US010751330B2

United States Patent
Zaid et al.

(10) Patent No.: US 10,751,330 B2
(45) Date of Patent: *Aug. 25, 2020

(54) HUMAN THERAPEUTIC AGENTS

(71) Applicant: Ankh Life Sciences Limited, Dublin (IE)

(72) Inventors: Gene H. Zaid, Sterling, KS (US); Thomas W. Burgoyne, Lake Zurich, IL (US)

(73) Assignee: Ankh Life Sciences Limited, Dublin 2 (IE)

( * ) Notice: Subject to any disclaimer, the term of this patent is extended or adjusted under 35 U.S.C. 154(b) by 0 days.

This patent is subject to a terminal disclaimer.

(21) Appl. No.: 16/724,979

(22) Filed: Dec. 23, 2019

(65) Prior Publication Data

US 2020/0147061 A1    May 14, 2020

Related U.S. Application Data

(63) Continuation of application No. 16/541,665, filed on Aug. 15, 2019, now Pat. No. 10,576,067, which is a continuation of application No. 16/213,774, filed on Dec. 7, 2018, now Pat. No. 10,471,049, which is a continuation of application No. 15/826,101, filed on Nov. 29, 2017, now abandoned, which is a continuation of application No. 15/337,987, filed on Oct. 28, 2016, now Pat. No. 9,907,786, which is a continuation of application No. PCT/IB2016/000723, filed on Apr. 20, 2016, and a continuation-in-part of application No. PCT/US2015/055968, filed on Oct. 16, 2015, and a continuation-in-part of application No. 14/721,011, filed on May 26, 2015, now Pat. No. 9,402,834, and a continuation-in-part of application No. 14/721,011, filed on May 26, 2015, now Pat. No. 9,402,834.

(60) Provisional application No. 62/184,051, filed on Jun. 24, 2015, provisional application No. 62/184,051, filed on Jun. 24, 2015, provisional application No. 62/161,090, filed on May 13, 2015, provisional application No. 62/161,090, filed on May 13, 2015, provisional application No. 62/066,686, filed on Oct. 21, 2014.

(51) Int. Cl.
| | |
|---|---|
| *A61K 31/435* | (2006.01) |
| *A61K 31/437* | (2006.01) |
| *A61K 45/06* | (2006.01) |
| *A61K 31/11* | (2006.01) |
| *A61K 31/12* | (2006.01) |
| *A61K 47/10* | (2017.01) |
| *A61K 31/4375* | (2006.01) |

(52) U.S. Cl.
CPC ............ *A61K 31/437* (2013.01); *A61K 31/11* (2013.01); *A61K 31/12* (2013.01); *A61K 31/4375* (2013.01); *A61K 45/06* (2013.01); *A61K 47/10* (2013.01)

(58) Field of Classification Search
None
See application file for complete search history.

(56) References Cited

U.S. PATENT DOCUMENTS

| | | | | |
|---|---|---|---|---|
| 10,471,049 | B2 * | 11/2019 | Zaid | A61K 31/11 |
| 10,507,200 | B1 * | 12/2019 | Zaid | A61K 31/11 |
| 16,724,935 | * | 12/2019 | Zaid | A61K 31/437 |
| 10,532,043 | B2 * | 1/2020 | Zaid | A61K 31/11 |
| 10,576,067 | B2 * | 3/2020 | Zaid | A61K 47/10 |

\* cited by examiner

*Primary Examiner* — Svetlana M Ivanova
(74) *Attorney, Agent, or Firm* — Hovey Williams LLP

(57) ABSTRACT

Human therapeutic treatment compositions comprise at least two of a curcumin component, a harmine component, and an isovanillin component, and preferably all three in combination. The agents are effective for the treatment of human conditions, especially human cancers.

24 Claims, 585 Drawing Sheets

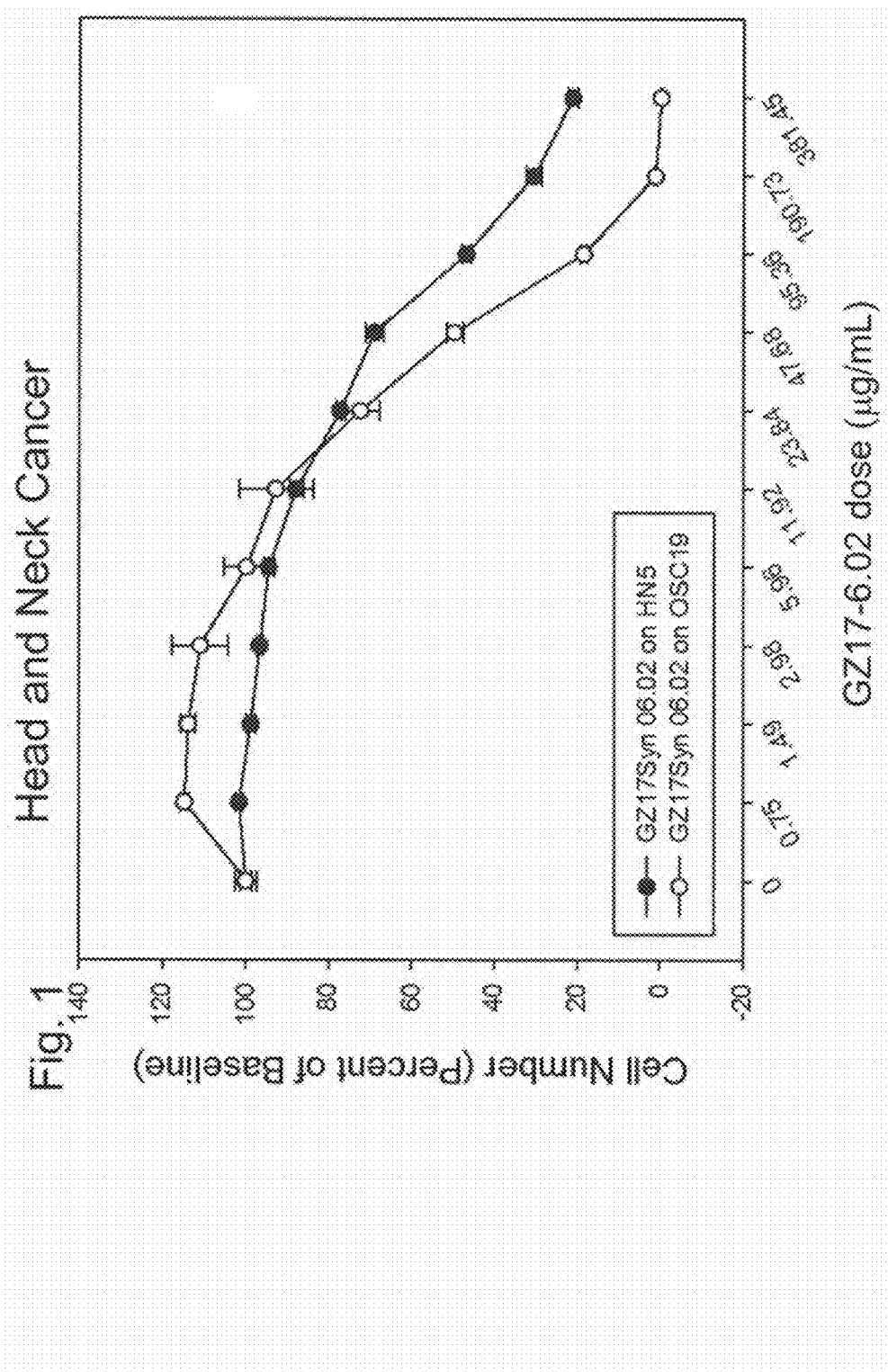

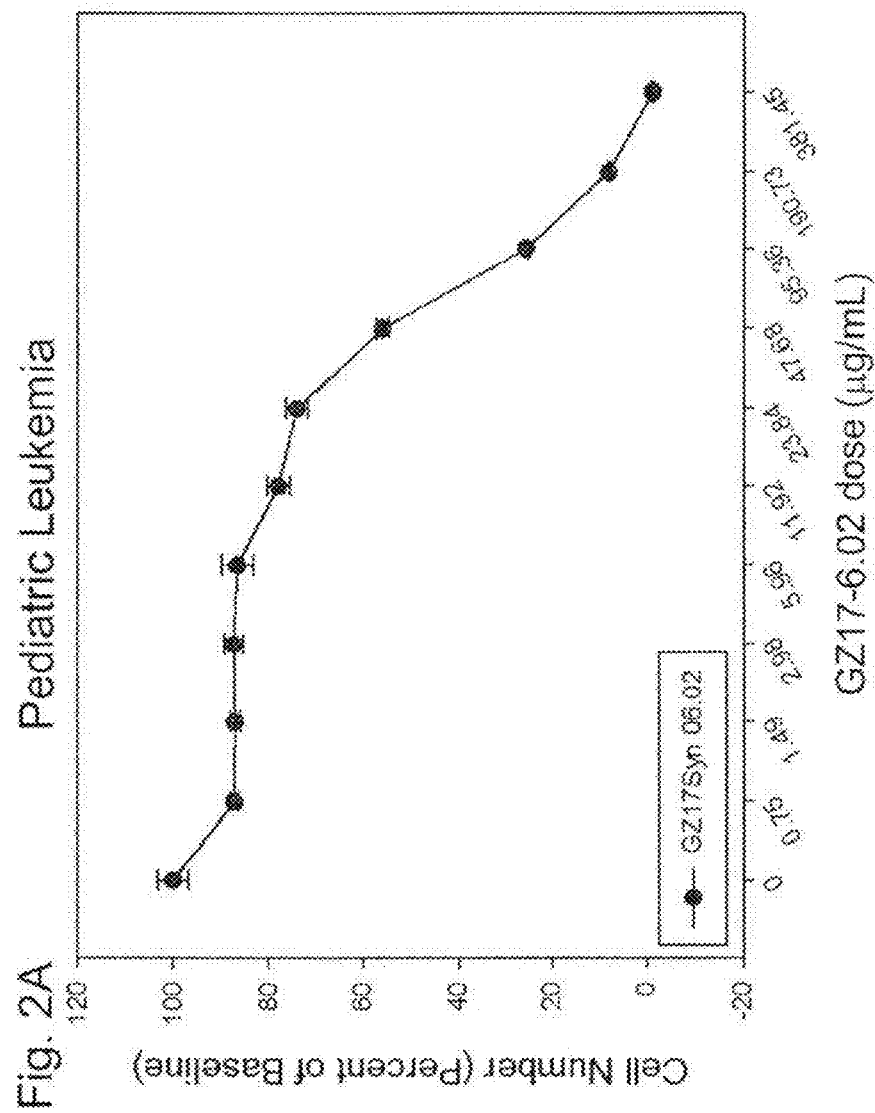

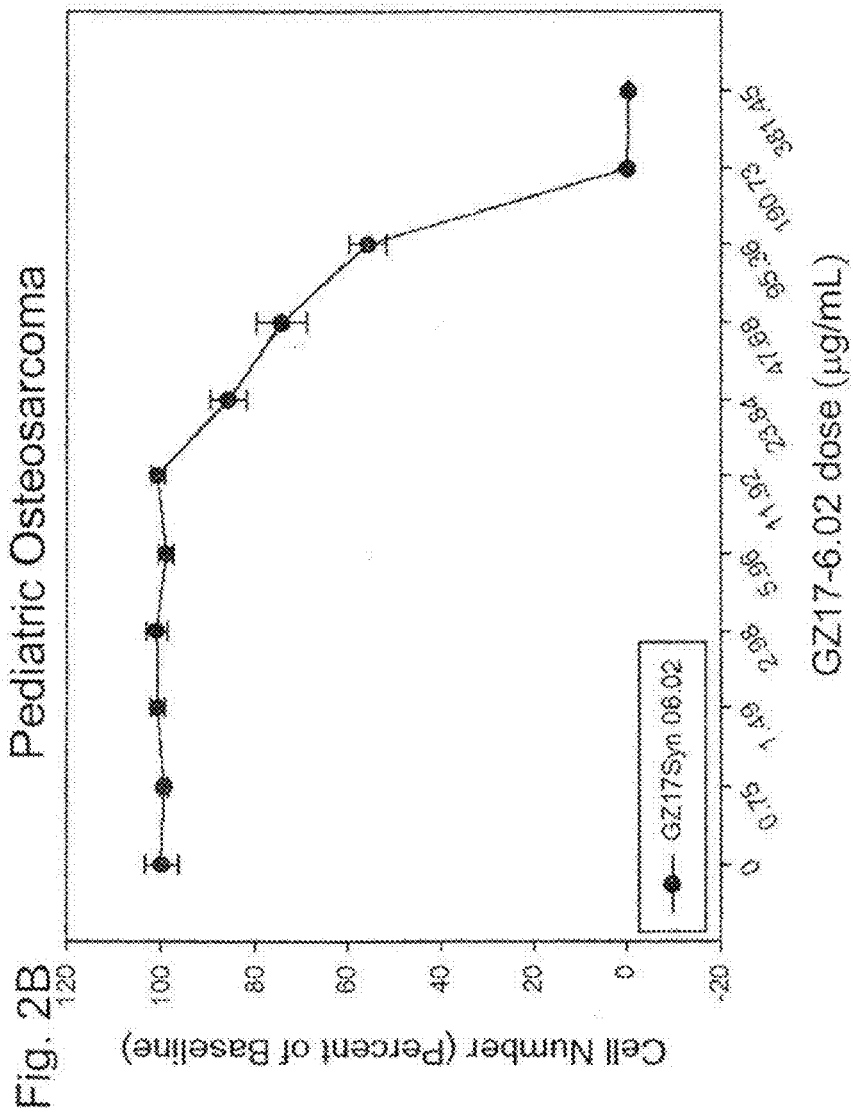

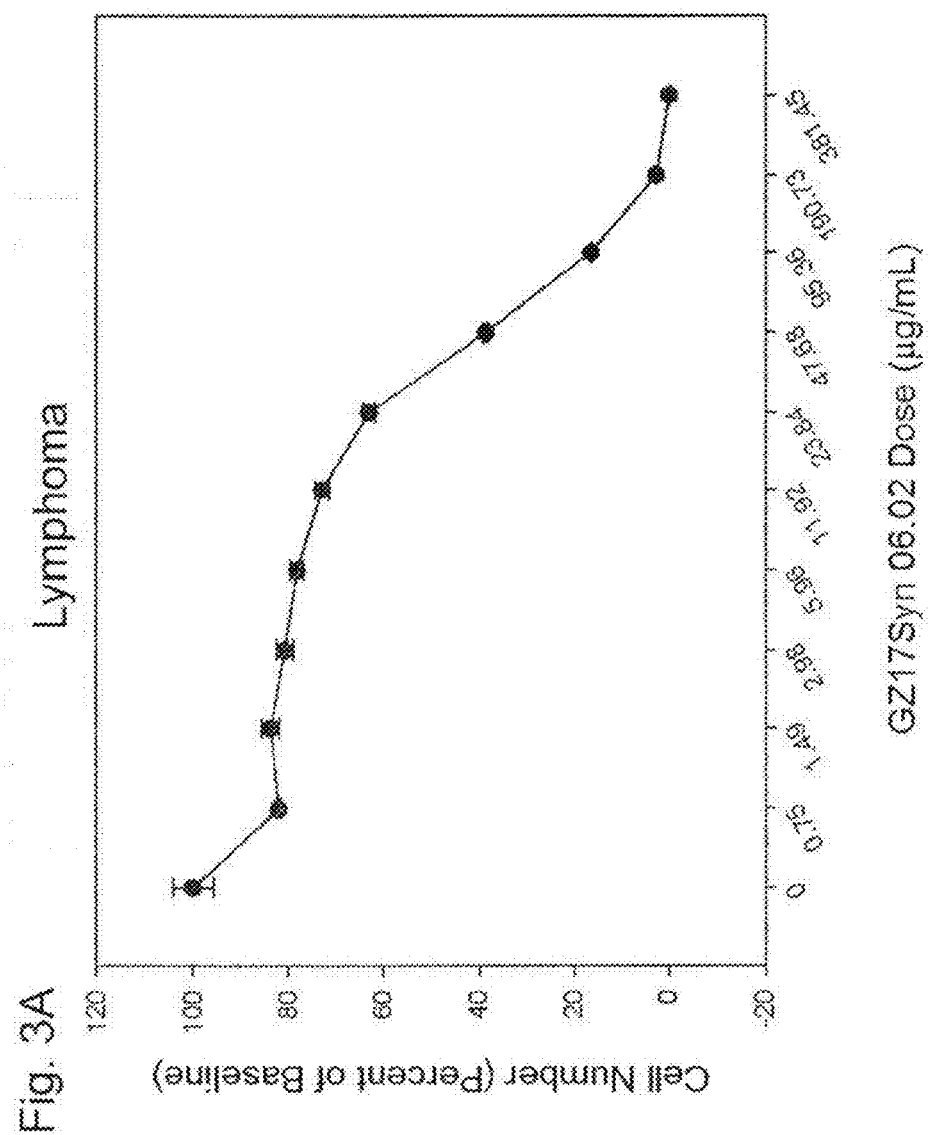

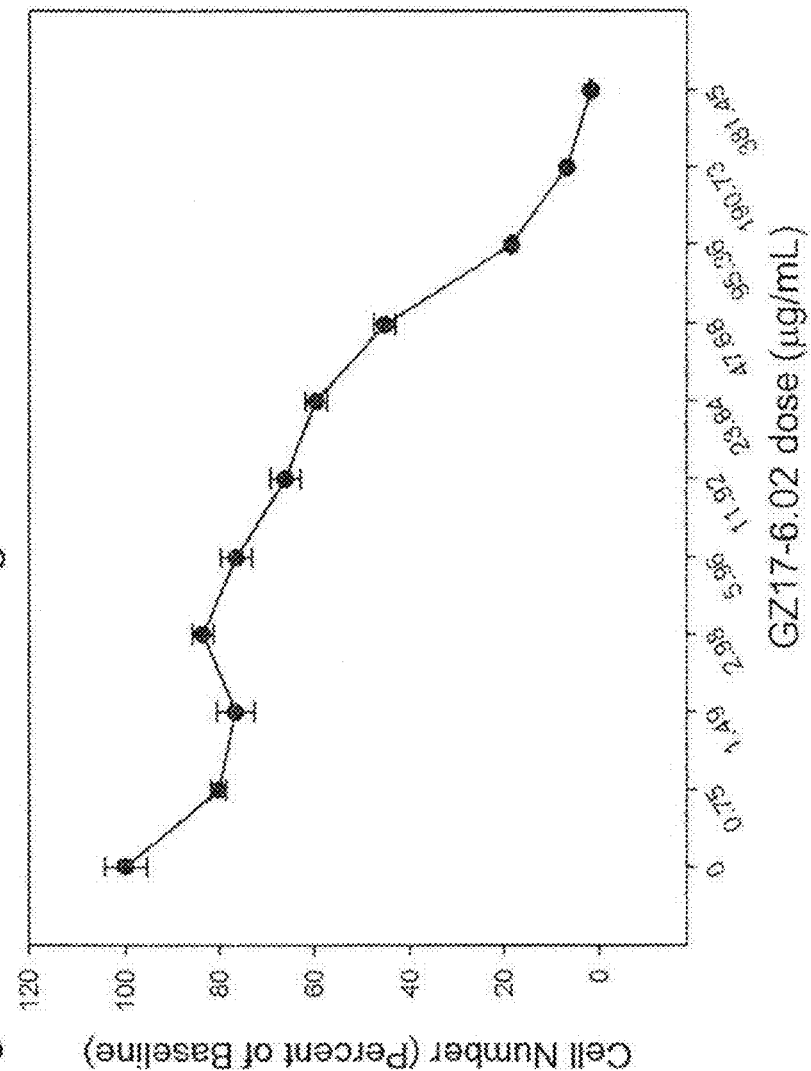

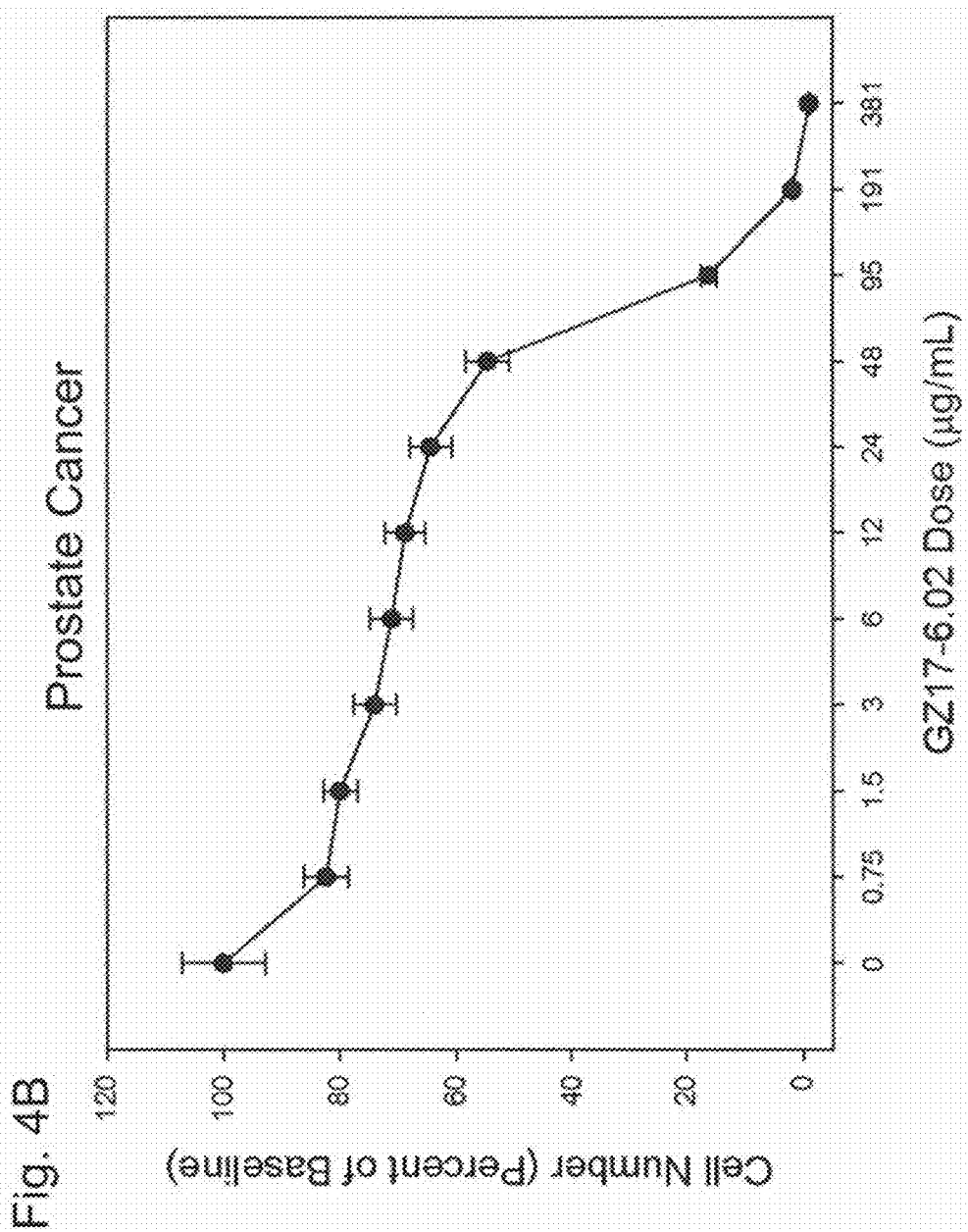

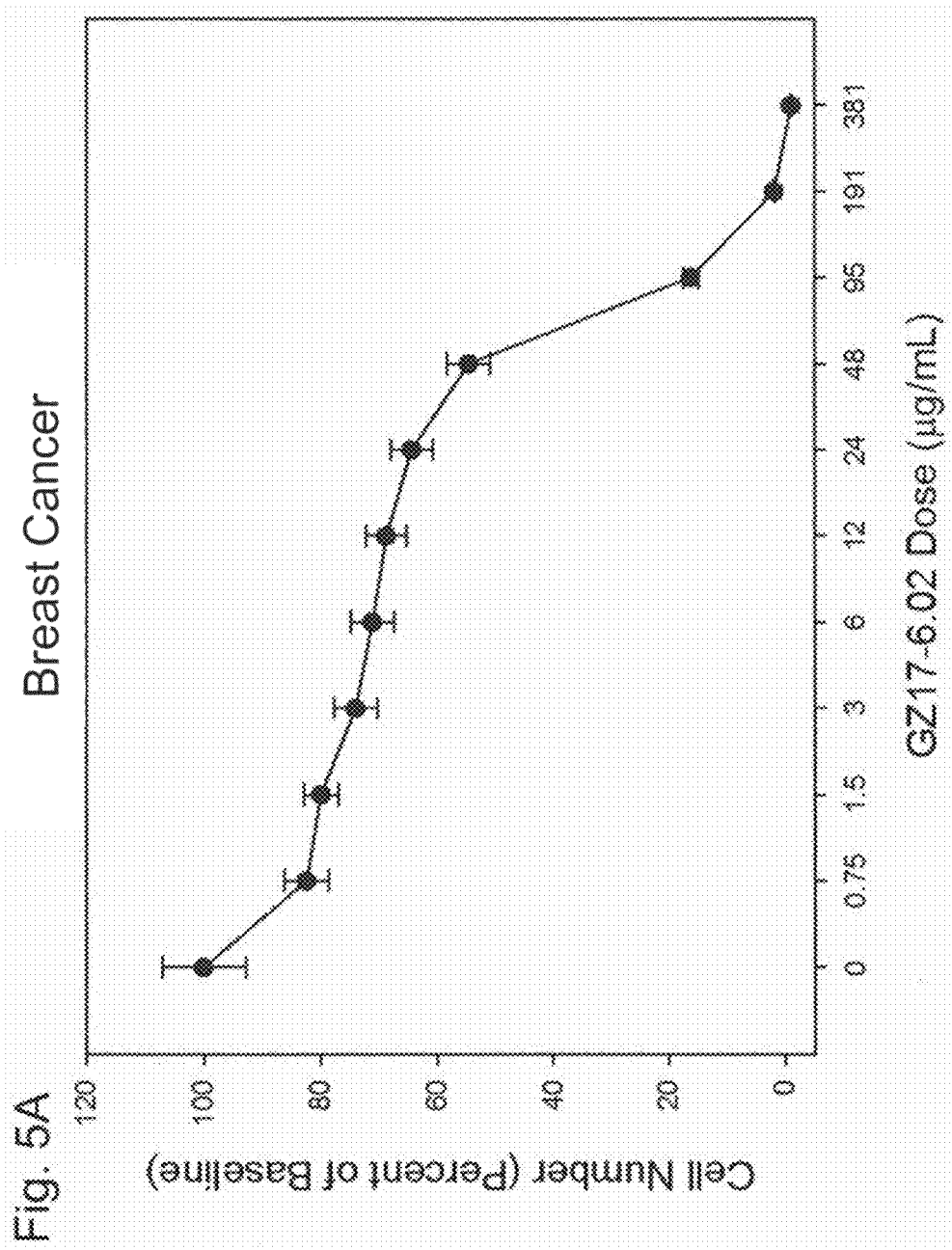

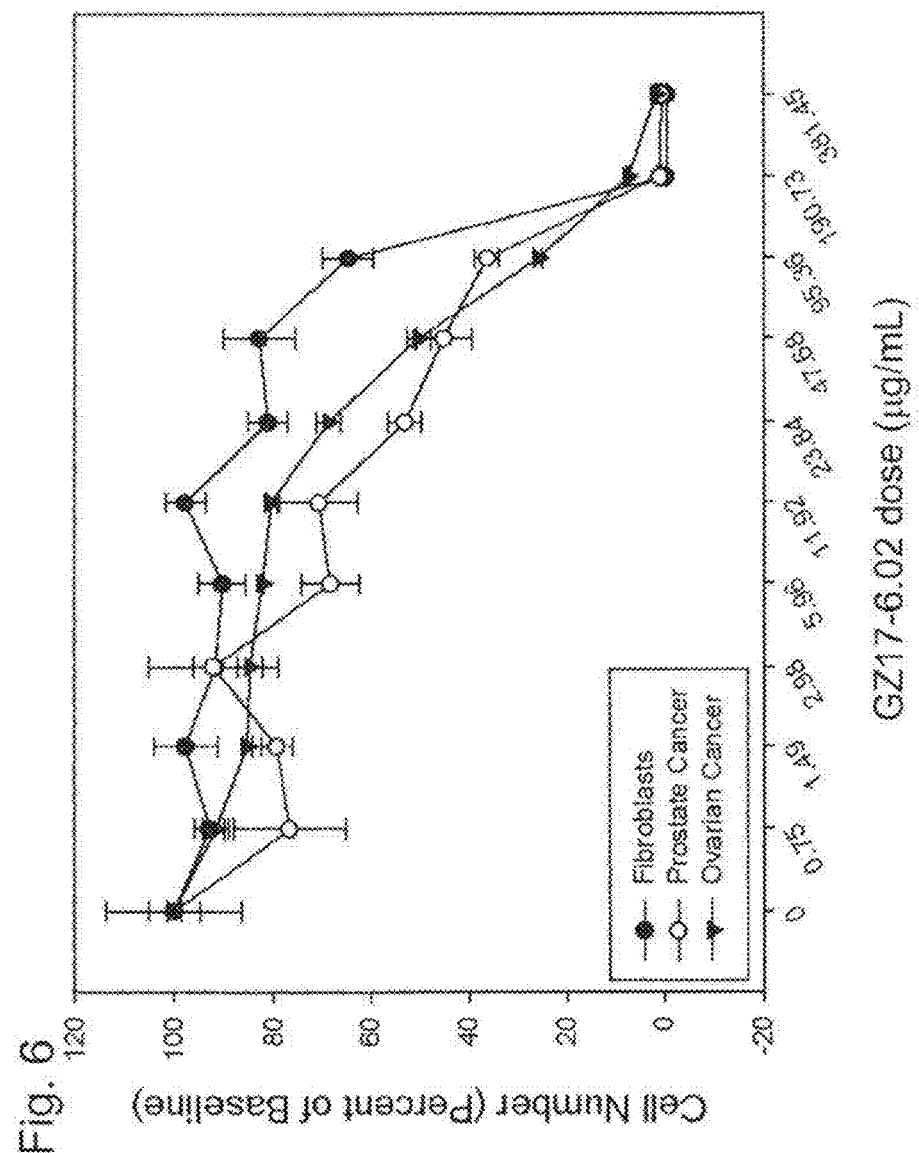

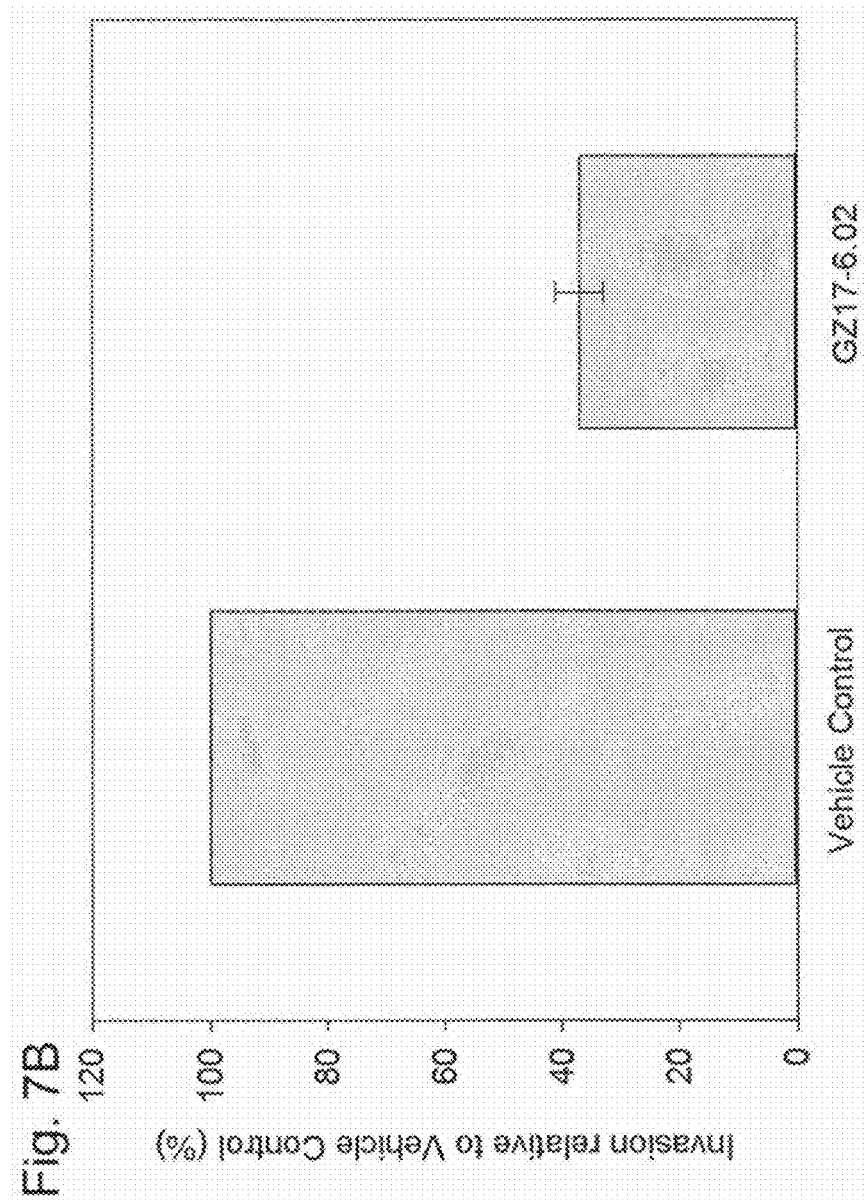

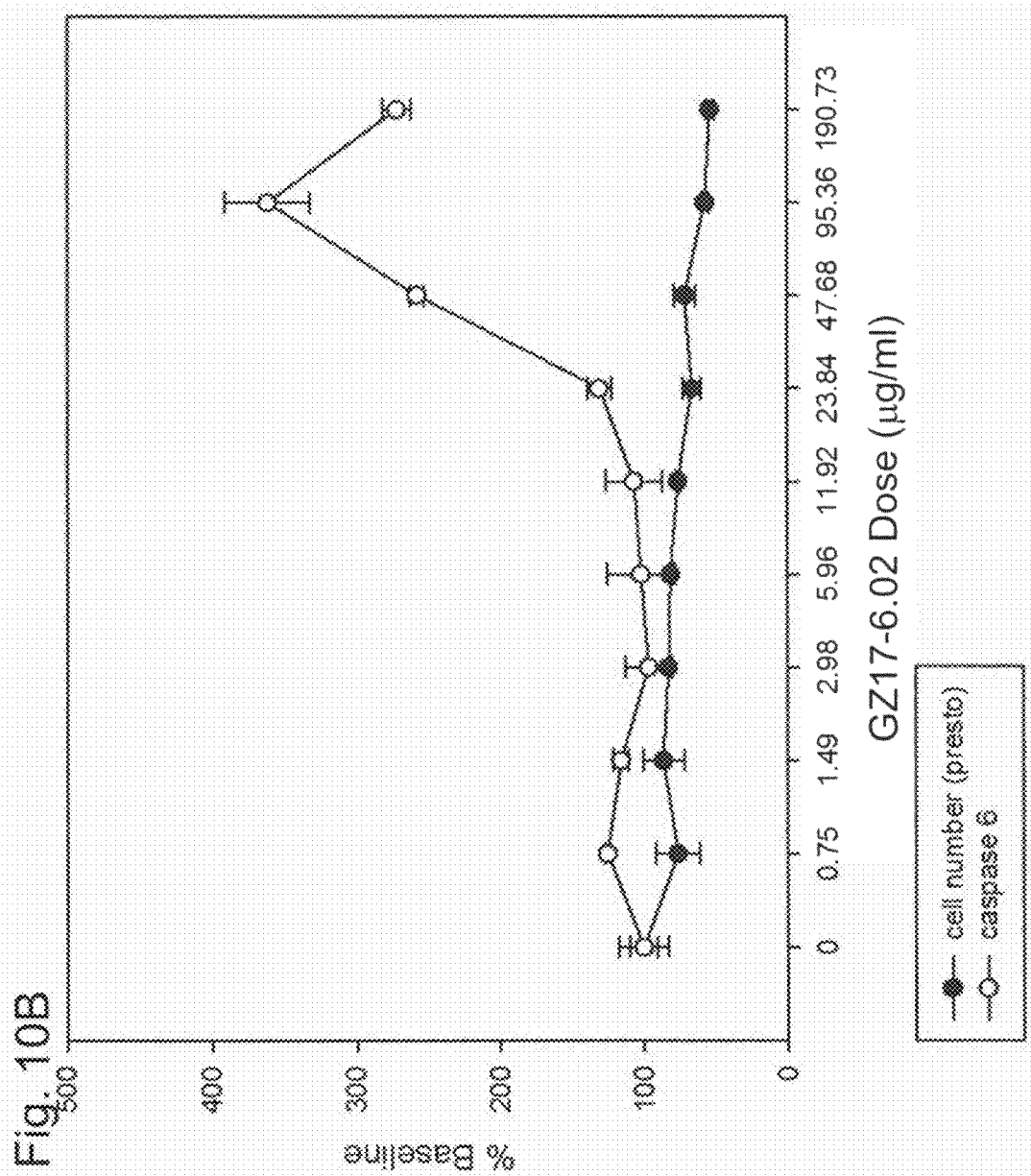

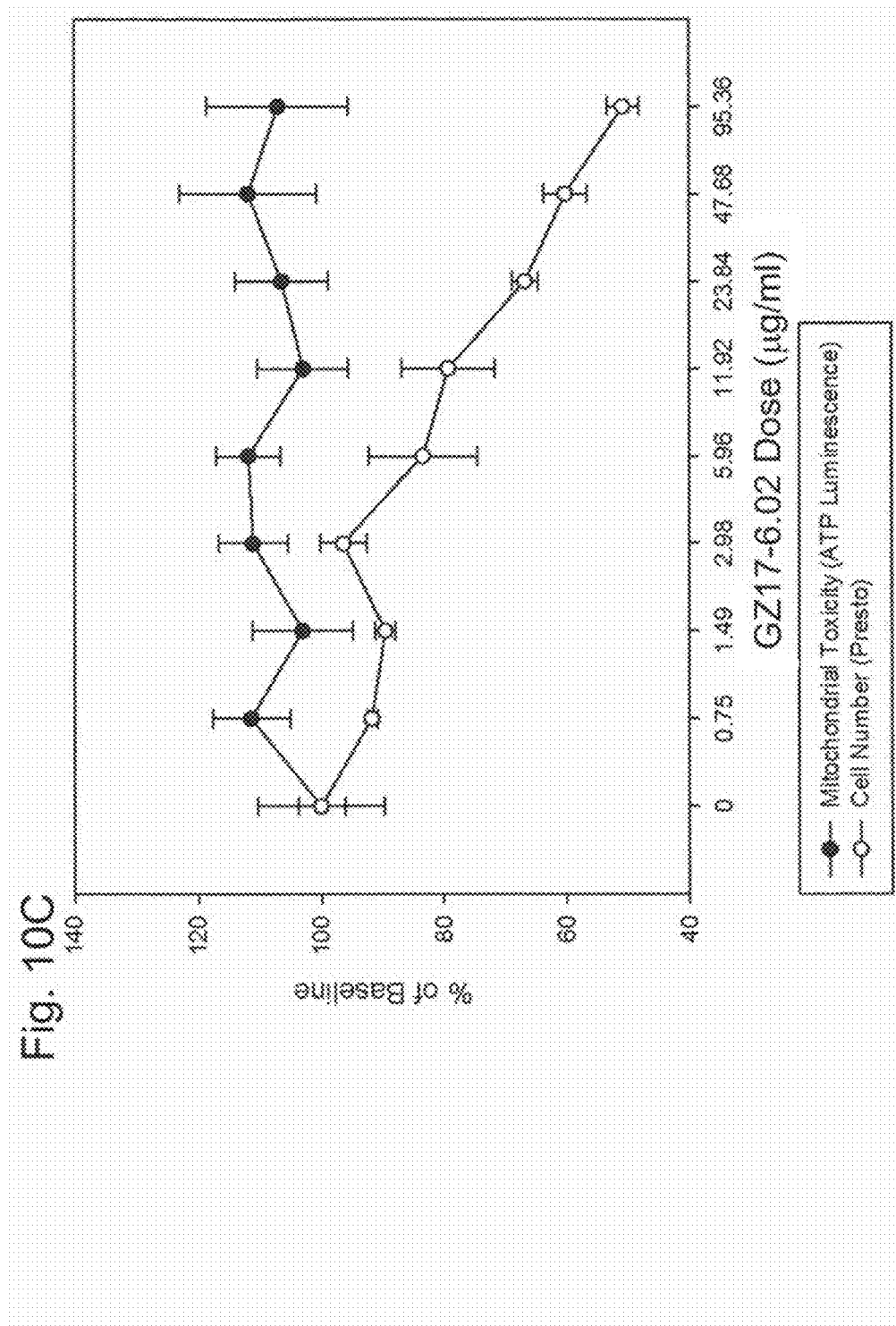

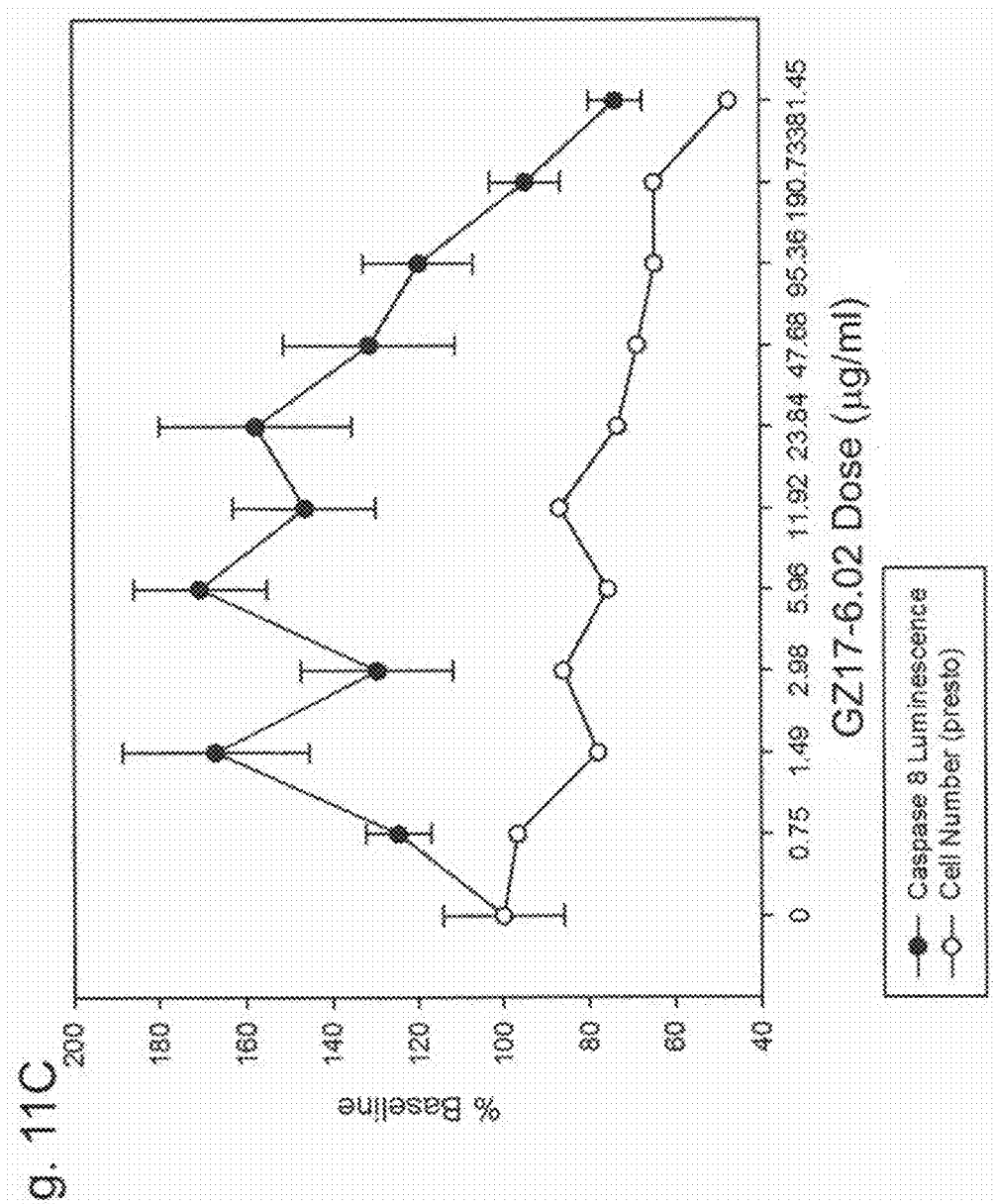

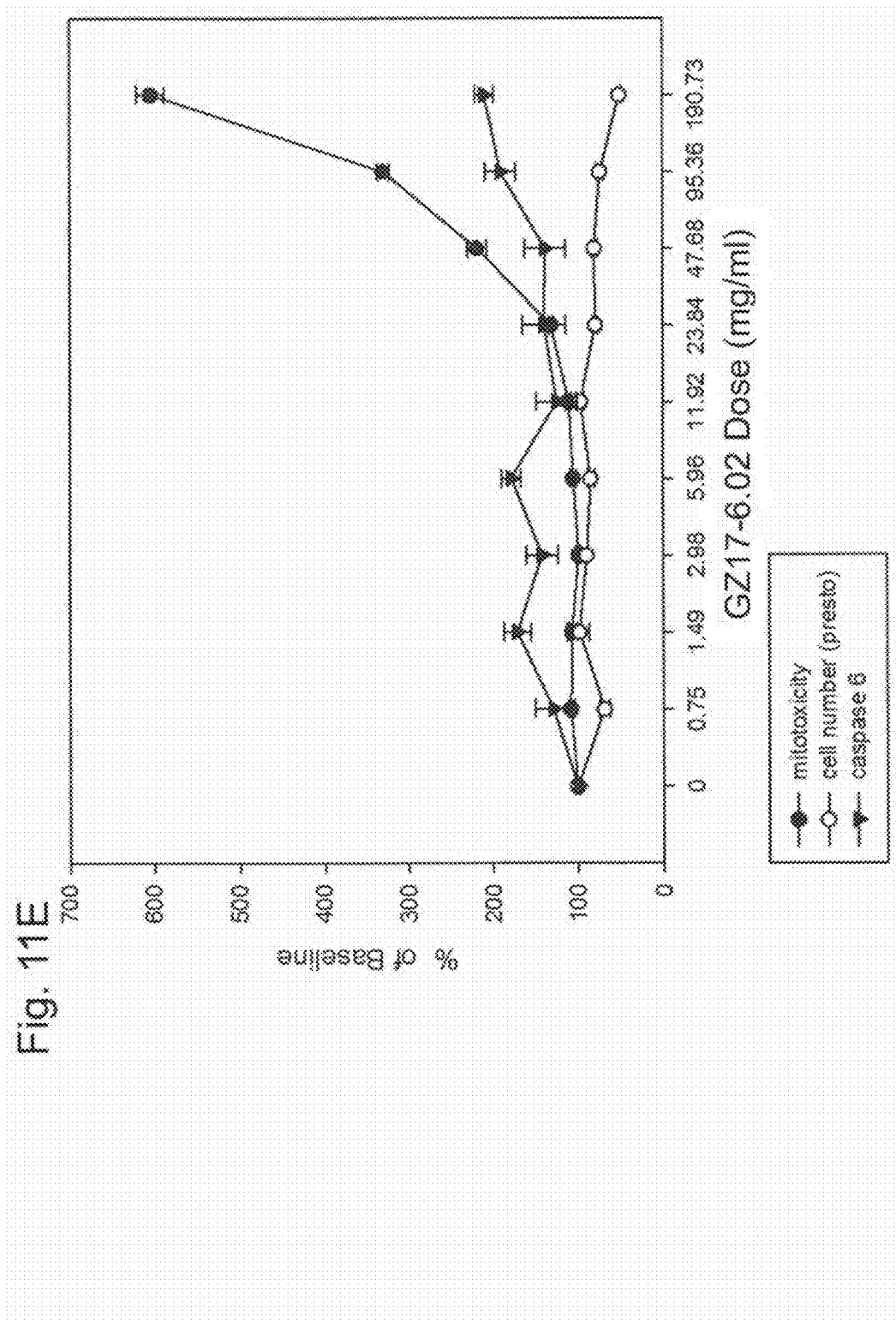

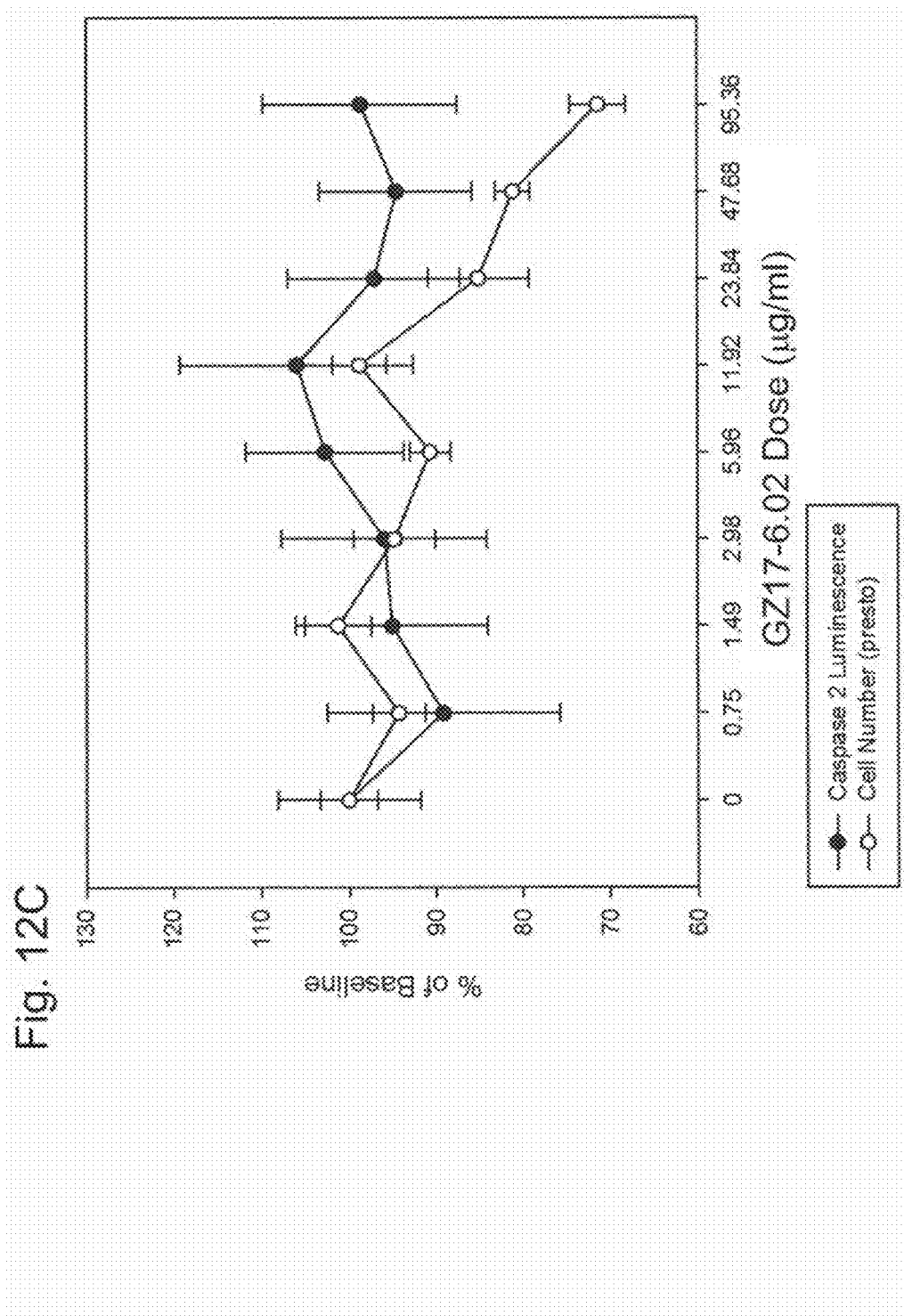

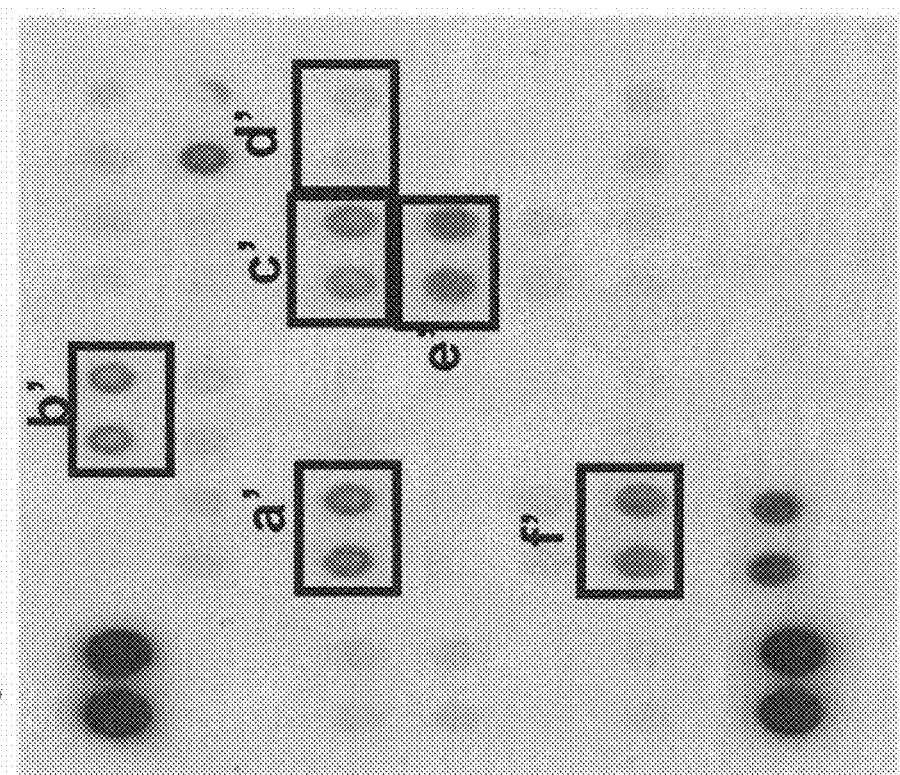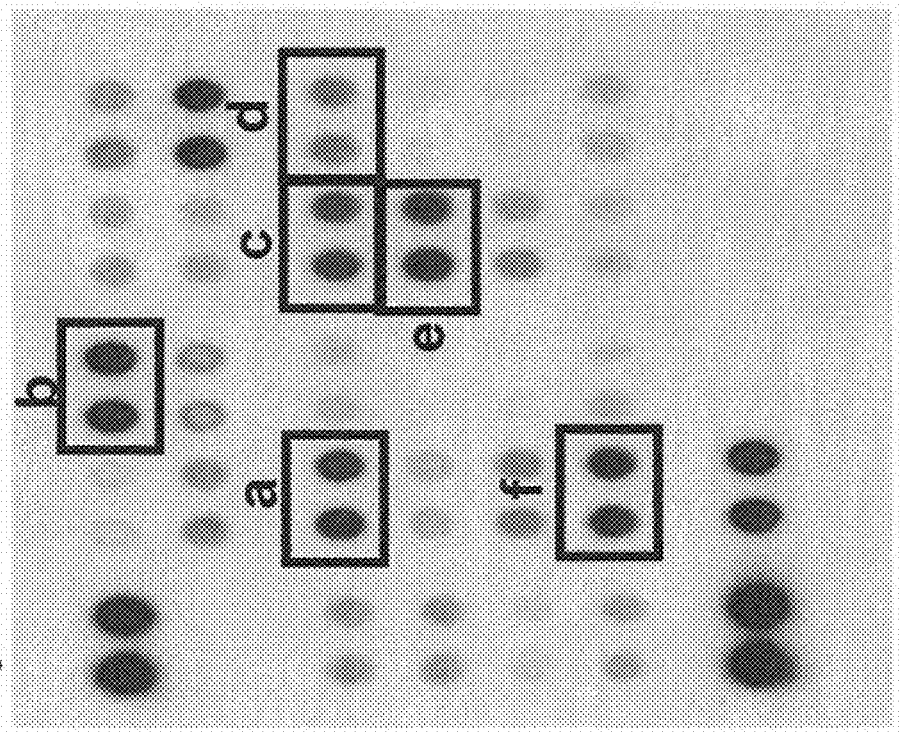

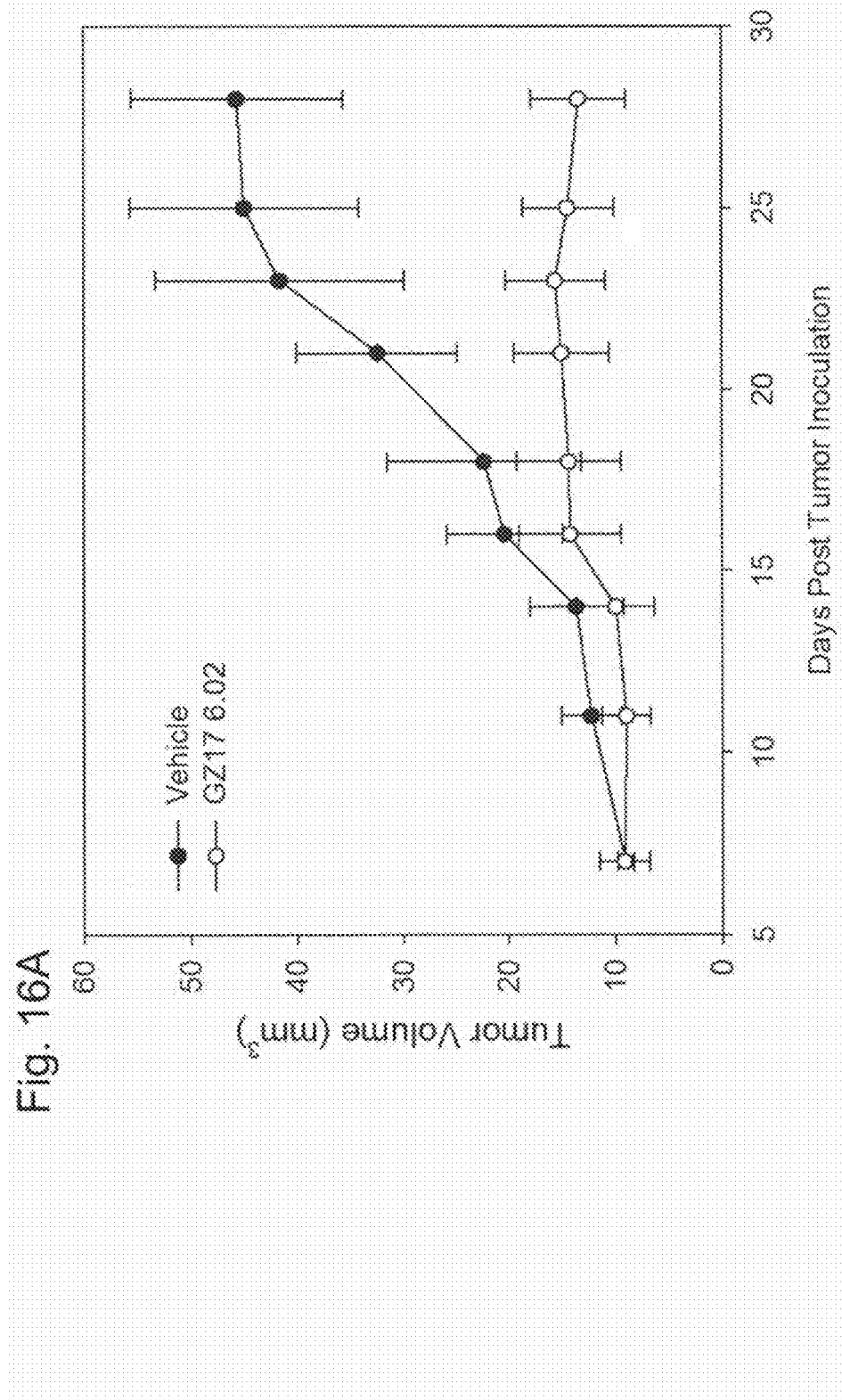

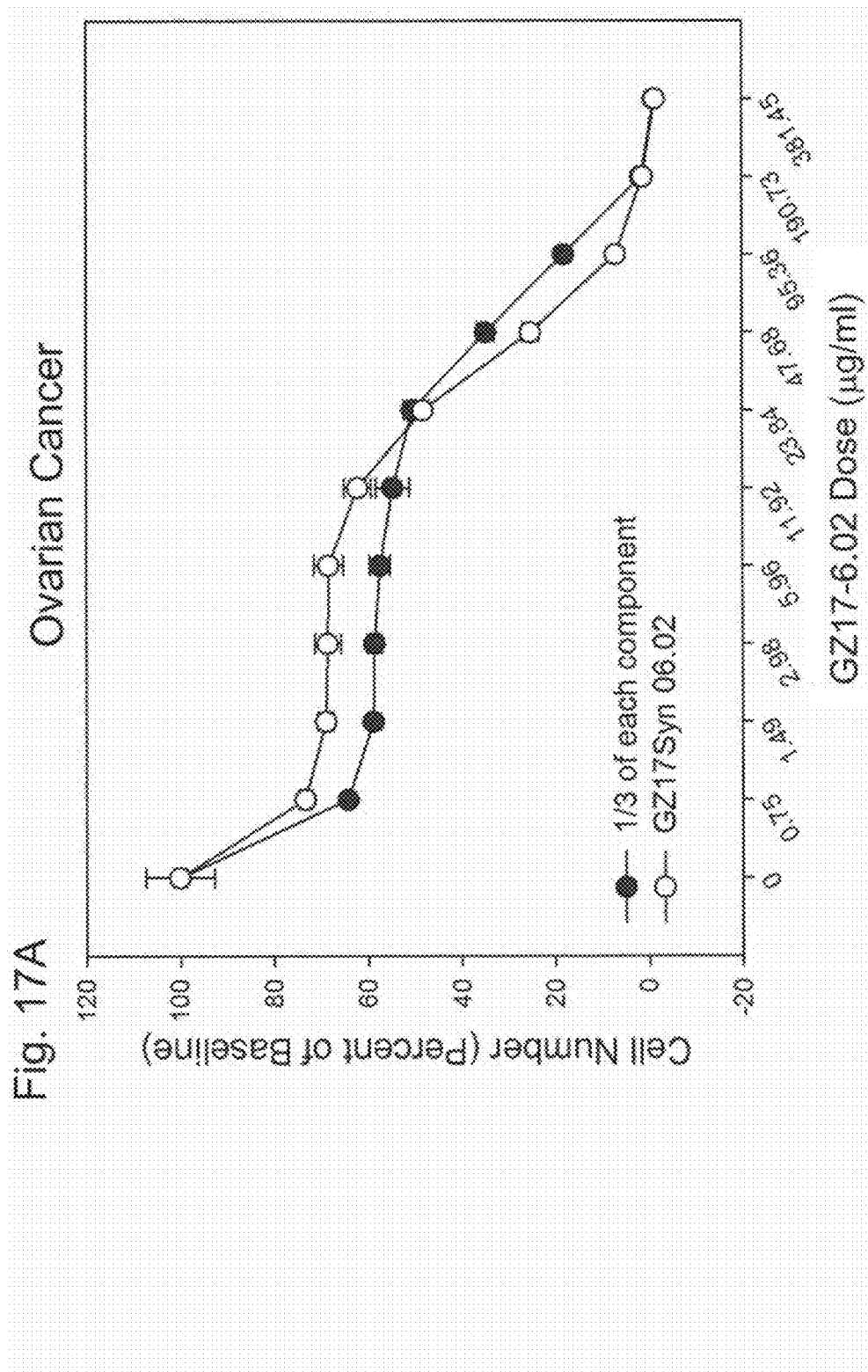

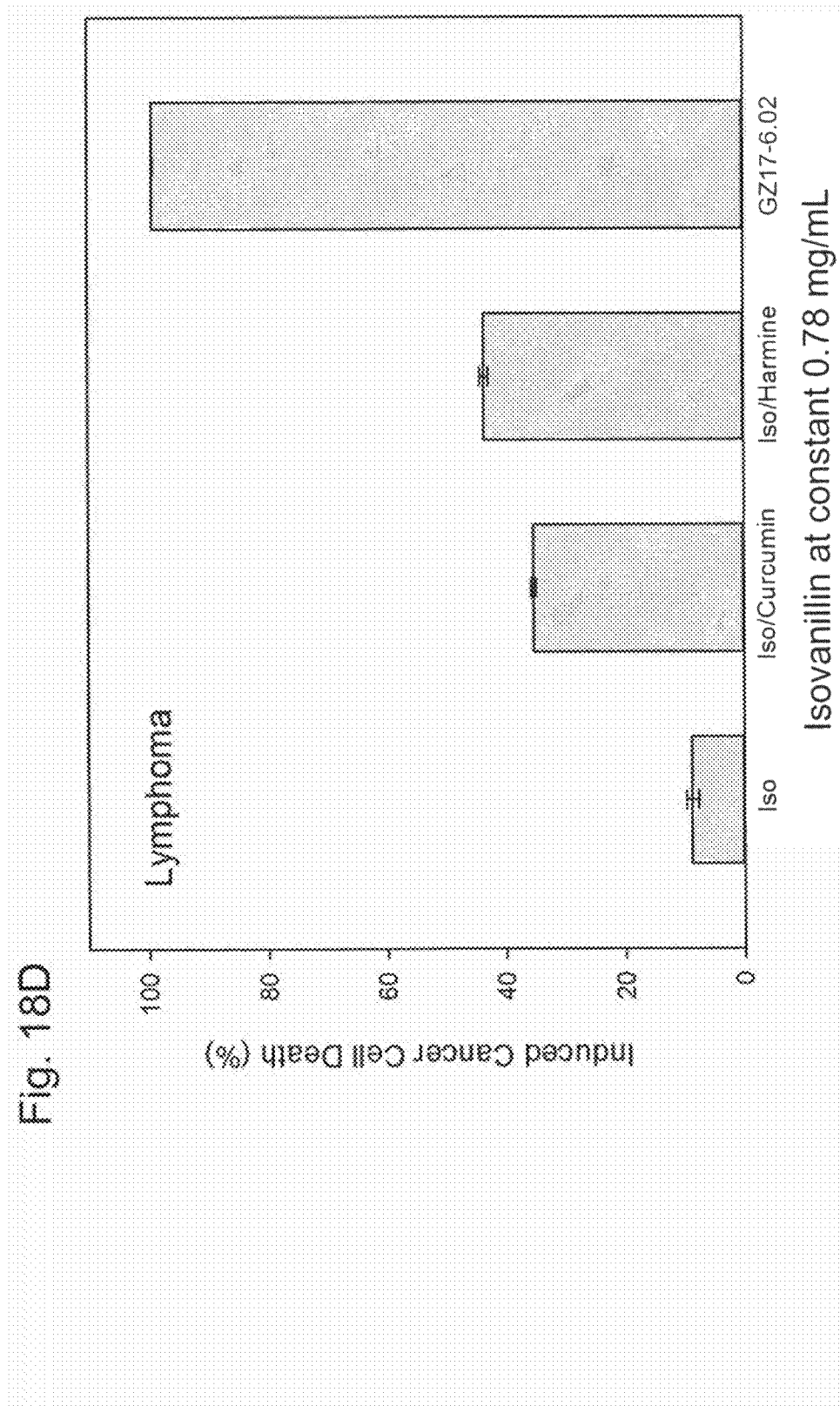

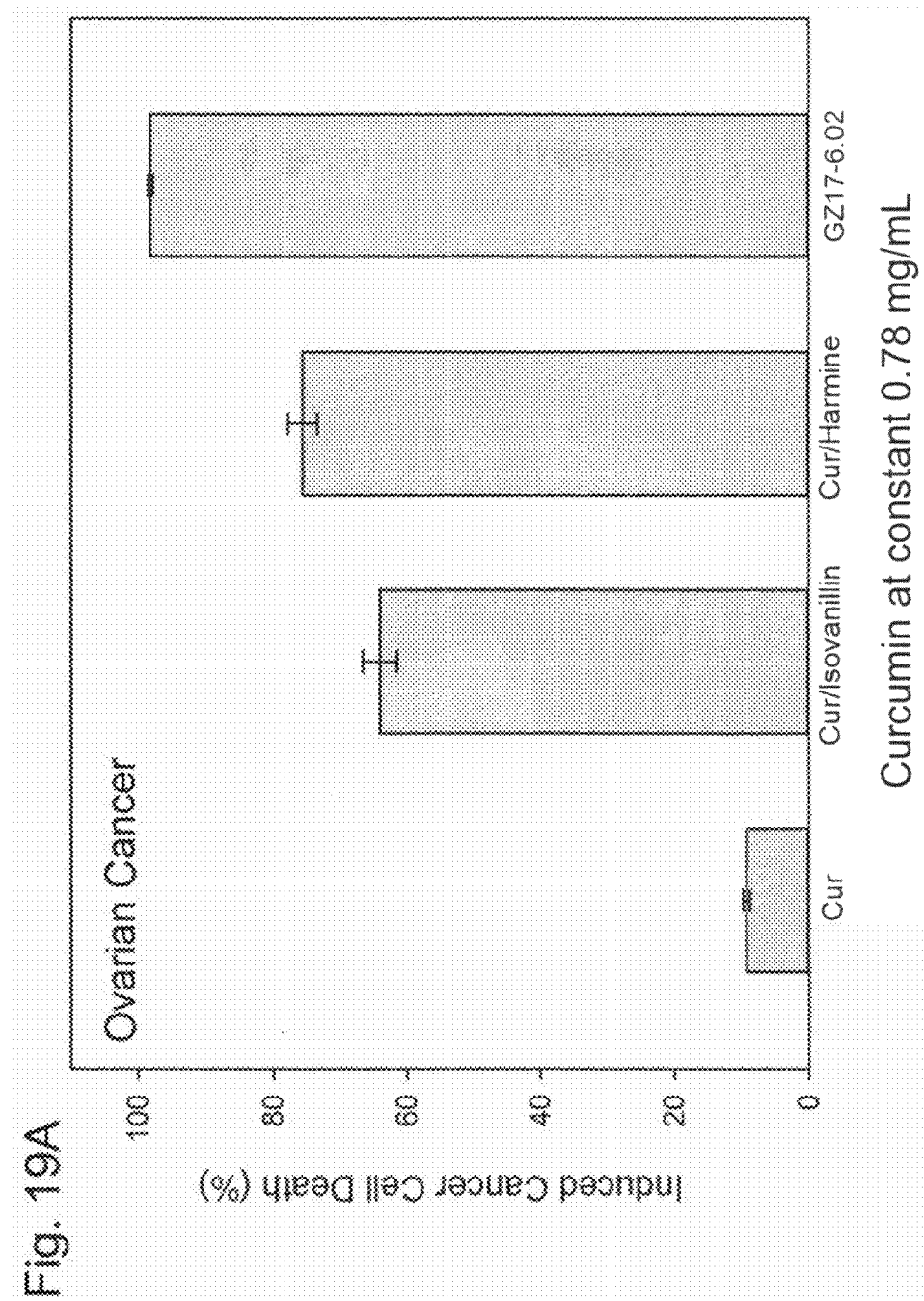

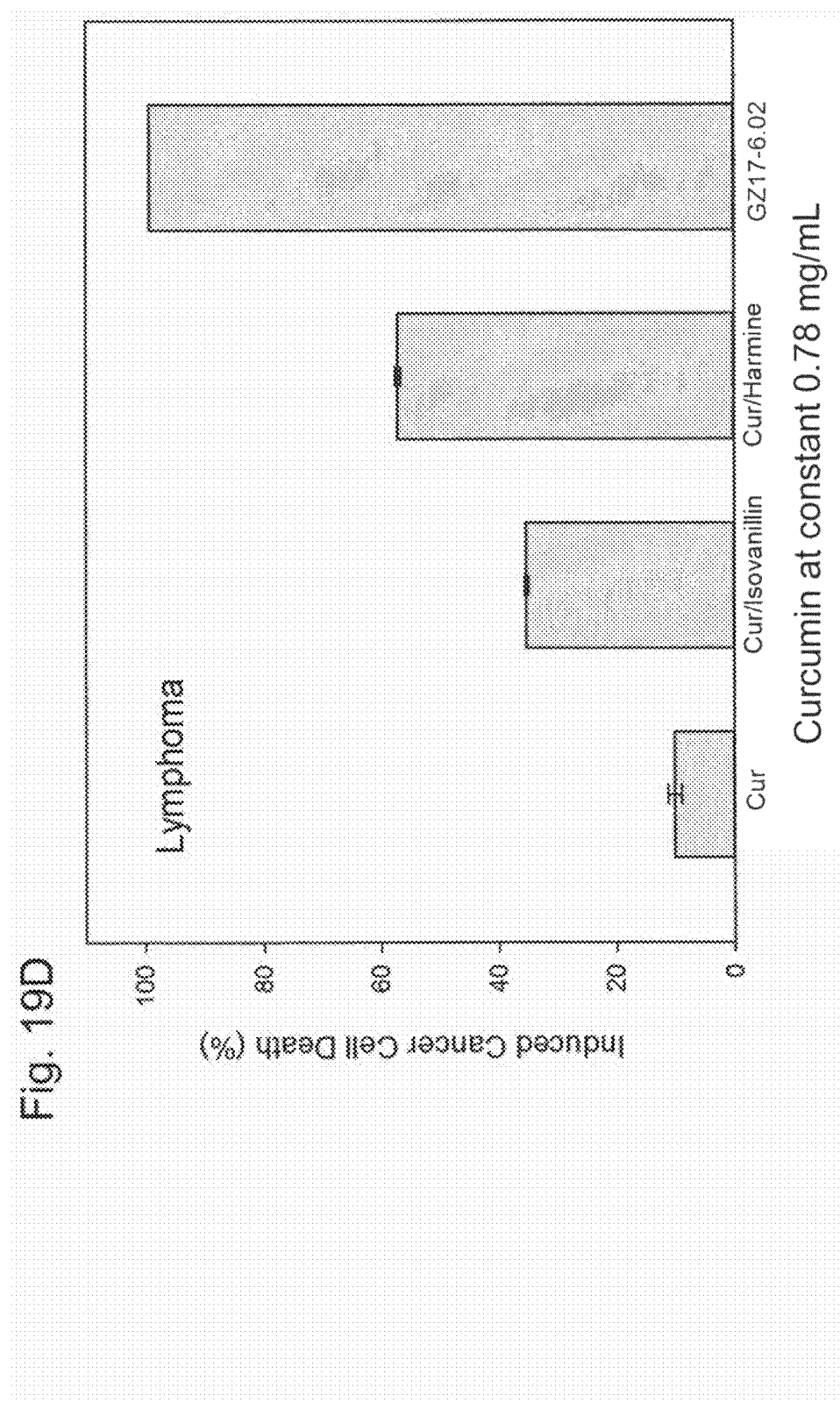

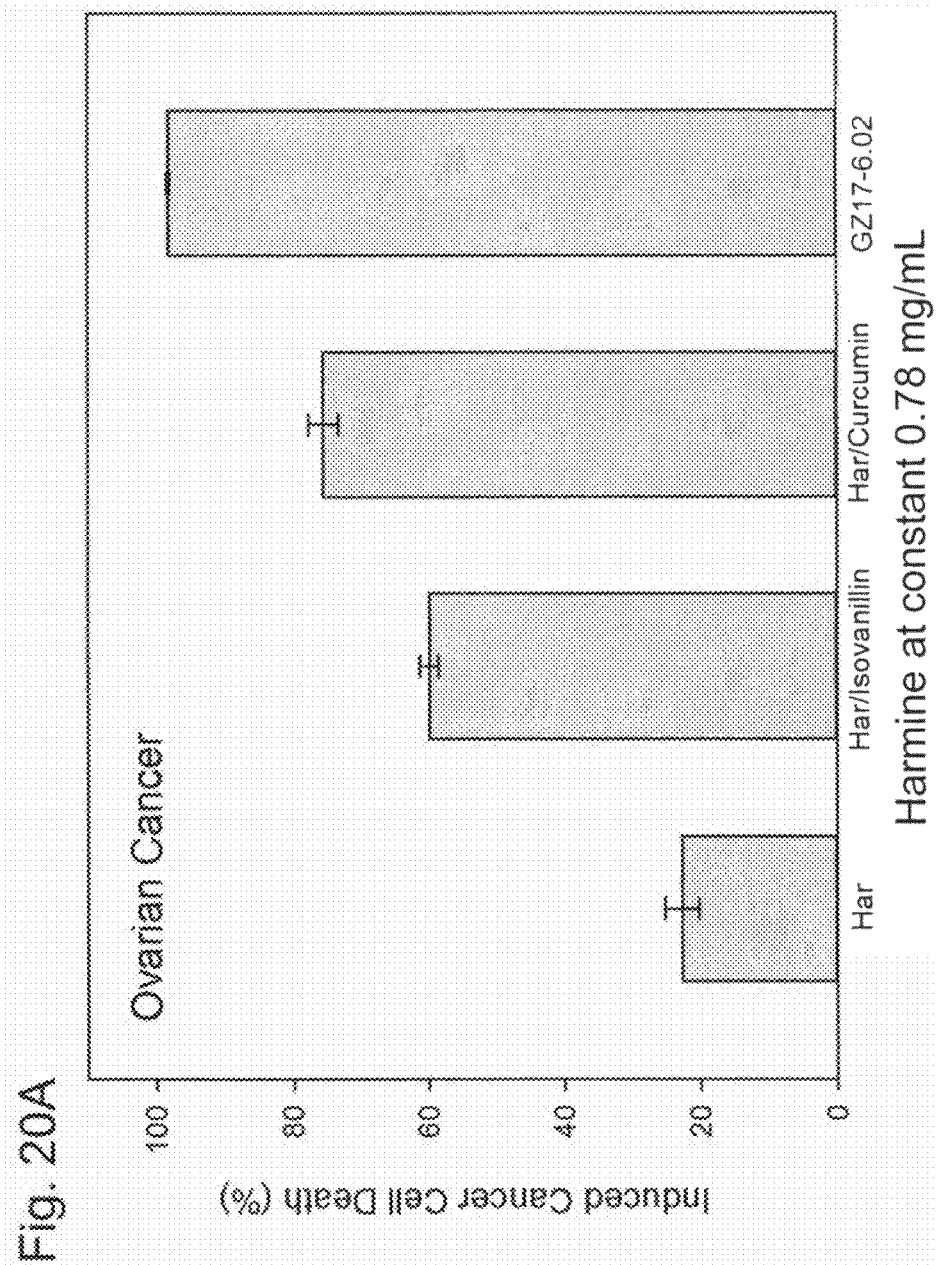

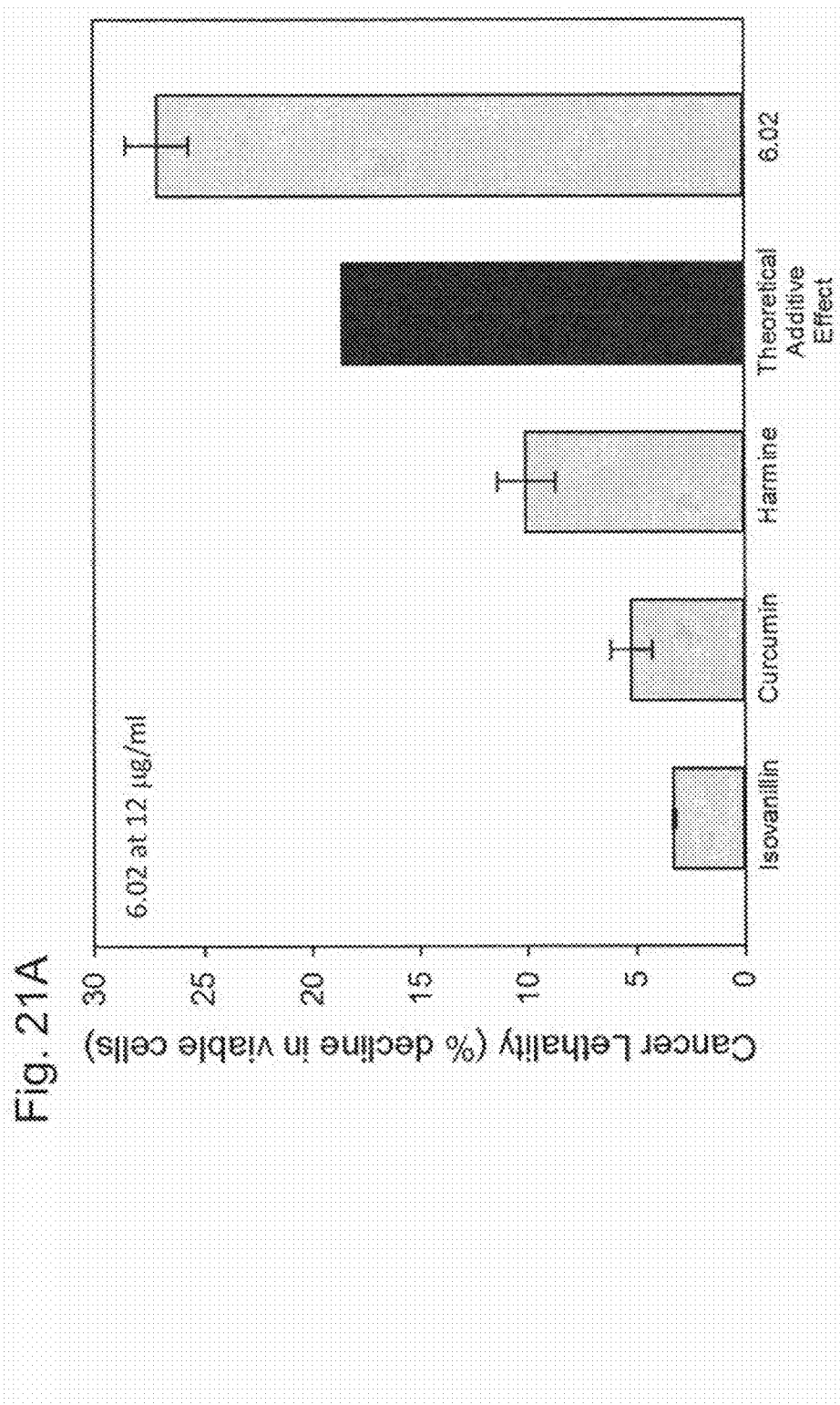

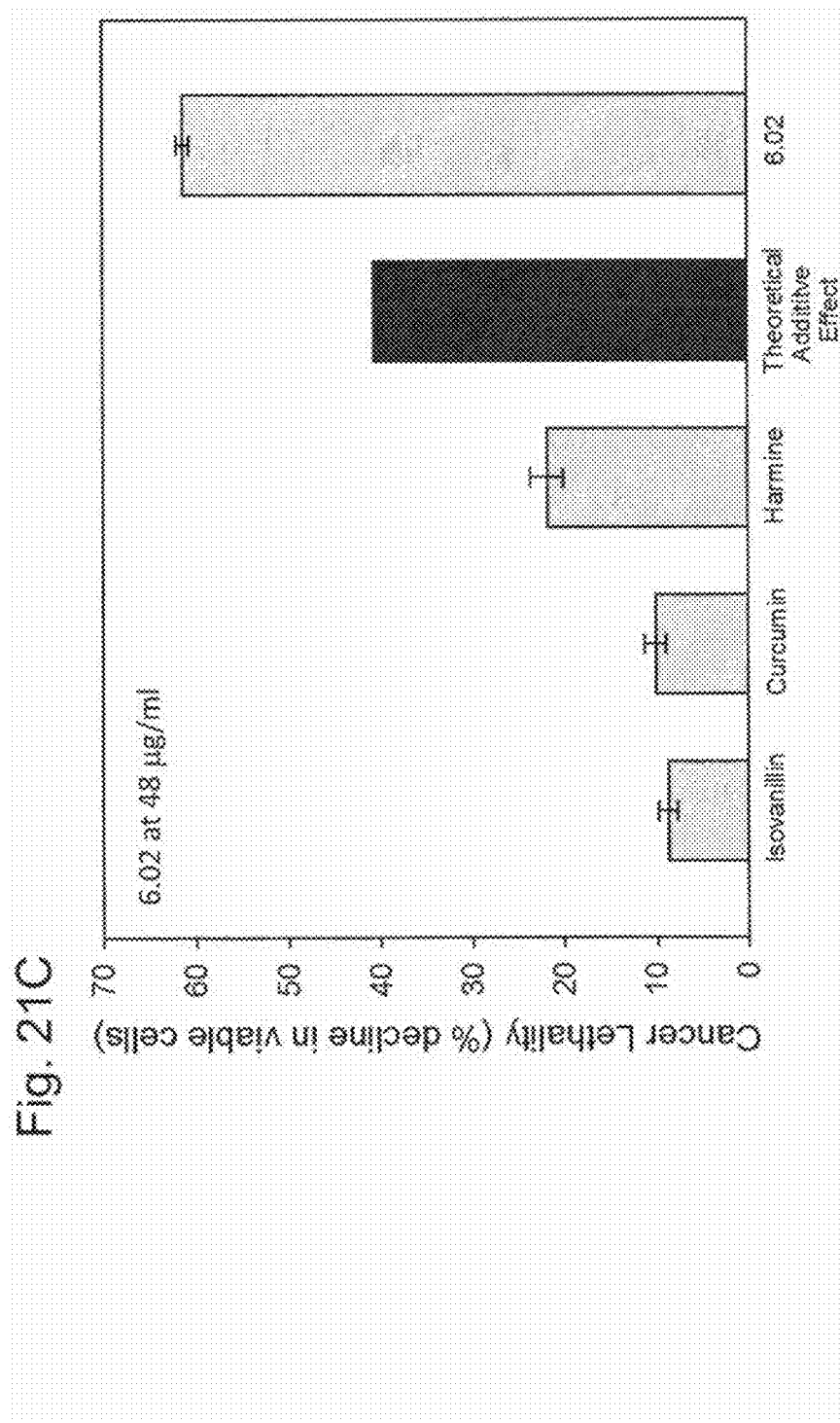

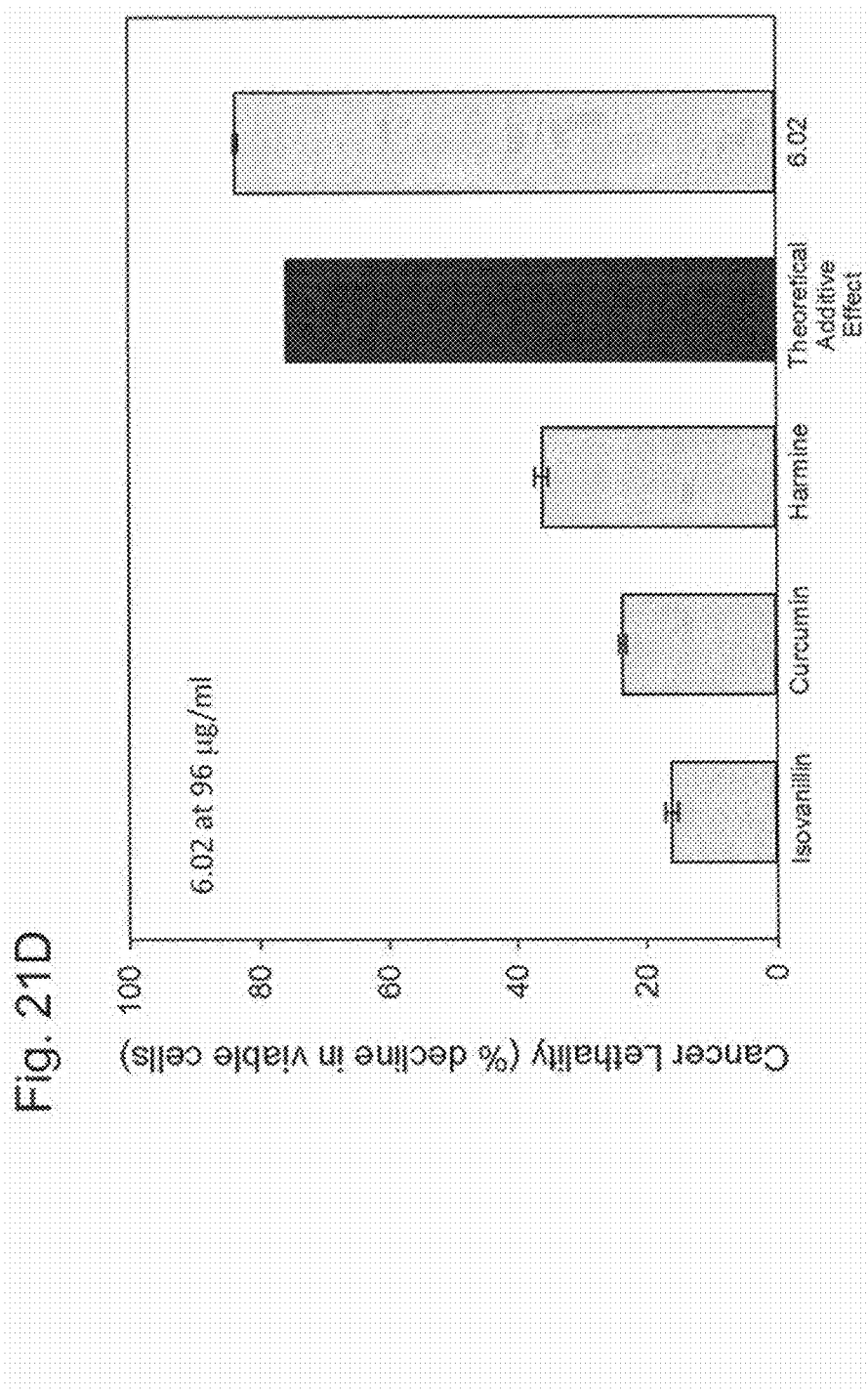

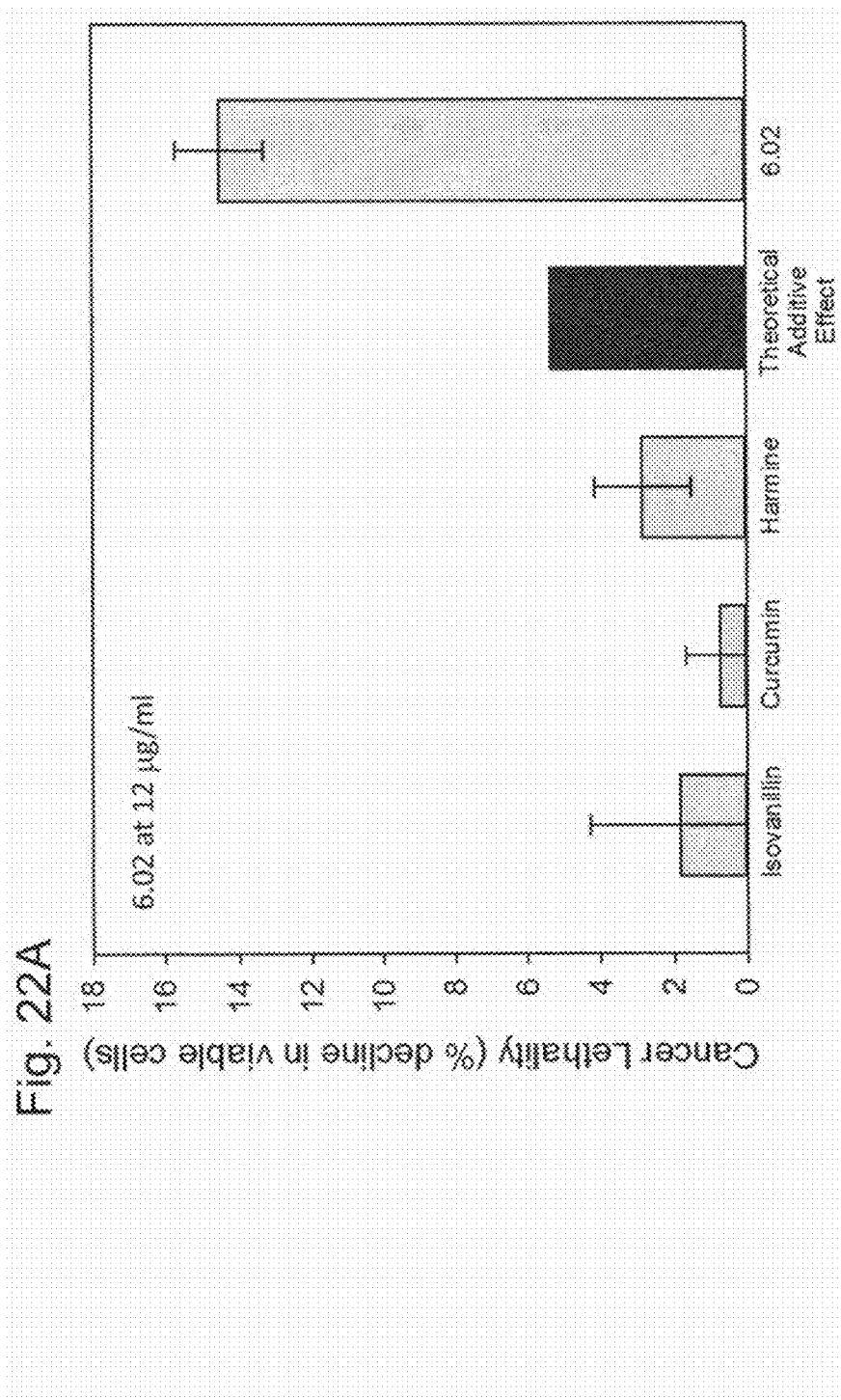

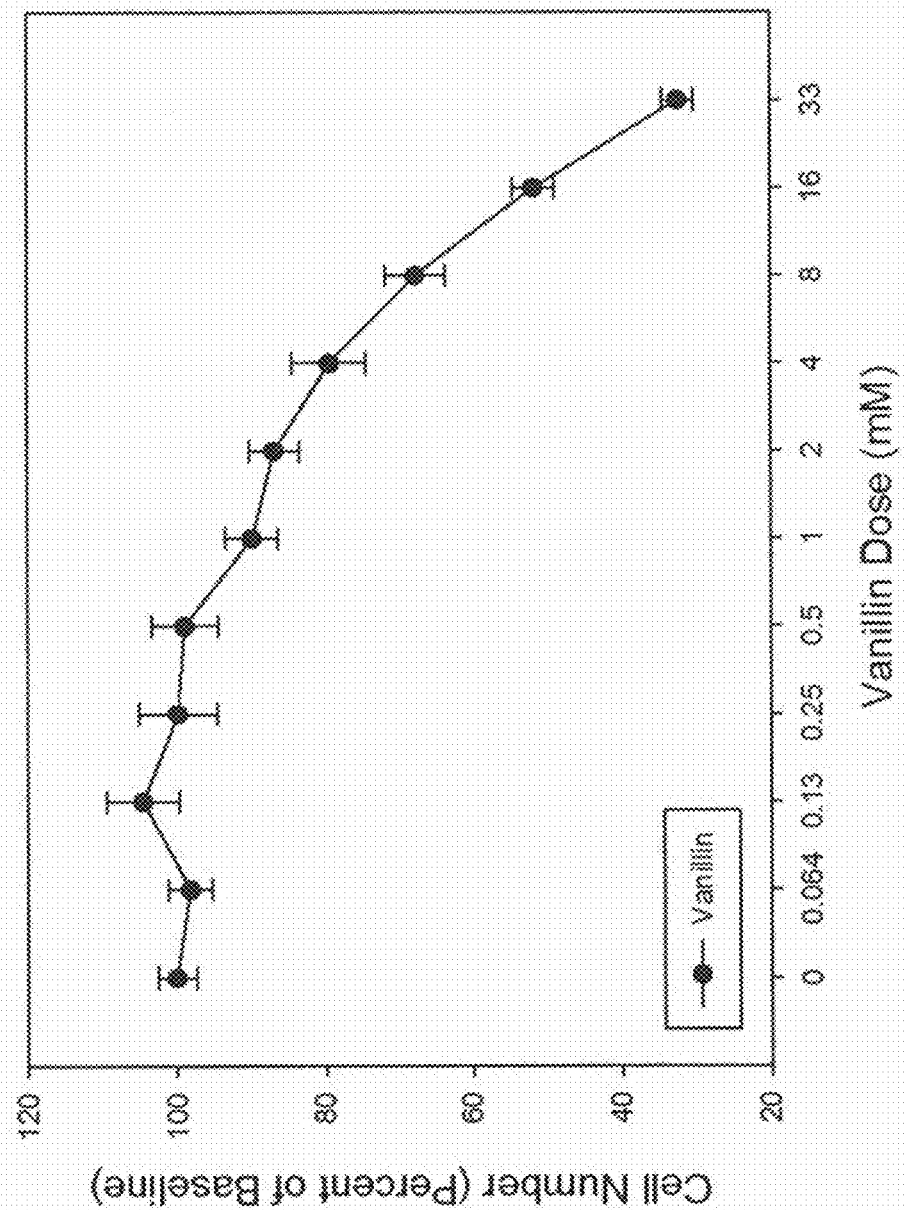
Fig. 23A Vanillin on Lung Cancer

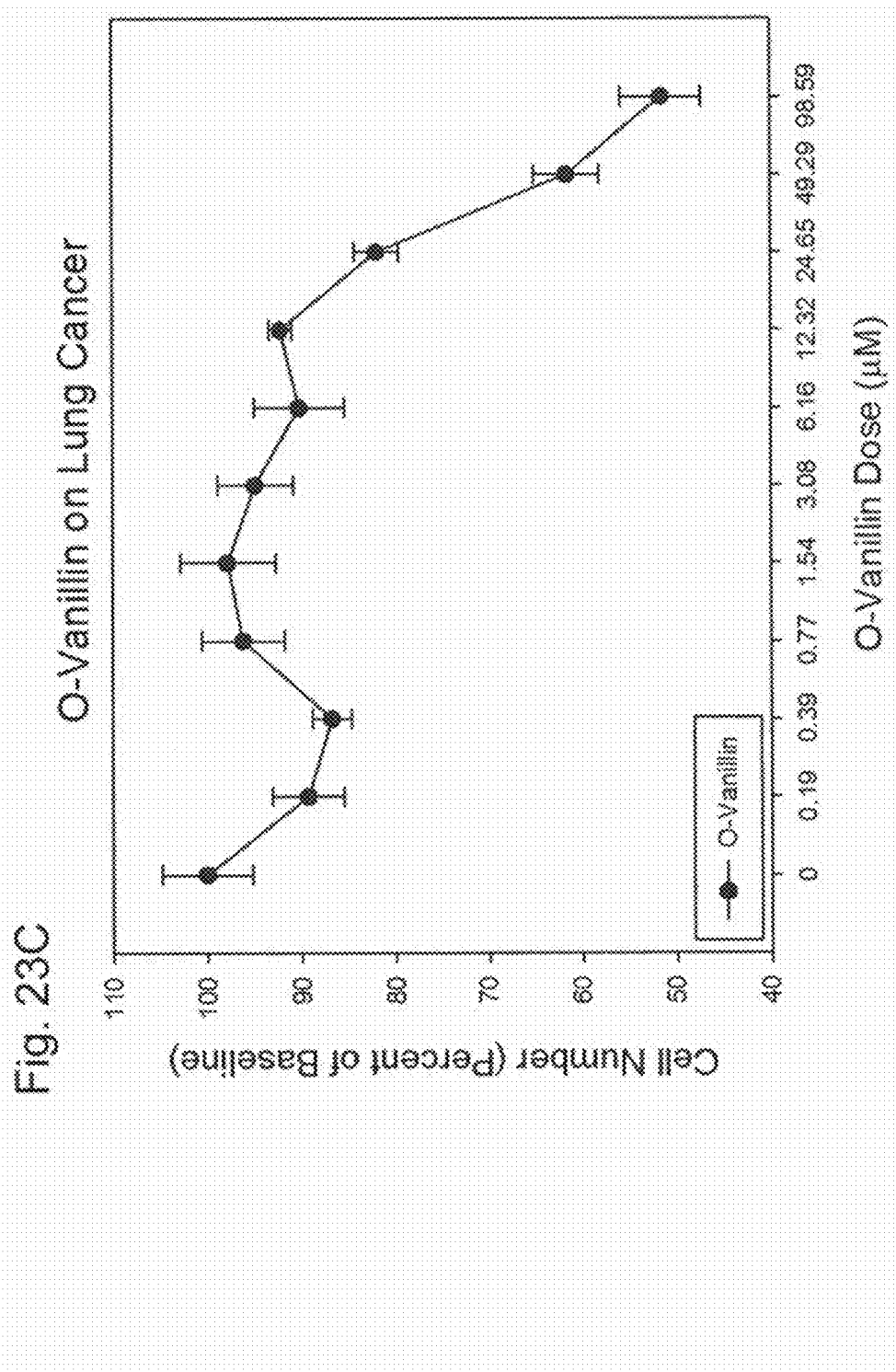
Fig. 23C O-Vanillin on Lung Cancer

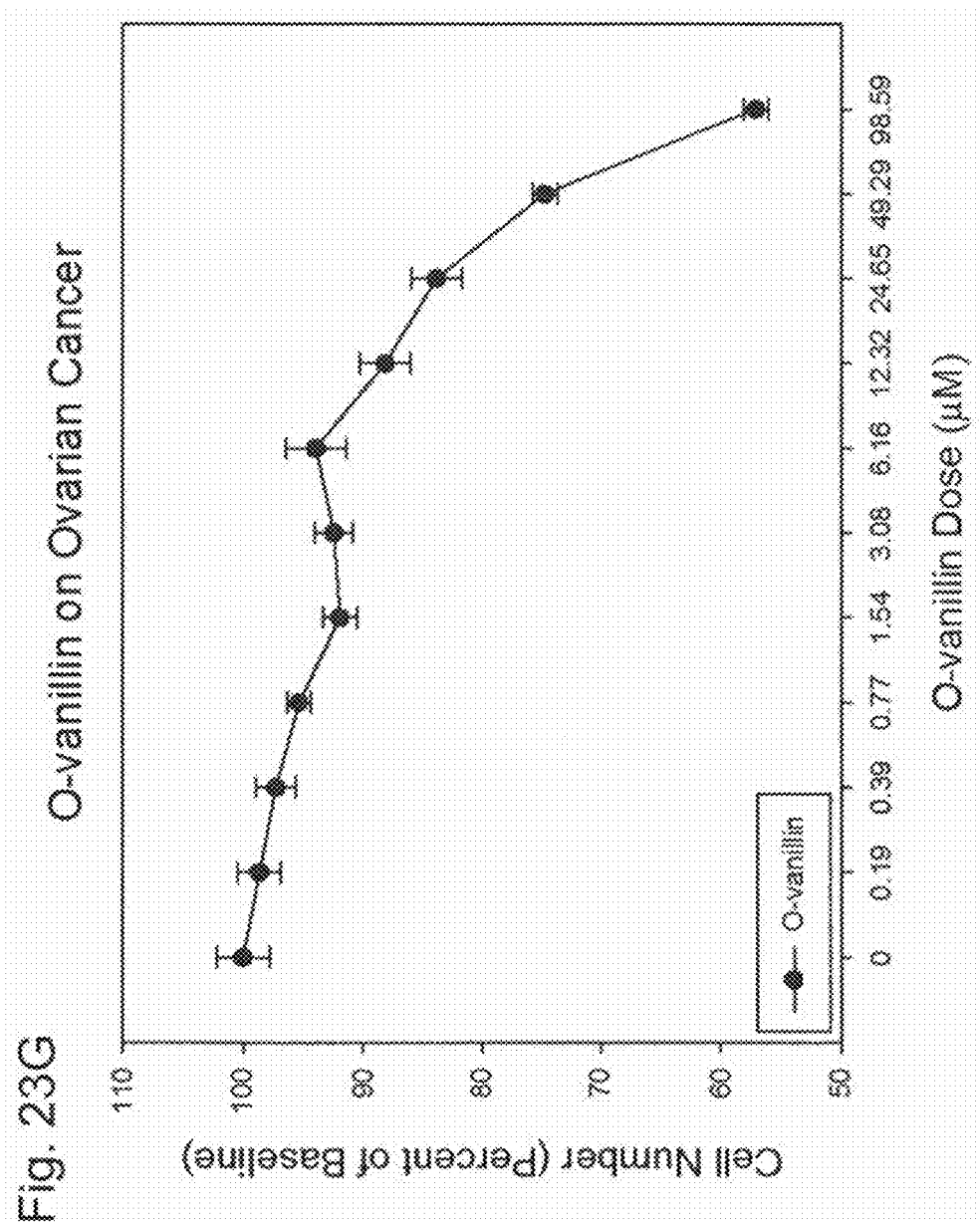

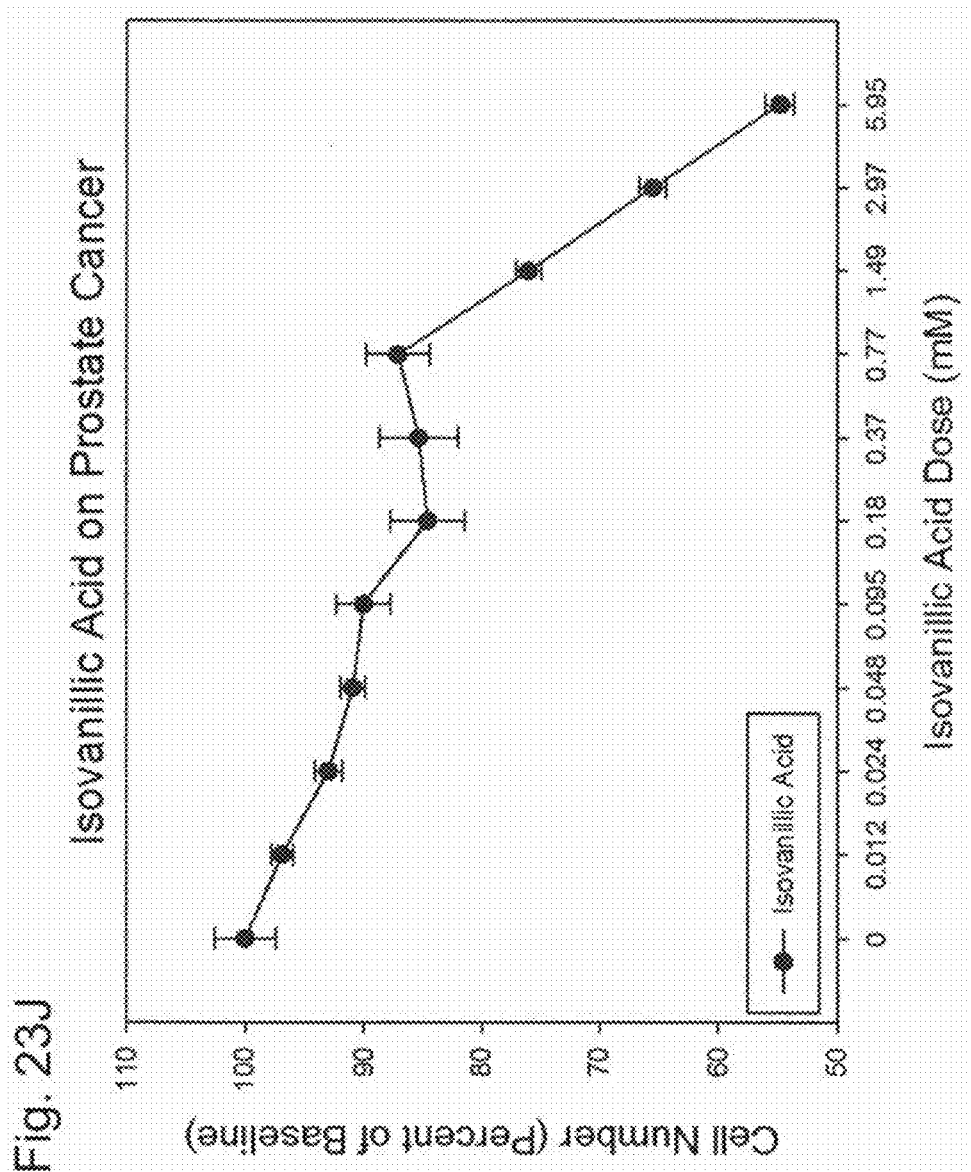

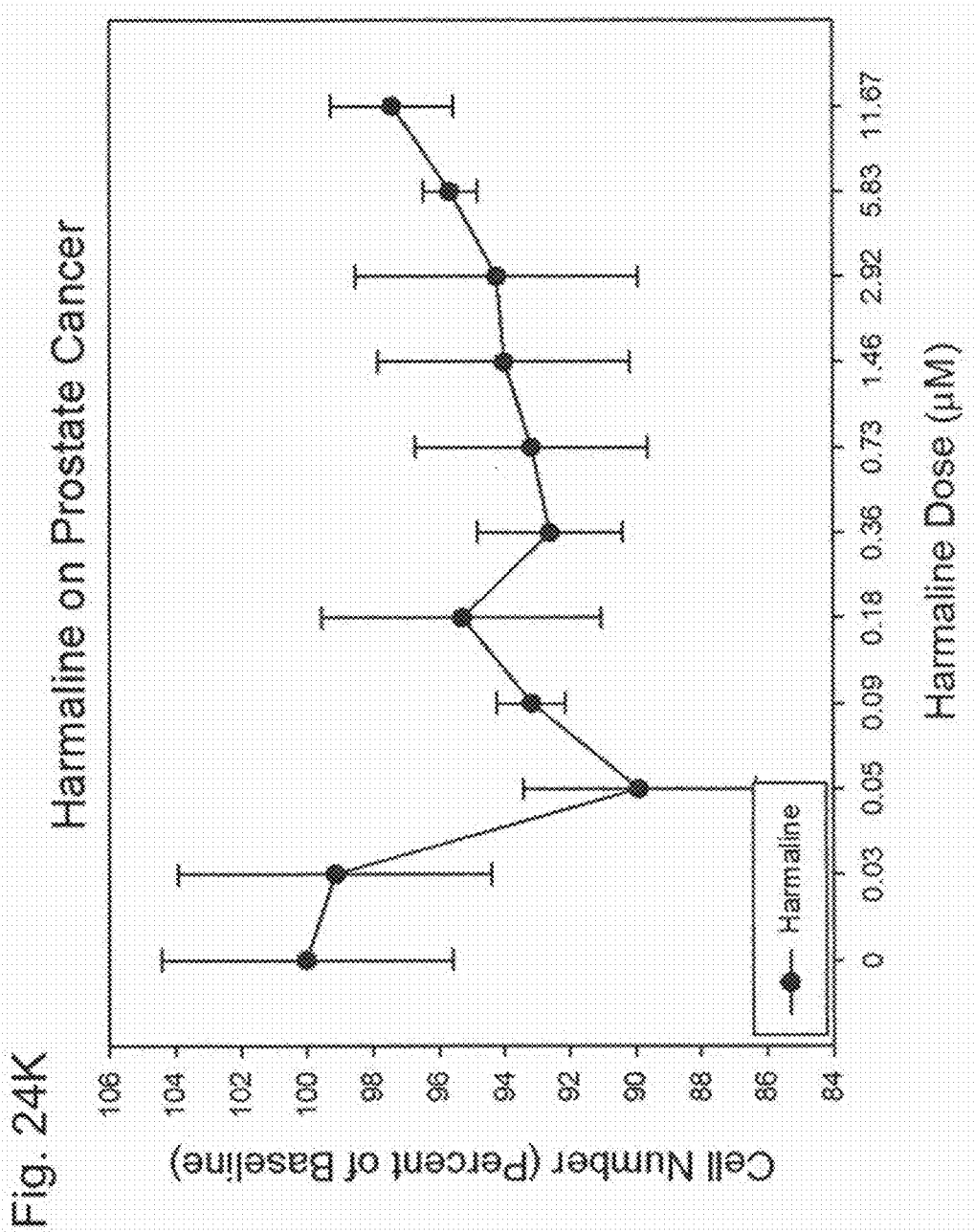

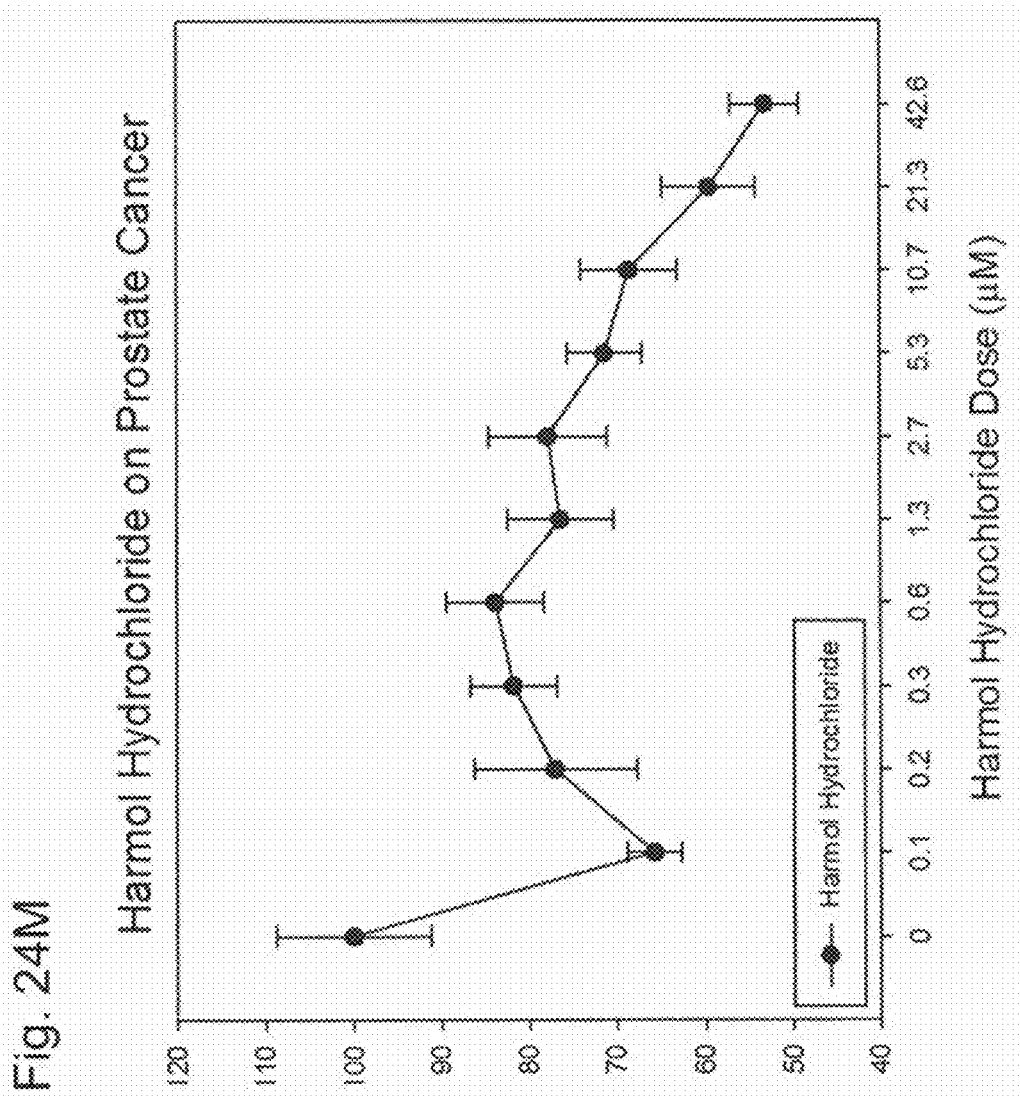

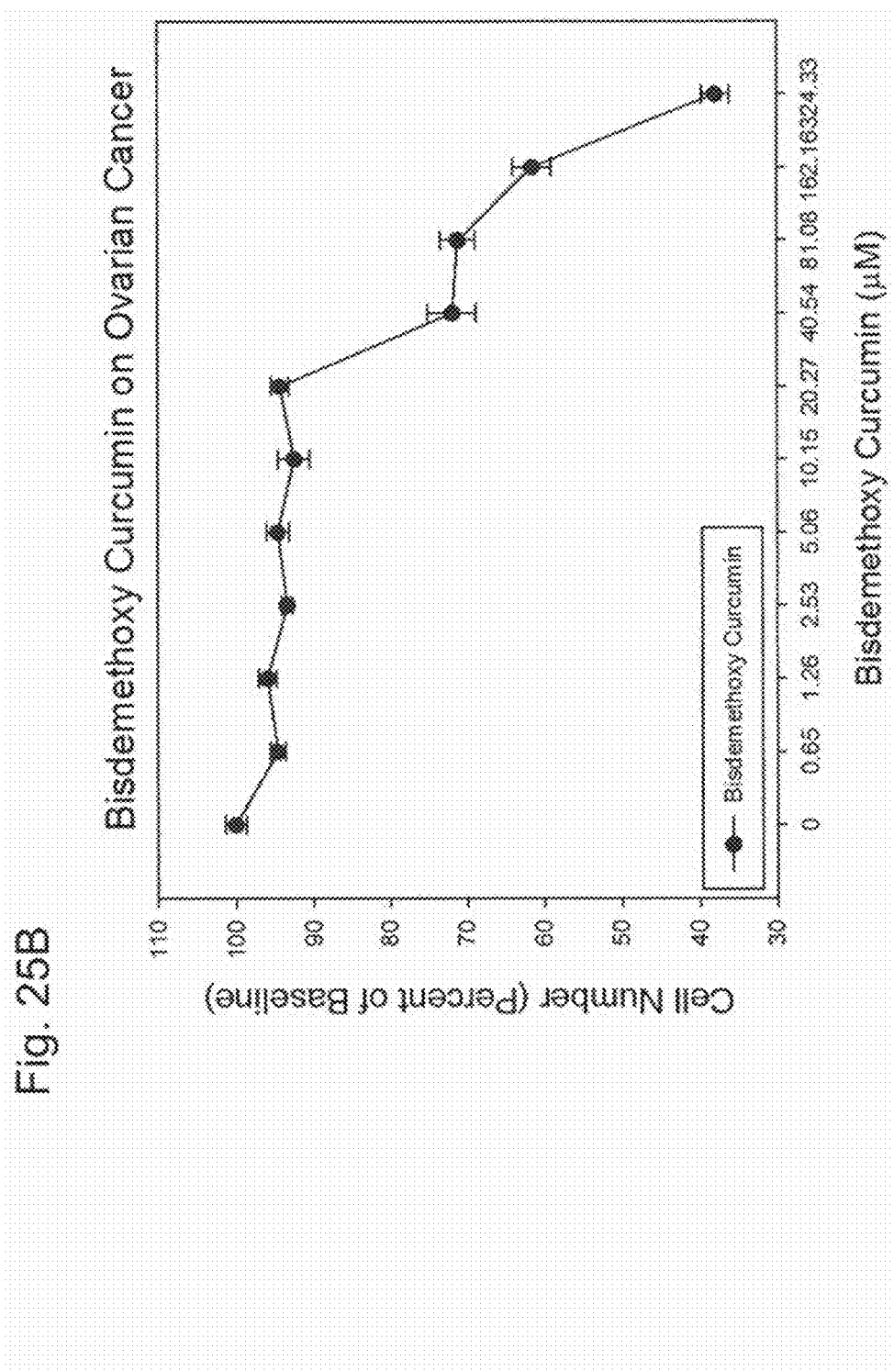

HUMAN THERAPEUTIC AGENTS

CROSS-REFERENCE TO RELATED APPLICATIONS

This application is a continuation of U.S. application Ser. No. 16/541,665 filed Aug. 15, 2019, which is a continuation of U.S. application Ser. No. 16,213,774 filed Dec. 7, 2018 (issued as U.S. Pat. No. 10,471,049 on Nov. 12, 2019), which is a continuation of U.S. application Ser. No. 15/826, 101 filed Nov. 29, 2017, which is a continuation of U.S. application Ser. No. 15/337,987 filed Oct. 28, 2016 (issued as U.S. Pat. No. 9,907,786 on Mar. 6, 2018), which is a continuation-in-part of PCT application SN PCT/US2015/055968 filed Oct. 16, 2015, which is a continuation-in-part of U.S. utility application Ser. No. 14/721,011 filed May 26, 2015 (issued Aug. 2, 2016 as U.S. Pat. No. 9,402,834), and which claims the benefit of U.S. Provisional Application, Ser. 62/184,051 filed Jun. 24, 2015, Ser. 62/161,090 filed May 13, 2015, and Ser. 62/066,686 filed Oct. 21, 2014. U.S. application Ser. No. 15/337,987 filed Oct. 28, 2016, is also a continuation of PCT Application SN PCT/IB2016/000723 filed Apr. 20, 2016, which is a continuation-in-part of U.S. utility application Ser. No. 14/721,011 filed May 26, 2015 (issued Aug. 2, 2016 as U.S. Pat. No. 9,402,834), and which claims the benefit of U.S. Provisional Application Ser. 62/184,051 filed Jun. 24, 2015, and Ser. 62/161,090 filed May 13, 2015. Each of the above provisional, non-provisional, and PCT applications is incorporated by reference herein in its entirety.

BACKGROUND OF THE INVENTION

Field of the Invention

The present invention relates to combination chemotherapeutics for treatment of humans, and especially for the treatment of human cancers, and corresponding methods for the treatment of humans suffering from cancers or other maladies. The invention further provides dosage forms and regimens for administration to human patients, and methods of formulating and administering such dosage forms to yield improvements in treatment outcomes. More particularly, the invention is concerned with the administration of specific chemotherapeutic dosage forms (e.g., liquid mixtures, capsules, pills, or tablets) containing one or more curcumin component(s), harmine component(s), and isovanillin component(s), and sub-combinations thereof.

Description of Related Art

Cancer is a generic term for a large group of diseases that can affect any part of the body. Other terms used are malignant tumors and neoplasms. One defining feature of cancer is the rapid creation of abnormal cells that grow beyond their usual boundaries, and which can then invade adjoining parts of the body and spread to other organs. This process is referred to as metastasis. Metastases are the major cause of death from cancer.

The transformation from a normal cell into a tumor cell is a multistage process, typically a progression from a pre-cancerous lesion to malignant tumors. These changes are the result of the interaction between a person's genetic factors and three categories of external agents, including:
  physical carcinogens, such as ultraviolet and ionizing radiation
  chemical carcinogens, such as asbestos, components of tobacco smoke, aflatoxin (a food contaminant) and arsenic (a drinking water contaminant)
  biological carcinogens, such as infections from certain viruses, bacteria or parasites.

Some examples of infections associated with certain cancers:
  Viruses: hepatitis B and liver cancer, Human Papilloma Virus (HPV) and cervical cancer, and human immunodeficiency virus (HIV) and Kaposi sarcoma.
  Bacteria: *Helicobacter pylori* and stomach cancer.
  Parasites: schistosomiasis and bladder cancer.

Aging is another fundamental factor for the development of cancer. The incidence of cancer rises dramatically with age, most likely due to a buildup of risks for specific cancers that increase with age. The overall risk accumulation is combined with the tendency for cellular repair mechanisms to be less effective as a person grows older.

Tobacco use, alcohol use, low fruit and vegetable intake, and chronic infections from hepatitis B (HBV), hepatitis C virus (HCV) and some types of Human Papilloma Virus (HPV) are leading risk factors for cancer in low- and middle-income countries. Cervical cancer, which is caused by HPV, is a leading cause of cancer death among women in low-income countries. In high-income countries, tobacco use, alcohol use, and being overweight or obese are major risk factors for cancer.

The most common cancer treatment modalities are surgery, chemotherapy, and radiation treatments. All of these techniques have significant drawbacks in terms of side effects and patient discomfort. For example, chemotherapy may result in significant decreases in white blood cell count (neutropenia), red blood cell count (anemia), and platelet count (thrombocytopenia). This can result in pain, diarrhea, constipation, mouth sores, hair loss, nausea, and vomiting.

Biological therapy (sometimes called immunotherapy, biotherapy, or biological response modifier therapy) is a relatively new addition to the family of cancer treatments. Biological therapies use the body's immune system, either directly or indirectly, to fight cancer or to lessen the side effects that may be caused by some cancer treatments.

During chemotherapies involving multiple-drug treatments, adverse drug events are common, and indeed toxicities related to drug-drug interactions are one of the leading causes of hospitalizations in the US. Obach, R. S. "Drug-Drug Interactions: An Important Negative Attribute in Drugs." *Drugs Today* 39.5 (2003): 308-338. In fact, in any single-month period, one-fifth of all surveyed adults in the USA reported an adverse drug response. Hakkarainen, K. M. et al. "Prevalence and Perceived Preventability of Self-Reported Adverse Drug Events—A Population-Based Survey of 7,099 Adults." *PLoS One* 8.9 (2013): e73166. A large-scale study of adults aged 57-85 found that 29% were taking more than five prescription medications and nearly 5% were at risk of major adverse drug-drug interactions. In the field of oncology, a review of over 400 cancer patients determined that 77% were taking drugs that were considered to have a moderately severe potential for adverse drug interactions, and 9% had major adverse drug interactions. Ghalib, M. S. et al. "Alterations of Chemotherapeutic Pharmocokinetic Profiles by Drug-Drug Interactions." *Expert Opin. Drug Metabl. Toxicol* 5.2 (2009): 109-130.

Such interactions are a global health problem, and the WHO has determined that negative drug interactions are leading causes of morbidity and mortality around the world, with up to 7% of all hospitalizations in the US due to negative drug interactions. A recent survey of a single hospital shows that 83% of hospitalized patients were prescribed drug combinations with the potential to cause adverse reactions. Patel, P. S. et al. "A Study of Potential Adverse Drug-Drug Interactions Among Prescribed Drugs in a Medicine Outpatient Department of a Tertiary Care Teaching Hospital." *J. Basic Clin. Pharm.* 5.2 (2014): 44-48.

Examples of famous negative drug interactions include the development of rhabdomyolysis, a severe muscle disease, when taking Simvastatin with Amiodarone. As a result, the FDA introduced a warning on the drug label about the interaction. The calcium channel blocker Mibefradif, taken for high blood pressure, was removed from the market because of the harmful interaction with drugs that work on the electrical activity of the heart.

Cancer cells are cells that, by definition, grow and divide without normal limitations. The unrestricted cell growth results in tumors, comprised of a variety of cell types. Treatments to fight cancer are frequently successful in killing the typical, differentiated cancer cells that form the majority of a solid tumor, otherwise known as the bulk cells. However even with the best treatment, the cancer may return a few months to years later (Prince, M. E. et al., "Cancer stem cells in head and neck squamous cell cancer." *J. Clin. Oncol.* 26.17 (2008):2871-2875). For example, recurrence is frequently the case for pancreatic and head and neck cancer. It is now hypothesized that one of the key factors in the recurrence rate for cancers is the presence of cancer stem cells.

Cancer stem cells were not identified until the late 1990s and show two important properties of stem cells: 1) cancer stem cells can self-renew and, 2) cancer stem cells can differentiate into any other cell type (Bandhavkar, S. "Cancer stem cells: a metastasizing menace." *Cancer Med.* (2016) doi:10.1002/cam4.629; Dick, J. E. "Stem cell concepts renew cancer research." *Blood.* 112 (2008):4793-4807). While they make up only a small percentage of the total number of cells in a tumor, they compromise a unique category of cancer cells that are more likely to be resistant to chemotherapy or radiation therapy. In fact, it is now believed that the majority of cells in tumors are not cancer-causing and cannot initiate new tumors (Bandhavkar). Only cancer stem cells appear to be tumor-initiators (Visvader, J. E. et al. "Cancer stem cells: Current status and evolving complexities." *Cell Stem Cell.* 10 (2012):717-728). Cancer stem cells have been shown to coordinate tumor cell growth, metastases (migration and invasion), and drug resistance (Cammarota, F. et al. "Mesenchymal stem/stromal cells in stromal evolution and cancer progression." *Stem Cells Int.* (2016):4824573). These cancer stem cells behave differently than non-cancerous stem cells in the person (Cammarota et al.), and have been described as the "roots of aggressive tumors for which we have no effective treatment" (Doherty, M. R. et al. "Cancer stem cell plasticity drives therapeutic resistance." *Cancers* 8,8 (2016) doi:10.3390). In general stem cells are naturally resistant to chemotherapies and radiation therapy (Diehn, M. et al. "Cancer stem cells and radiotherapy: new insights into tumor radioresistance." *J. Natl. Cancer Inst.* 98 (2016):1775-1757; Mery, B. et al. "Targeting head and neck tumoral stem cells: From biological aspects to therapeutic perspectives." *World J Stem Cells* 8.1 (2016):13-21), because they have chemical pumps that remove the chemotherapies out of the cells, thus they can have no effect on the stem cells. They also have a slow rate of turnover, and most radiation and chemotherapies are designed to only kill cells that are rapidly dividing, such as the majority of the cells within the tumor. These characteristics explain, on a large scale, how stem cells associated with cancer are resistant to chemotherapy.

Current anticancer therapies may directly cause cancer cells to die or just inhibit their growth (Bandhavkar). If the anticancer therapy fails to target and remove the cancer stem cells, then relapse and drug resistance ensues. Selectively targeting and eliminating cancer stem cells would theoretically treat the primary tumors and halt any chance of recurrence (Mery et al.). Yet, the ability to kill cancer stem cells is currently considered a significant clinical challenge. Some recent evidence suggests that traditional chemotherapies can even induce the generation of new stem cells within tumors potentially making the cancer return faster (Doherty et. al).

Identification of the regulatory mechanisms and signaling pathways involved in cancer stem cells (CSCs) will help in designing novel agents to target this refractory cell population in pancreatic cancers. Cancer stem cells are capable of self-renewal and generating tumors resembling the primary tumor (Ponnurangam, S. et al. "Quinomycin A targets Notch signaling pathway in pancreatic cancer stem cells." Oncotarget 7.3 (2015):3217-3232). The sphere-forming assays have been widely used to identify stem cells based on their reported capacity to evaluate self-renewal and differentiation.

U.S. Pat. No. 8,039,025 describes cancer treatments in the form of extracts of *Arum palaestinum* Boiss, supplemented with individual amounts of β-sitosterol, isovanillin, and linoleic acid, and this patent is incorporated by reference herein in its entirety.

Despite the immense amount of worldwide research and efforts to stem the tide of cancer and its side effects, the disease in its many manifestations continues to be a huge problem. Therefore, any new cancer treatment having a curative affect and/or the ability to ameliorate cancer symptoms and improve the lifestyle of patients is highly significant and important.

SUMMARY OF THE INVENTION

The present invention provides improved chemotherapeutics for treatment of humans, and especially in the treatment of human cancers, with novel combinations of compounds, which are useful against a wide variety of different cancers with minimal or nonexistent adverse side effects. Generally speaking, the chemotherapeutics of the invention comprise respective quantities of at least two of, curcumin component(s), harmine component(s), and isovanillin component(s). The preferred chemotherapeutics include all three of these components, but sub-combinations thereof are also useful, i.e., therapeutics comprising curcumin component(s) and harmine component(s), curcumin component(s) and isovanillin component(s), and harmine component(s) and isovanillin component(s). In particularly preferred embodiments, the active components of the compositions (i.e., those having a significant therapeutic effect) consist essentially of curcumin, harmine, and isovanillin components in the case of three-component compositions, and consist essentially of two of the three components in the case of the two-component compositions. Preferably, the at least one curcumin component comprises curcumin, the at least one harmine component comprises harmine, and the at least one isovanillin component comprises isovanillin or vanillin.

The invention also provides new methods for treatment of cancers by administration of appropriate quantities of the anti-cancer compositions hereof. Hence, the compositions are particularly designed for use in the treatment of cancers, and the compositions can be used for the manufacture of medicaments of anti-cancer therapeutic applications. In addition, the invention provides pharmaceutical compositions for the treatment of cancers comprising administering therapeutically effective amounts of the new compositions, prepared by processes known per se, with a pharmaceutically acceptable carrier.

Curcumin (CAS #458-37-7) is a diaryl heptanoid, and has the molecular formula C21H20O6. Curcumin occurs as a part of a curcuminoid plant extract containing curcumin, demethoxycurcumin, and bis-demethoxycurcumin. One commercially available effective curcuminoid is sold as "Curcumin from Curcuma Longa (Turmeric)," which contains greater than 65% by weight curcumin, as determined by HPLC analysis.

Harmine (CAS #442-51-3) is a methoxy methyl pyrido indole belonging to the O-carboline family of compounds, and has the molecular formula C13H12N2O. Harmine occurs in a number of different plants native to the Middle East and South America.

Isovanillin (CAS #621-59-0) is a phenolic aldehyde vanillin isomer, and has the molecular formula C8H8O3.

A "chemotherapeutic" or "chemotherapeutic agent" as used herein refers to the combinations of chemical compounds described herein as useful in the treatment of human conditions, especially human cancers. Chemotherapeutics may be cytostatic, selectively toxic or destructive of cancerous tissue and/or cells, but also include indiscriminately cytotoxic compounds used in cancer treatments.

The combination therapeutic agents of the invention have been found to be effective in the treatment of a broad spectrum of human cancers, and also to other conditions, such as elevated PSA counts in men. The broad scope of utility with the agents of the invention is in itself highly unusual. However, this feature, together with the nonexistent or minimal side effects induced by the agents, represents a startling development in the art.

BRIEF DESCRIPTION OF THE DRAWINGS

FIG. 32B is a graph of cell number versus dosage amounts of GZ17-8.14, illustrating the effect thereof in inducing the death of lung cancer;

FIG. 32C is a graph of cell number versus dosage amounts of GZ17-8.14, illustrating the effect thereof in inducing the death of prostate cancer;

FIG. 32D is a graph of cell number versus dosage amounts of GZ17-8.14, illustrating the effect thereof in inducing the death of head and neck cancer;

FIG. 32E is a graph of cell number versus dosage amounts of GZ17-8.14, illustrating the effect thereof in inducing the death of breast cancer;

FIG. 32F is a graph of cell number versus dosage amounts of GZ17-8.14, illustrating the effect thereof in inducing the death of leukemia;

FIG. 32G is a graph of cell number versus dosage amounts of GZ17-8.14, illustrating the effect thereof in inducing the death of lymphoma;

FIG. 33A is a graph of cell number versus dosage amounts of GZ17-8.15, illustrating the effect thereof in inducing the death of ovarian cancer;

FIG. 33B is a graph of cell number versus dosage amounts of GZ17-8.15, illustrating the effect thereof in inducing the death of lung cancer;

FIG. 33C is a graph of cell number versus dosage amounts of GZ17-8.15, illustrating the effect thereof in inducing the death of prostate cancer;

FIG. 33D is a graph of cell number versus dosage amounts of GZ17-8.15, illustrating the effect thereof in inducing the death of head and neck cancer;

FIG. 33E is a graph of cell number versus dosage amounts of GZ17-8.15, illustrating the effect thereof in inducing the death of breast cancer;

FIG. 33F is a graph of cell number versus dosage amounts of GZ17-8.15, illustrating the effect thereof in inducing the death of leukemia;

Figure 8:
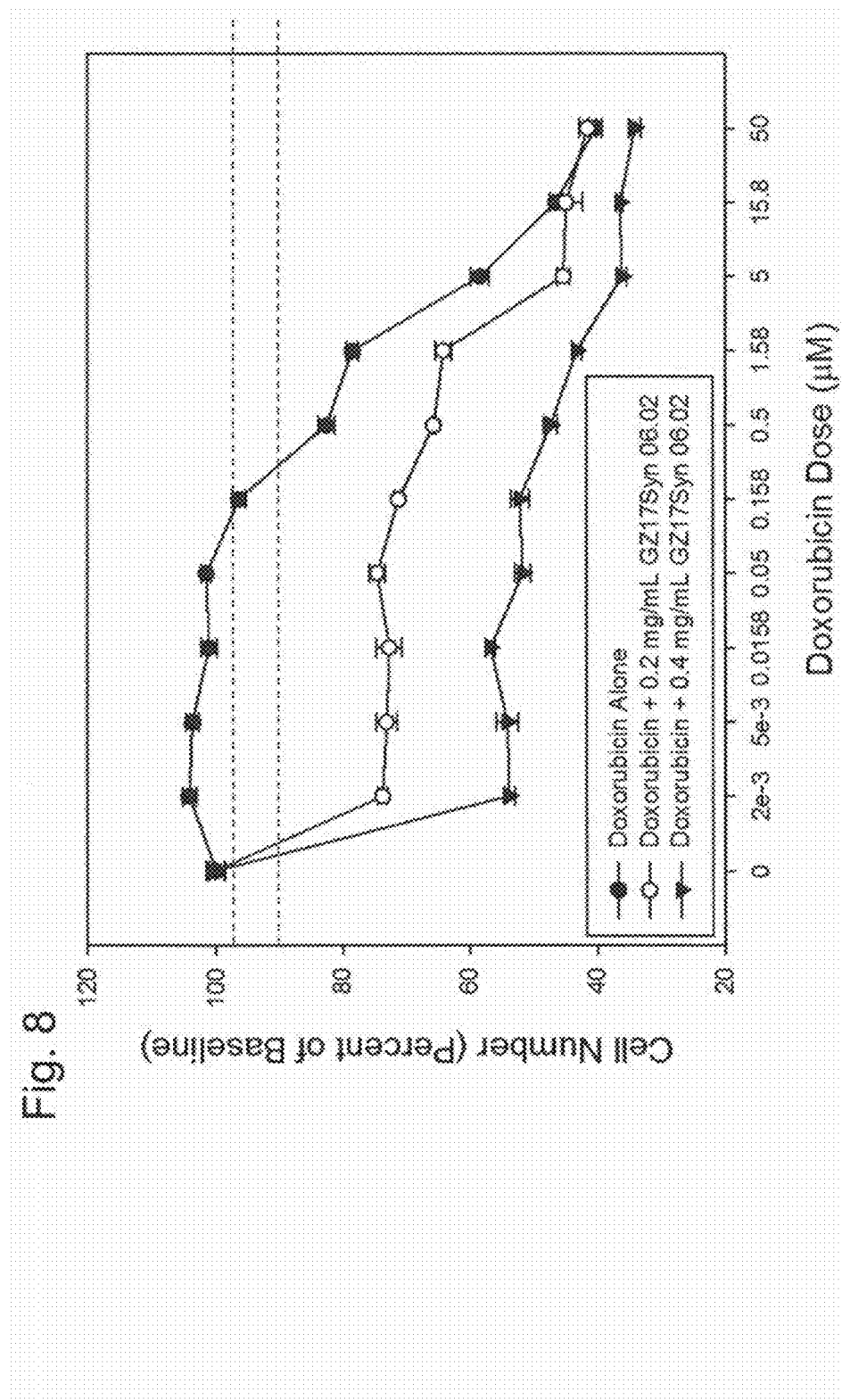
FIG. 8 is a graph of normalized cell number versus increasing doxorubicin doses alone and with the addition of two different concentrations of GZ17-6.02, as described in Example 8.
Figure 13:
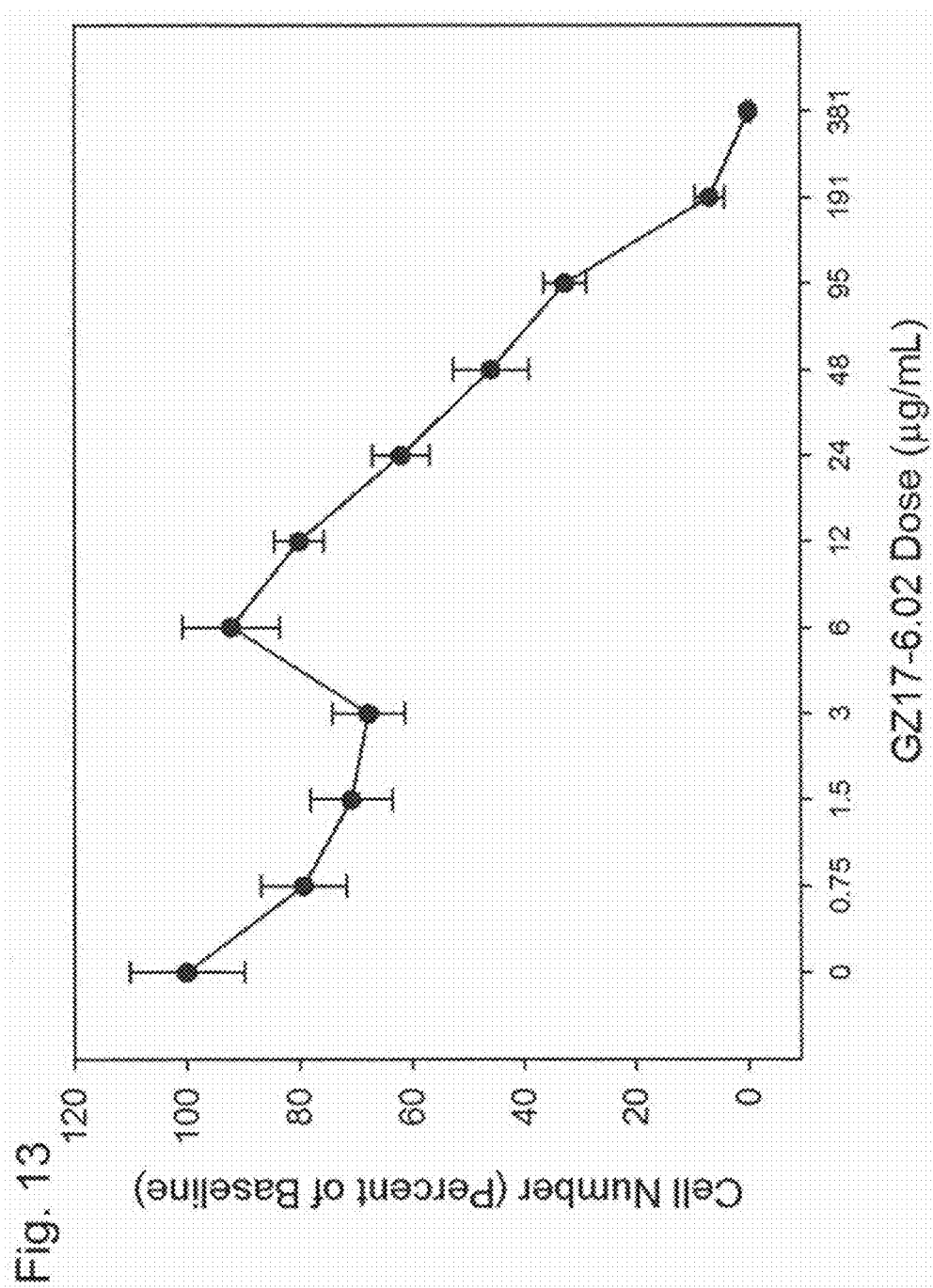
FIG. 13 is a graph illustrating the mechanisms of human head and neck cancer cells death by application of GZ17-6.02, as explained in Example 13.
Figure 26:
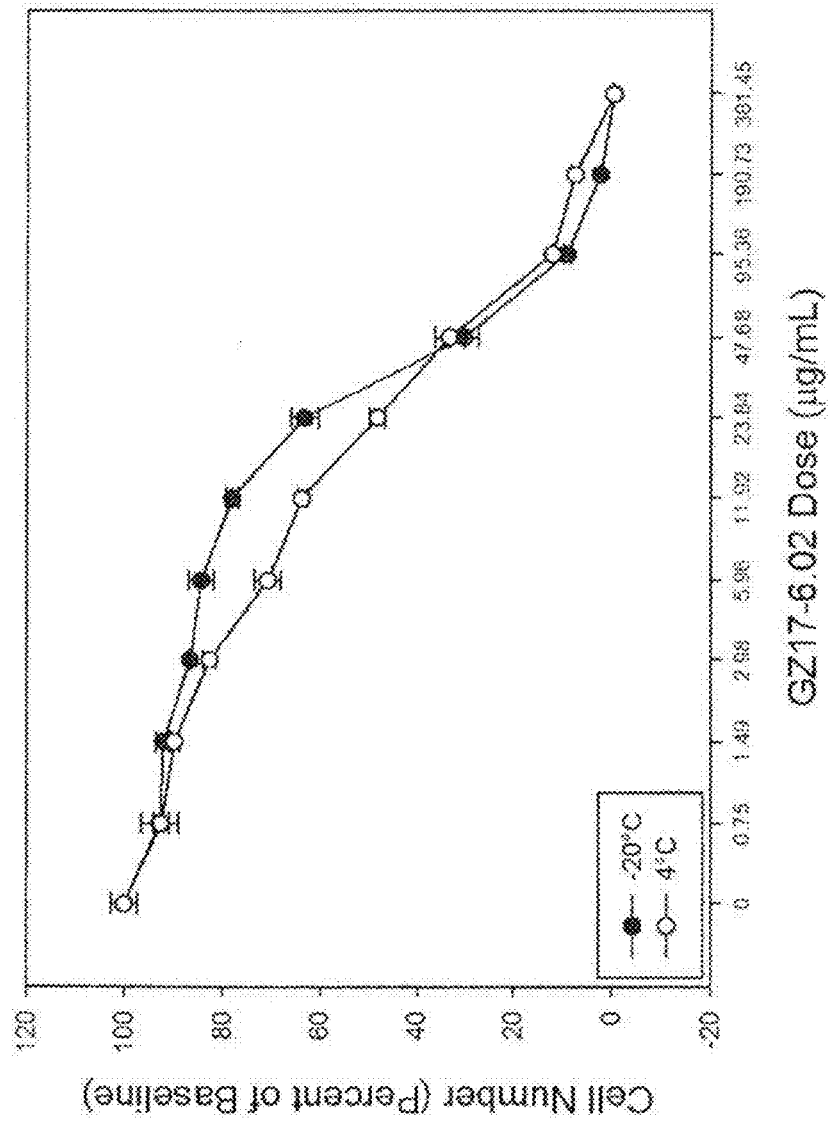
FIG. 26 is a graph of ovarian cancer cell number versus dosage amounts of GZ17-6.02 where the product was stored at varying temperatures over two months, confirming that the product has long-term stability.
Figure 27:
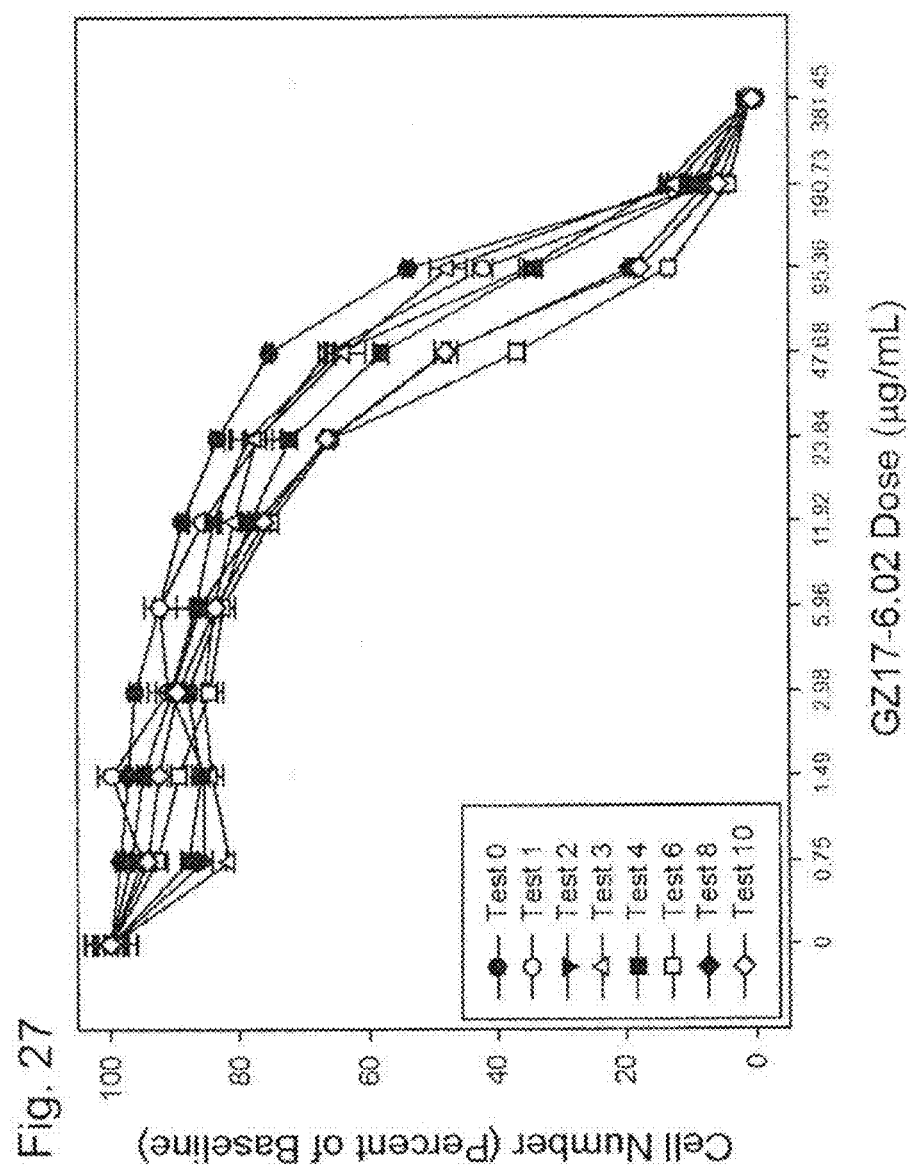
FIG. 27 is a graph of ovarian cancer cell number versus dosage amounts of GZ17-6.02, where the GZ17-6.02 was subjected to a series of successive freeze/thaw cycles, confirming that the product has excellent freeze/thaw stability.
Figure 33A:
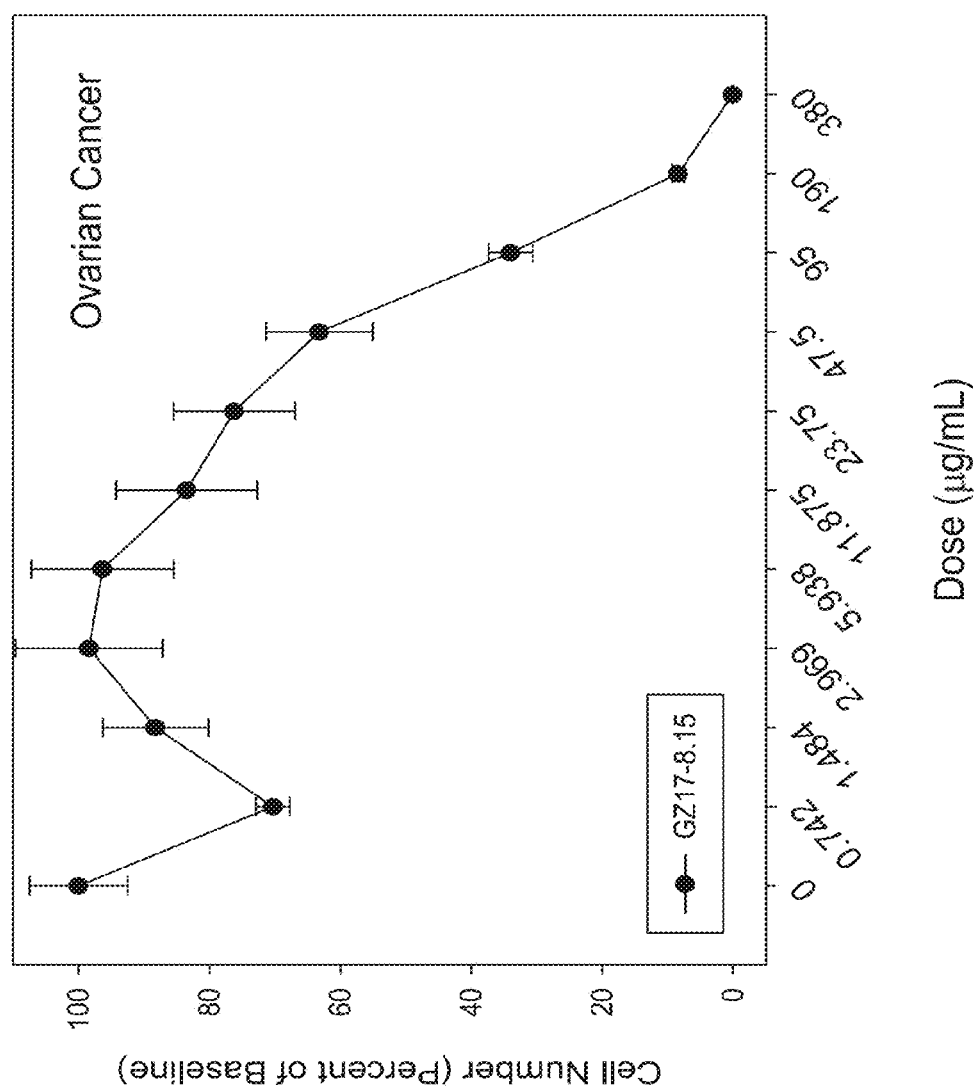
Figure 33B:
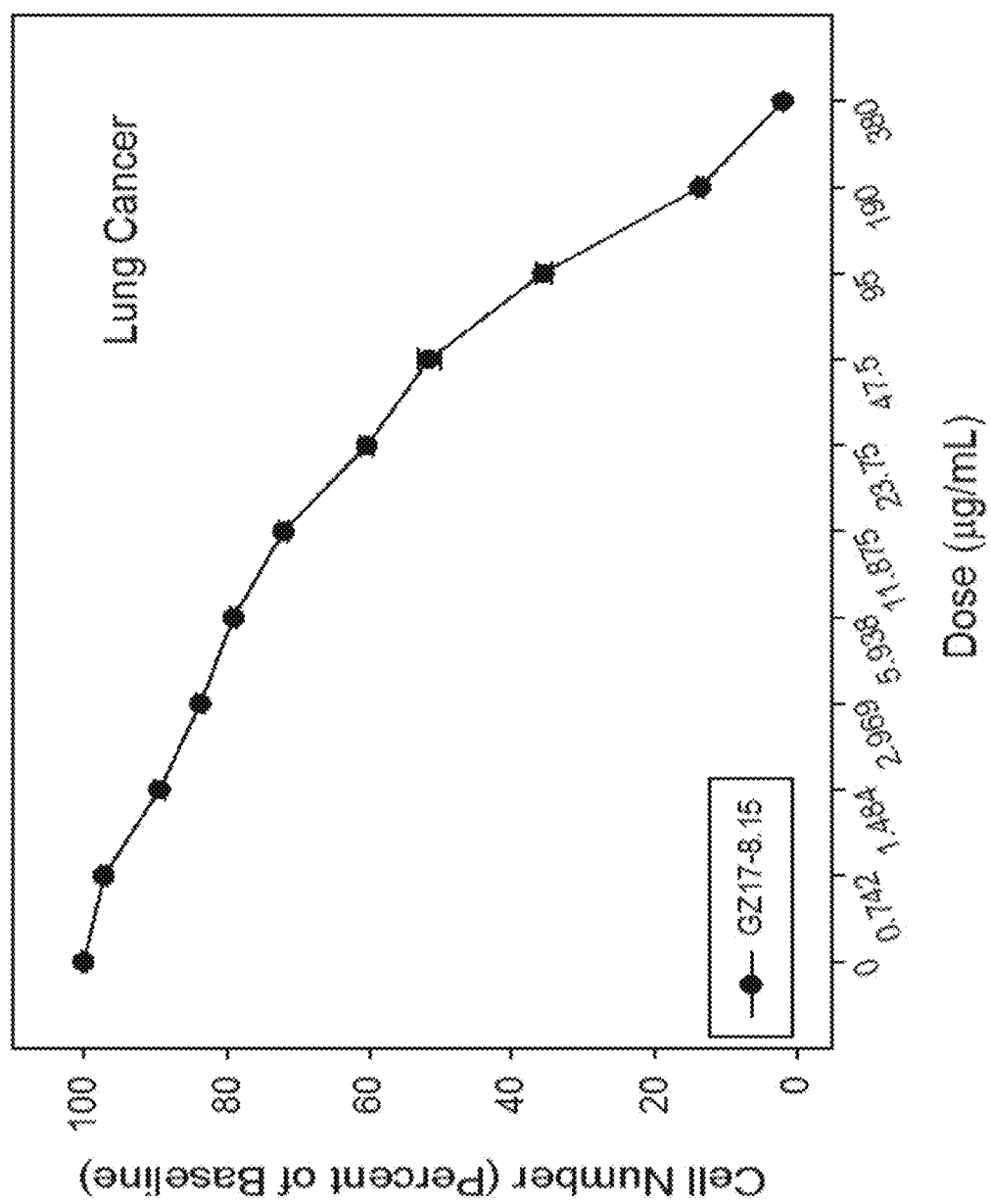
Figure 33C:
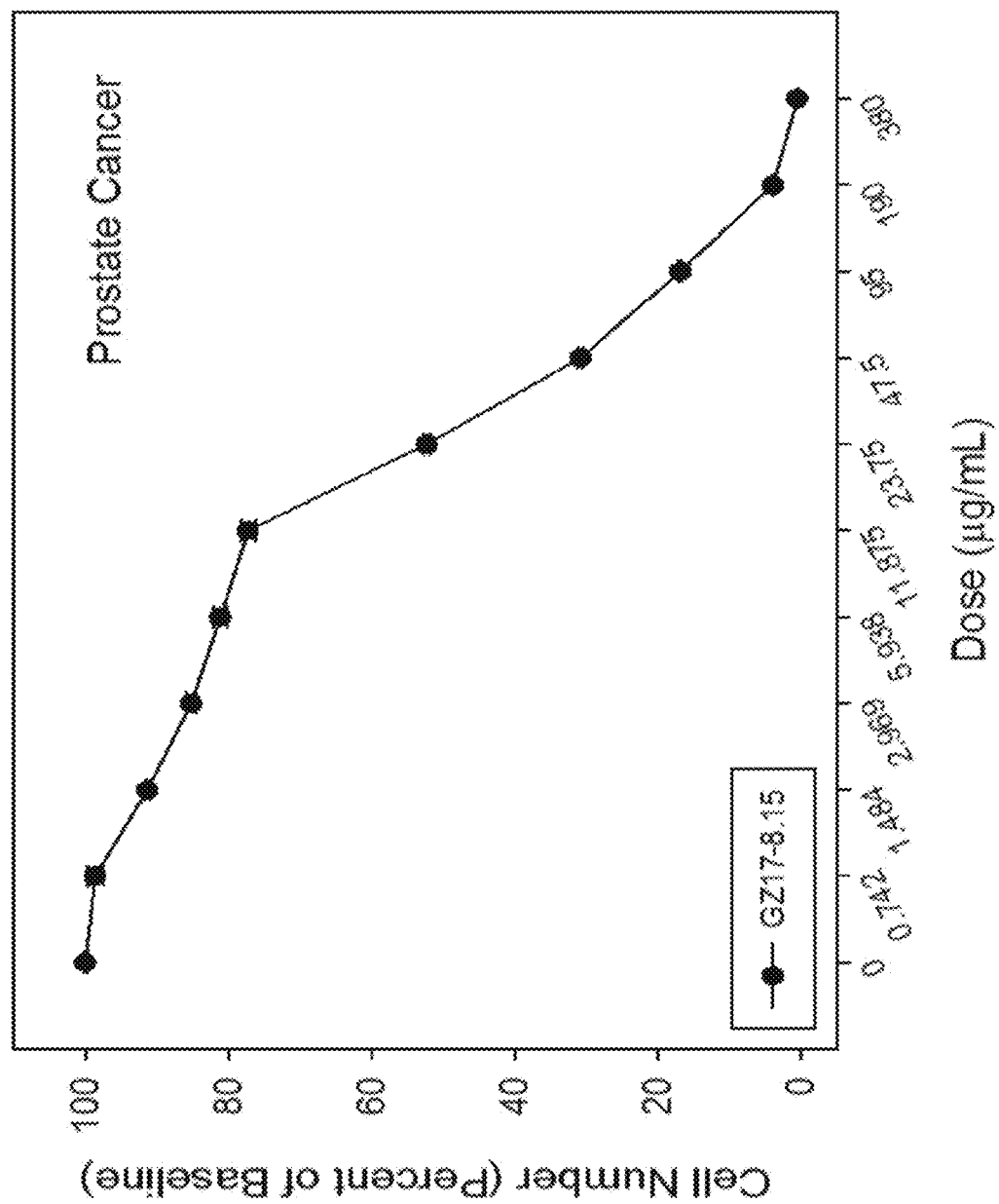
Figure 33D:
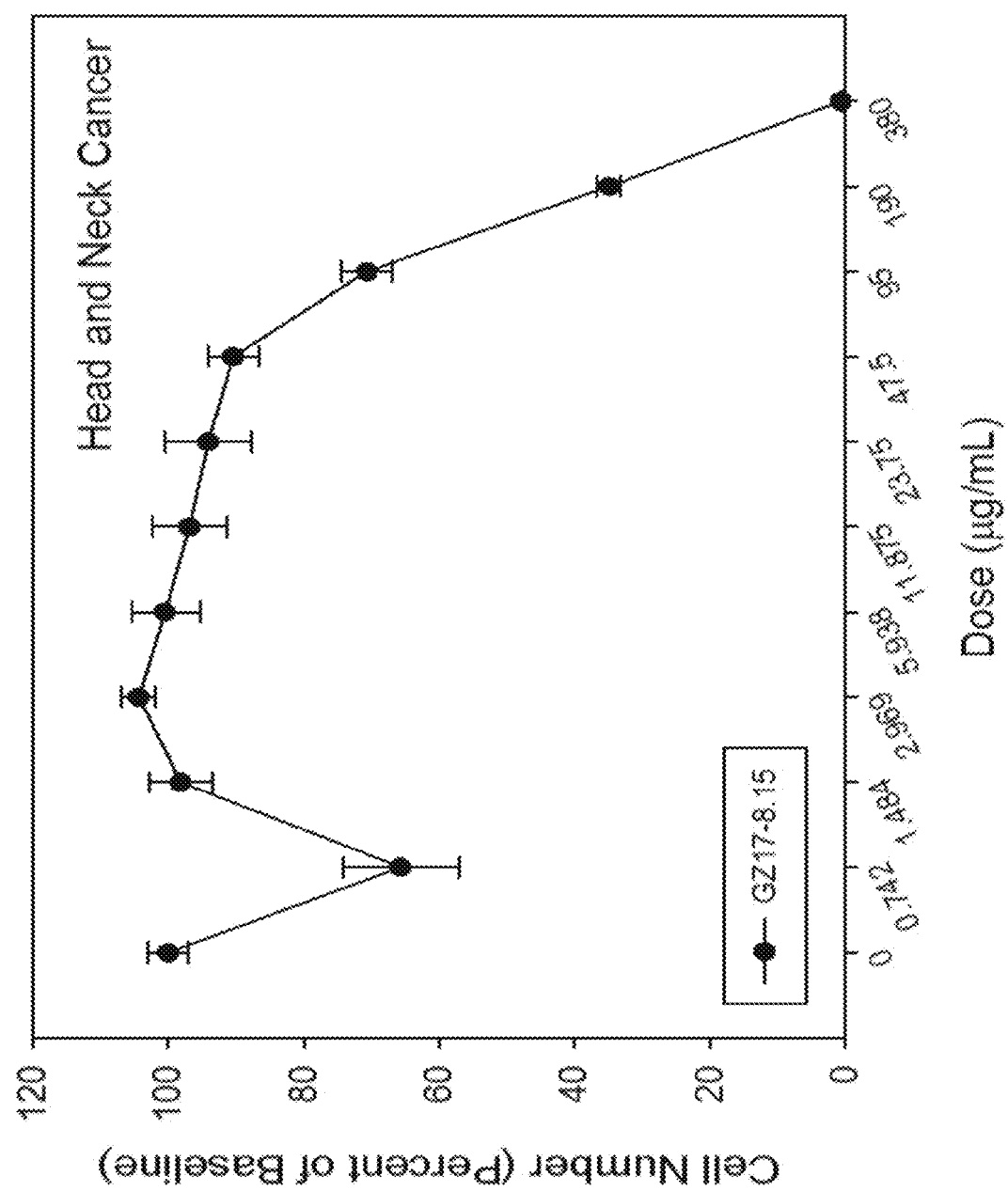
Figure 33E:
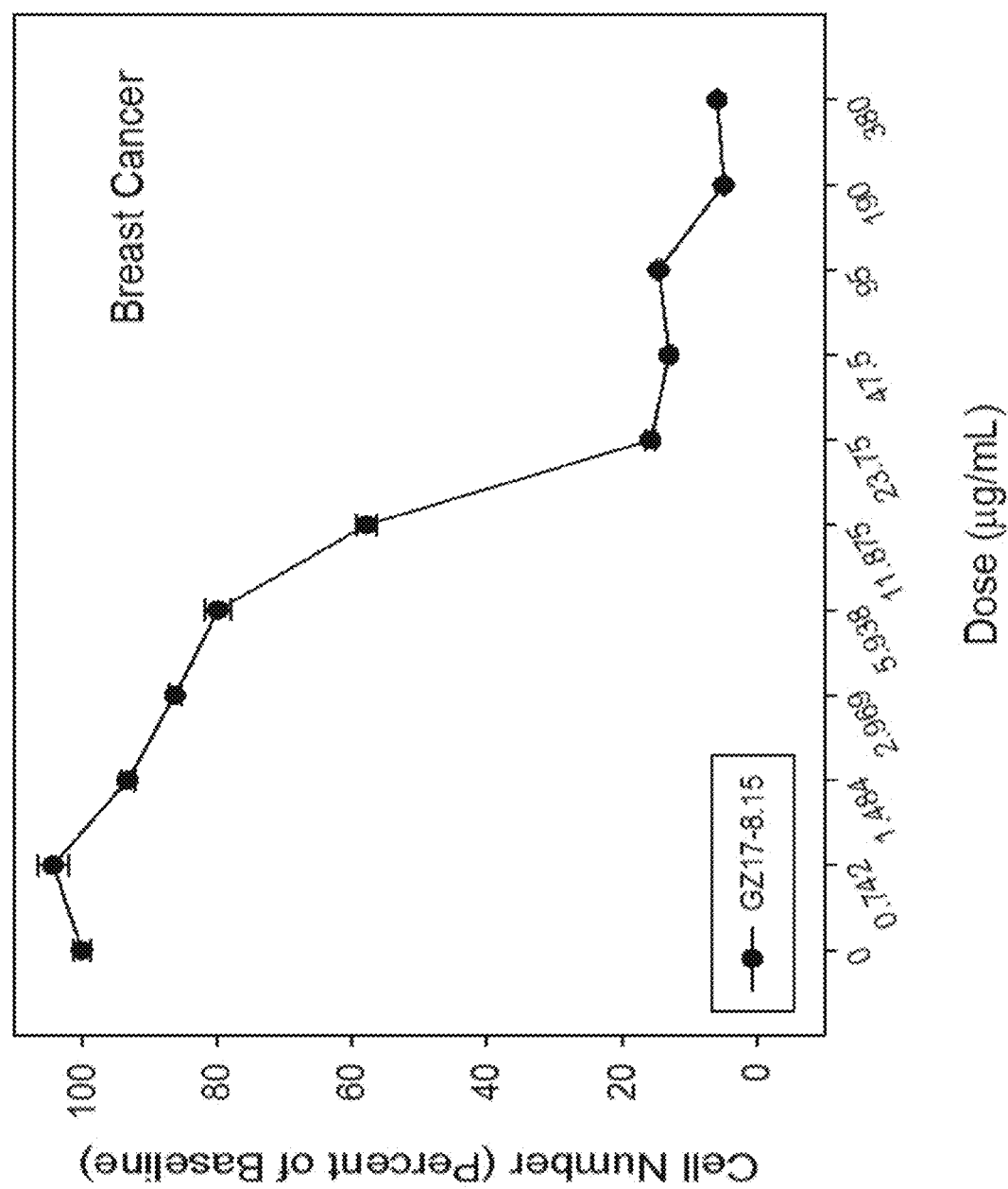
Figure 33F:
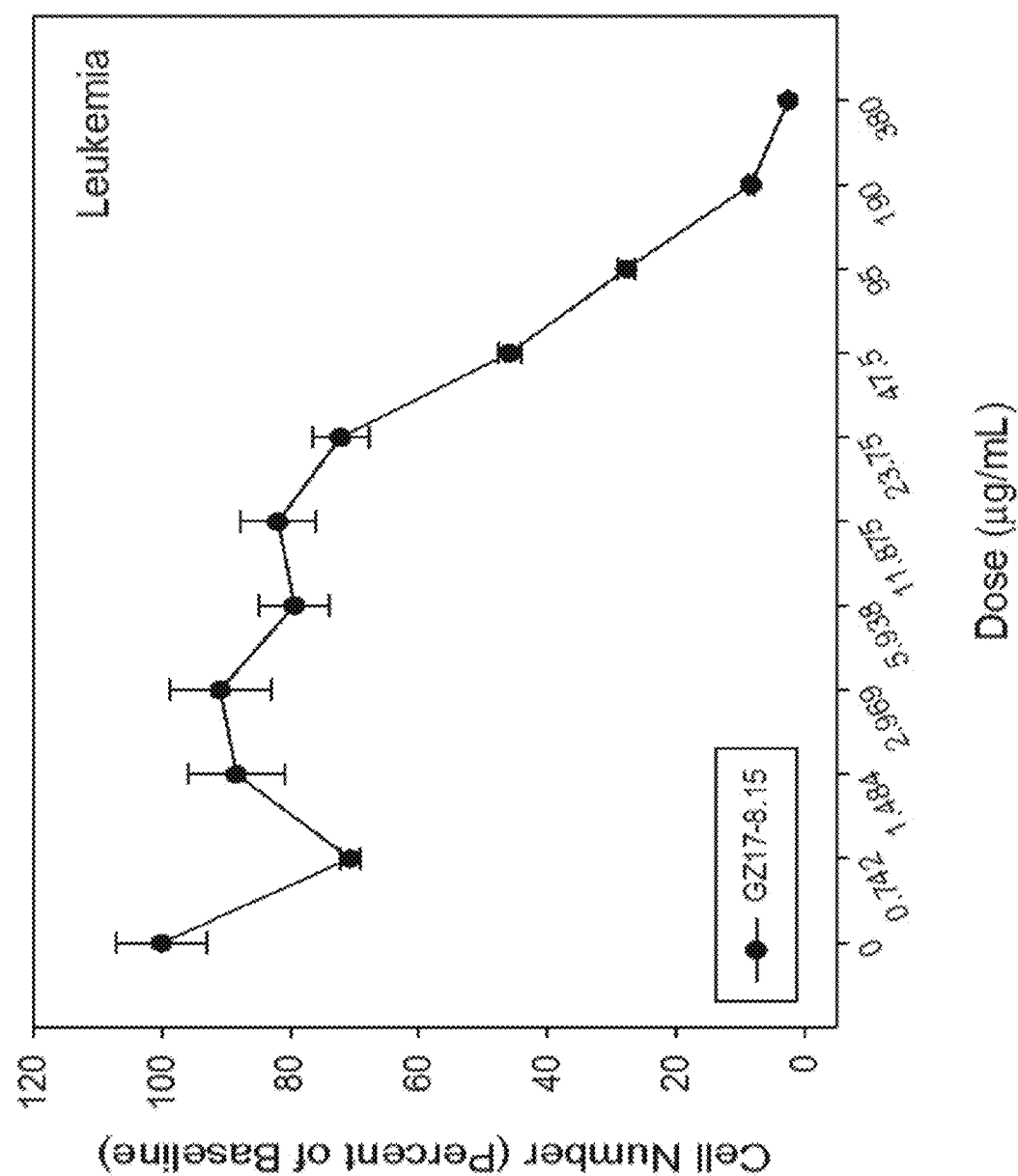
Figure 33G:
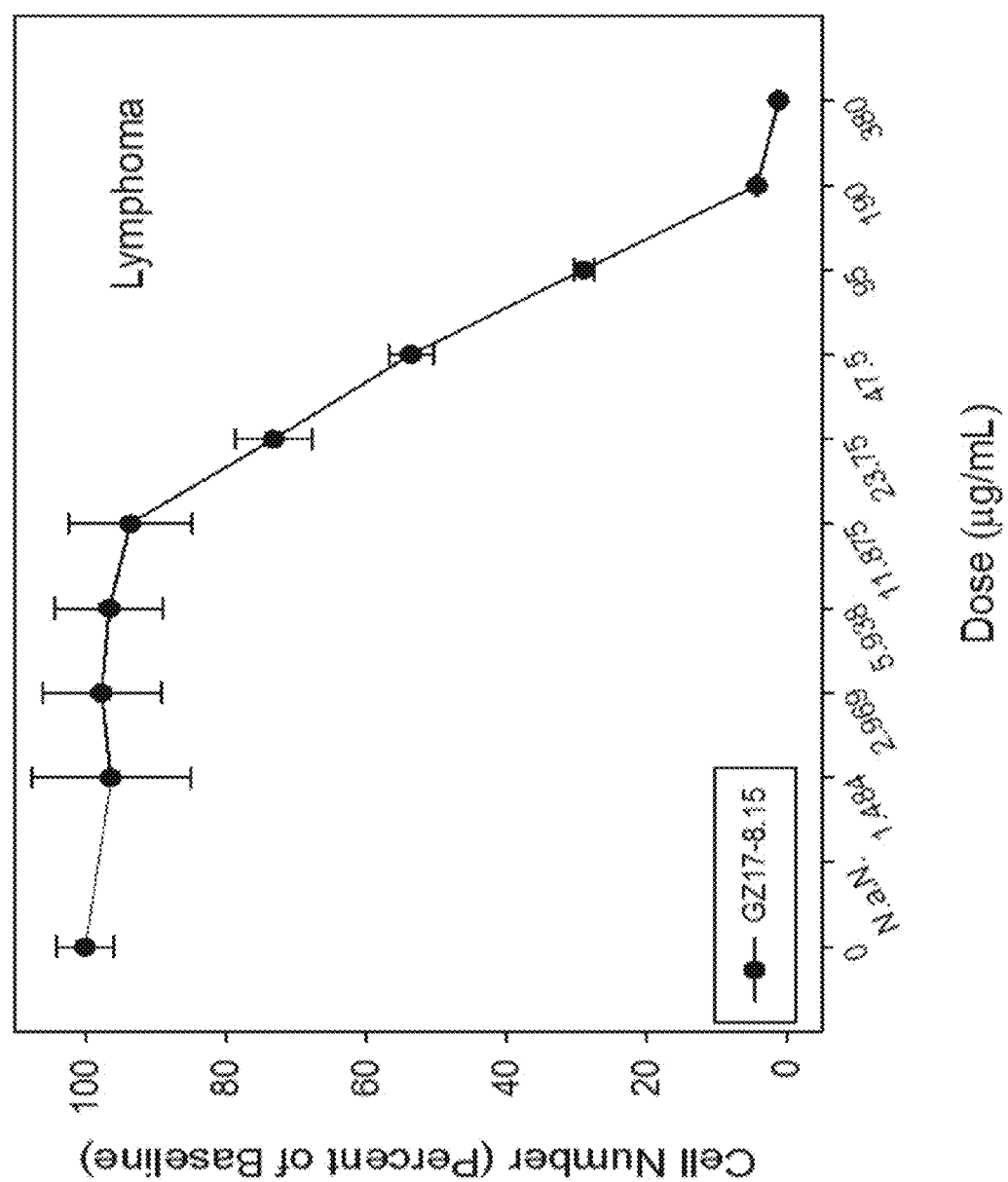
Figure 34A:
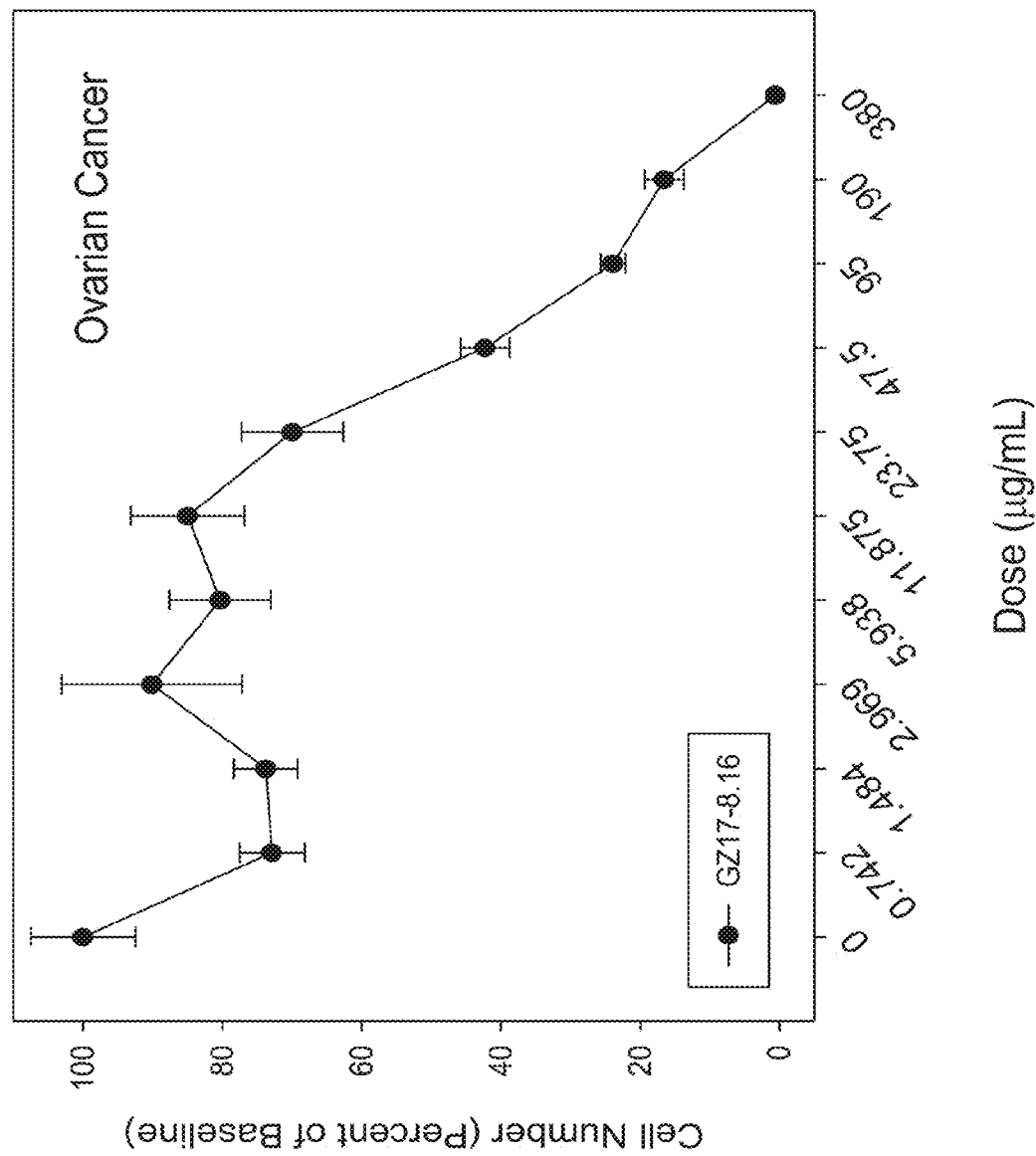
Figure 34B:
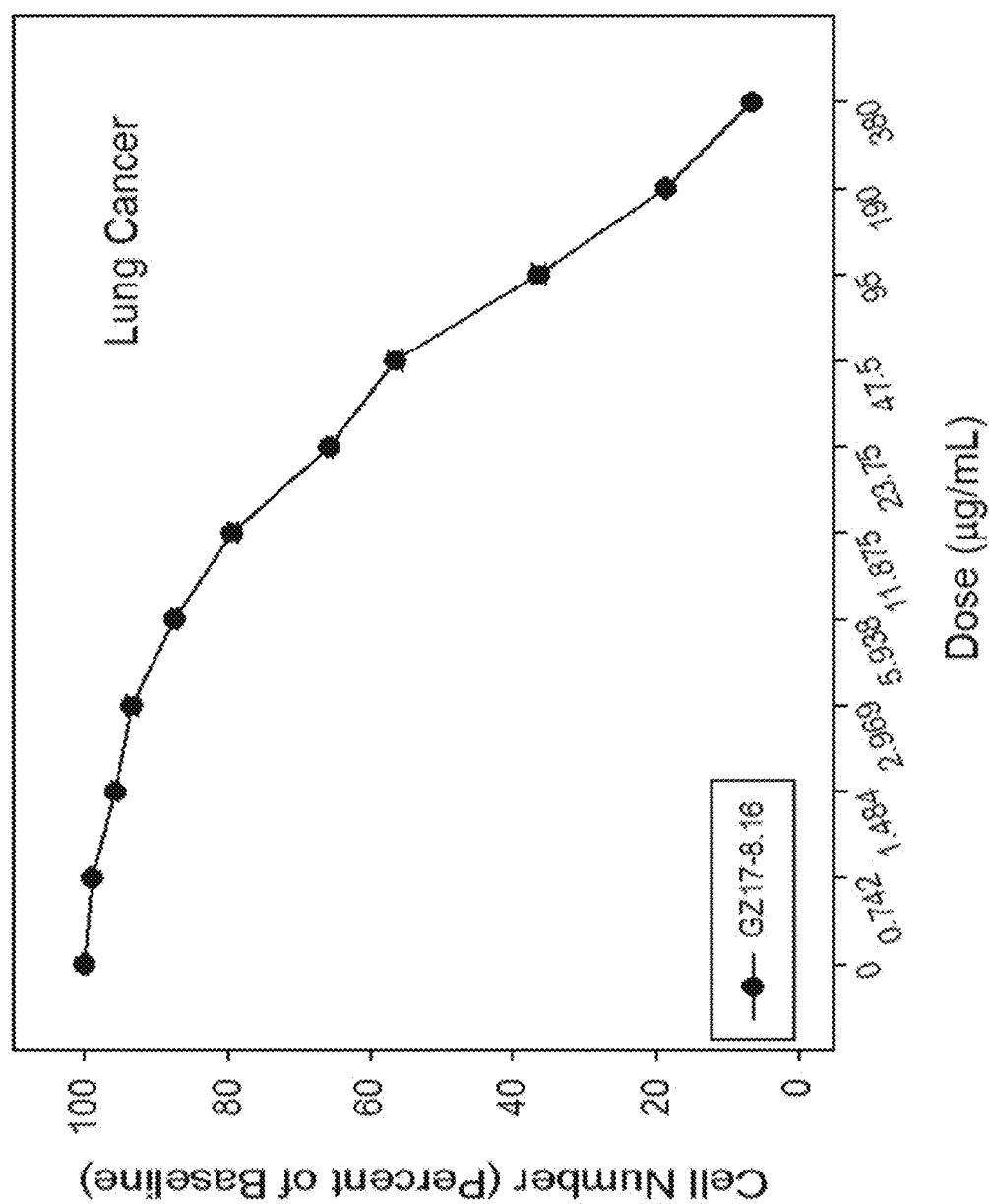
Figure 34C:
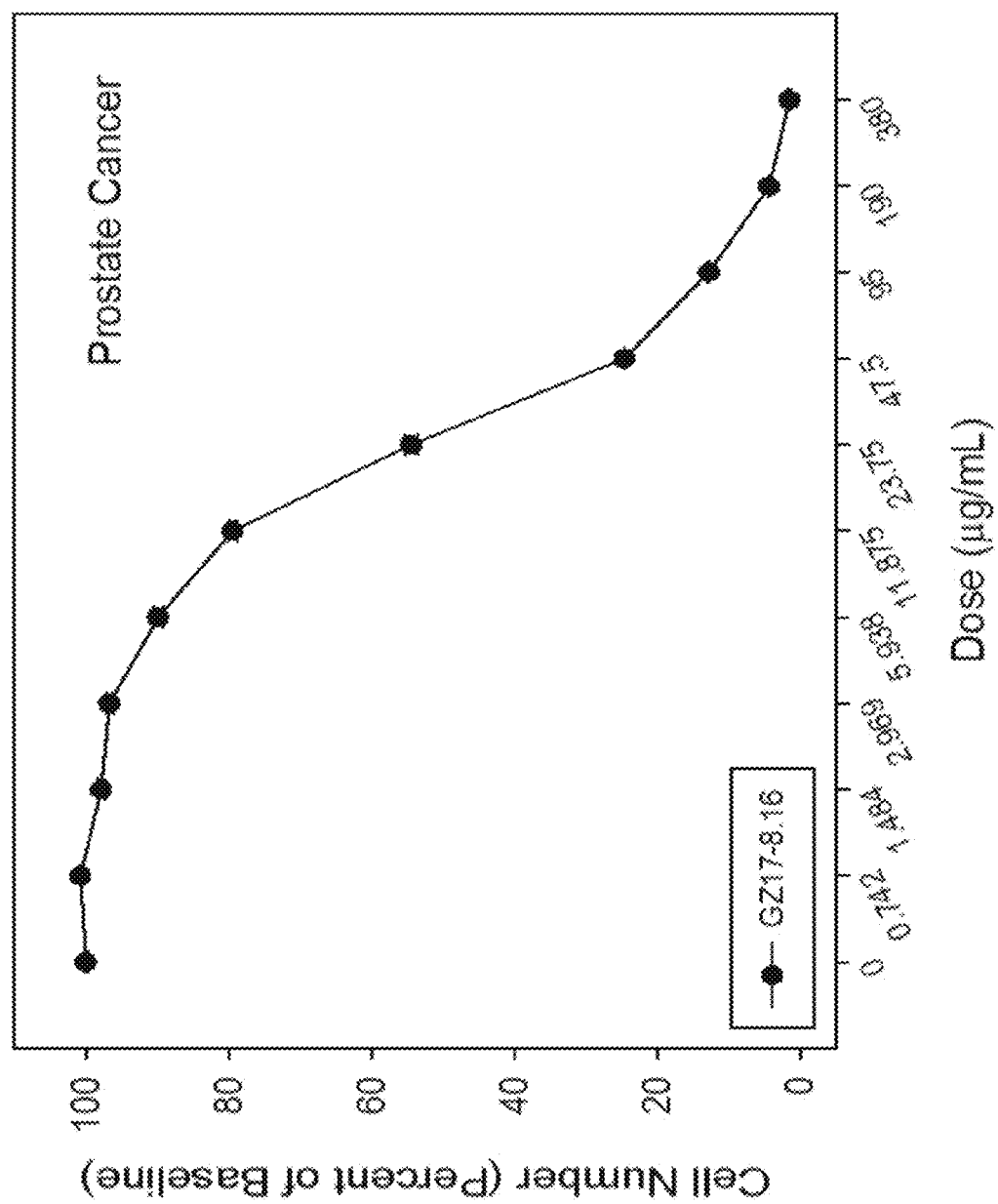
Figure 34D:
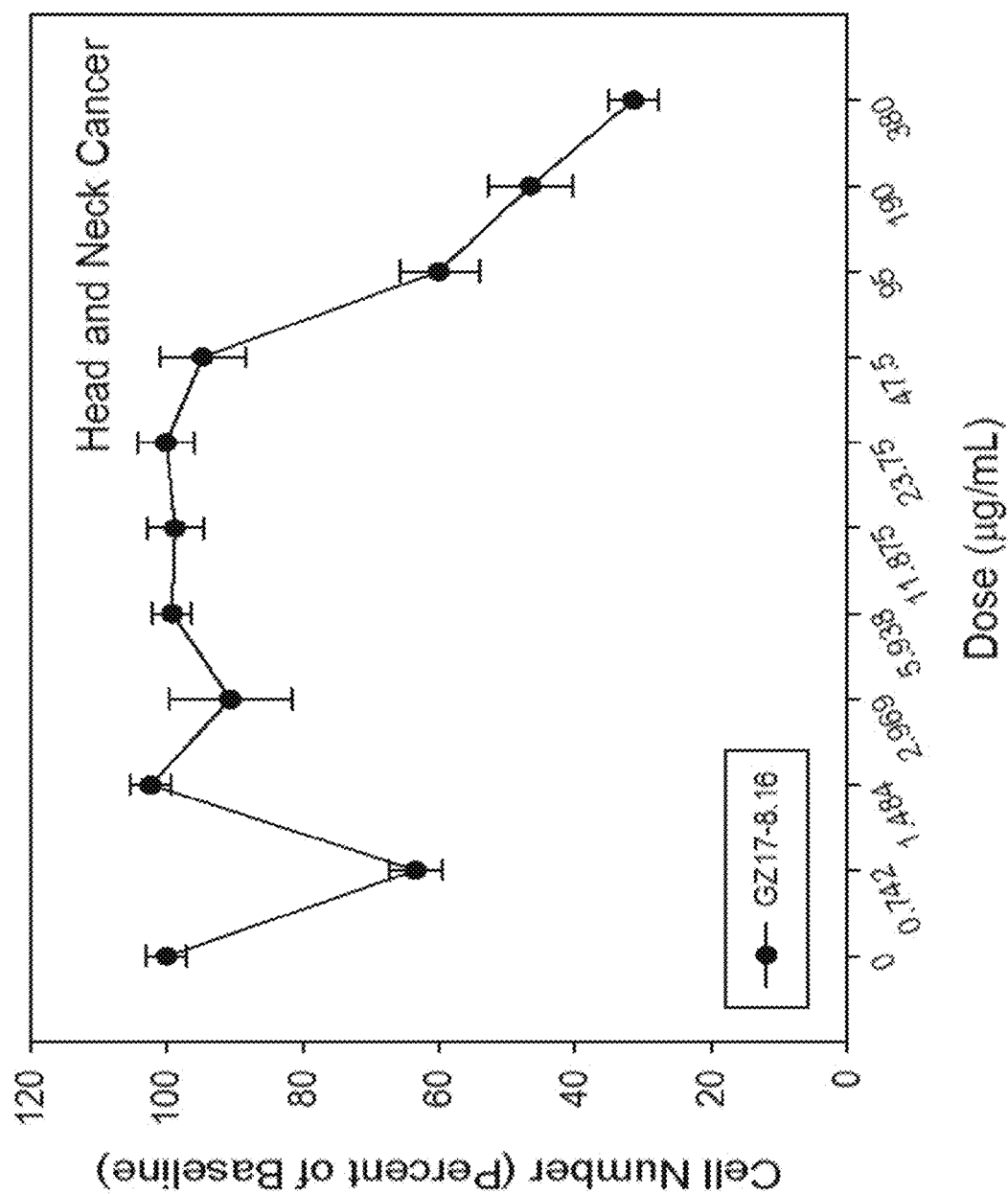
Figure 34E:
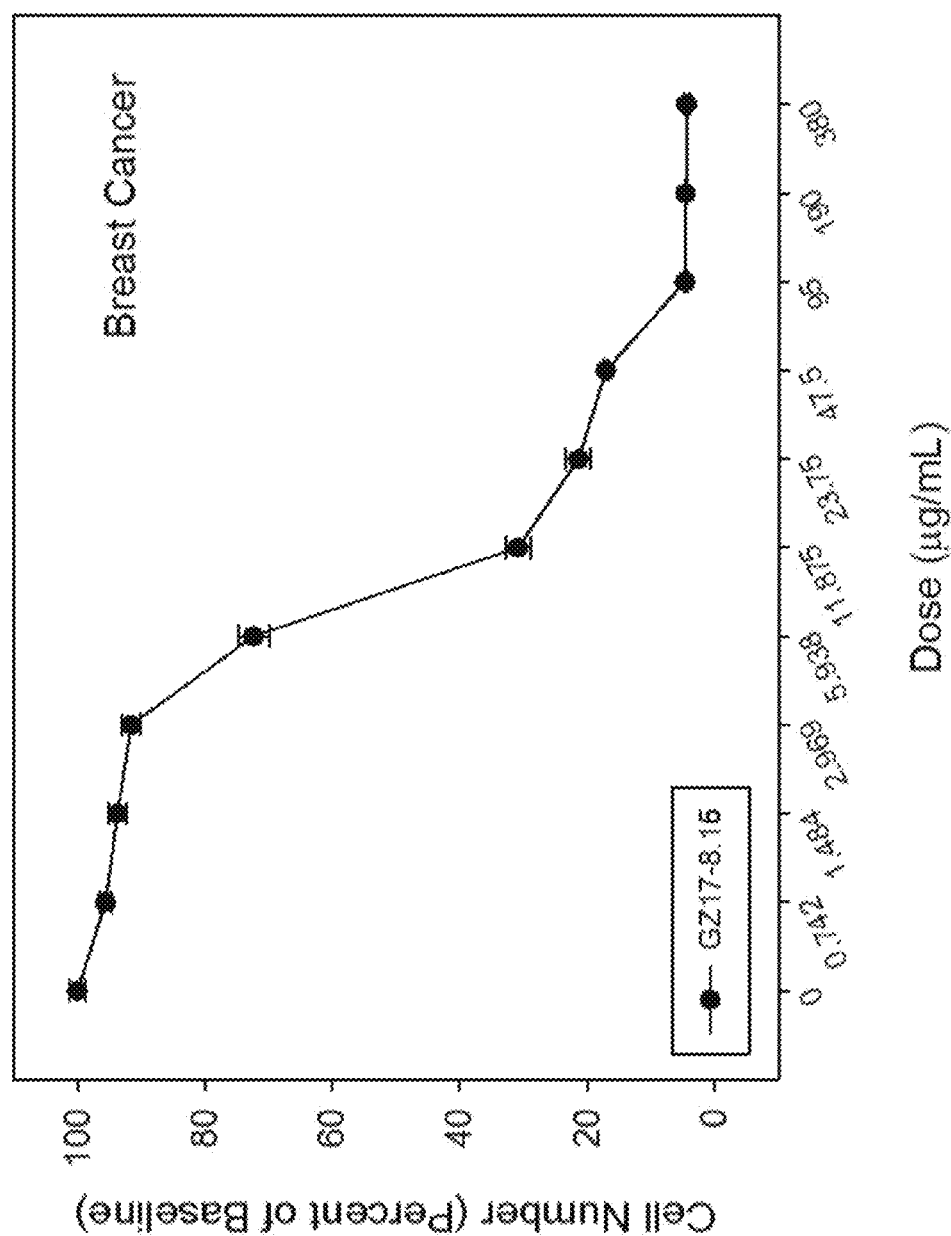
Figure 34F:
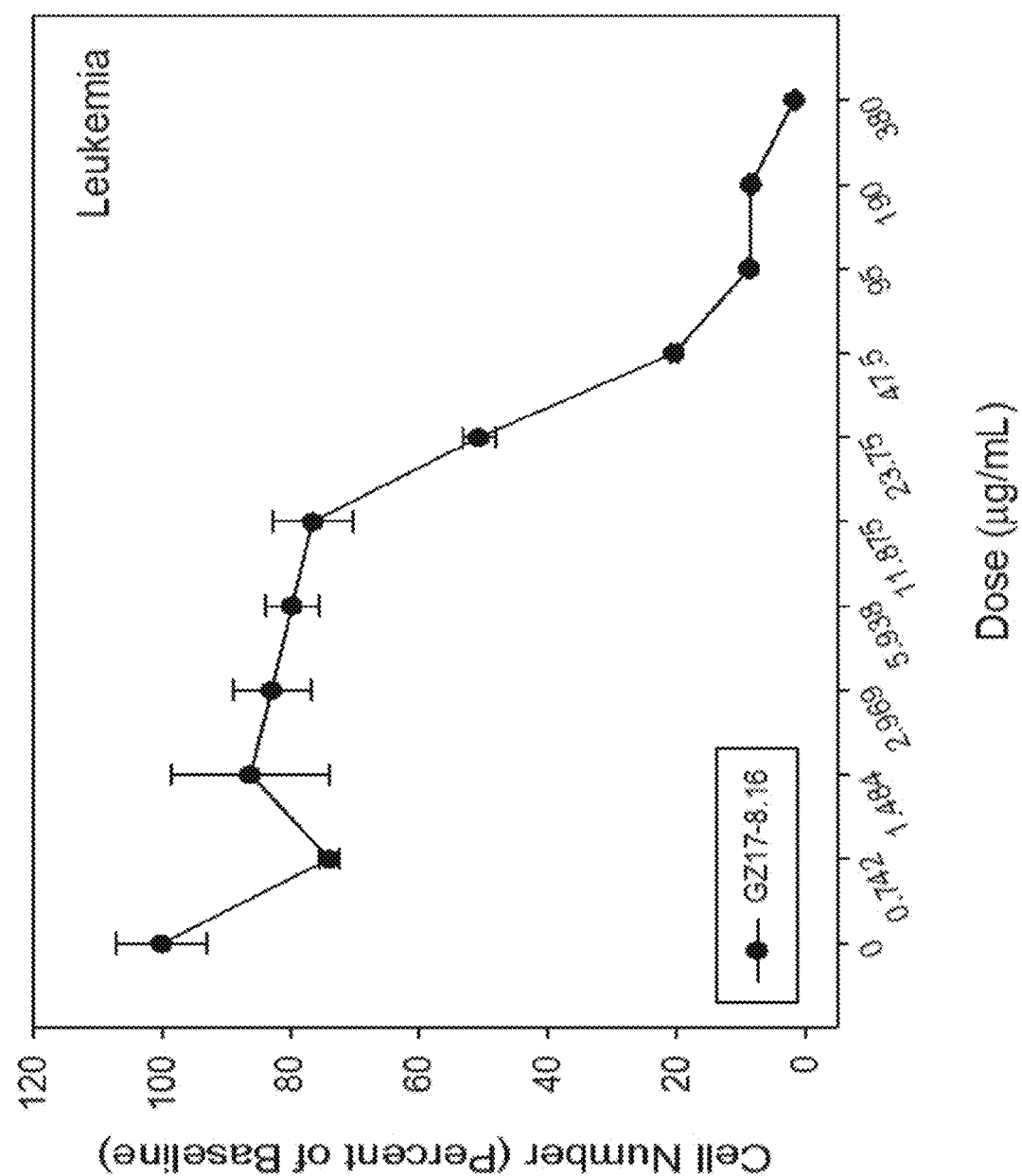
Figure 34G:
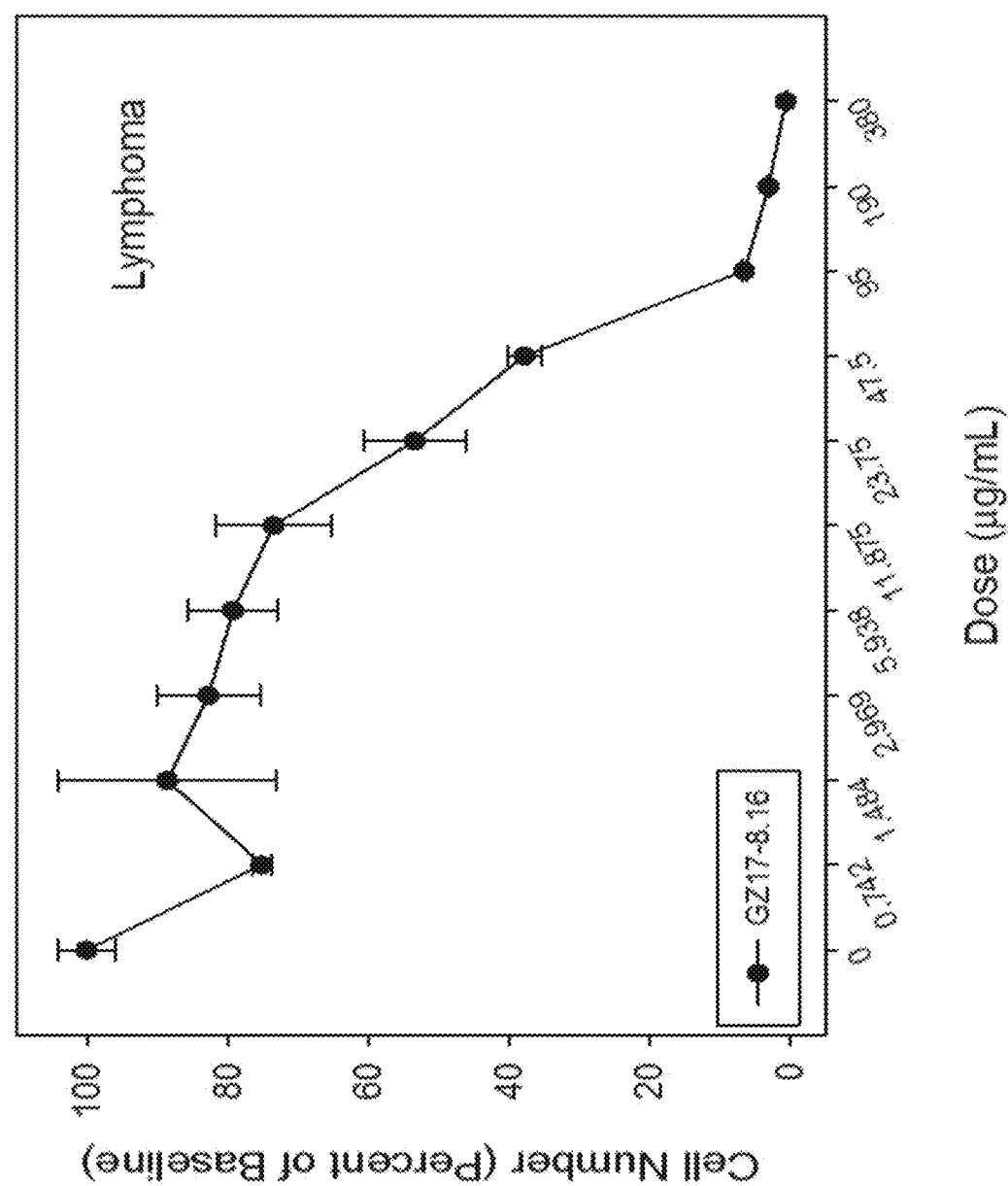
Figure 35A:
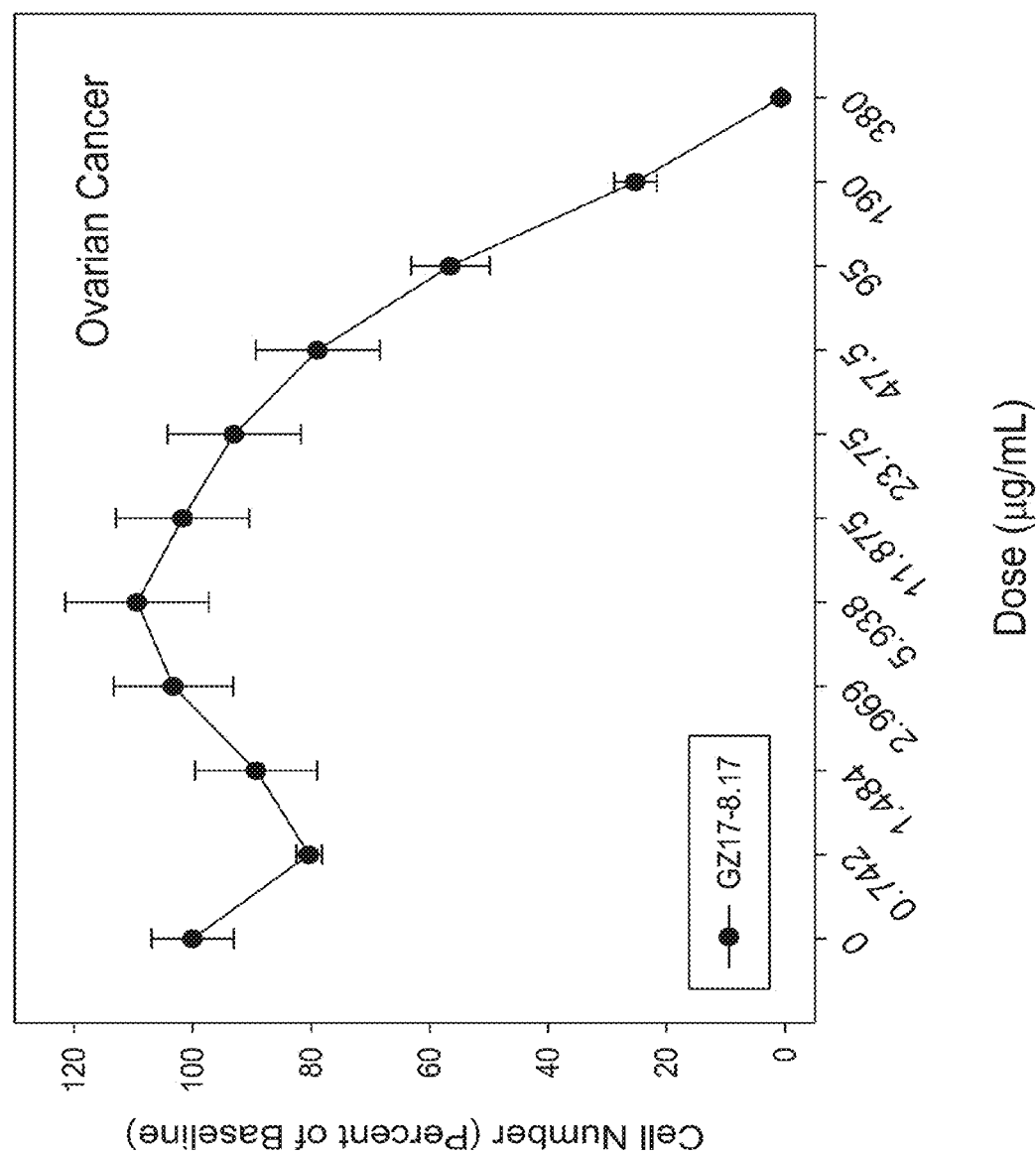
Figure 35B:
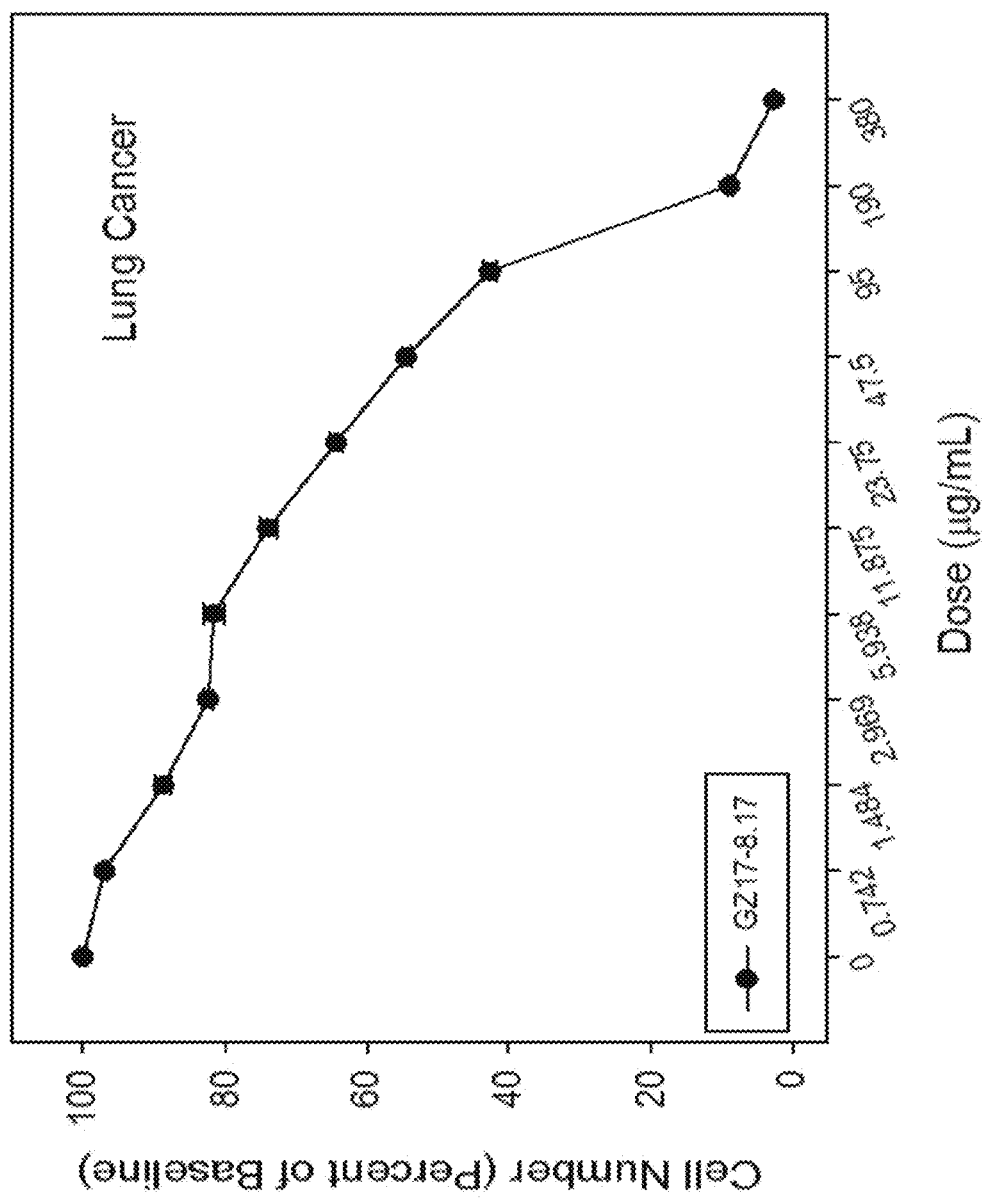
Figure 35C:
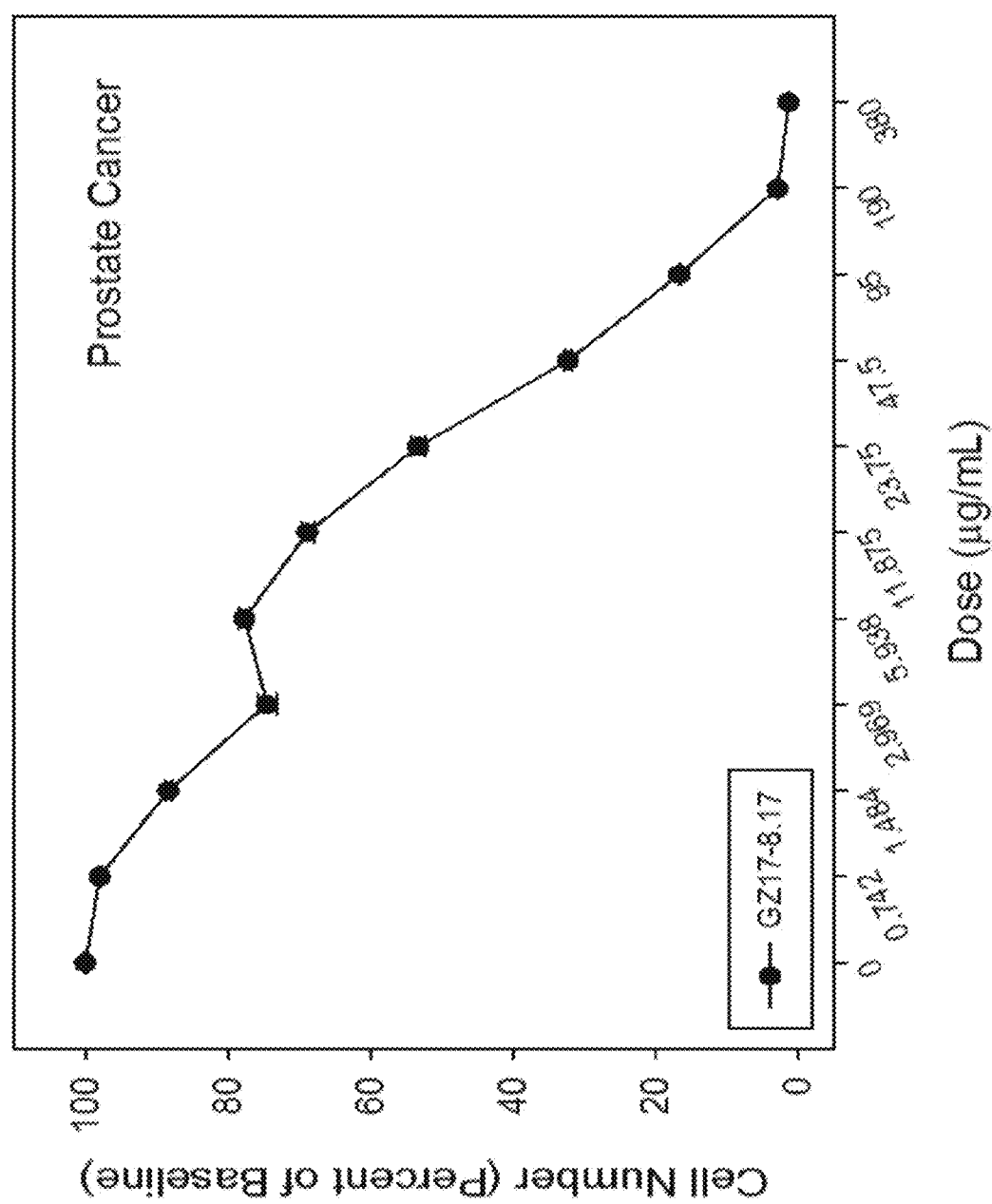
Figure 35D:
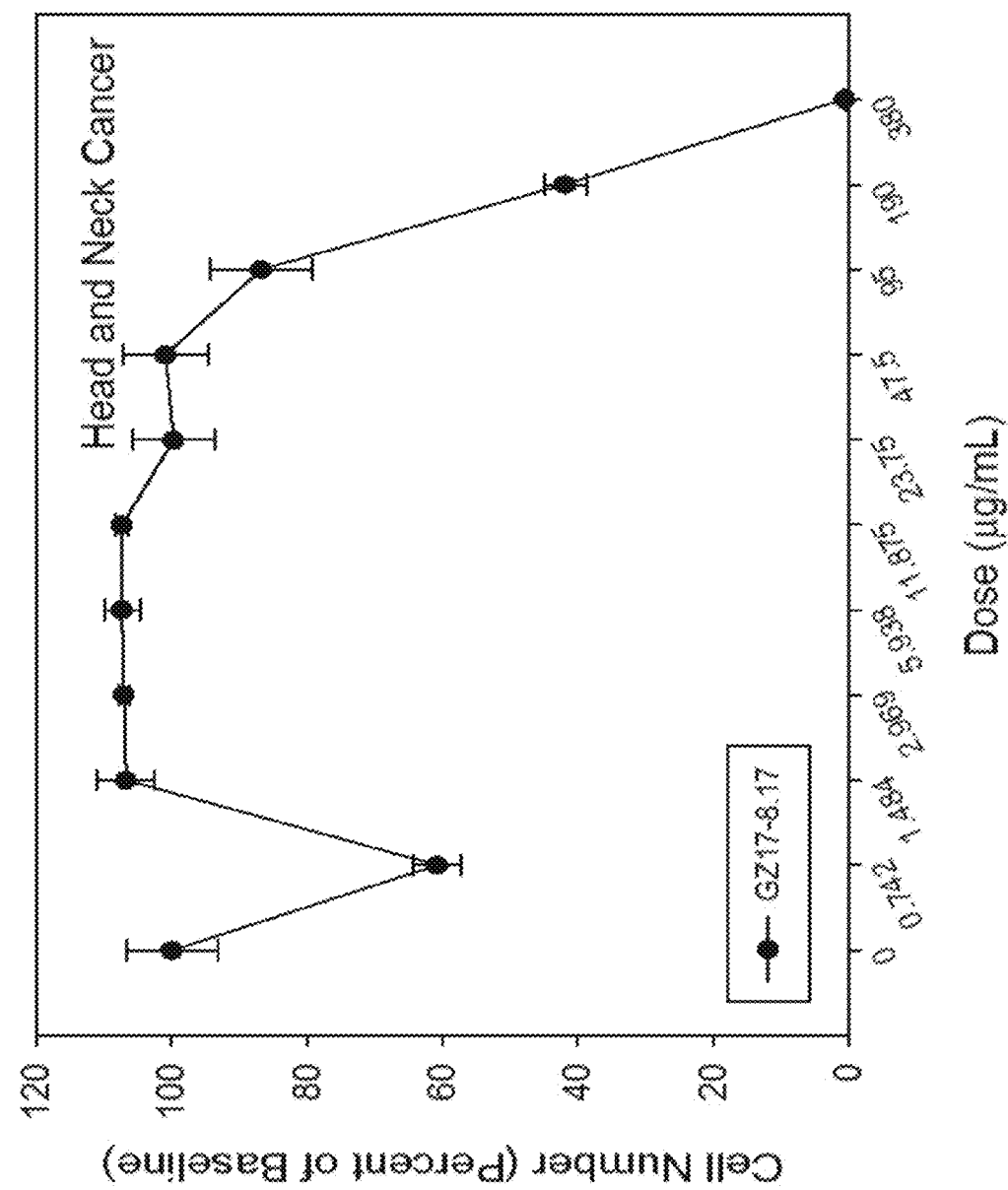
Figure 35E:
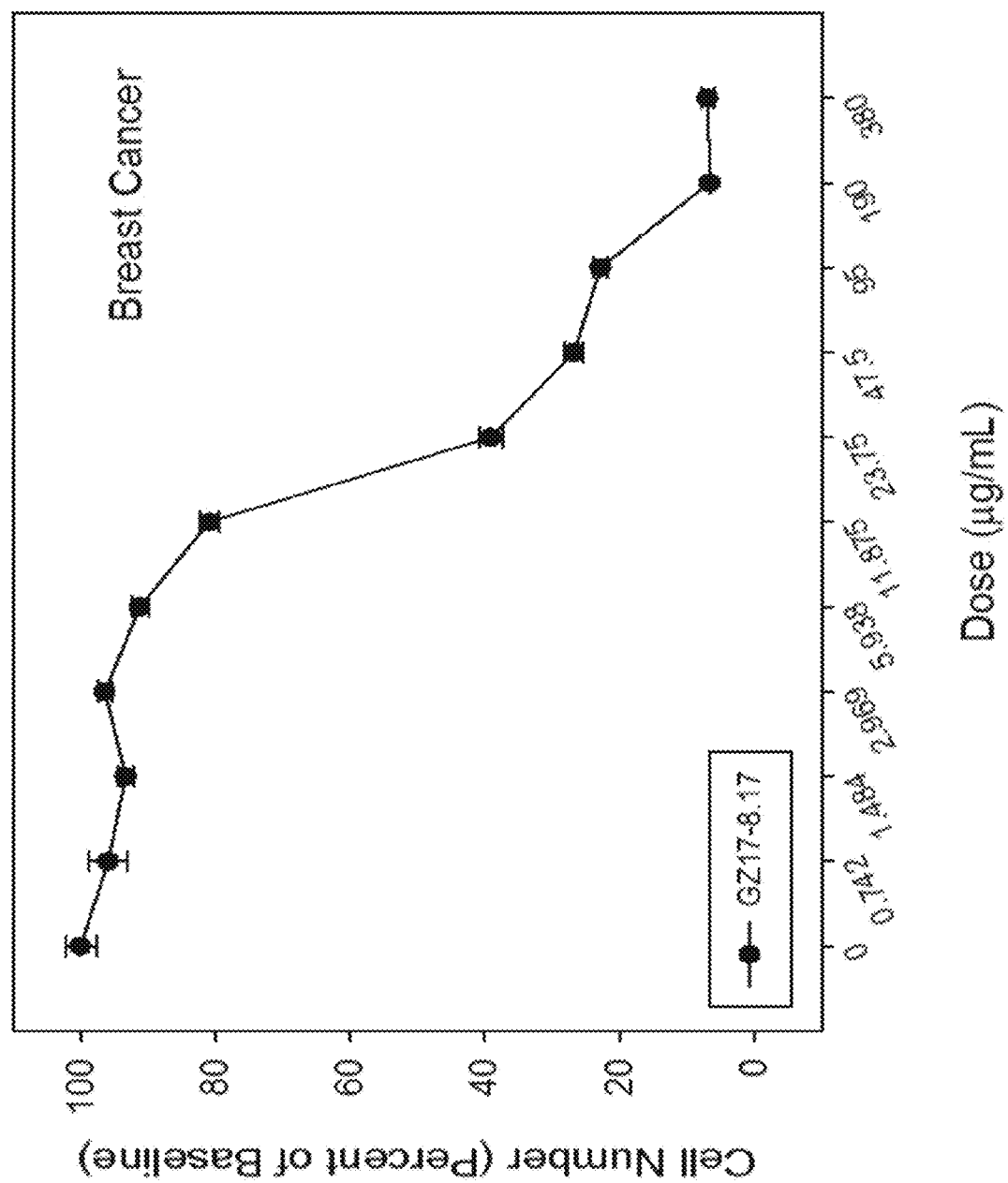
Figure 35F:
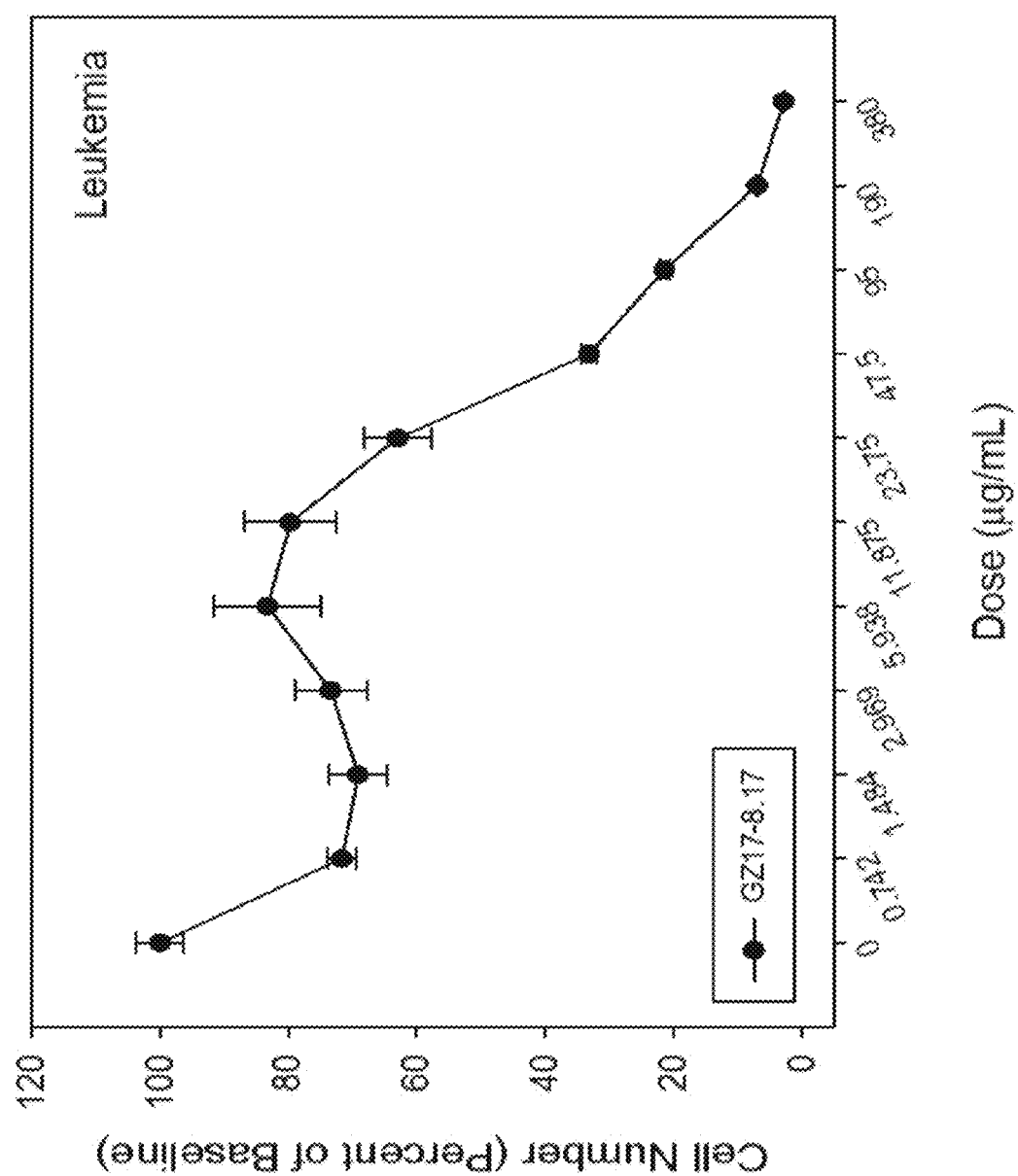
Figure 35G:
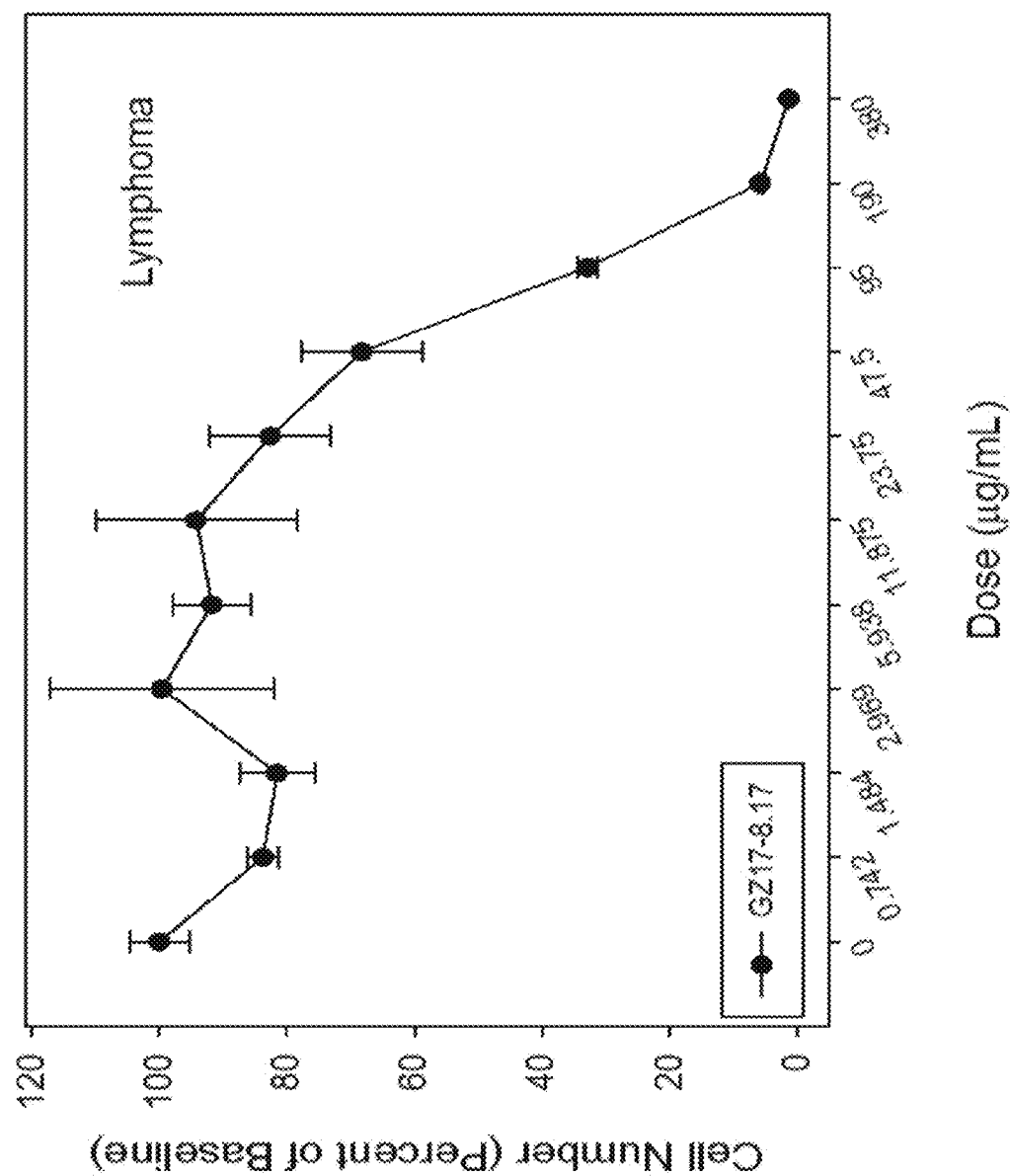
Figure 36A:
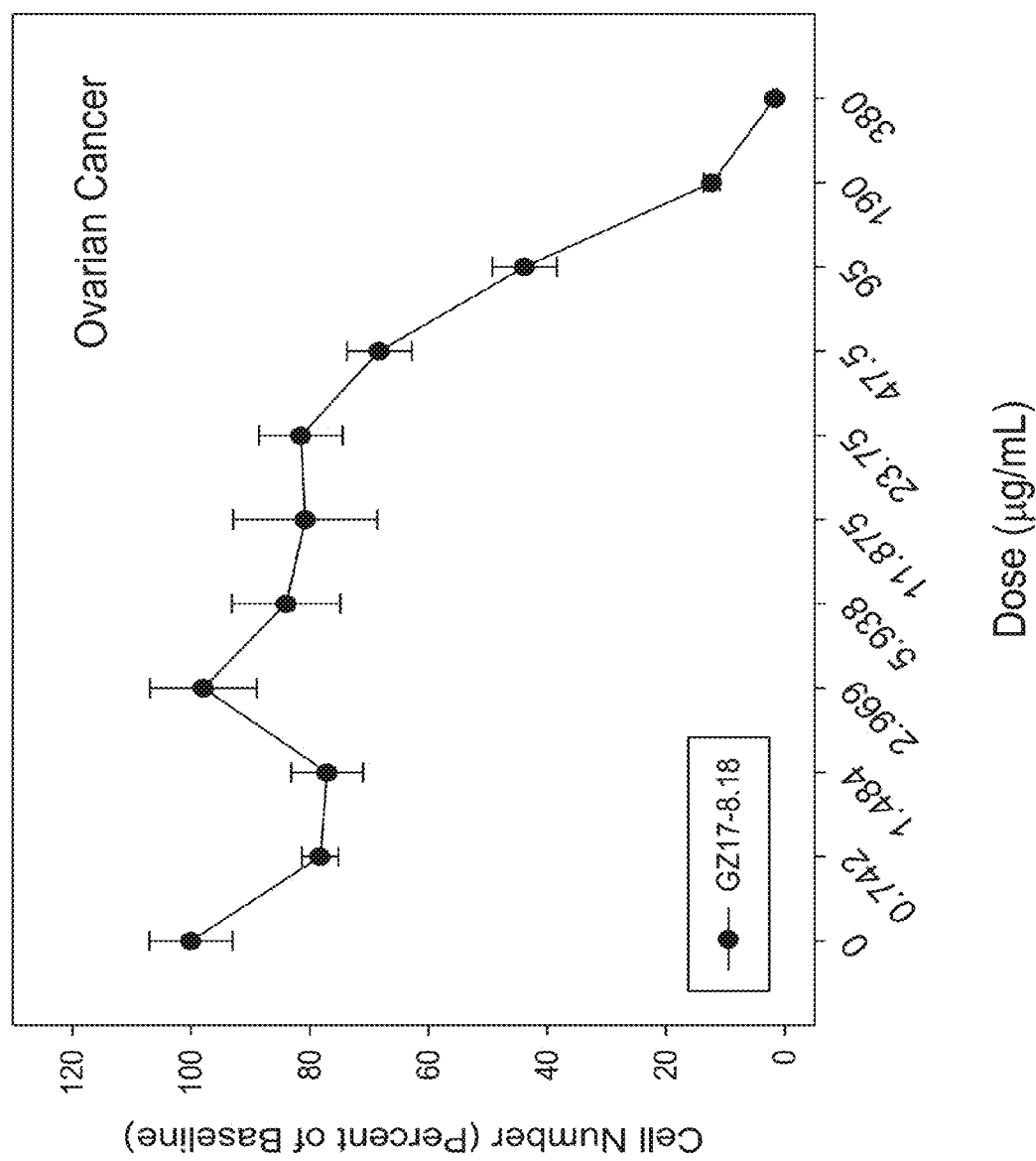
Figure 36B:
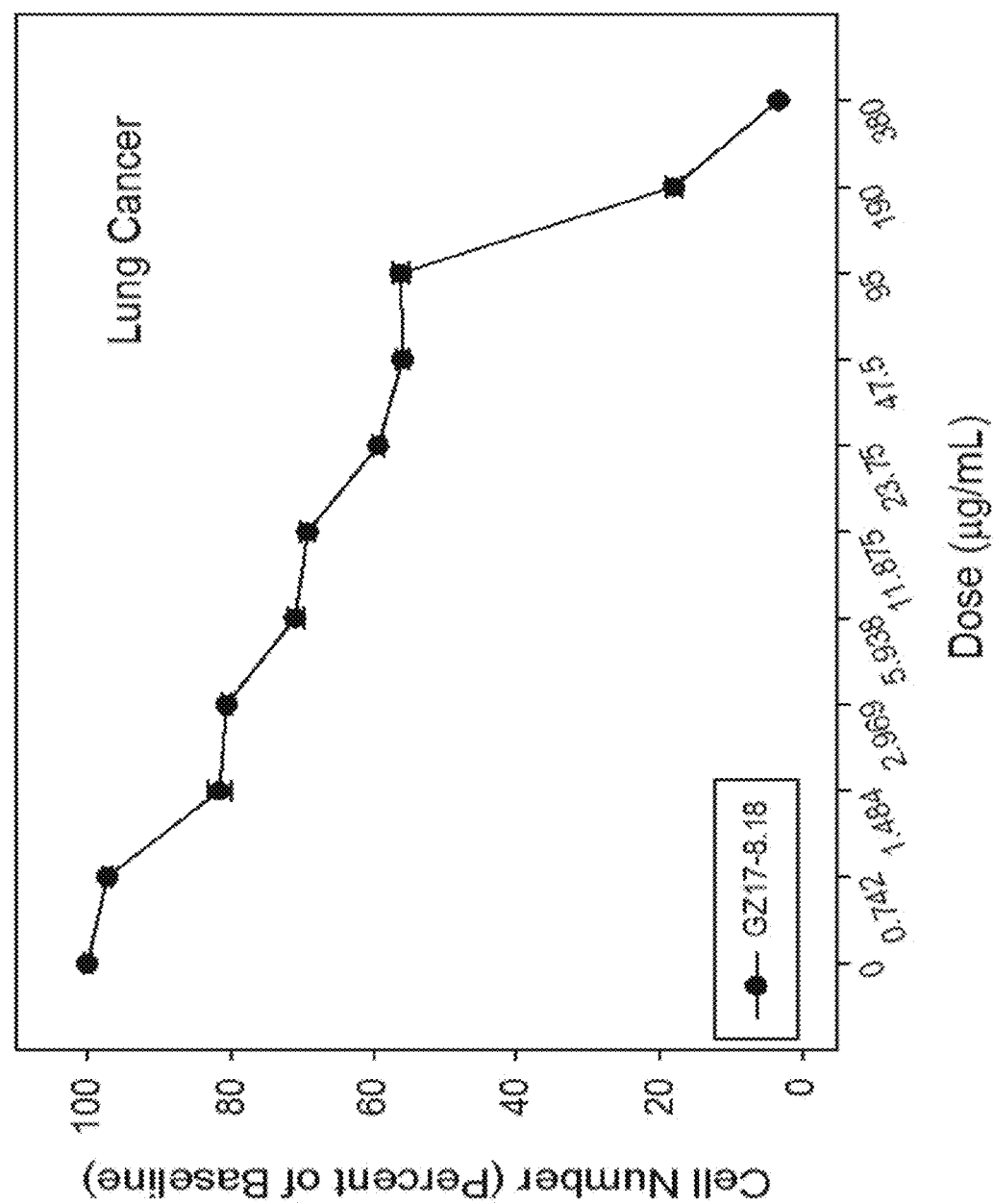
Figure 36C:
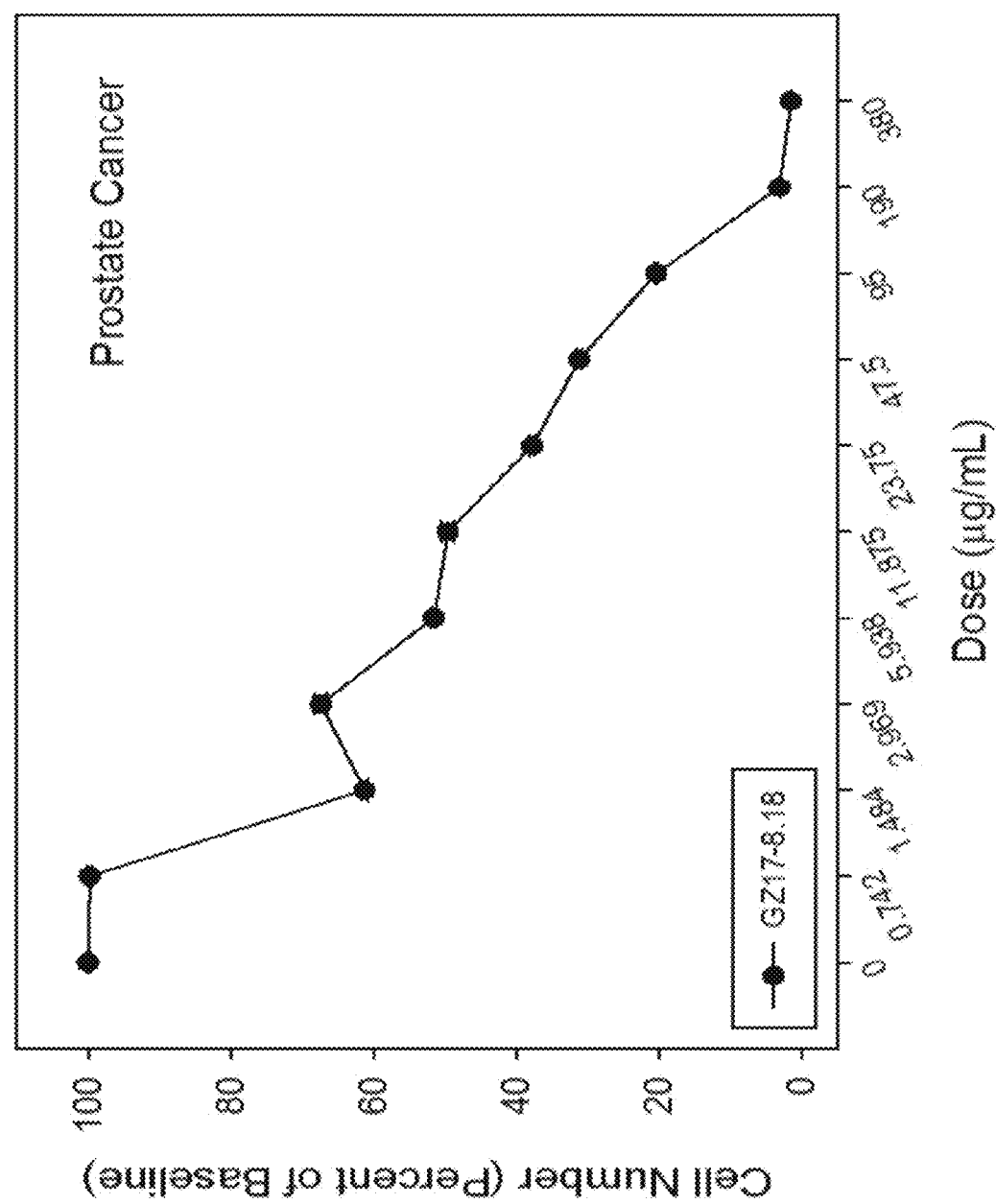
Figure 36D:
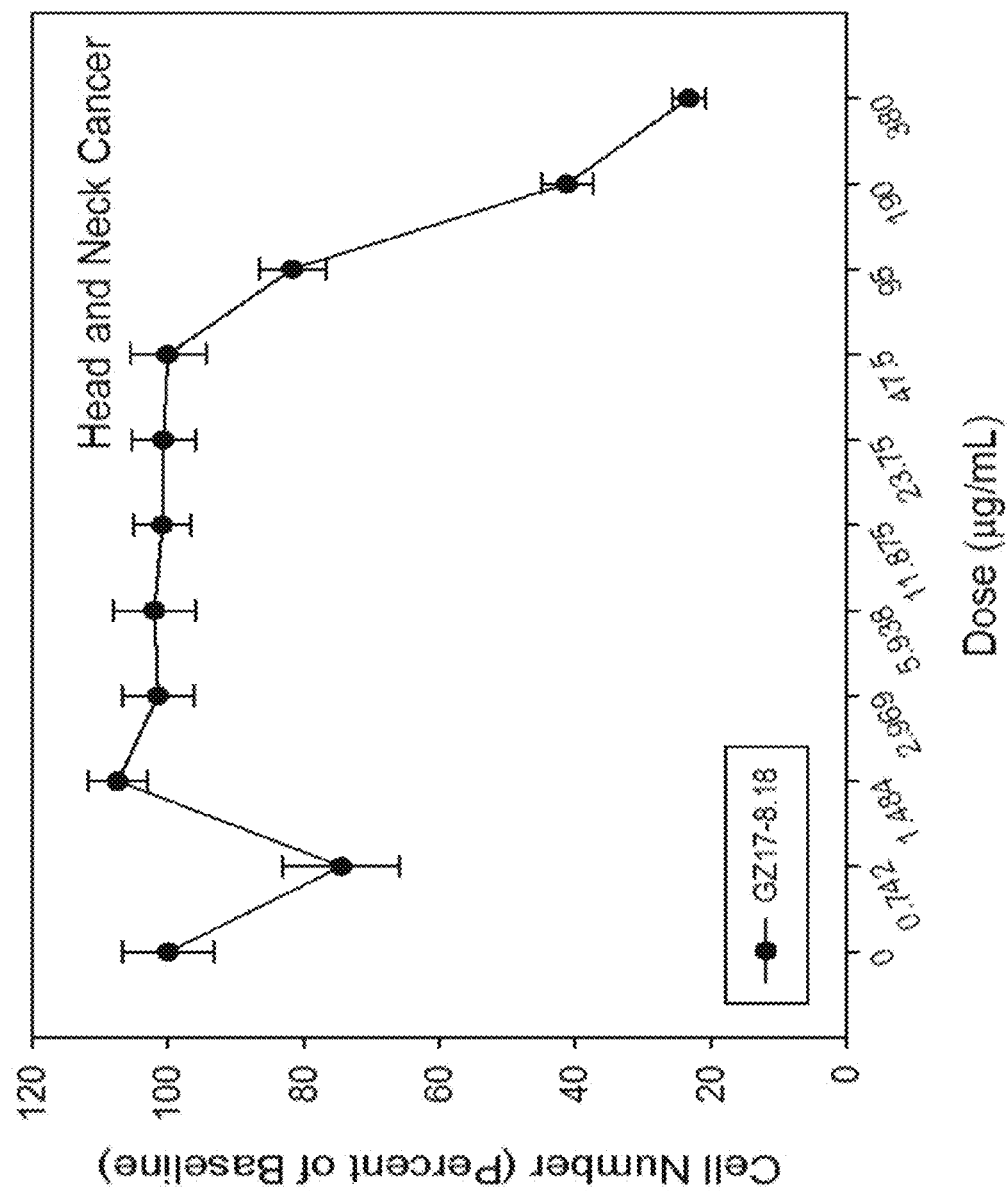
Figure 36E:
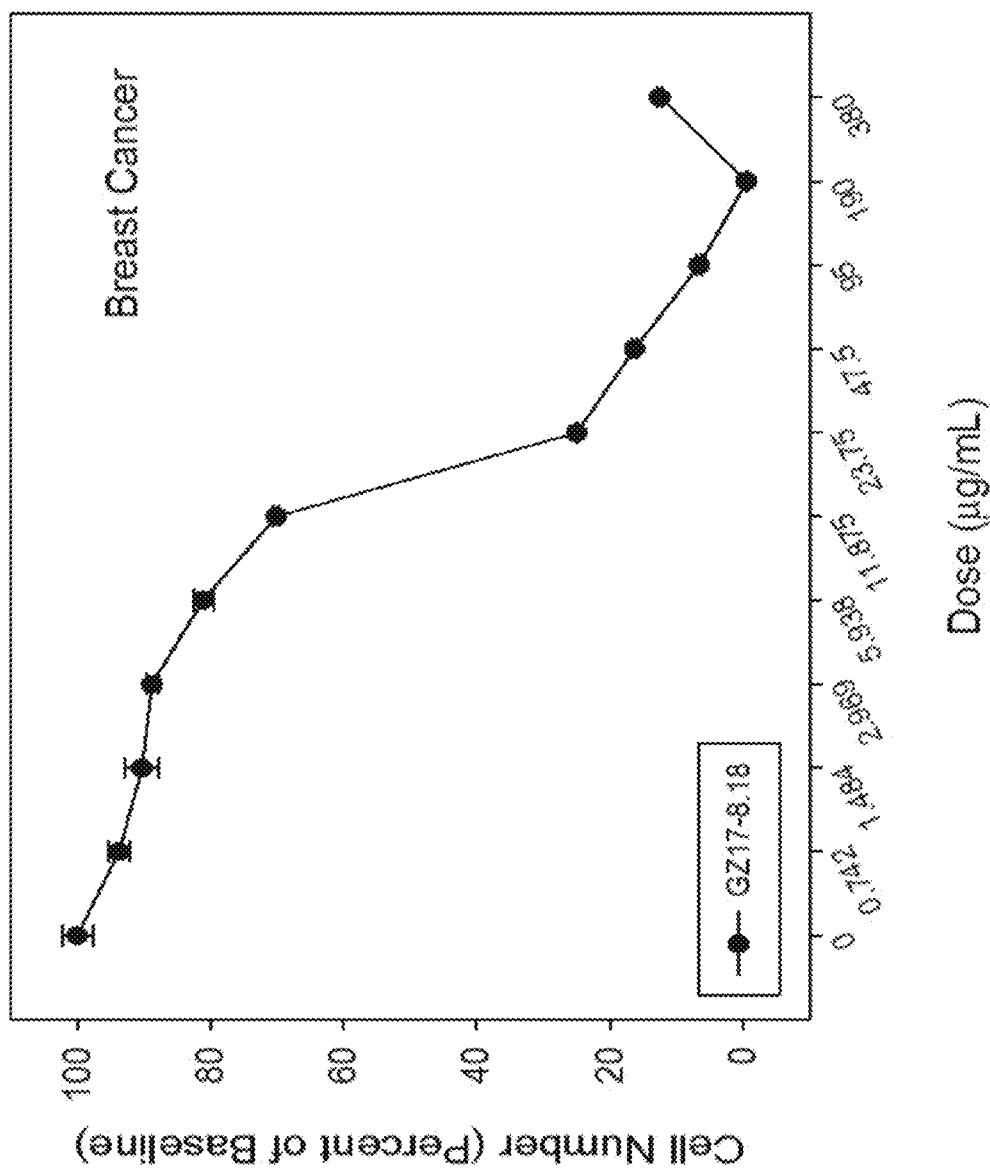
Figure 36F:
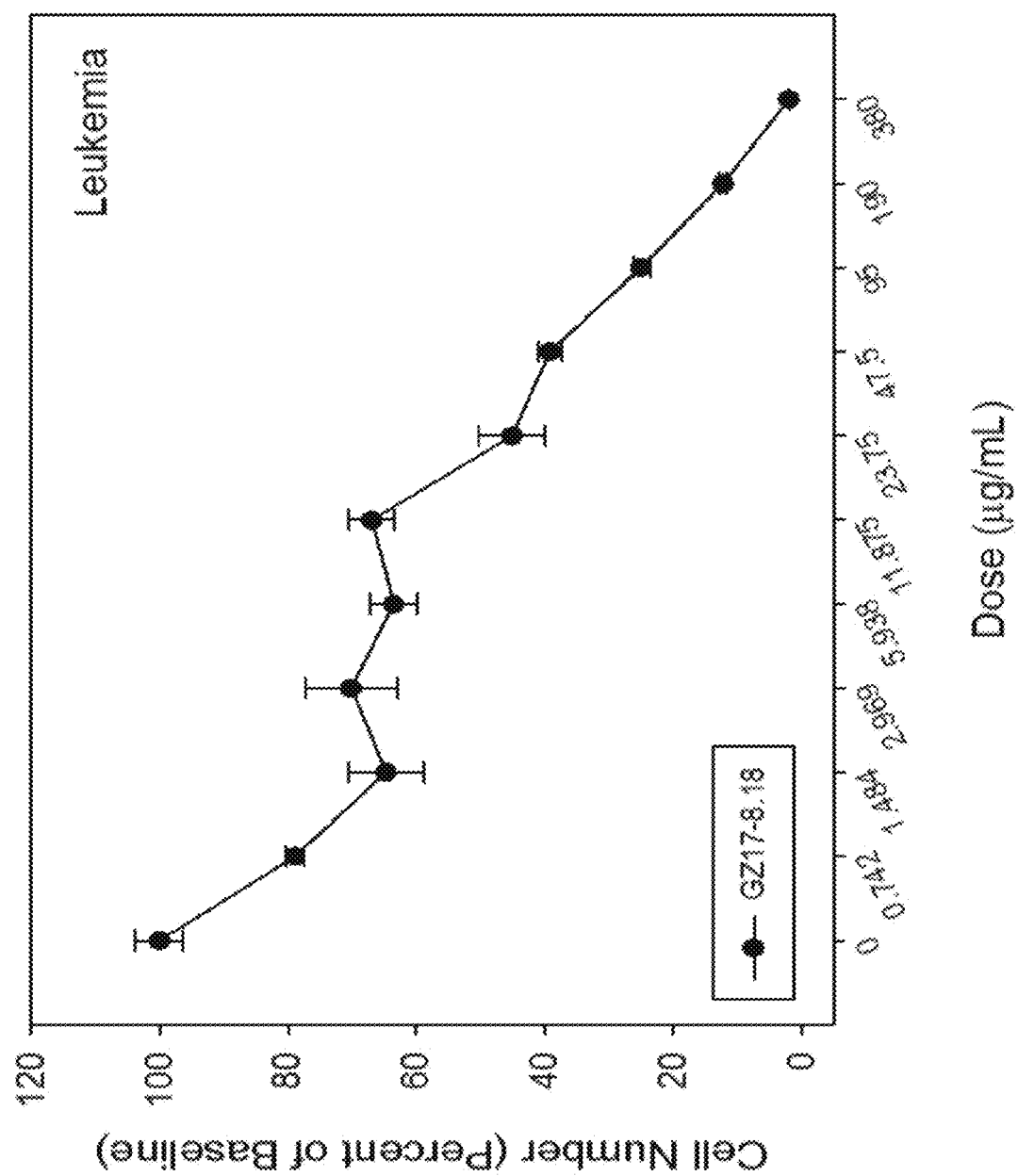
Figure 36G:
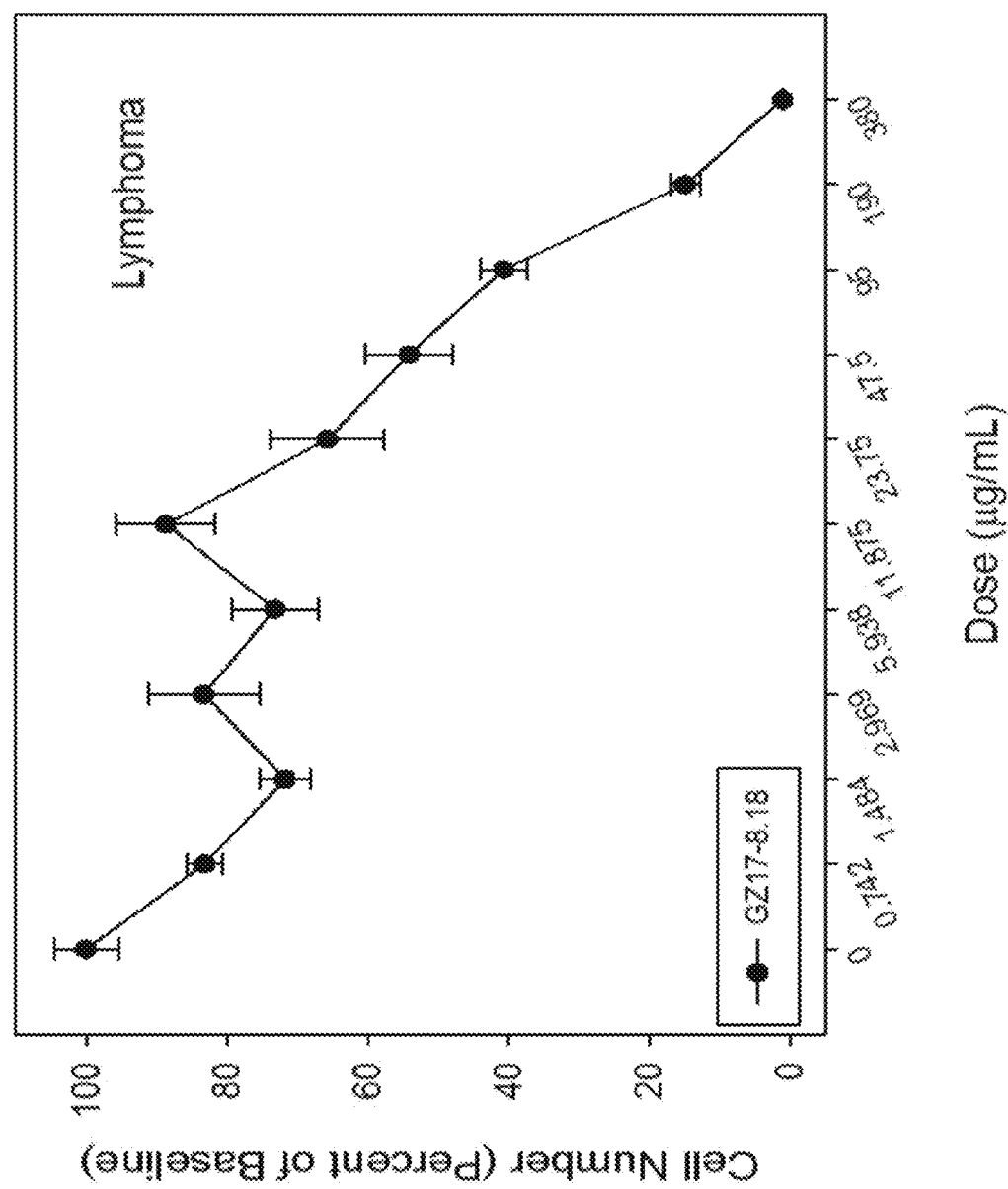
Figure 37A:
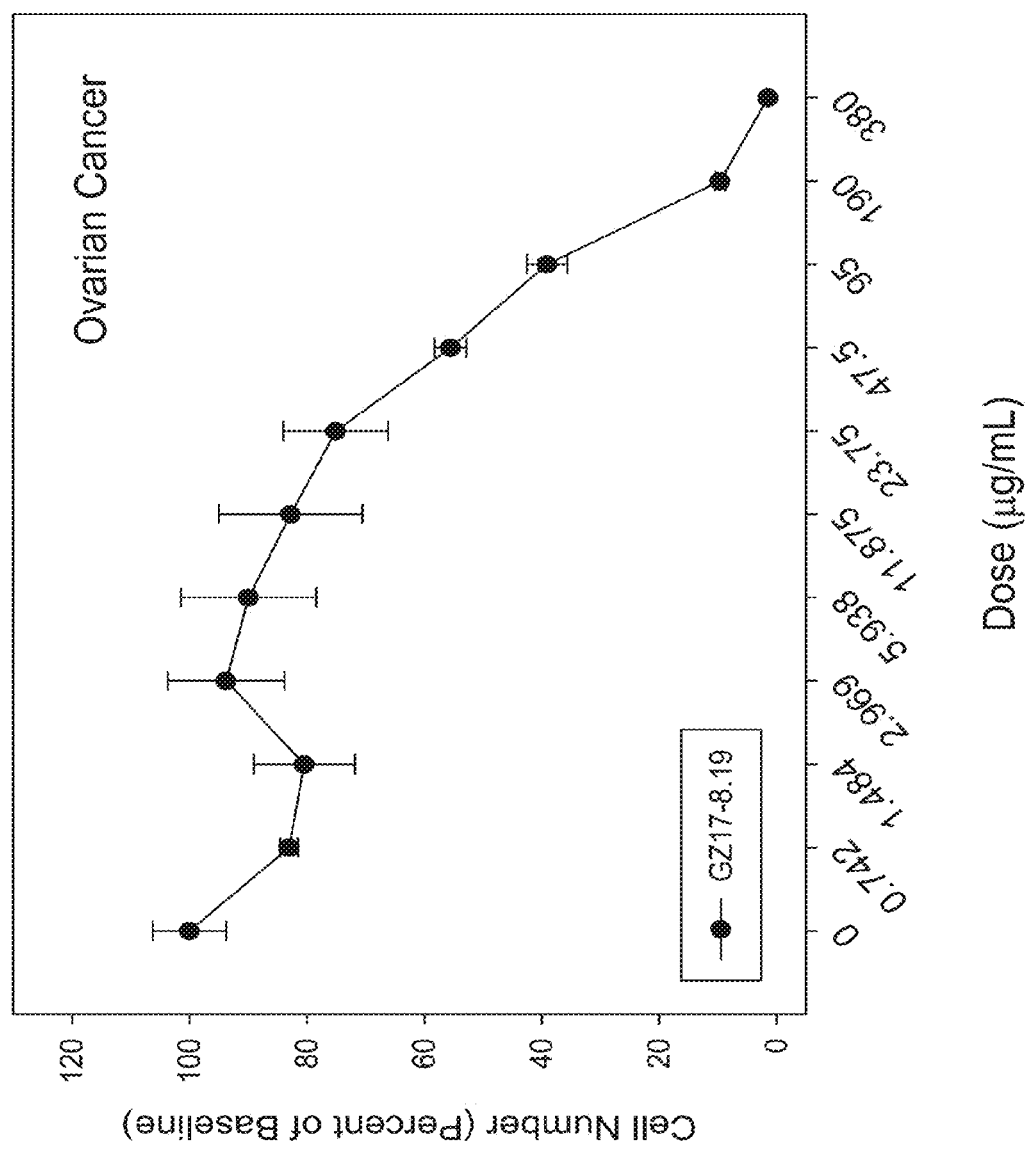
Figure 37B:
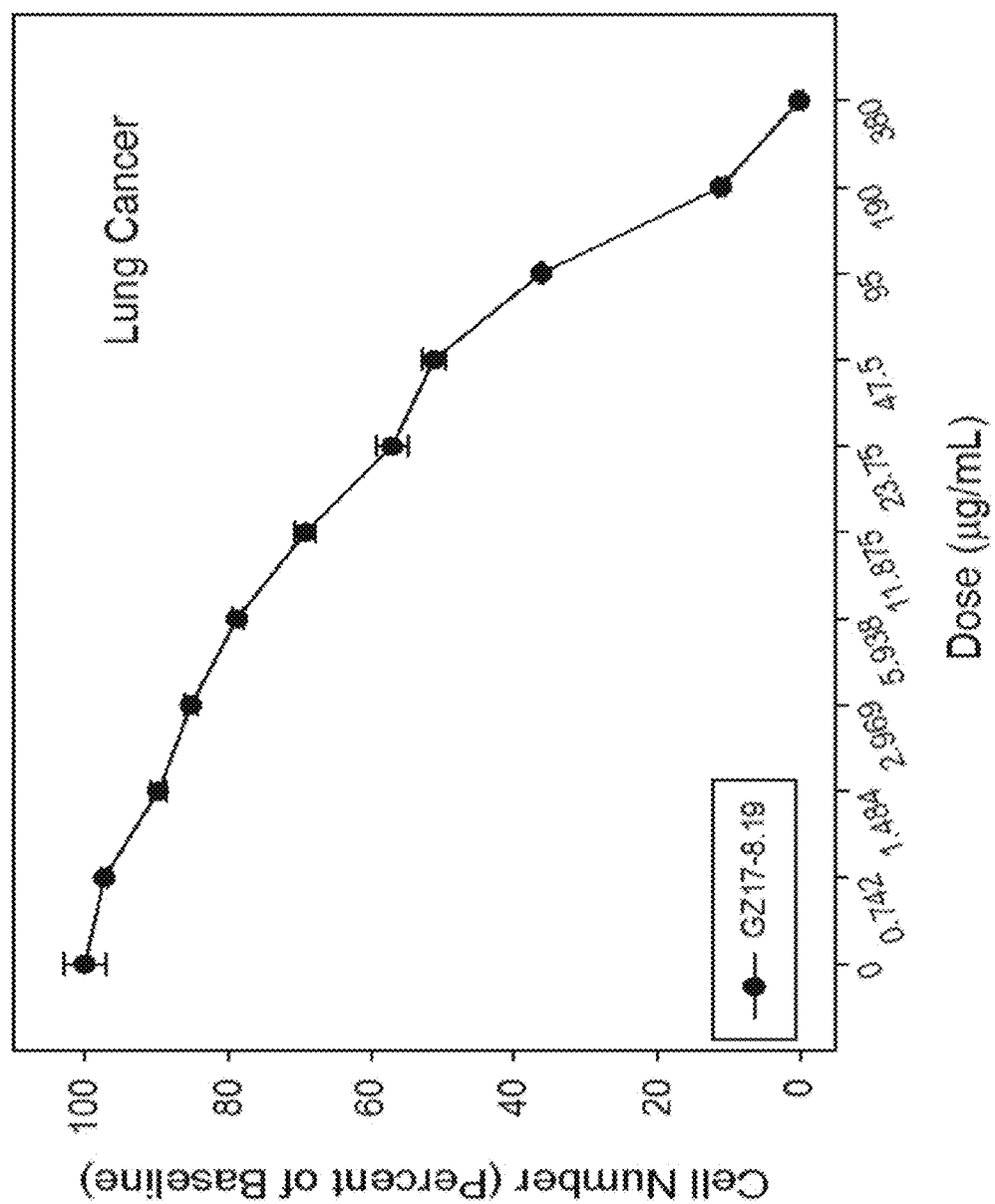
Figure 37C:
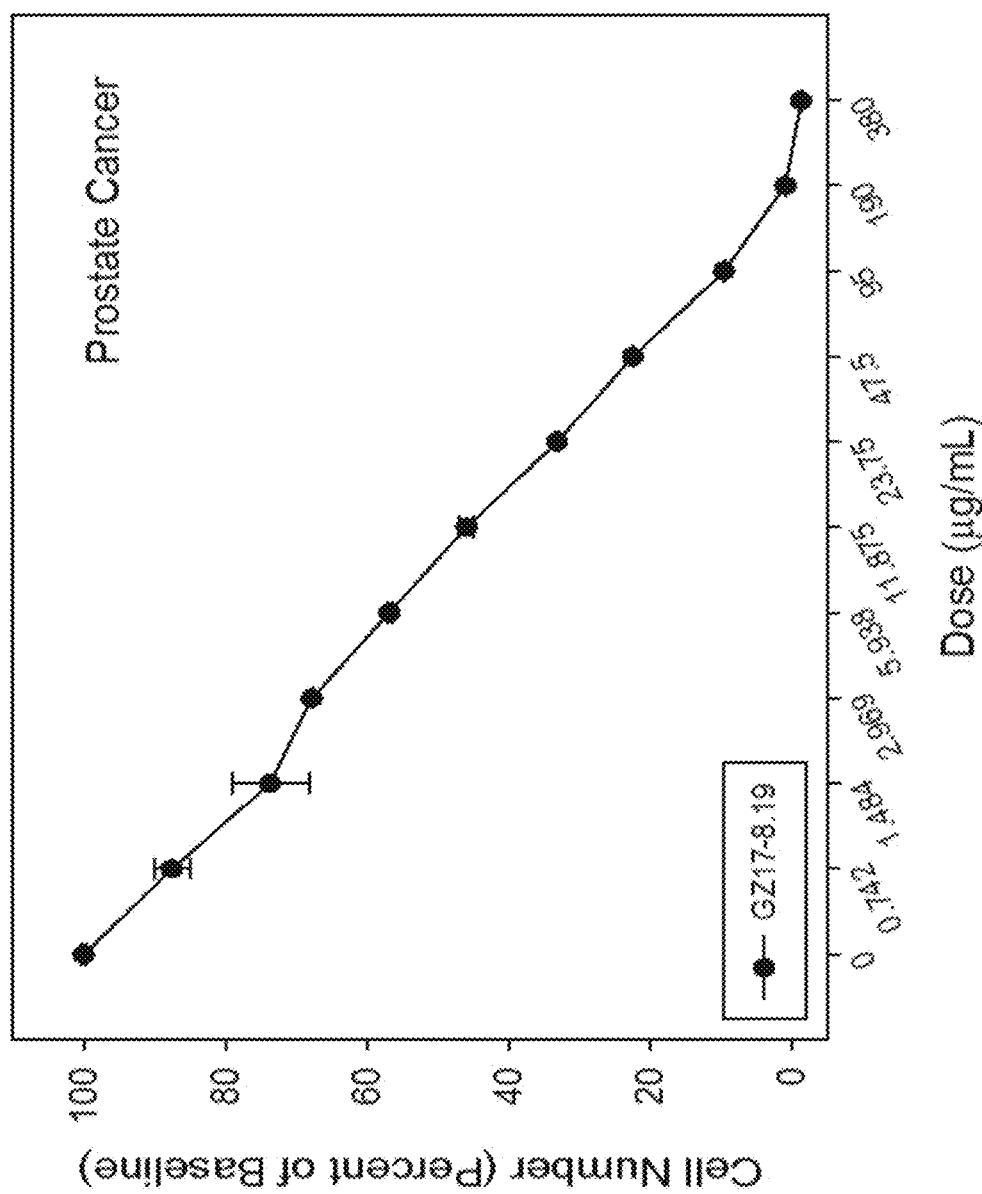
Figure 37D:
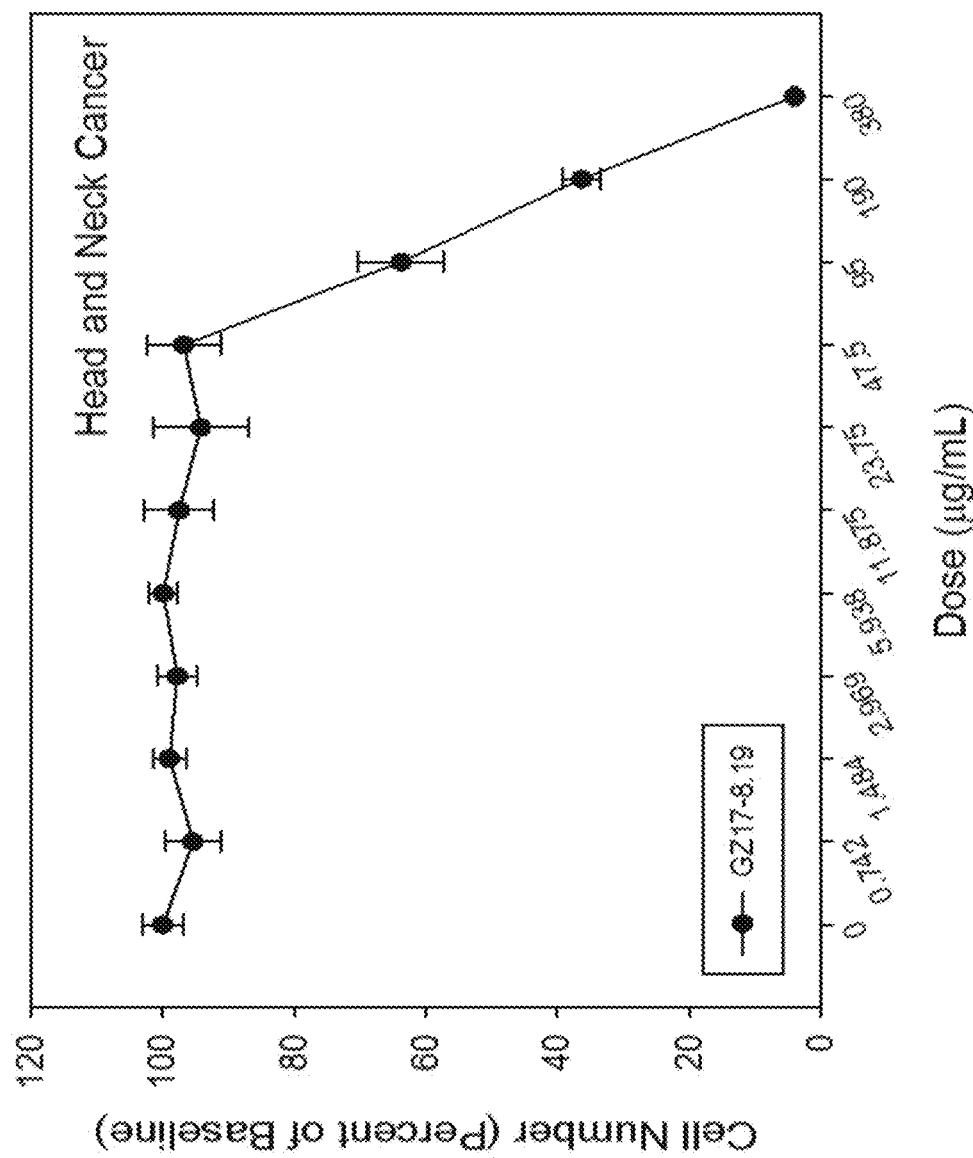
Figure 37E:
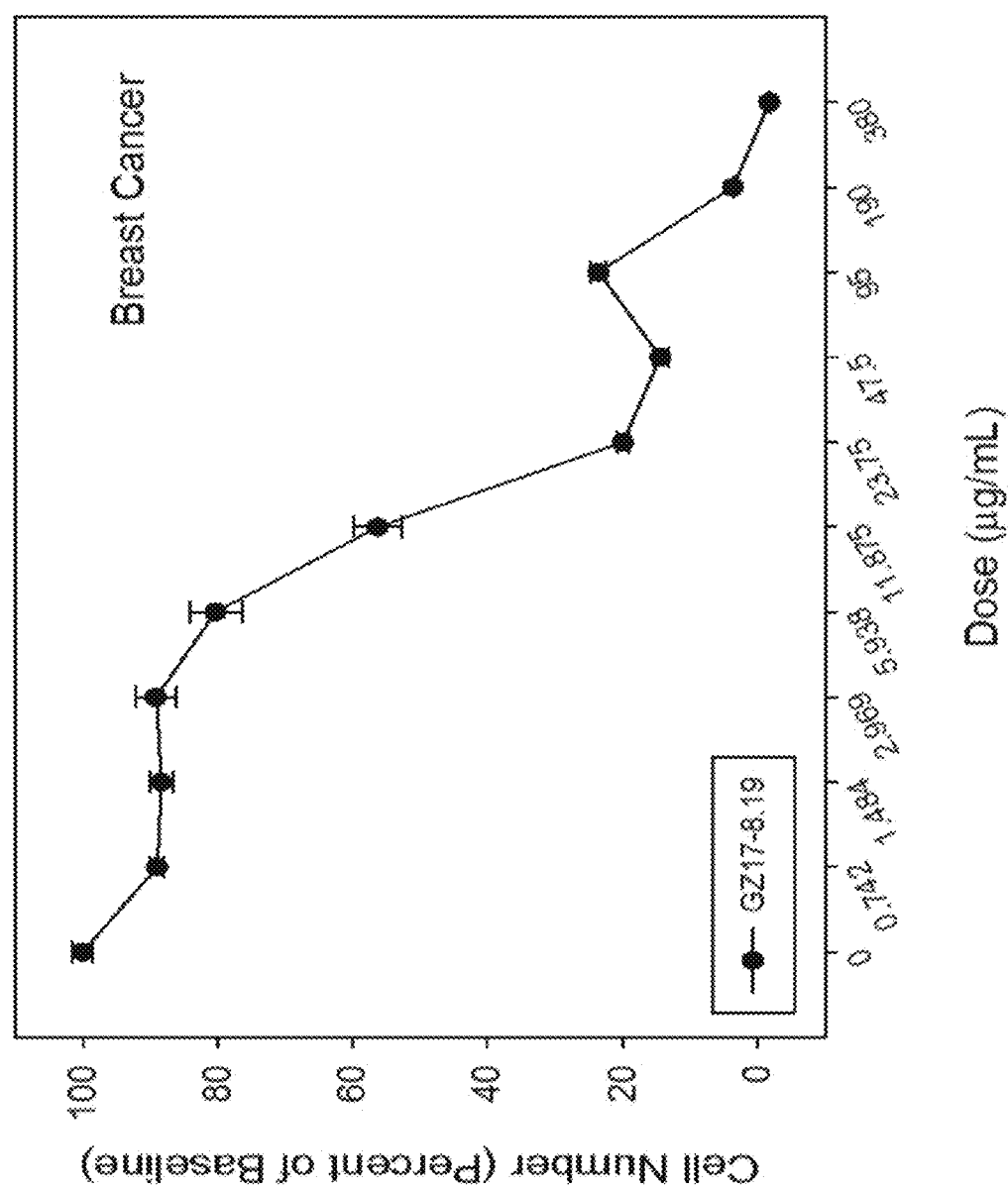
Figure 37F:
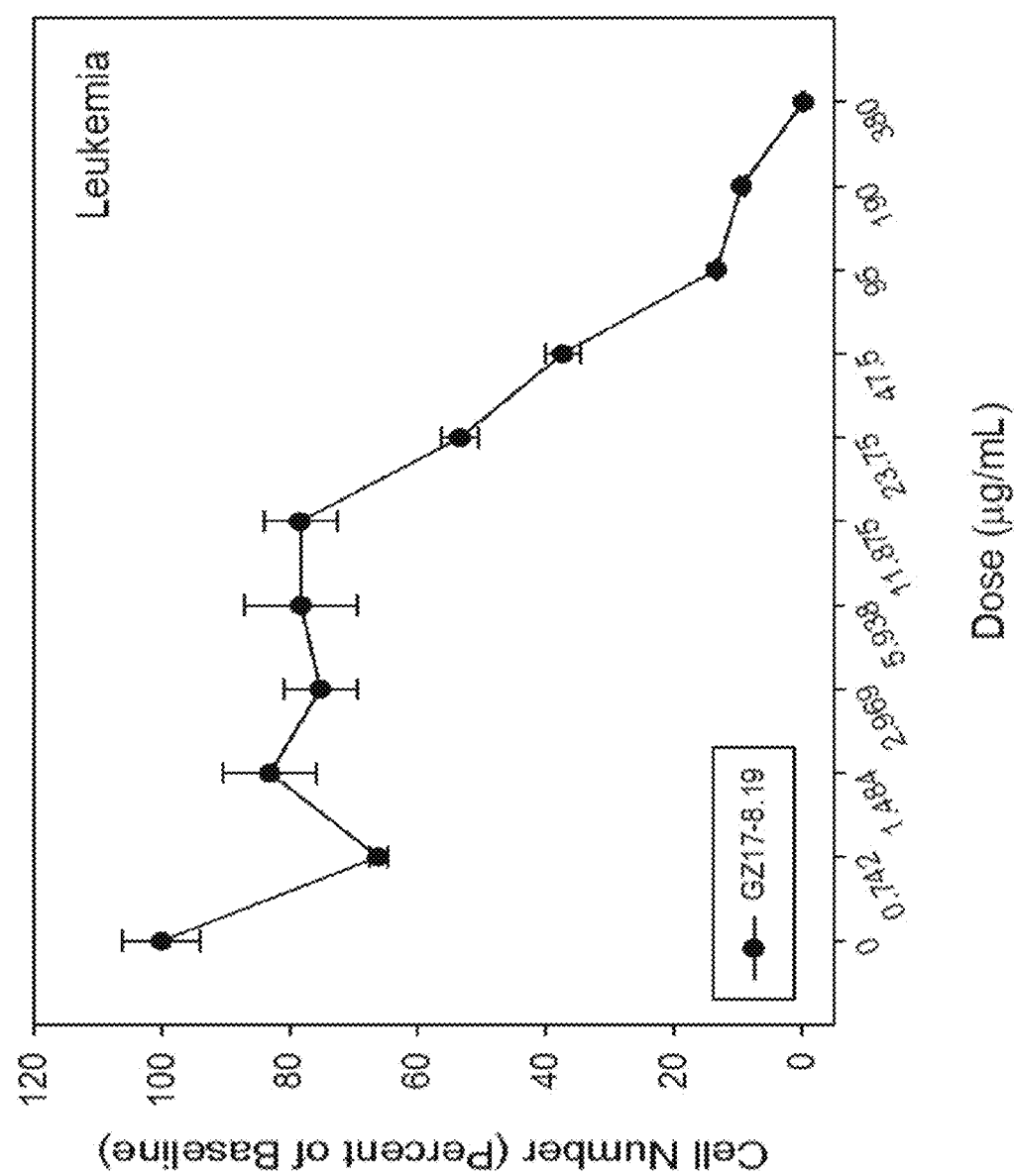
Figure 37G:
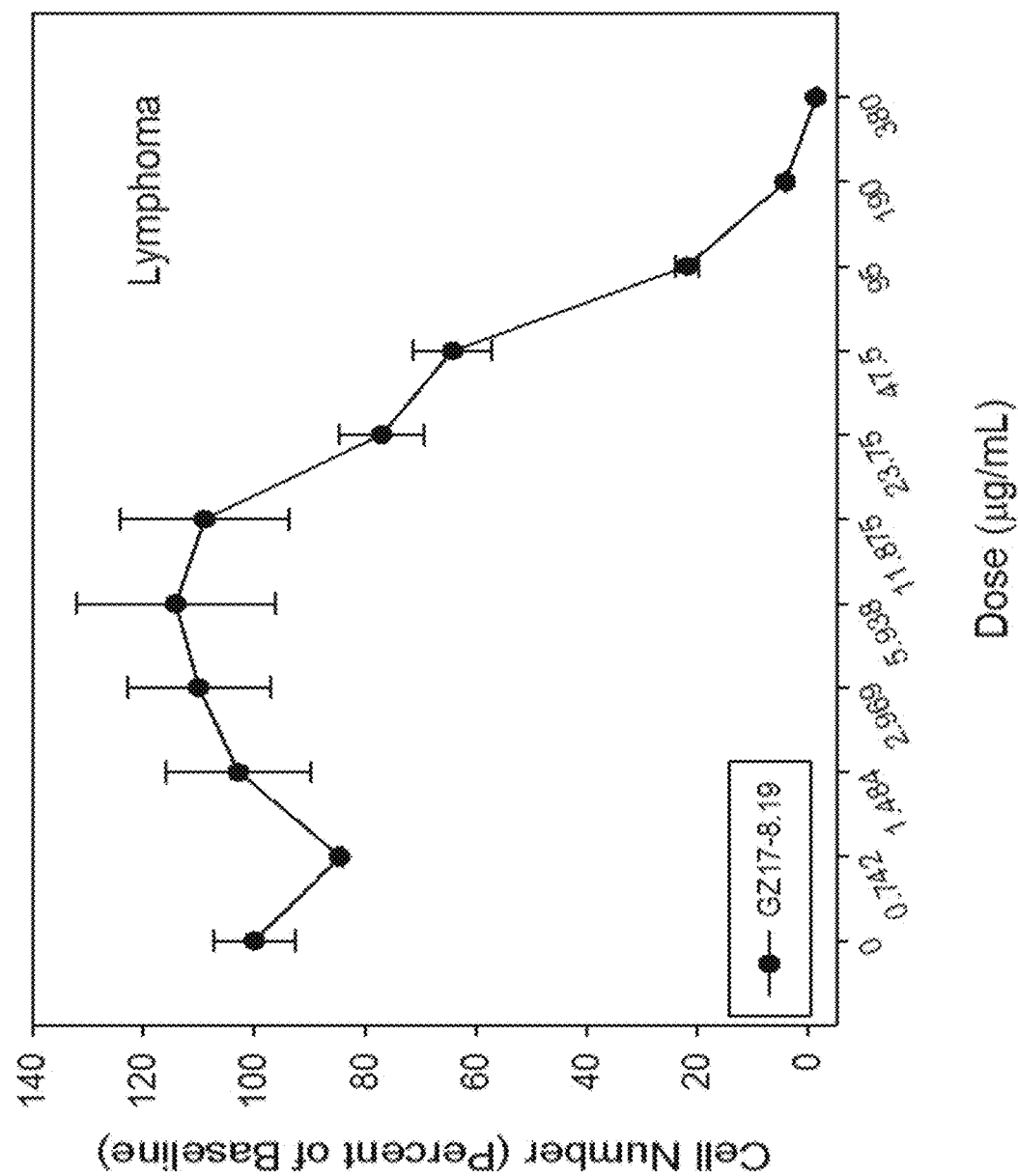
Figure 38A:
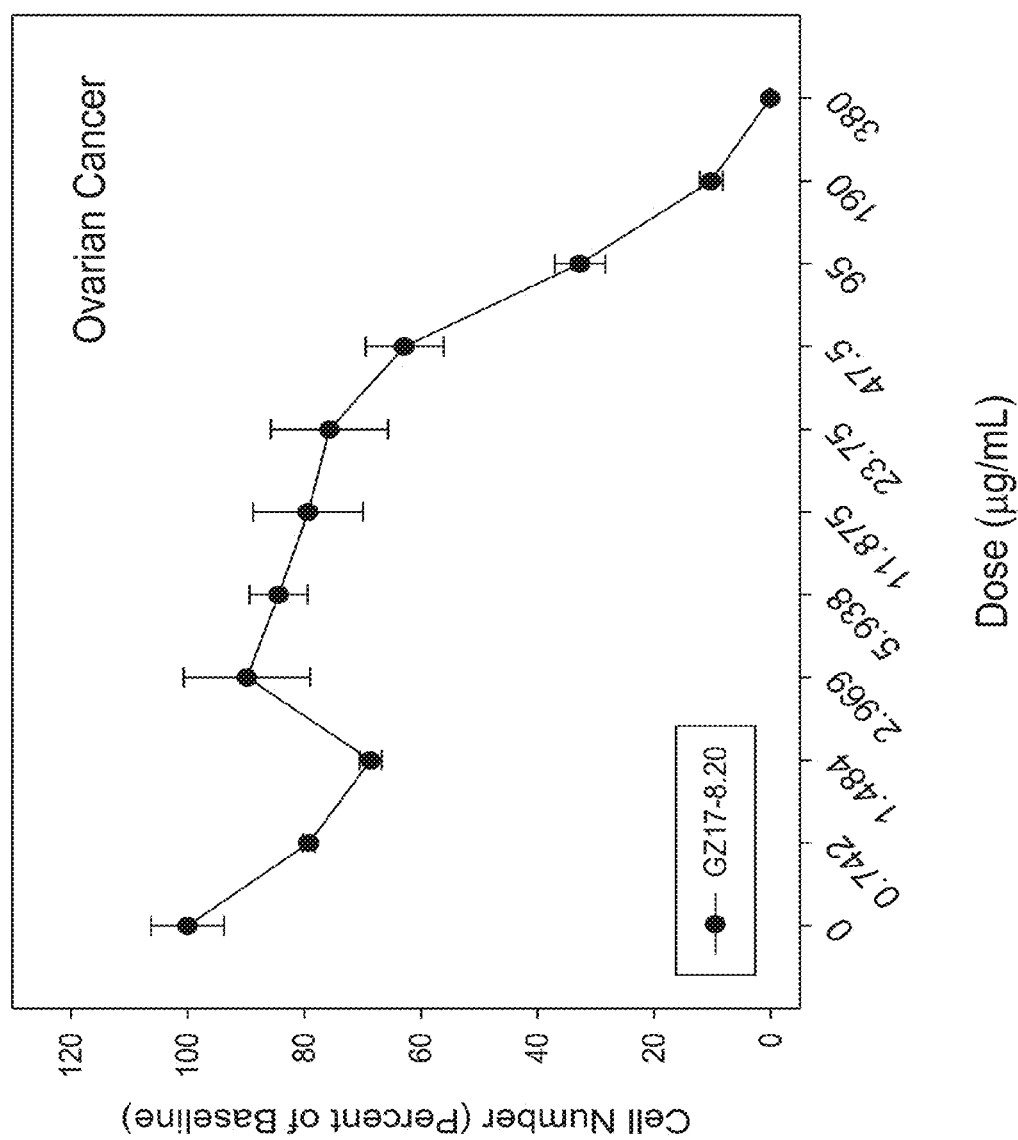
Figure 38B:
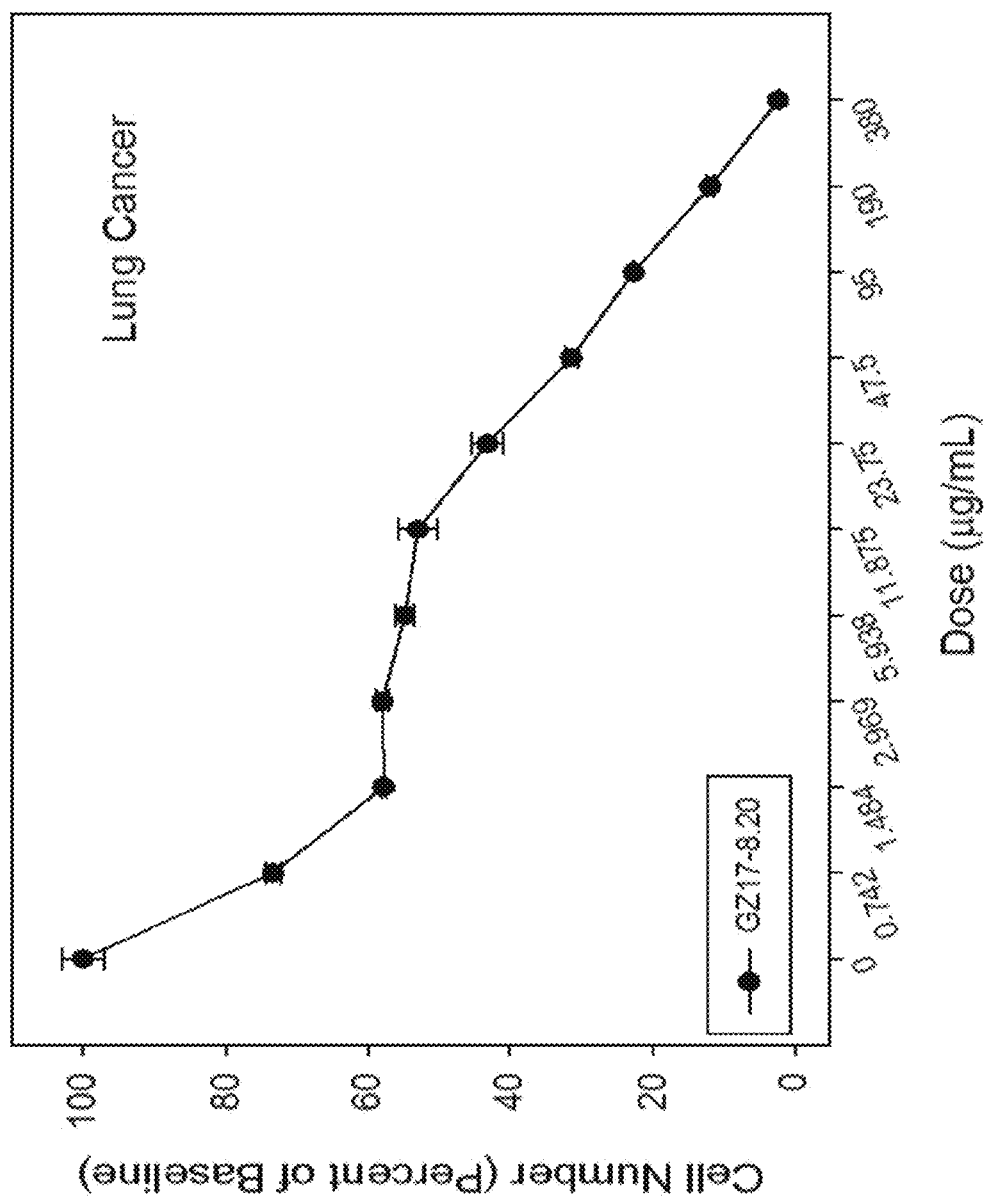
Figure 38C:
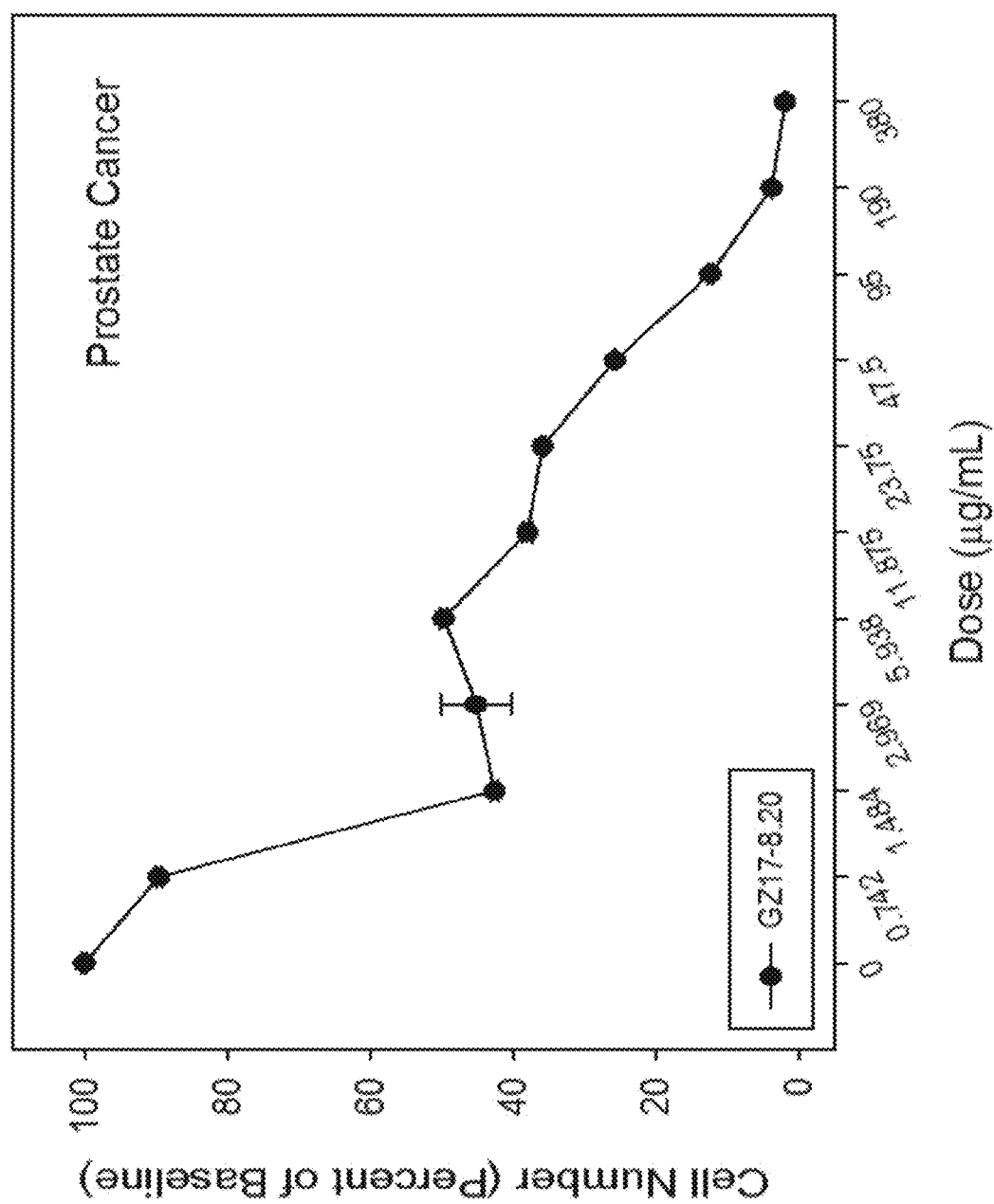
Figure 38D:
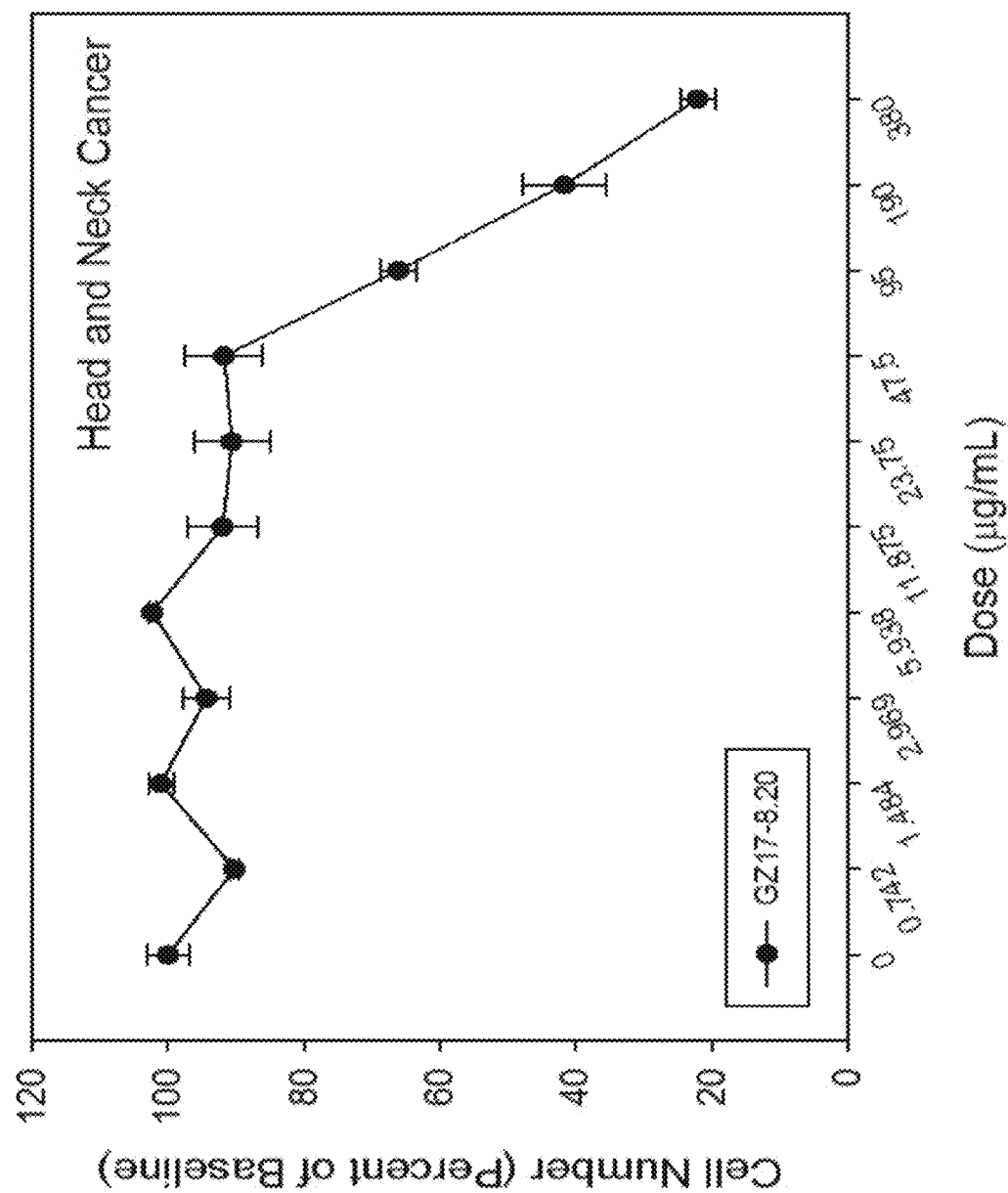
Figure 38E:
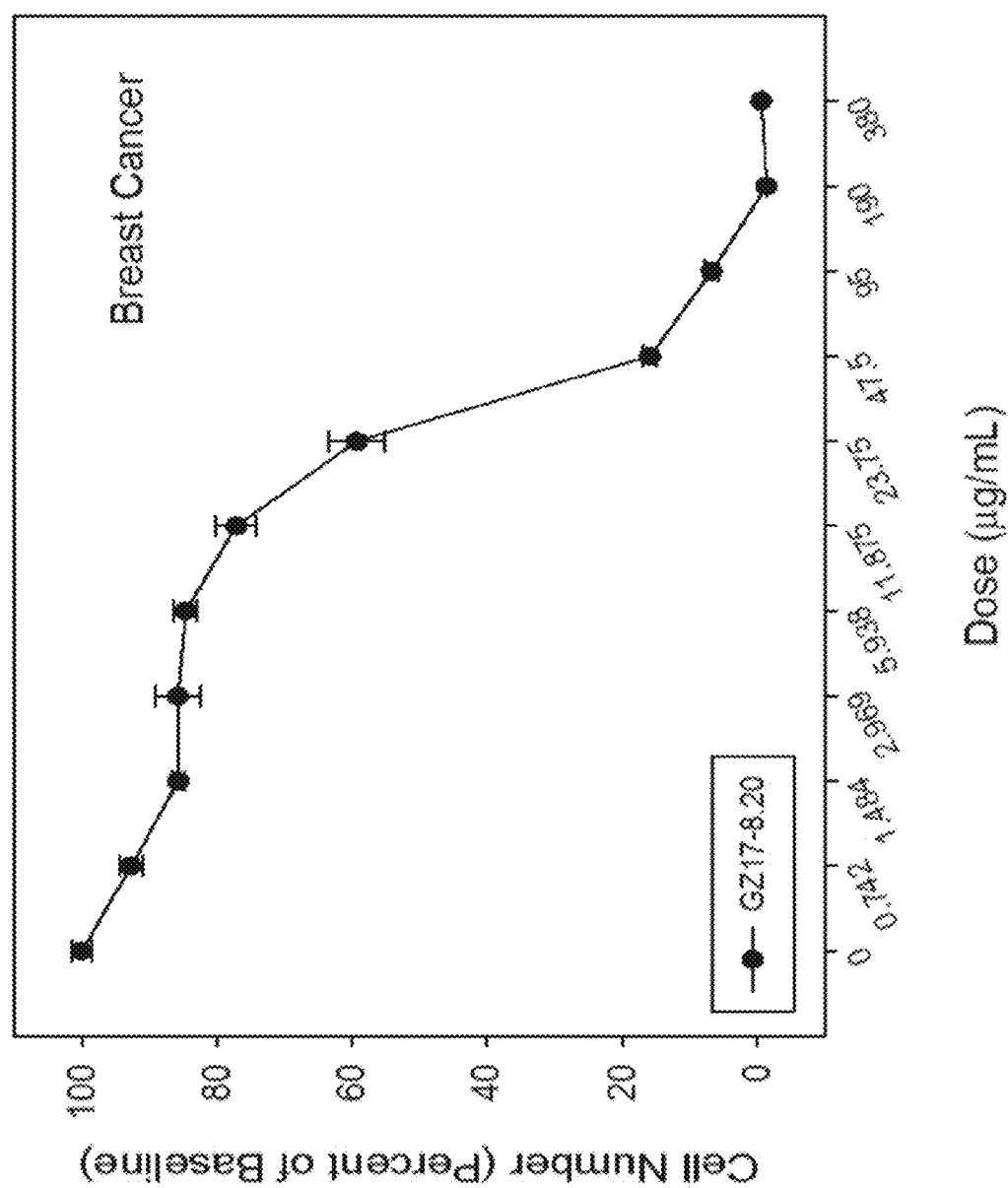
Figure 38F:
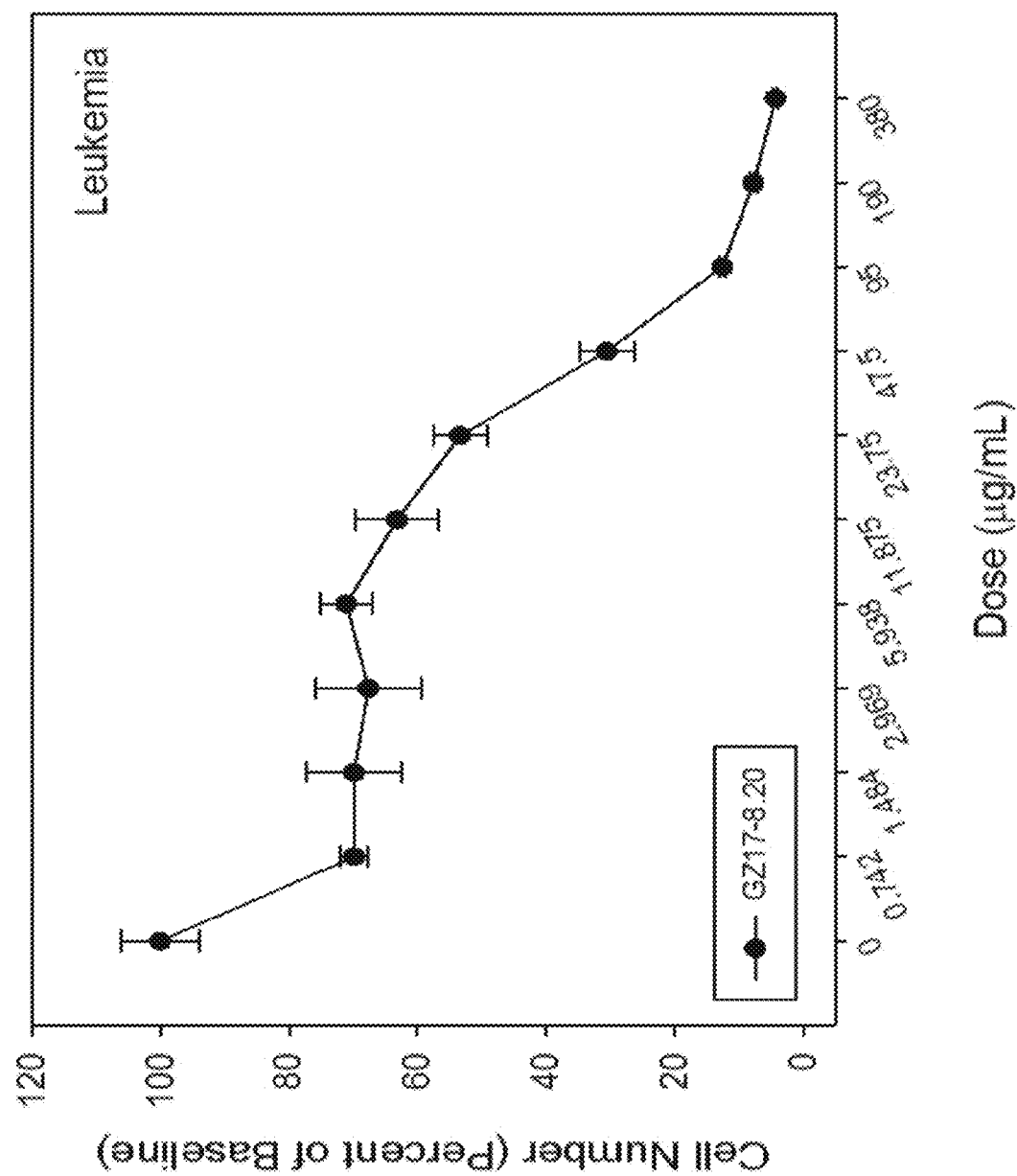
Figure 38G:
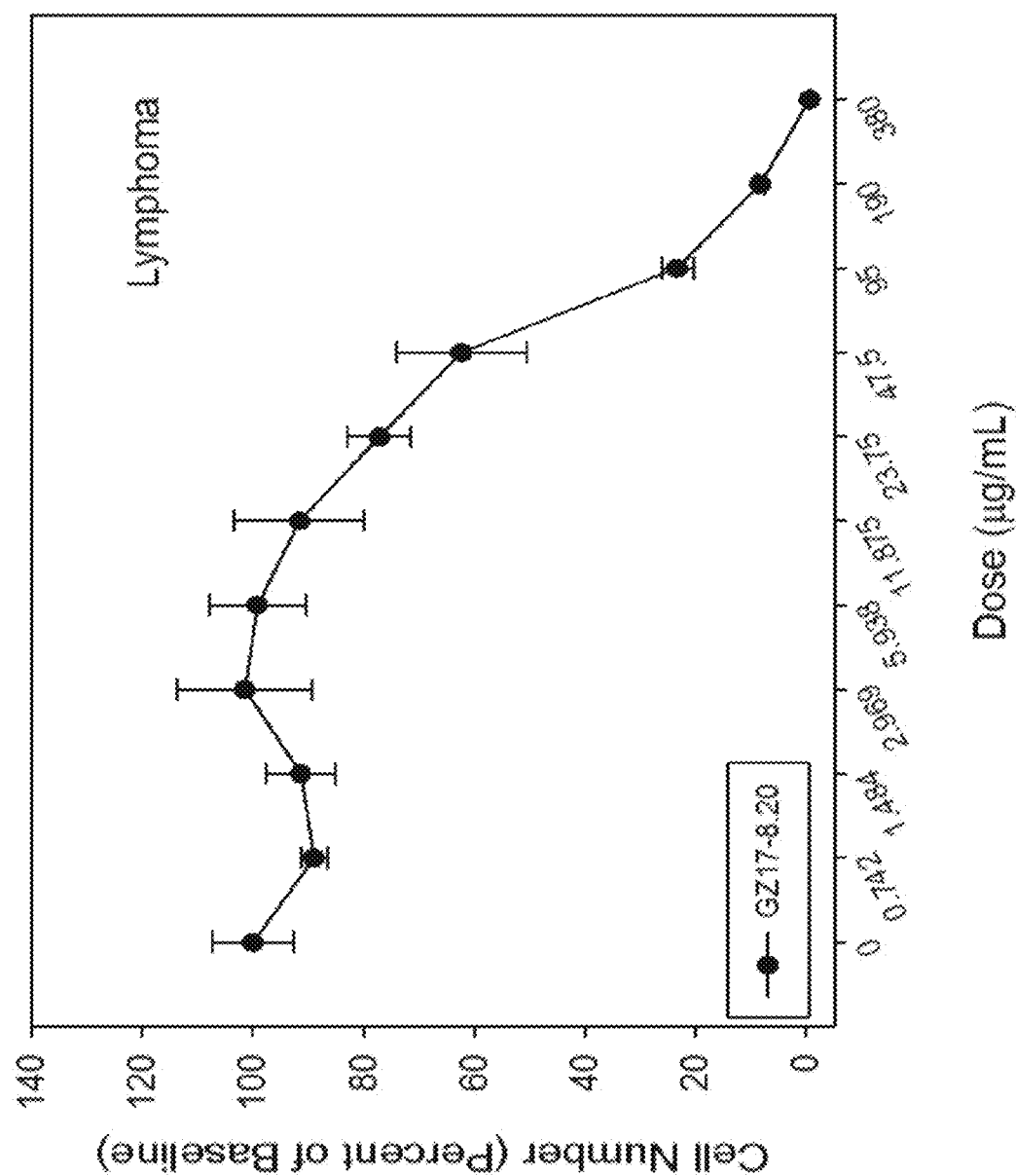
Figure 39A:
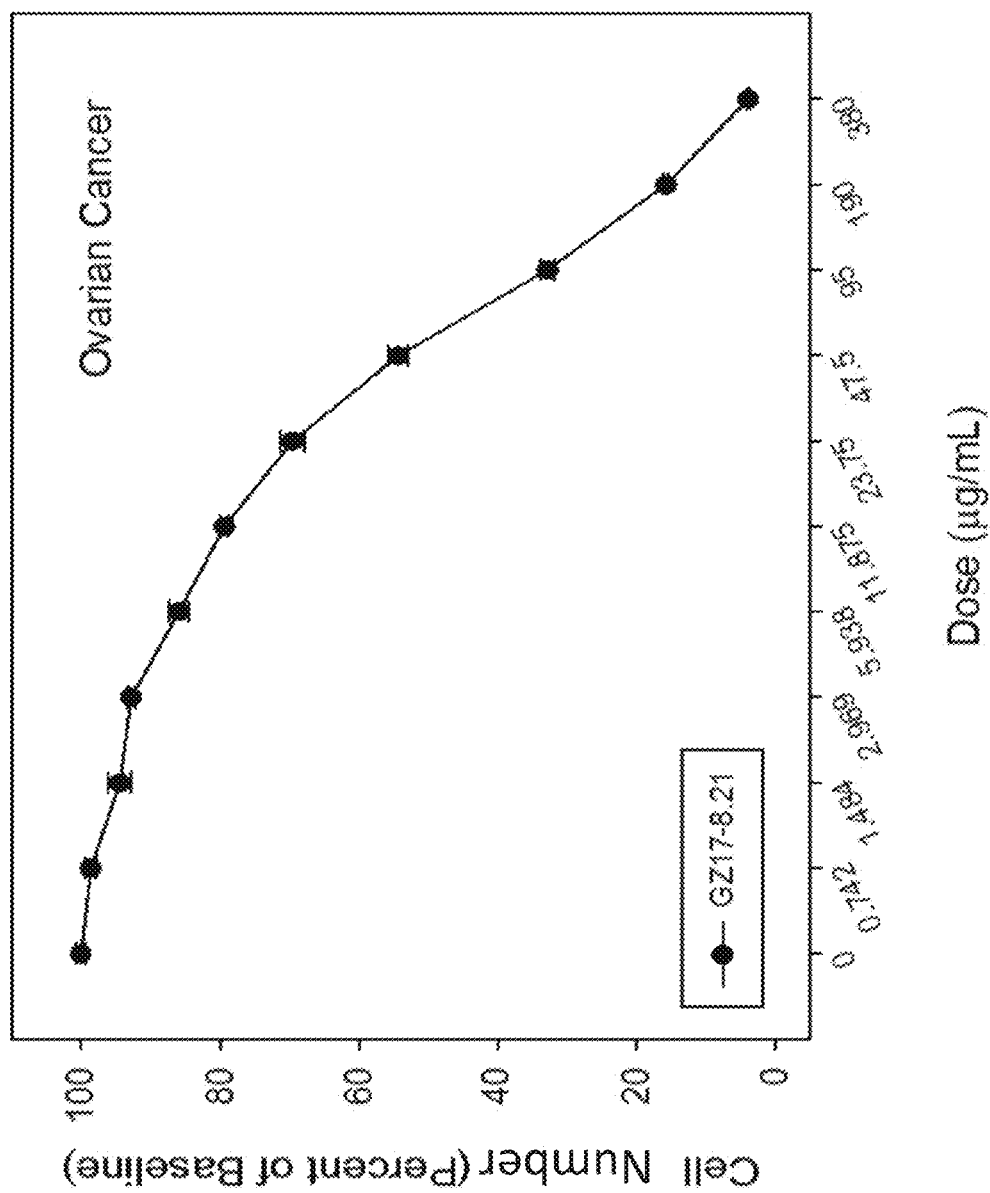
Figure 39B:
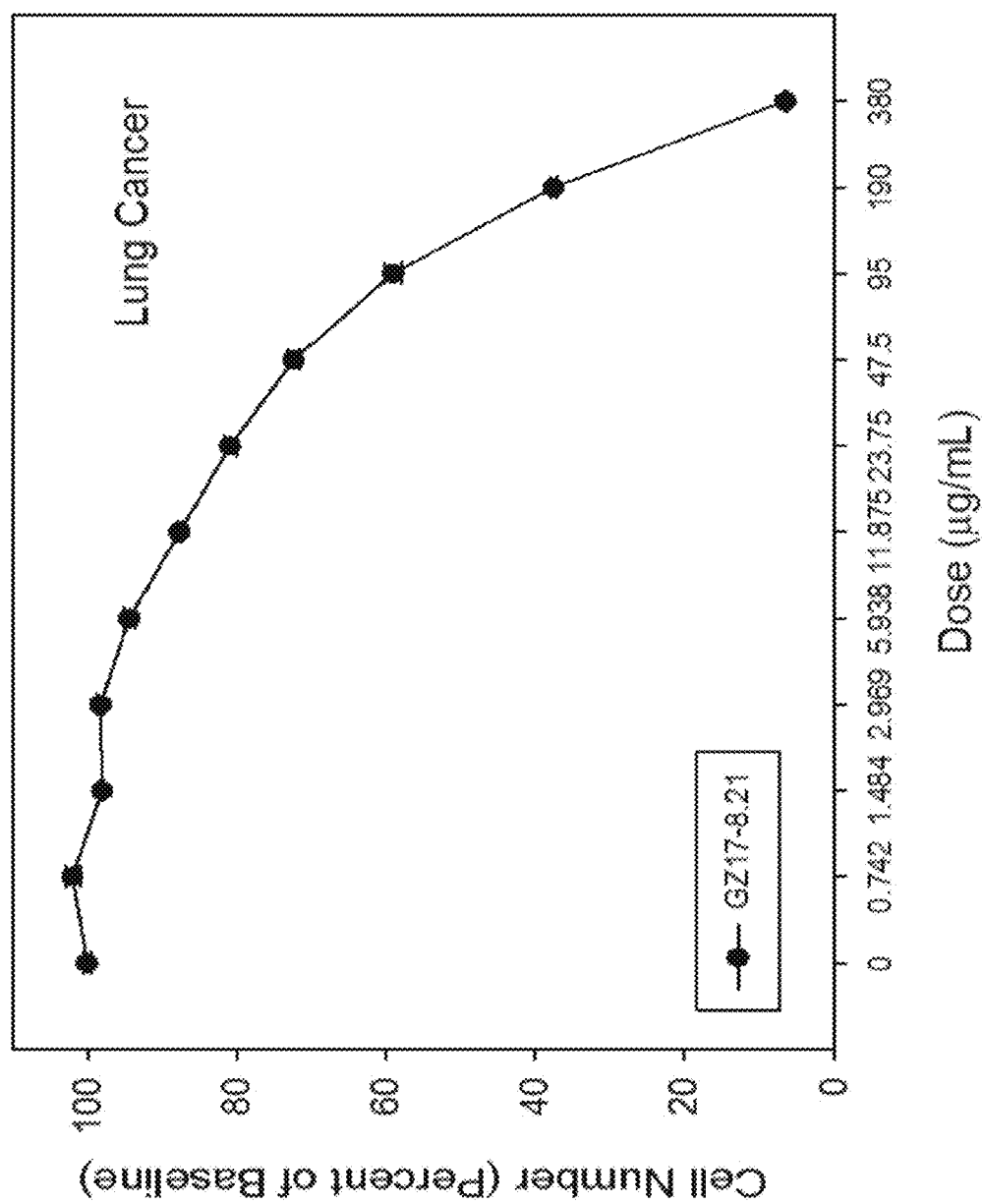
Figure 39C:
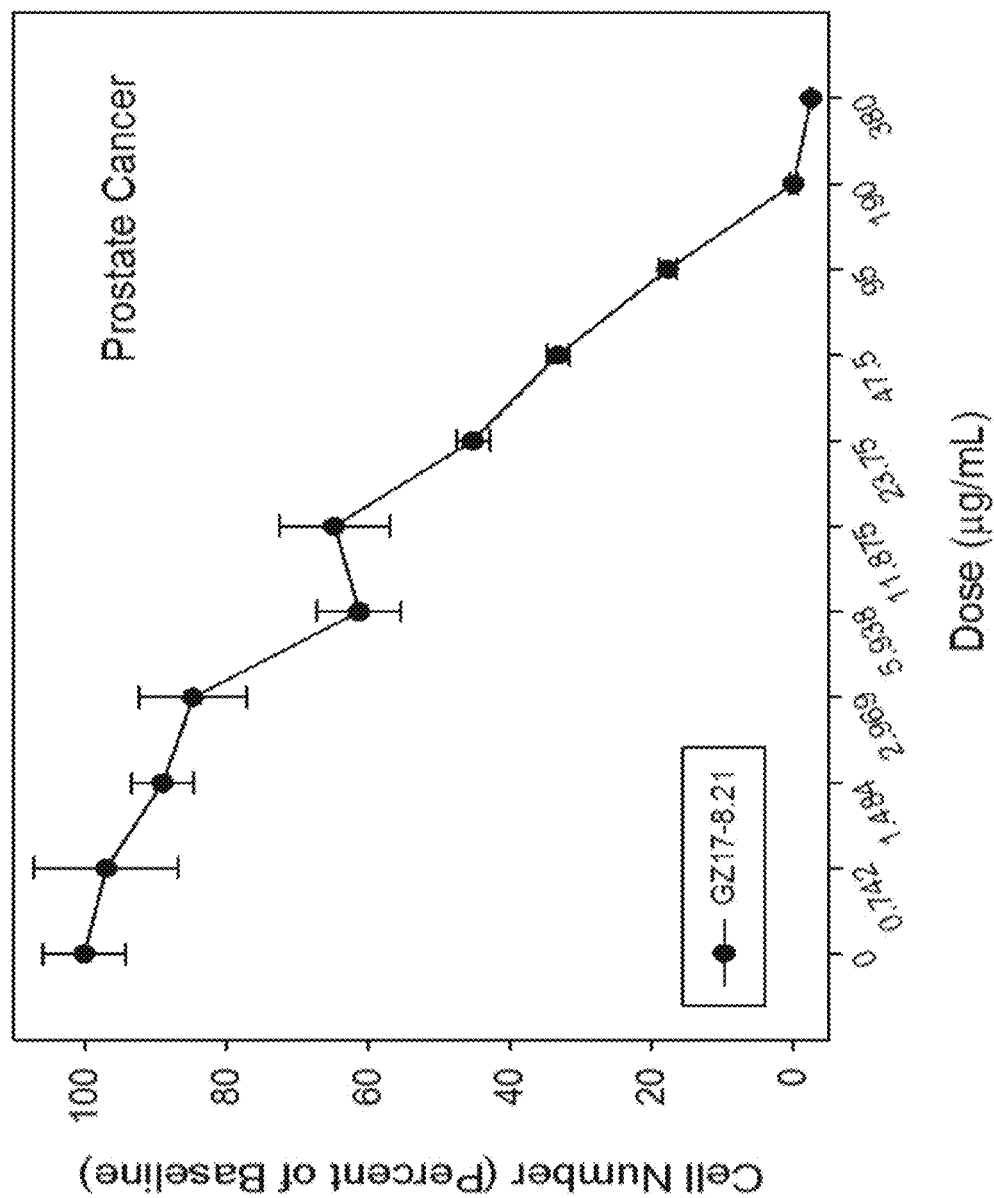
Figure 39D:
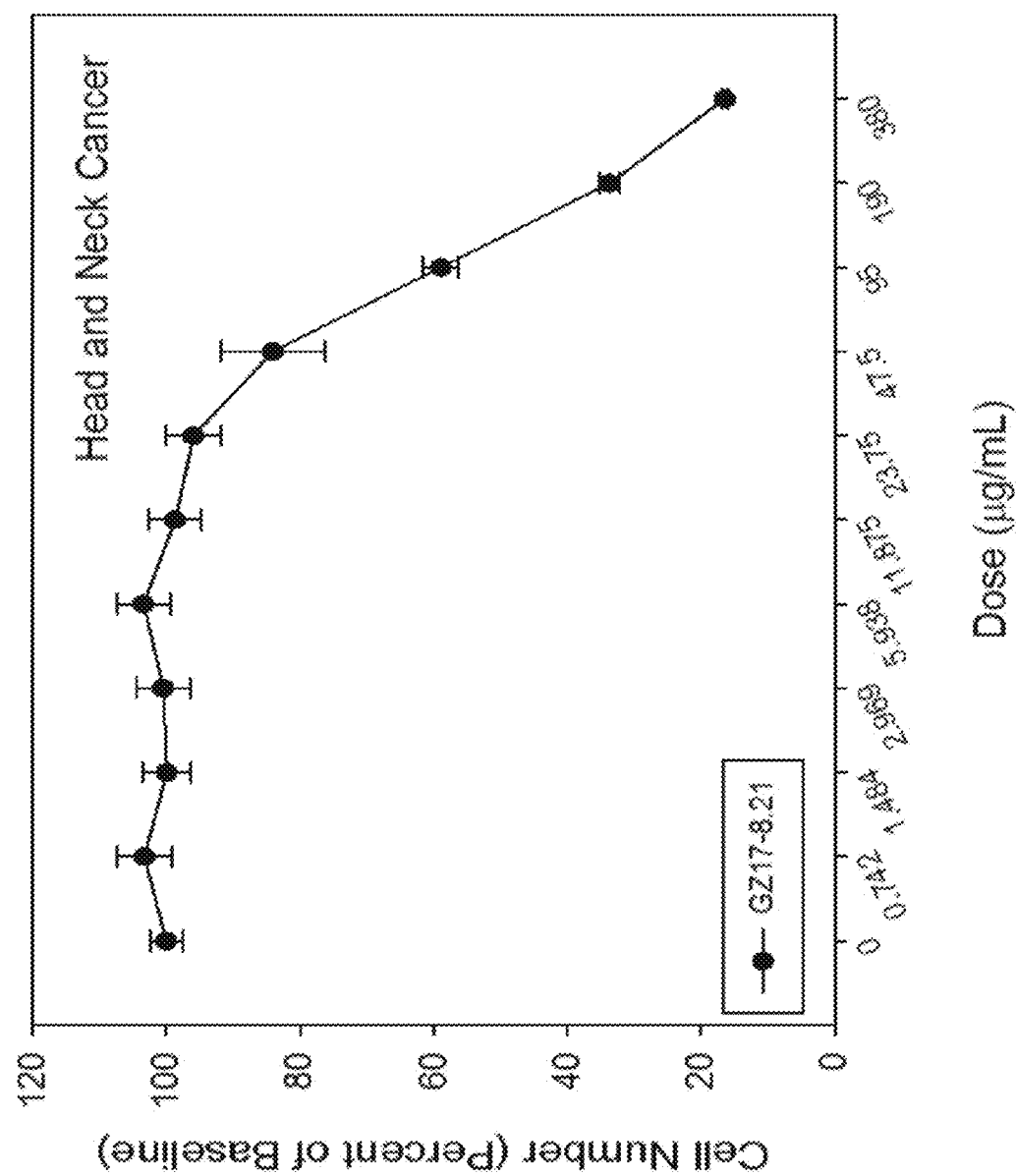
Figure 39E:
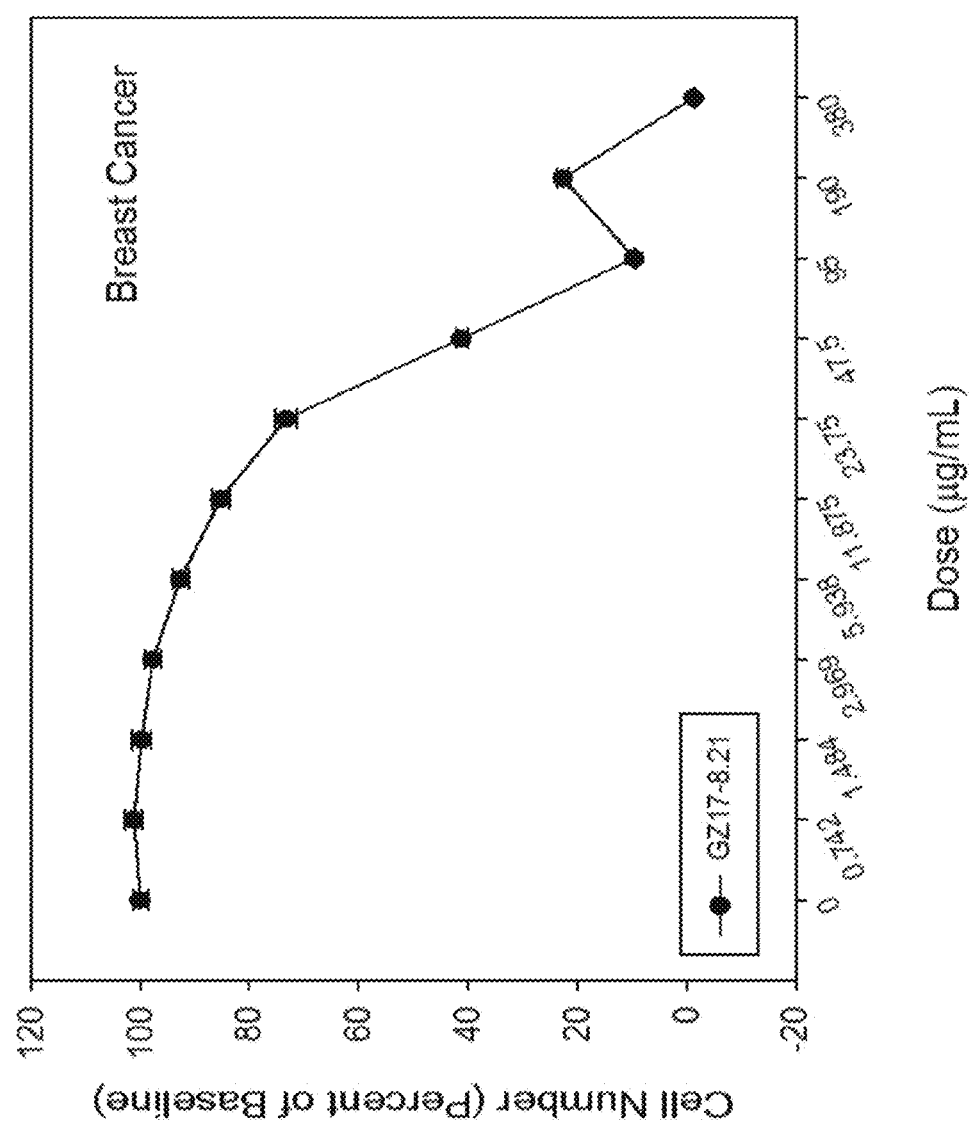
Figure 39F:
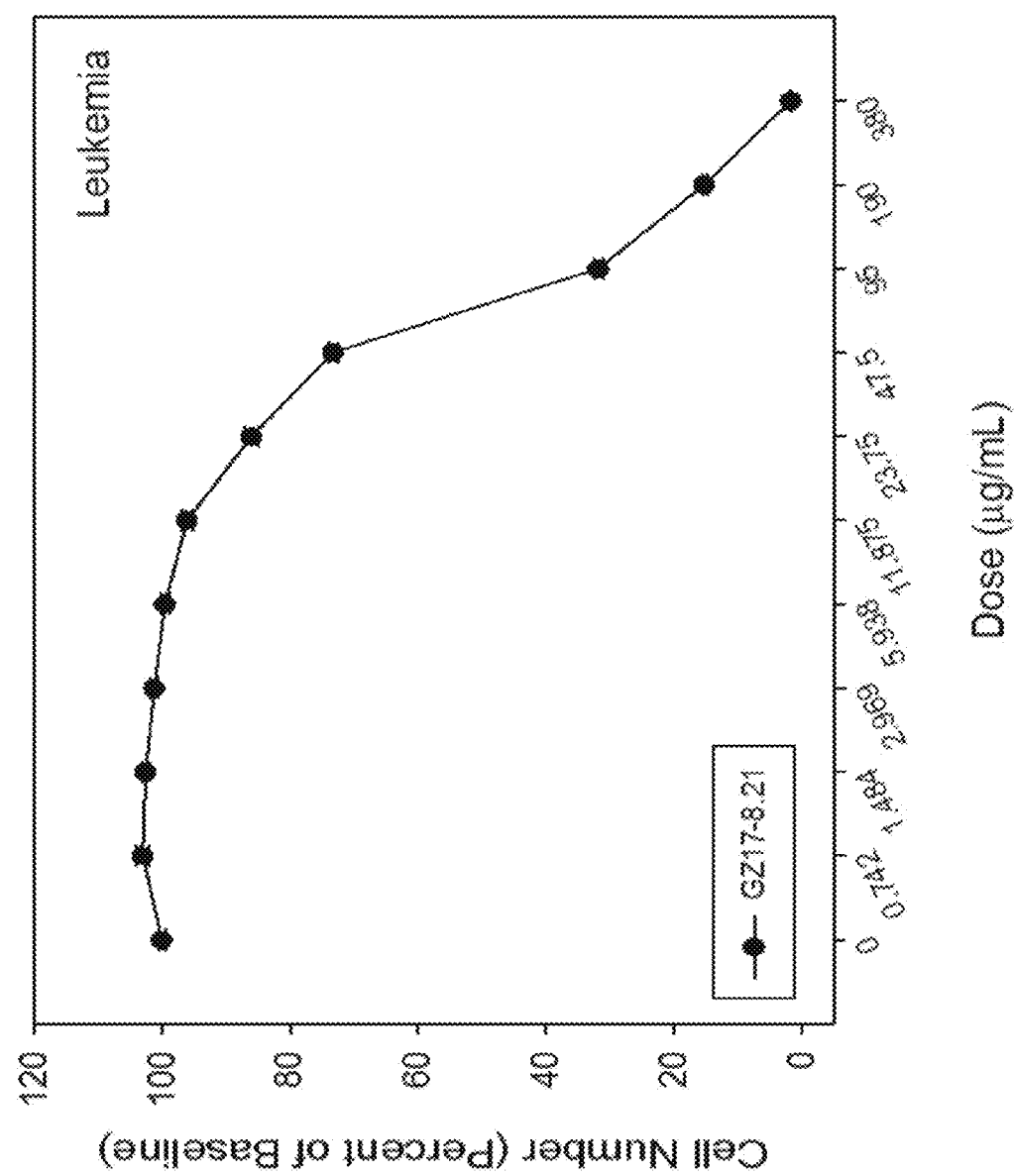
Figure 39G:
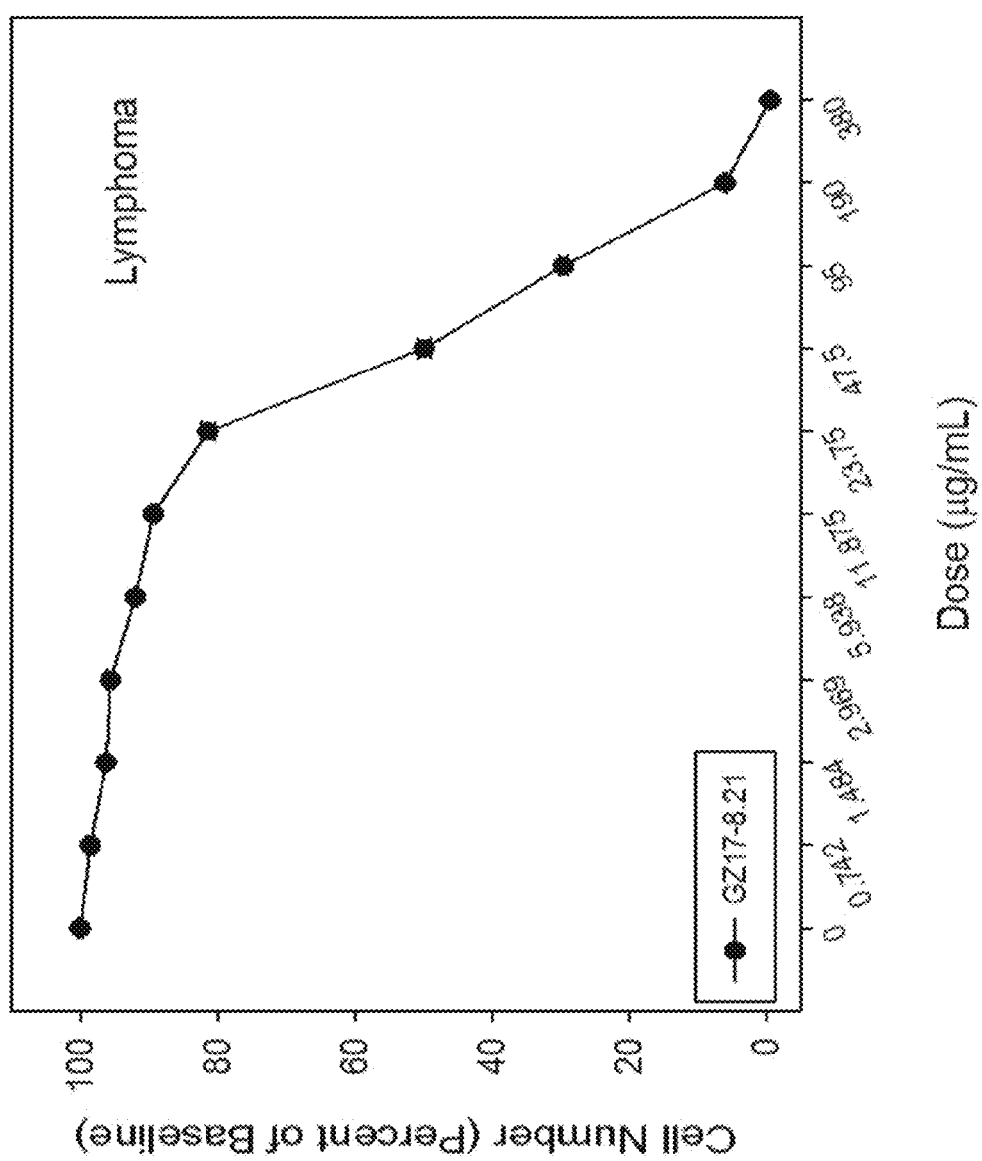
Figure 40A:
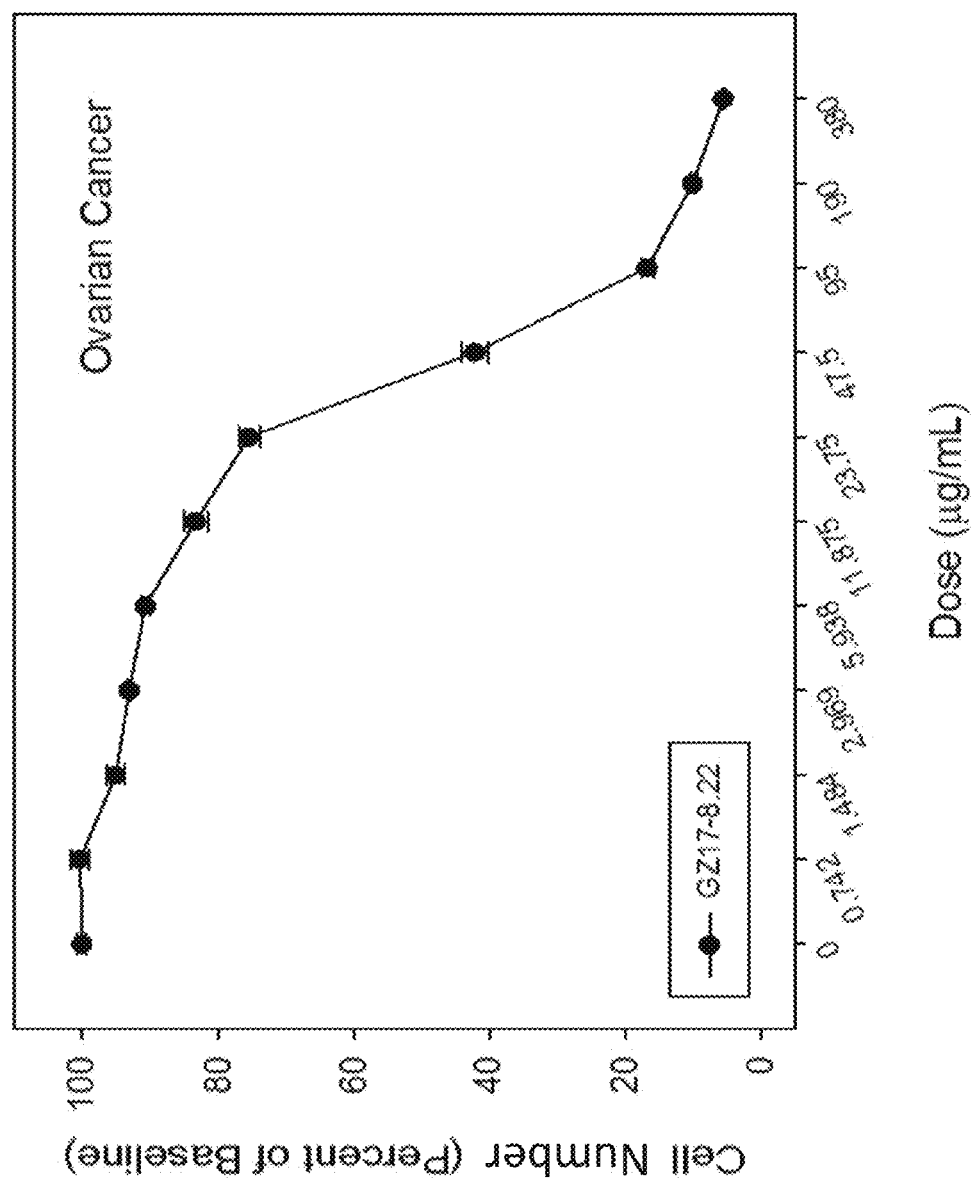
Figure 40B:
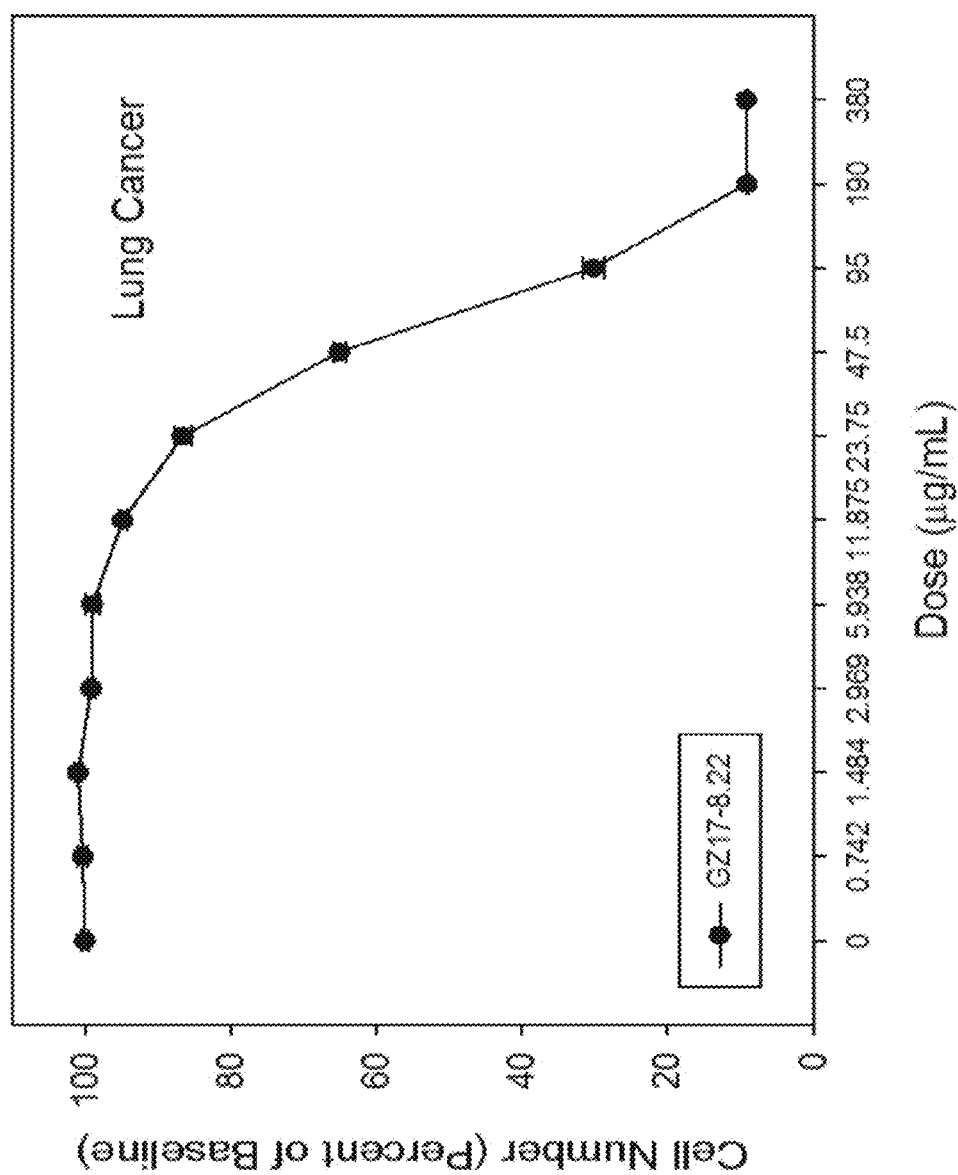
Figure 40C:
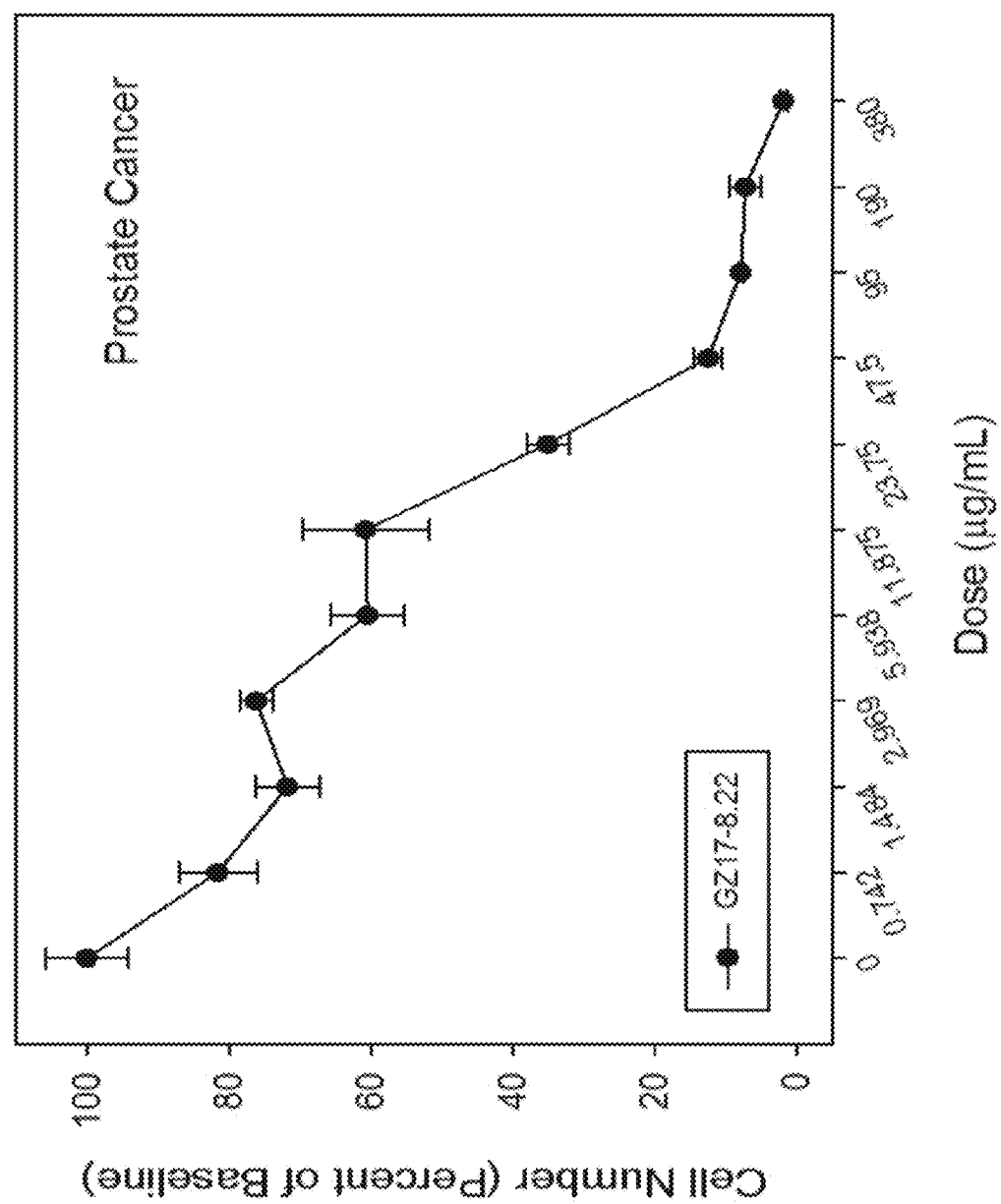
Figure 40D:
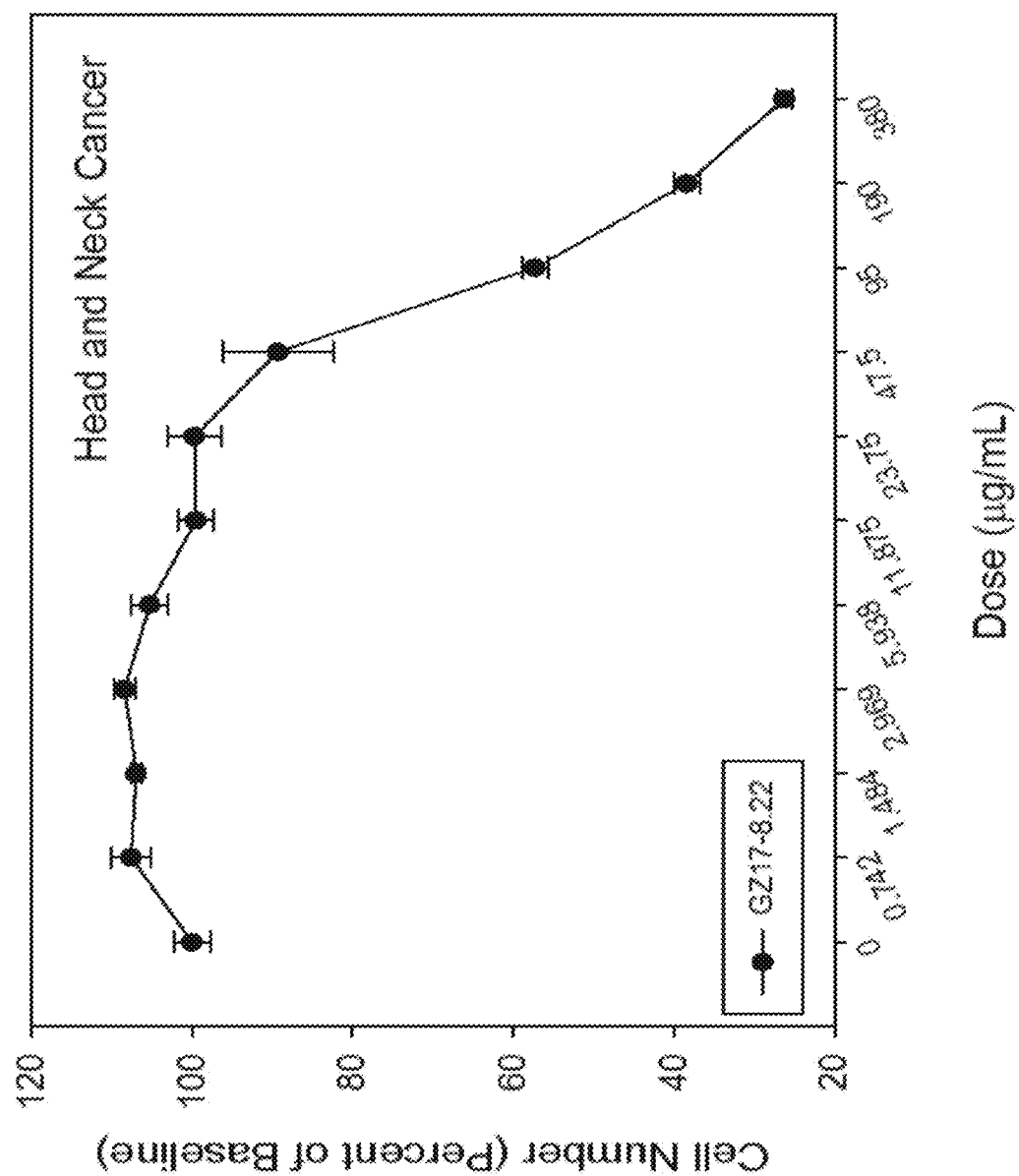
Figure 40E:
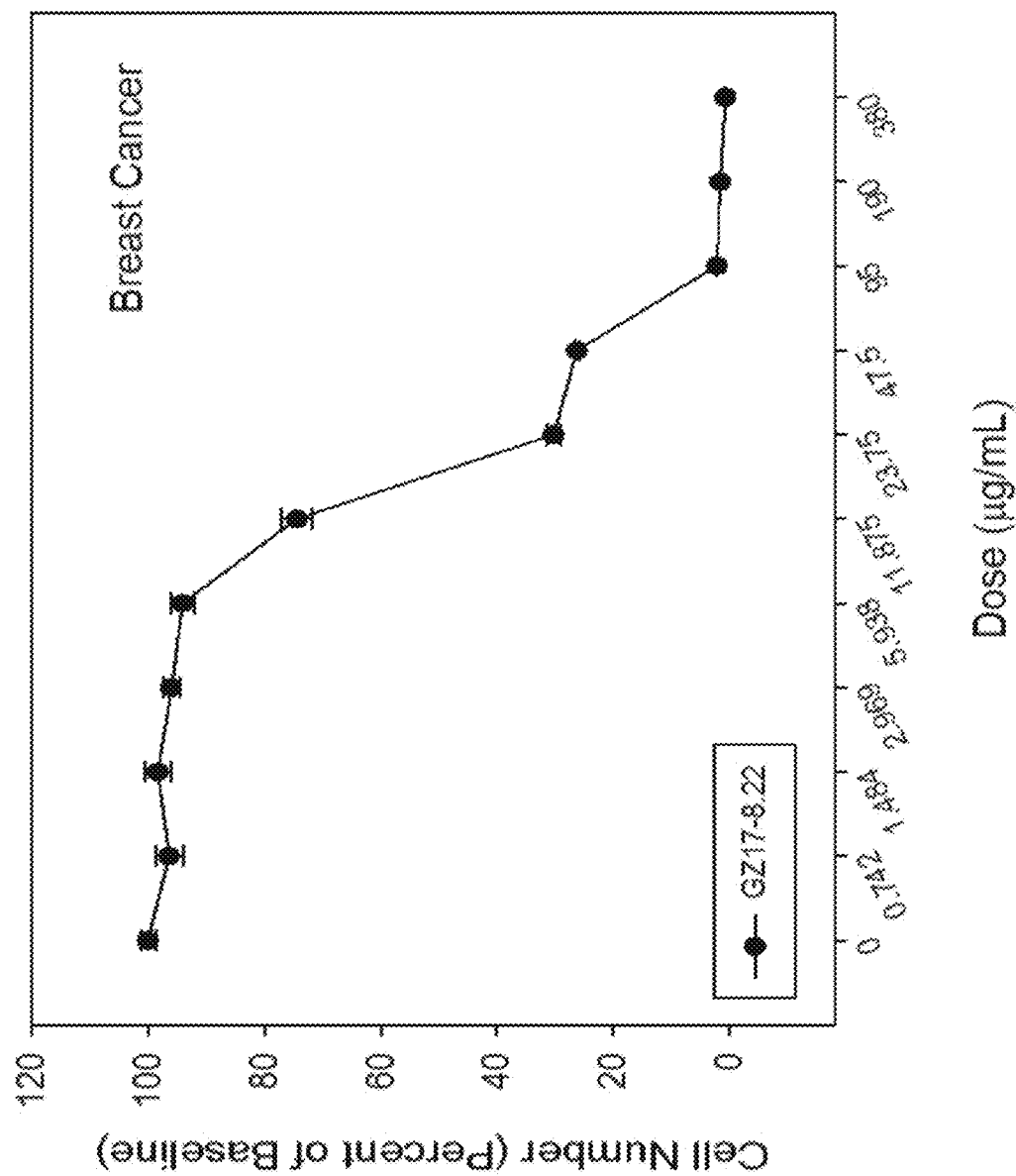
Figure 40F:
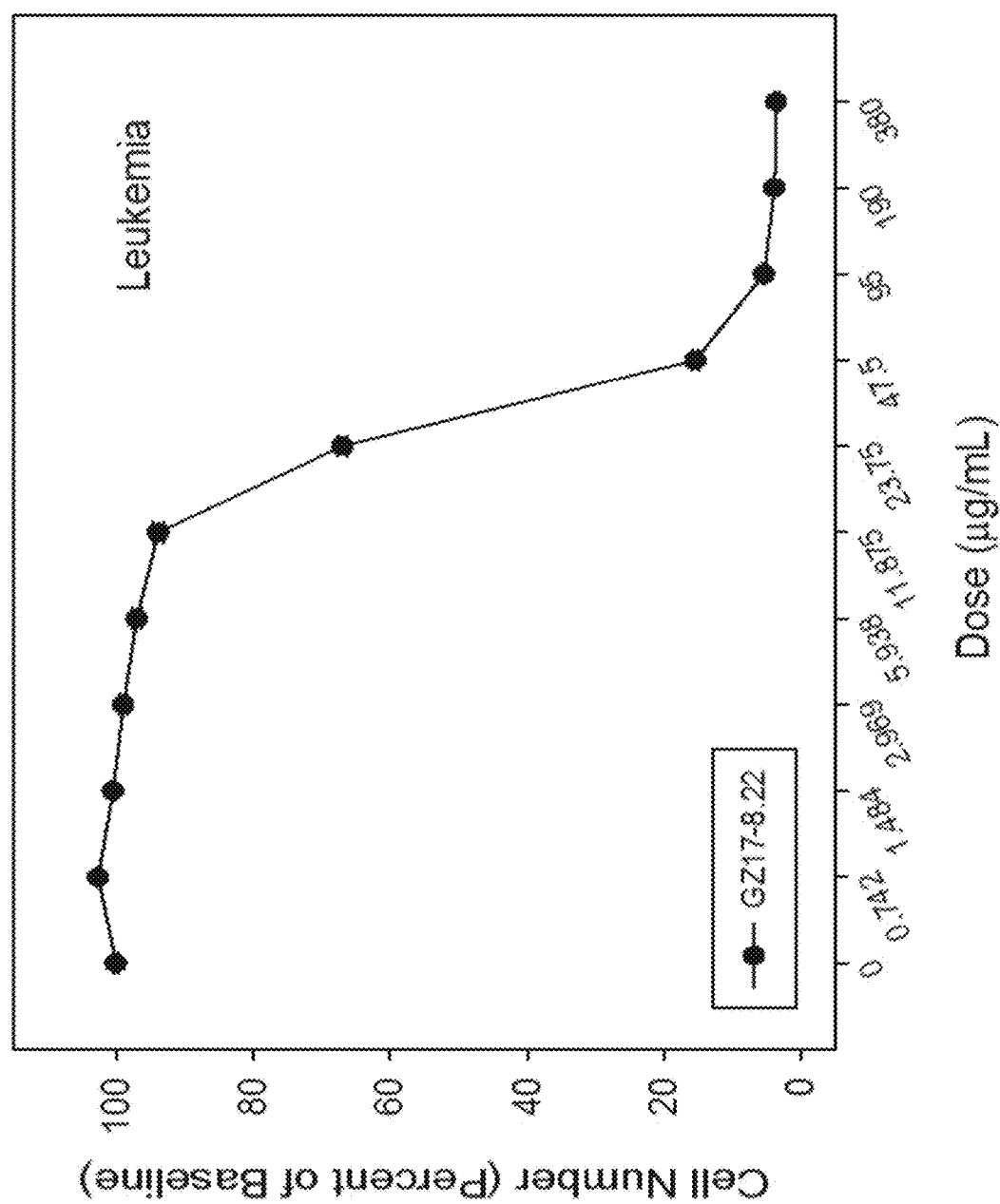
Figure 40G:
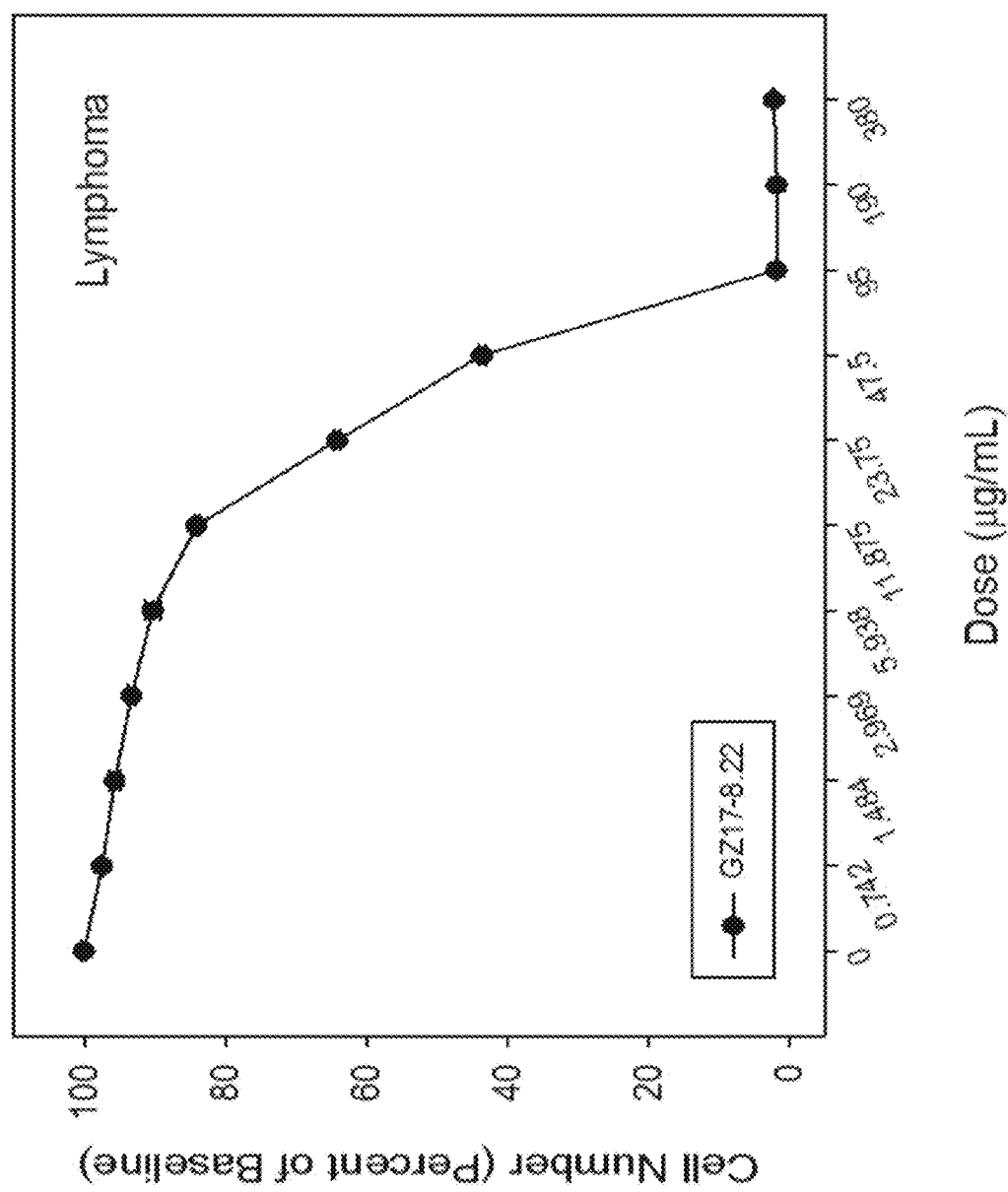
Figure 41A:
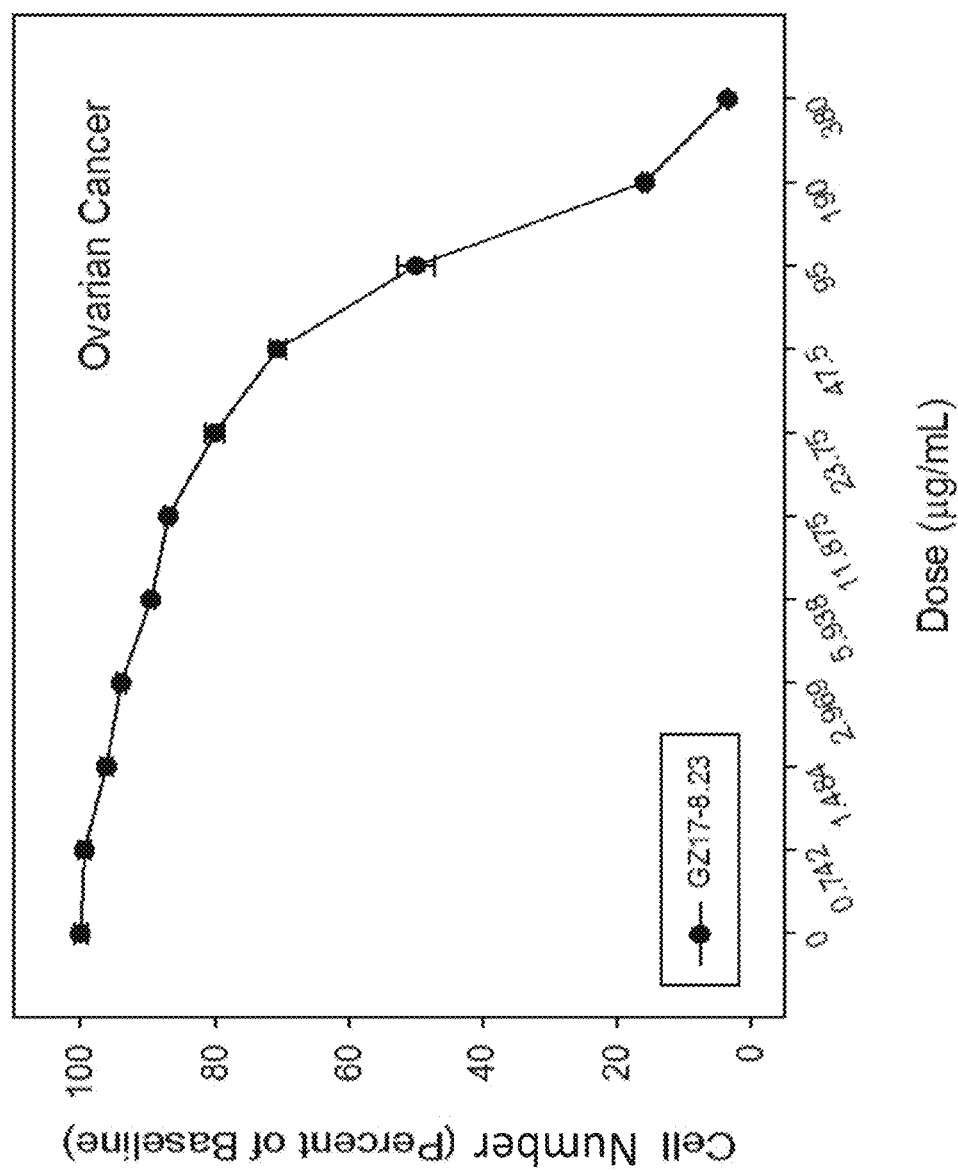
Figure 41B:
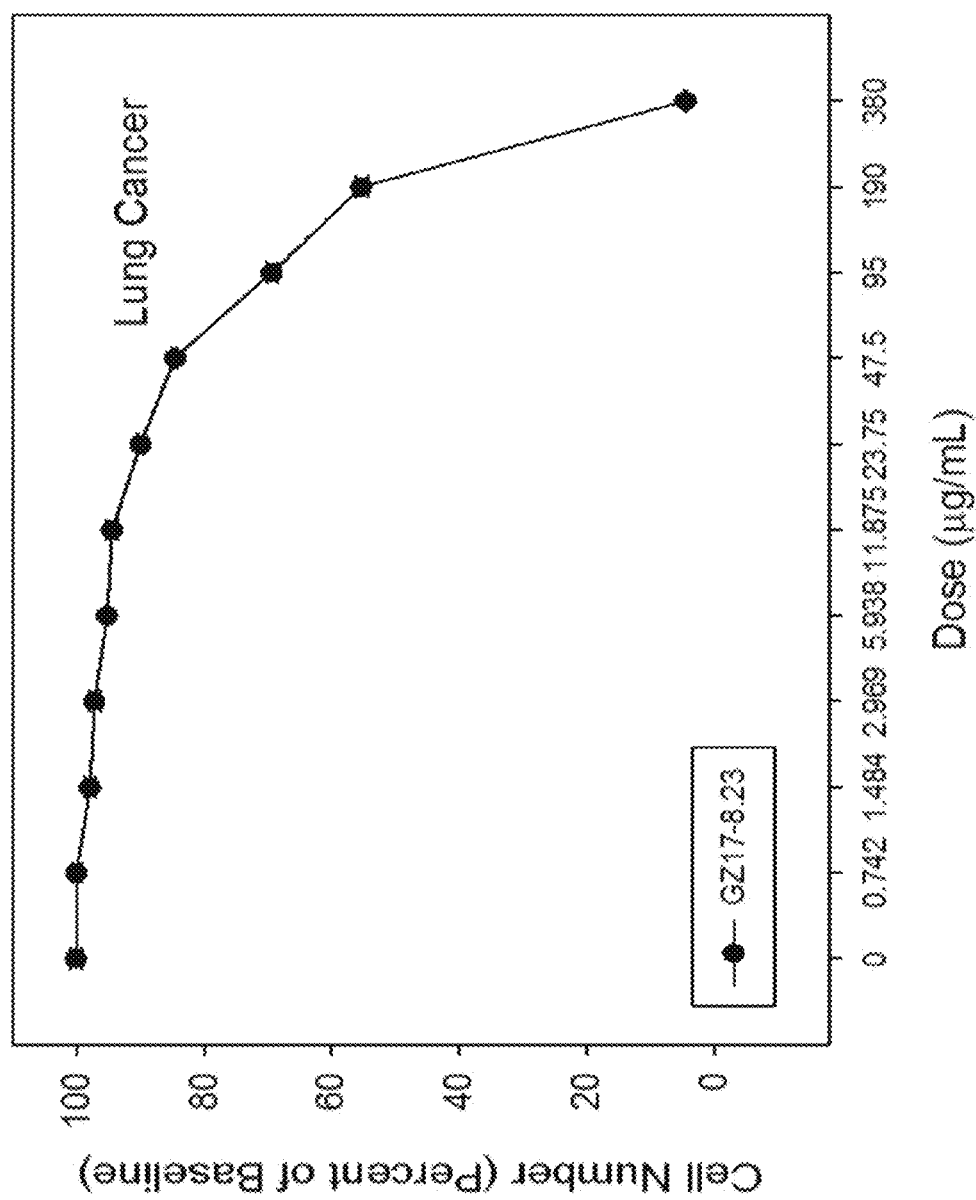
Figure 41C:
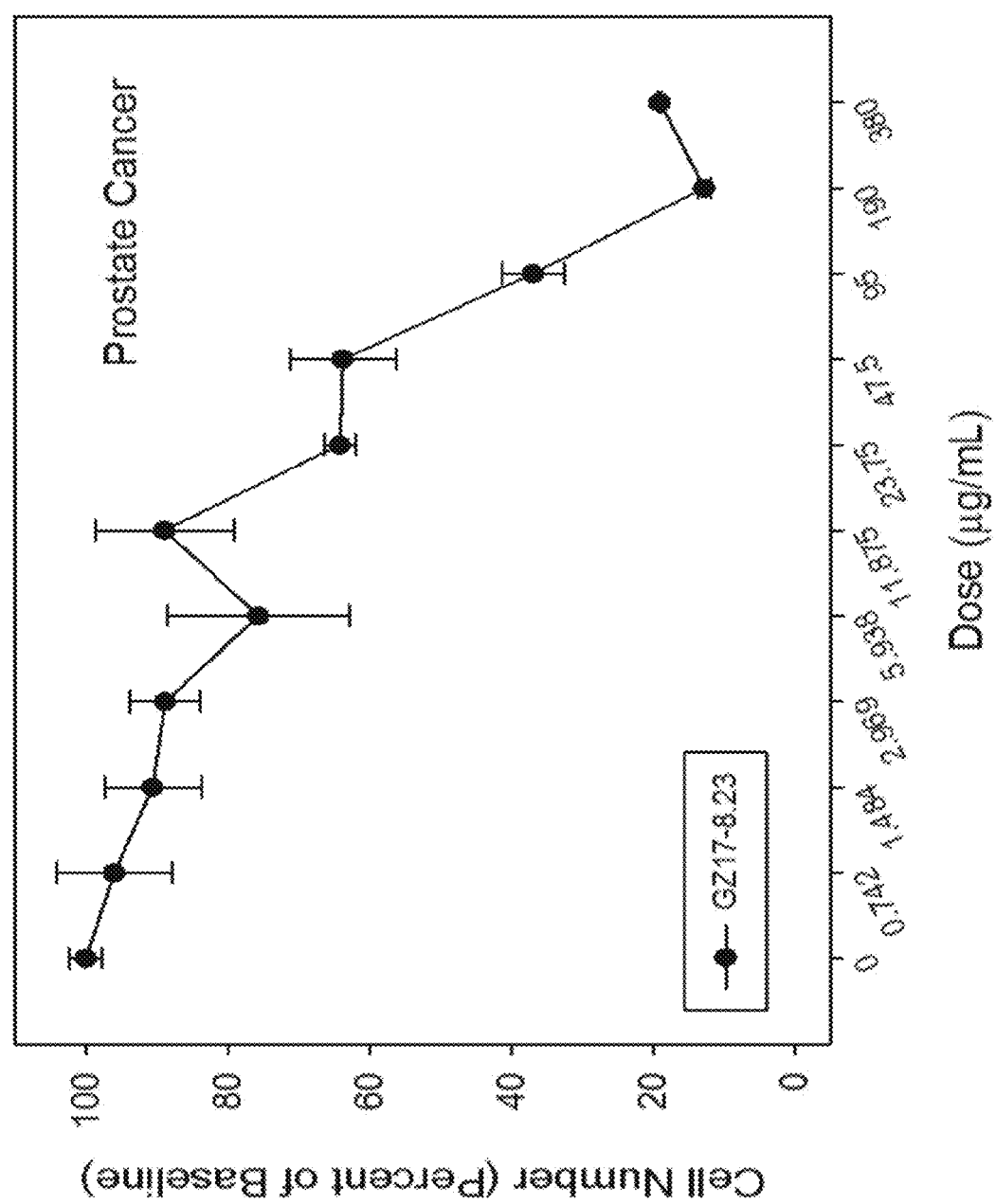
Figure 41D:
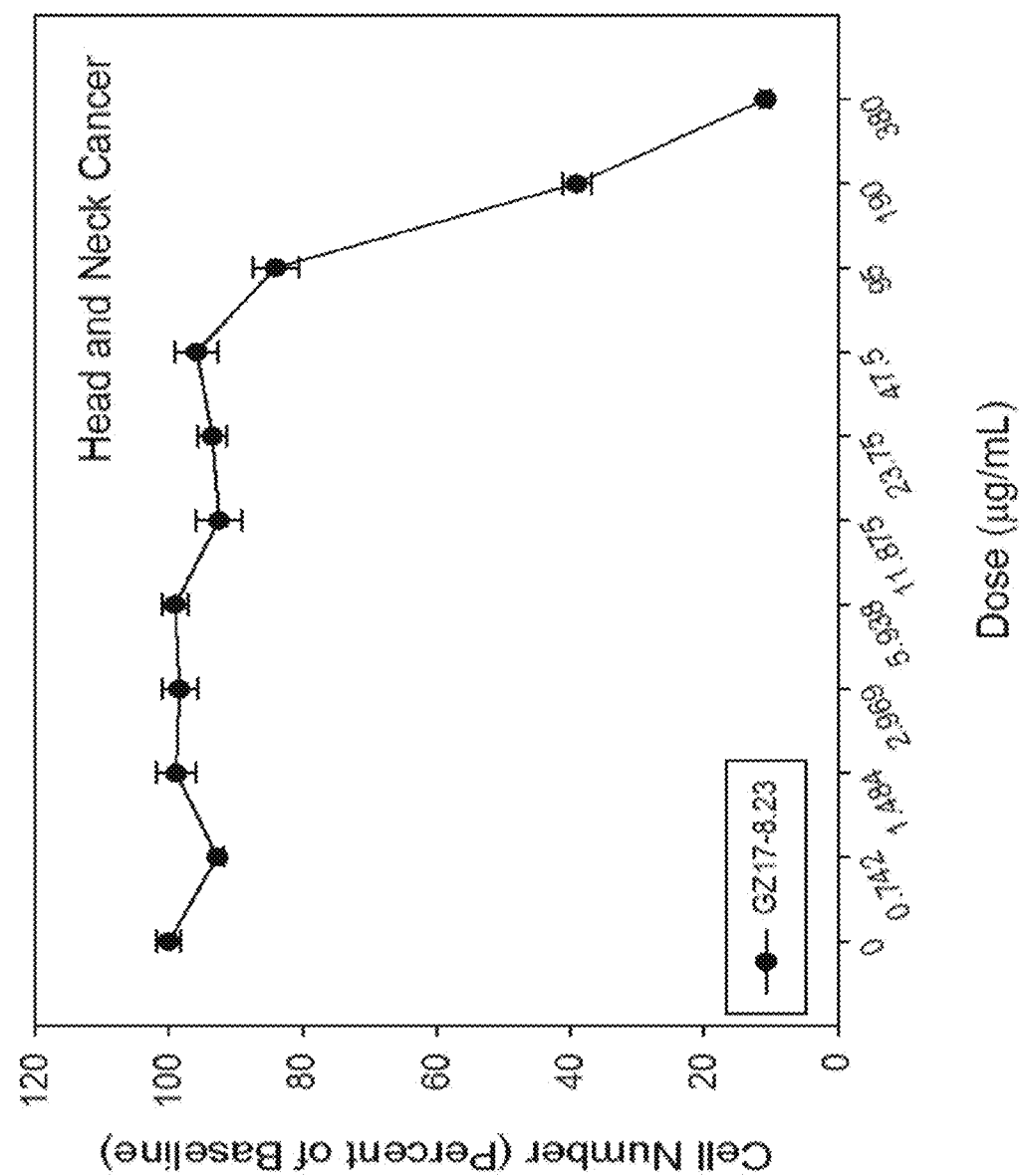
Figure 41E:
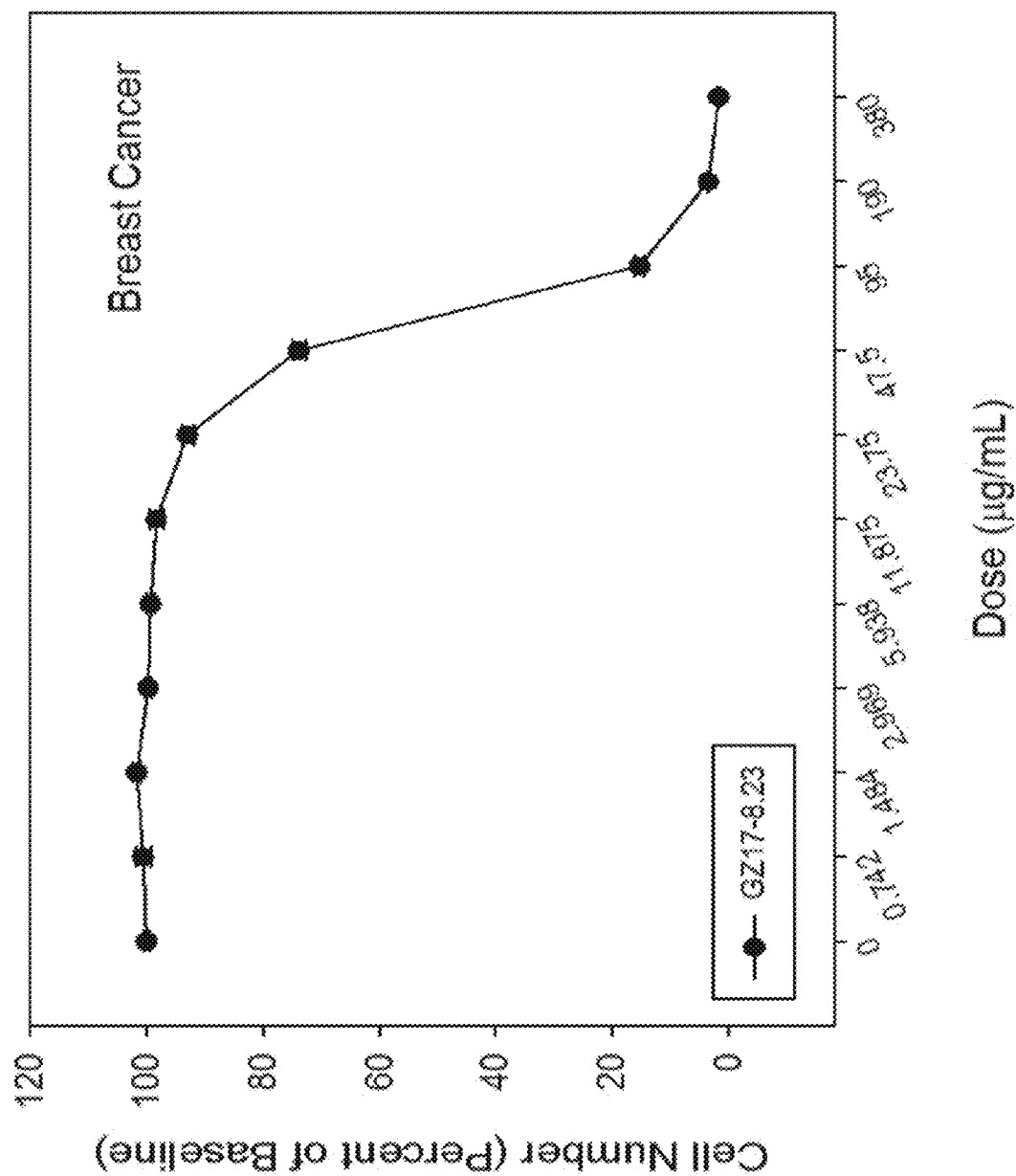
Figure 41F:
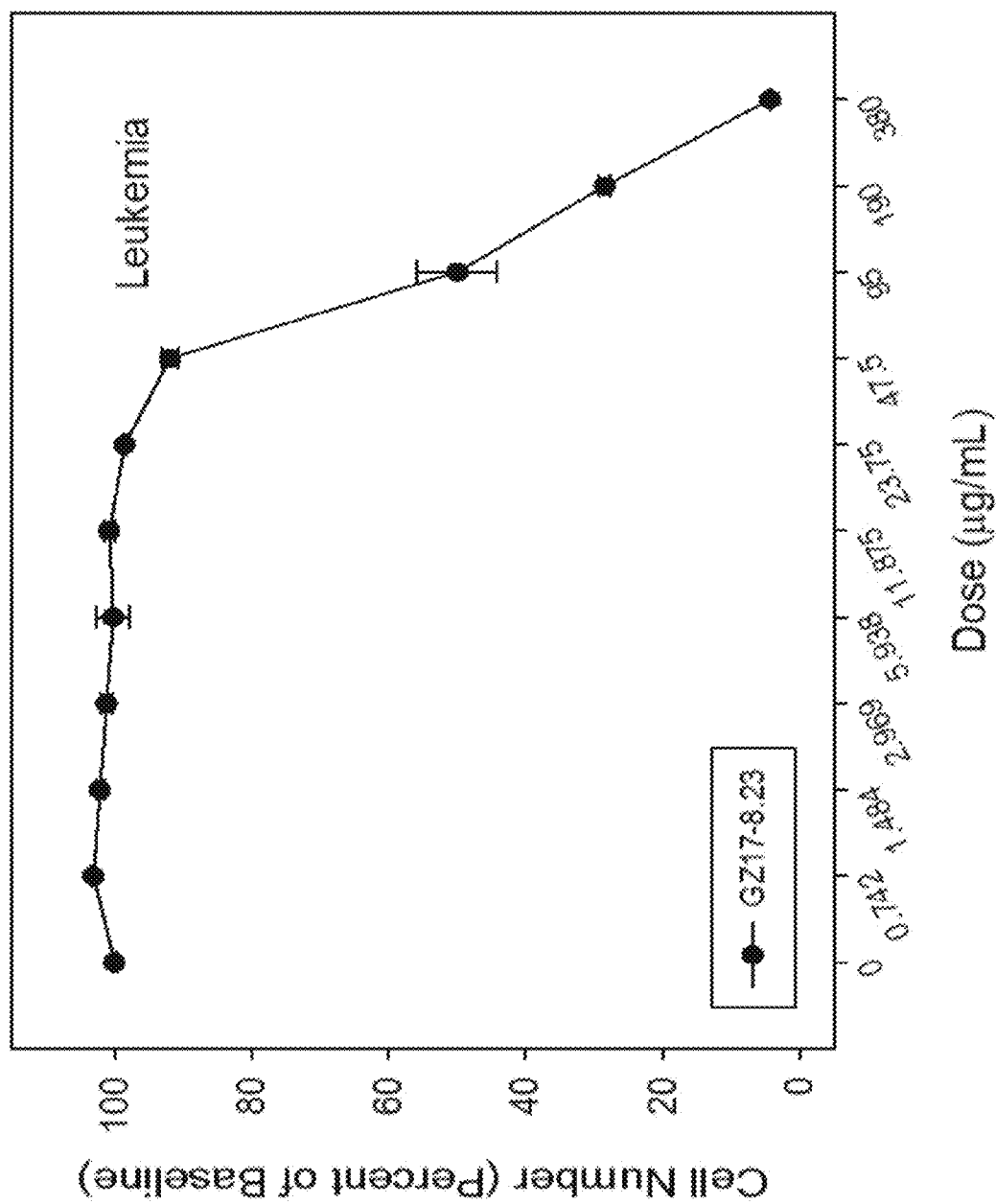
Figure 41G:
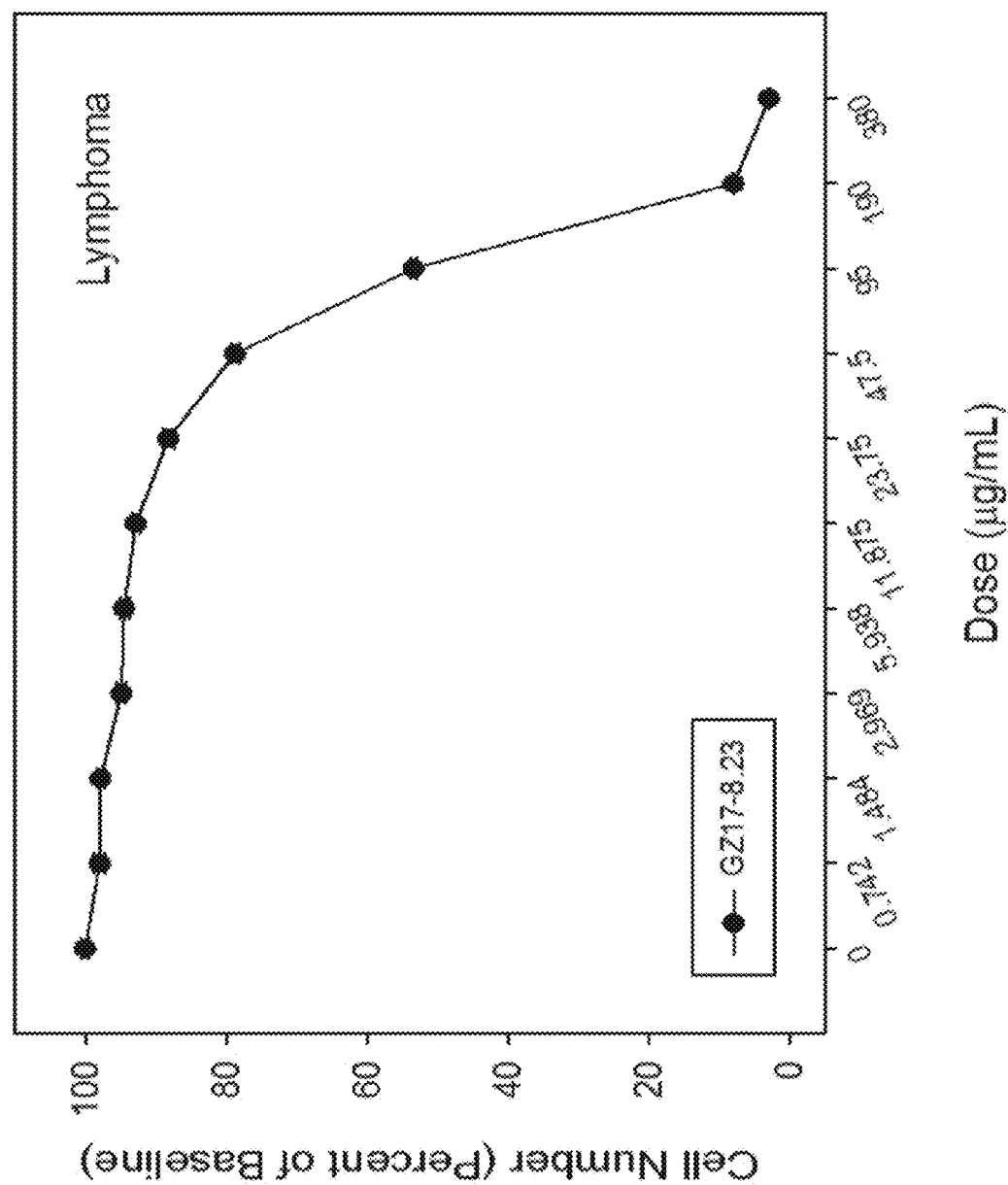
Figure 42A:
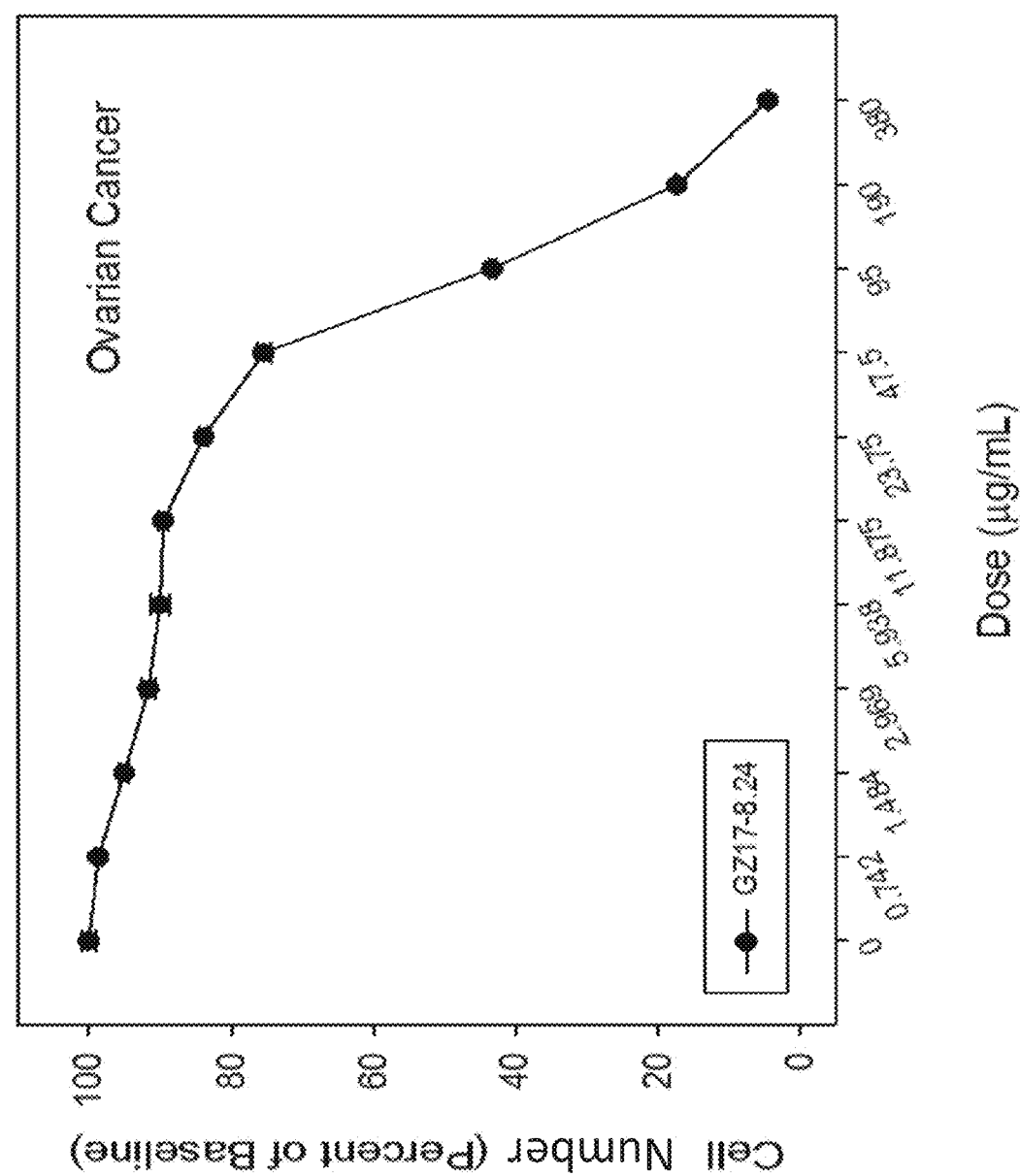
Figure 42B:
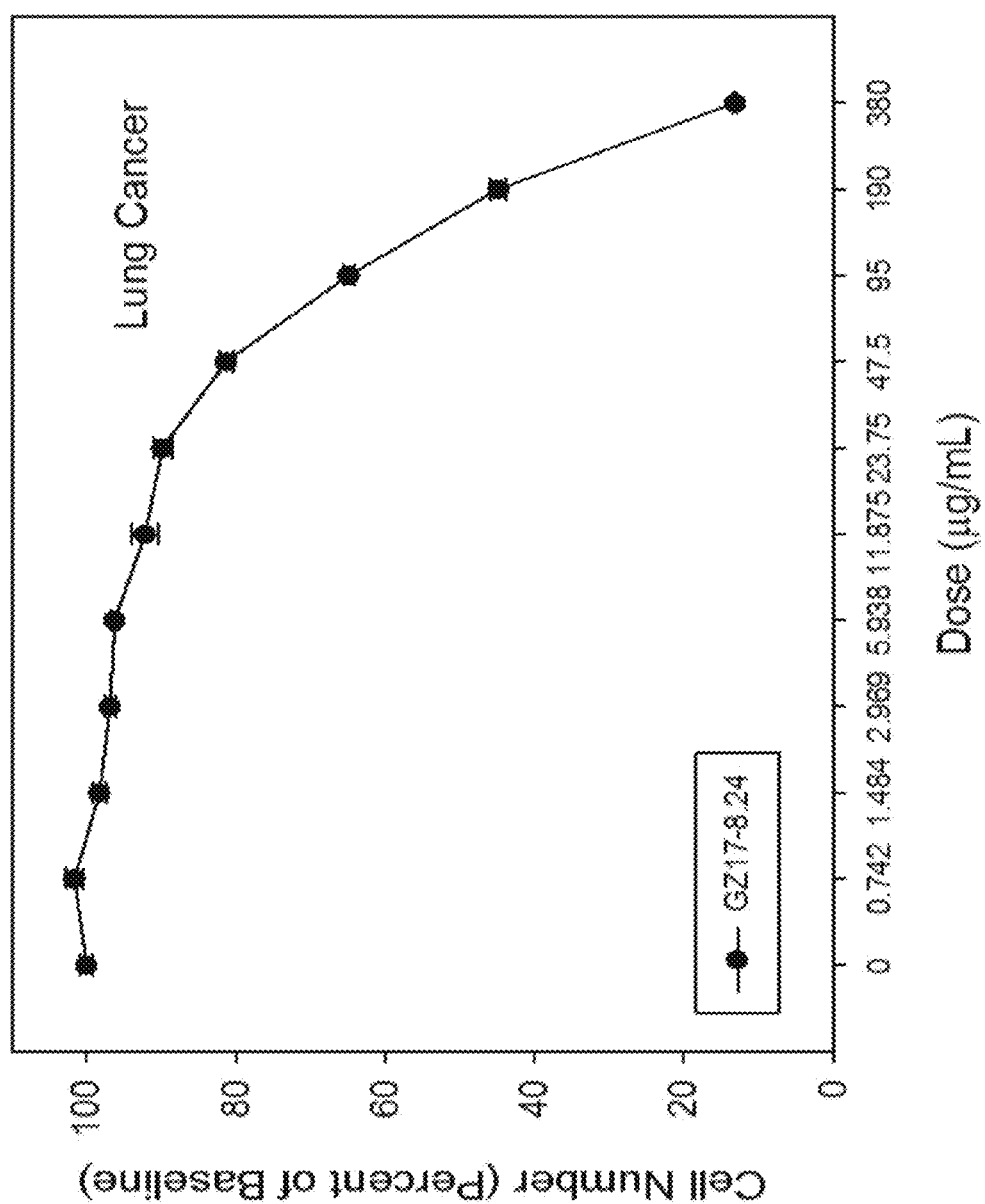
Figure 42C:
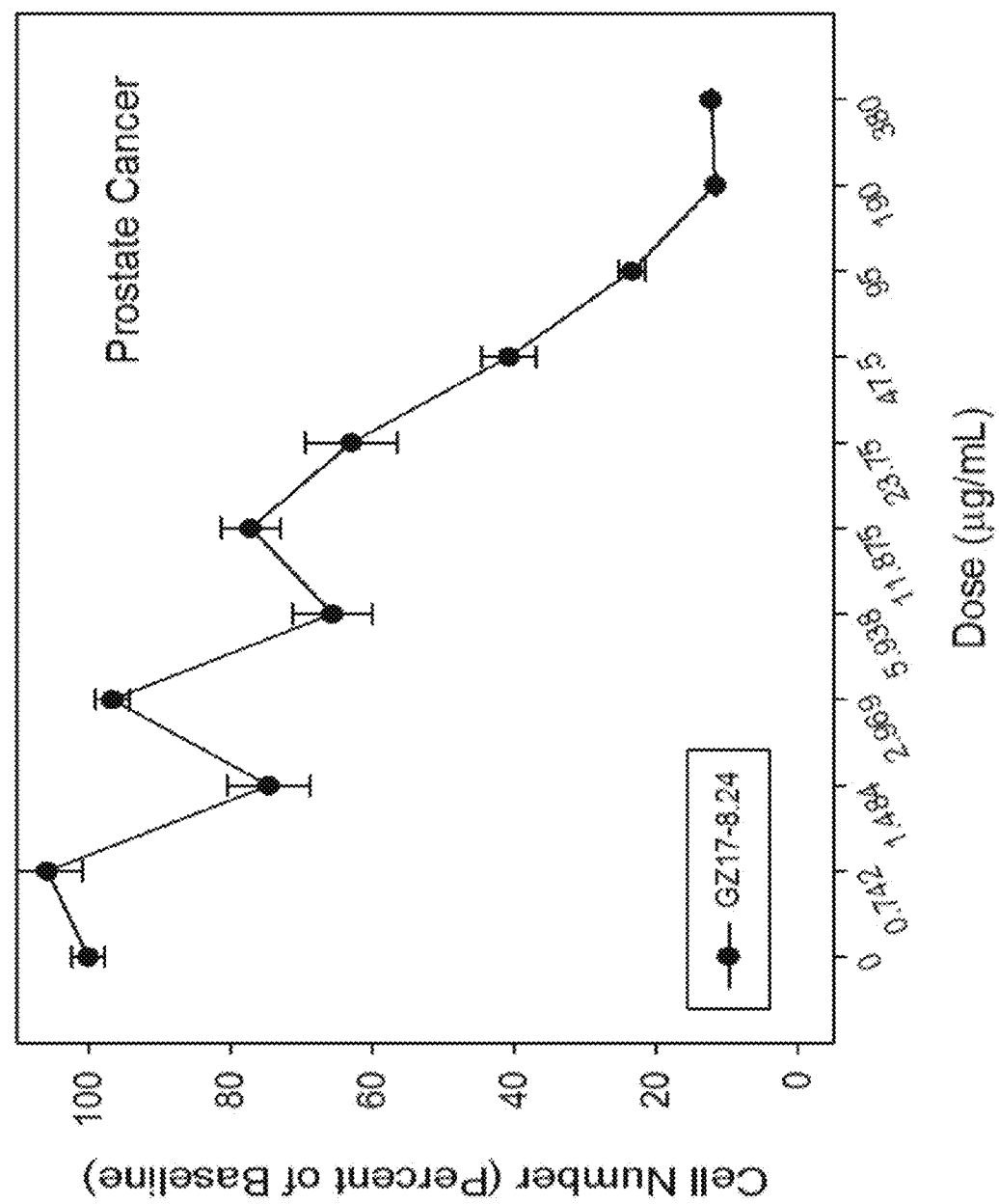
Figure 42D:
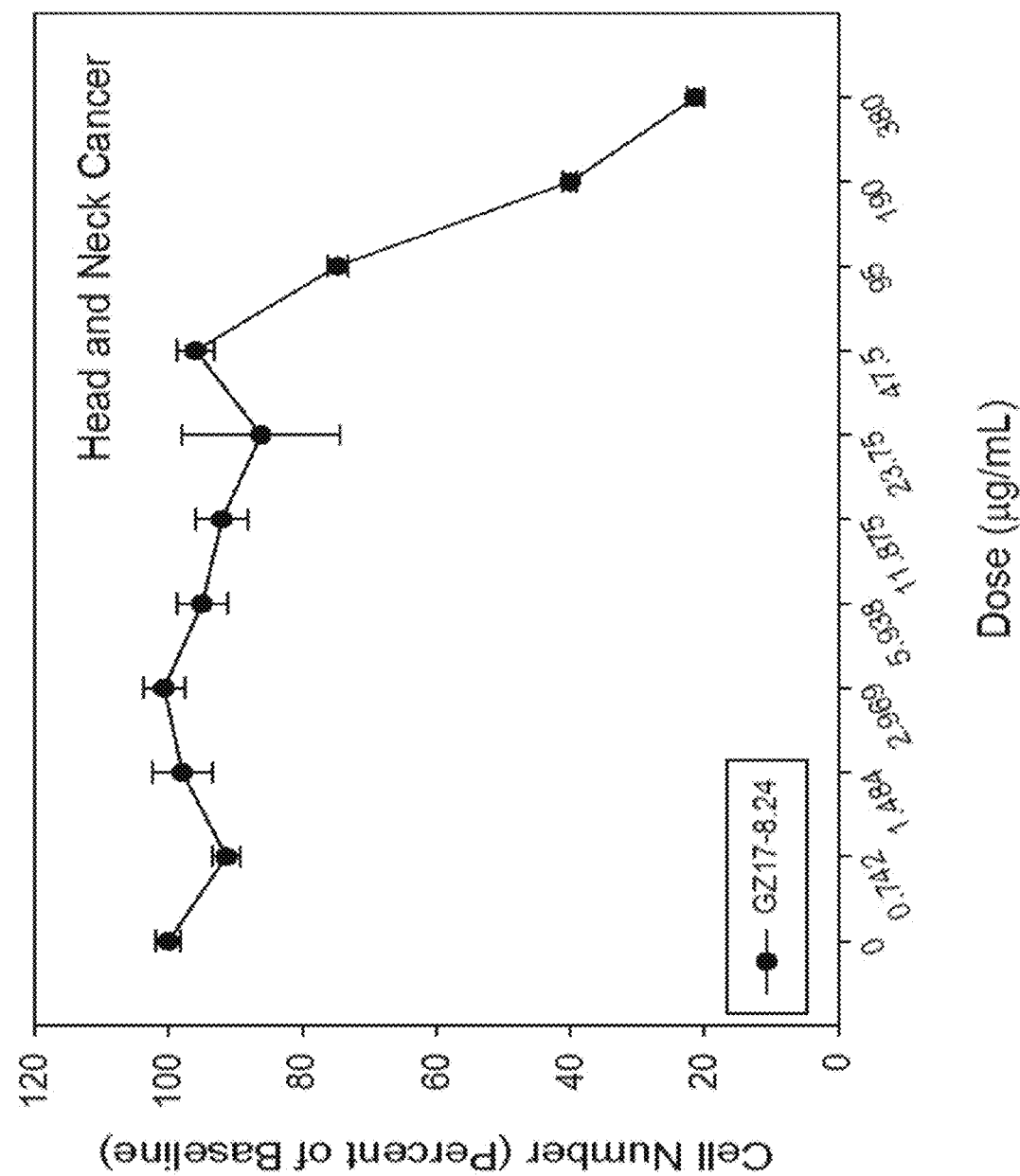
Figure 42E:
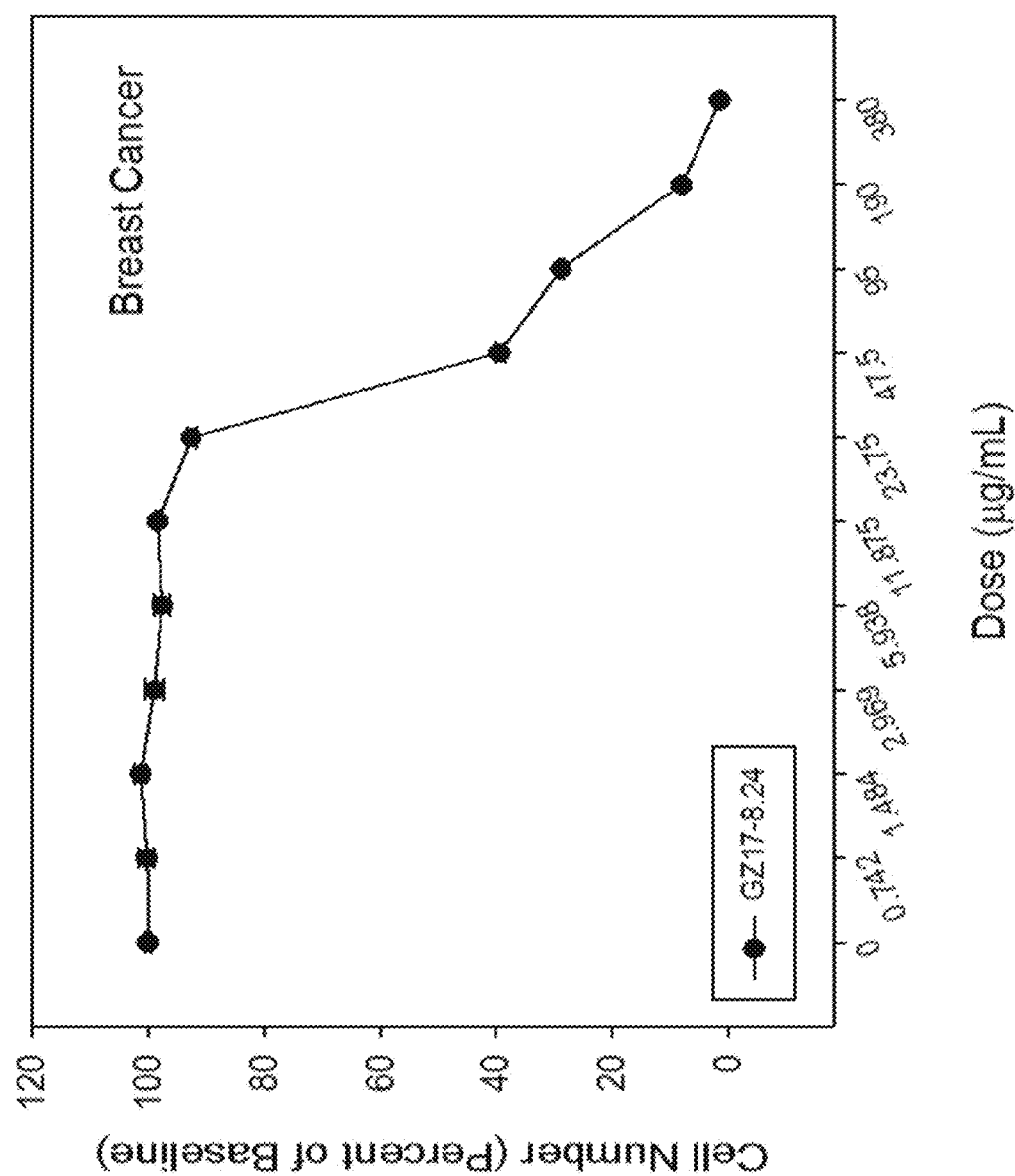
Figure 42F:
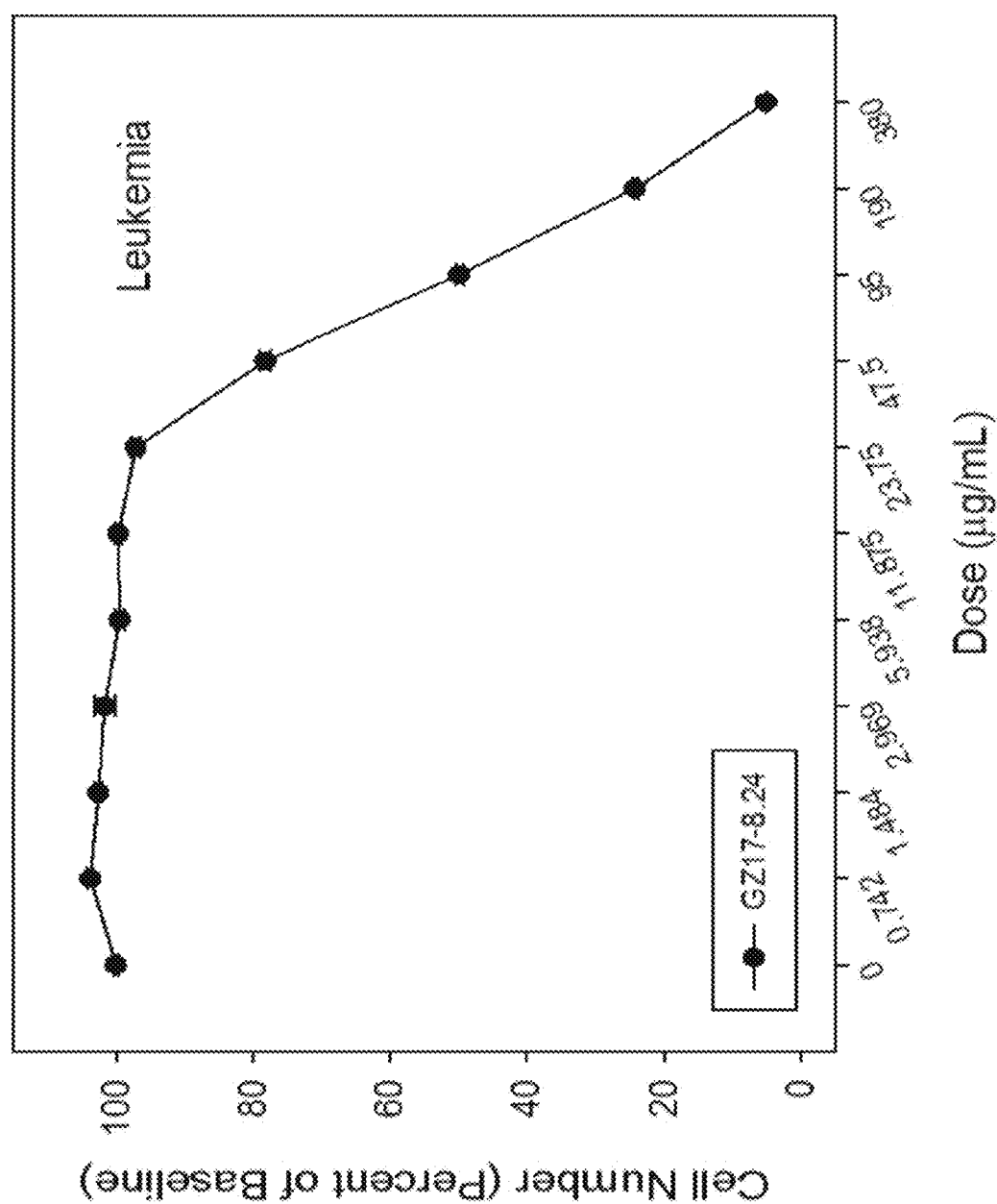
Figure 42G:
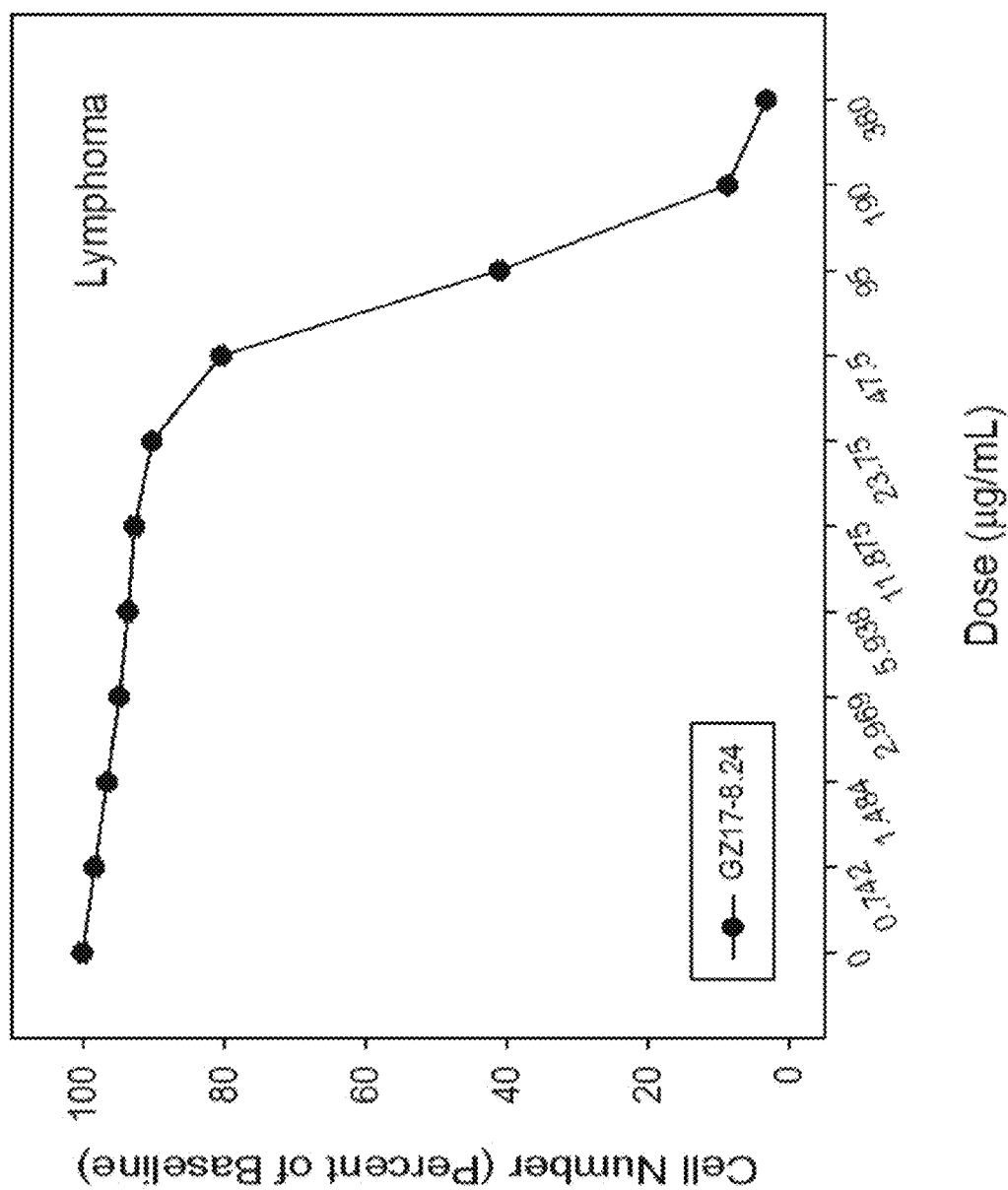
Figure 43A:
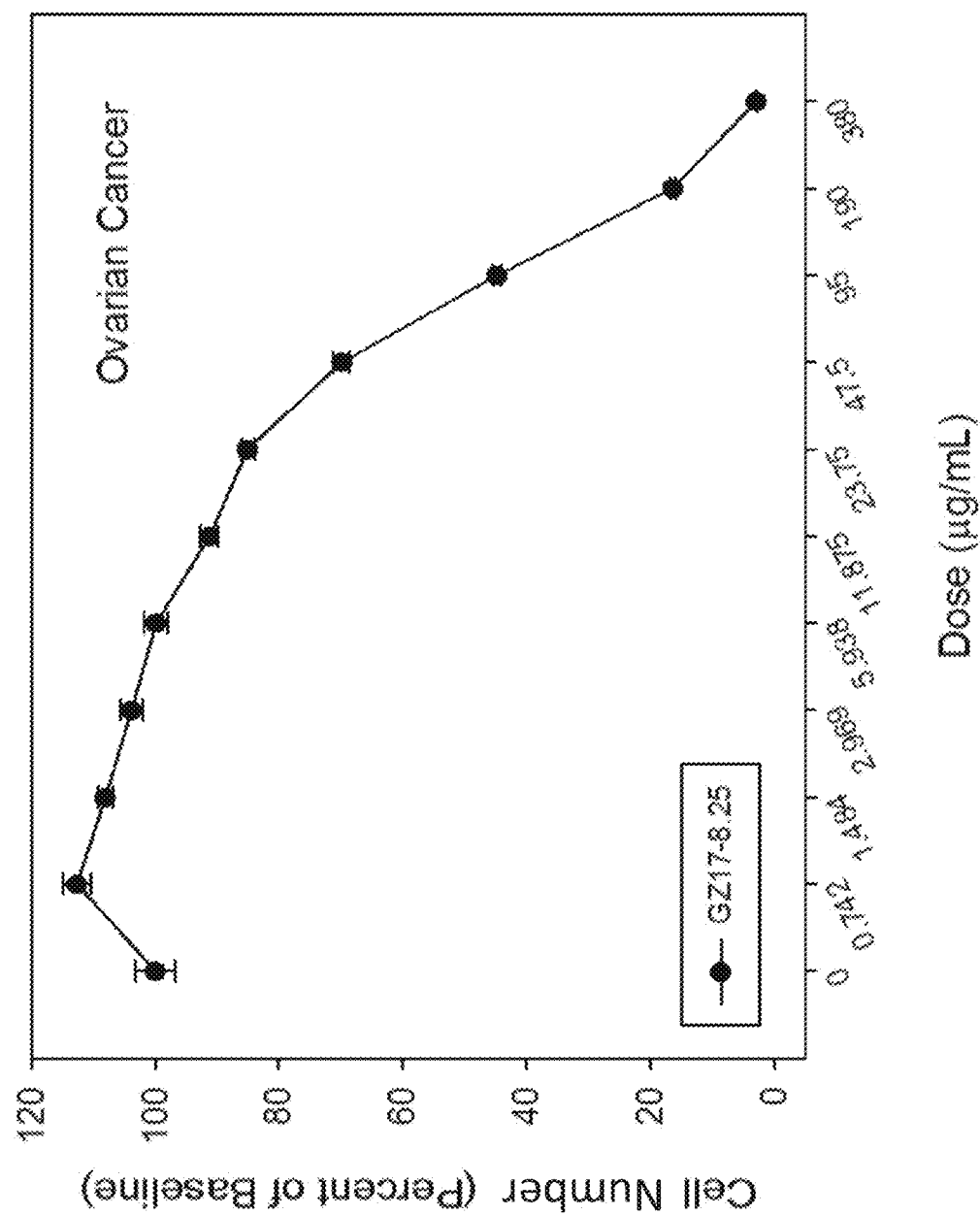
Figure 43B:
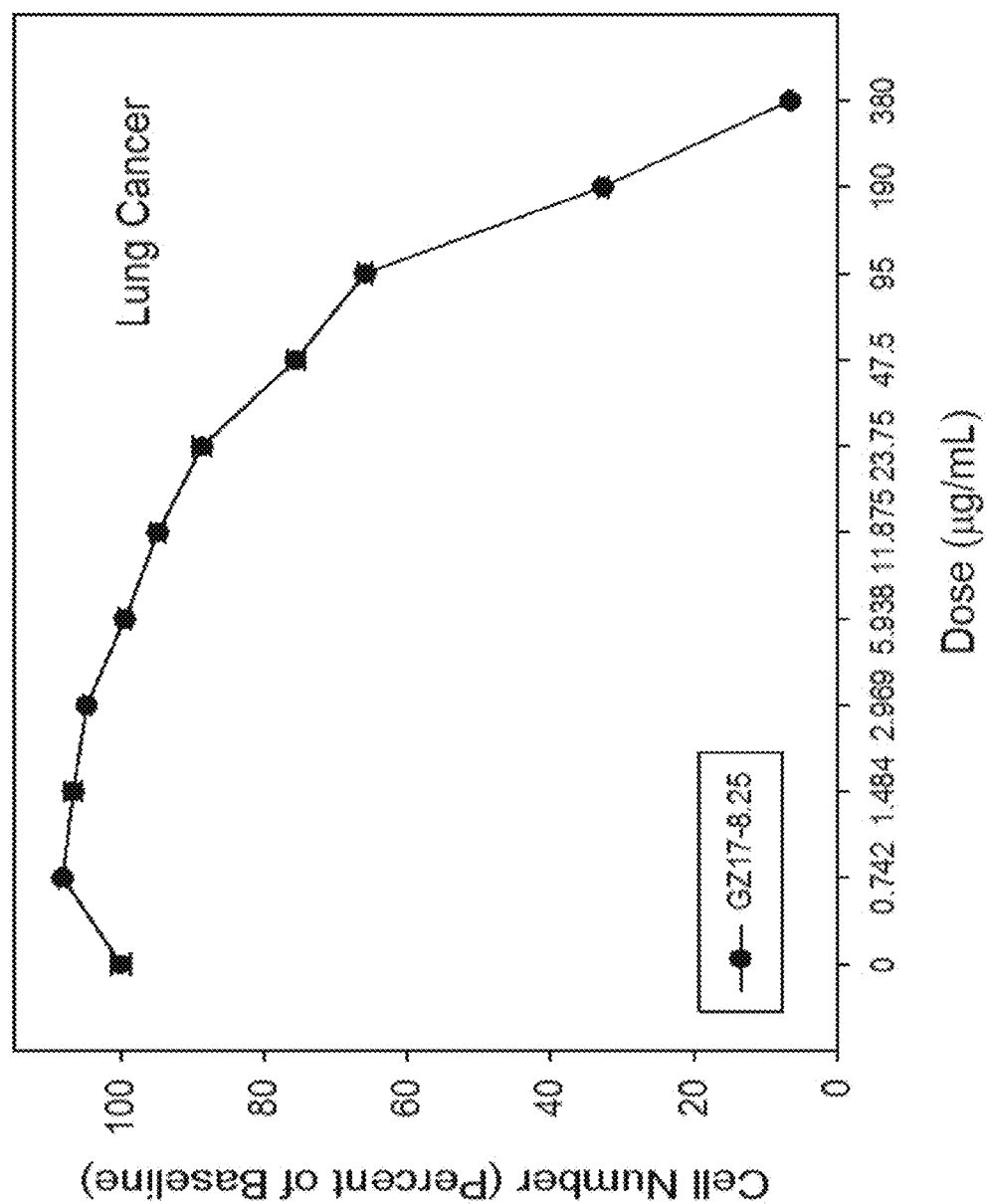
Figure 43C:
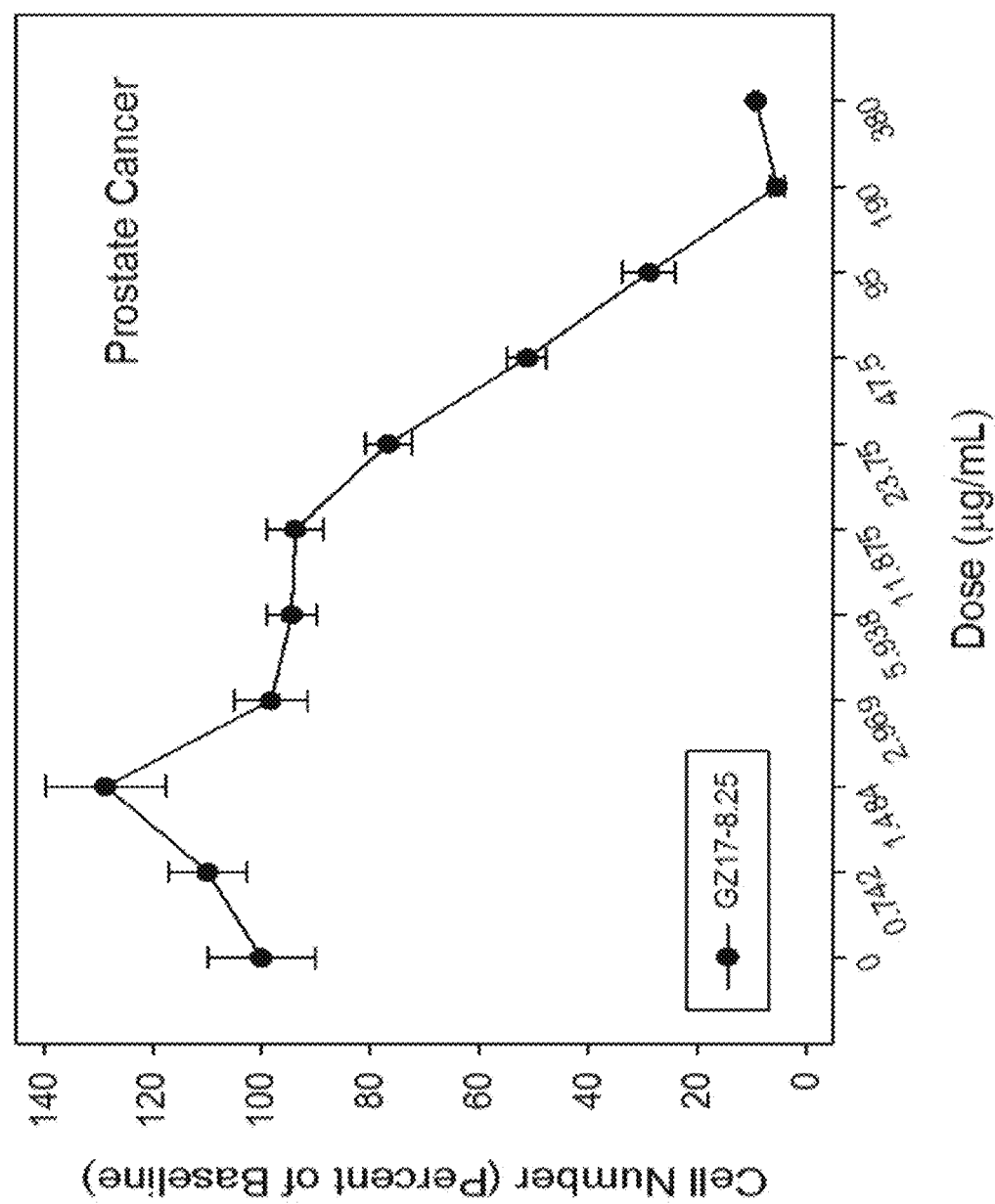
Figure 43D:
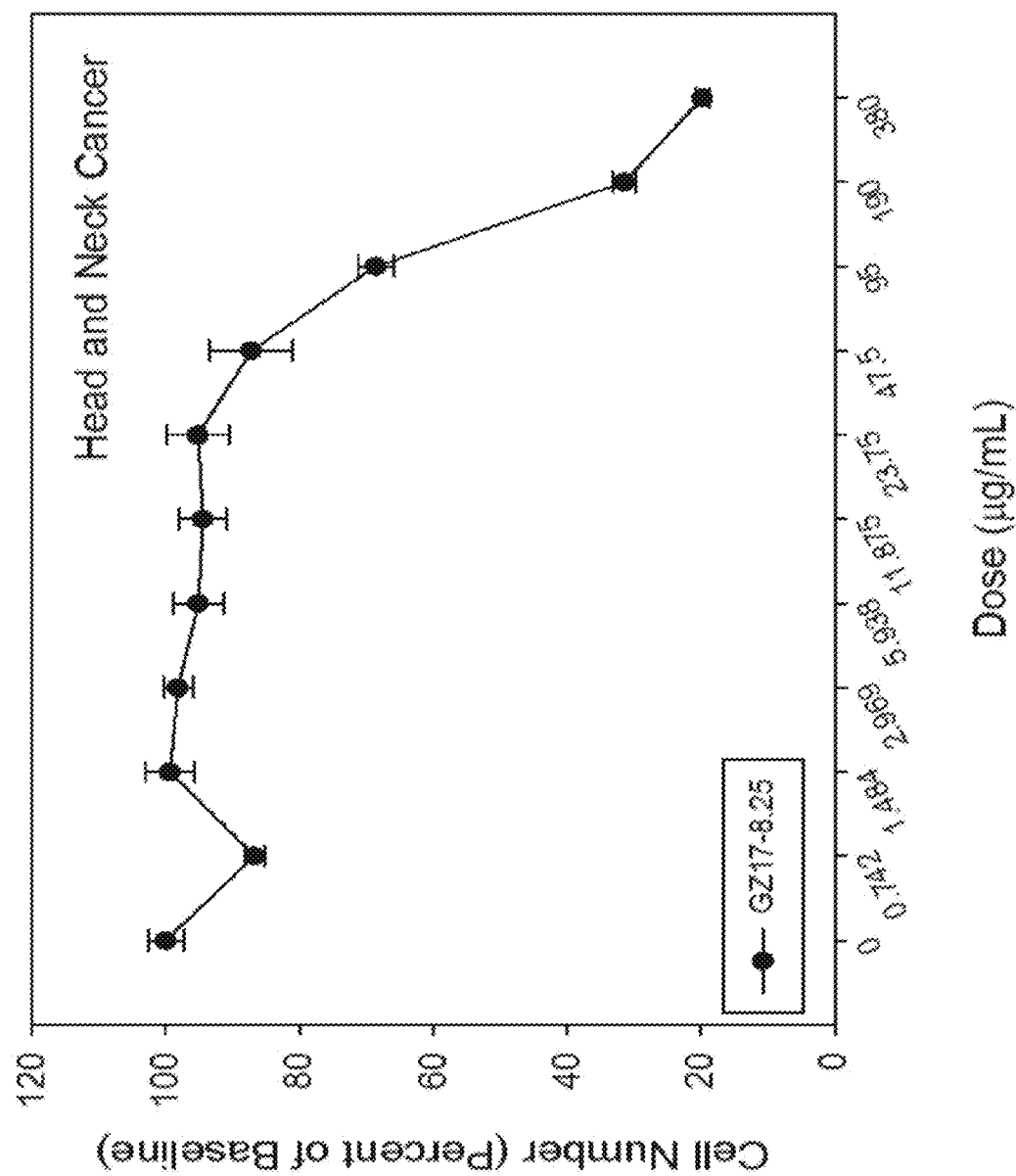
Figure 43E:
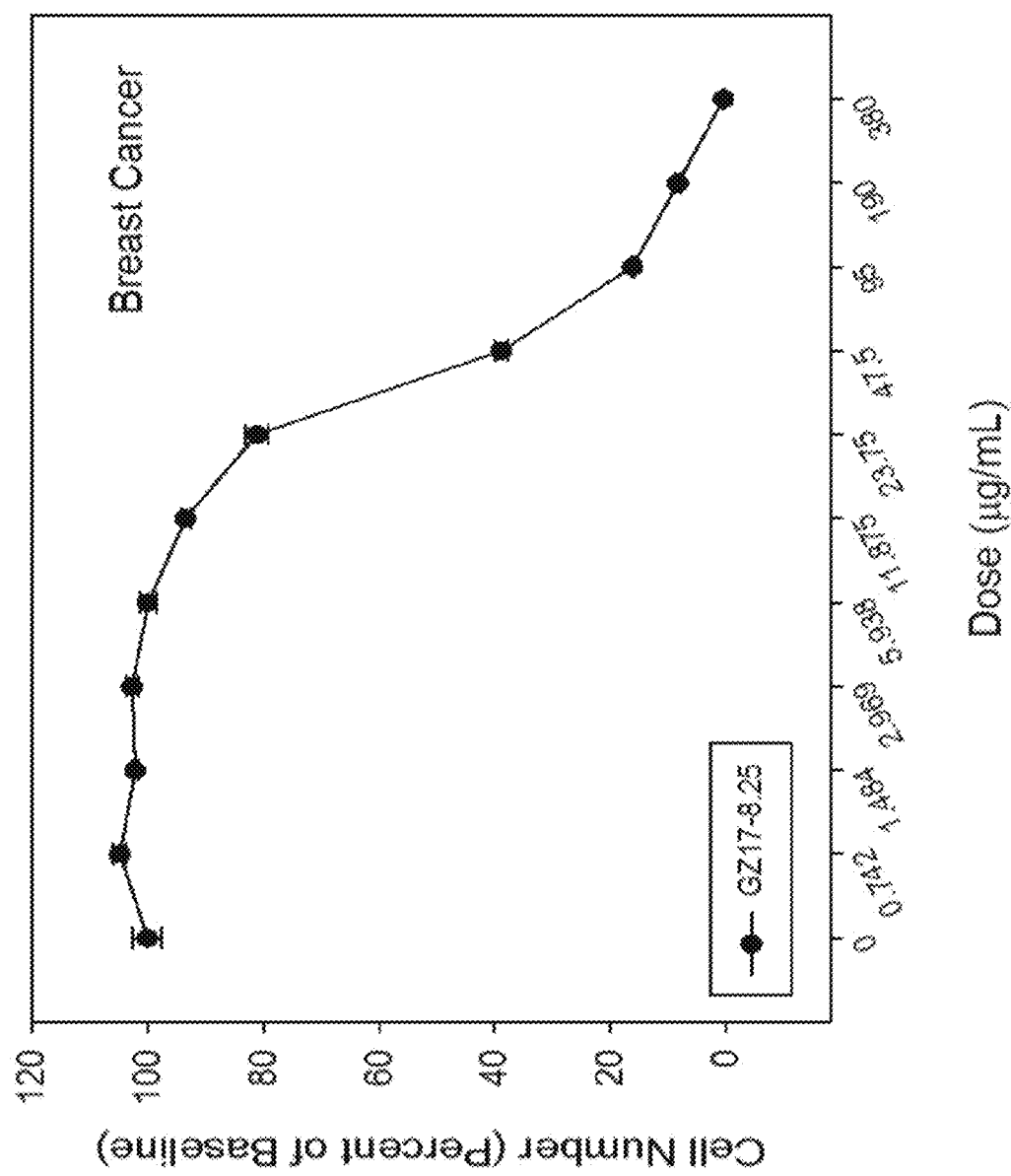
Figure 43F:
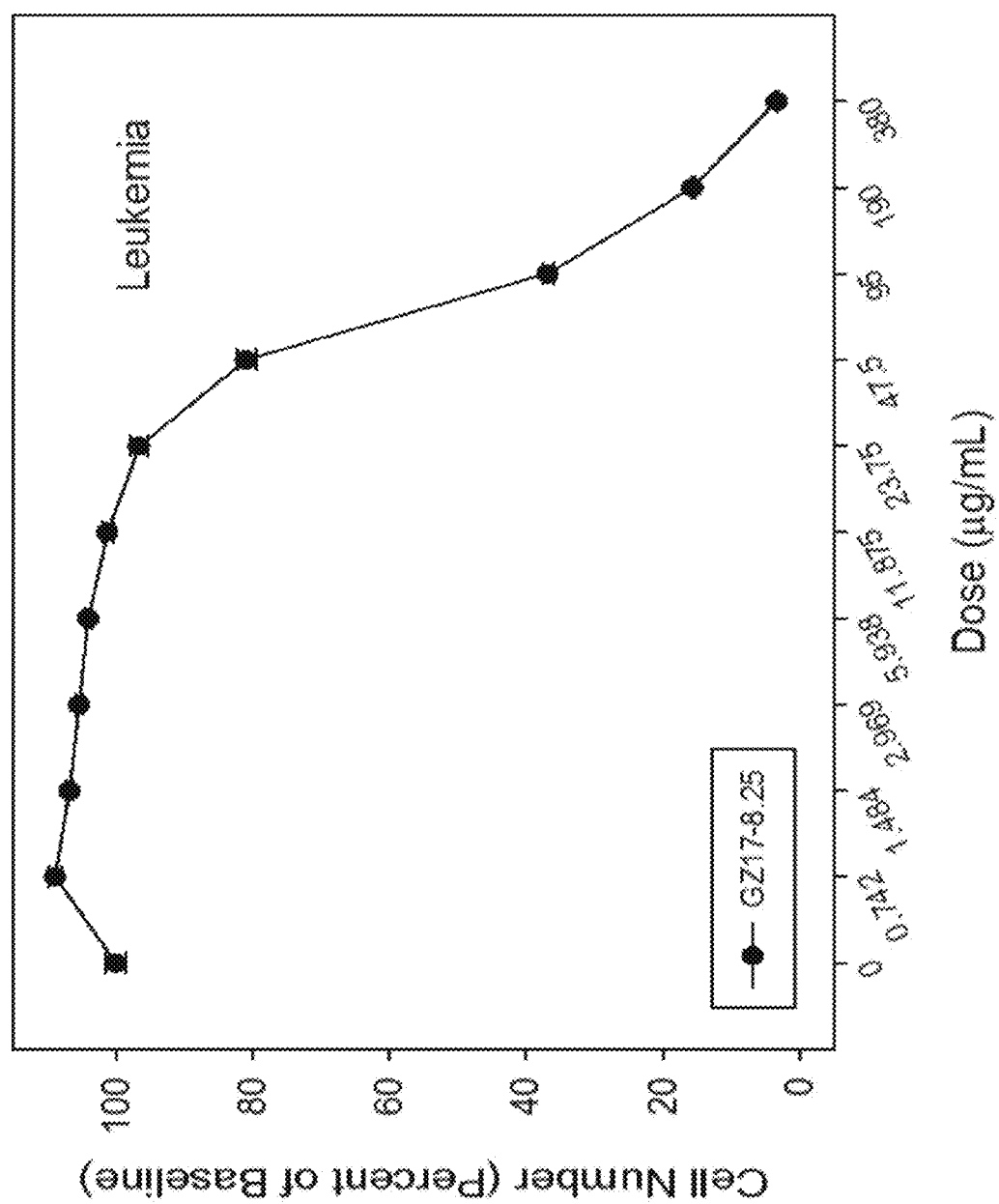
Figure 43G:
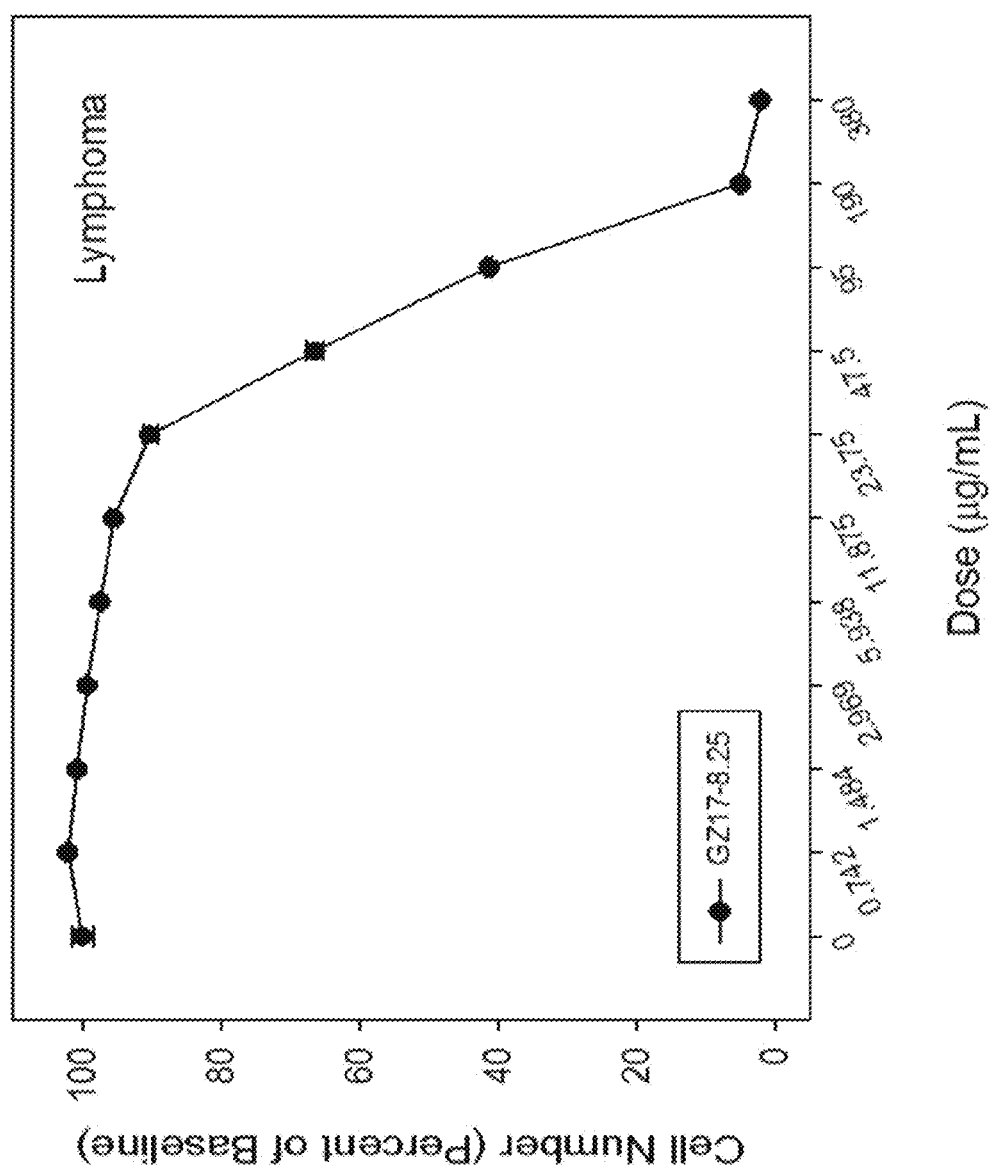
Figure 44A:
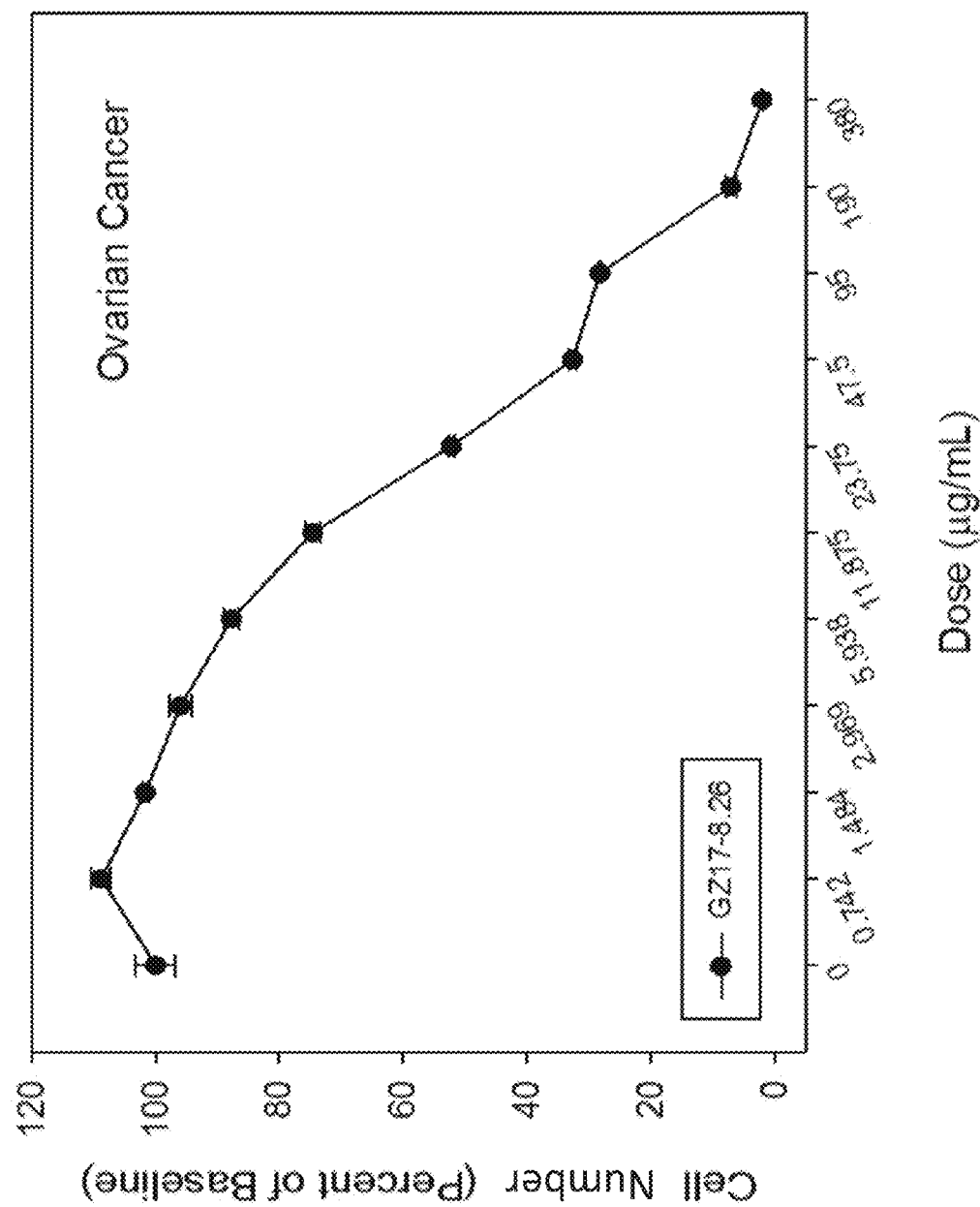
Figure 44B:
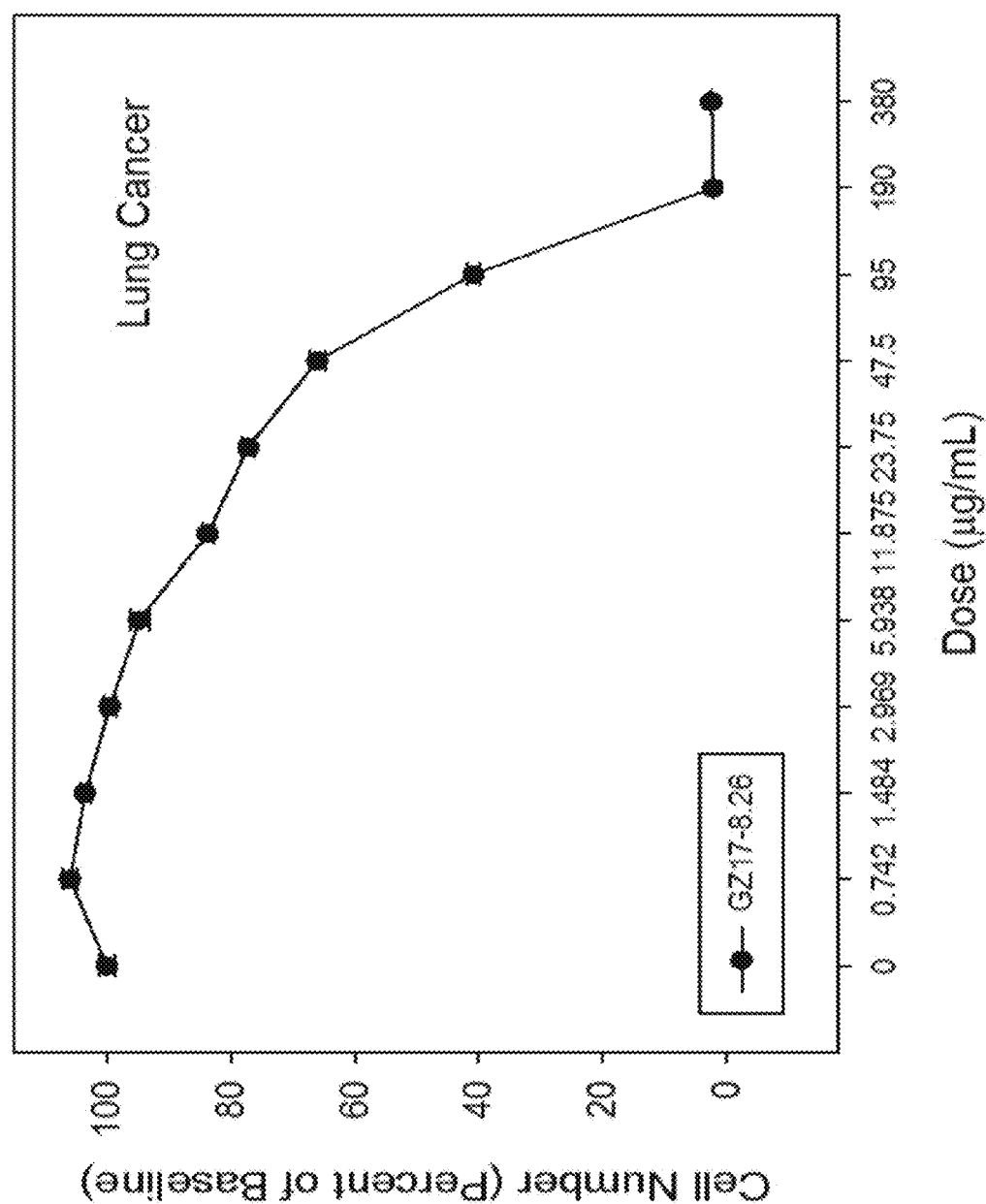
Figure 44C:
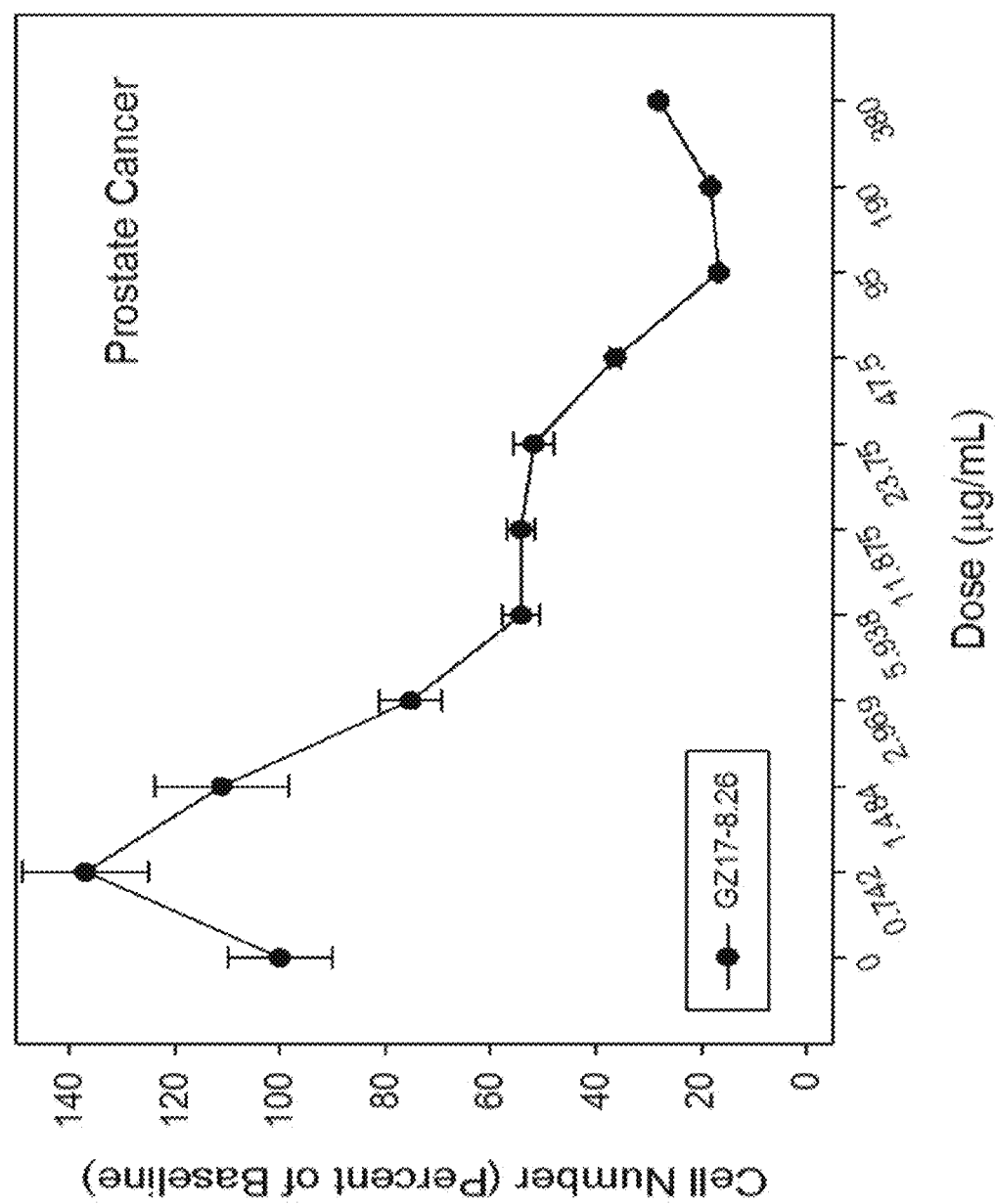
Figure 44D:
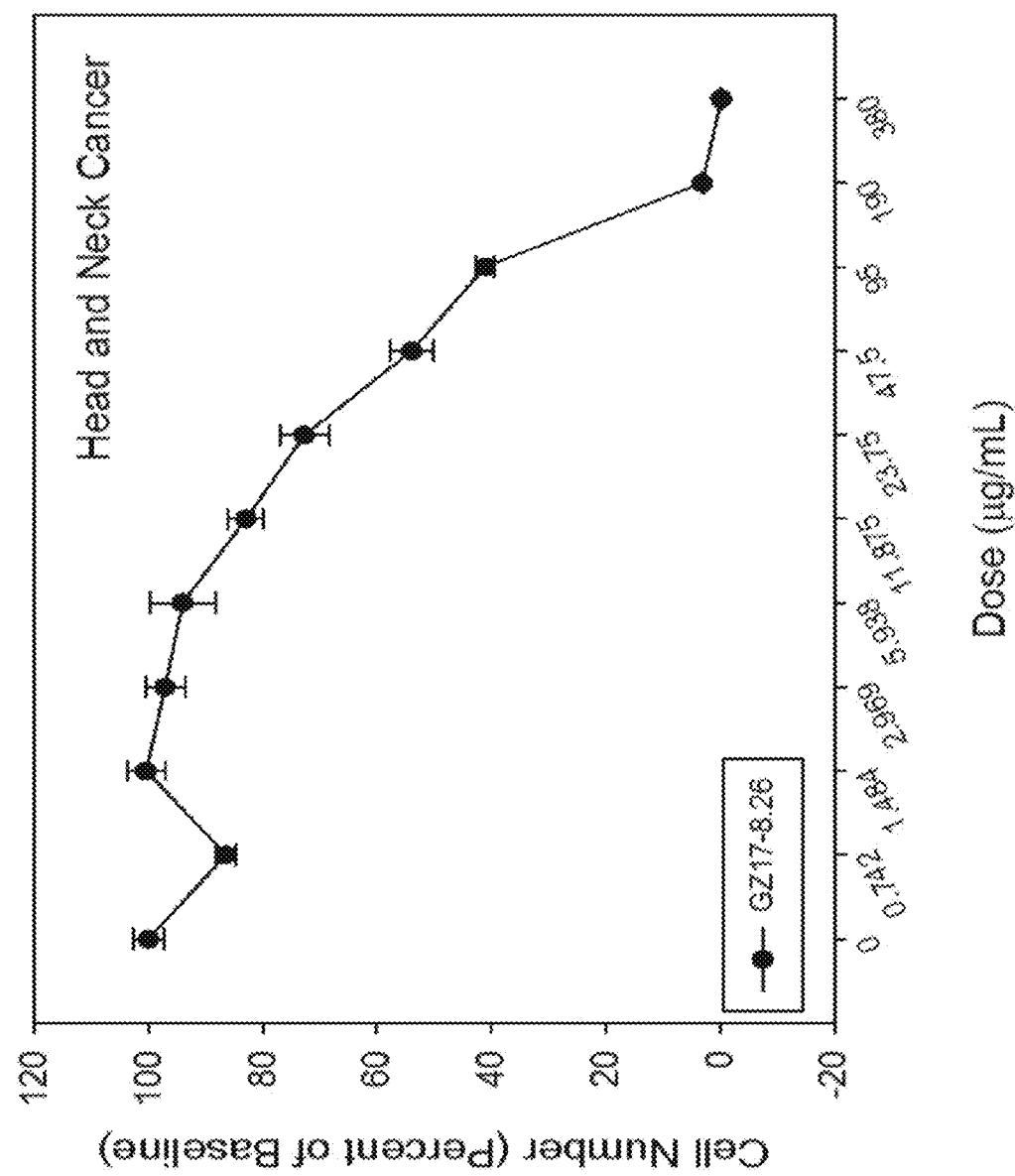
Figure 44E:
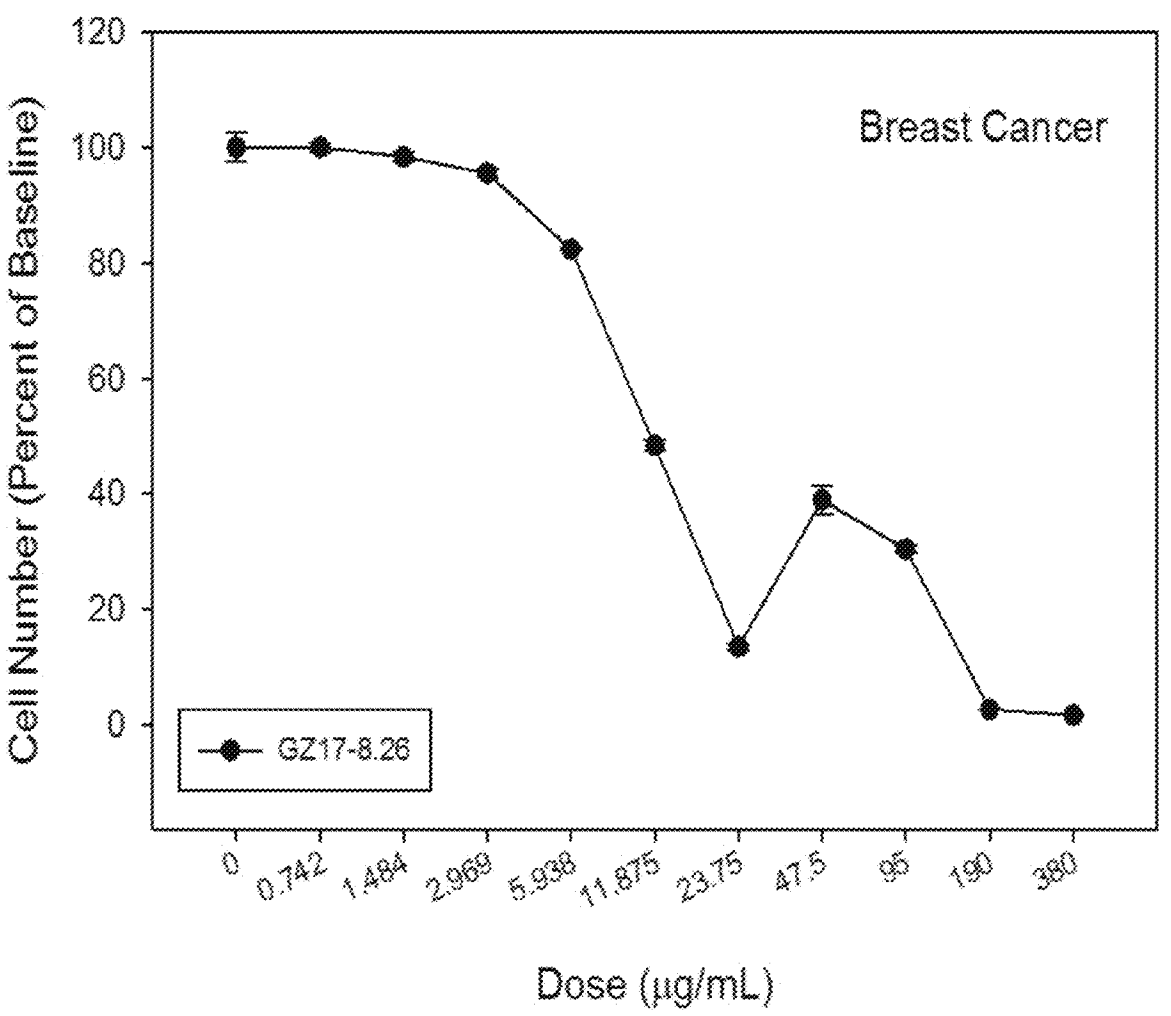
Figure 44F:
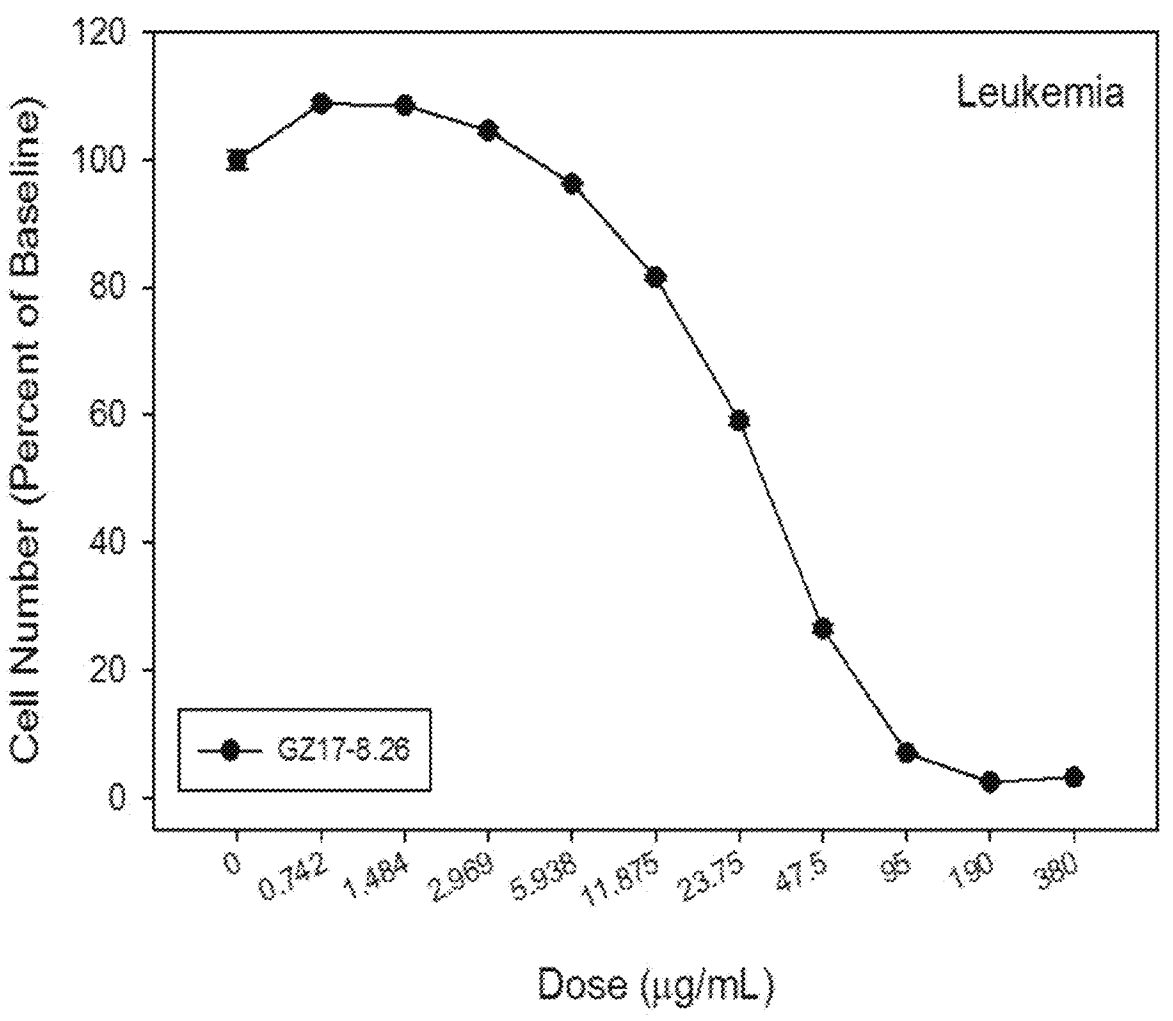
Figure 44G:
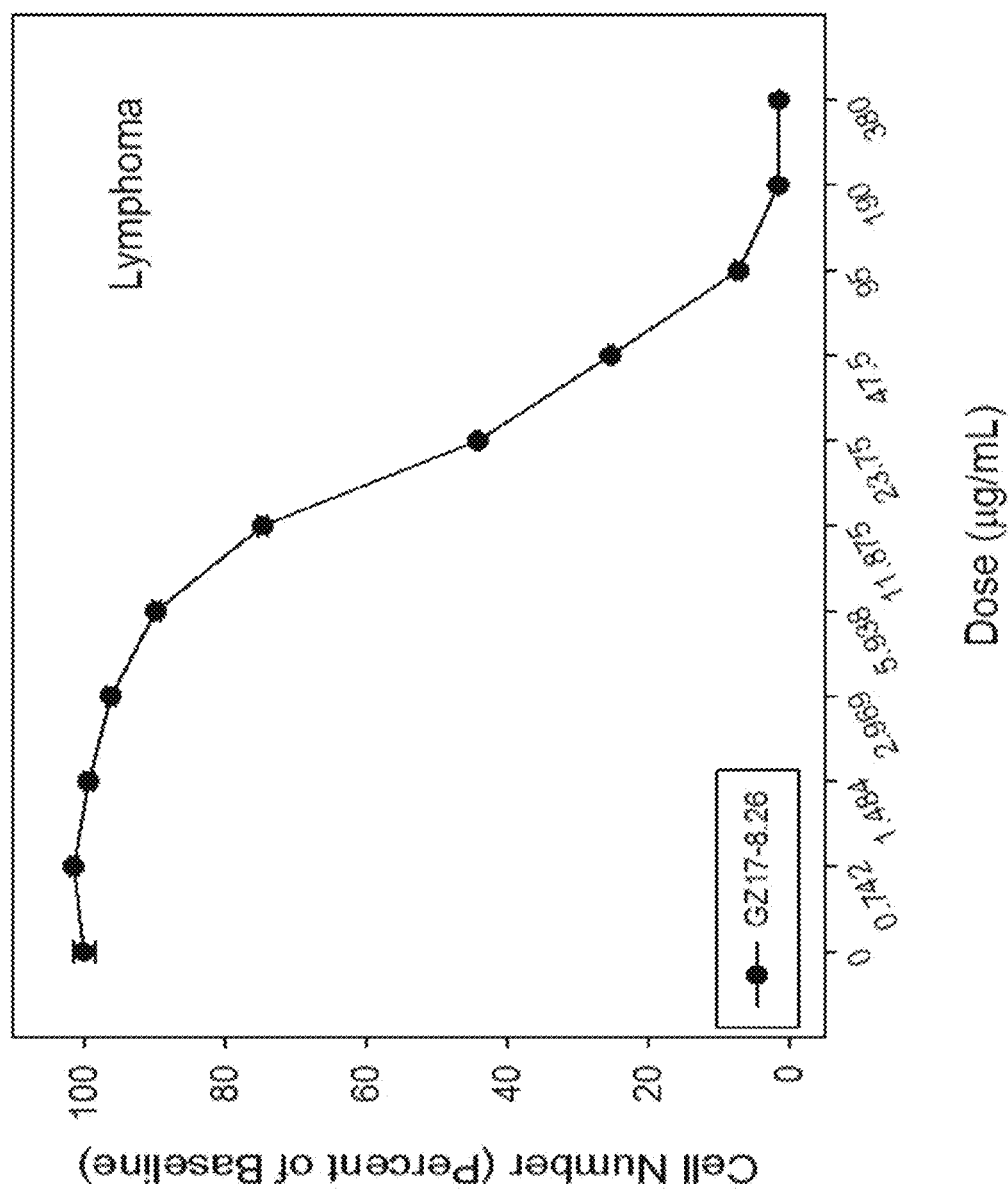
Figure 45A:
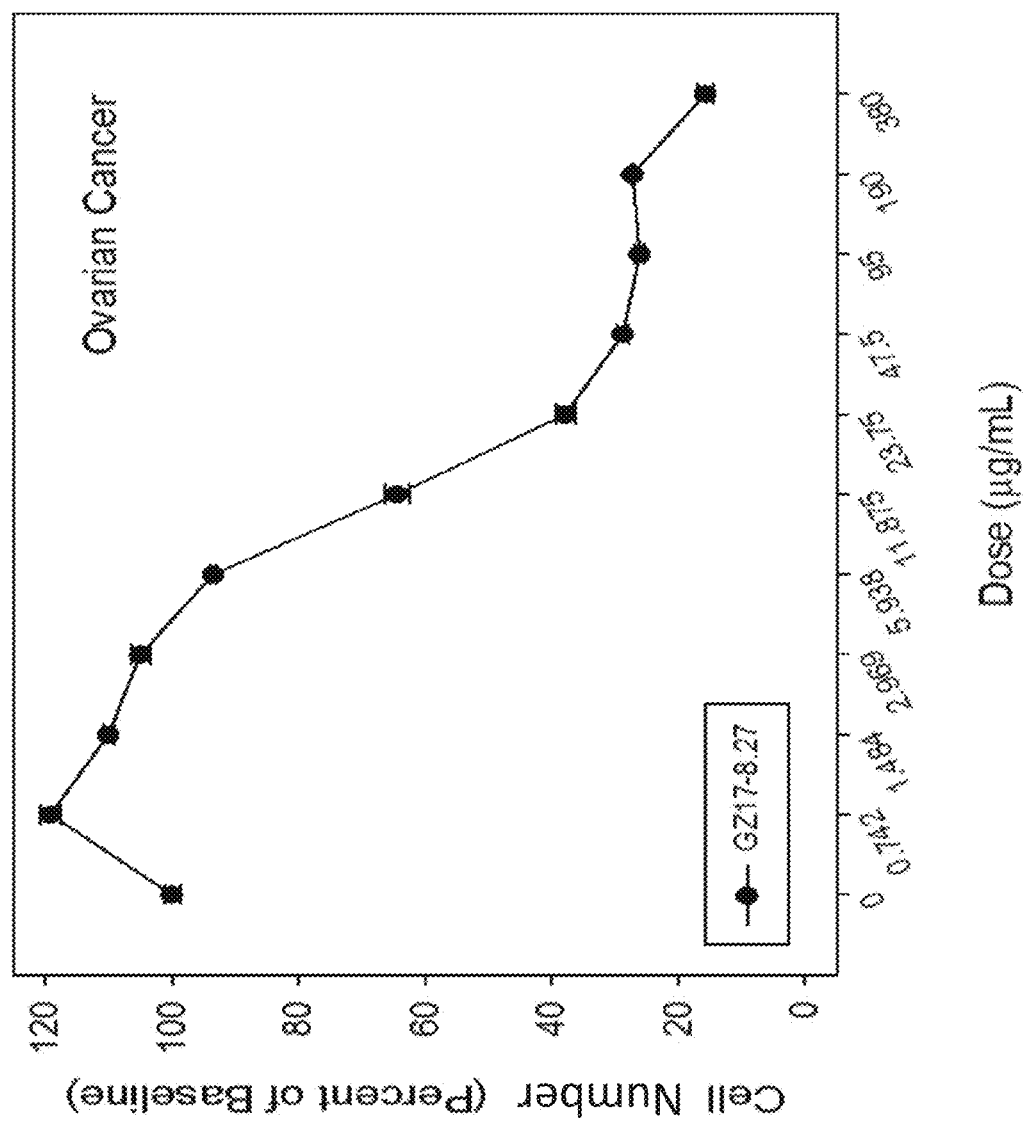
Figure 45B:
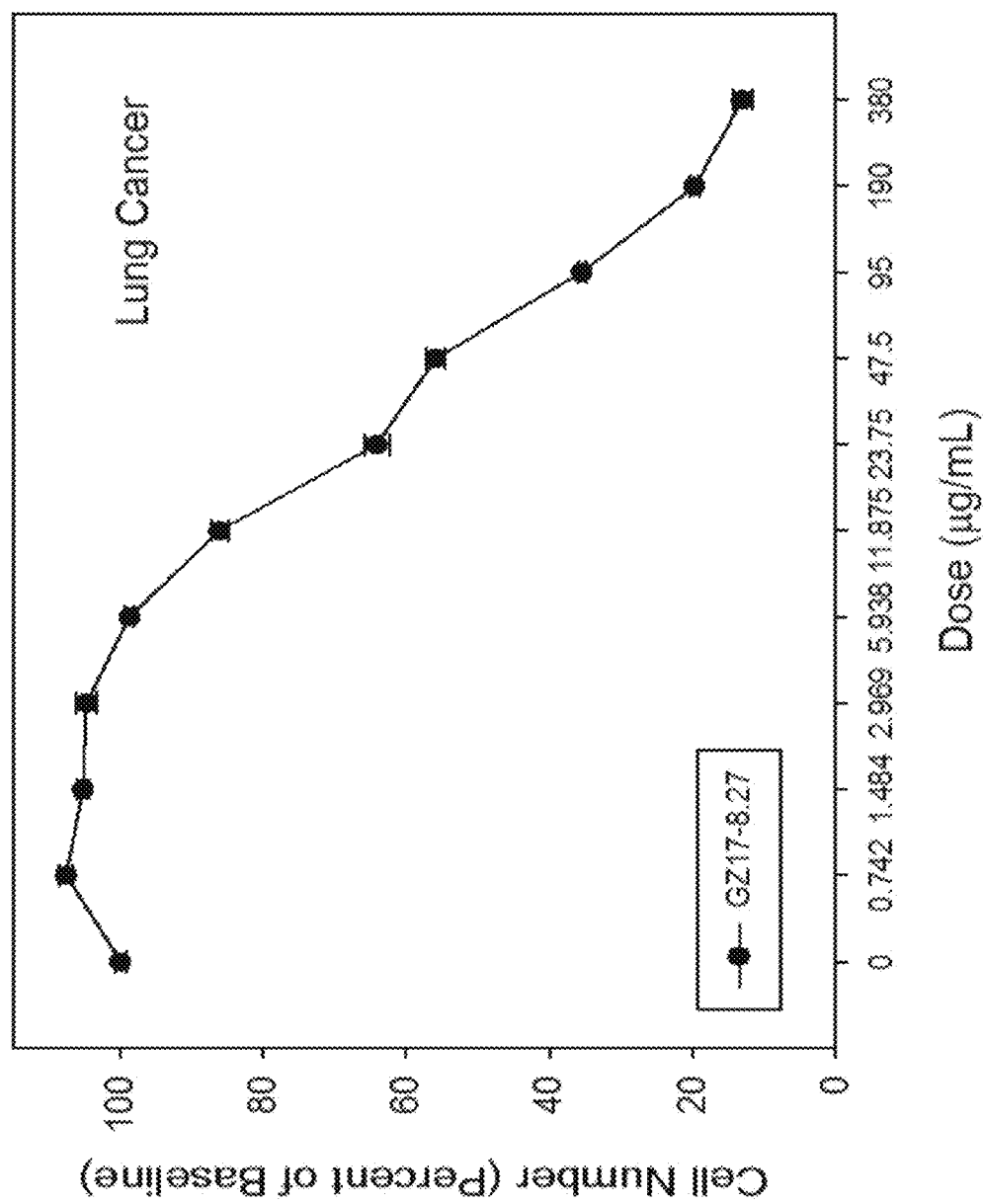
Figure 45C:
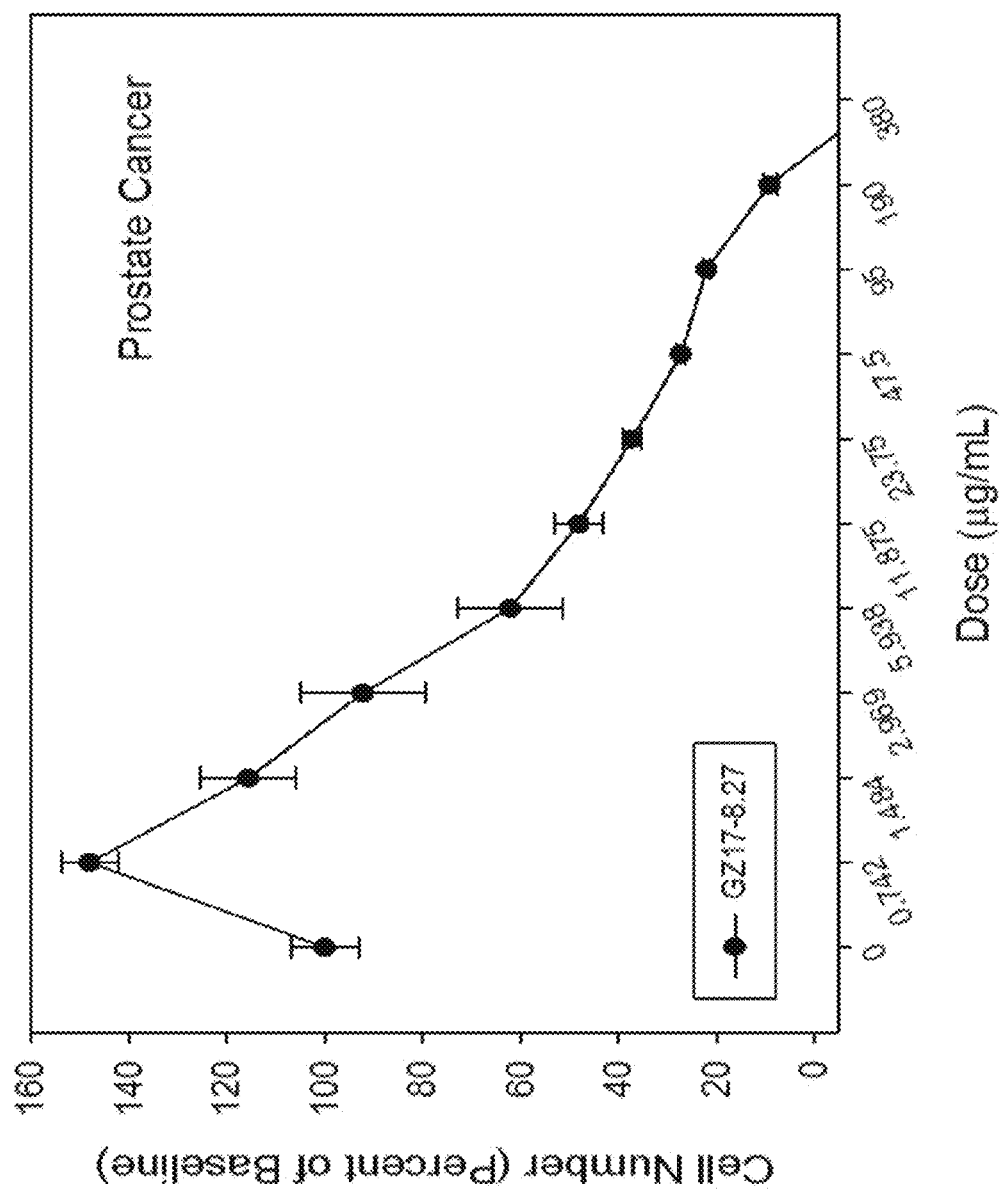
Figure 45D:
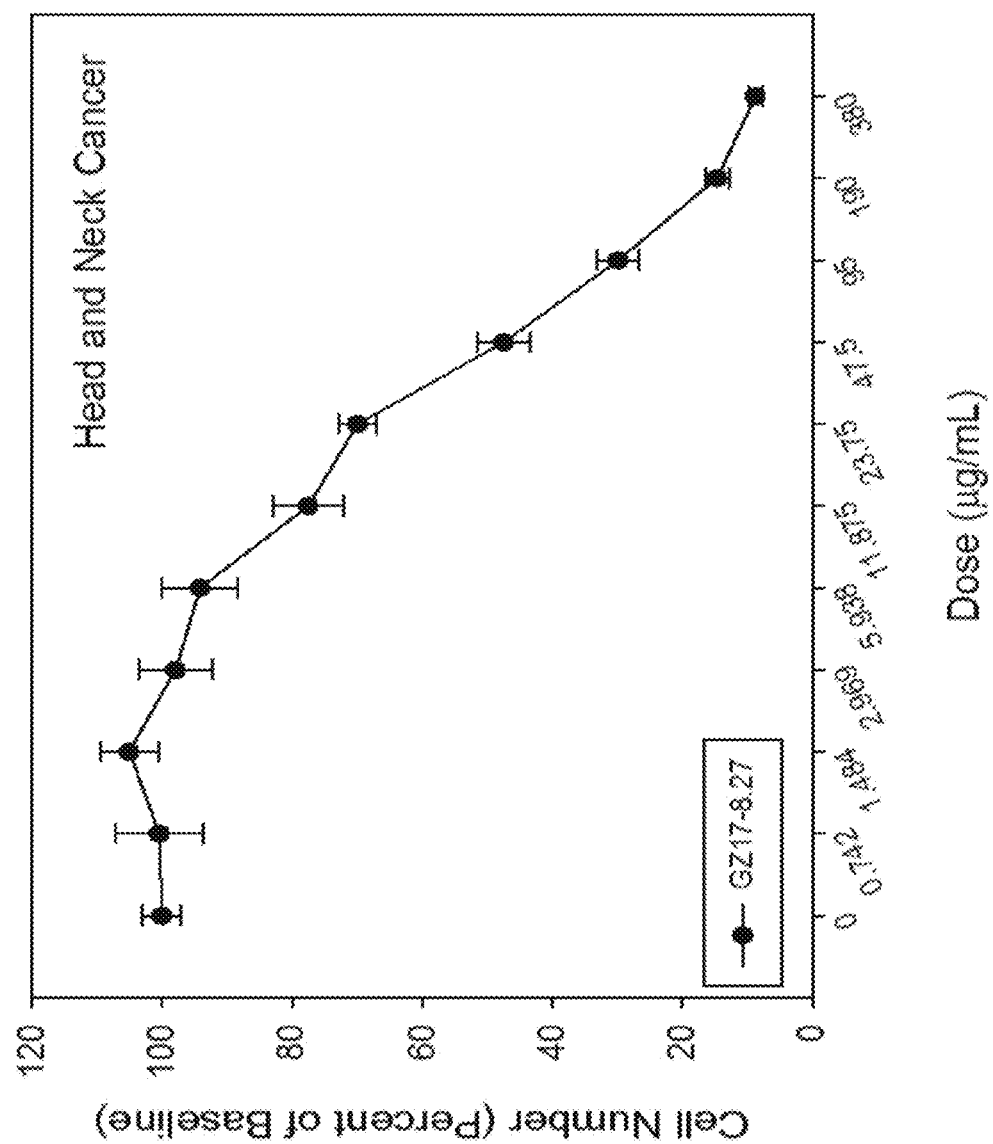
Figure 45E:
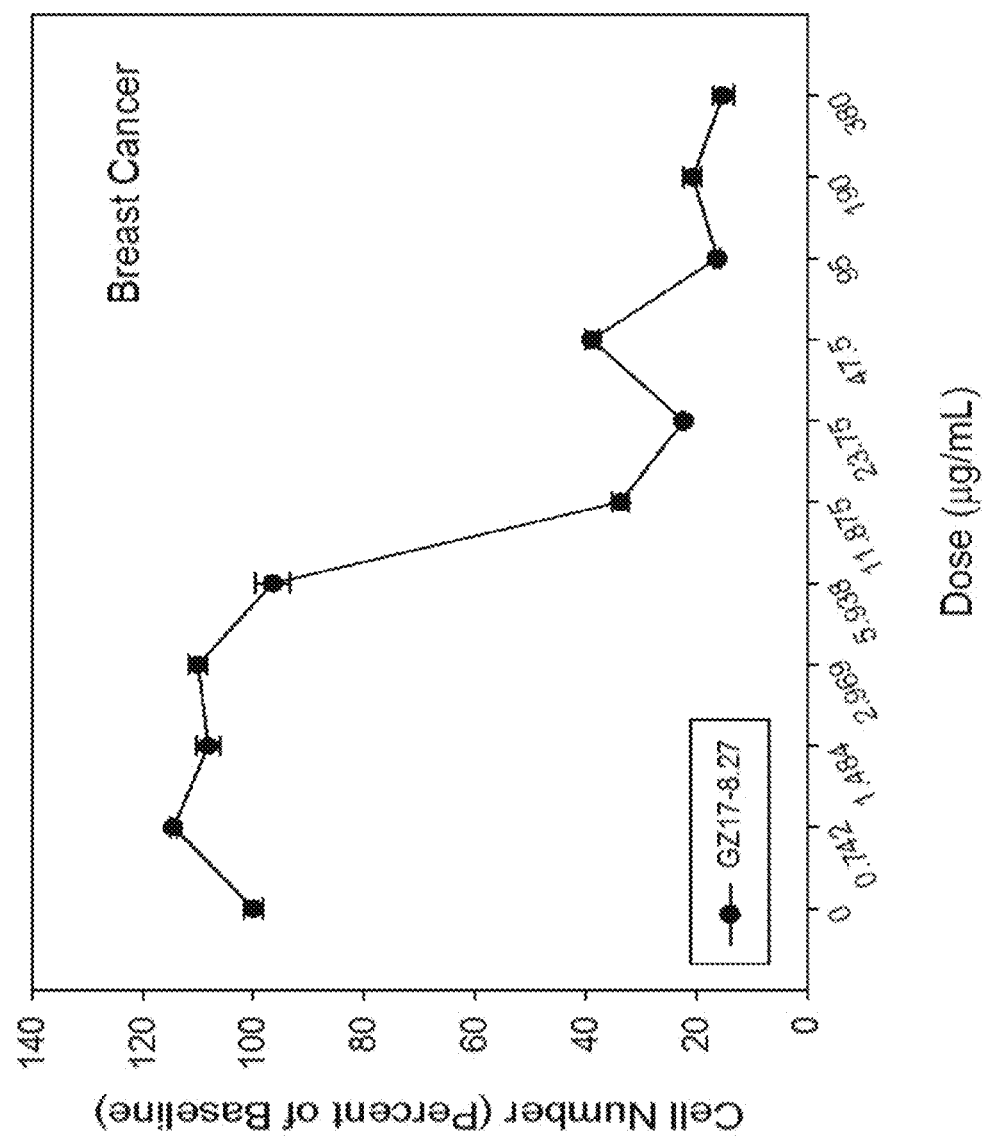
Figure 45F:
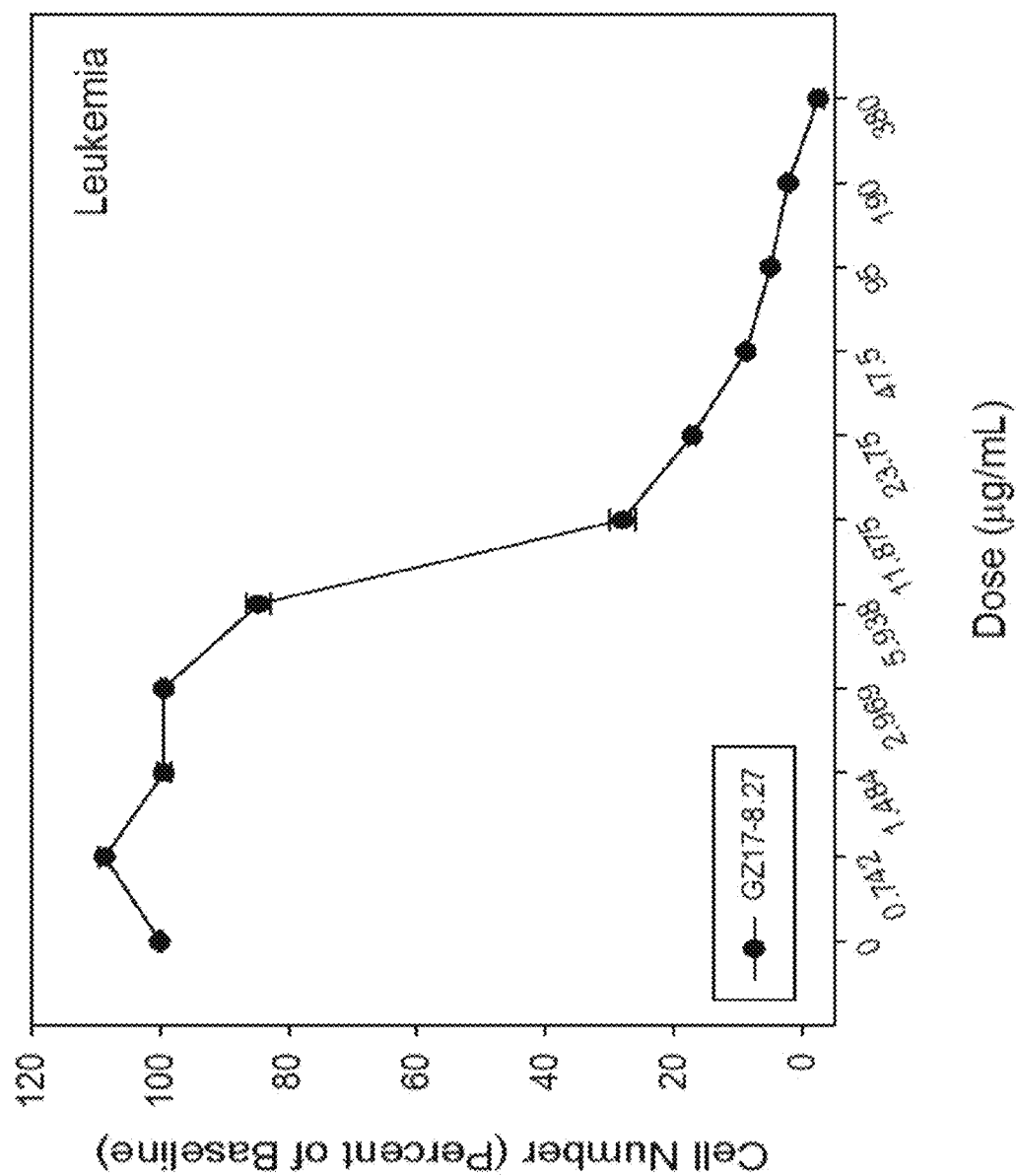
Figure 45G:
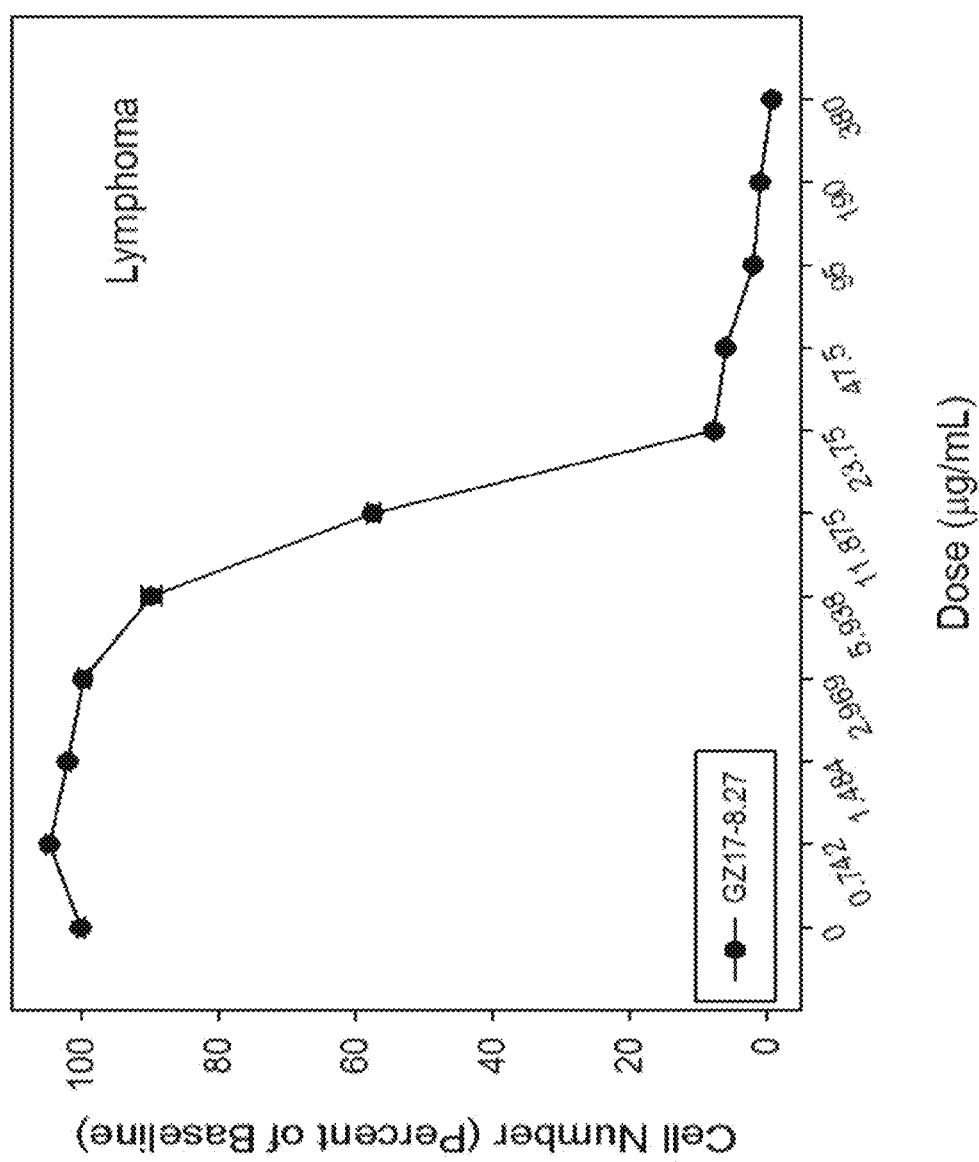
Figure 46A:
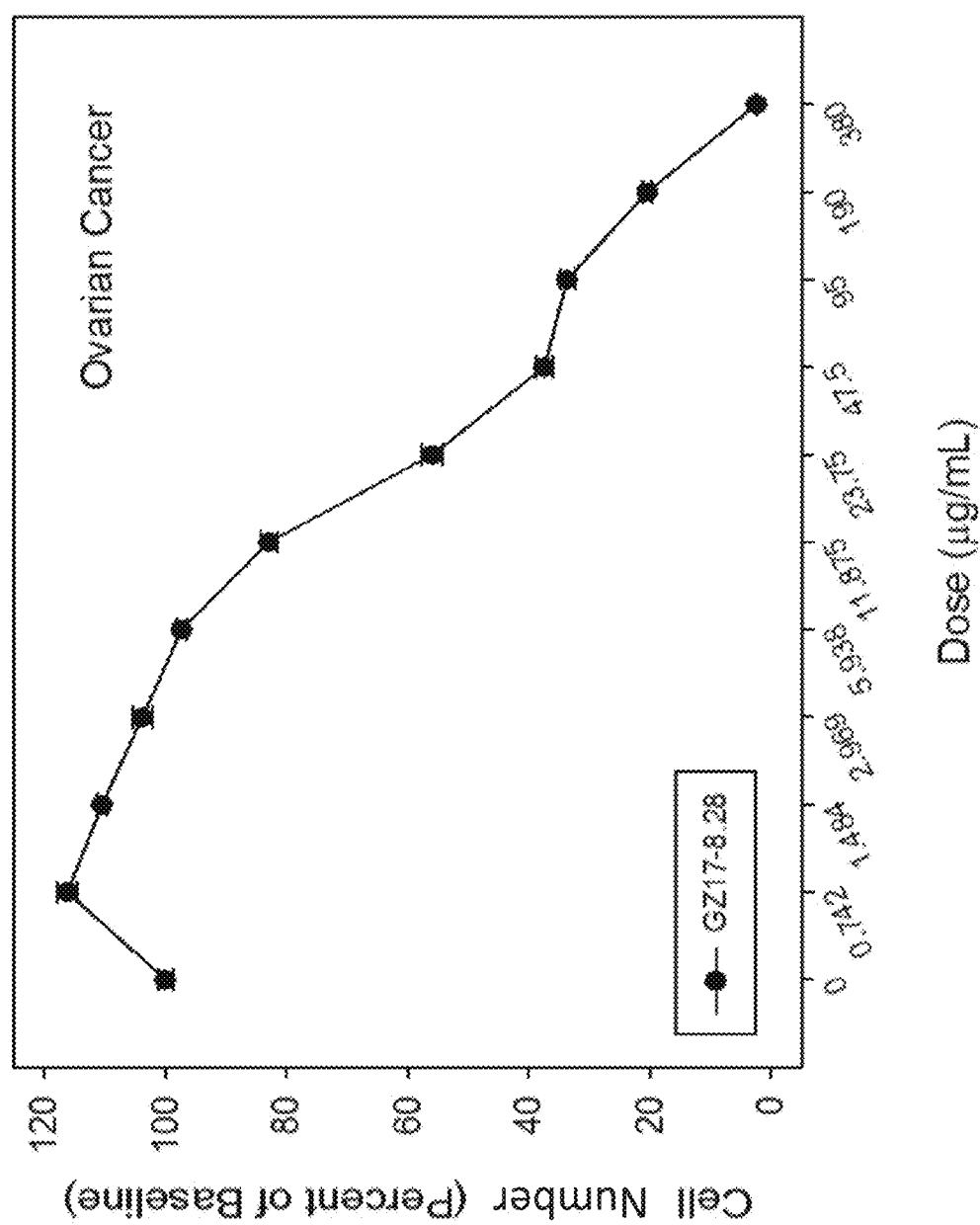
Figure 46B:
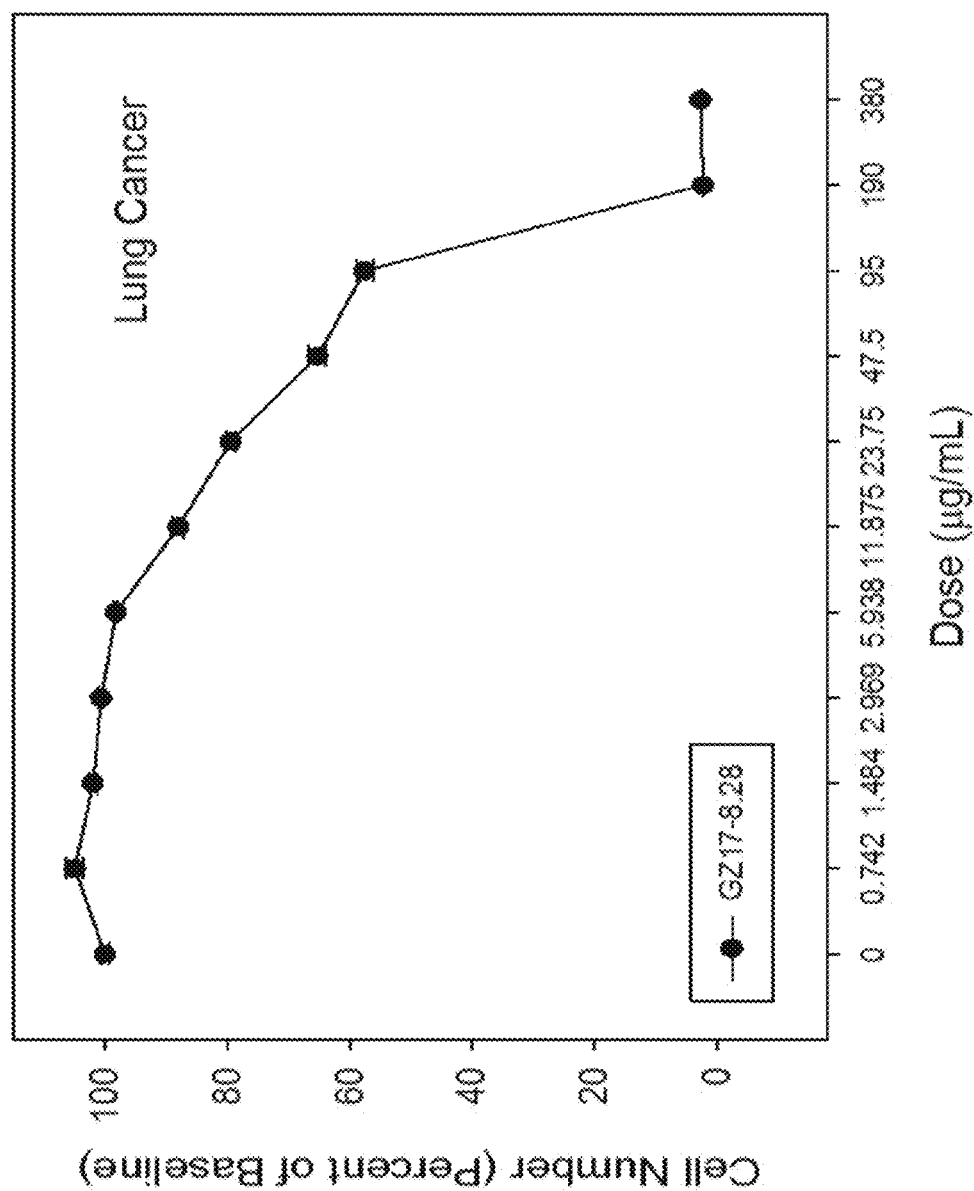
Figure 46C:
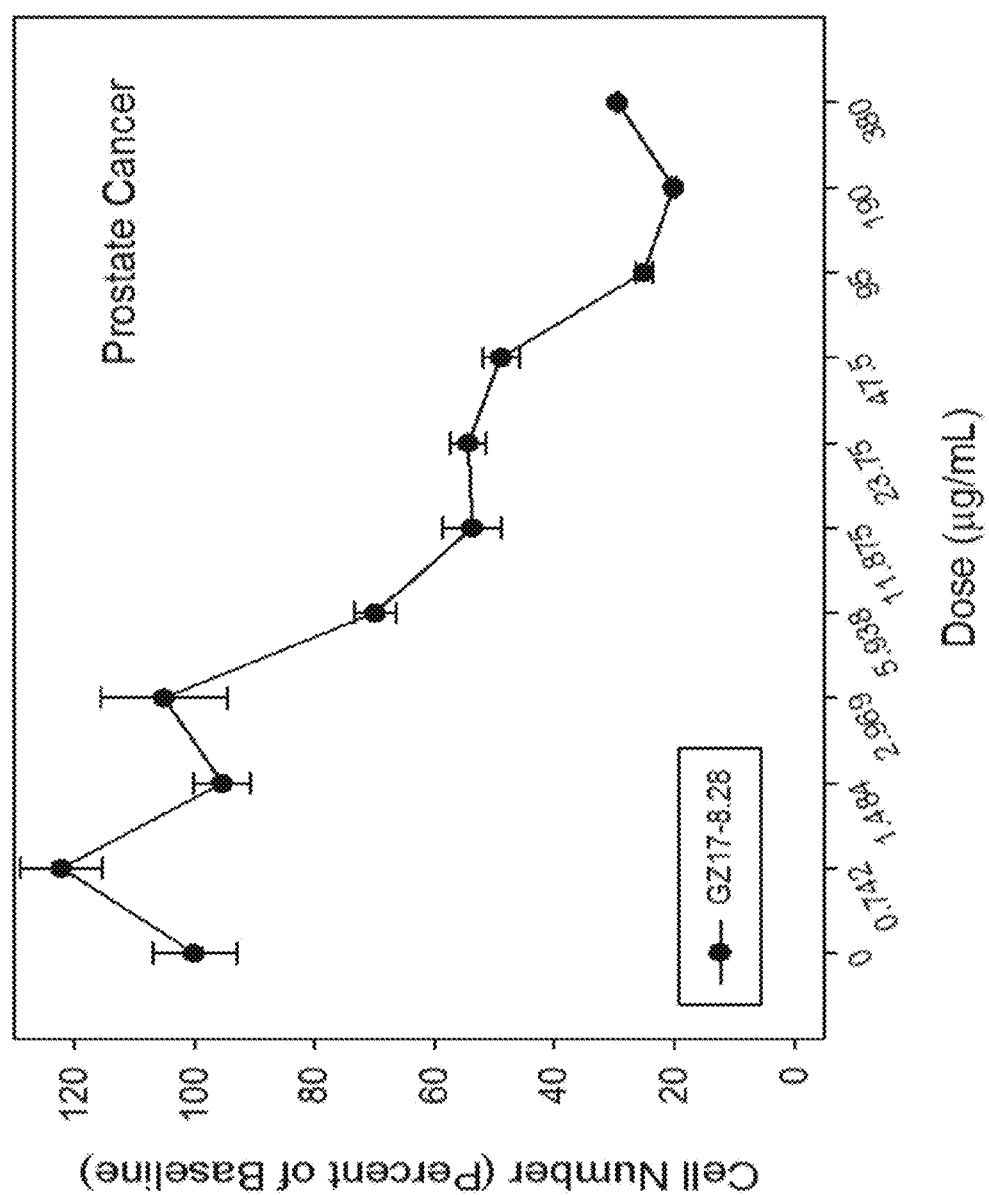
Figure 46D:
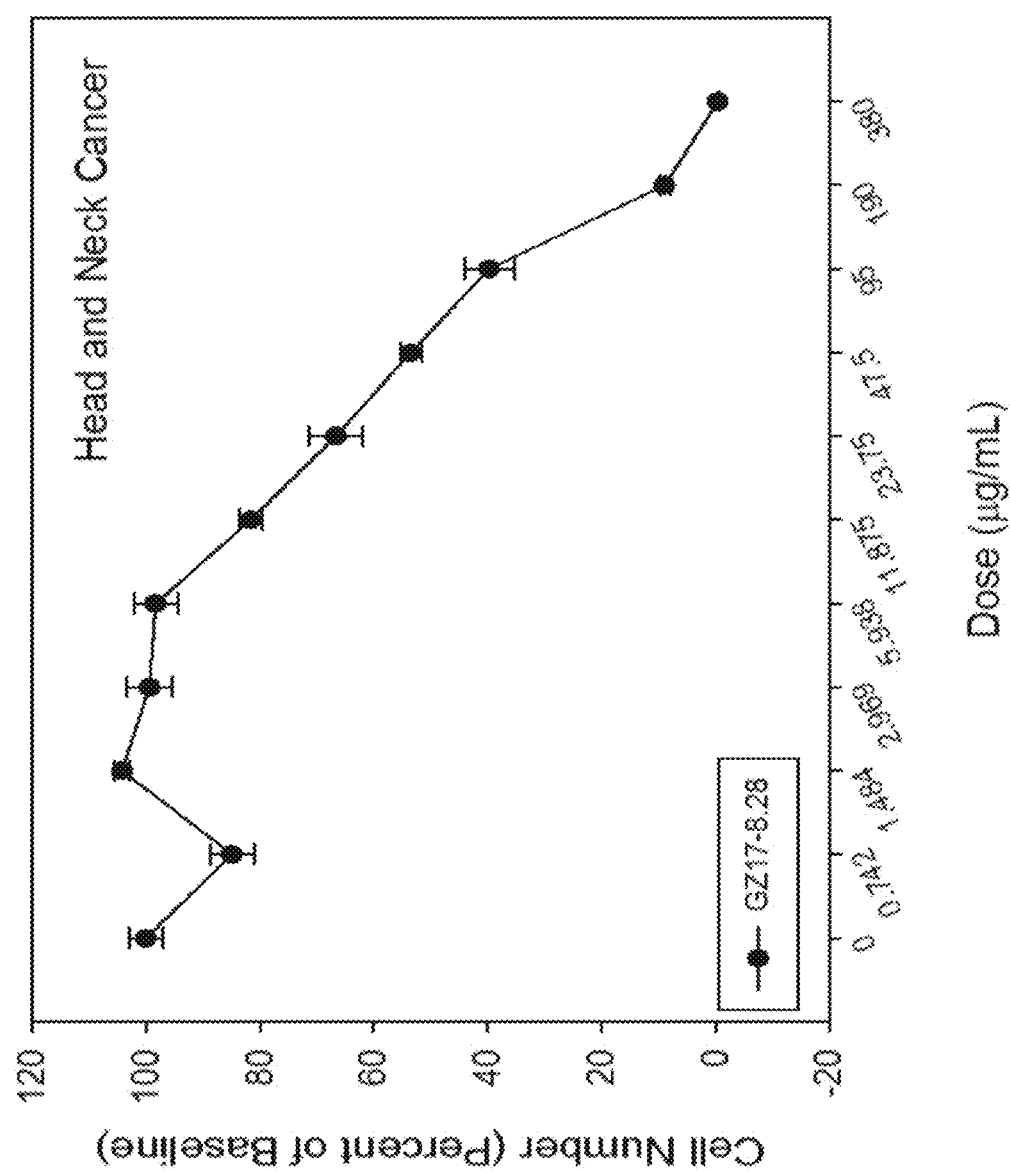
Figure 46E:
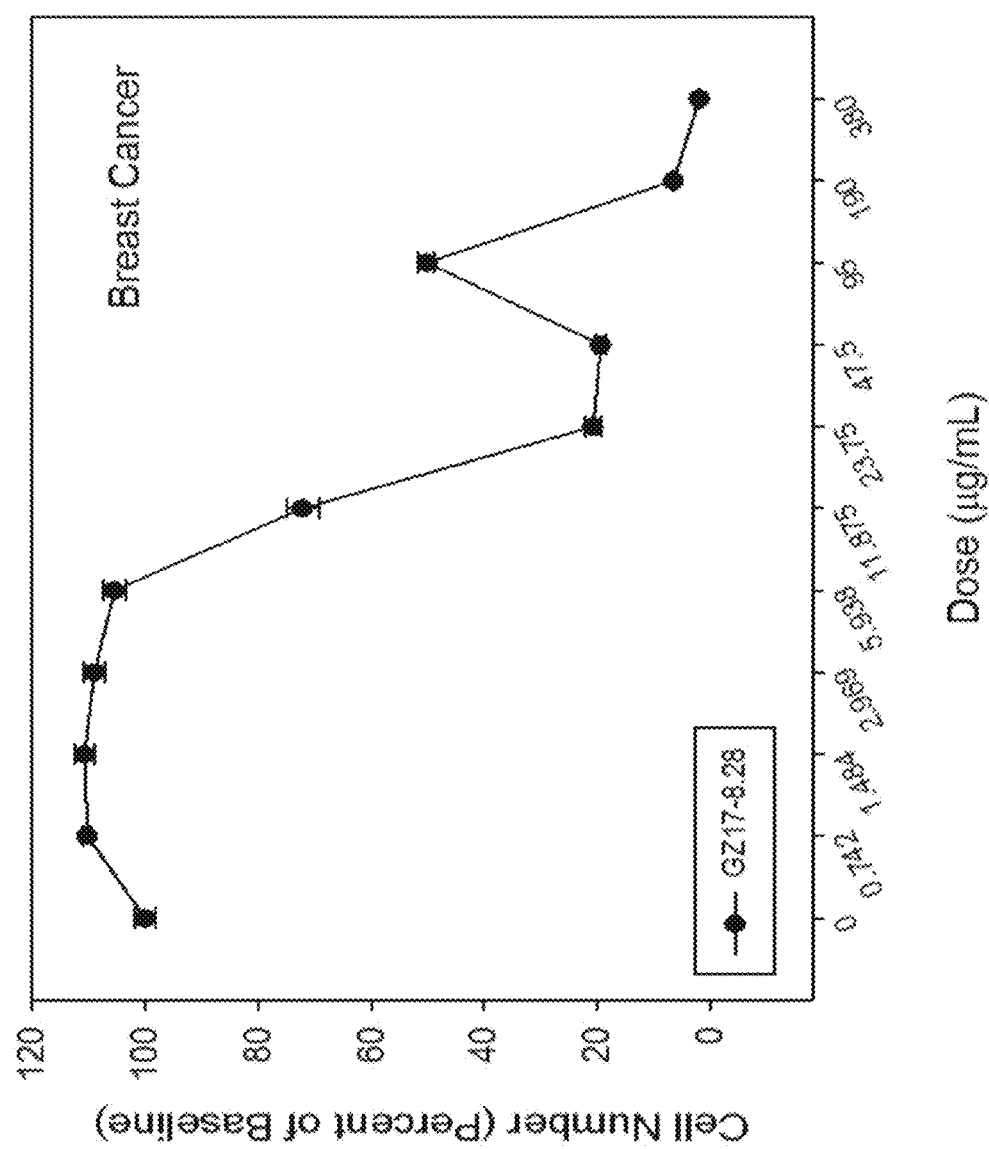
Figure 46F:
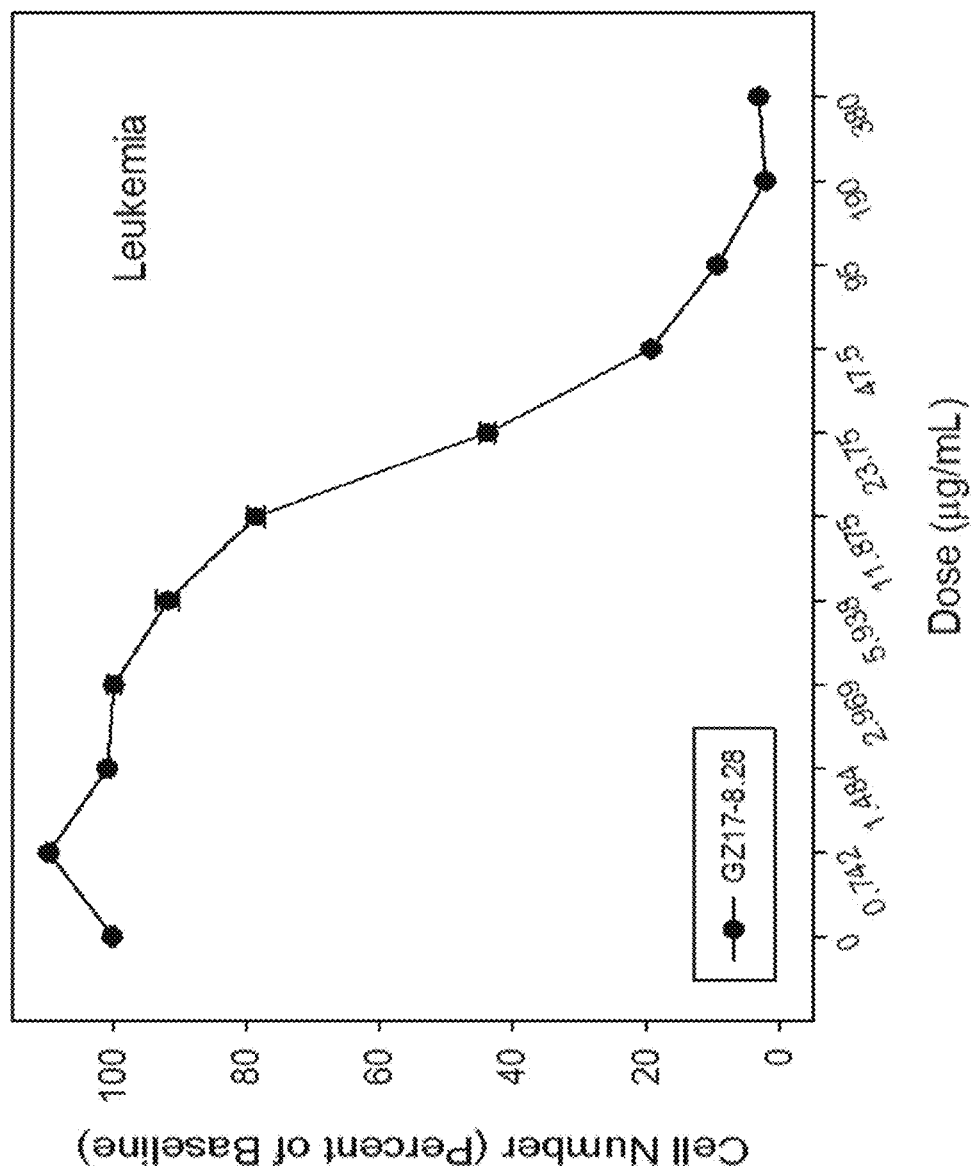
Figure 46G:
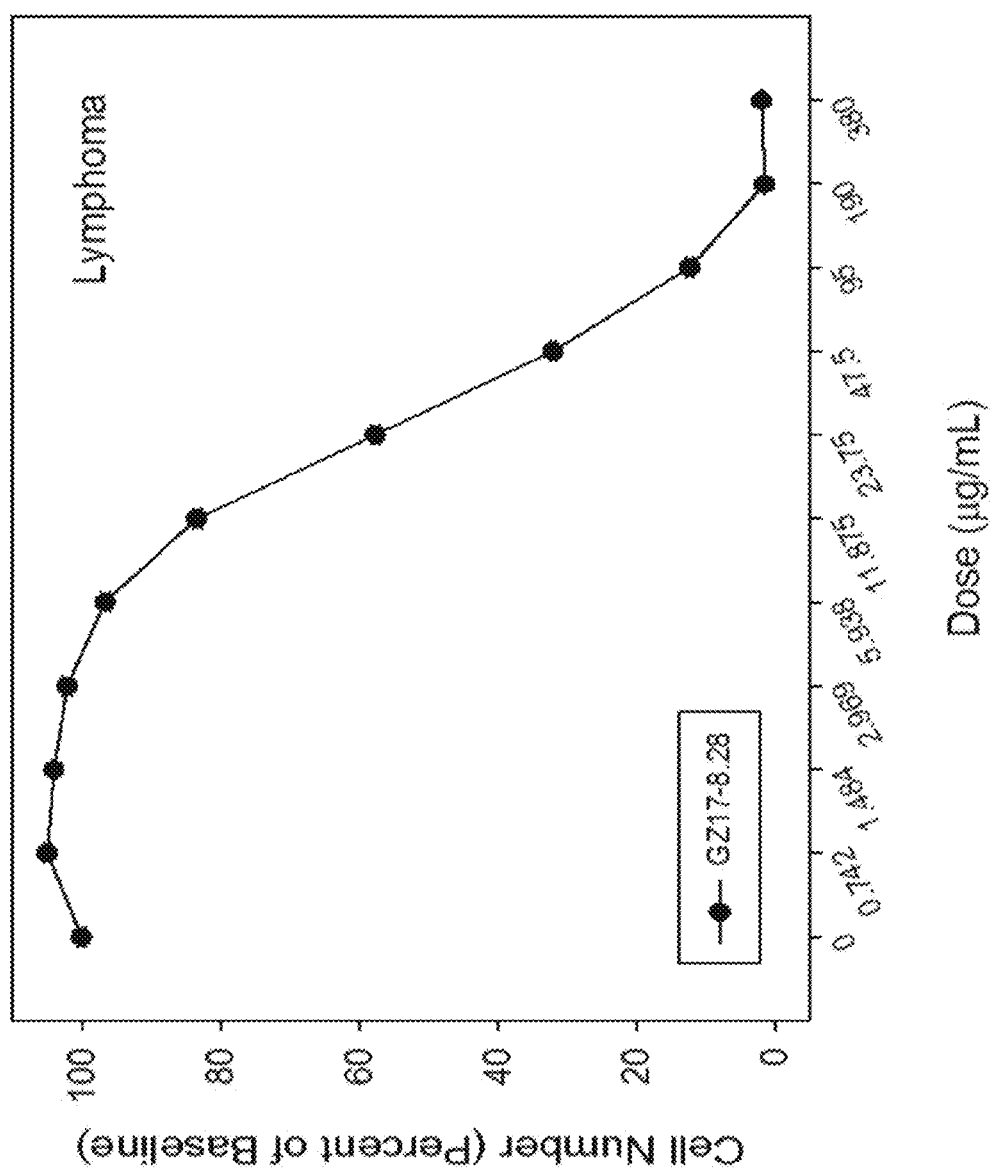
Figure 47A:
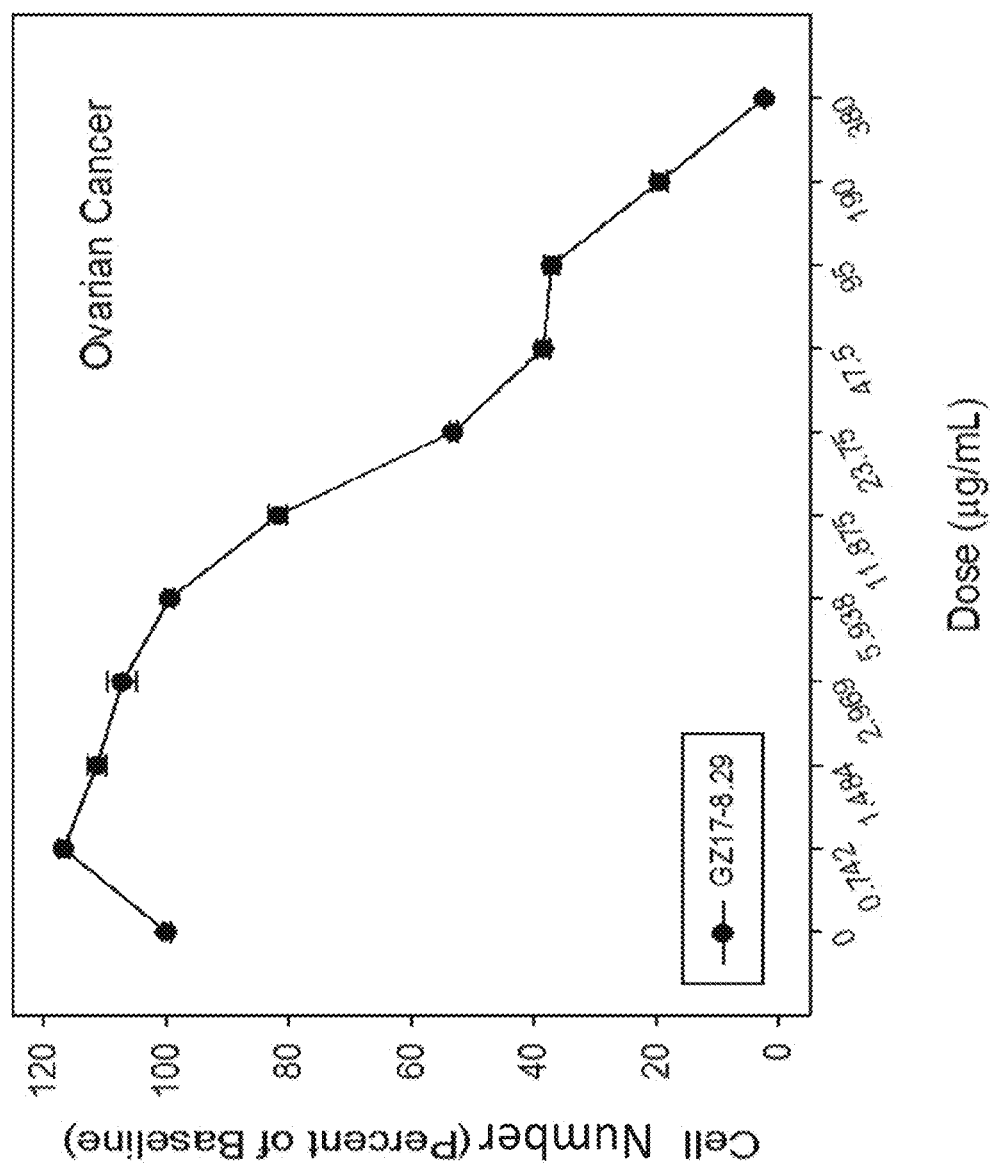
Figure 47B:
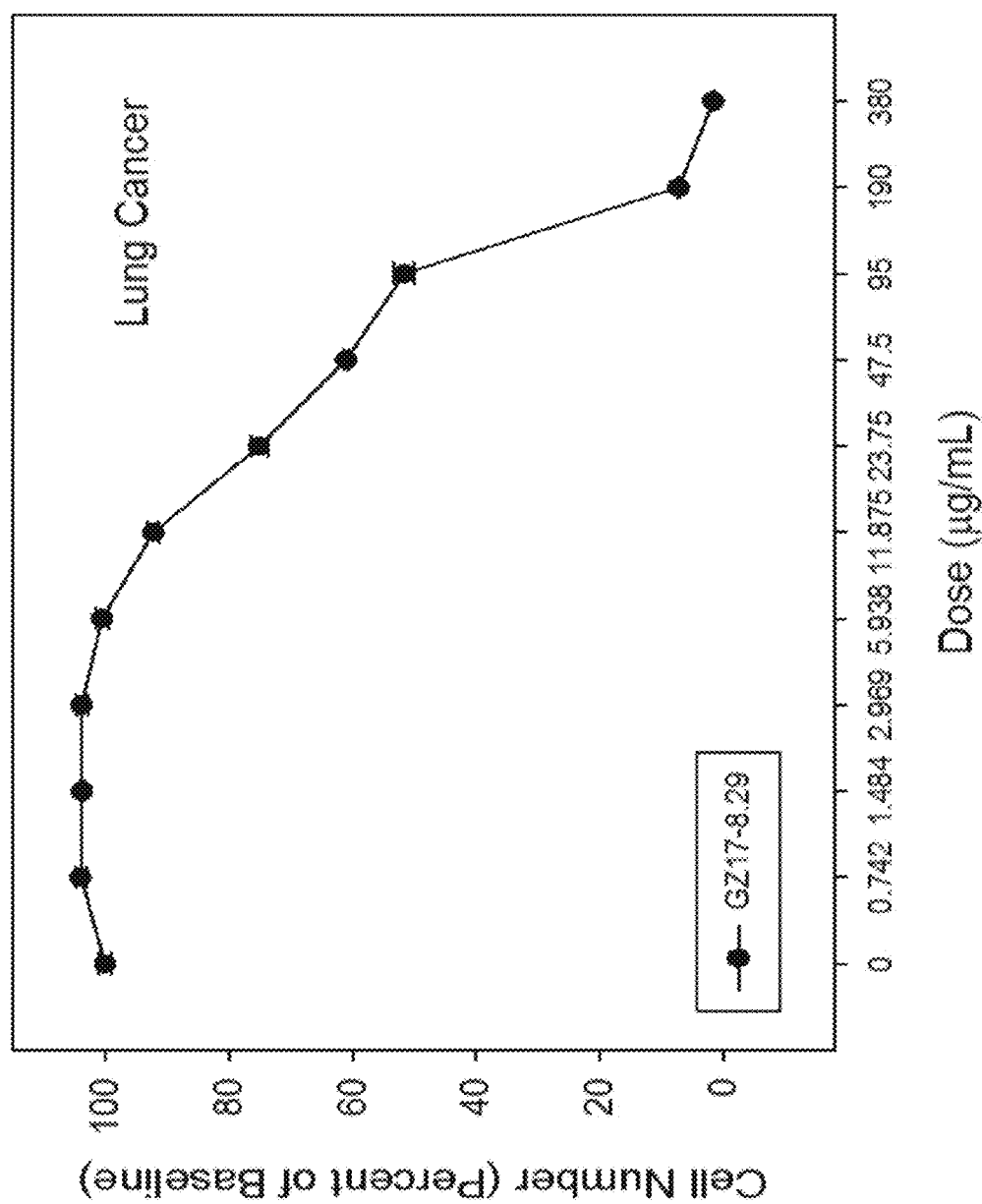
Figure 47C:
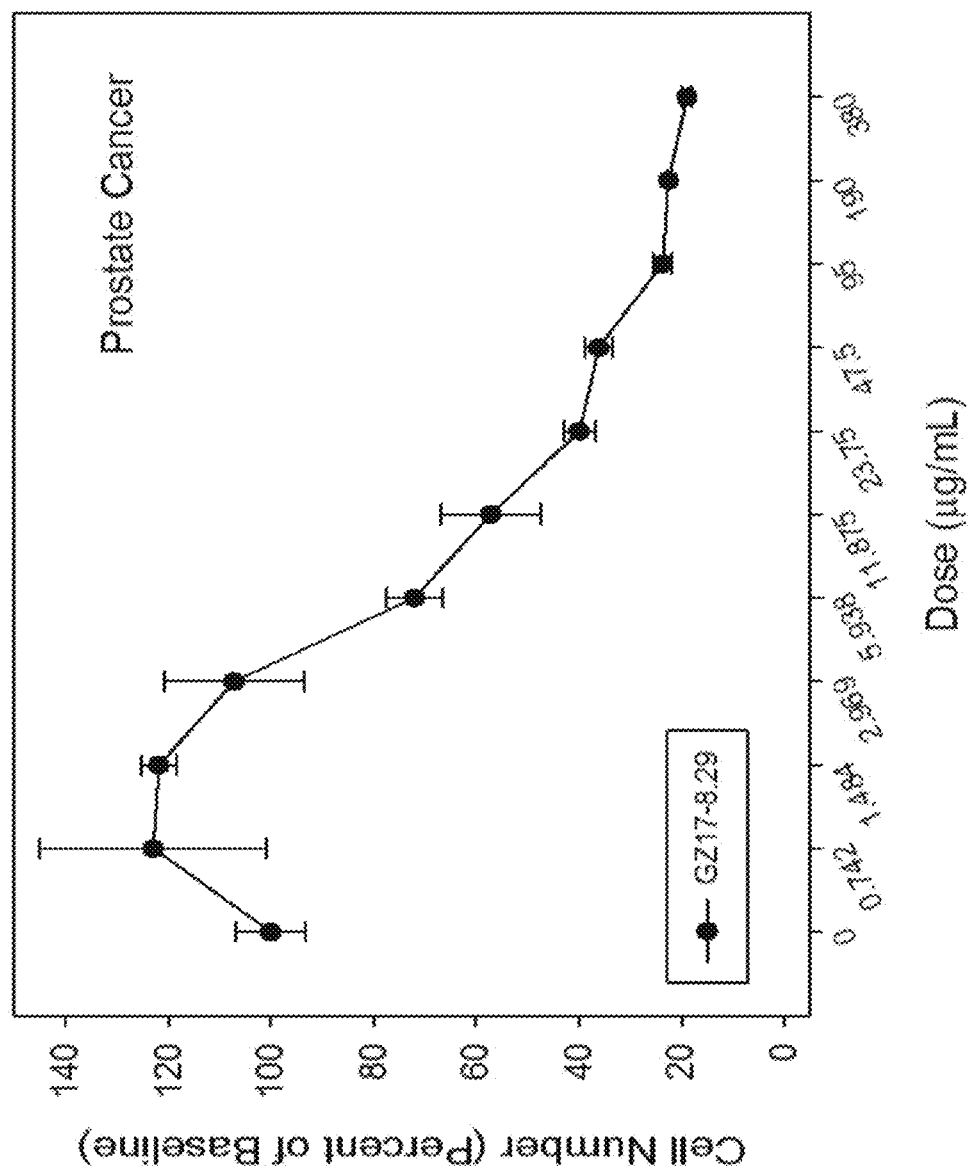
Figure 47D:
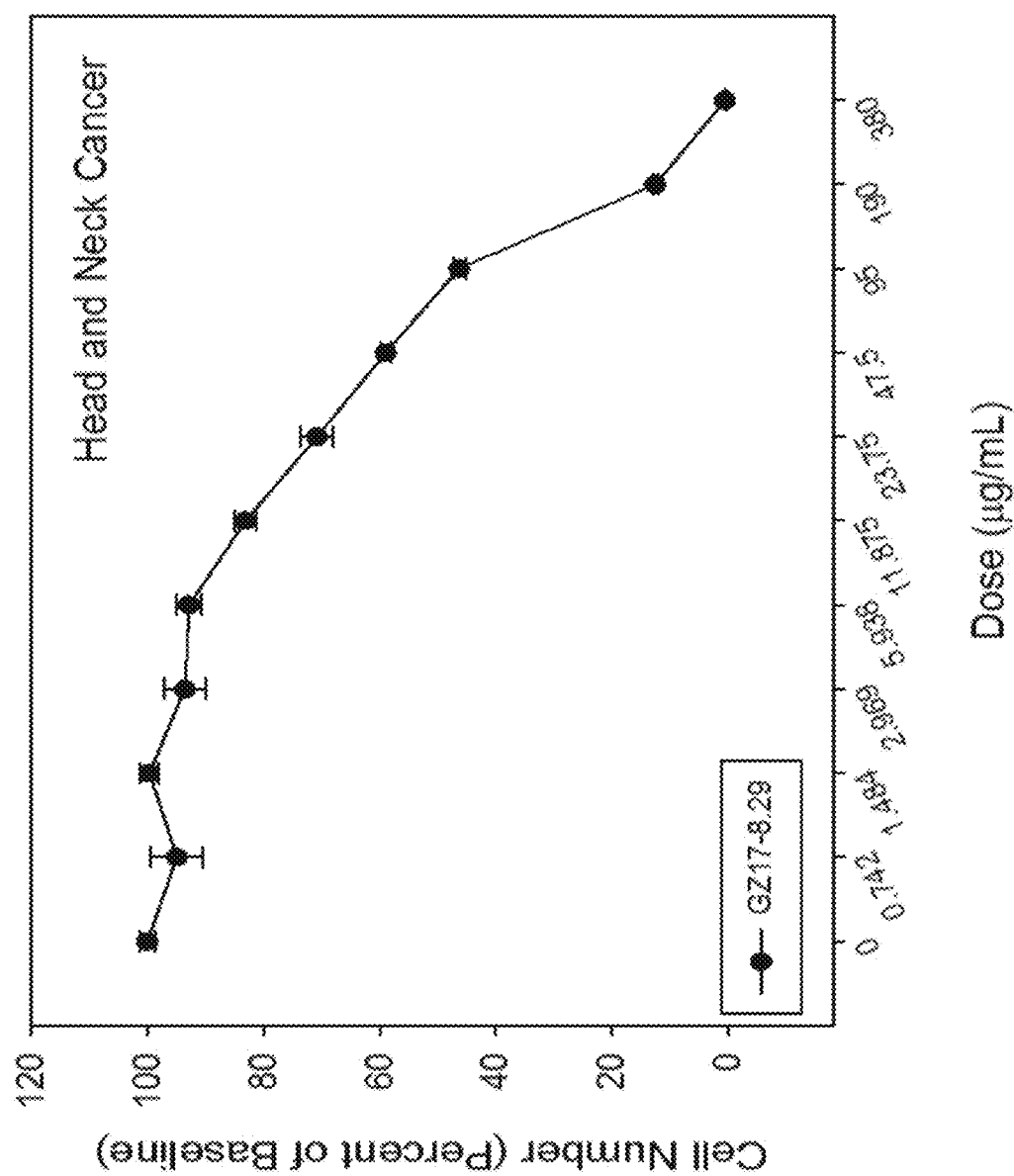
Figure 47E:
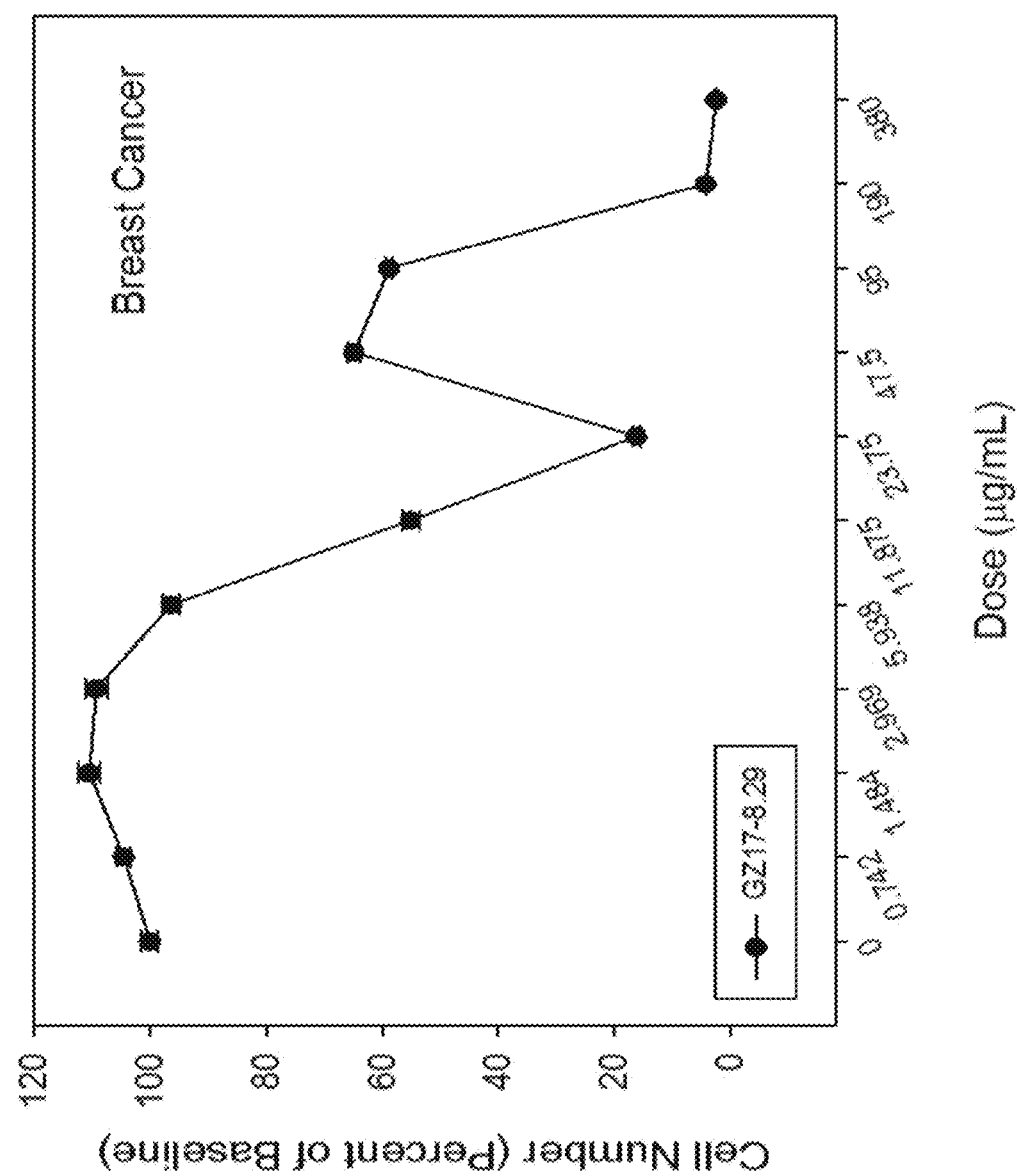
Figure 47F:
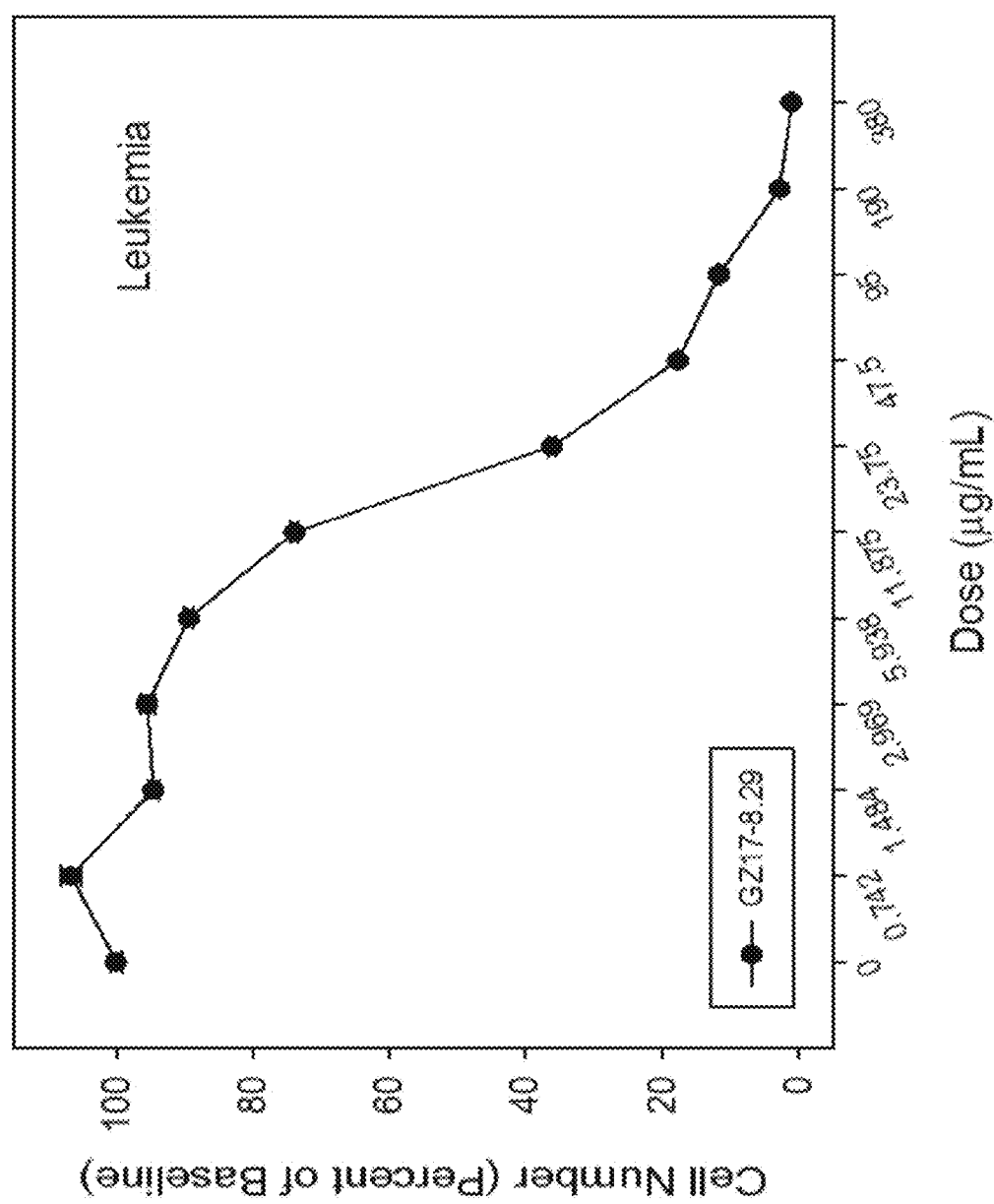
Figure 47G:
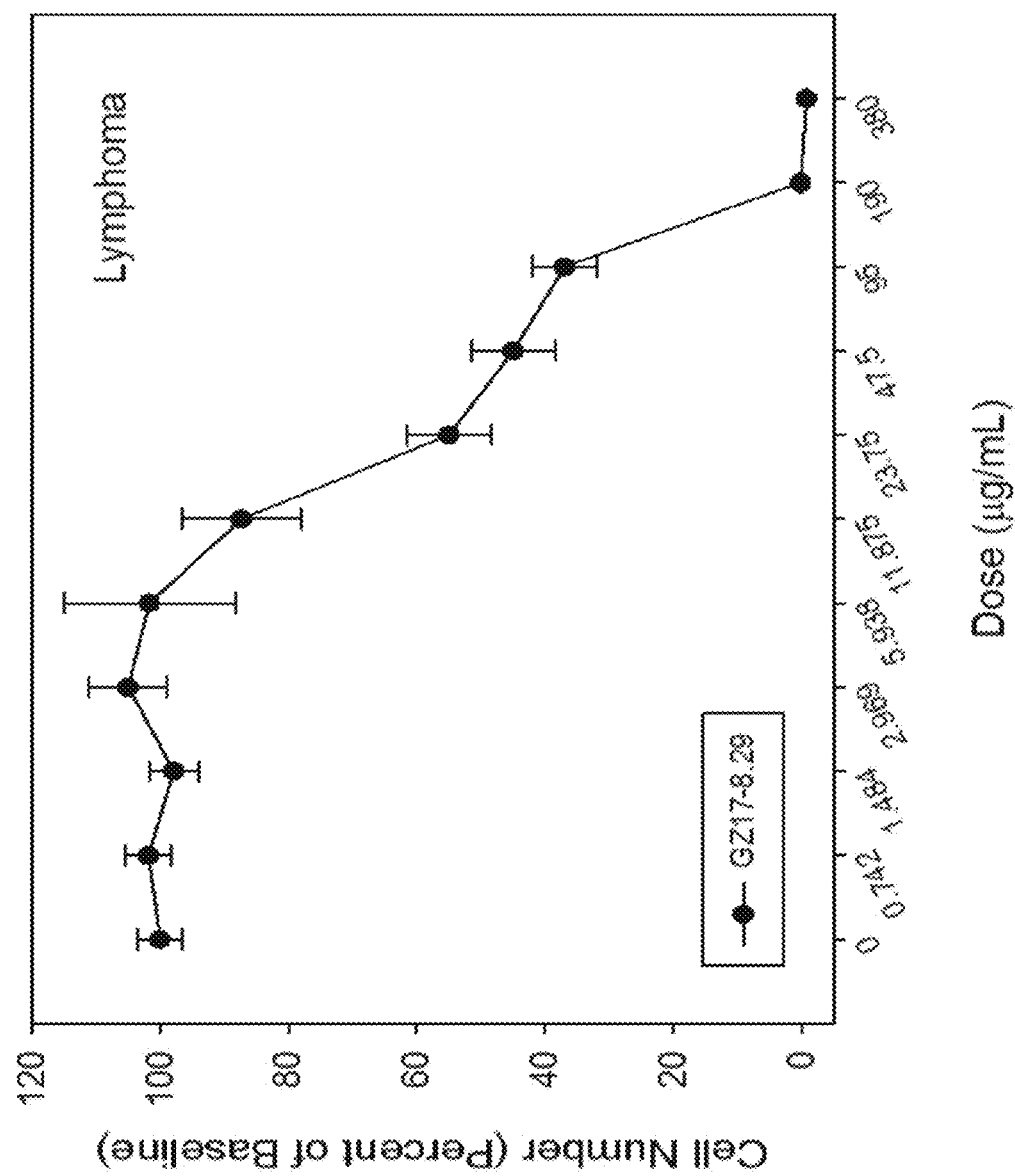
Figure 48A:
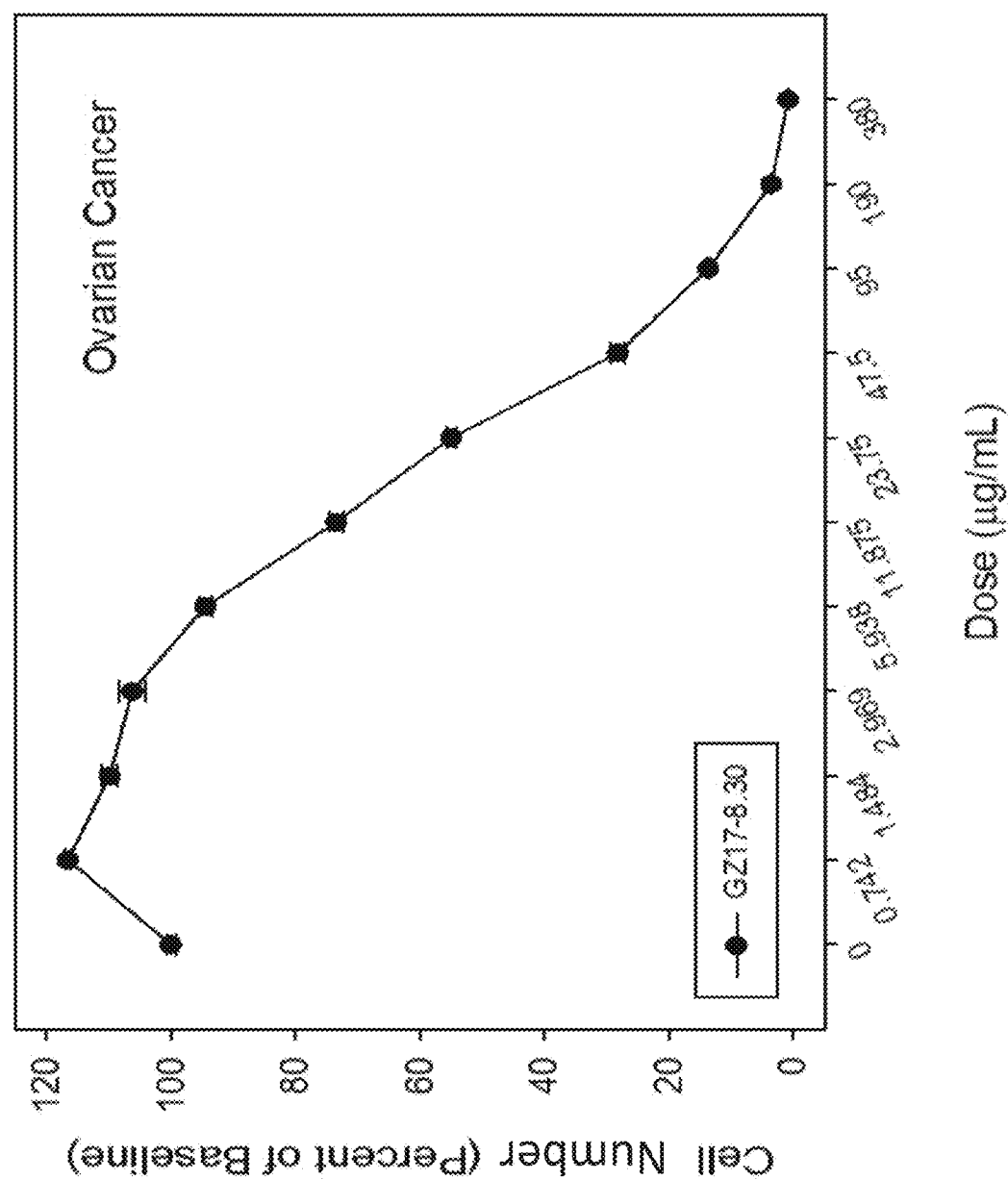
Figure 48B:
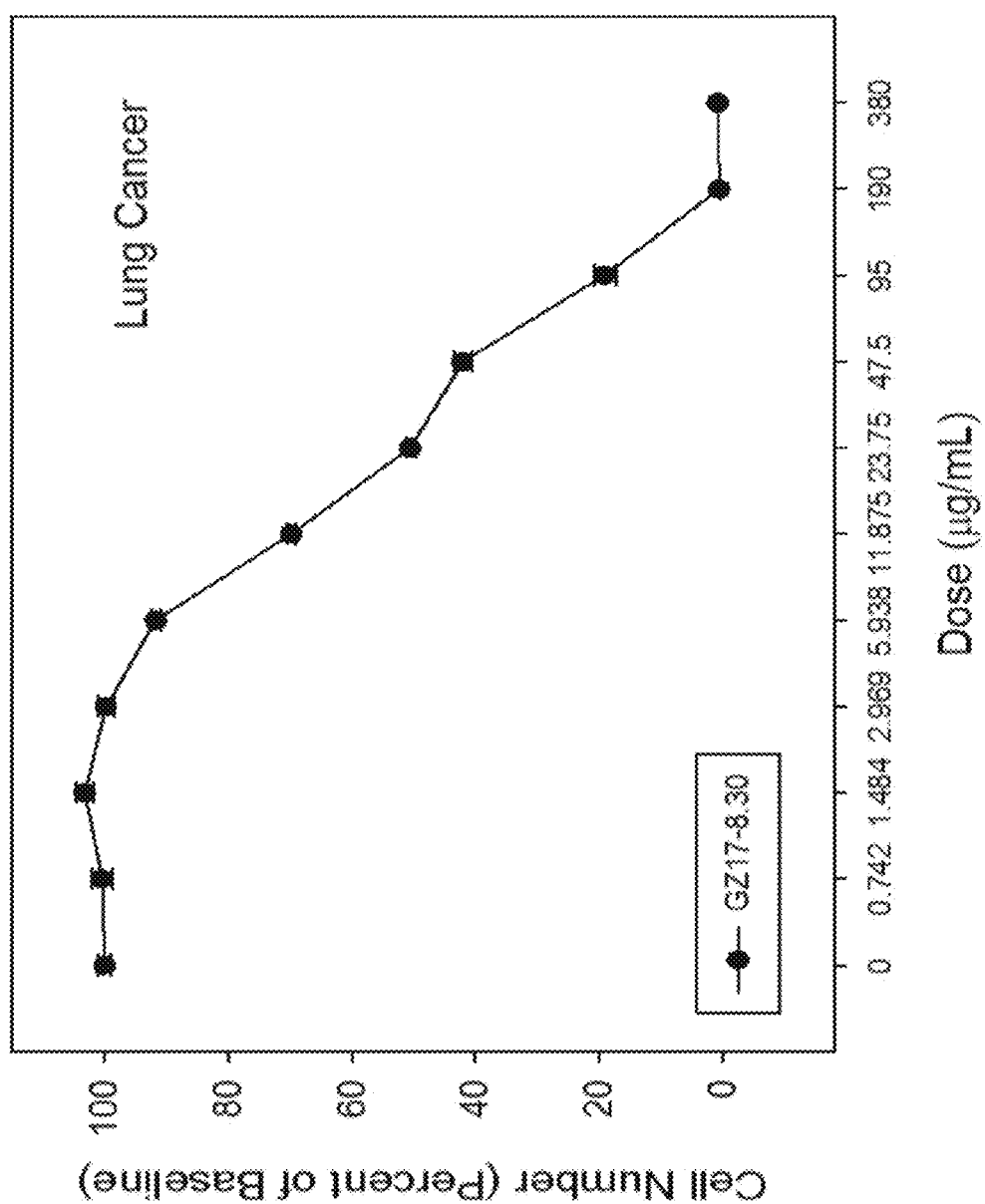
Figure 48C:
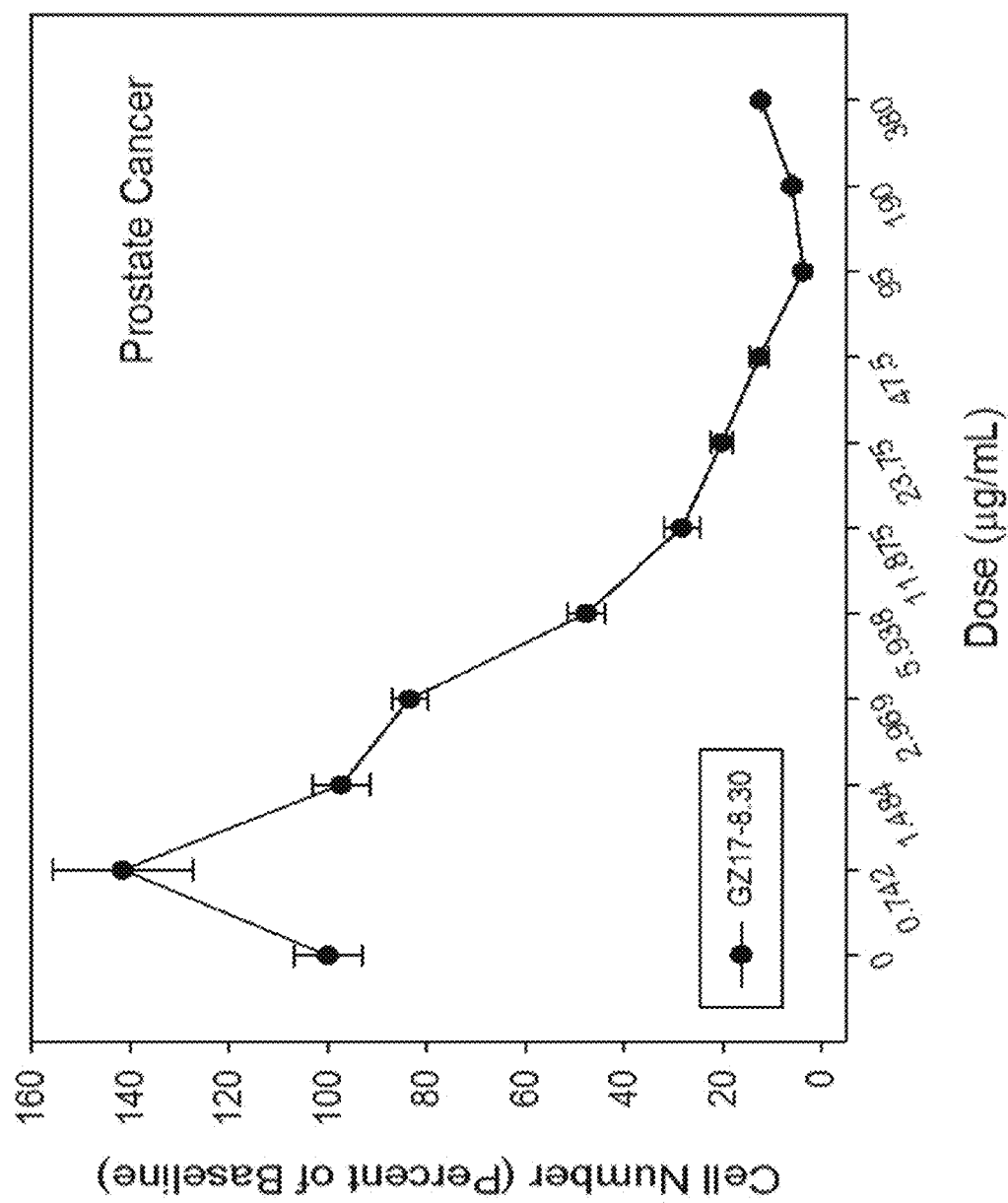
Figure 48D:
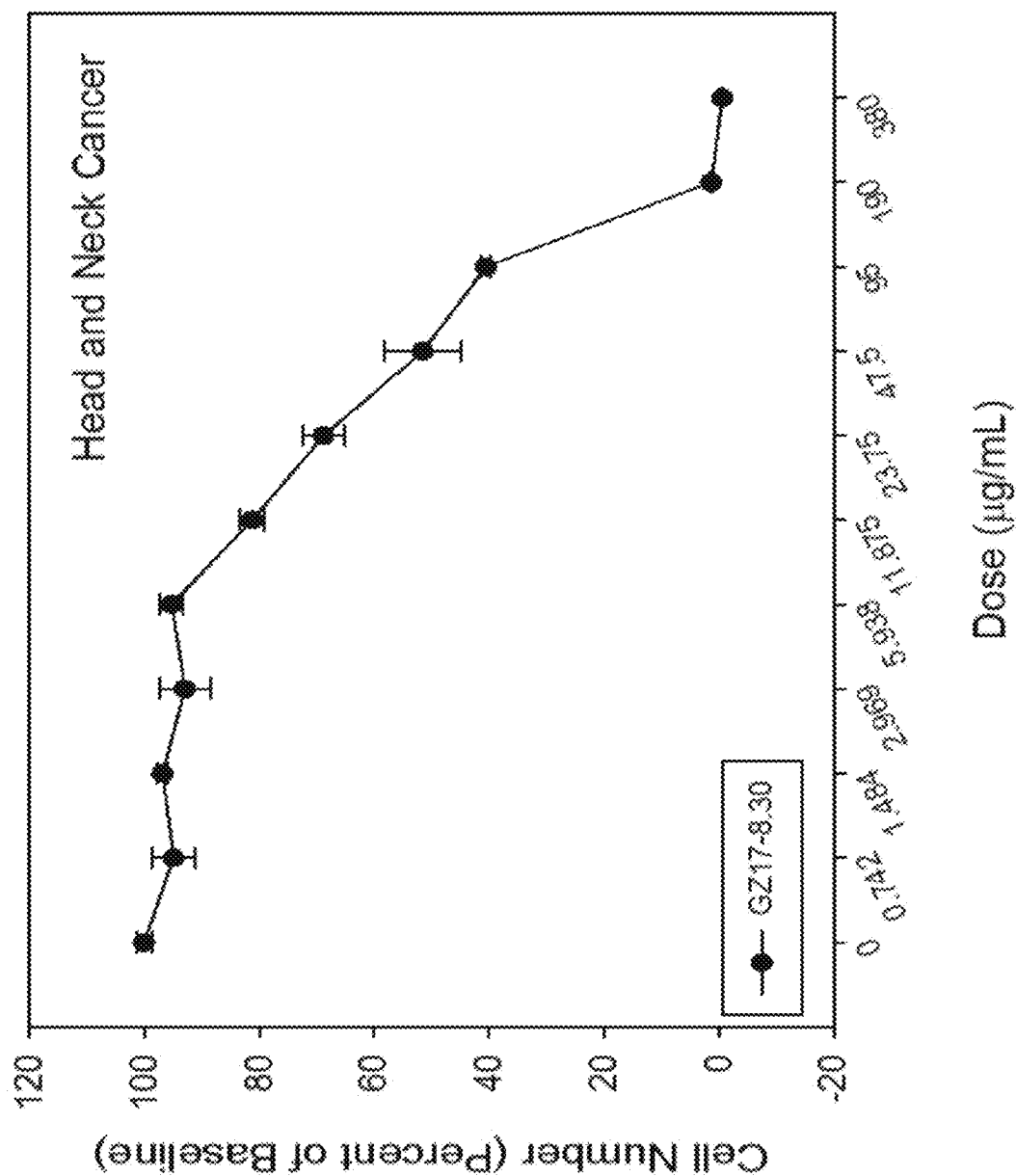
Figure 48E:
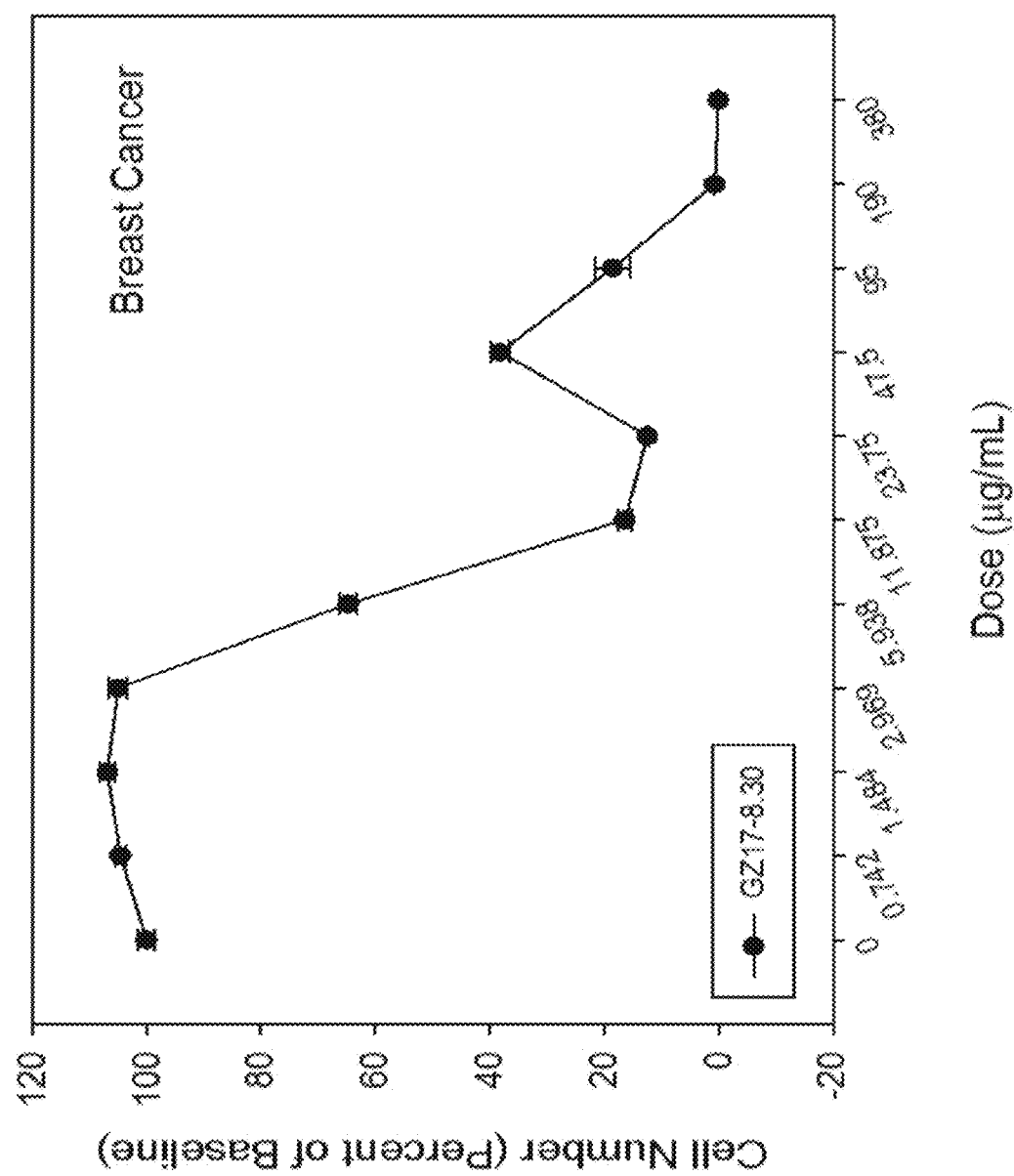
Figure 48F:
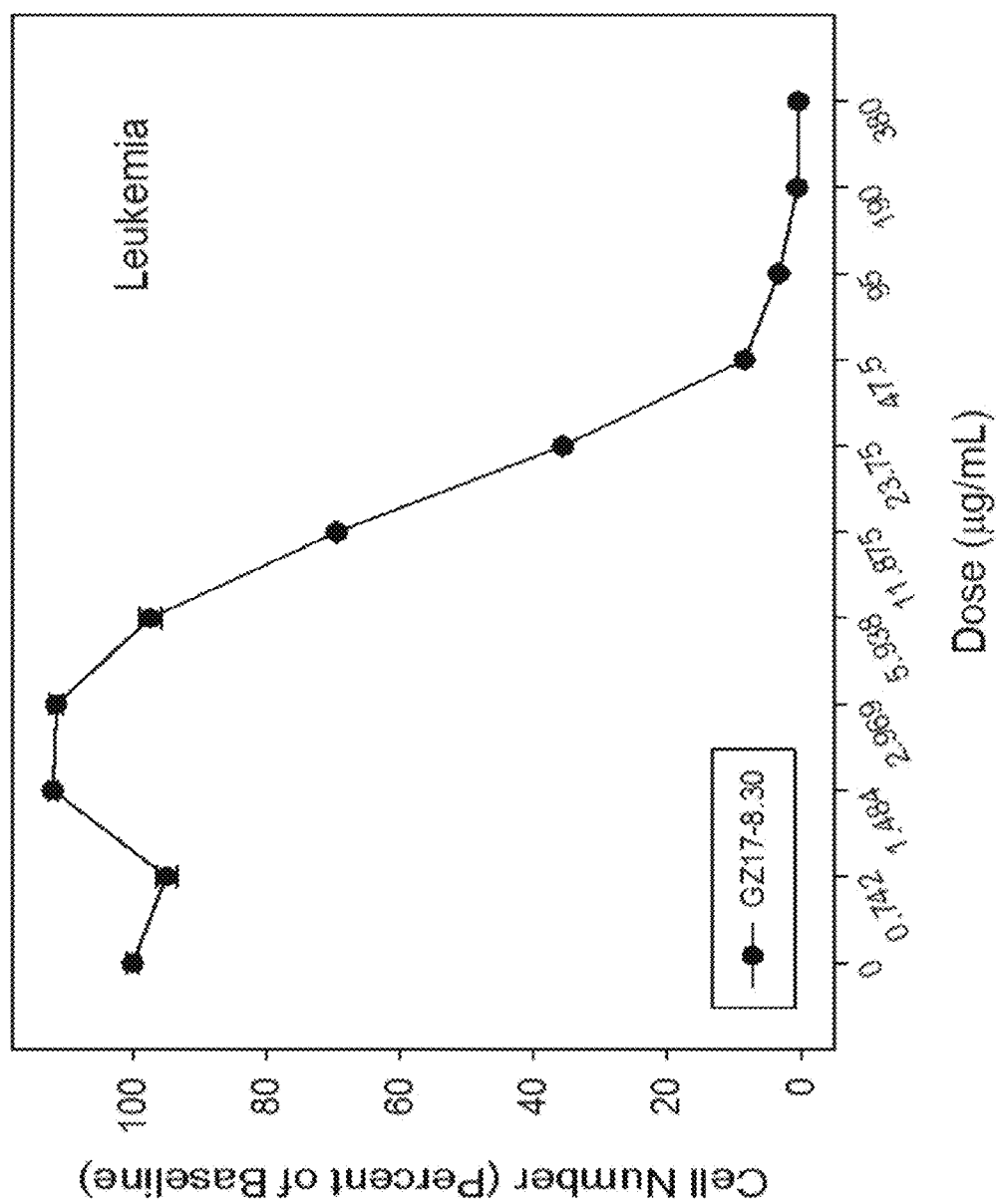
Figure 48G:
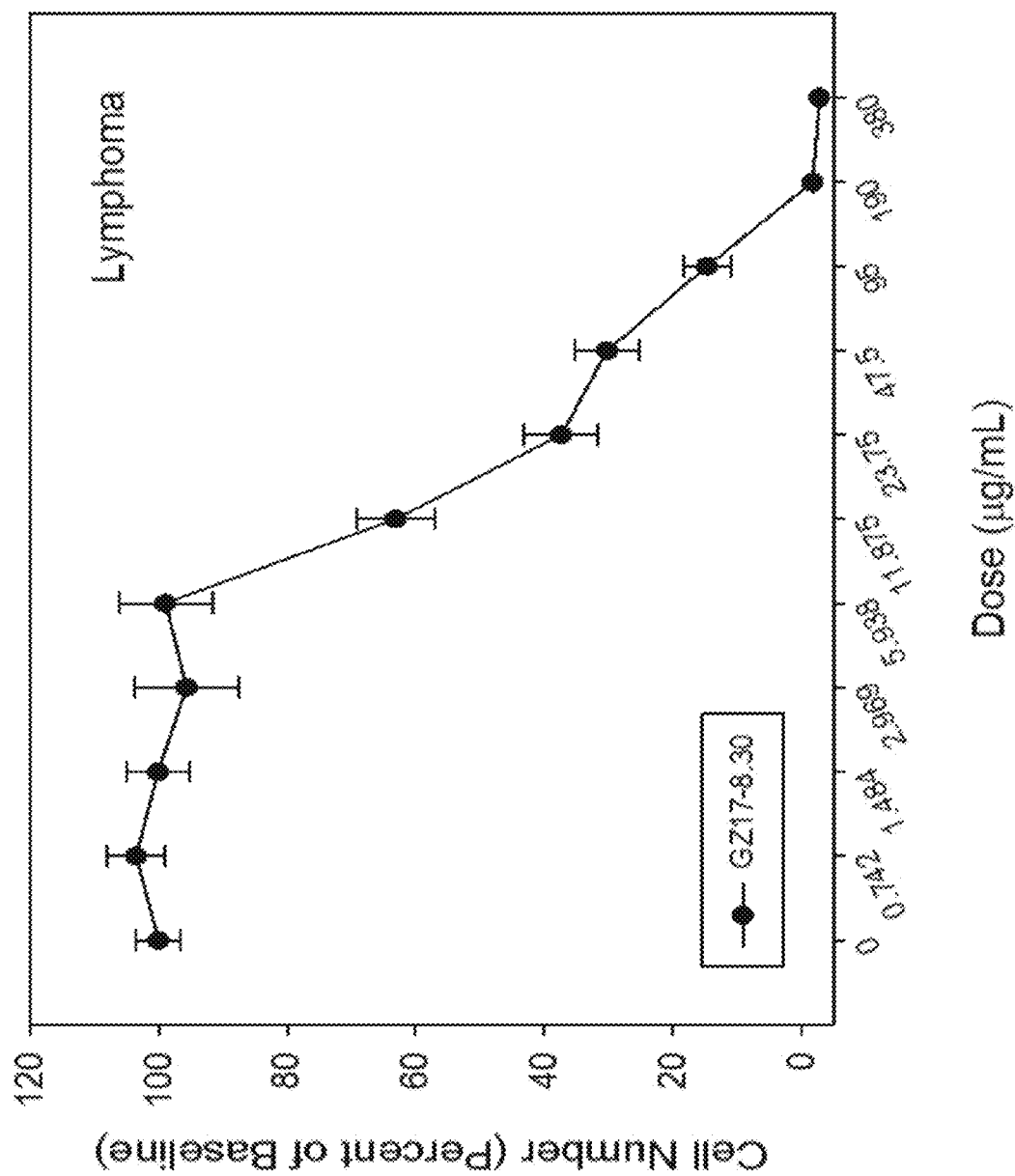
Figure 49A:
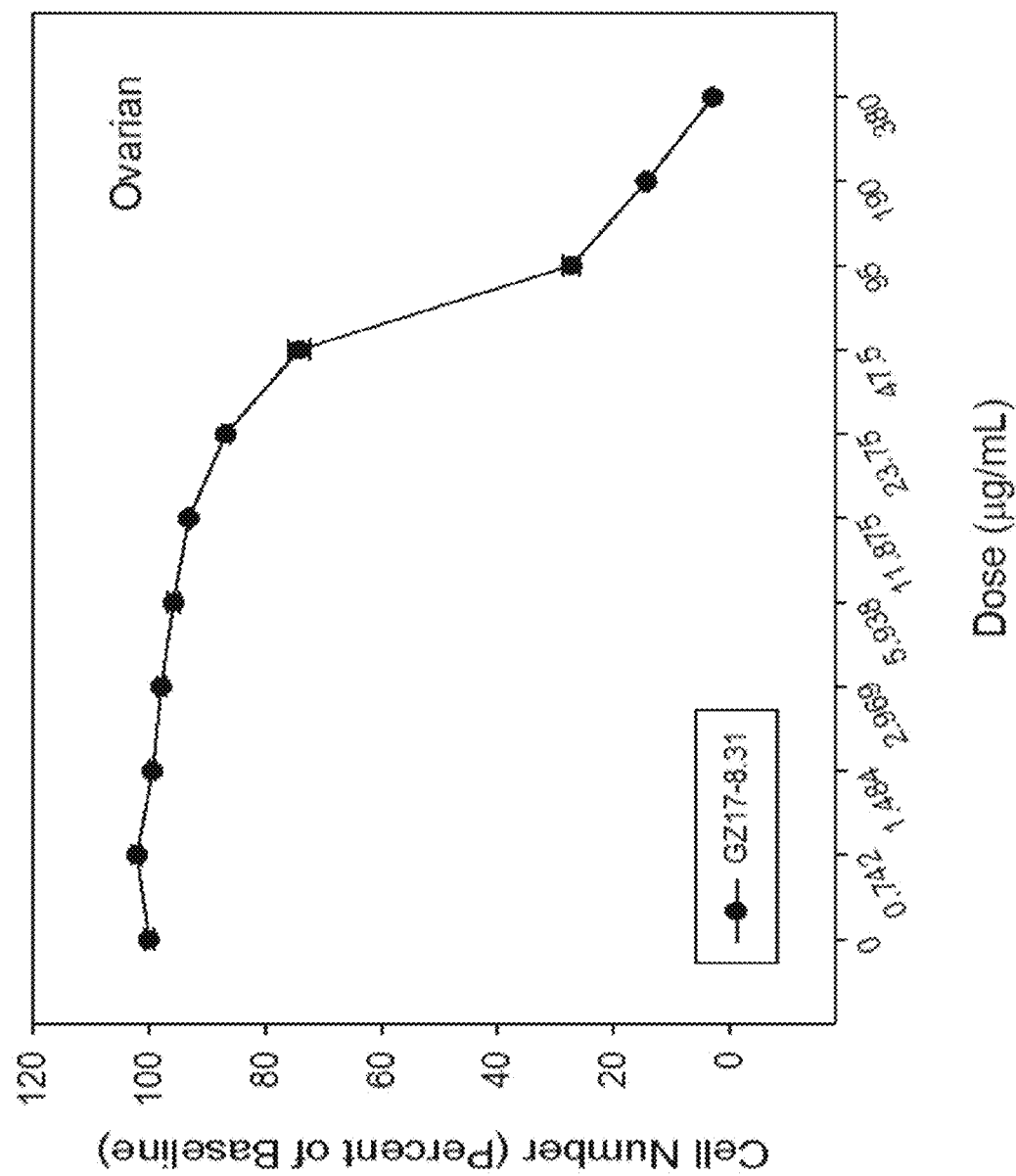
Figure 49B:
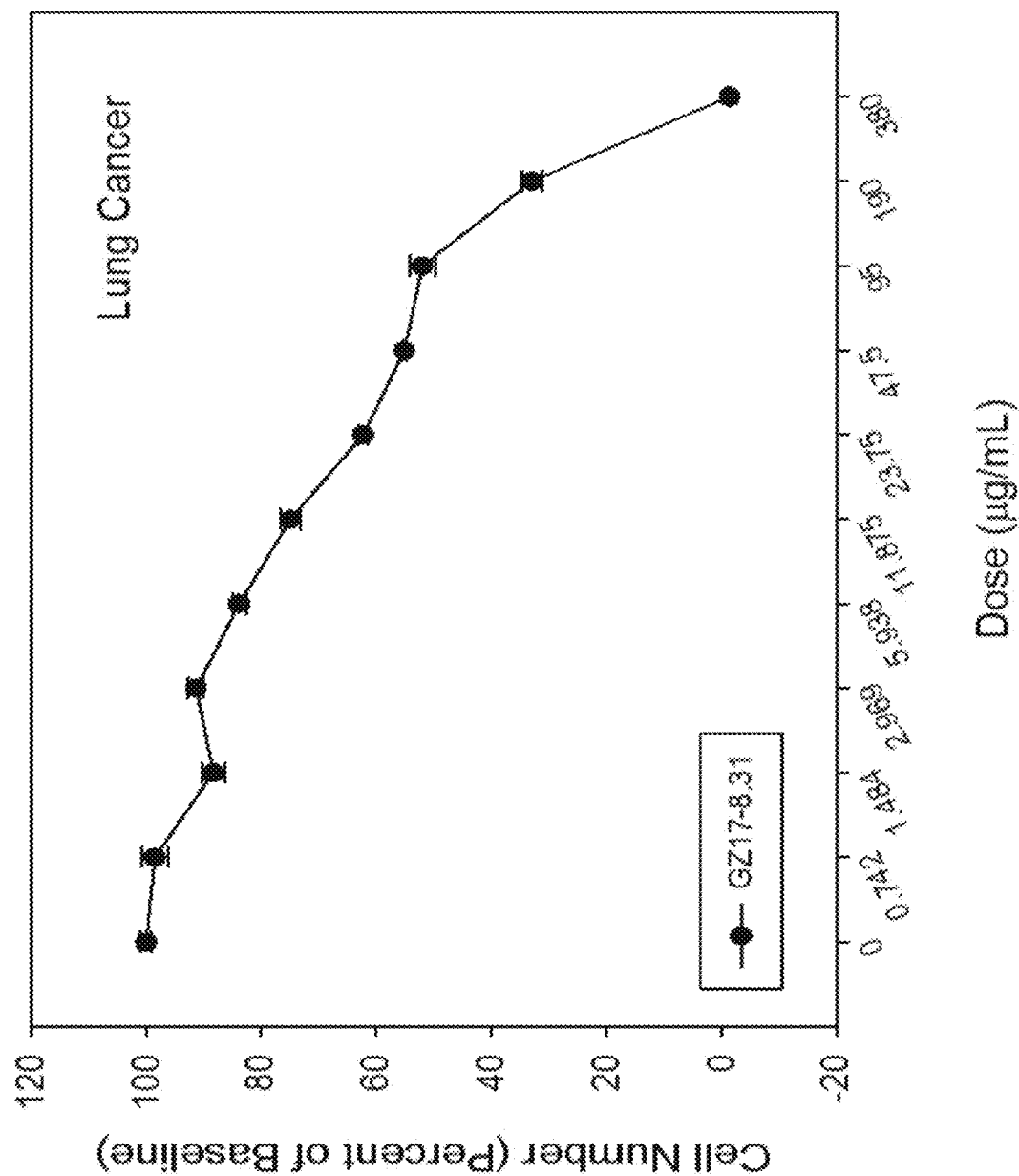
Figure 49C:
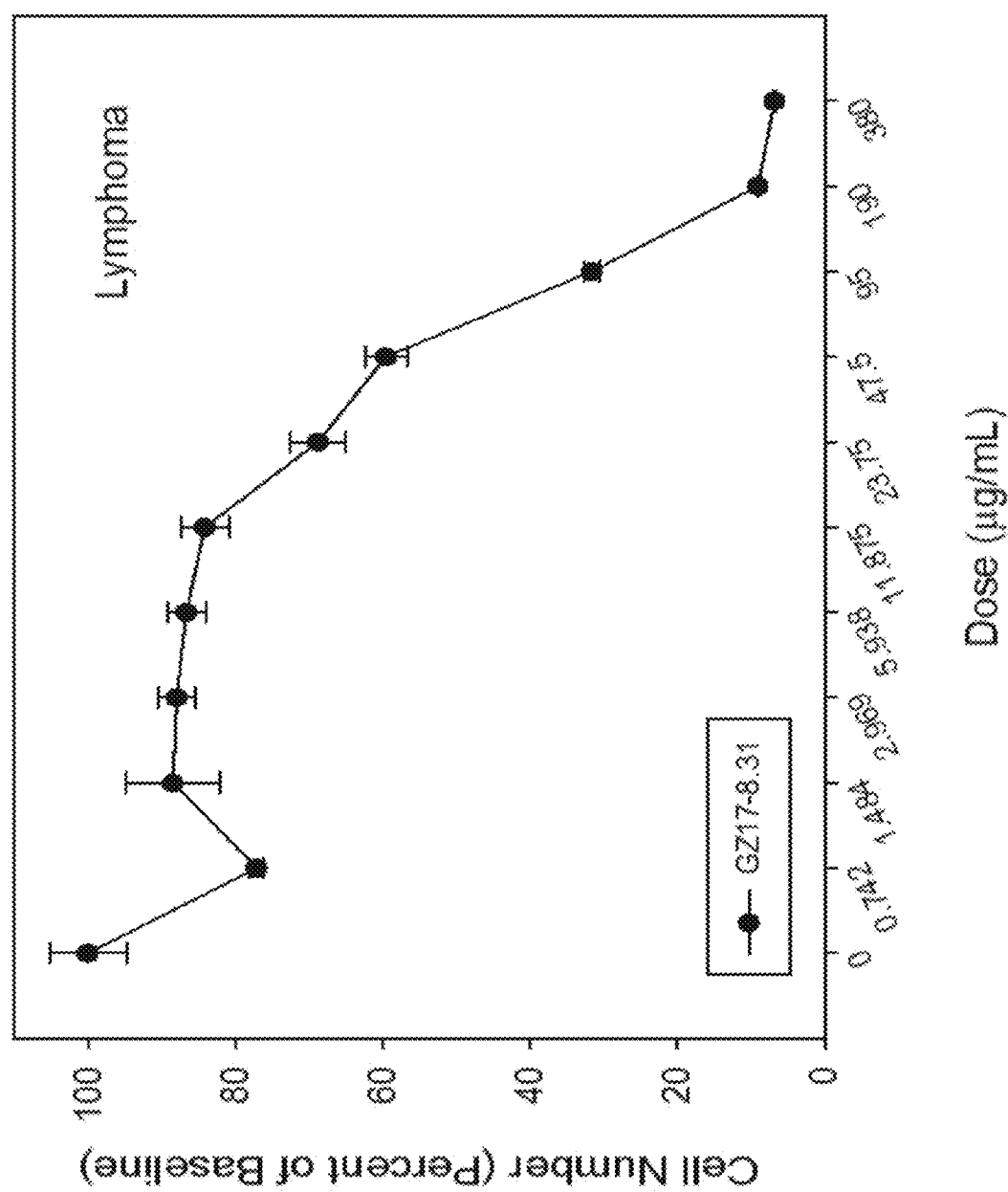
Figure 49D:
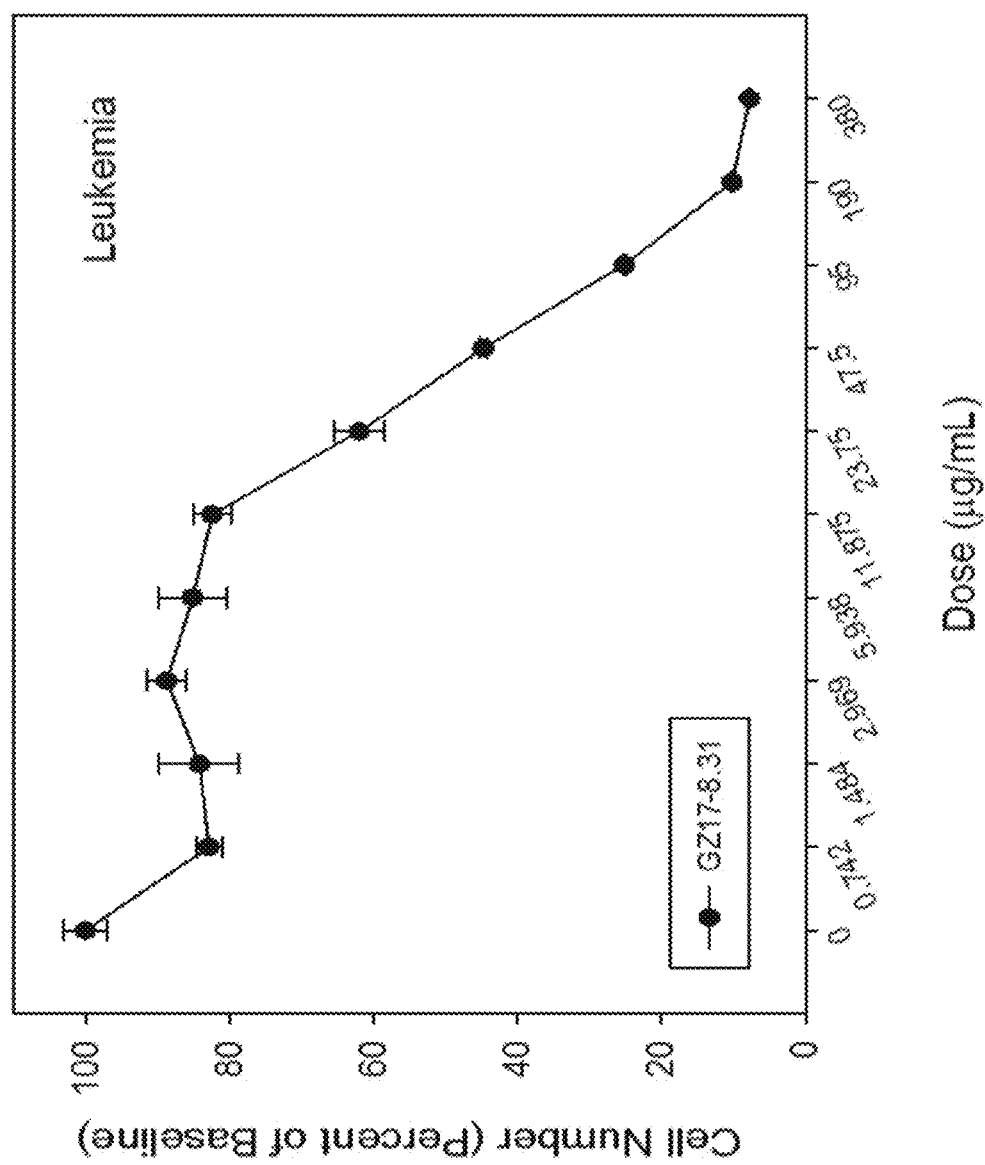
Figure 50A:
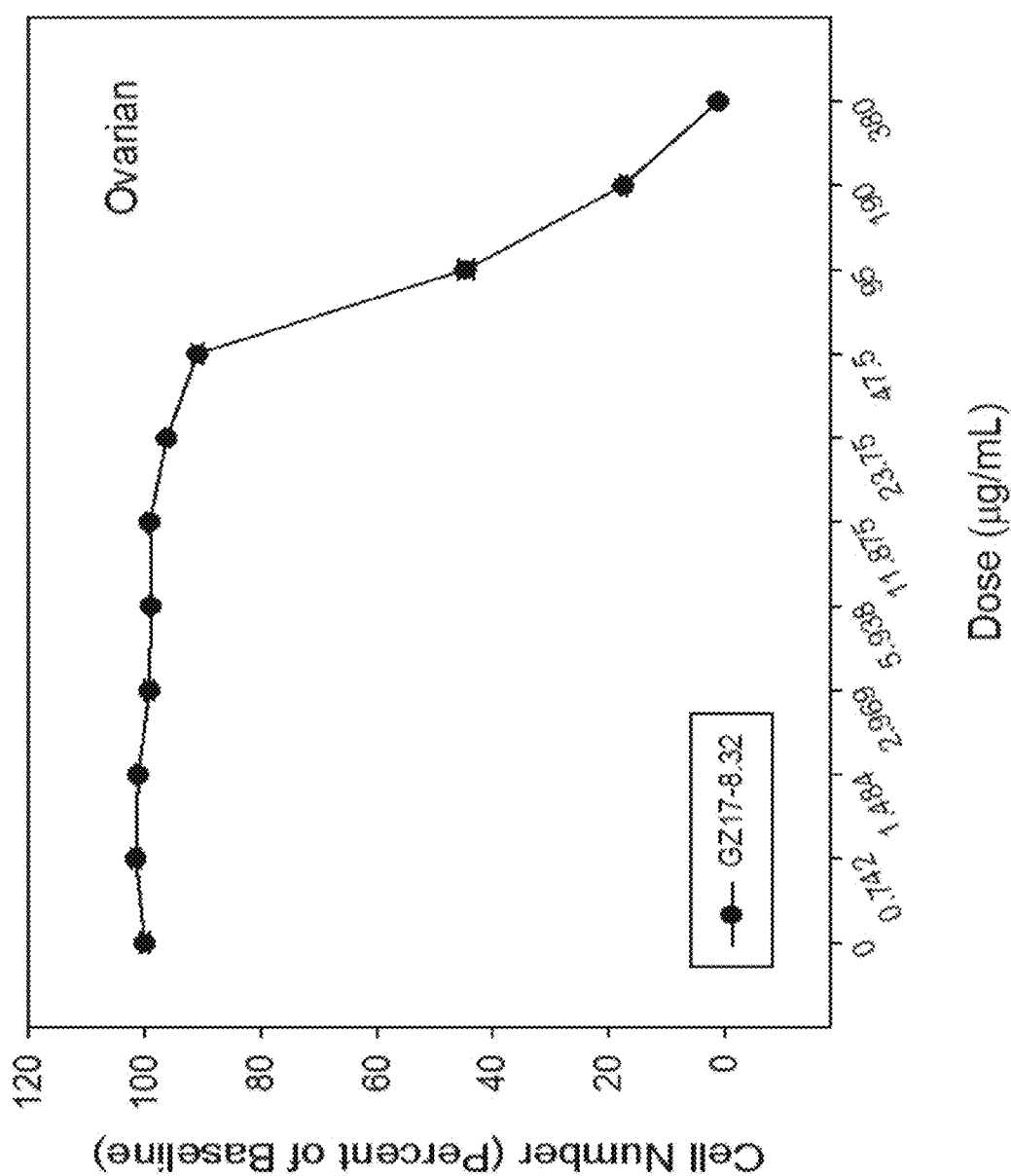
Figure 50B:
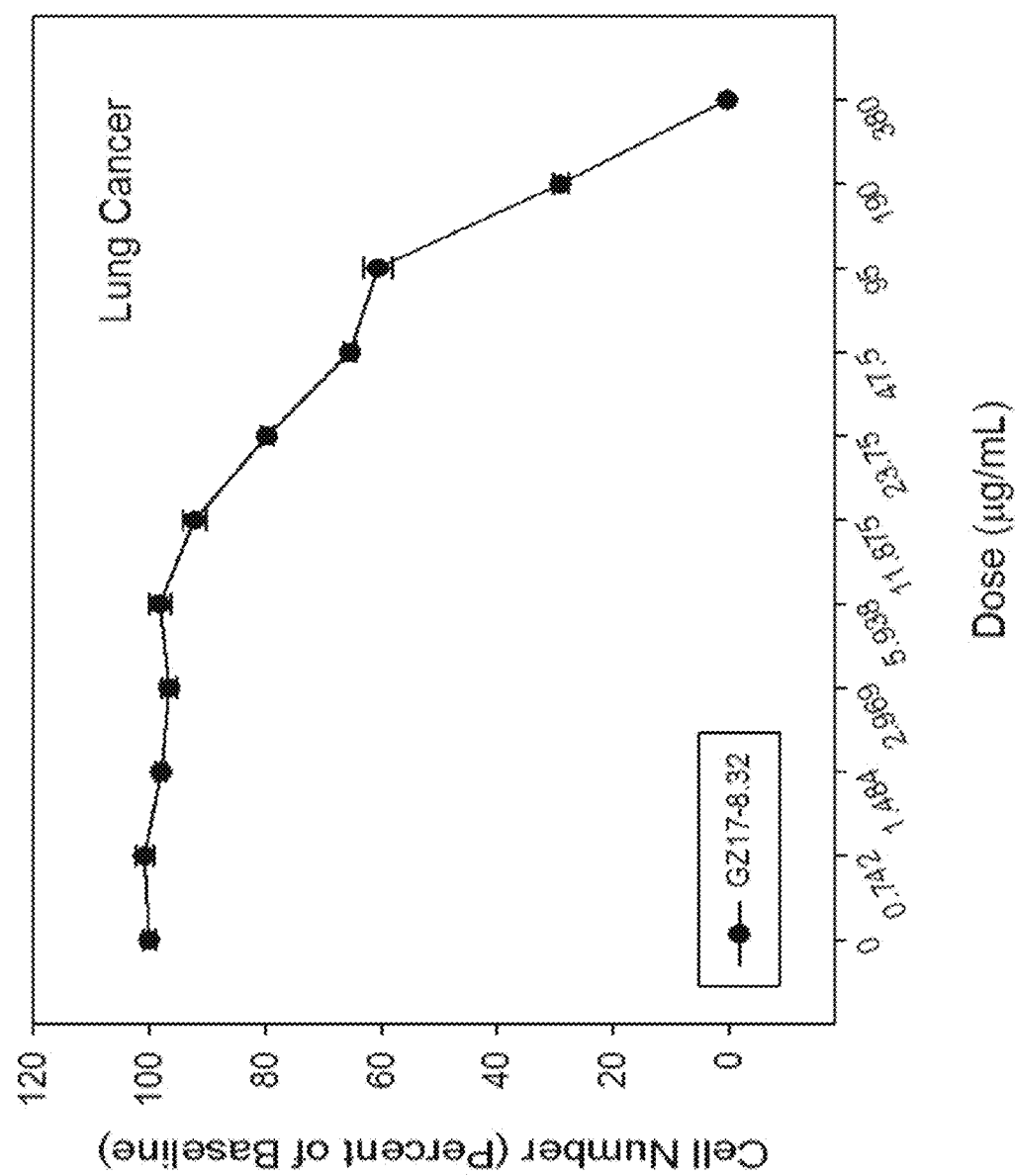
Figure 50C:
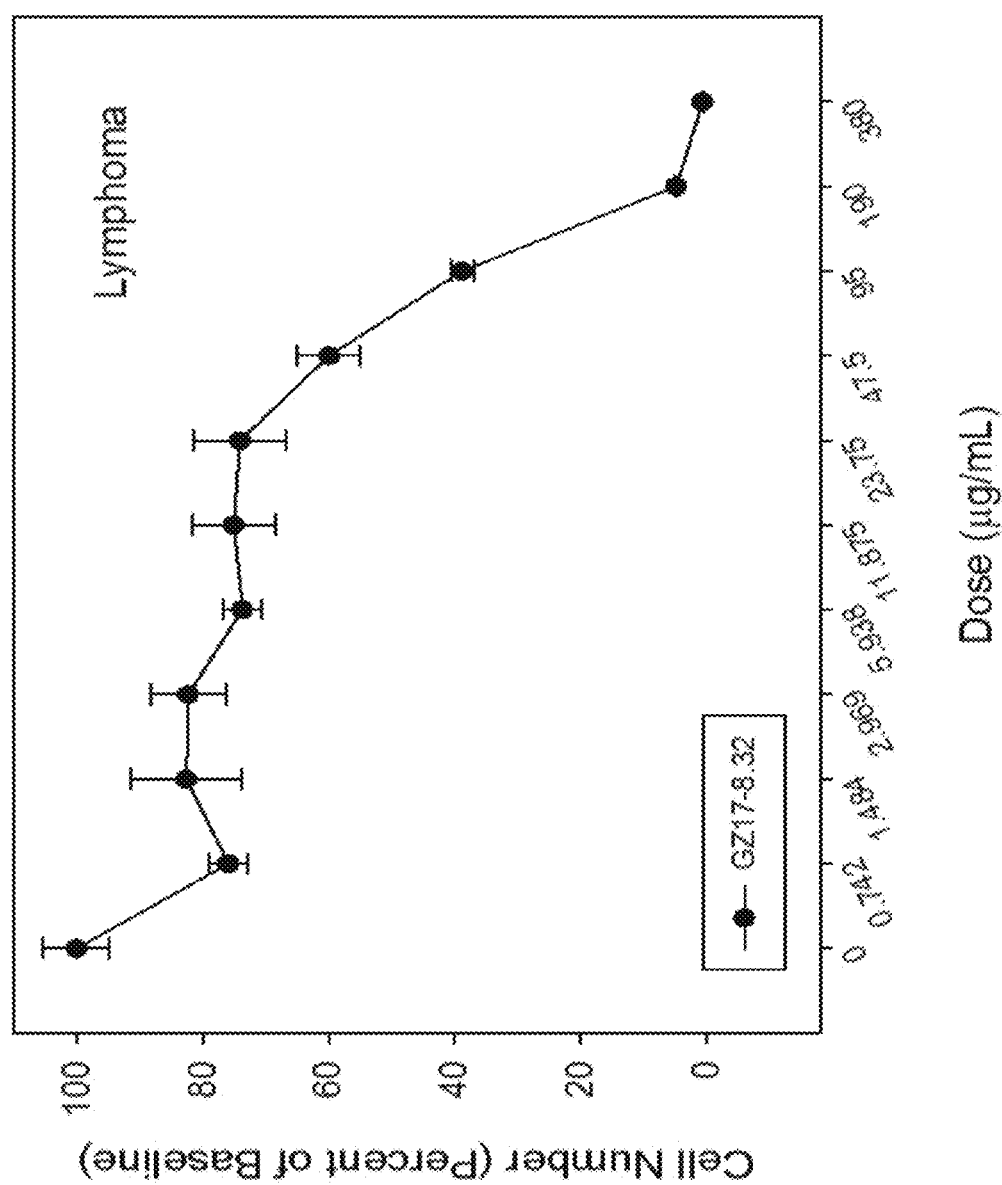
Figure 50D:
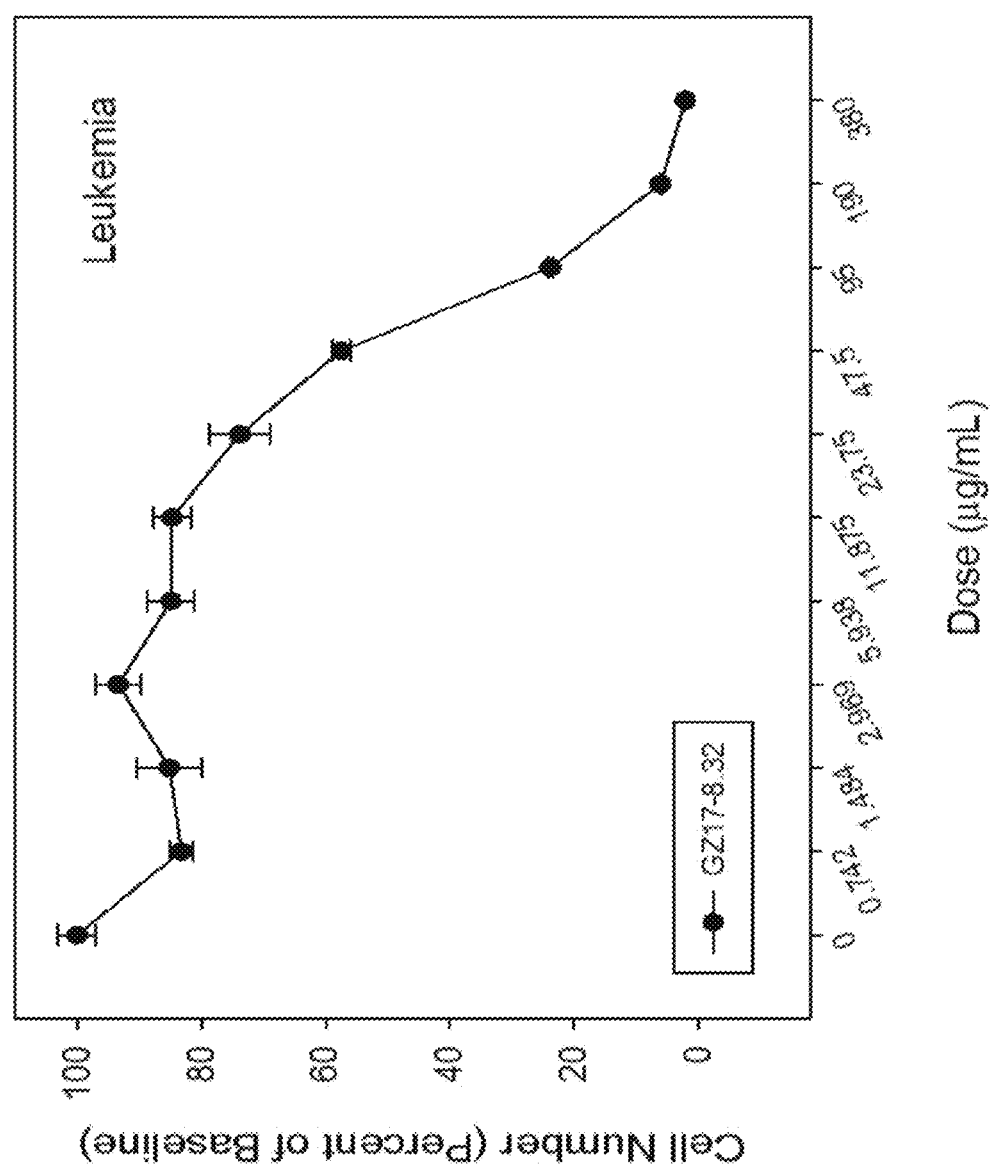
Figure 51A:
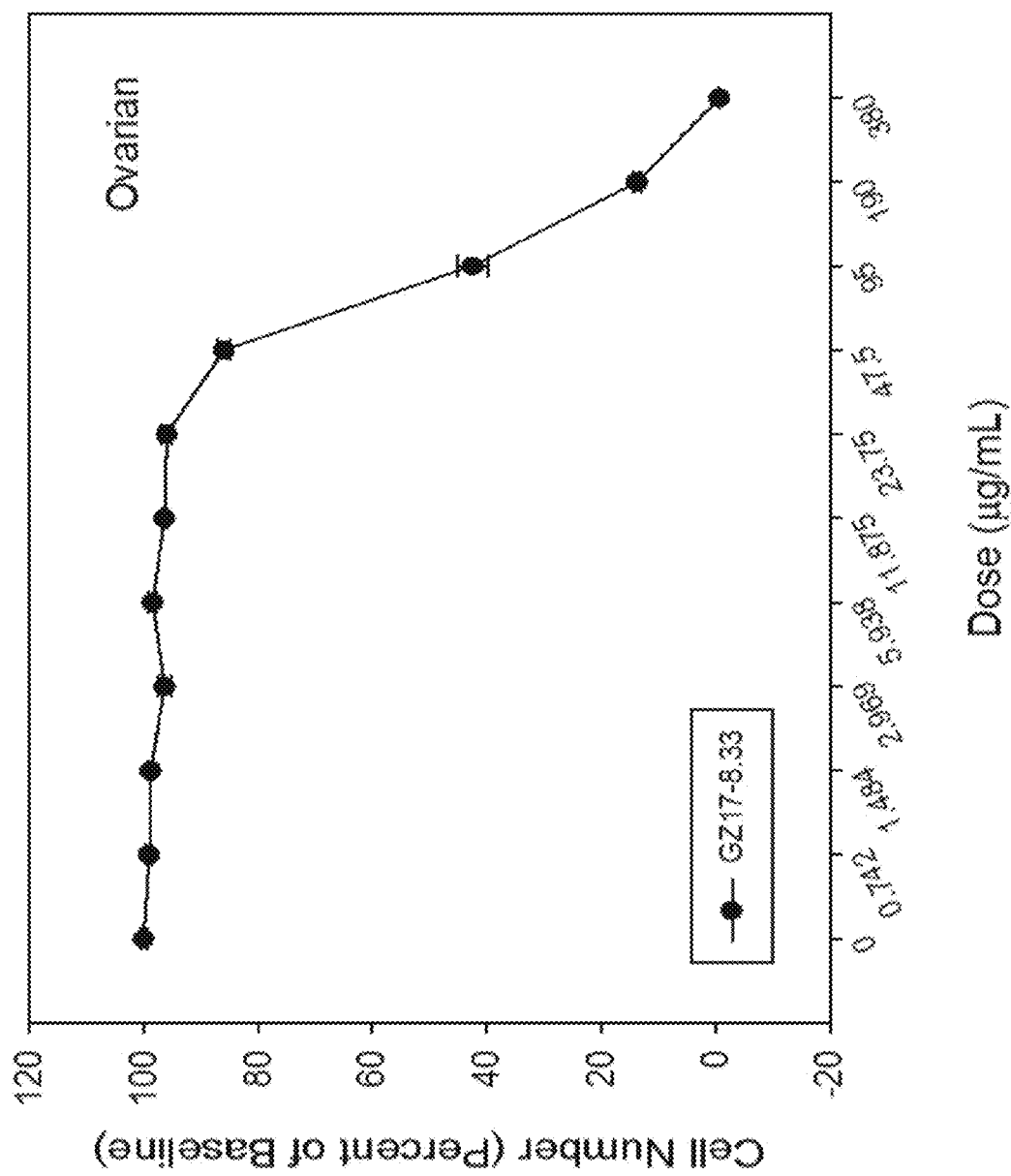
Figure 51B:
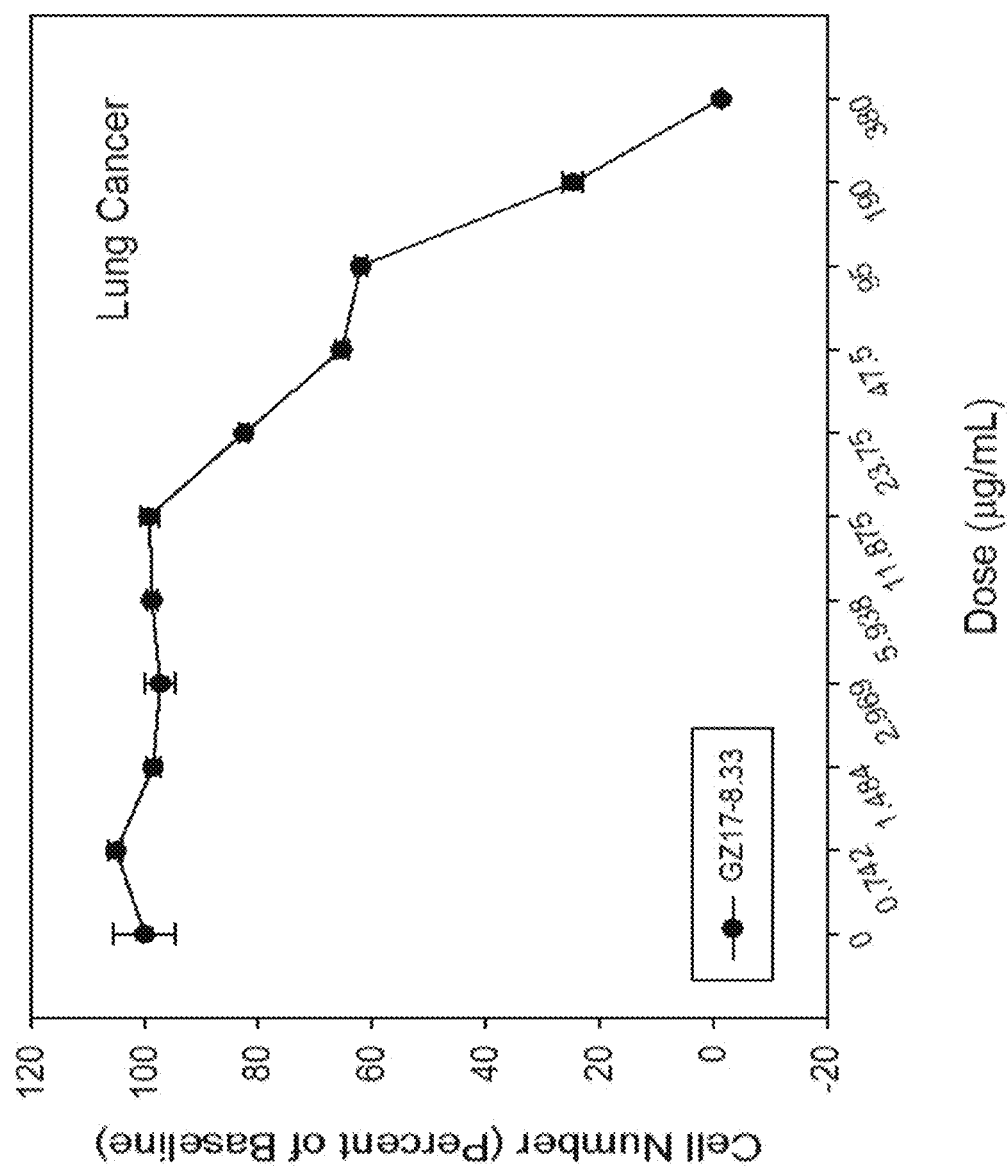
Figure 51C:
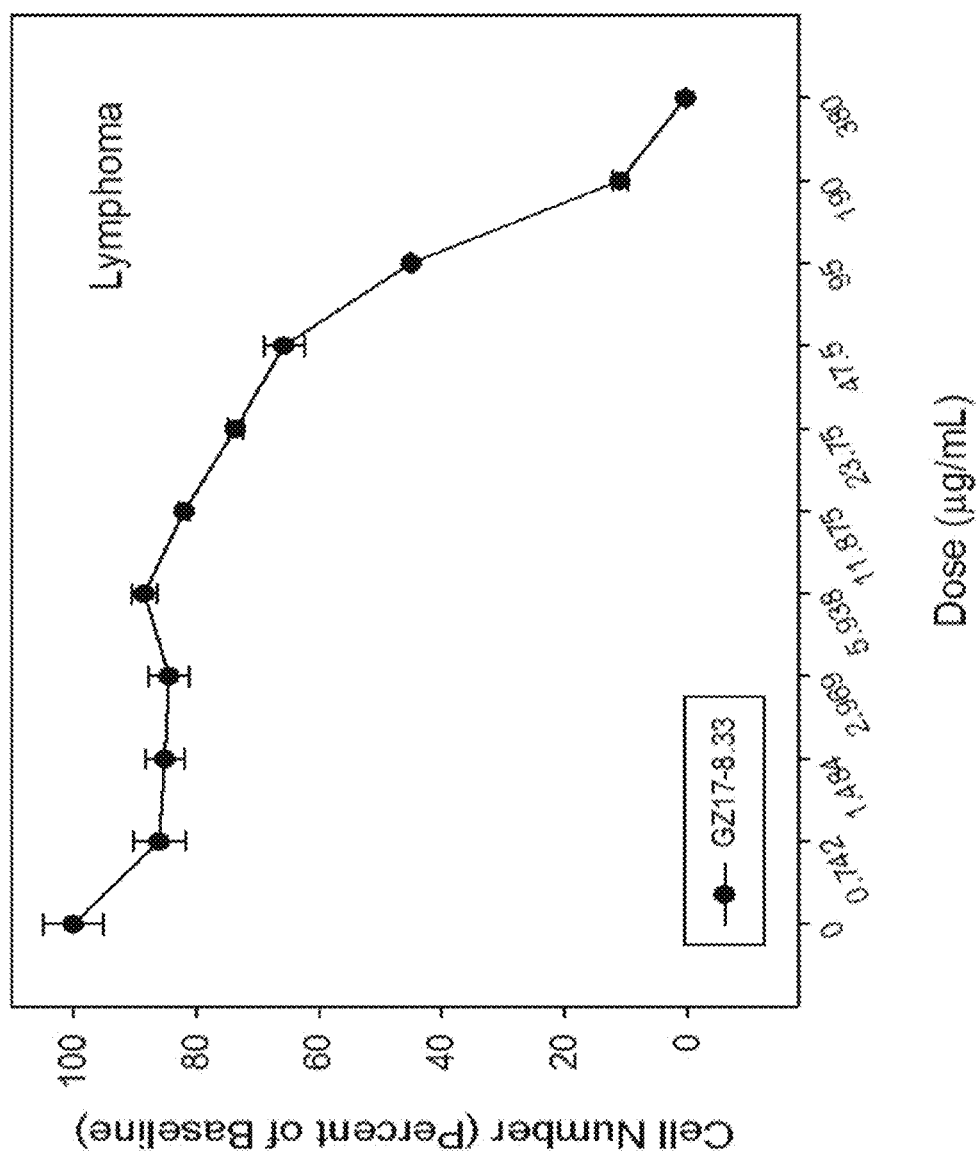
Figure 51D:
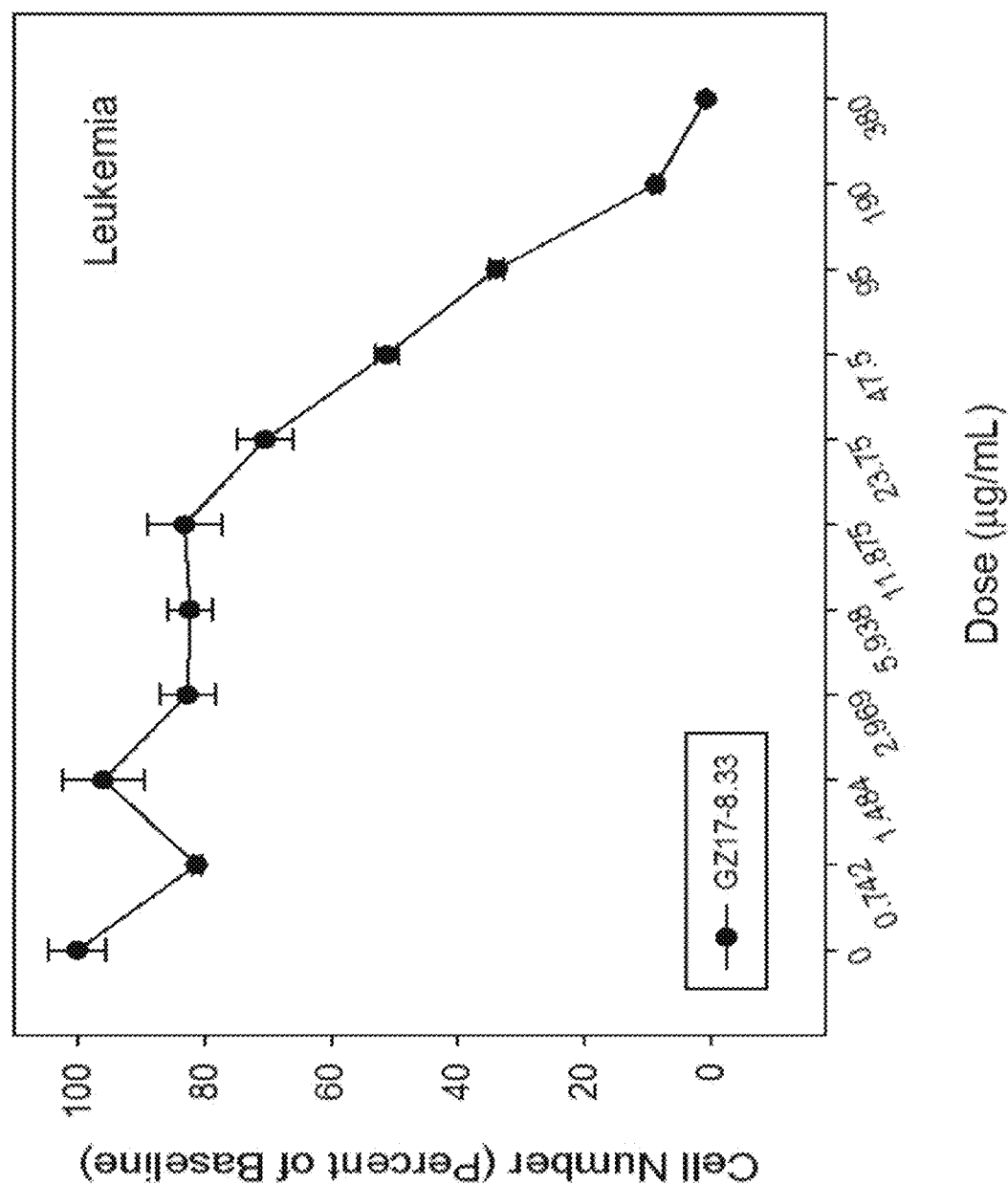
Figure 52A:
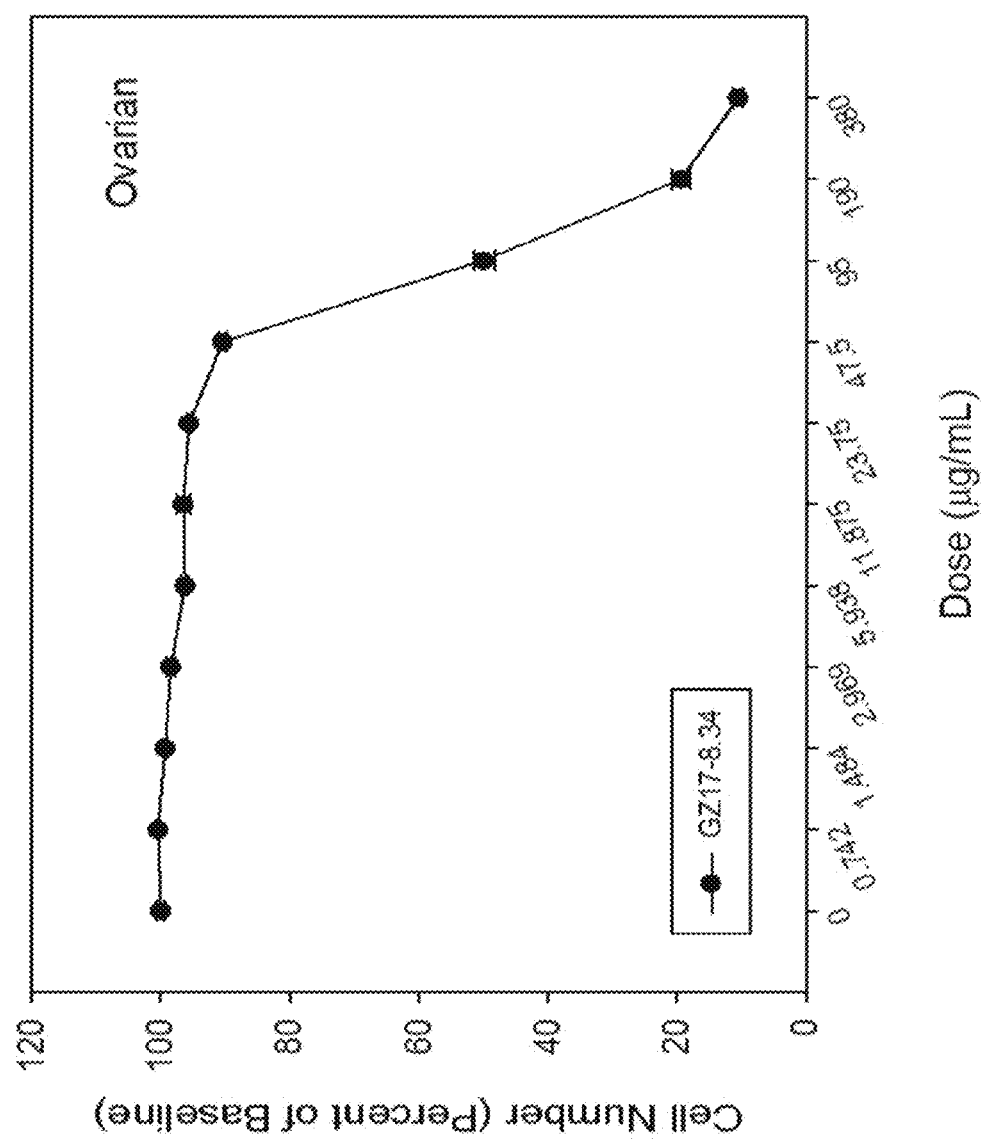
Figure 52B:
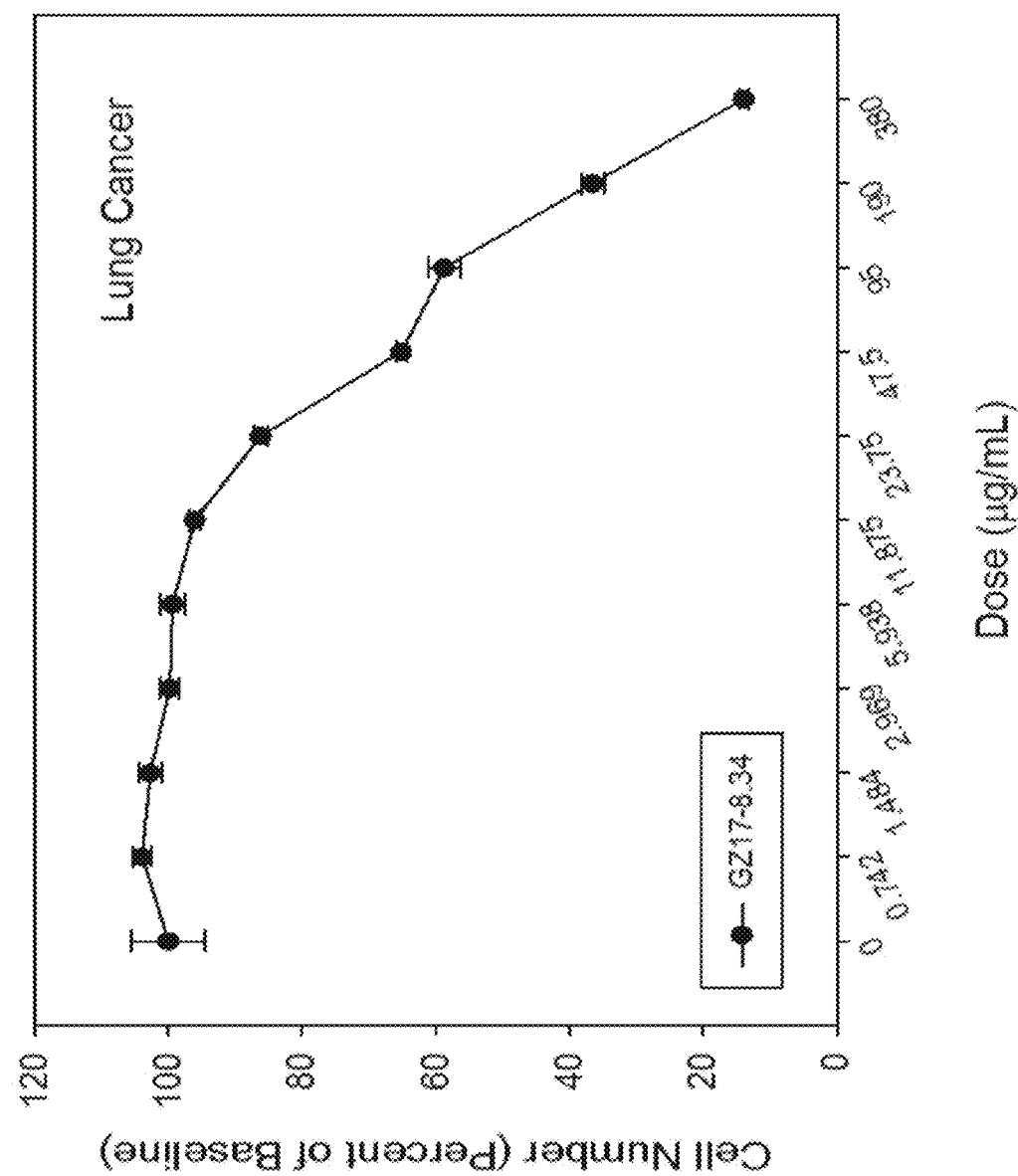
Figure 52C:
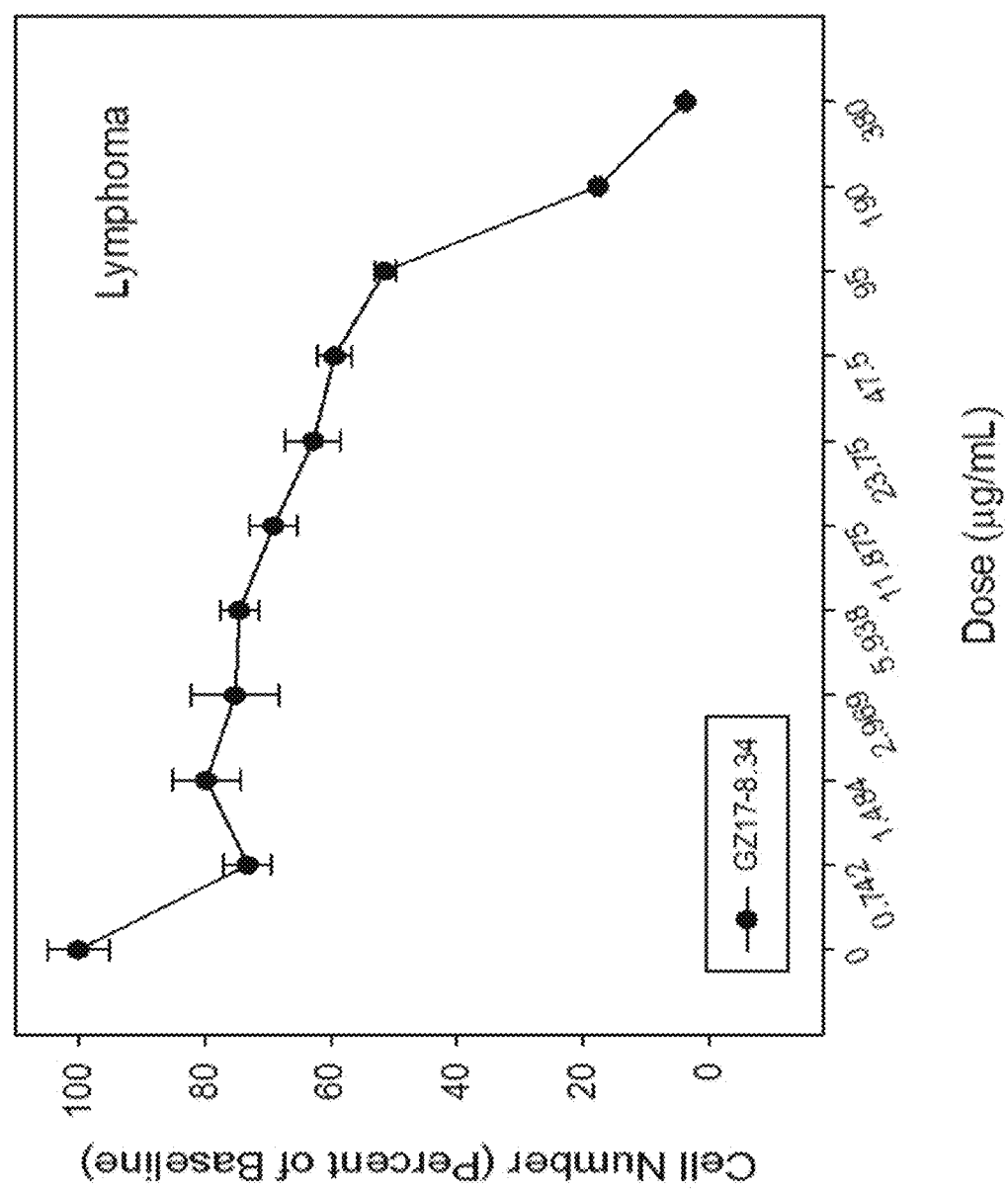
Figure 52D:
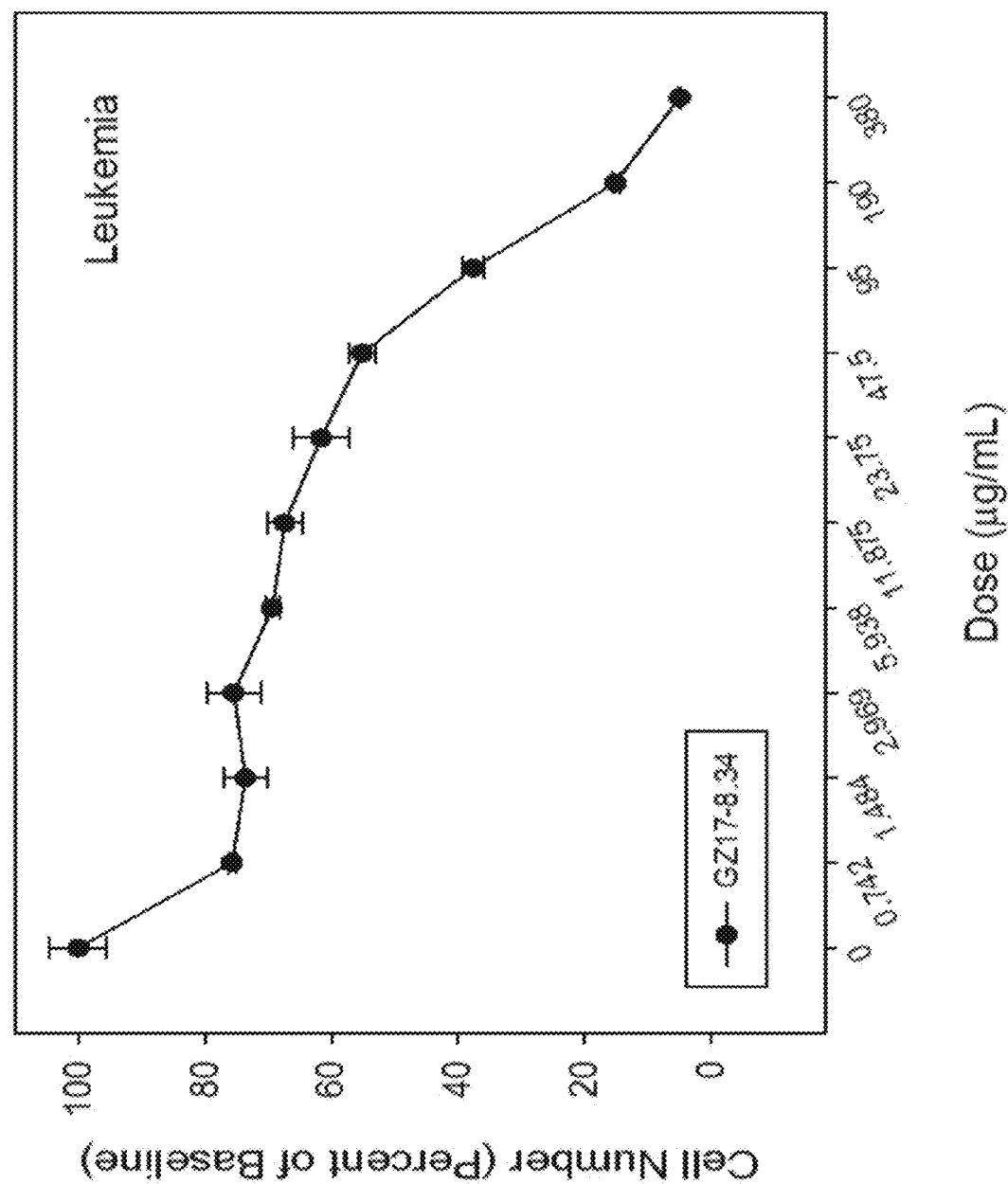
Figure 53A:
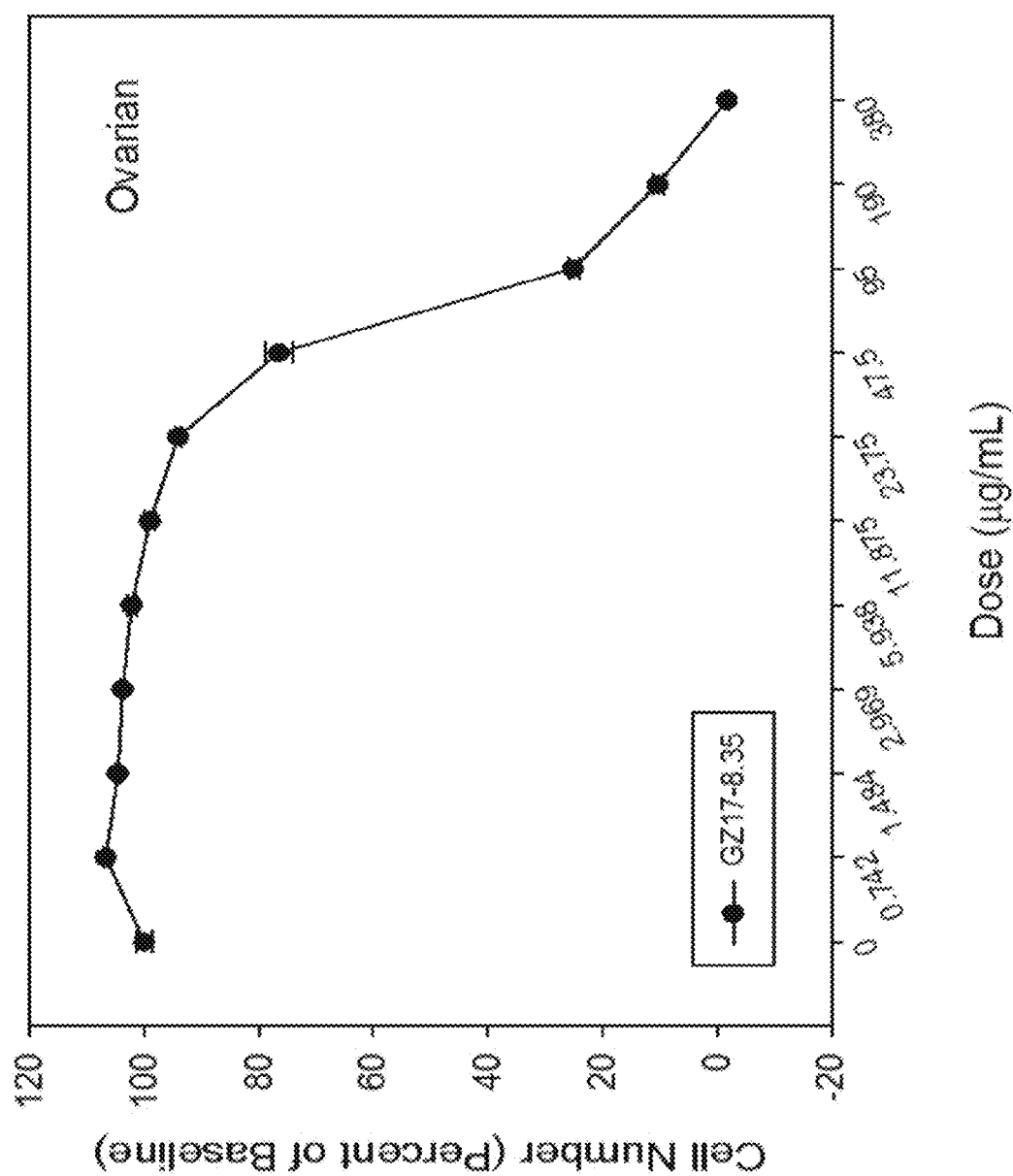
Figure 53B:
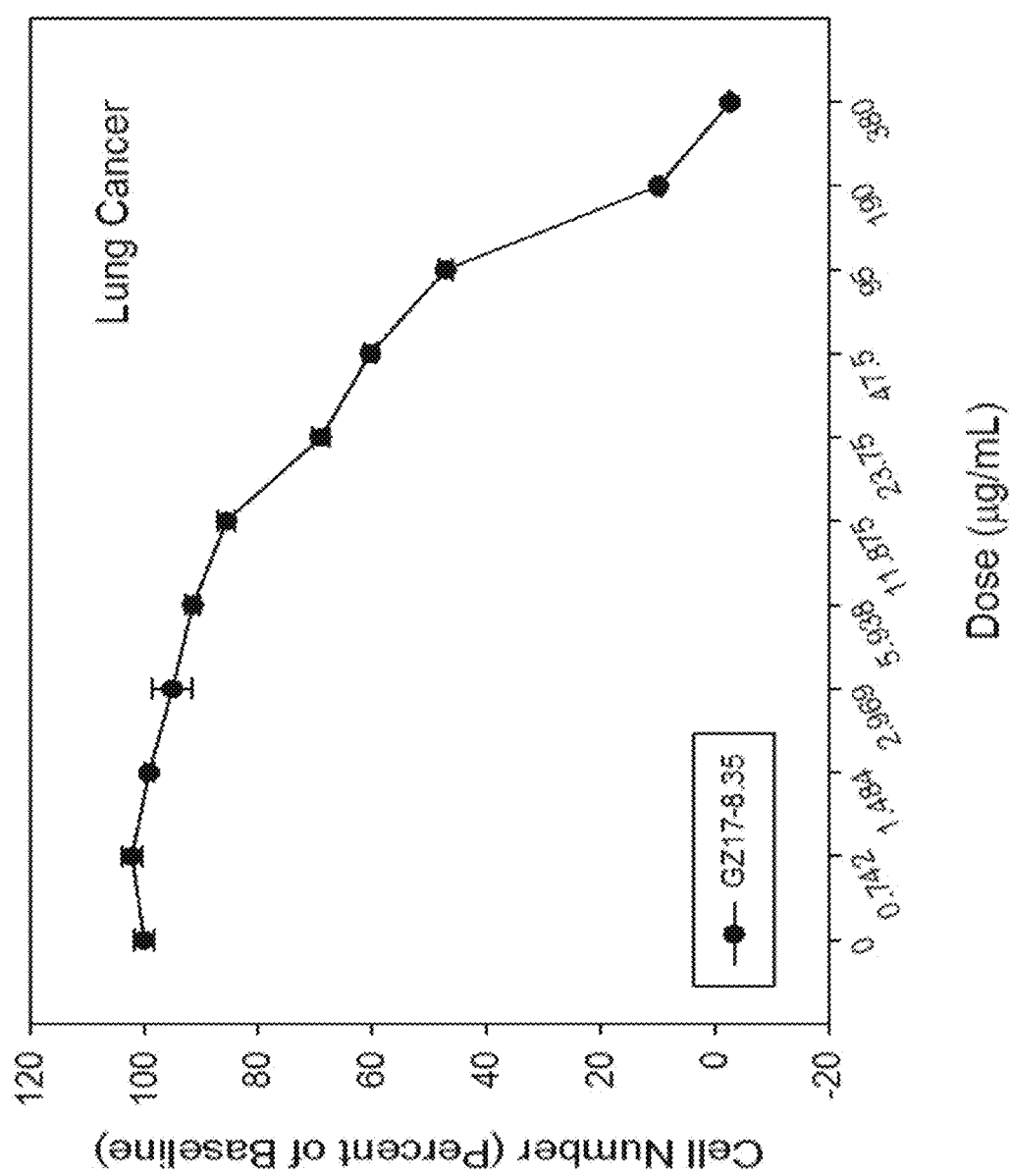
Figure 53C:
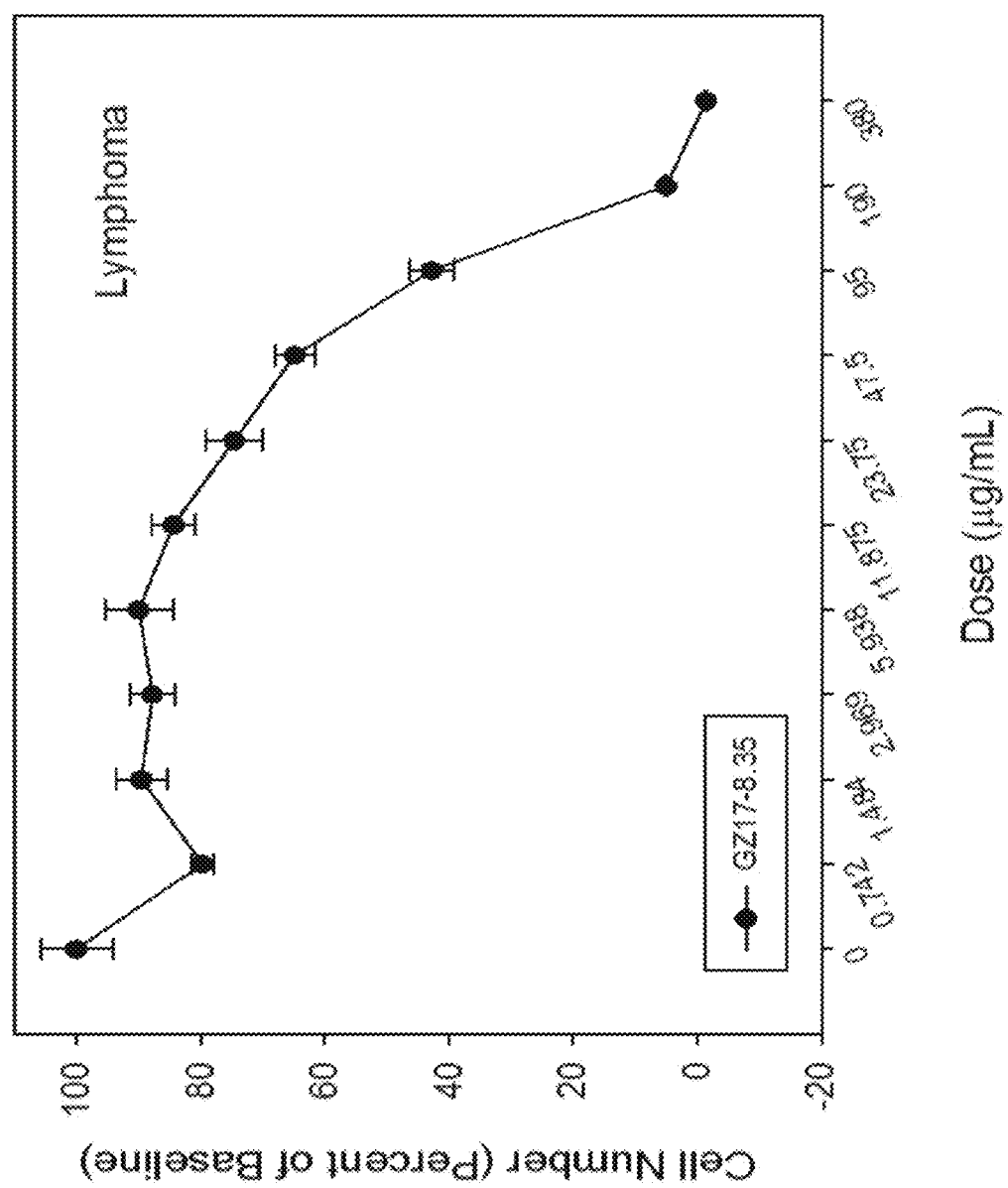
Figure 53D:
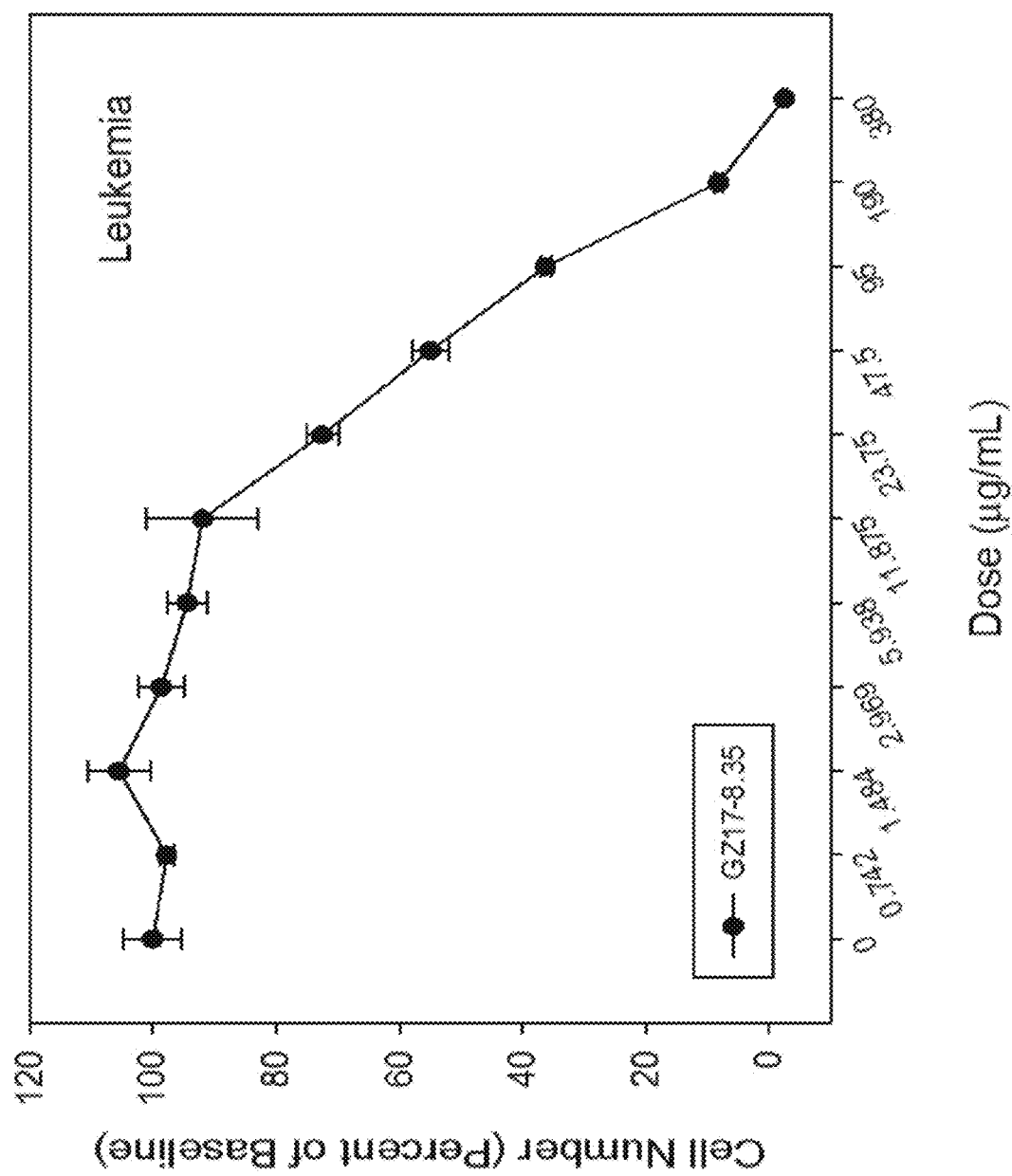
Figure 54A:
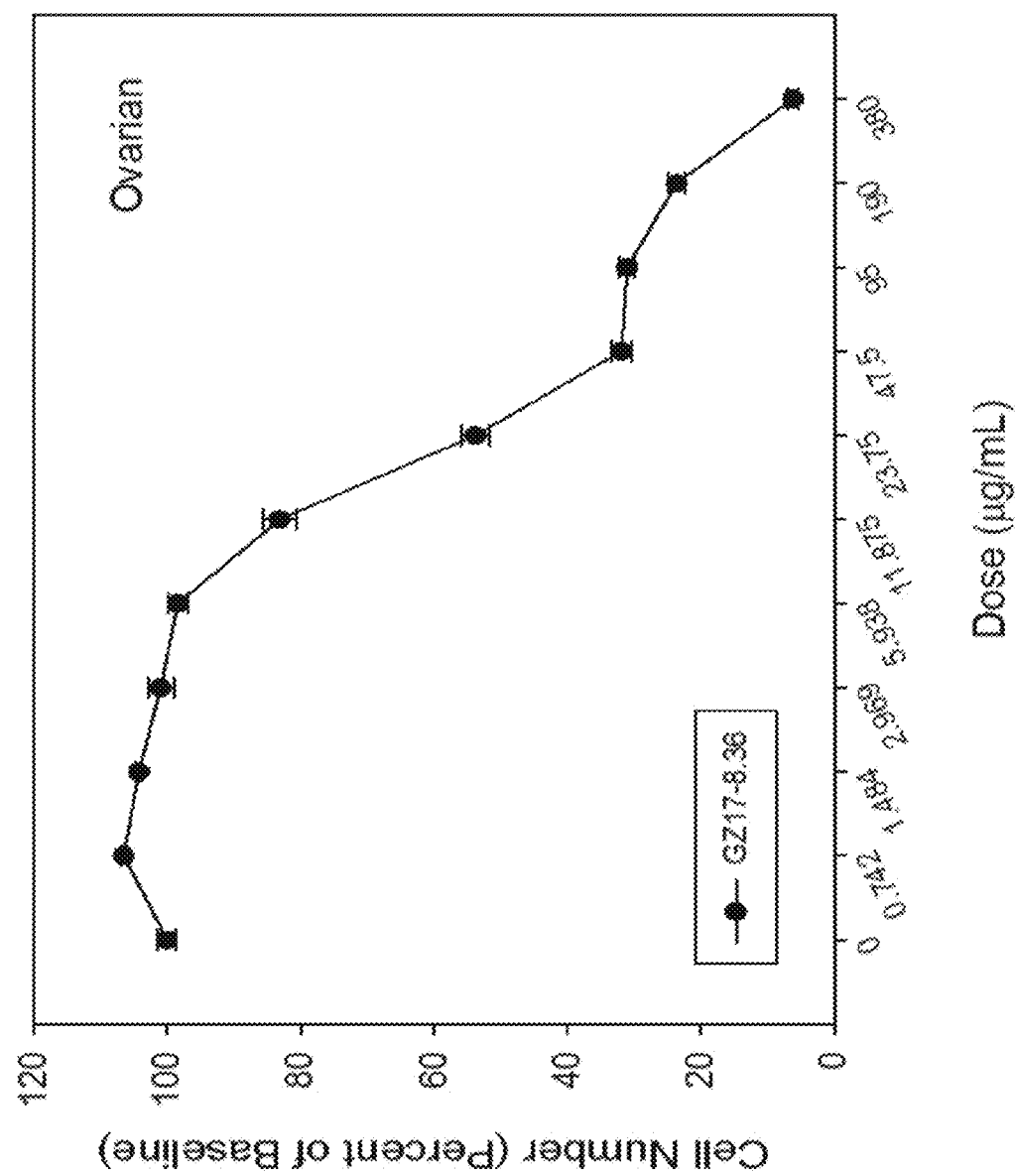
Figure 54B:
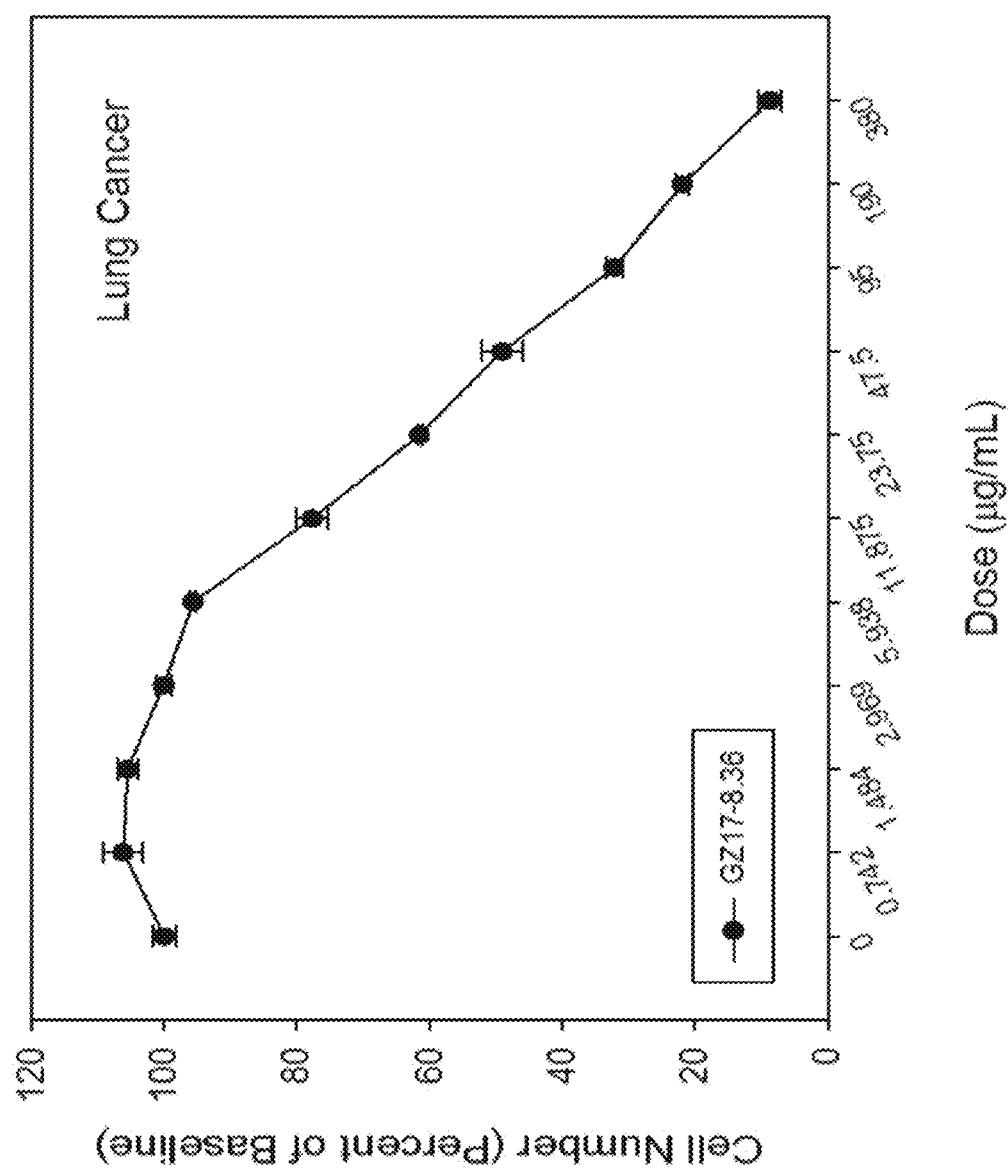
Figure 54C:
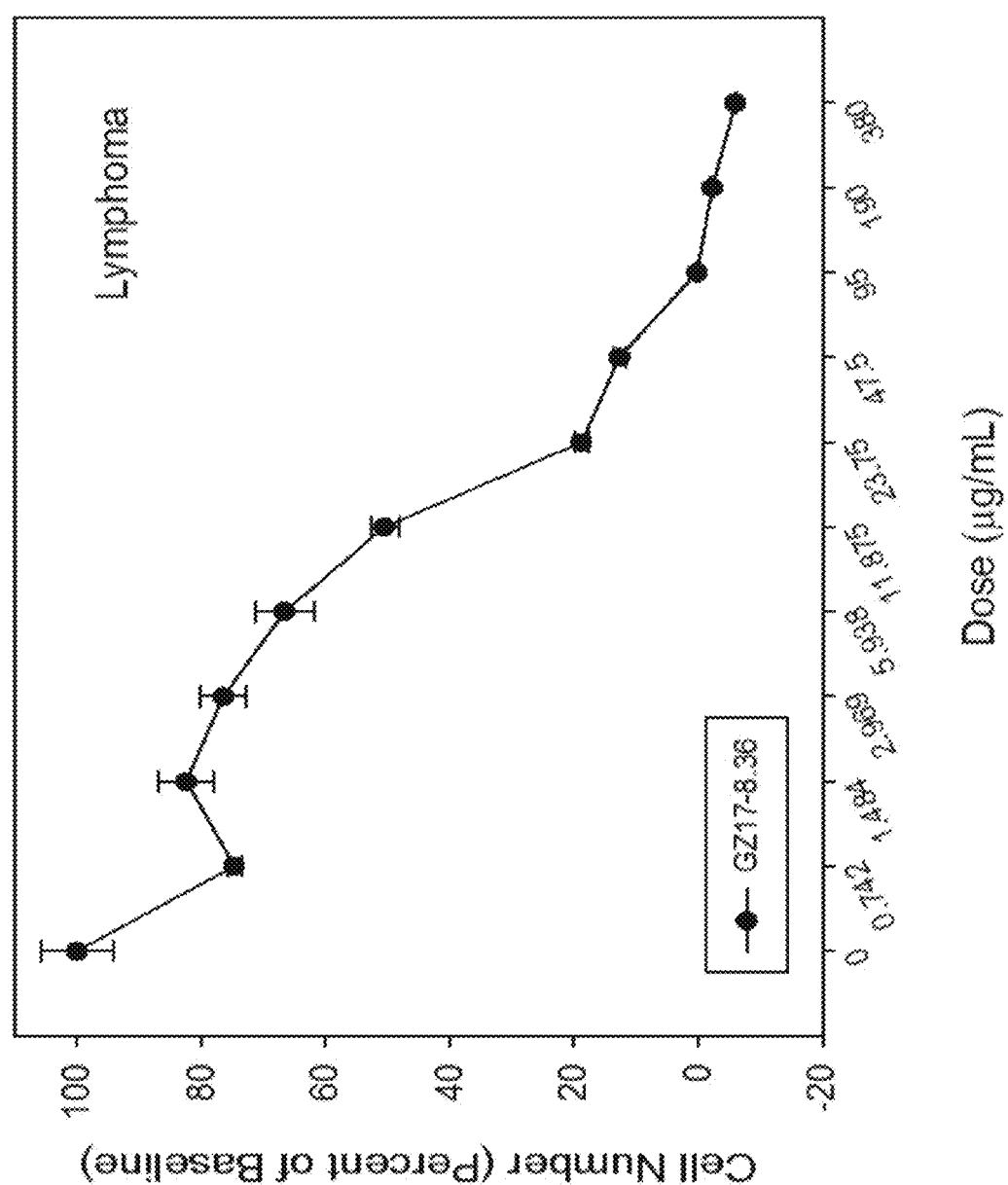
Figure 54D:
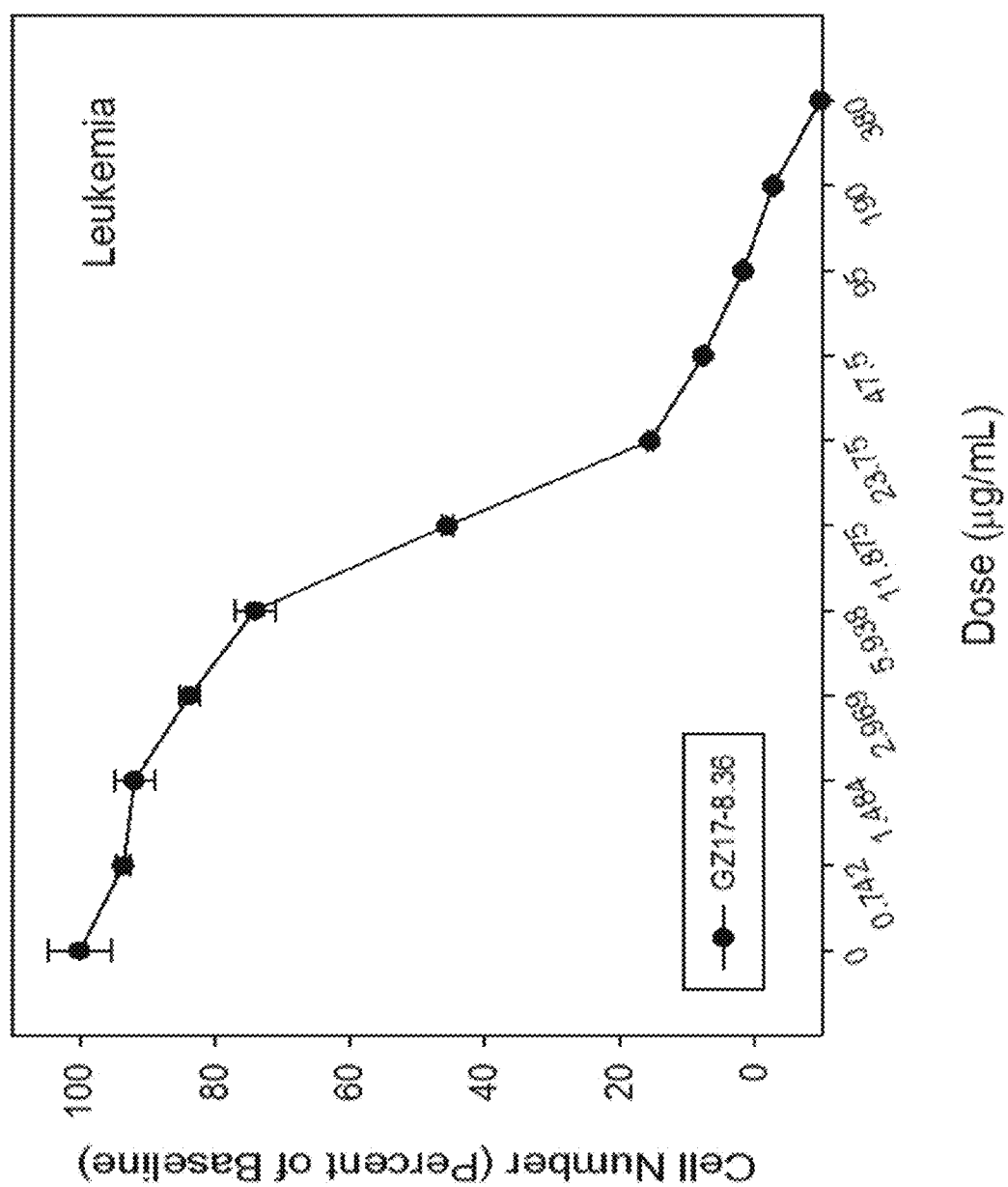
Figure 55A:
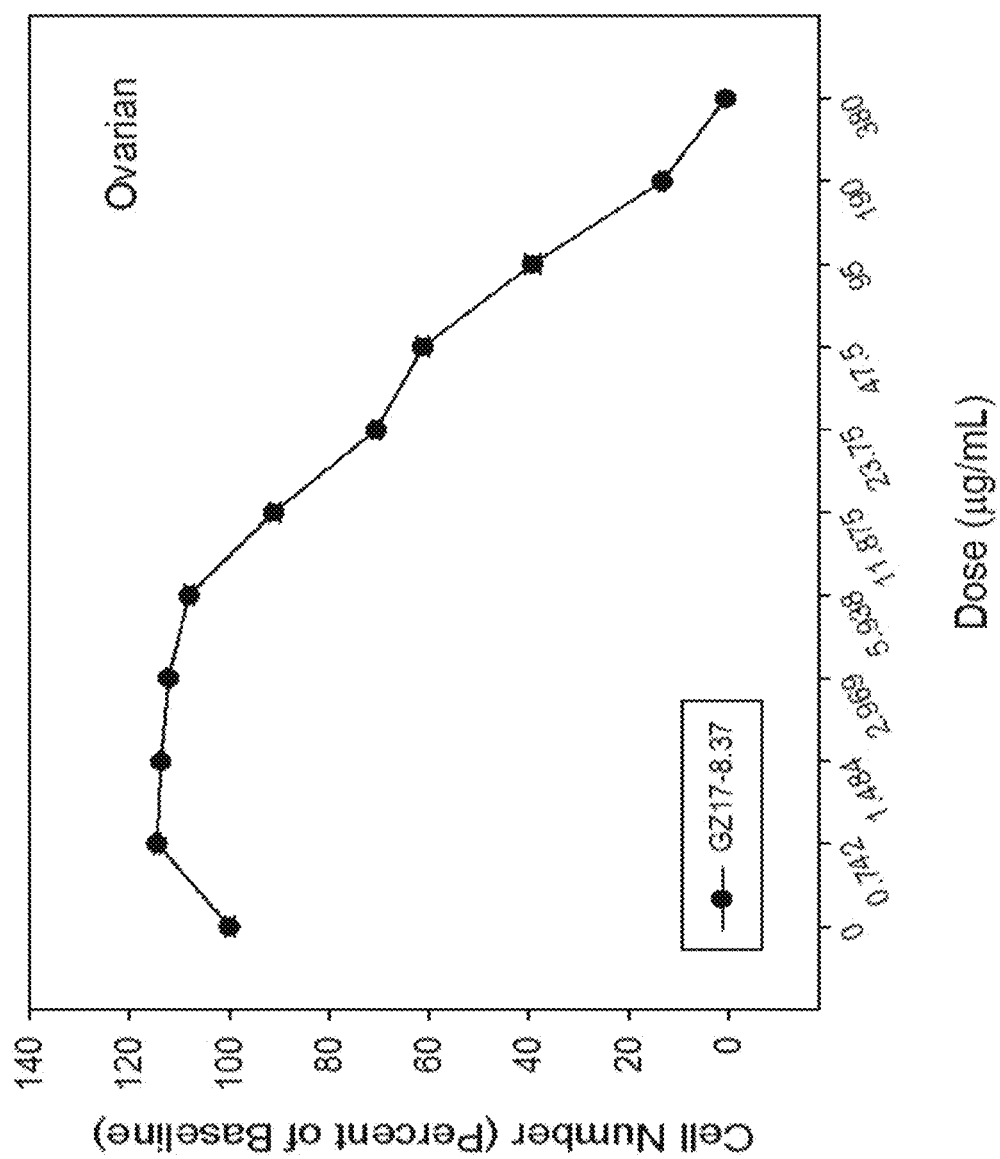
Figure 55B:
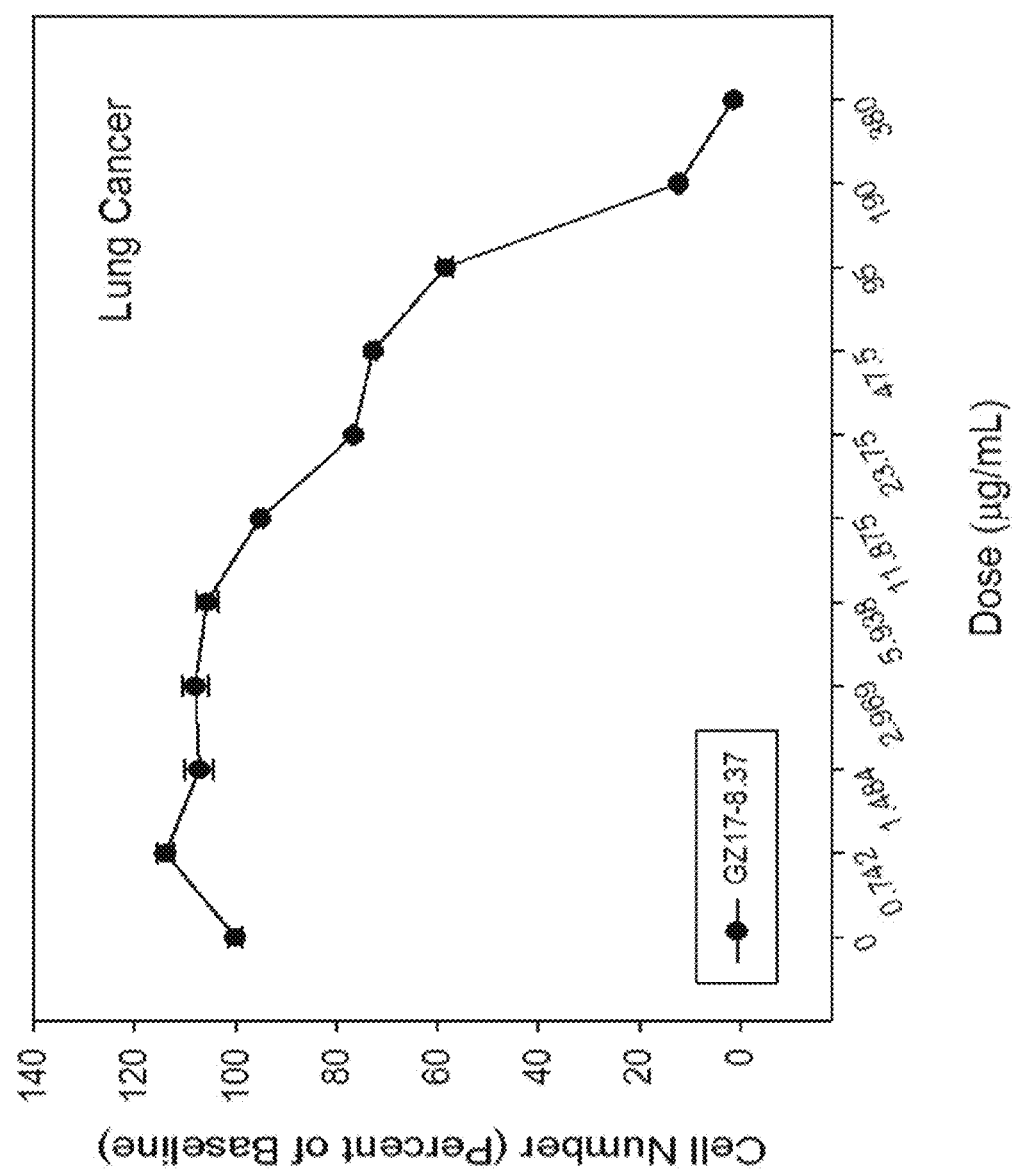
Figure 55C:
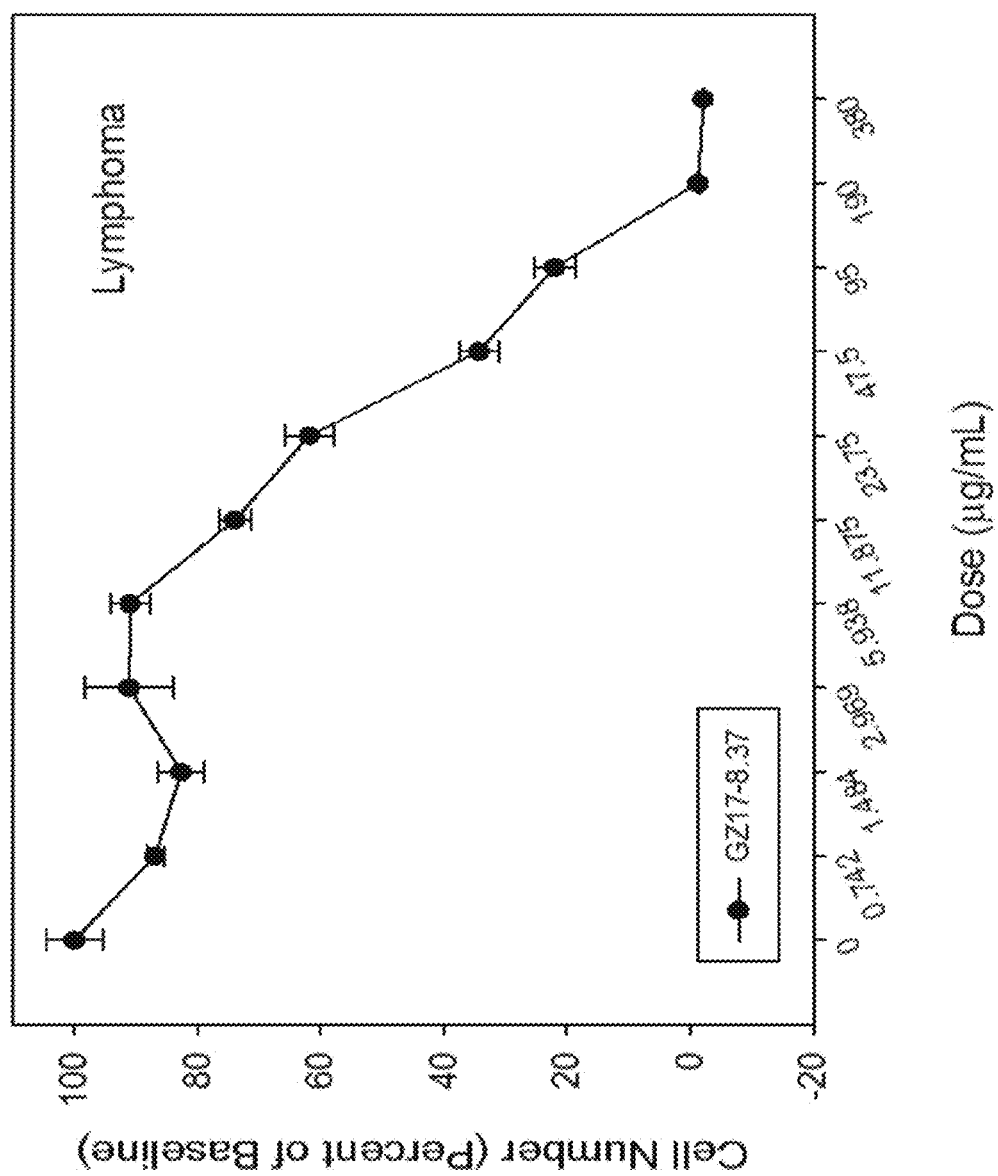
Figure 55D:
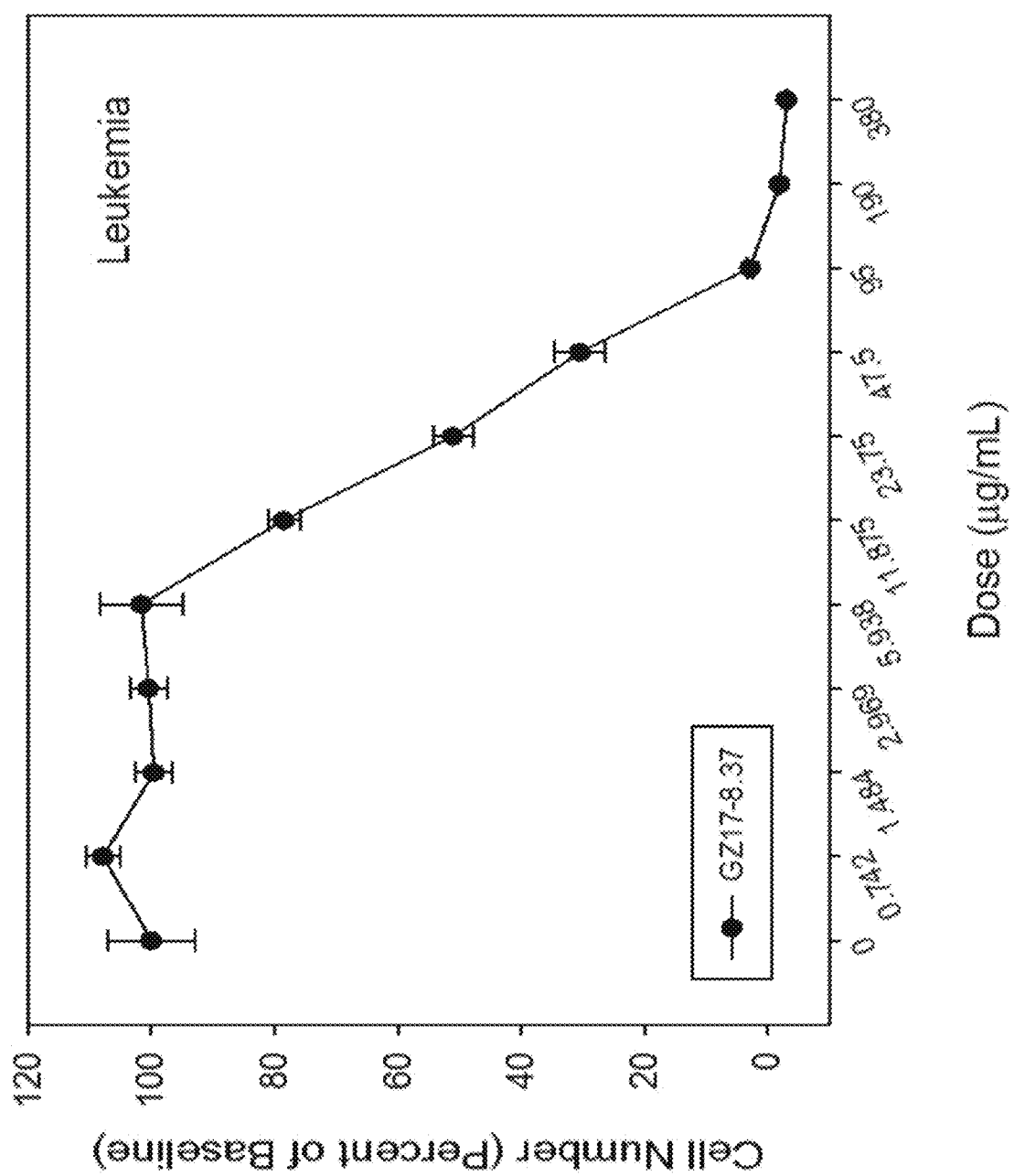
Figure 56A:
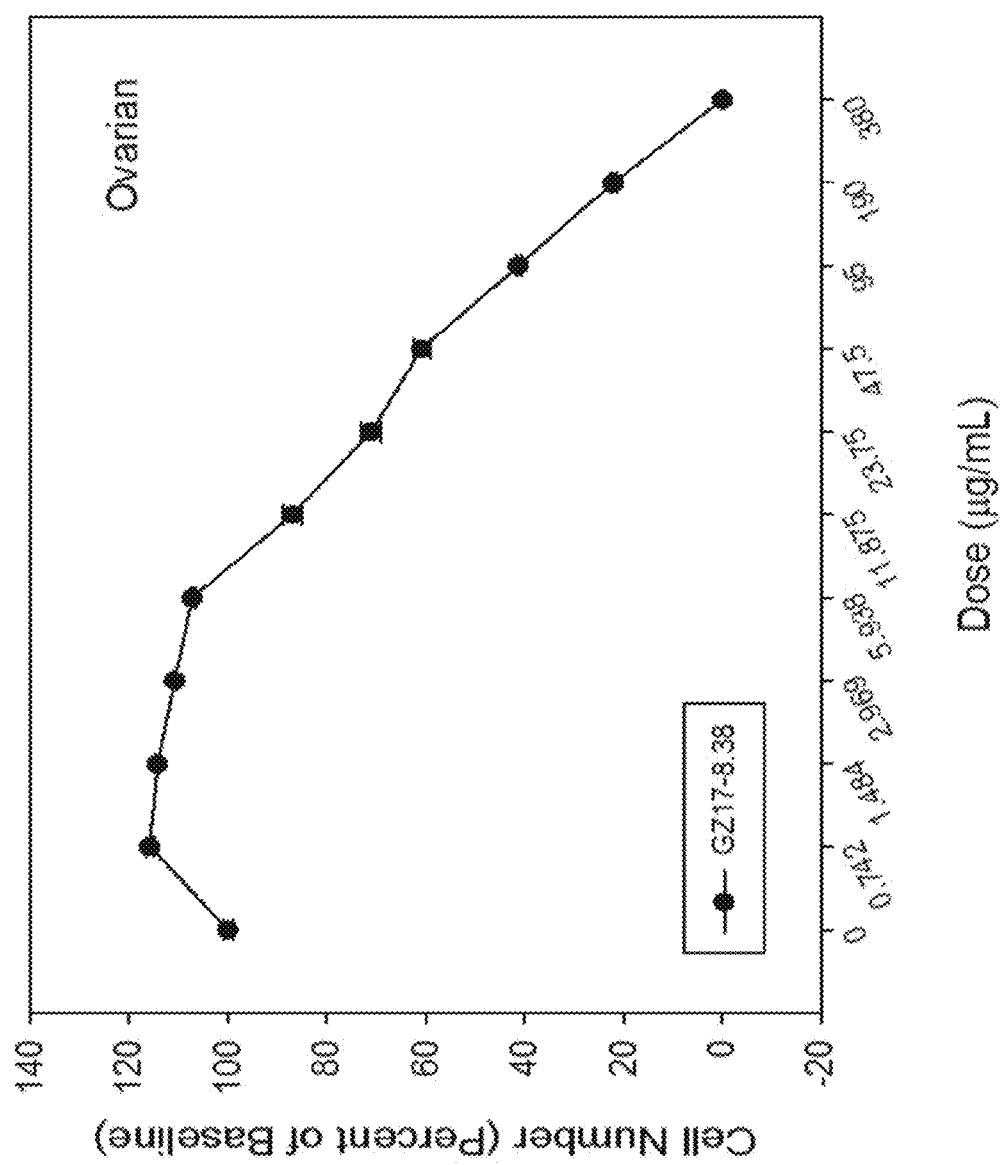
Figure 56B:
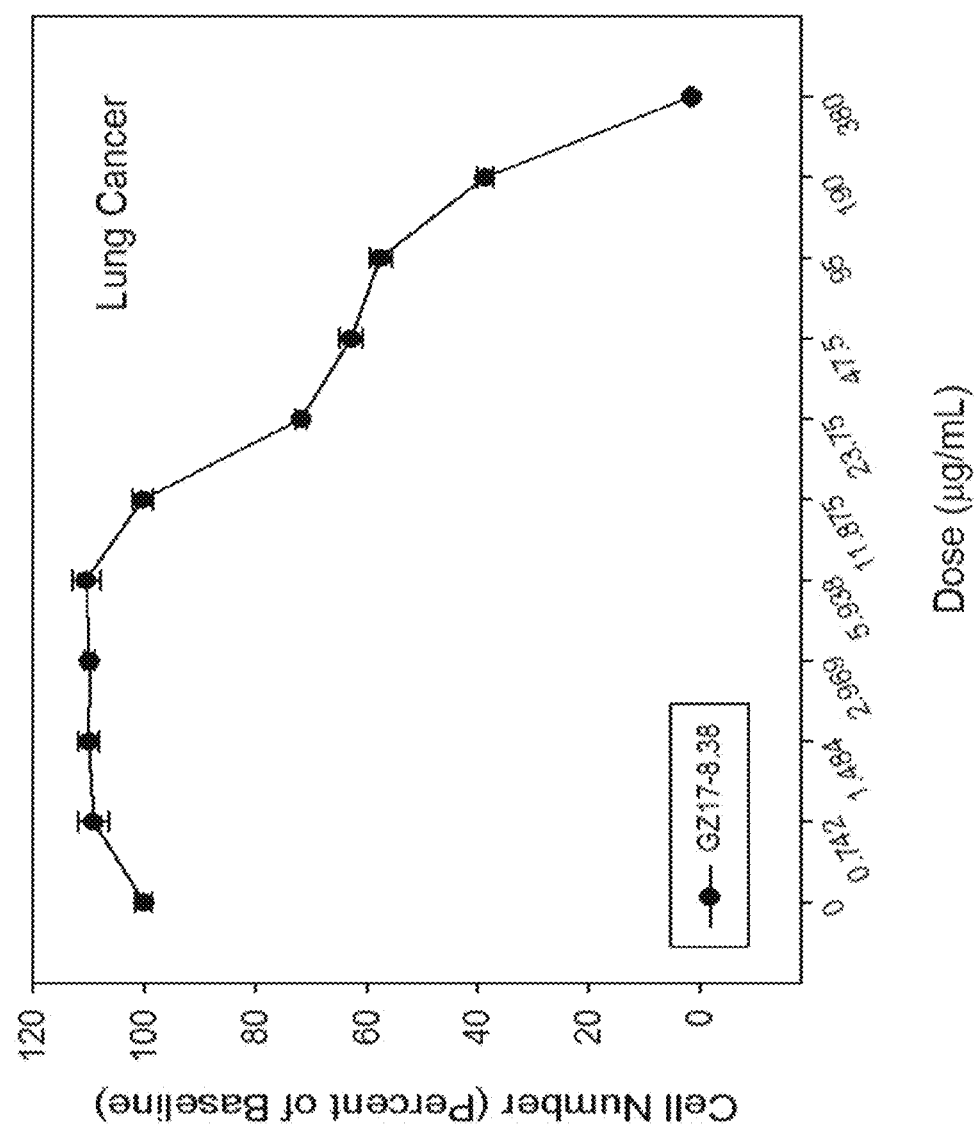
Figure 56C:
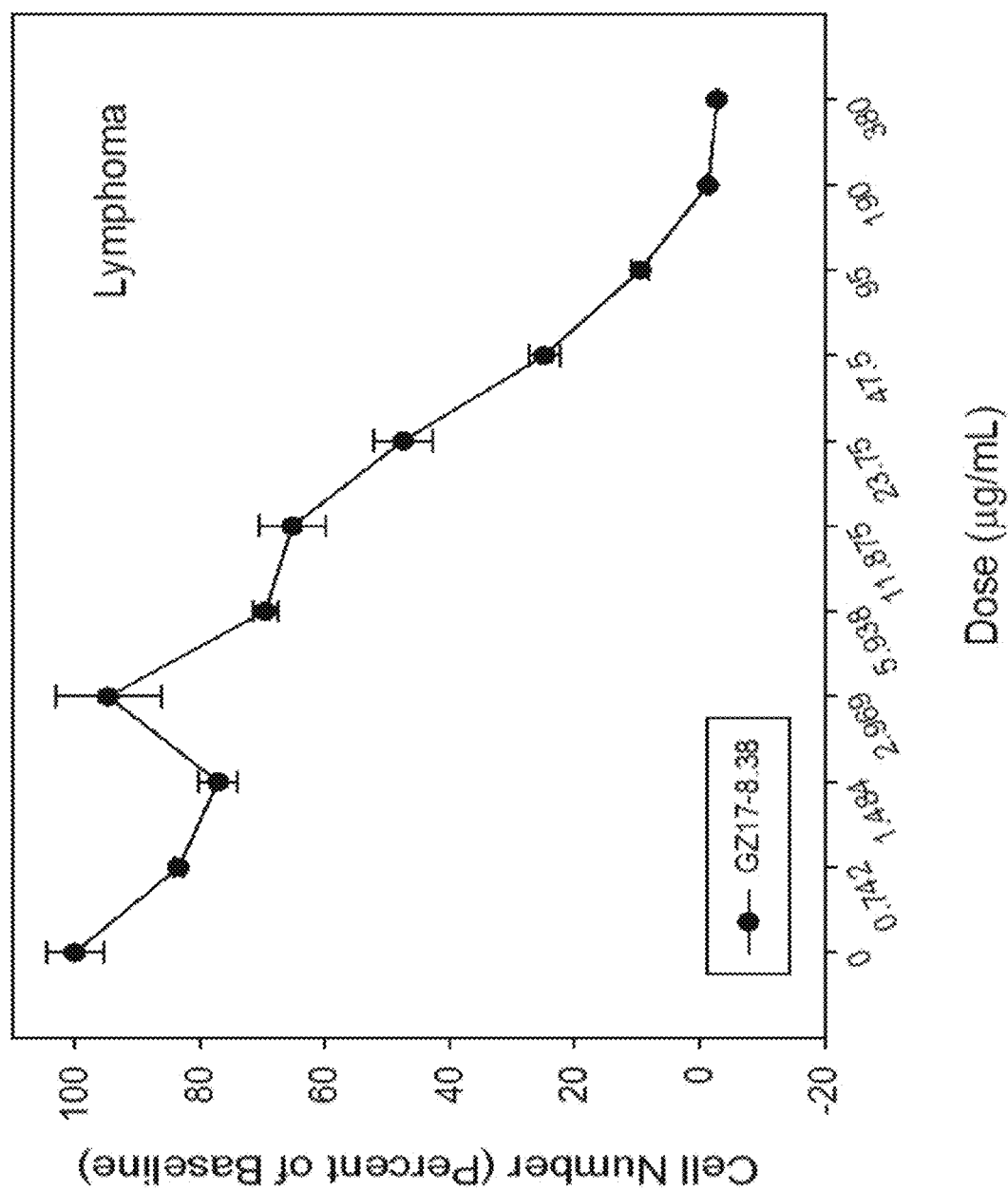
Figure 56D:
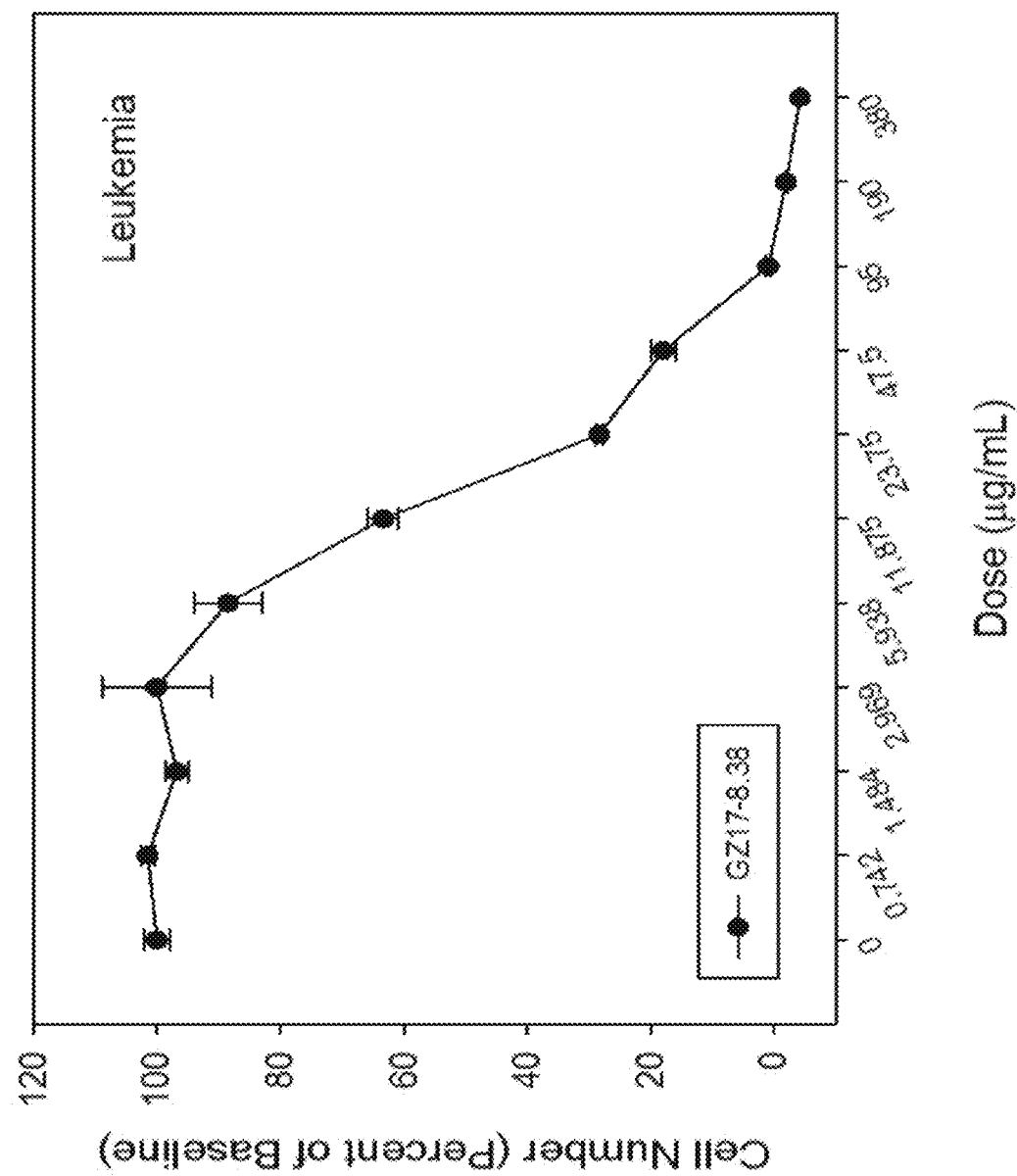
Figure 57A:
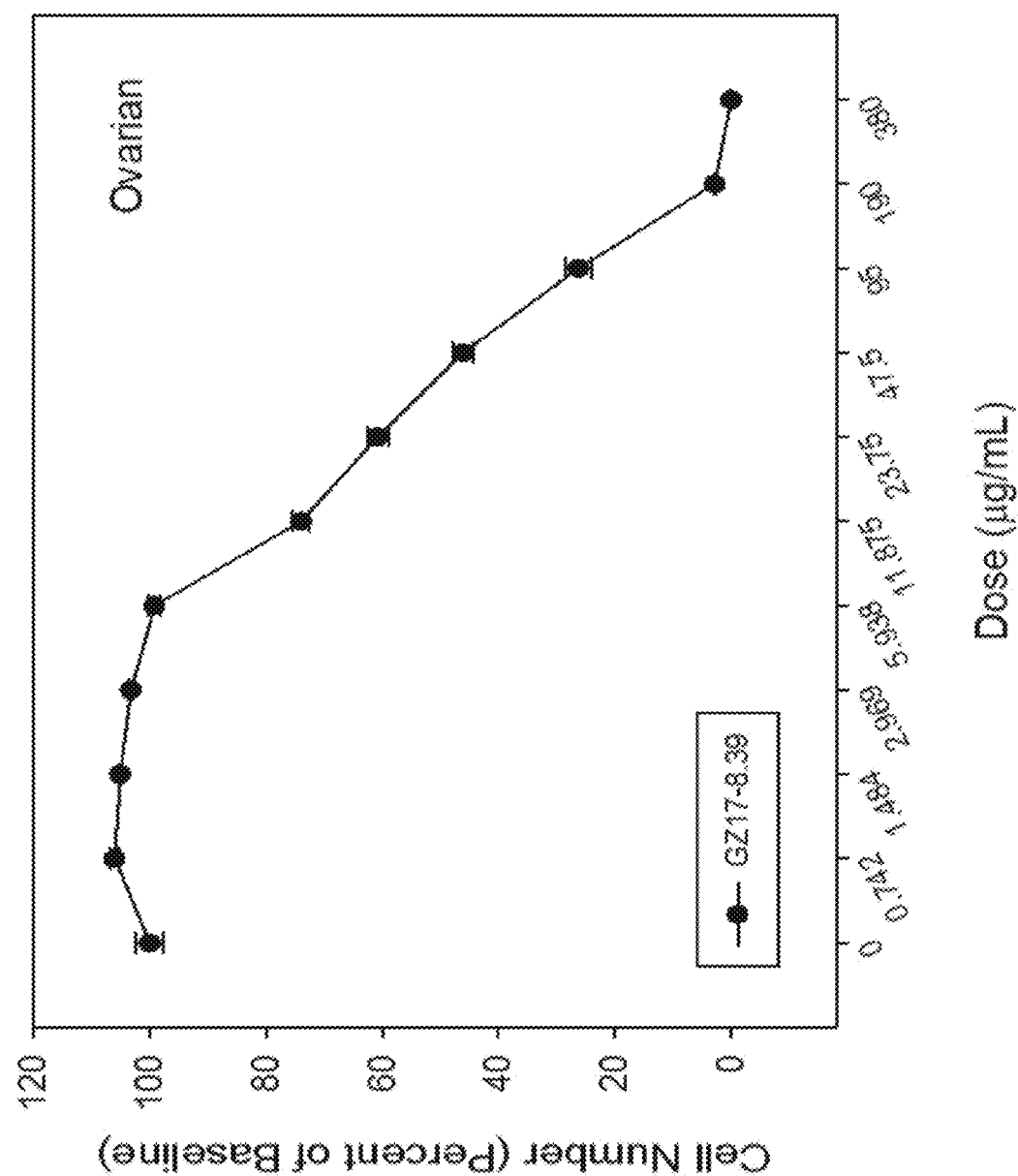
Figure 57B:
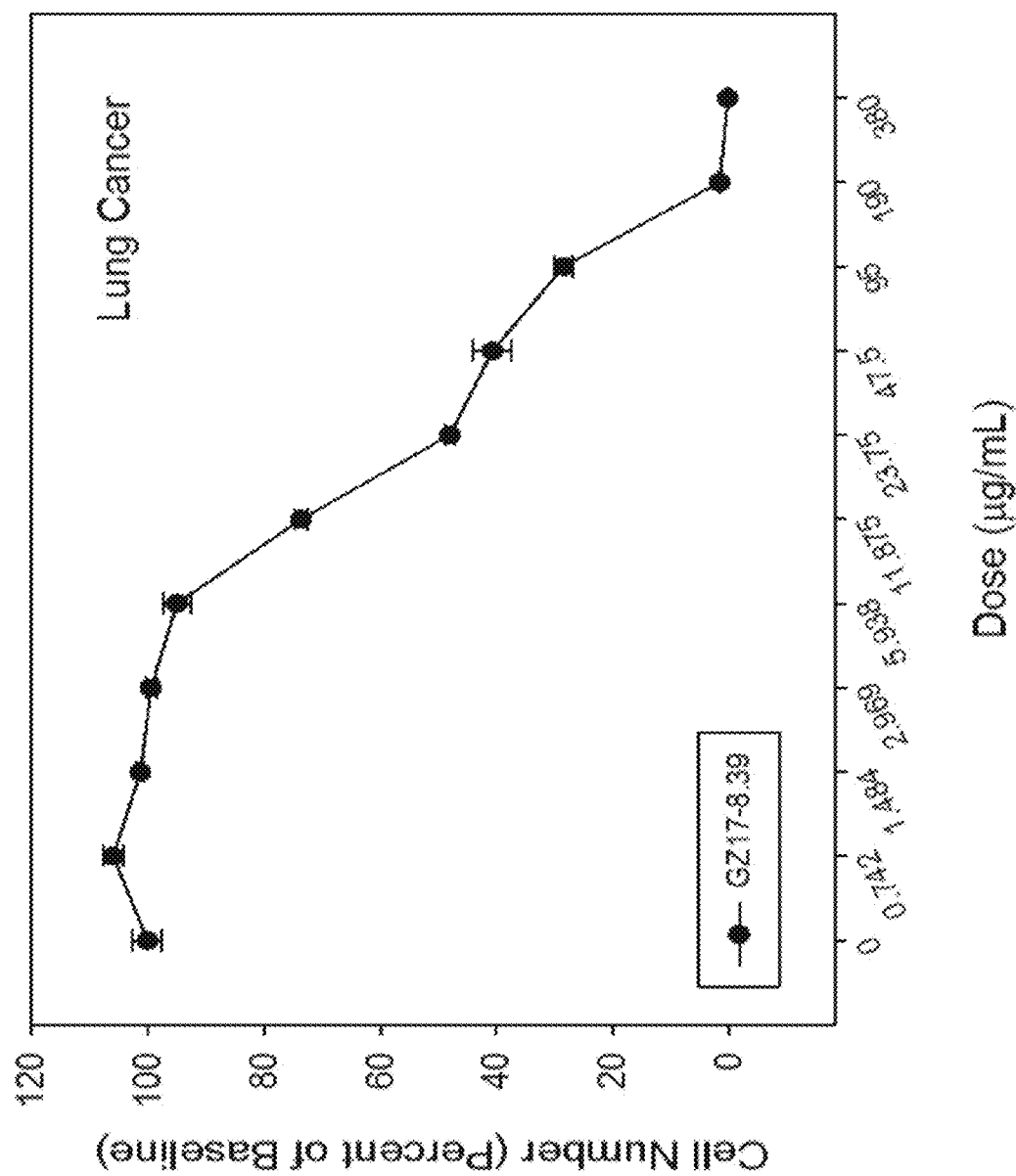
Figure 57C:
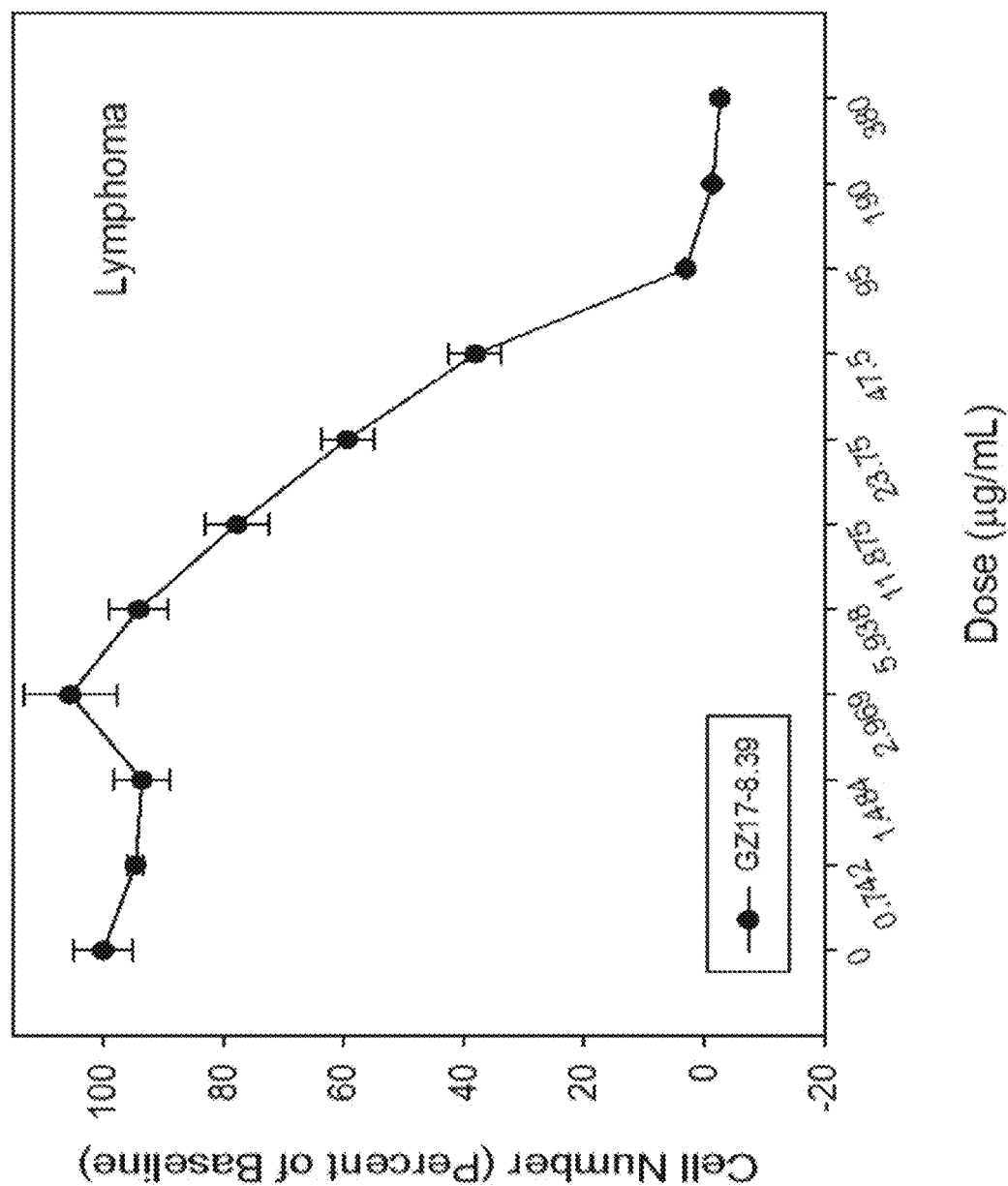
Figure 57D:
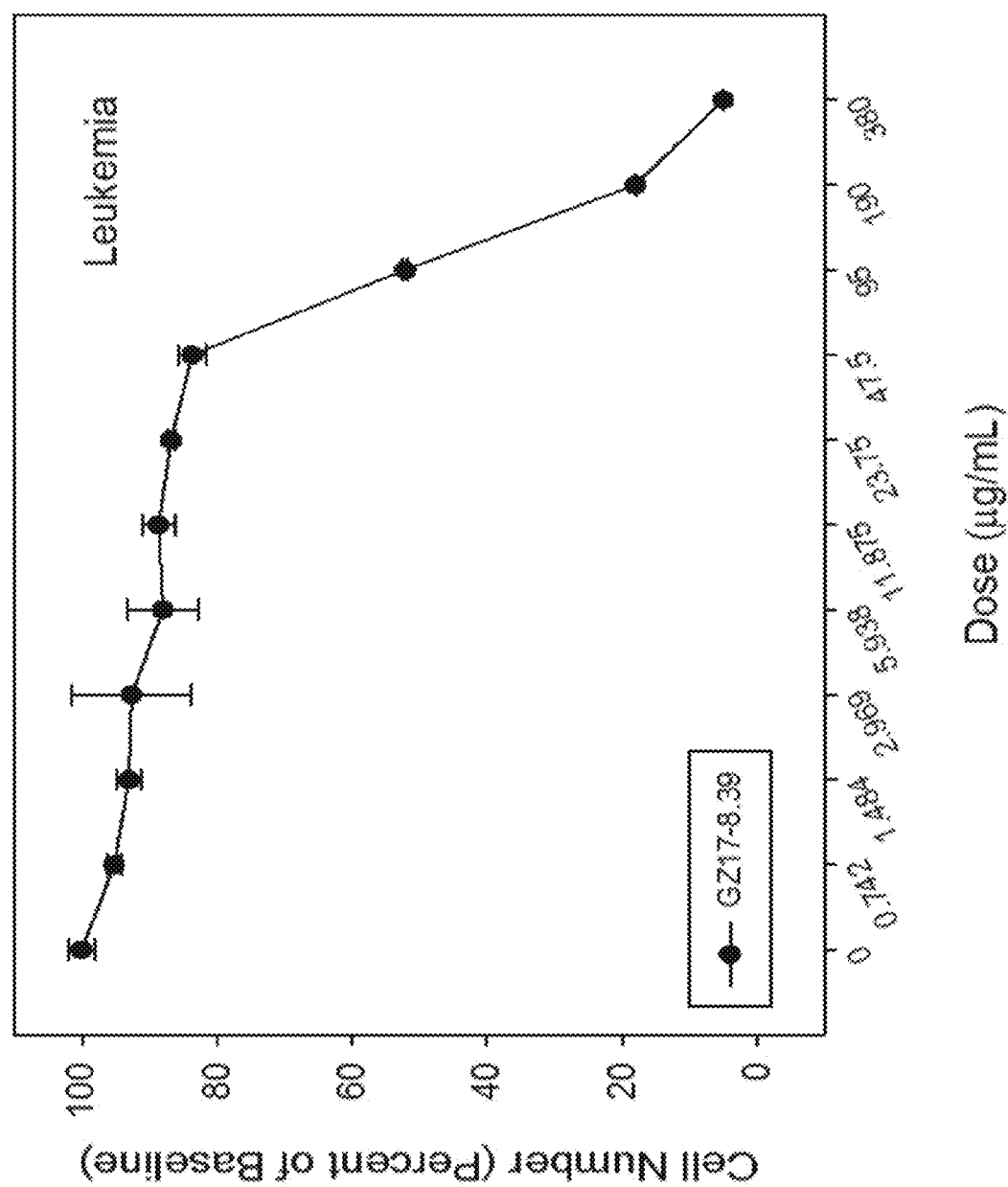
Figure 58A:
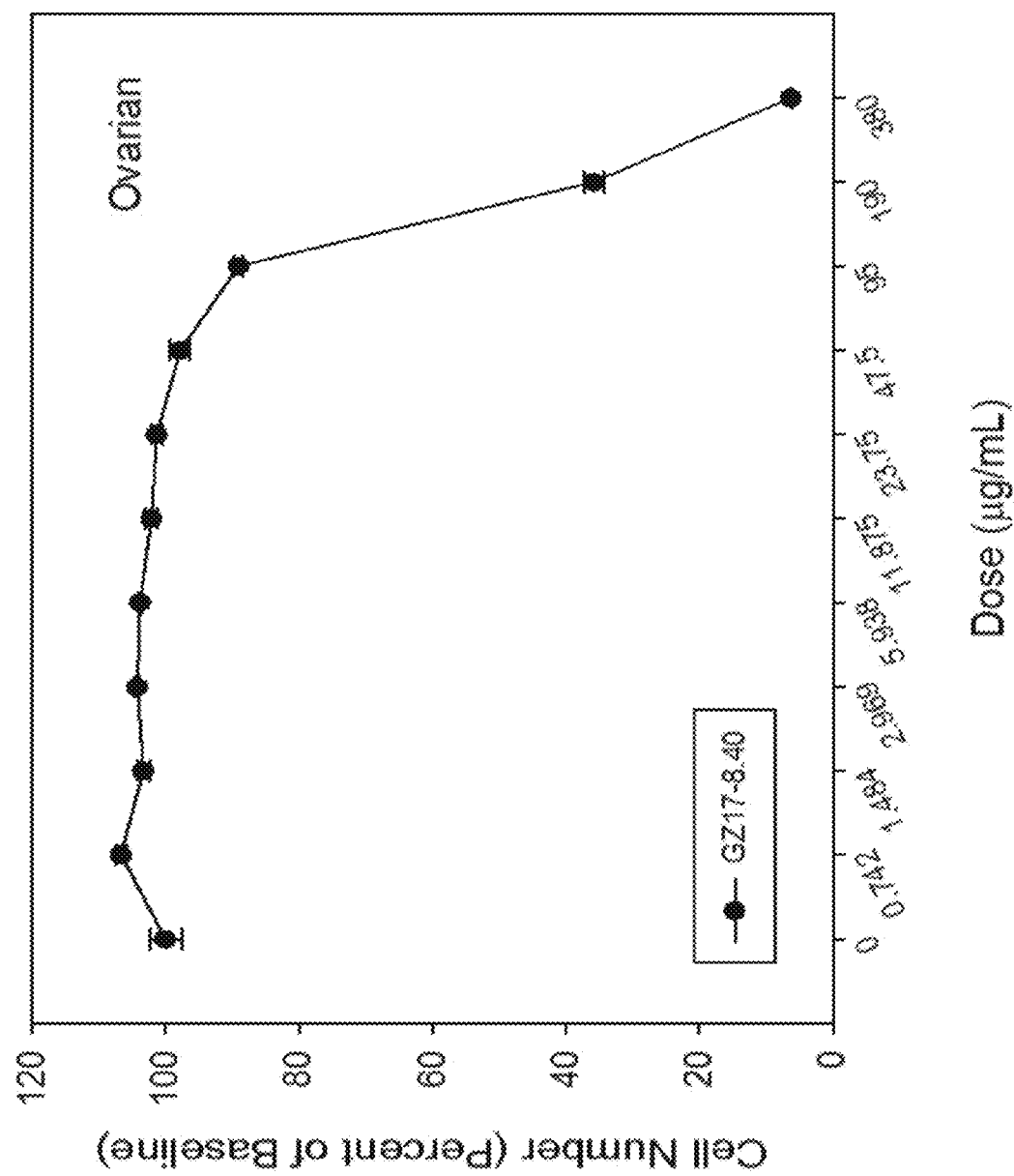
Figure 58B:
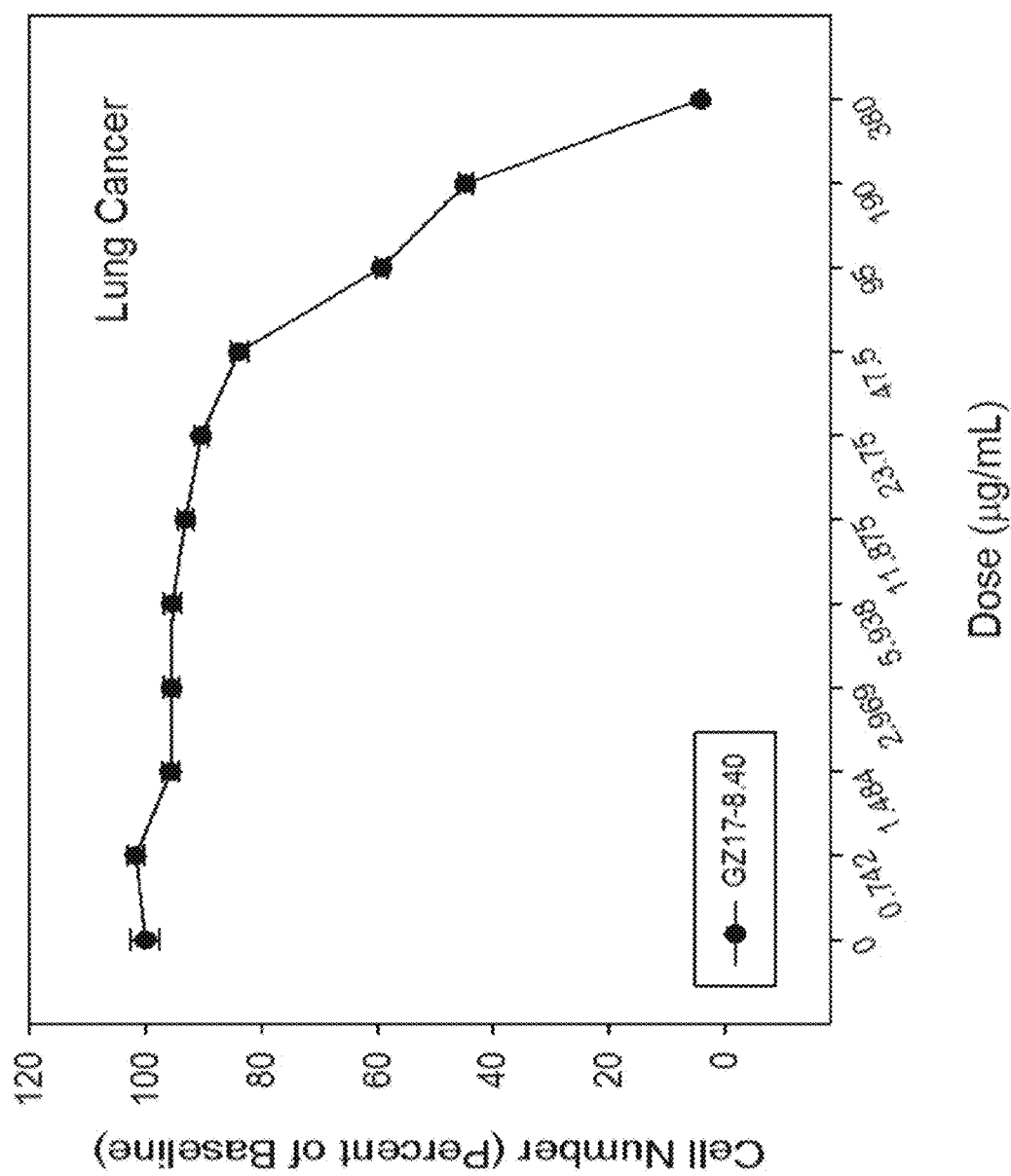
Figure 58C:
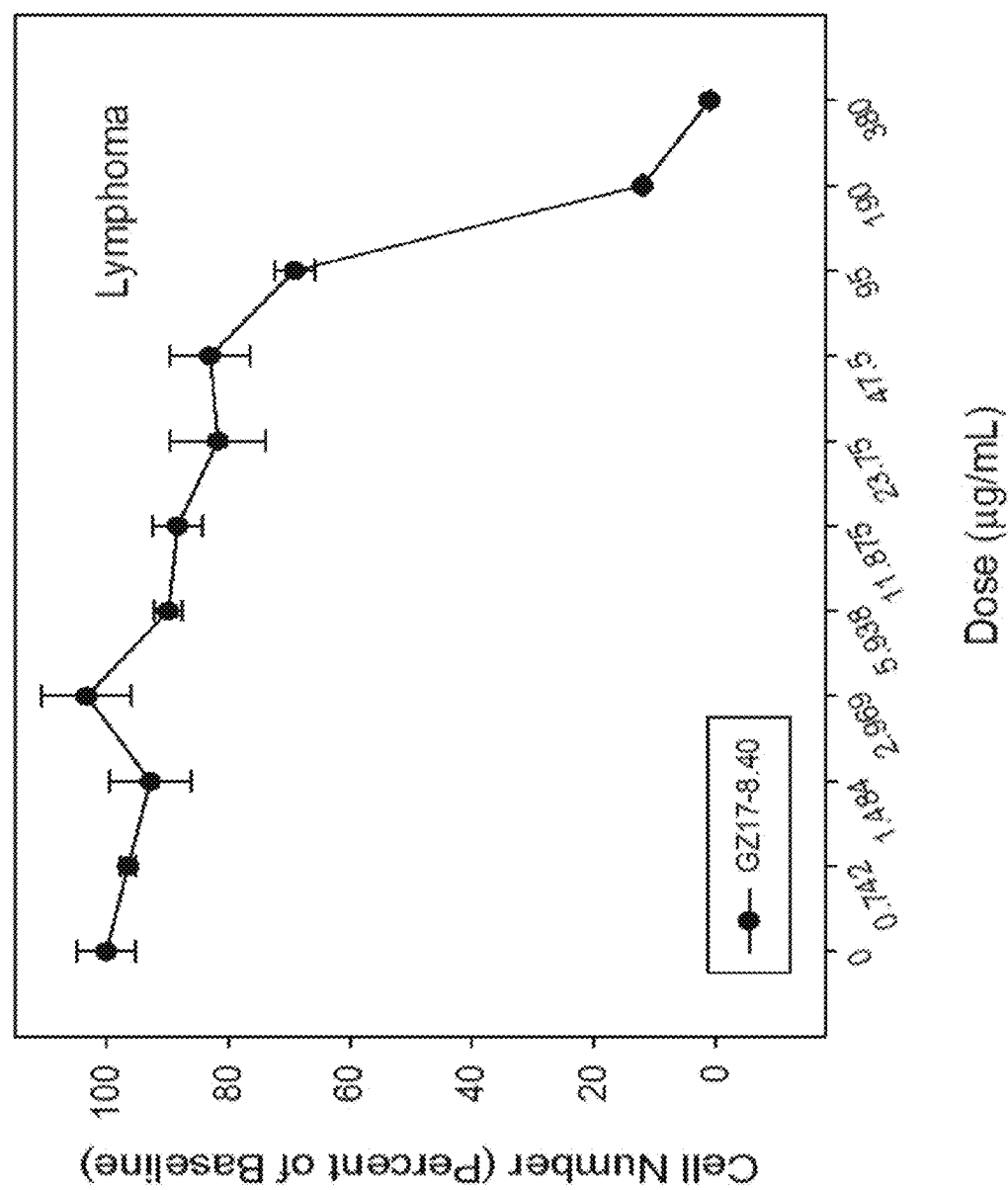
Figure 58D:
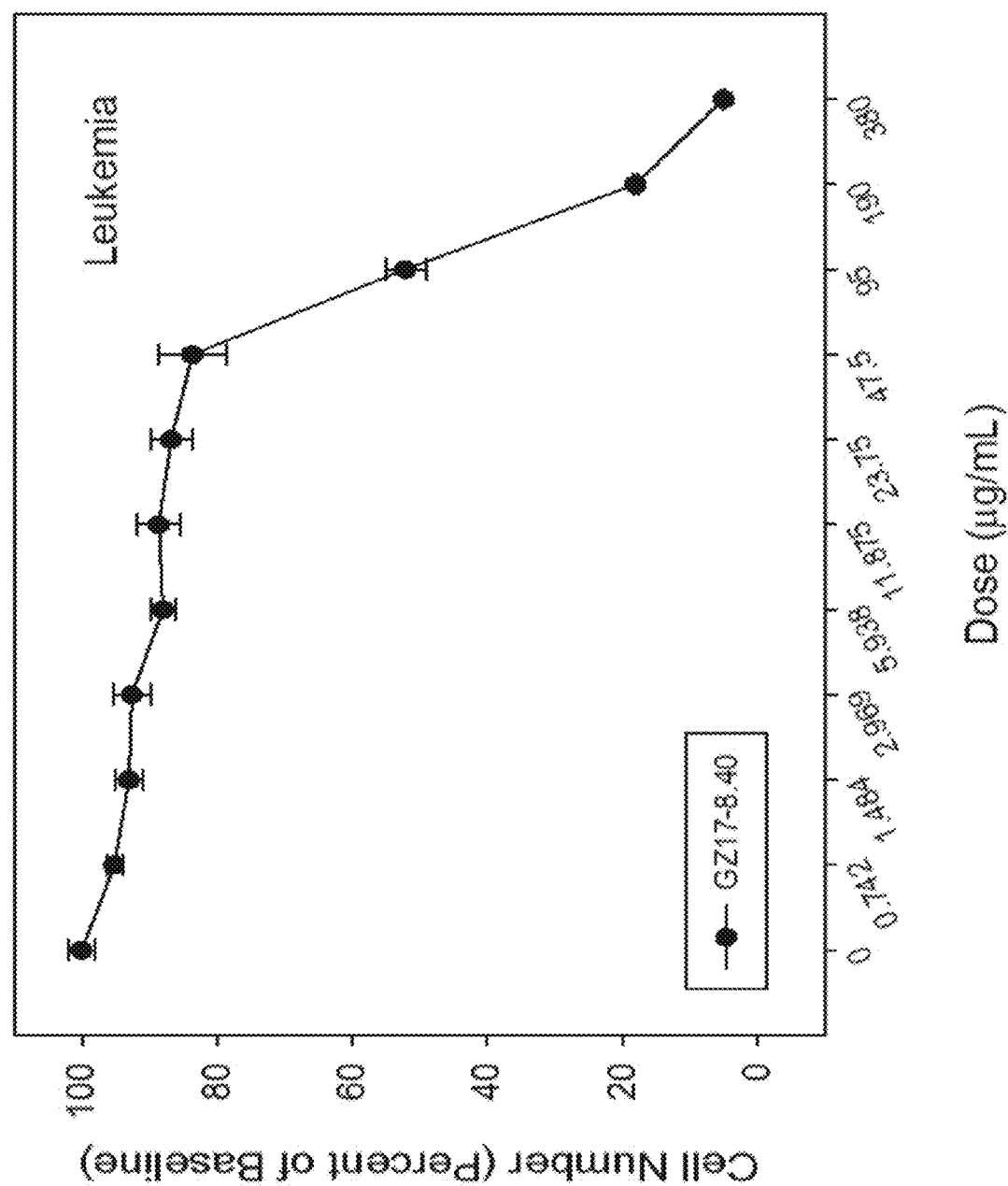
Figure 59A:
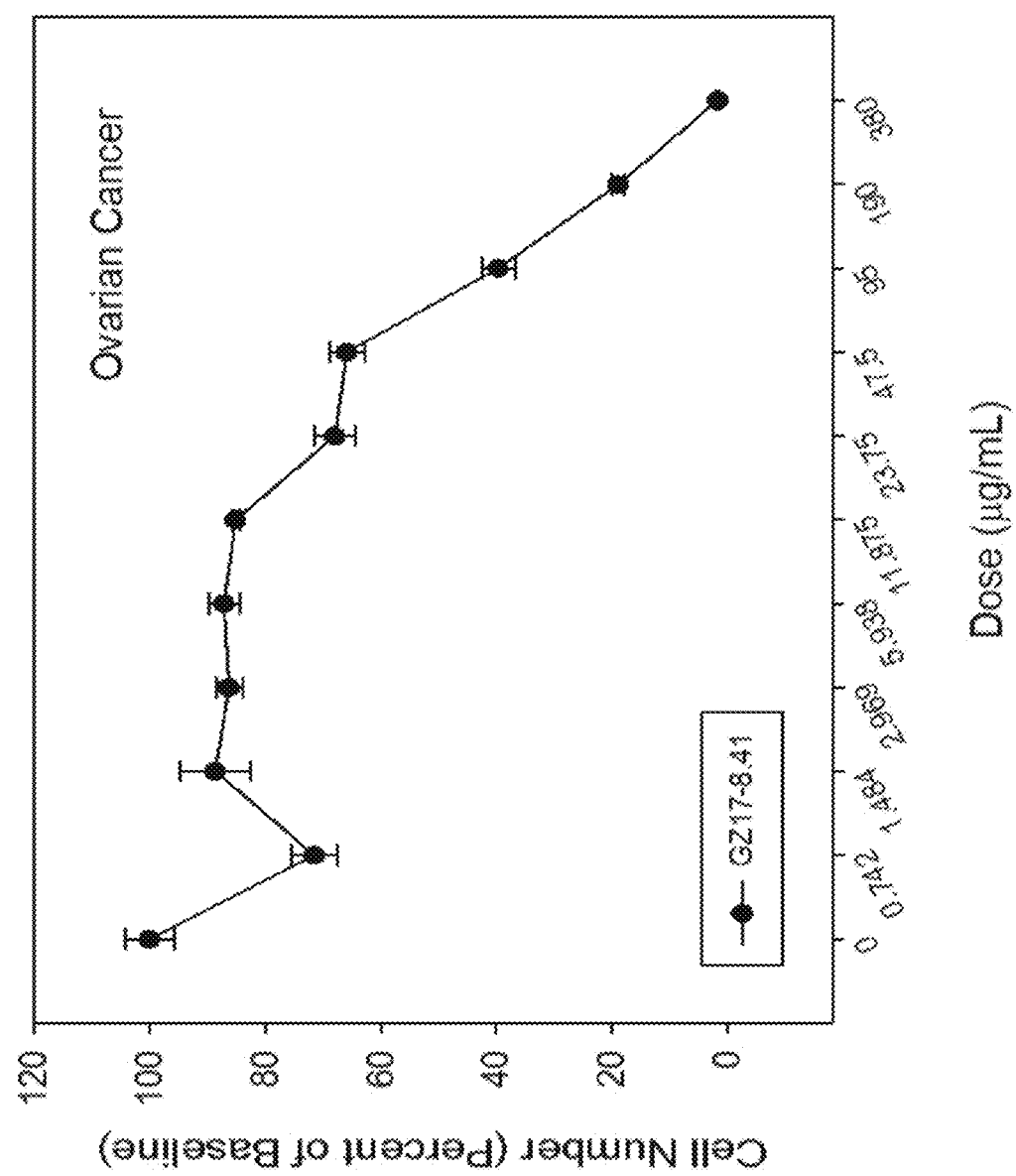
Figure 59B:
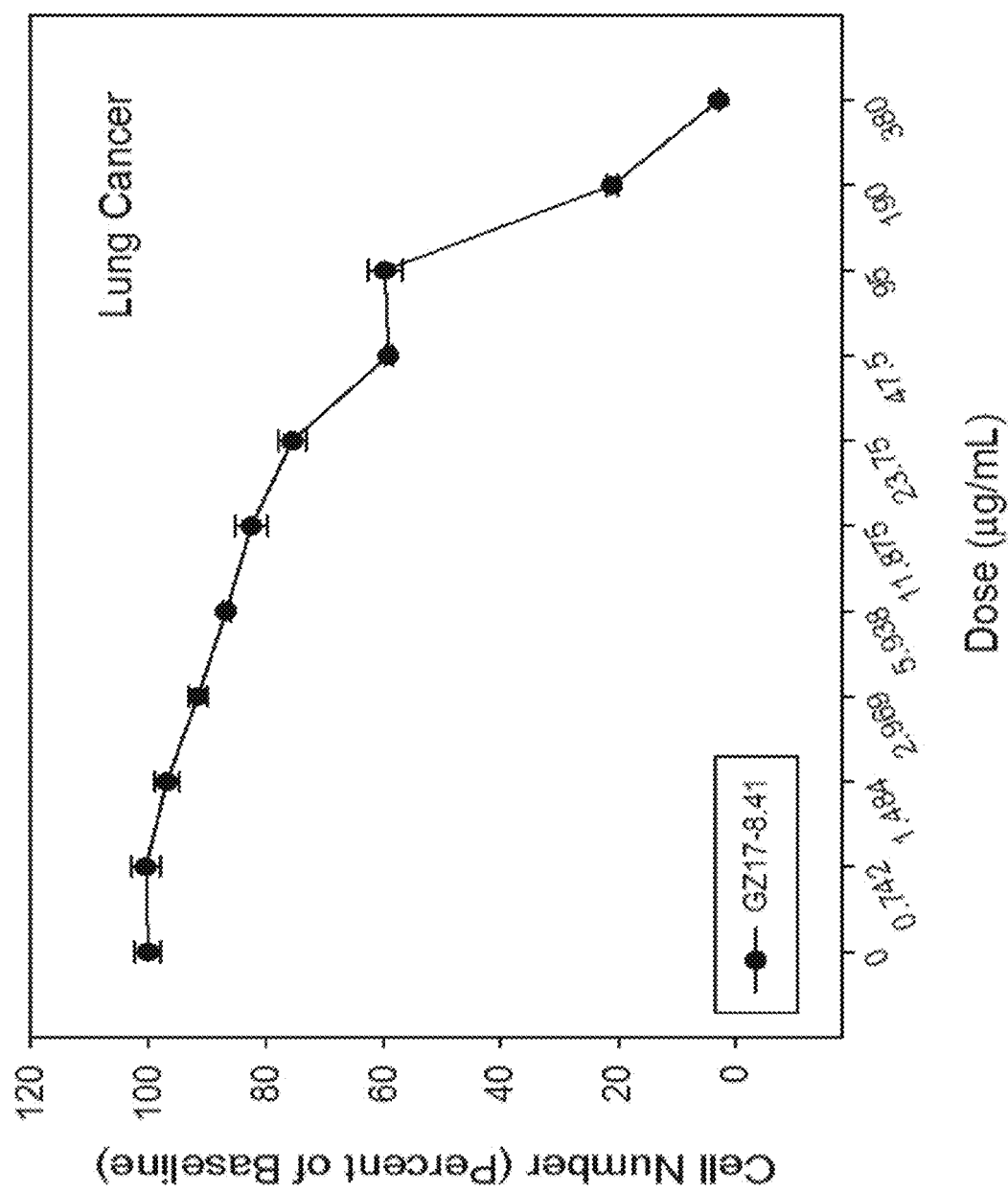
Figure 59C:
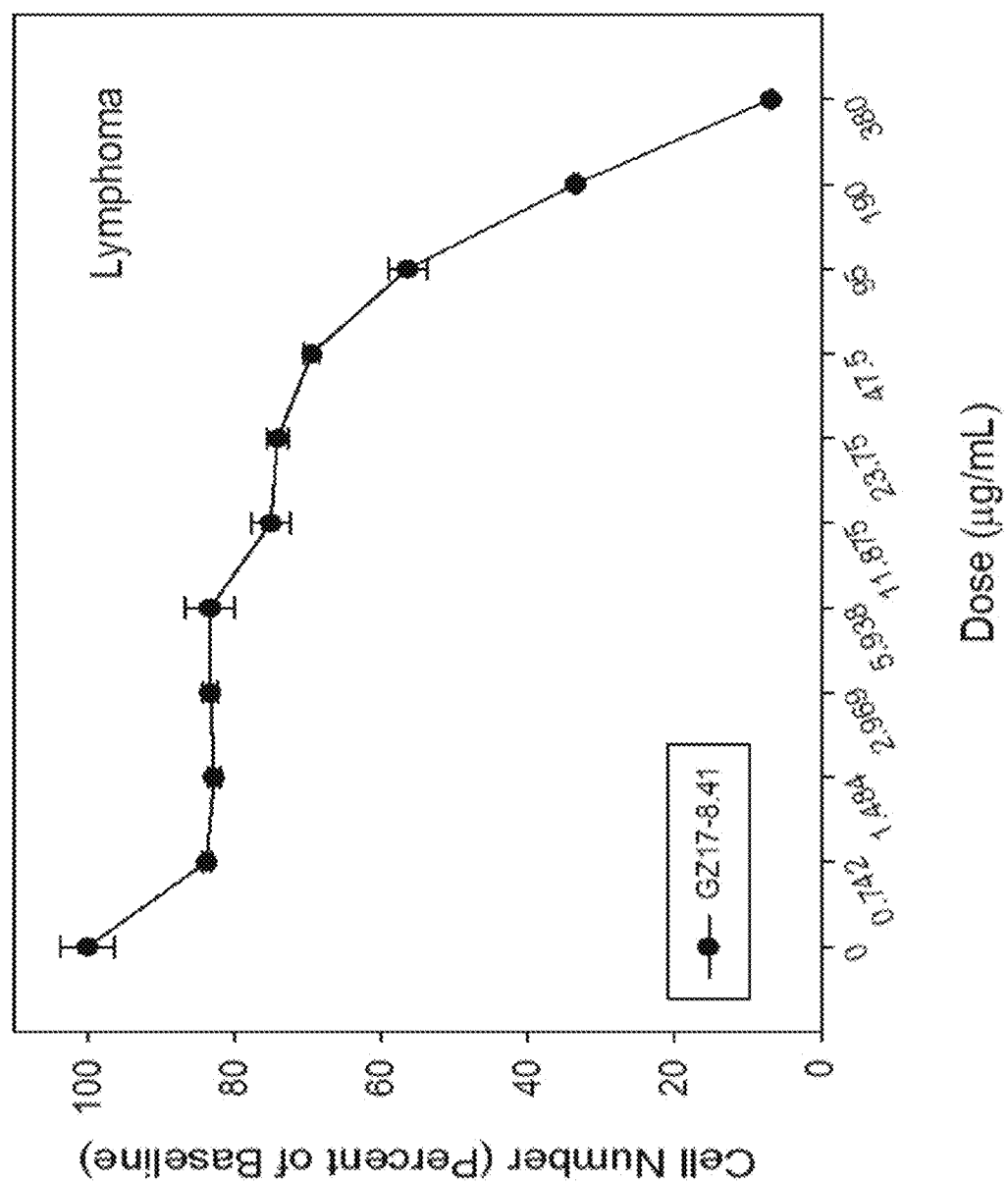
Figure 59D:
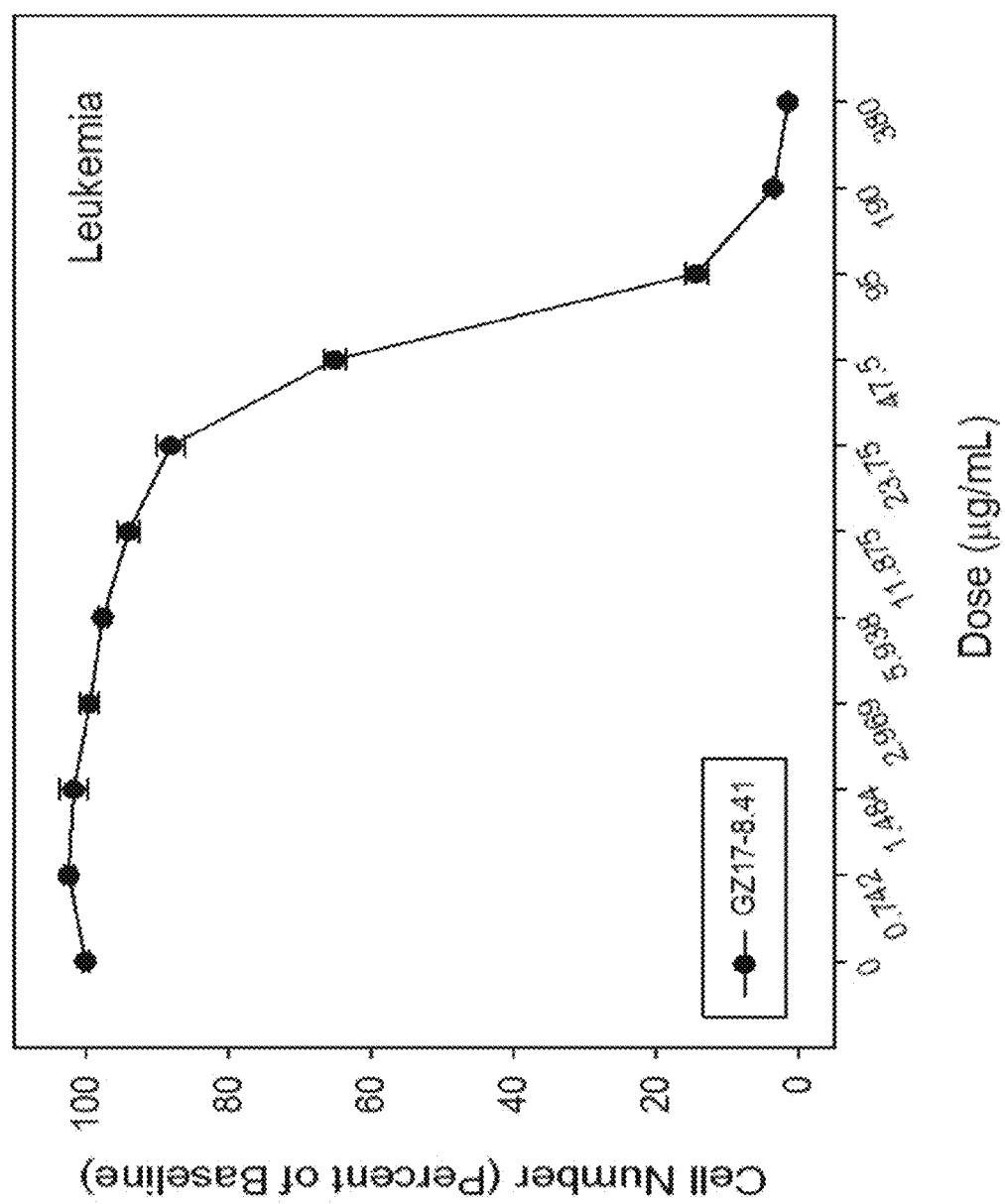
Figure 60A:
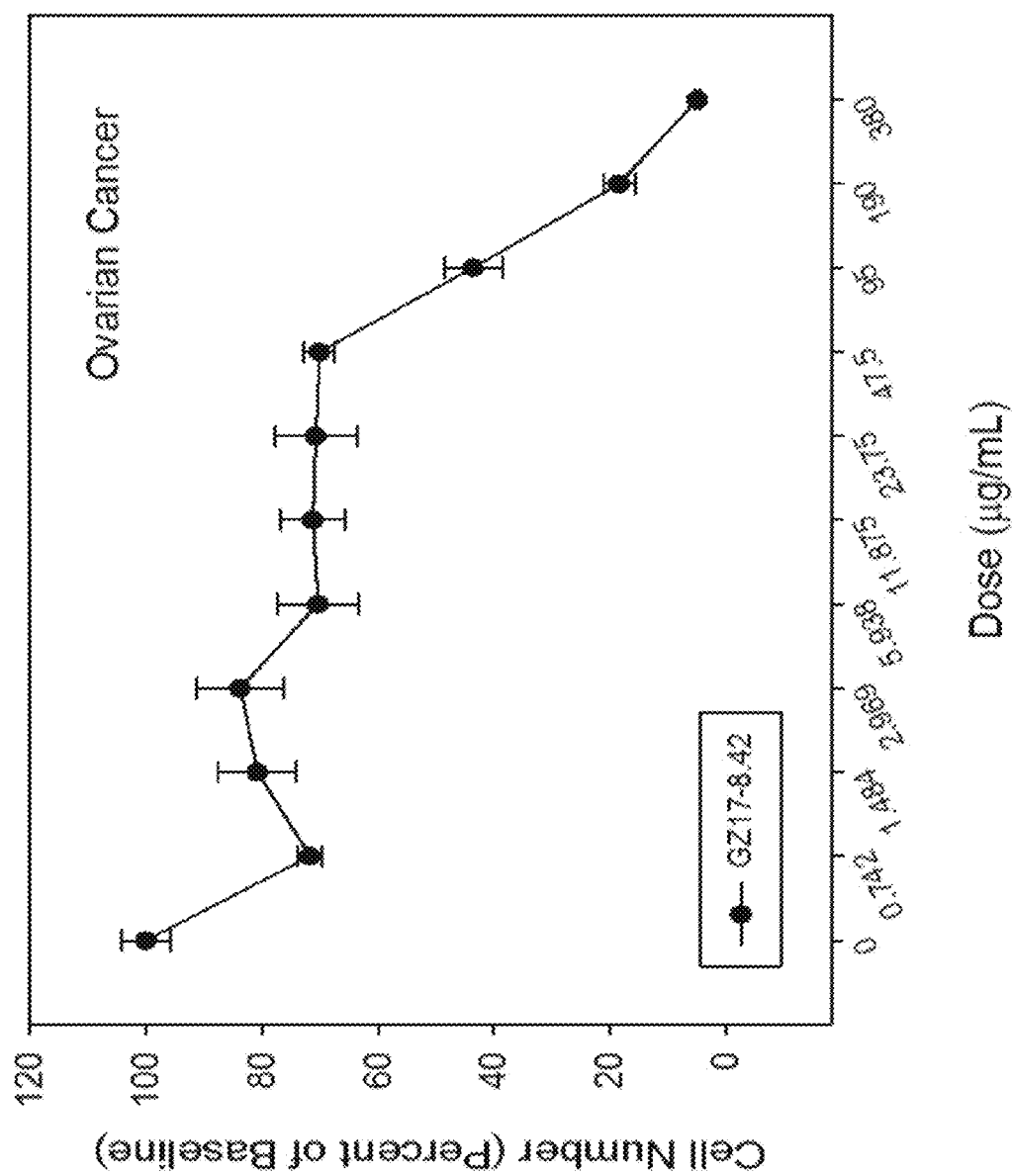
Figure 60B:
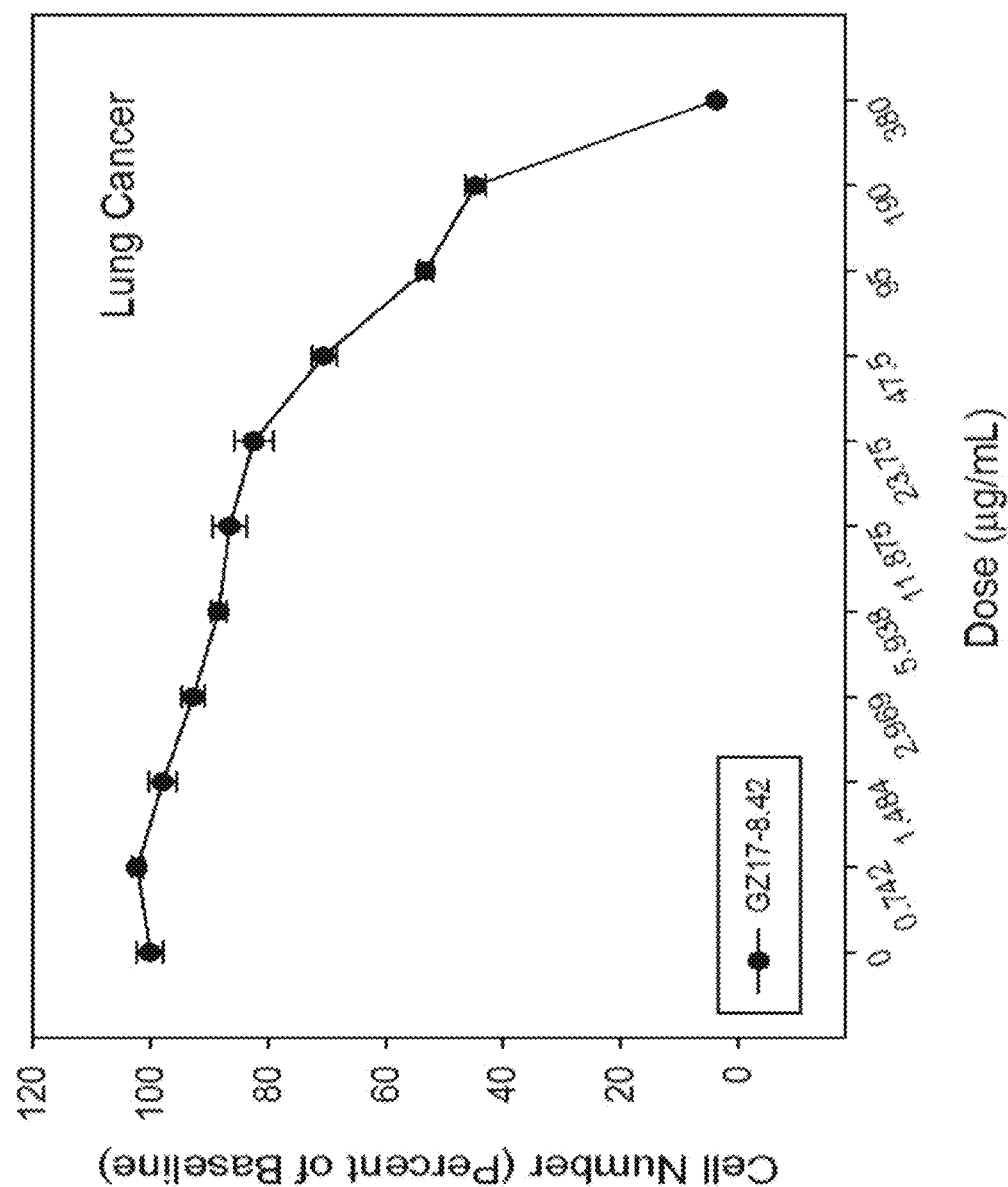
Figure 60C:
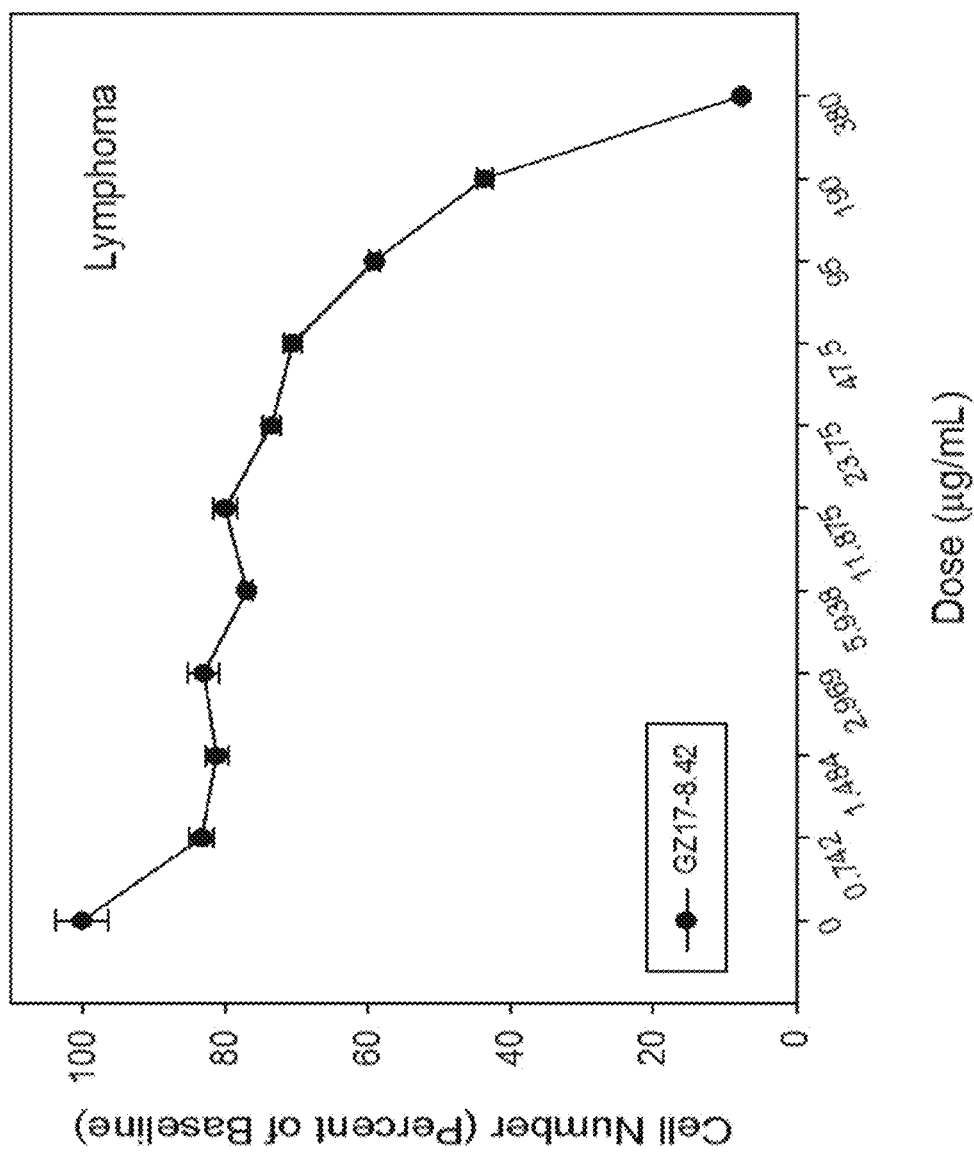
Figure 60D:
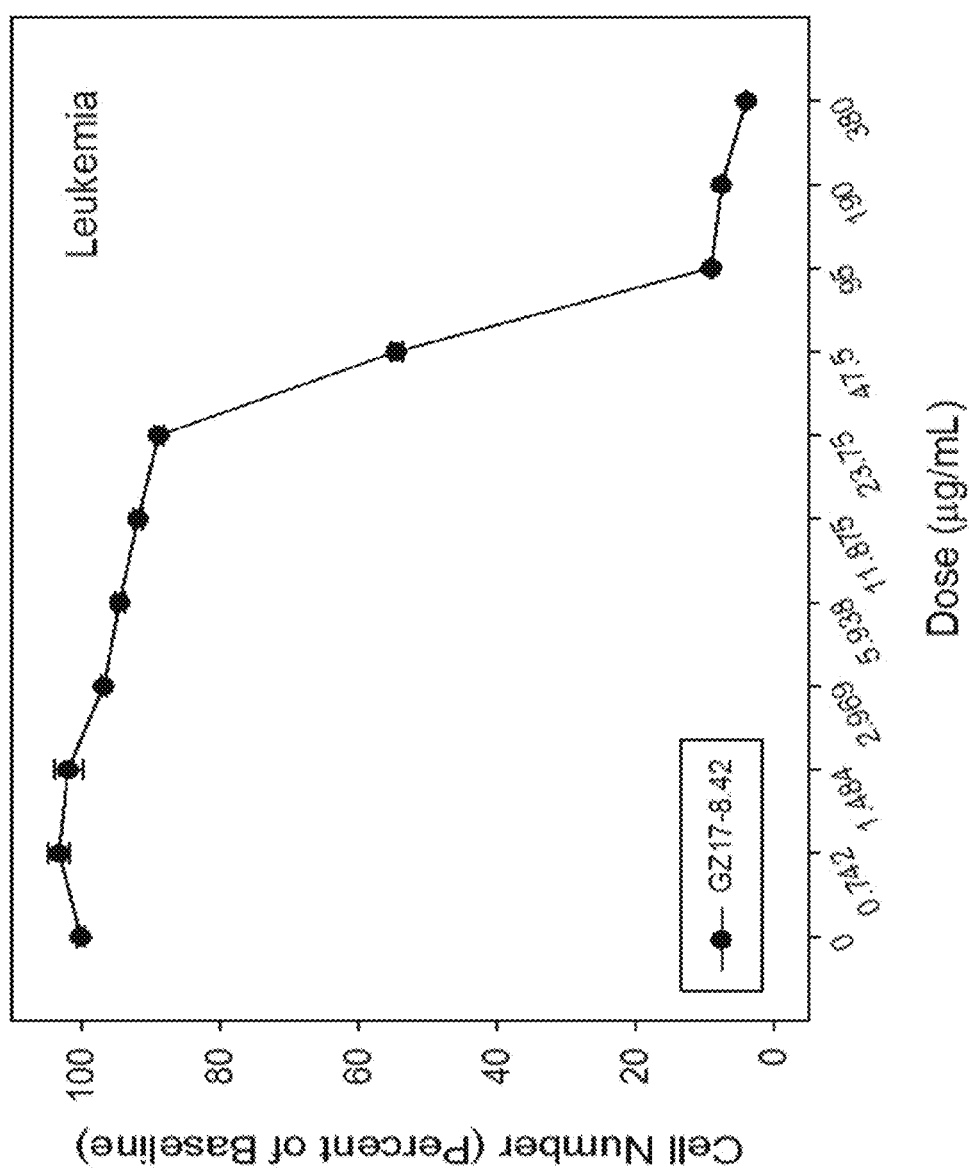
Figure 61A:
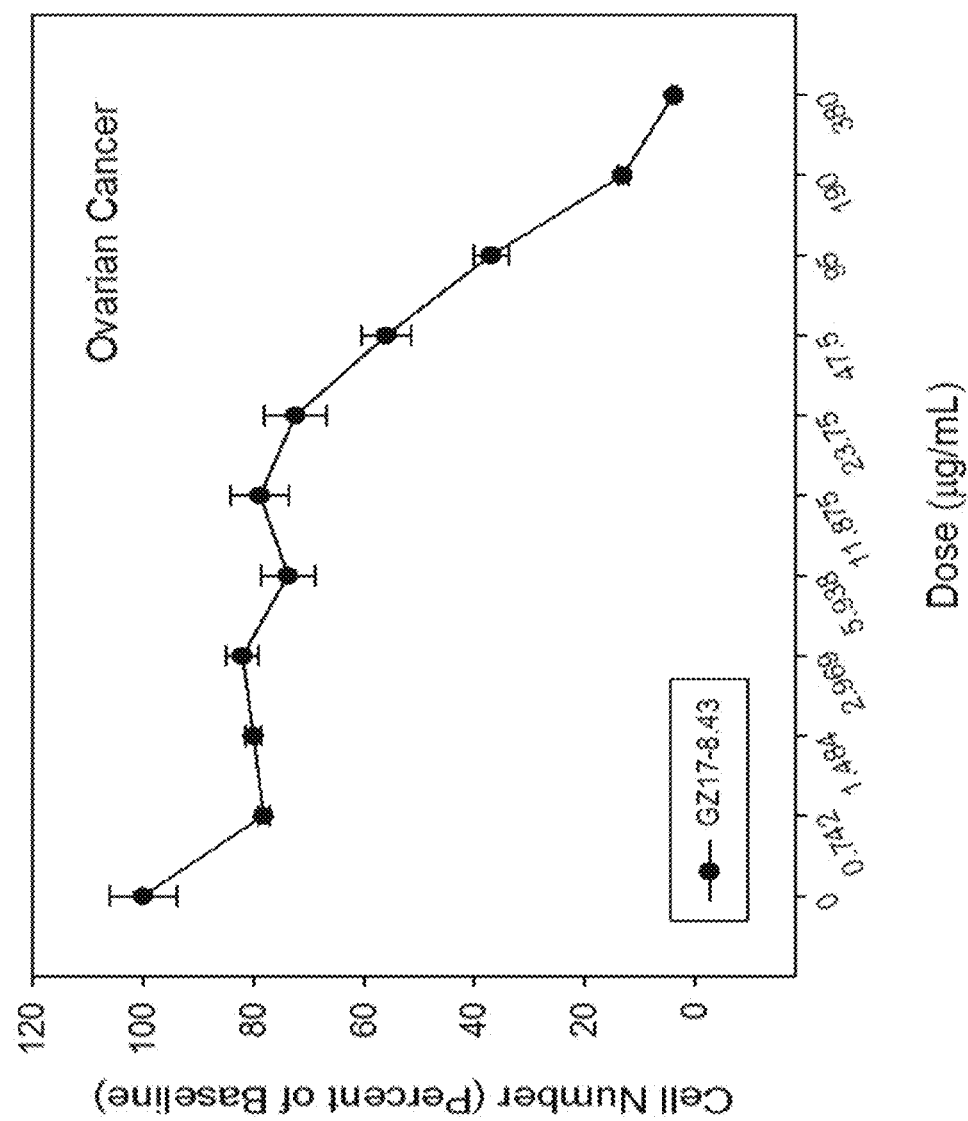
Figure 61B:
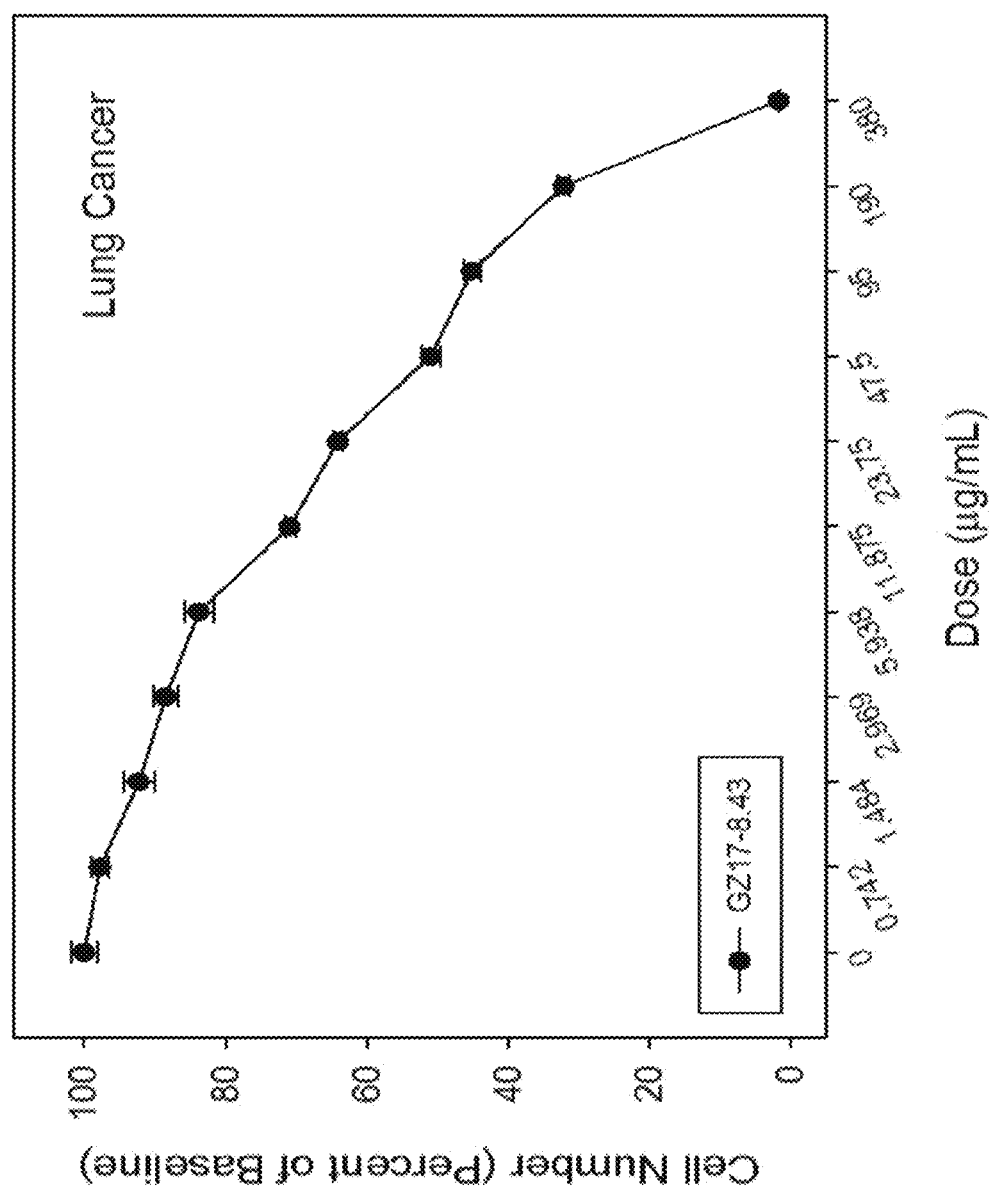
Figure 61C:
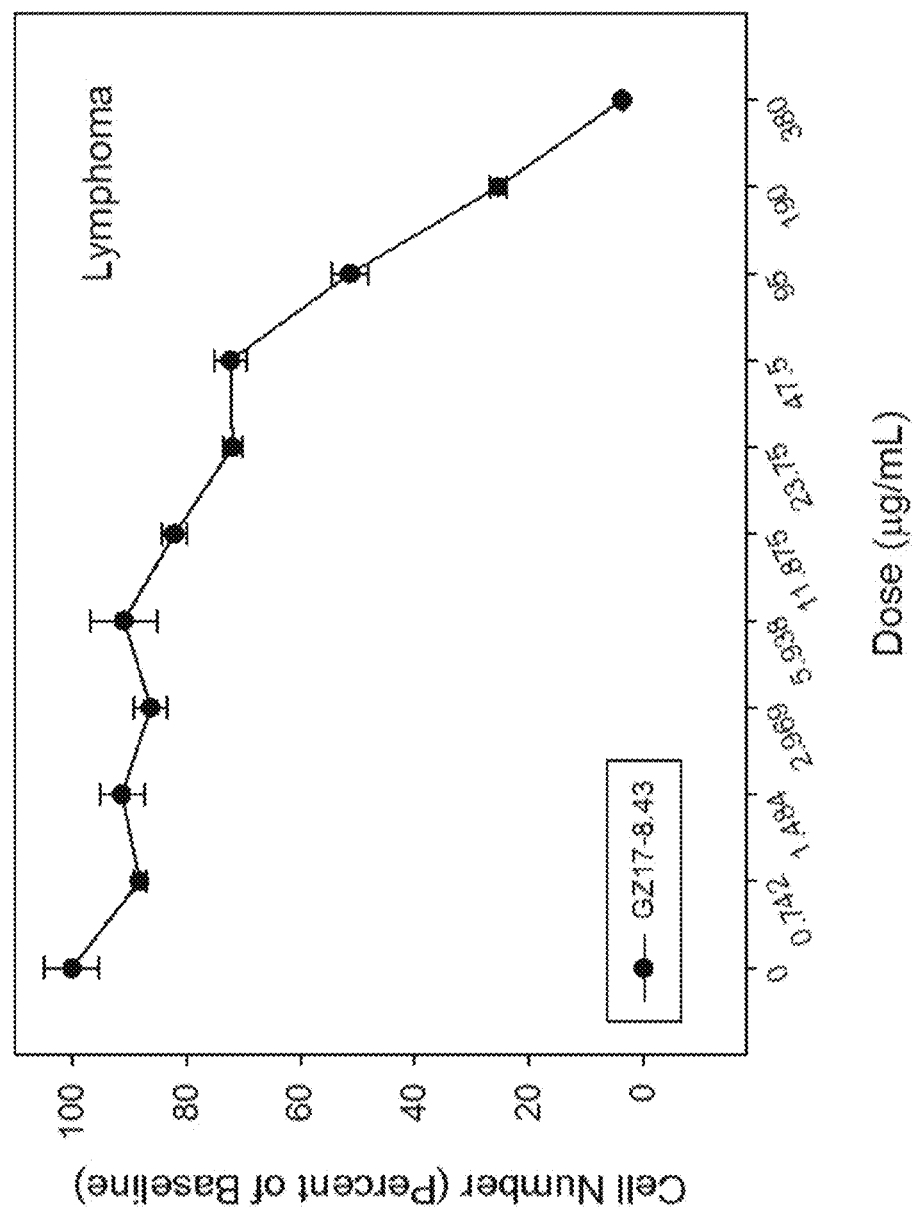
Figure 61D:
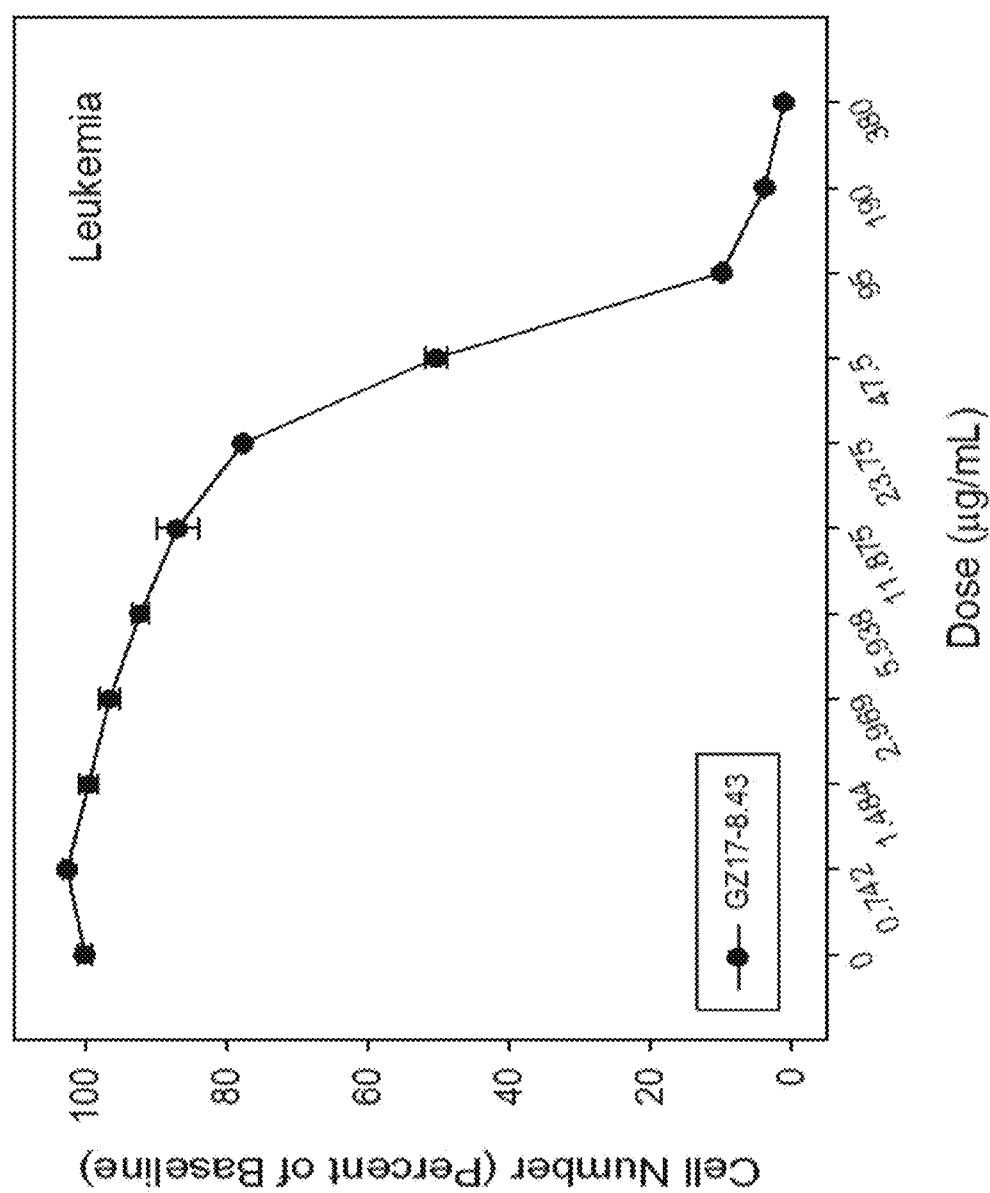
Figure 62A:
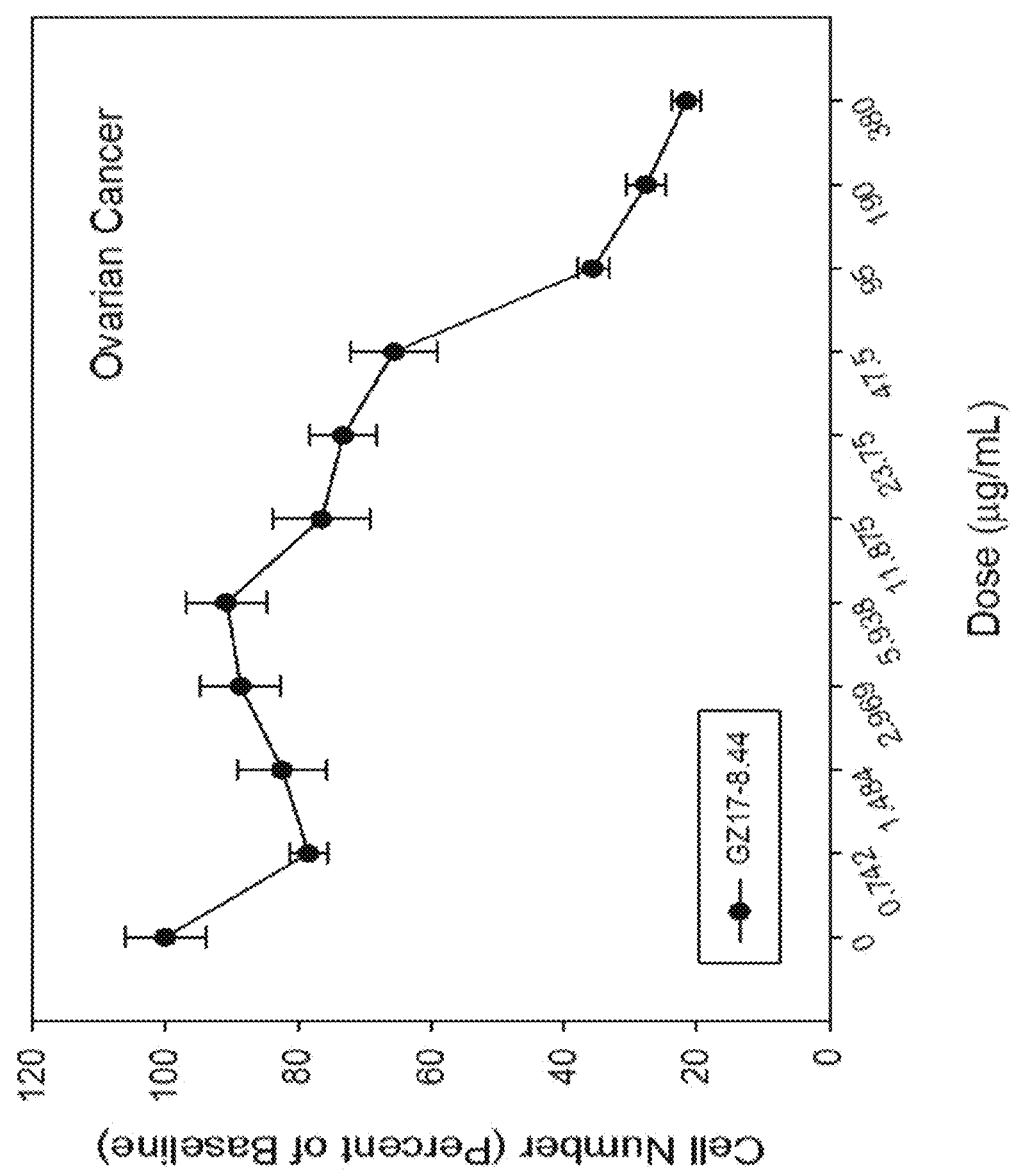
Figure 62B:
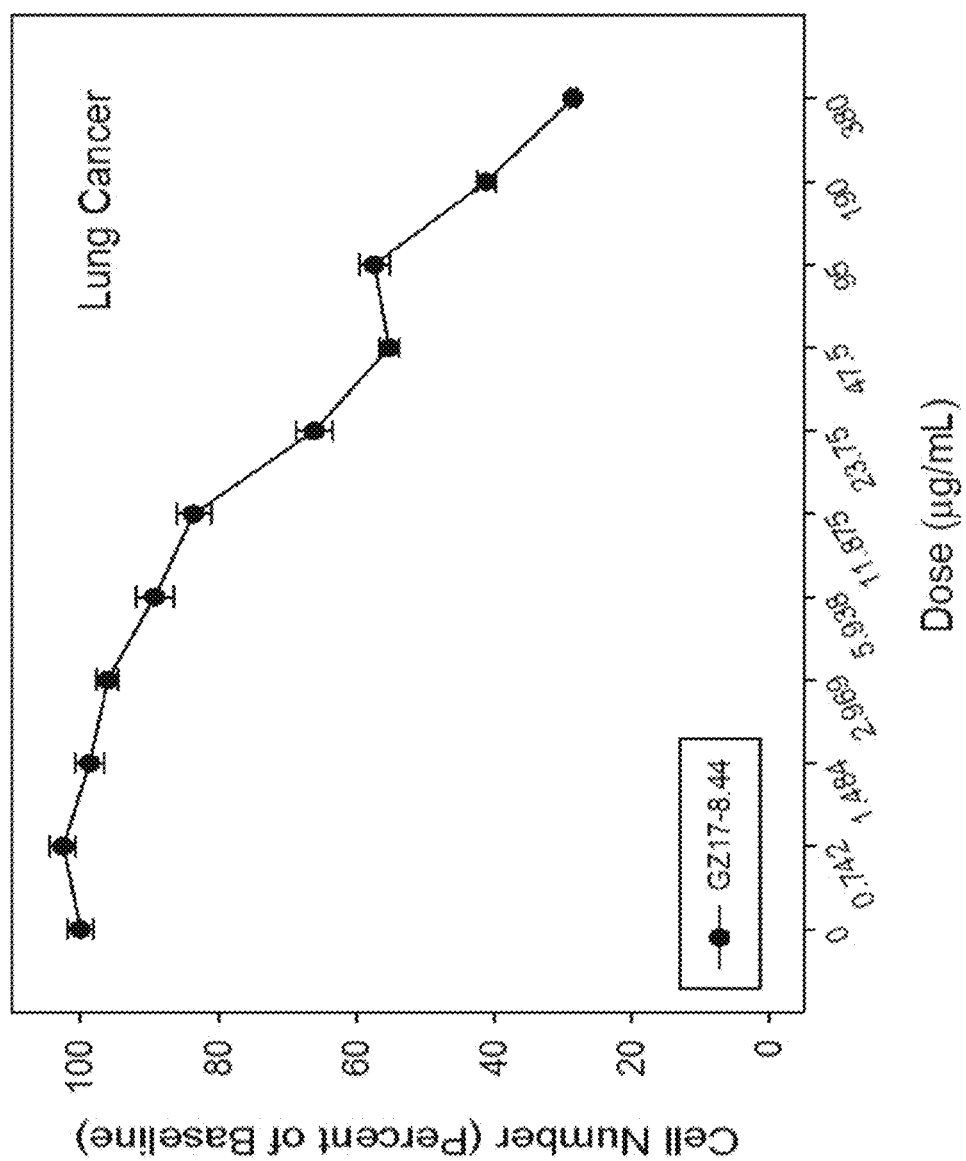
Figure 62C:
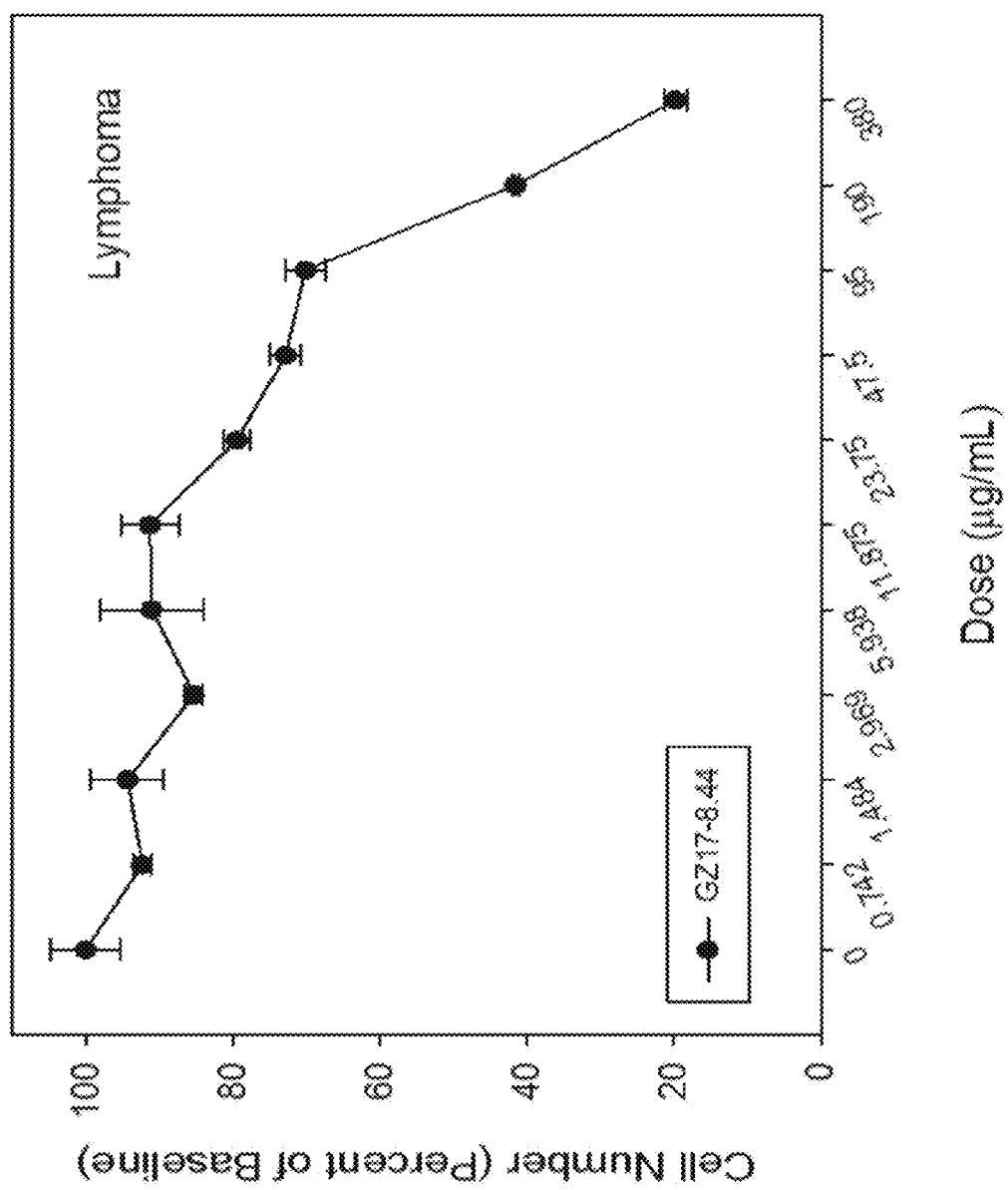
Figure 62D:
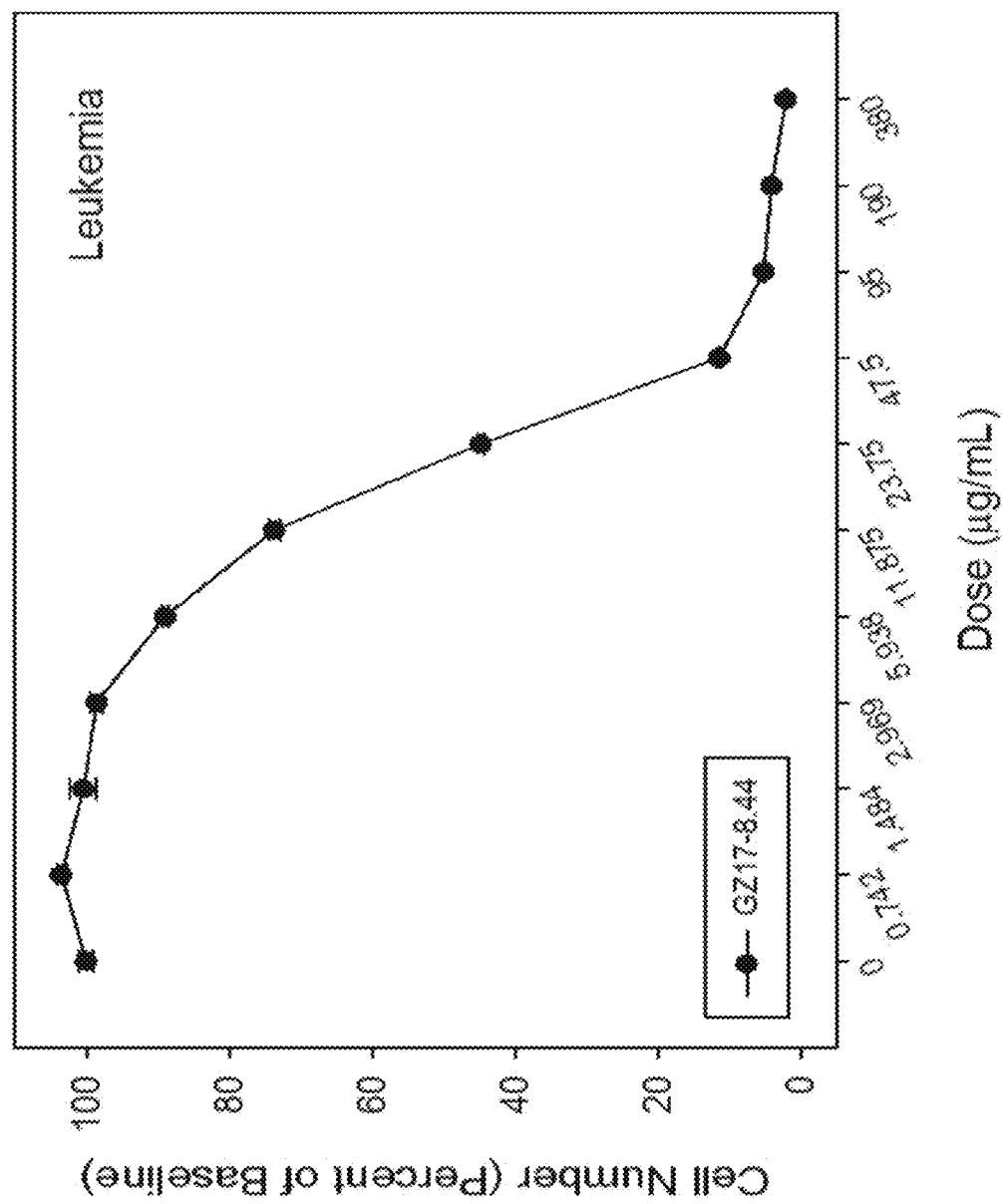
Figure 63A:
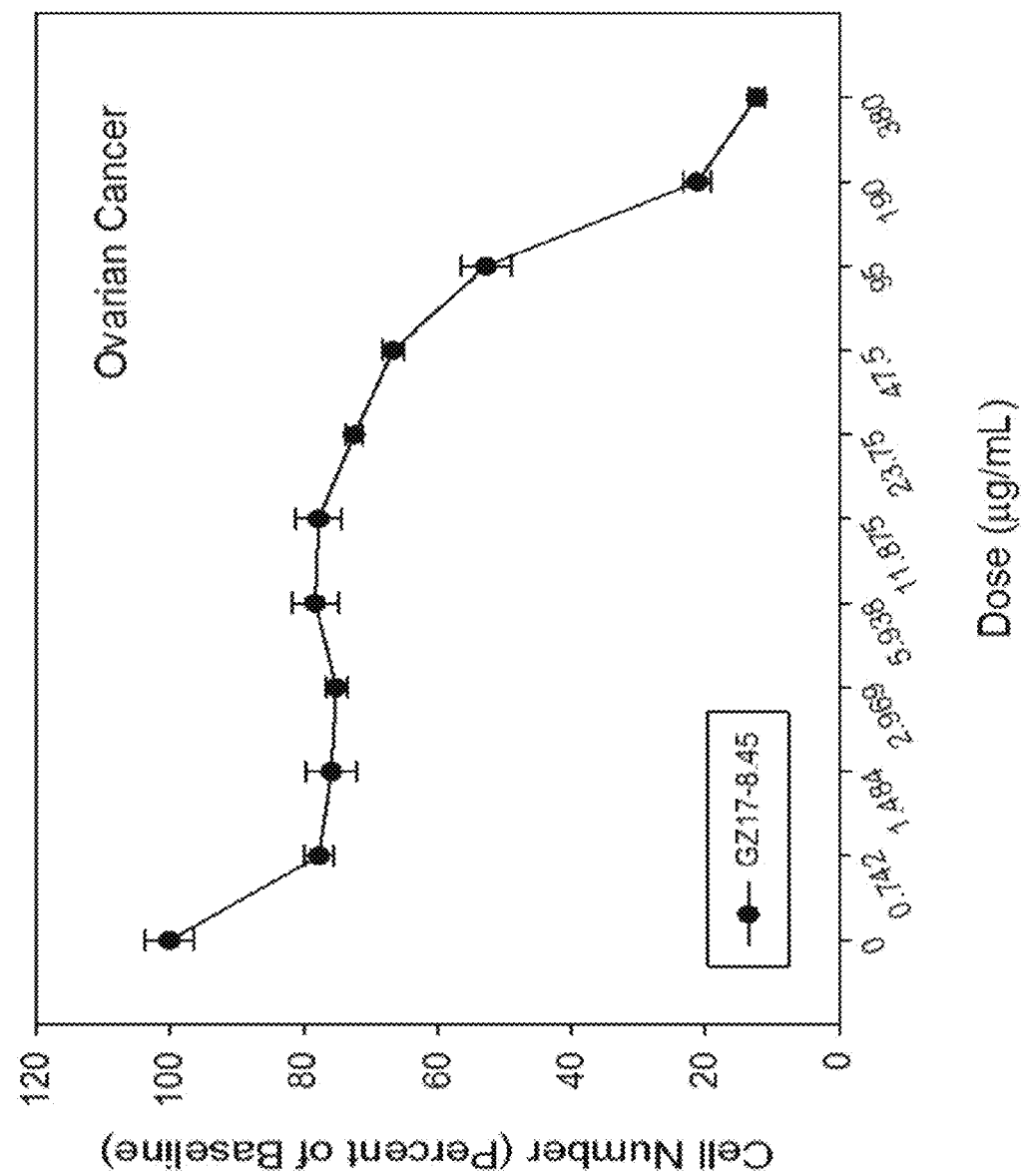
Figure 63B:
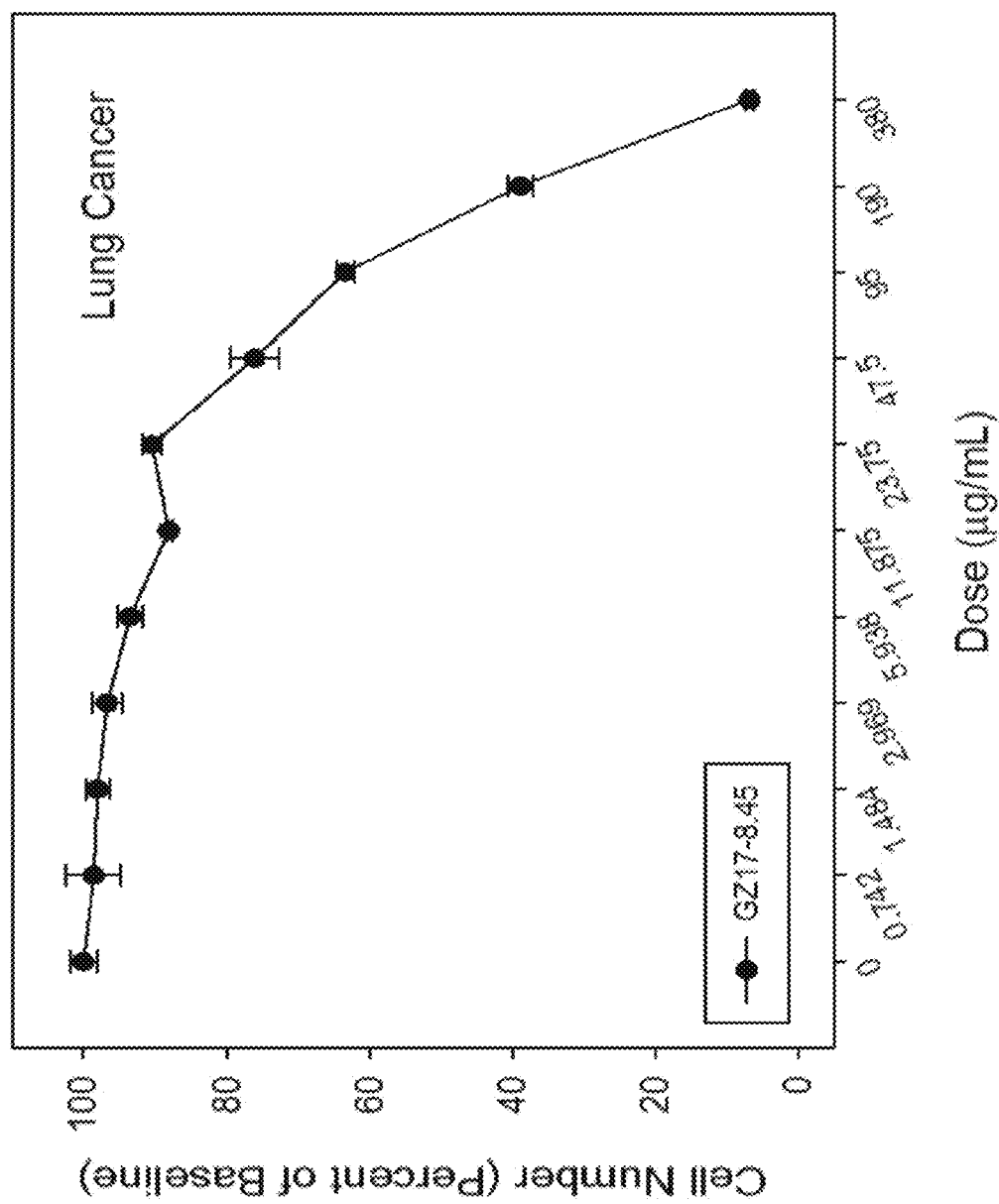
Figure 63C:
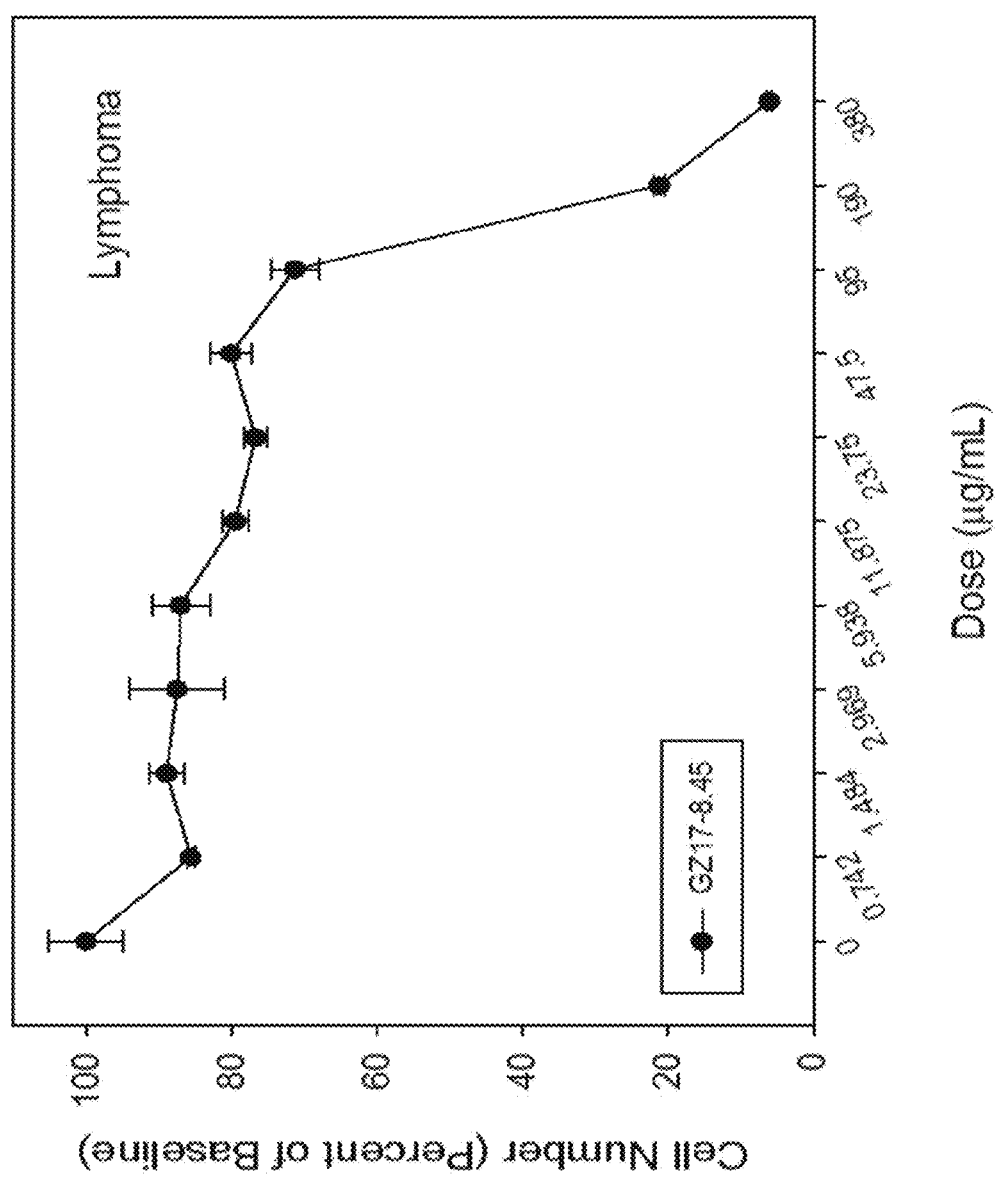
Figure 63D:
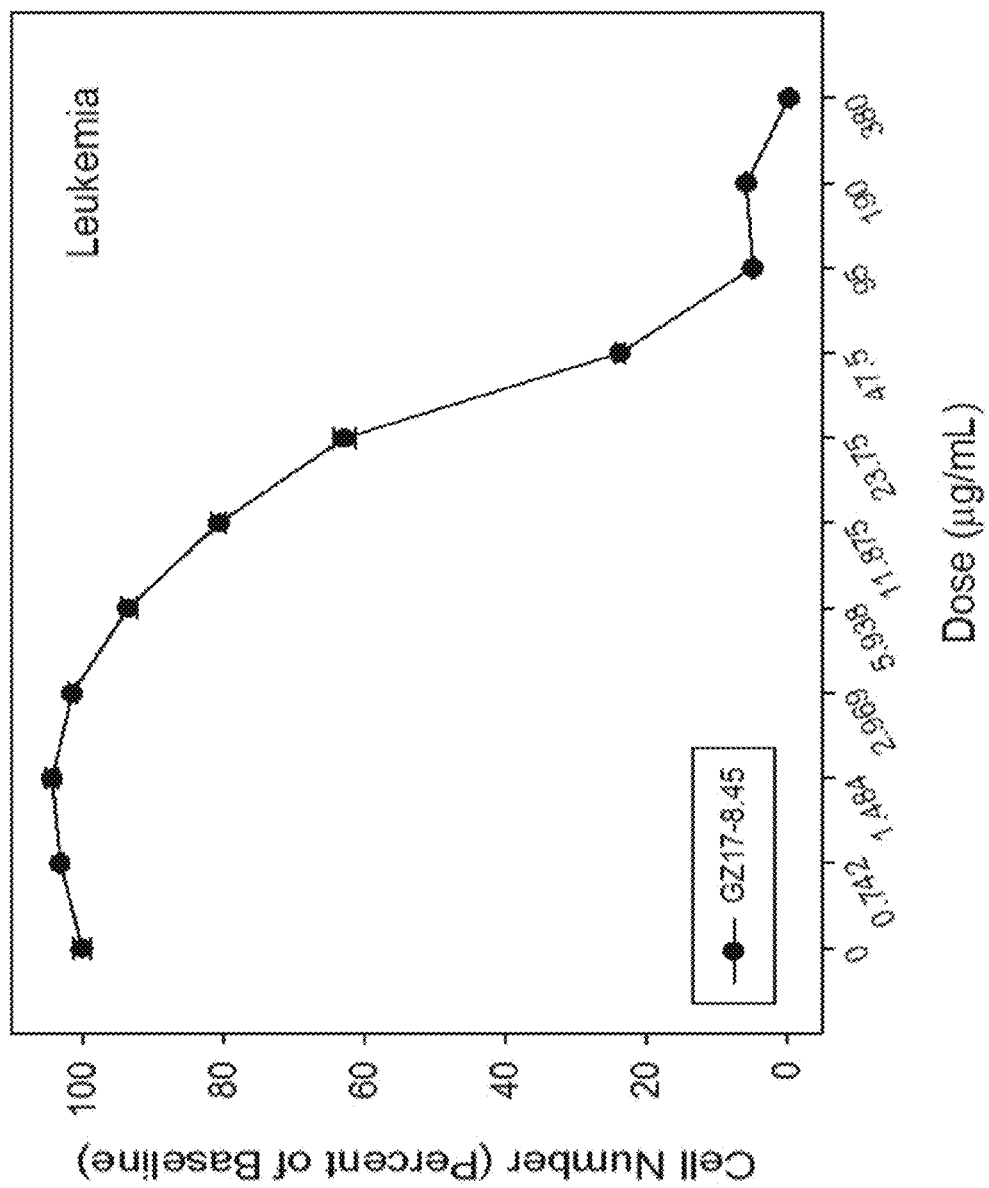
Figure 64A:
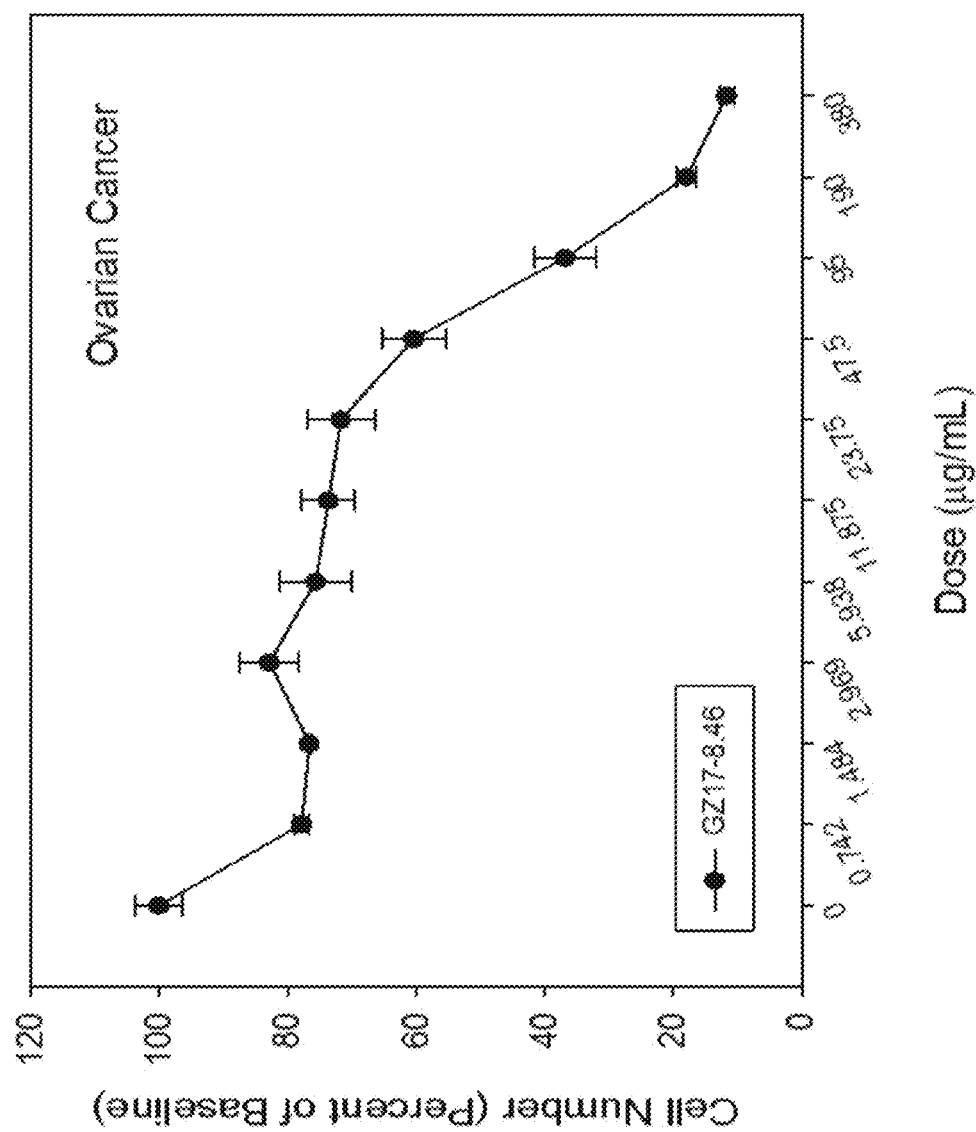
Figure 64B:
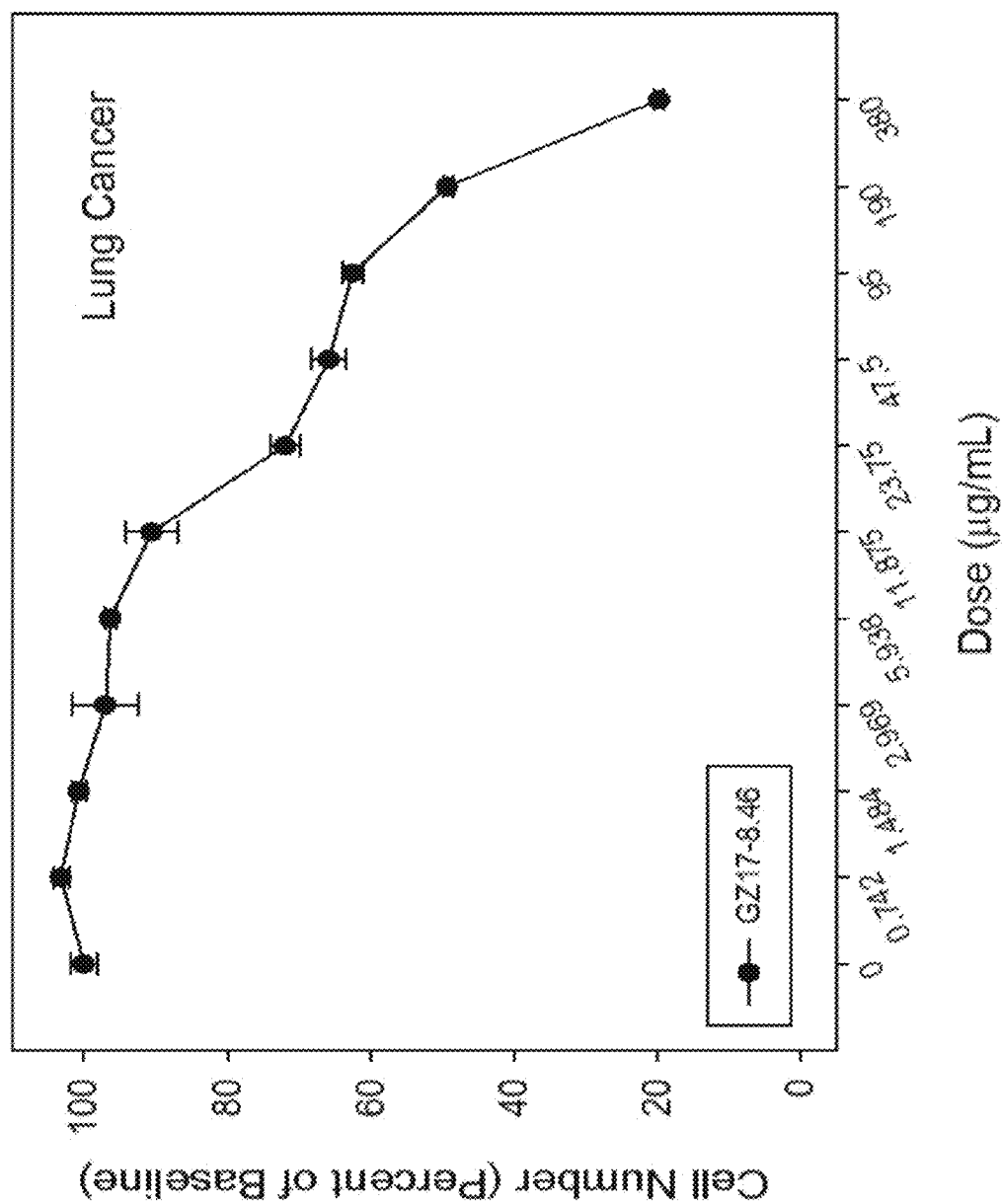
Figure 64C:
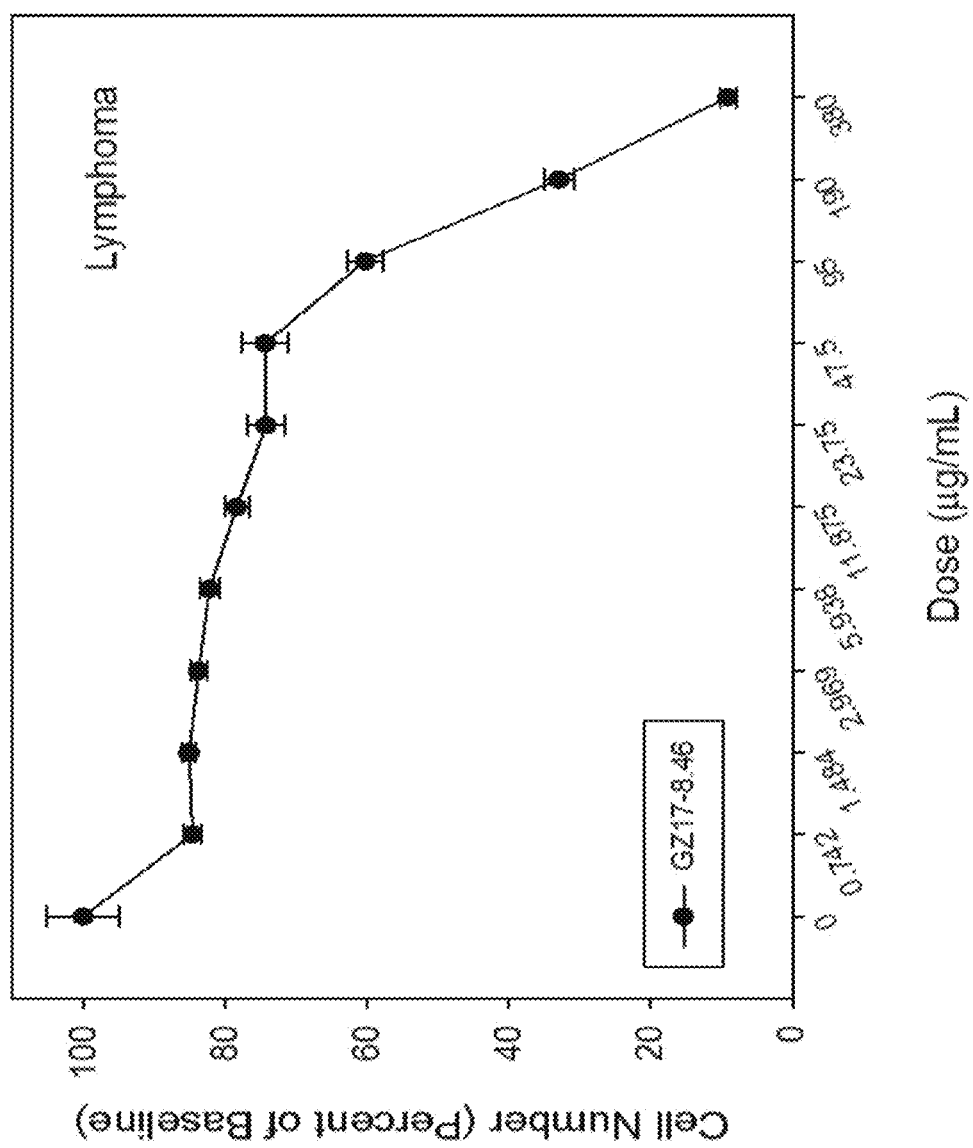
Figure 64D:
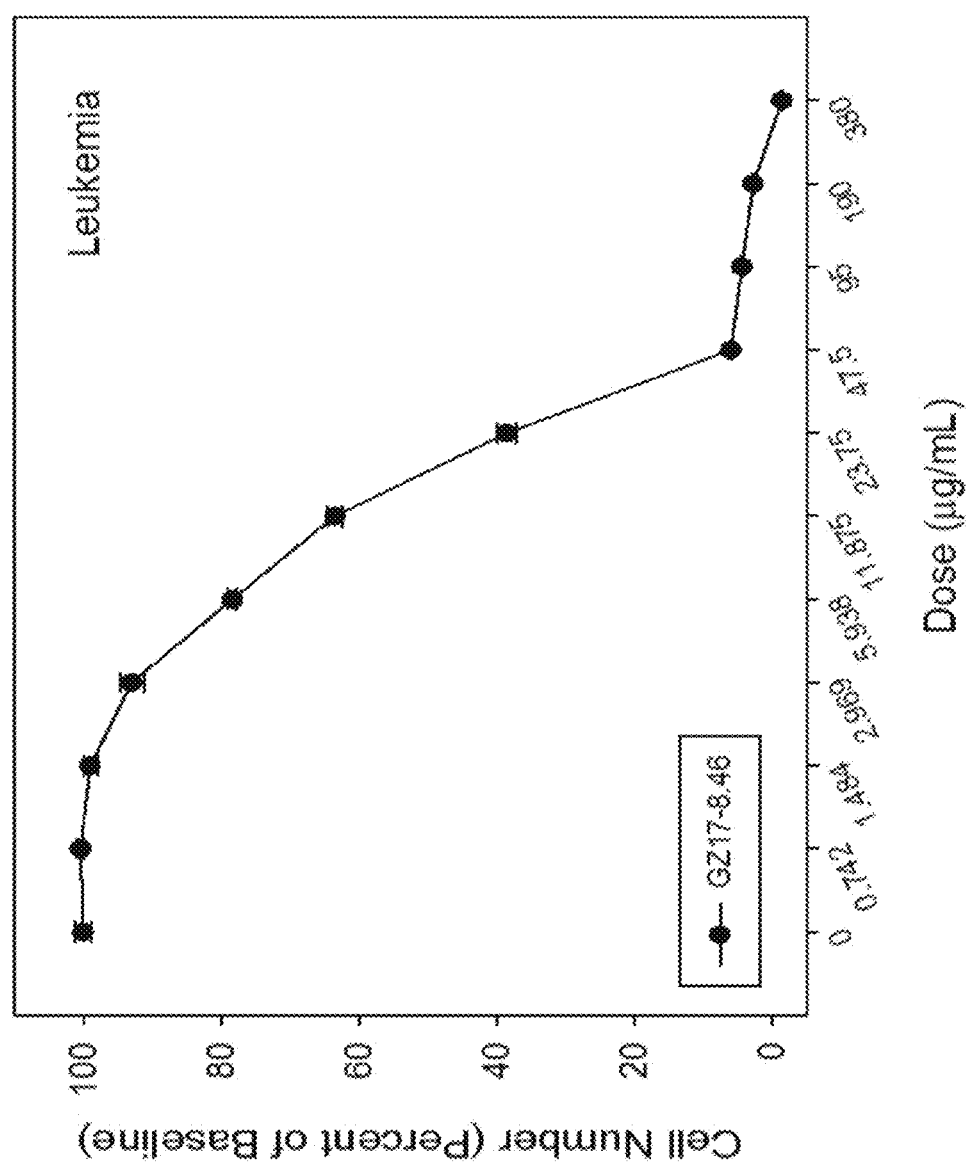
Figure 65A:
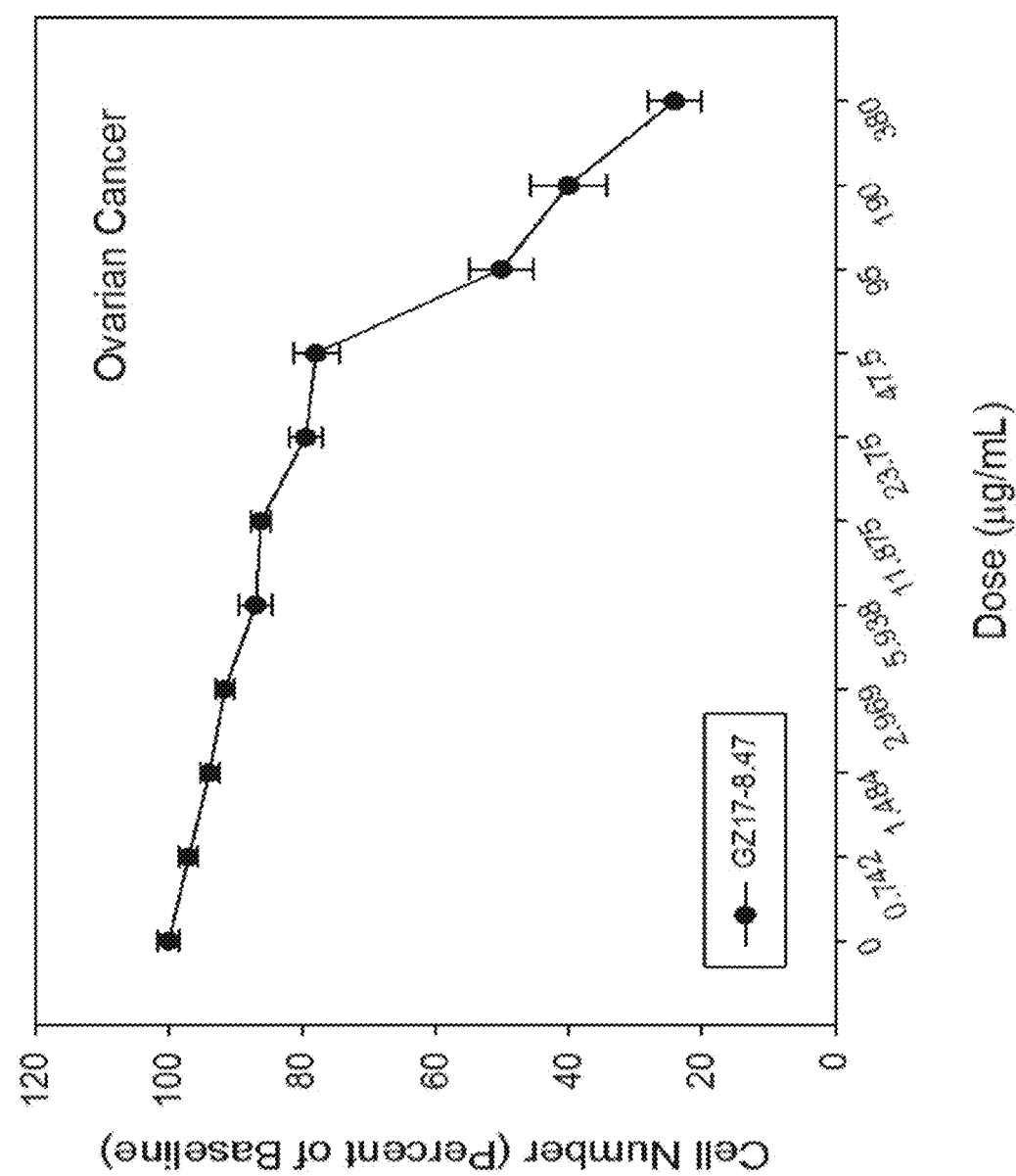
Figure 65B:
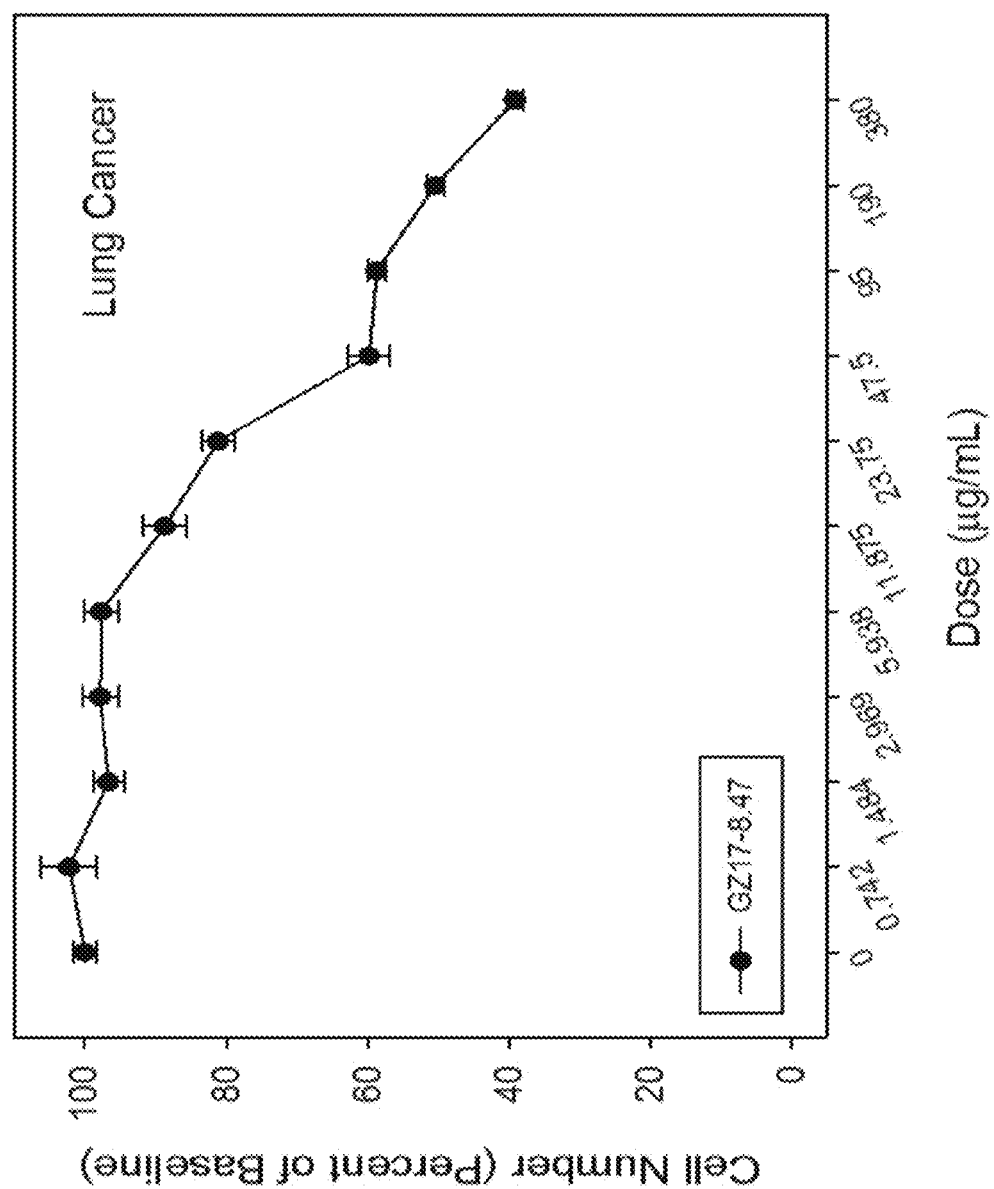
Figure 65C:
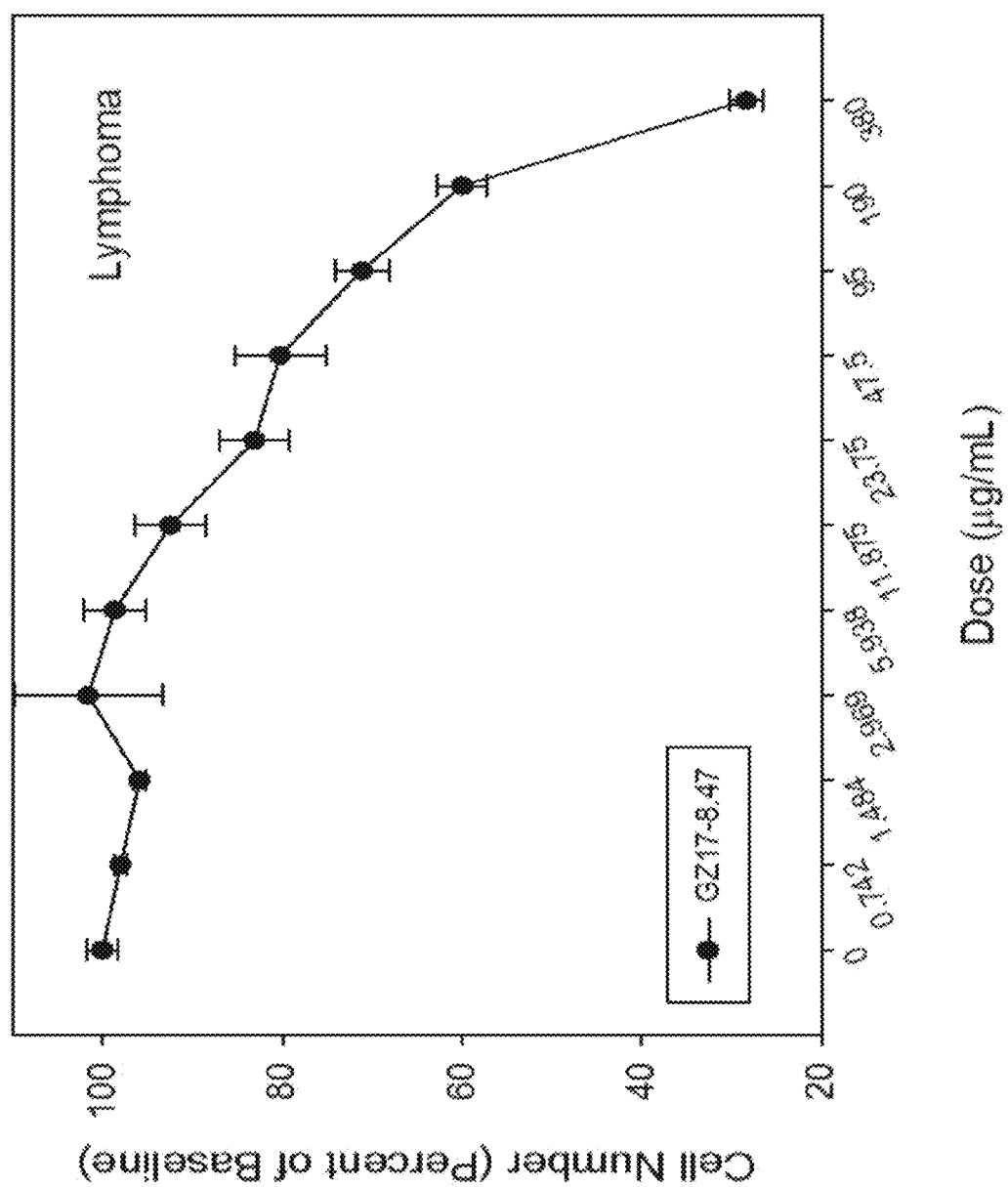
Figure 65D:
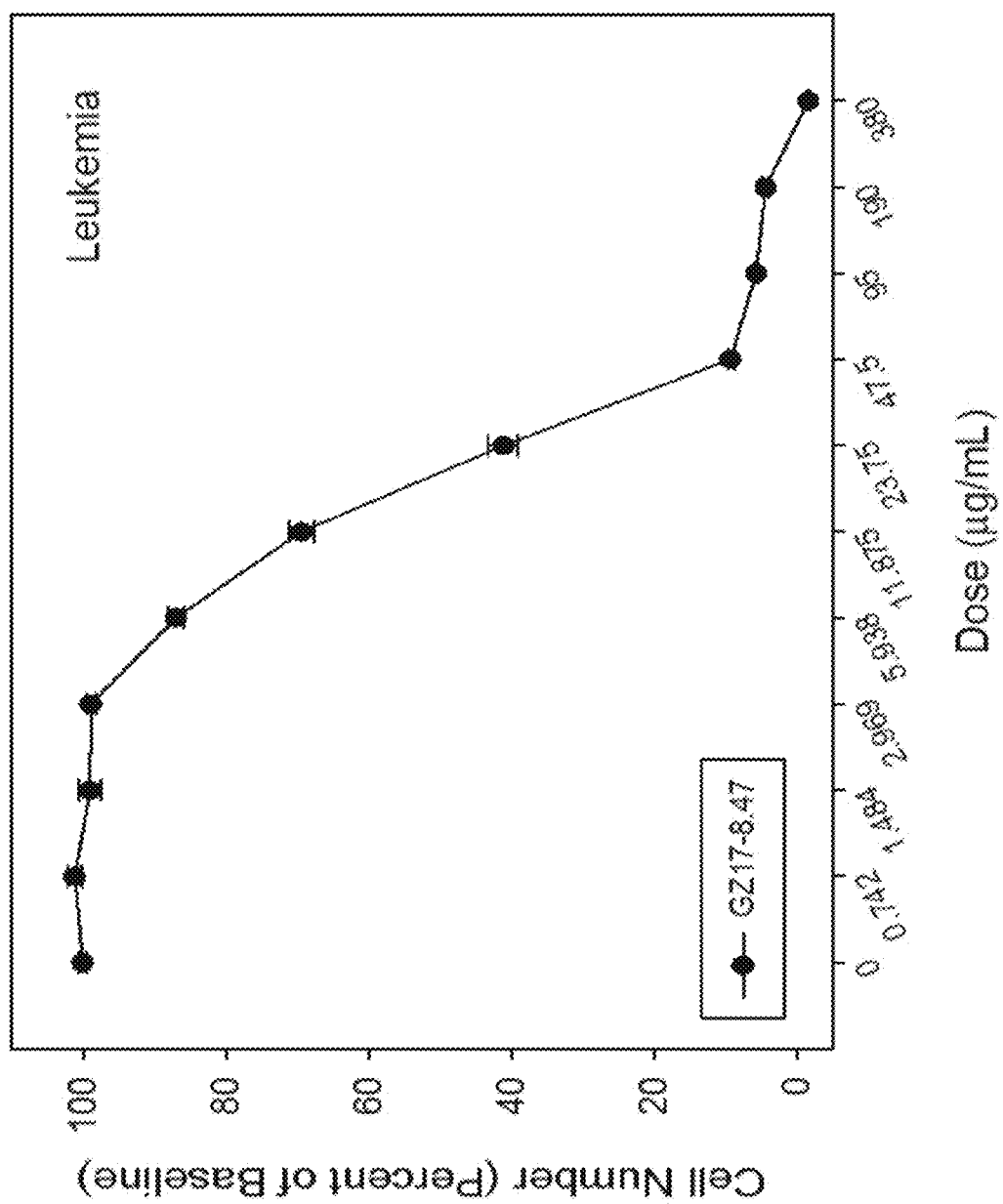
Figure 66A:
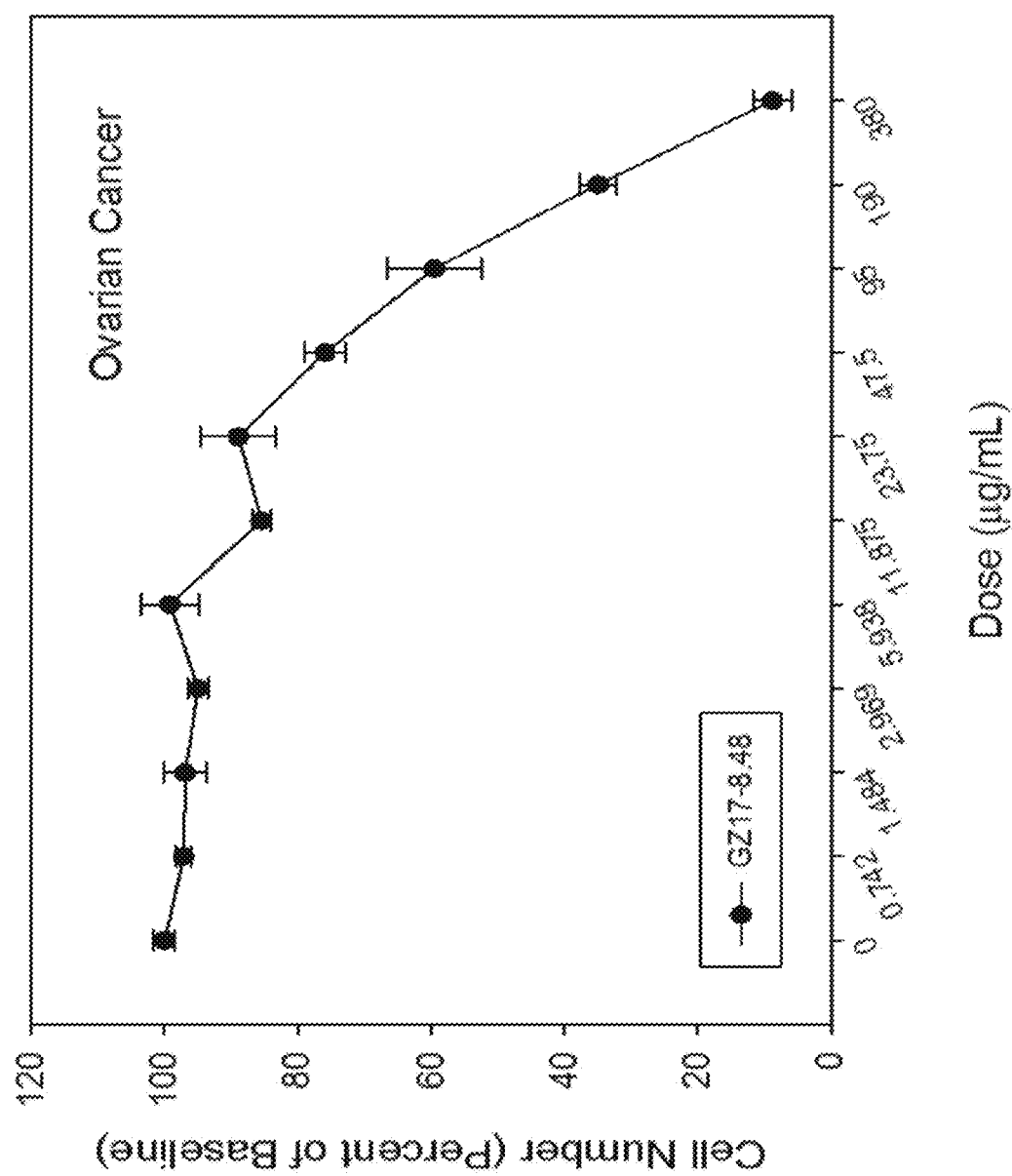
Figure 66B:
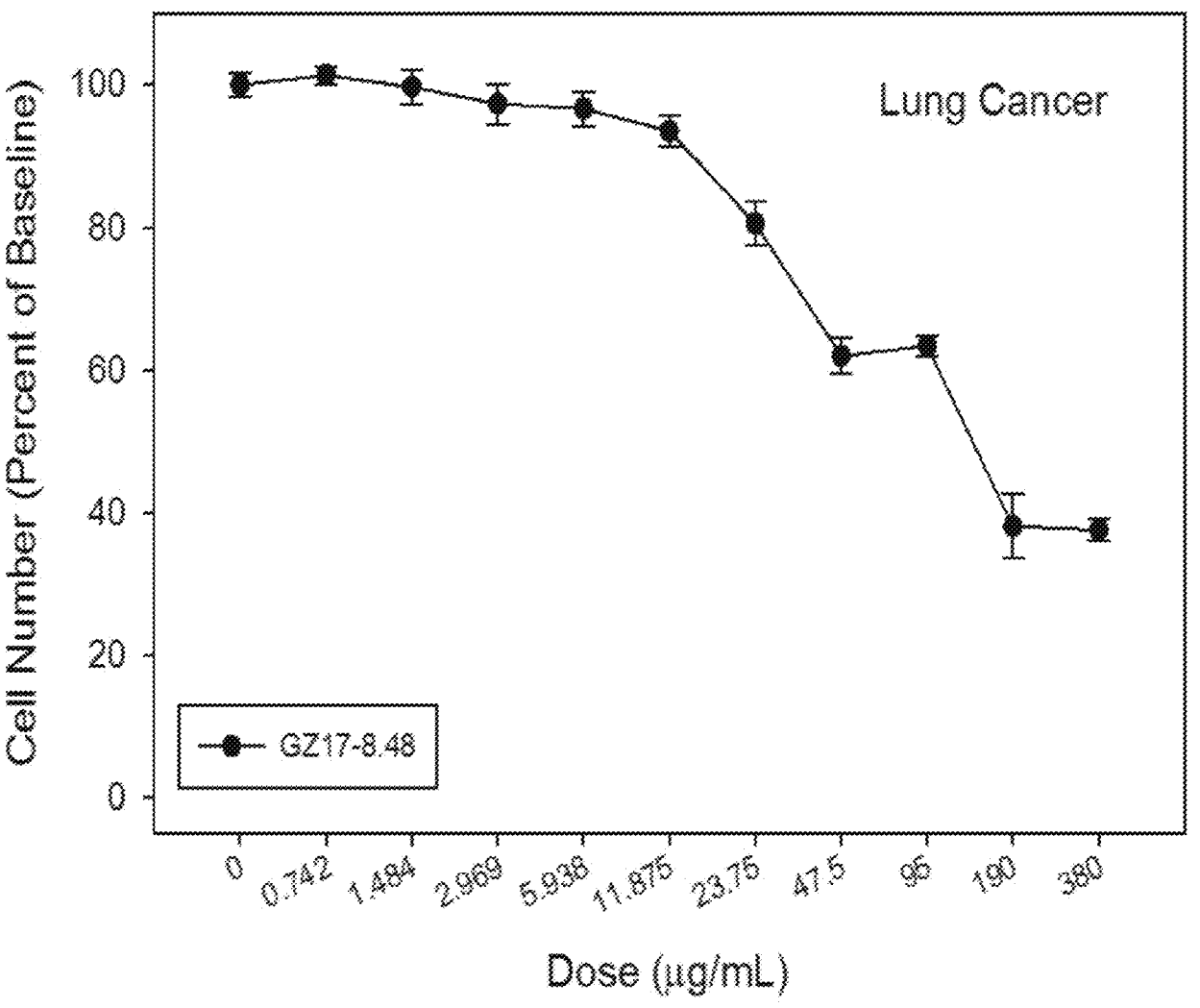
Figure 66C:
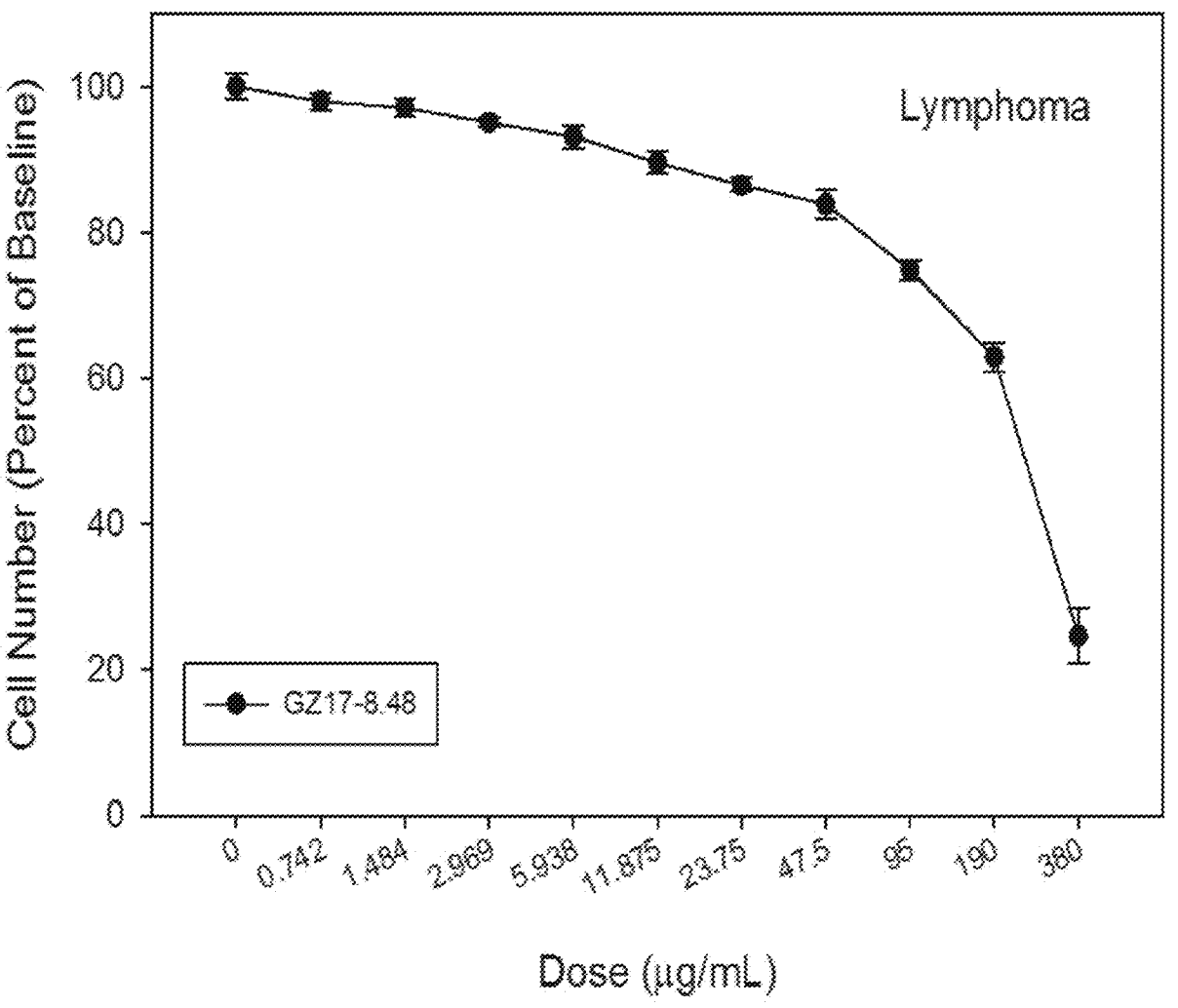
Figure 66D:
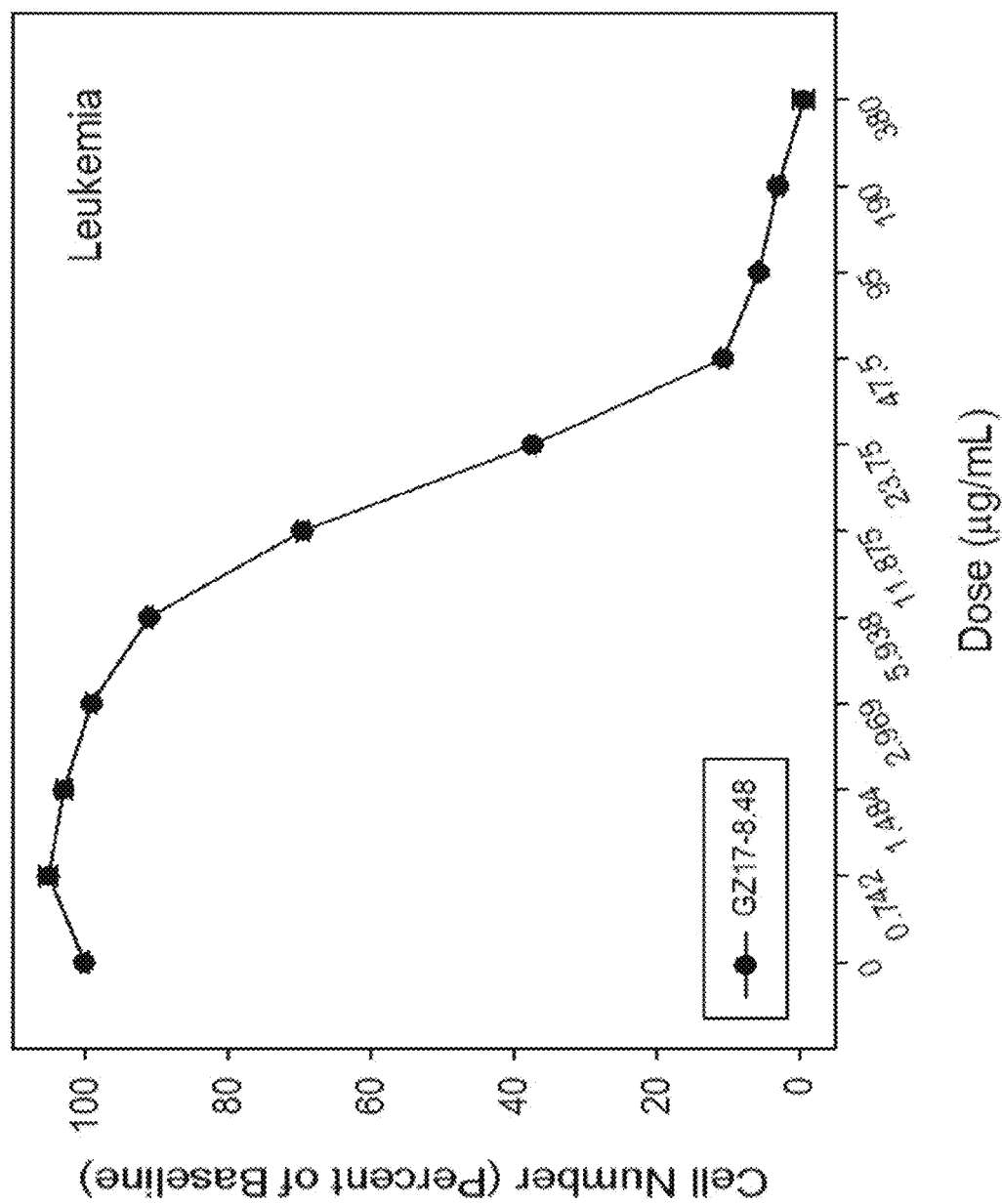
Figure 67A:
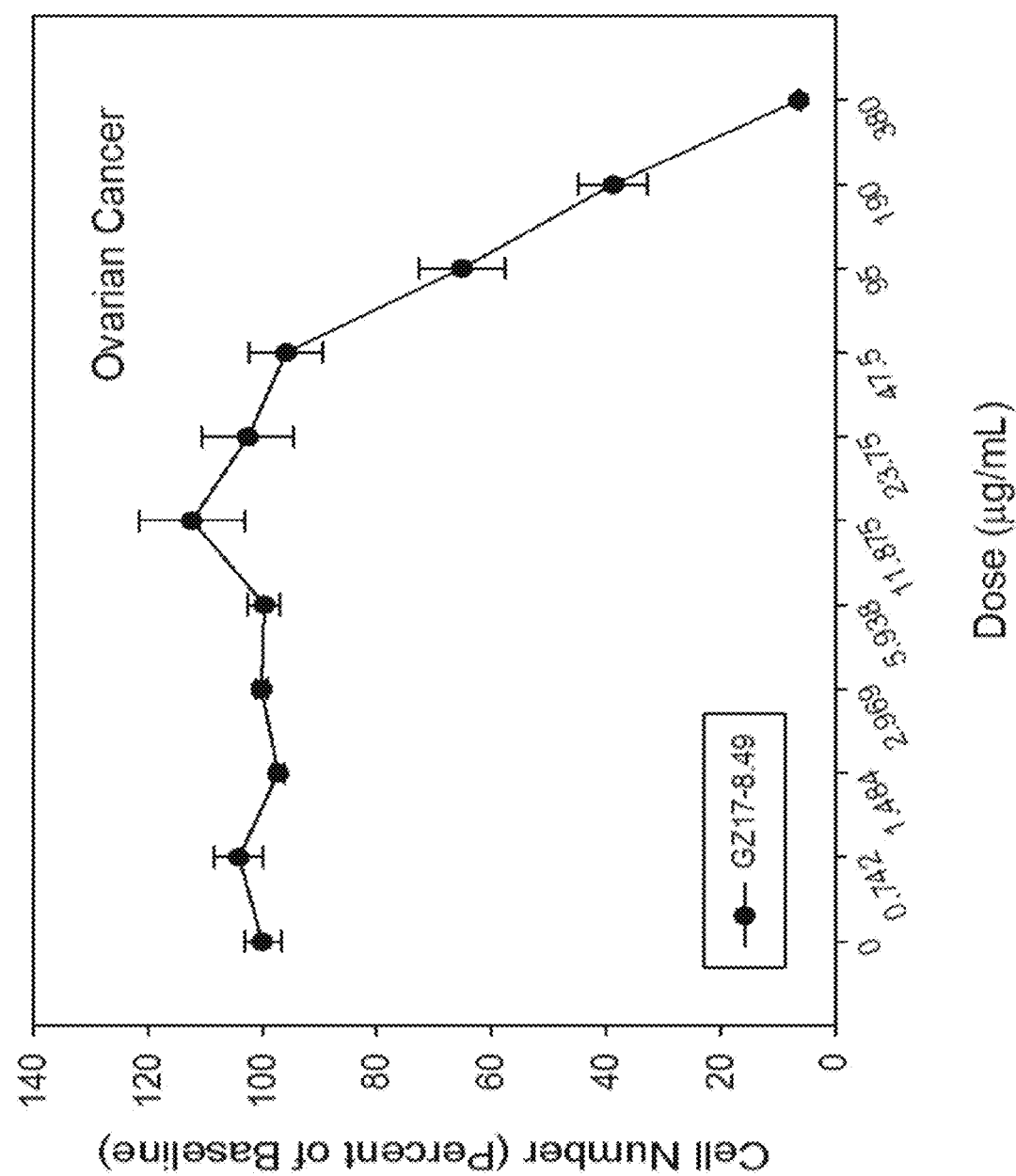
Figure 67B:
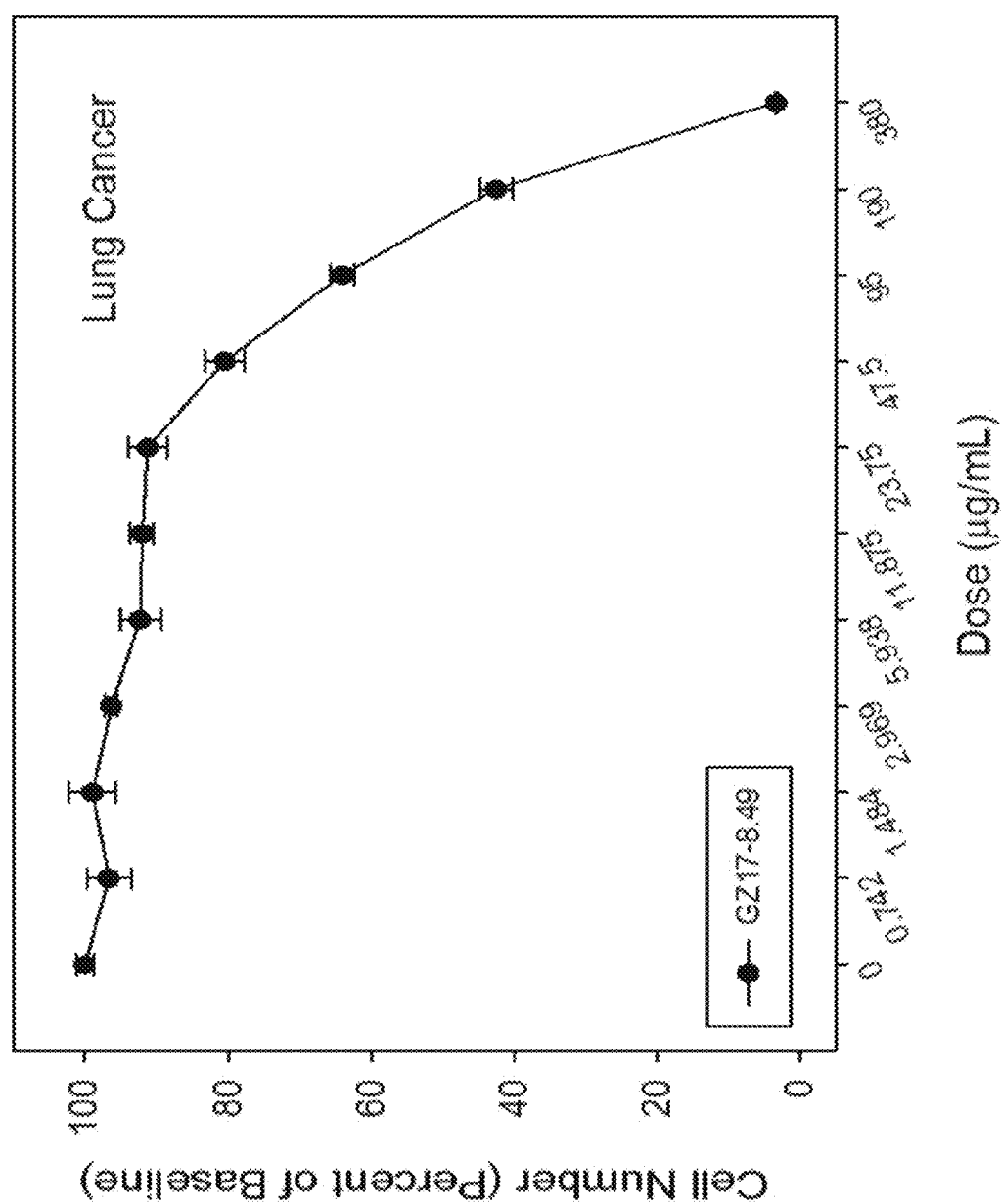
Figure 67C:
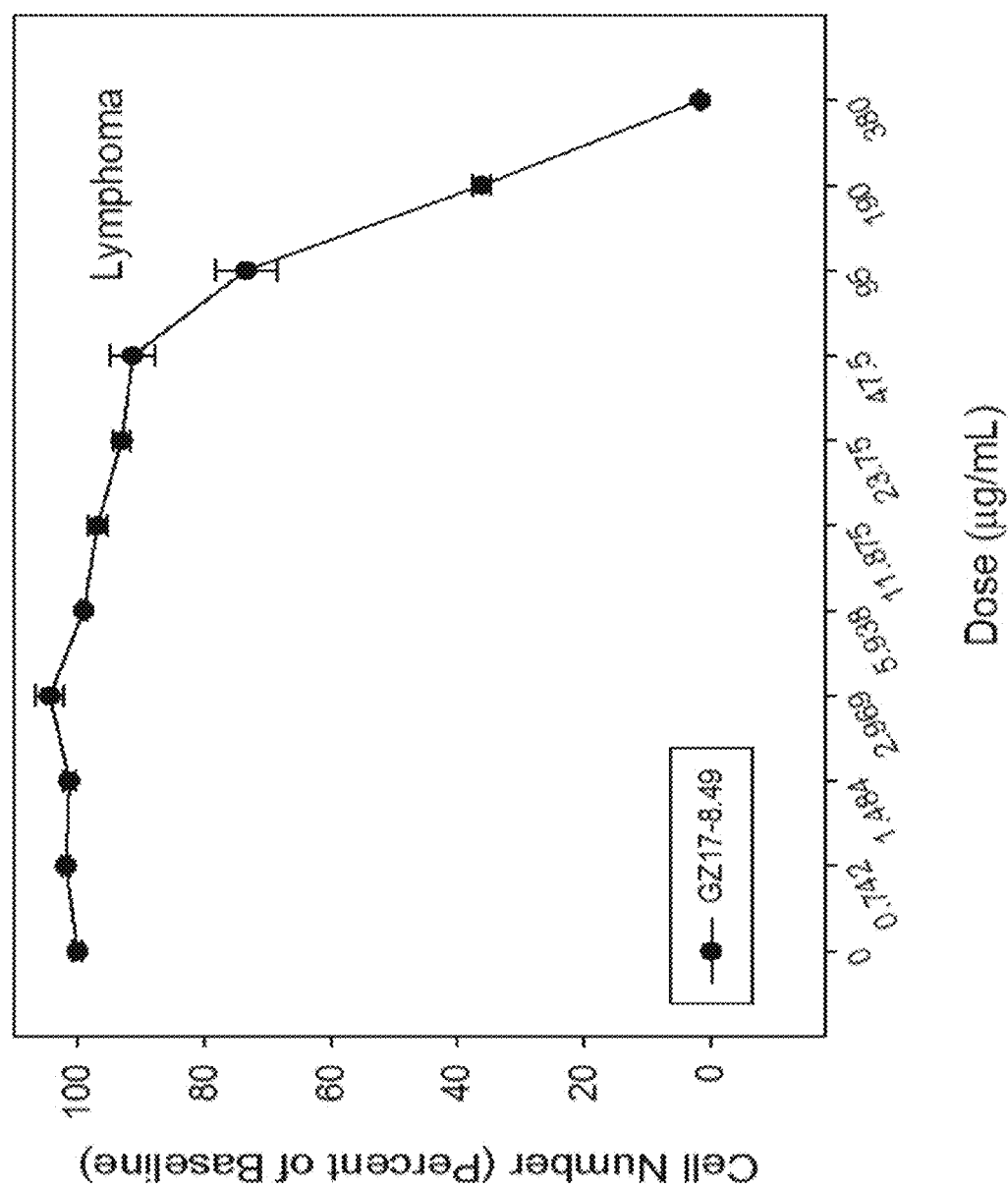
Figure 67D:
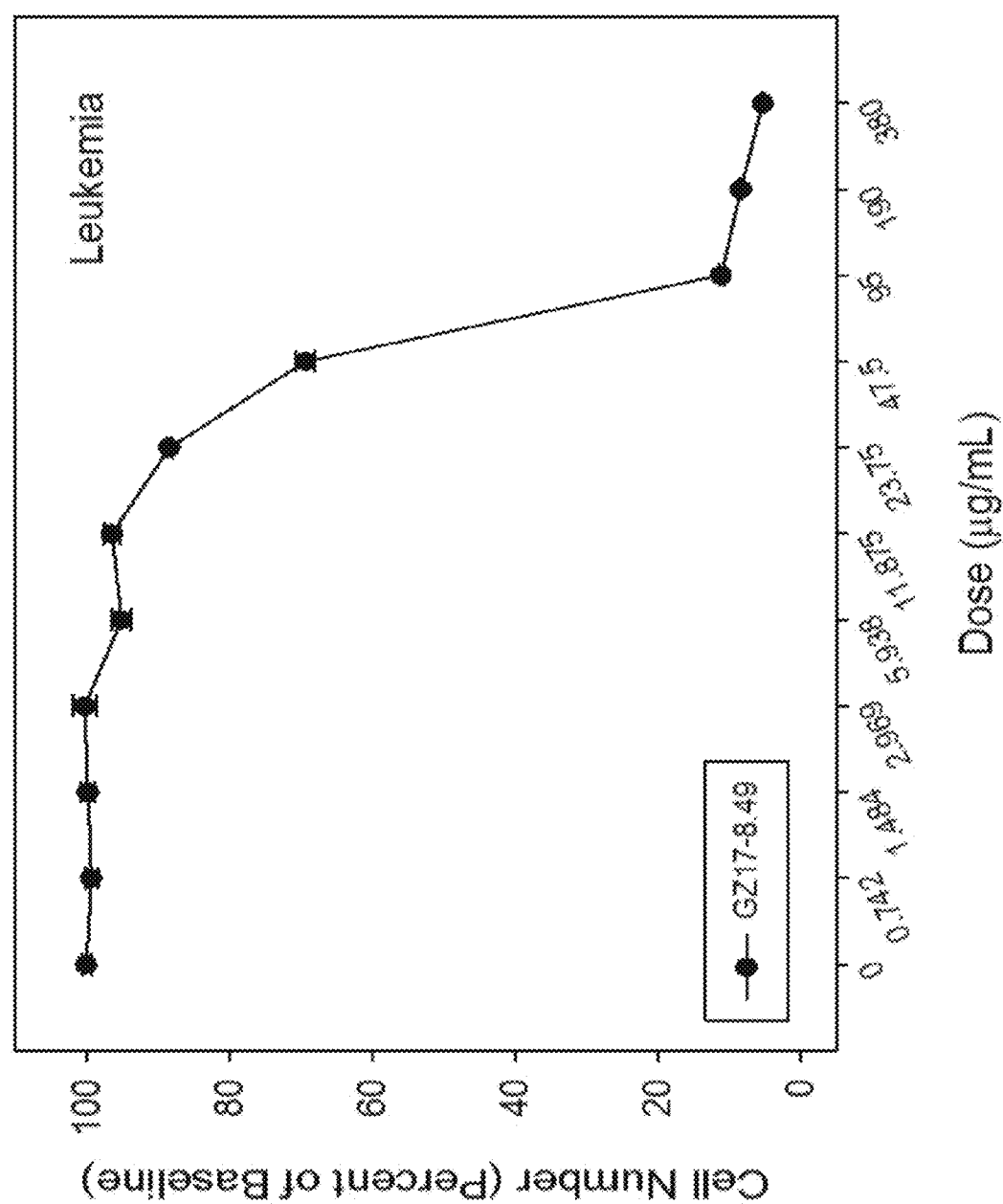
Figure 68A:
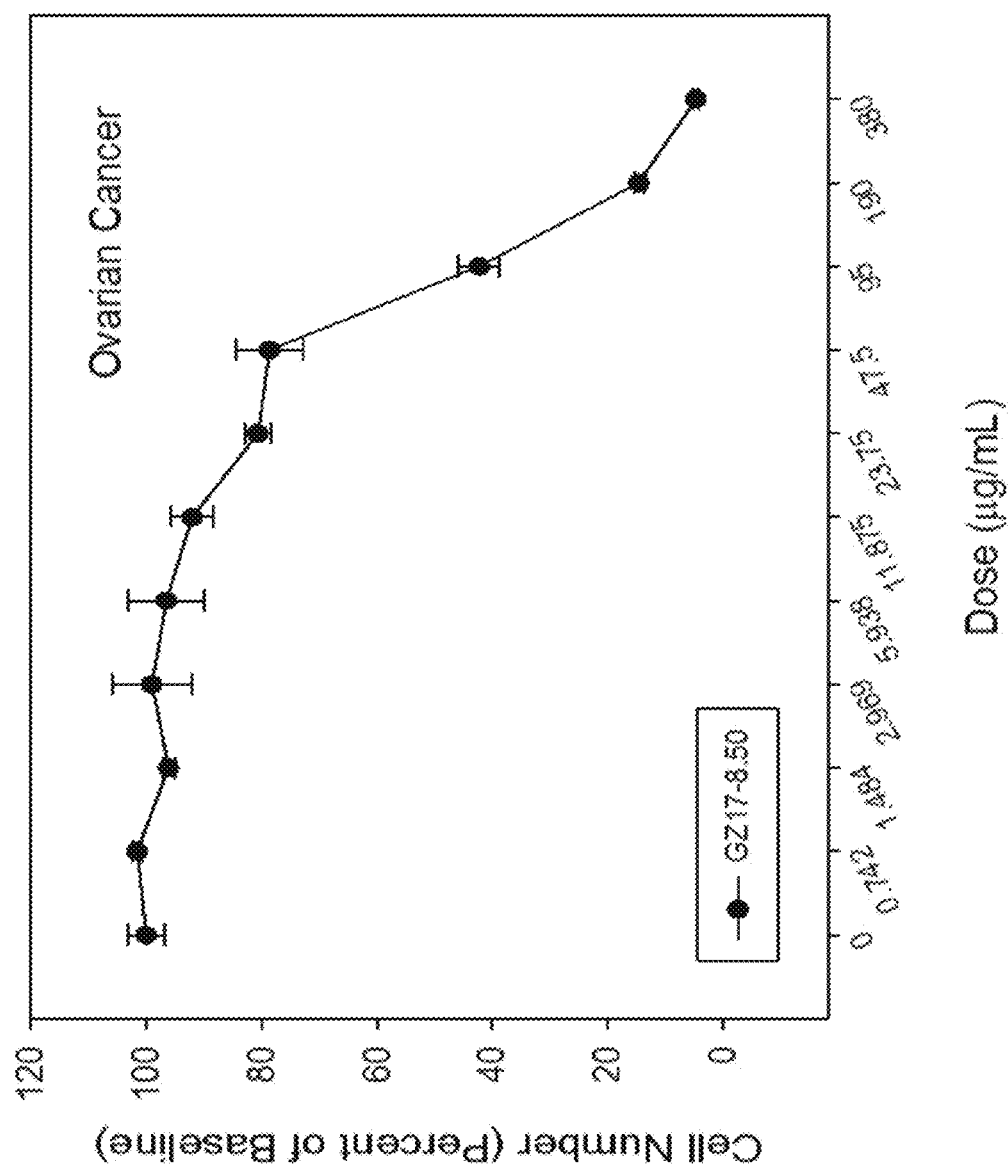
Figure 68B:
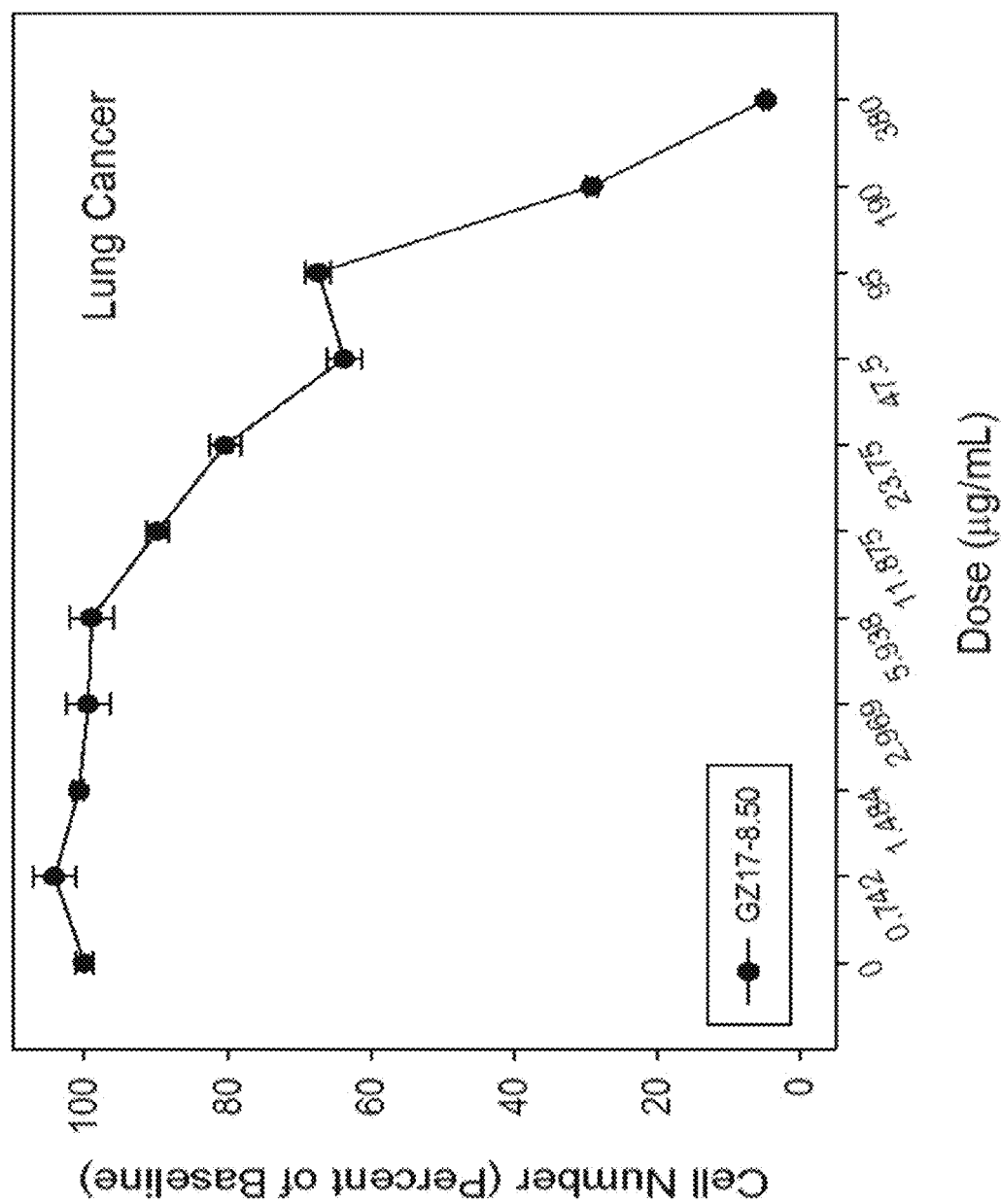
Figure 68C:
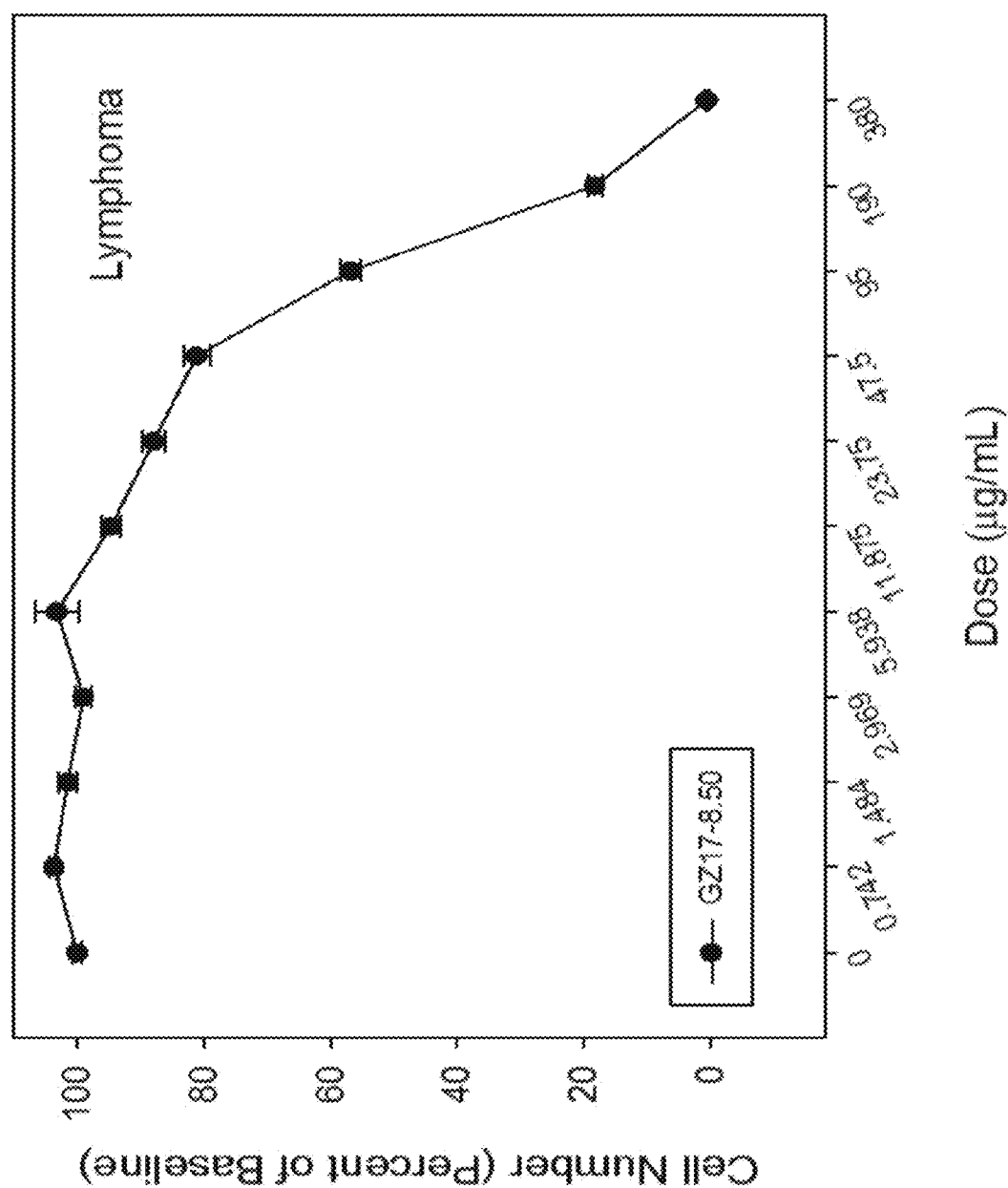
Figure 68D:
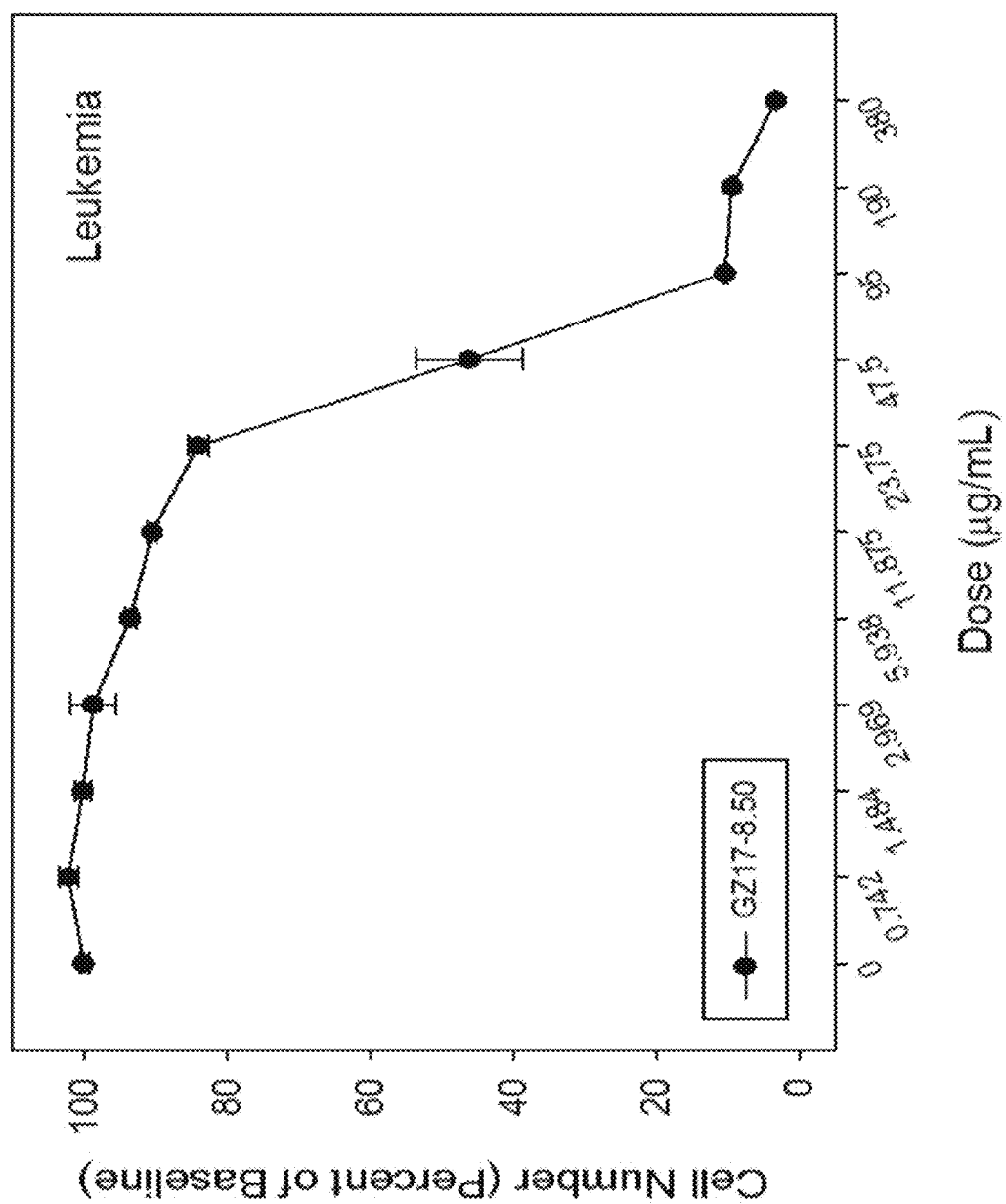
Figure 69A:
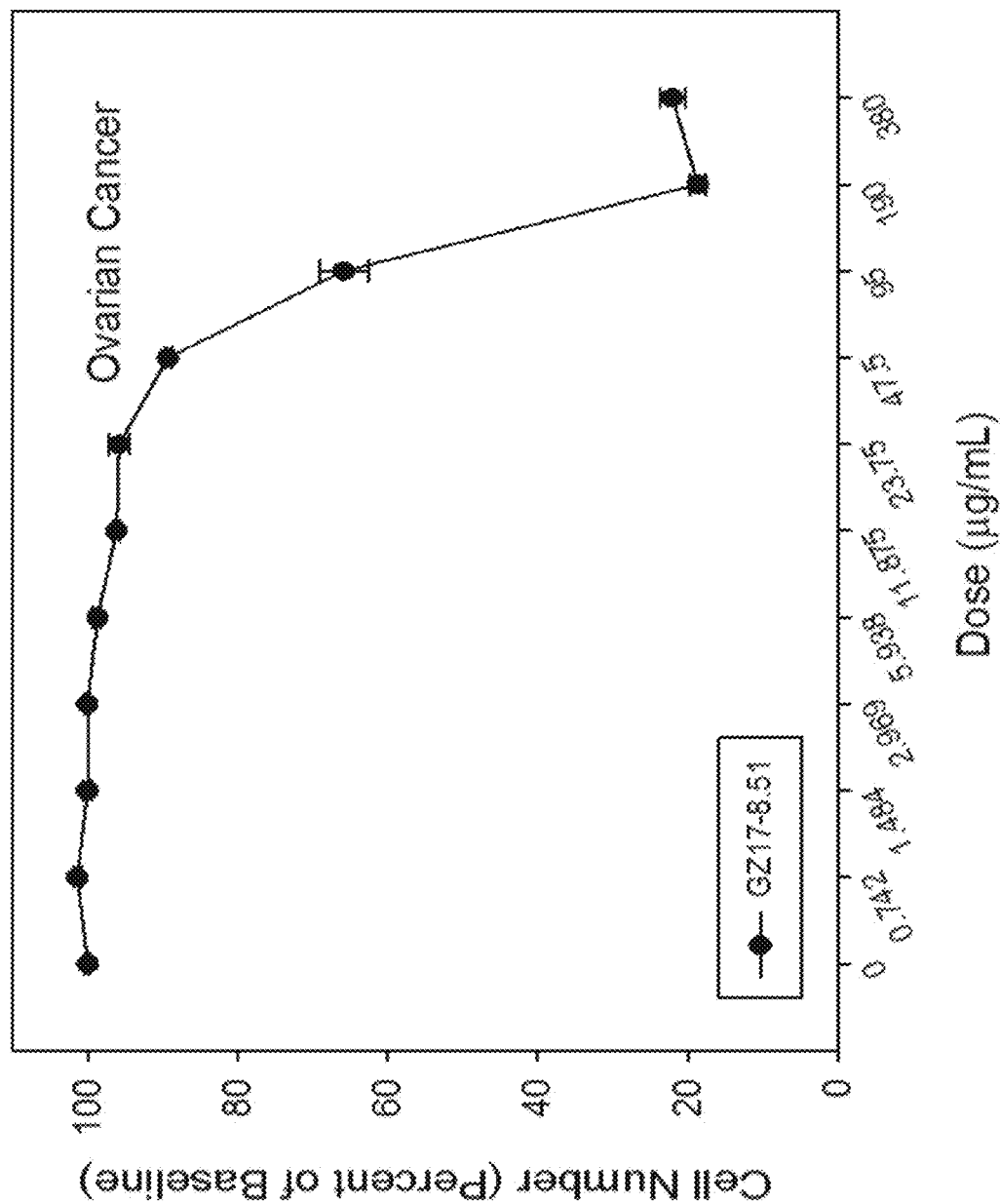
Figure 69B:
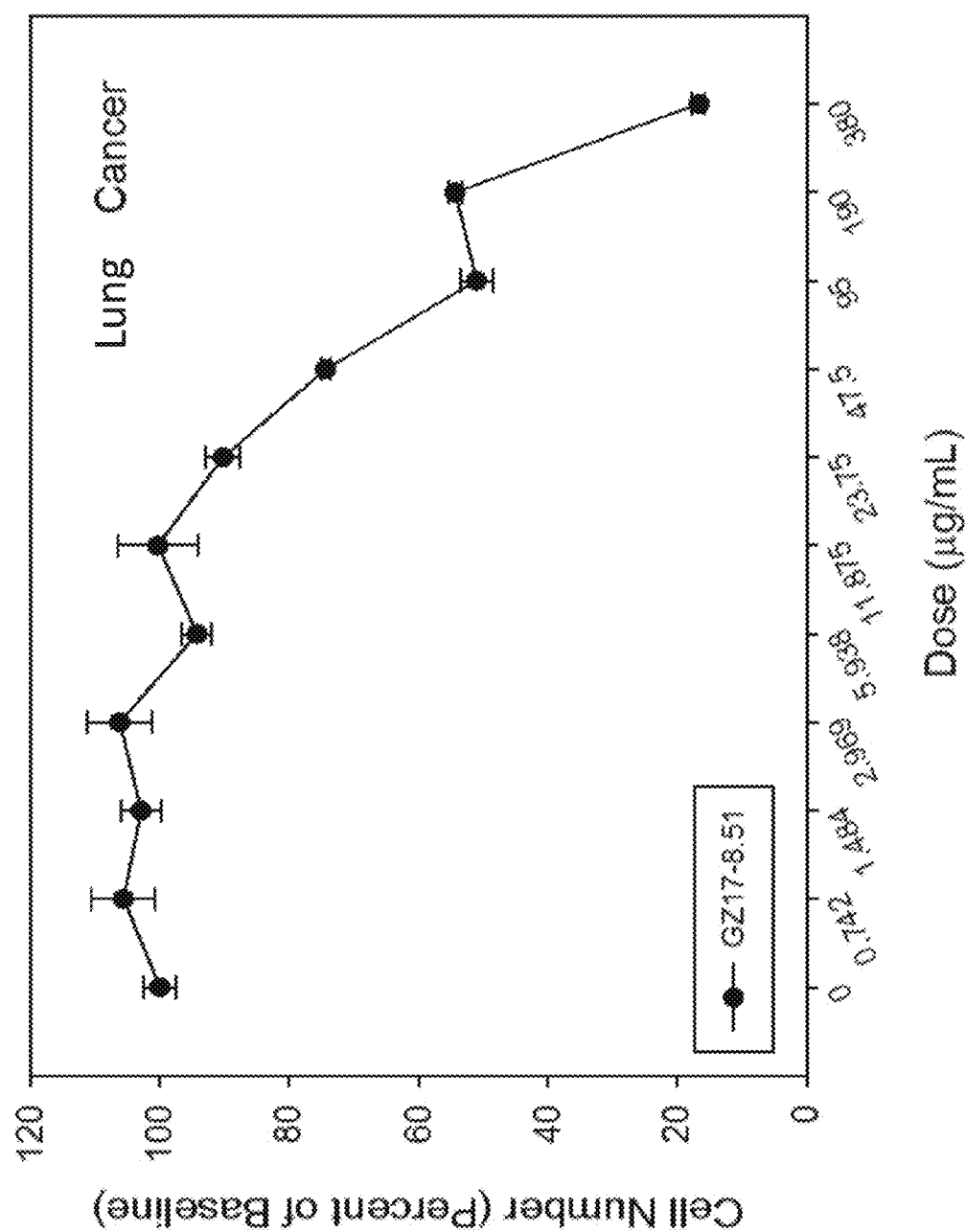
Figure 69C:
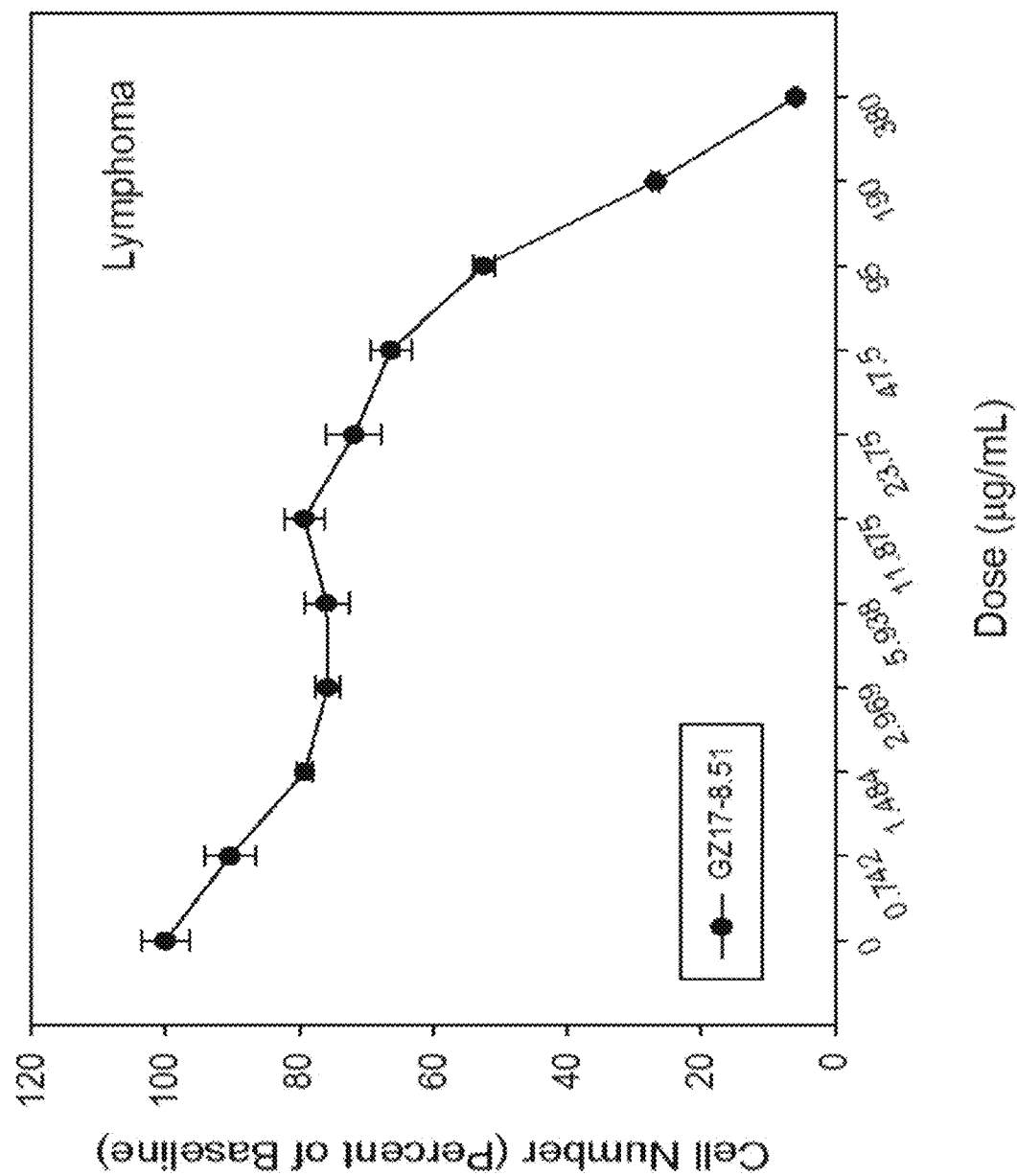
Figure 69D:
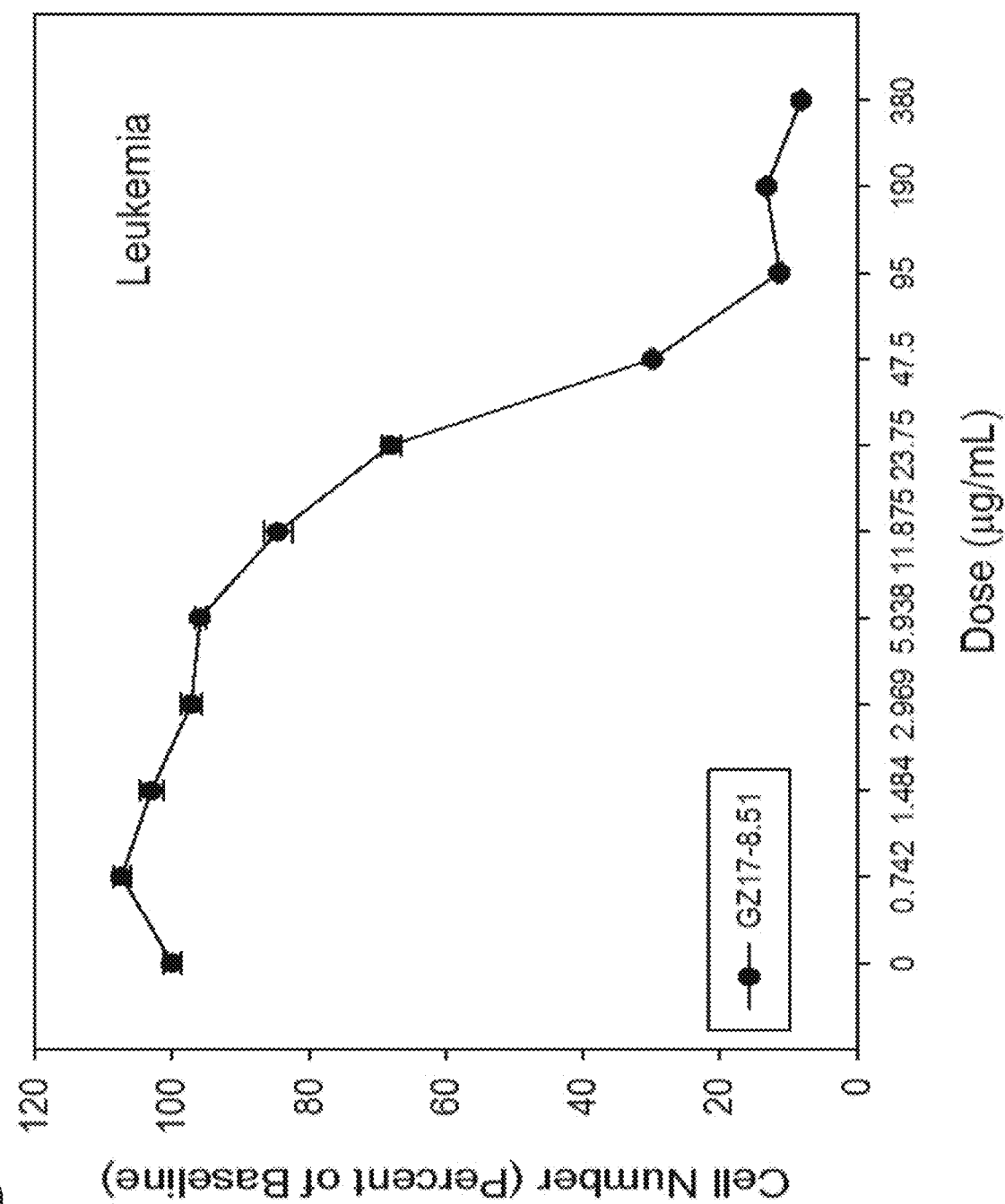
Figure 70A:
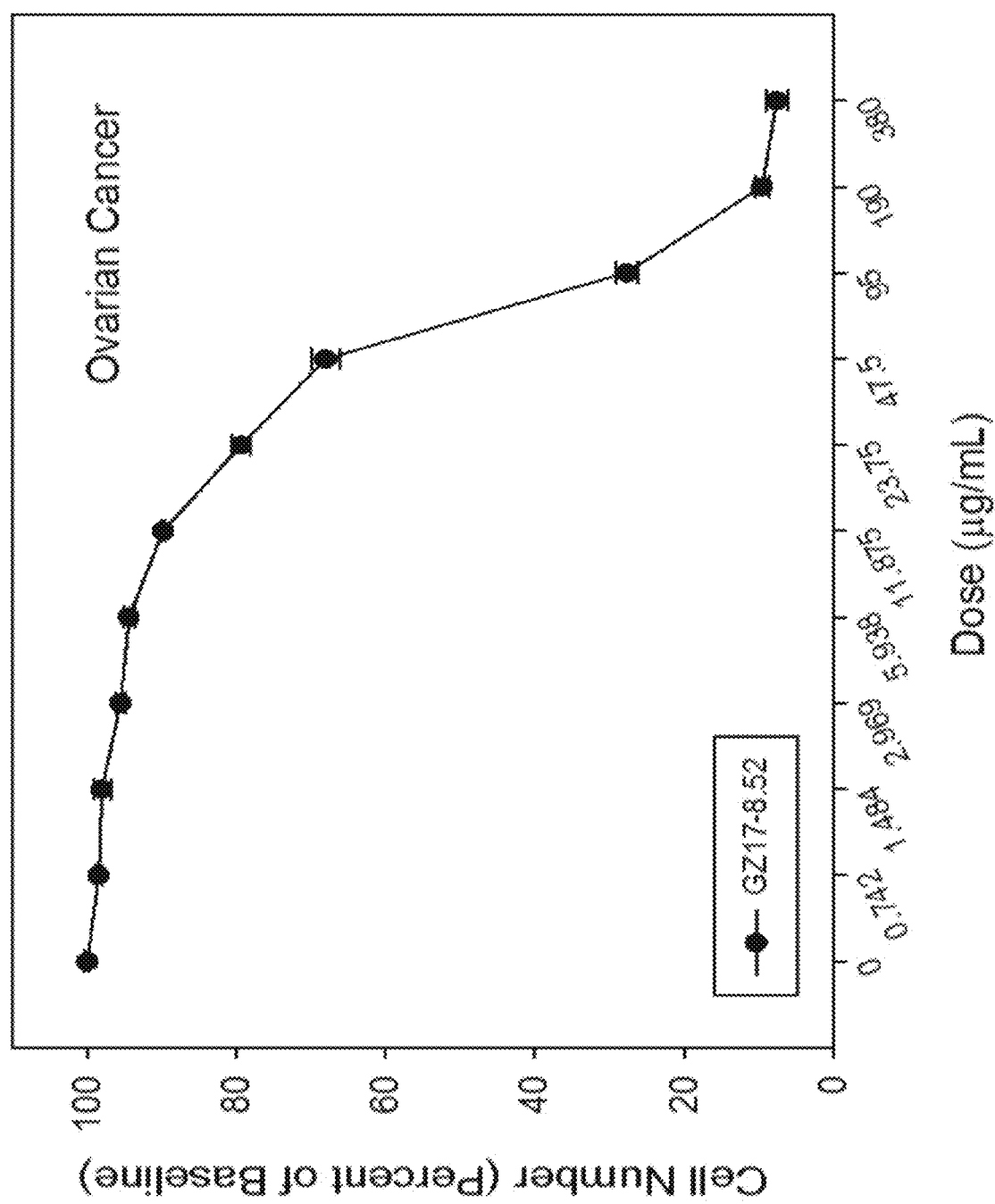
Figure 70B:
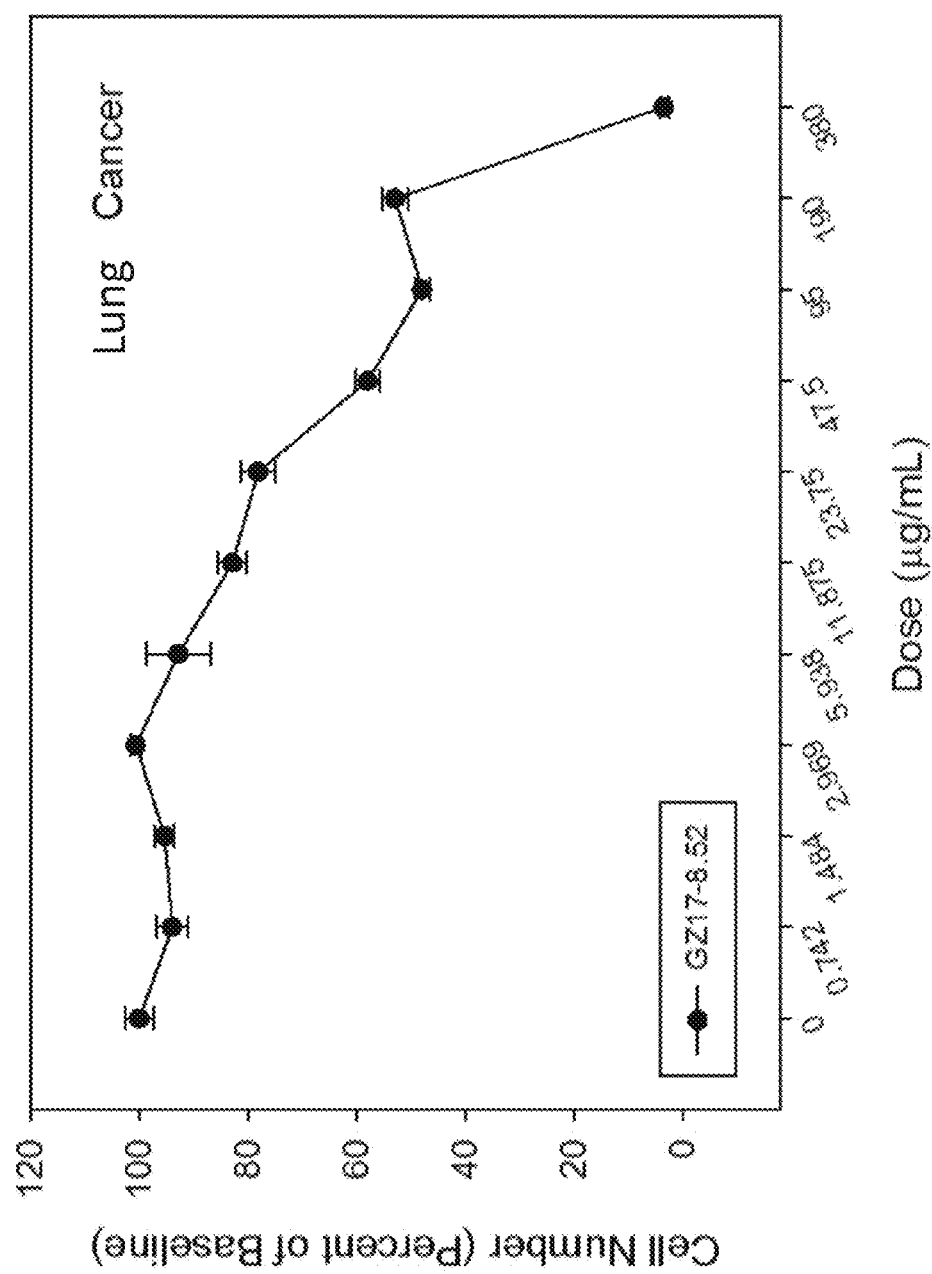
Figure 70C:
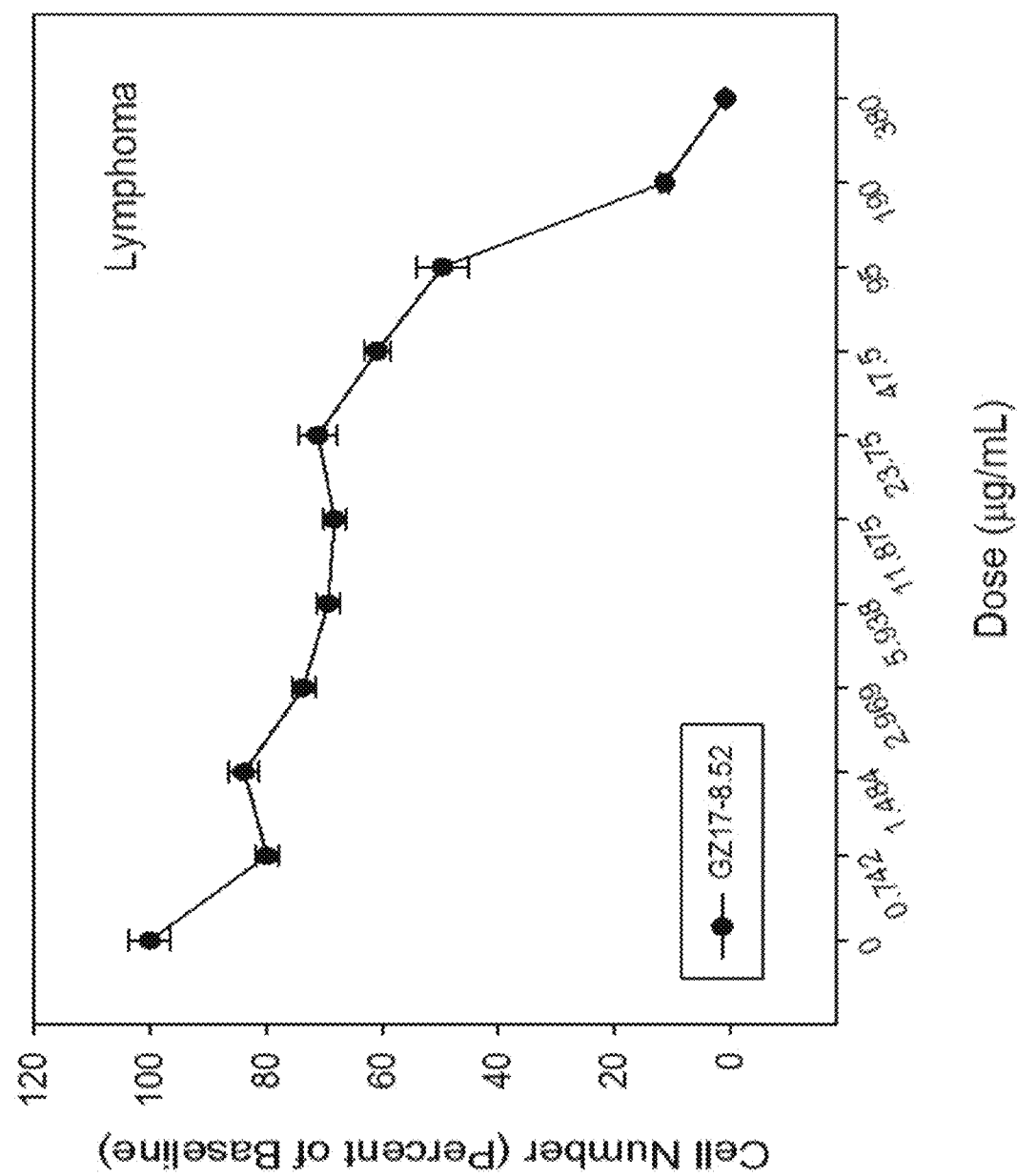
Figure 70D:
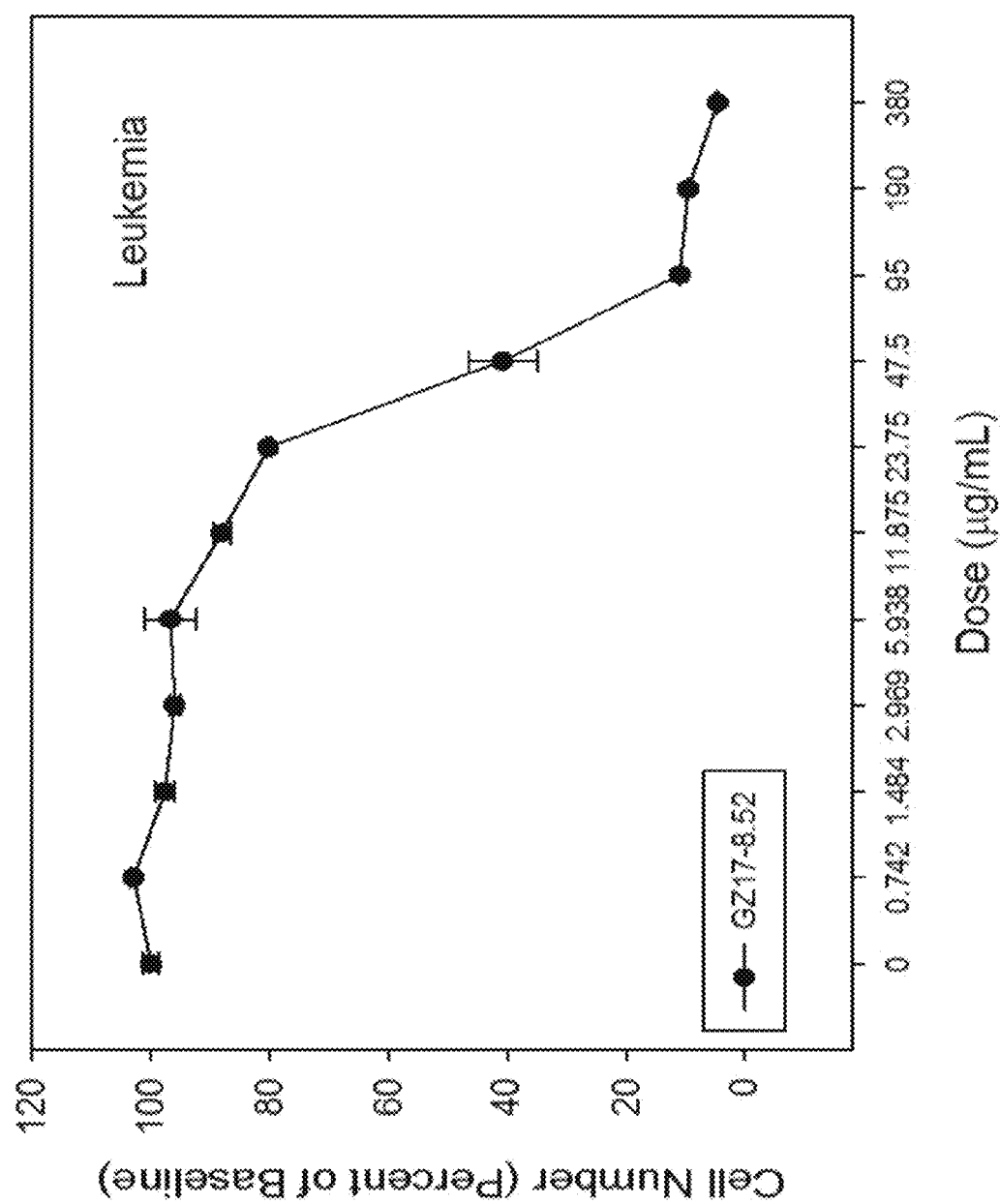
Figure 71A:
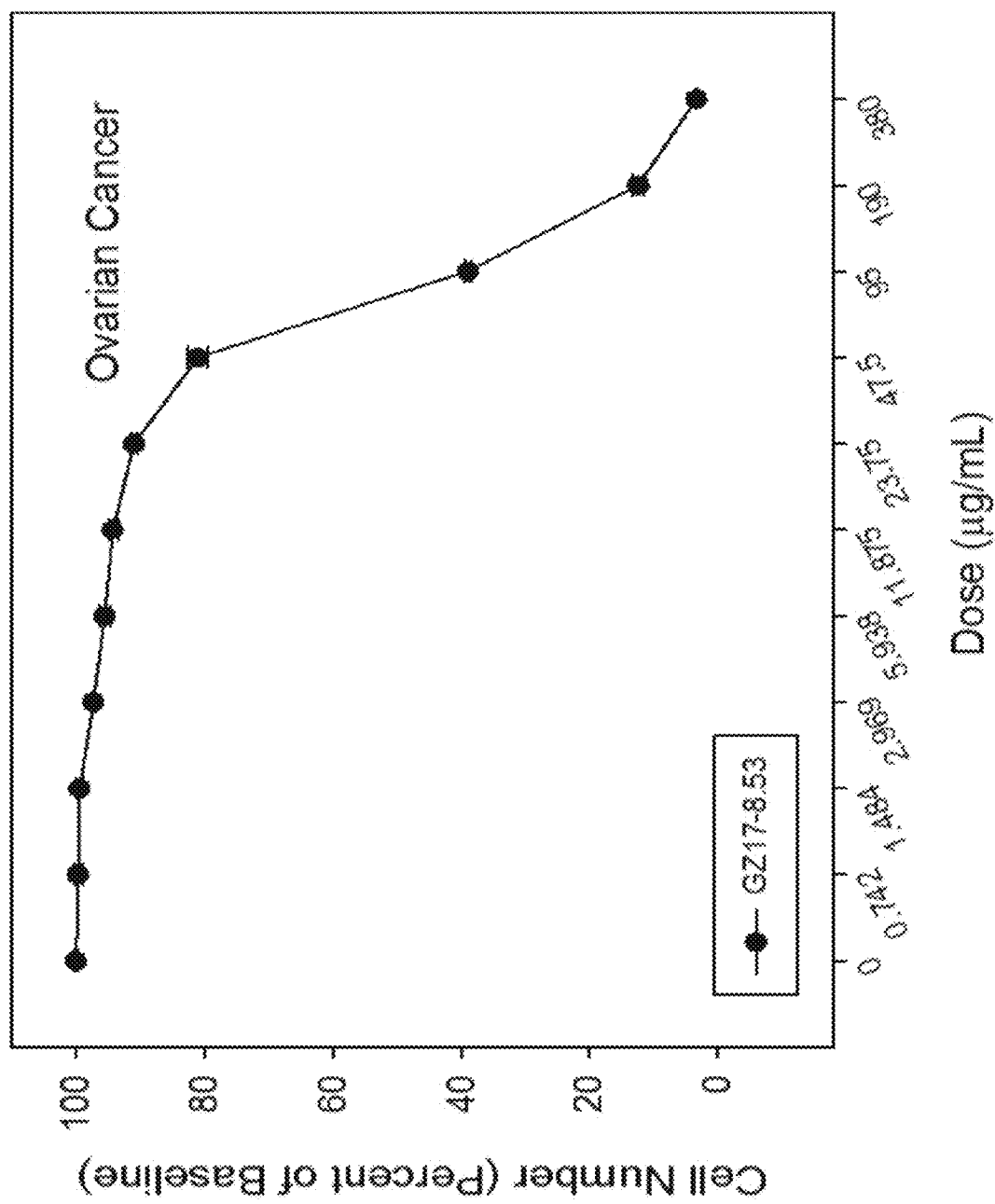
Figure 71B:
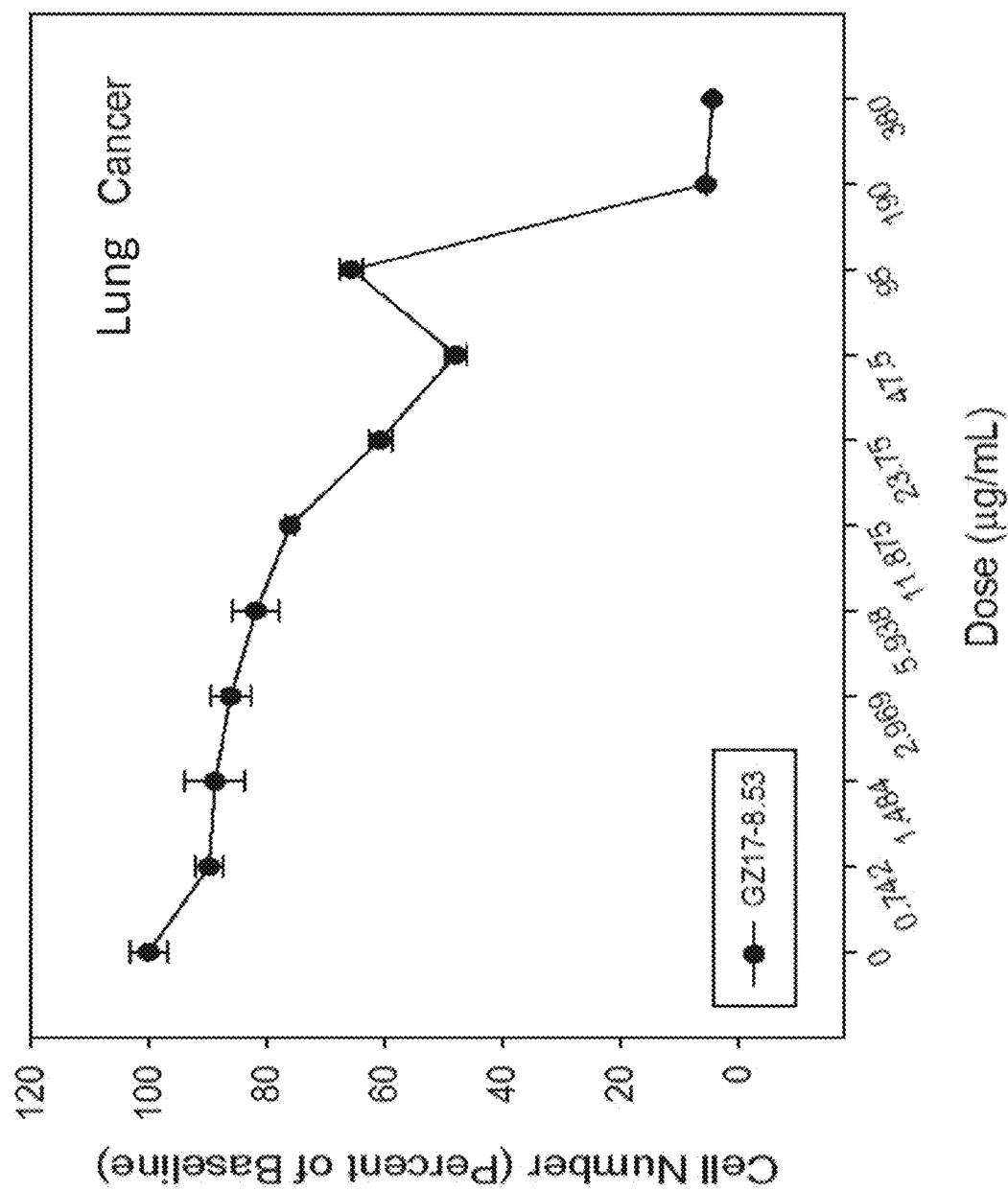
Figure 71C:
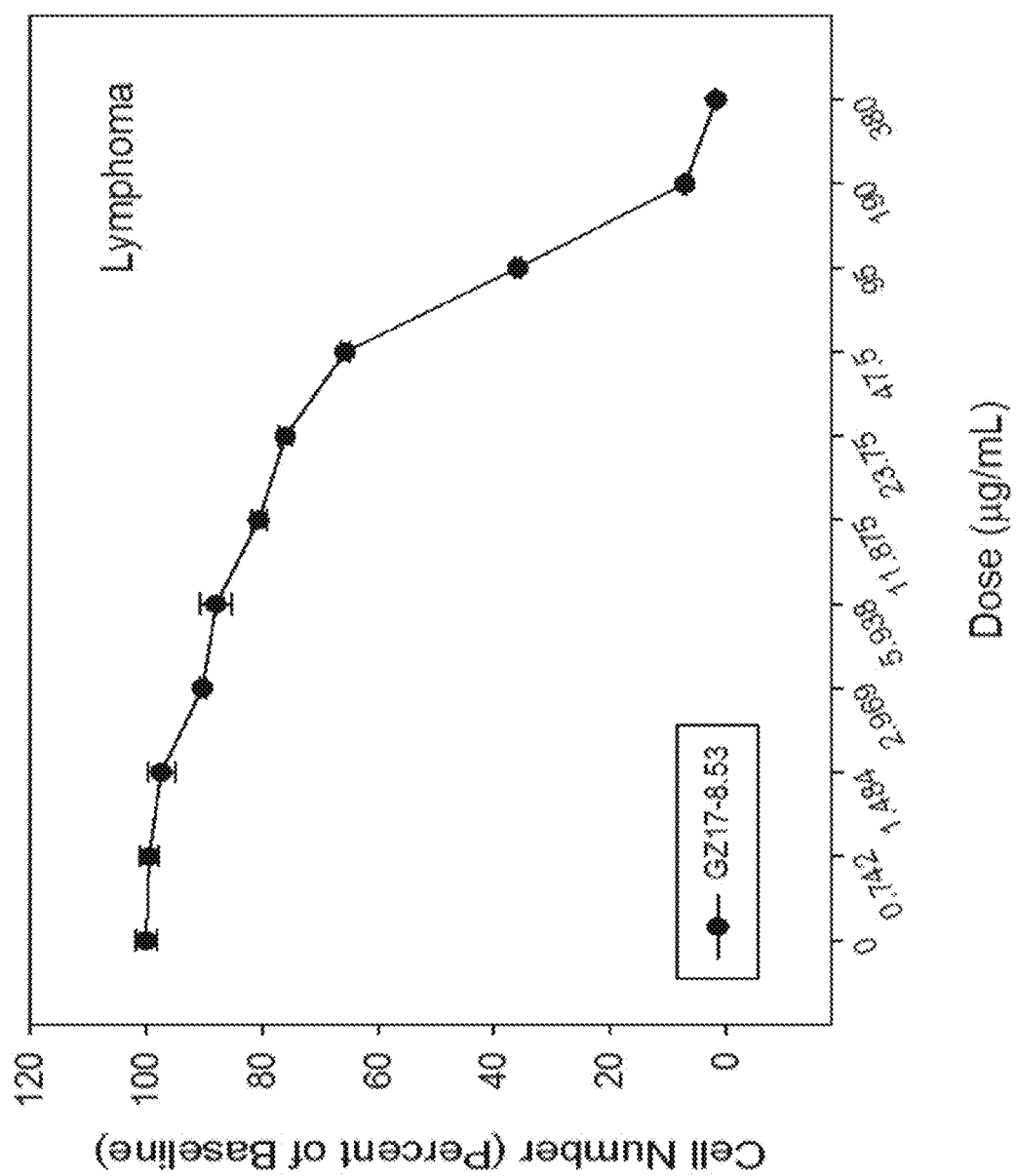
Figure 71D:
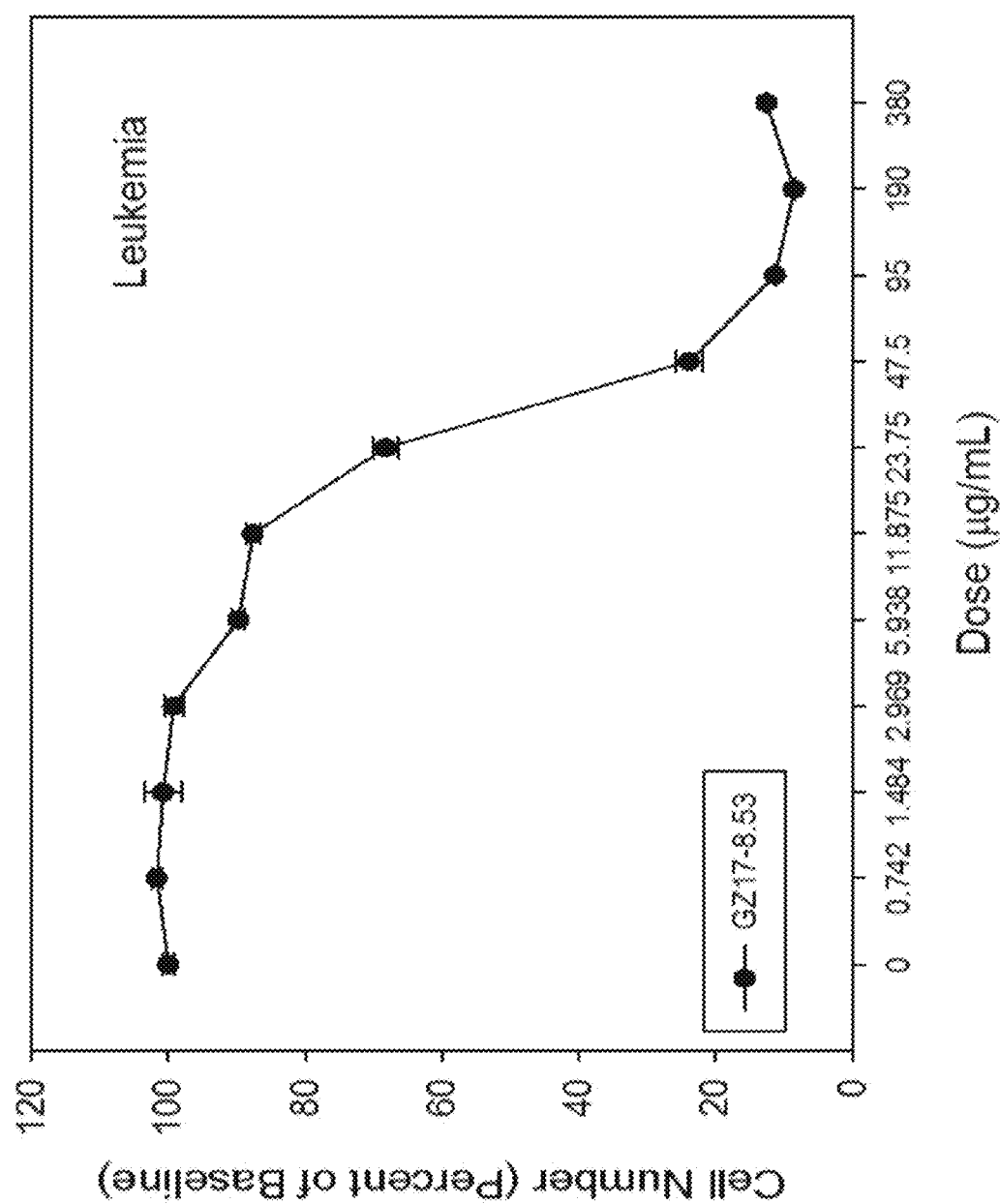
Figure 72A:
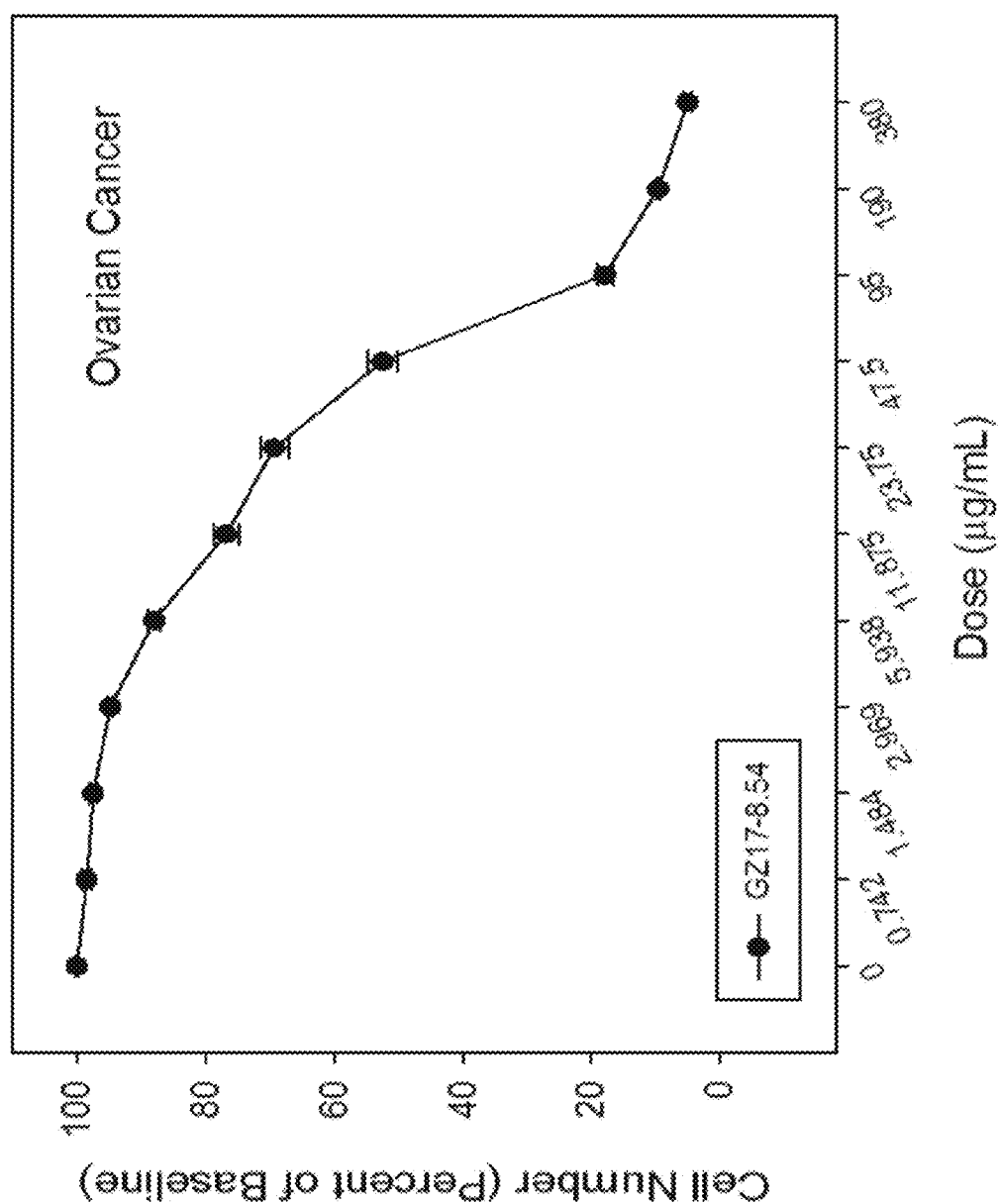
Figure 72B:
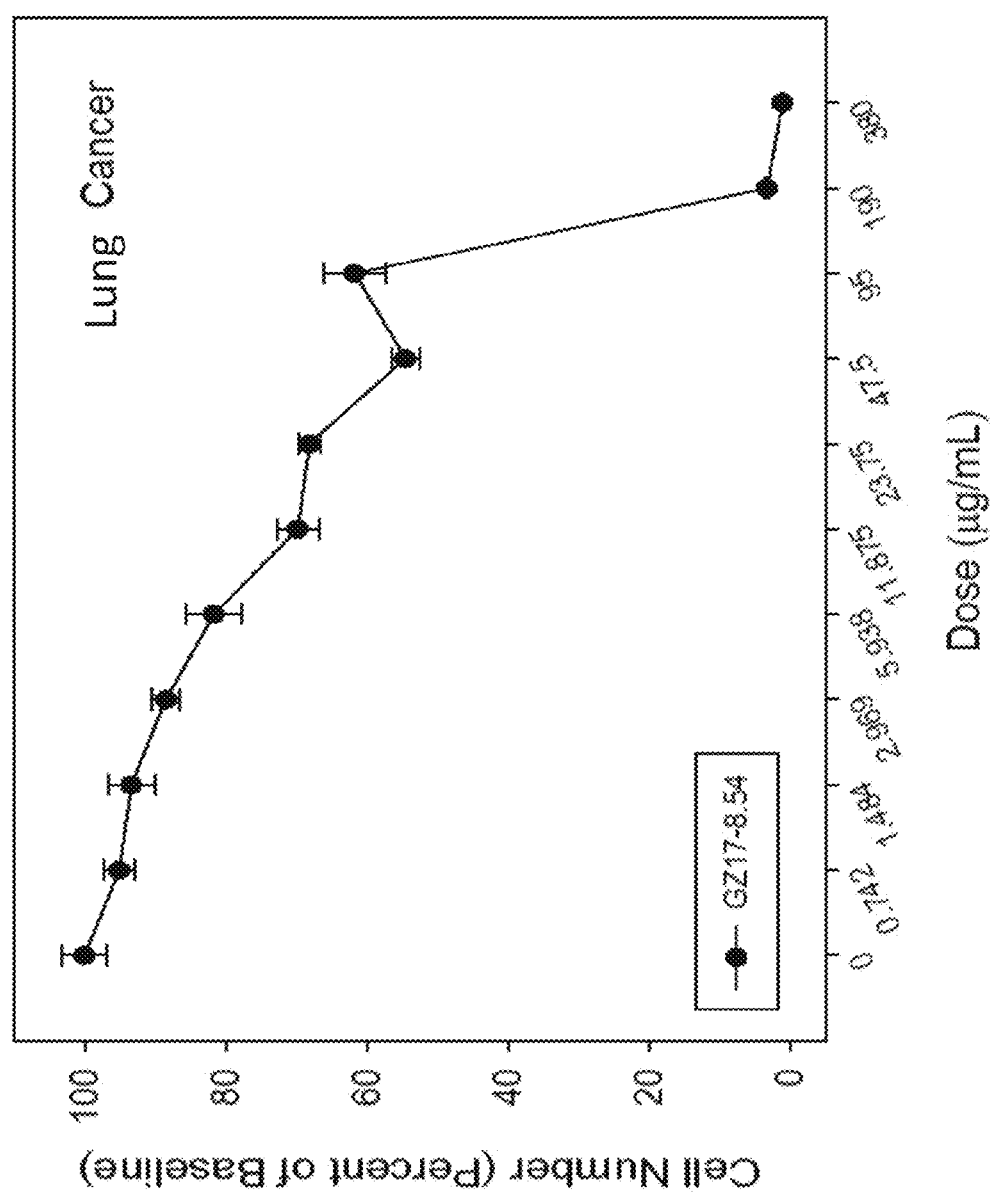
Figure 72C:
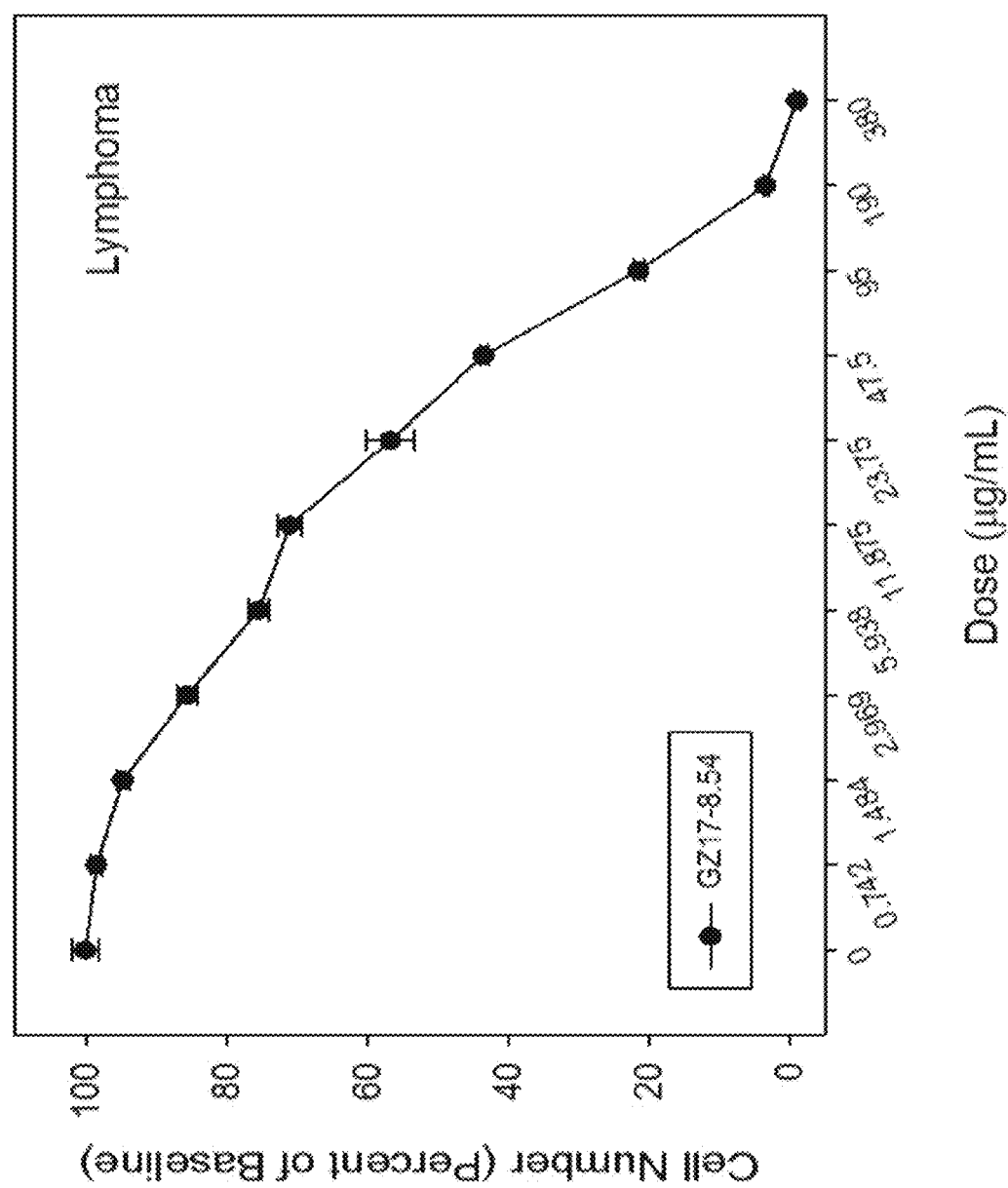
Figure 72D:
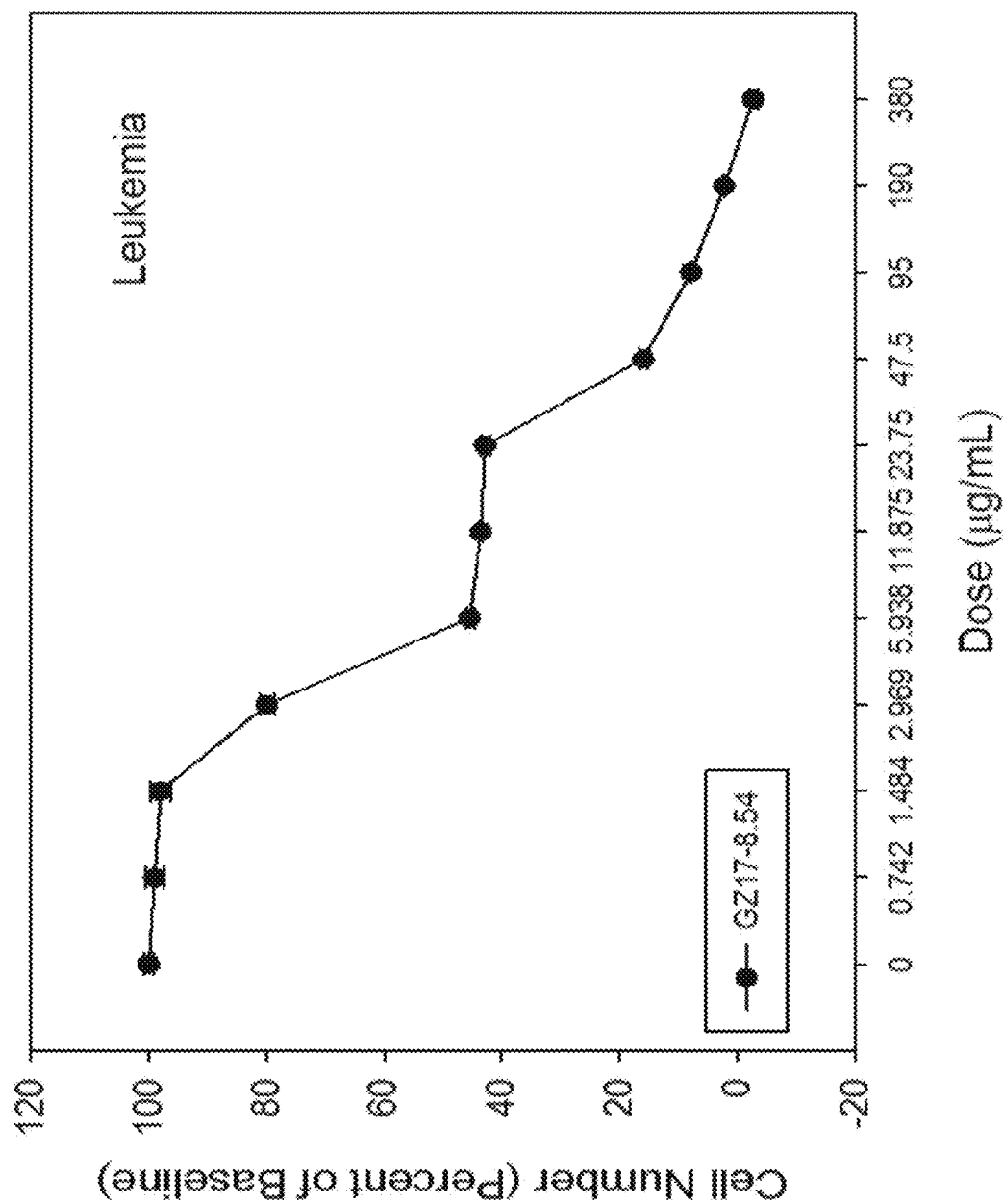
Figure 73A:
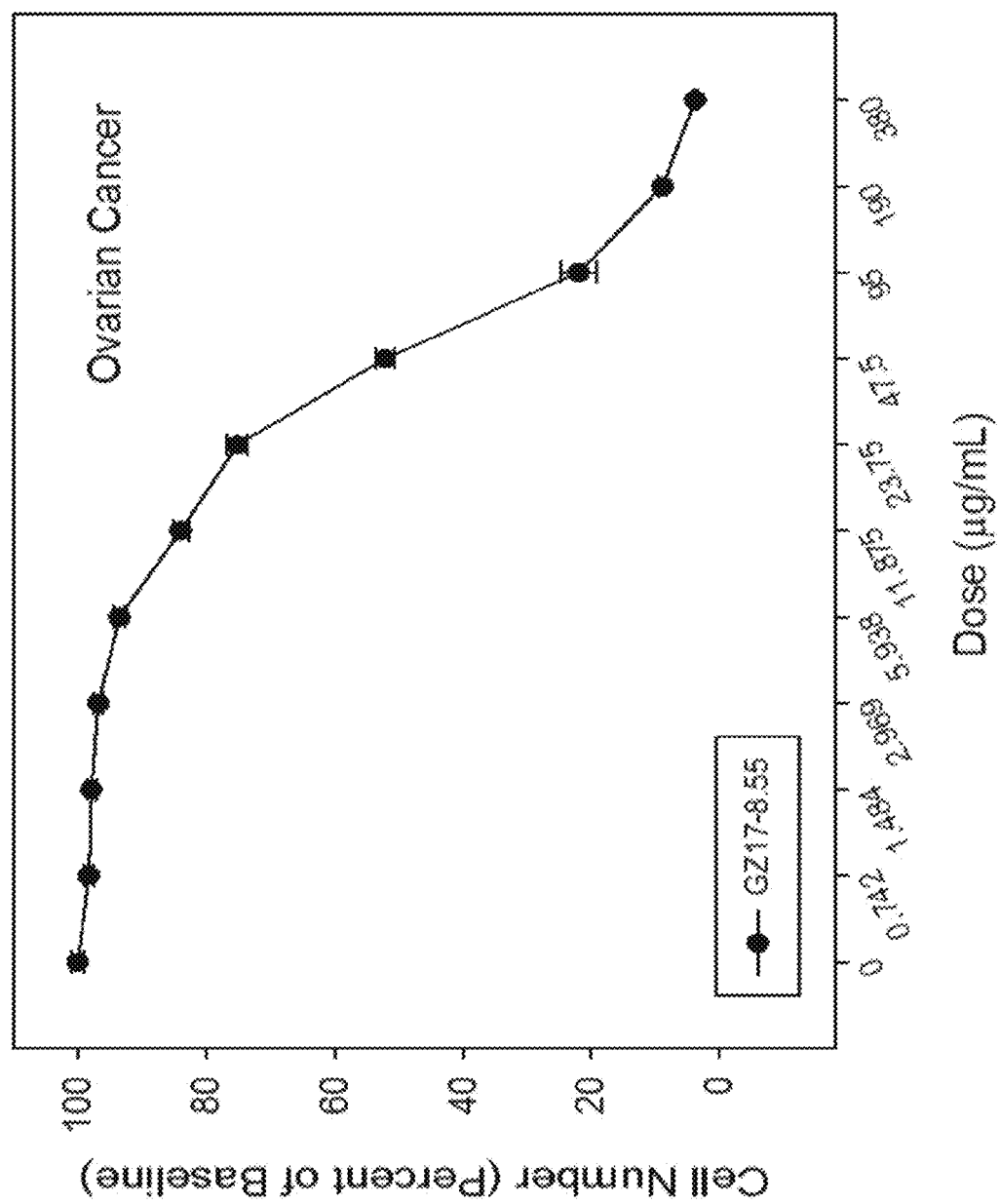
Figure 73B:
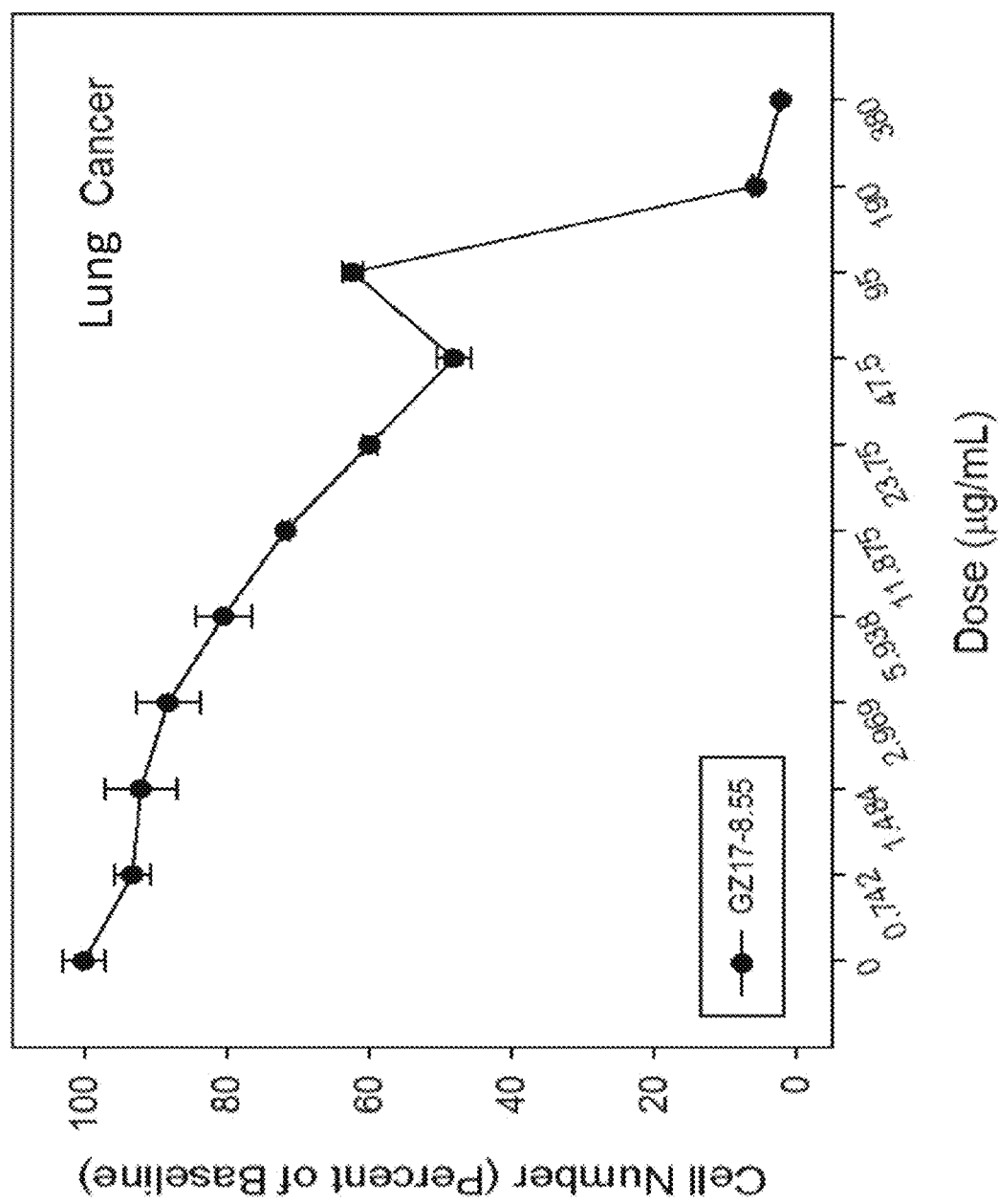
Figure 73C:
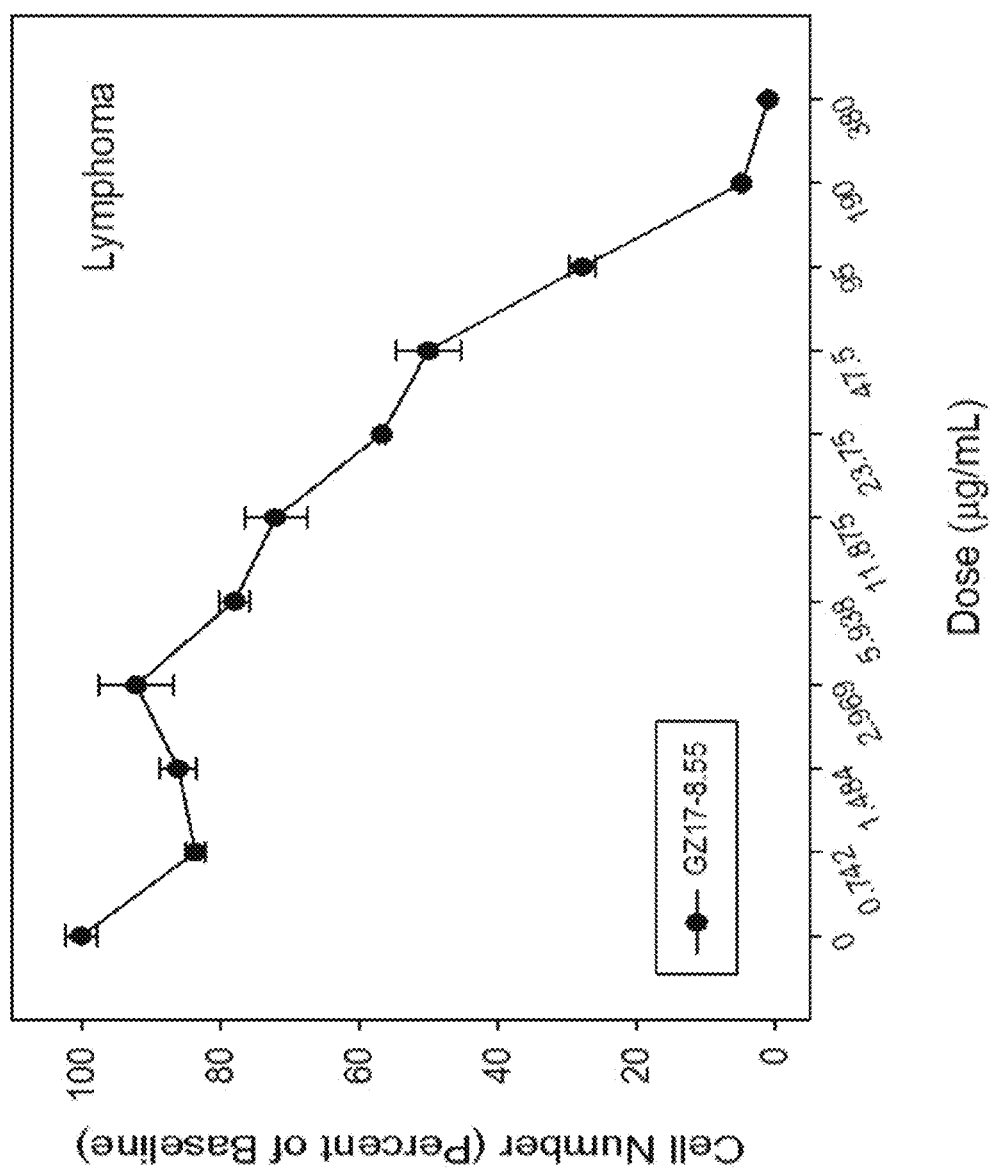
Figure 73D:
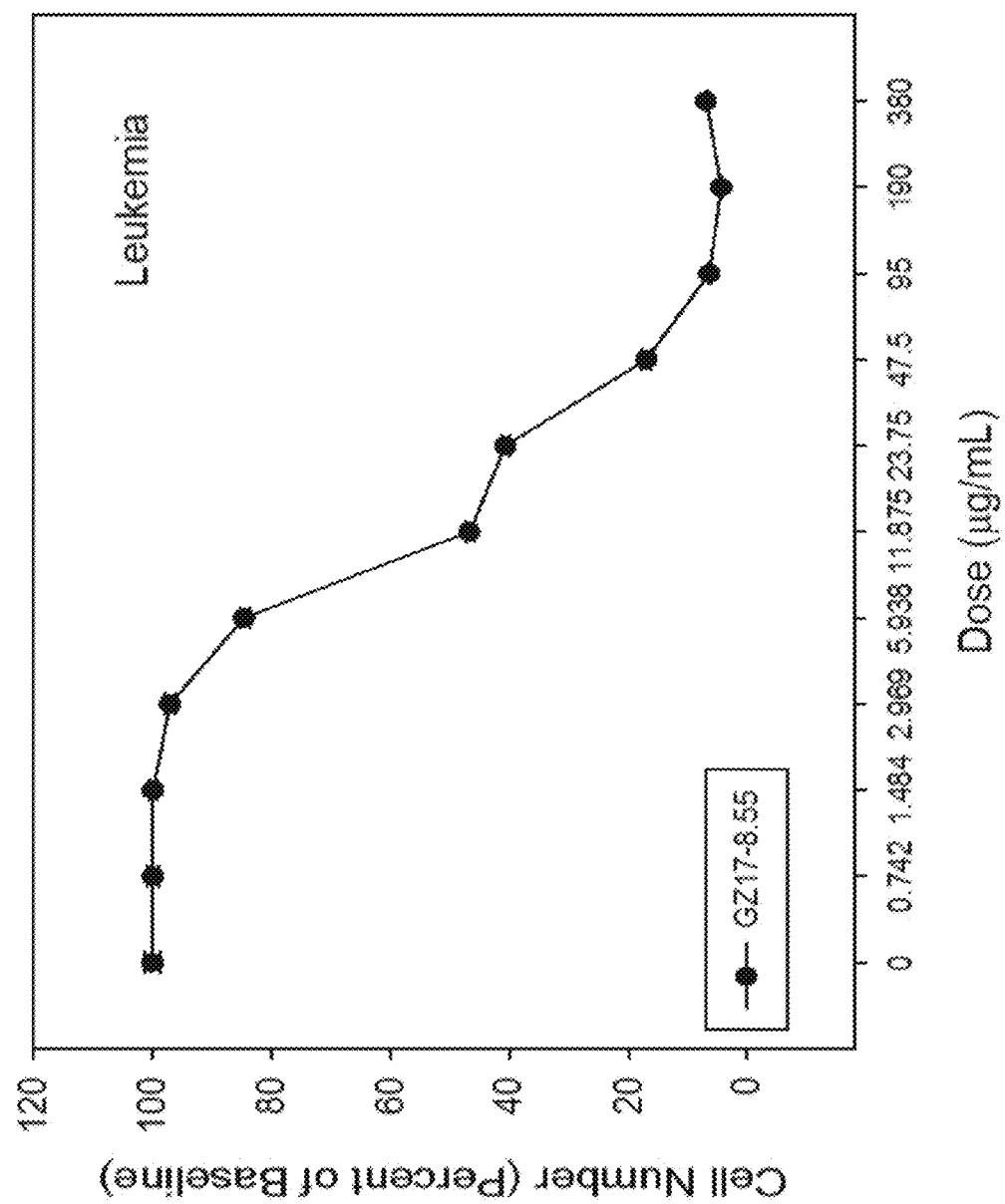
Figure 74A:
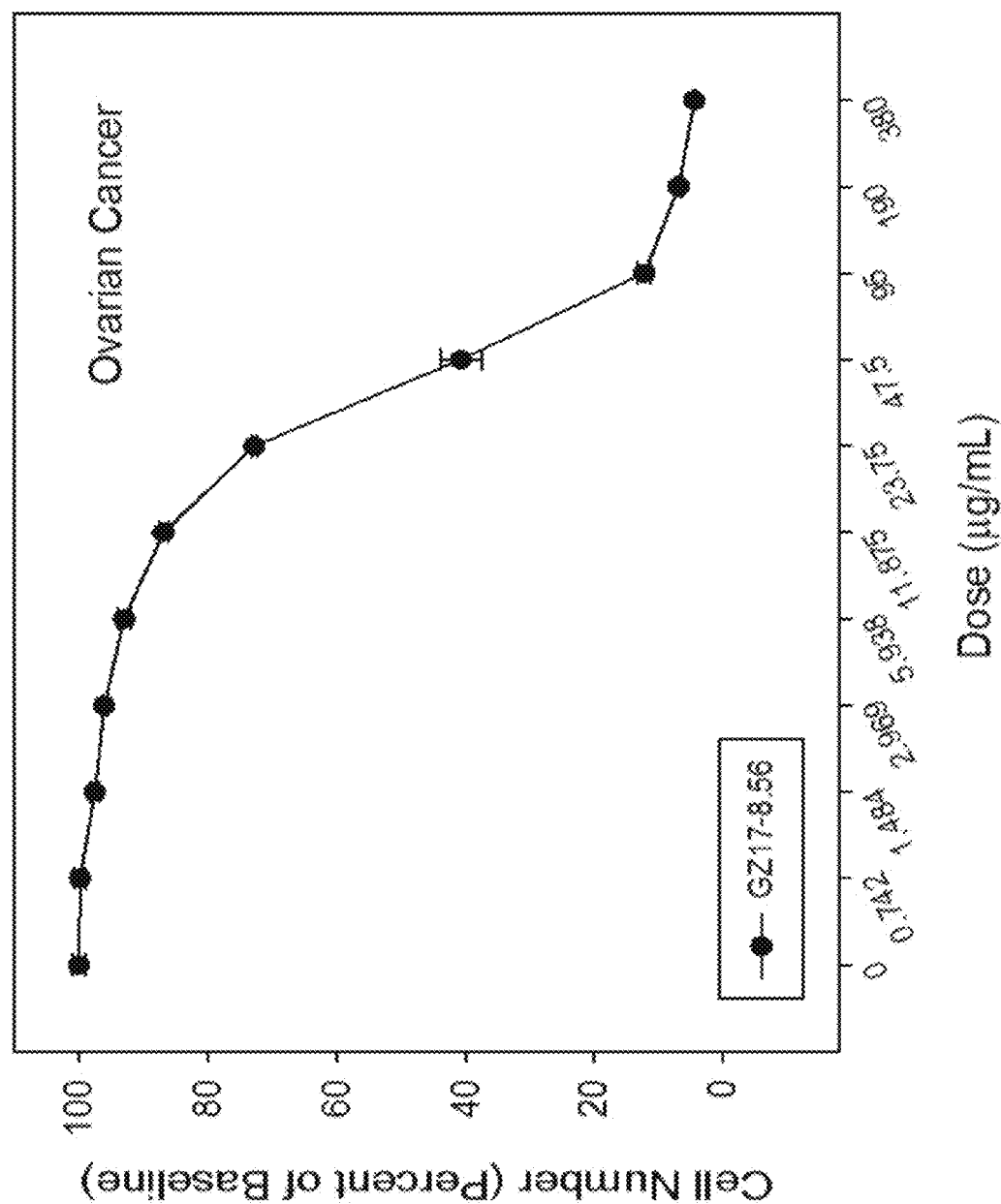
Figure 74B:
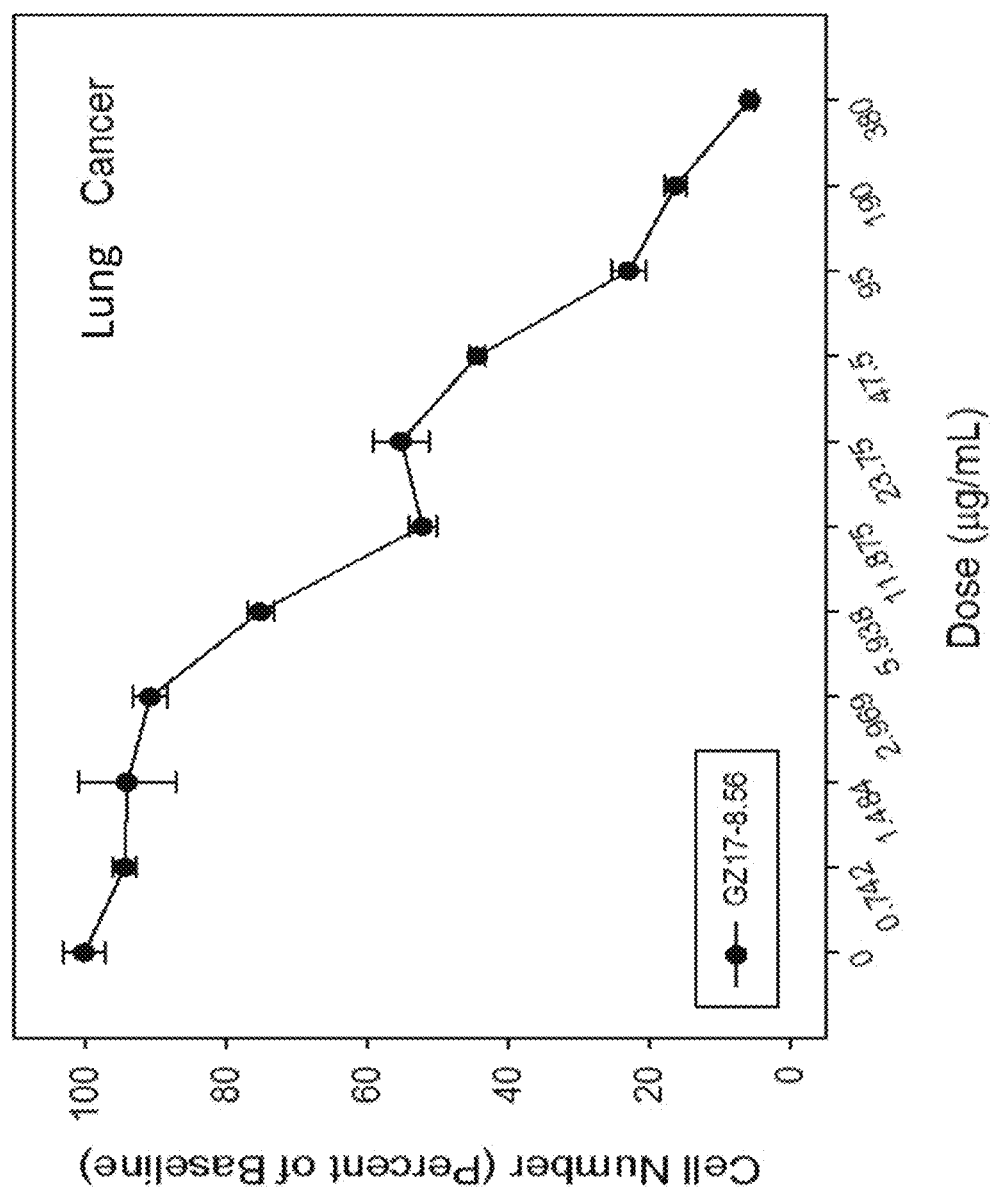
Figure 74C:
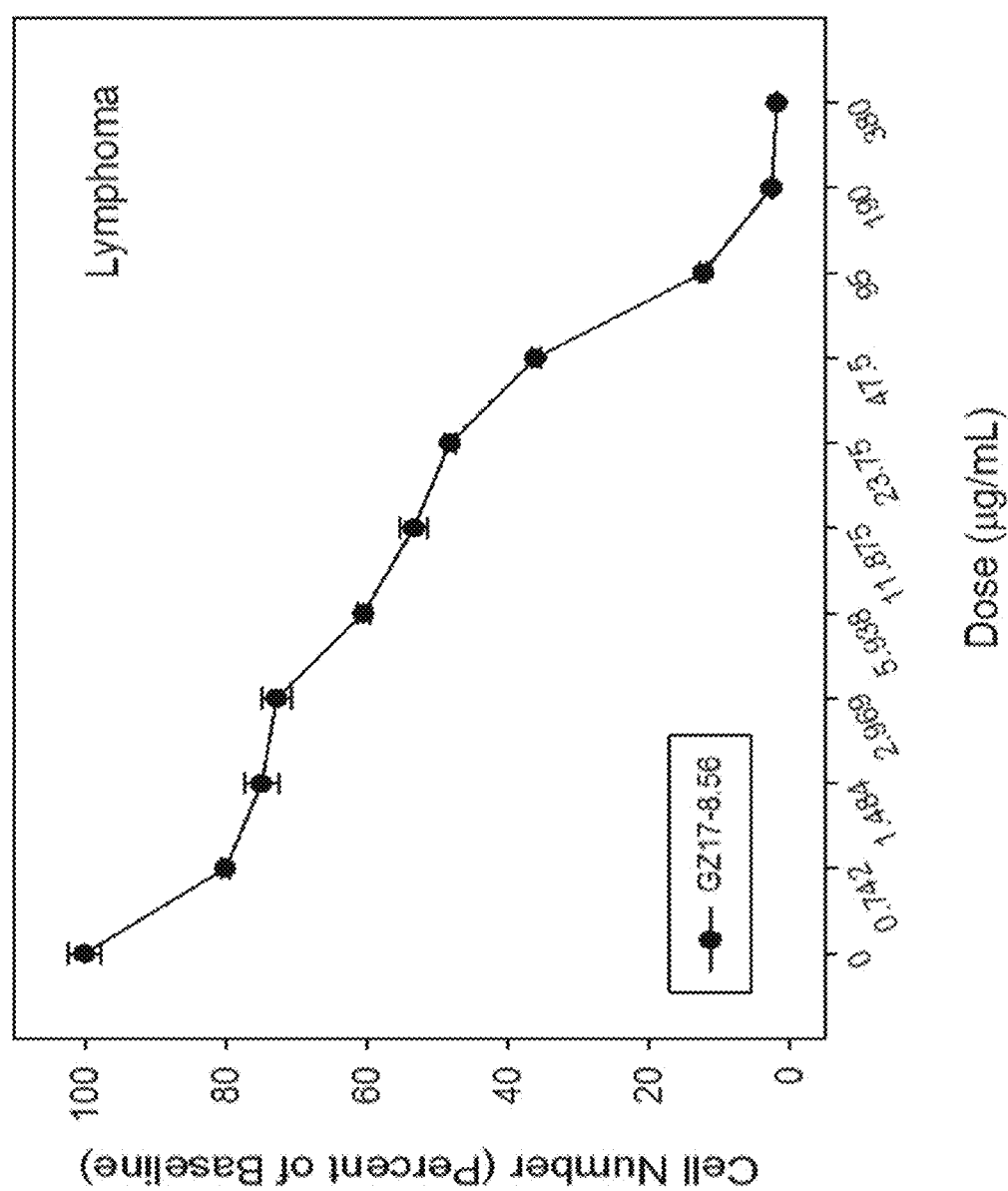
Figure 74D:
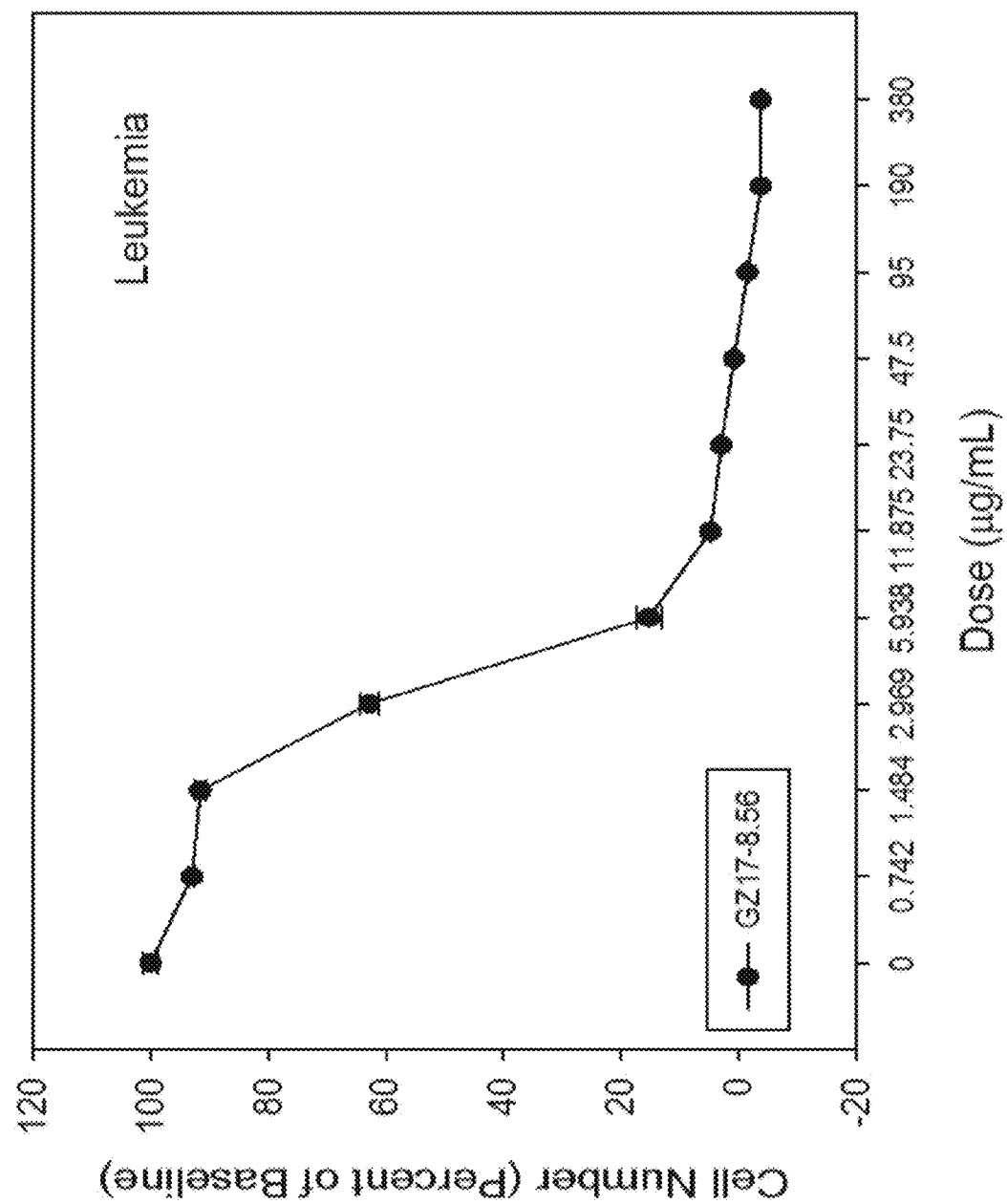
Figure 75A:
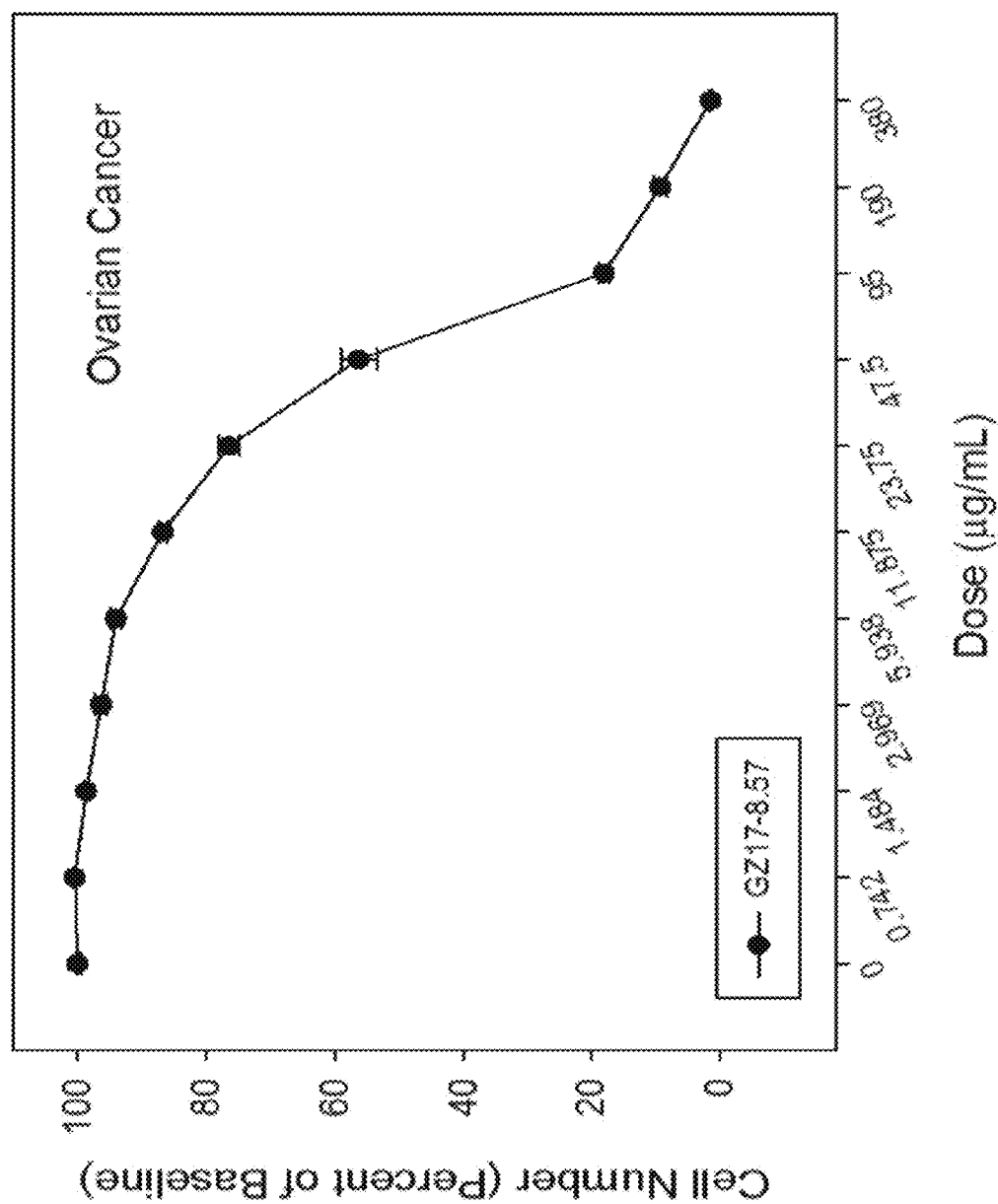
Figure 75B:
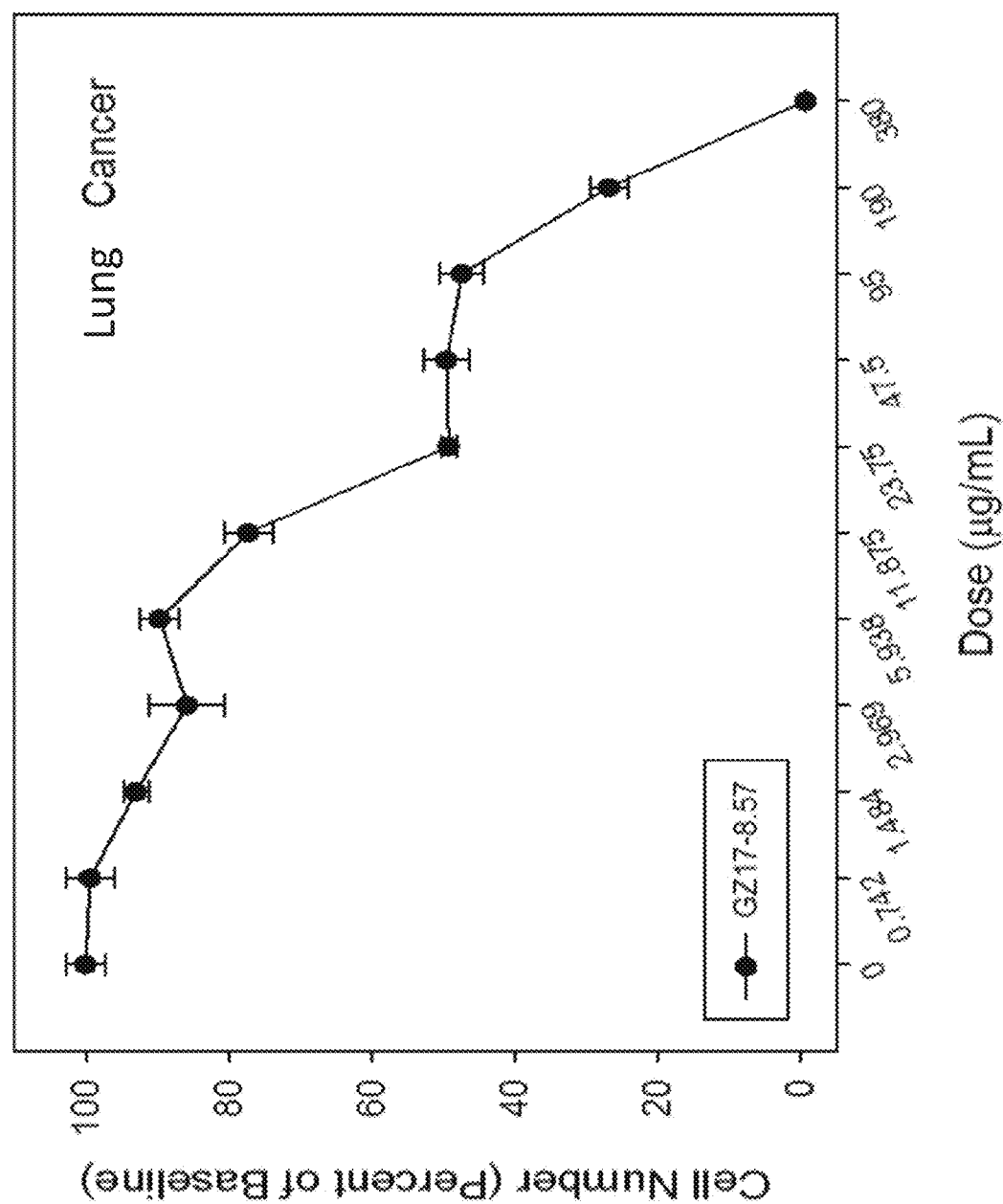
Figure 75C:
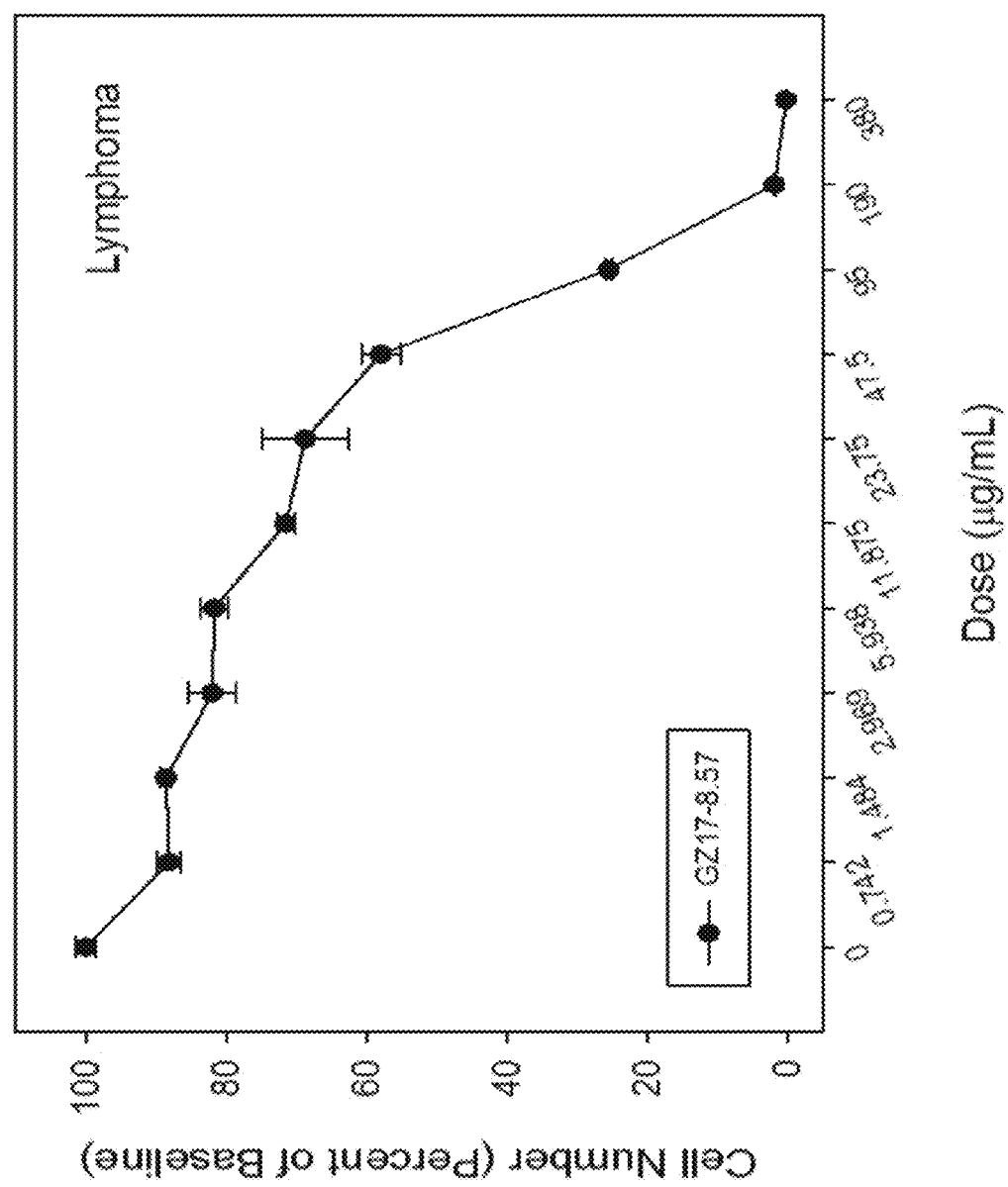
Figure 75D:
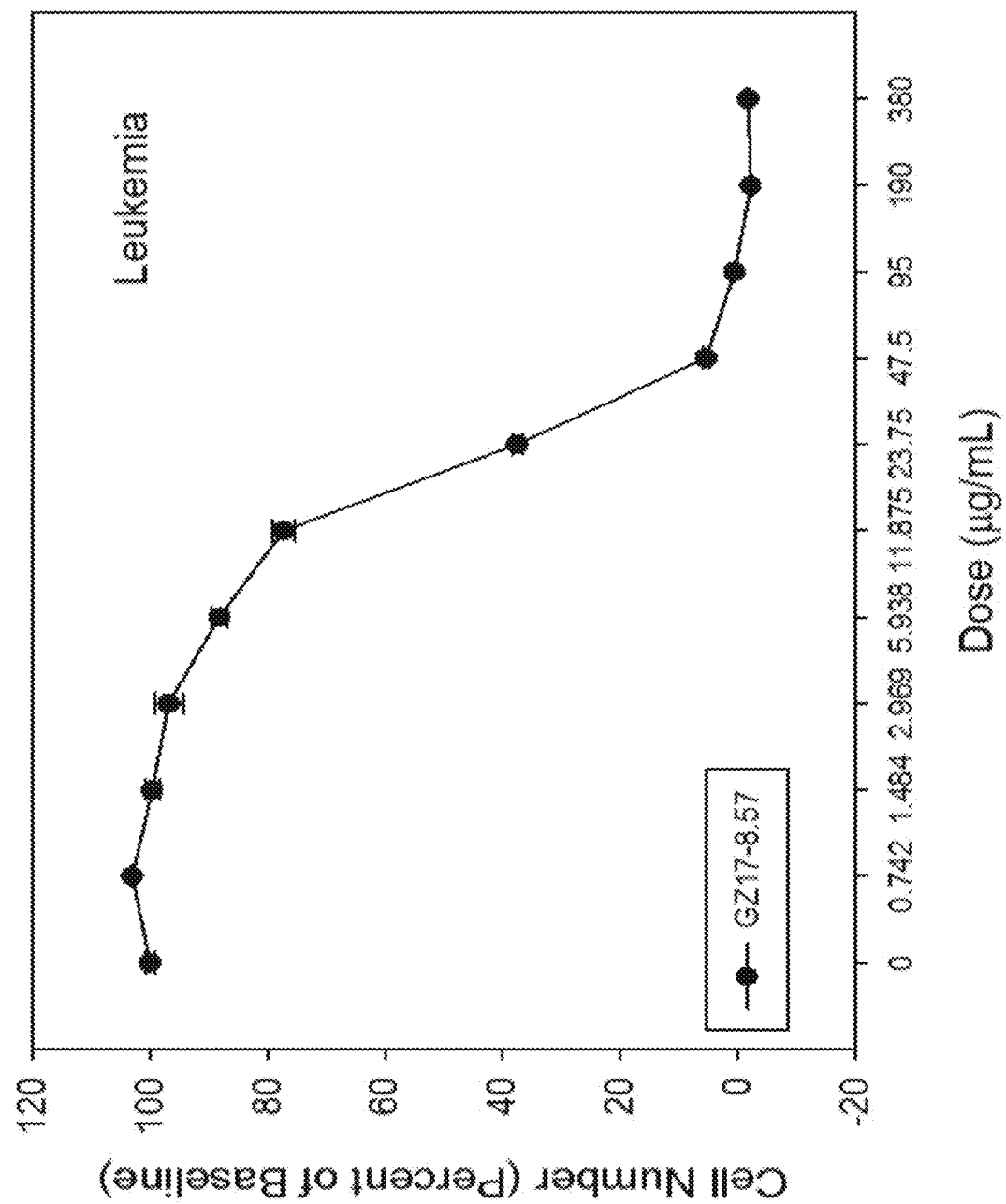
Figure 76A:
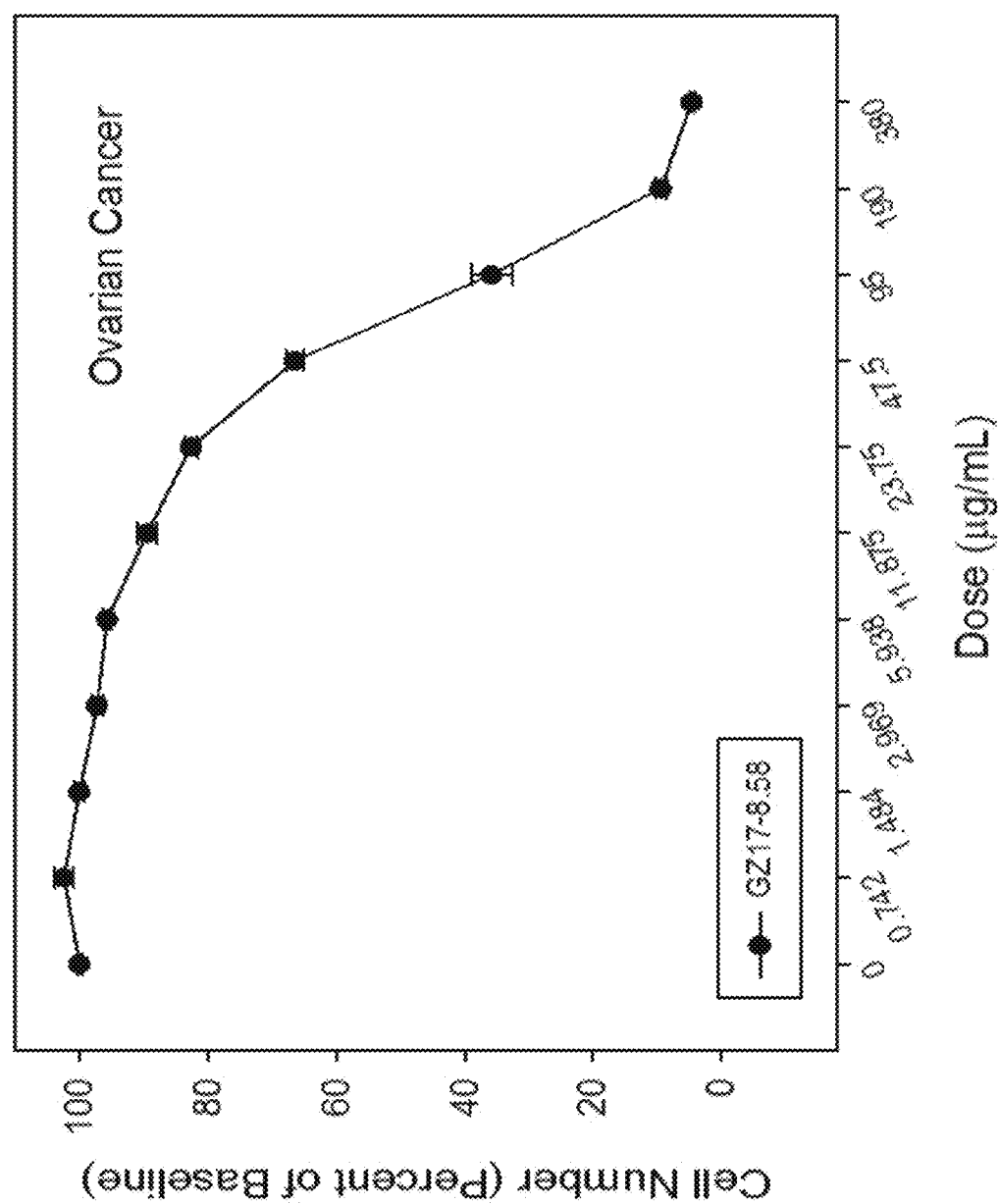
Figure 76B:
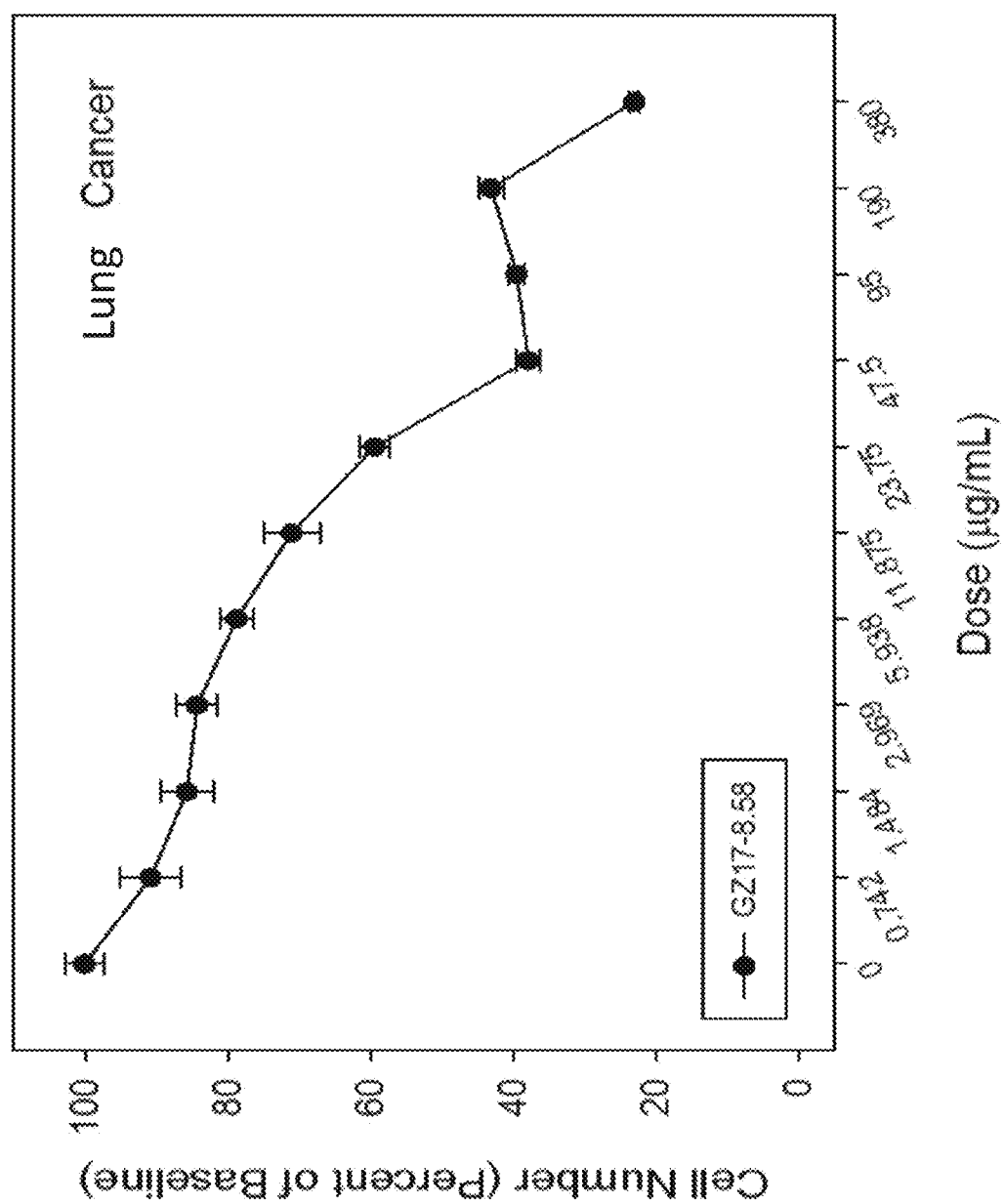
Figure 76C:
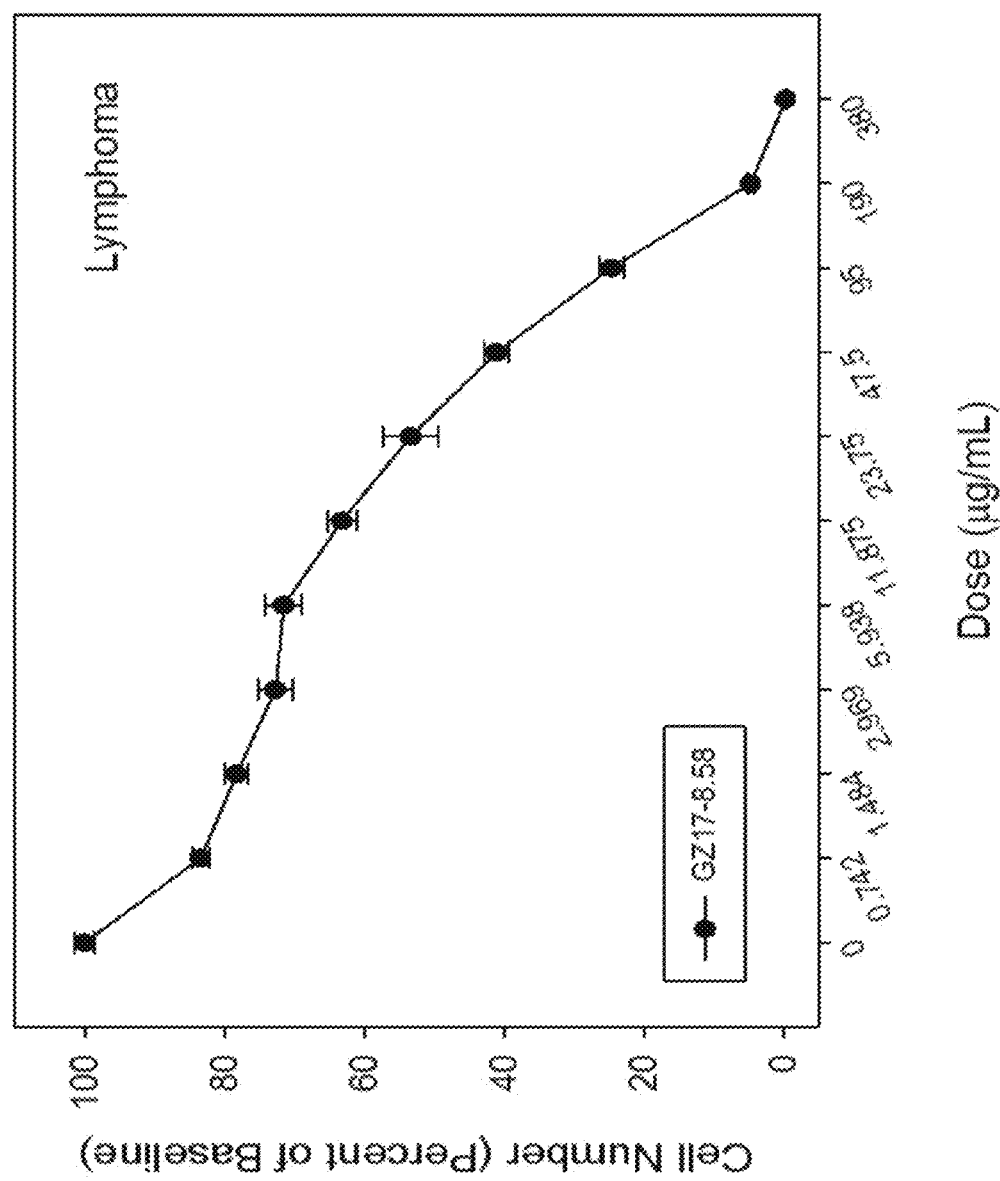
Figure 76D:
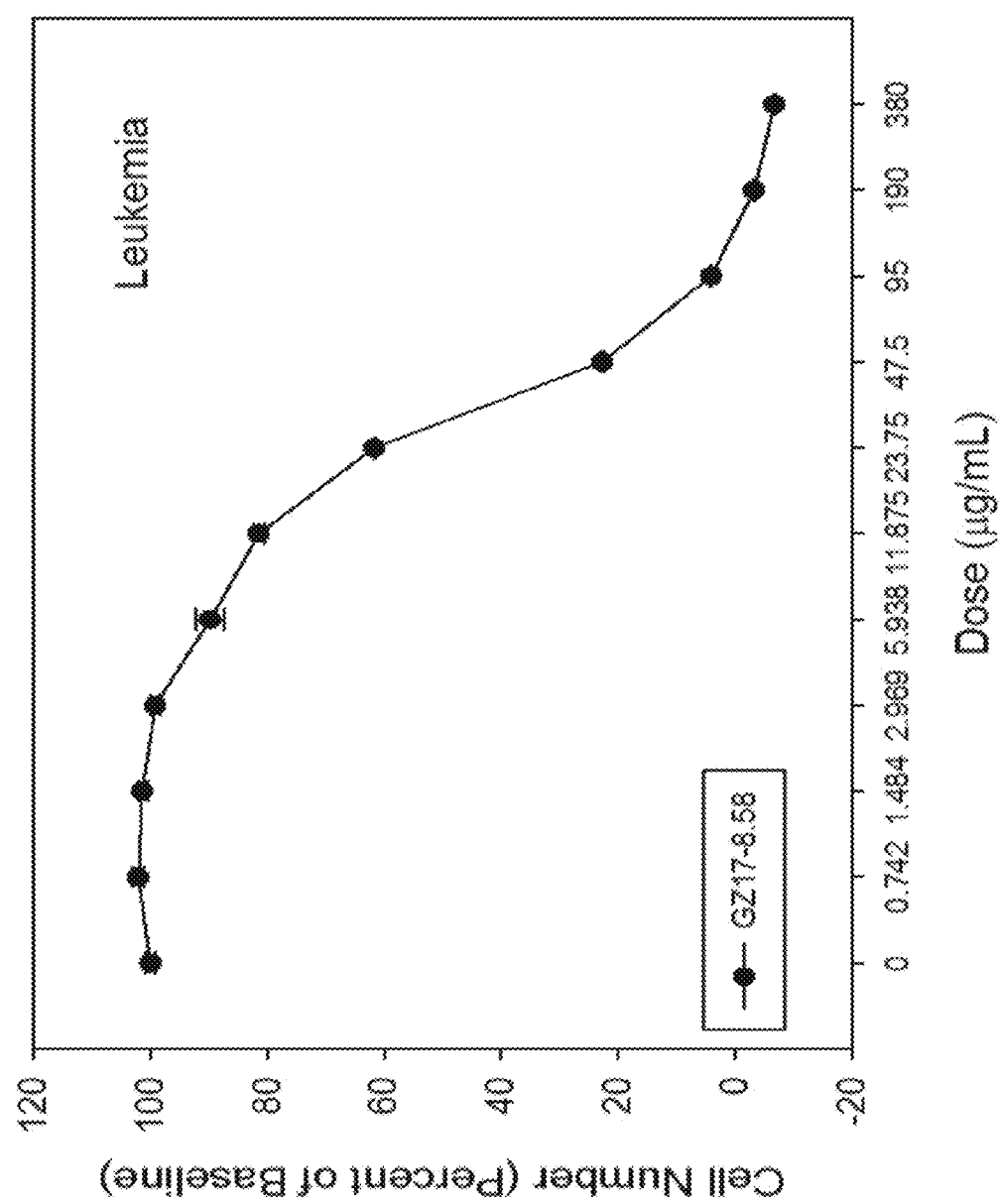
Figure 77A:
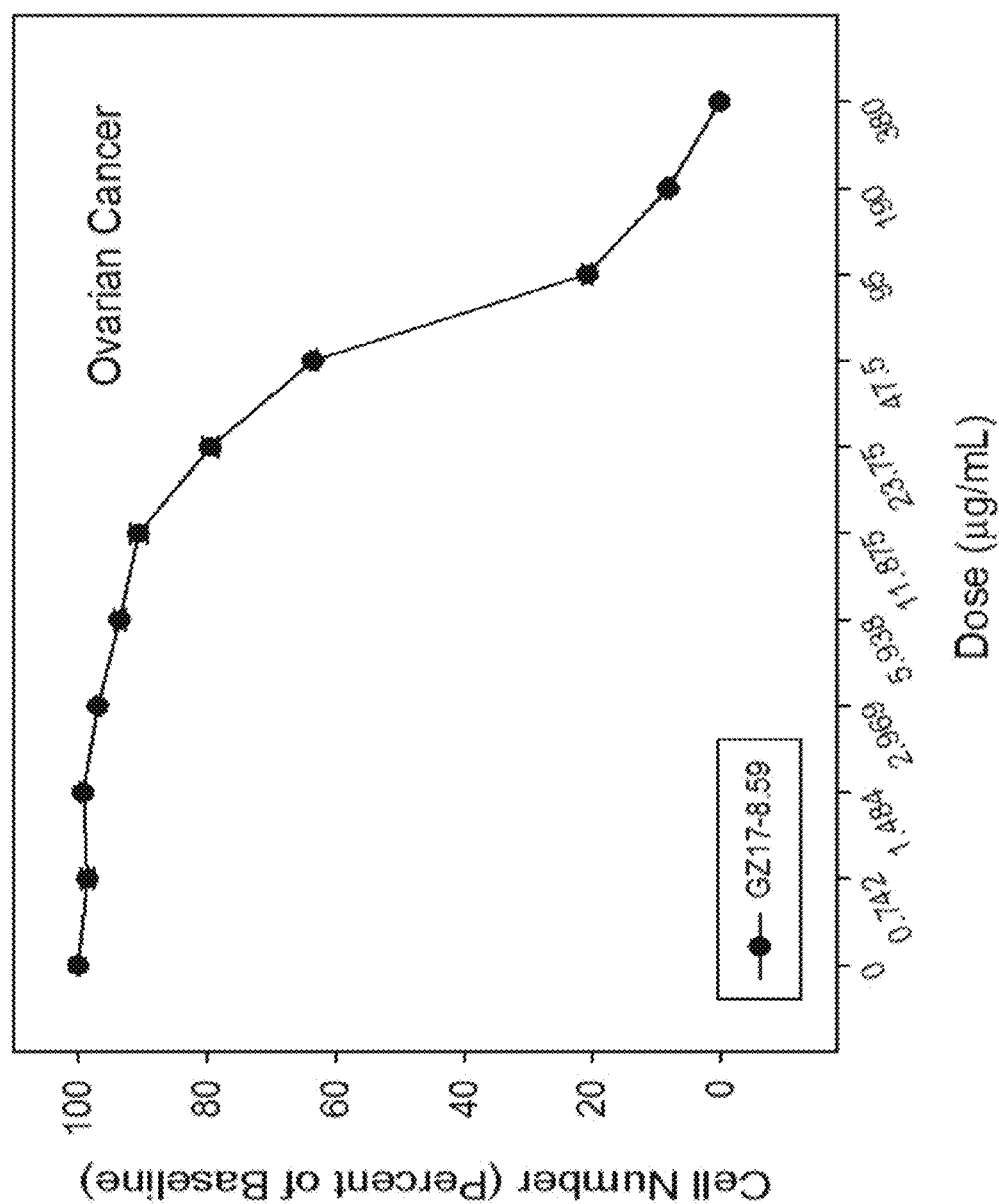
Figure 77B:
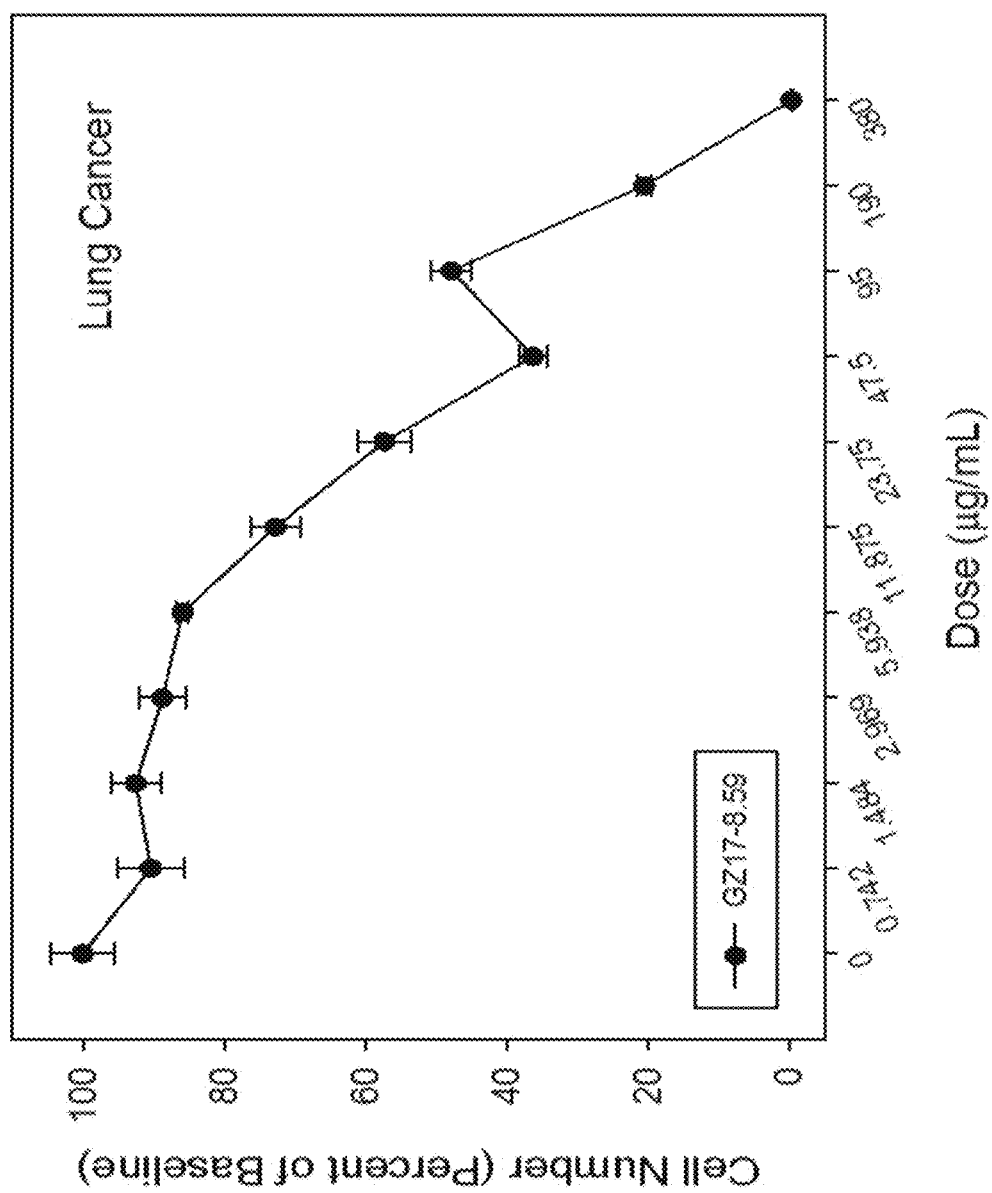
Figure 77C:
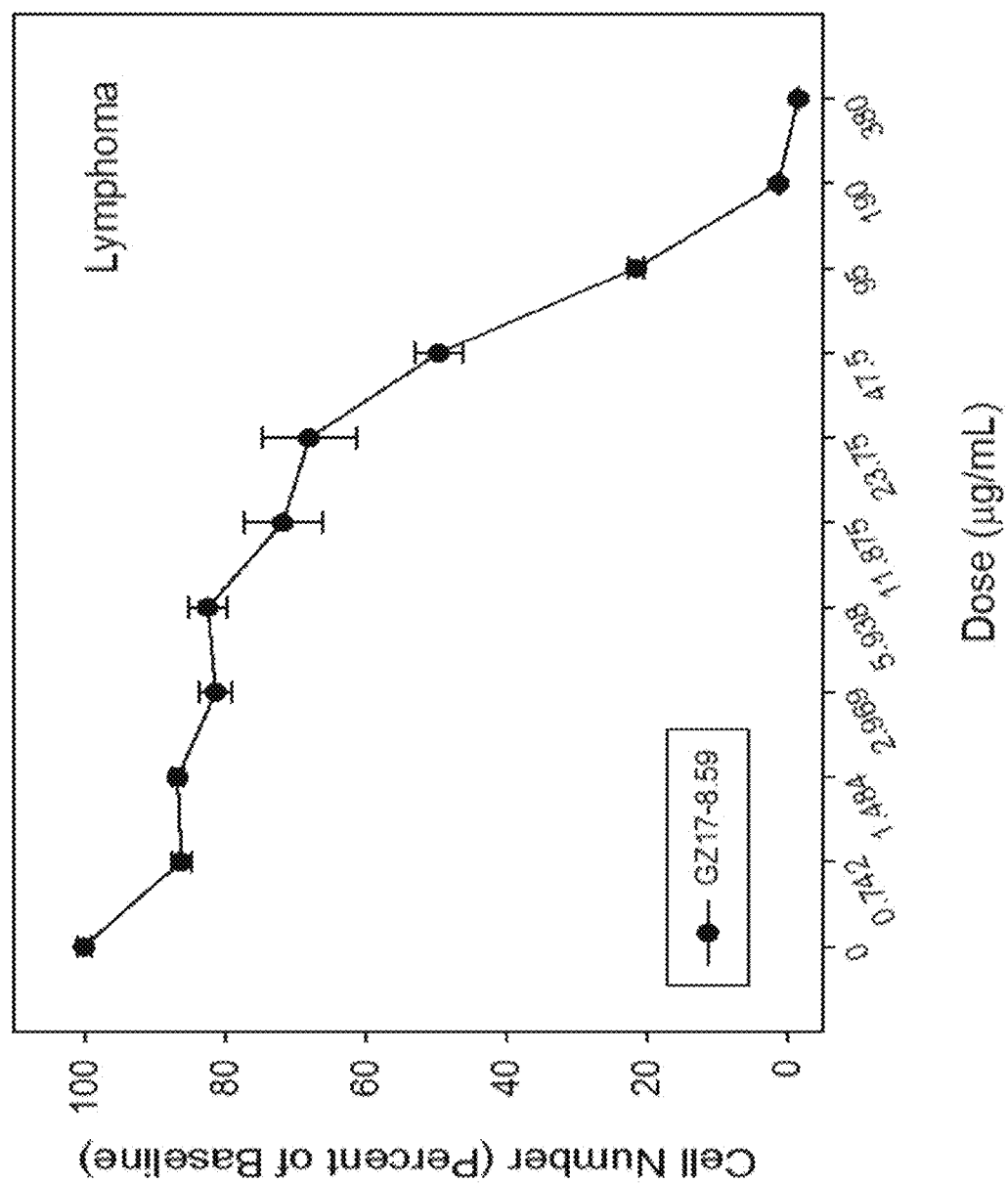
Figure 77D:
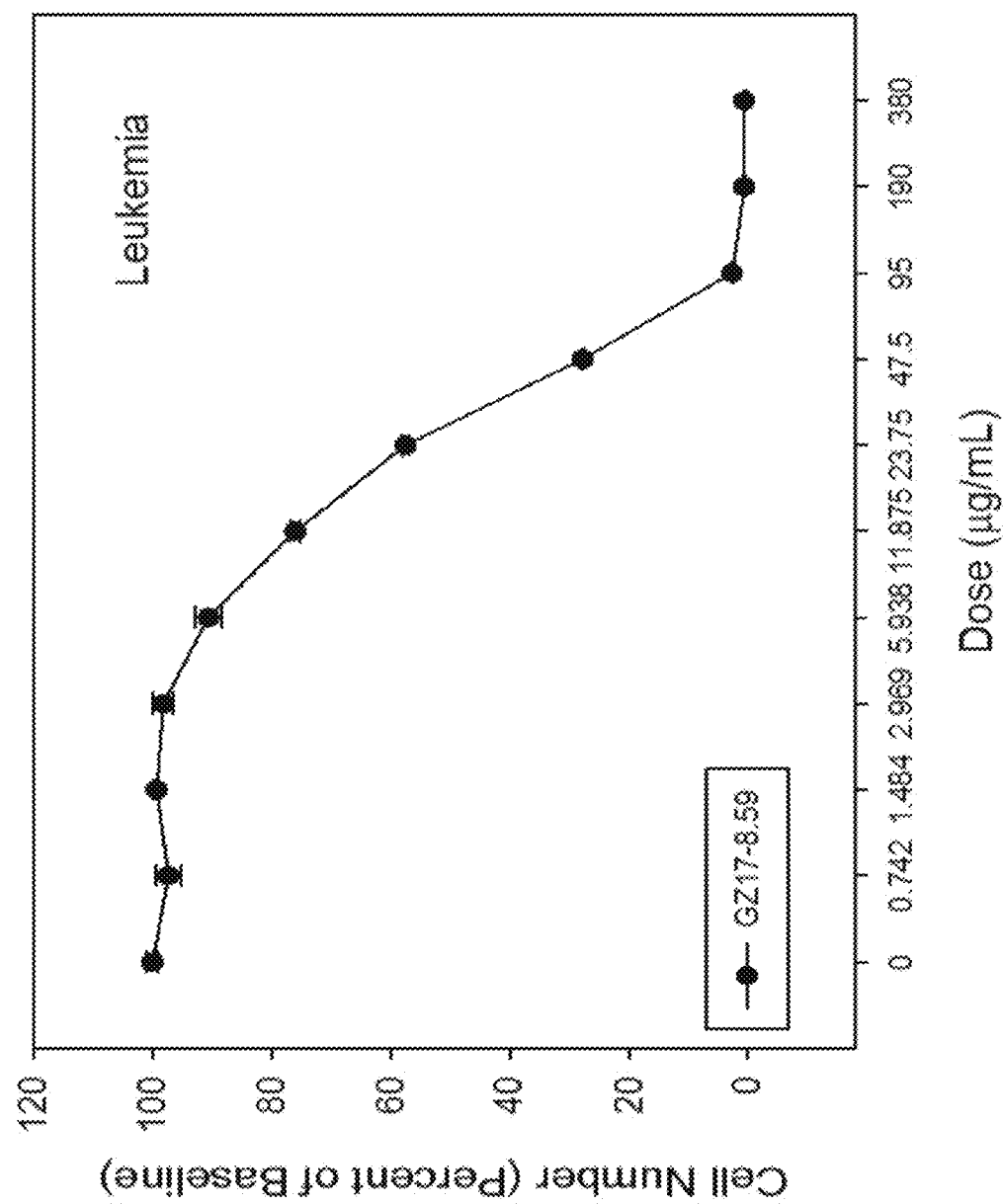
Figure 78A:
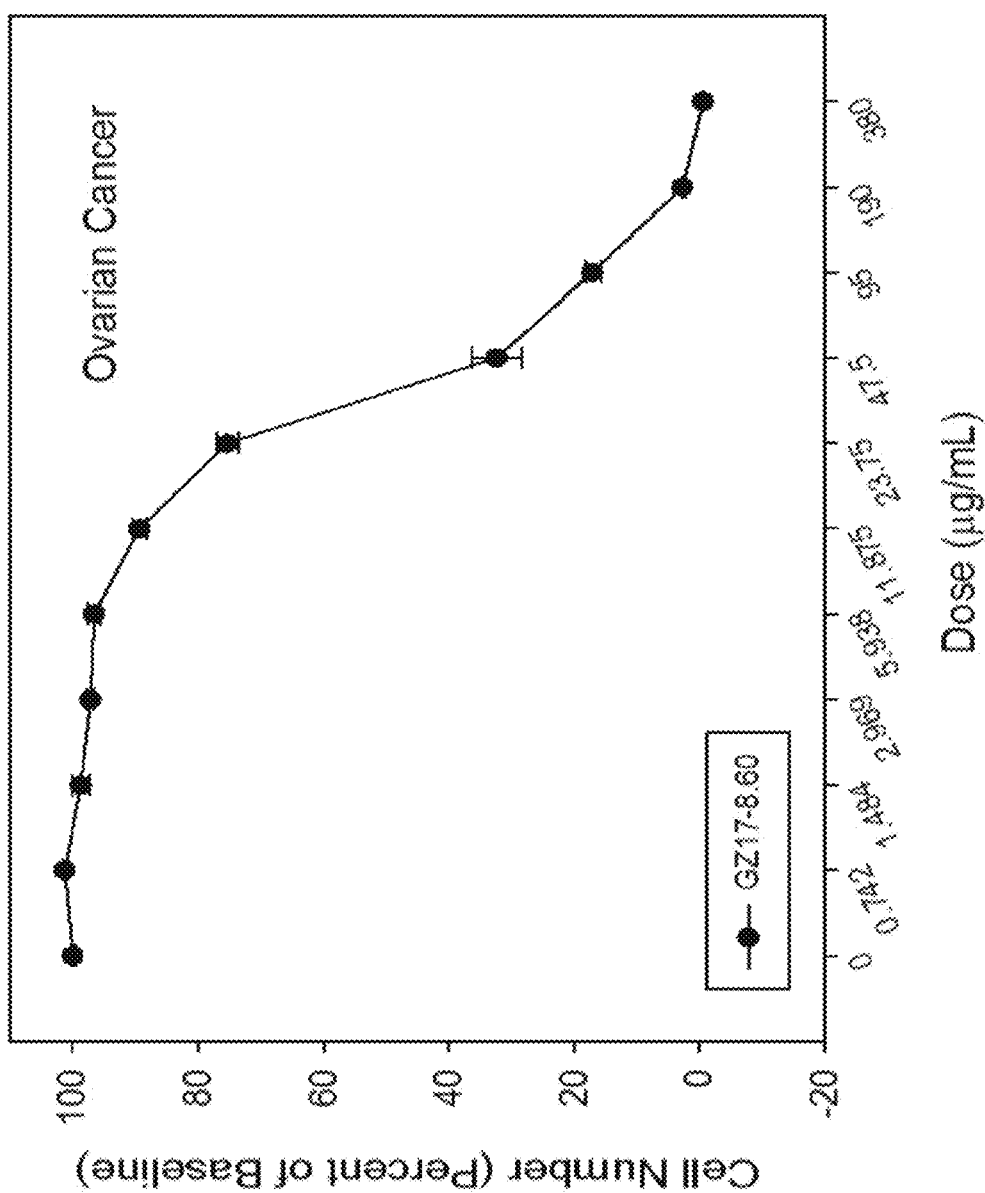
Figure 78B:
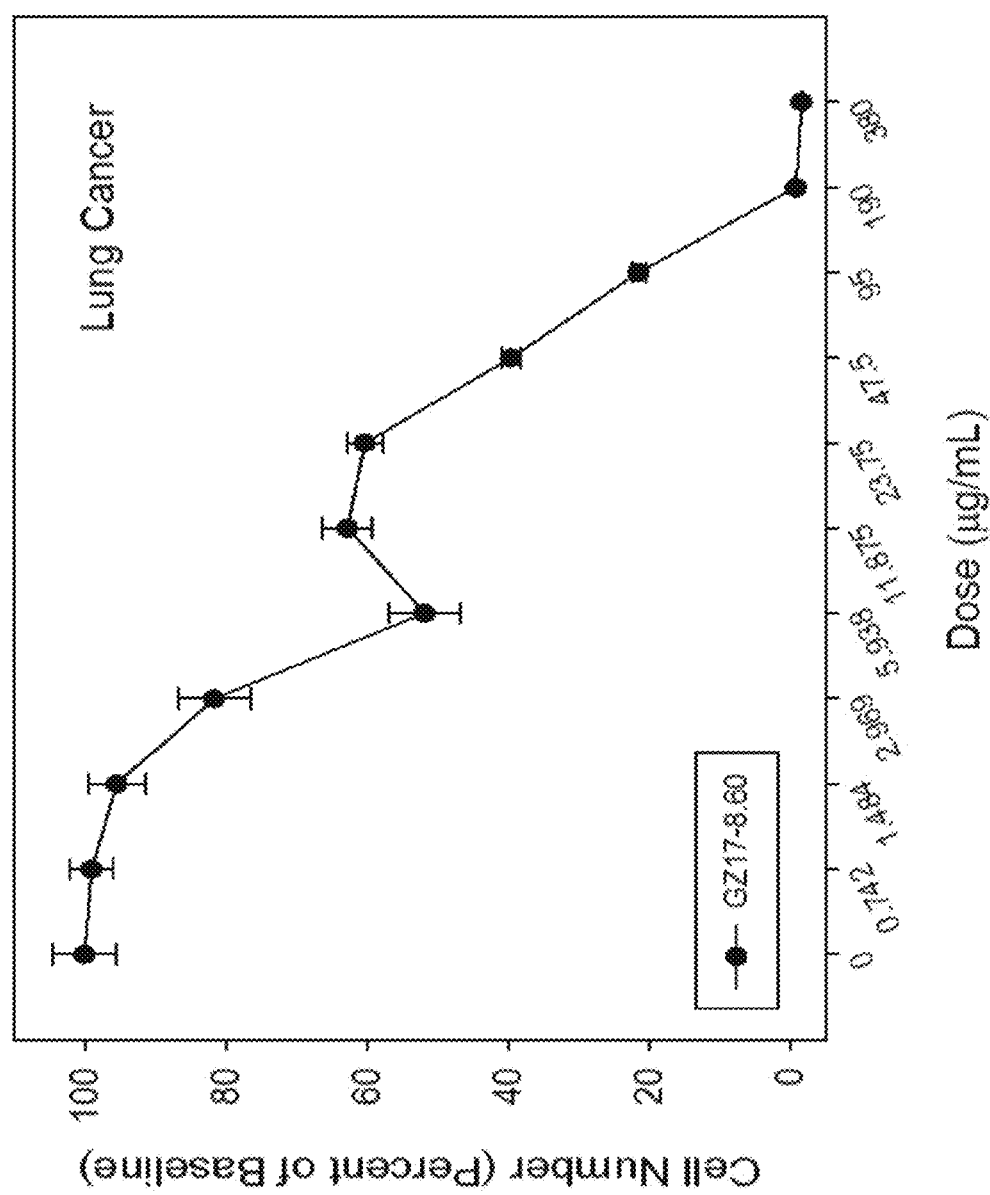
Figure 78C:
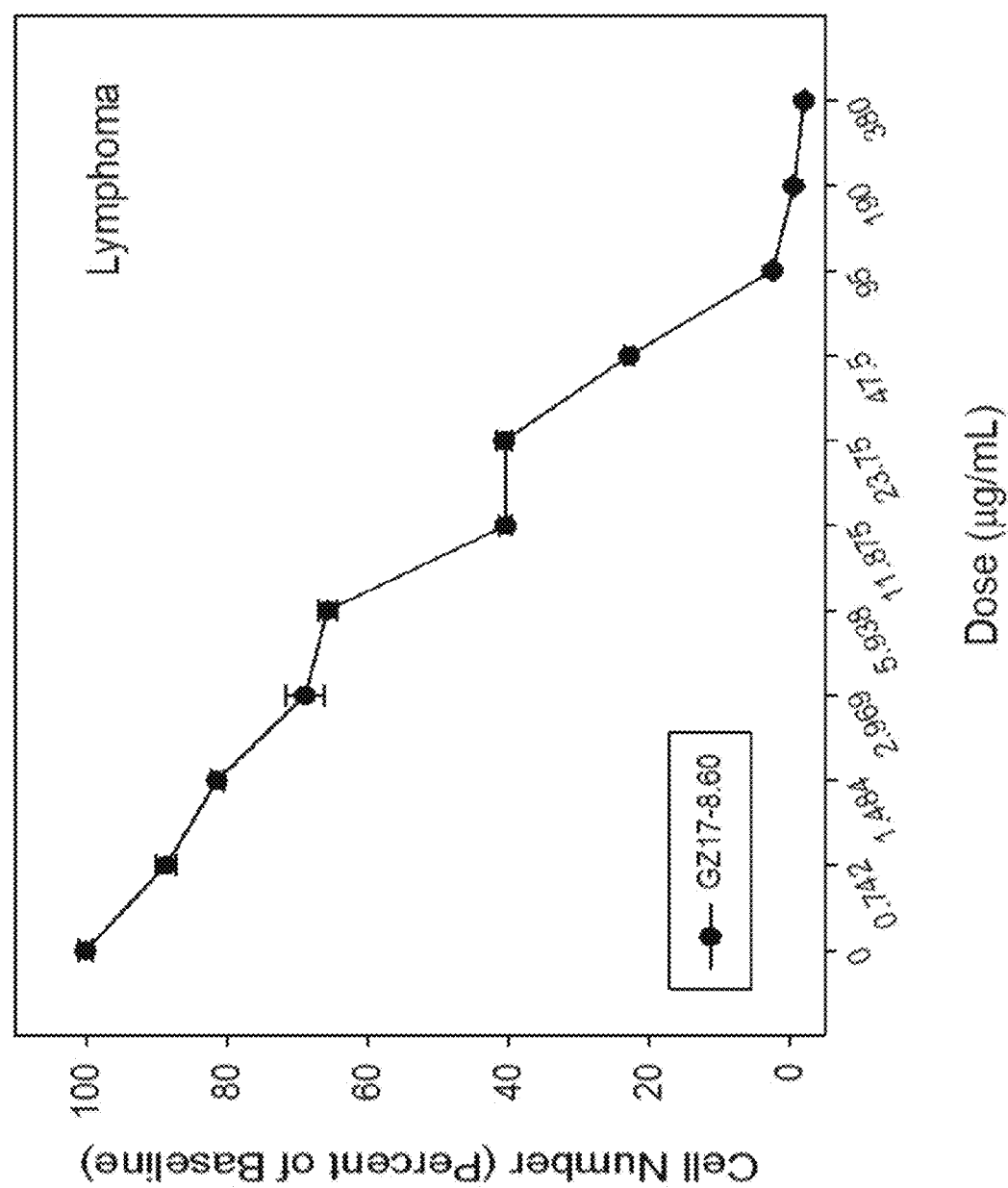
Figure 78D:
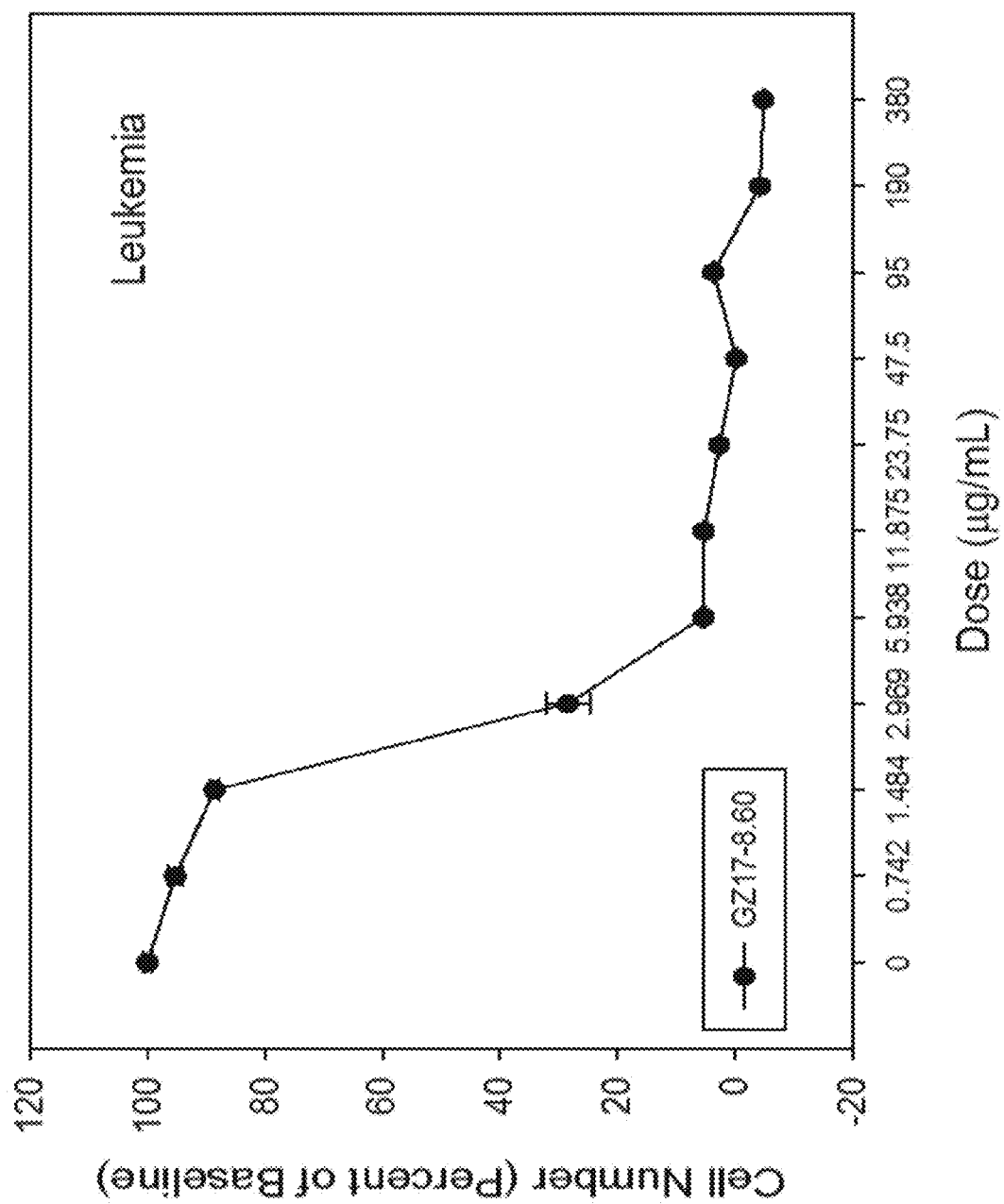
Figure 79A:
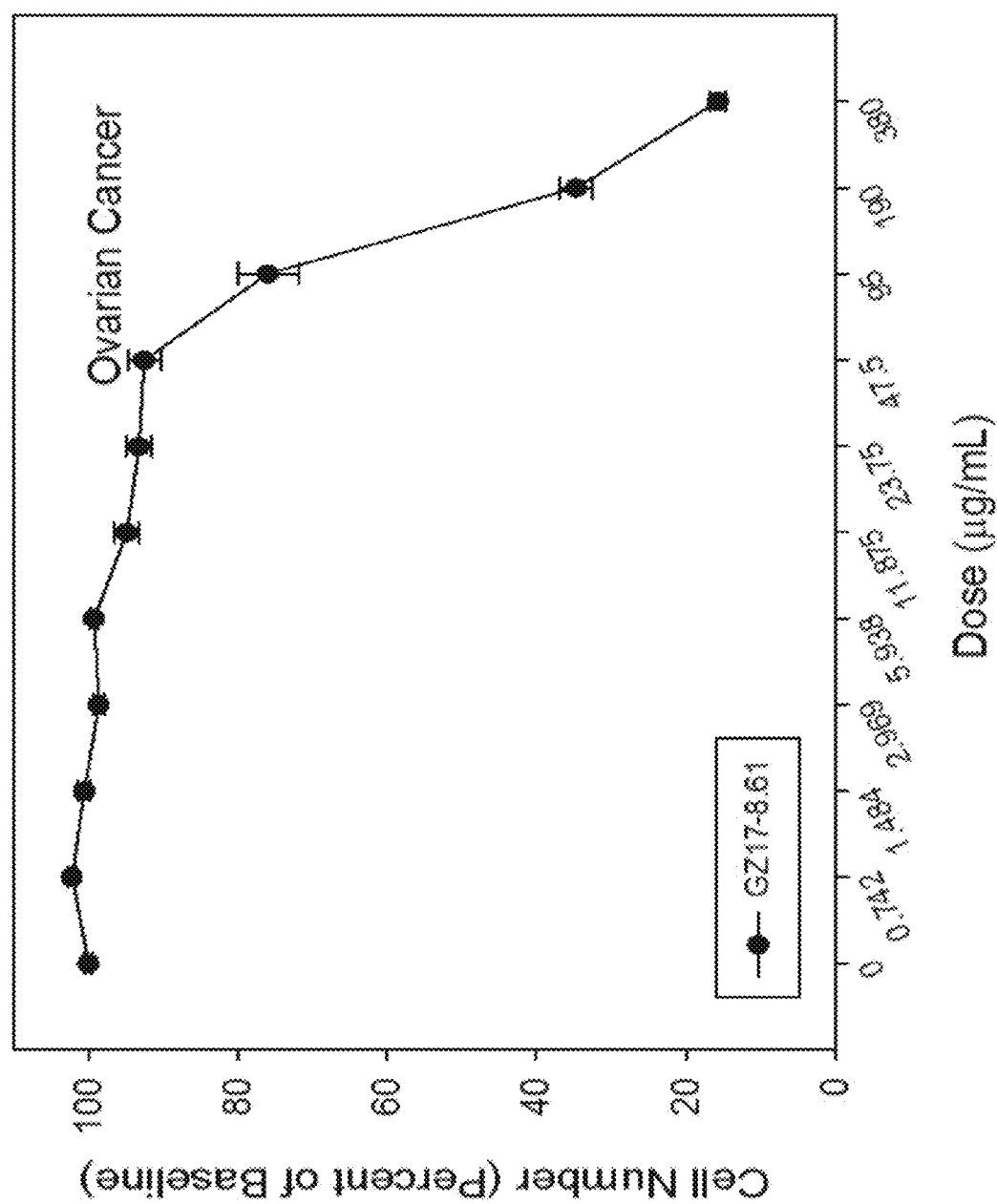
Figure 79B:
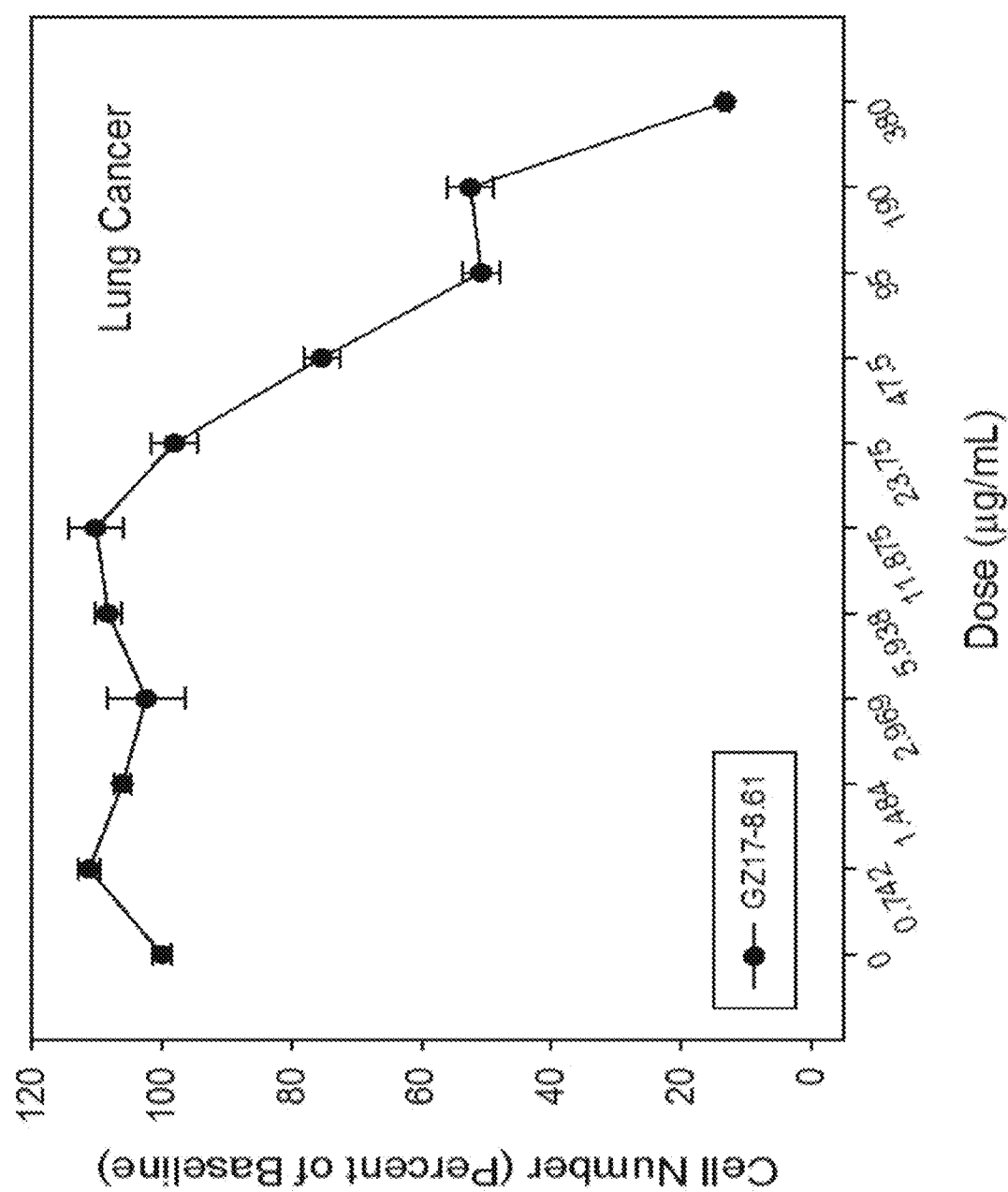
Figure 79C:
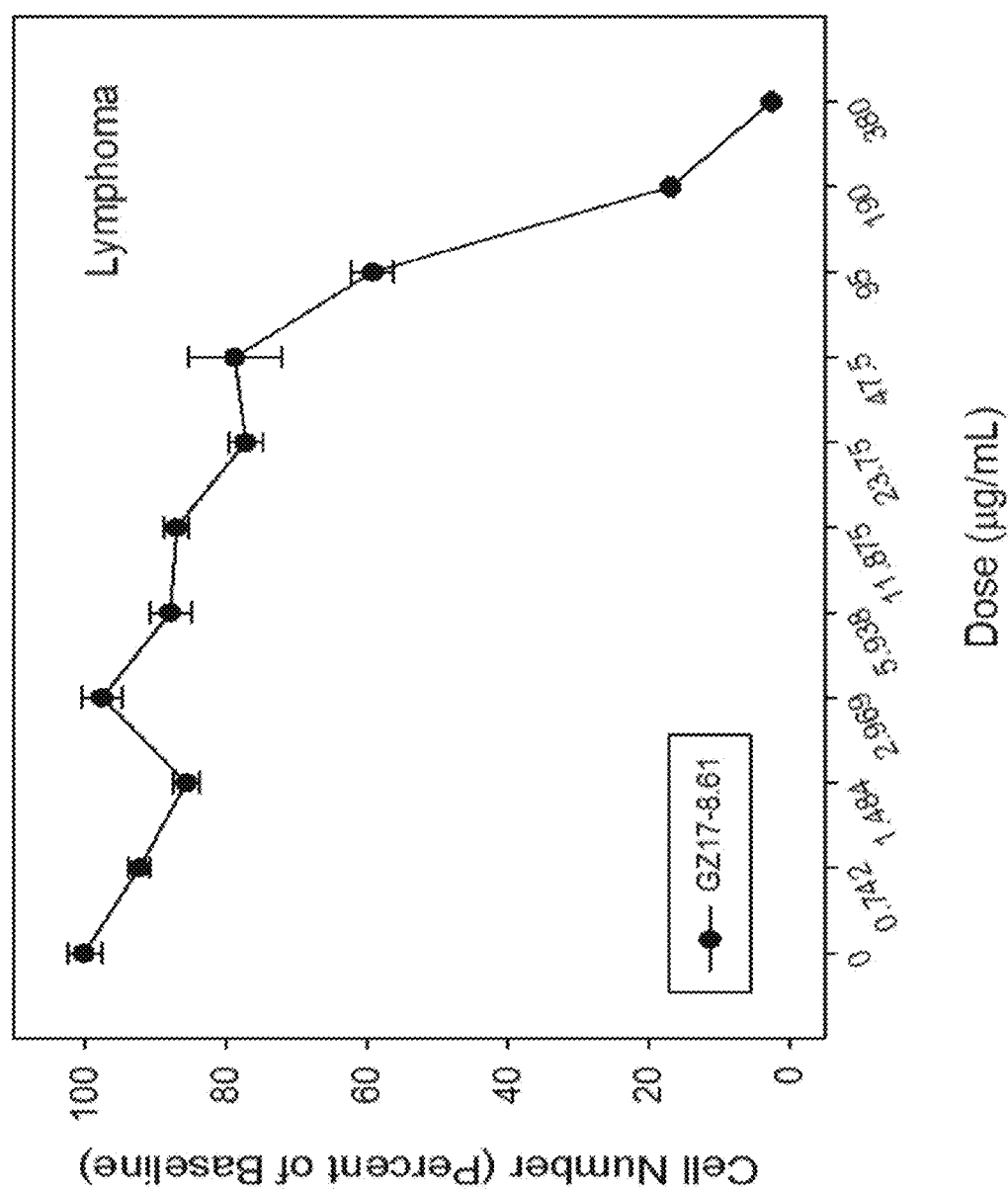
Figure 79D:
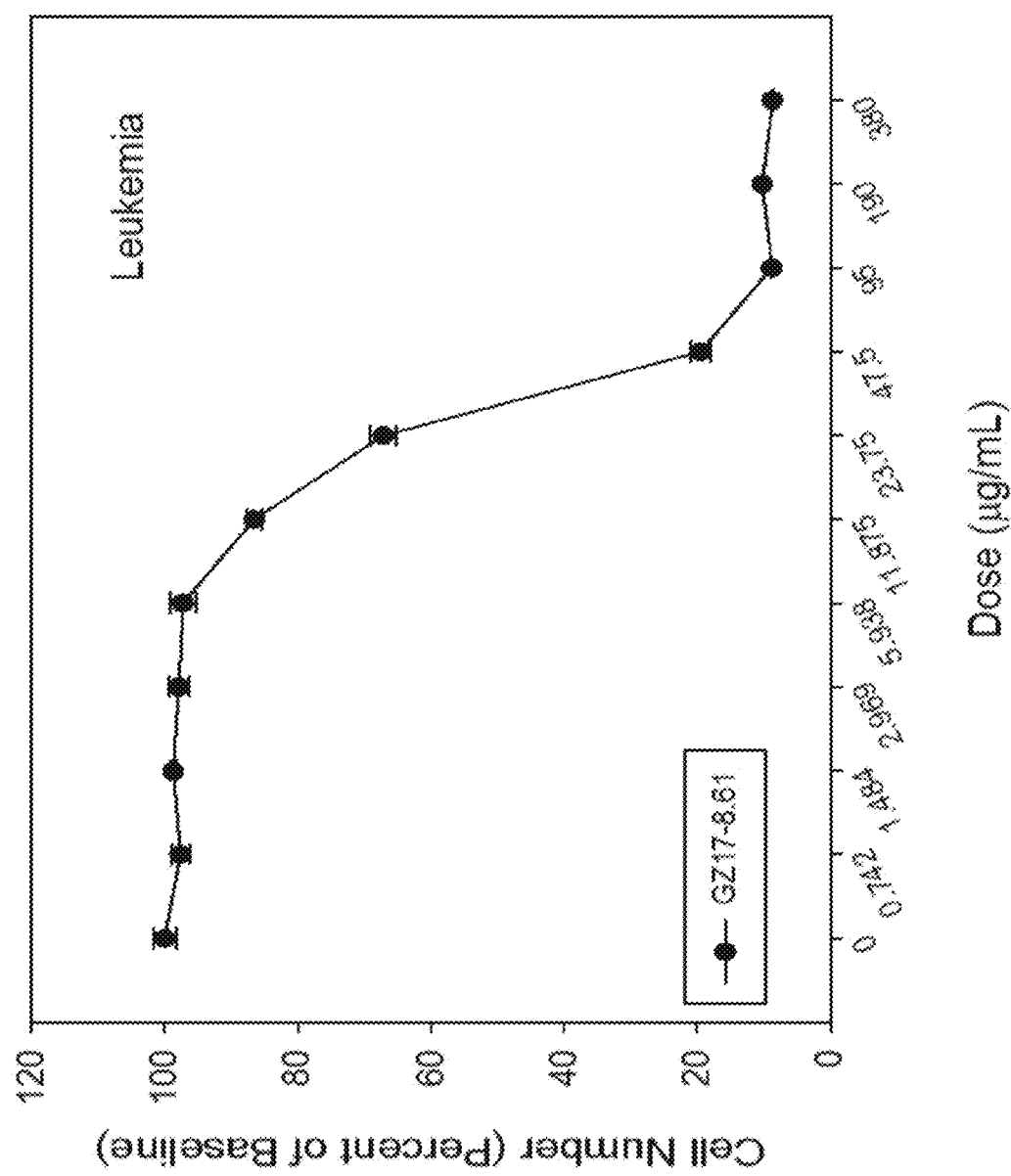
Figure 80A:
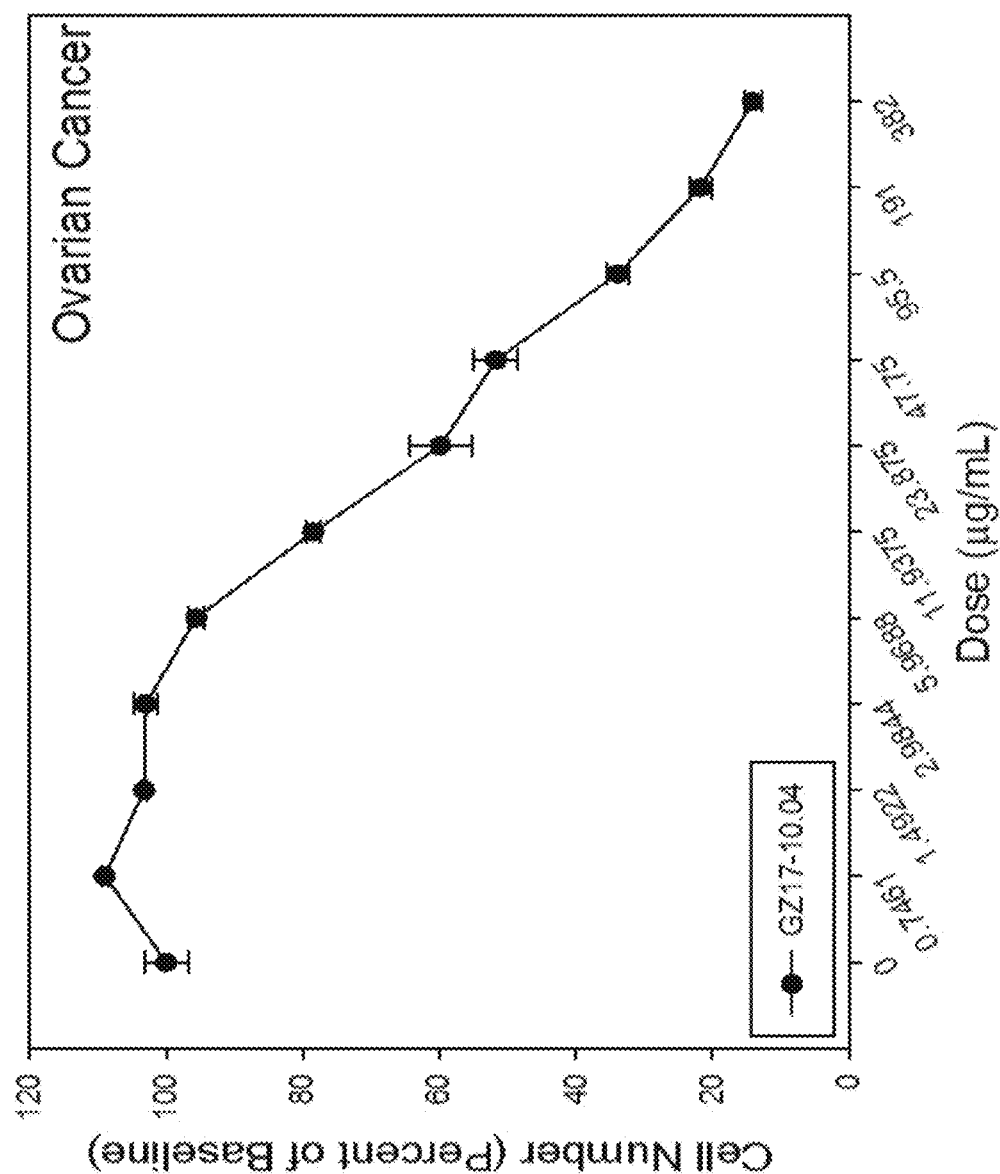
Figure 80B:
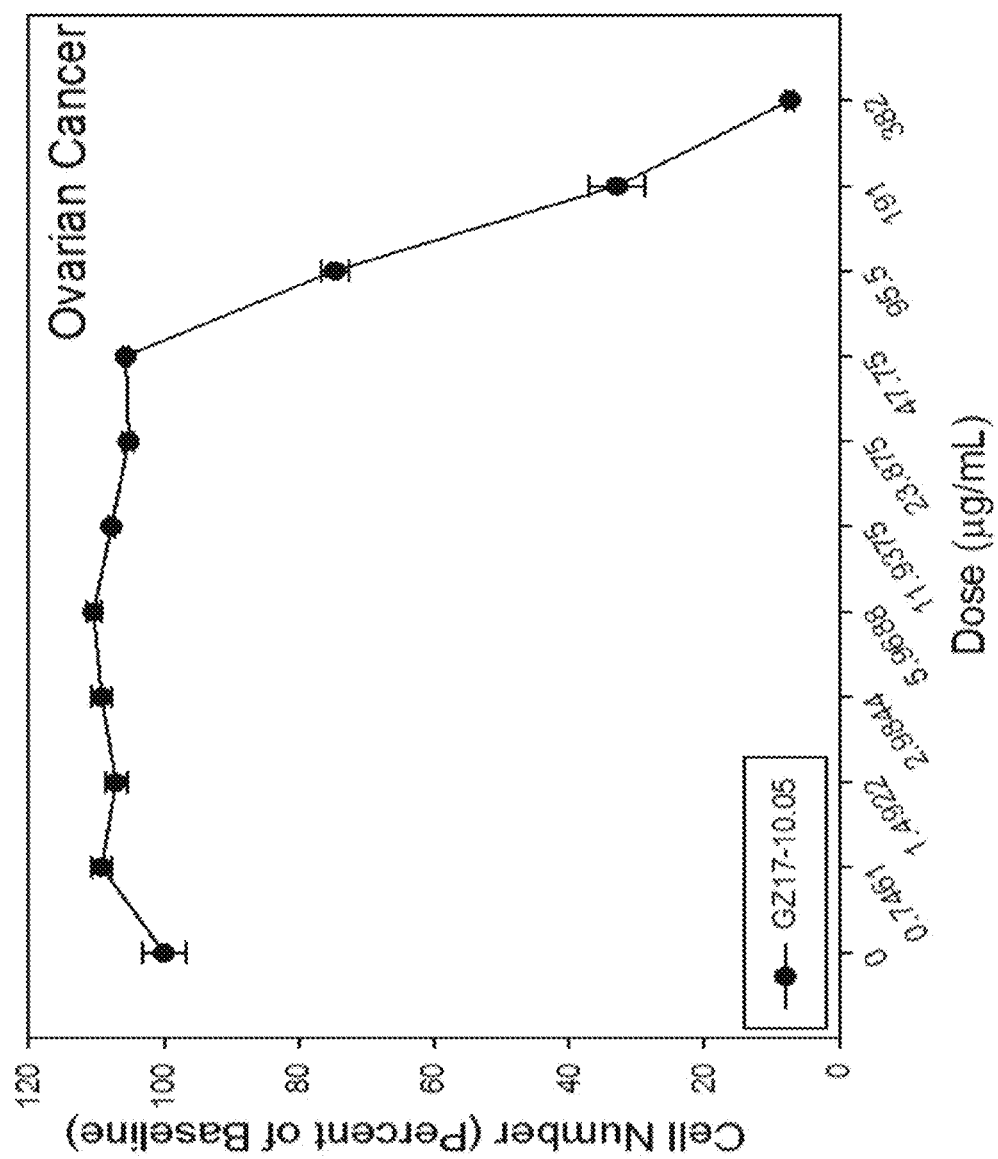
Figure 80C:
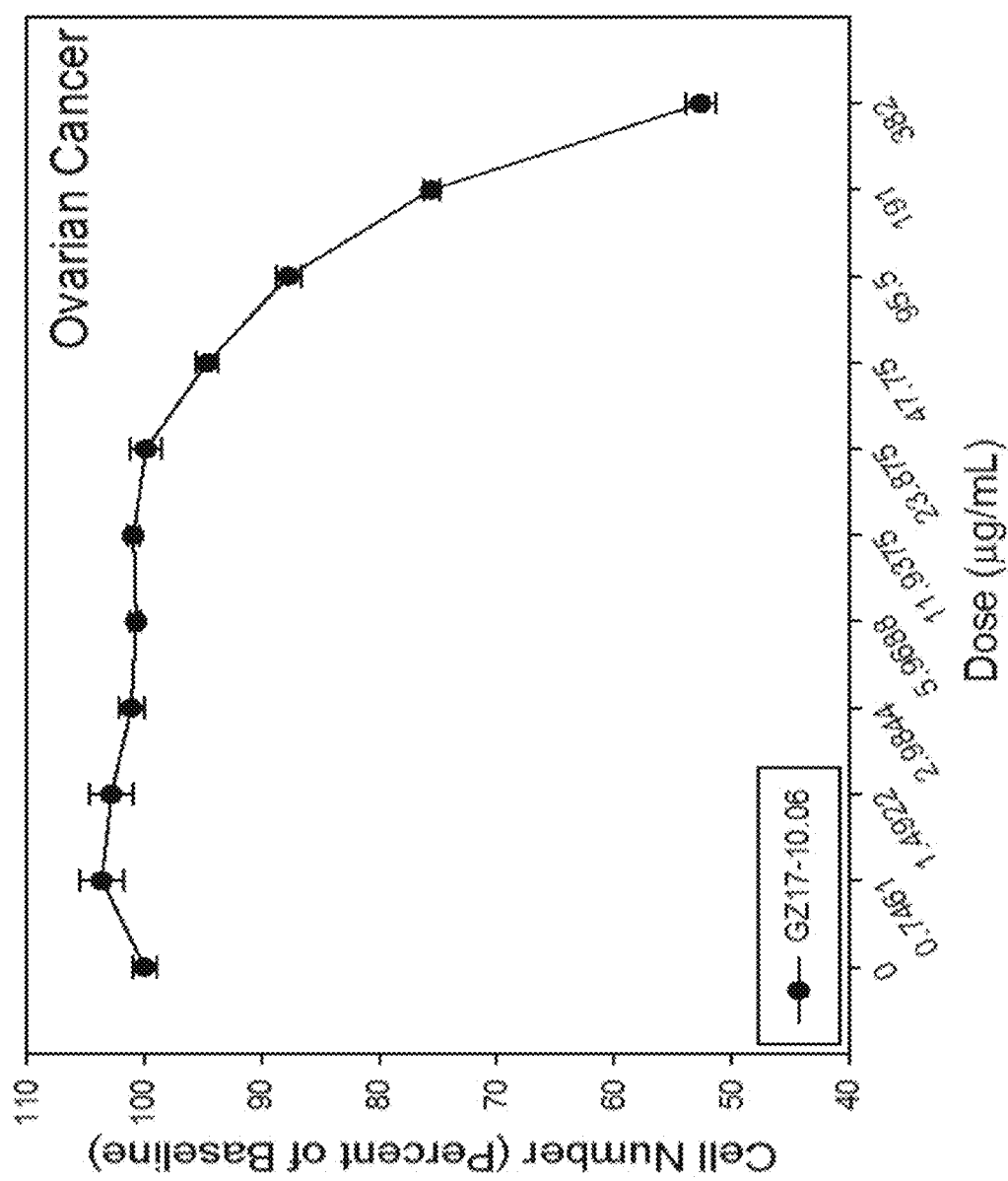
Figure 80D:
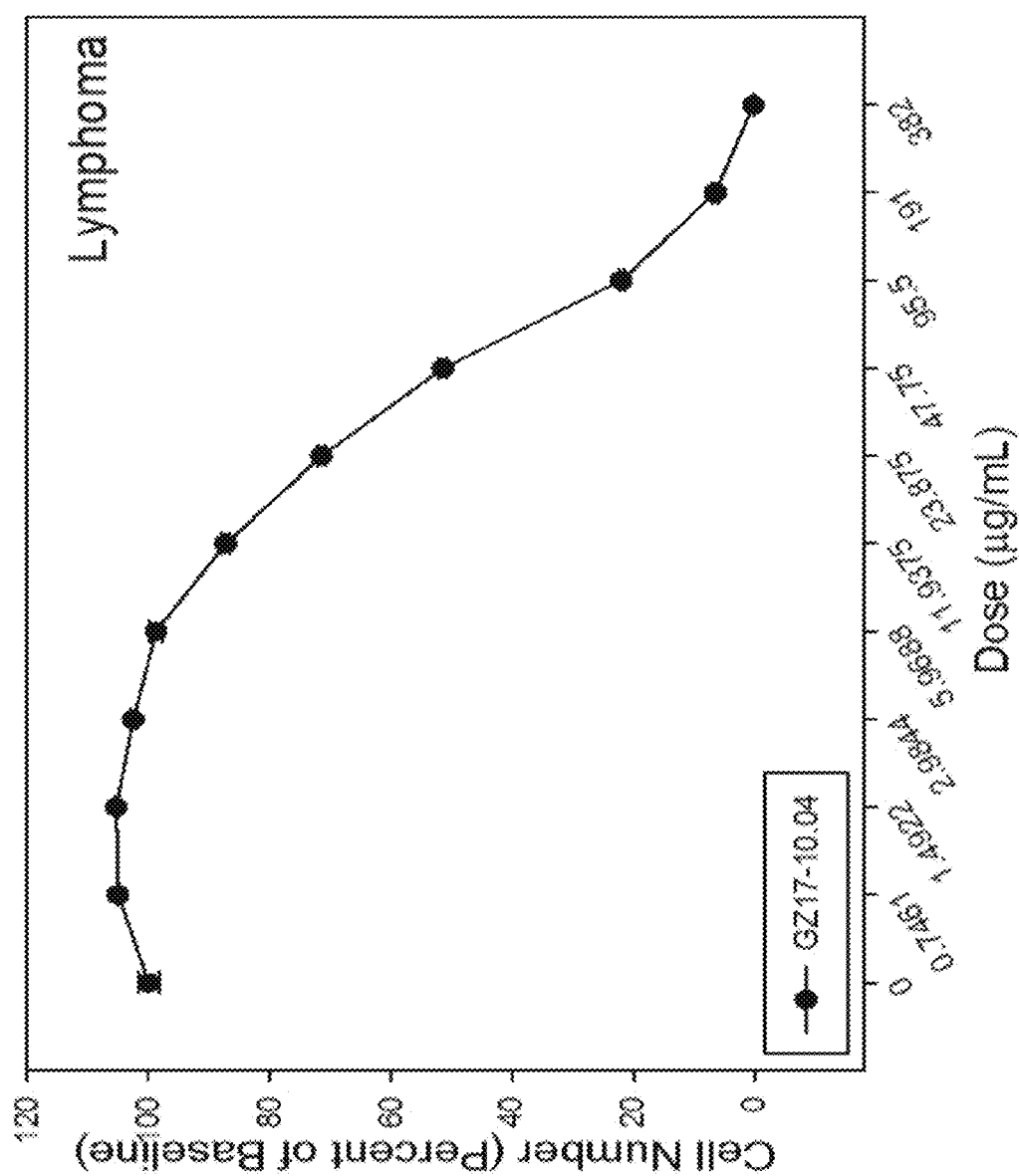
Figure 80E:
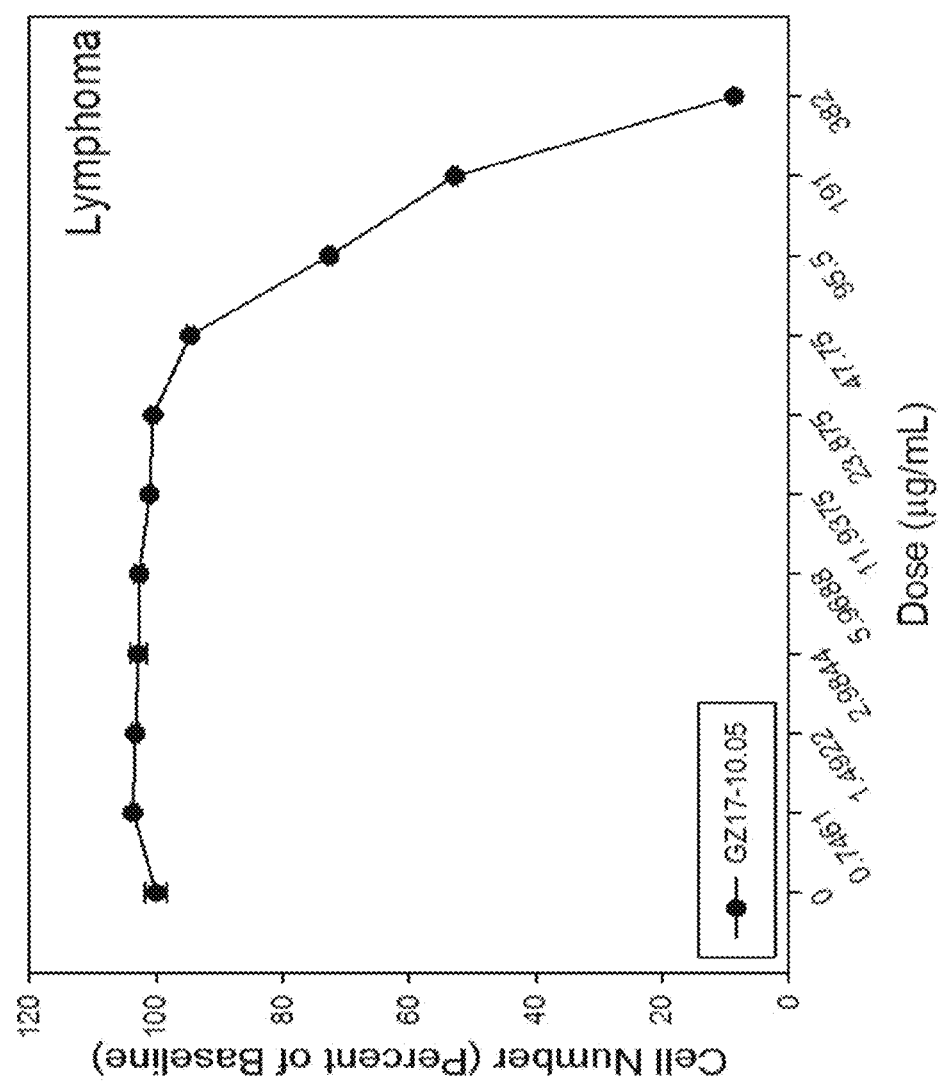
Figure 80F:
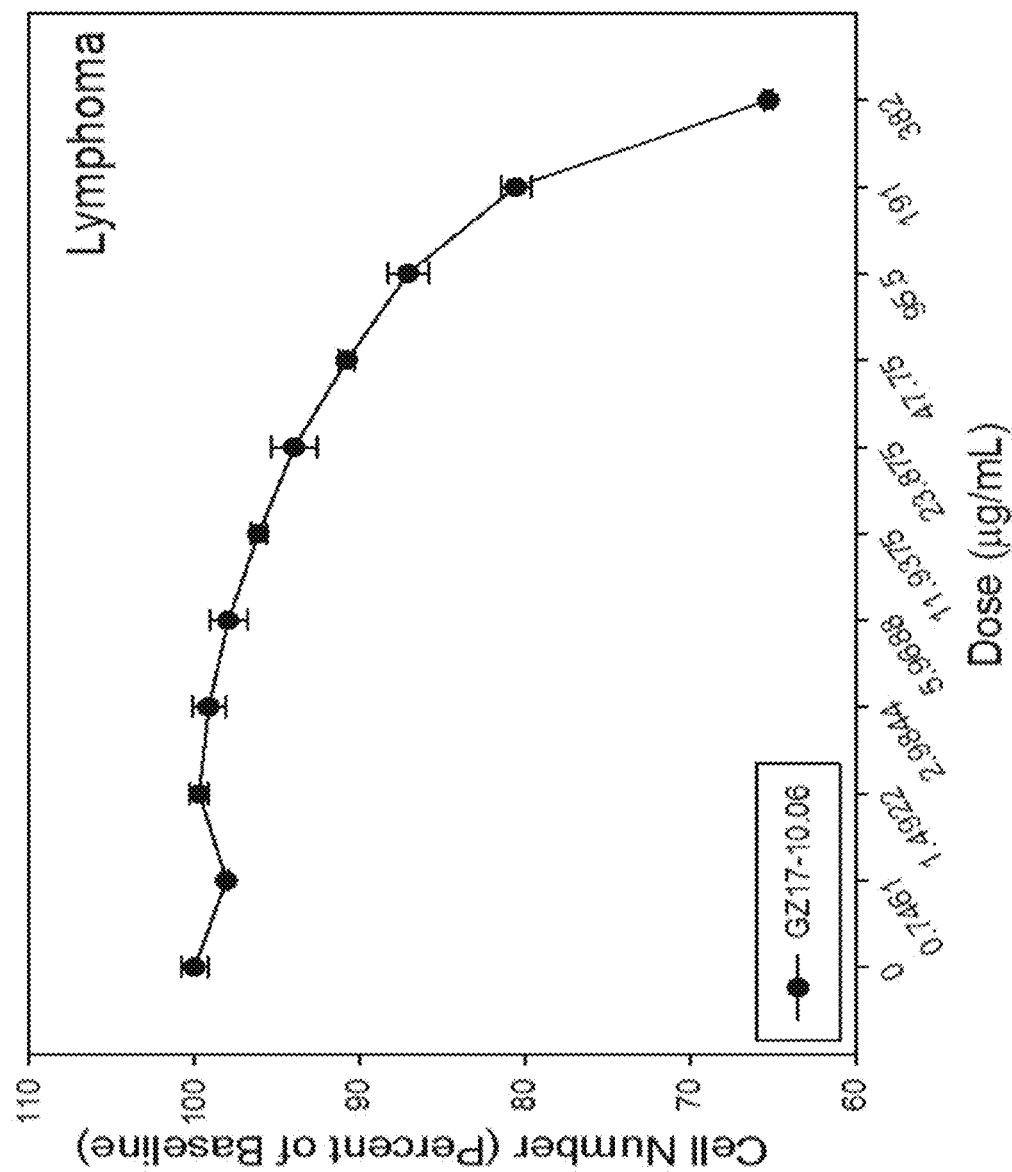
Figure 80G:
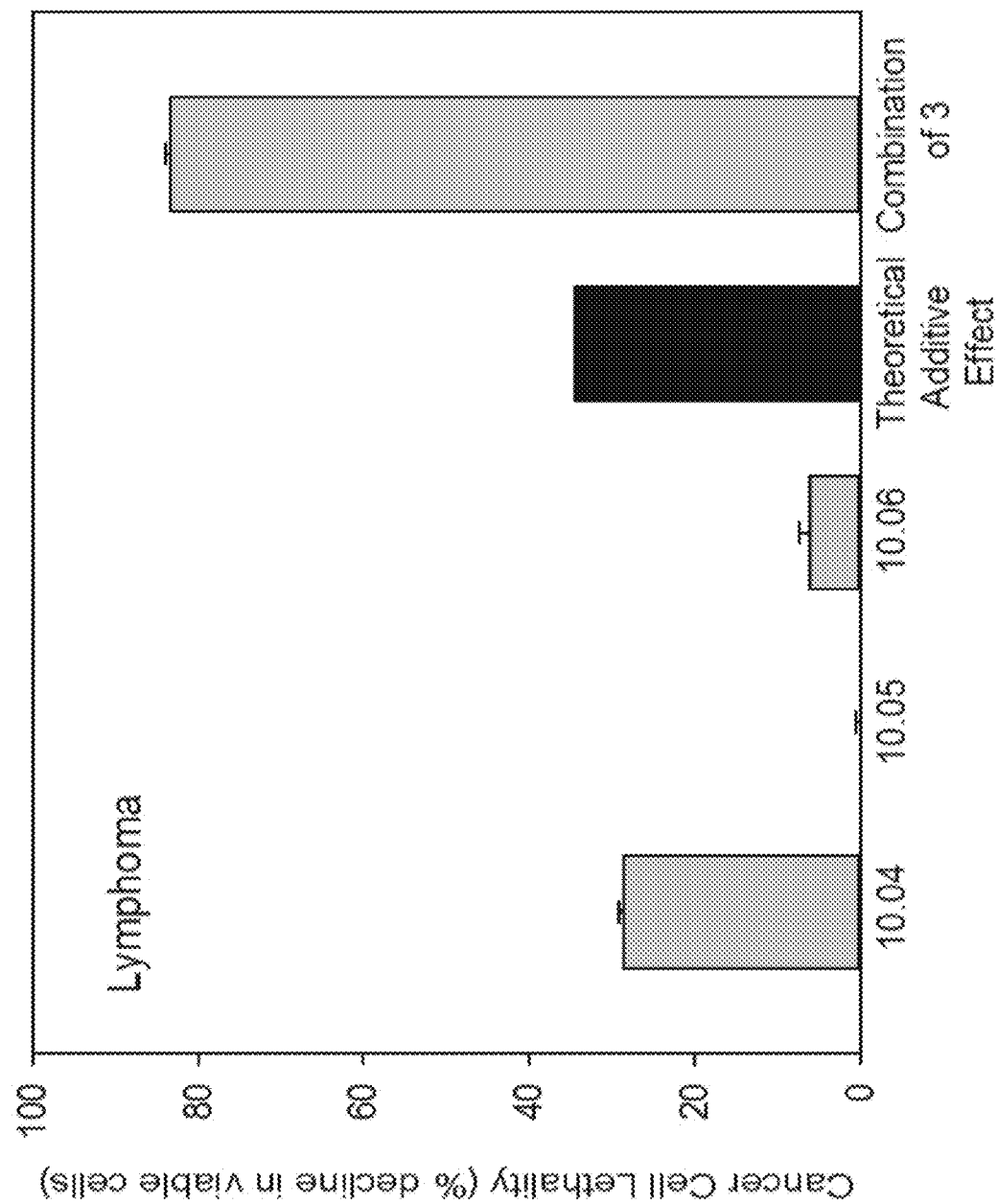
Figure 80H:
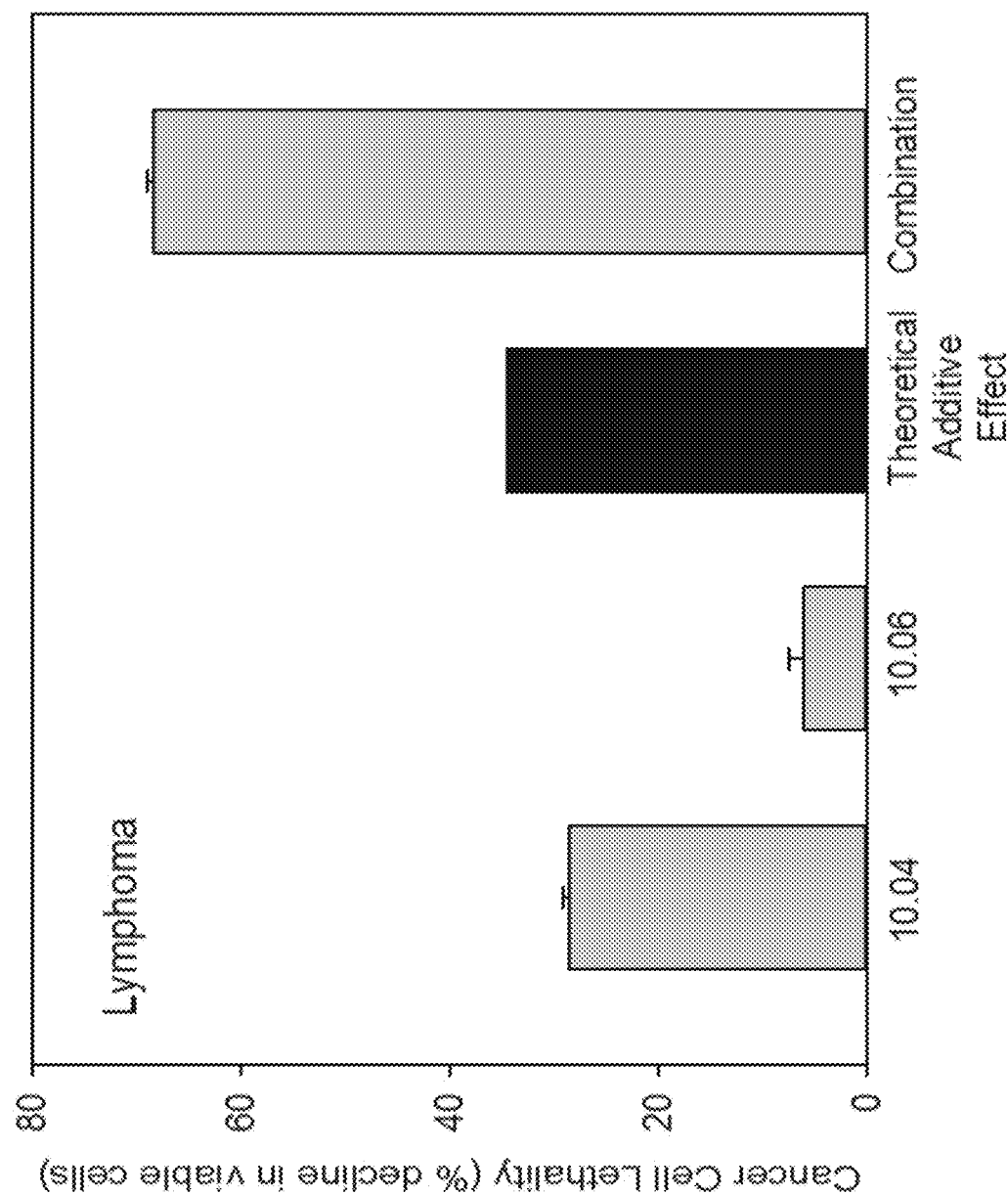
Figure 80I:
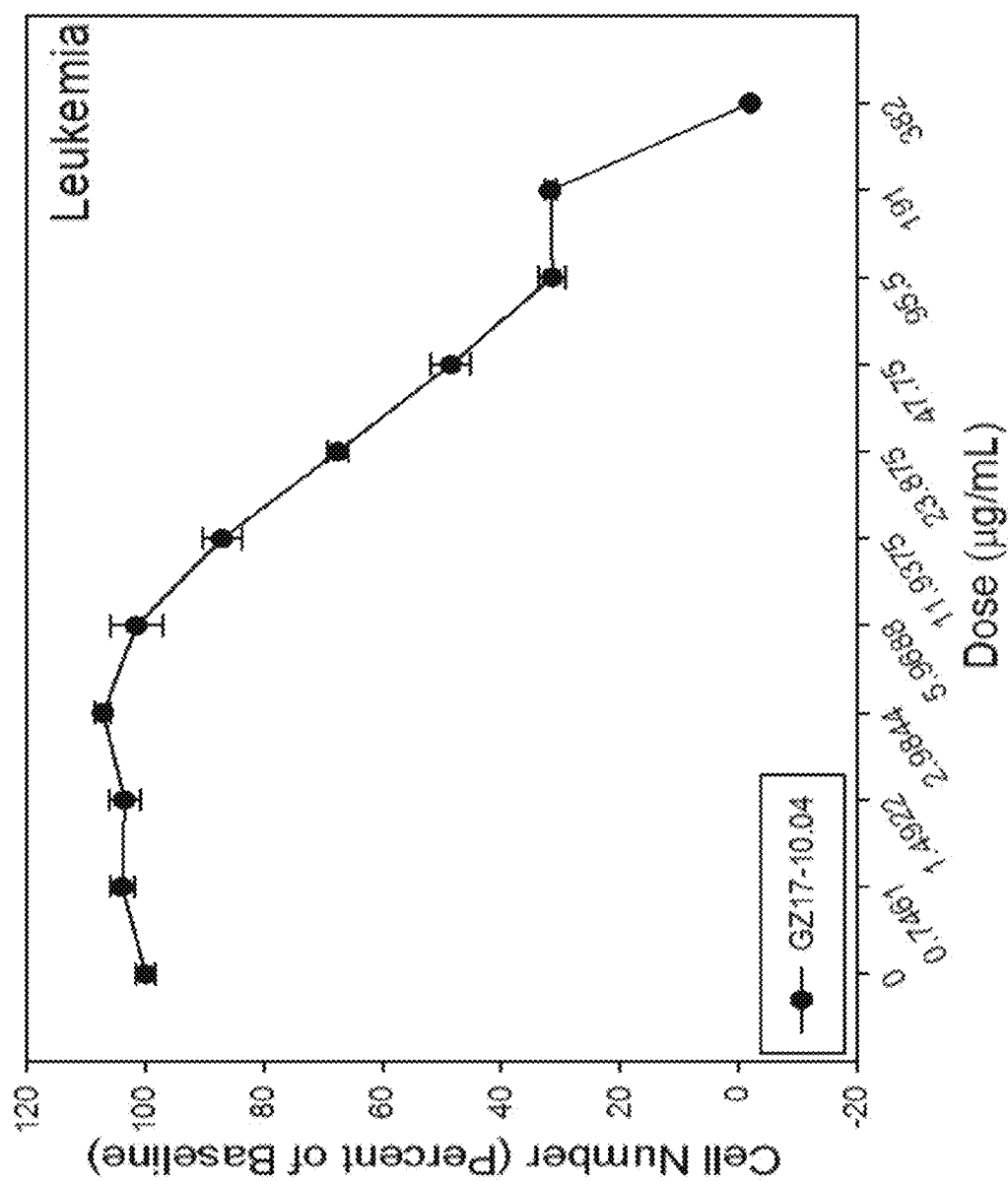
Figure 80J:
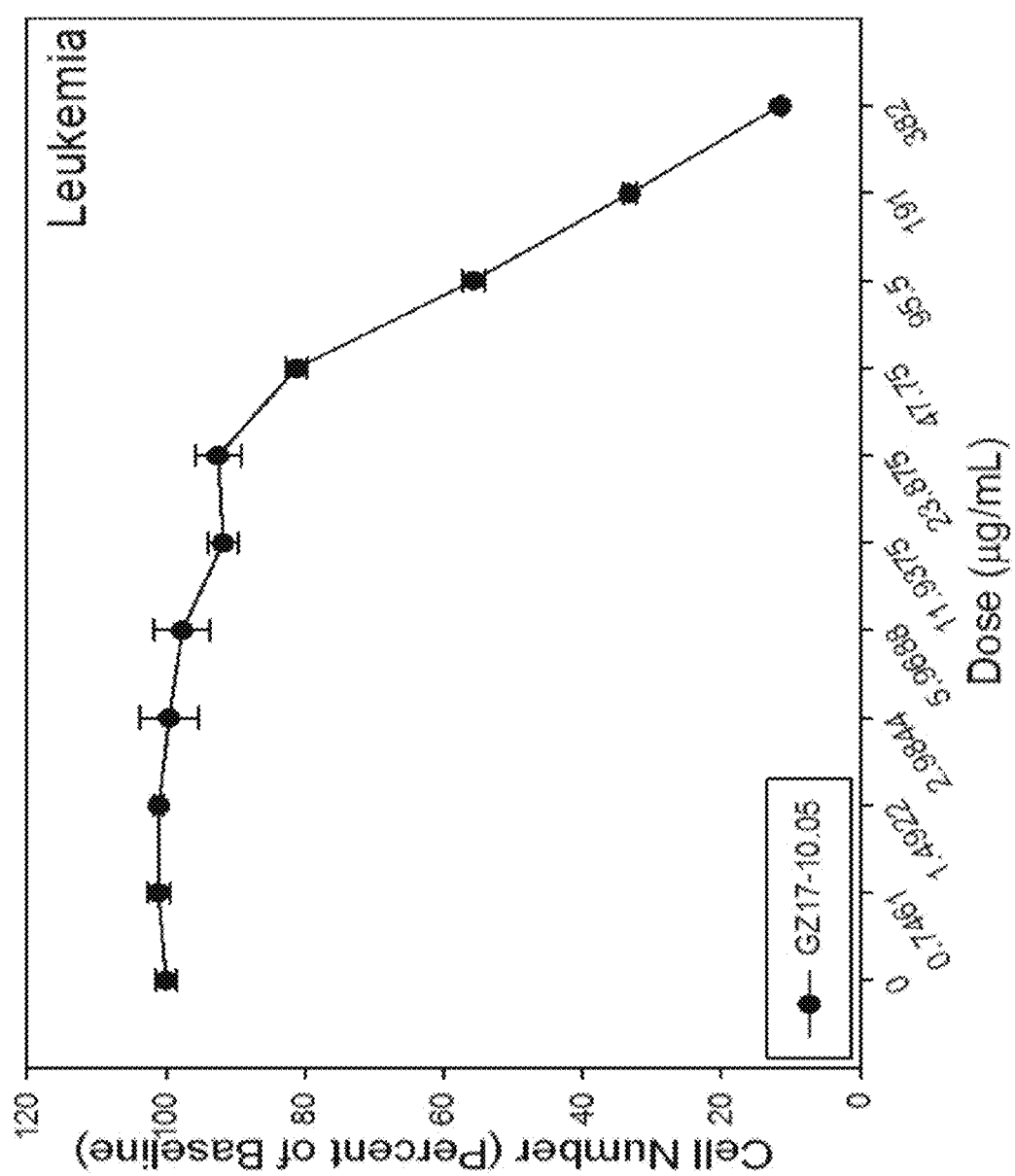
Figure 80K:
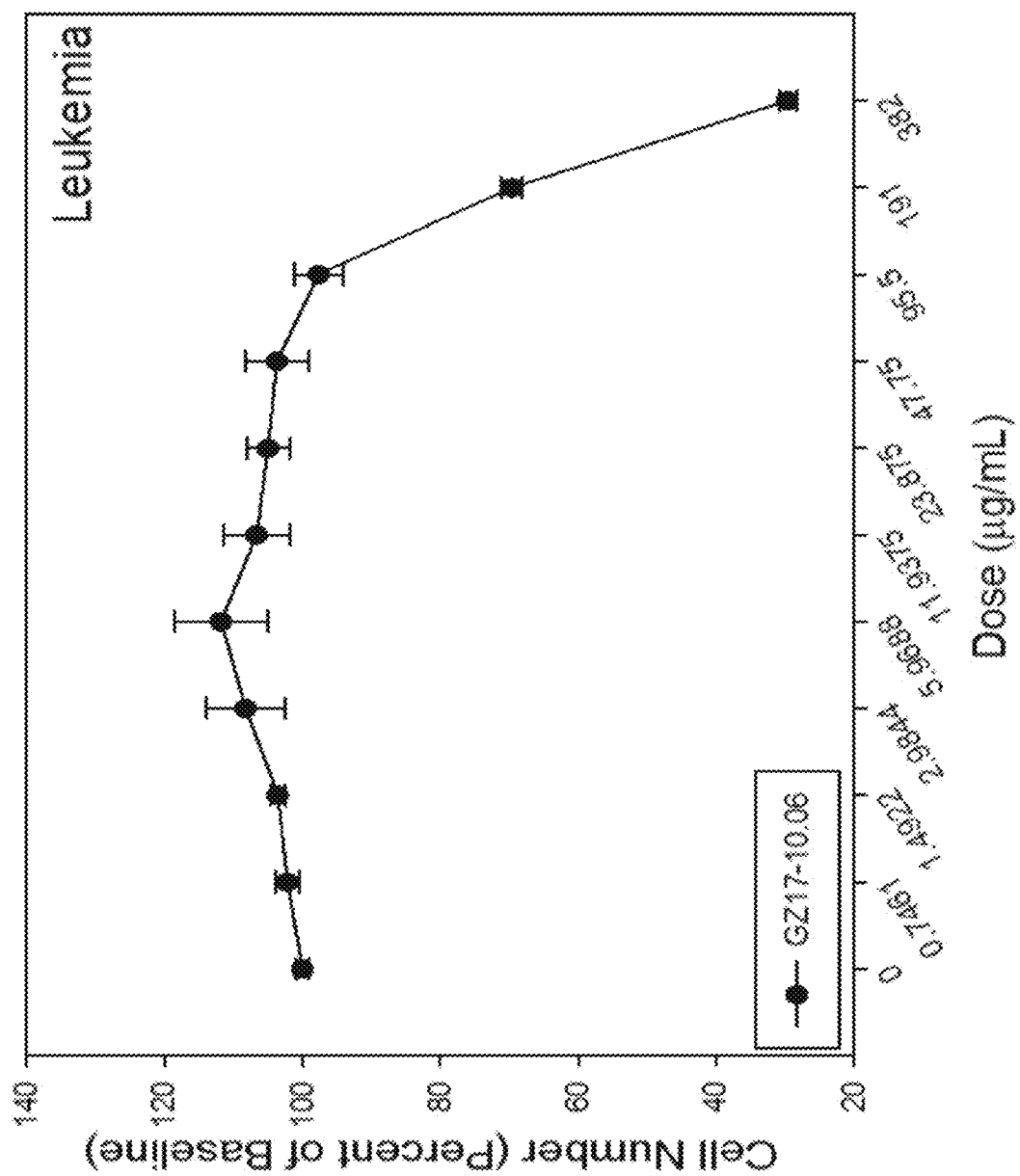
Figure 80L:
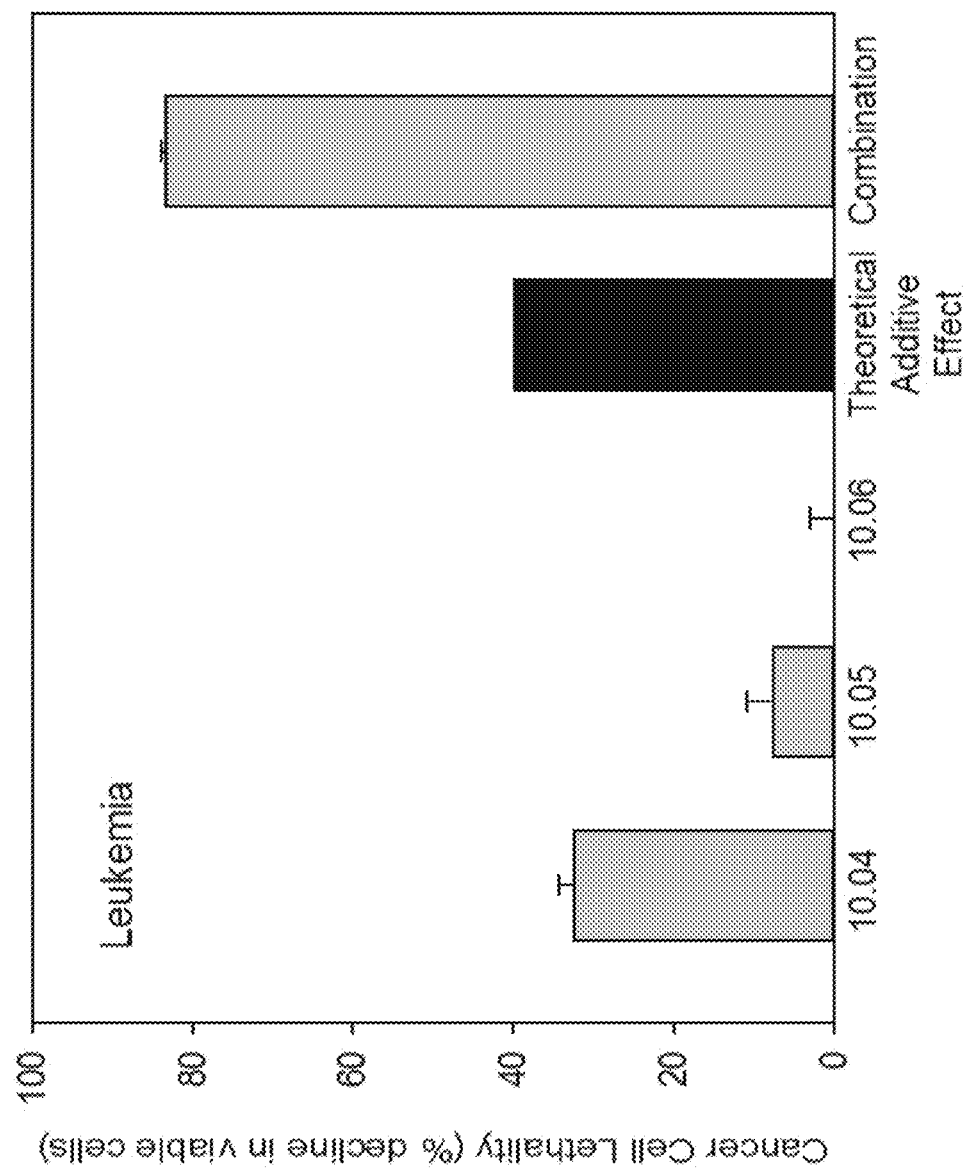
Figure 80M:
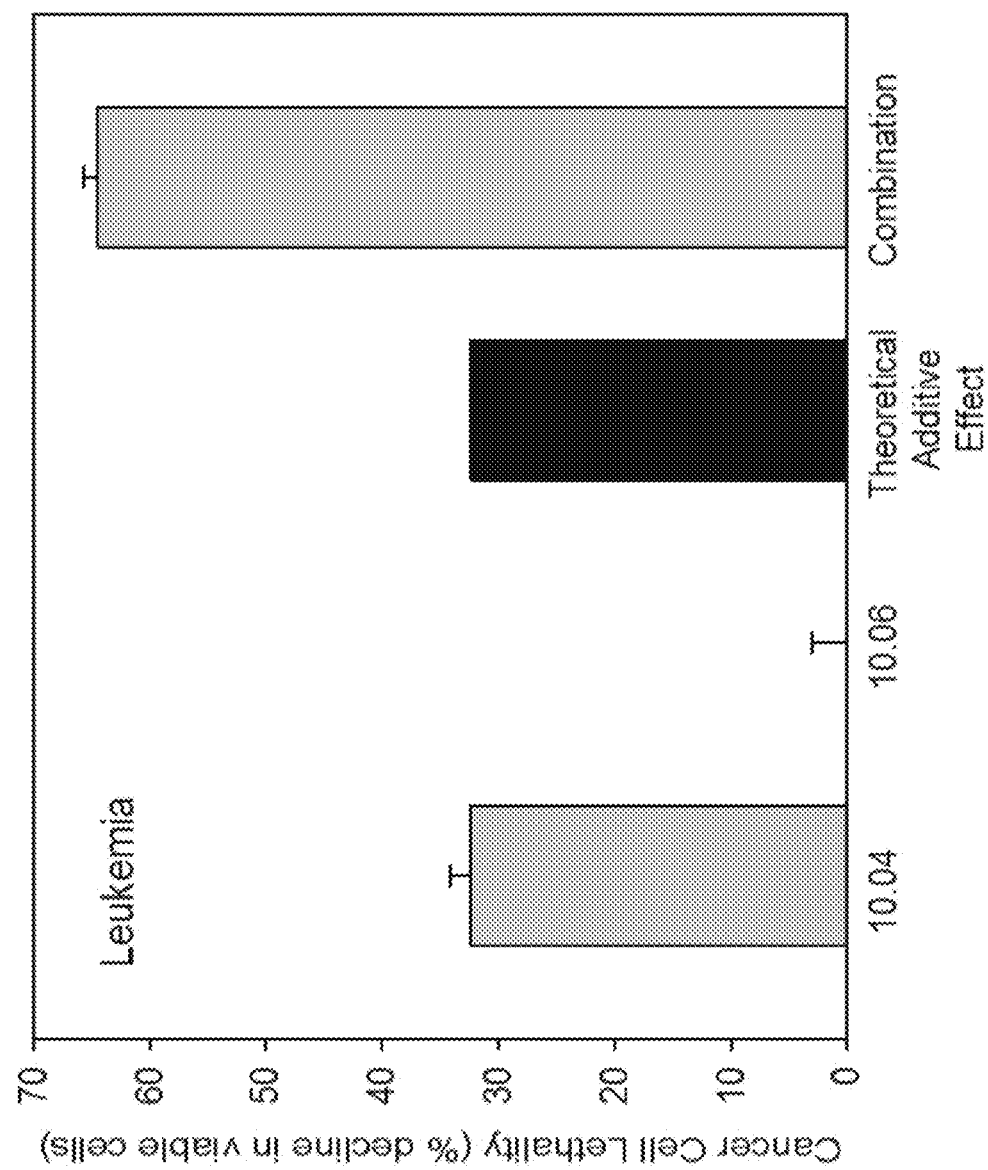
Figure 80N:
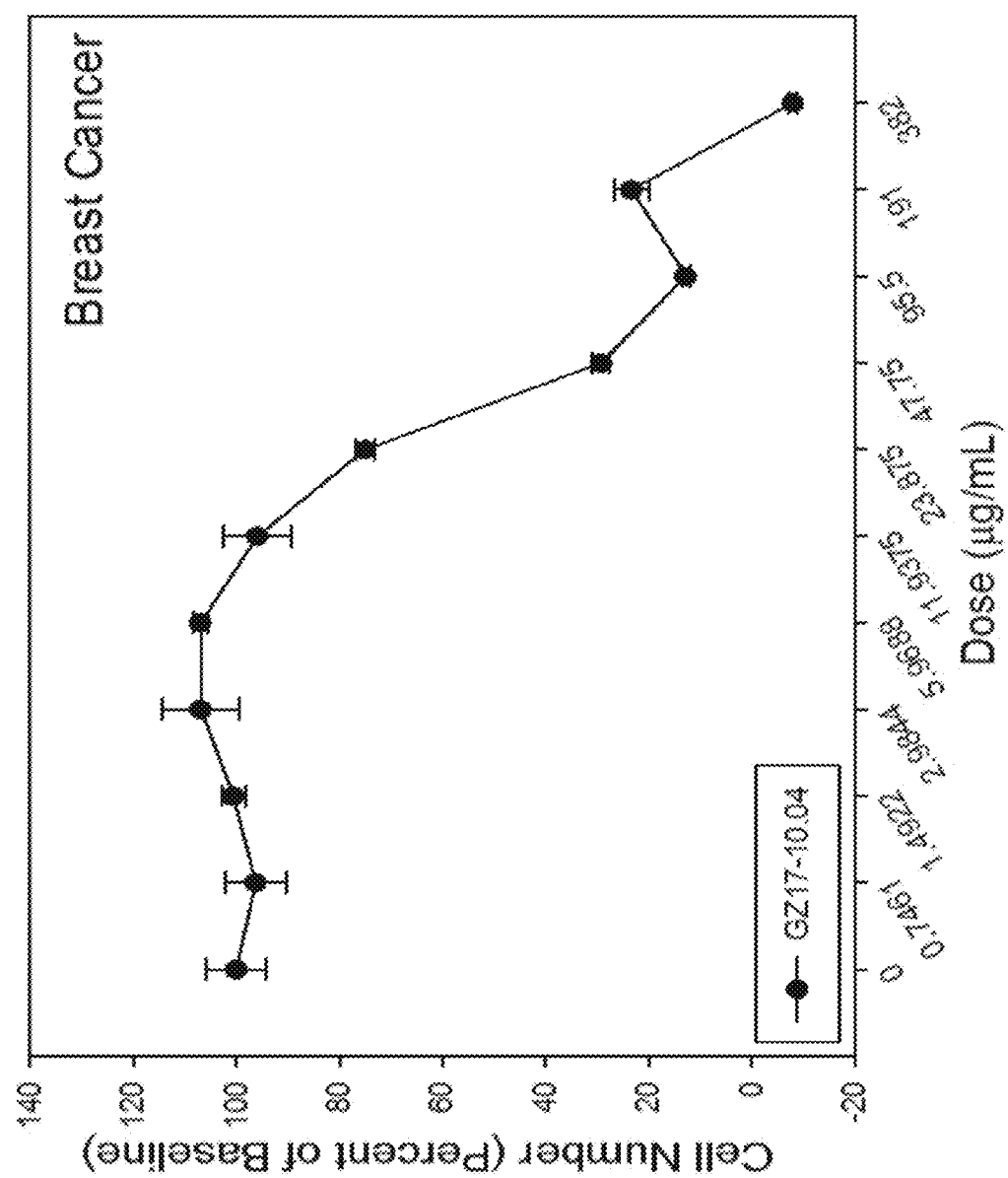
Figure 800:
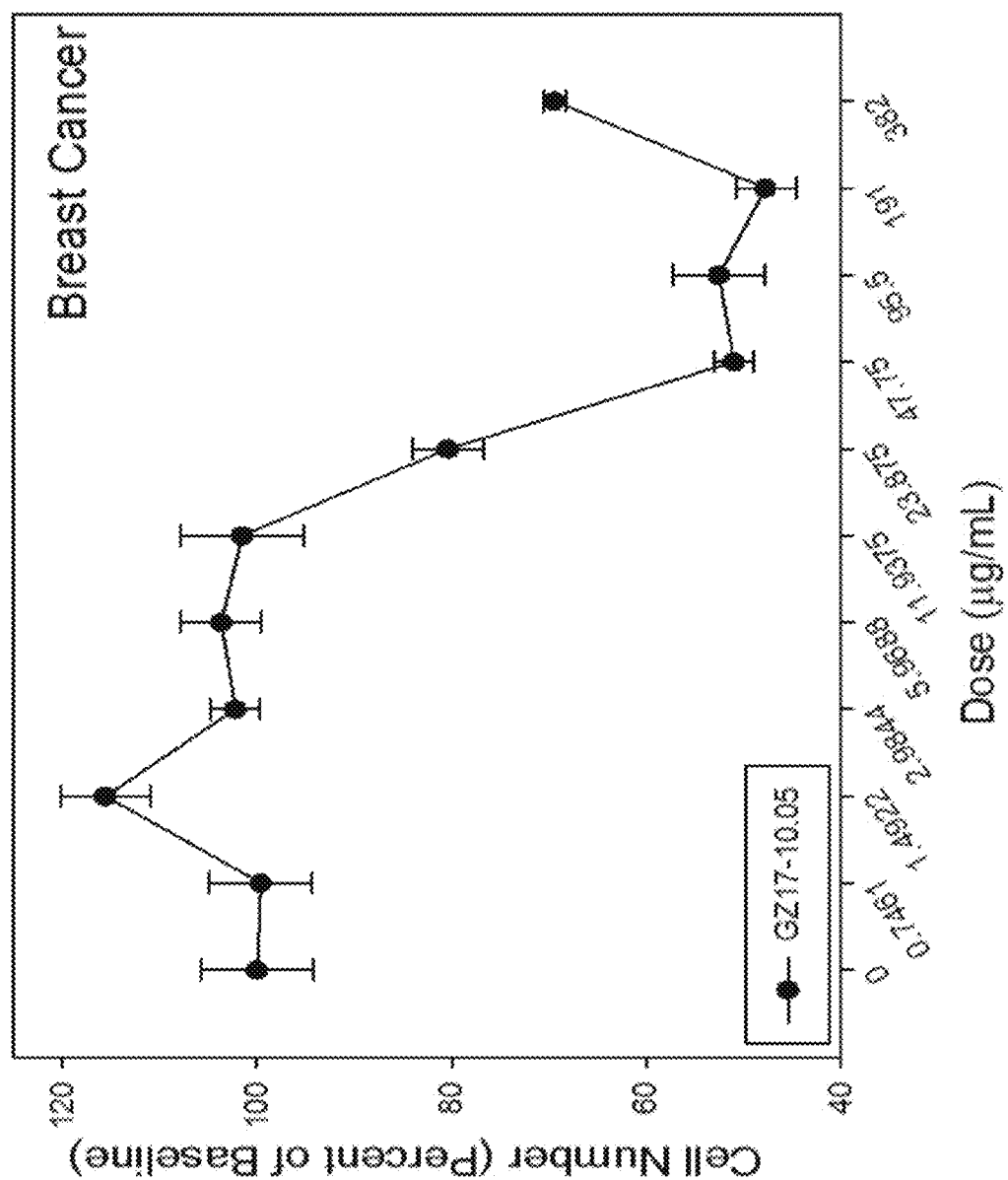
Figure 80P:
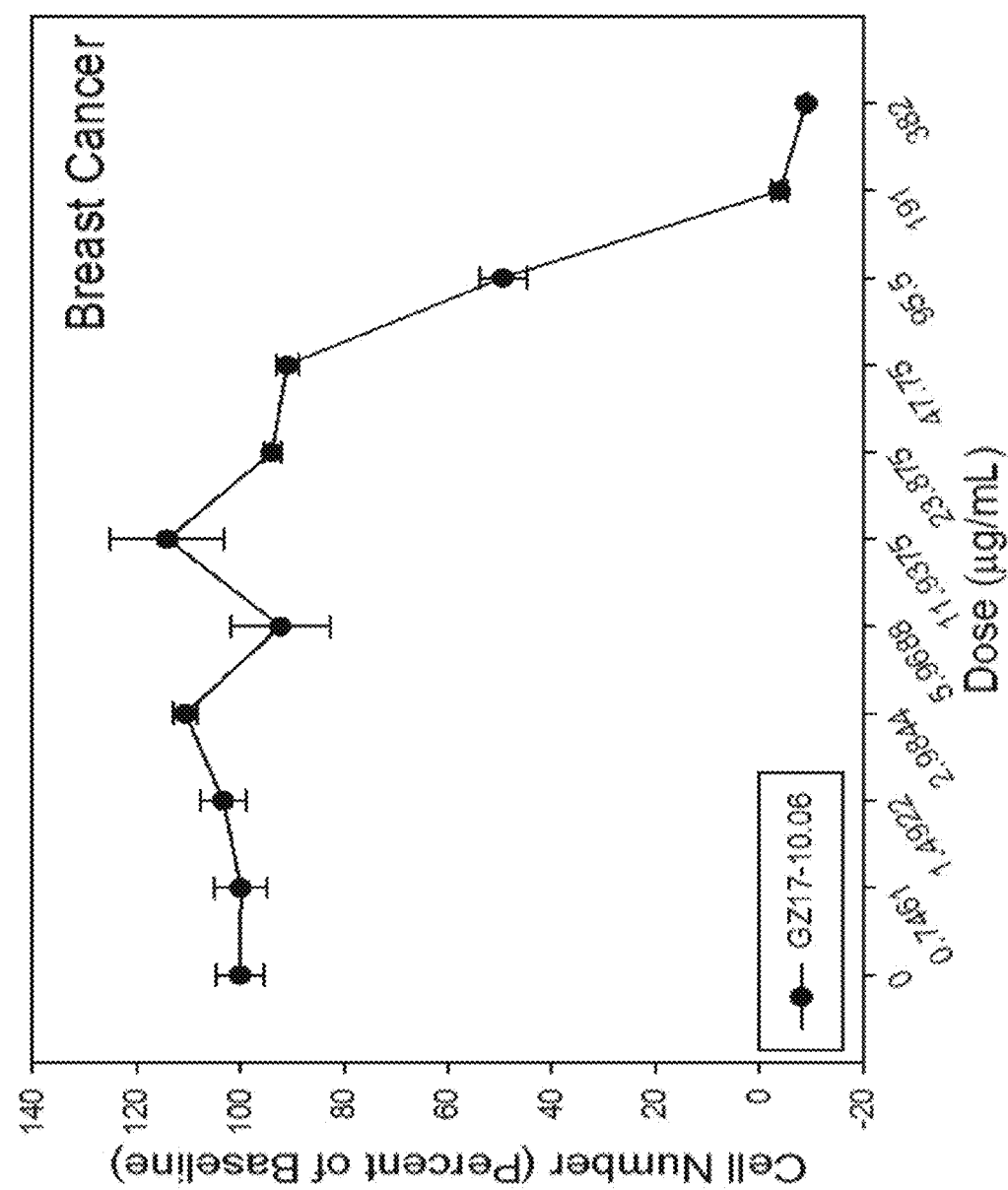
Figure 80Q:
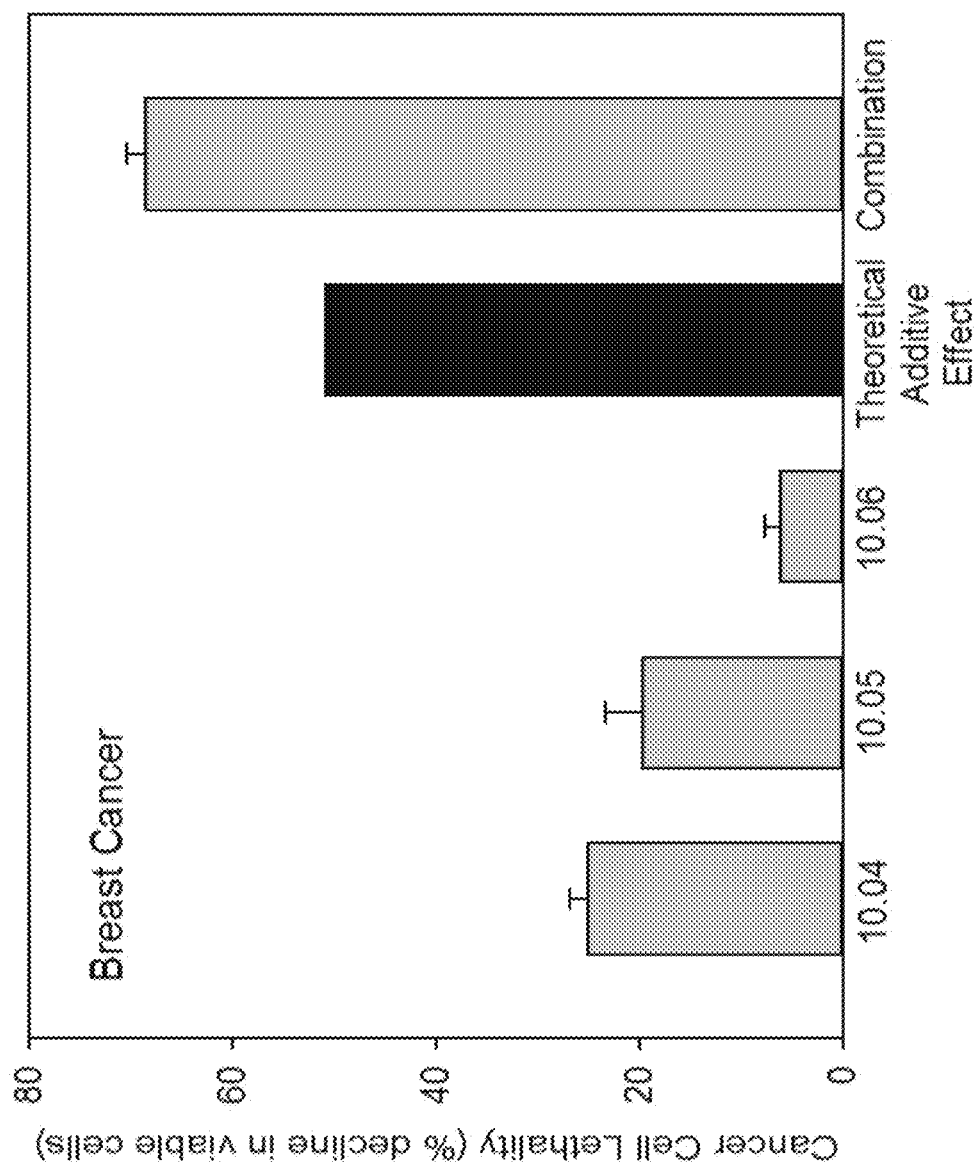
Figure 80R:
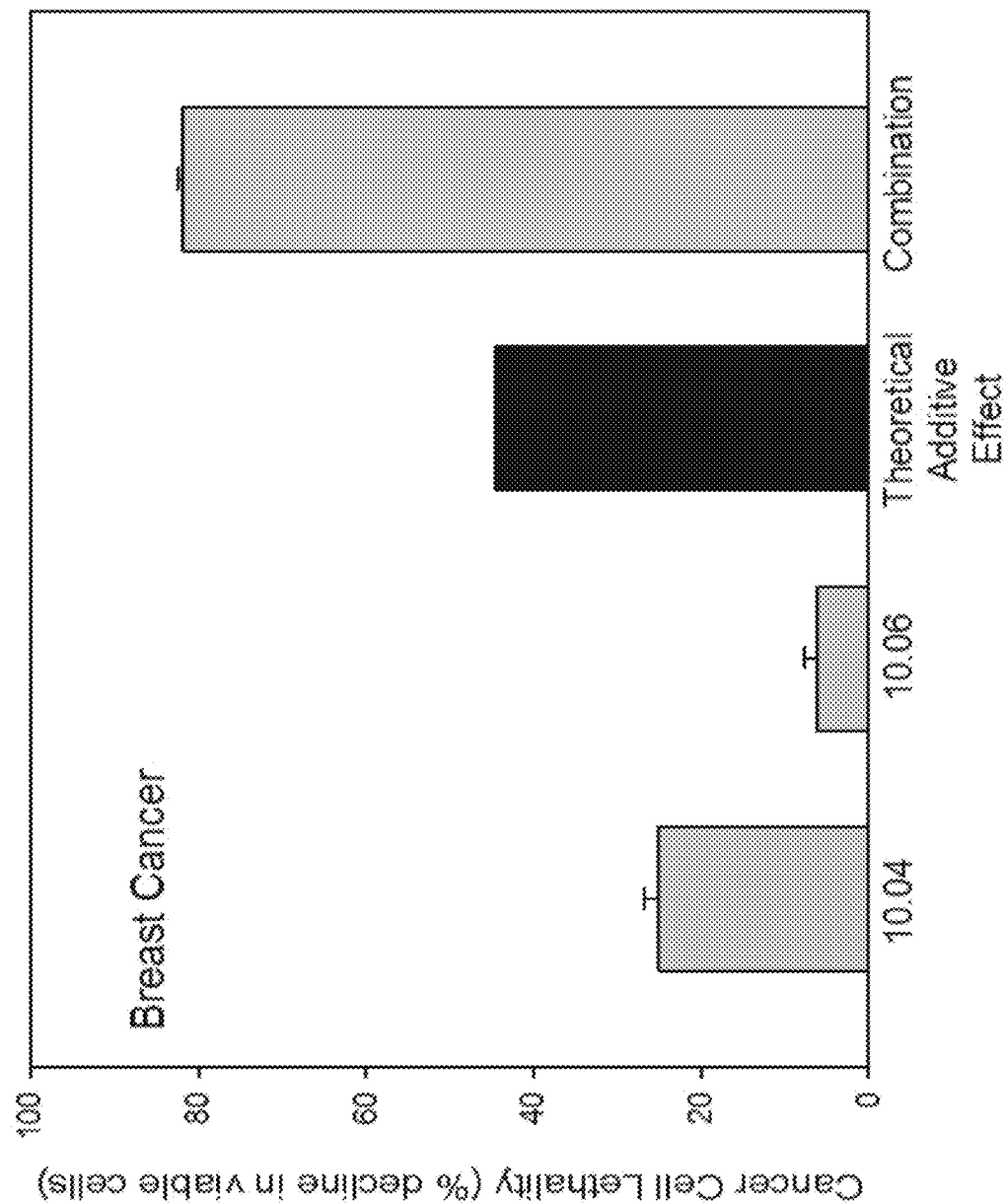
Figure 81A:
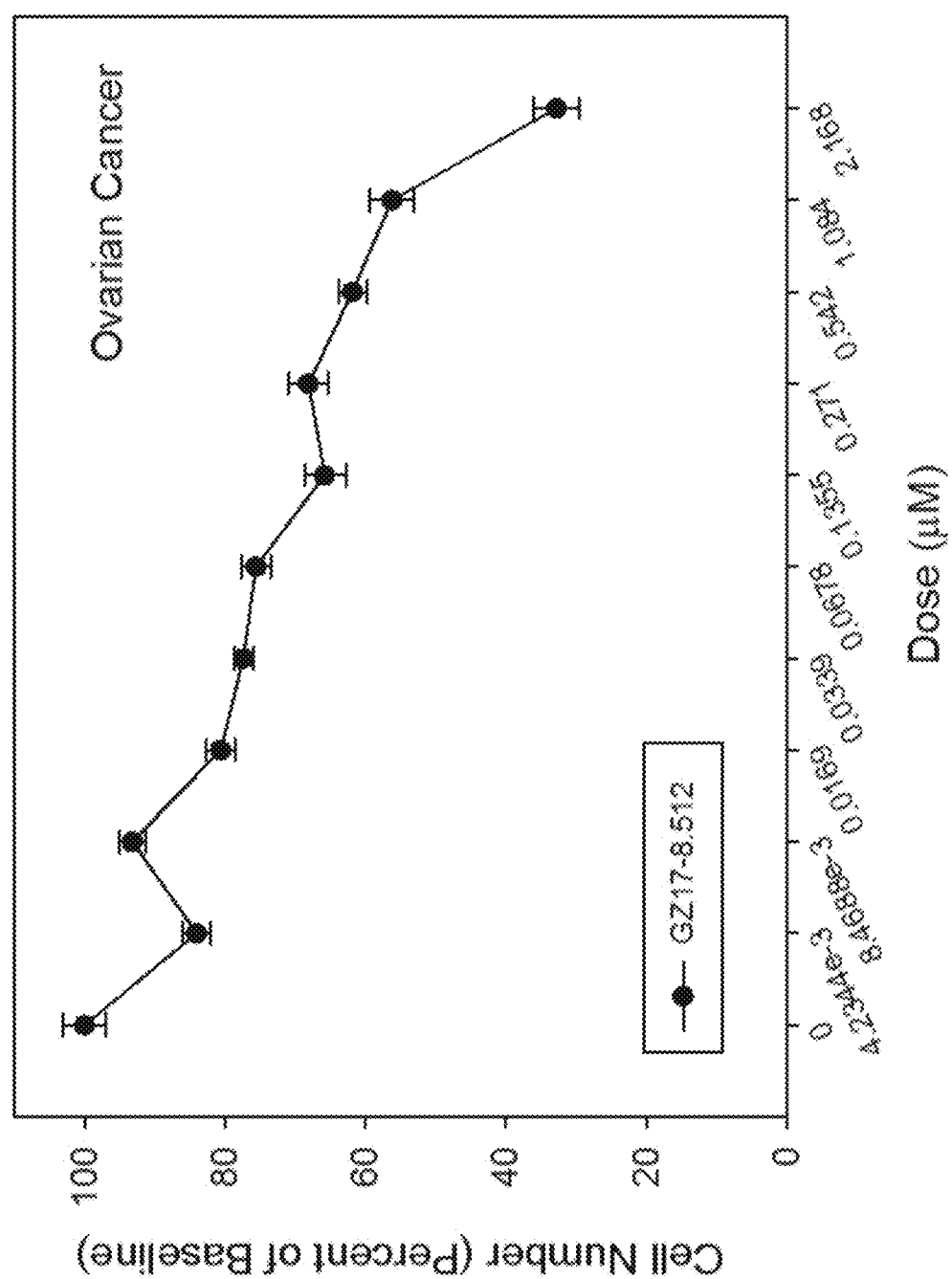
Figure 81B:
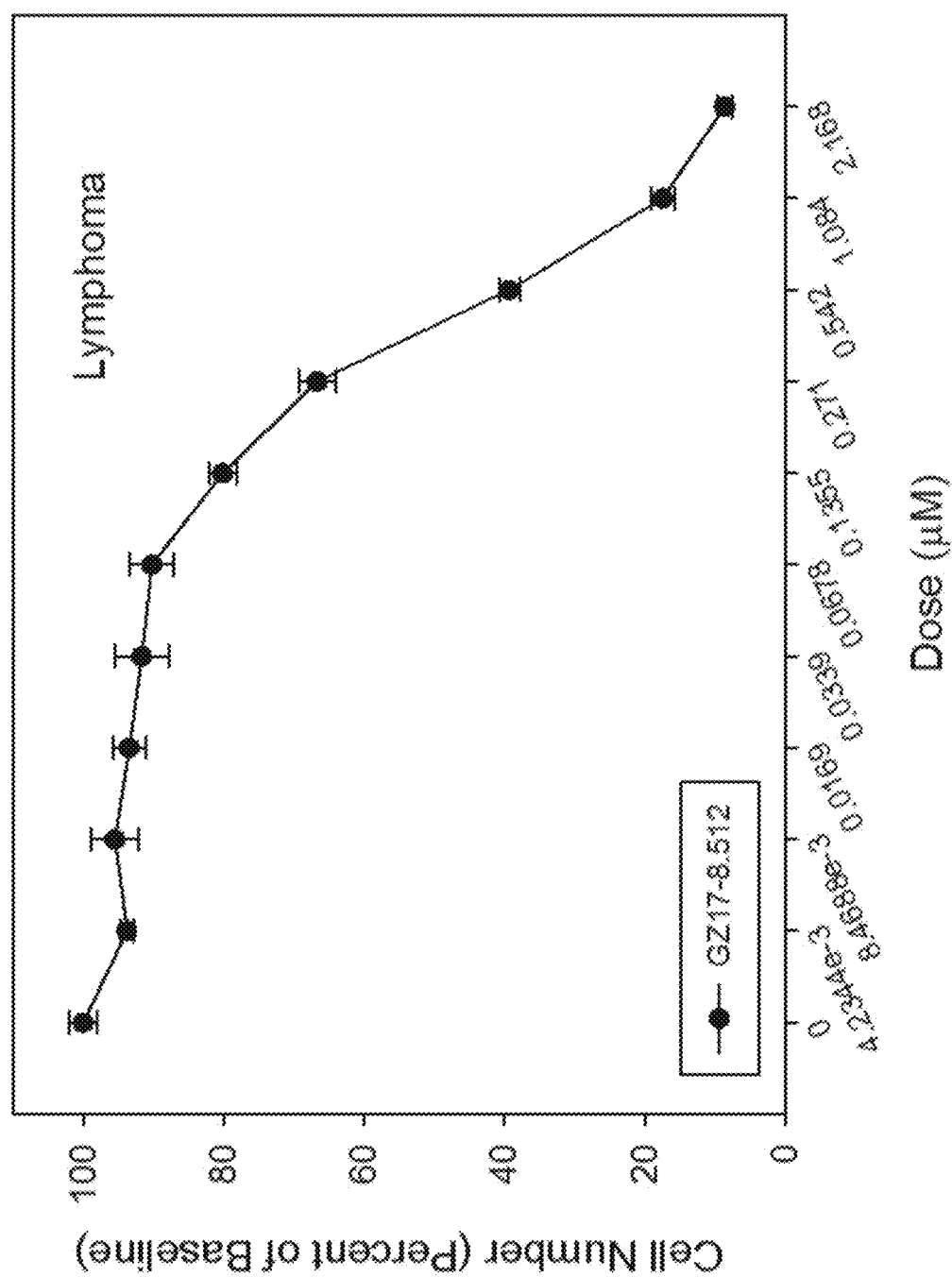
Figure 81C:
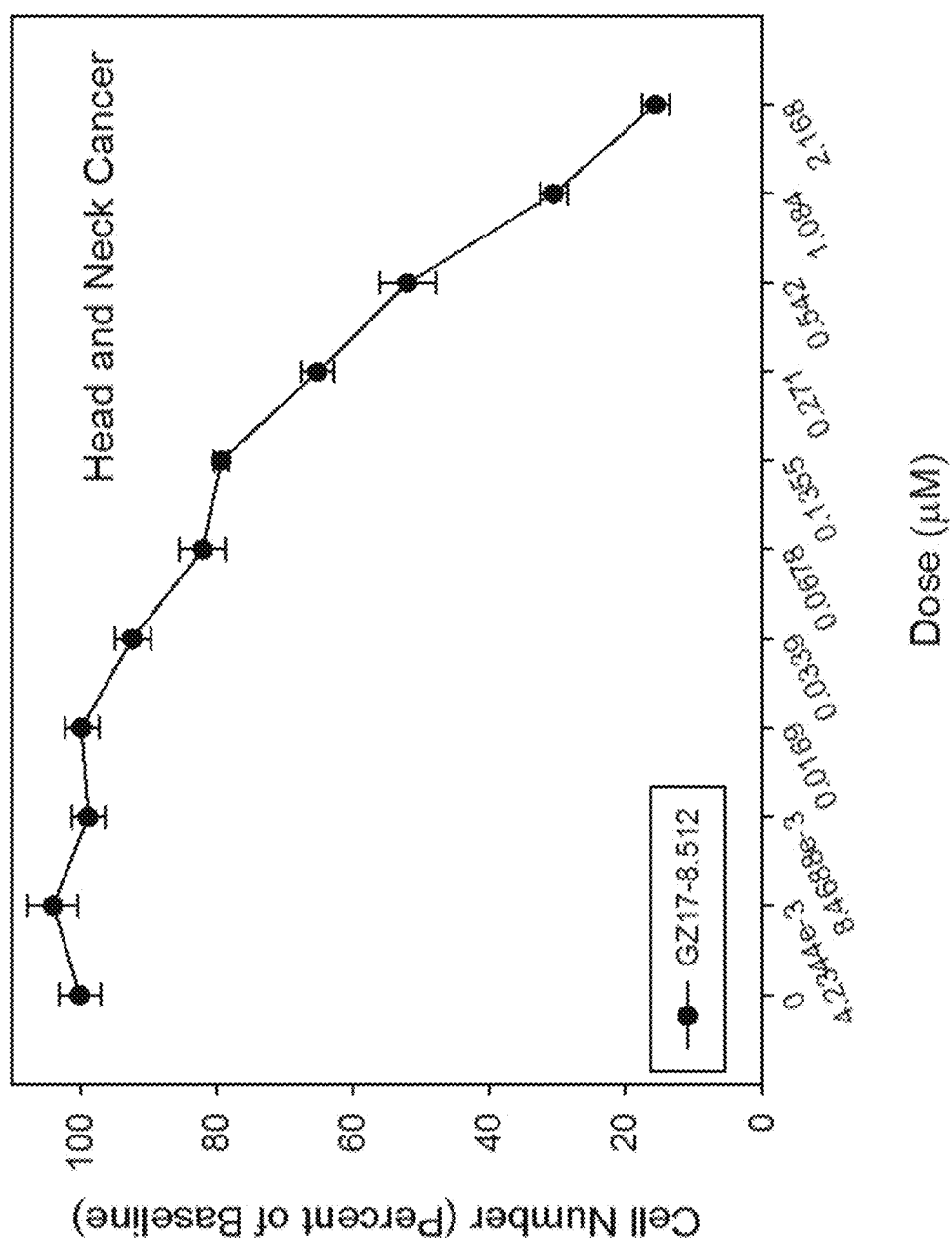
Figure 81D:
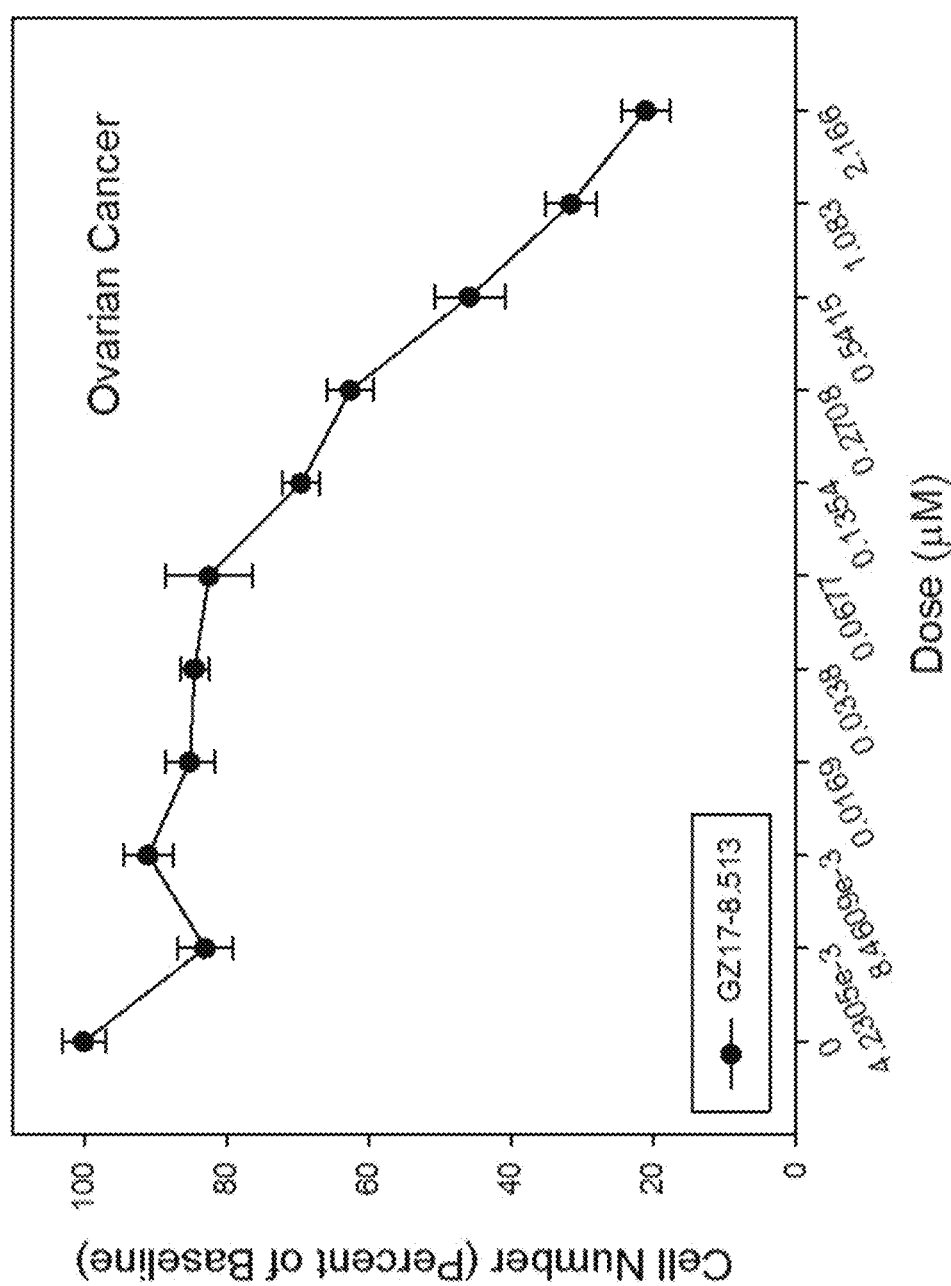
Figure 81E:
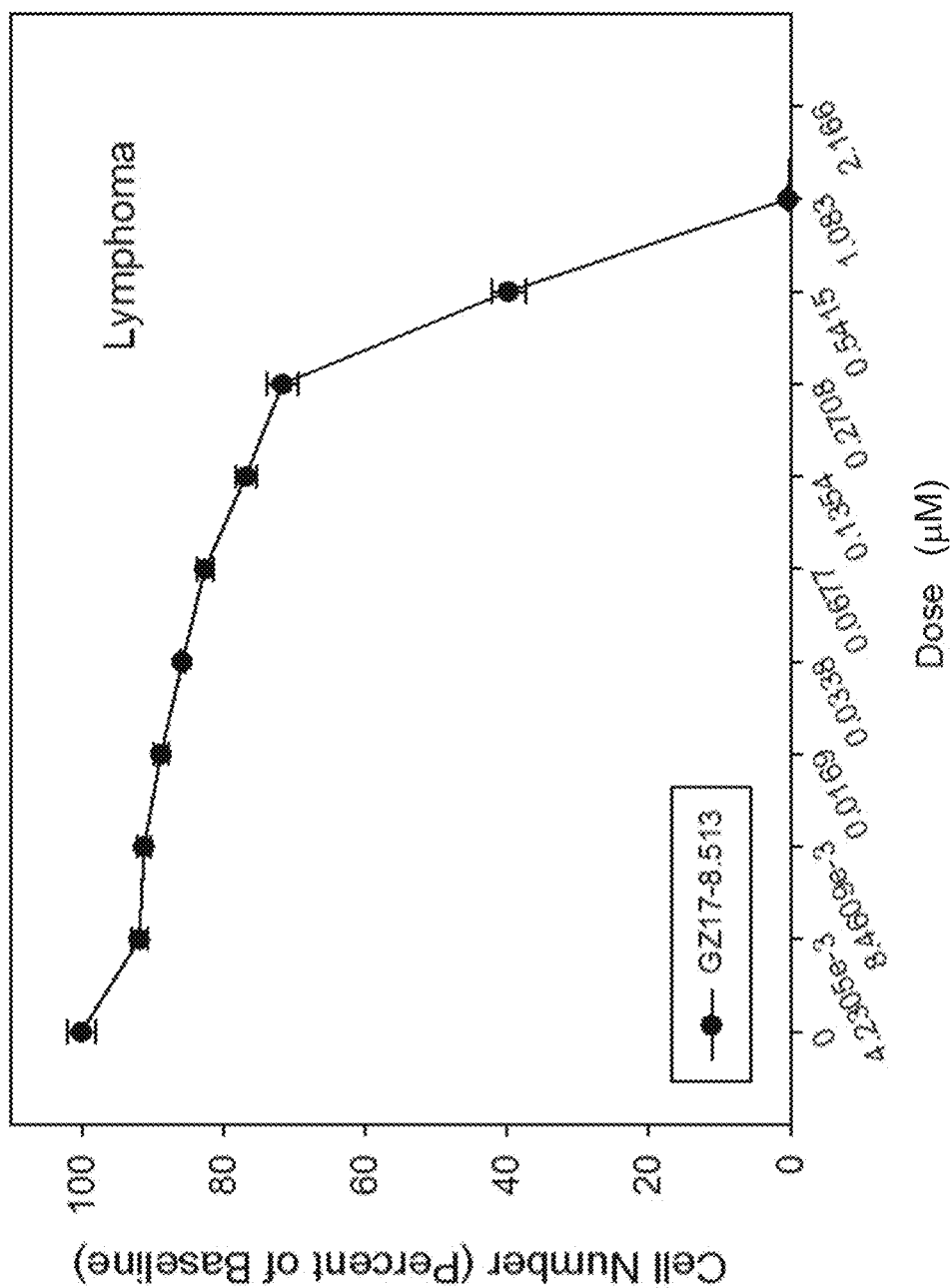
Figure 81F:
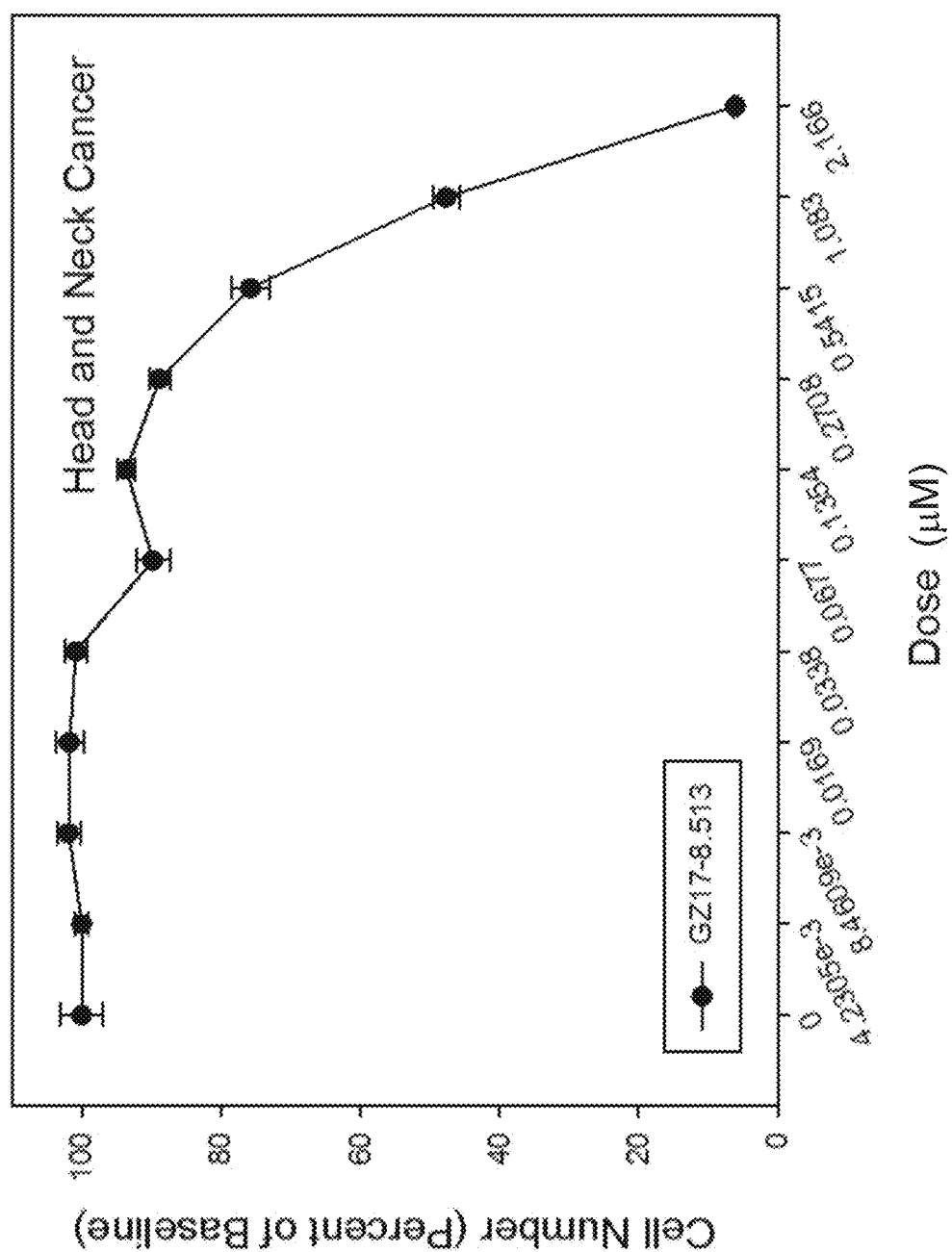
Figure 81G:
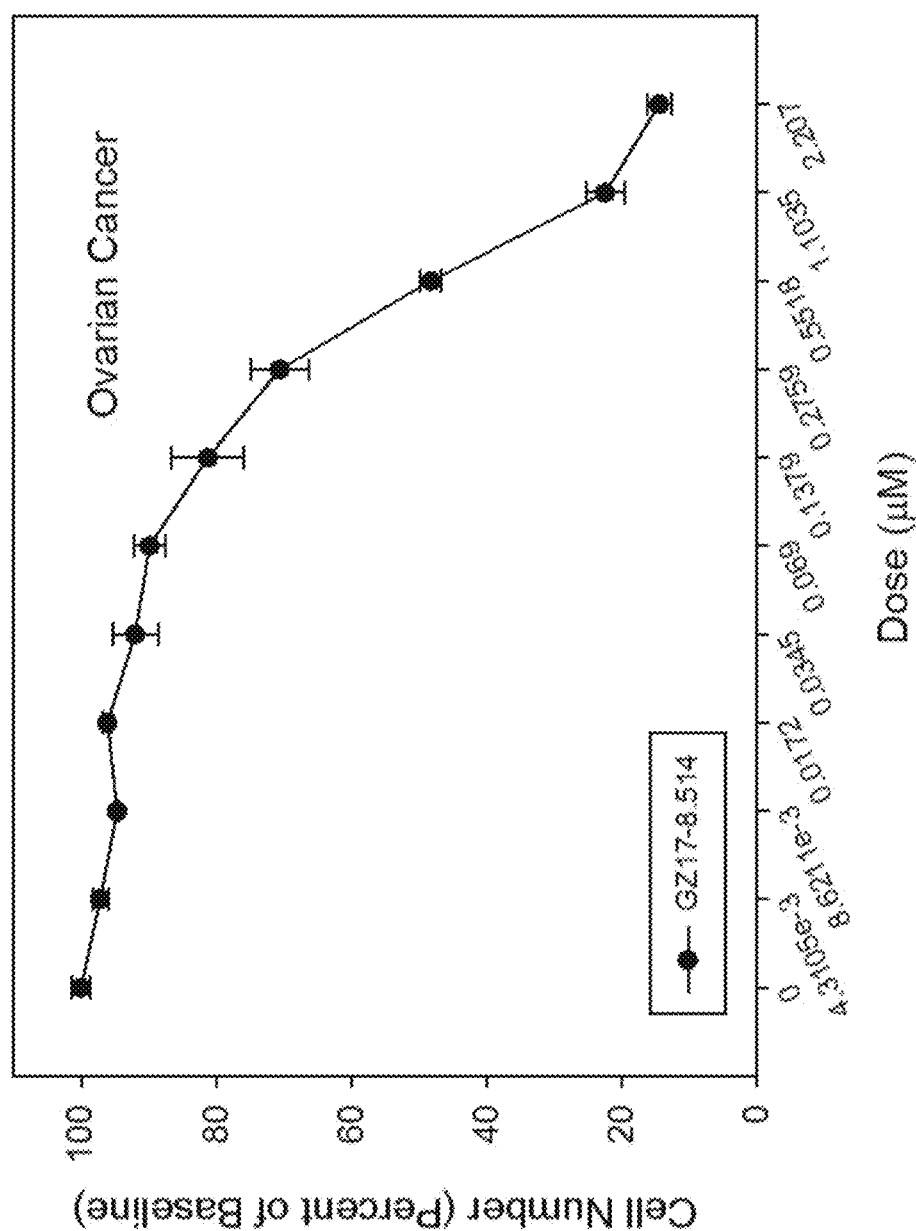
Figure 81H:
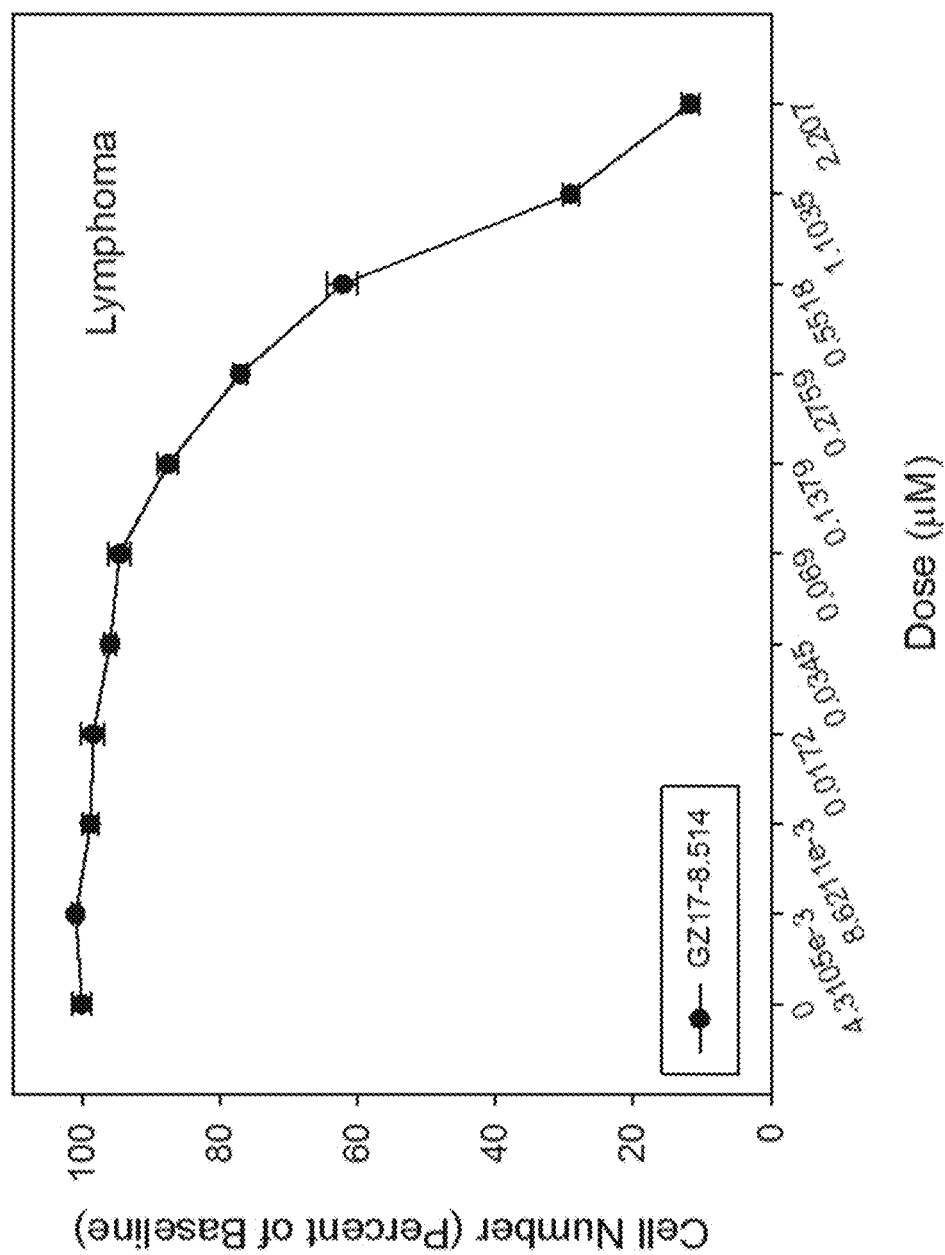
Figure 81I:
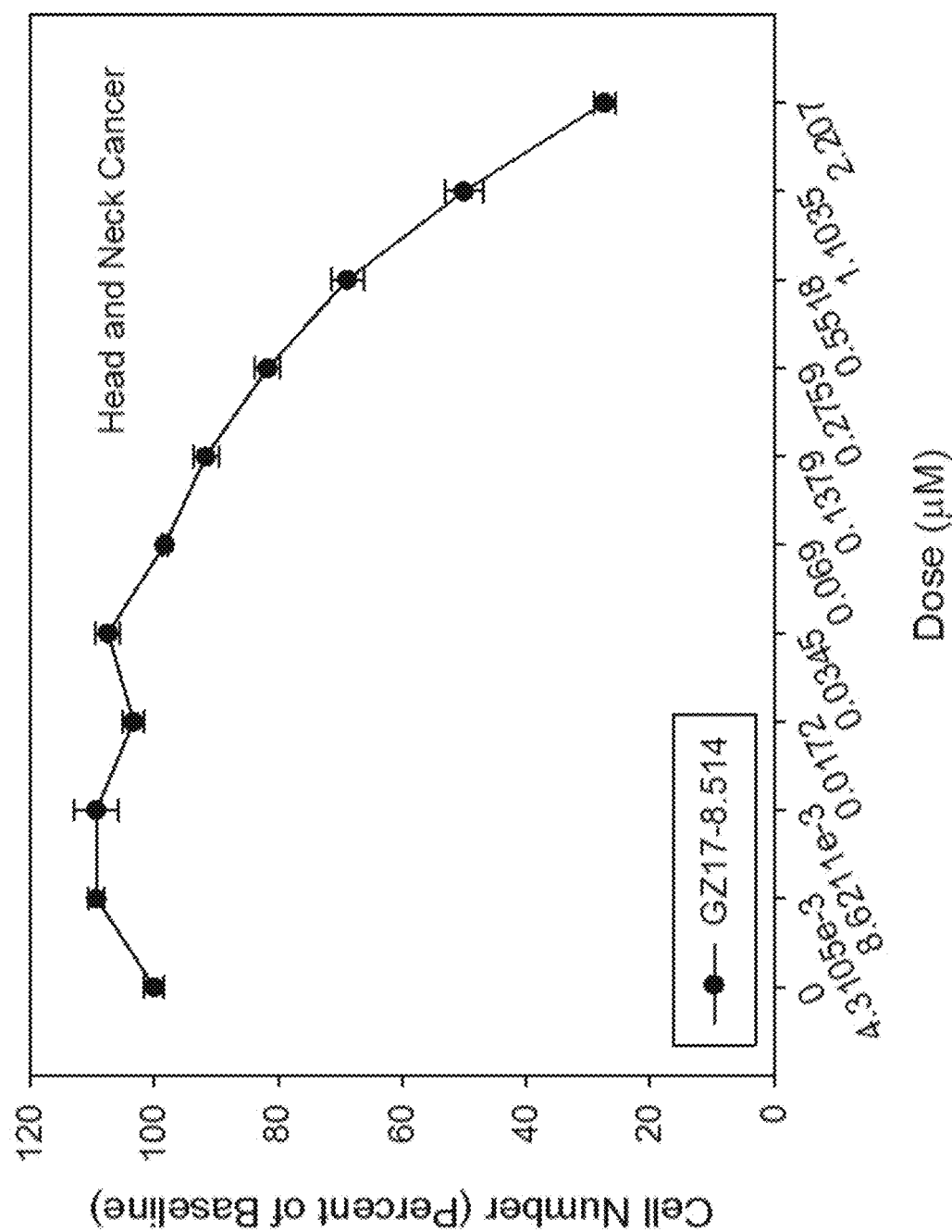
Figure 81J:
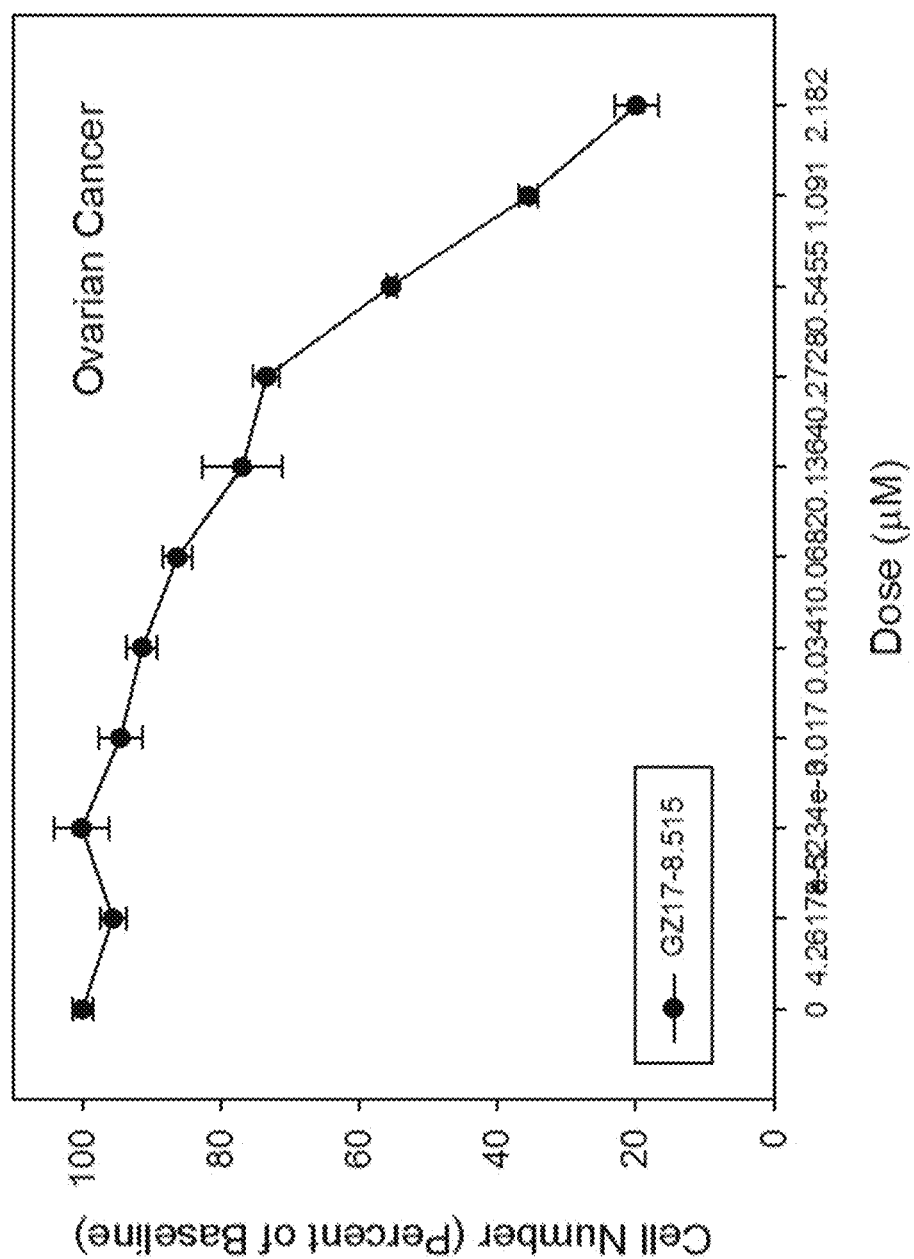
Figure 81K:
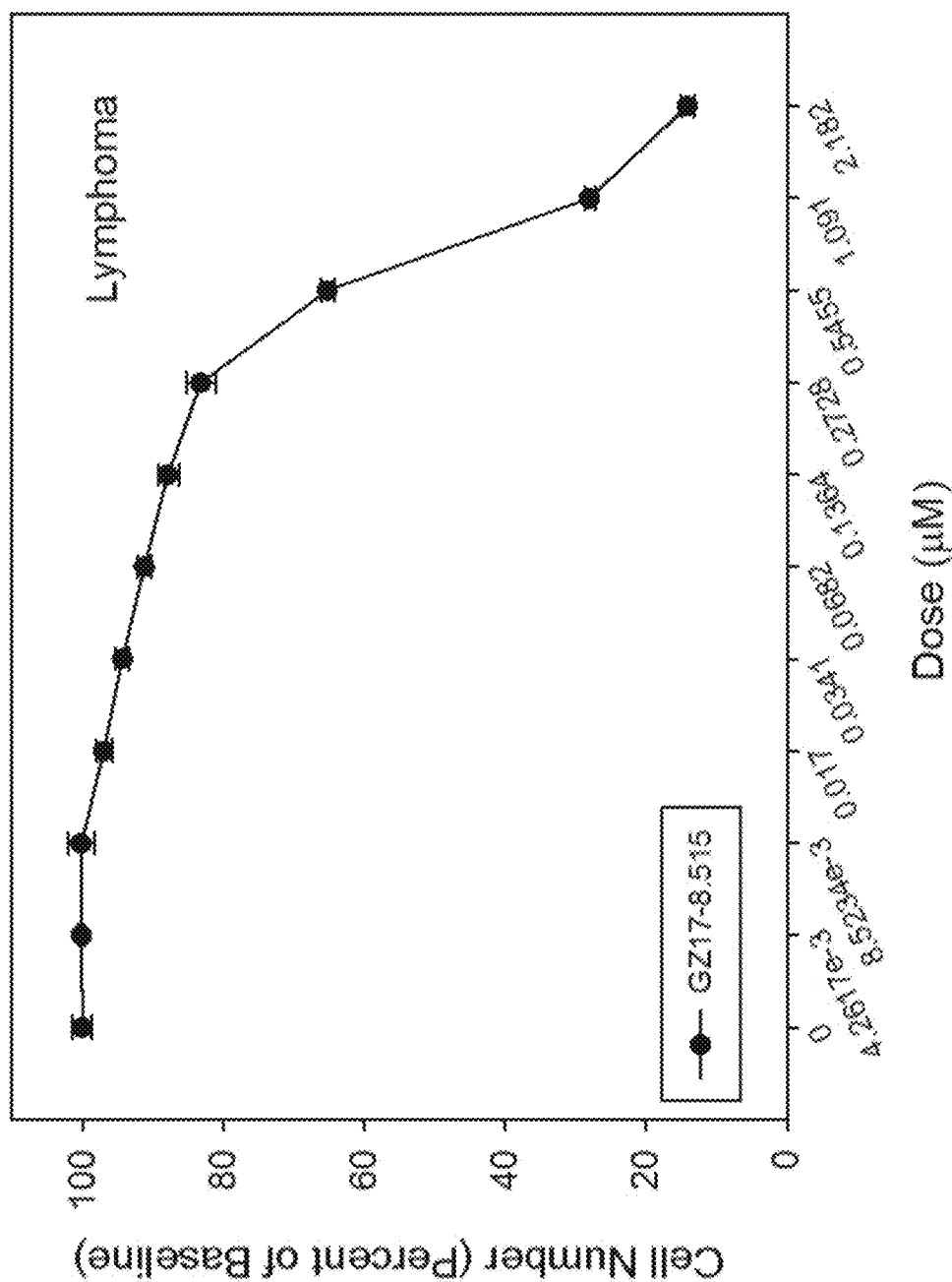
Figure 81L:
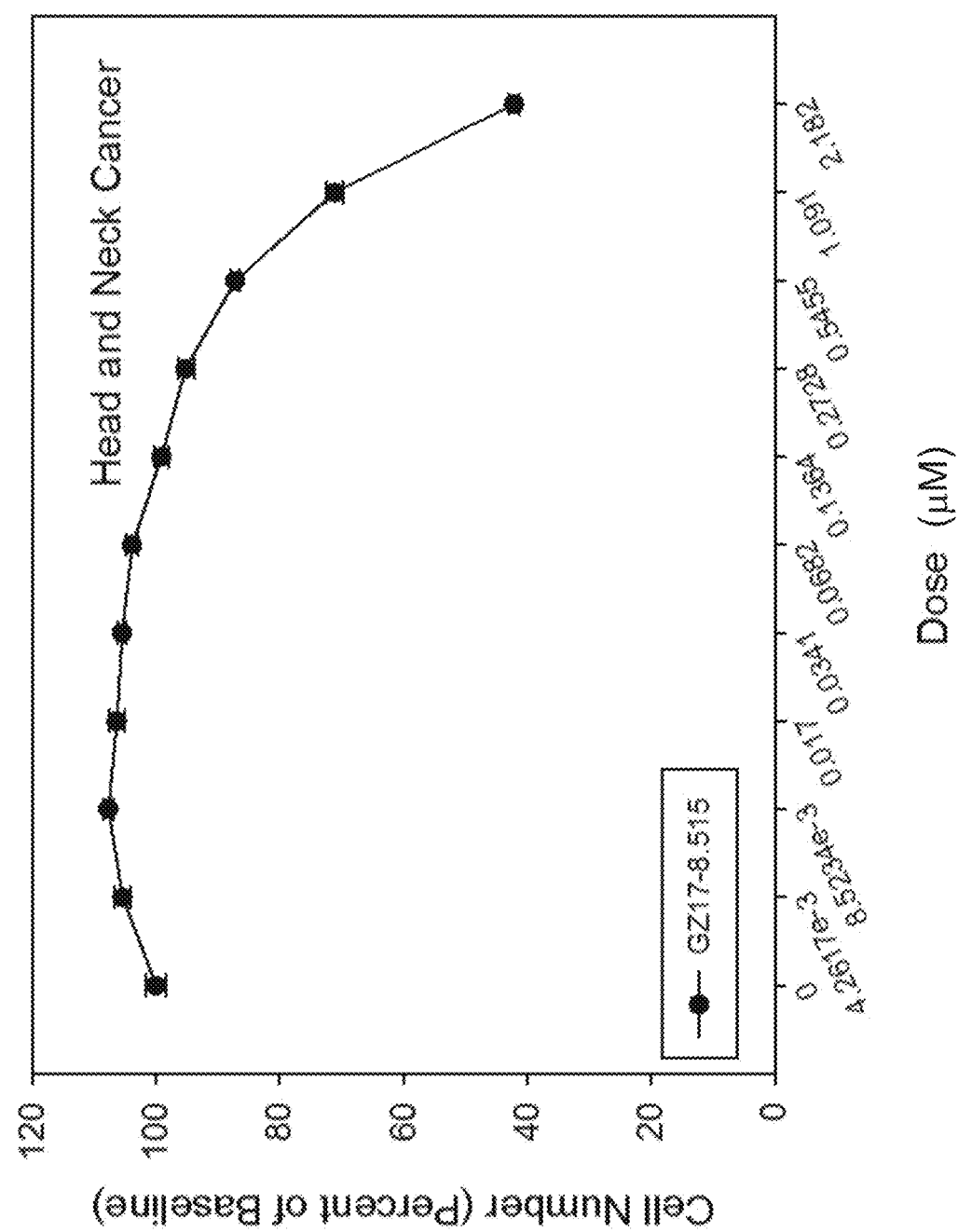
Figure 81M:
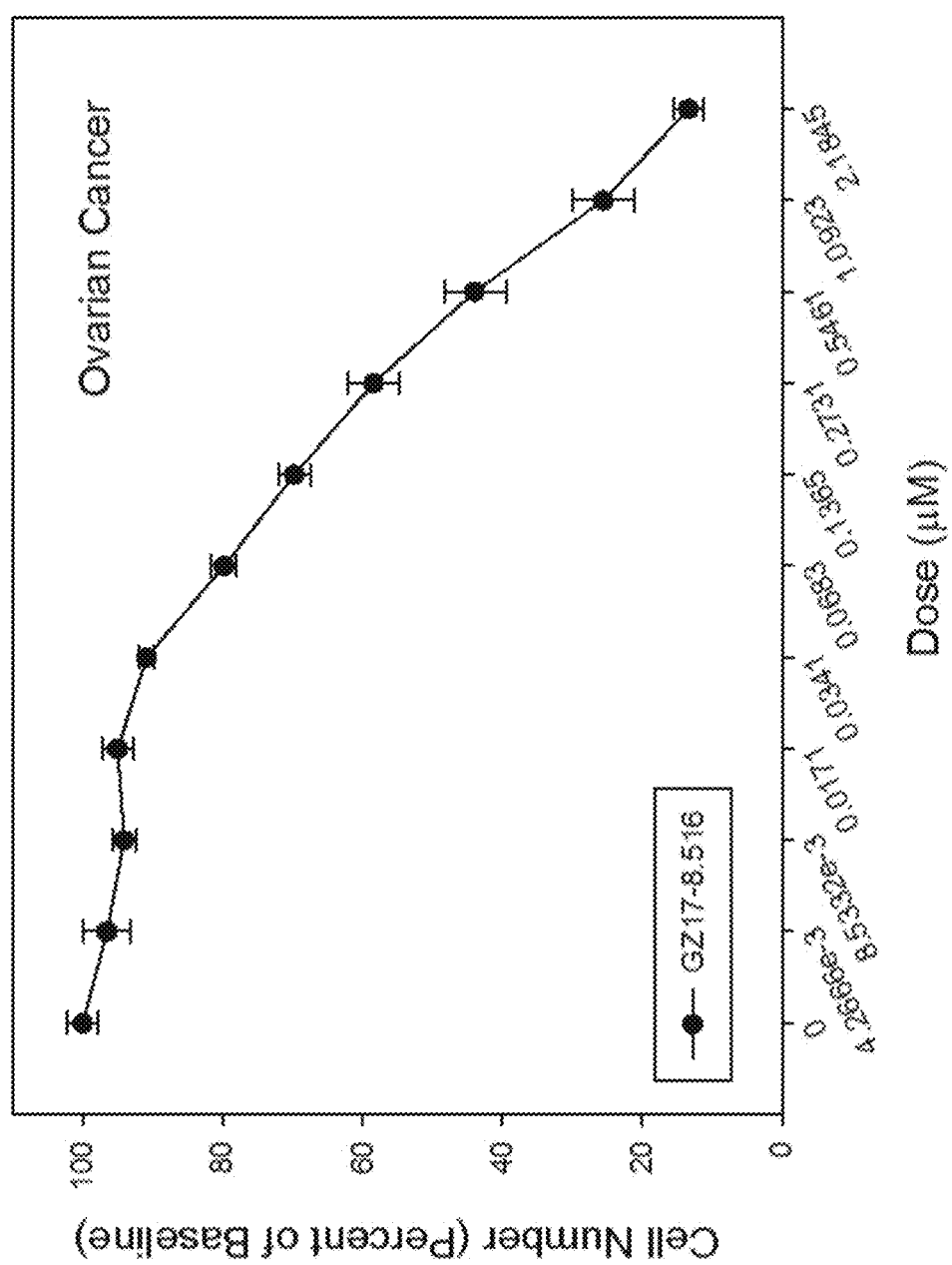
Figure 81N:
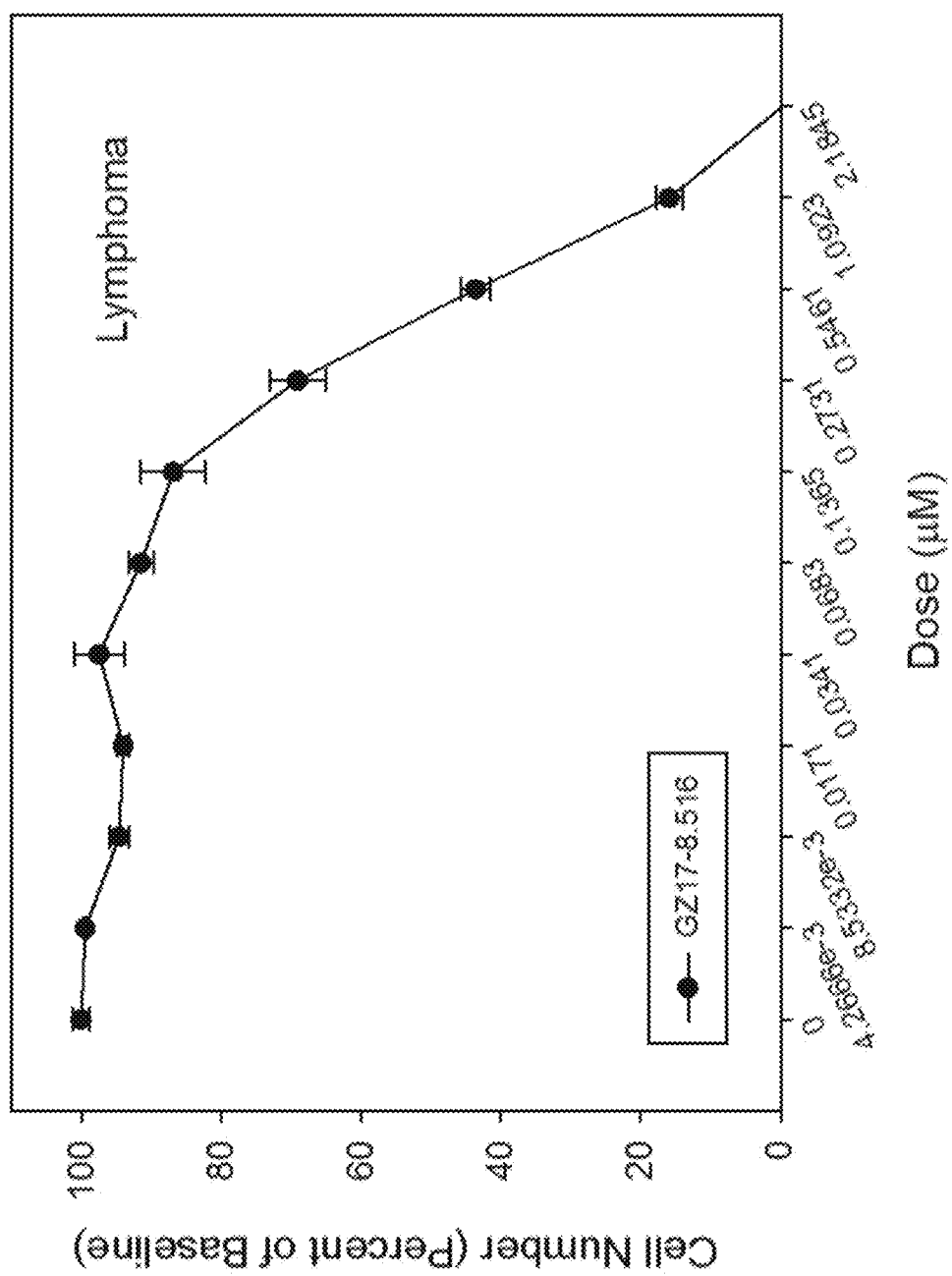
Figure 810:
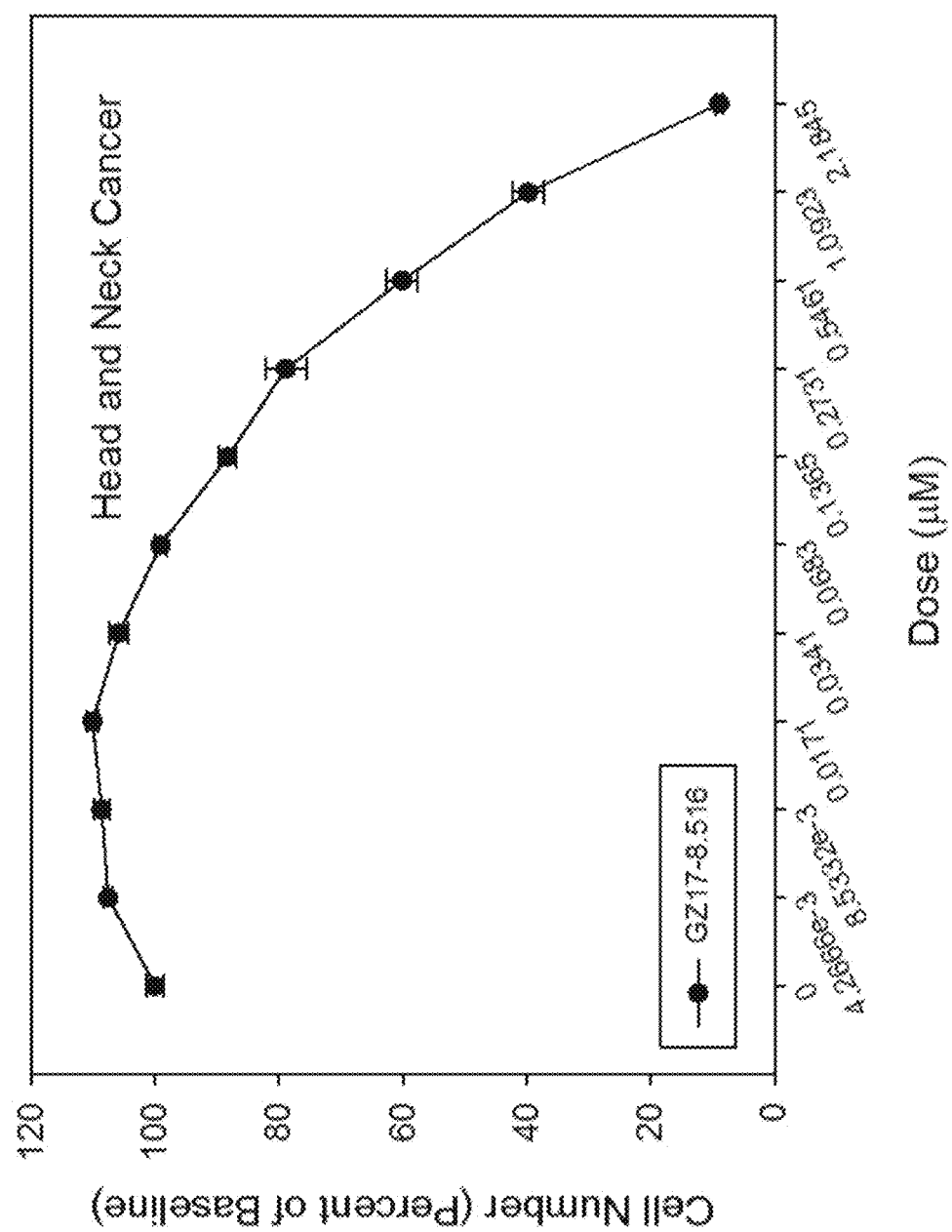
Figure 81P:
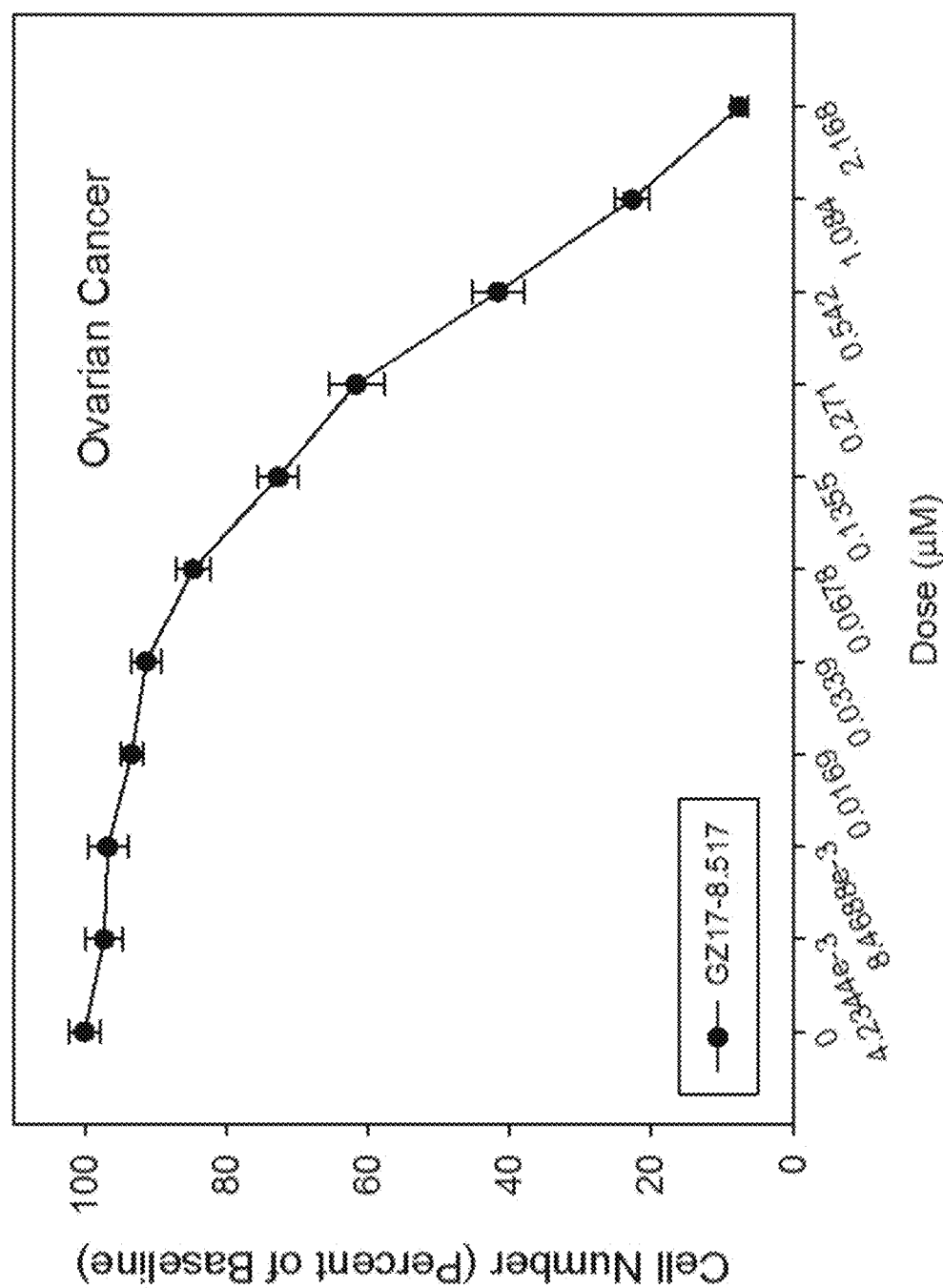
Figure 81Q:
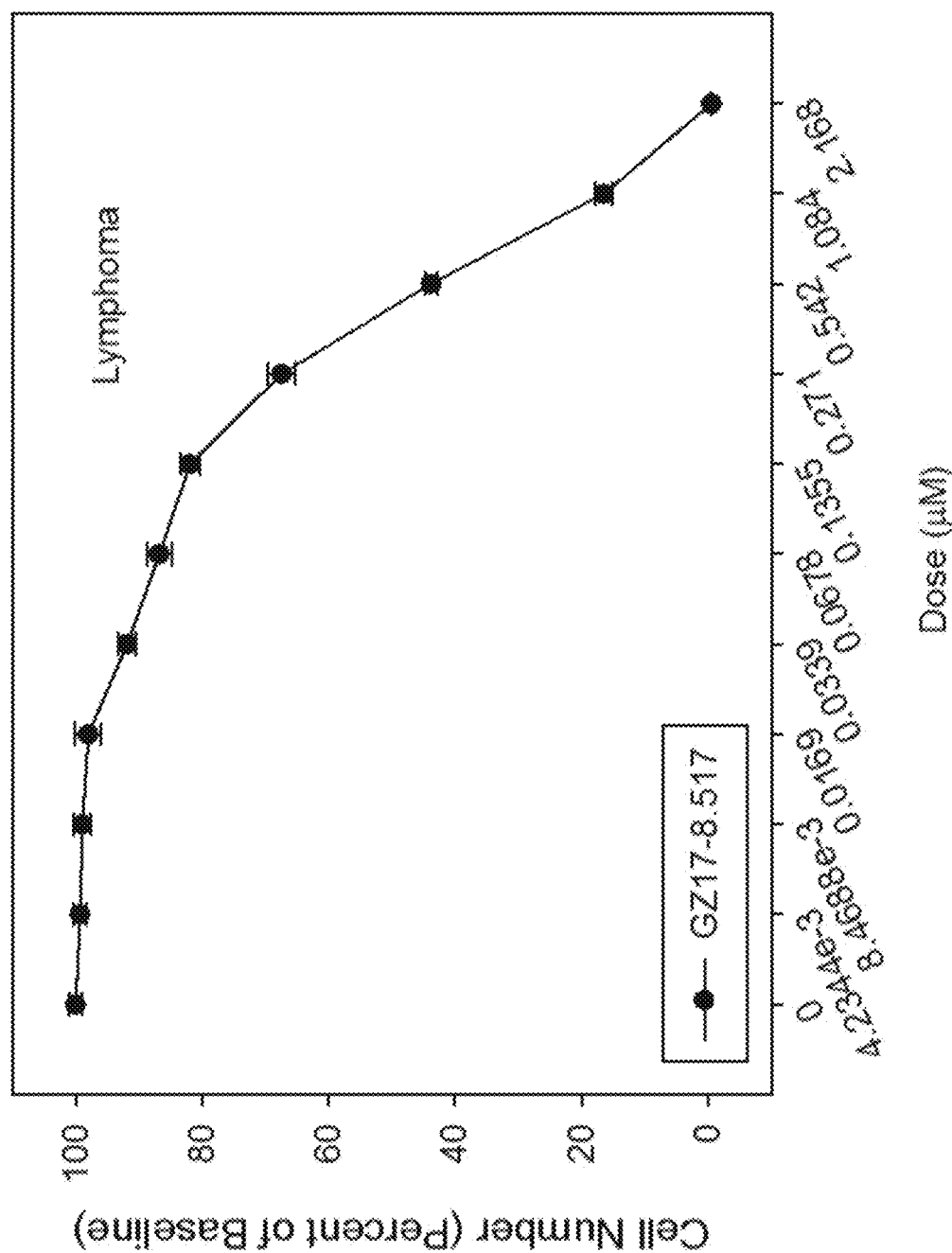
Figure 81R:
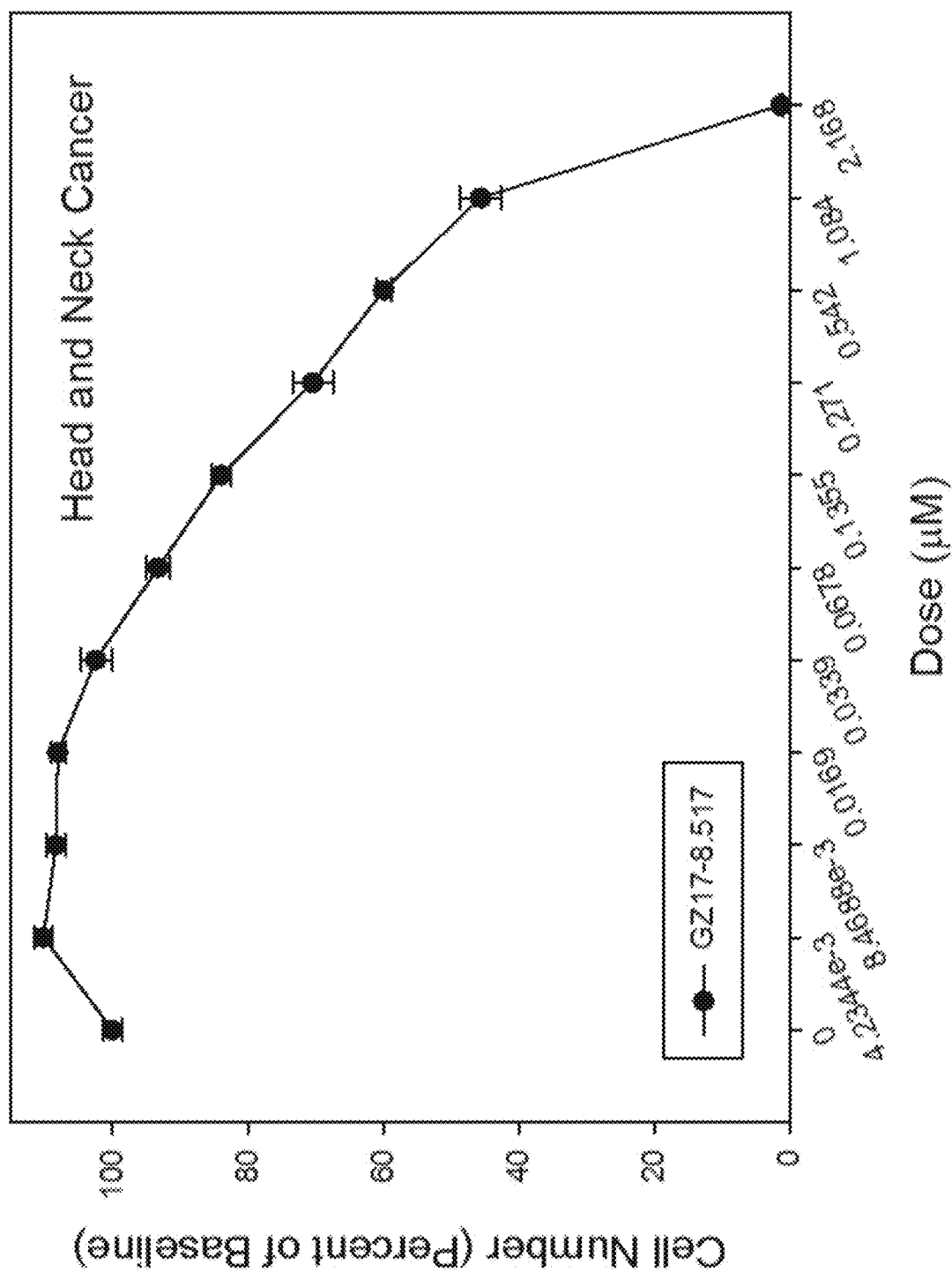
Figure 81S:
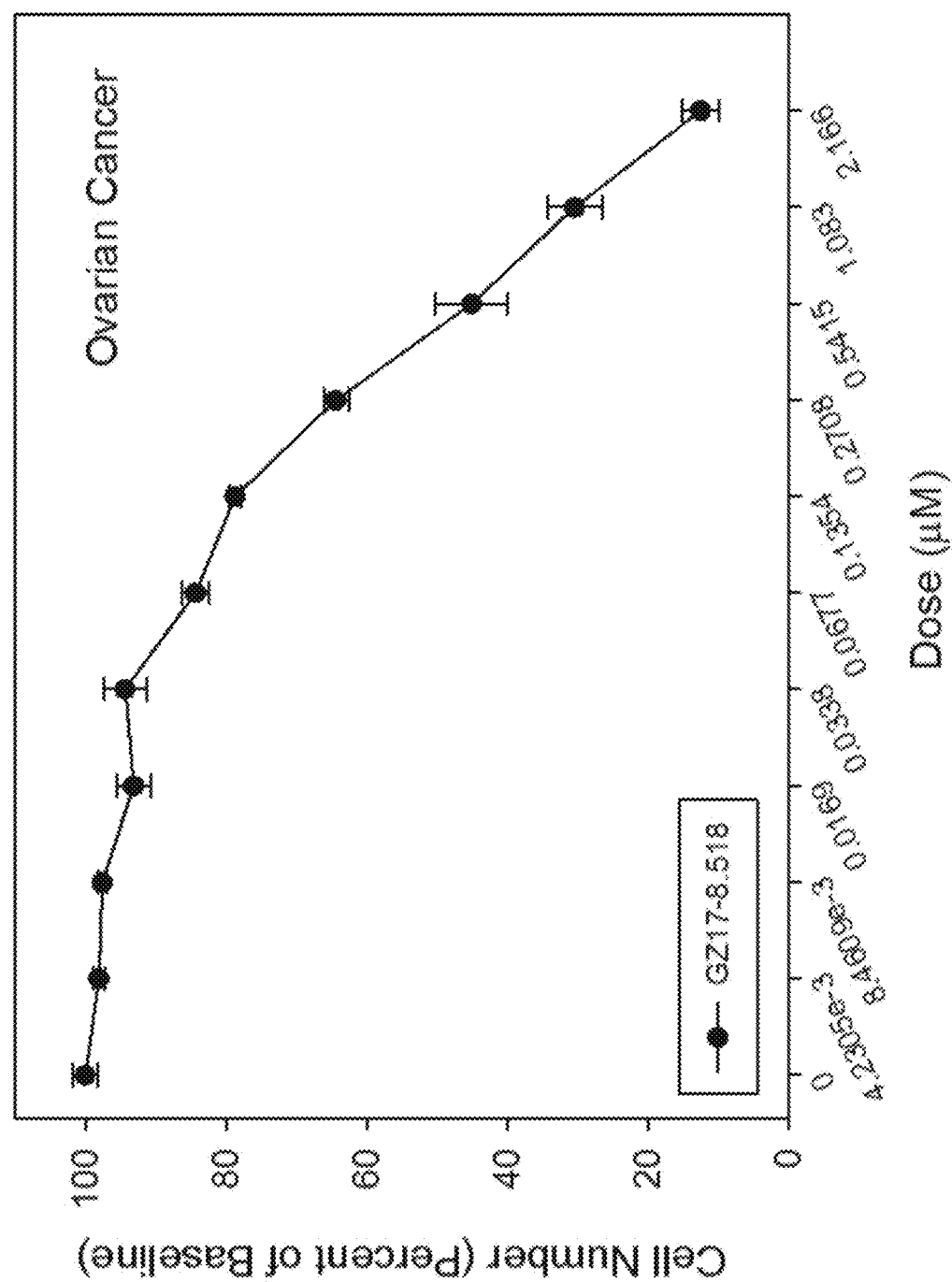
Figure 81T:
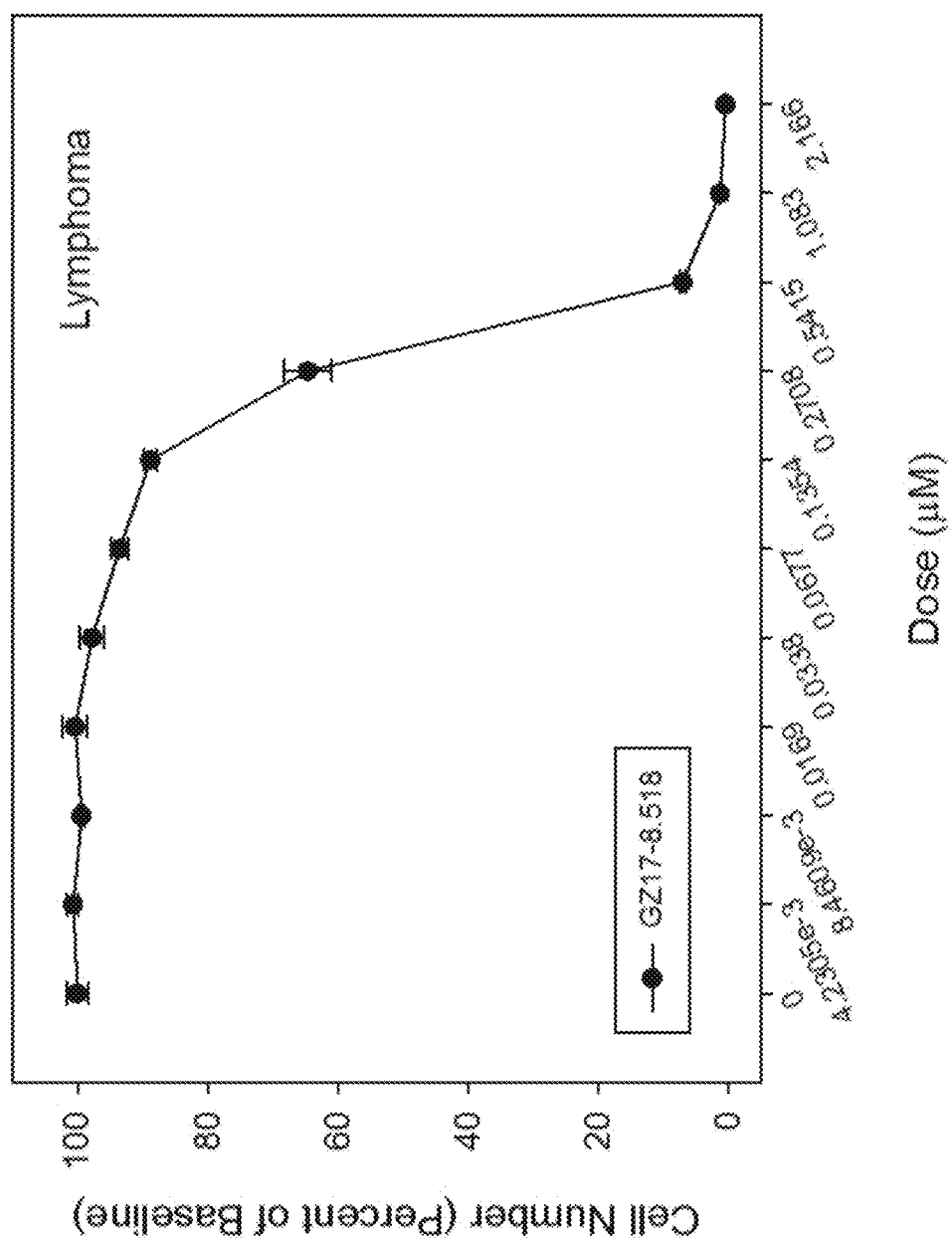
Figure 81U:
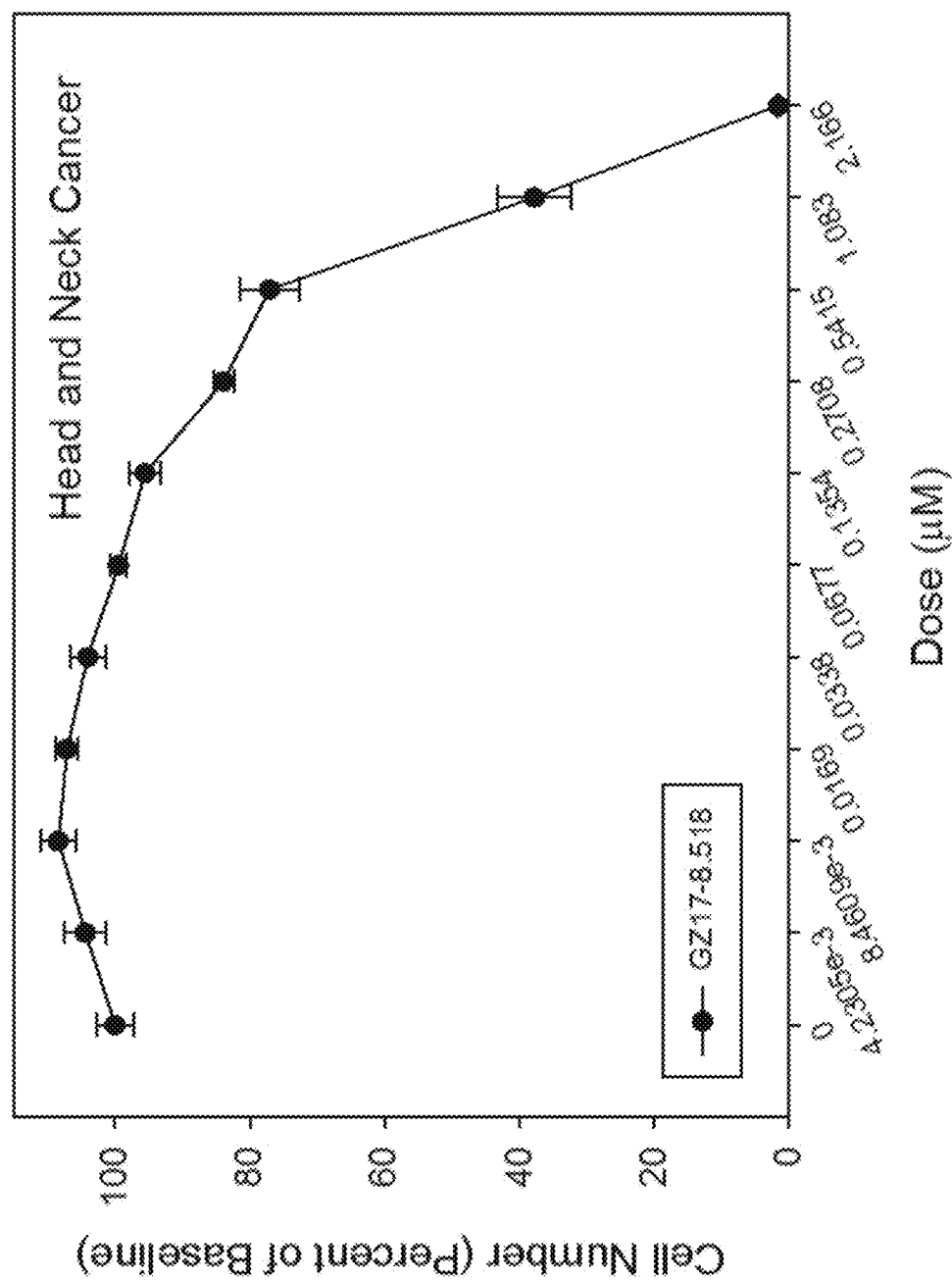
Figure 81V:
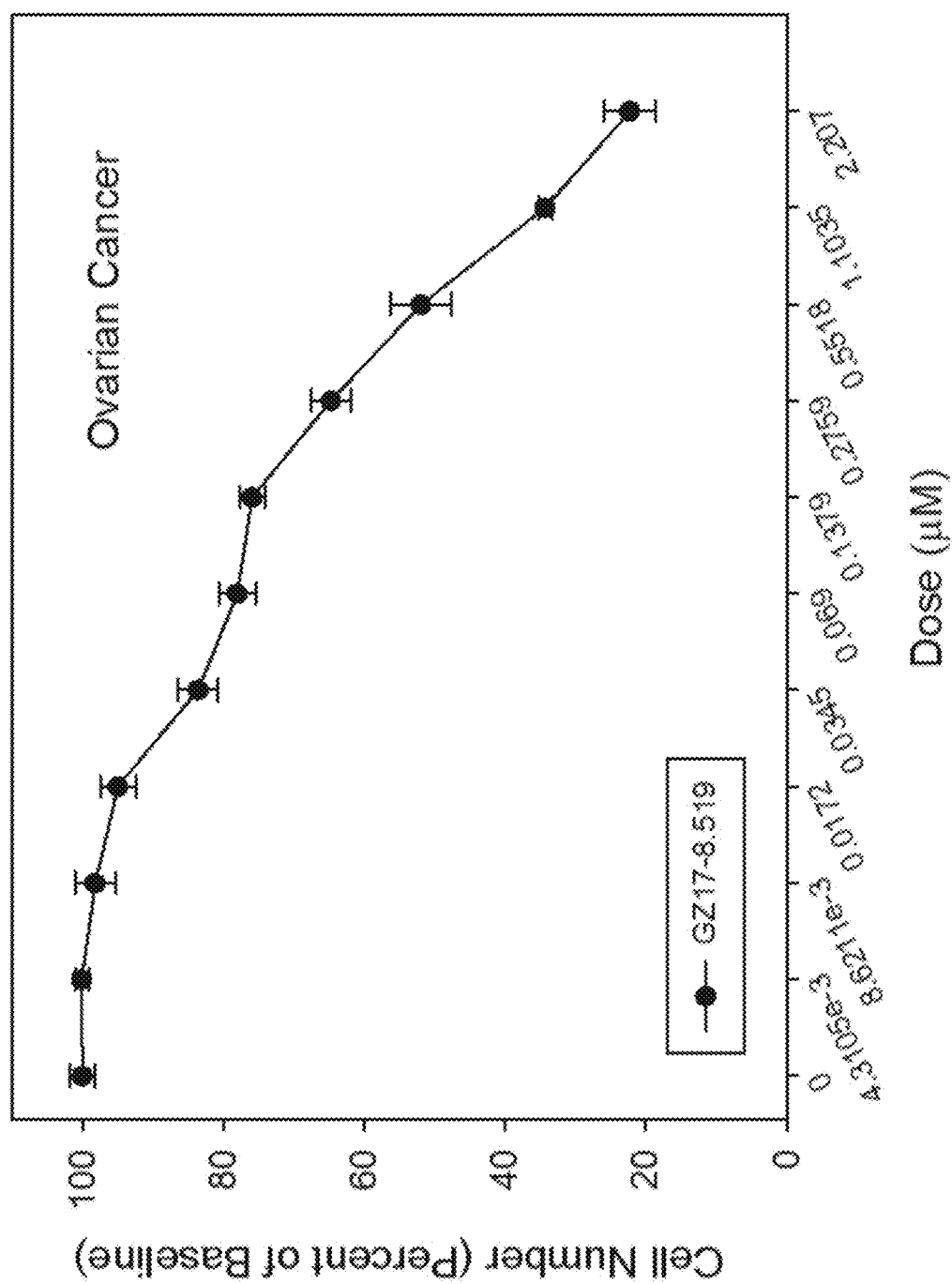
Figure 81W:
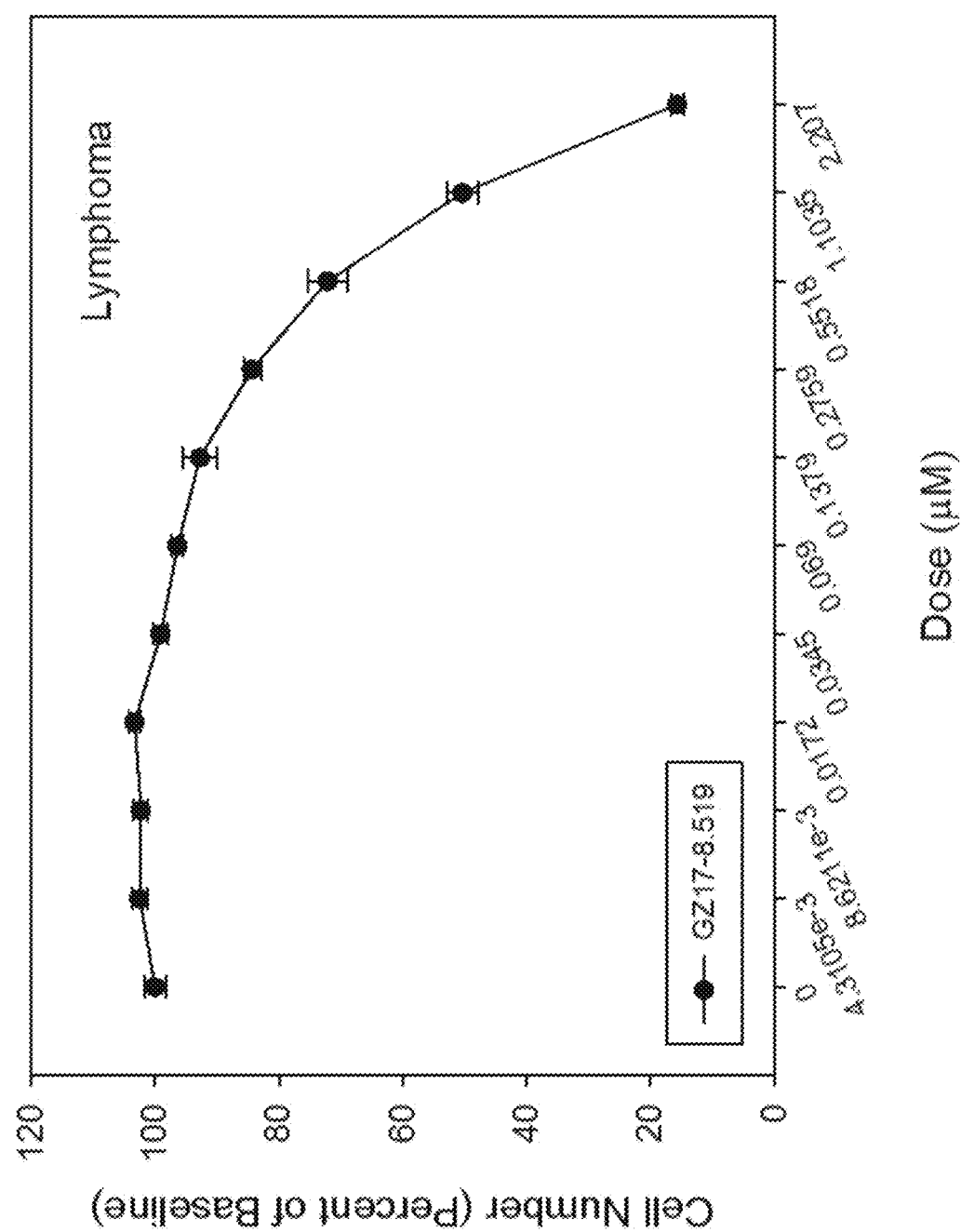
Figure 81X:
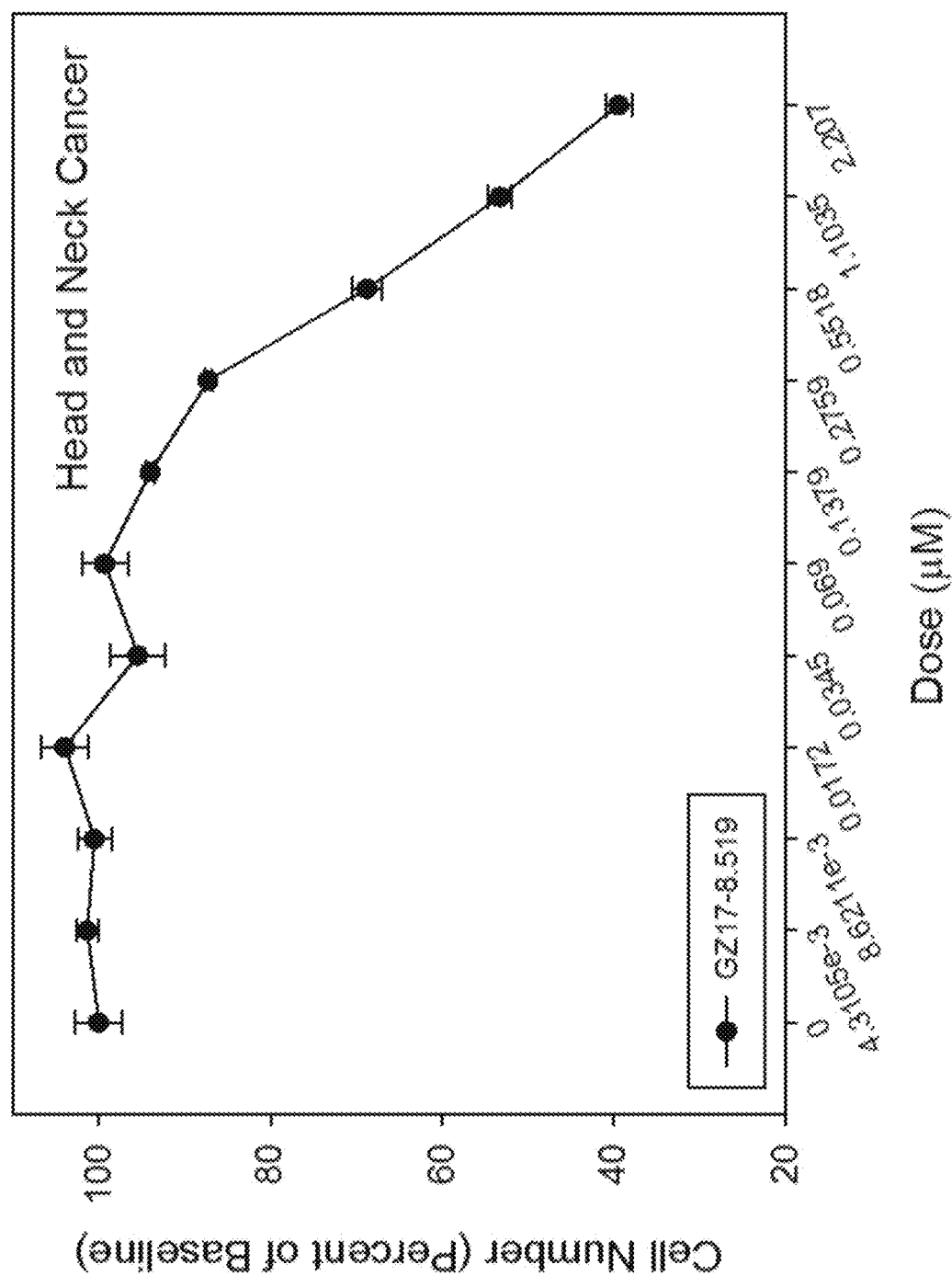
Figure 81Y:
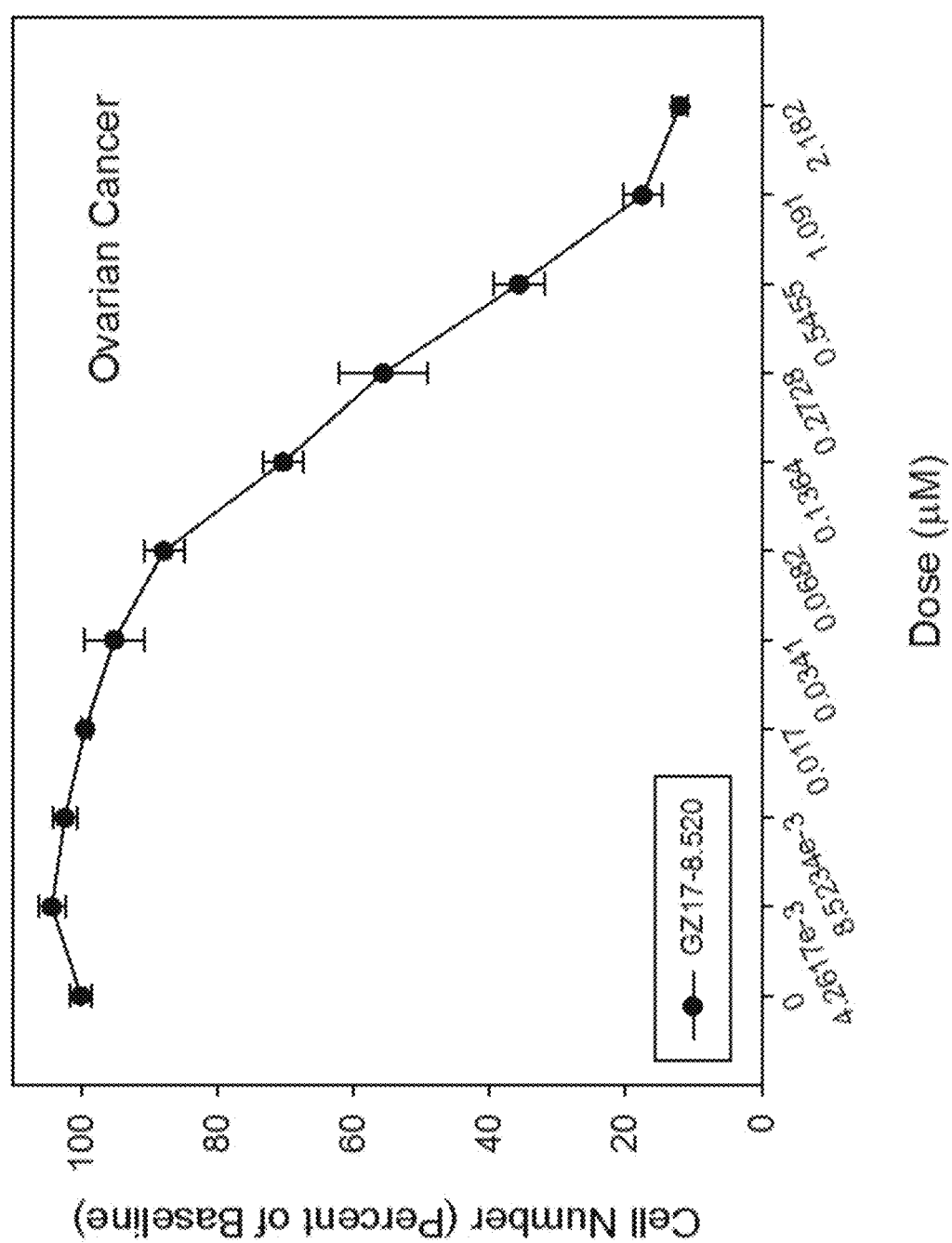
Figure 81Z:
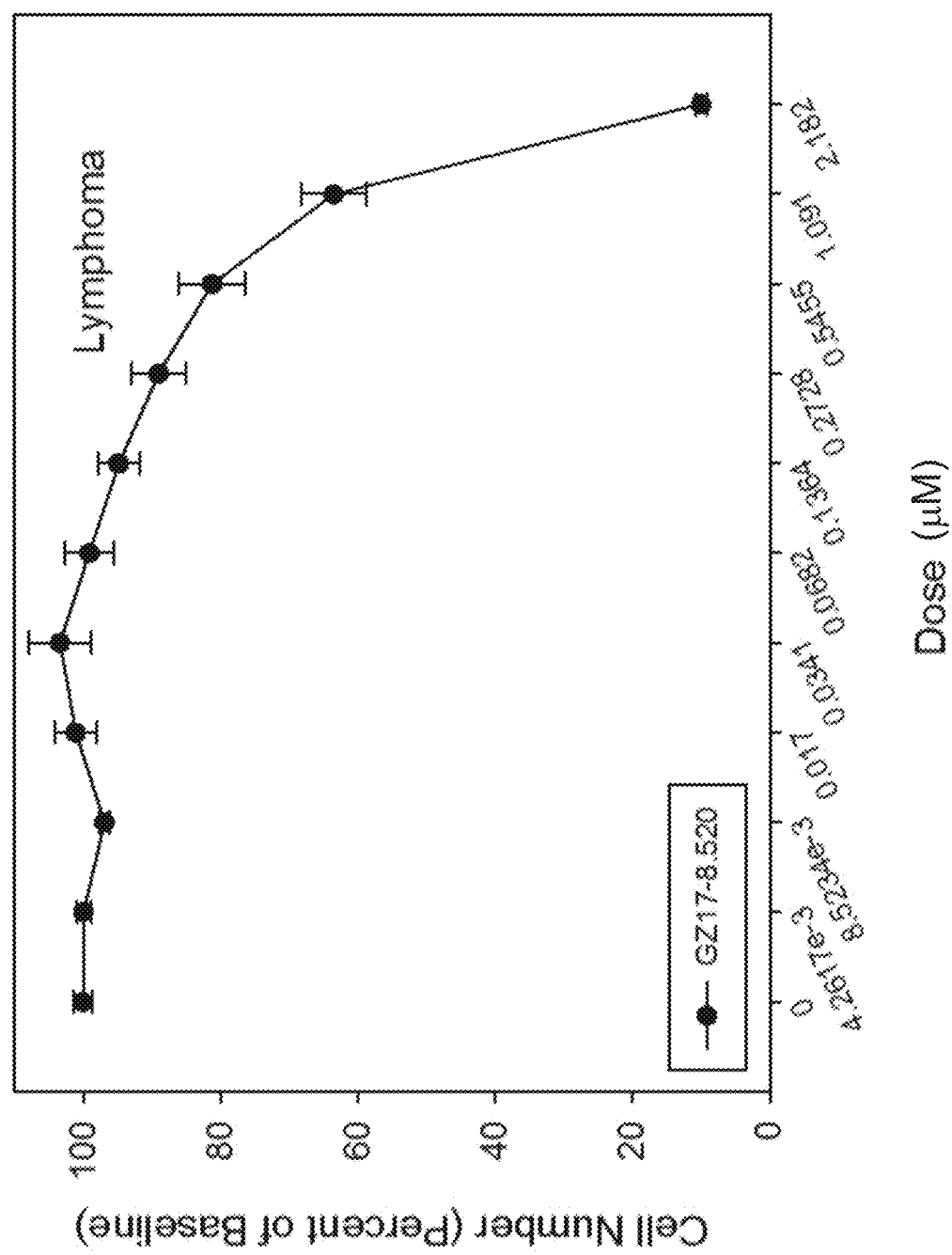
Figure 81A:
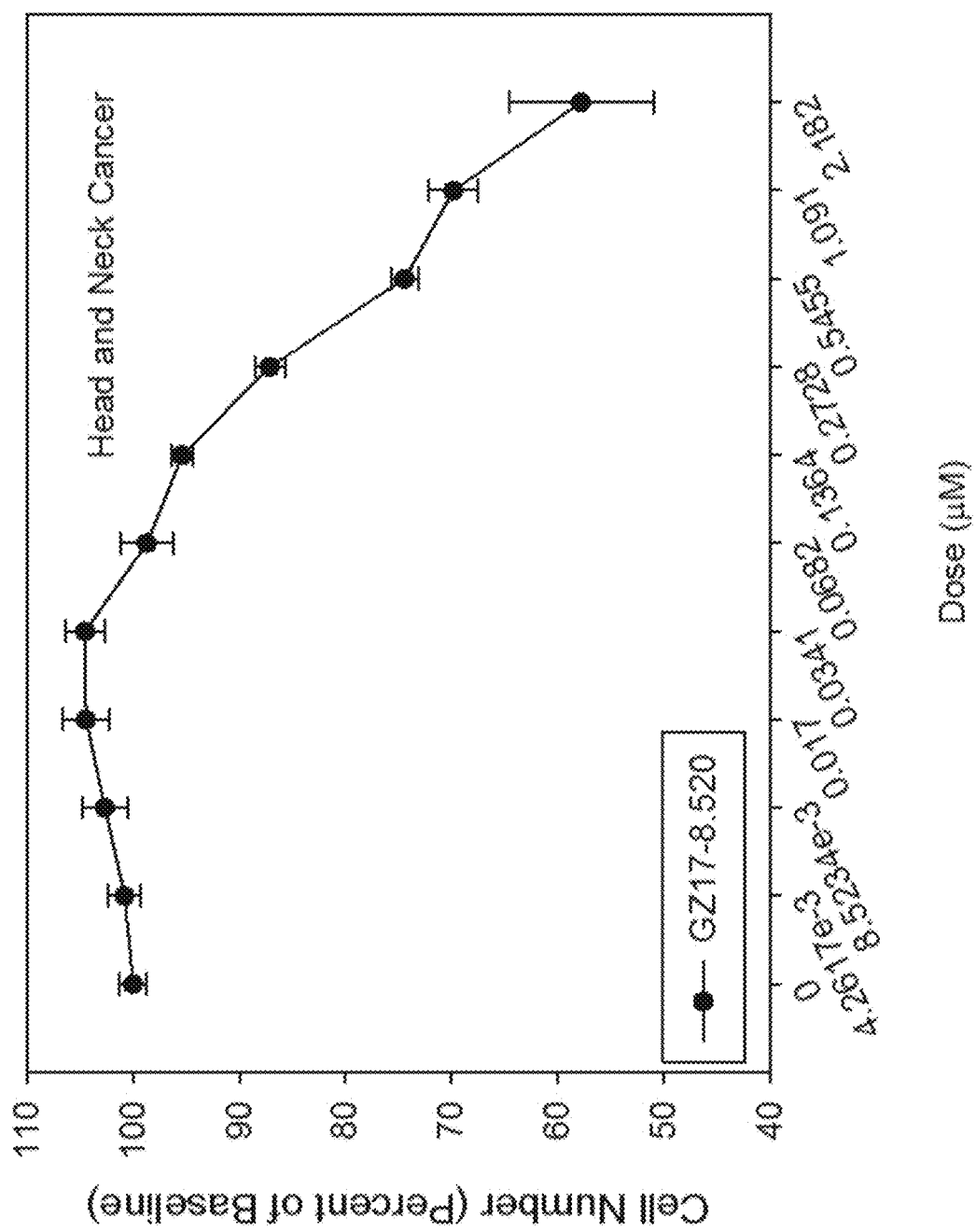
Figure 81B:
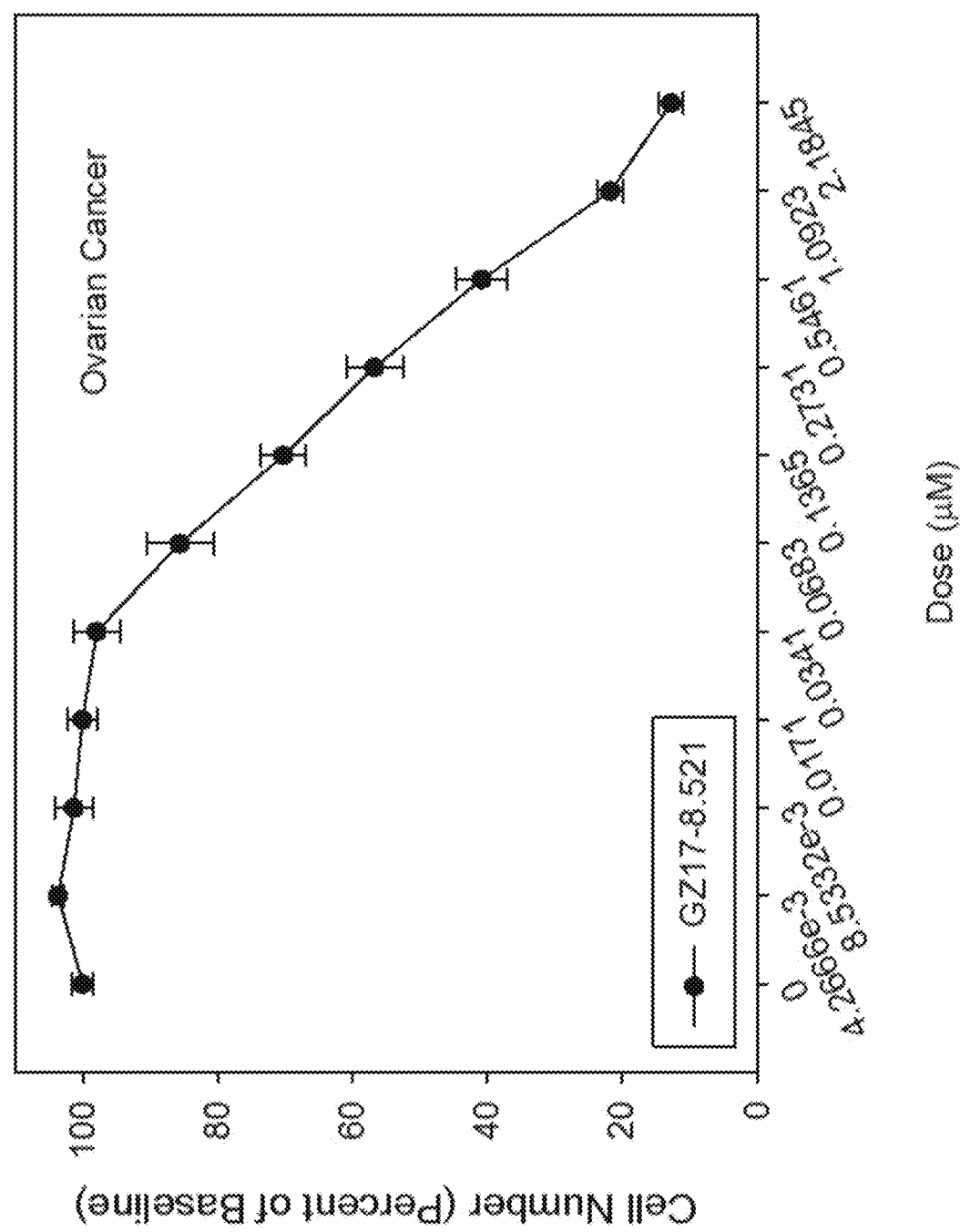
Figure 81C:
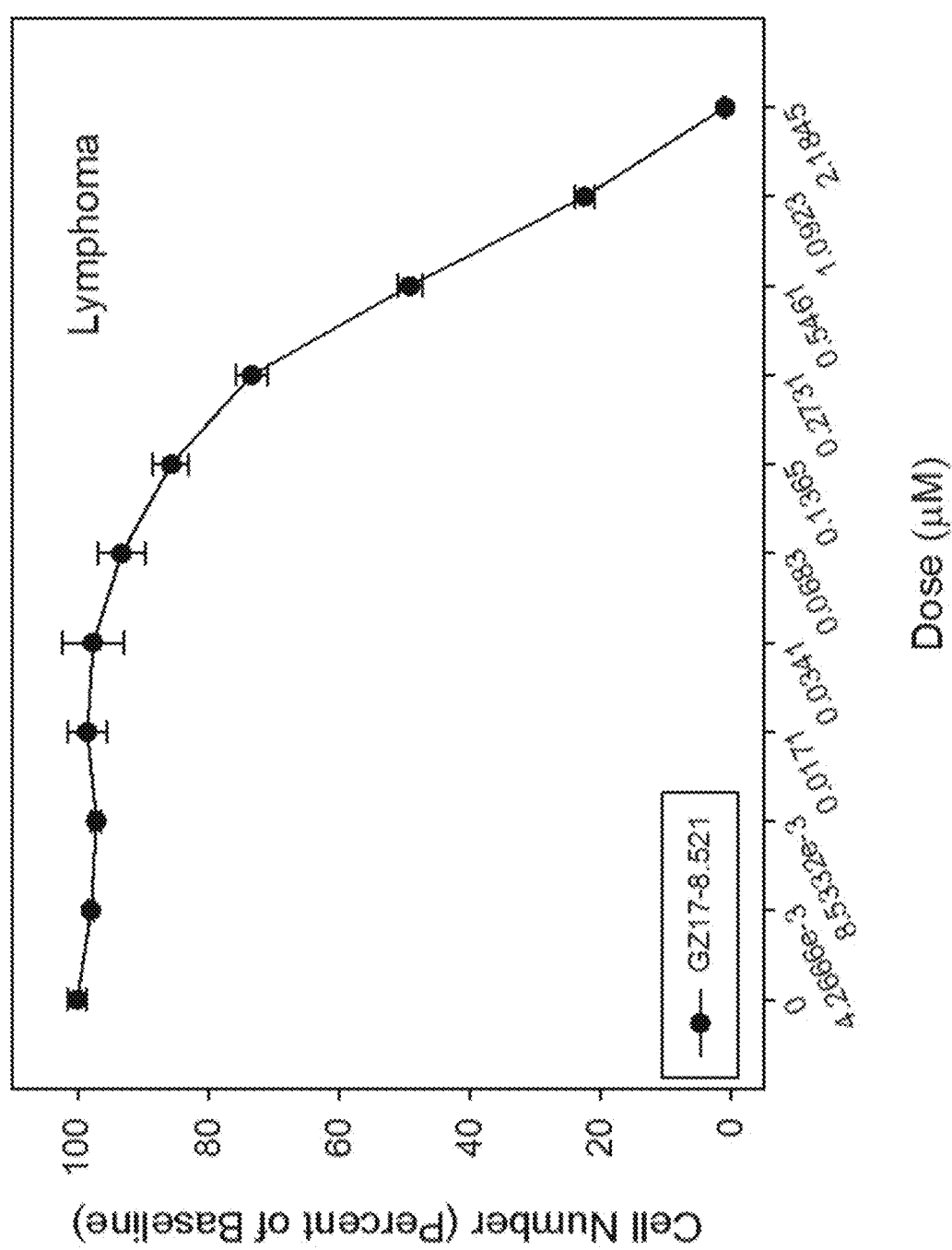
Figure 81D:
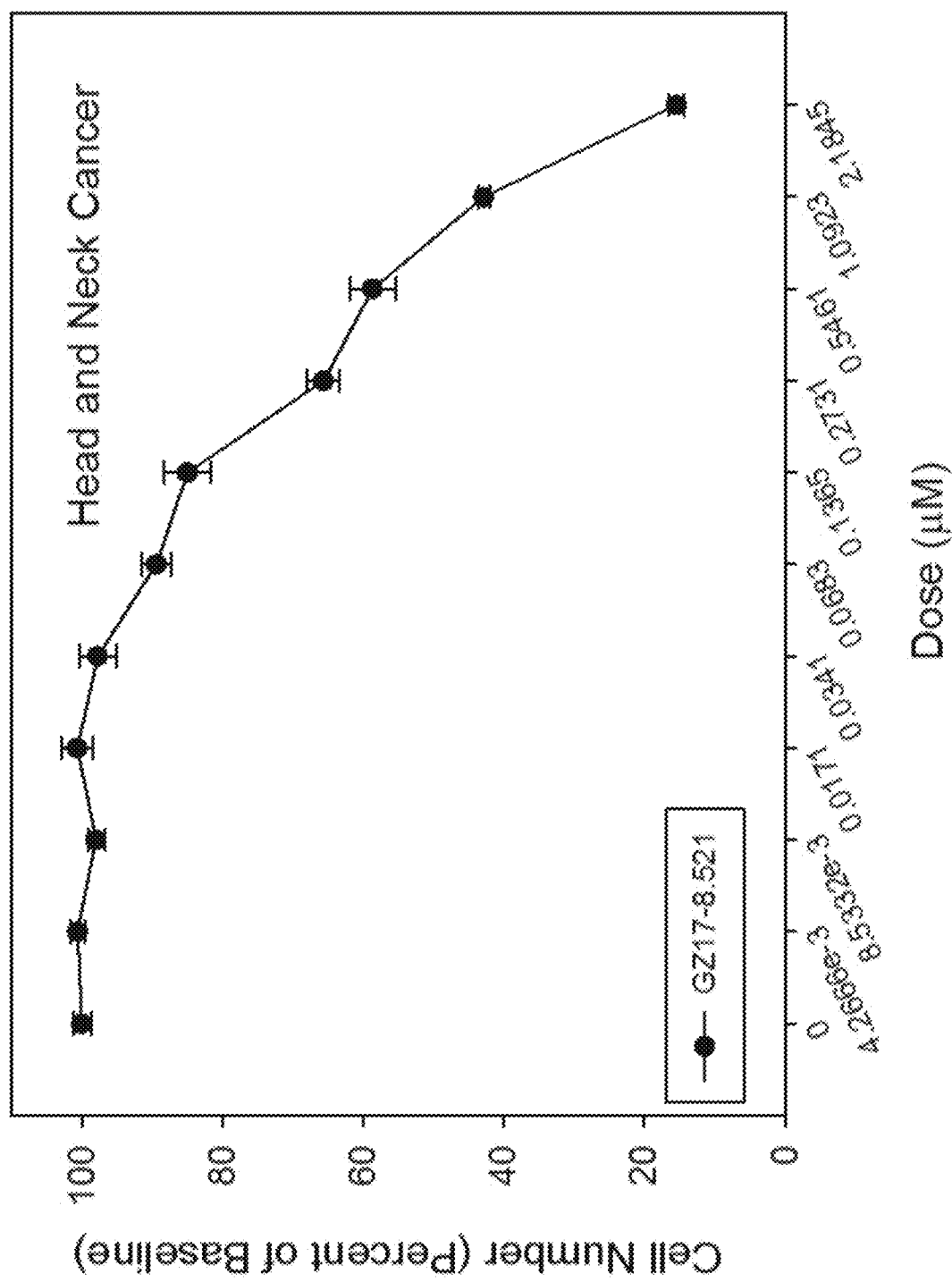
Figures 1, 82:
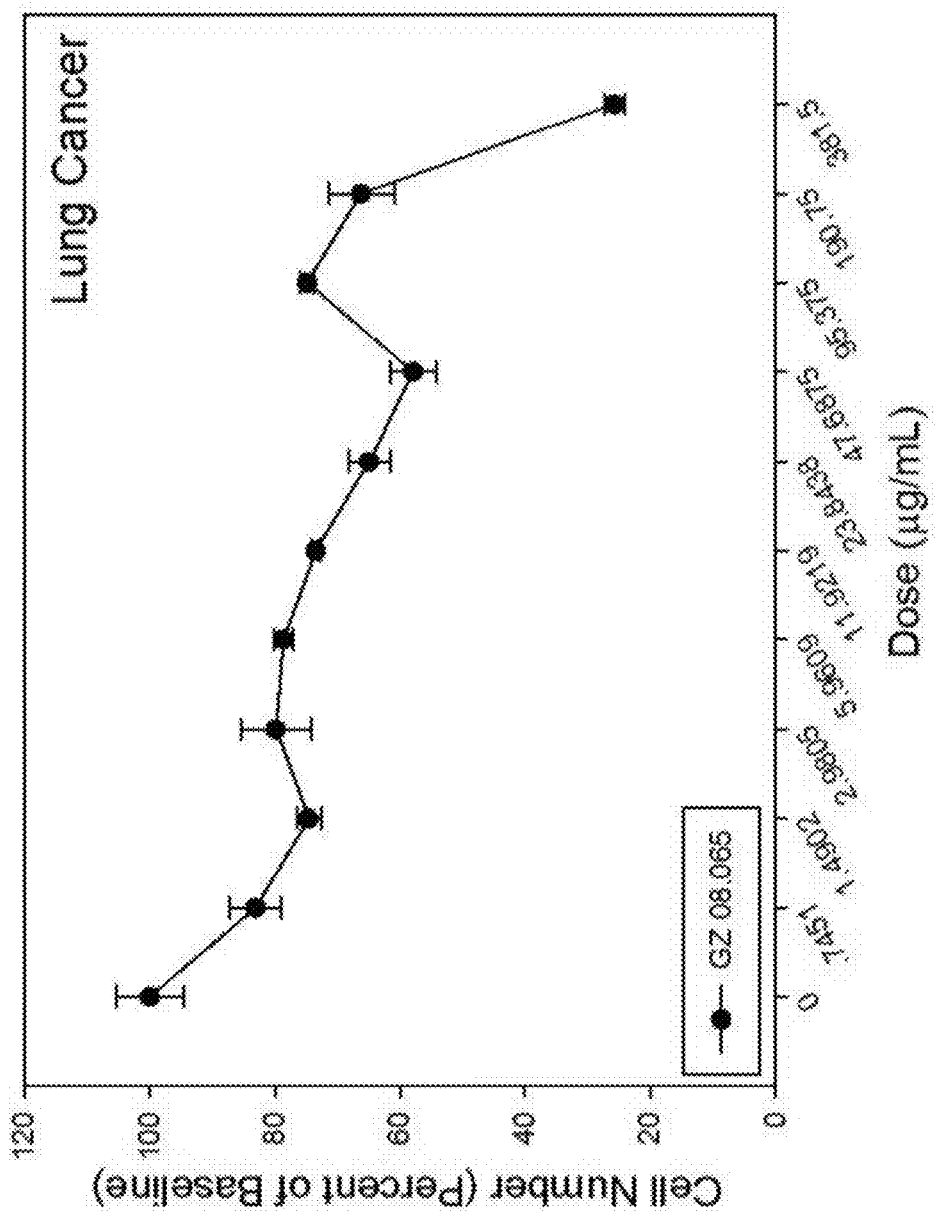
FIG. 1 is a graph of cell number versus dosage amounts of GZ17-6.02, illustrating the effect thereof in inducing the death of two different types of human head and neck cancer cells, as described in Example 1.
Figures 2, 82:
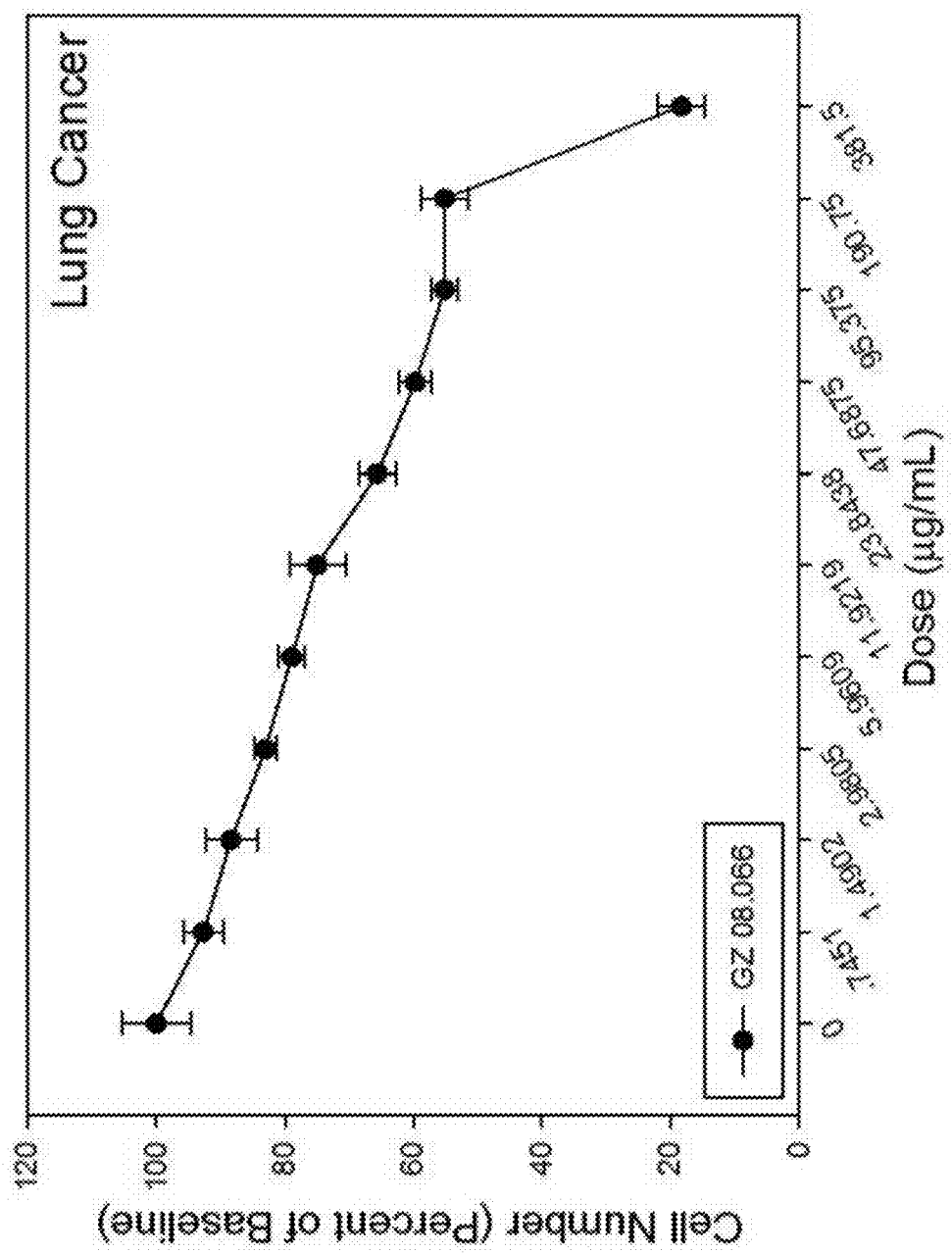
FIG. 2A is a graph of cell number versus dosage amounts of GZ17-6.02, illustrating the effect thereof GZ17-6.02 in inducing the death of pediatric leukemia cells, as described in Example 2.
FIG. 2B is a graph of cell number versus dosage amounts of GZ17-6.02, illustrating the effect thereof GZ17-6.02 in inducing the death of pediatric osteosarcoma cells, as described in Example 2.
Figures 3, 82:
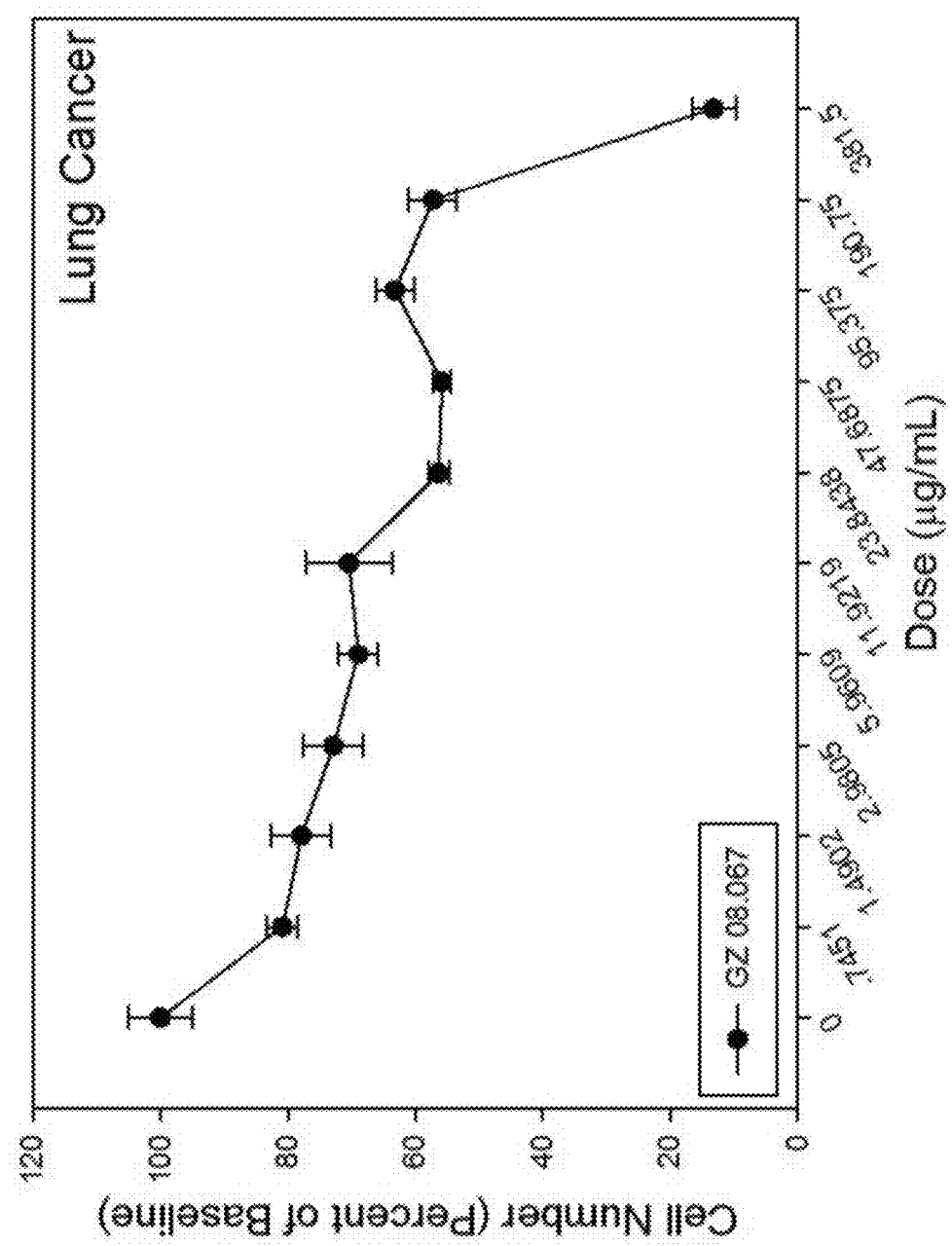
FIG. 3A is a graph of cell number versus dosage amounts of GZ17-6.02, illustrating the effect thereof GZ17-6.02 in inducing the death of lymphoma cells, as described in Example 3.
FIG. 3B is a graph of cell number versus dosage amounts of GZ17-6.02, illustrating the effect thereof GZ17-6.02 in inducing the death of lung cancer cells, as described in Example 3.
Figures 4, 82:
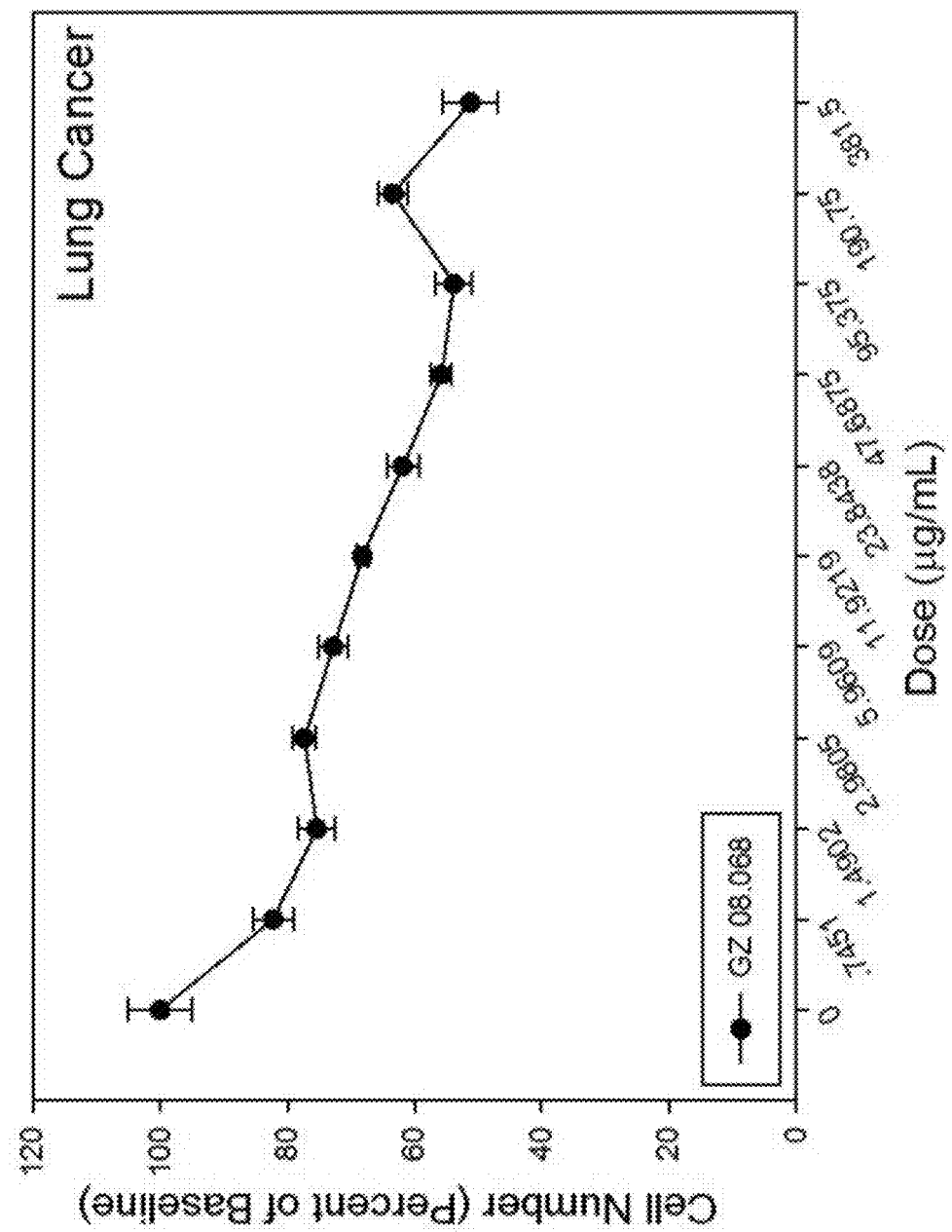
FIG. 4B is a graph of cell number versus dosage amounts of GZ17-6.02, illustrating the effect thereof in inducing the death of prostate cancer cells, as described in Example 4.
Figures 5, 82:
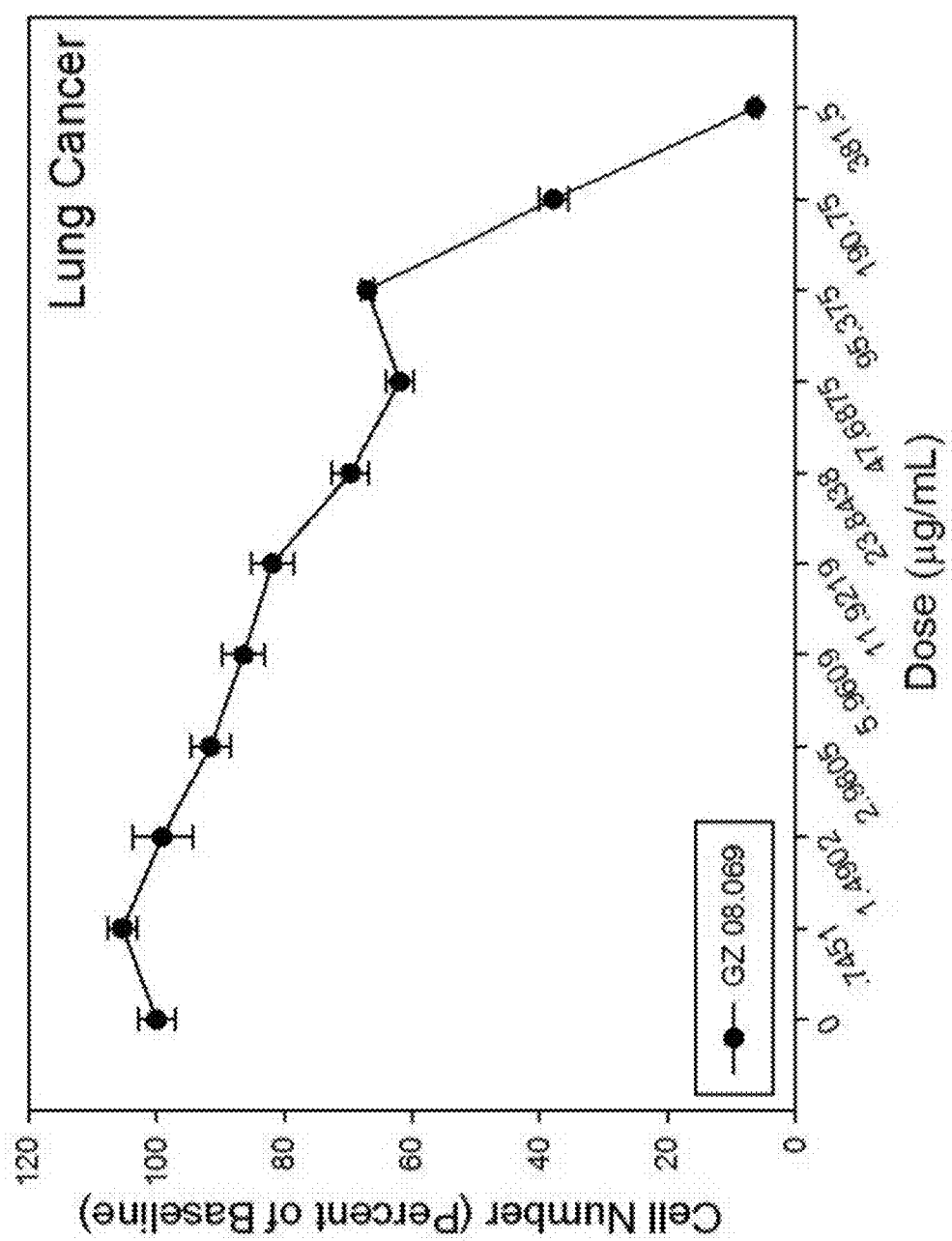
FIG. 5A is a graph of cell number versus dosage amounts of GZ17-6.02, illustrating the effect thereof in inducing the death of human breast cancer cells, as described in Example 5.
Figures 6, 82:
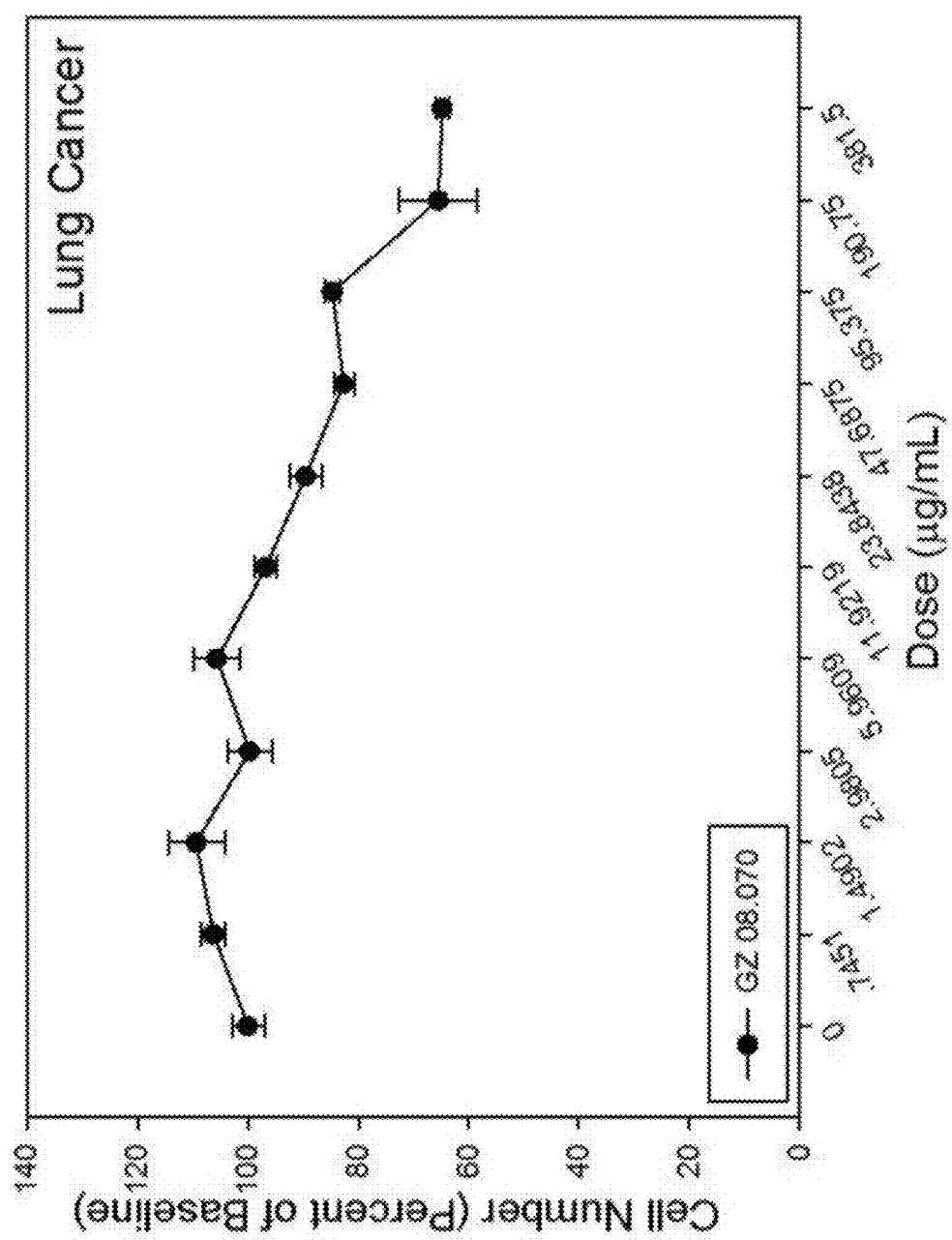
FIG. 6 is a graph of cell number versus doses of GZ17-6.02 illustrating the relative effects thereof in inducing cell death in prostate cancer and ovarian cancer cells, as compared with non-cancerous fibroblasts, as described in Example 6.
Figures 7, 82:
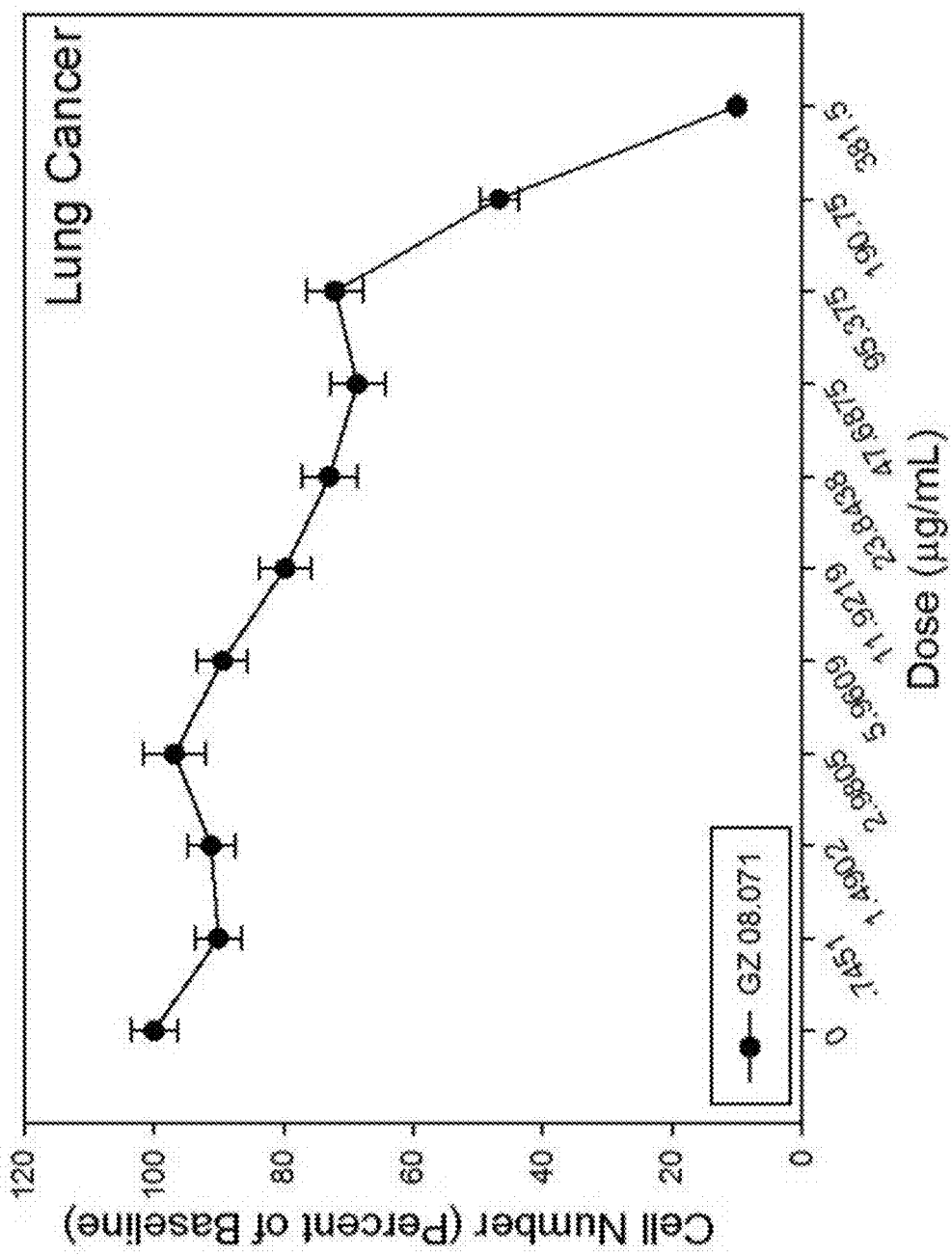
FIG. 7B is a graph illustrating the effect of GZ17-6.02 in preventing invasion of head and neck cancer cells, as described in Example 7.
Figures 8, 82:
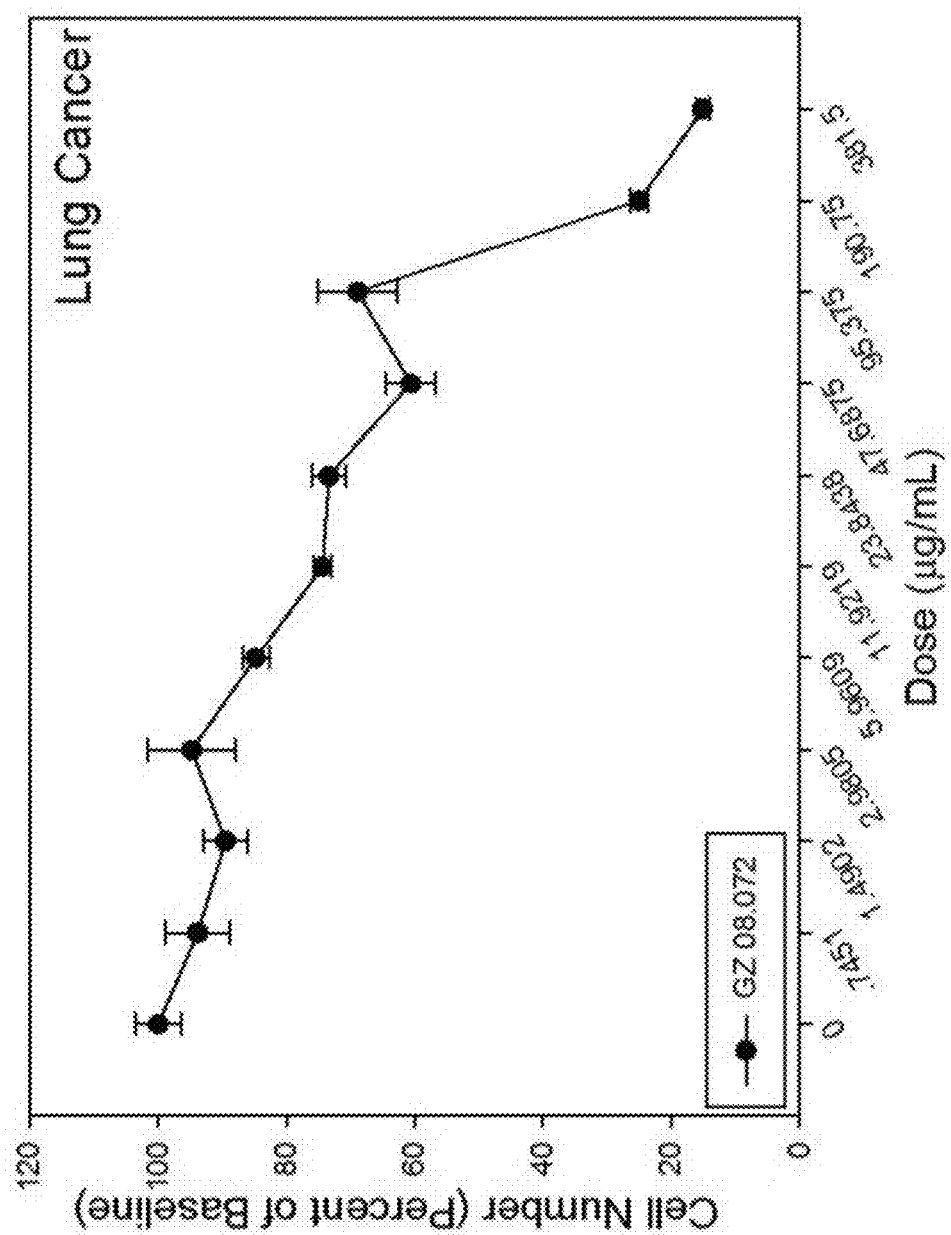
Figures 9, 82:
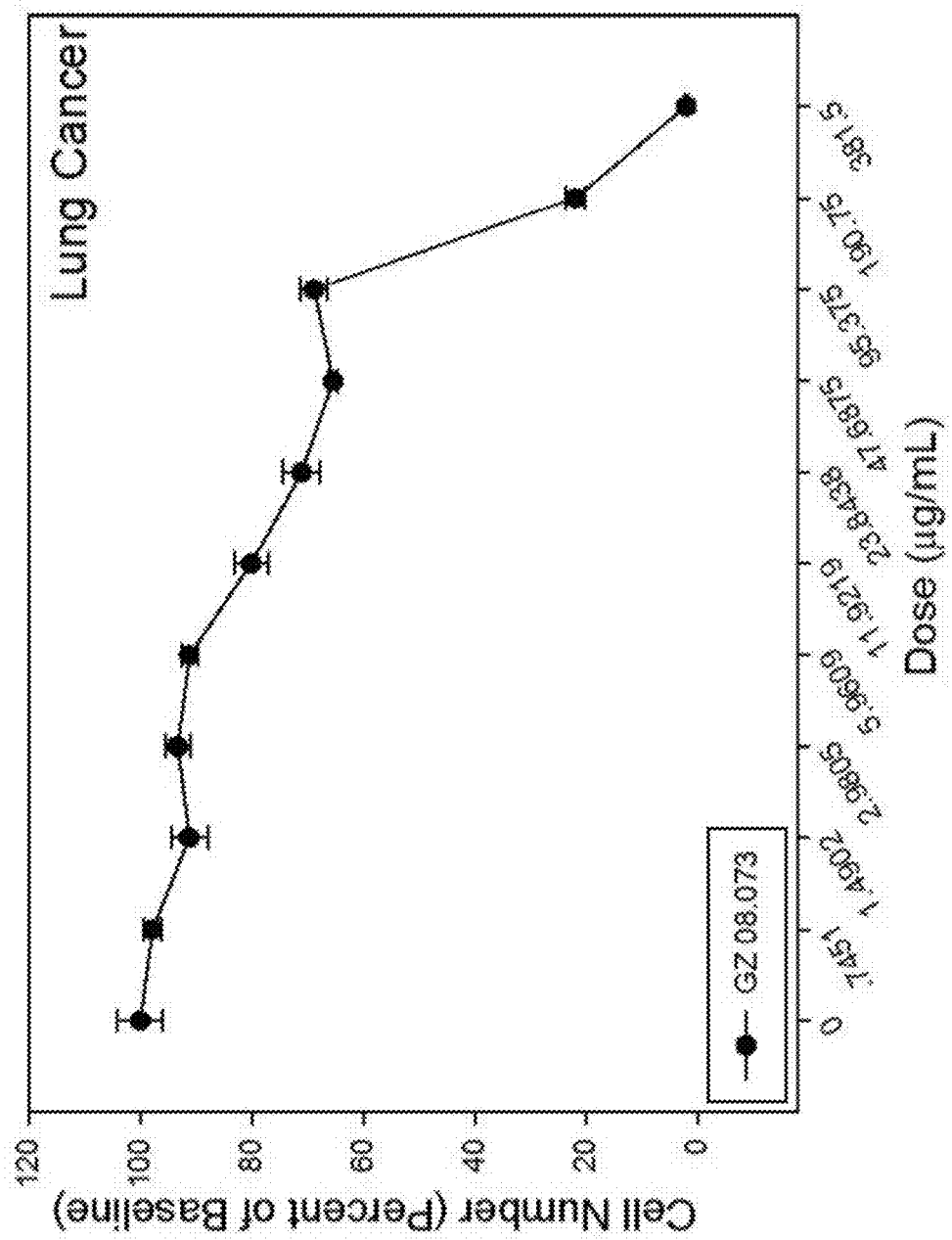
Figures 10, 82:
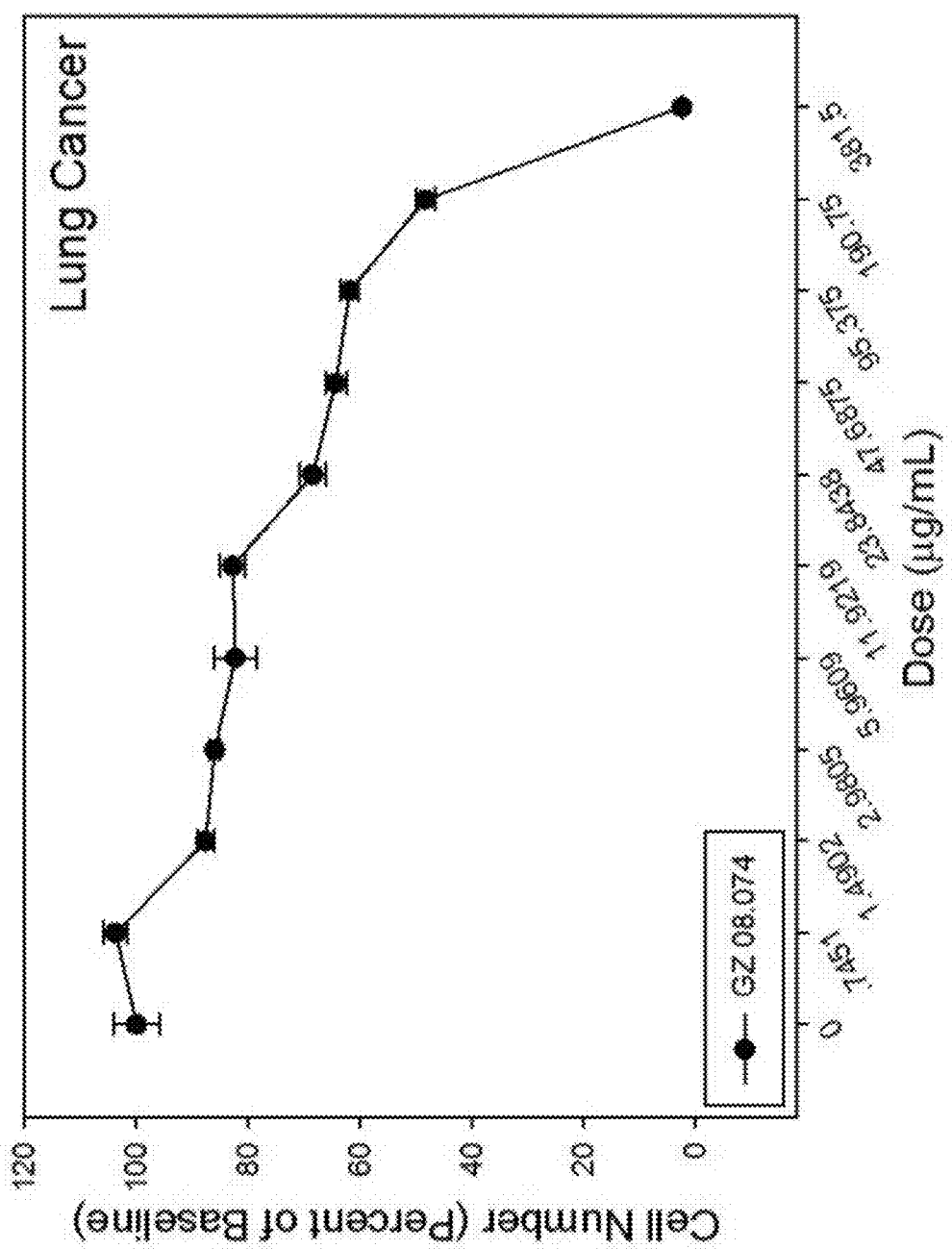
FIG. 10B is a graph illustrating that caspase 6 concentrations increased in response to GZ17-6.02 in lung cancer cells, as described in Example 10.
FIG. 10C is a graph illustrating that ATP levels, as a marker of mitochondrial toxicity, were not increased by GZ17-6.02 in lung cancer cells, as described in Example 10.
Figures 11, 82:
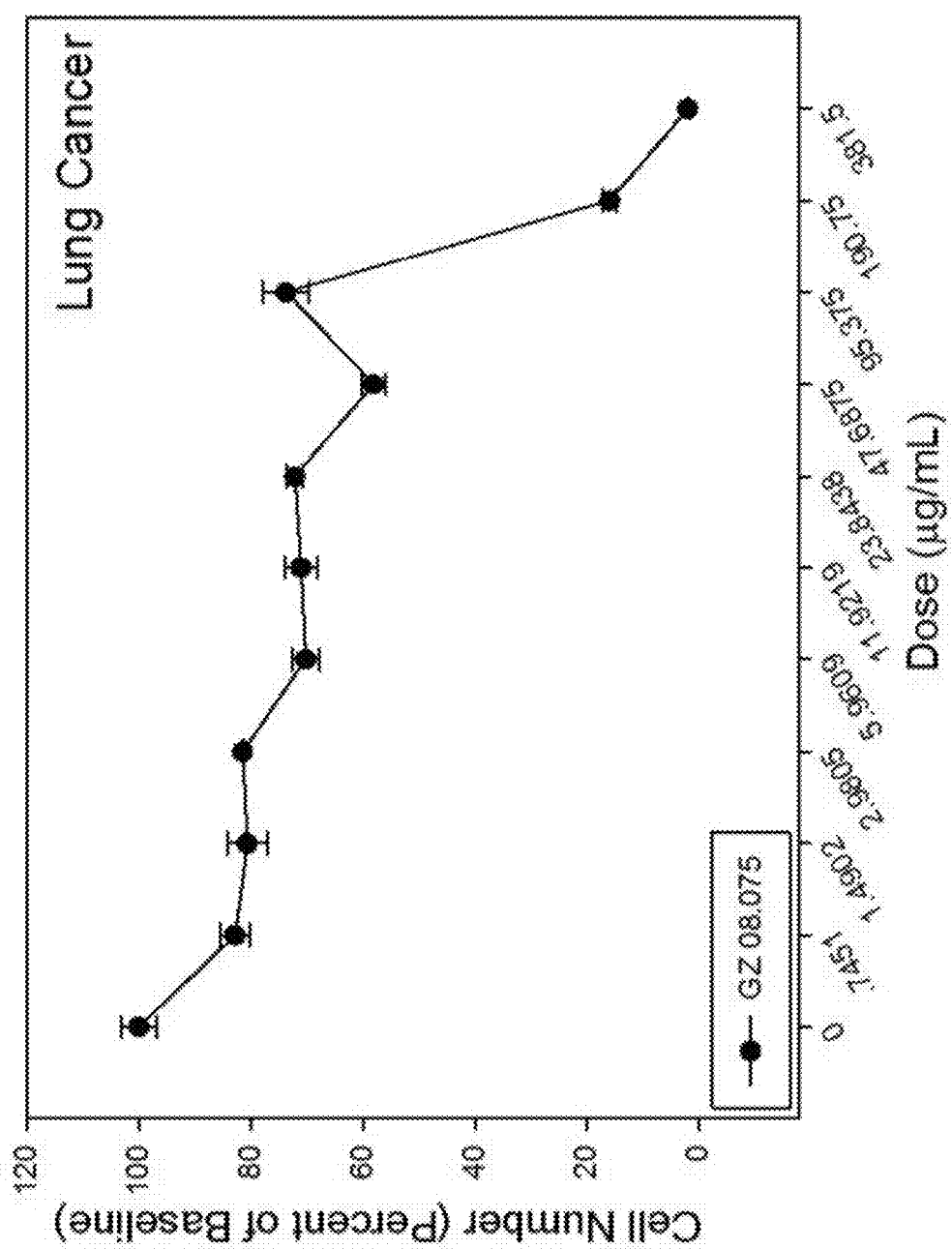
FIG. 11C is a graph illustrating the mechanisms of ovarian cancer cells death by application of GZ17-6.02, as explained in Example 11.
FIG. 11E is a graph illustrating the mechanisms of ovarian cancer cells death by application of GZ17-6.02, as explained in Example 11.
Figures 12, 82:
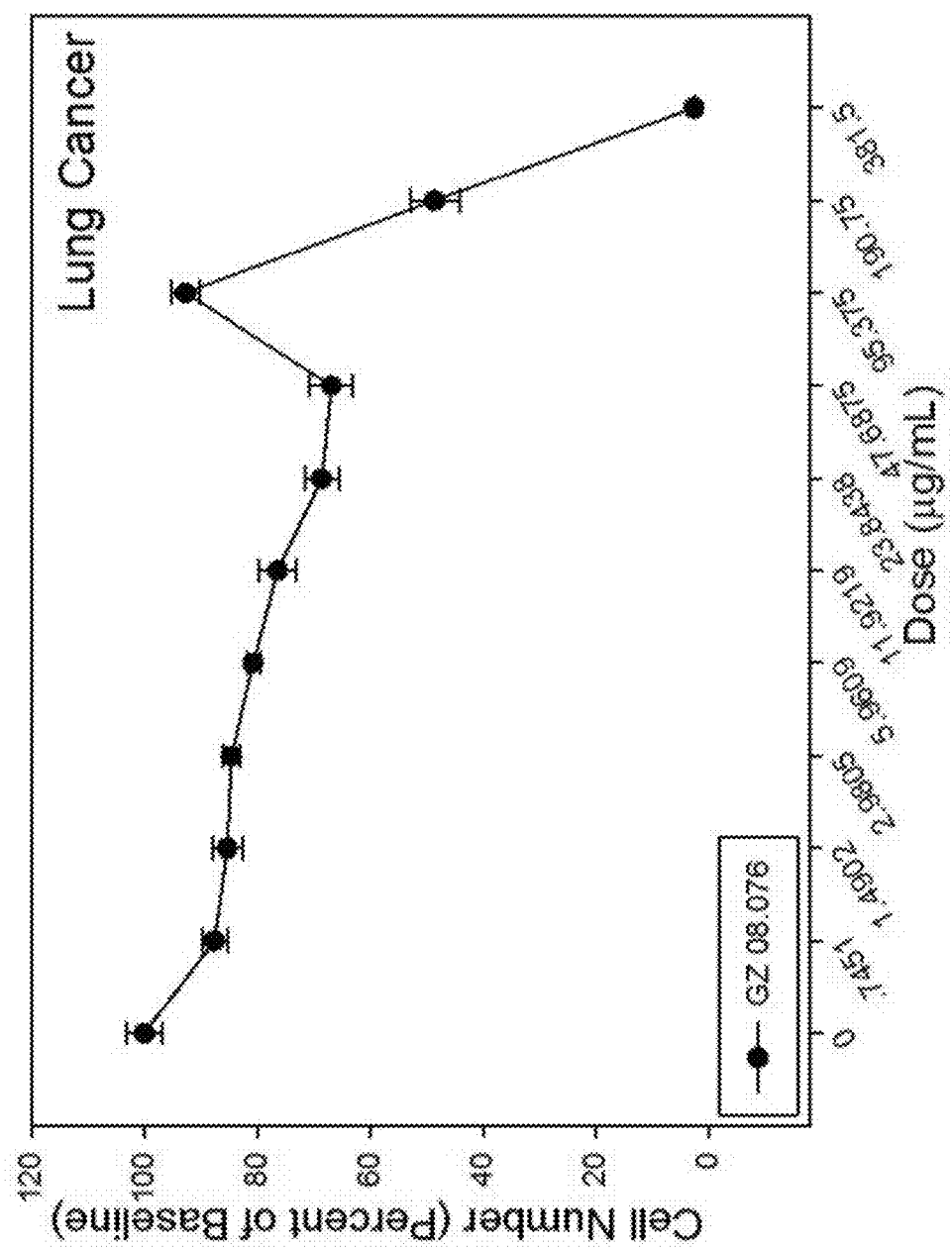
FIG. 12C is a graph illustrating the mechanisms of osteosarcoma cells death by application of GZ17-6.02, as explained in Example 12.
Figures 13, 82:
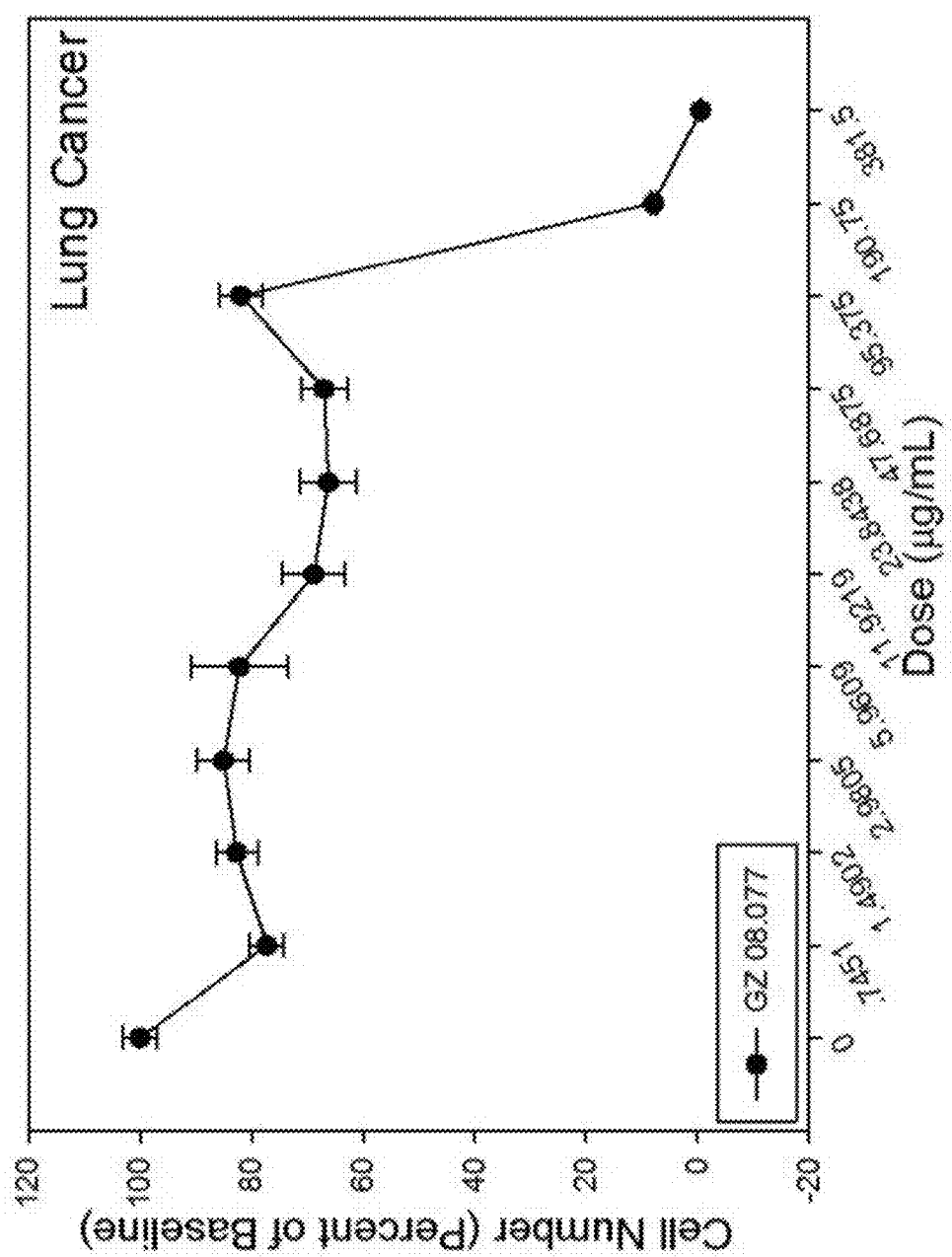
Figures 14, 82:
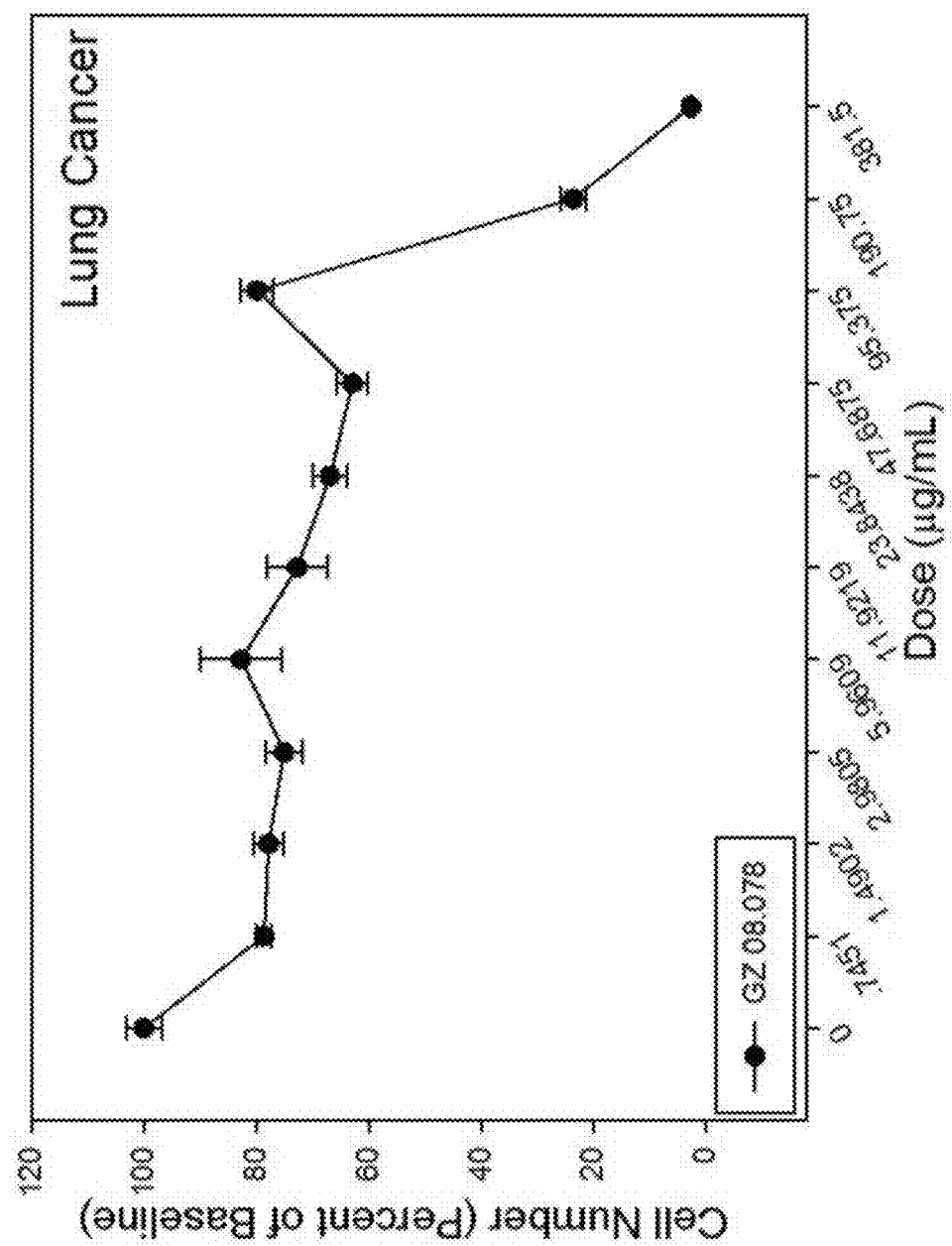
FIG. 14A is a control quantitative dot-blot, which measures the relative amount of proteins, known to be involved in cell proliferation described in Example 14, where the proteins were epidermal growth factor receptor (EGFR), extracellular-signal-regulated kinase (ERK1/2), the catalytic subunit of AMP-activated kinase (AMPKα2), β-catenin, and Chk-2.
FIG. 14B is a quantitative dot-block similar to that described in FIG. 14A, but illustrating the amounts of the test proteins upon application of GZ17-6.02, as described in Example 14.
Figures 15, 82:
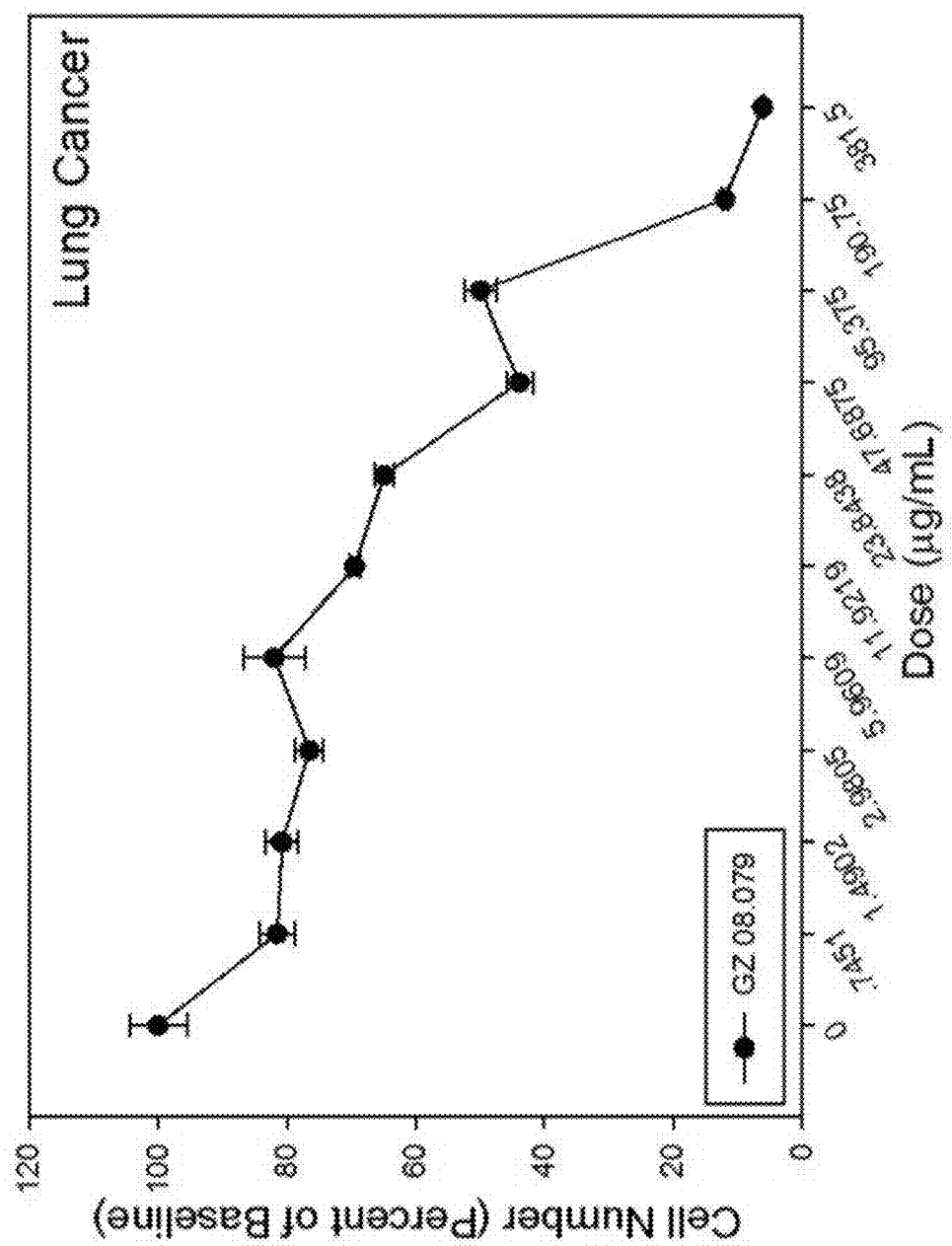
Figures 16, 82:
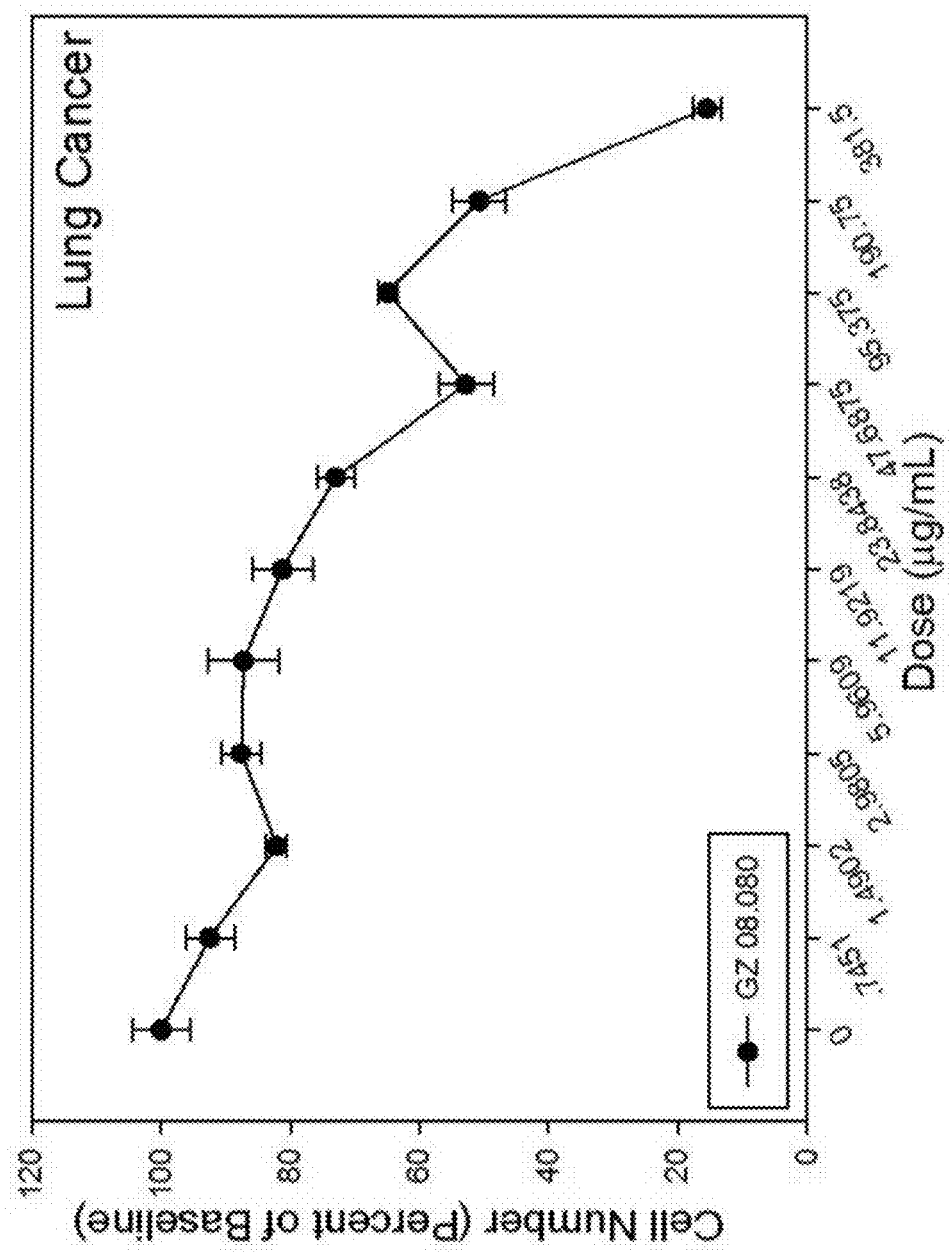
FIG. 16A is a comparative graph of tumor volume versus days after cancer cell inoculation in mice, between control inoculations (ethanol vehicle) and test inoculations containing the vehicle and GZ17-6.02, illustrating the dramatic reduction in tumor volumes in the test mice, as explained in Example 16.
Figures 17, 82:
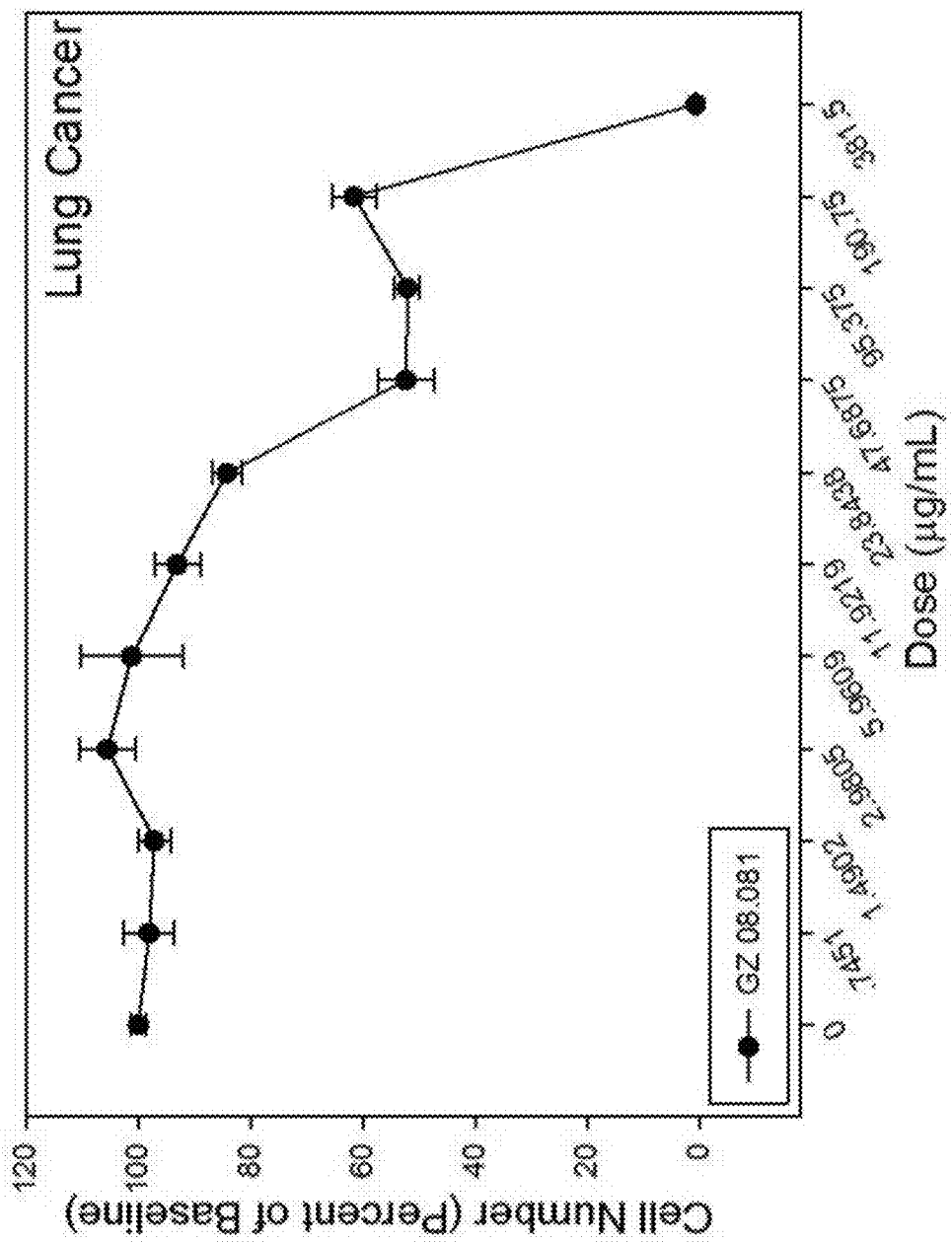
FIG. 17A is a graph of cell number versus dosage amounts of GZ17-6.02 (open circles) versus a combined product including ⅓ by weight of each GZ17-6.02 component (filled circles), tested on ovarian cancer cells, as described in Example 4.
Figures 18, 82:
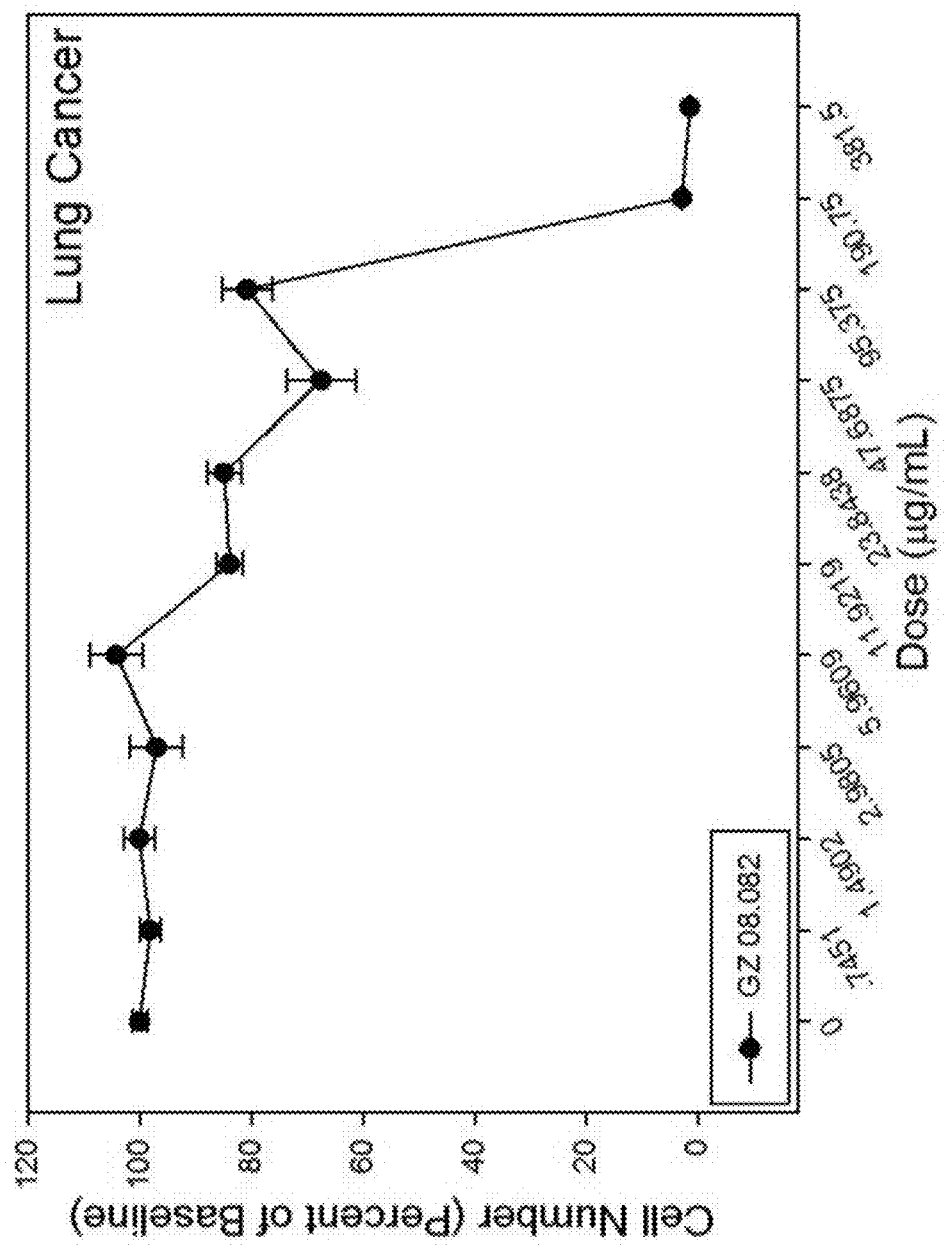
FIG. 18D is a graph of percent lymphoma cancer cell death versus different component combinations of GZ17-6.02, illustrating results using isovanillin alone, and two-component products respectively including isovanillin plus curcumin, and isovanillin plus harmine, where the isovanillin concentration was held constant throughout.
Figures 19, 82:
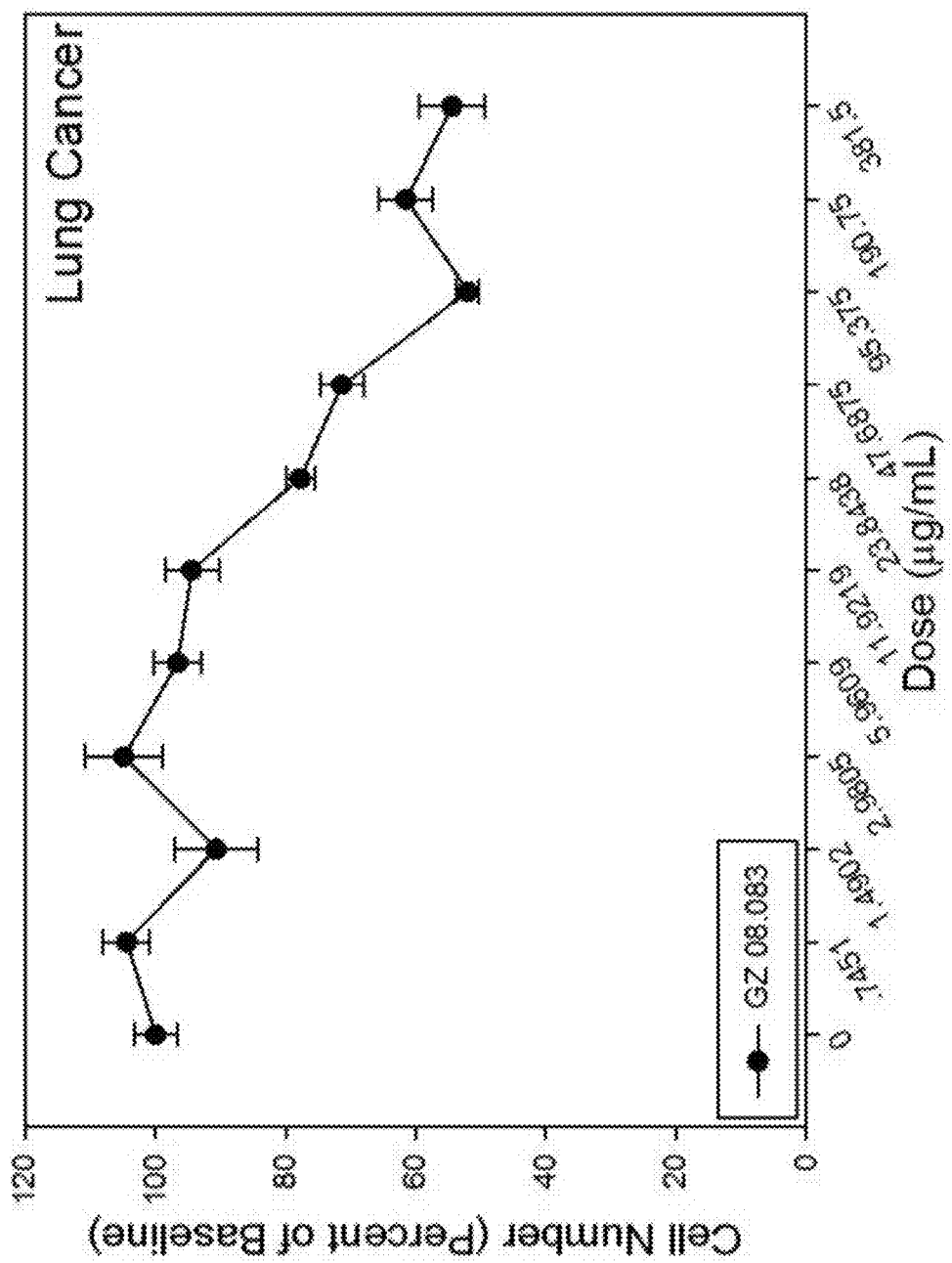
FIG. 19A is a graph of percent ovarian cancer cell death versus different component combinations of GZ17-6.02, illustrating results using curcumin alone, and two-component products respectively including curcumin plus isovanillin, and curcumin plus harmine, where the curcumin concentration was held constant throughout.
FIG. 19D is a graph of percent lymphoma cancer cell death versus different component combinations of GZ17-6.02, illustrating results using curcumin alone, and two-component products respectively including curcumin plus isovanillin, and curcumin plus harmine, where the curcumin concentration was held constant throughout.
Figures 20, 82:
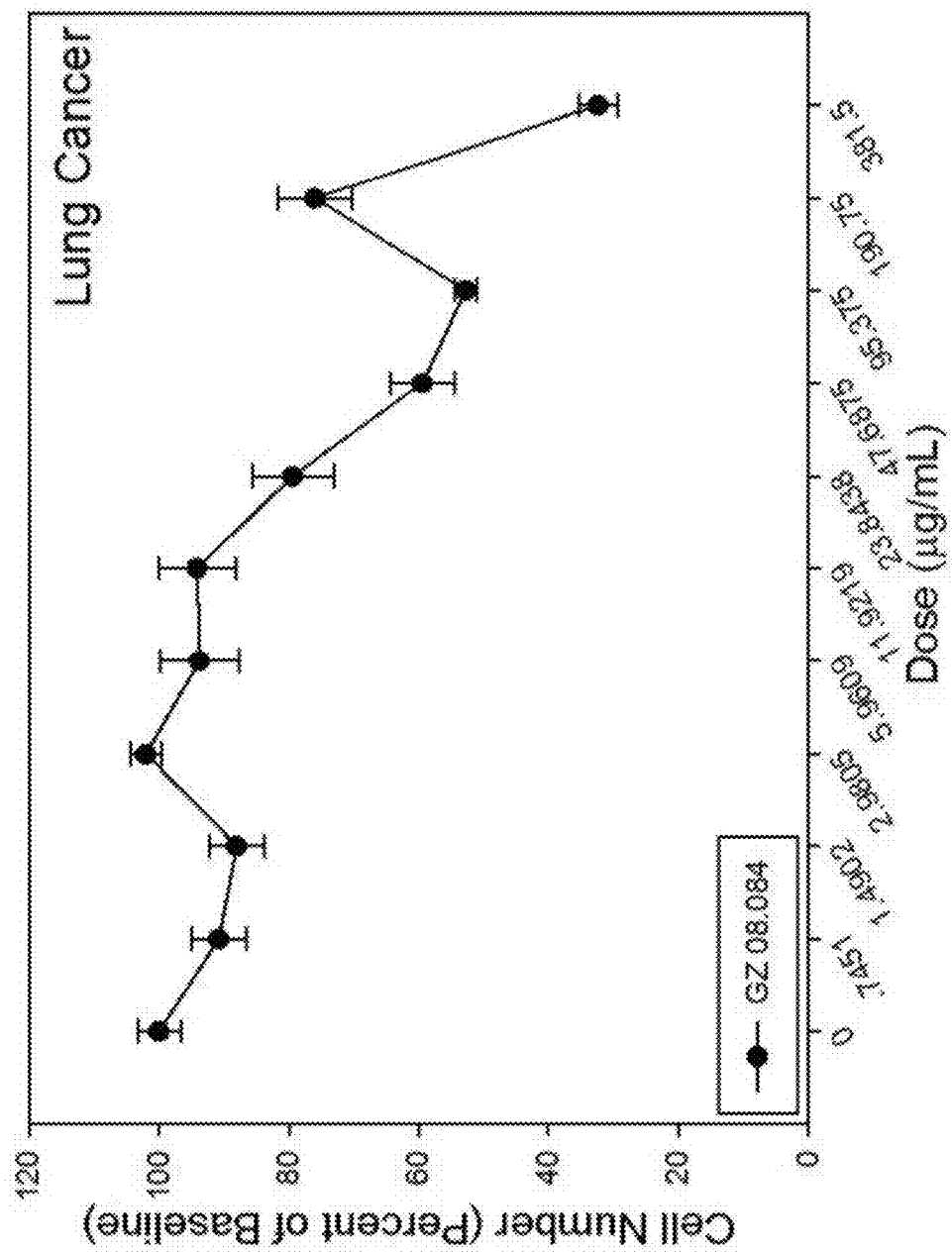
FIG. 20A is a graph of percent ovarian cancer cell death versus different component combinations of GZ17-6.02, illustrating results using harmine alone, and two-component products respectively including harmine plus isovanillin, and harmine plus curcumin, where the harmine concentration was held constant throughout.
Figures 21, 82:
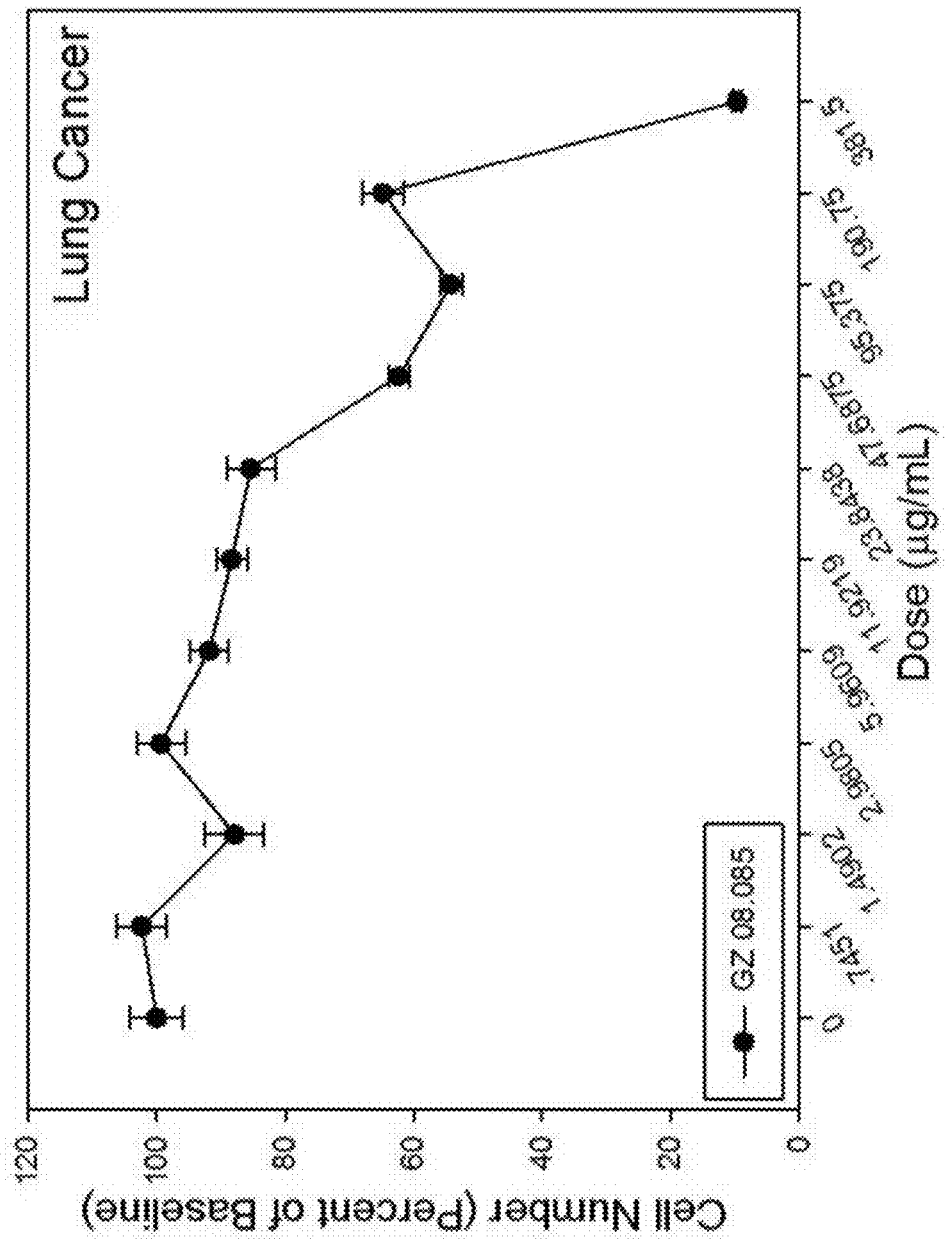
FIG. 21A is a graph of lymphoma cancer cell lethality using GZ17-6.02 at a dosage rate of 12 μg/mL, and using the three components of GZ17-6.02 individually at the concentration present in GZ17-6.02, and further illustrating the theoretical additive effect of the three components versus GZ17-6.02.
FIG. 21C is a graph of lymphoma cancer cell lethality using GZ17-6.02 at a dosage rate of 48 μg/mL, and using the three components of GZ17-6.02 individually at the concentration present in GZ17-6.02, and further illustrating the theoretical additive effect of the three components versus GZ17-6.02.
FIG. 21D is a graph of lymphoma cancer cell lethality using GZ17-6.02 at a dosage rate of 96 μg/mL, and using the three components of GZ17-6.02 individually at the concentration present in GZ17-6.02, and further illustrating the theoretical additive effect of the three components versus GZ17-6.02.
Figures 22, 82:
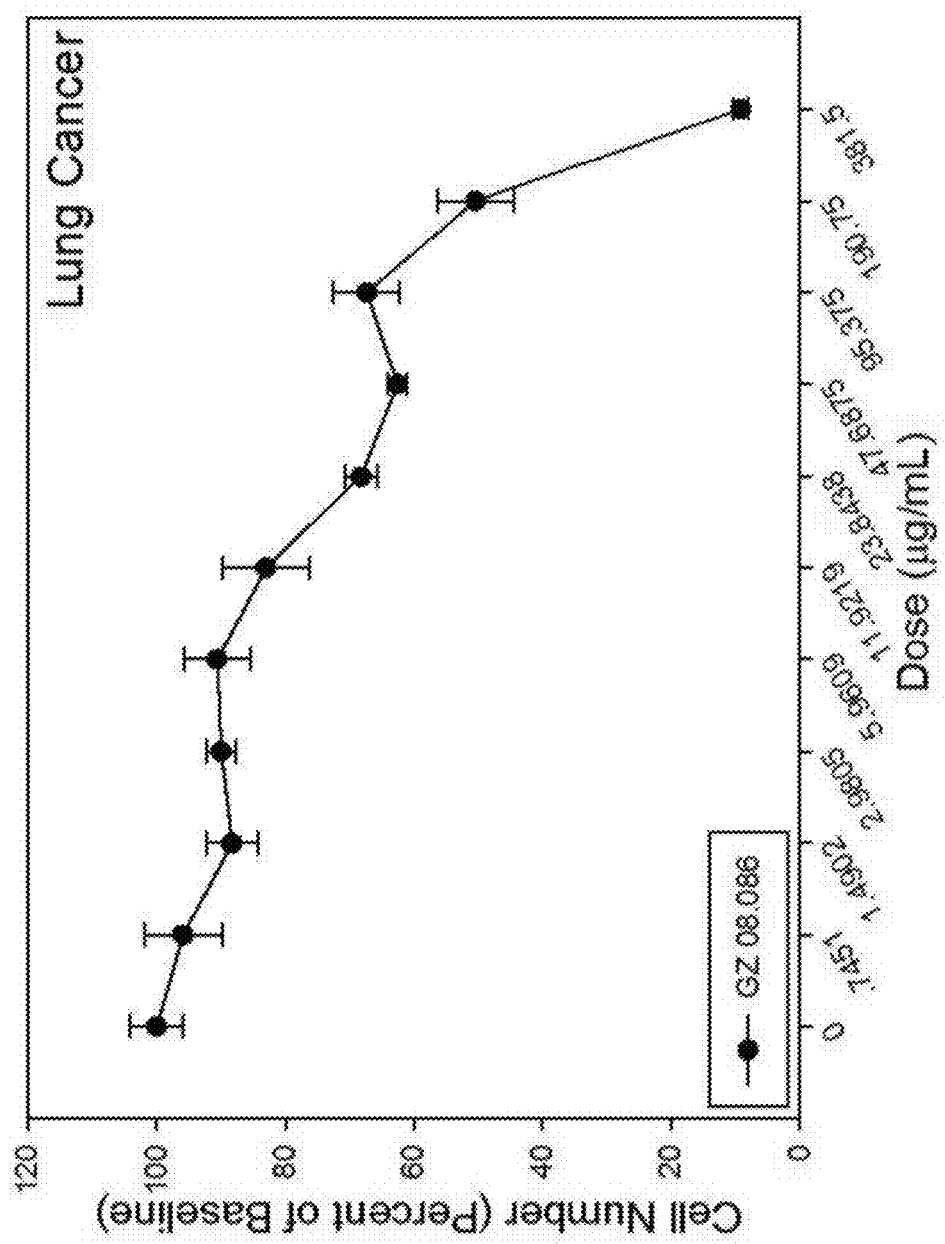
FIG. 22A is a graph of ovarian cancer cell lethality using GZ17-6.02 at a dosage rate of 12 μg/mL, and using the three components of GZ17-6.02 individually at the concentration present in GZ17-6.02, and further illustrating the theoretical additive effect of the three components versus GZ17-6.02.
Figures 23, 82:
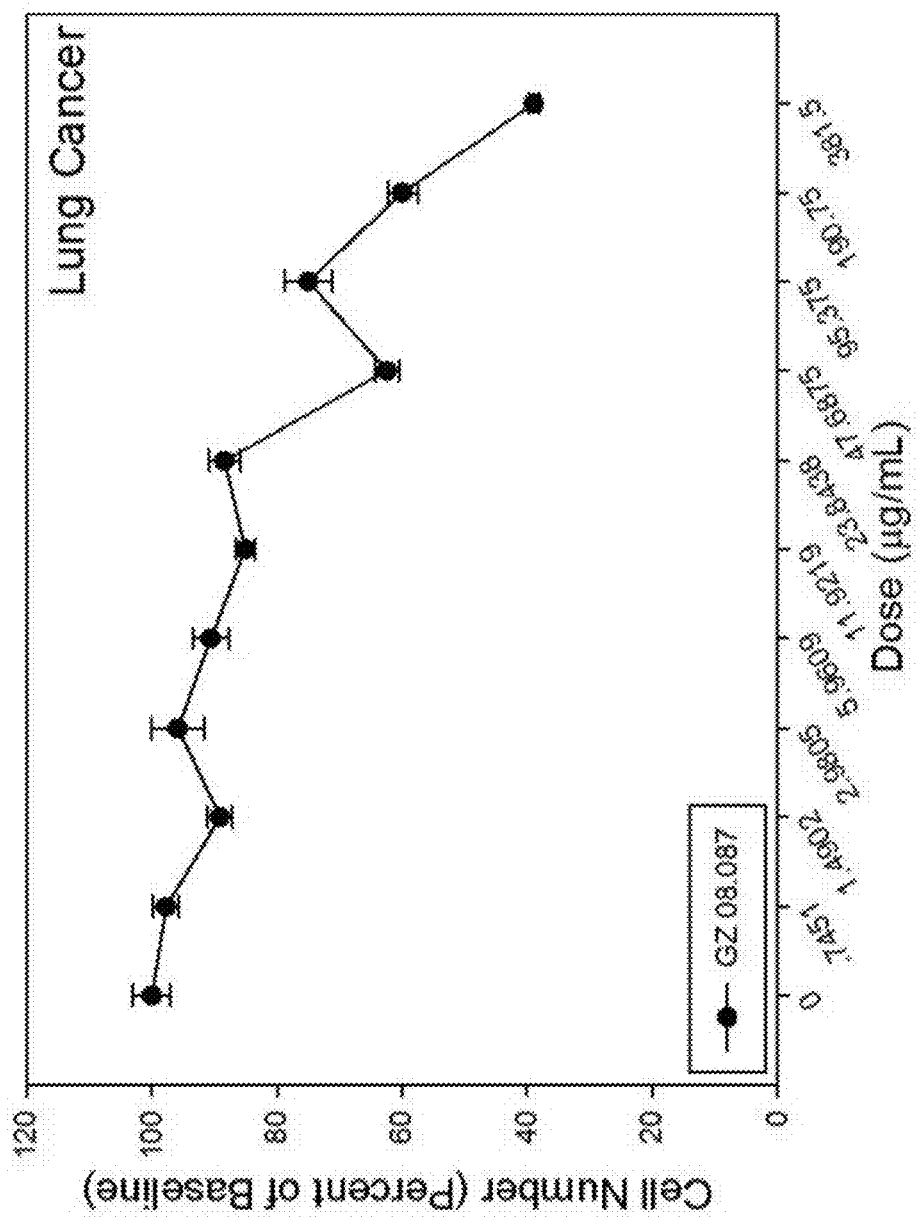
FIG. 23A is a graph of lung cancer cell number versus increasing dosage amounts of vanillin alone, as described in Example 1.
FIG. 23C is a graph of lung cancer cell number versus increasing dosage amounts of O-vanillin alone, as described in Example 1.
FIG. 23G is a graph of ovarian cancer cell number versus increasing dosage amounts of O-vanillin alone, as described in Example 1.
FIG. 23J is a graph of prostate cancer cell number versus increasing dosage amounts of isovanillic acid alone, as described in Example 1.
Figures 24, 82:
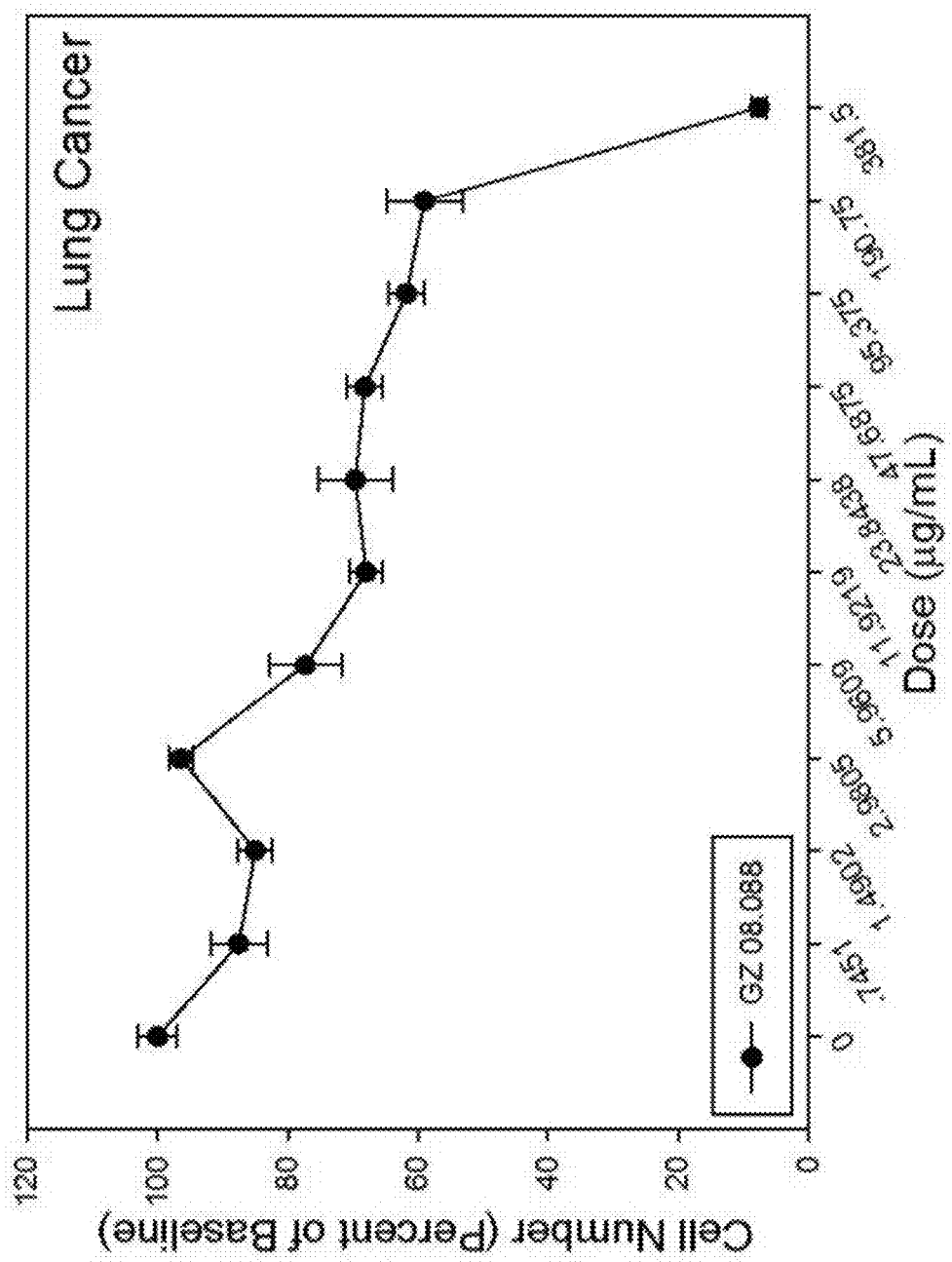
FIG. 24K is a graph of prostate cancer cell number versus increasing dosage amounts of harmaline alone, as described in Example 1.
FIG. 24M is a graph of prostate cancer cell number versus increasing dosage amounts of harmol hydrochloride alone, as described in Example 1.
Figures 25, 82:
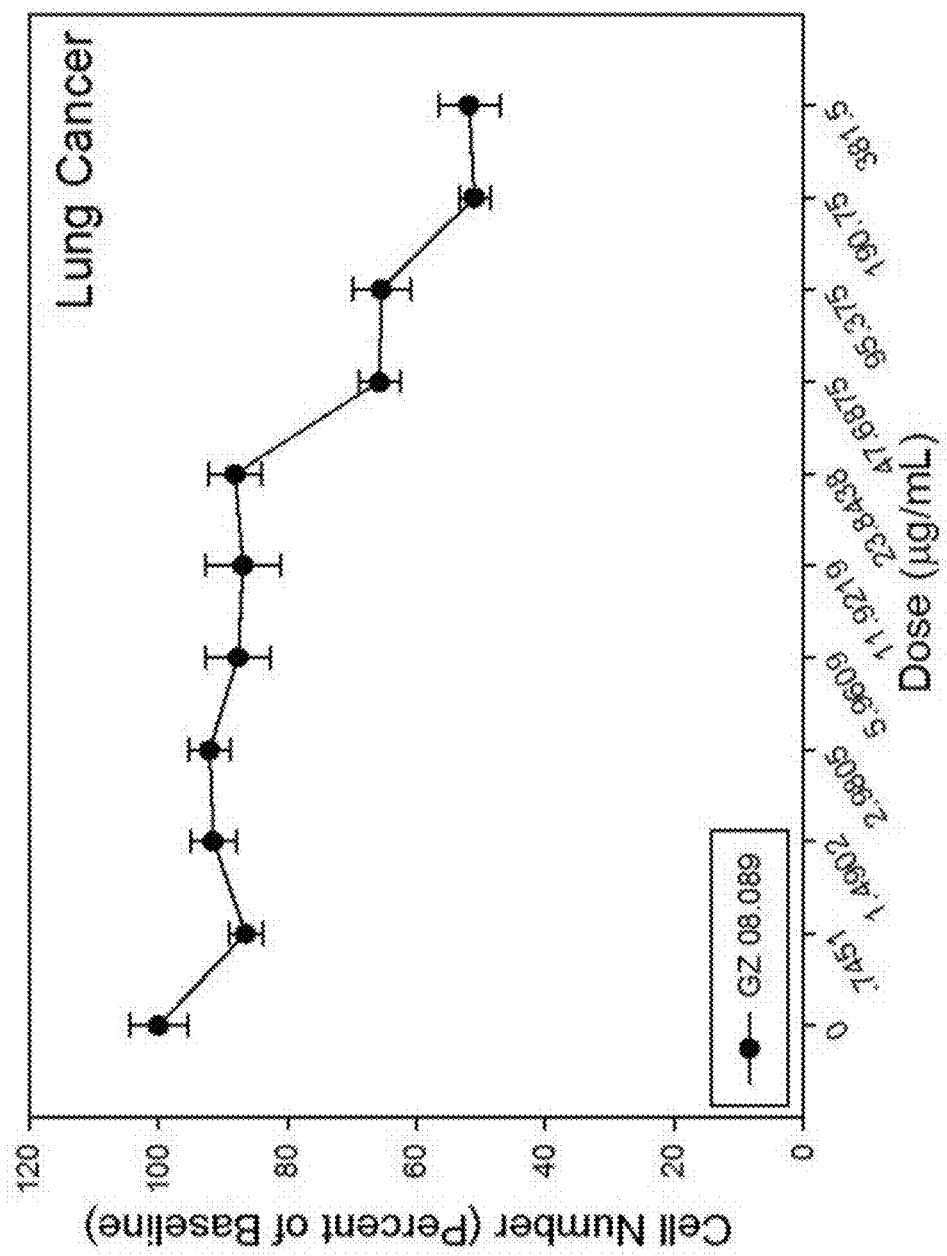
FIG. 25B is a graph of ovarian cancer cell number versus increasing dosage amounts of bisdemethoxy curcumin alone, as described in Example 1.
Figures 26, 82:
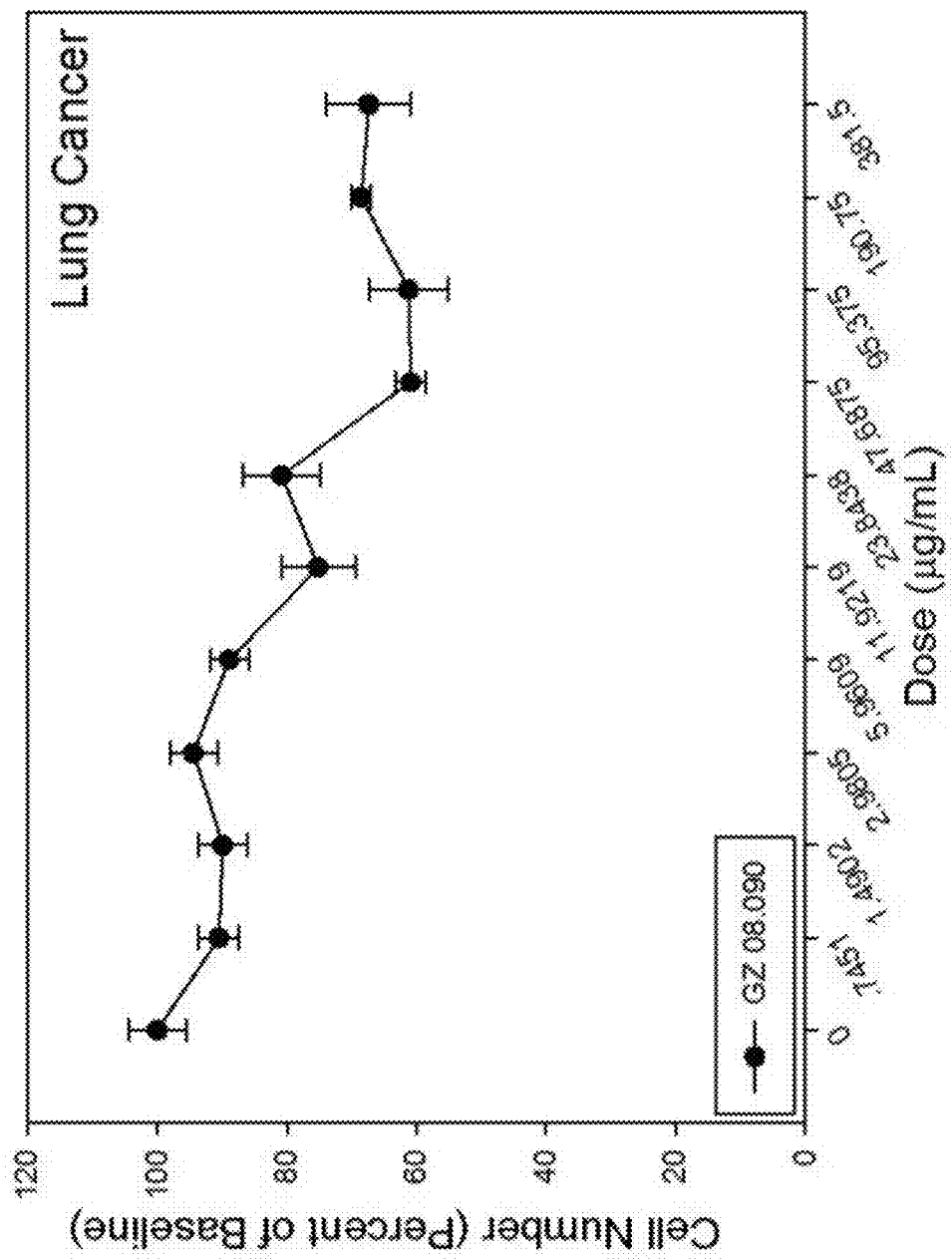
Figures 27, 82:
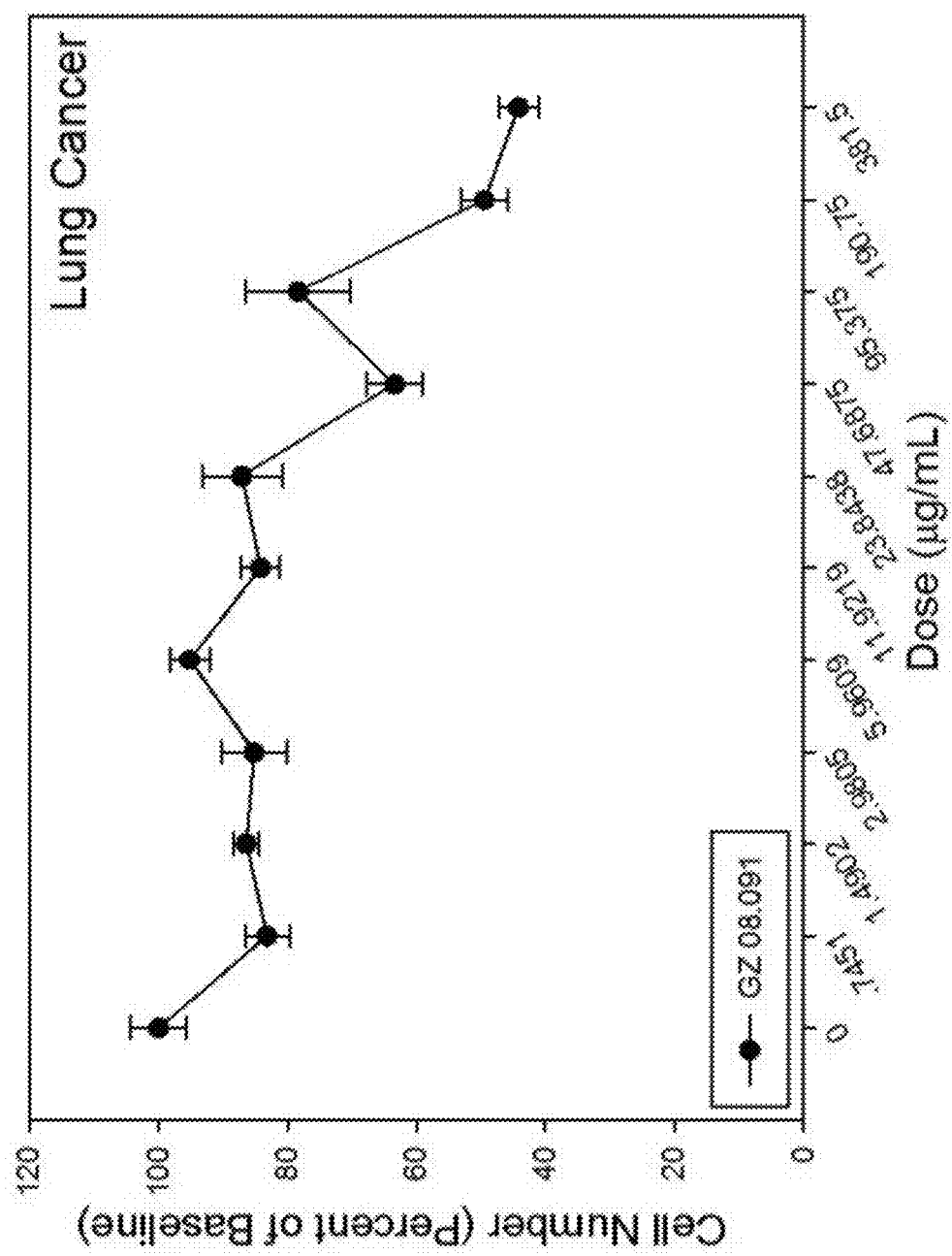
Figures 28, 82:
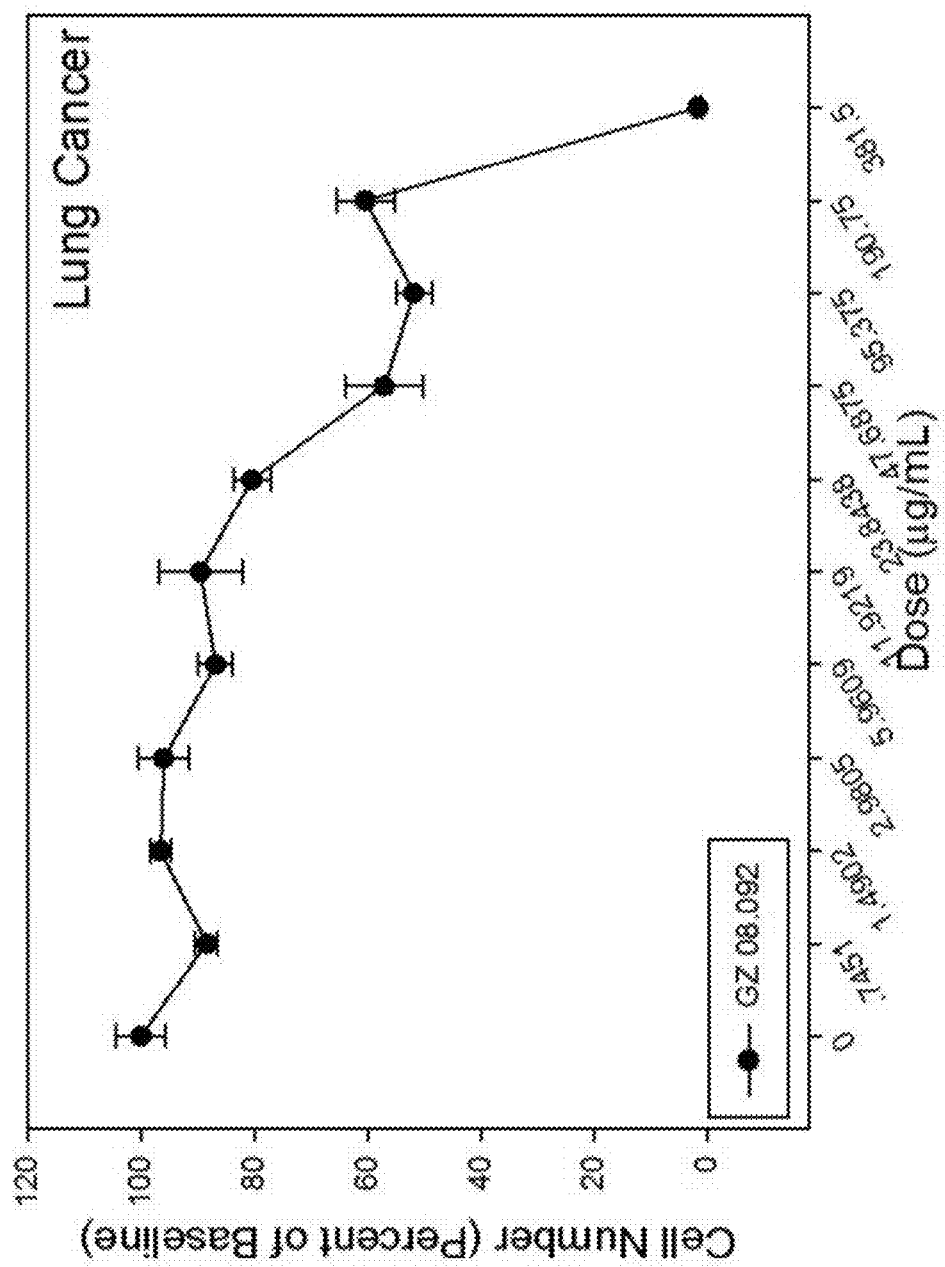
Figures 29, 82:
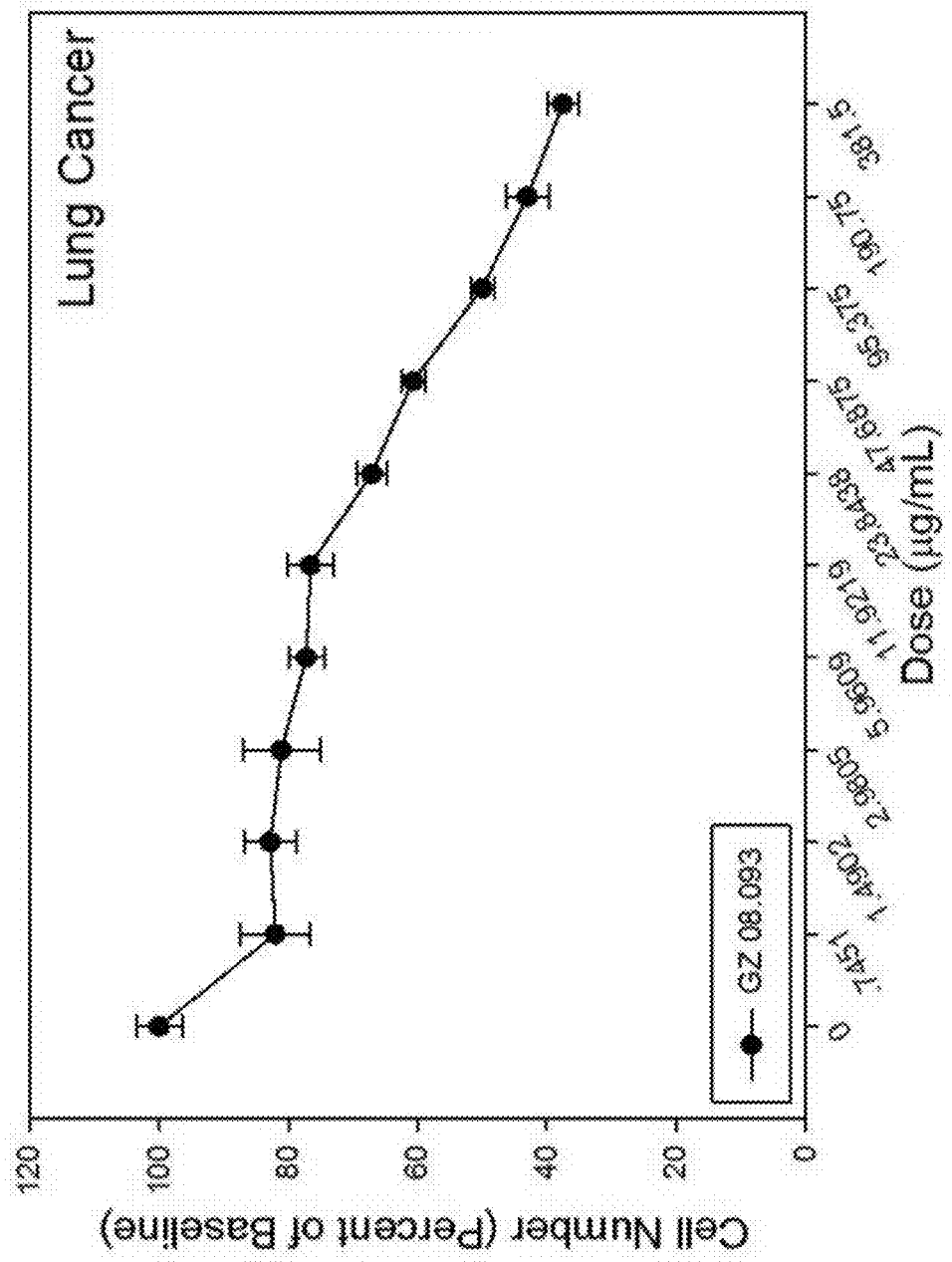
Figures 30, 82:
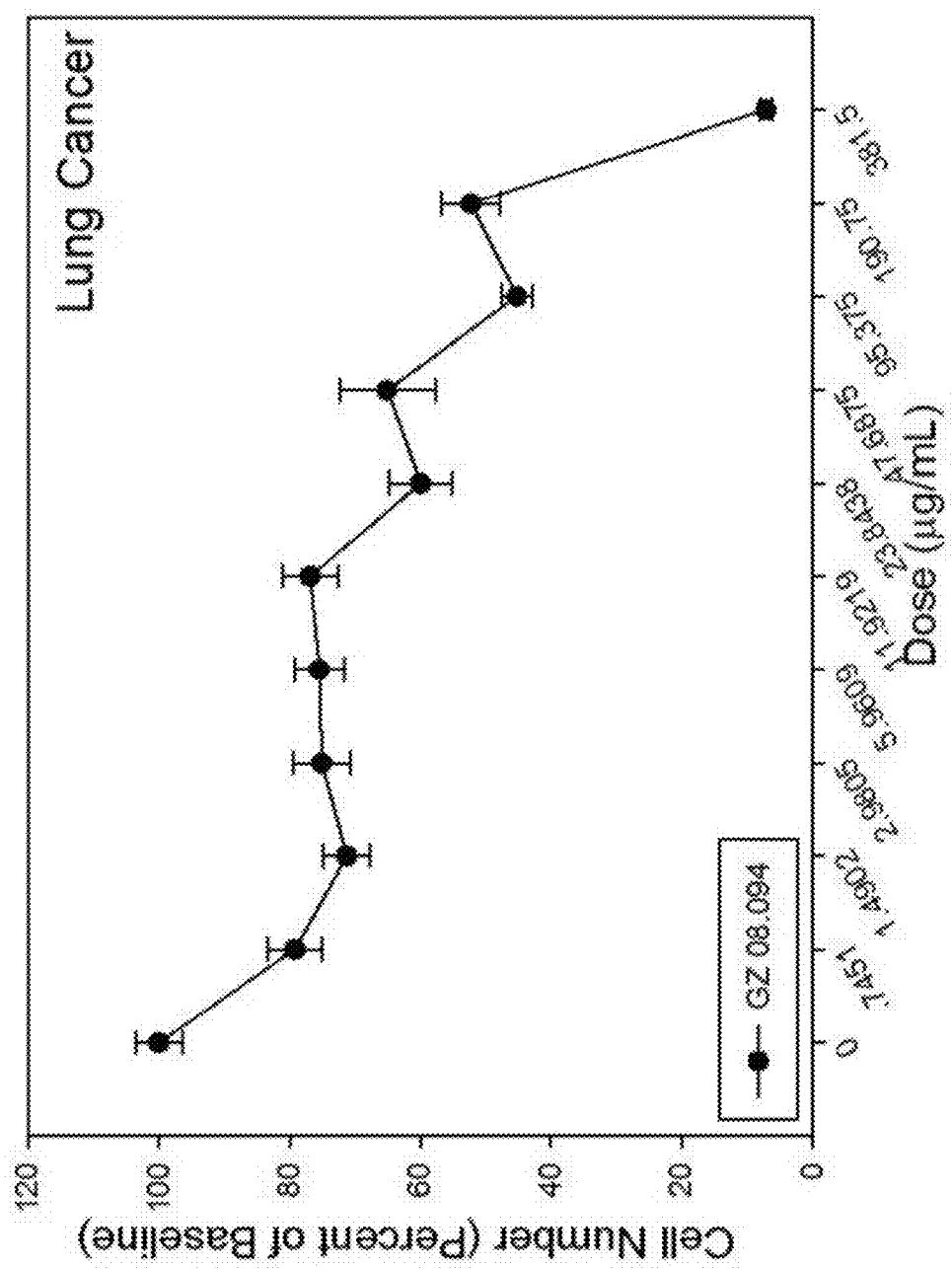
Figures 31, 82:
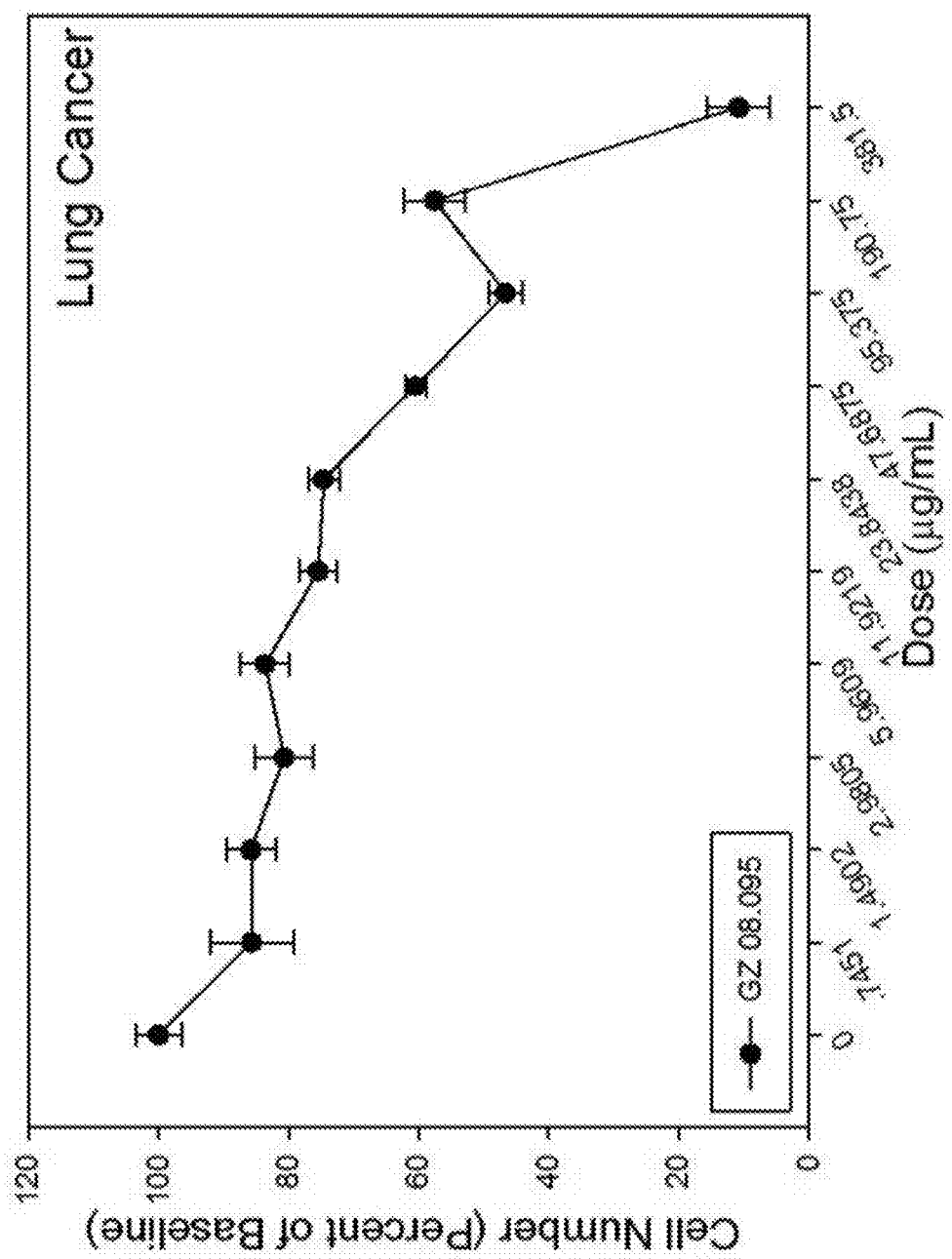
Figures 32, 82:
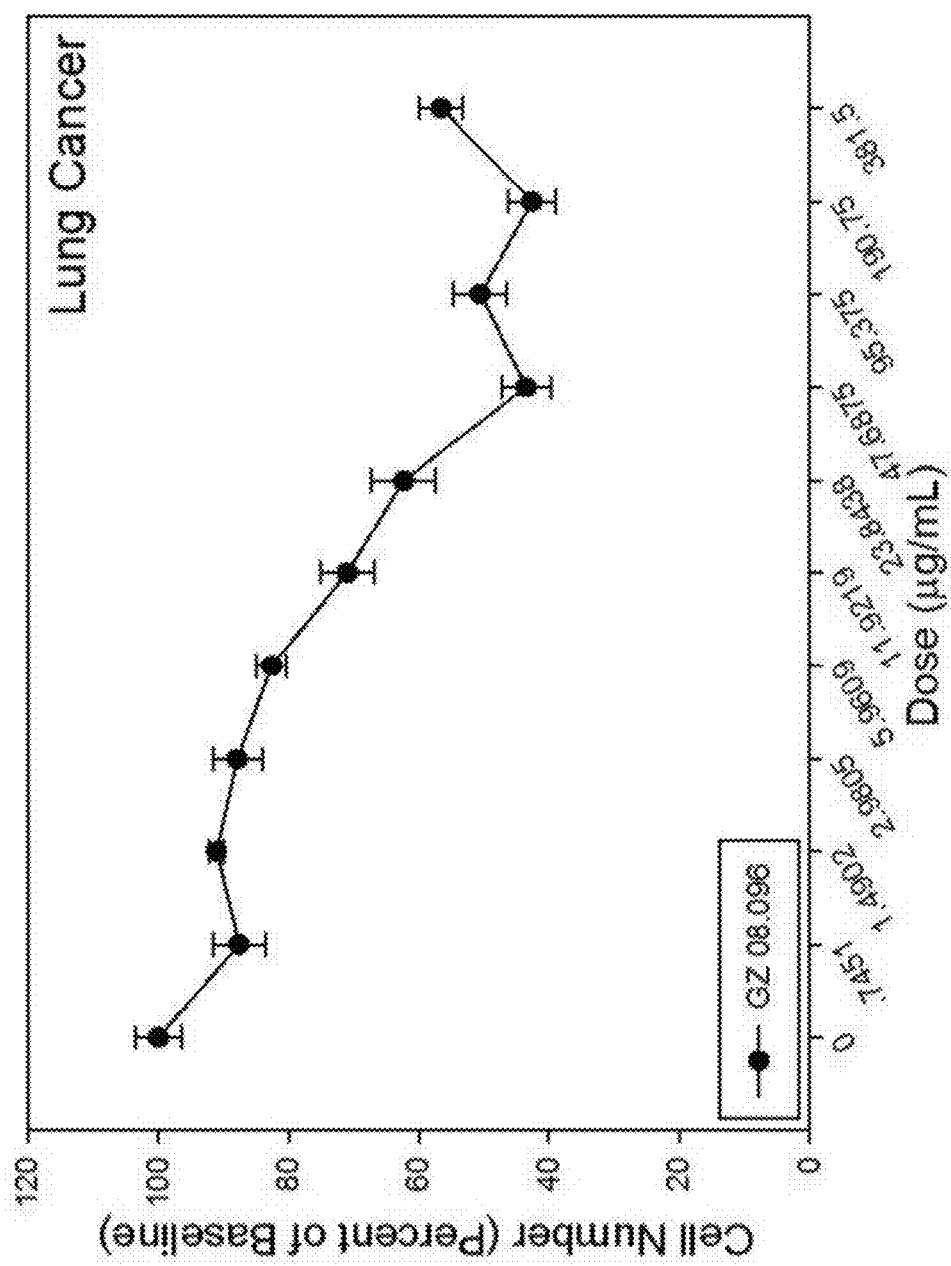
Figures 33, 82:
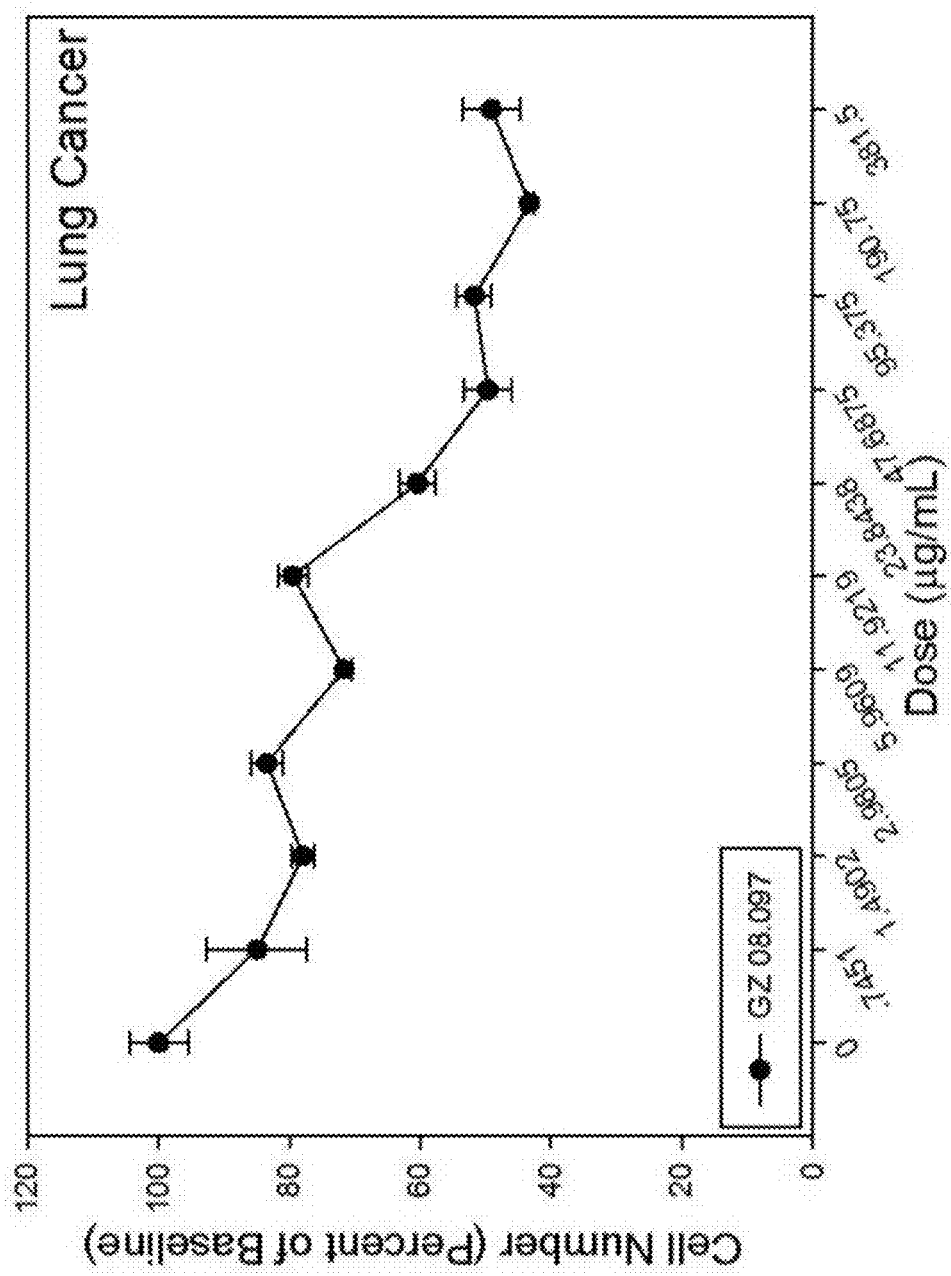
Figures 34, 82:
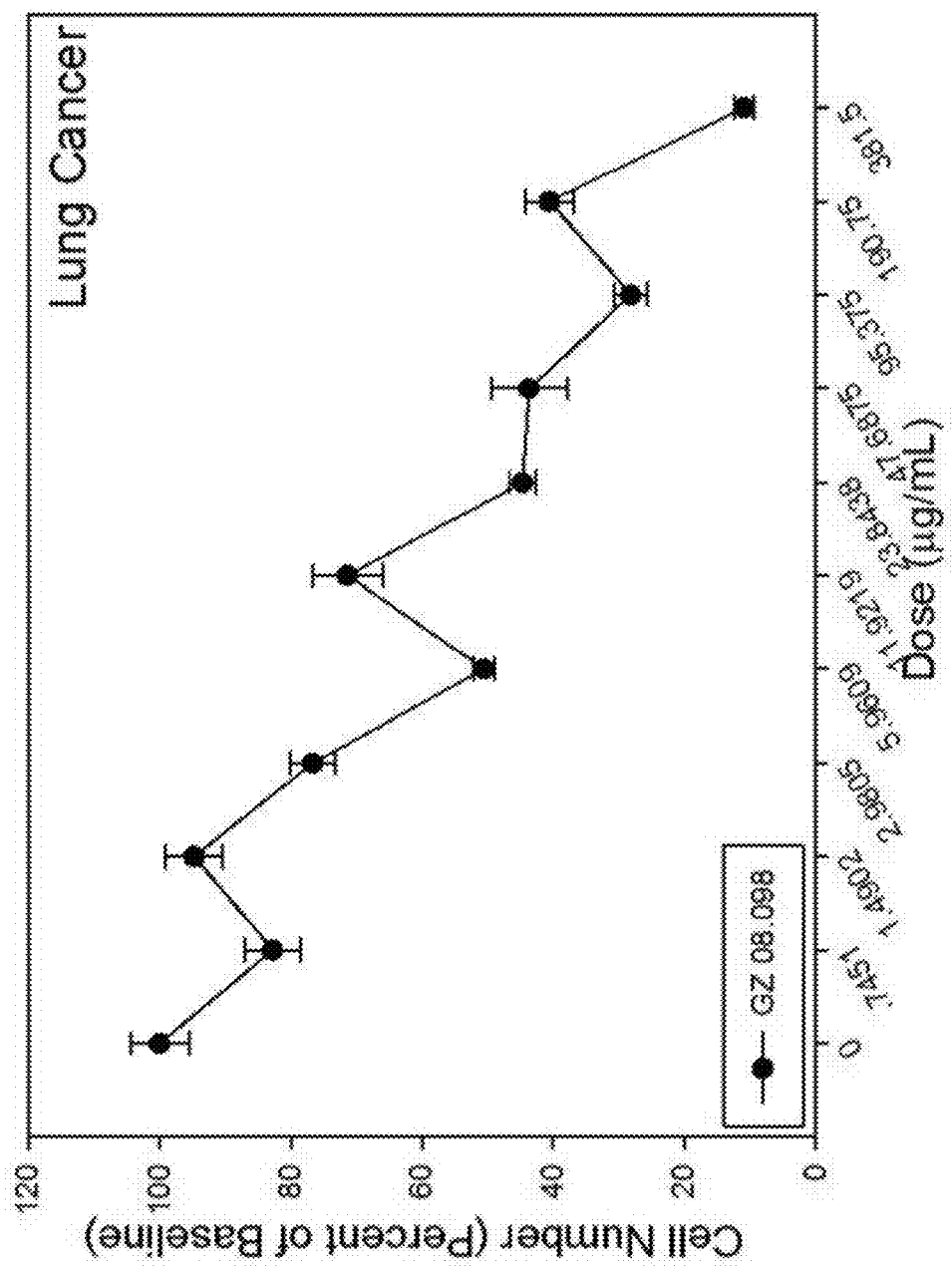
Figures 35, 82:
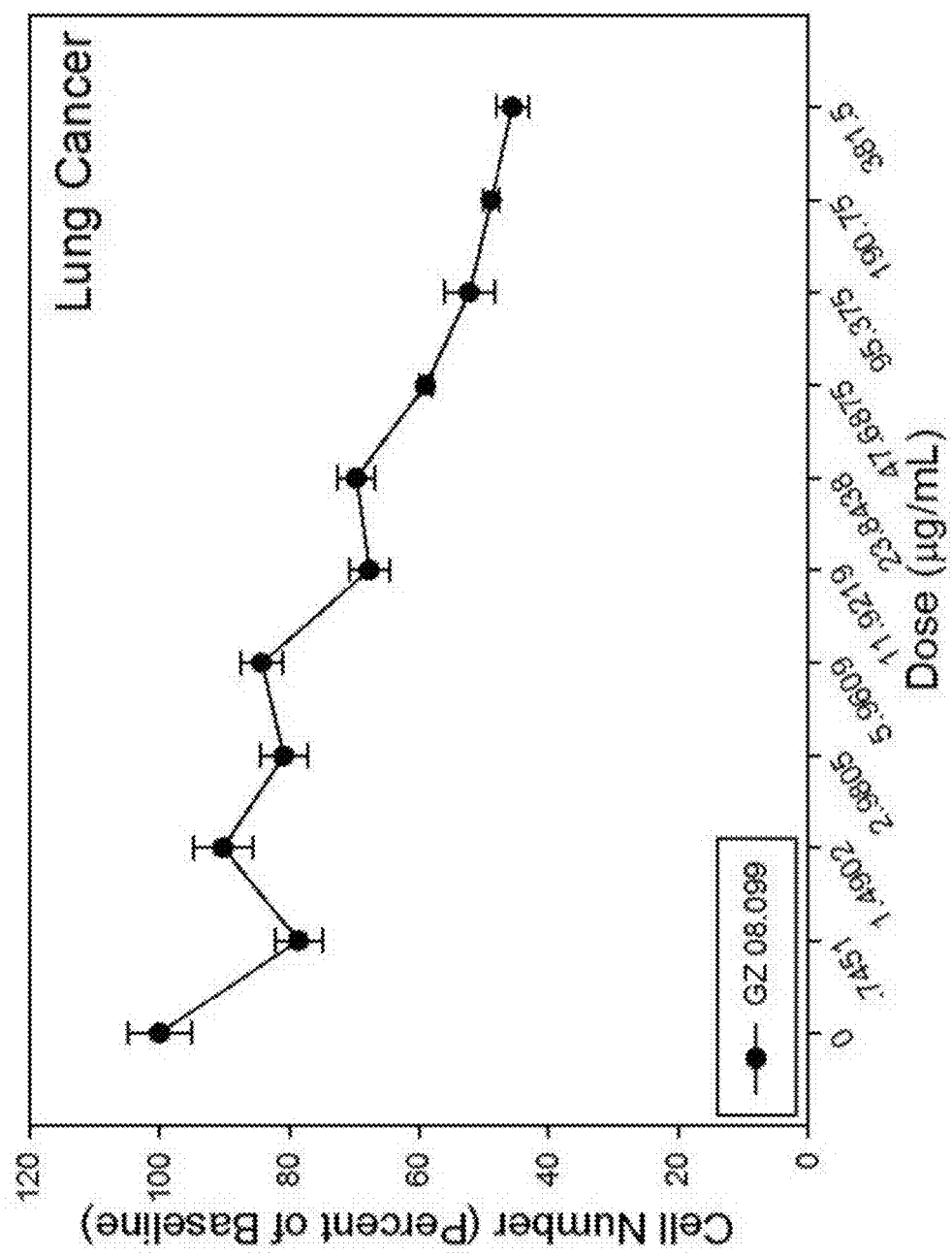
Figures 36, 82:
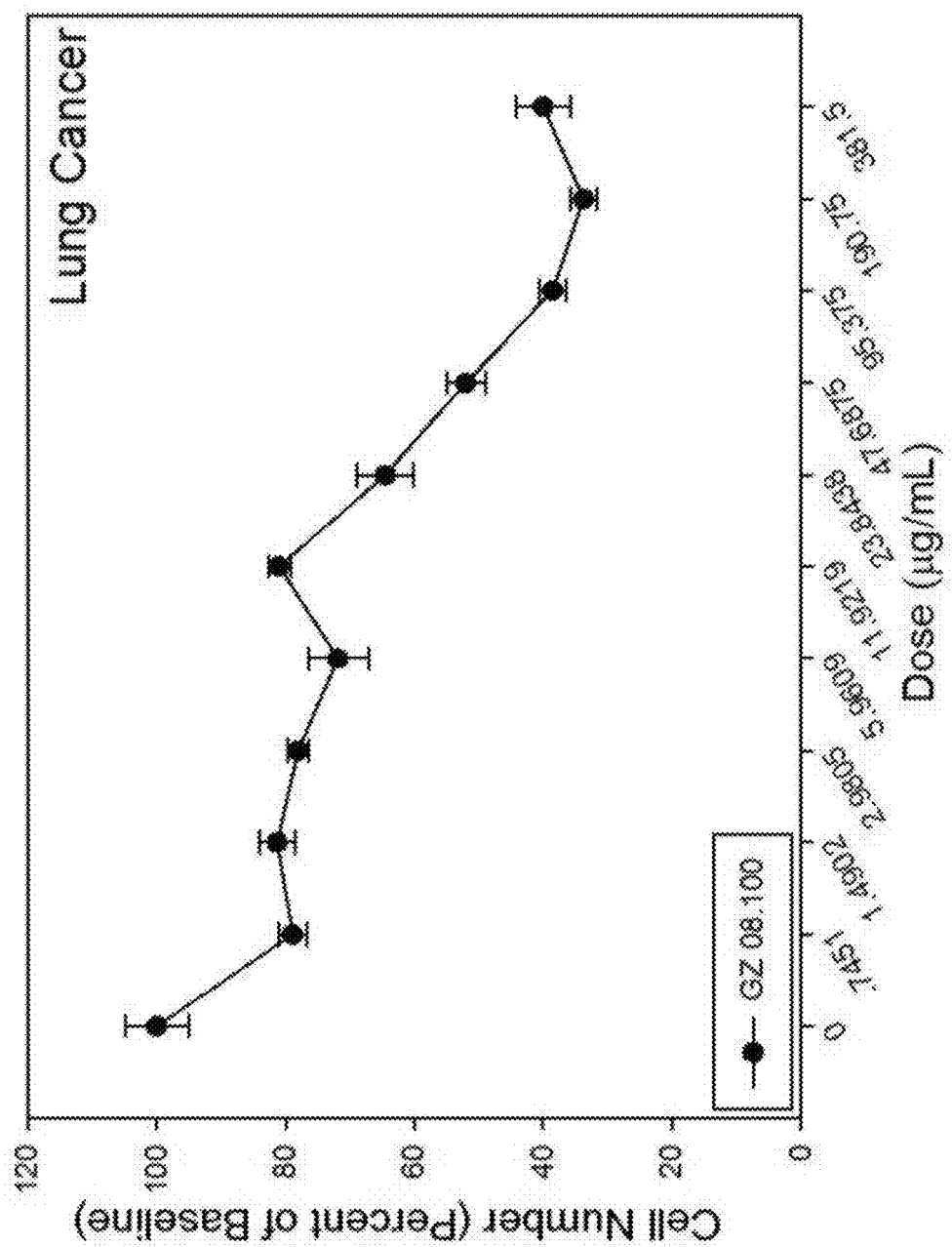
Figures 37, 82:
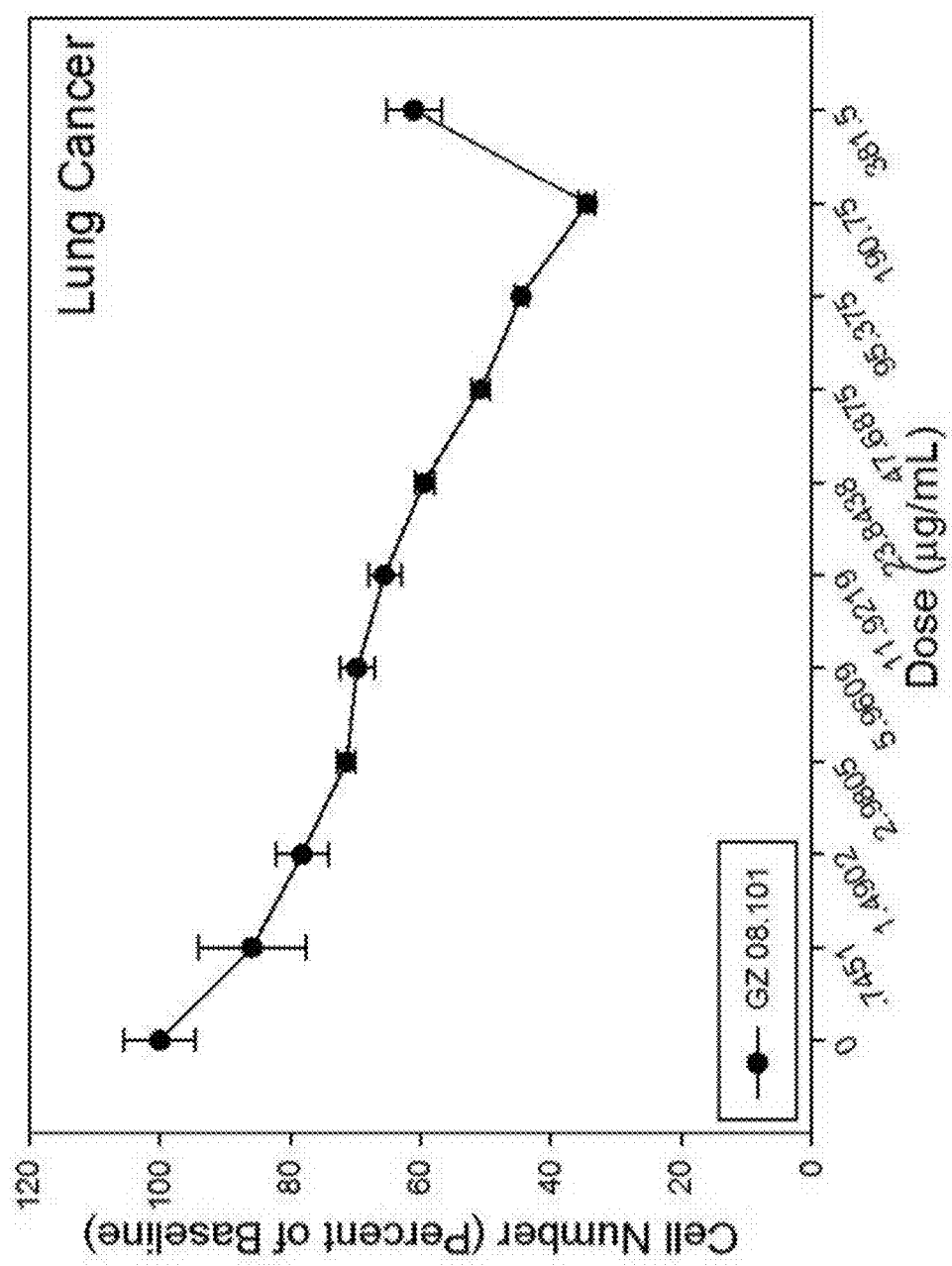
Figures 38, 82:
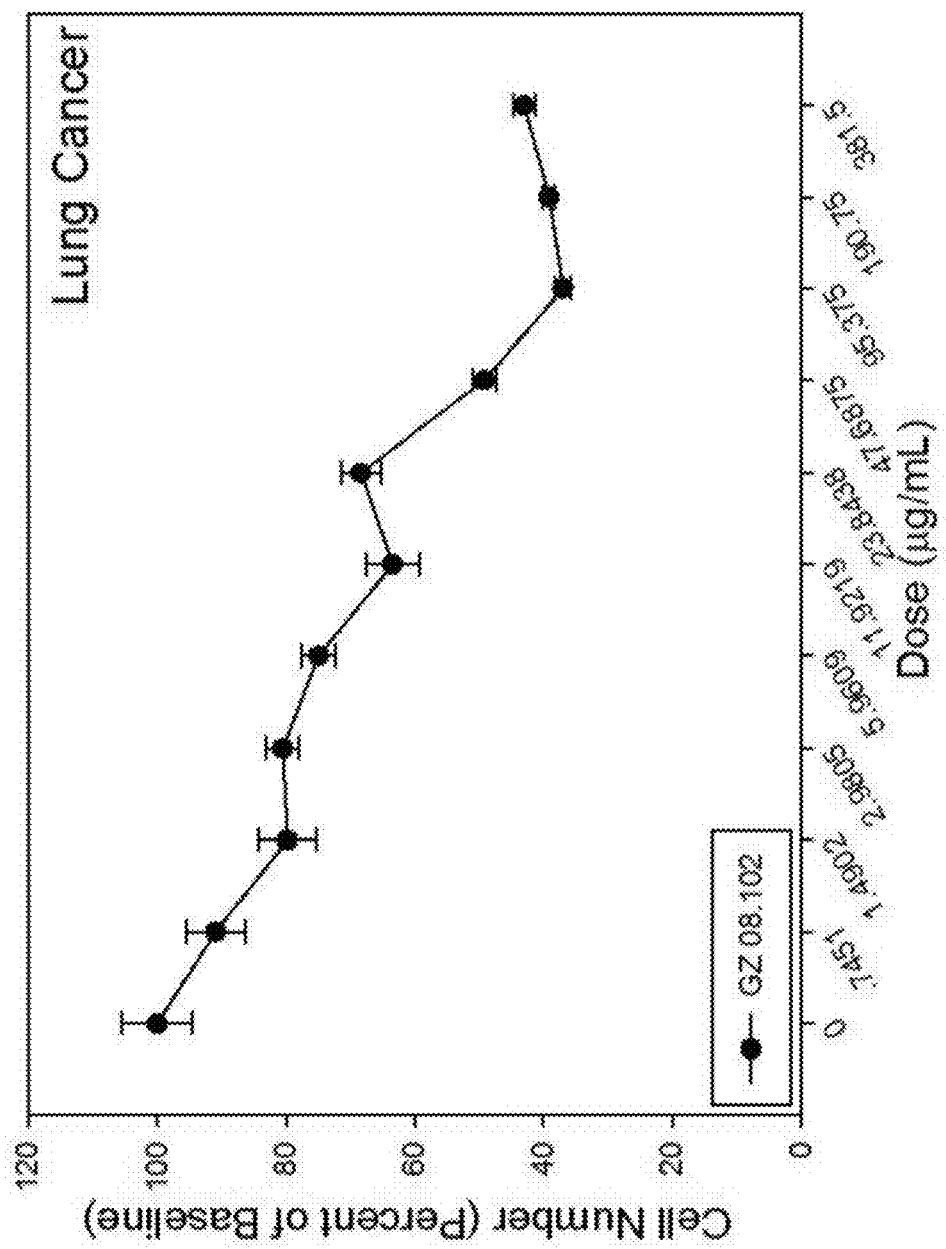
Figures 39, 82:
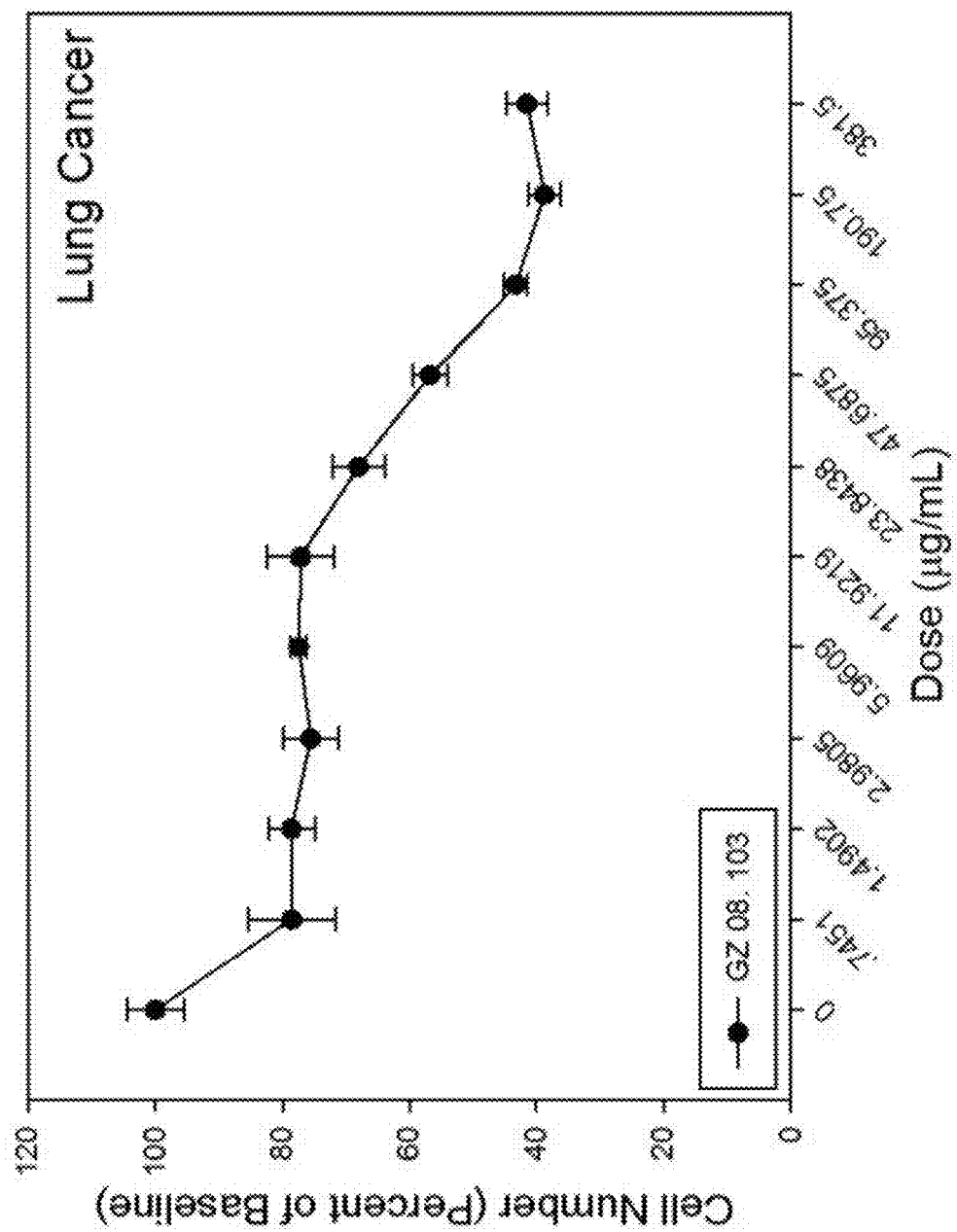
Figures 40, 82:
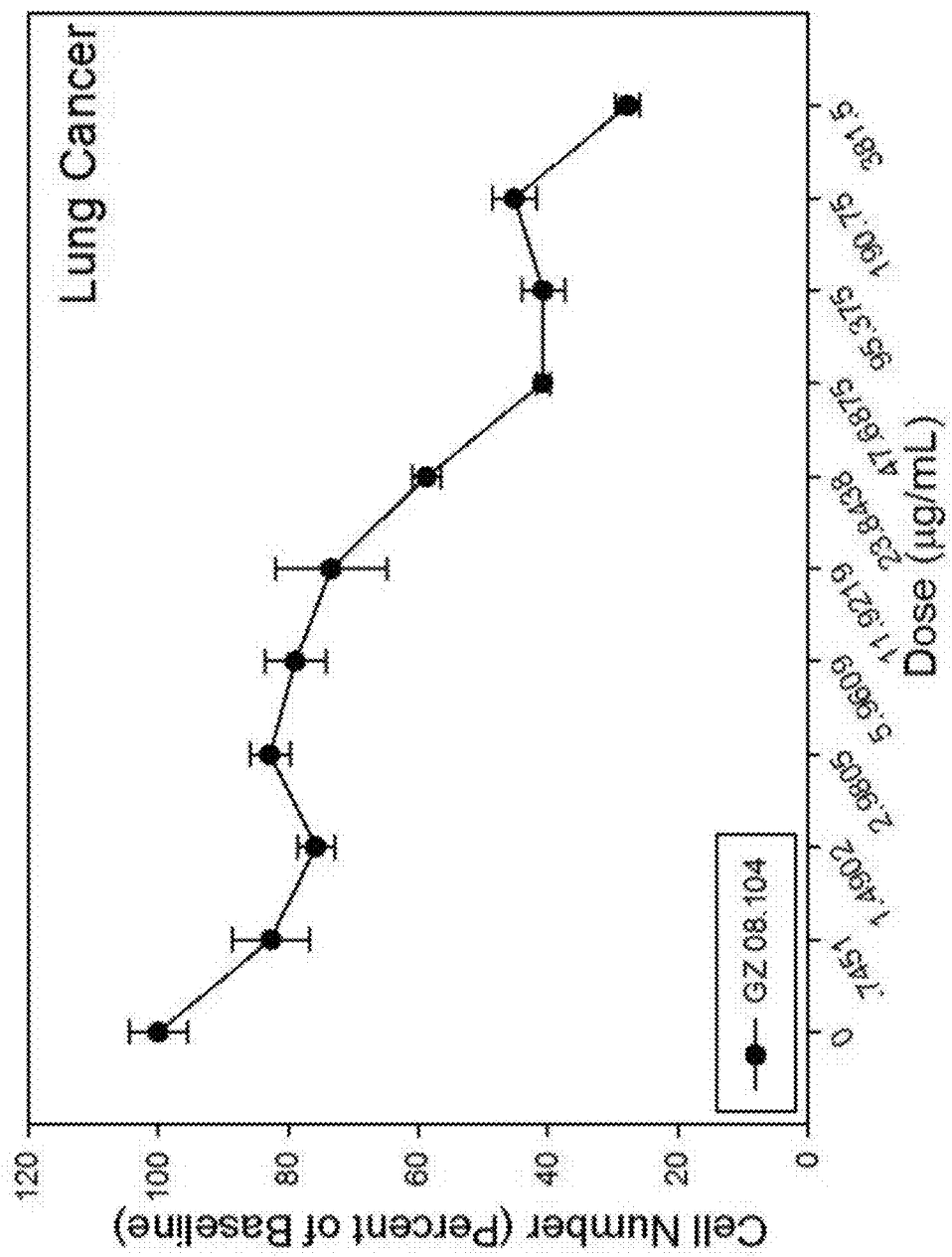
Figures 41, 82:
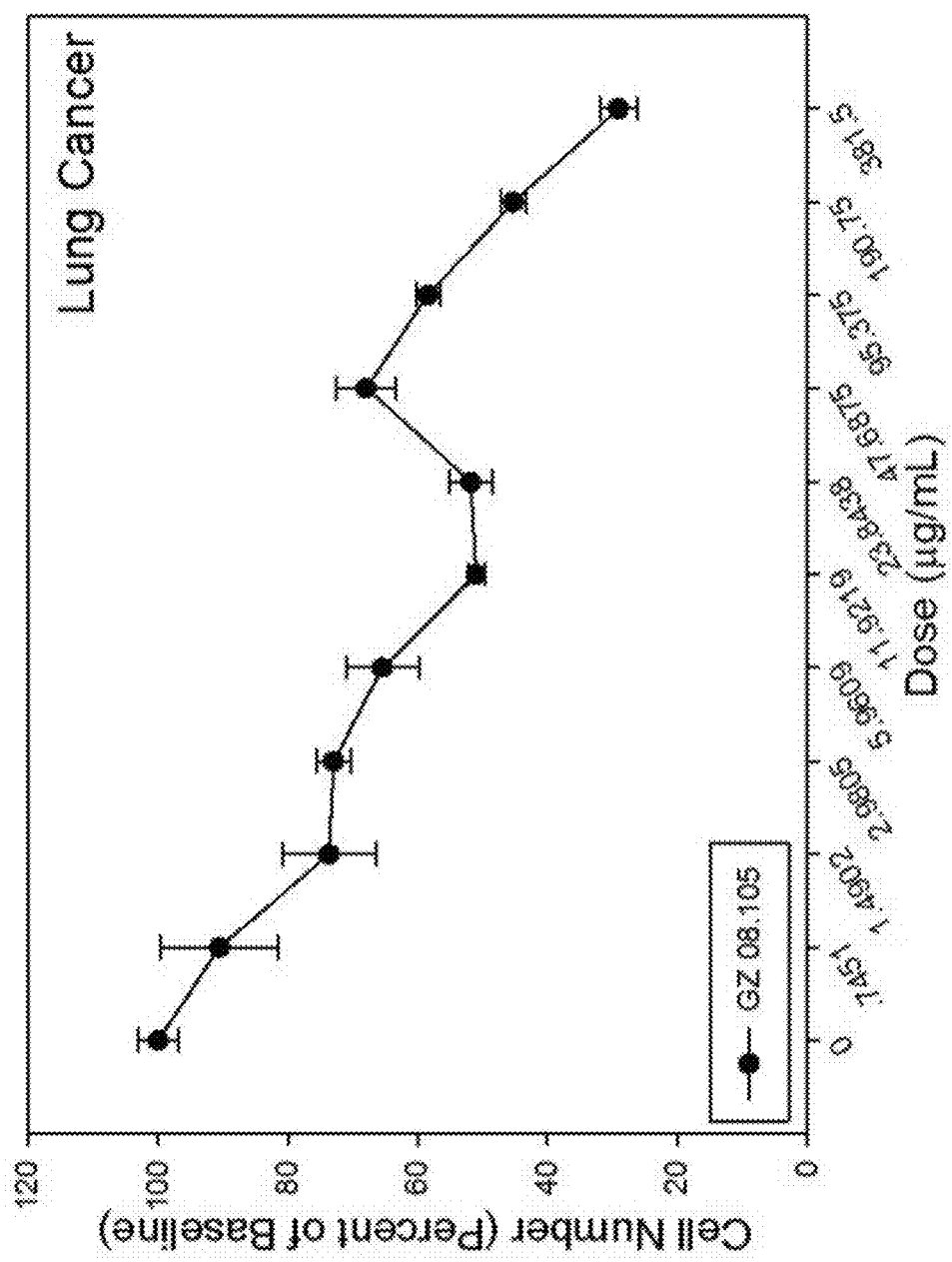
Figures 42, 82:
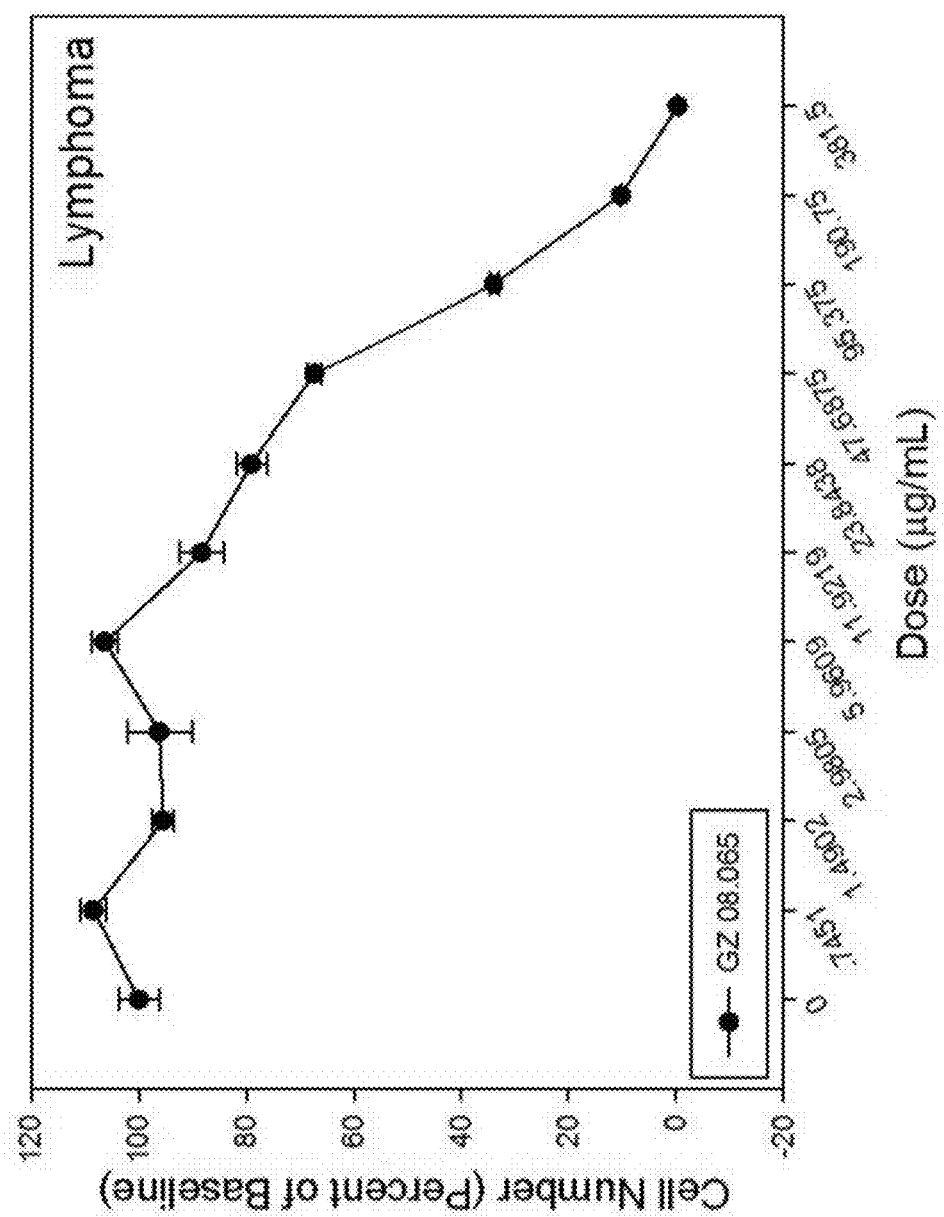
Figures 43, 82:
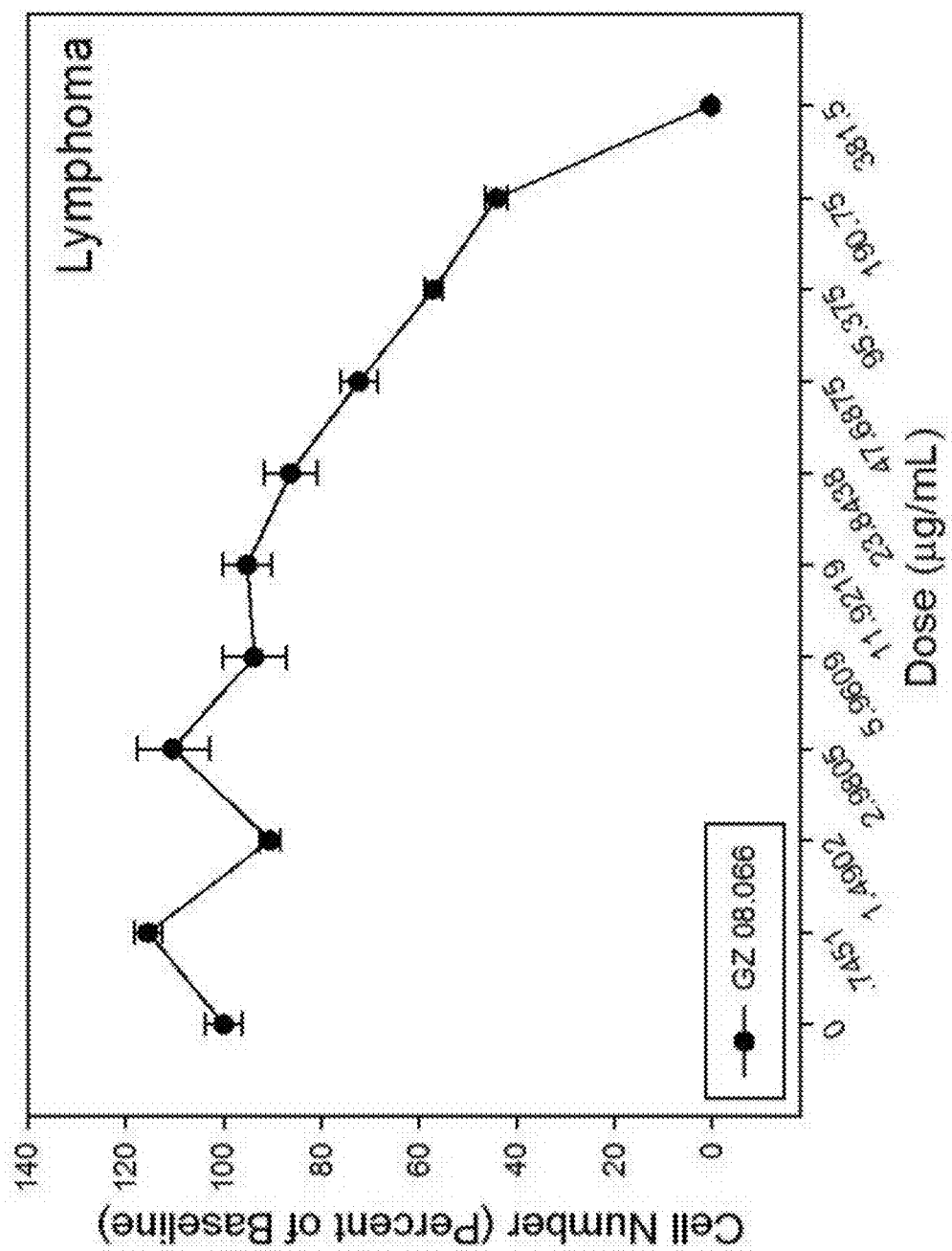
Figures 44, 82:
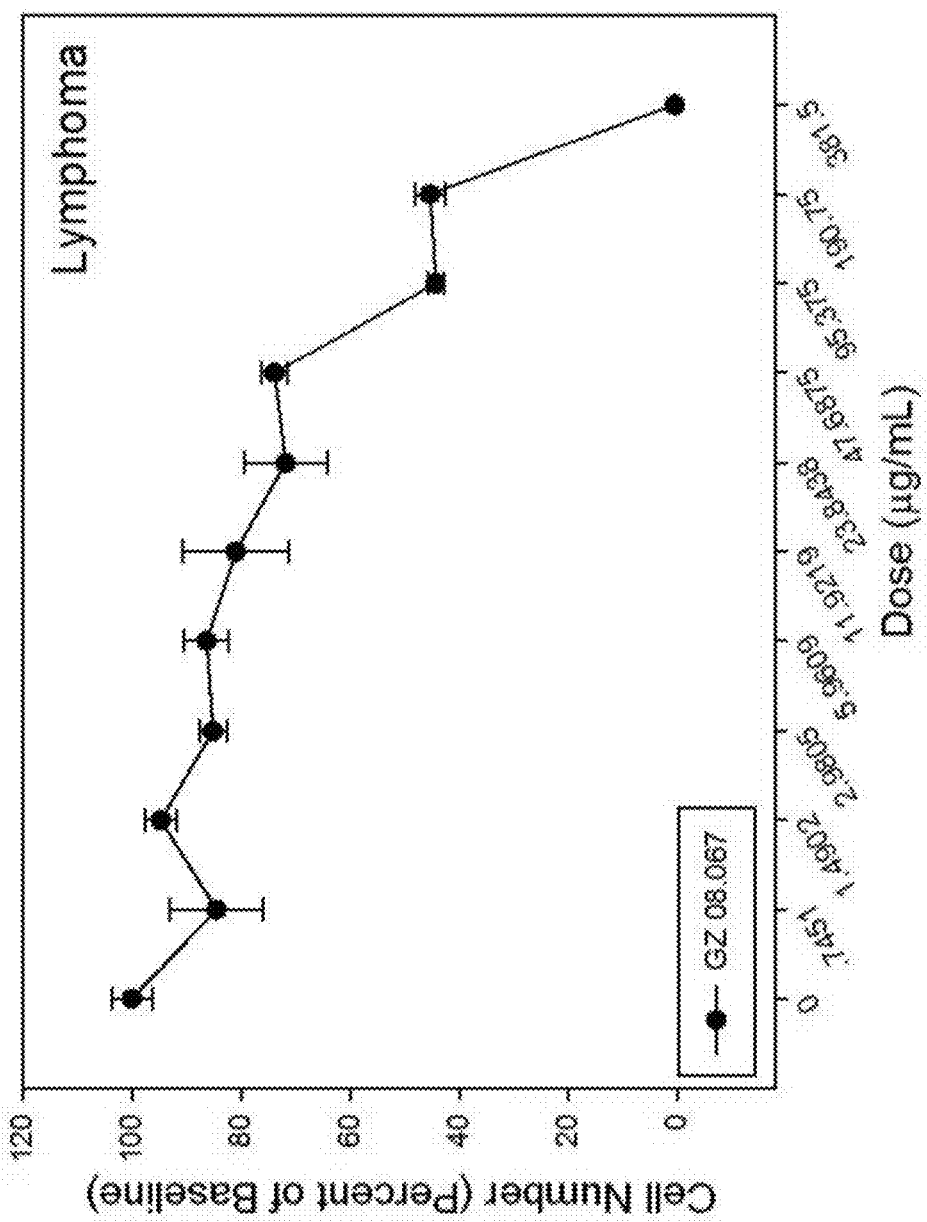
Figures 45, 82:
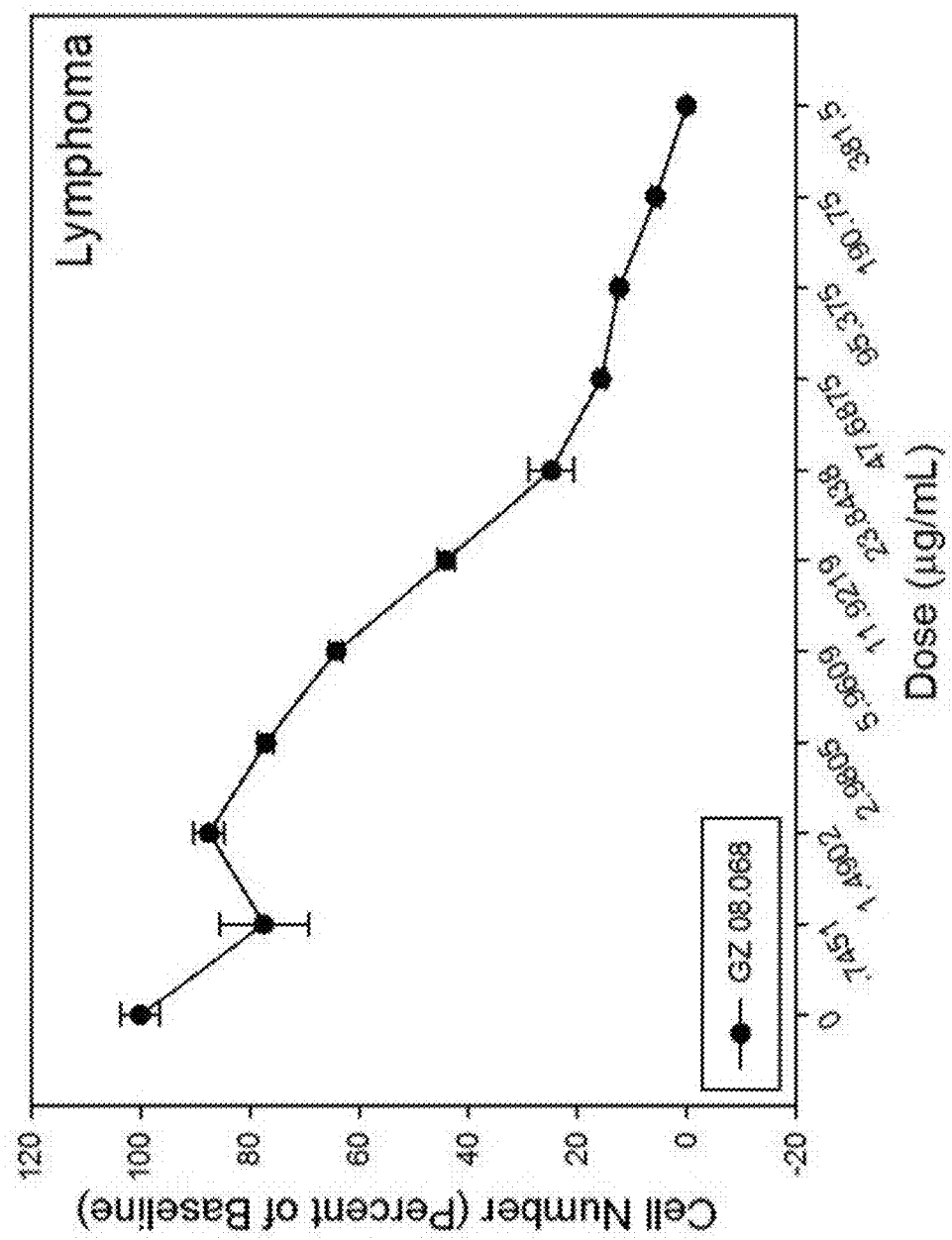
Figures 46, 82:
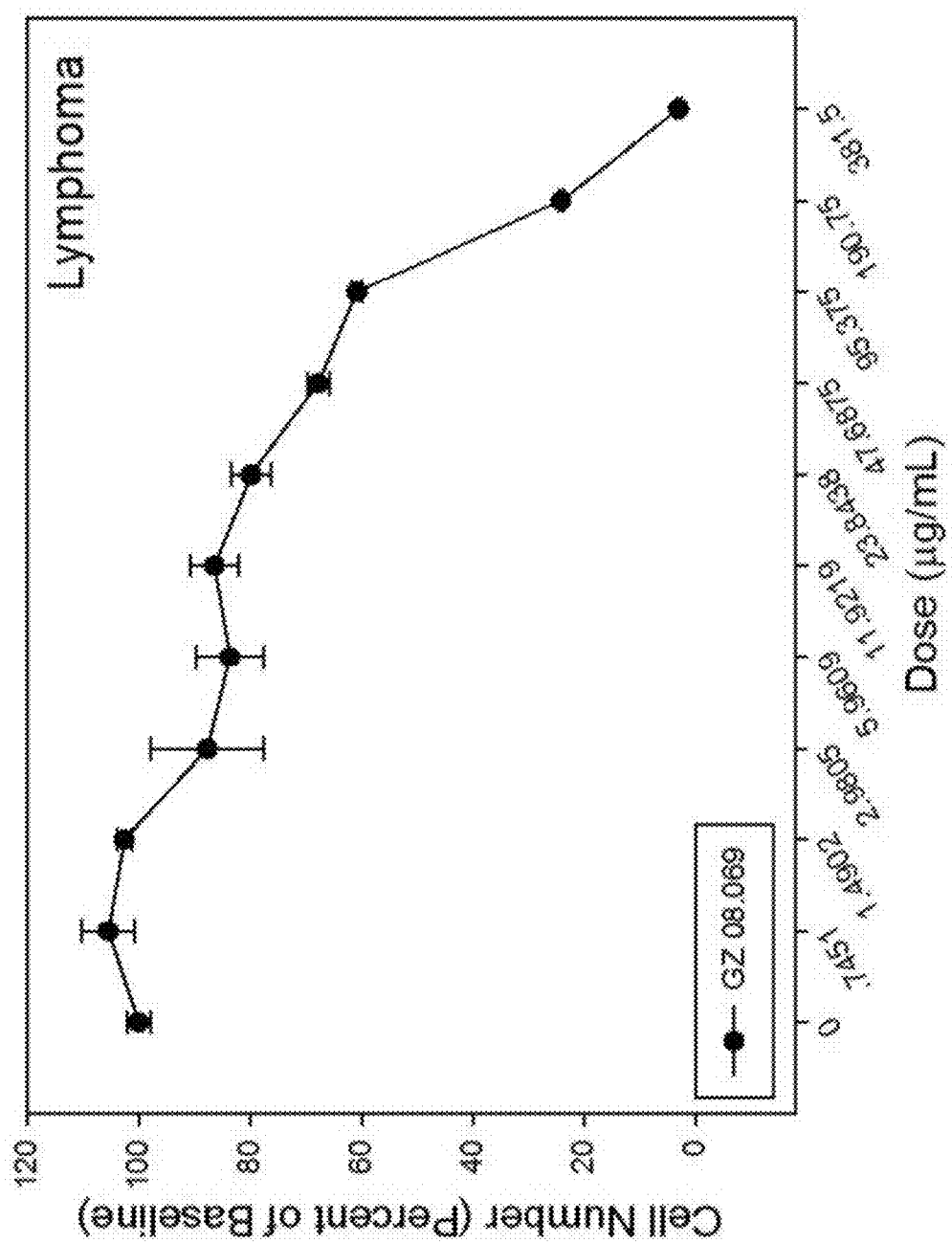
Figures 47, 82:
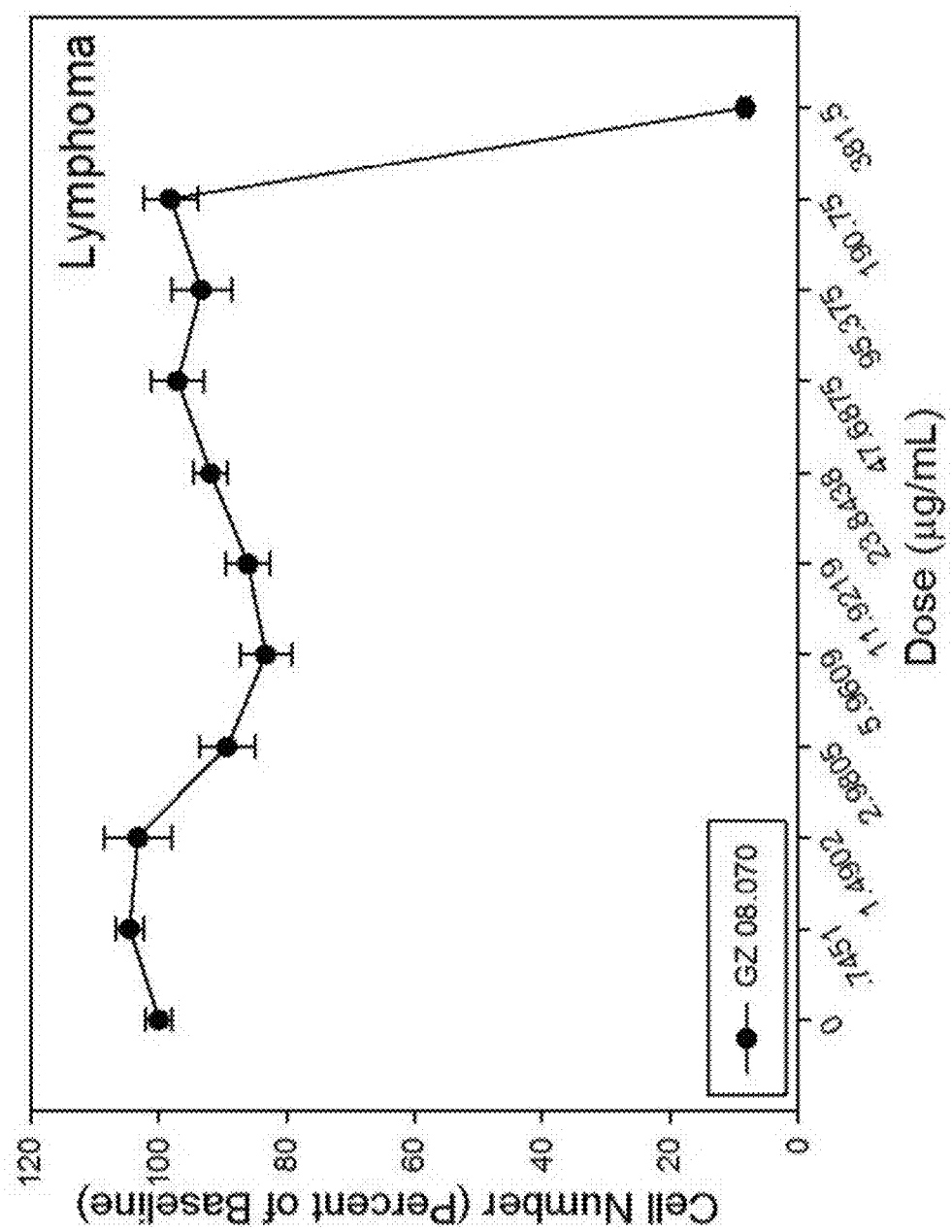
Figures 48, 82:
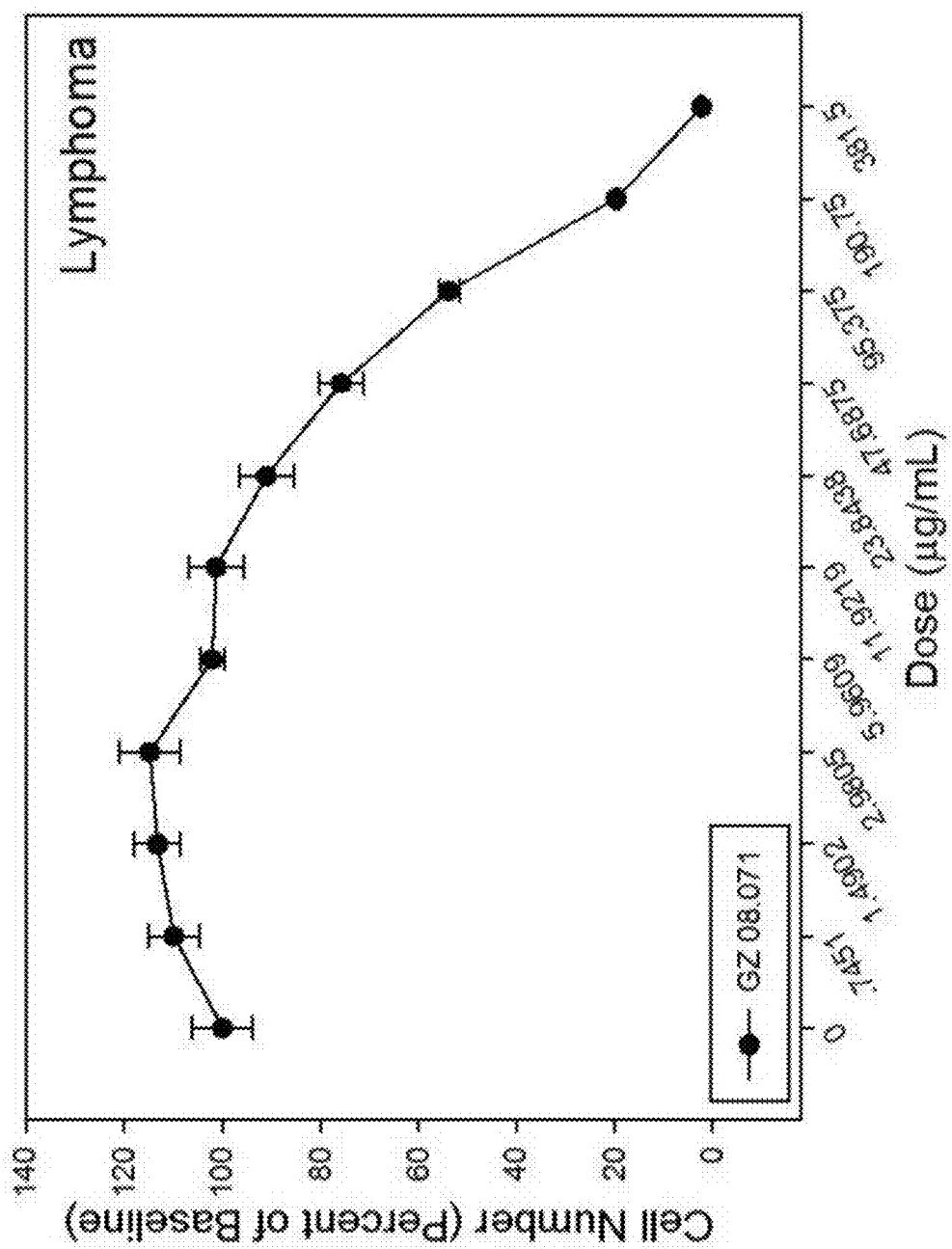
Figures 49, 82:
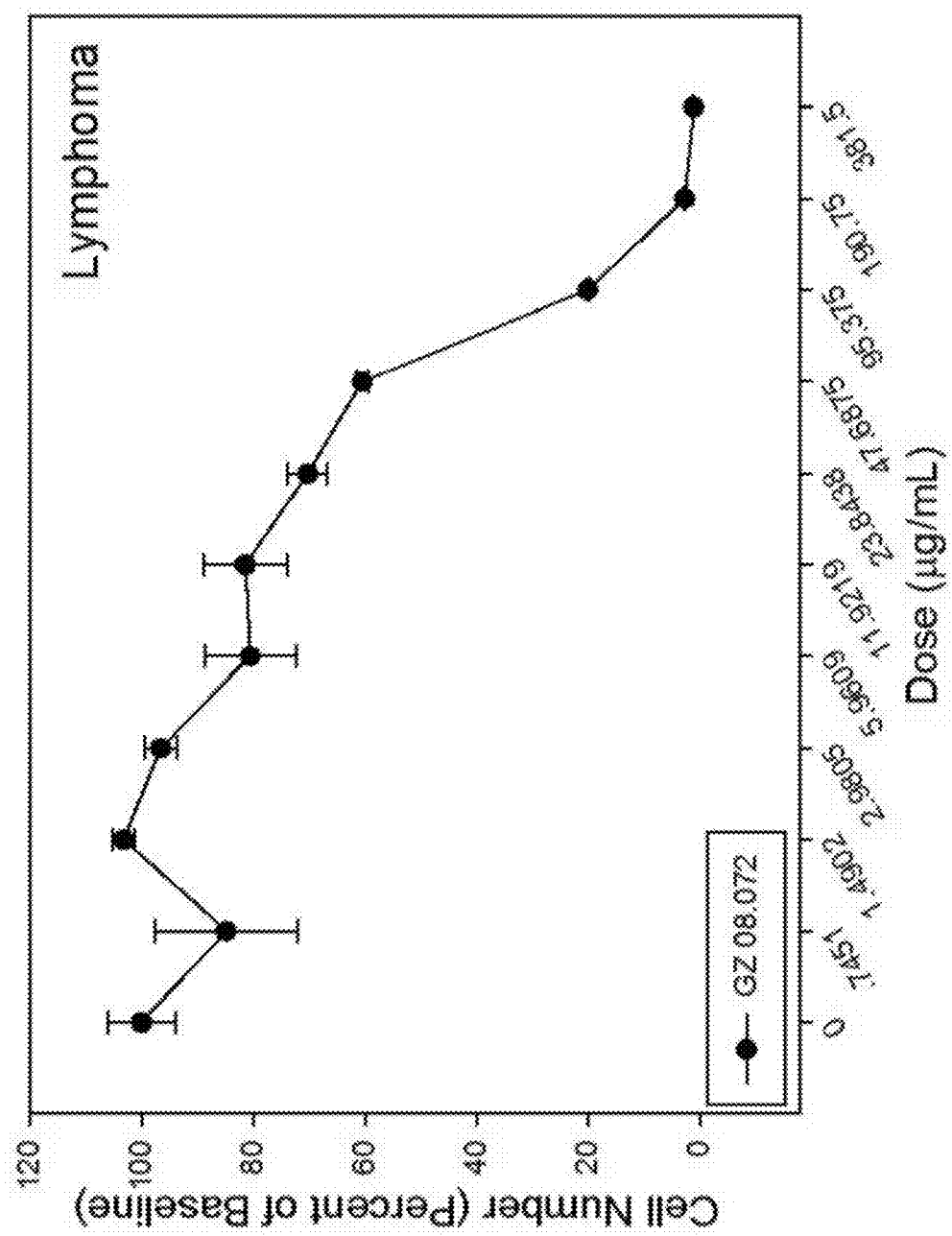
Figures 50, 82:
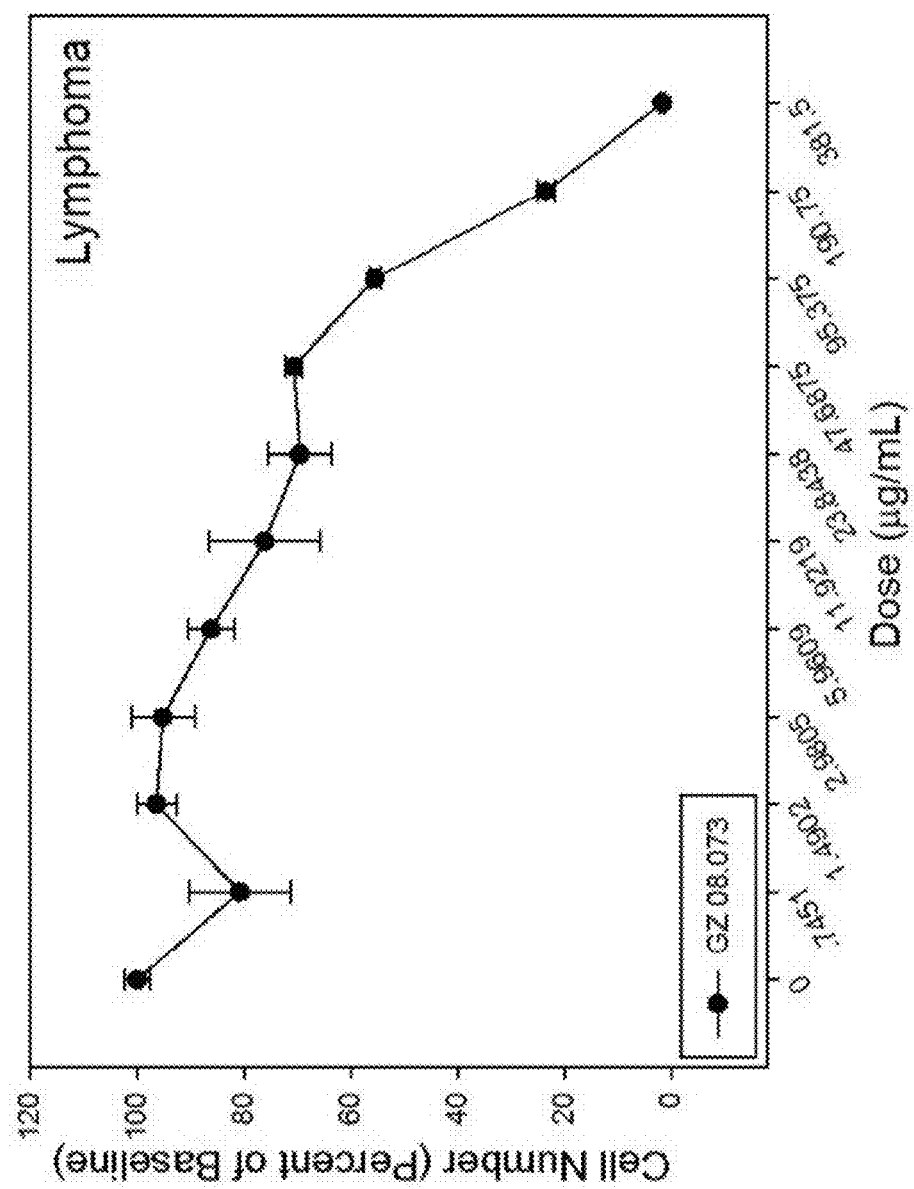
Figures 51, 82:
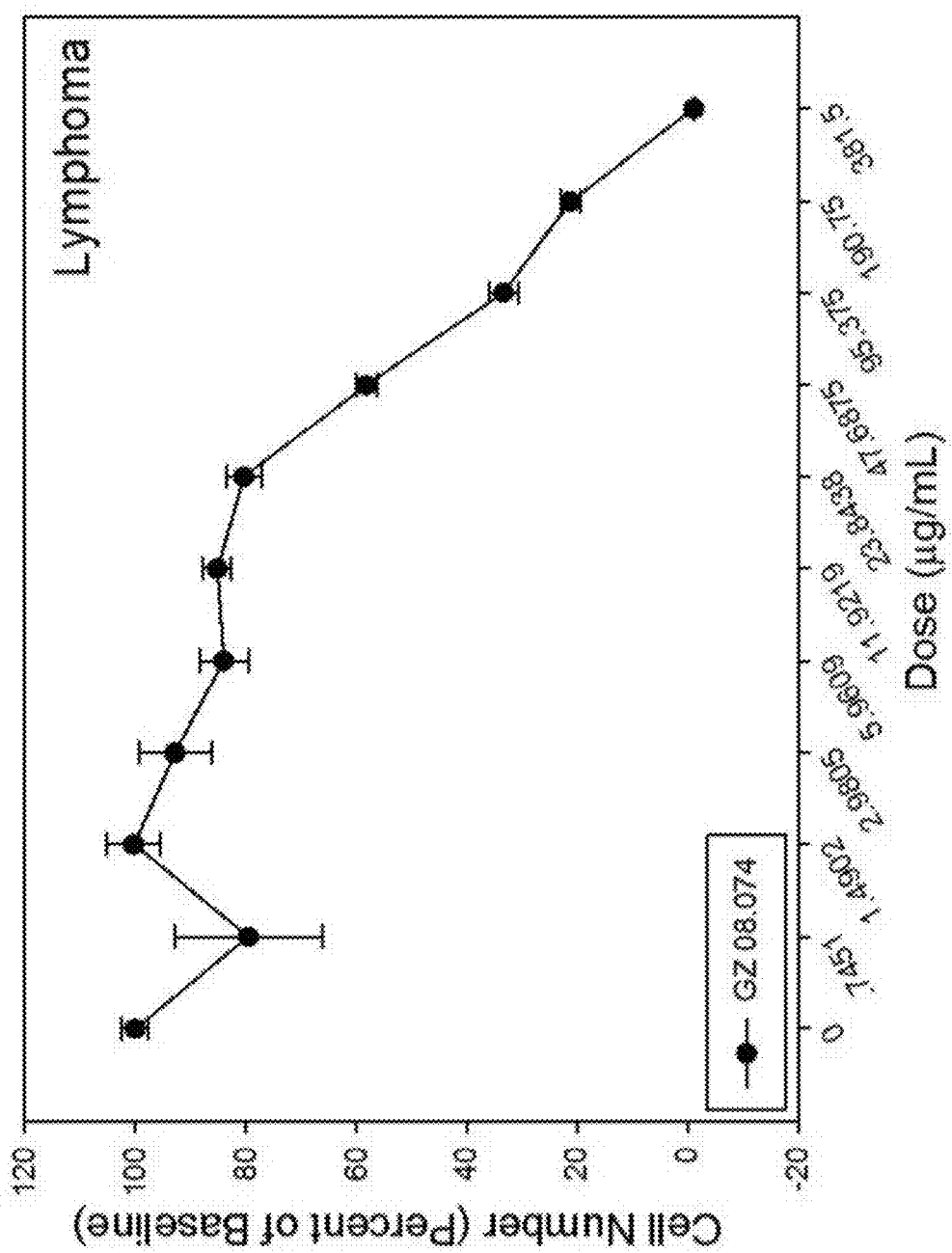
Figures 52, 82:
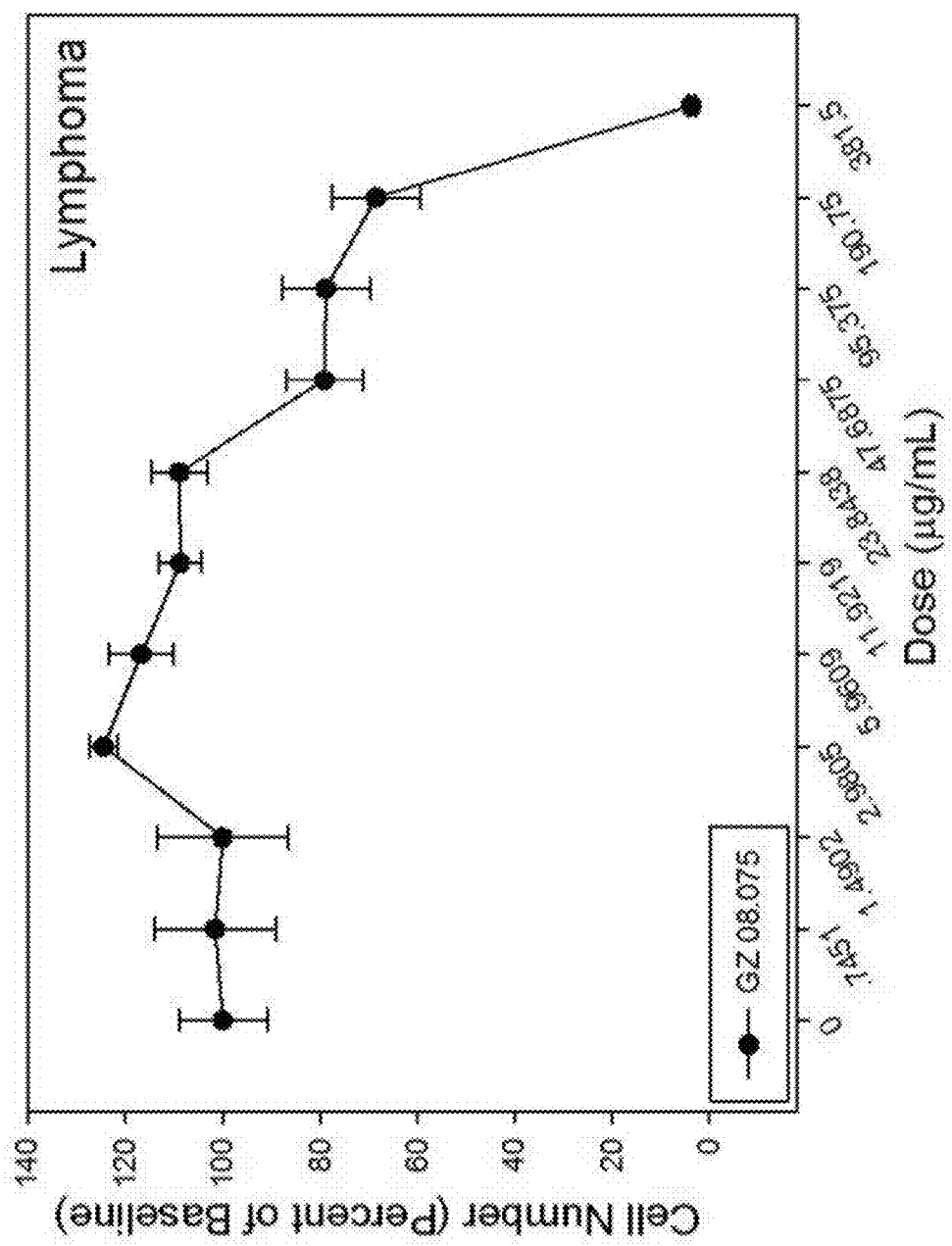
Figures 53, 82:
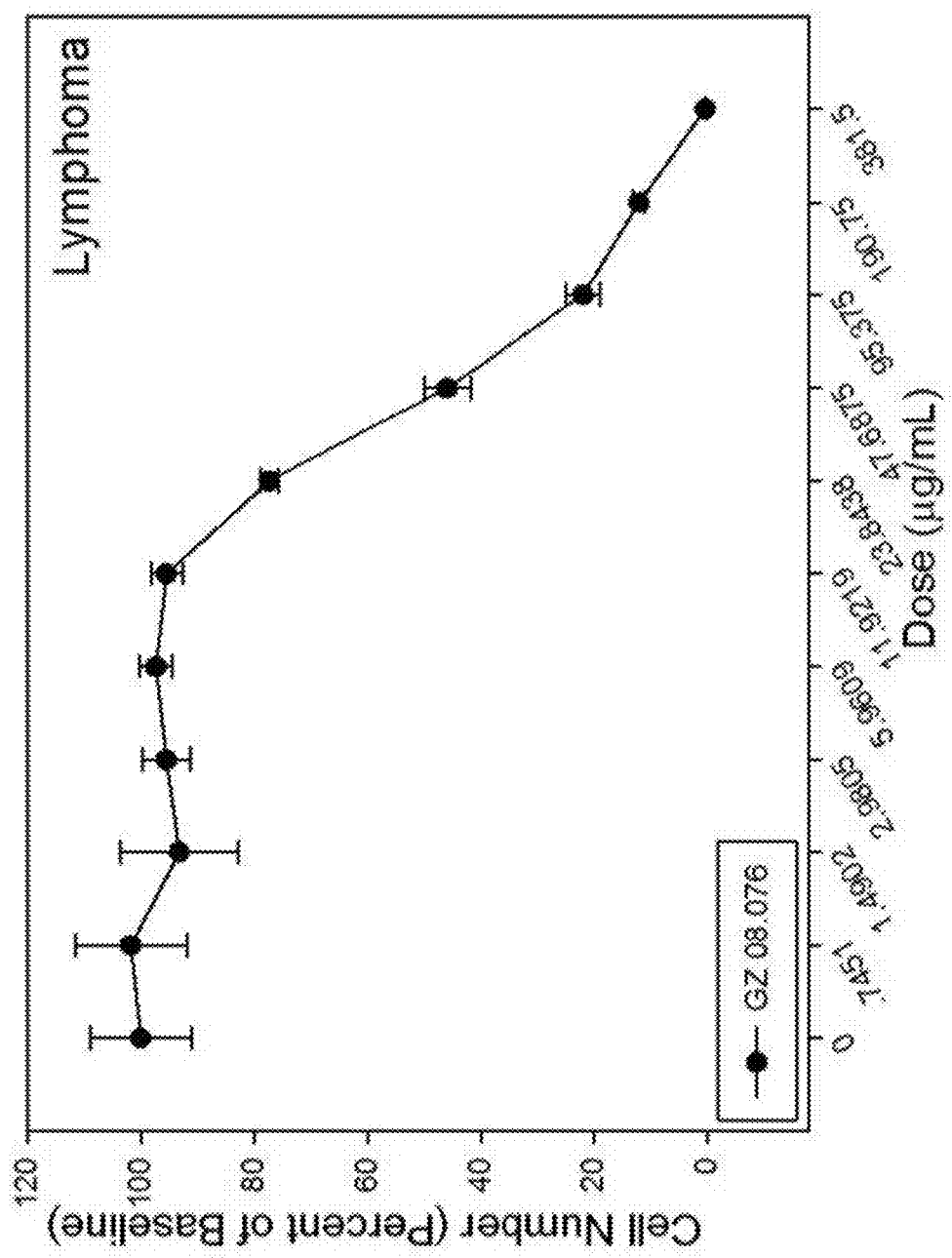
Figures 54, 82:
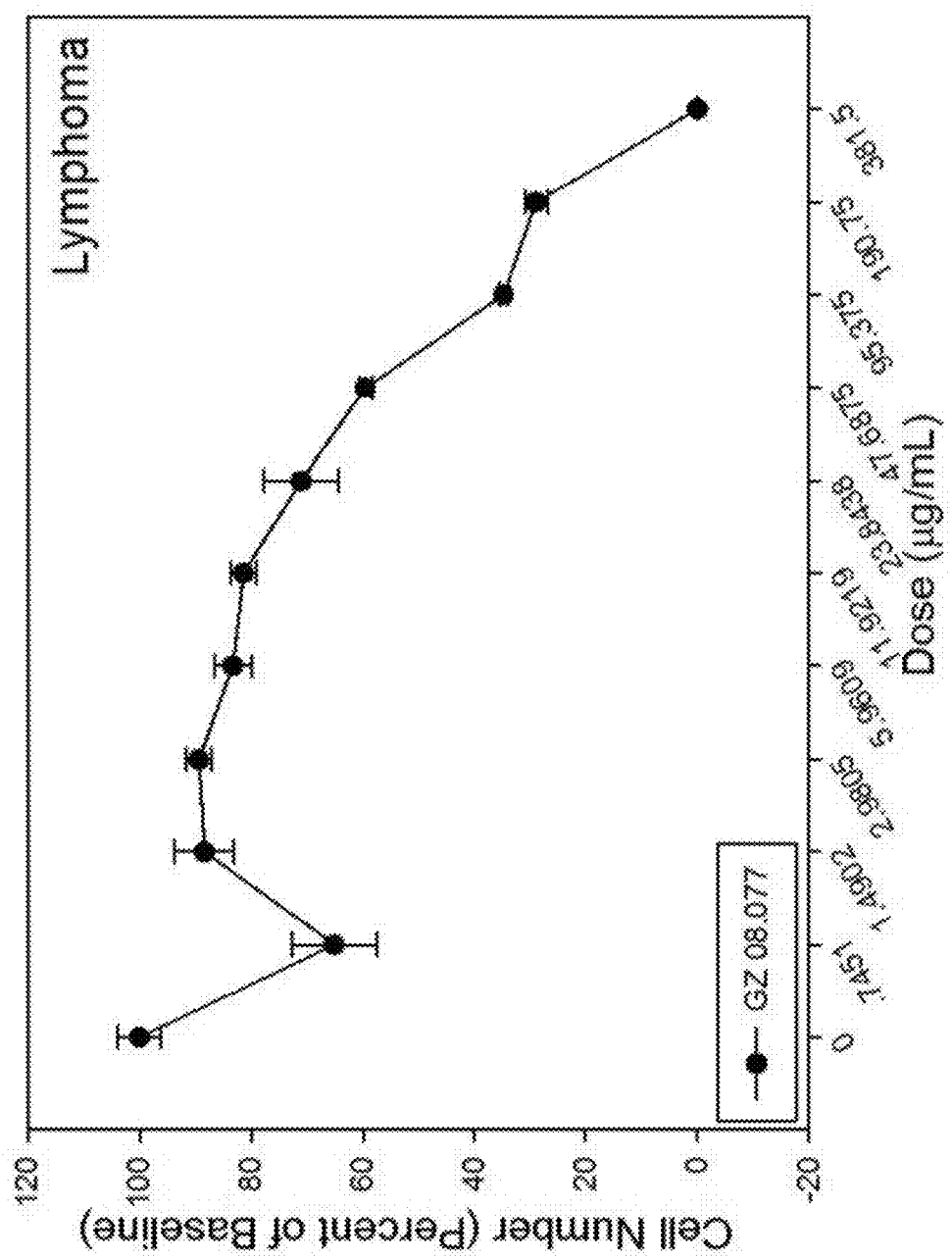
Figures 55, 82:
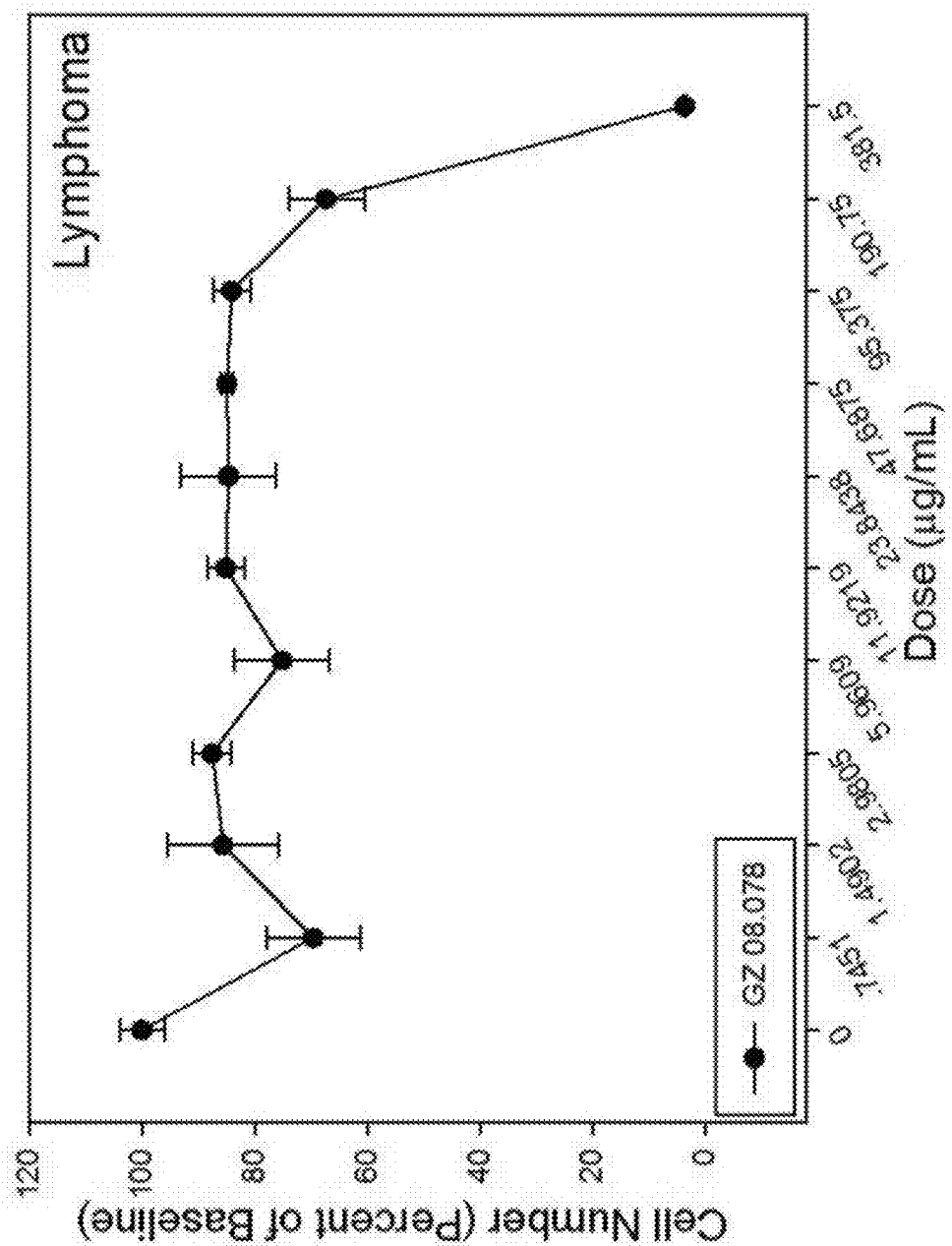
Figures 56, 82:
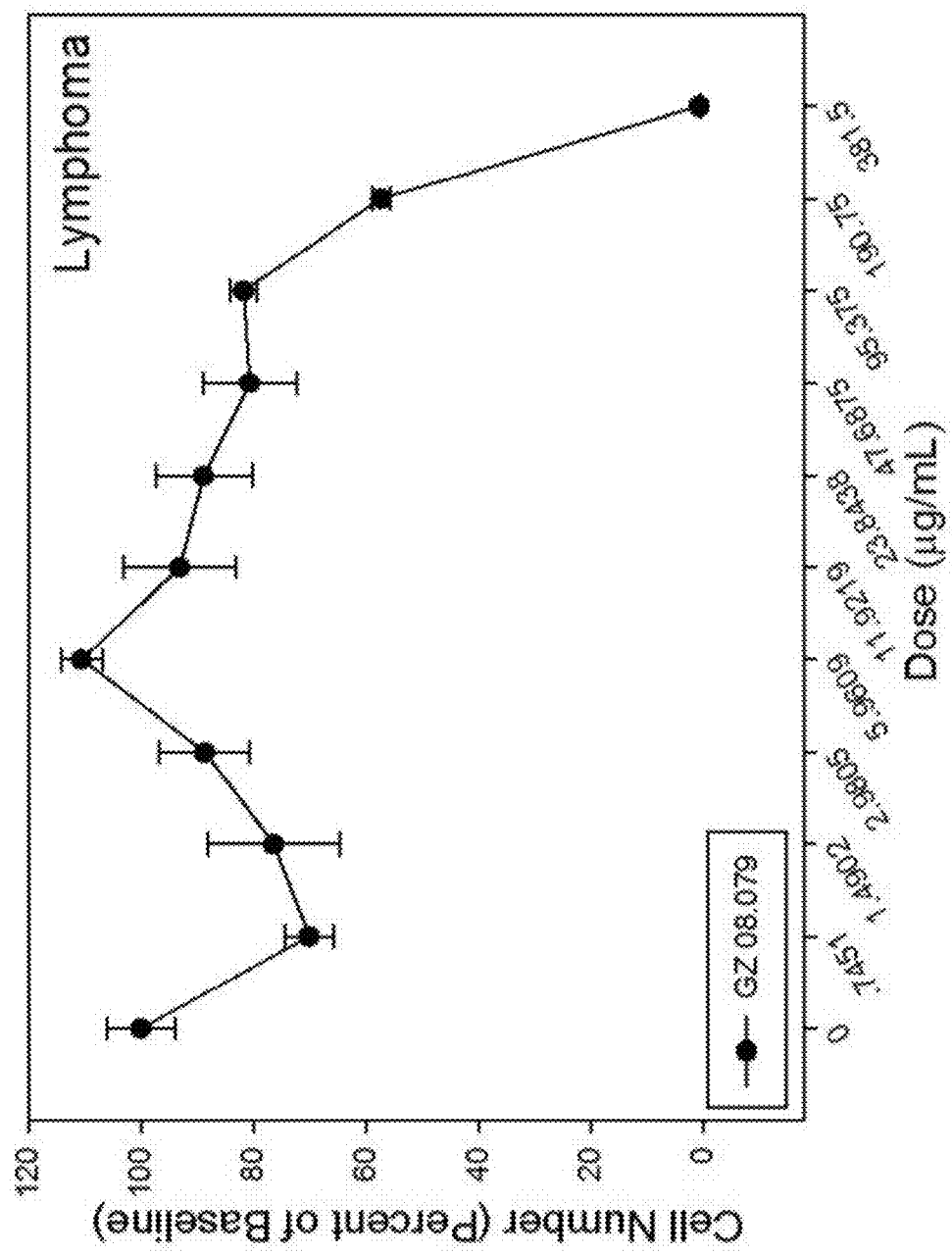
Figures 57, 82:
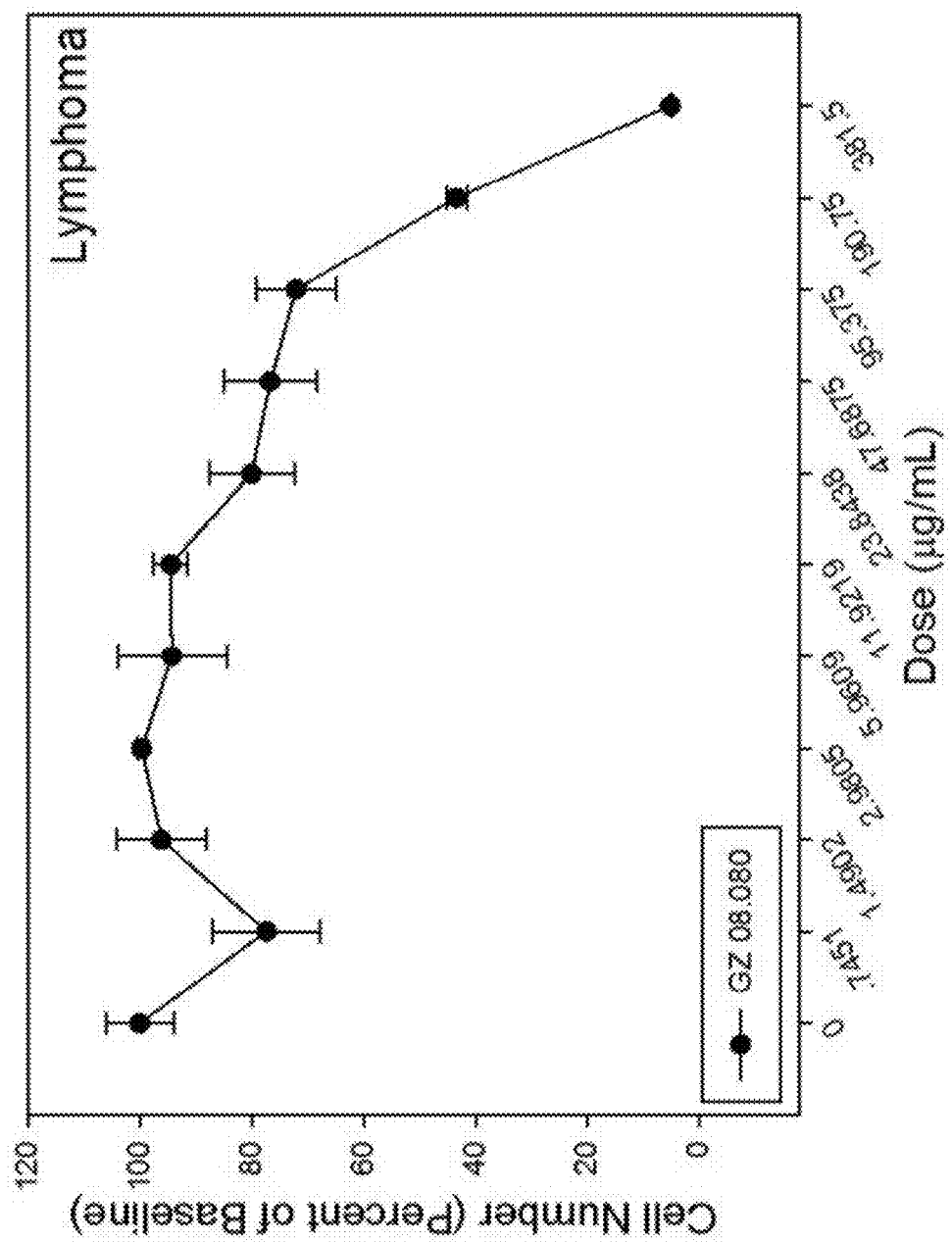
Figures 58, 82:
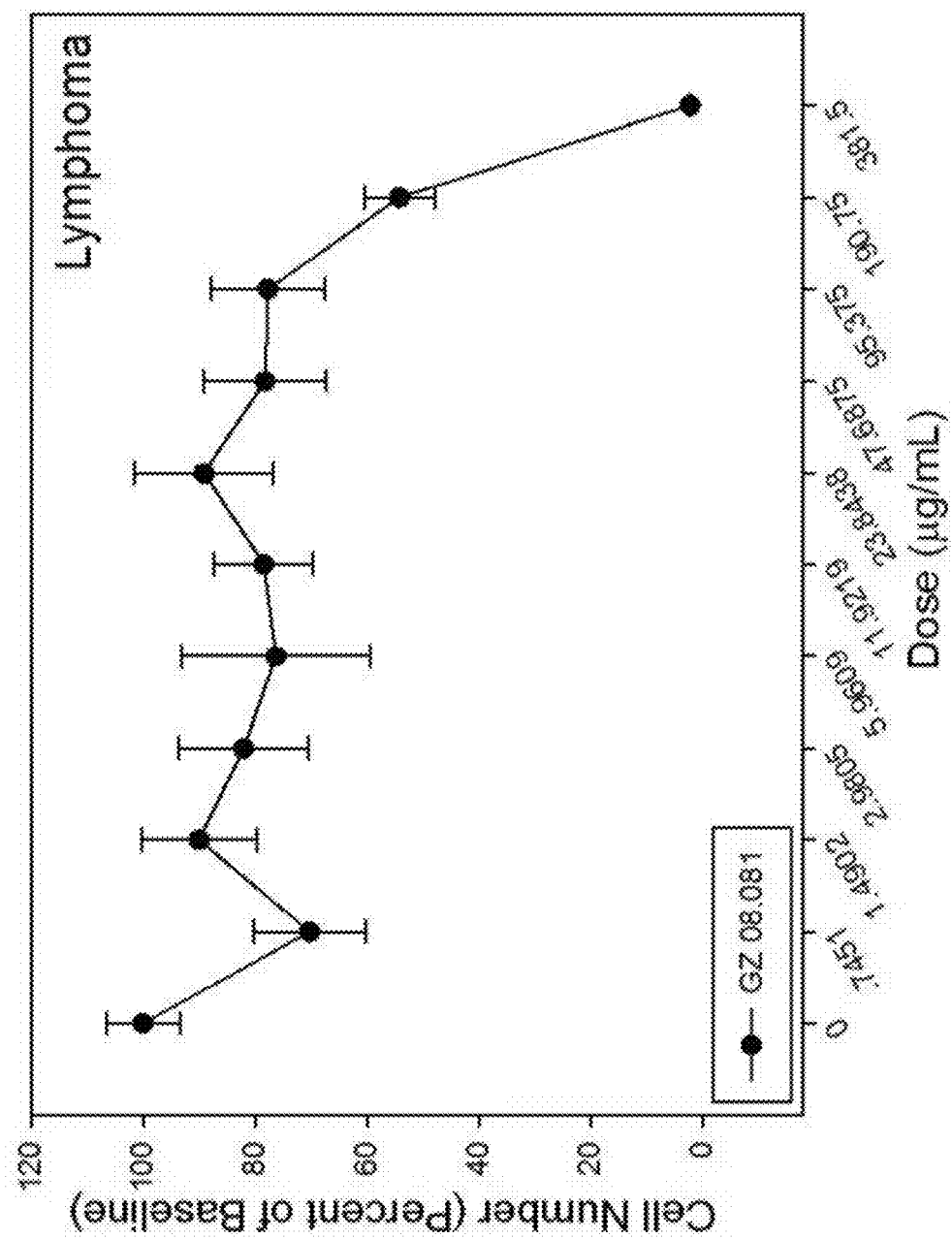
Figures 59, 82:
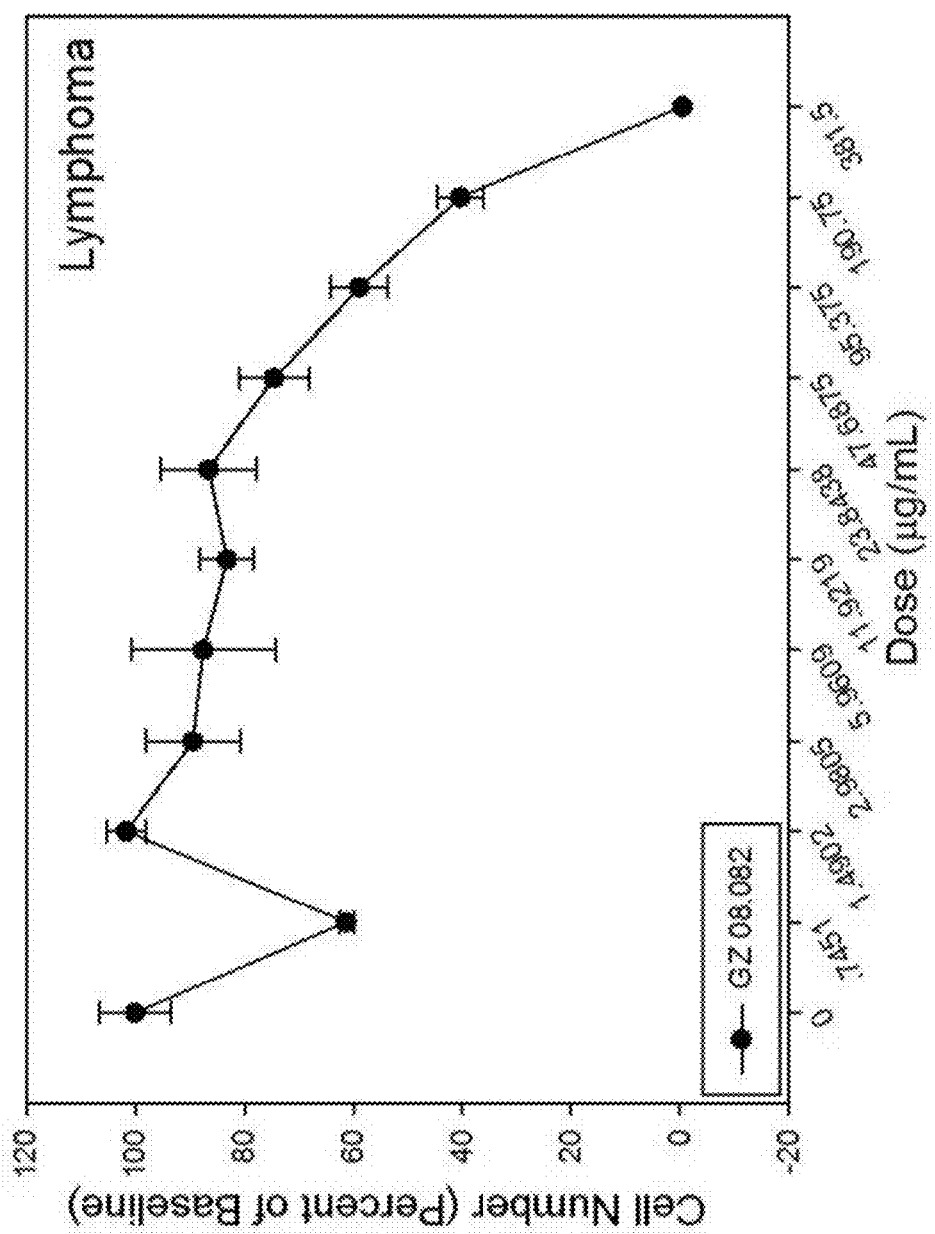
Figures 60, 82:
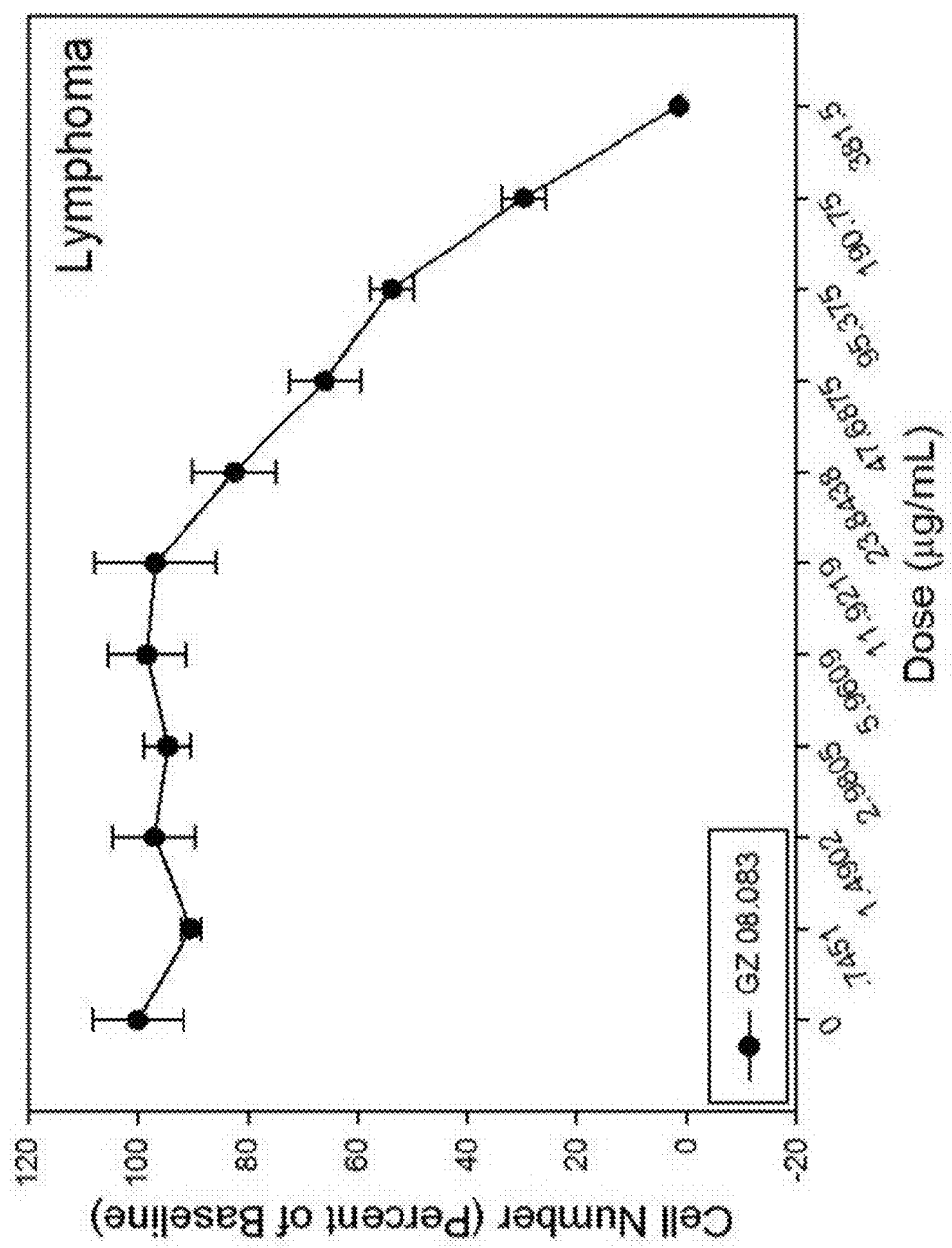
Figures 61, 82:
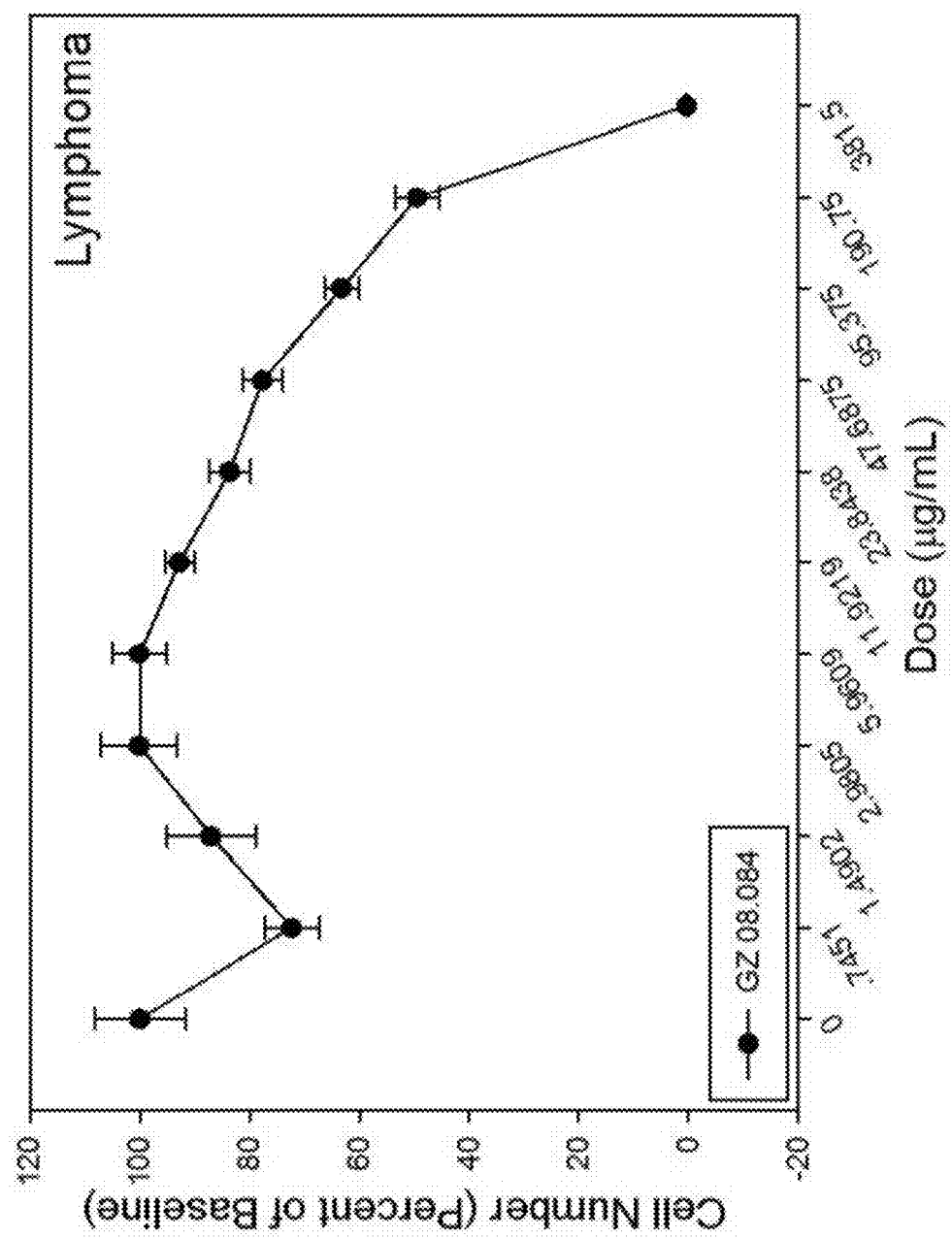
Figures 62, 82:
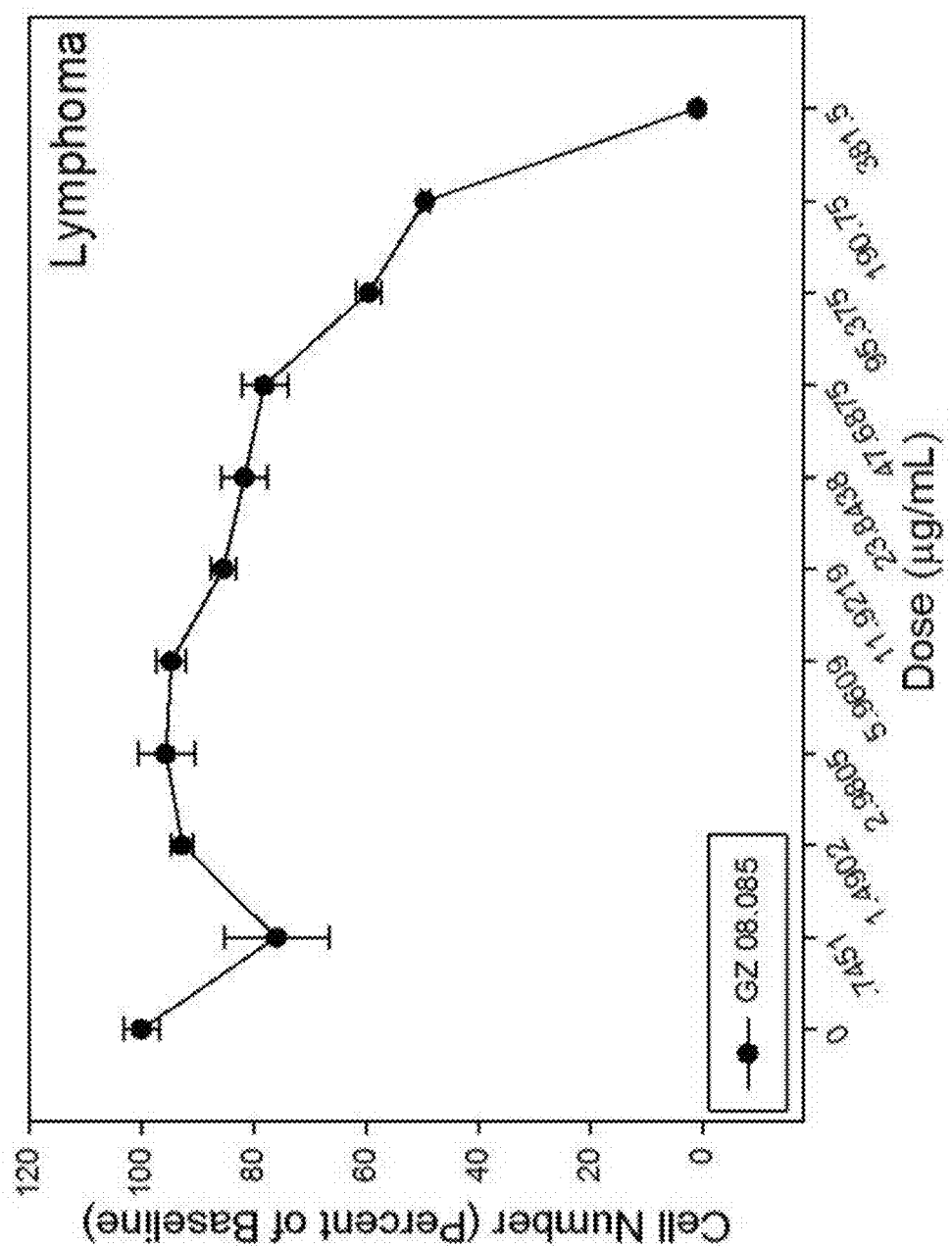
Figures 63, 82:
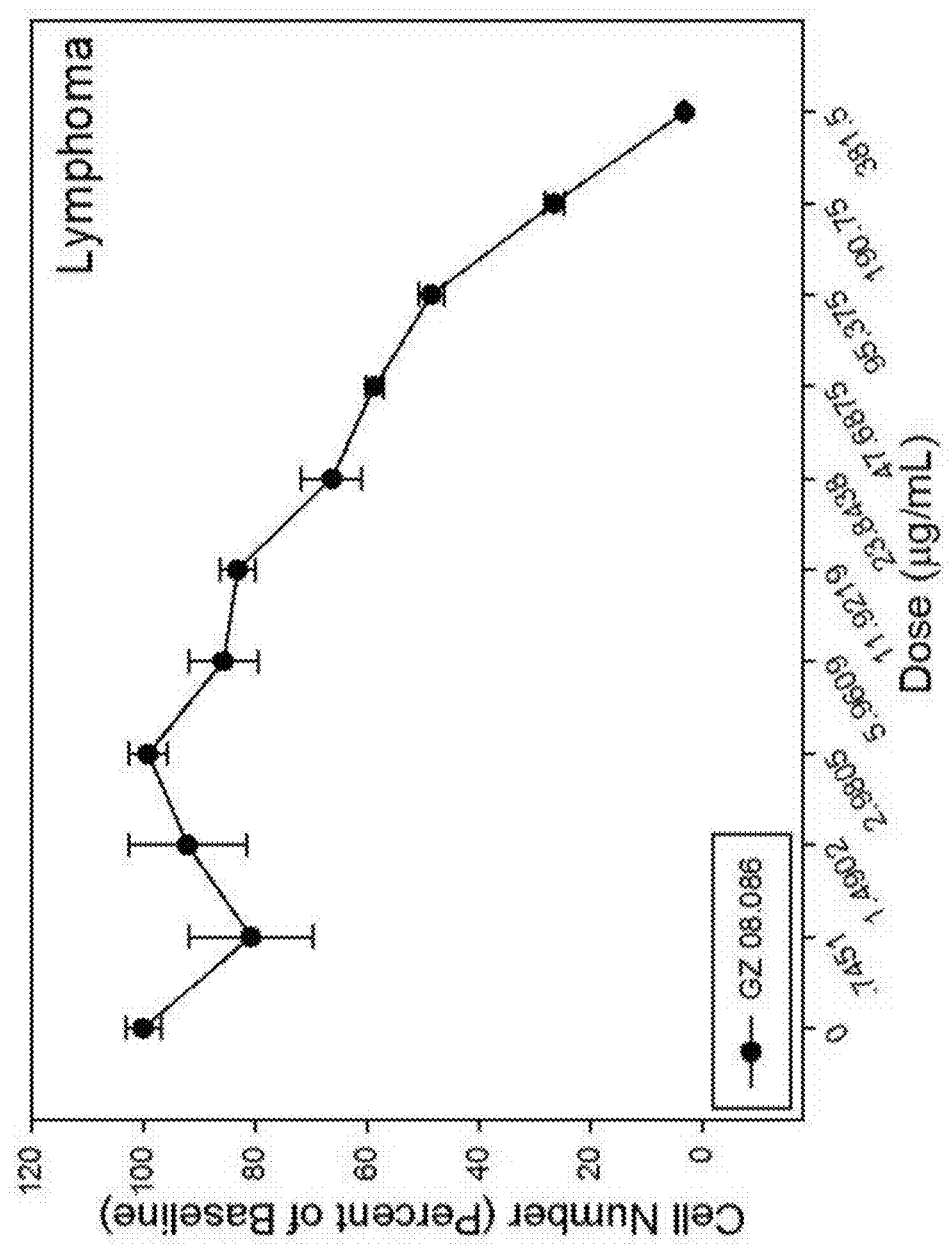
Figures 64, 82:
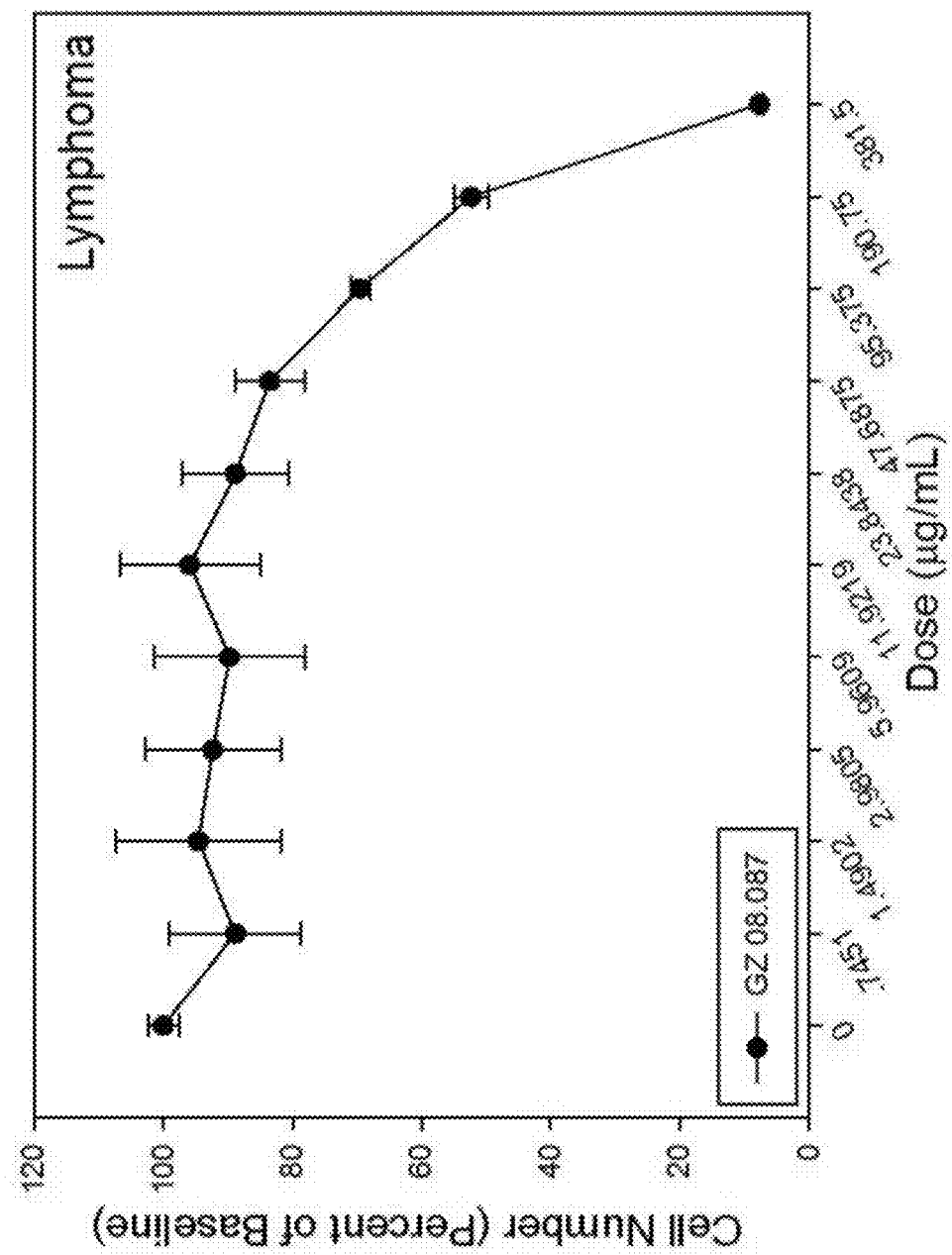
Figures 65, 82:
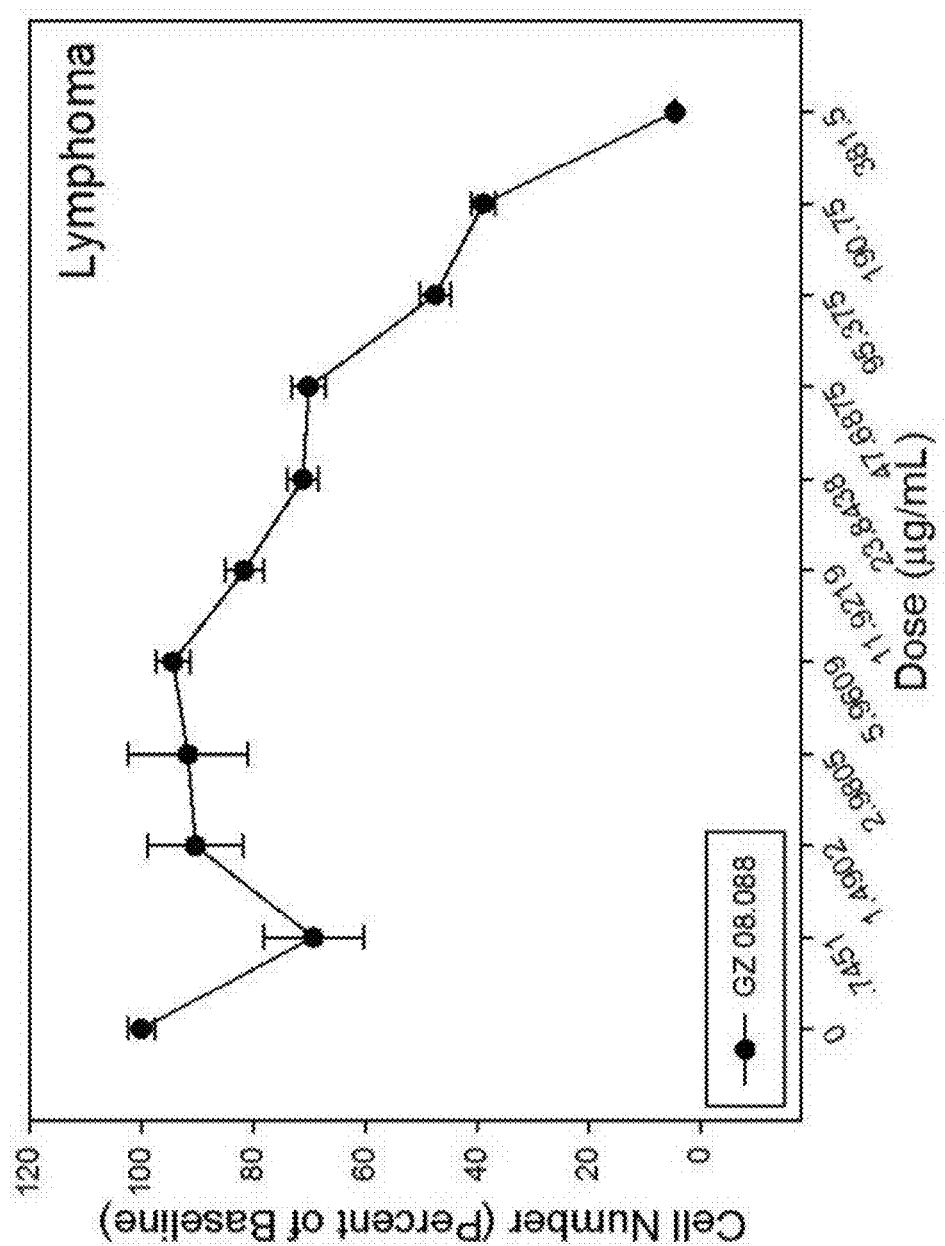
Figures 66, 82:
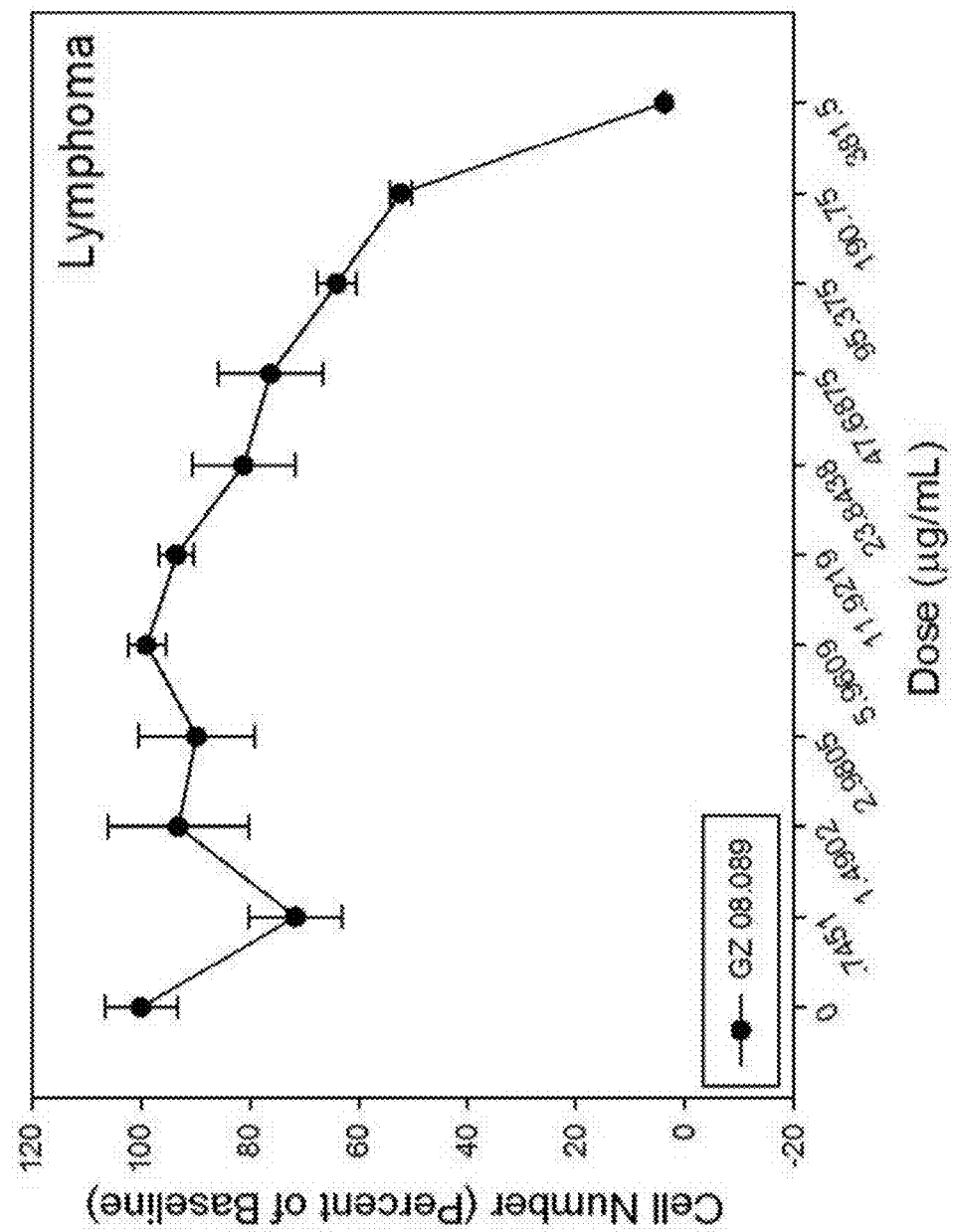
Figures 67, 82:
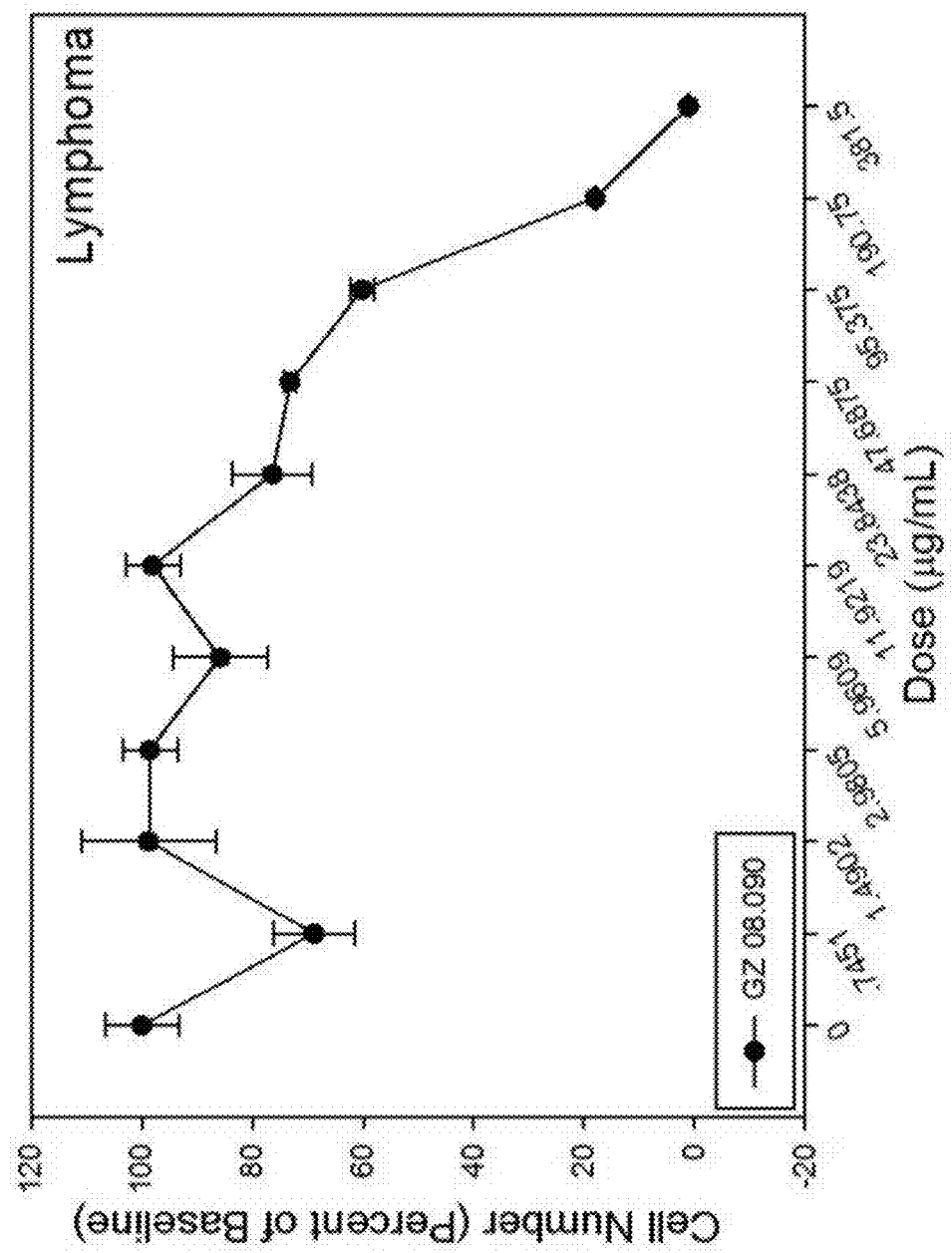
Figures 68, 82:
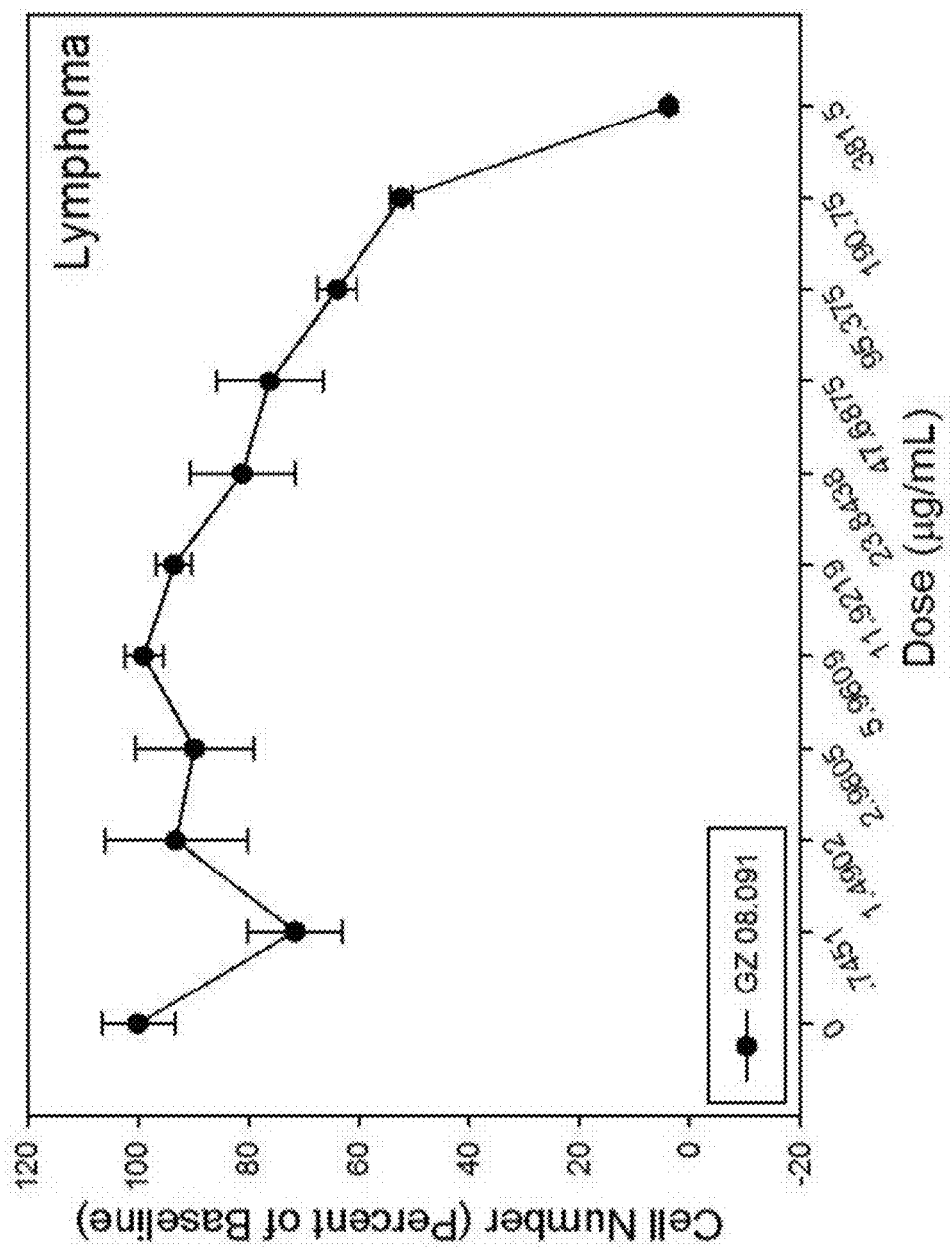
Figures 69, 82:
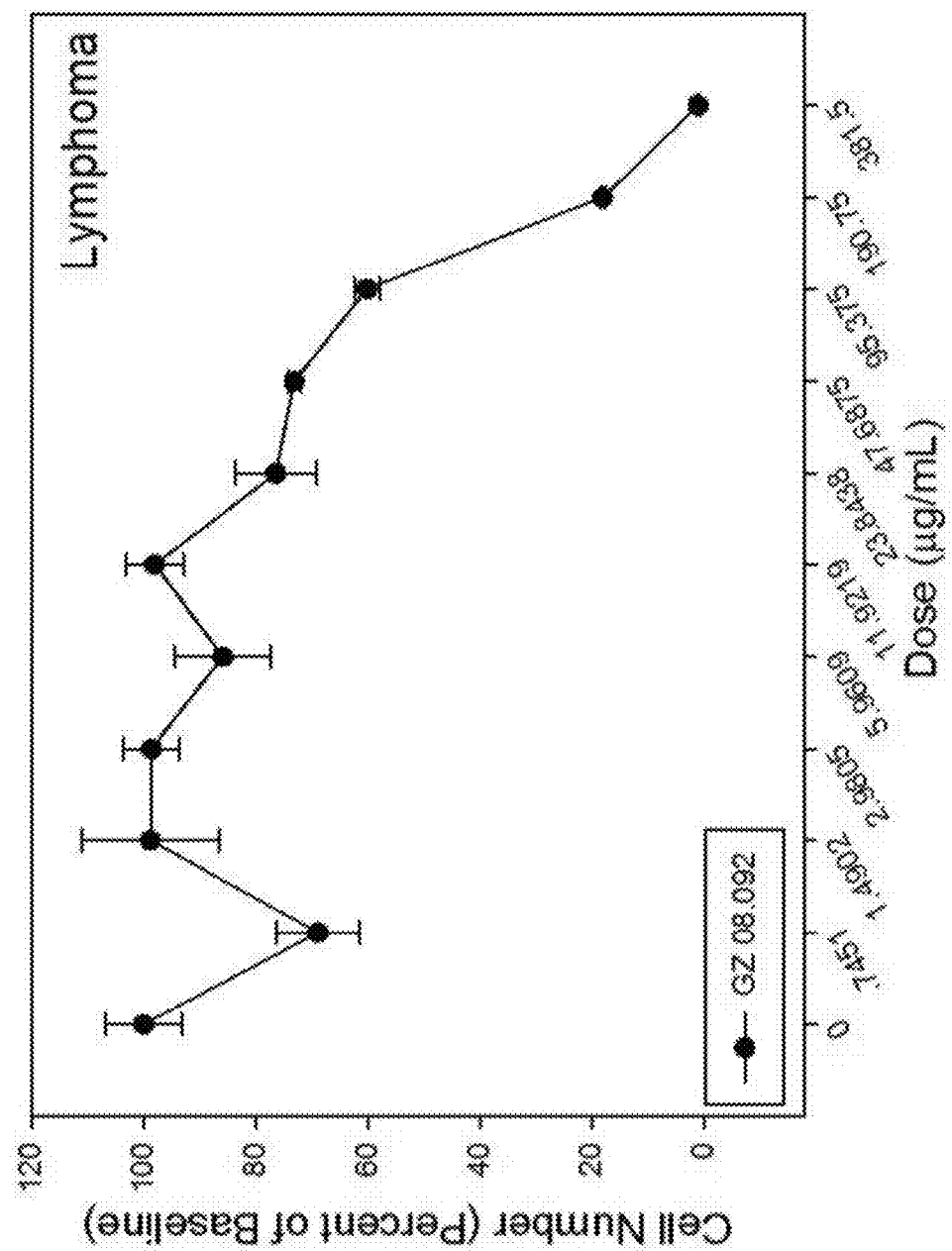
Figures 70, 82:
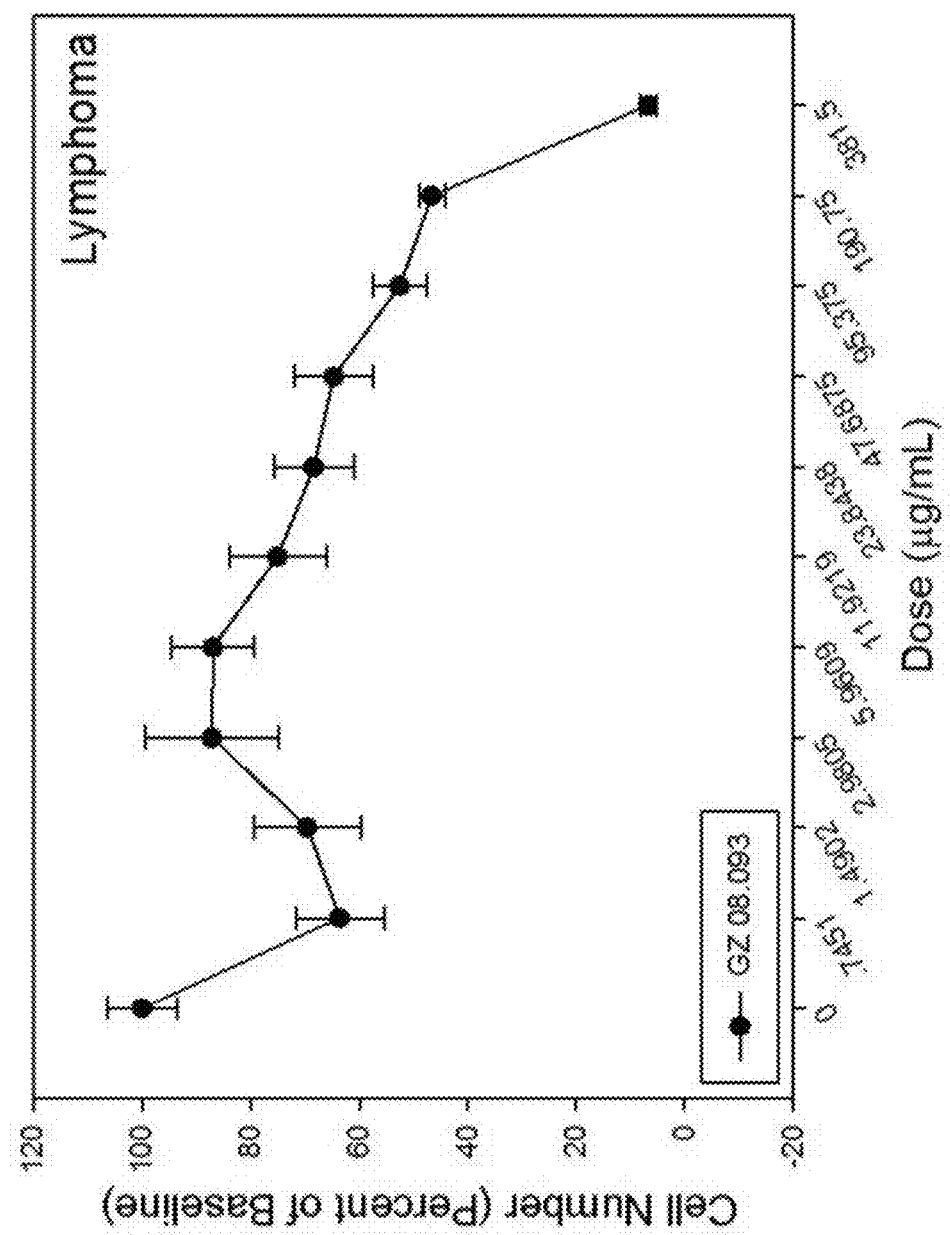
Figures 71, 82:
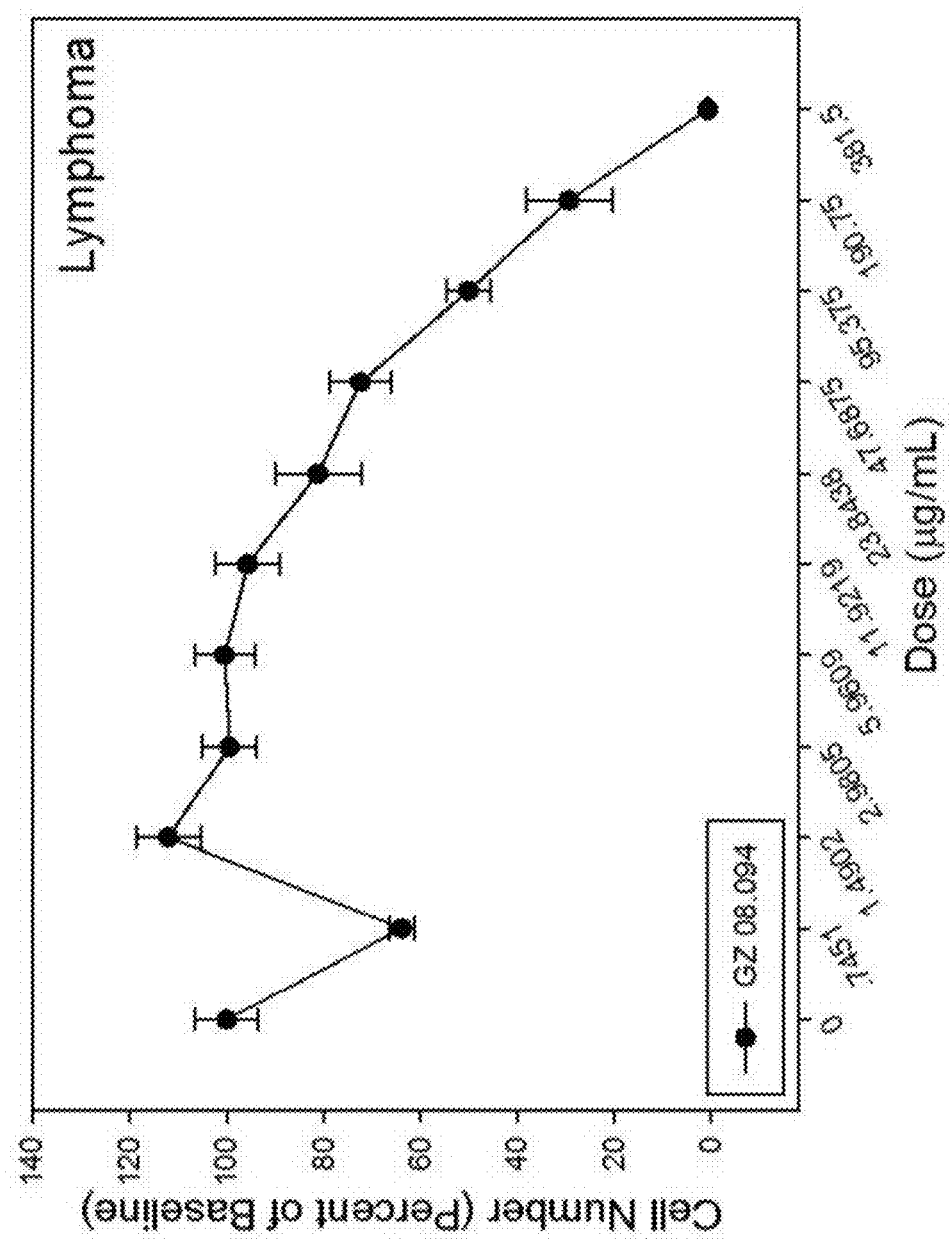
Figures 72, 82:
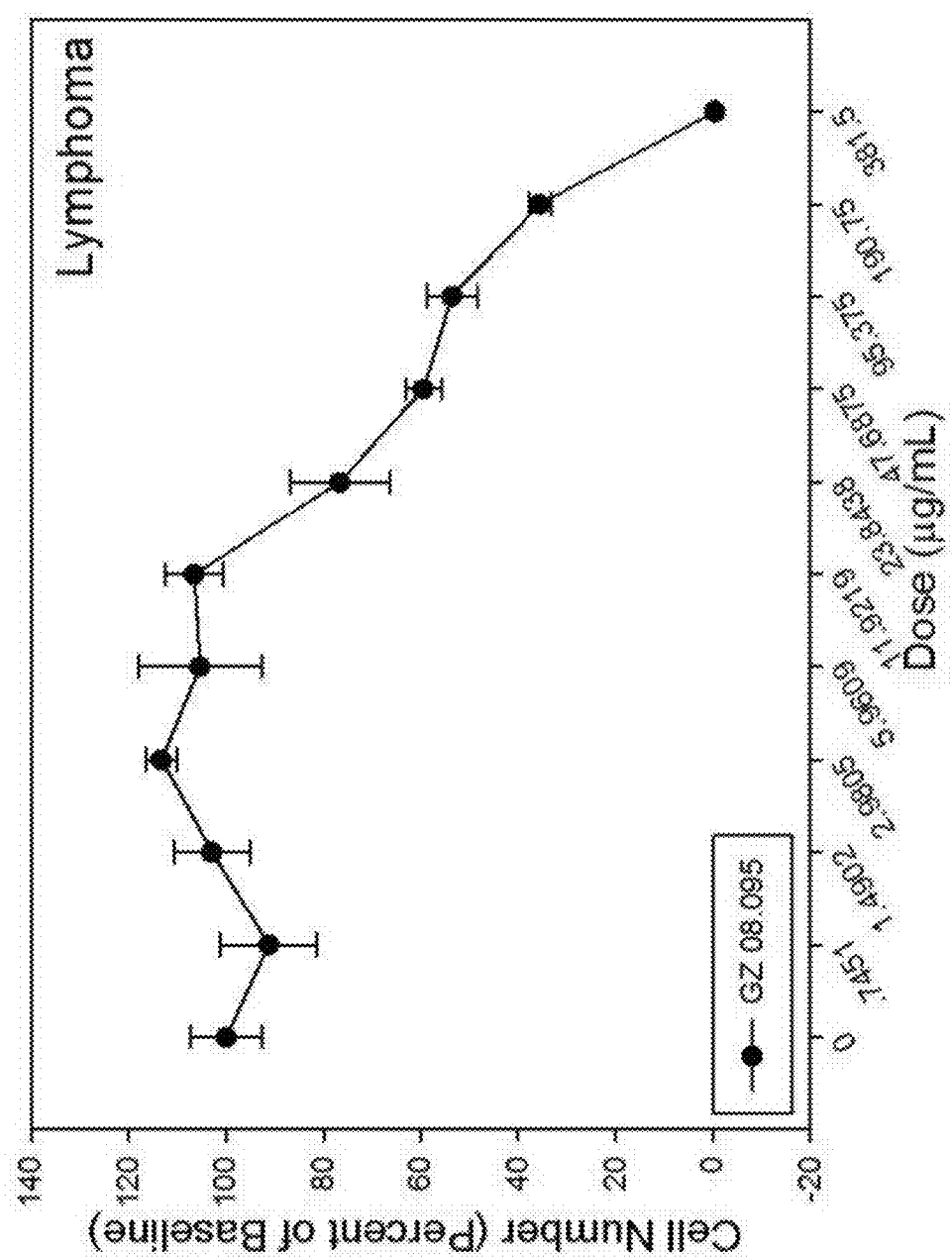
Figures 73, 82:
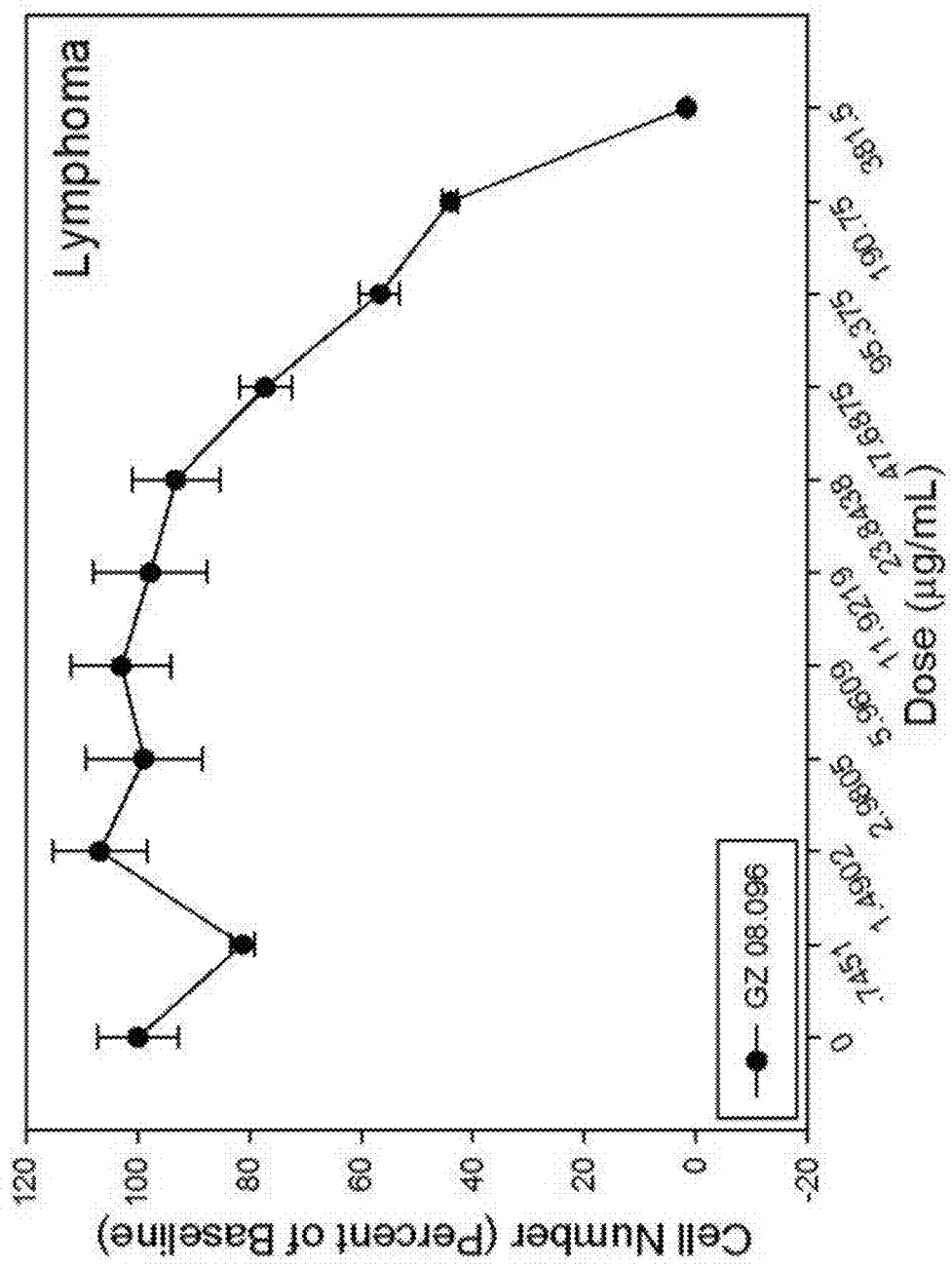
Figures 74, 82:
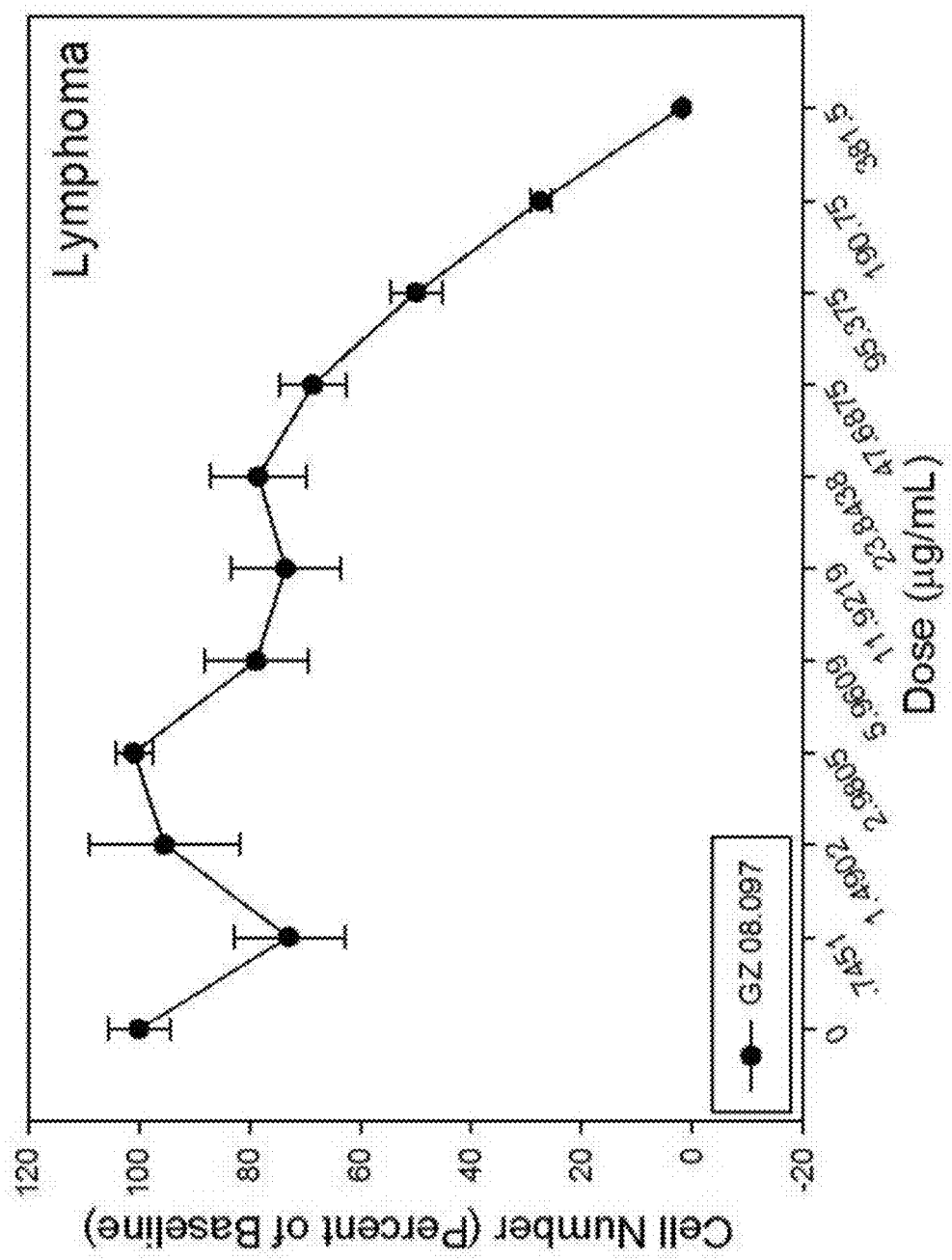
Figures 75, 82:
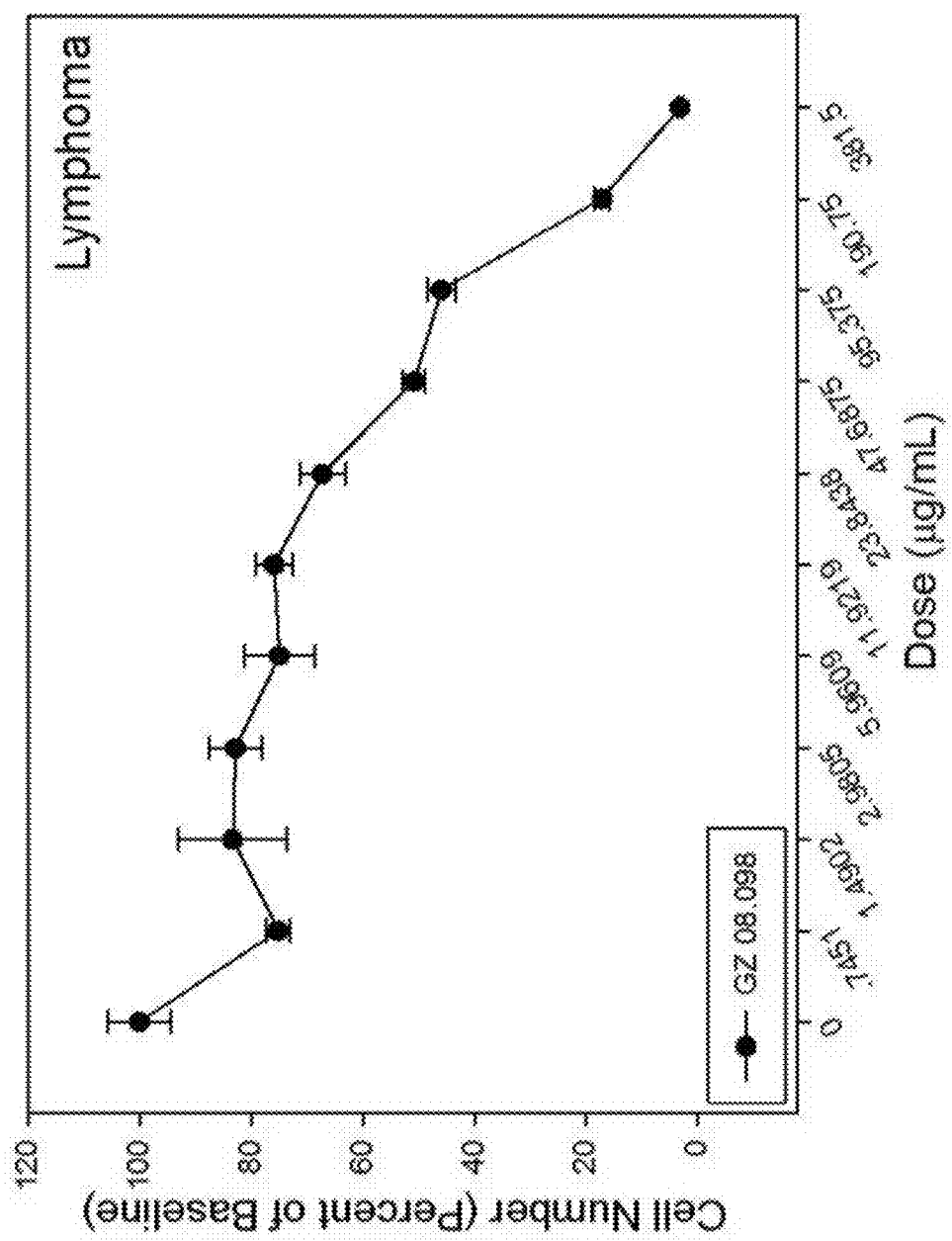
Figures 76, 82:
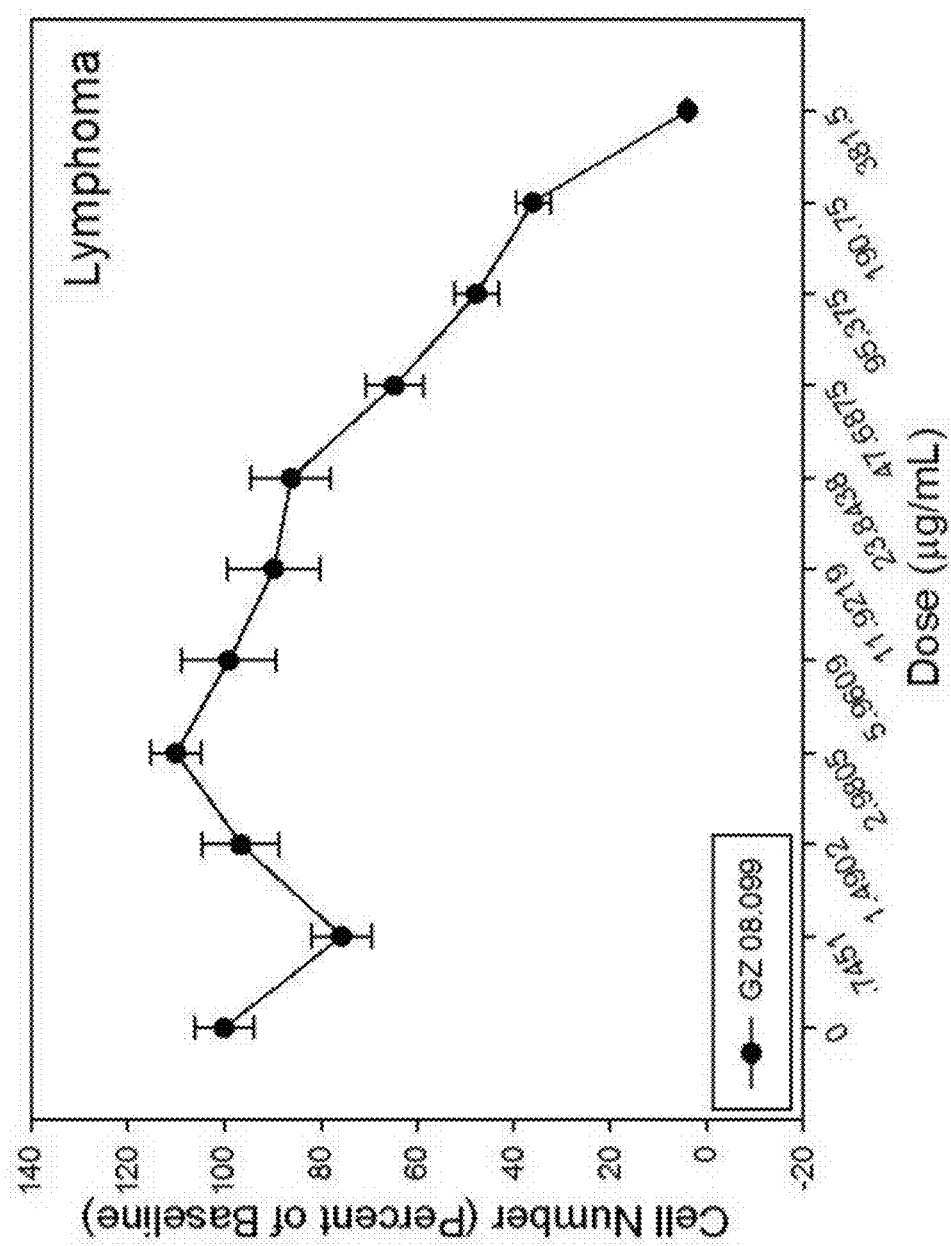
Figures 77, 82:
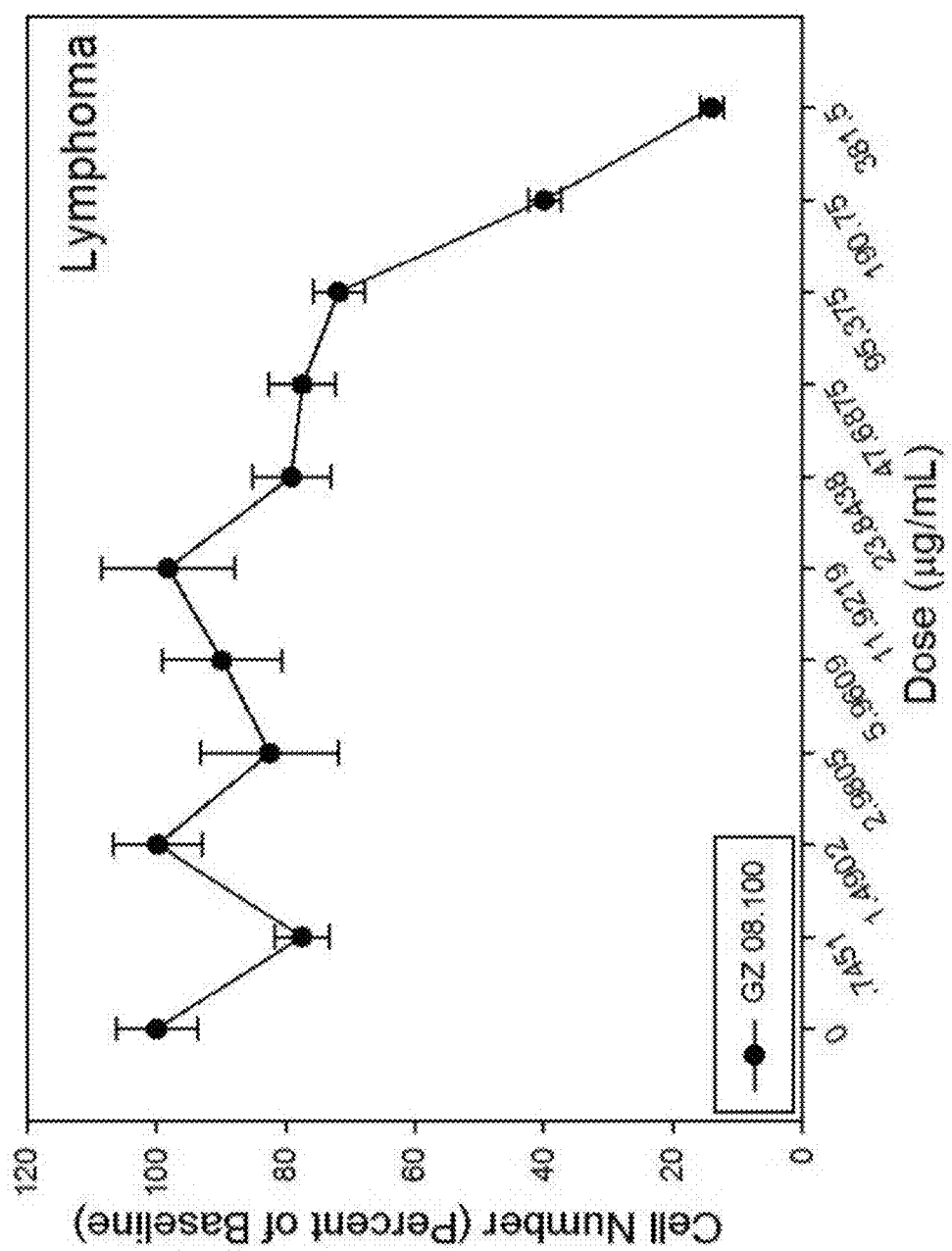
Figures 78, 82:
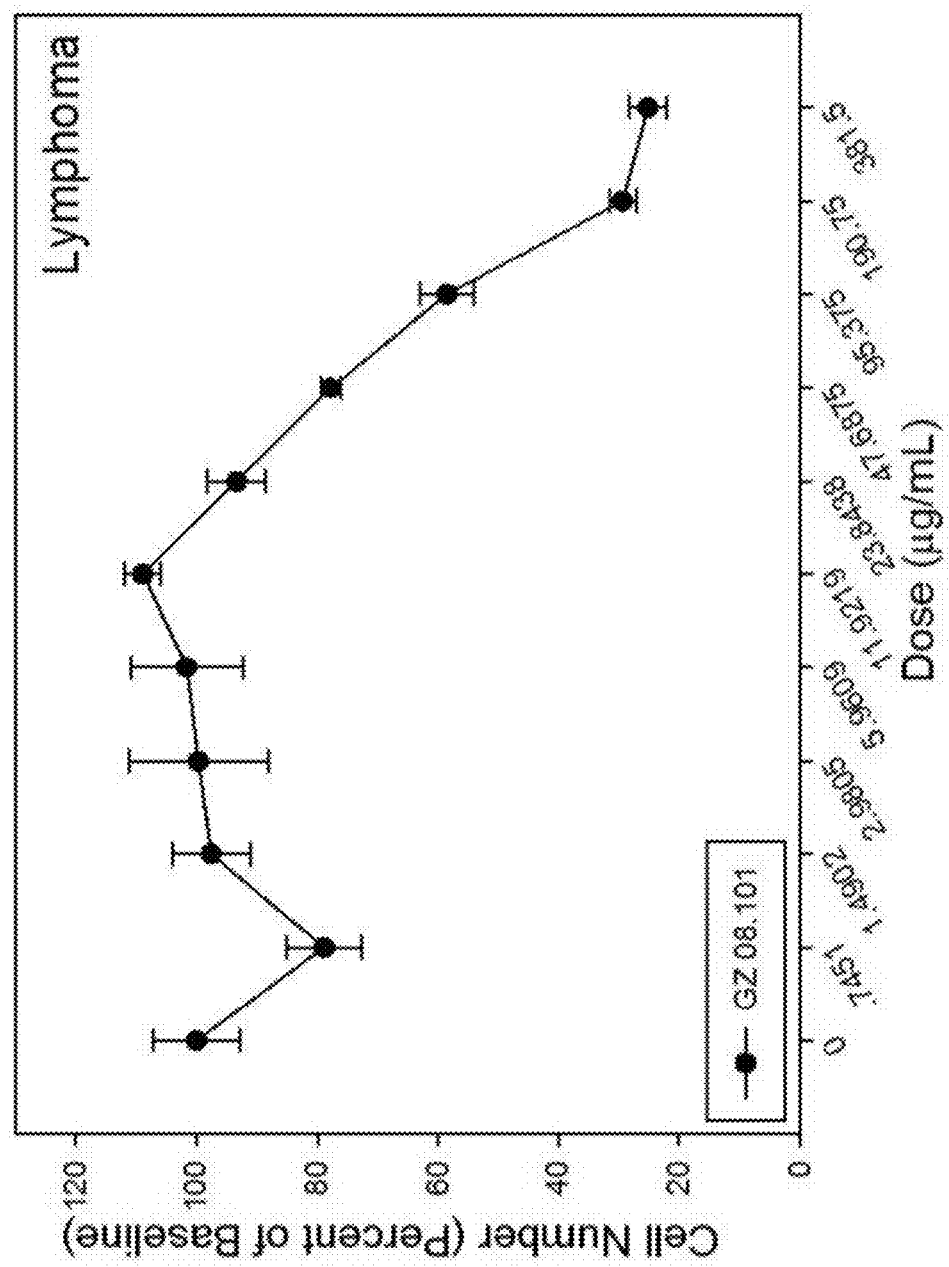
Figures 79, 82:
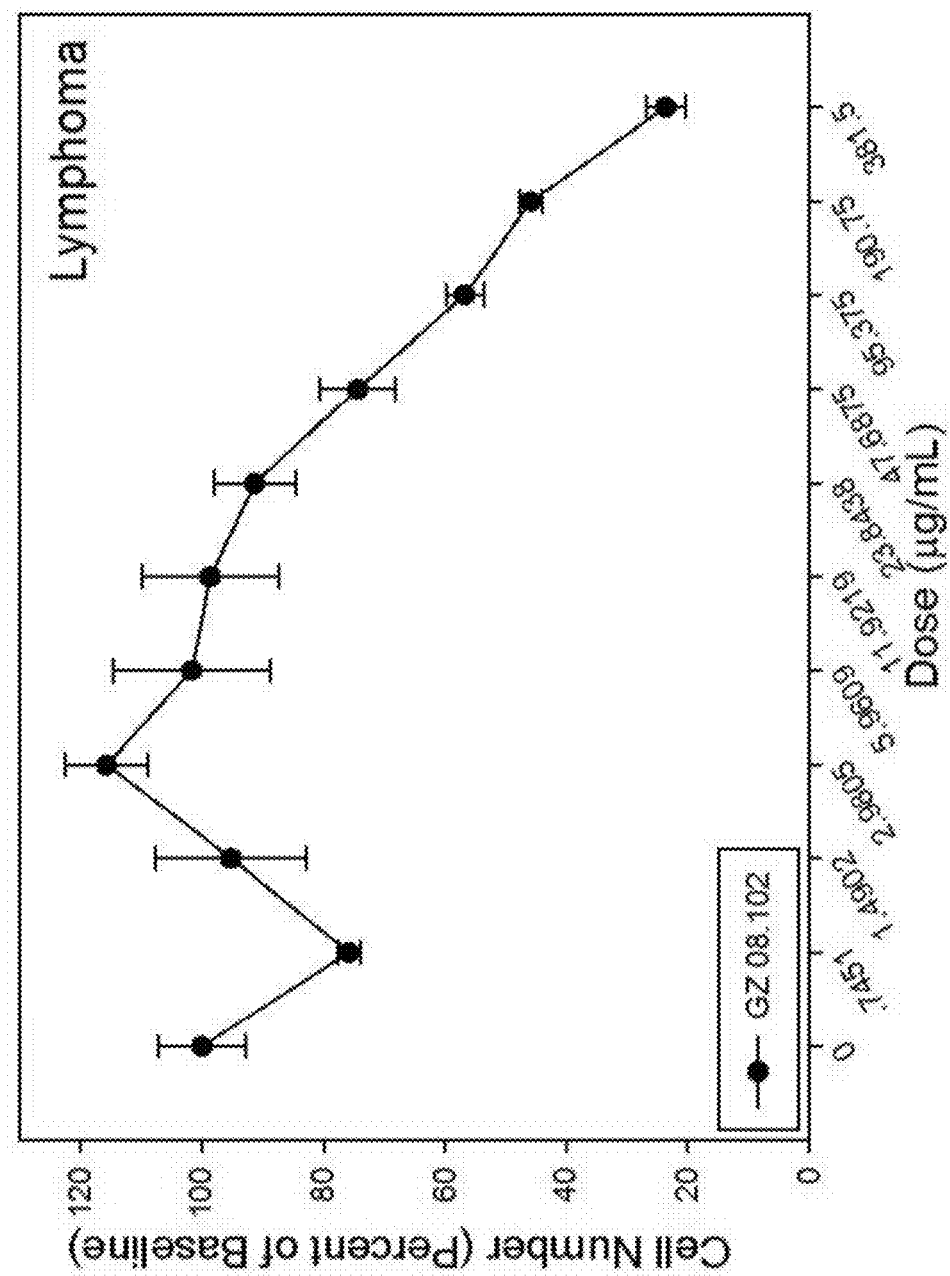
Figures 80, 82:
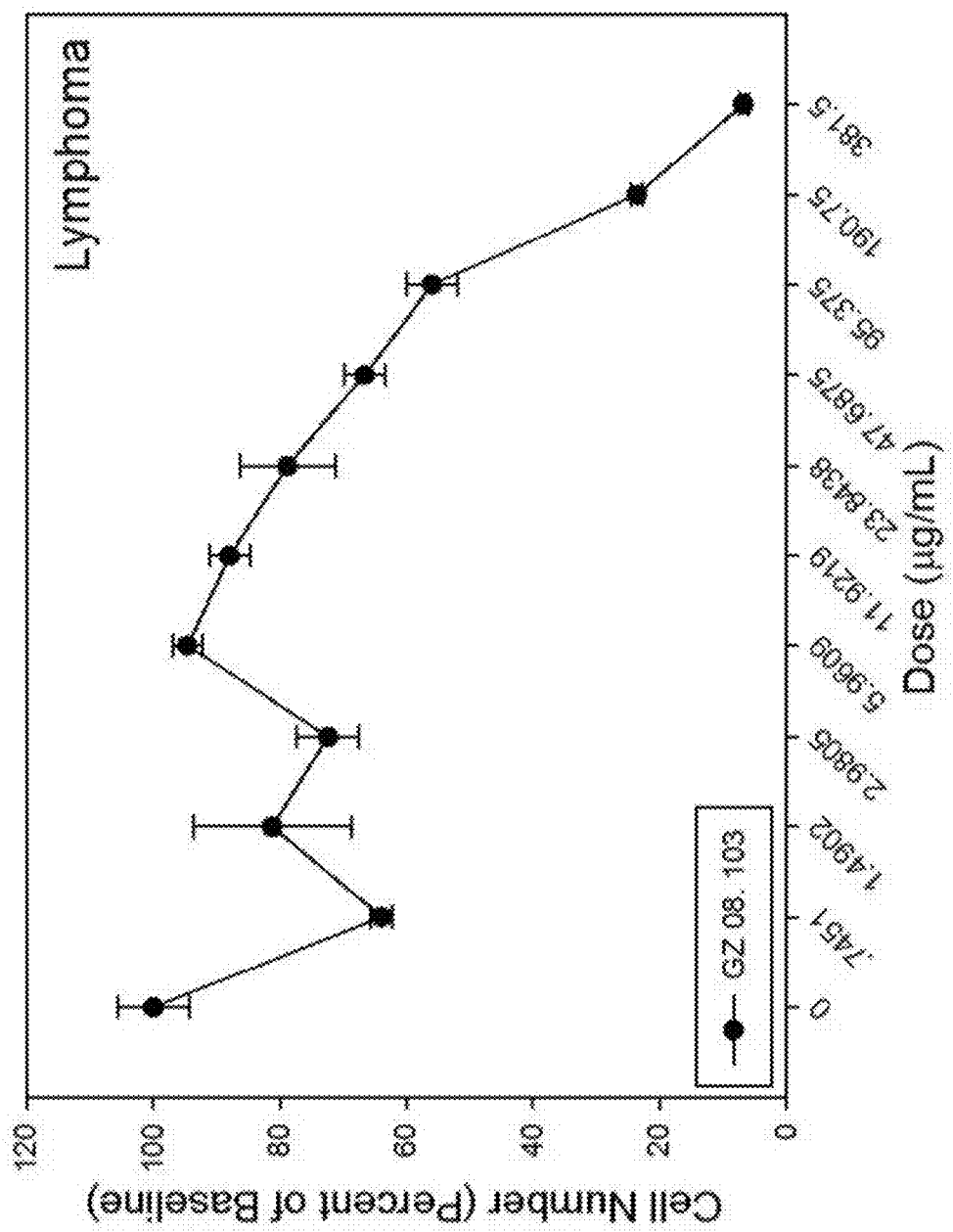
Figures 81, 82:
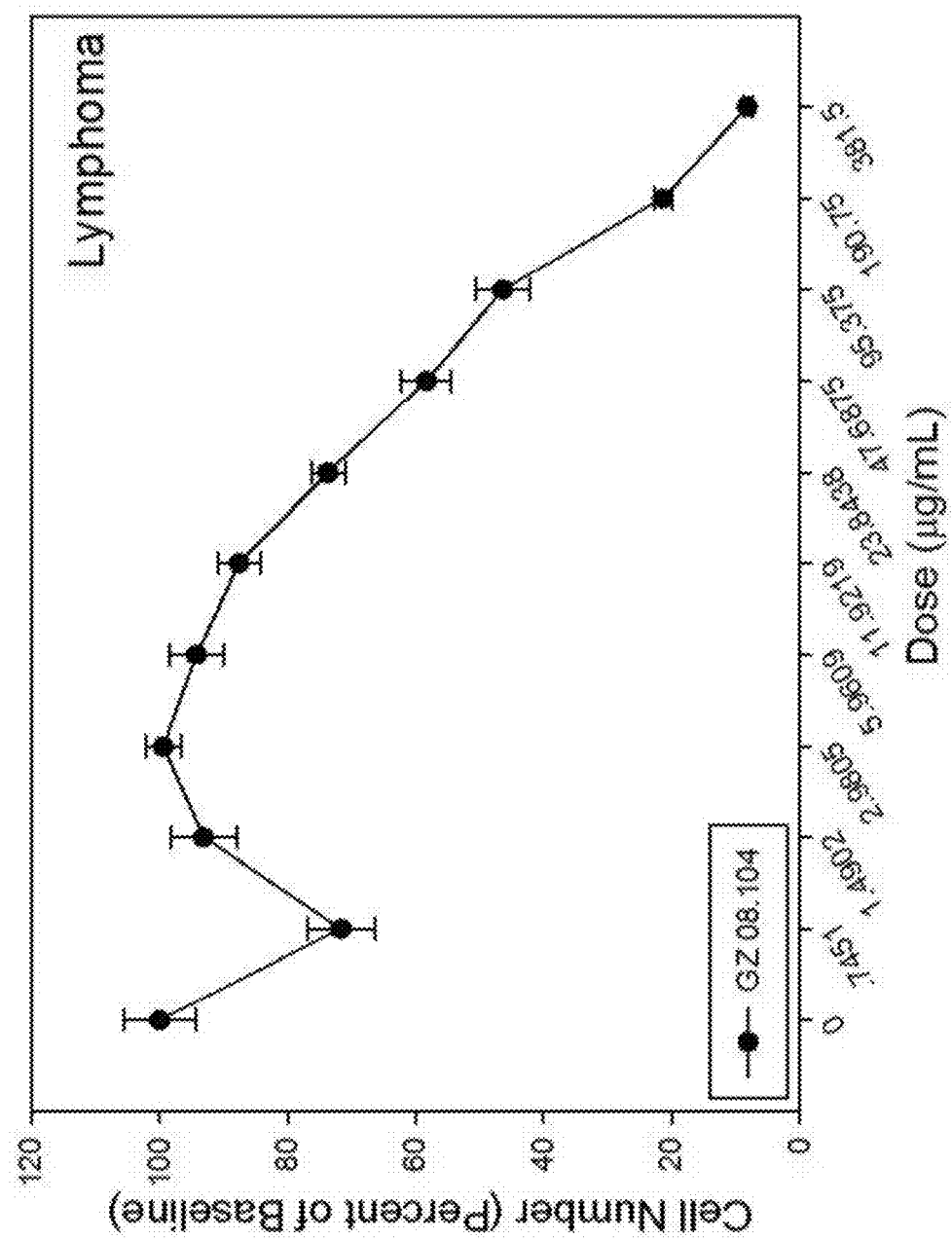
Figure 82:
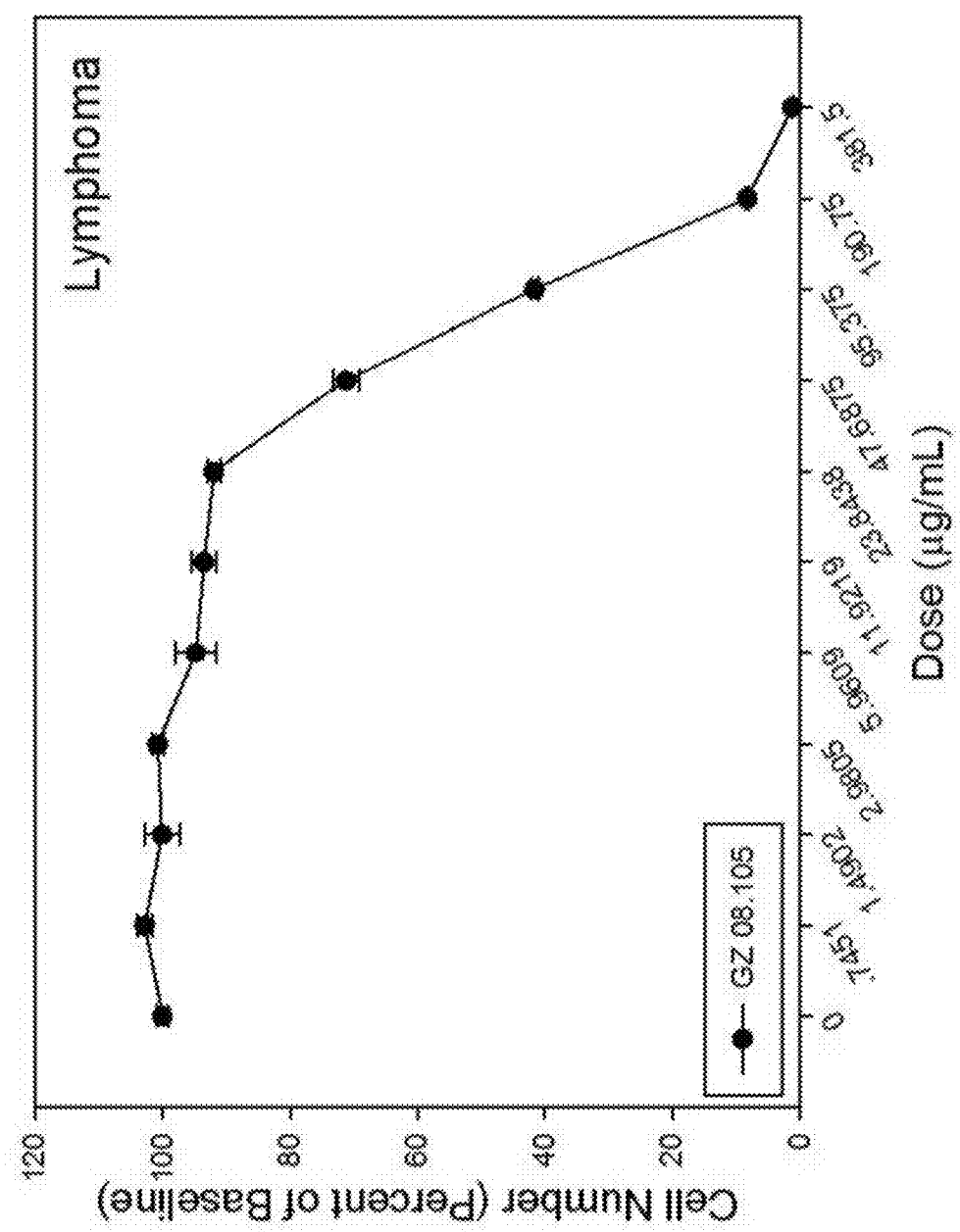
Figures 82, 83:
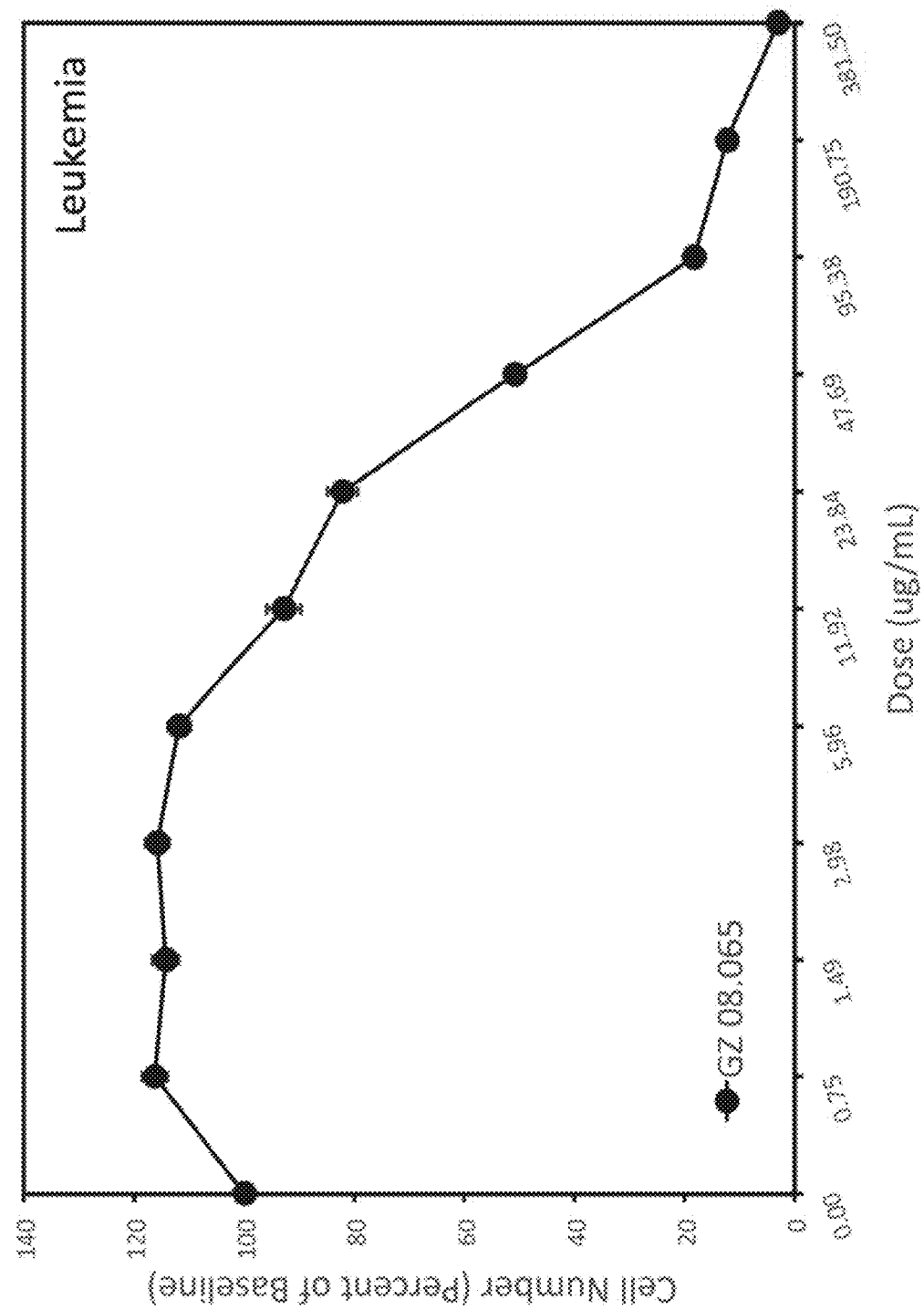
Figures 82, 83, 84:
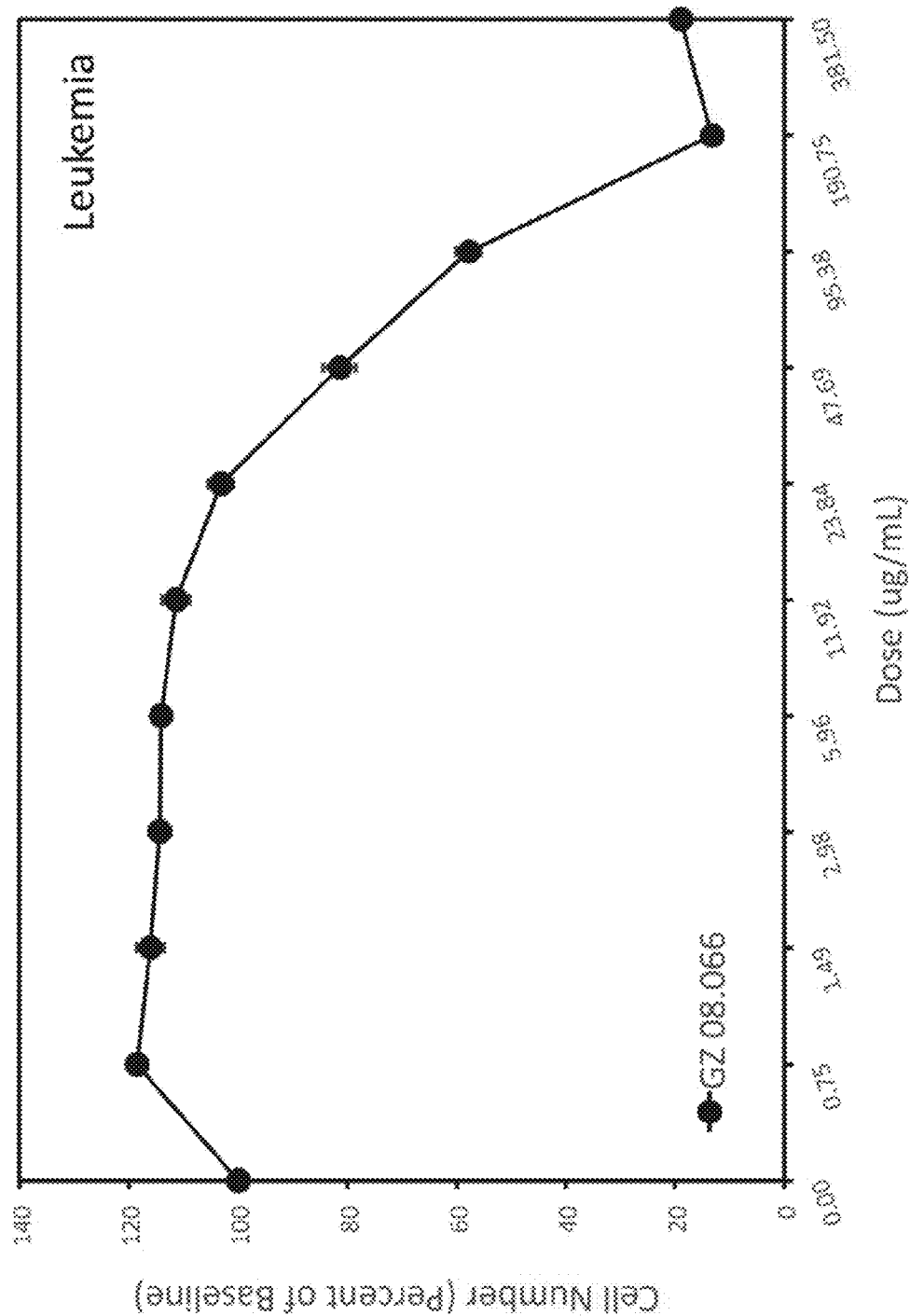
Figures 82, 83, 84, 85:
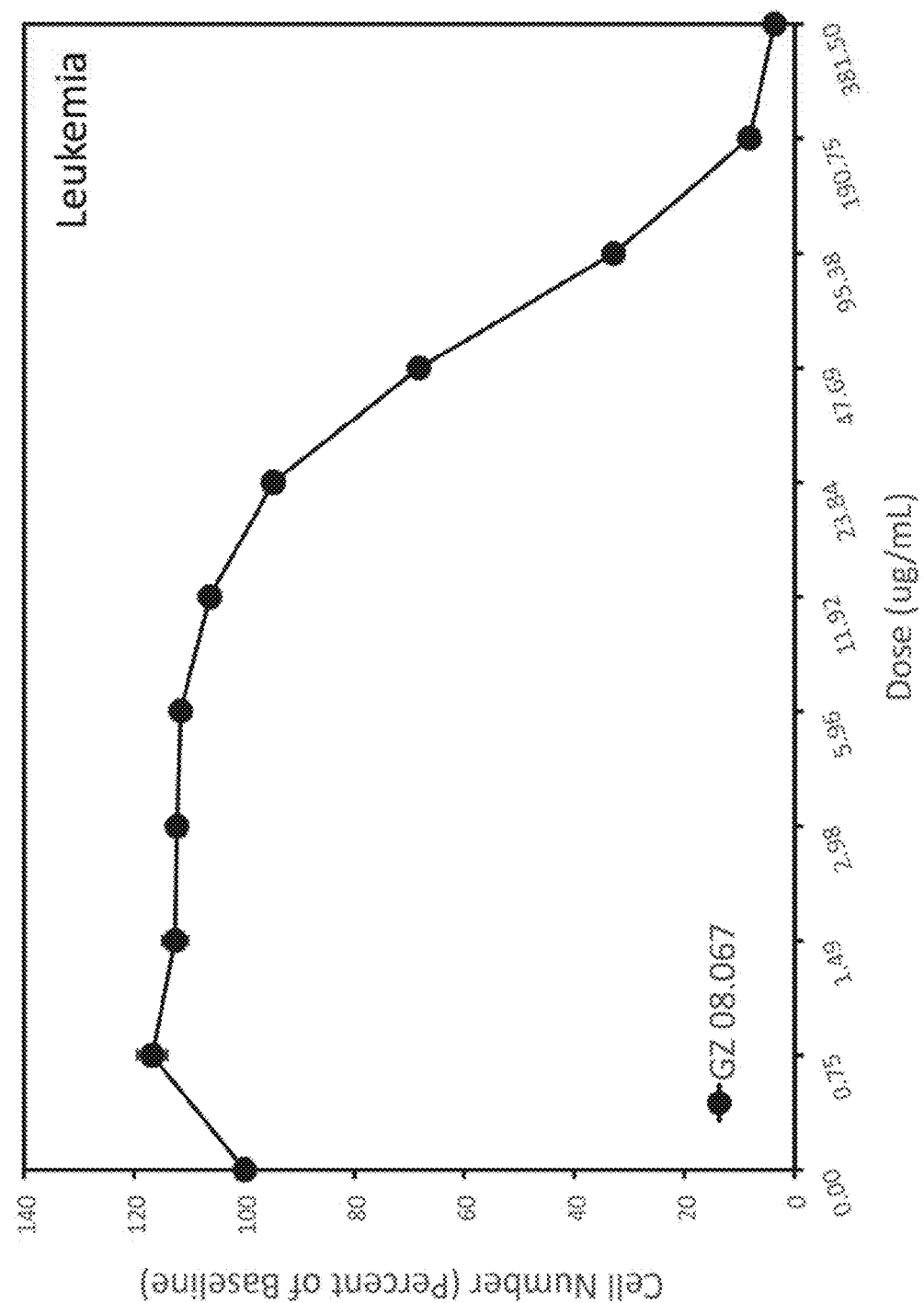
Figures 82, 83, 84, 85, 86:
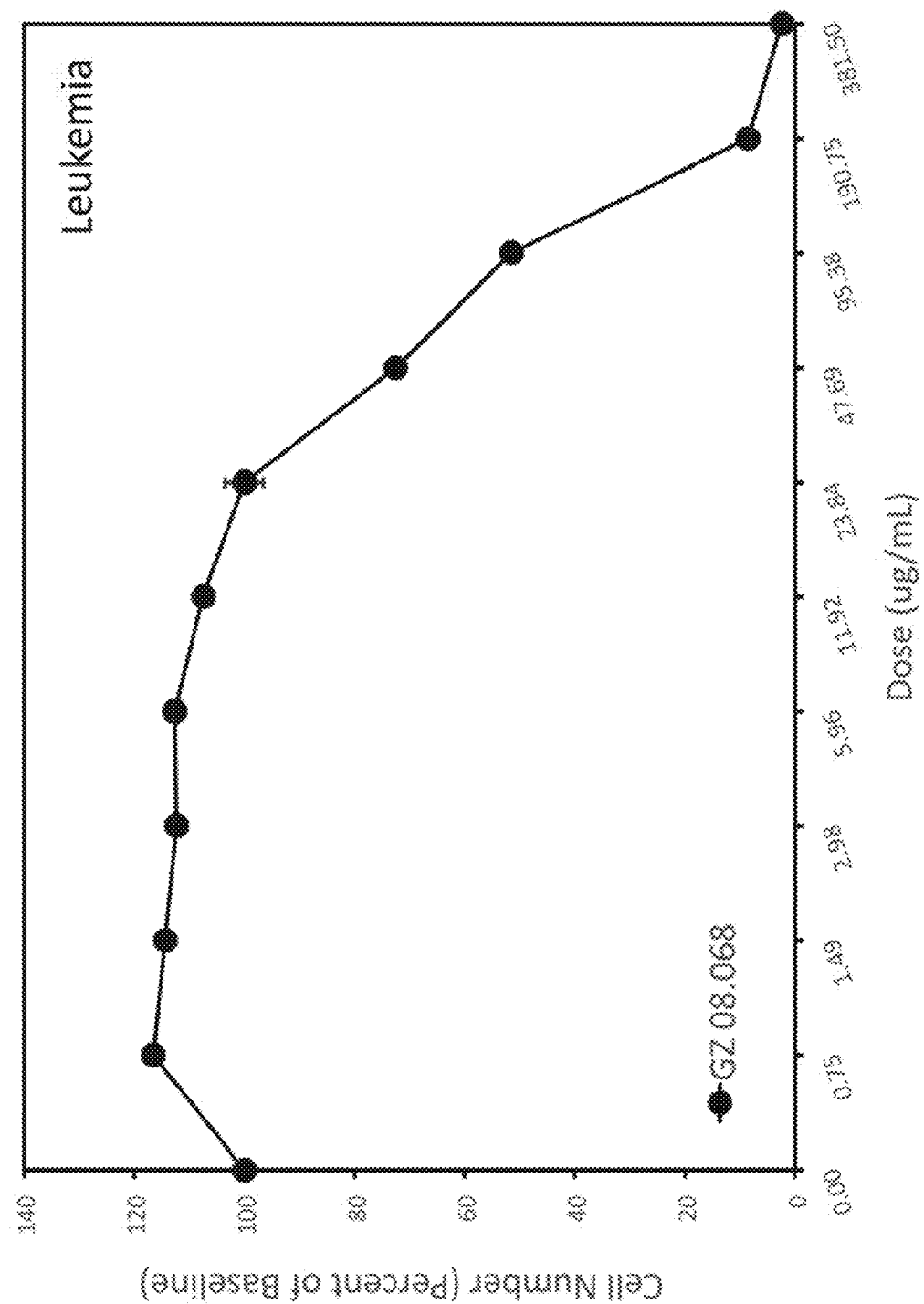
Figures 82, 83, 84, 85, 86, 87:
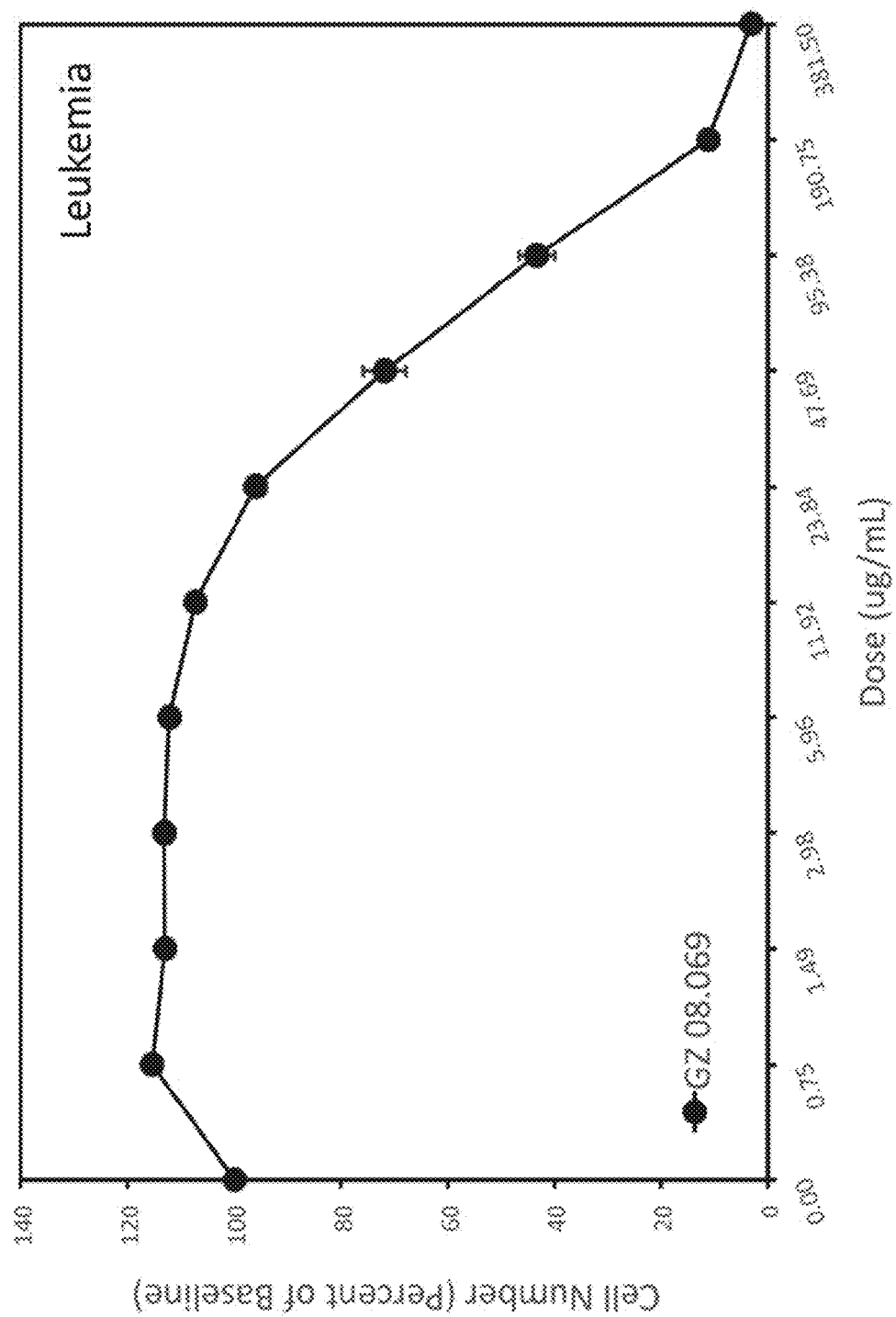
Figures 82, 83, 84, 85, 86, 87, 88:
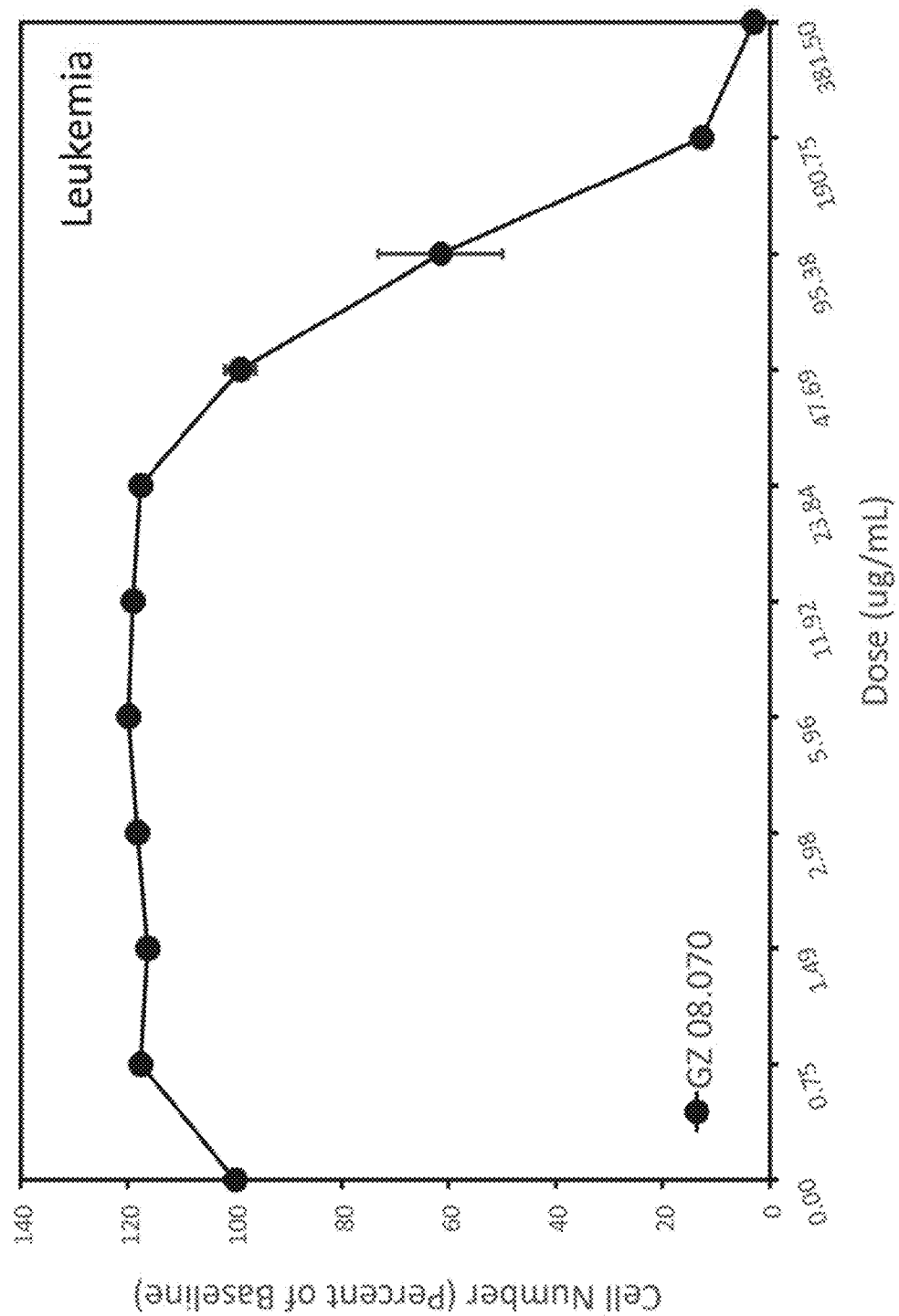
Figures 82, 83, 84, 85, 86, 87, 88, 89:
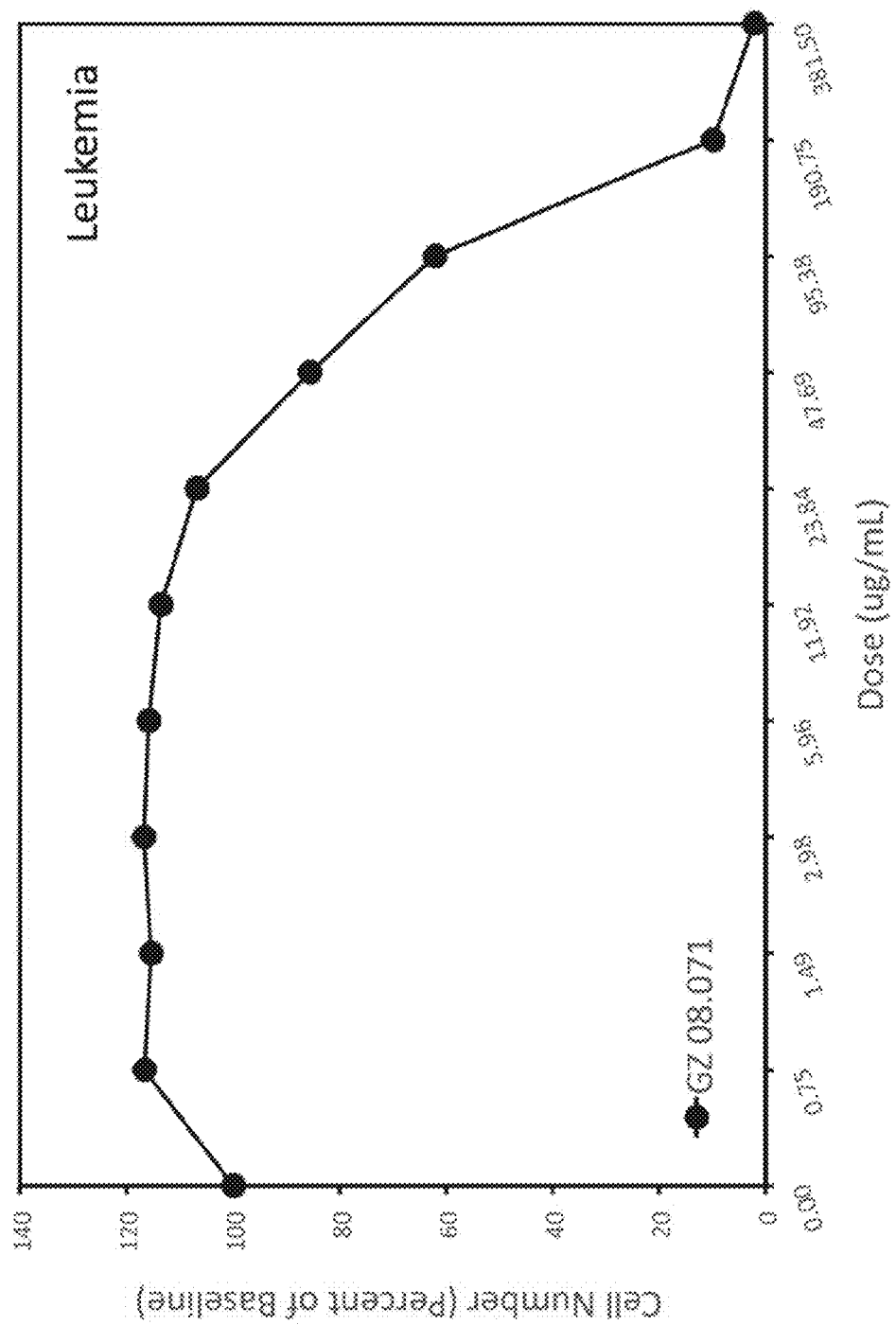
Figures 82, 83, 84, 85, 86, 87, 88, 89, 90:
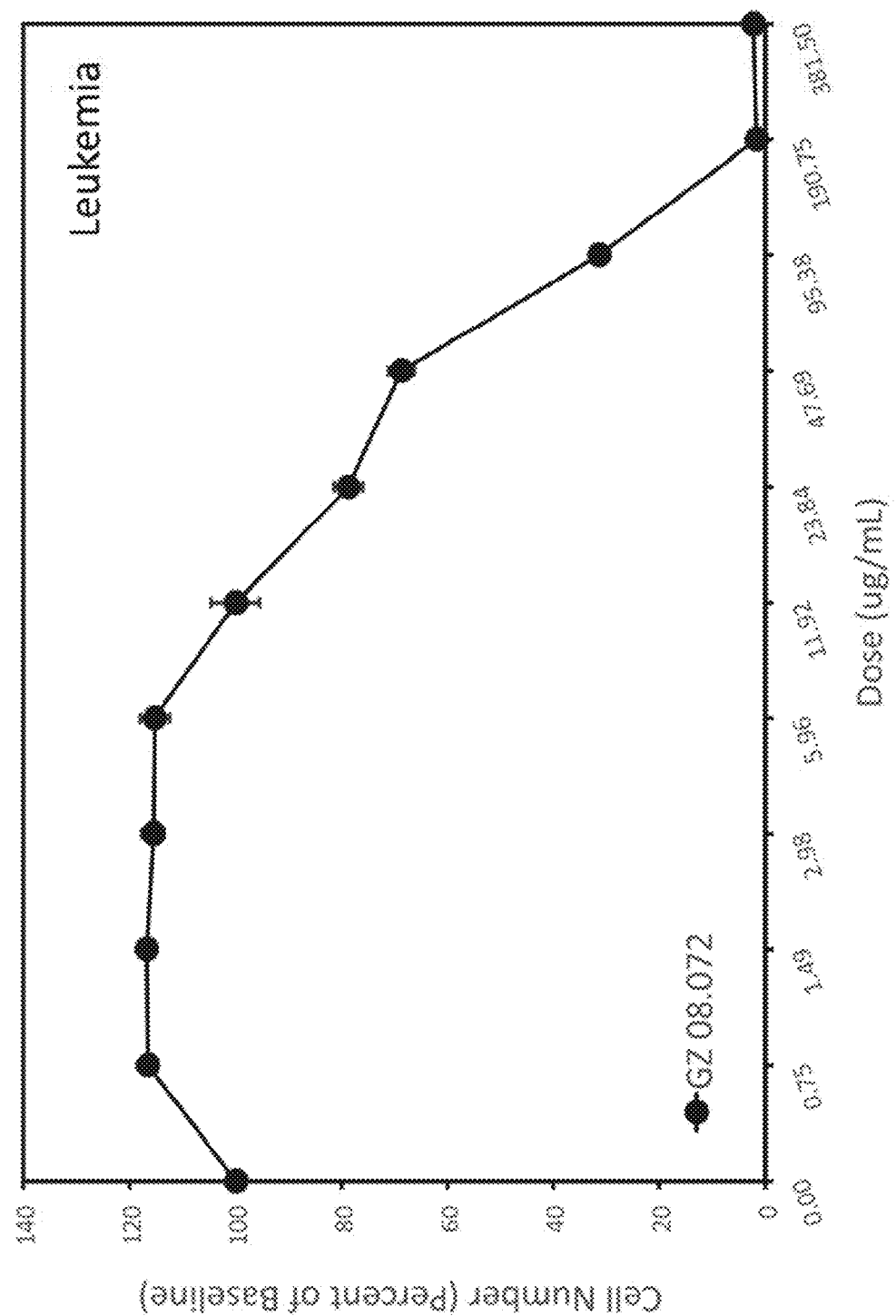
Figures 82, 83, 84, 85, 86, 87, 88, 89, 90, 91:
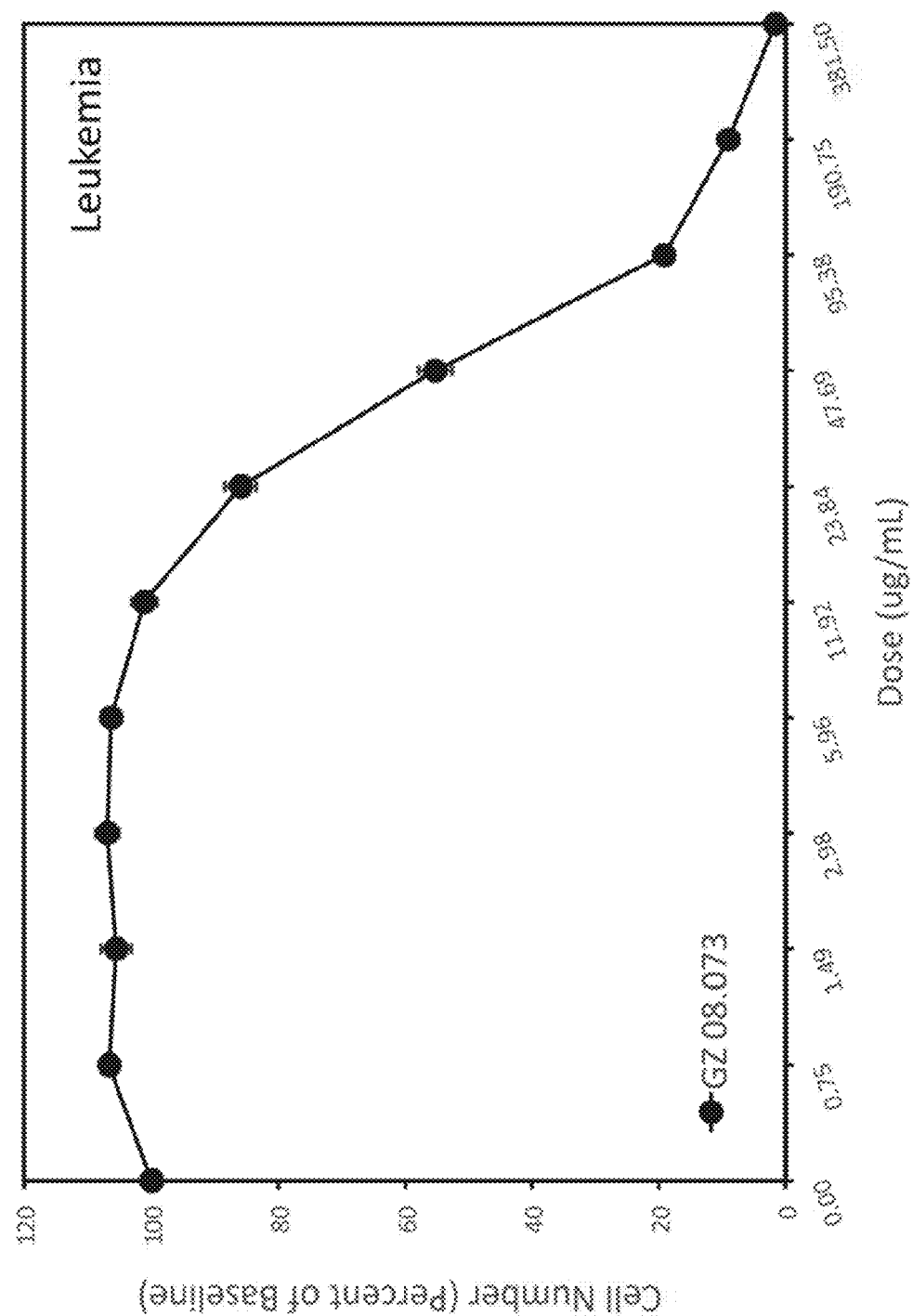
Figures 82, 83, 84, 85, 86, 87, 88, 89, 90, 91, 92:
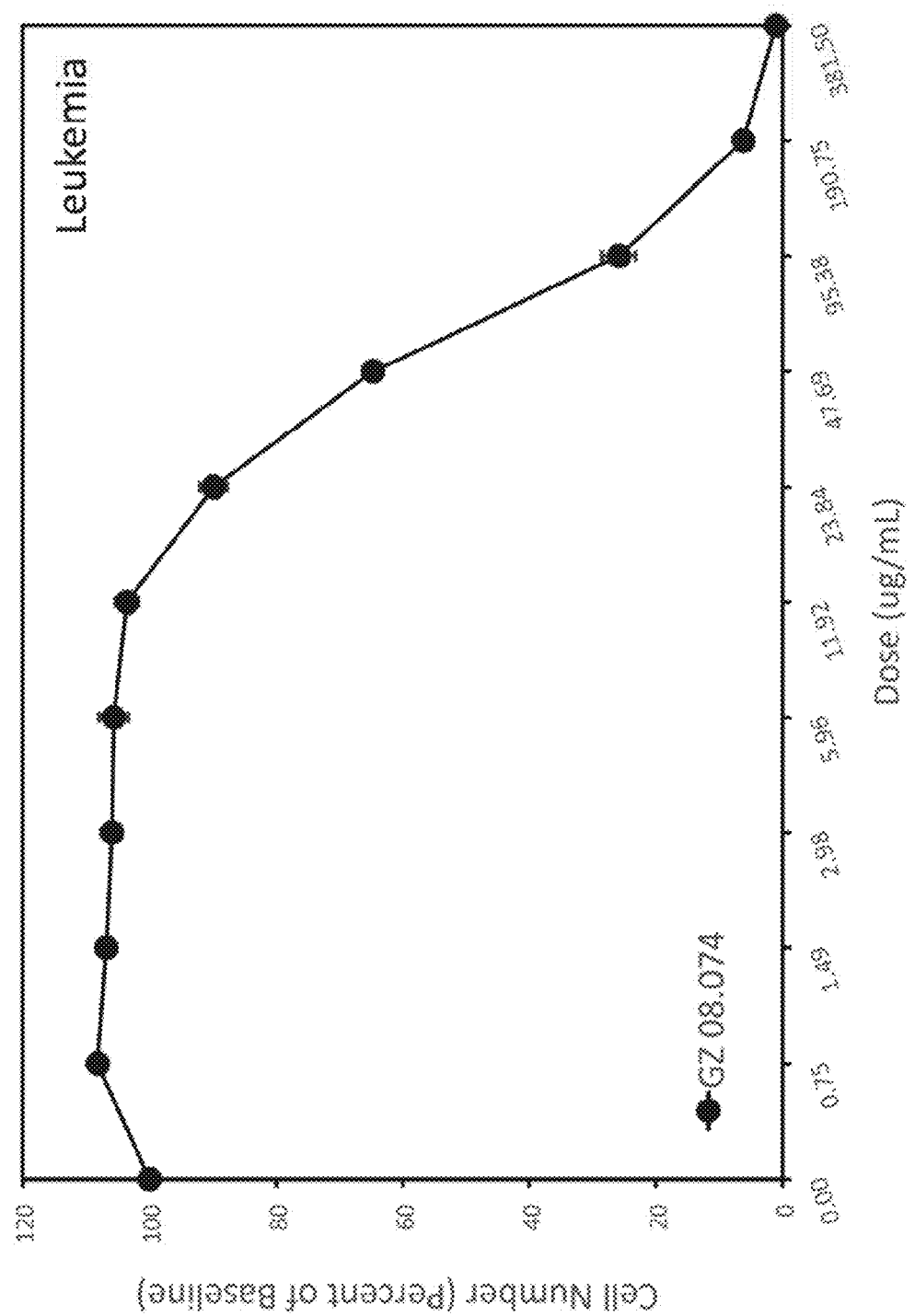
Figures 82, 83, 84, 85, 86, 87, 88, 89, 90, 91, 92, 93:
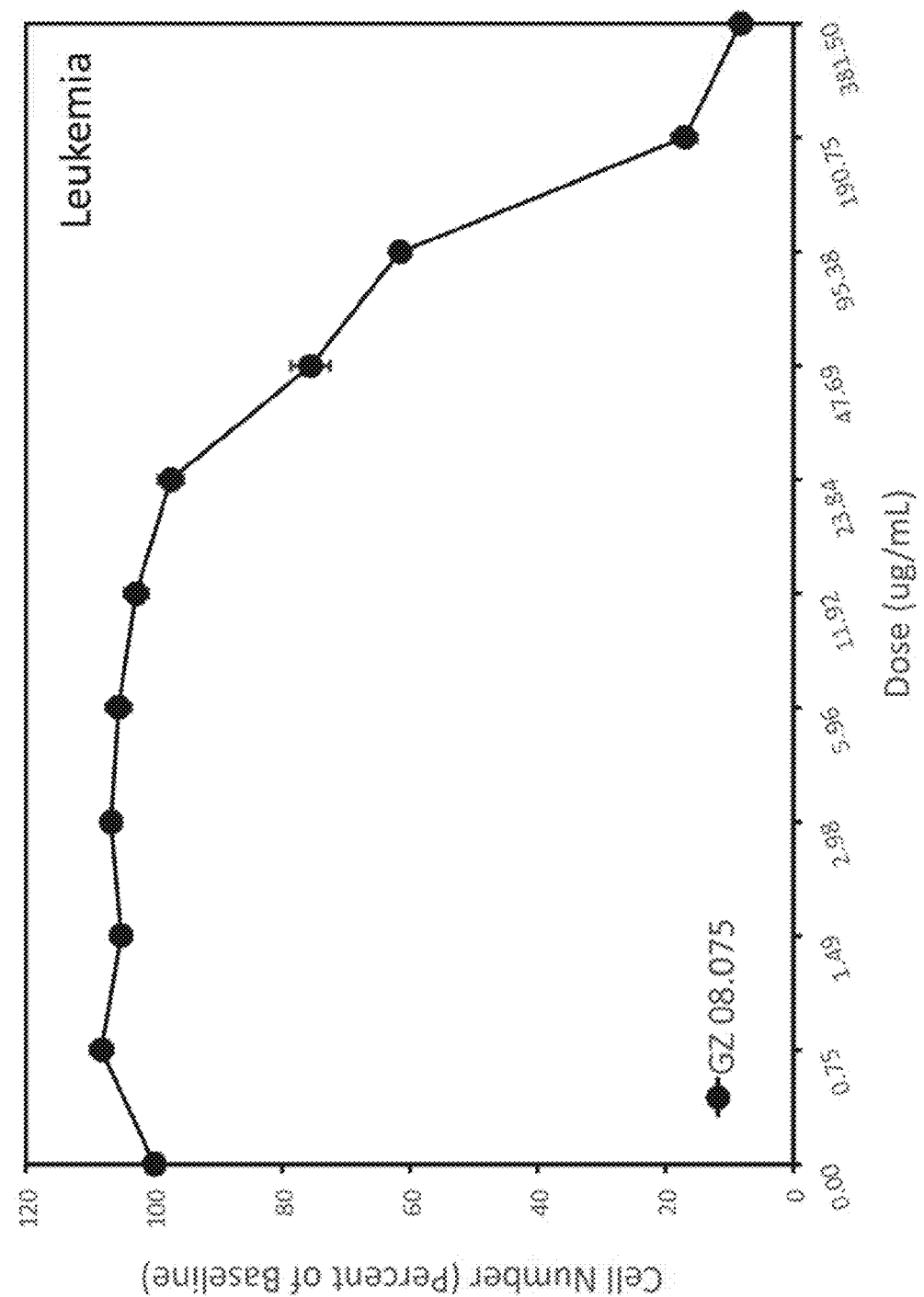
Figures 82, 83, 84, 85, 86, 87, 88, 89, 90, 91, 92, 93, 94:
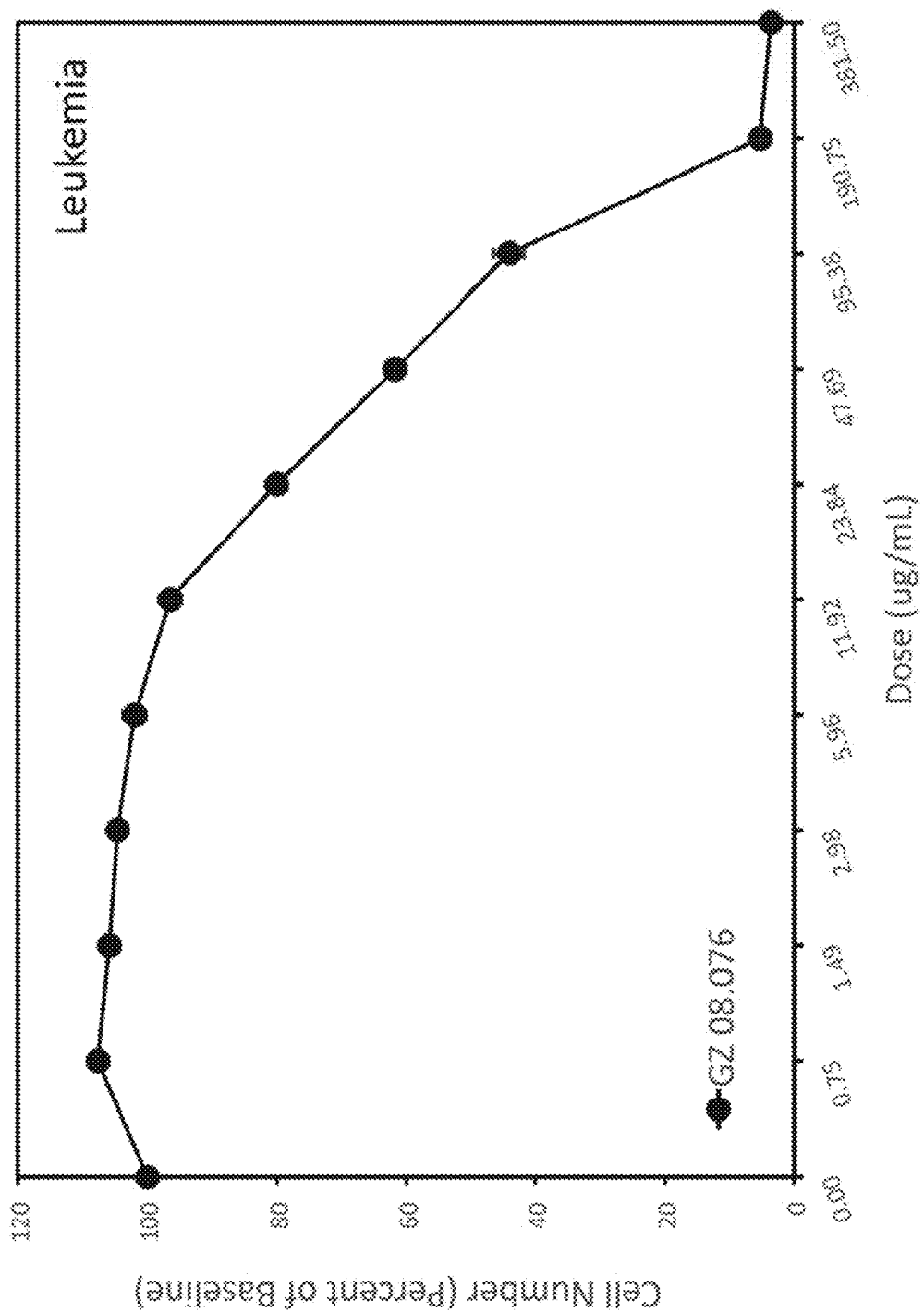
Figures 82, 83, 84, 85, 86, 87, 88, 89, 90, 91, 92, 93, 94, 95:
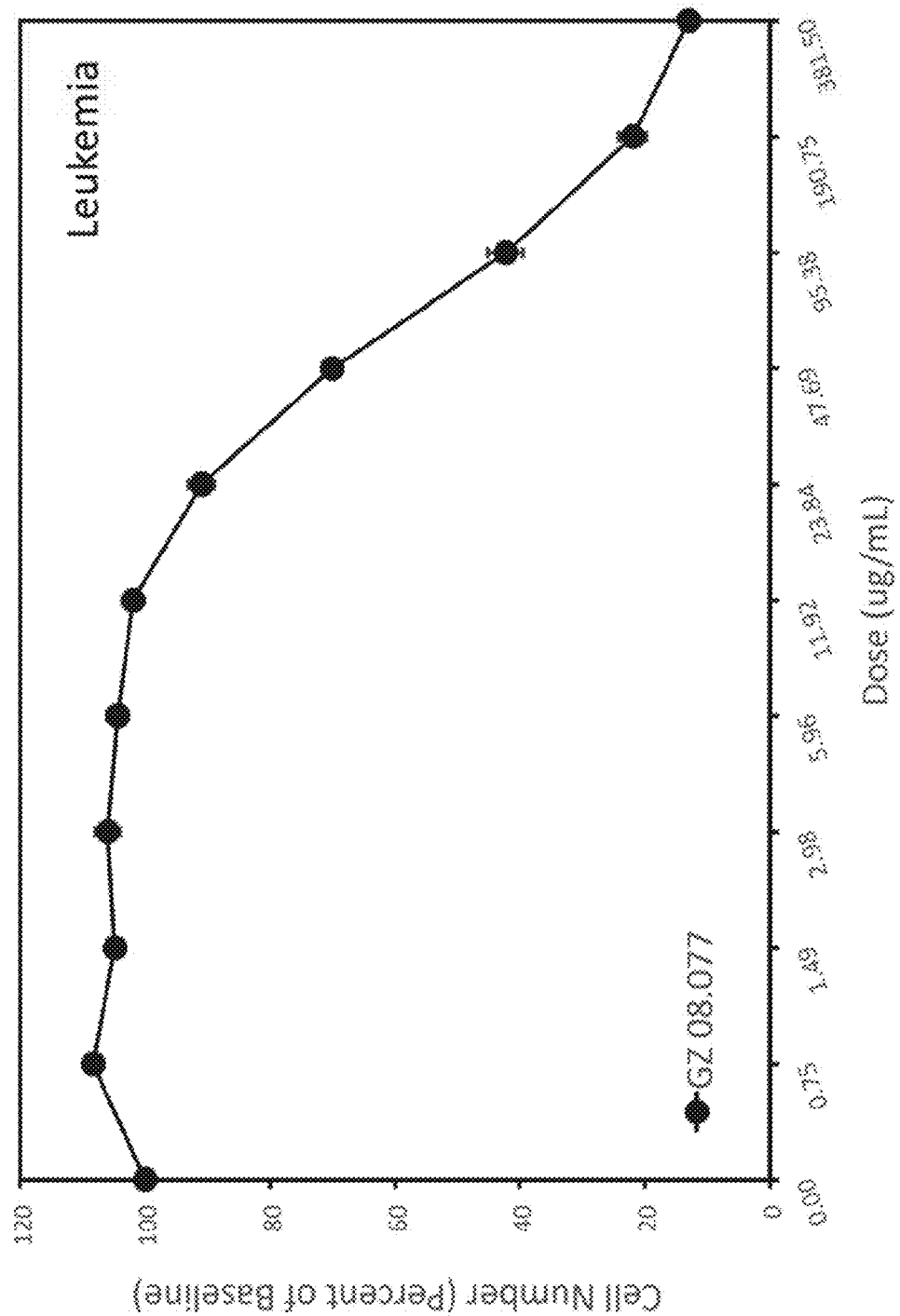
Figures 82, 83, 84, 85, 86, 87, 88, 89, 90, 91, 92, 93, 94, 95, 96:
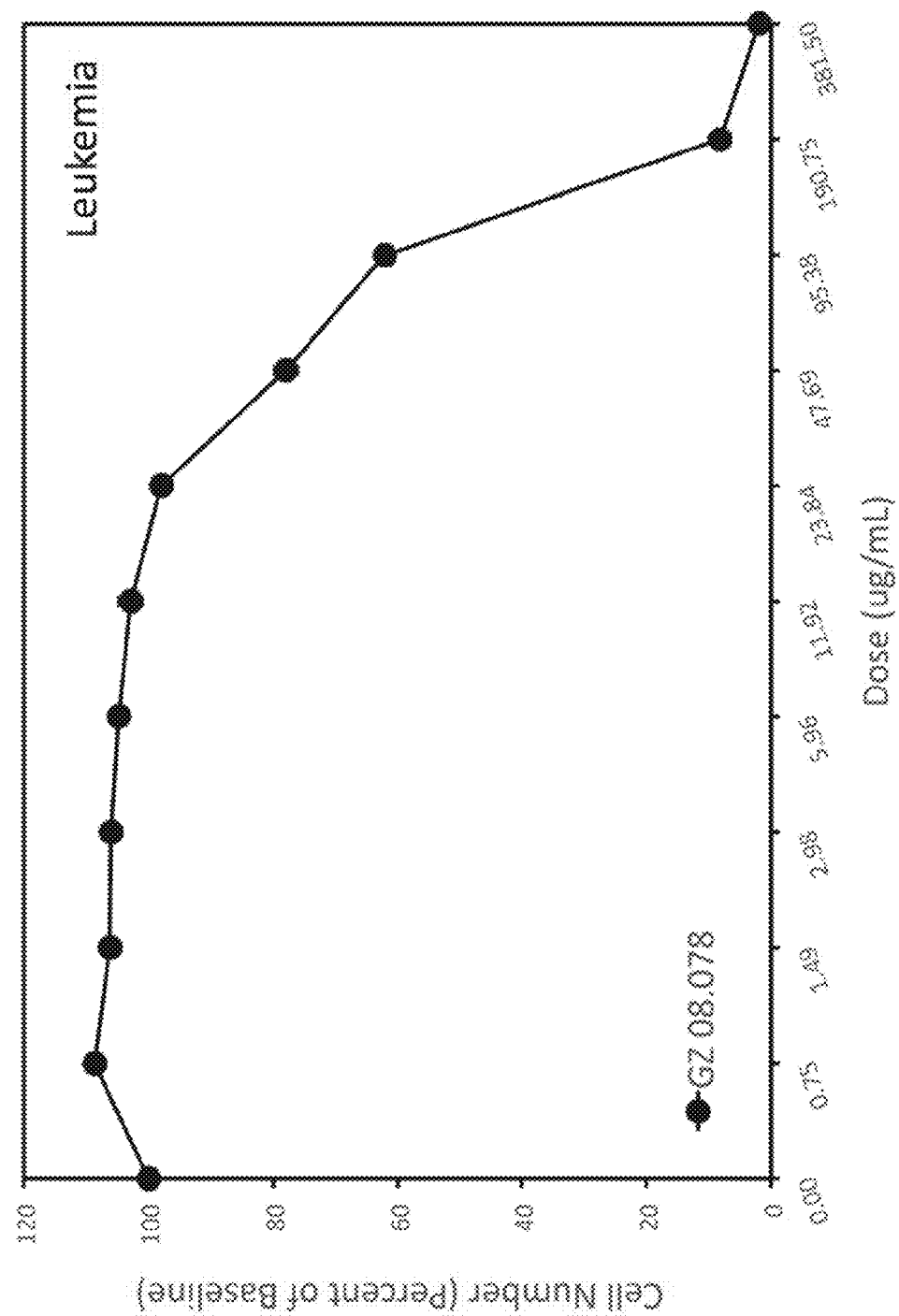
Figures 82, 83, 84, 85, 86, 87, 88, 89, 90, 91, 92, 93, 94, 95, 96, 97:
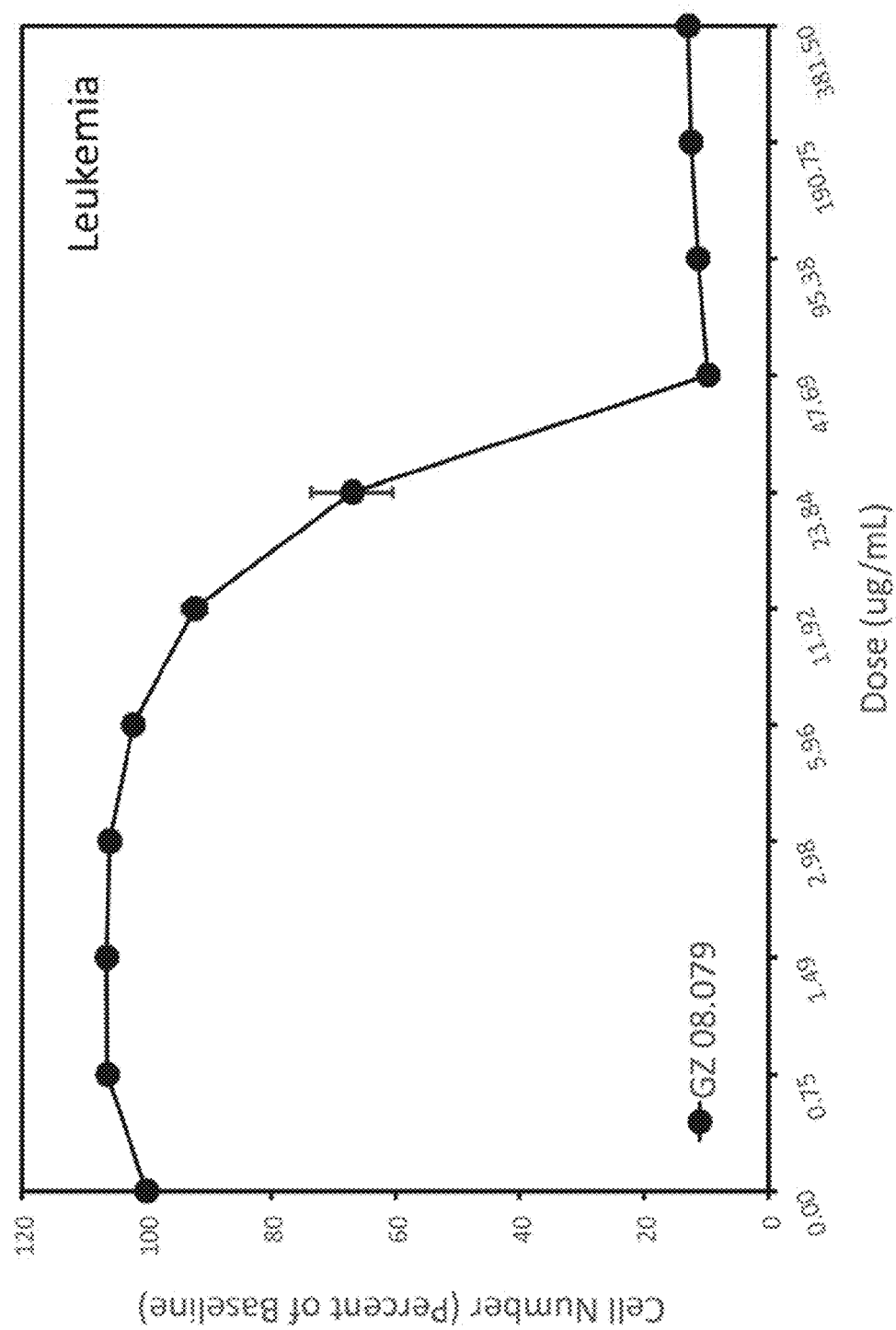
Figures 82, 83, 84, 85, 86, 87, 88, 89, 90, 91, 92, 93, 94, 95, 96, 97, 98:
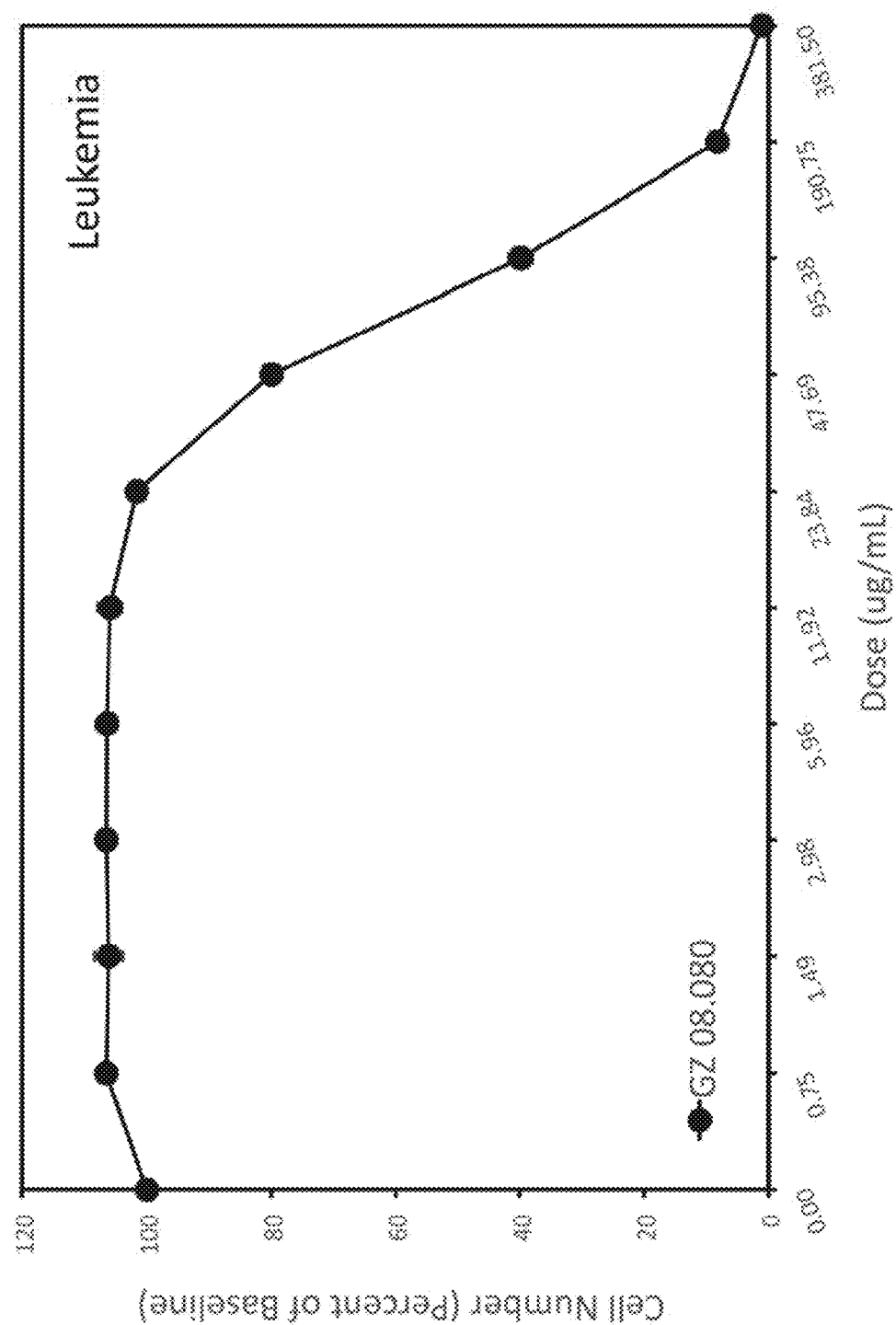
Figures 82, 83, 84, 85, 86, 87, 88, 89, 90, 91, 92, 93, 94, 95, 96, 97, 98, 99:
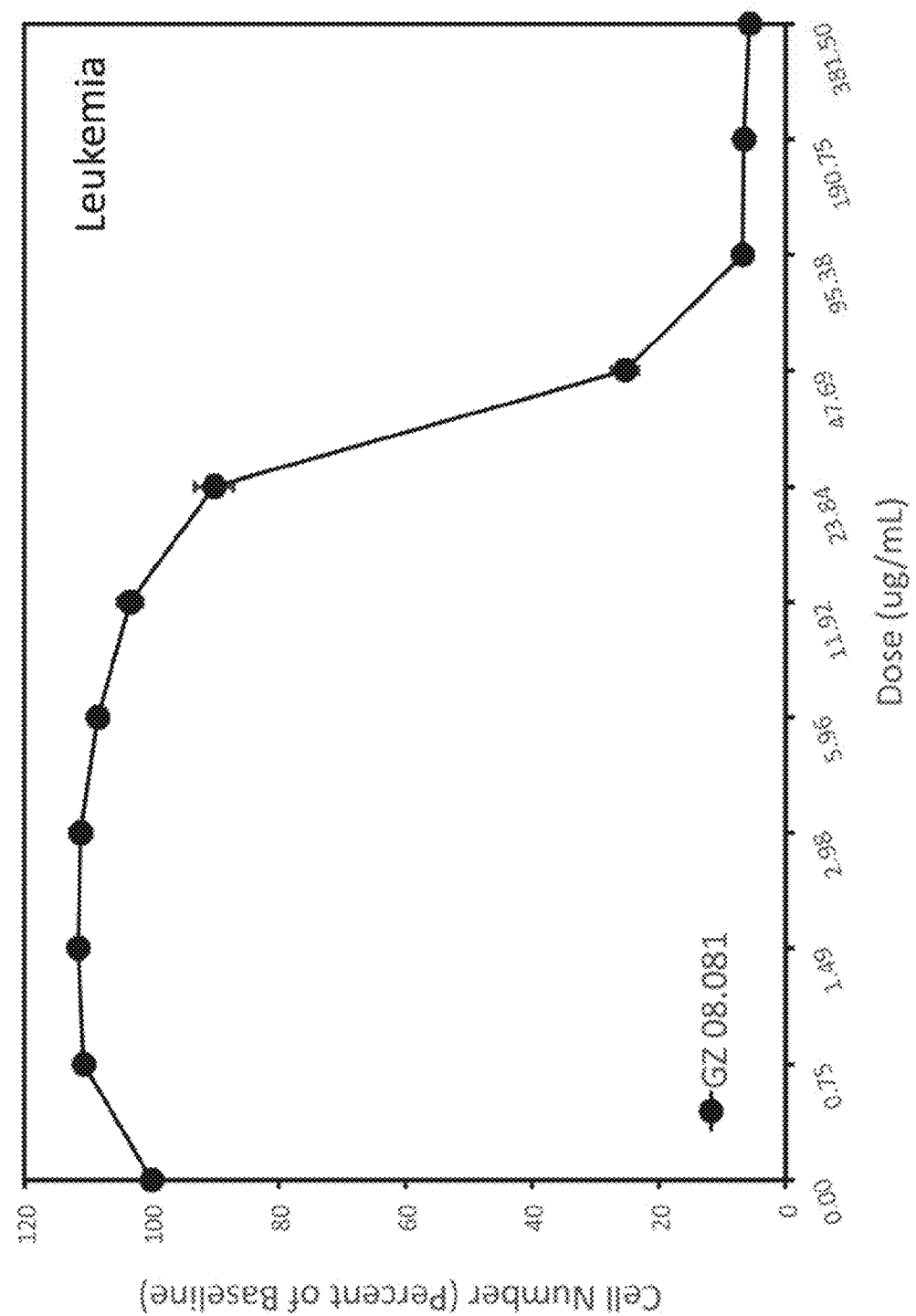
Figures 82, 83, 84, 85, 86, 87, 88, 89, 90, 91, 92, 93, 94, 95, 96, 97, 98, 99, 100:
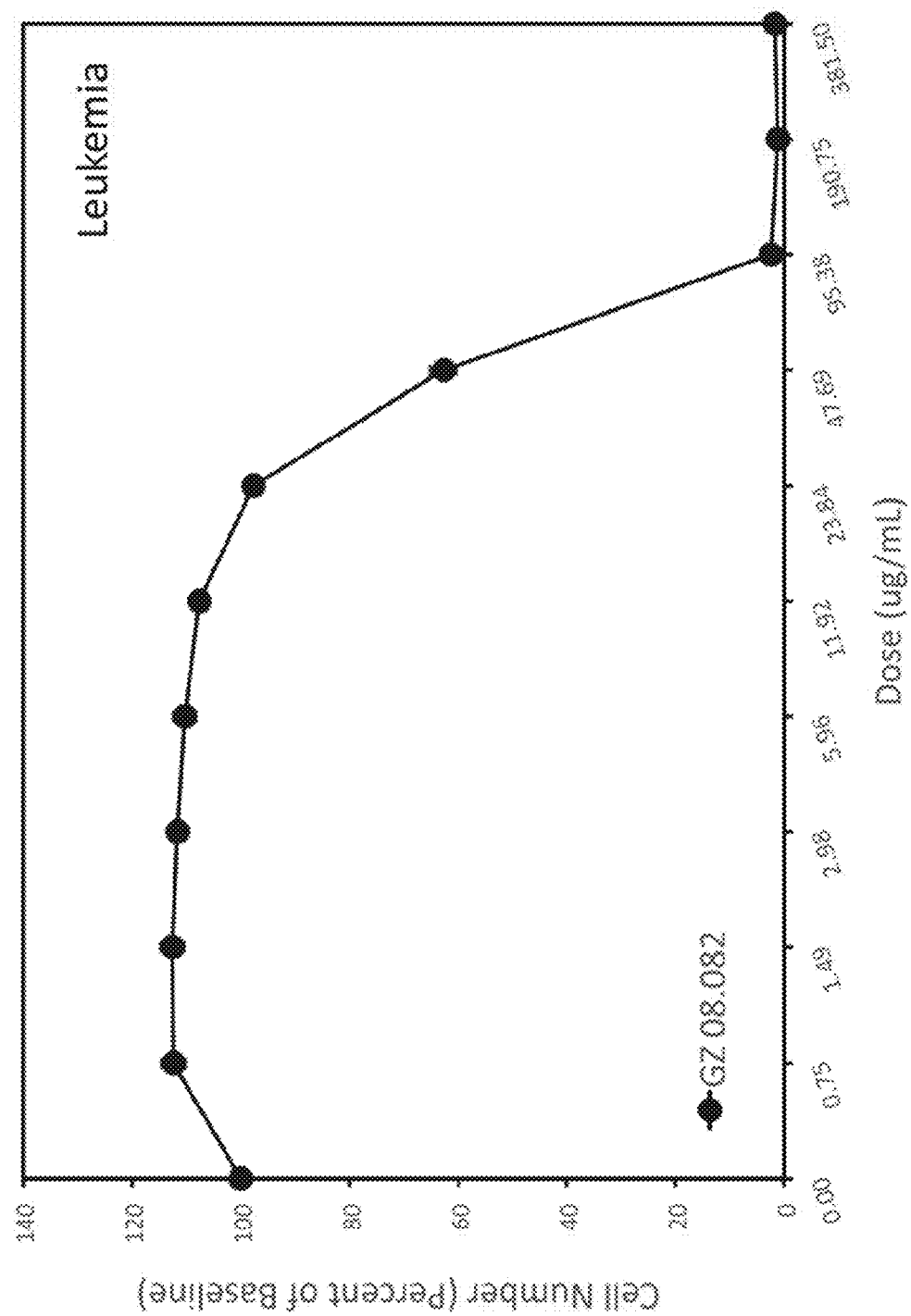
Figures 82, 83, 84, 85, 86, 87, 88, 89, 90, 91, 92, 93, 94, 95, 96, 97, 98, 99, 100, 101:
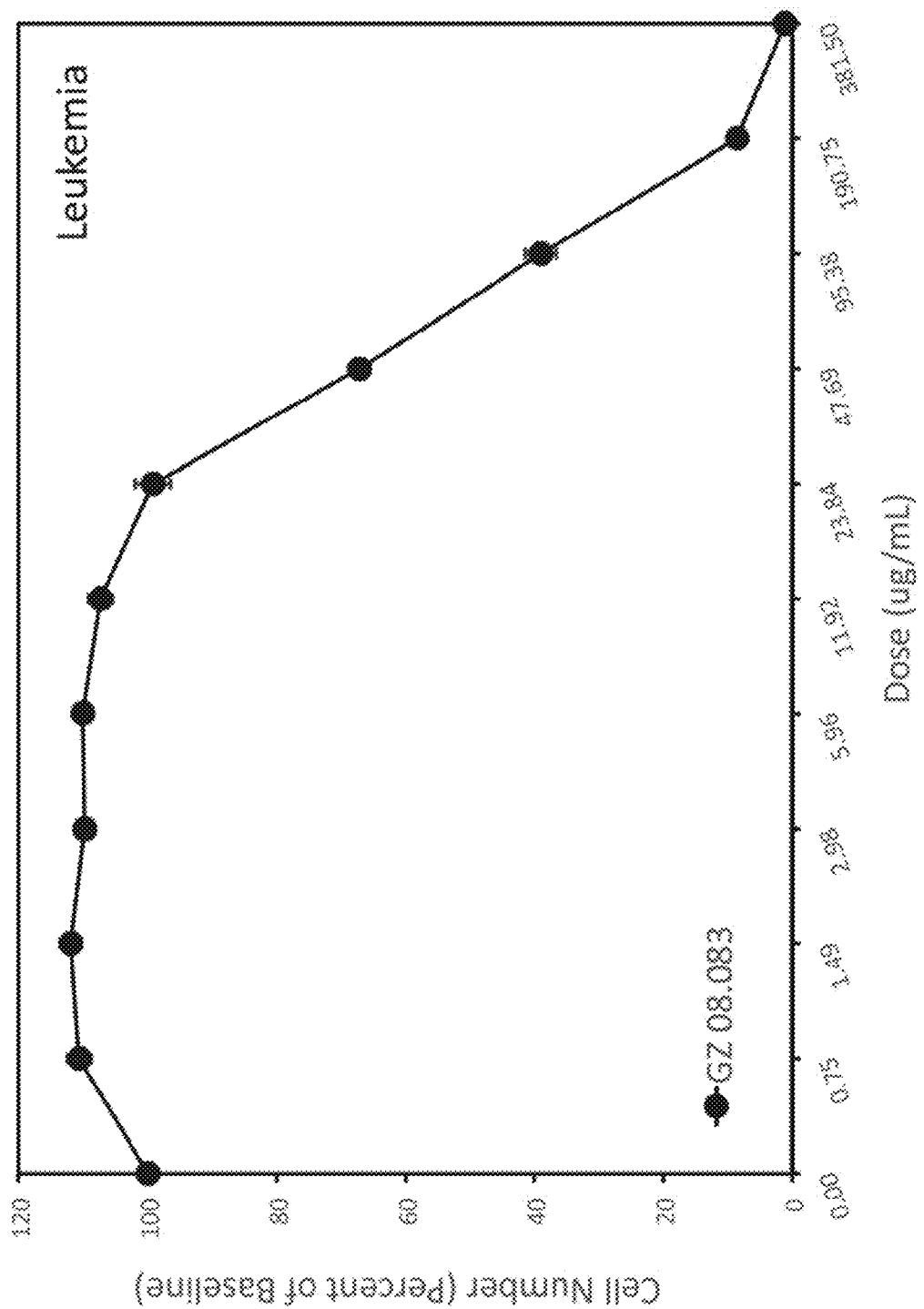
Figures 82, 83, 84, 85, 86, 87, 88, 89, 90, 91, 92, 93, 94, 95, 96, 97, 98, 99, 100, 101, 102:
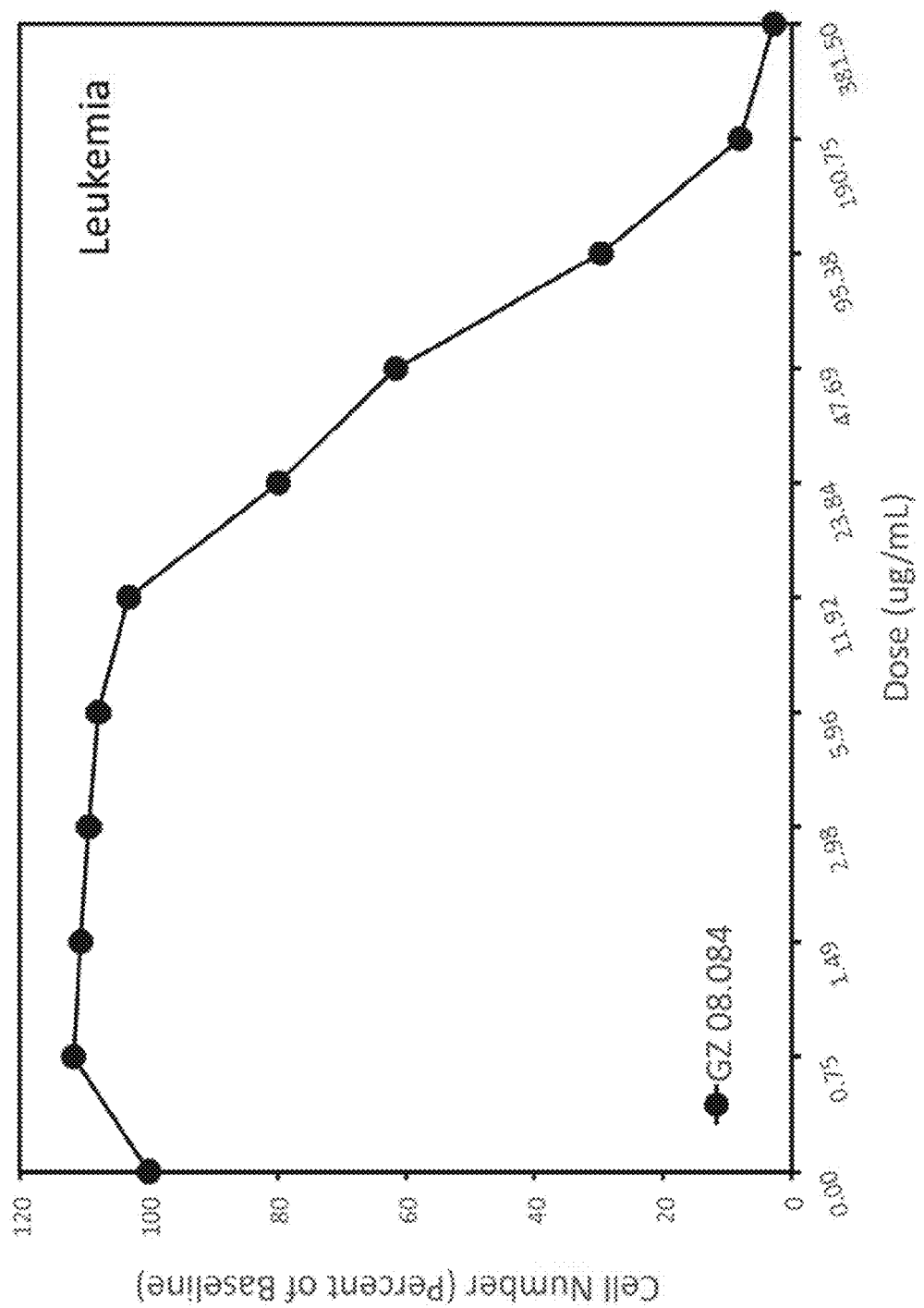
Figures 82, 83, 84, 85, 86, 87, 88, 89, 90, 91, 92, 93, 94, 95, 96, 97, 98, 99, 100, 101, 102, 103:
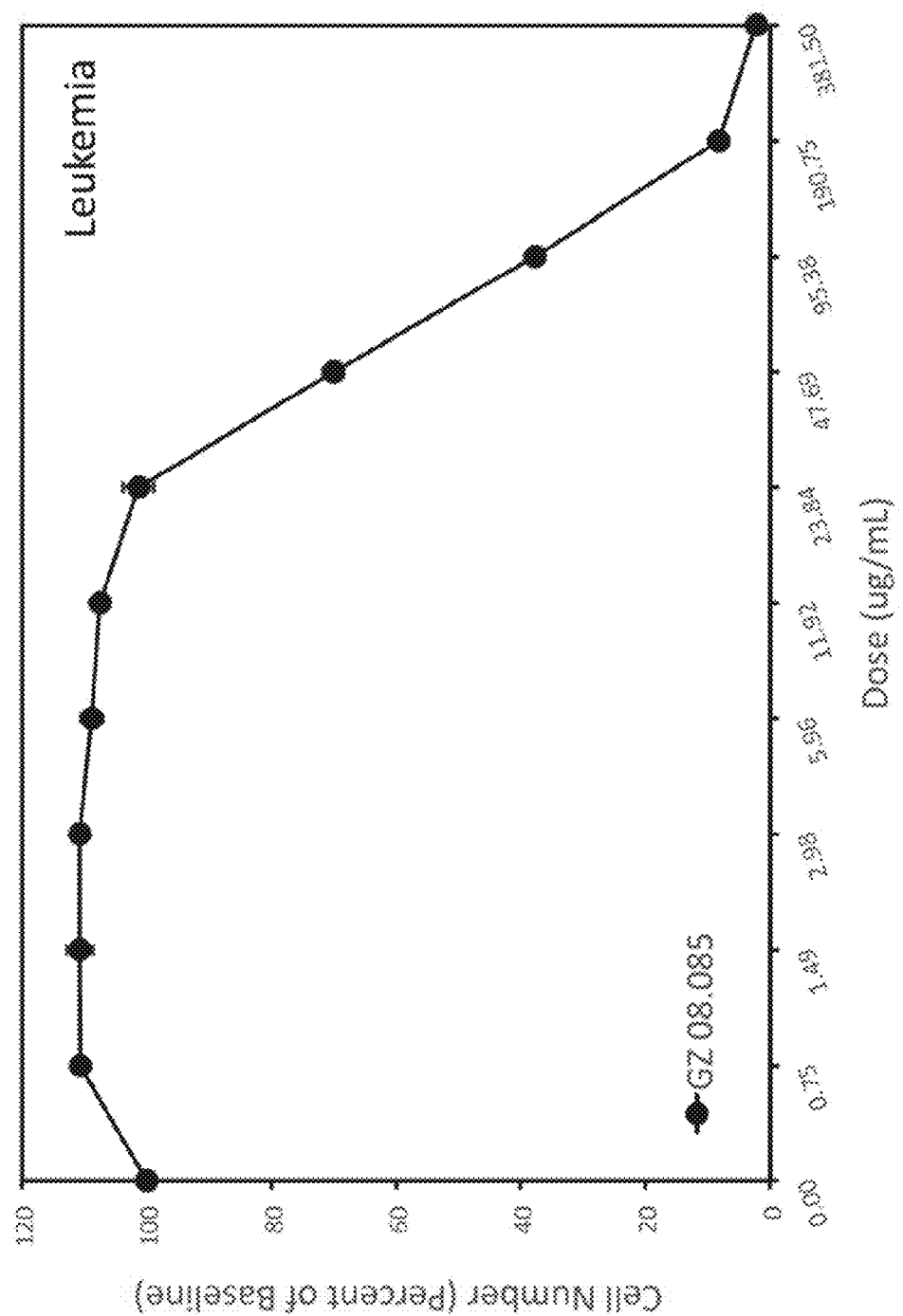
Figures 82, 83, 84, 85, 86, 87, 88, 89, 90, 91, 92, 93, 94, 95, 96, 97, 98, 99, 100, 101, 102, 103, 104:
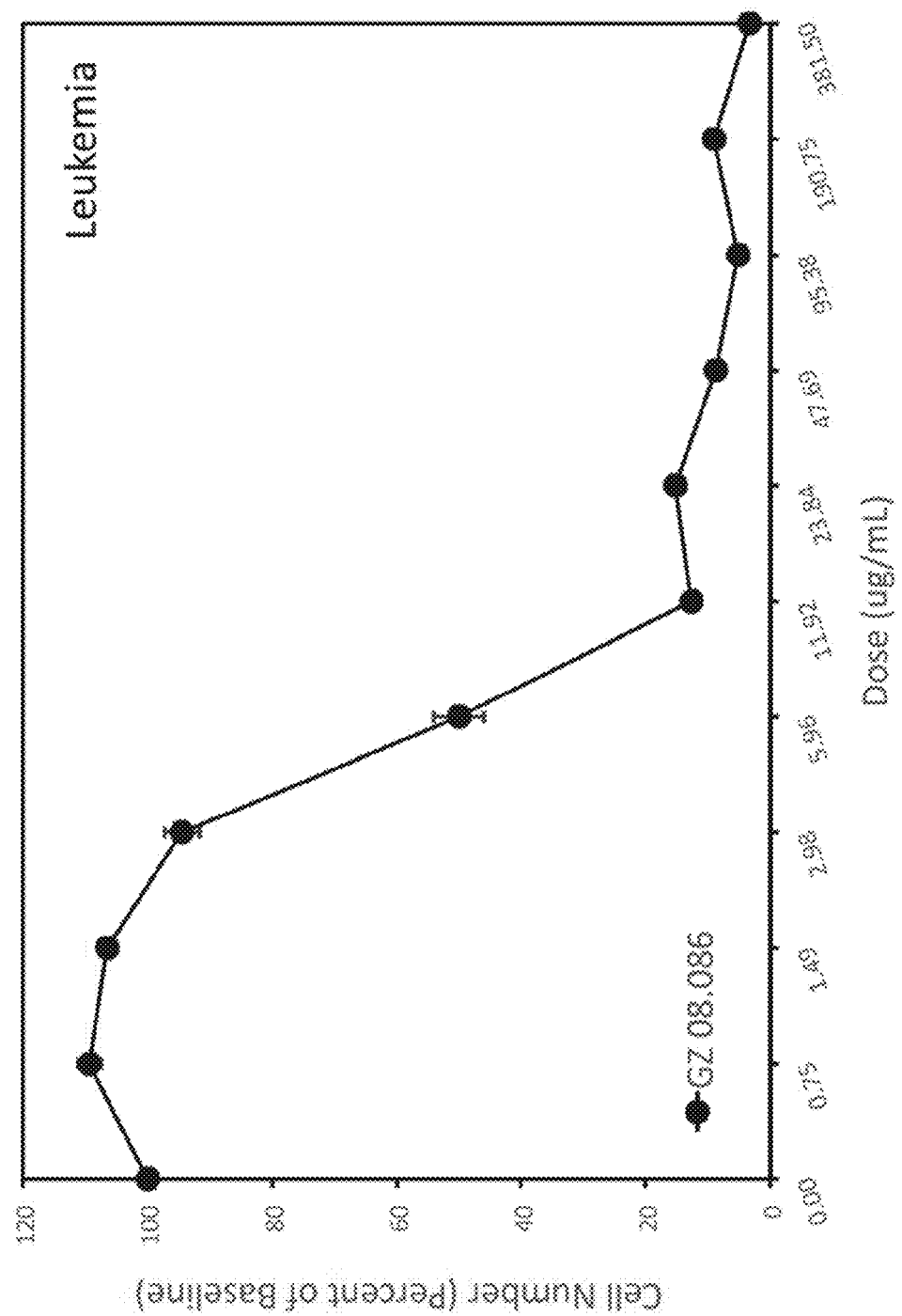
Figures 82, 83, 84, 85, 86, 87, 88, 89, 90, 91, 92, 93, 94, 95, 96, 97, 98, 99, 100, 101, 102, 103, 104, 105:
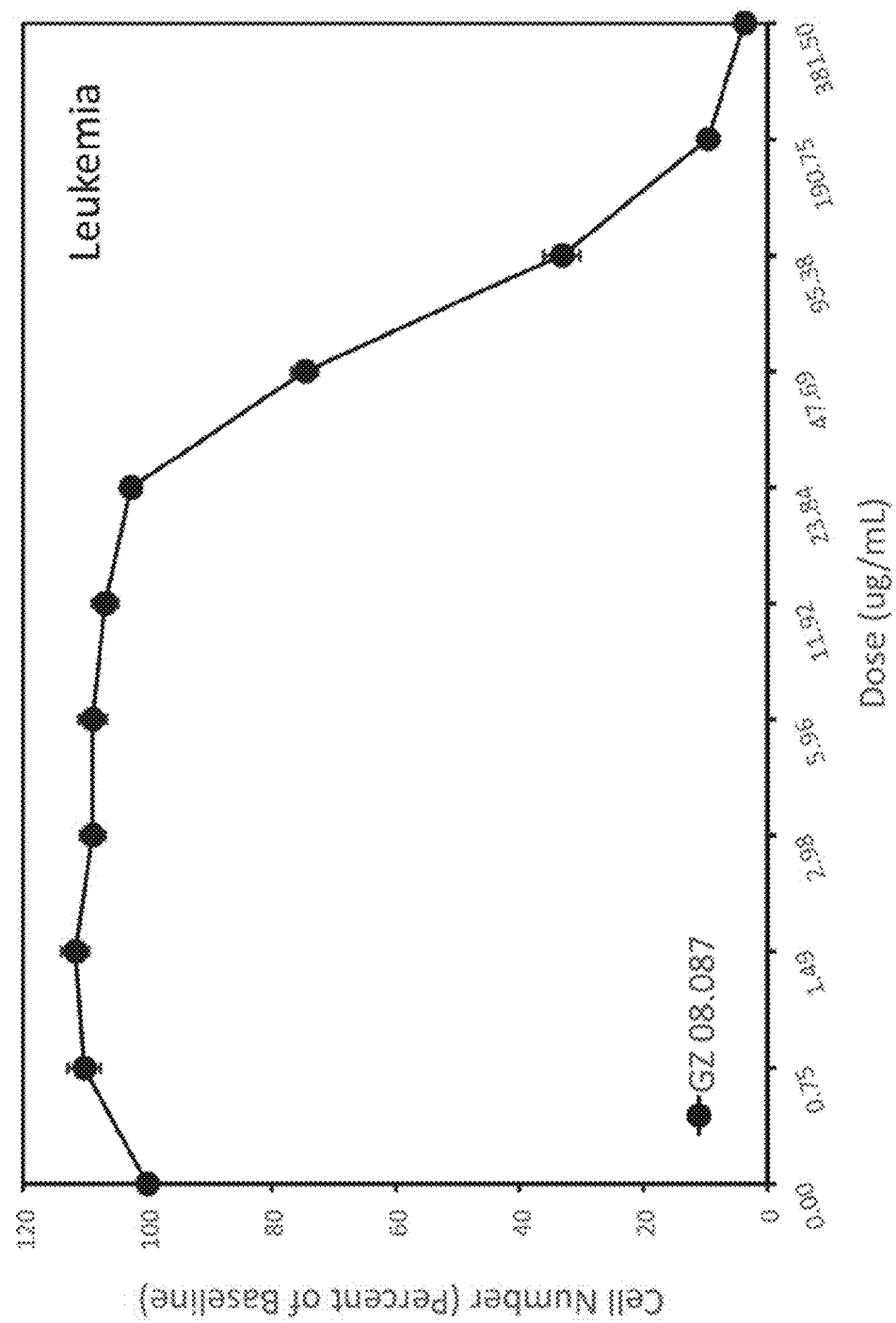
Figures 82, 83, 84, 85, 86, 87, 88, 89, 90, 91, 92, 93, 94, 95, 96, 97, 98, 99, 100, 101, 102, 103, 104, 105, 106:
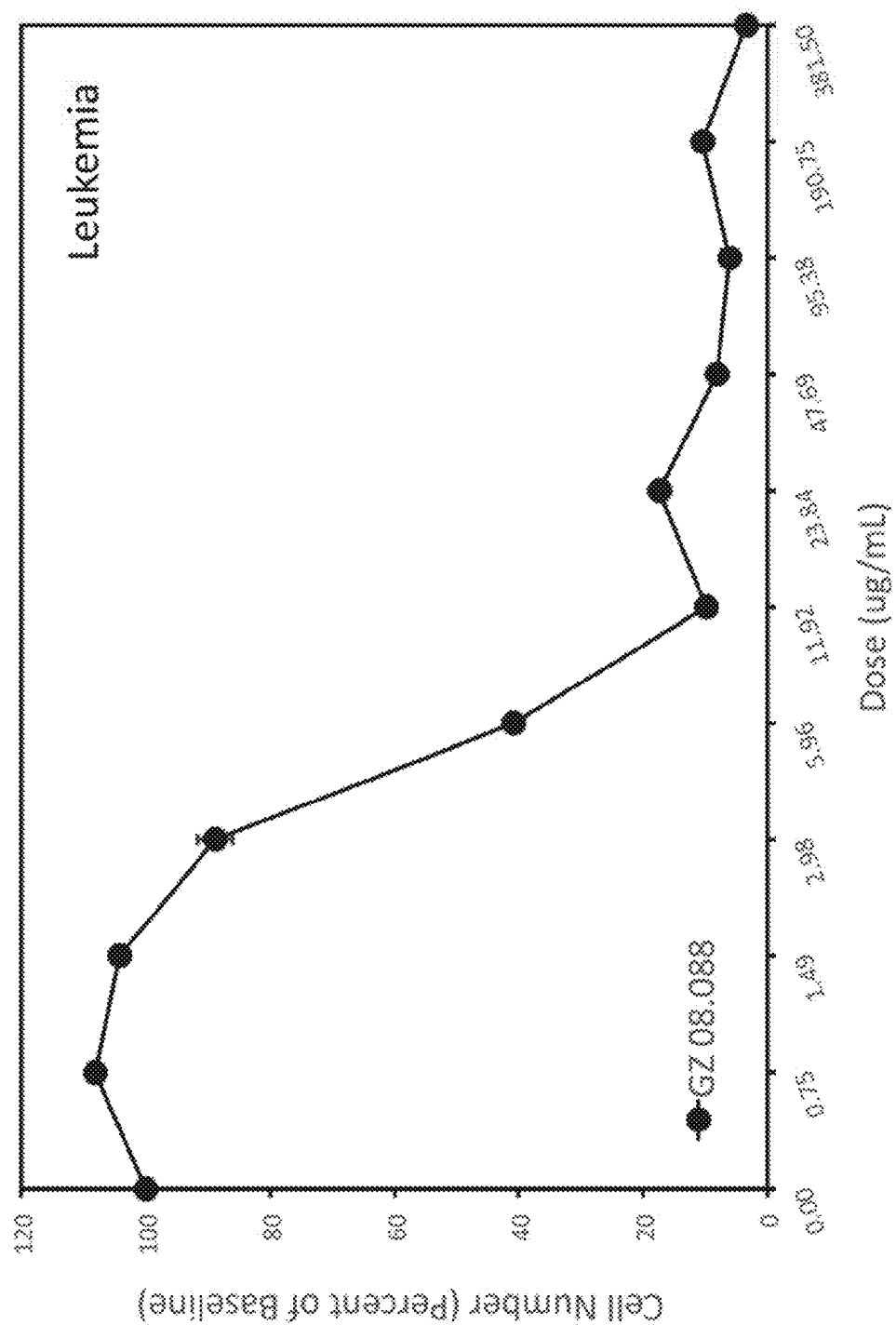
Figures 82, 83, 84, 85, 86, 87, 88, 89, 90, 91, 92, 93, 94, 95, 96, 97, 98, 99, 100, 101, 102, 103, 104, 105, 106, 107:
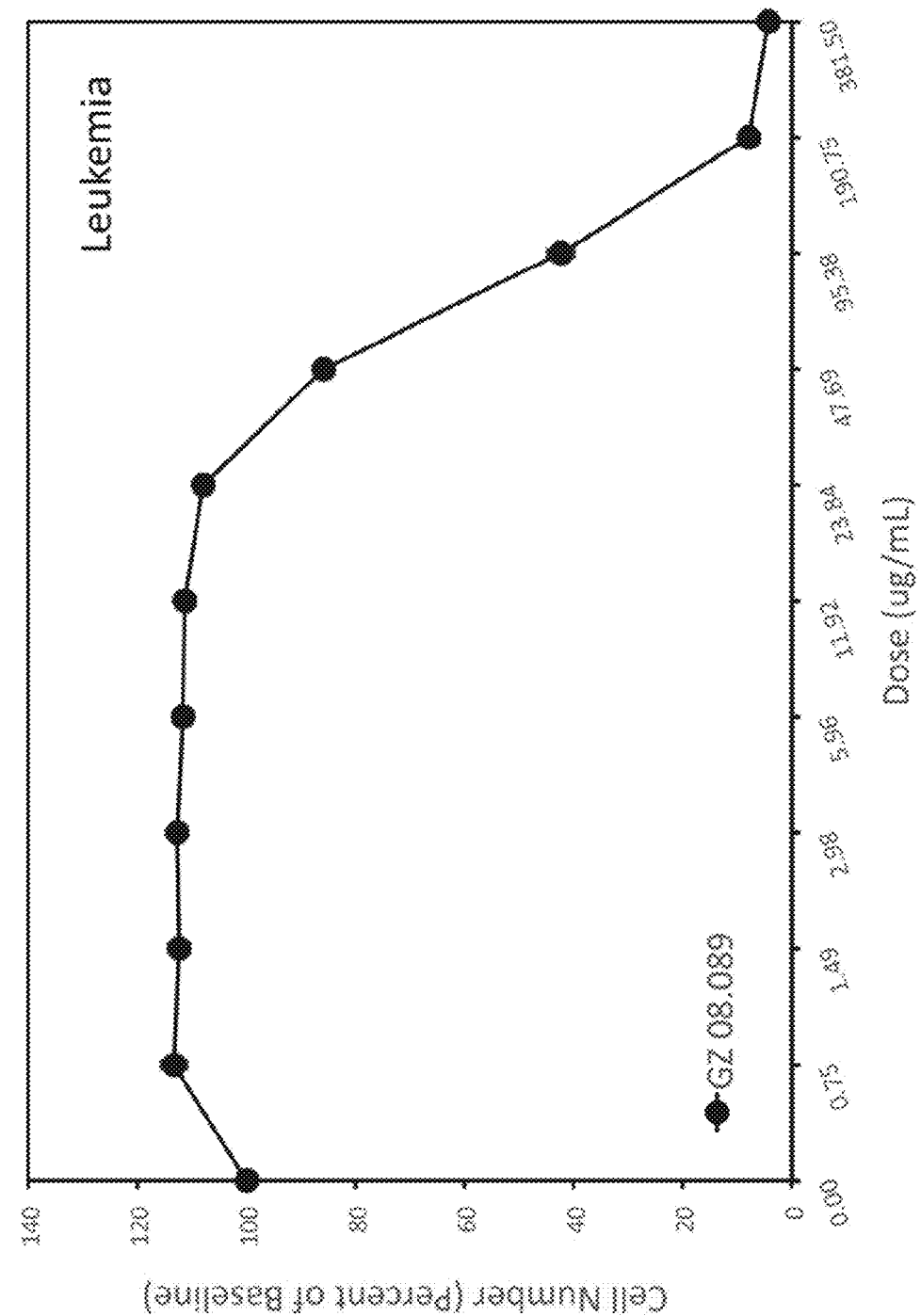
Figures 82, 83, 84, 85, 86, 87, 88, 89, 90, 91, 92, 93, 94, 95, 96, 97, 98, 99, 100, 101, 102, 103, 104, 105, 106, 107, 108:
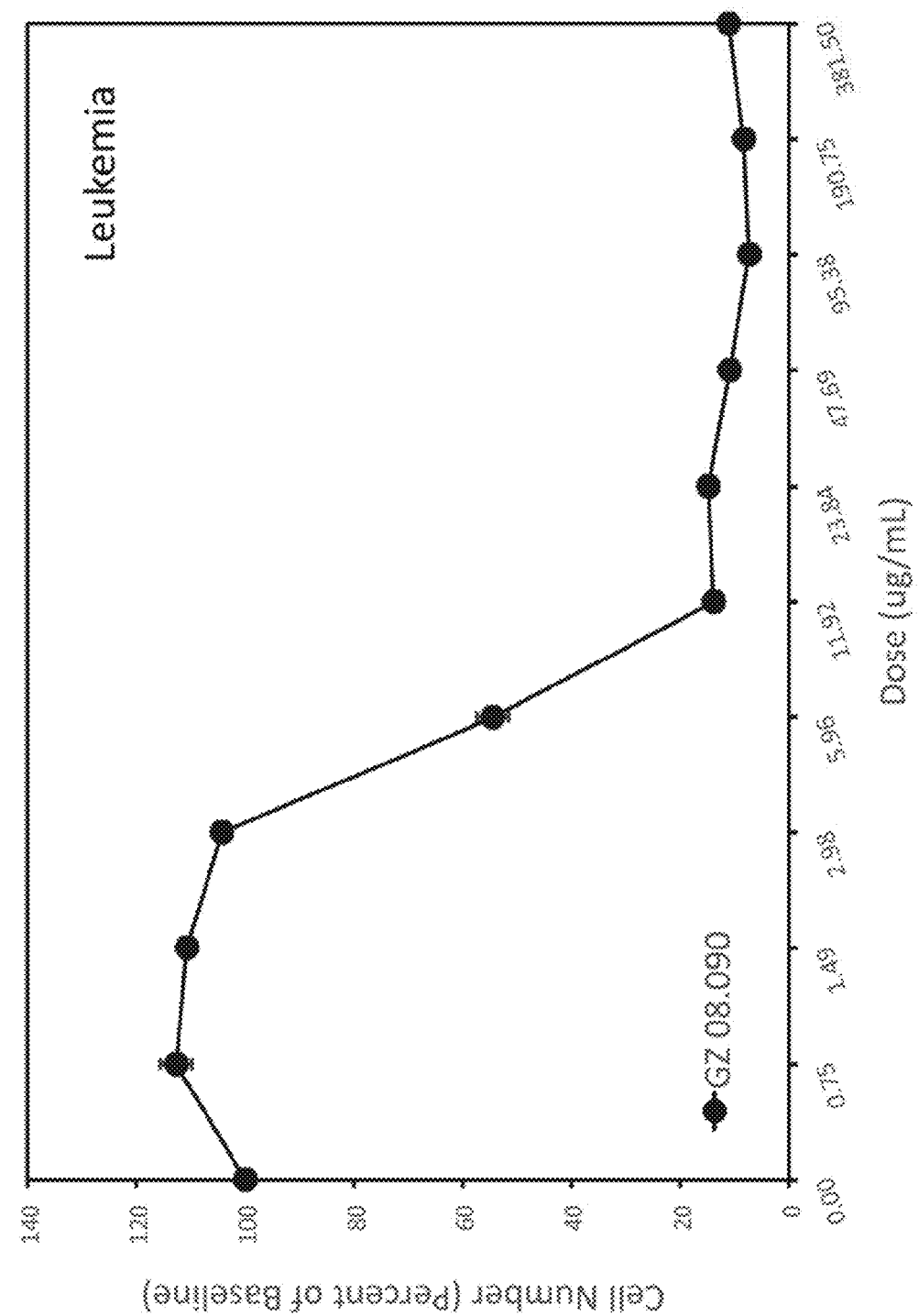
Figures 82, 83, 84, 85, 86, 87, 88, 89, 90, 91, 92, 93, 94, 95, 96, 97, 98, 99, 100, 101, 102, 103, 104, 105, 106, 107, 108, 109:
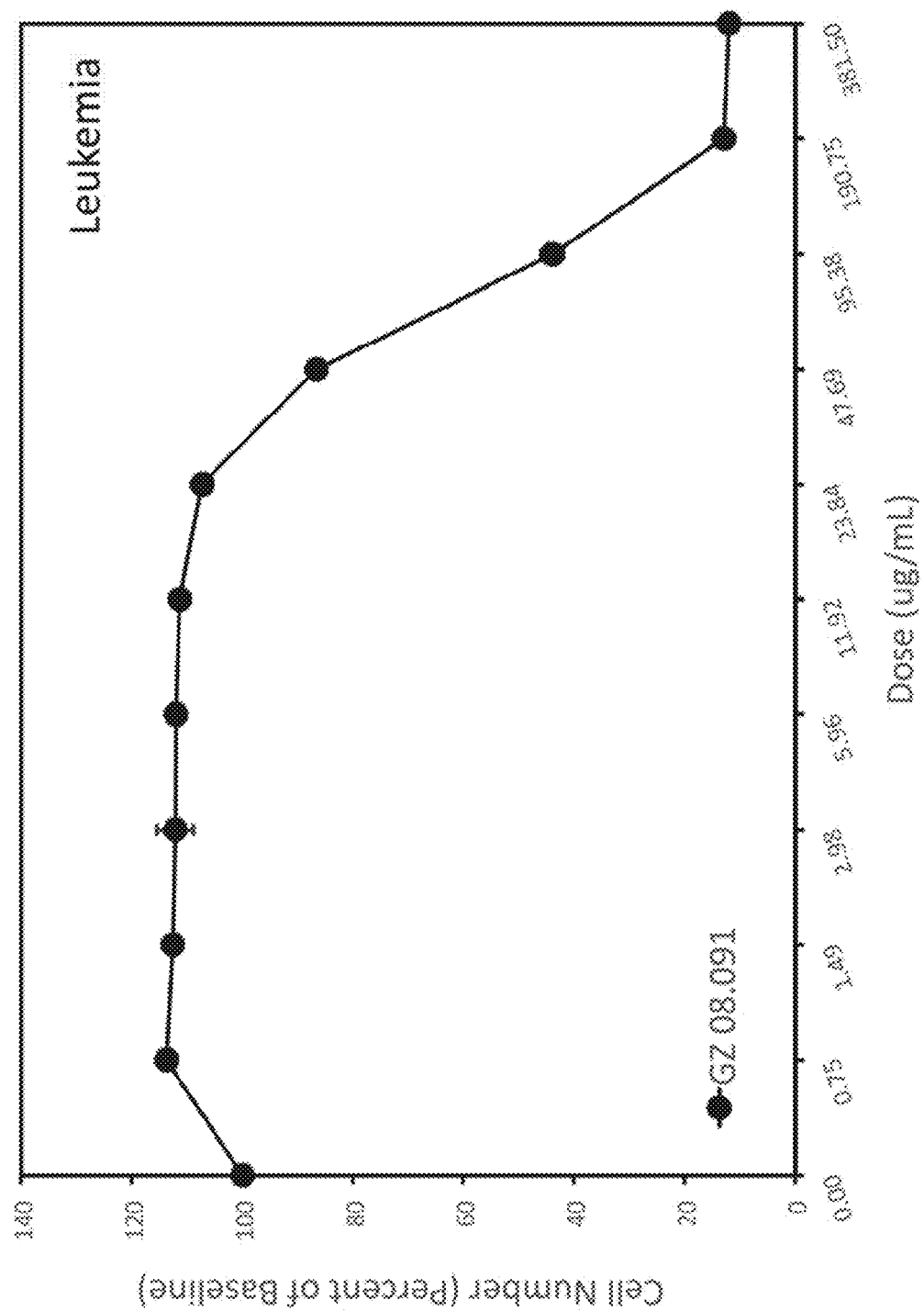
Figures 82, 83, 84, 85, 86, 87, 88, 89, 90, 91, 92, 93, 94, 95, 96, 97, 98, 99, 100, 101, 102, 103, 104, 105, 106, 107, 108, 109, 110:
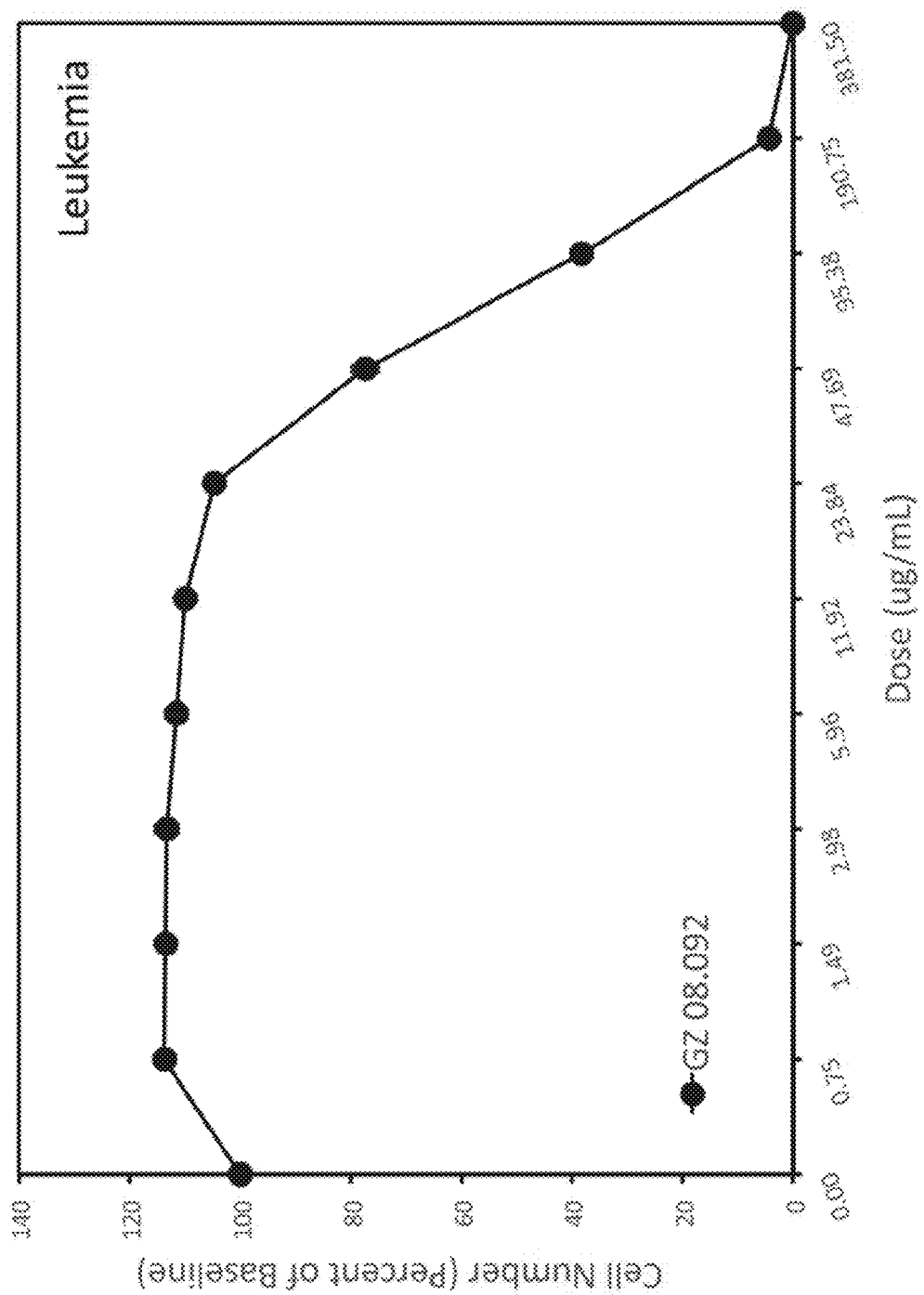
Figures 82, 83, 84, 85, 86, 87, 88, 89, 90, 91, 92, 93, 94, 95, 96, 97, 98, 99, 100, 101, 102, 103, 104, 105, 106, 107, 108, 109, 110, 111:
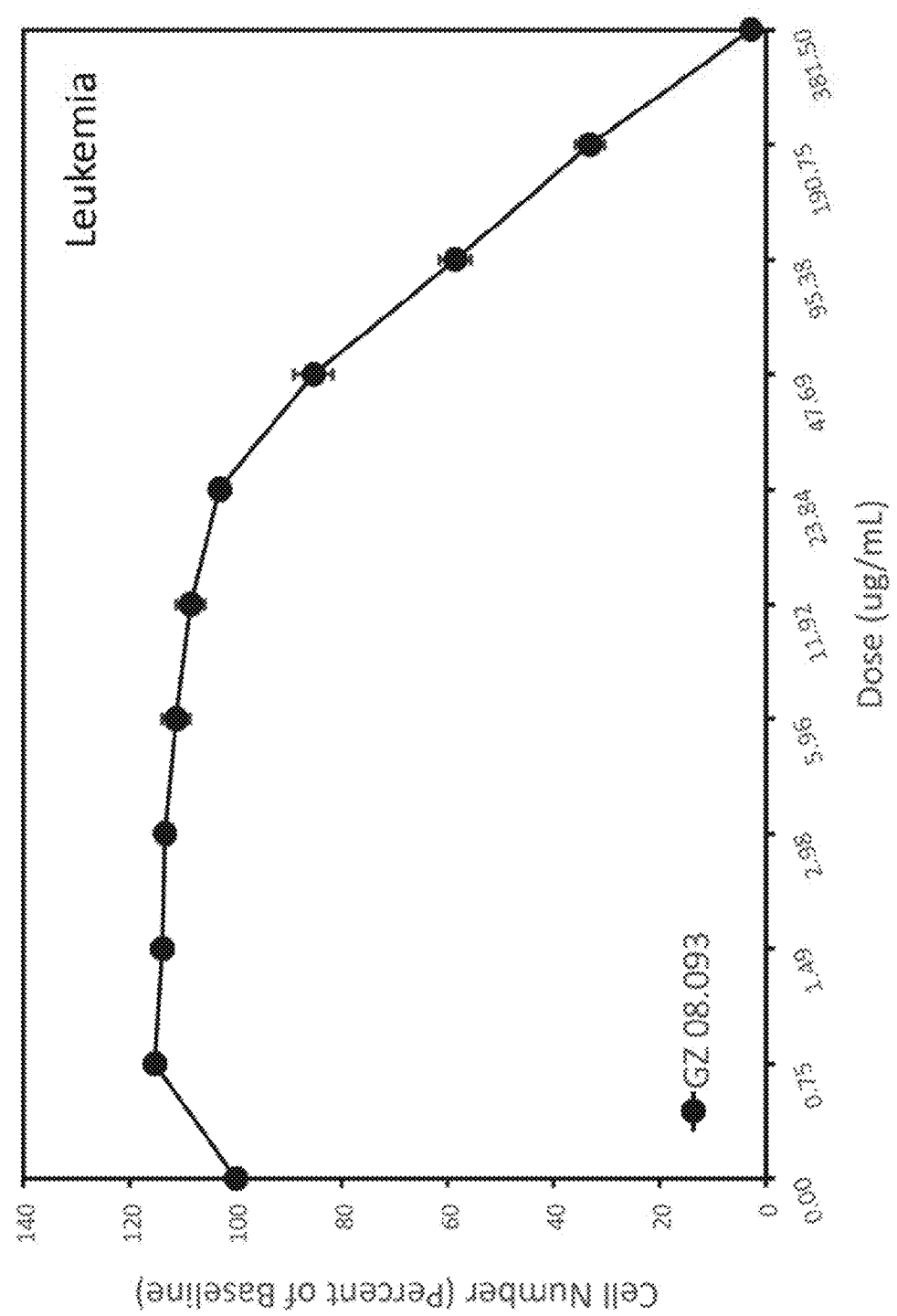
Figures 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112:
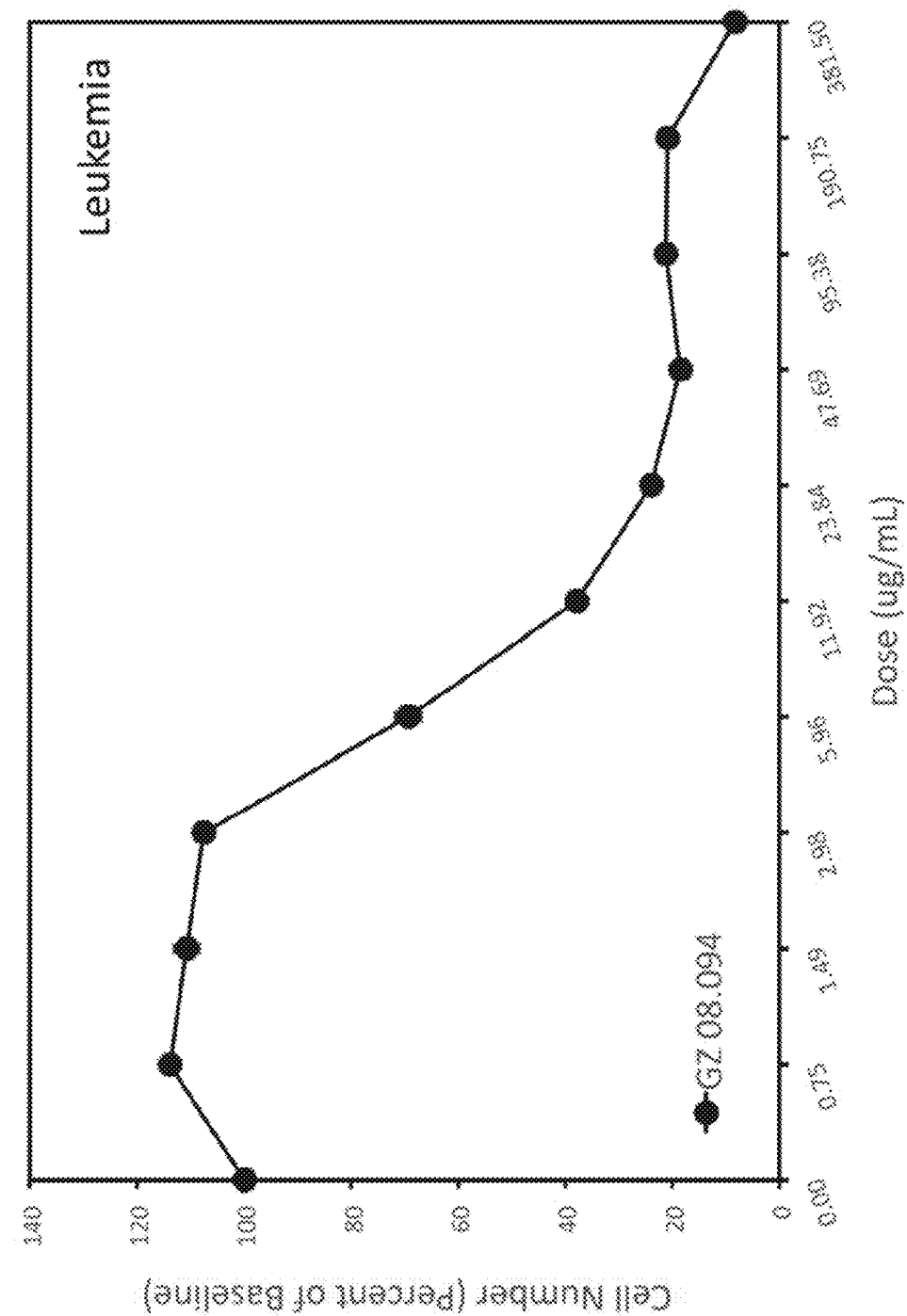
Figures 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113:
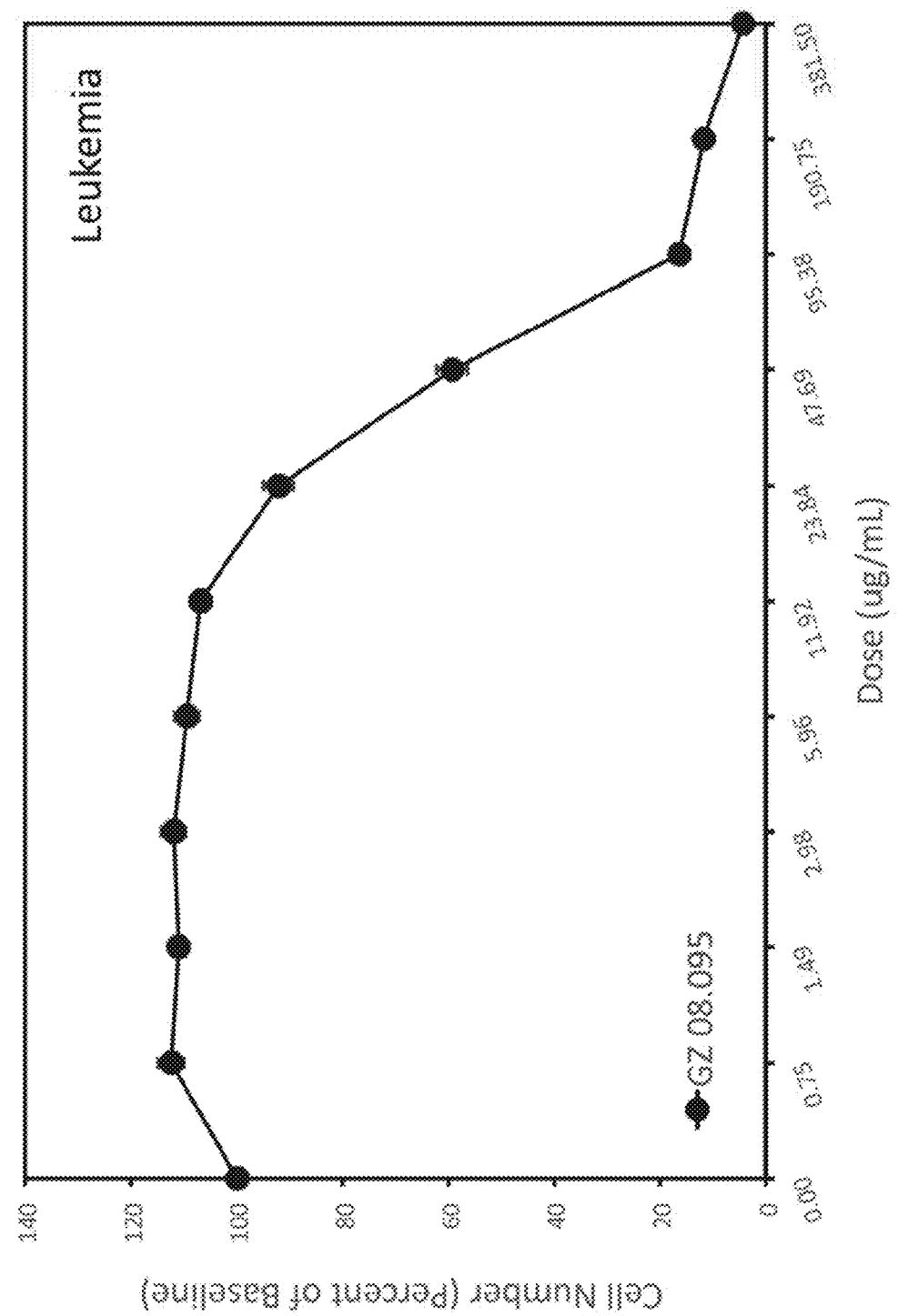
Figures 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114:
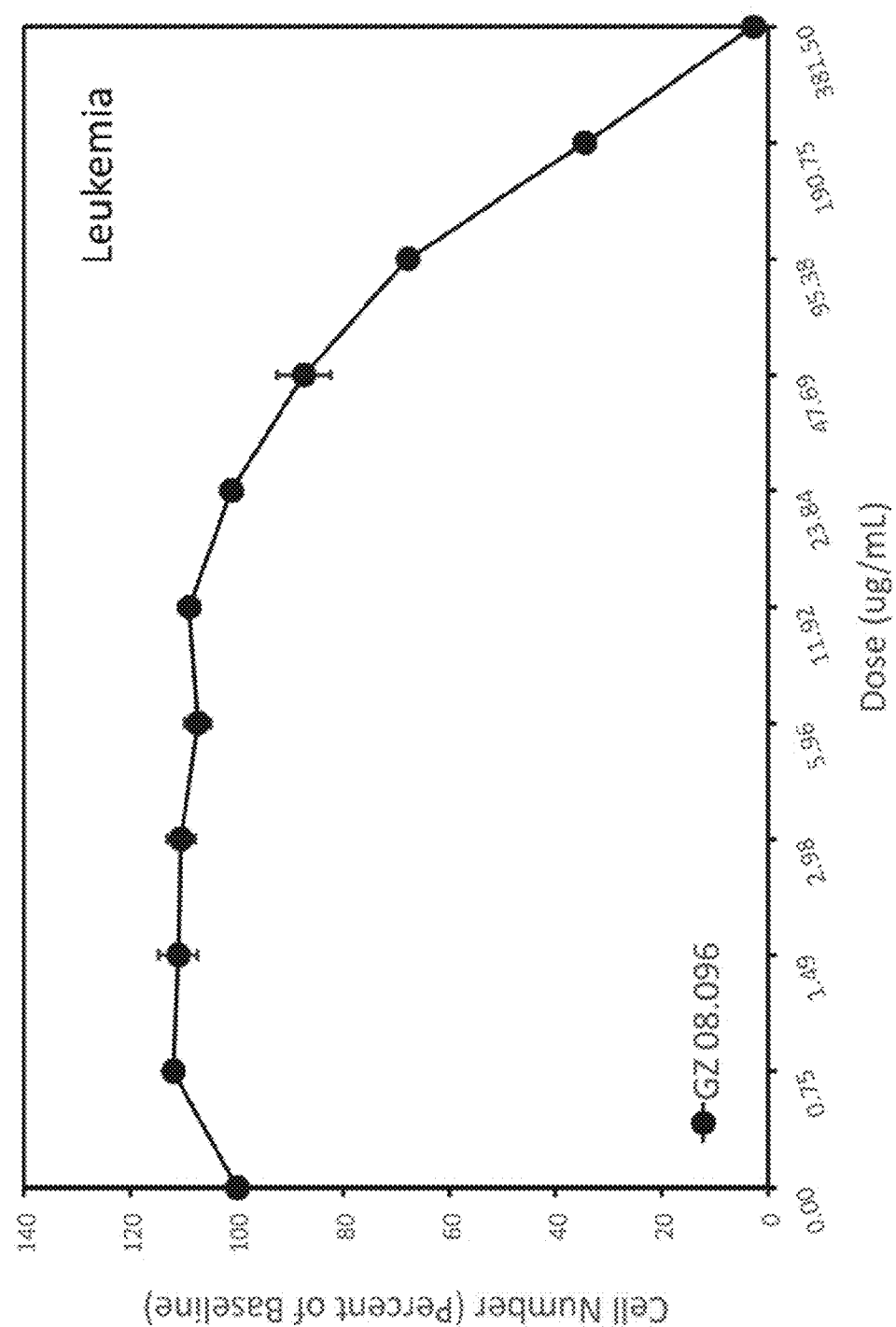
Figures 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115:
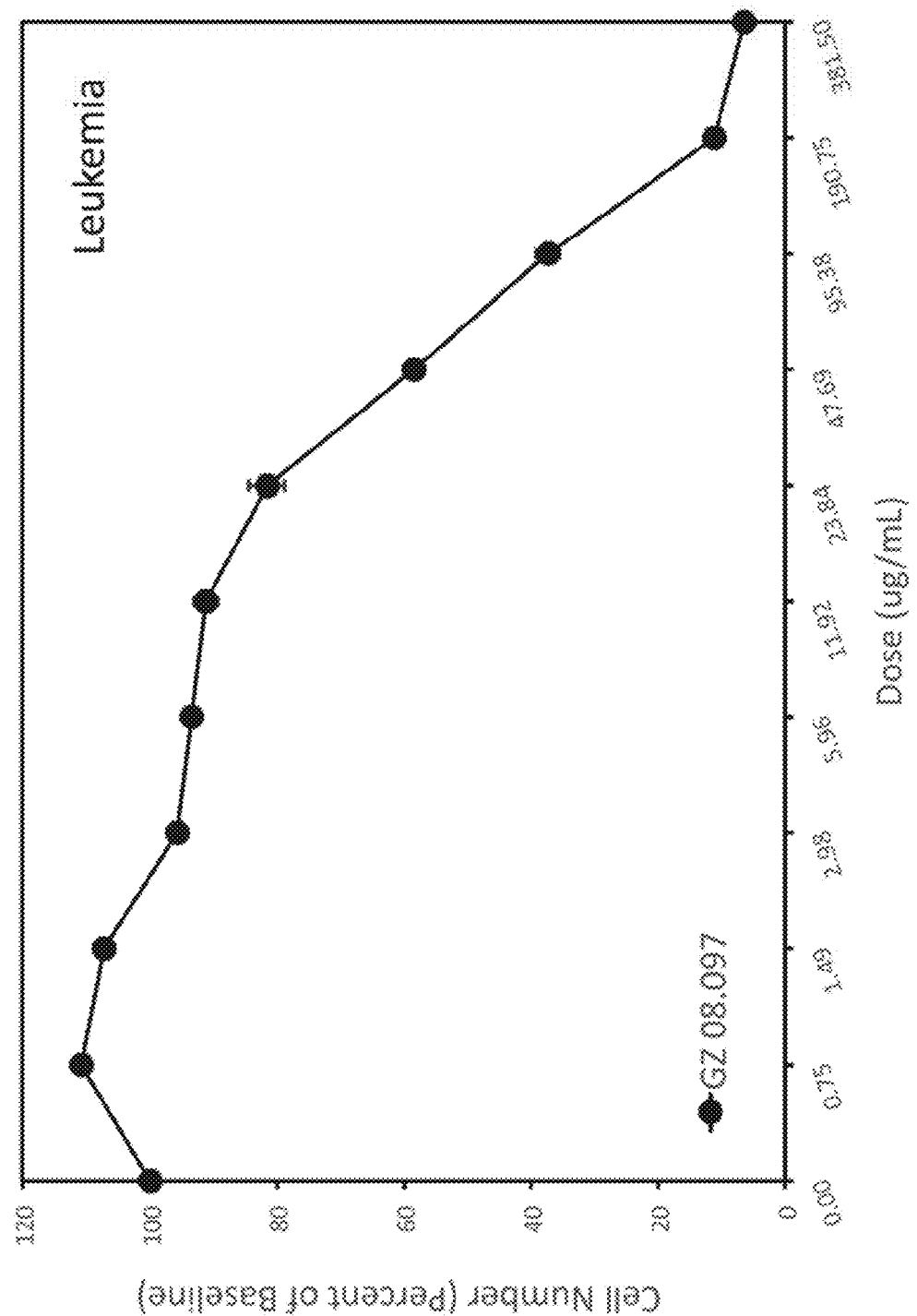
Figures 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116:
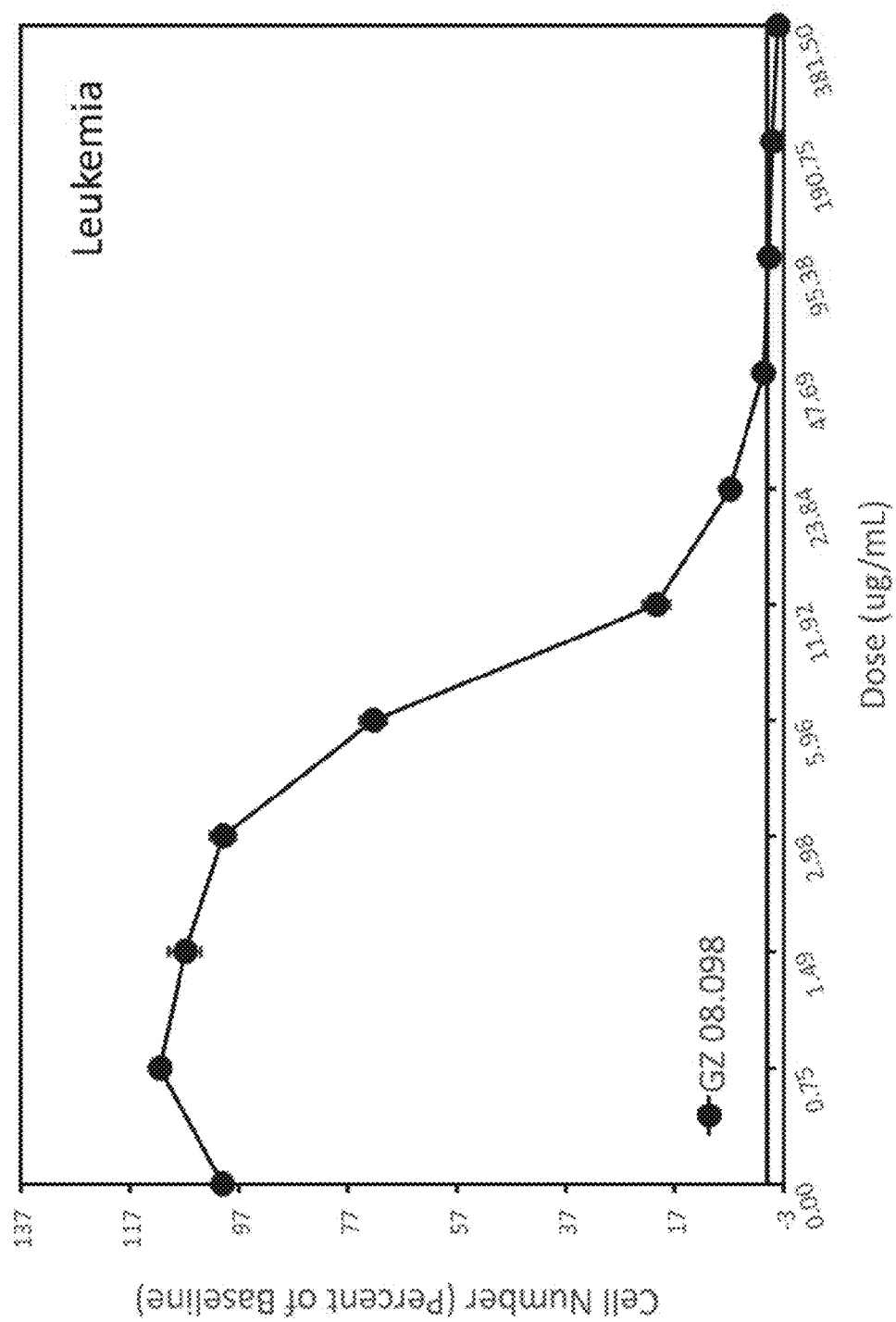
Figures 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117:
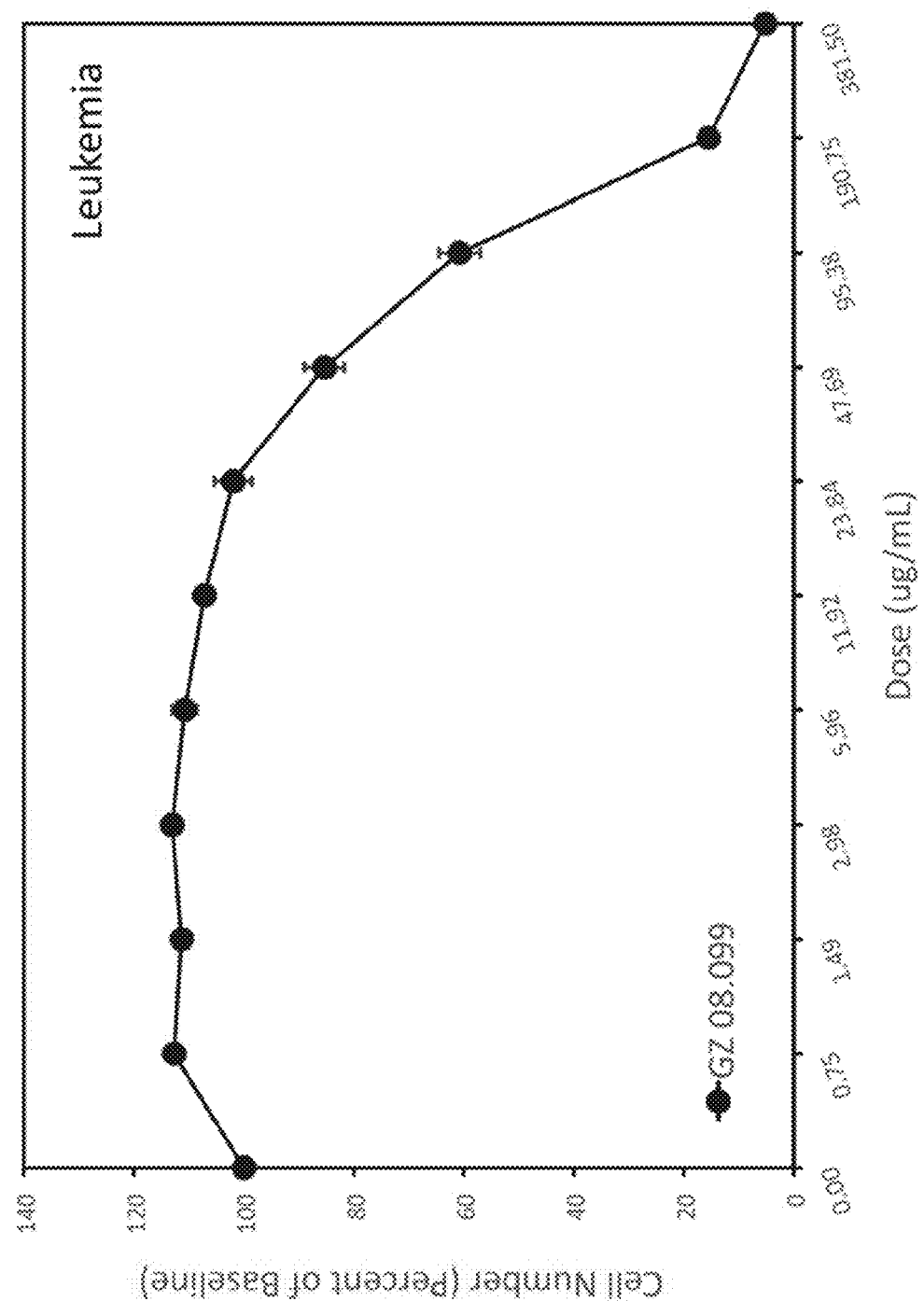
Figures 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118:
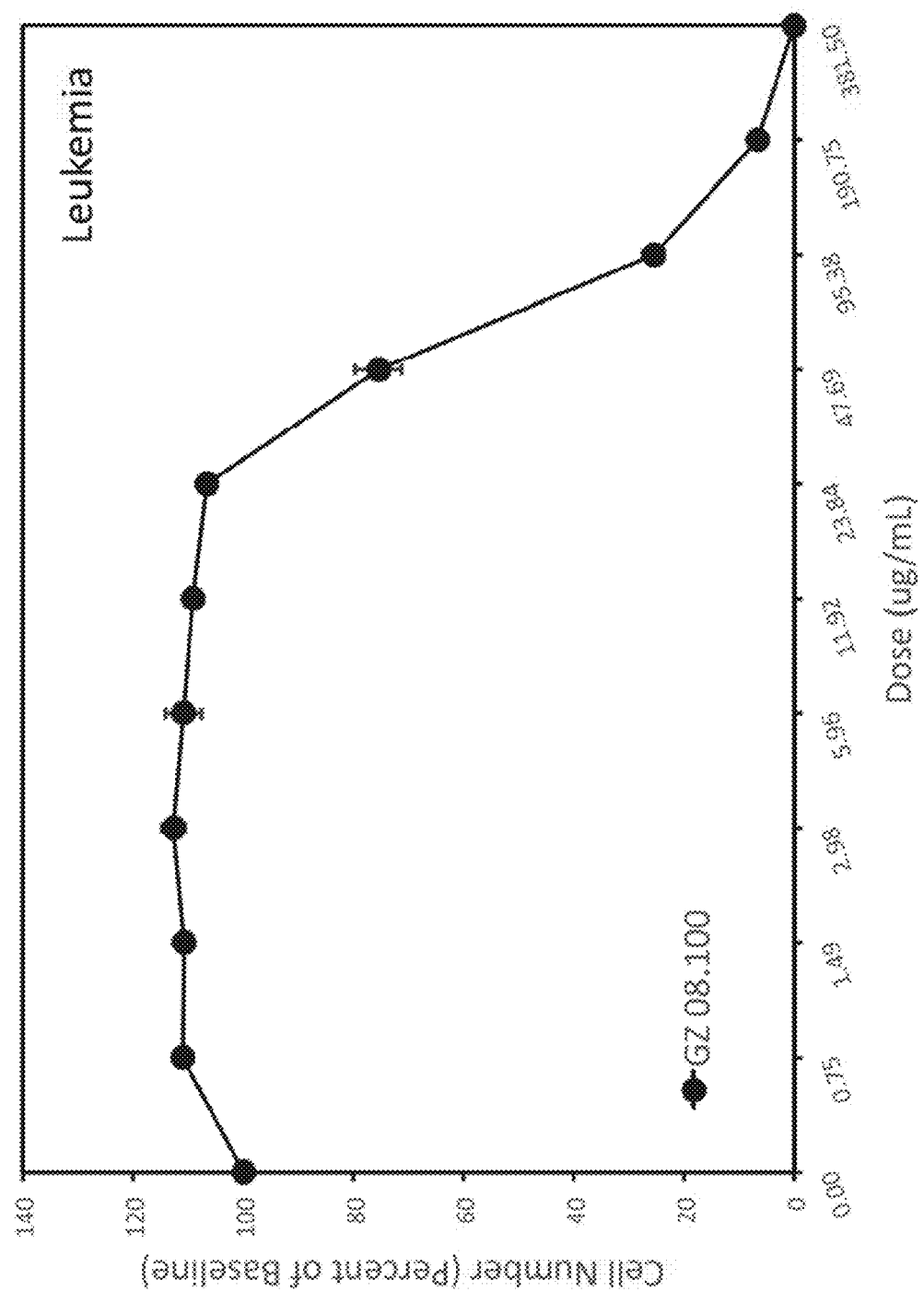
Figures 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119:
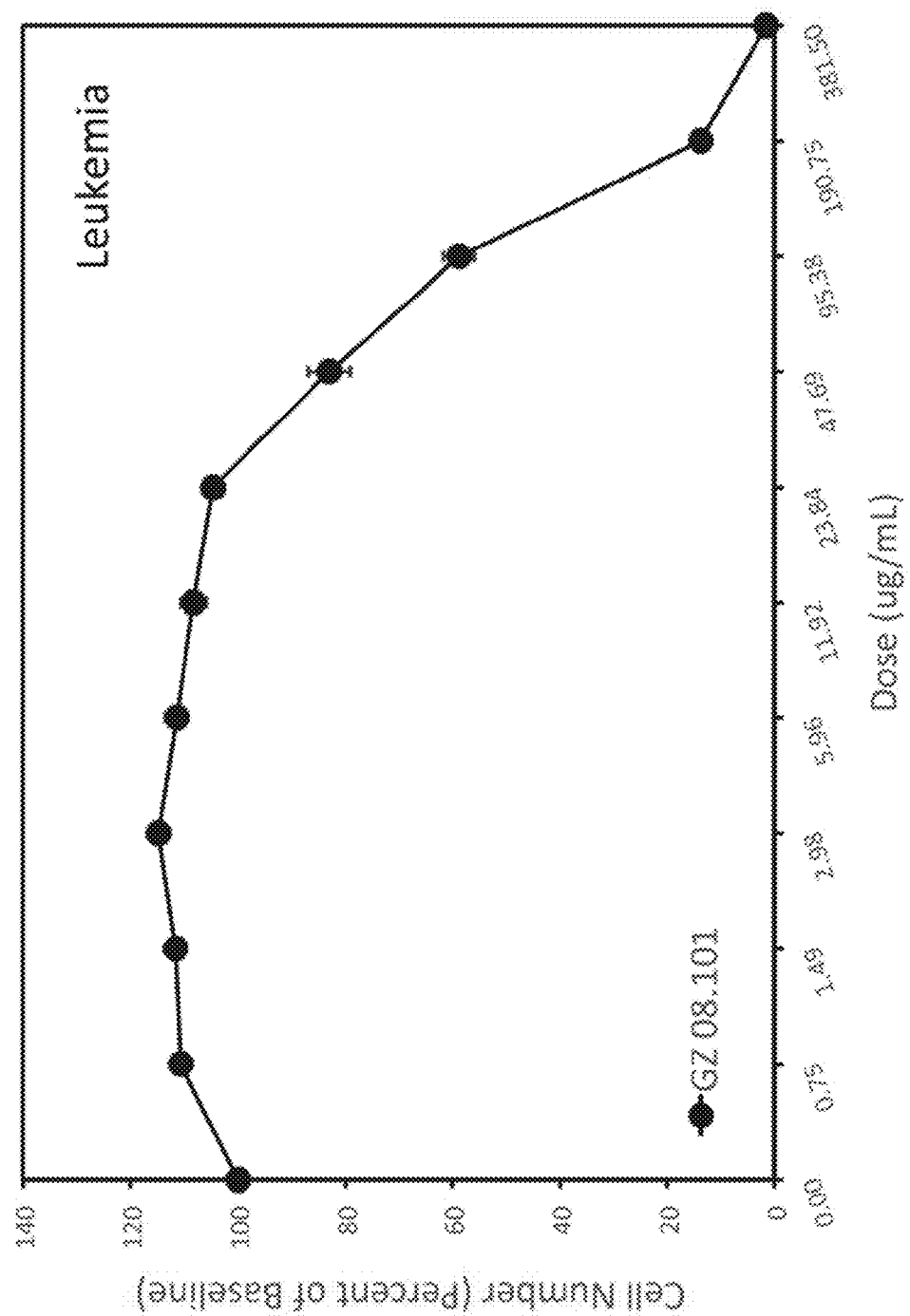
Figures 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120:
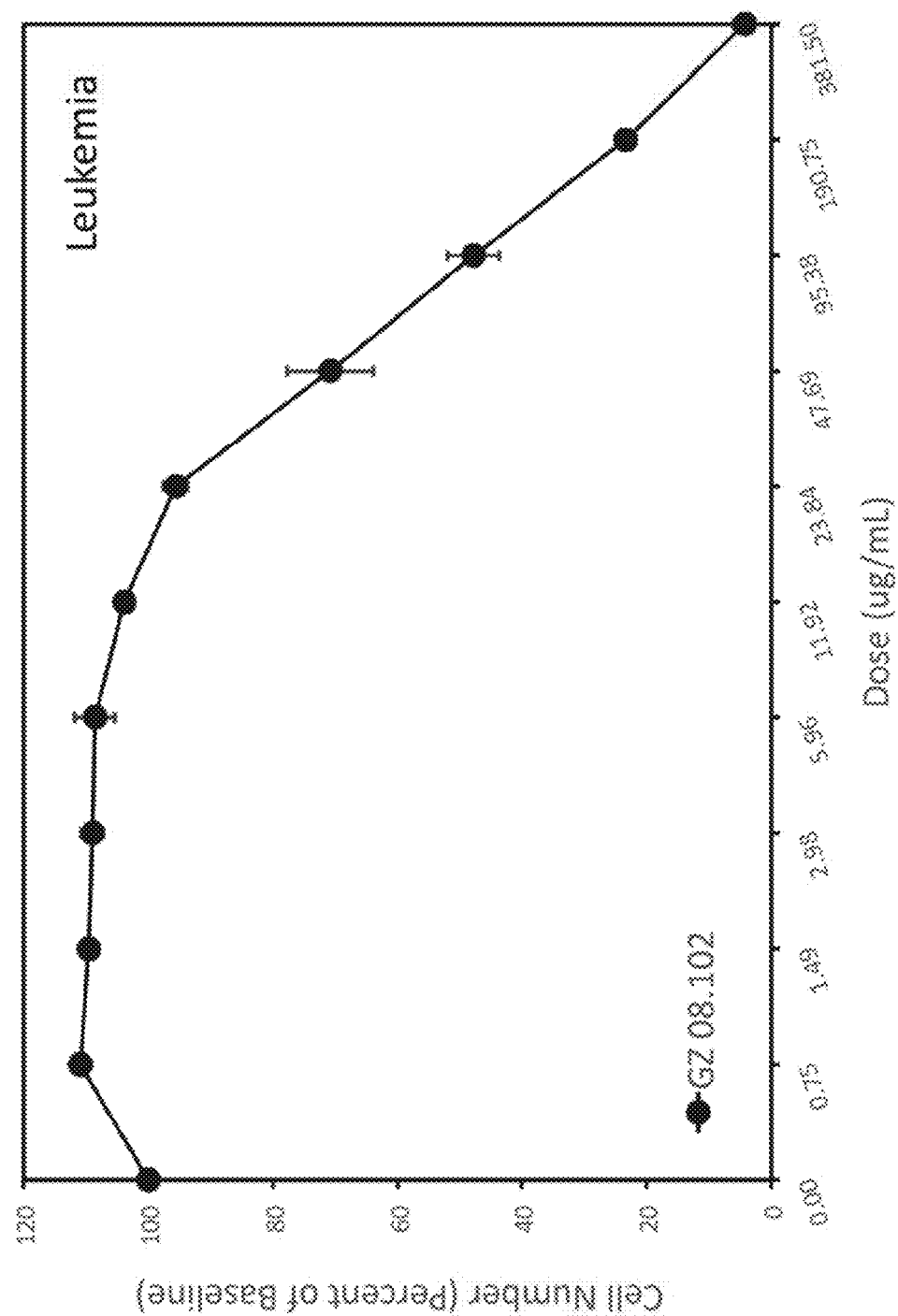
Figures 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121:
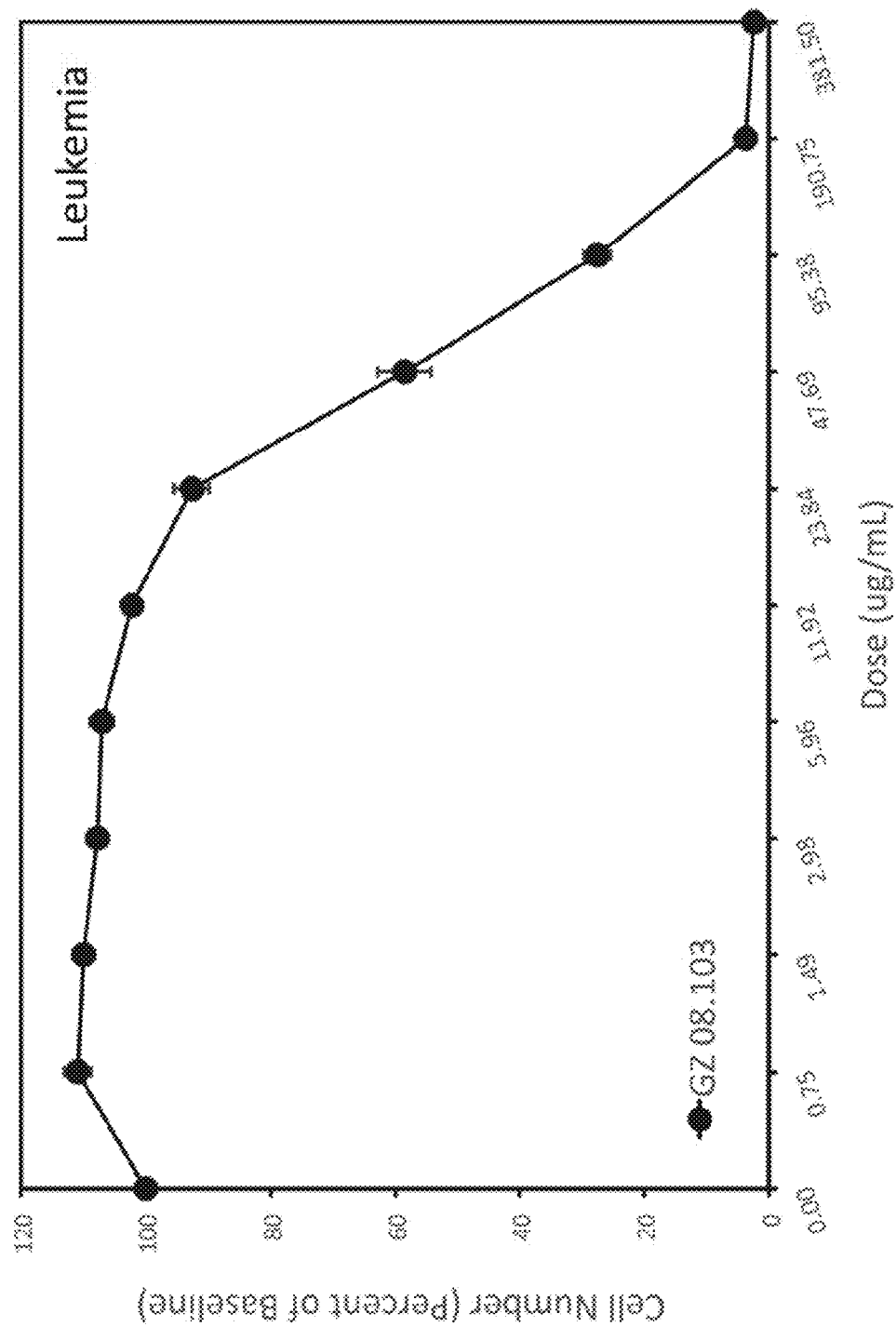
Figures 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122:
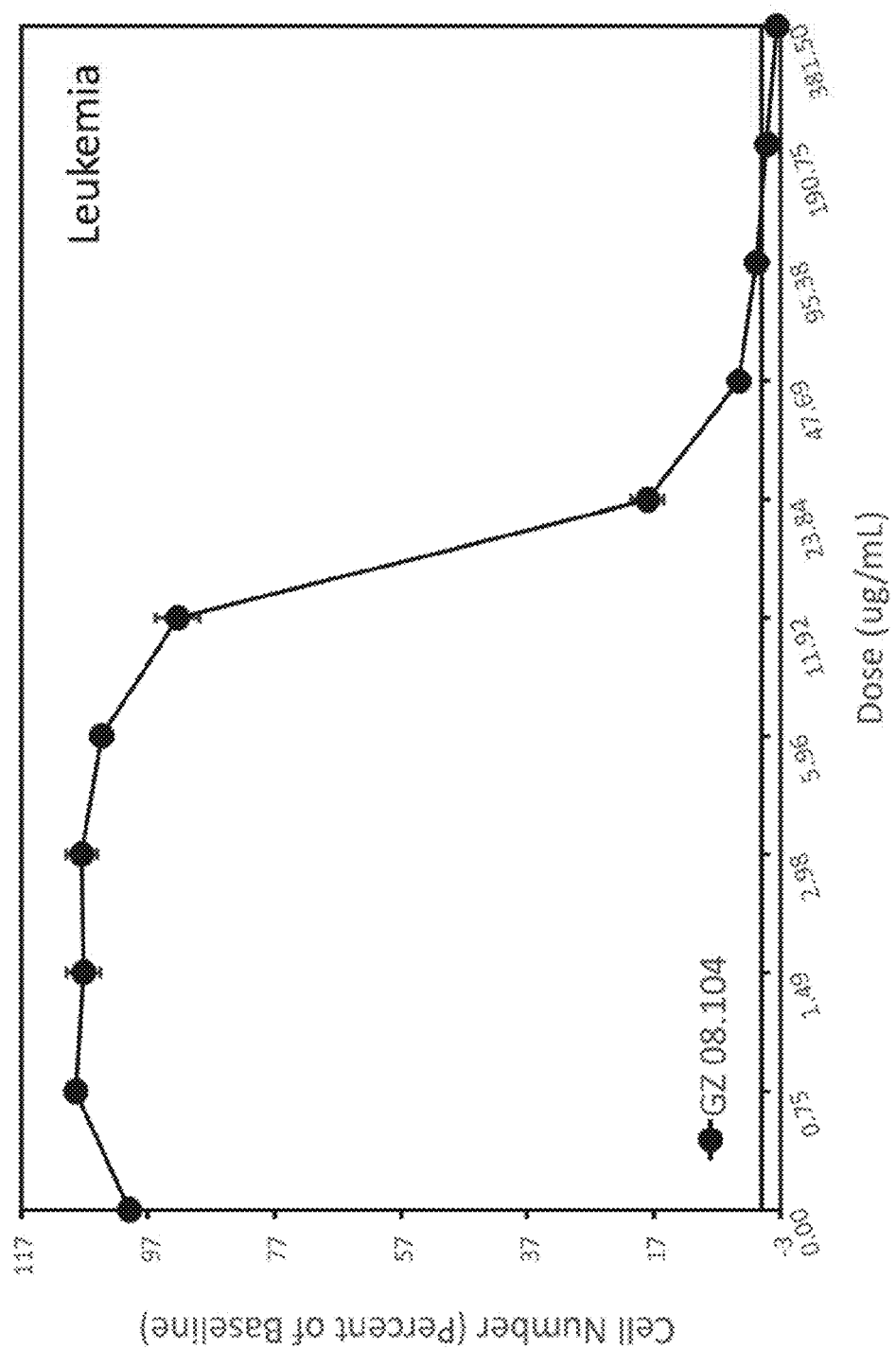
Figures 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123:
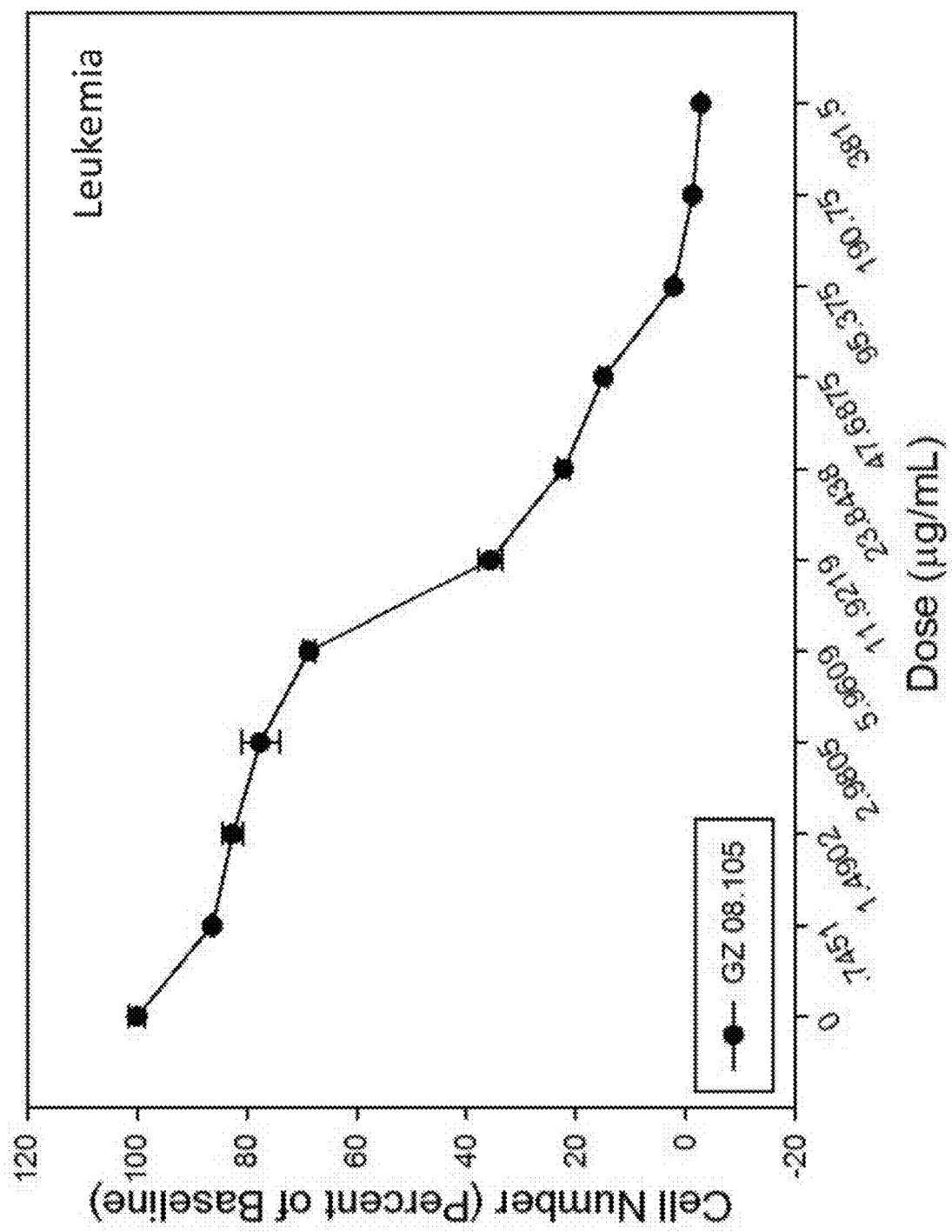
Figures 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124:
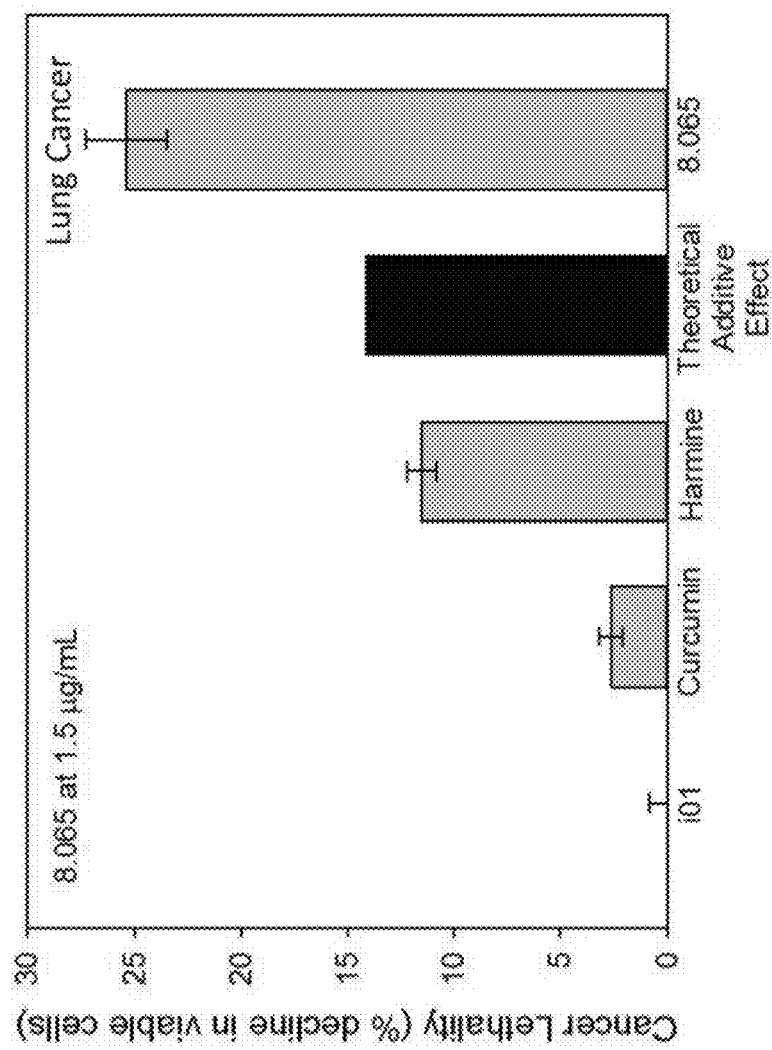
Figures 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125:
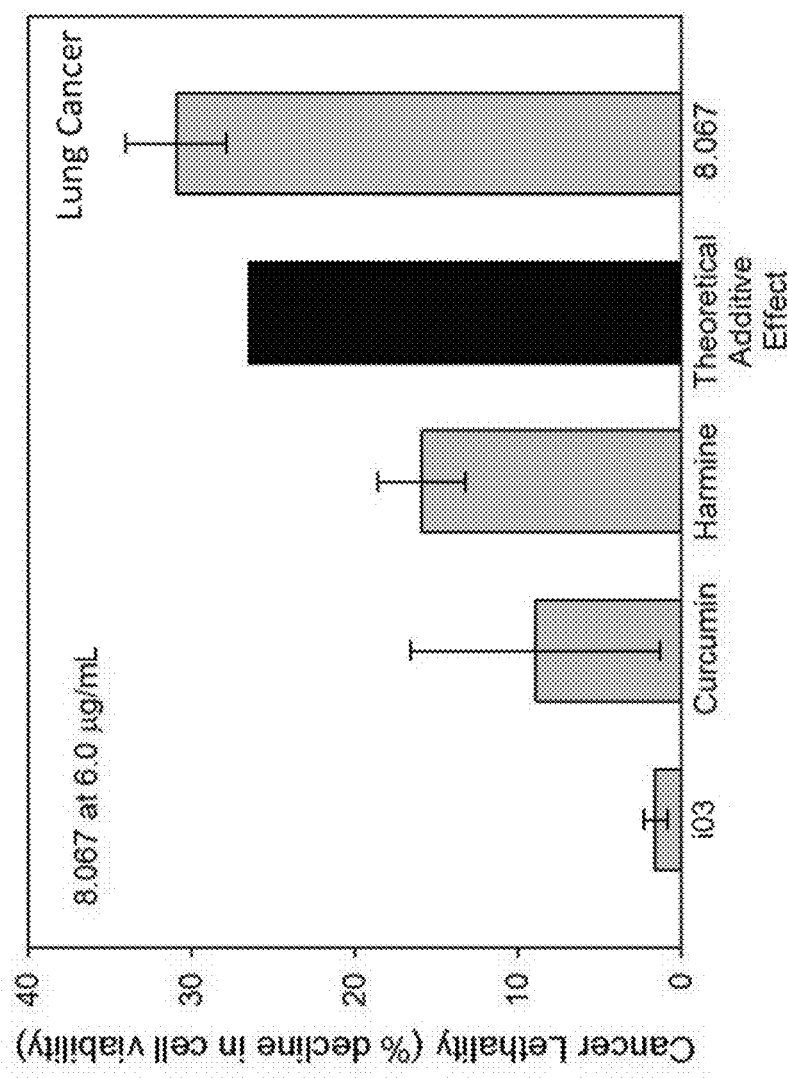
Figures 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126:
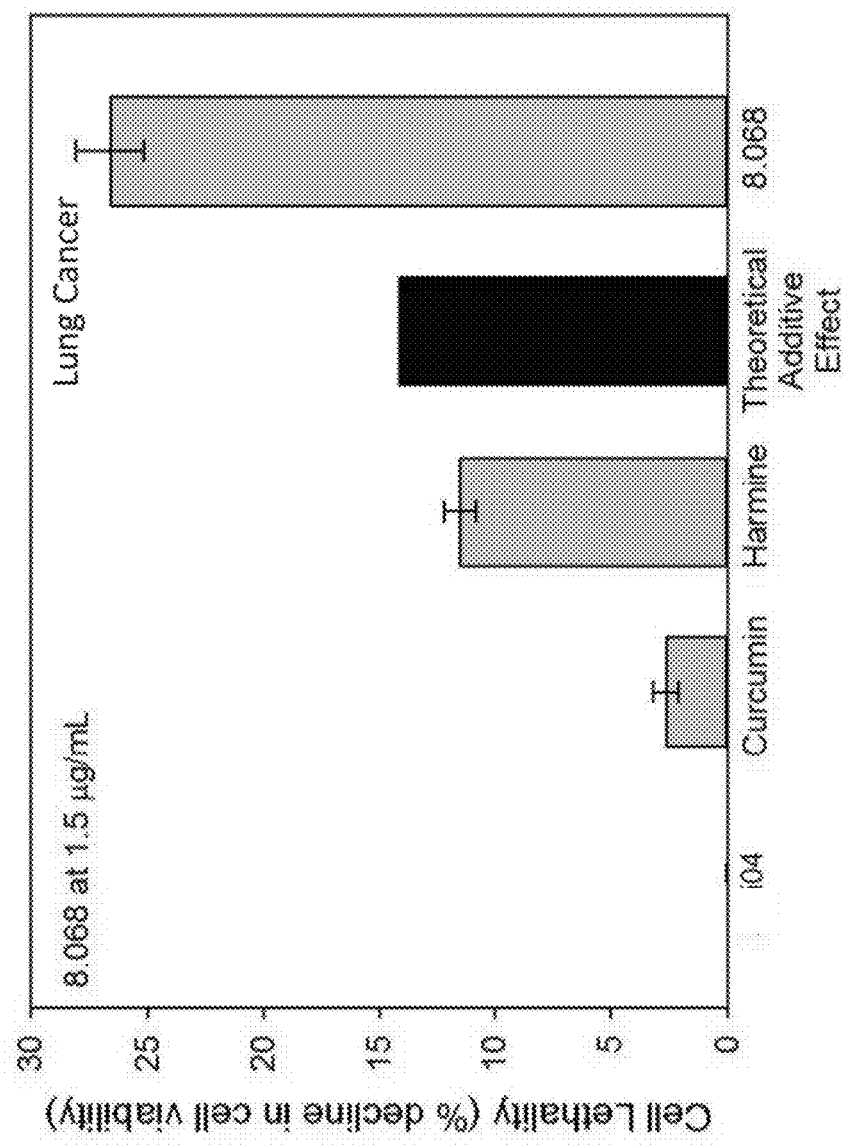
Figures 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127:
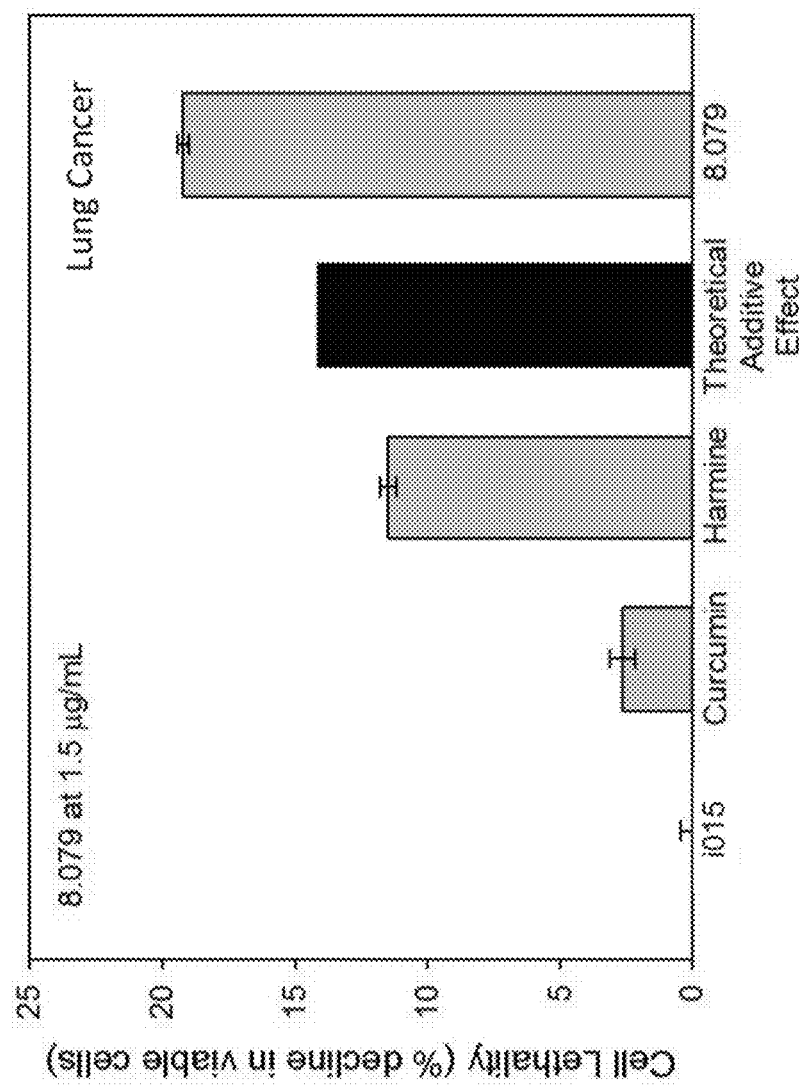
Figures 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128:
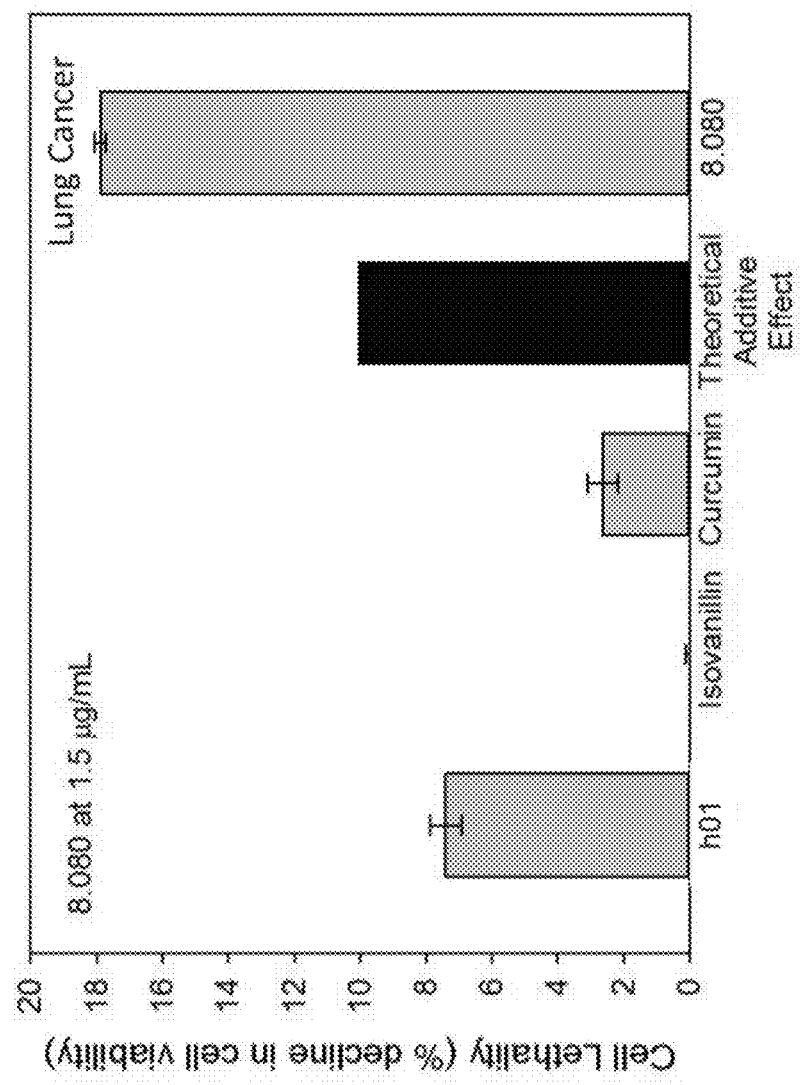
Figures 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129:
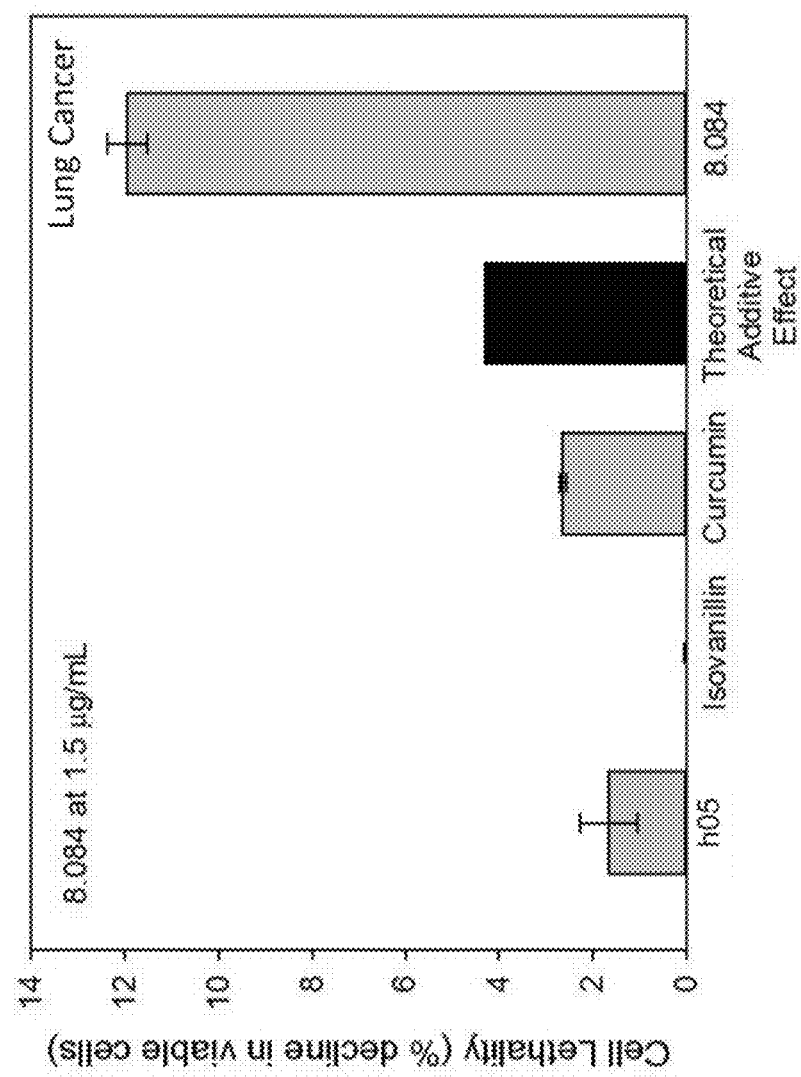
Figures 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130:
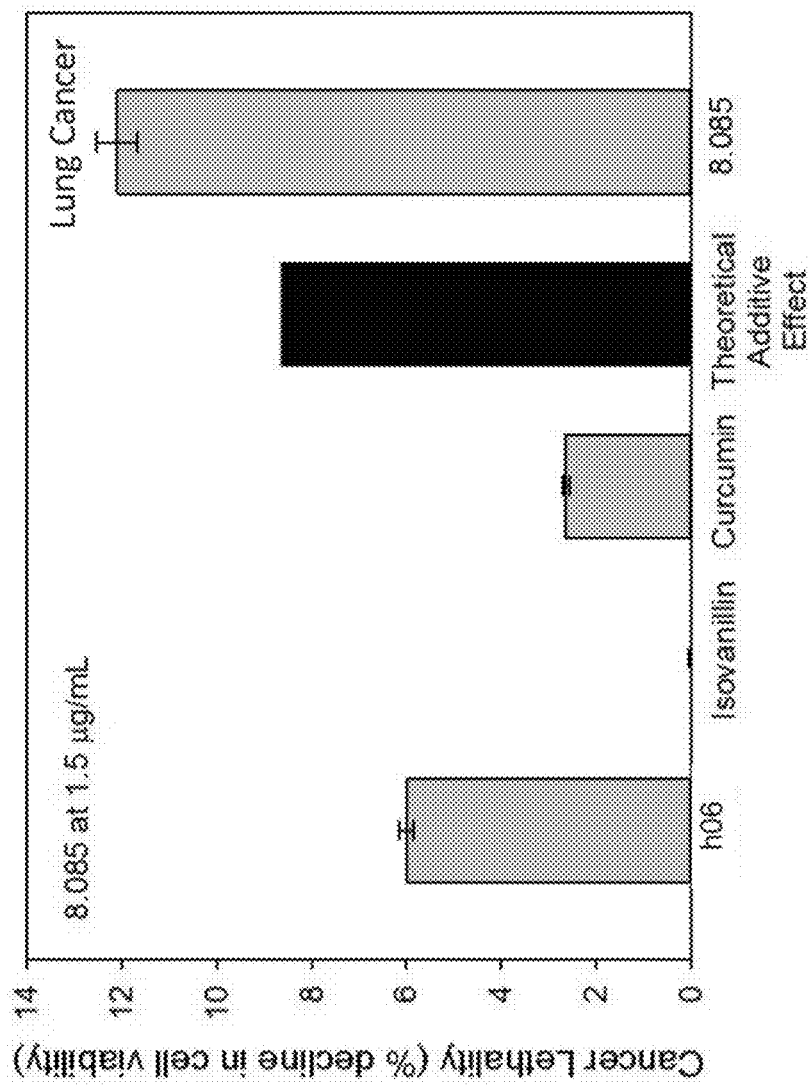
Figures 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131:
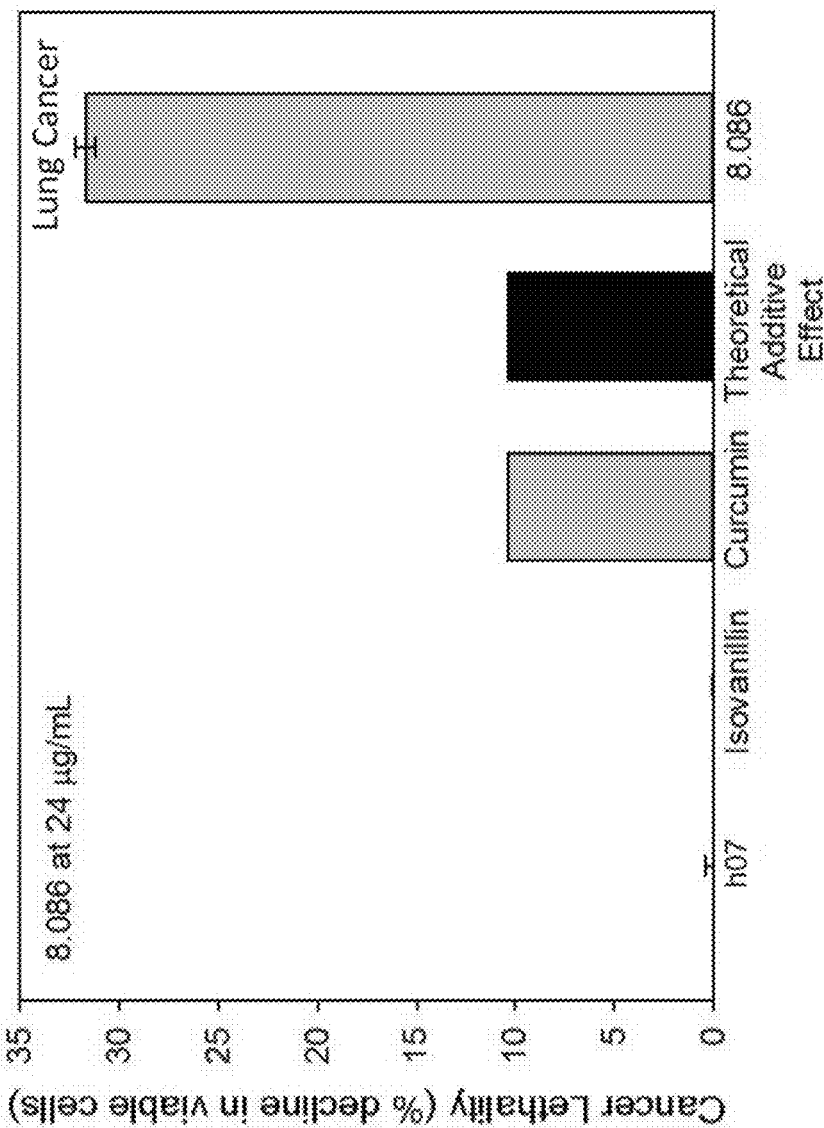
Figures 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132:
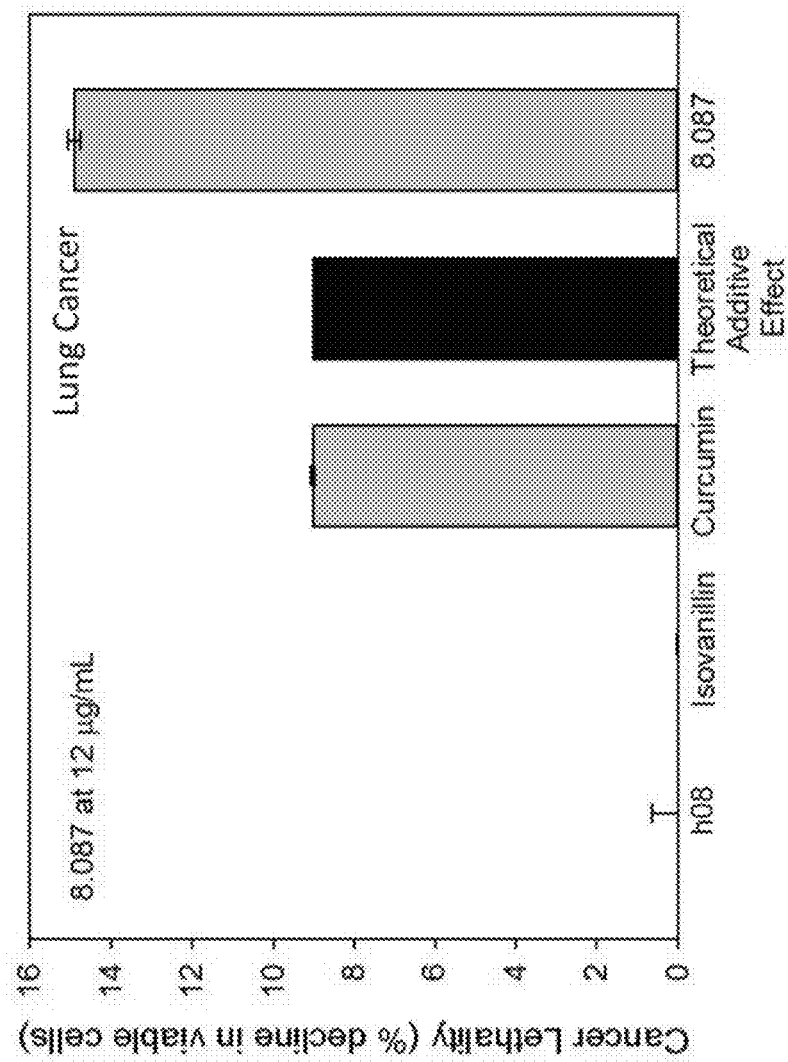
Figures 82, 133:
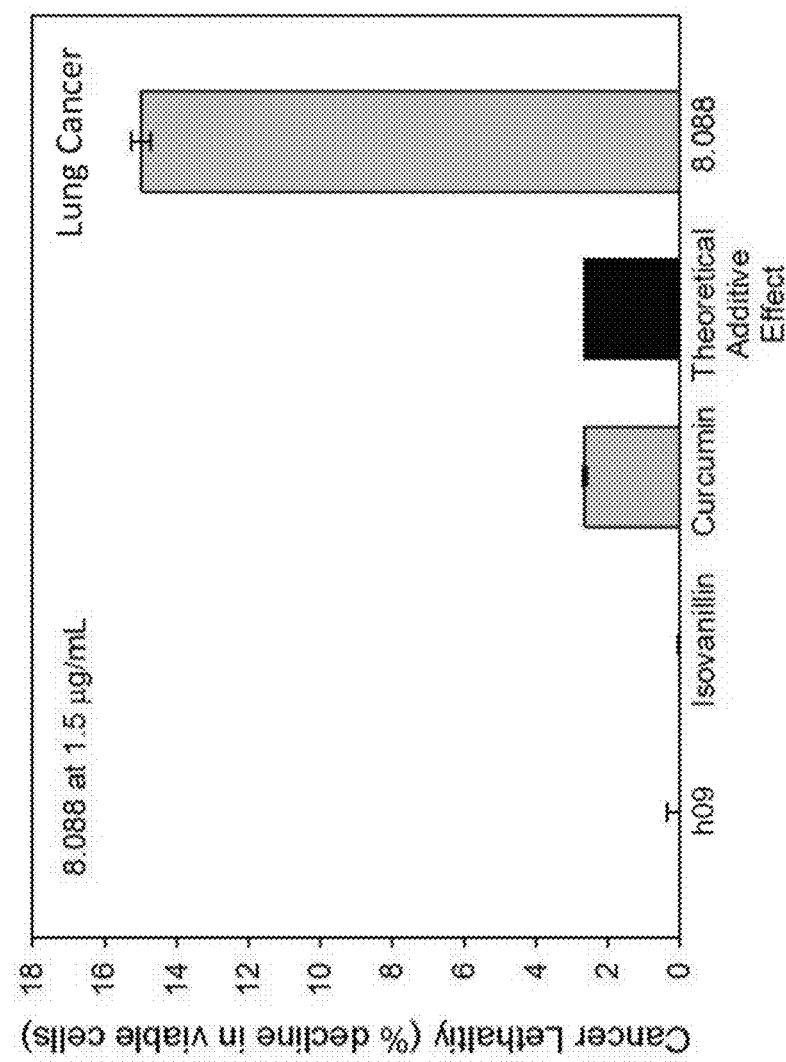
Figures 82, 134:
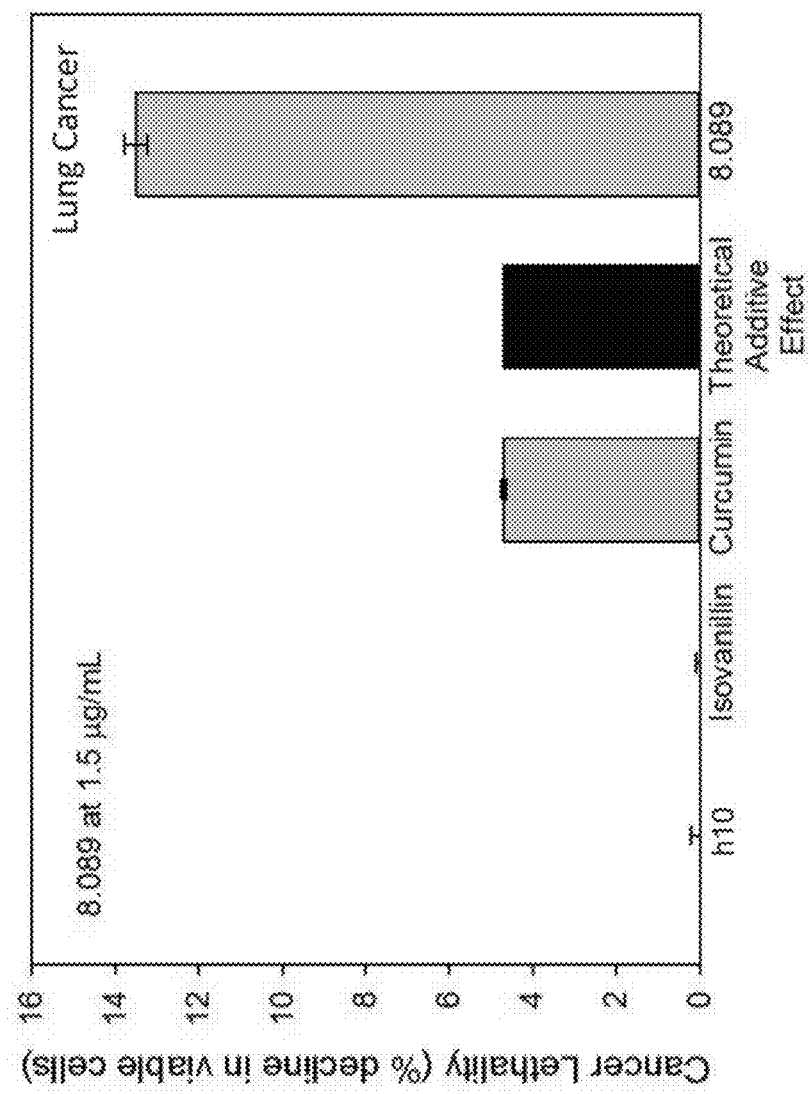
Figures 82, 135:
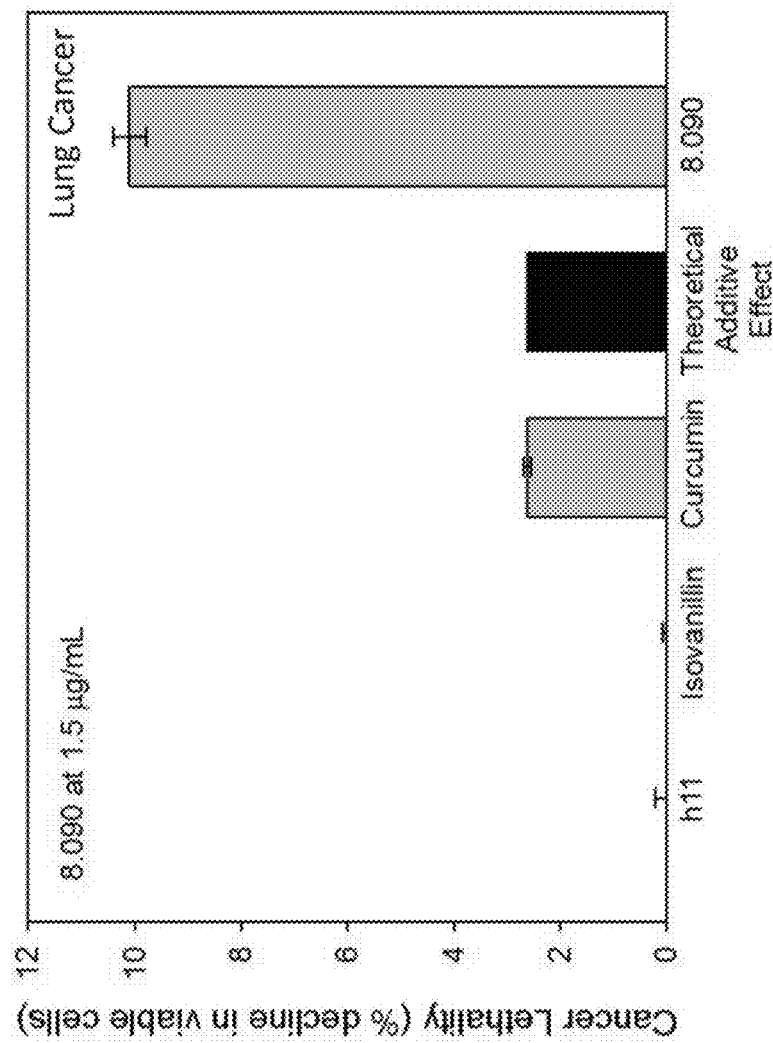
Figures 82, 136:
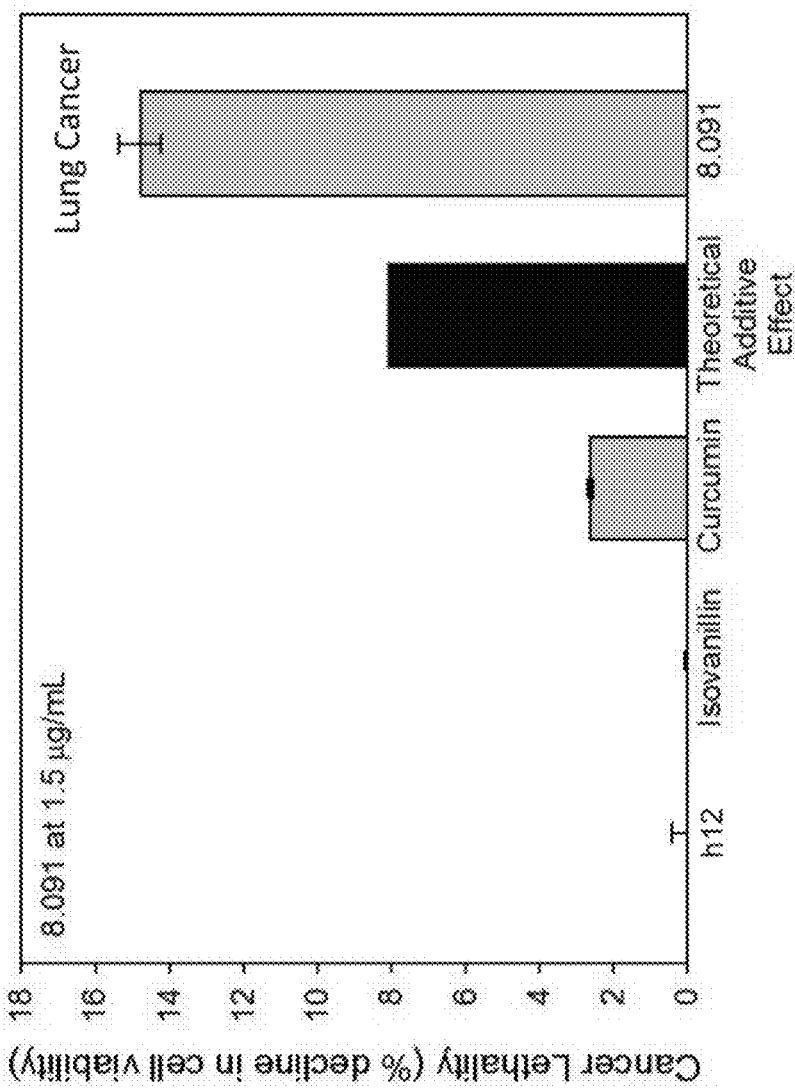
Figures 82, 137:
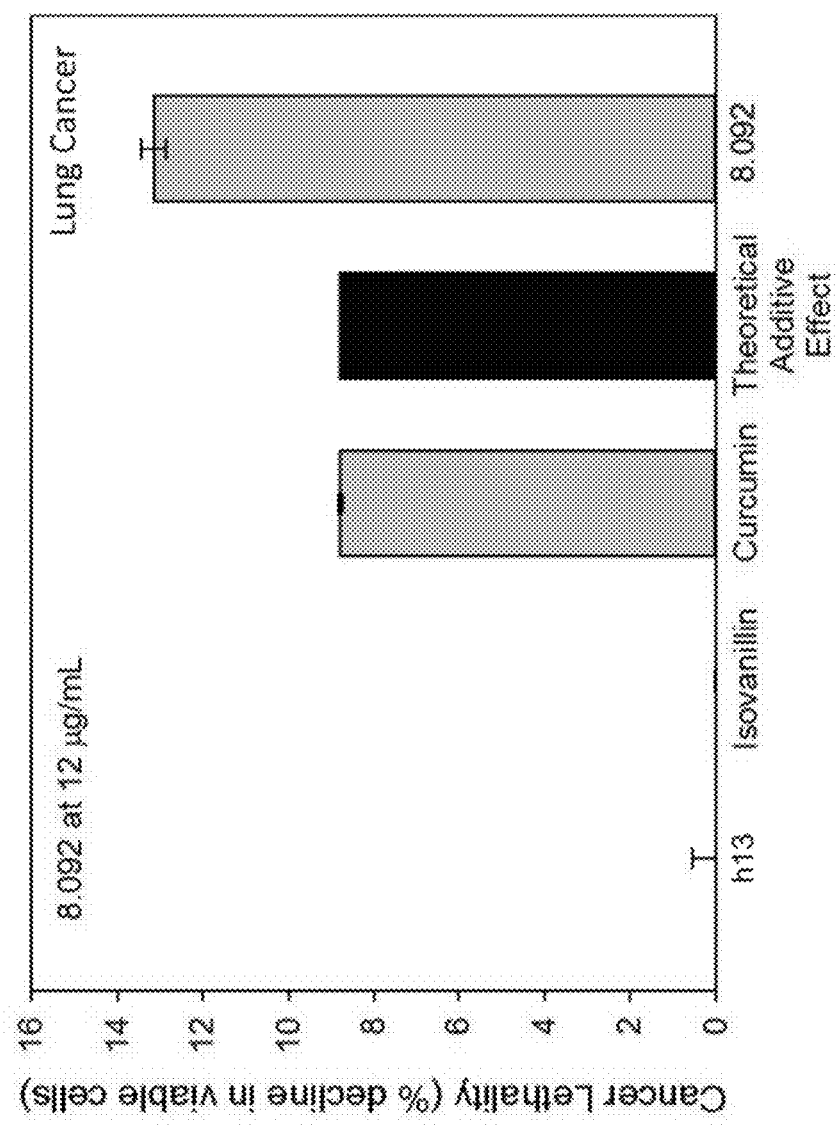
Figures 82, 138:
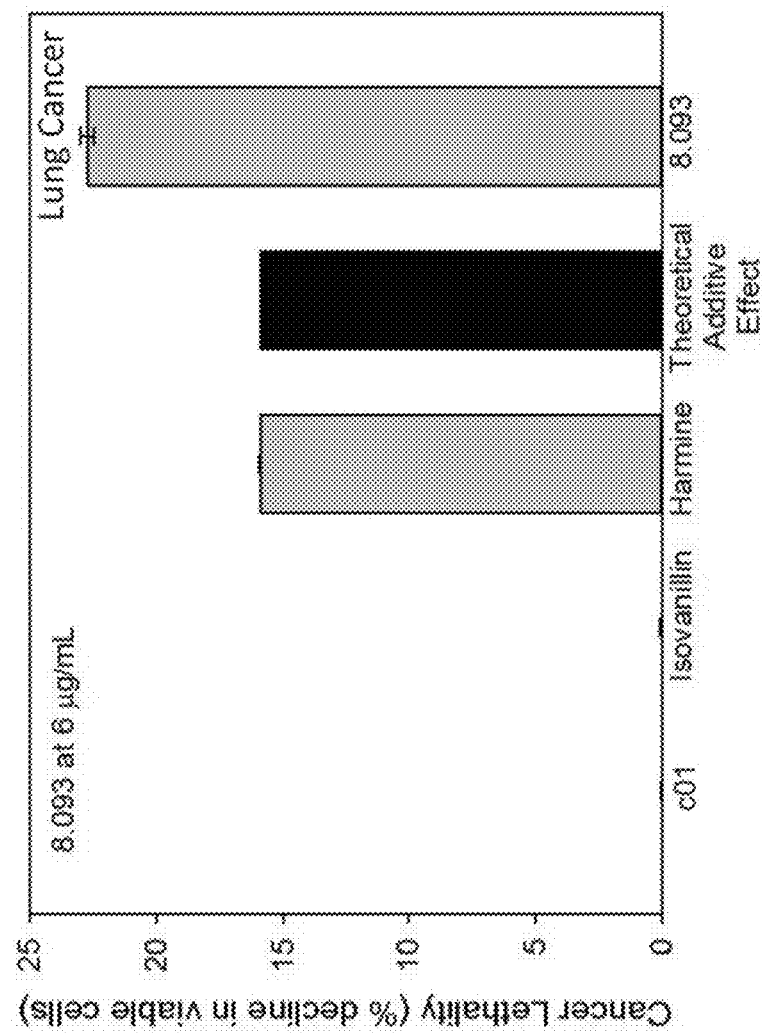
Figures 82, 139:
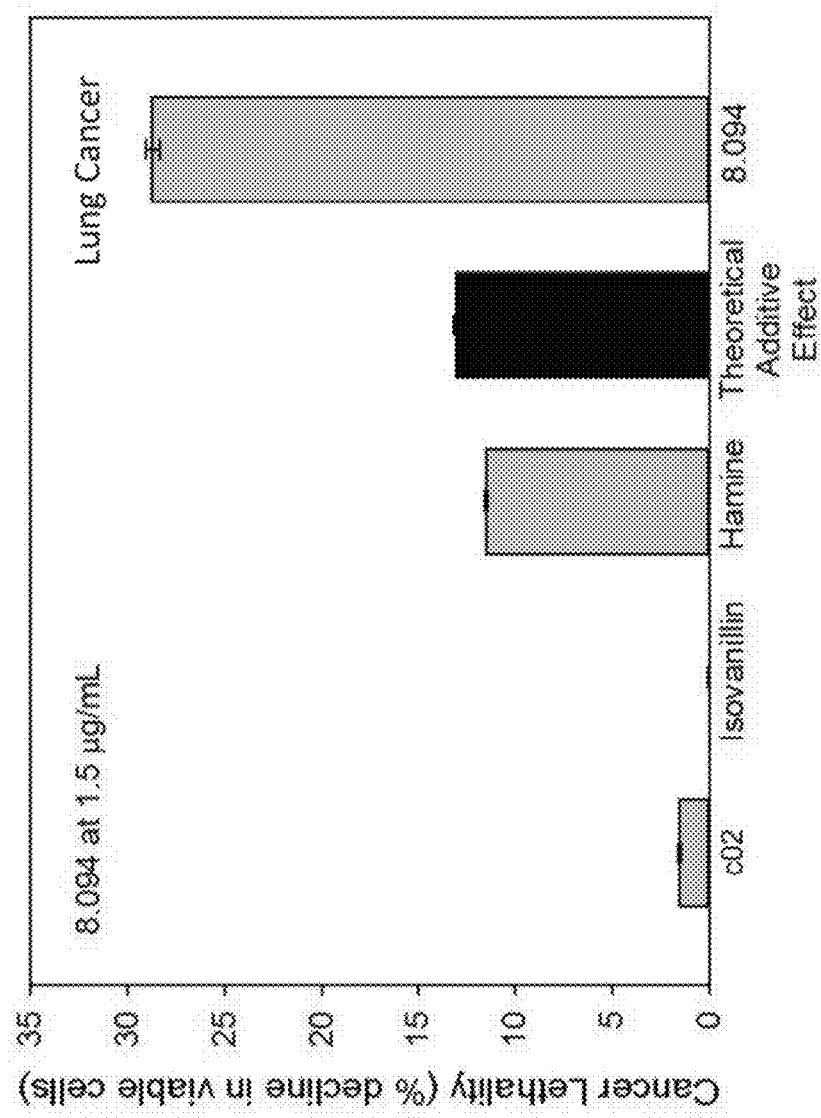
Figures 82, 140:
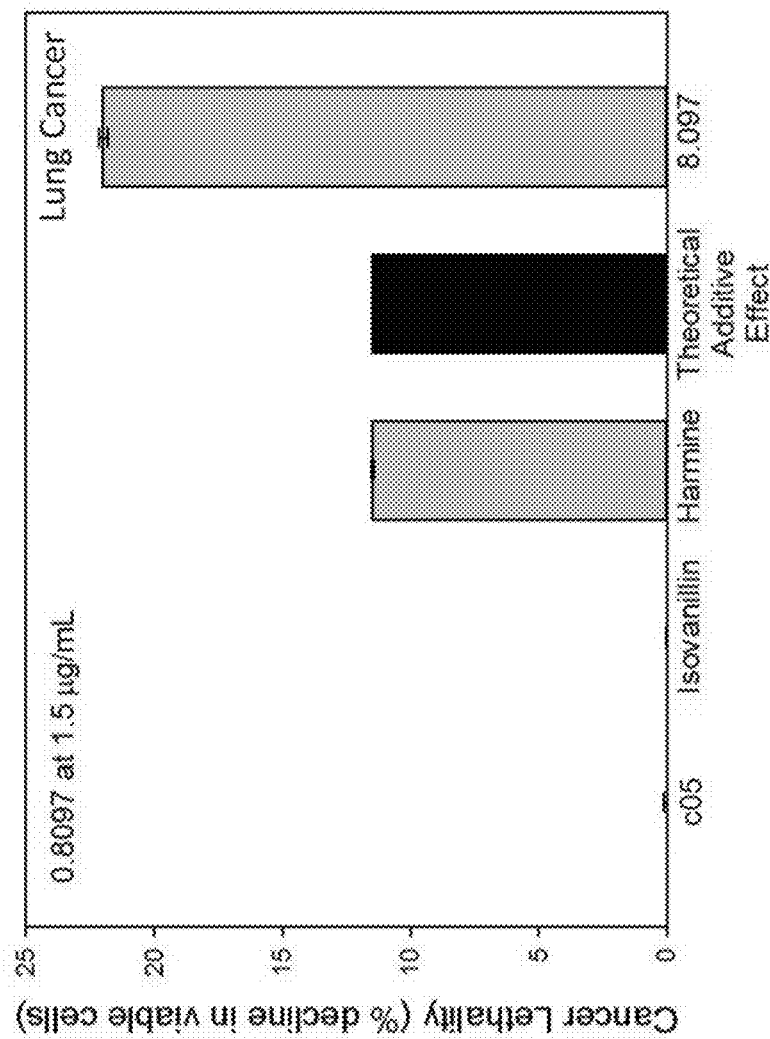
Figures 82, 141:
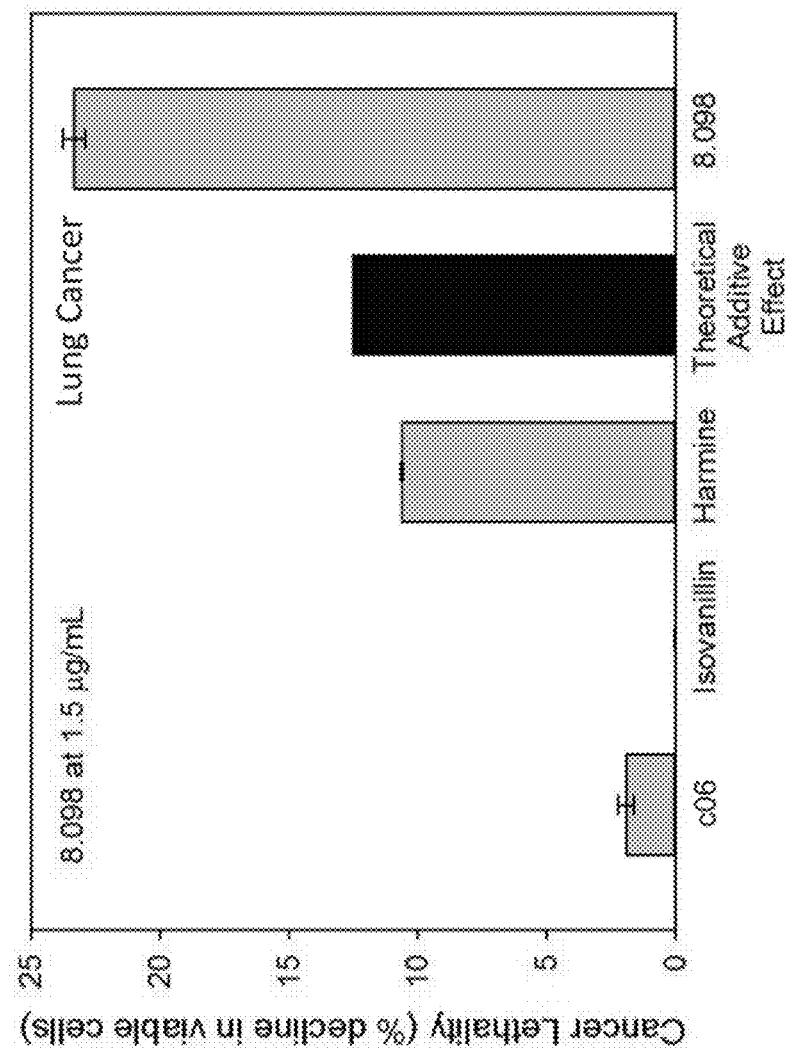
Figures 82, 142:
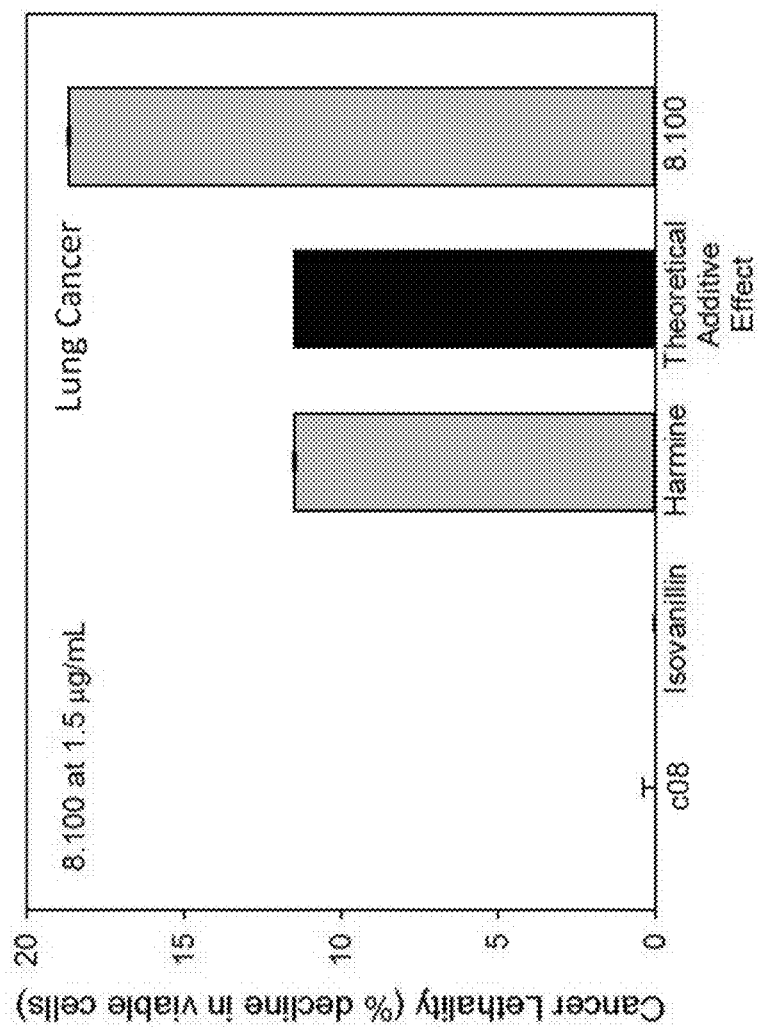
Figures 82, 143:
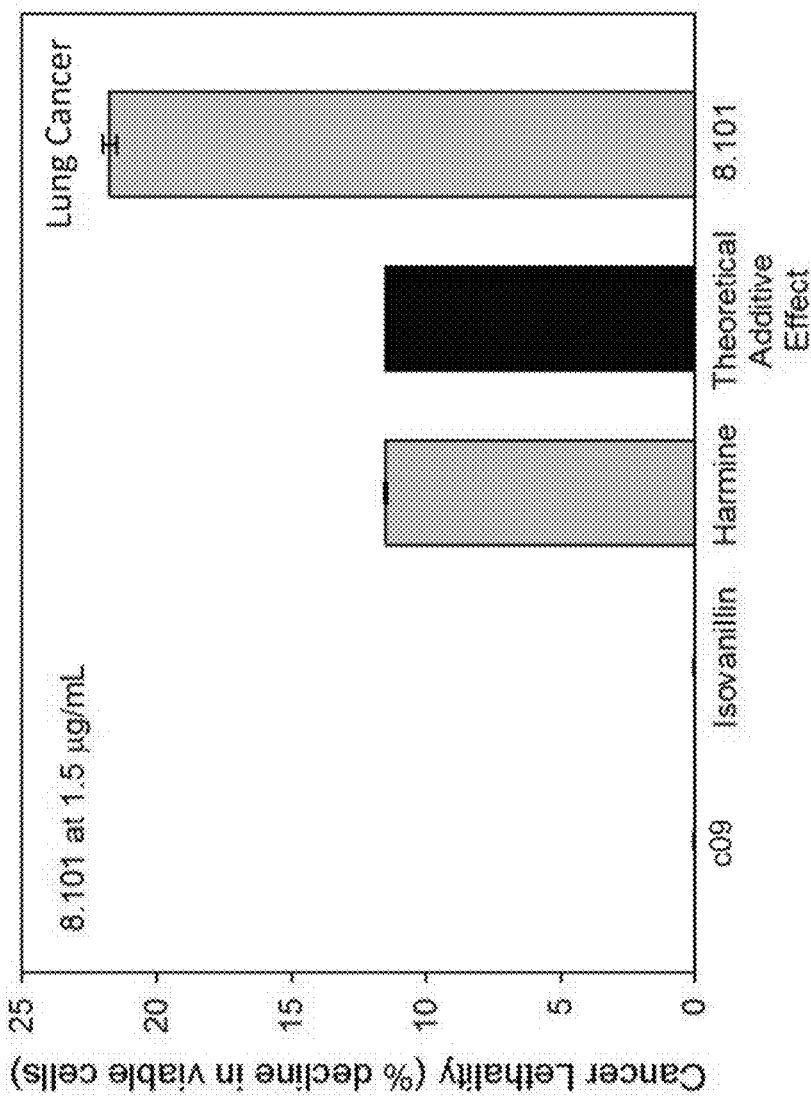
Figures 82, 144:
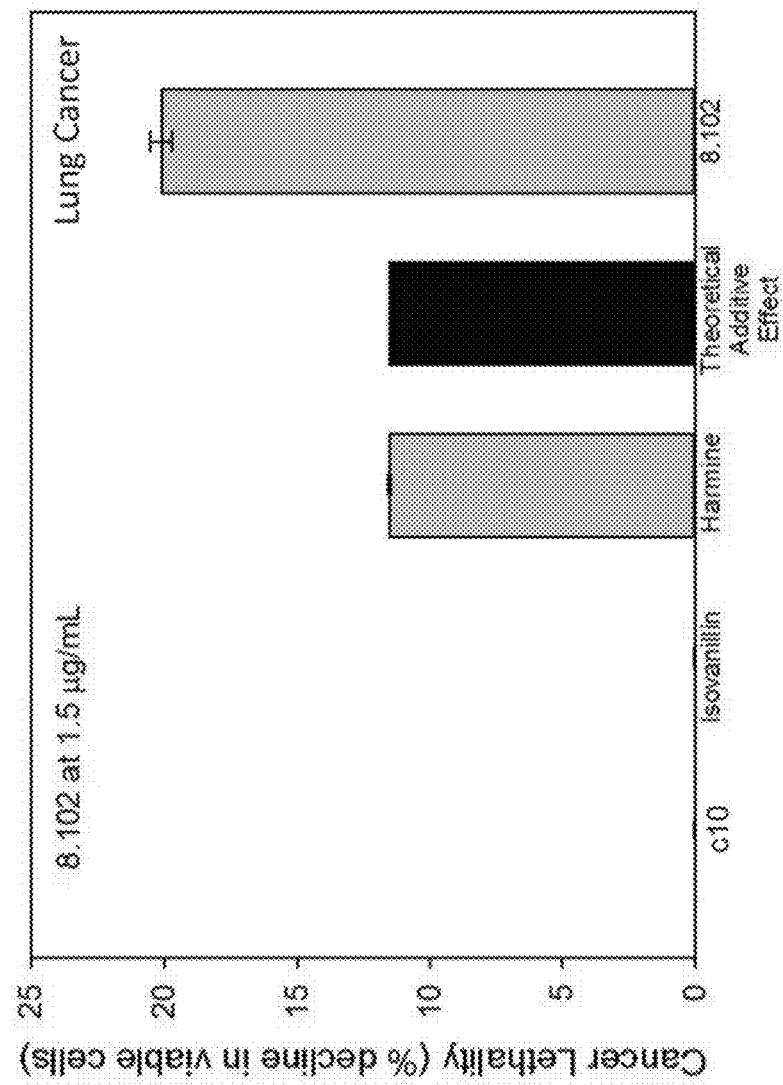
Figures 82, 145:
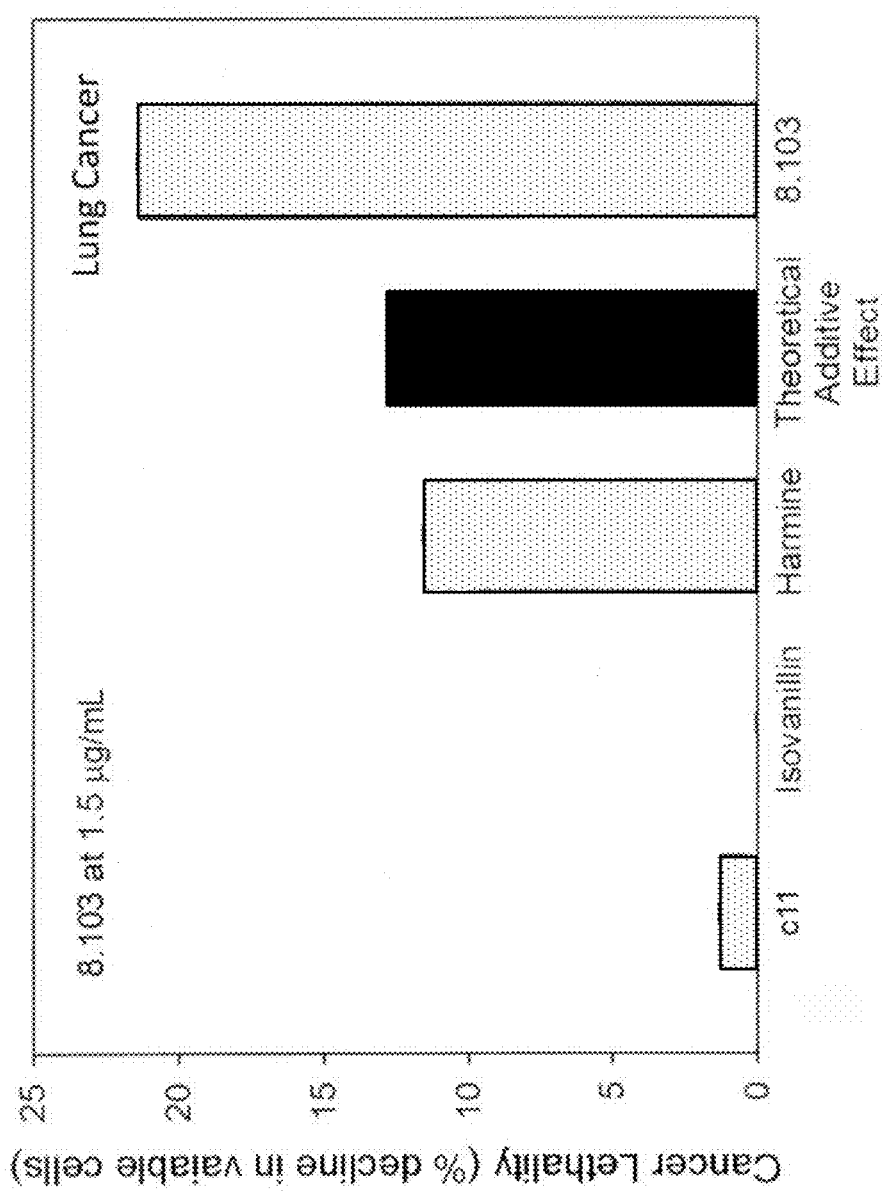
Figures 82, 146:
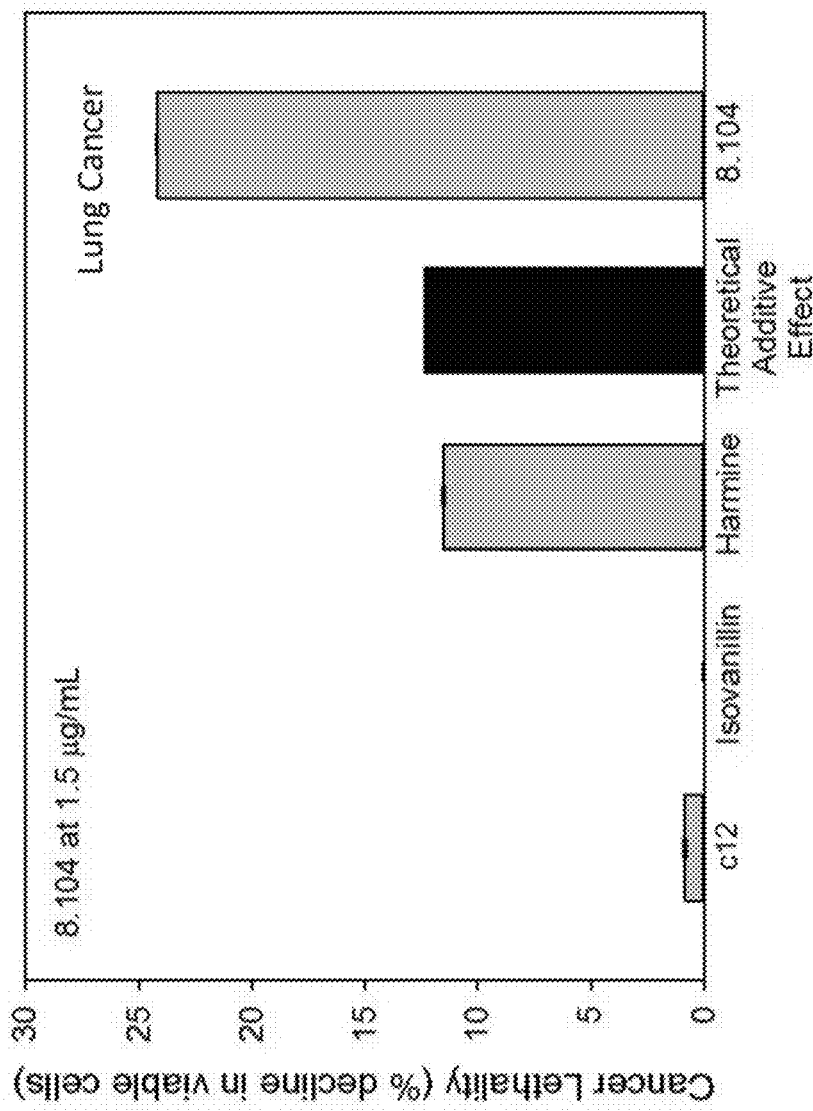
Figures 82, 147:
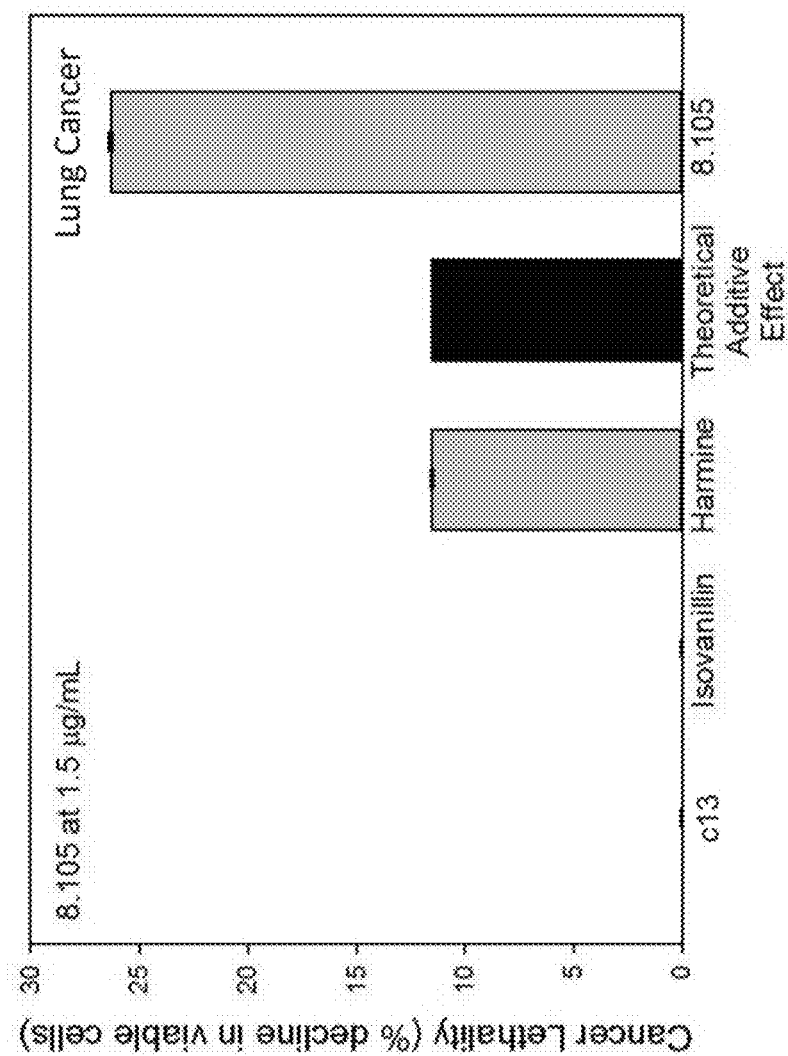
Figures 82, 148:
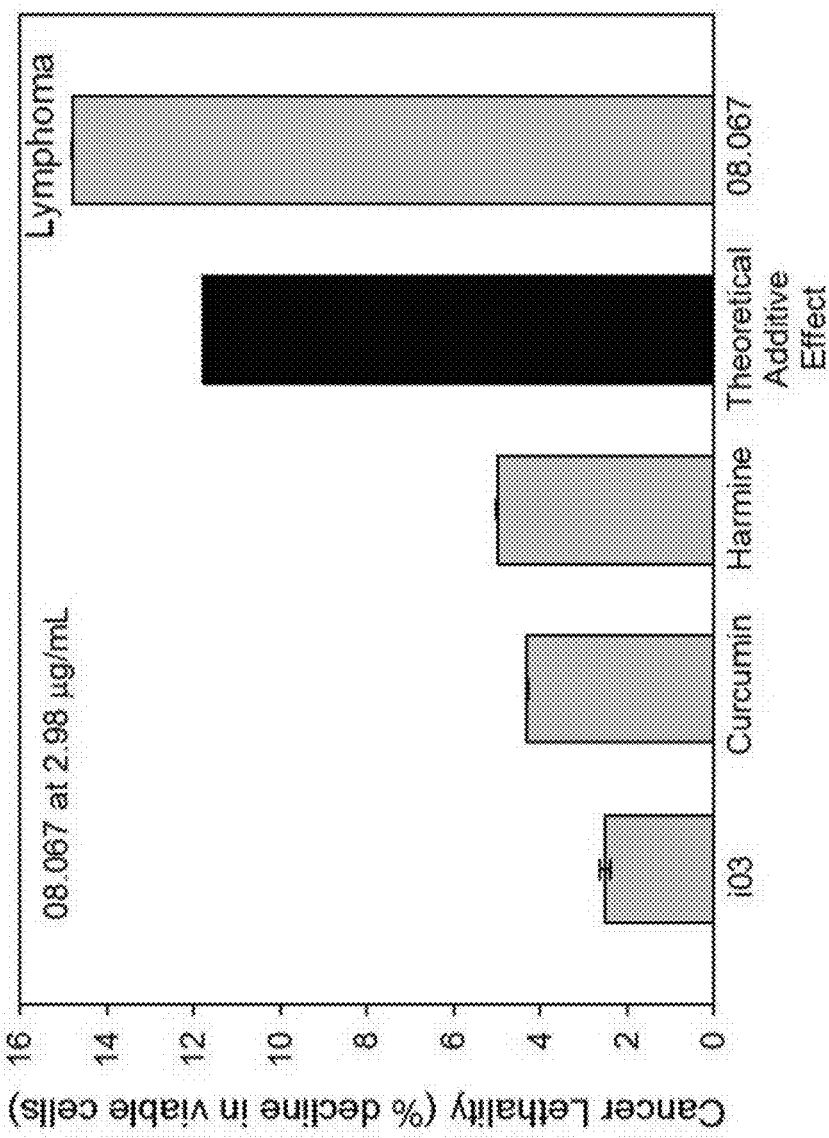
Figures 82, 149:
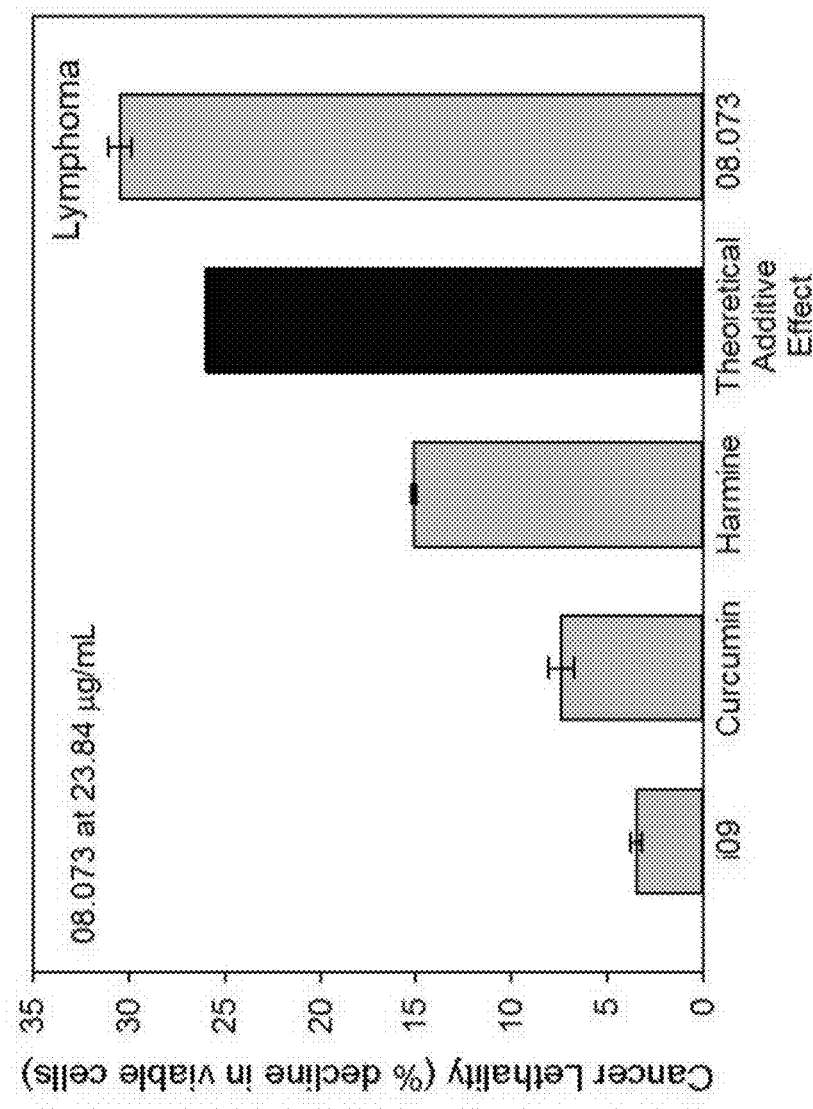
Figures 82, 150:
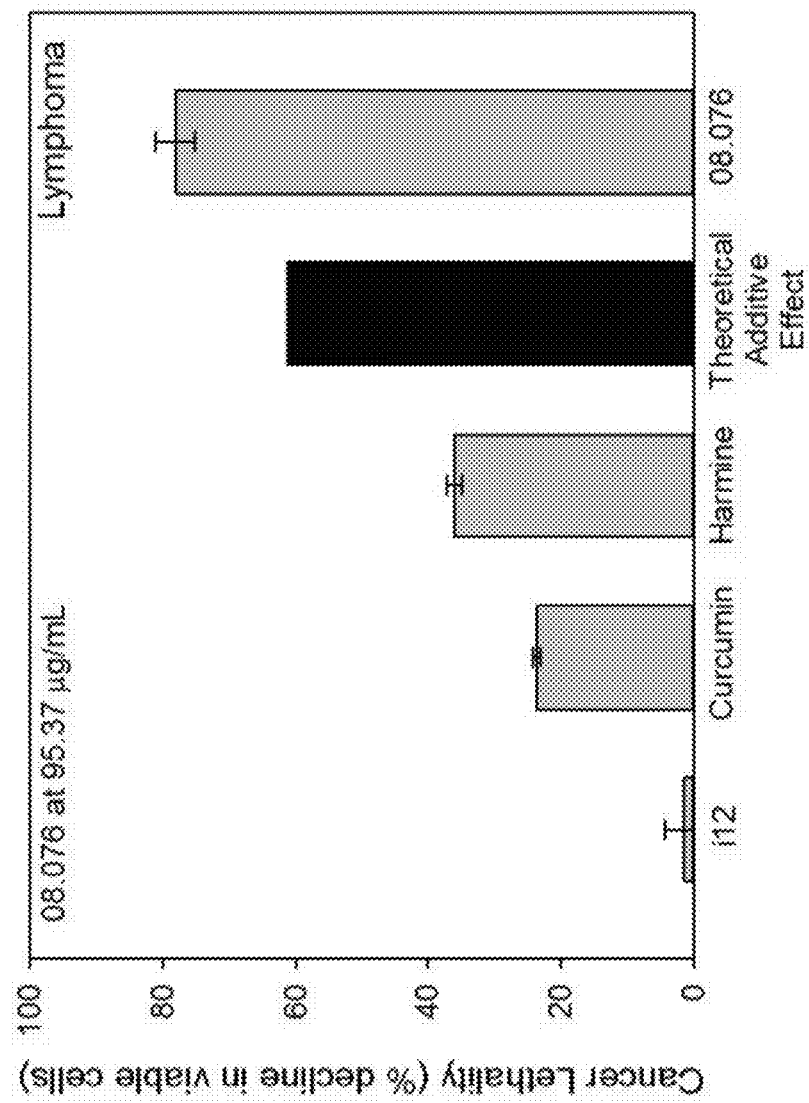
Figures 82, 151:
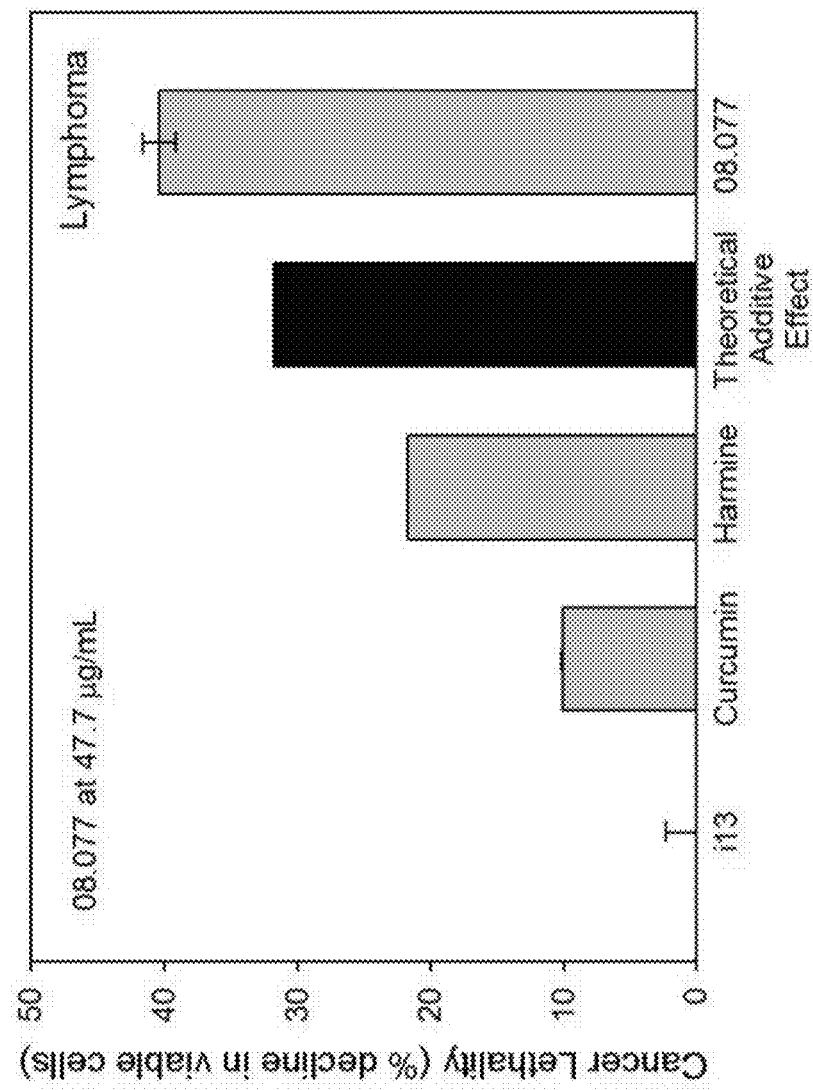
Figures 82, 152:
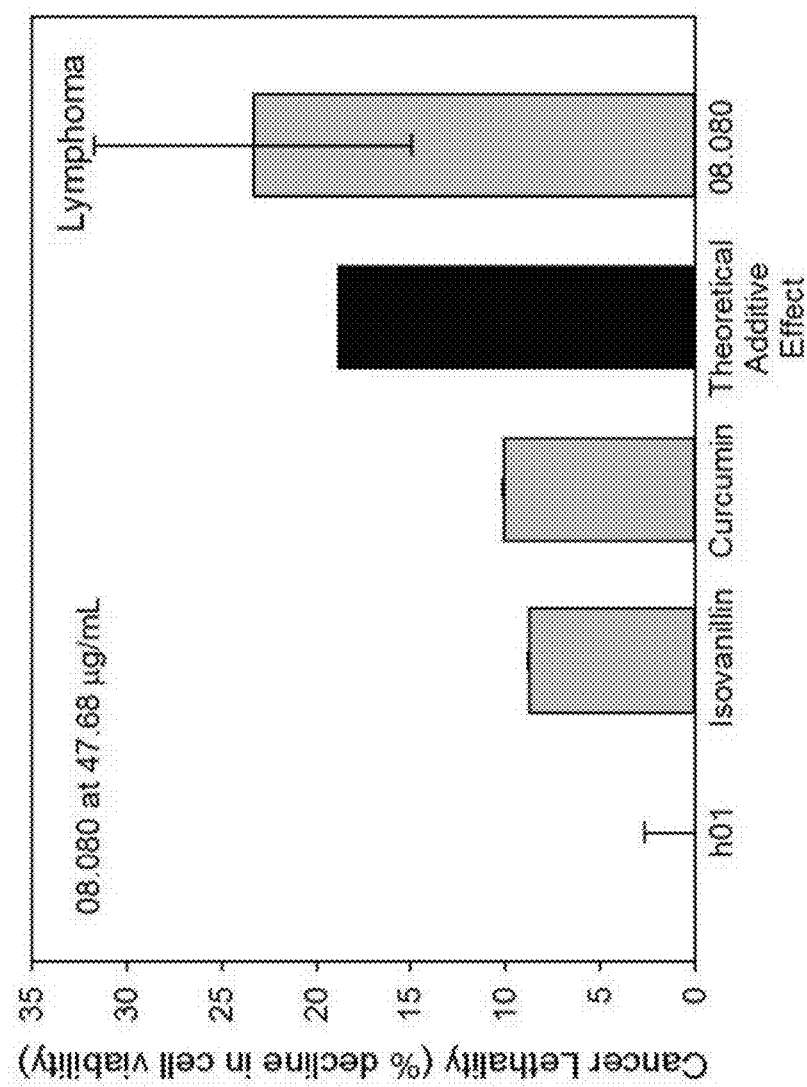
Figures 82, 153:
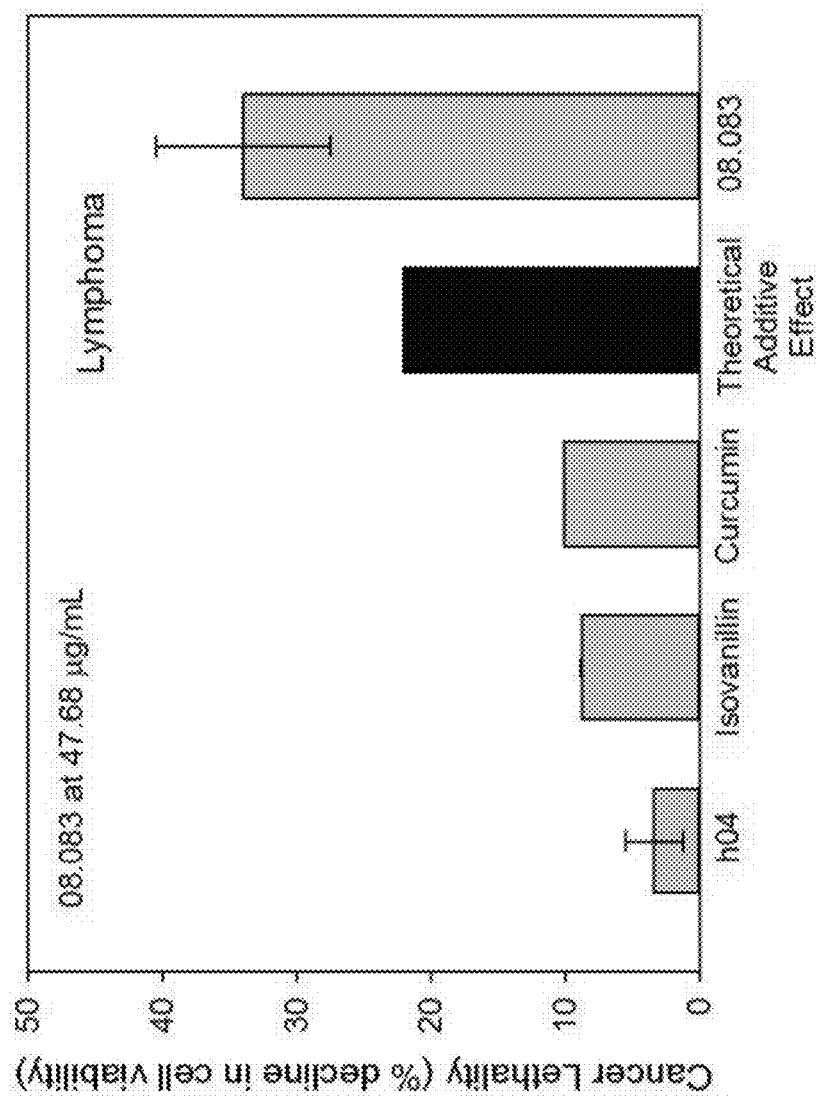
Figures 82, 154:
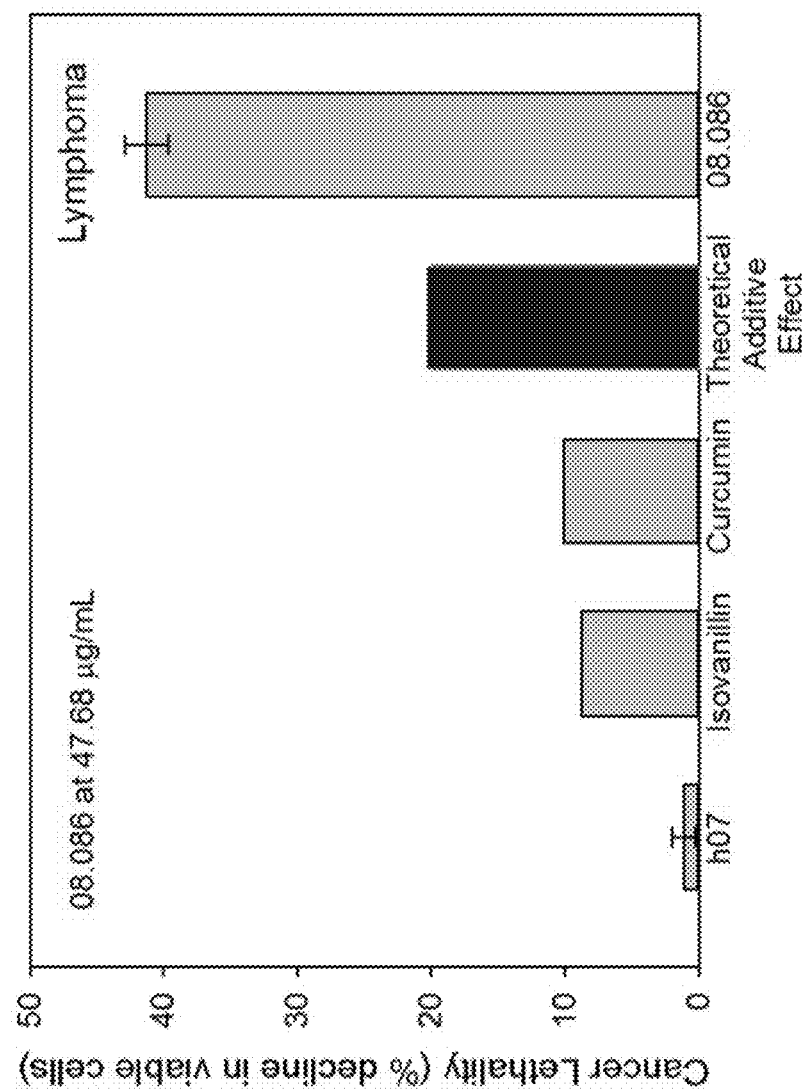
Figures 82, 155:
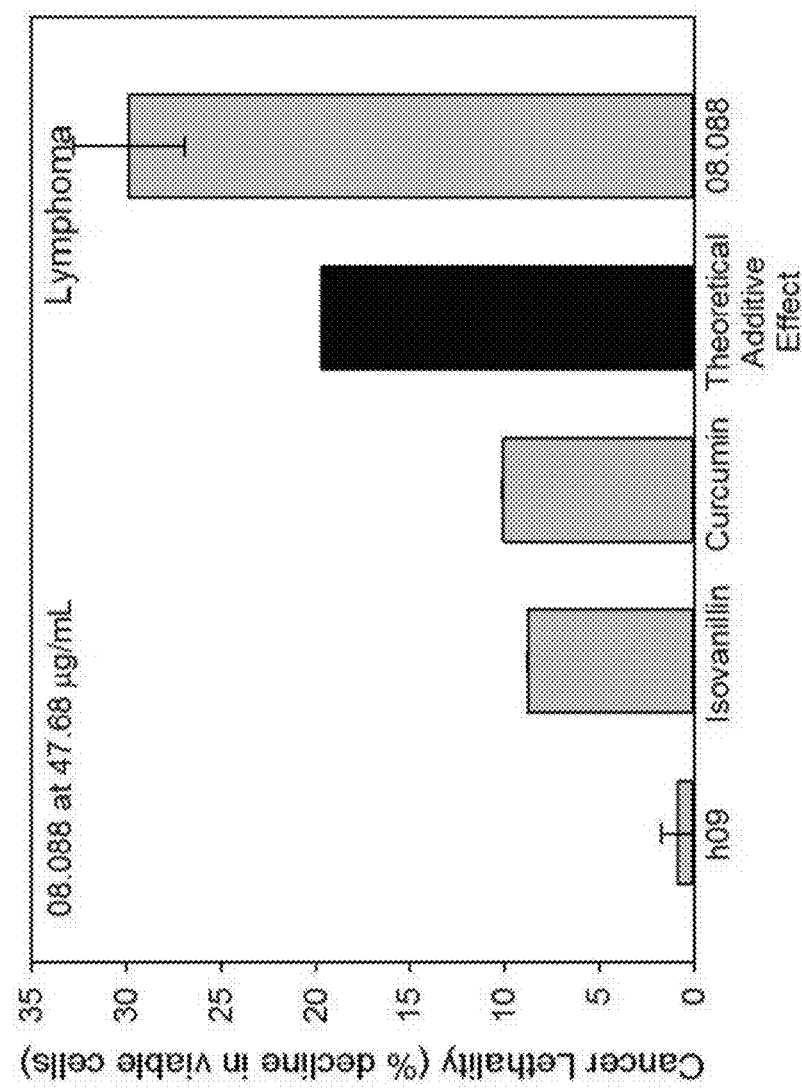
Figures 82, 156:
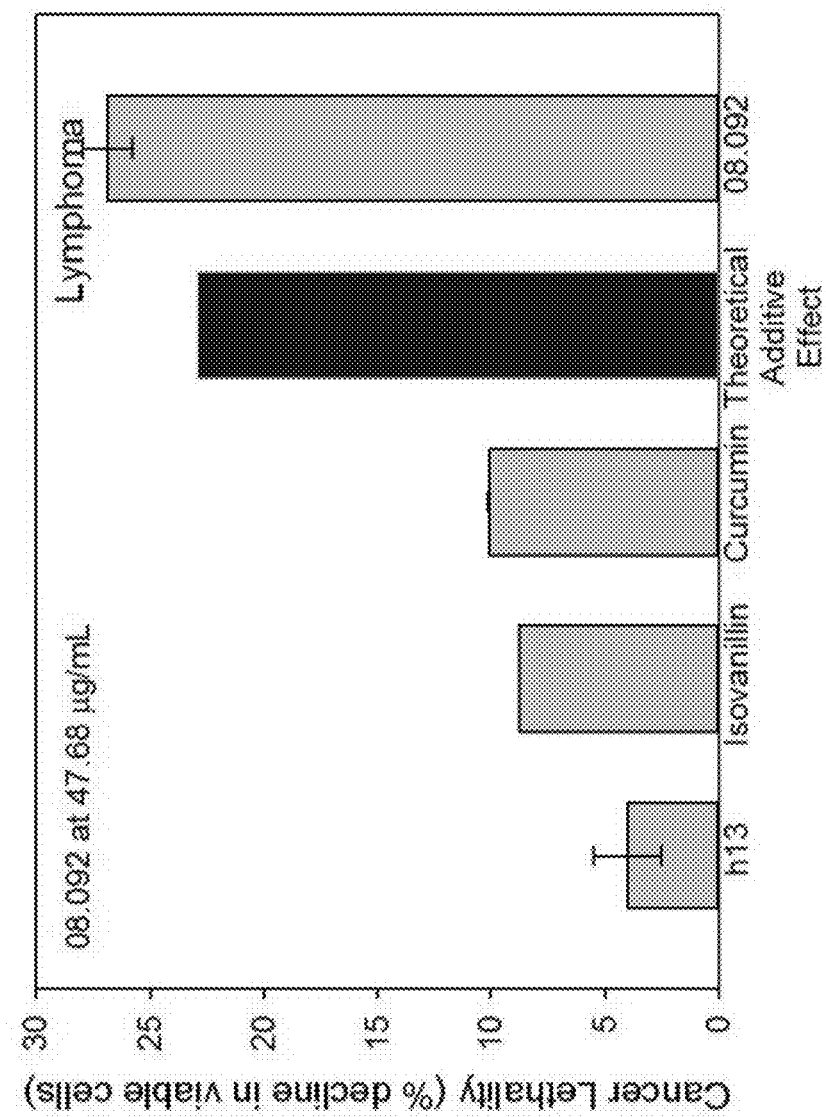
Figures 82, 157:
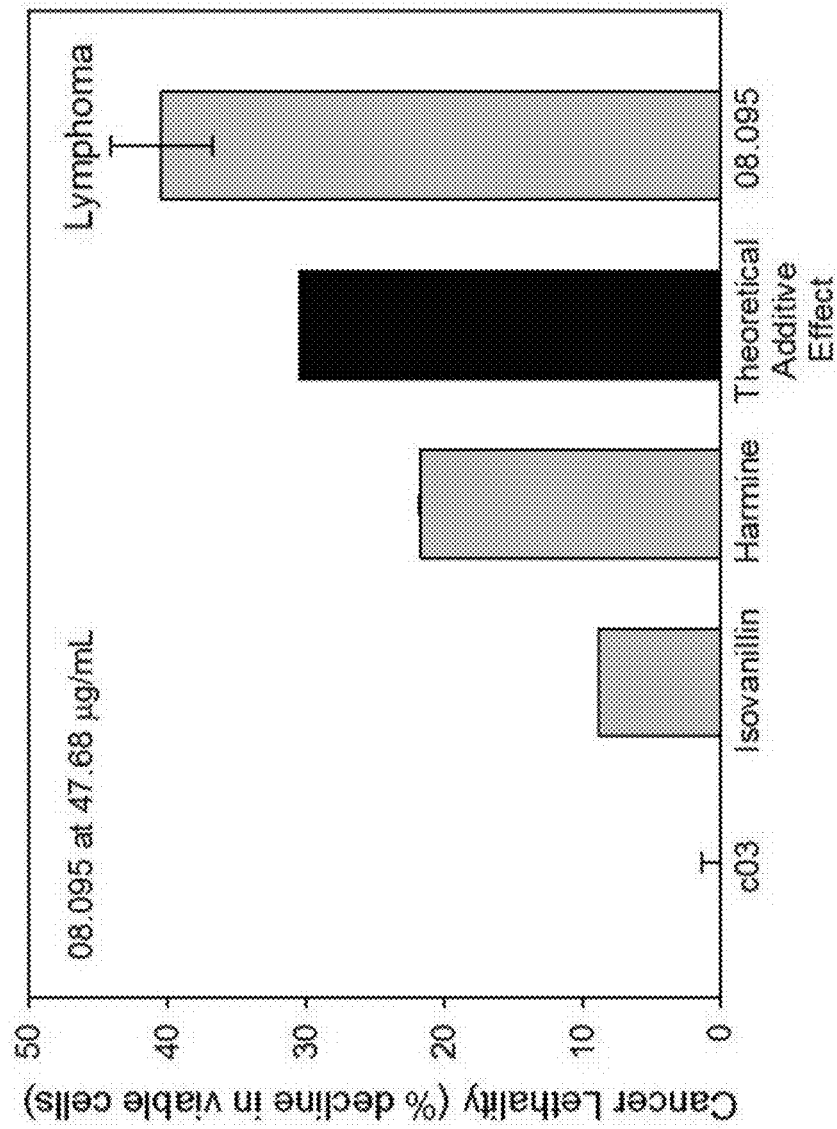
Figures 82, 158:
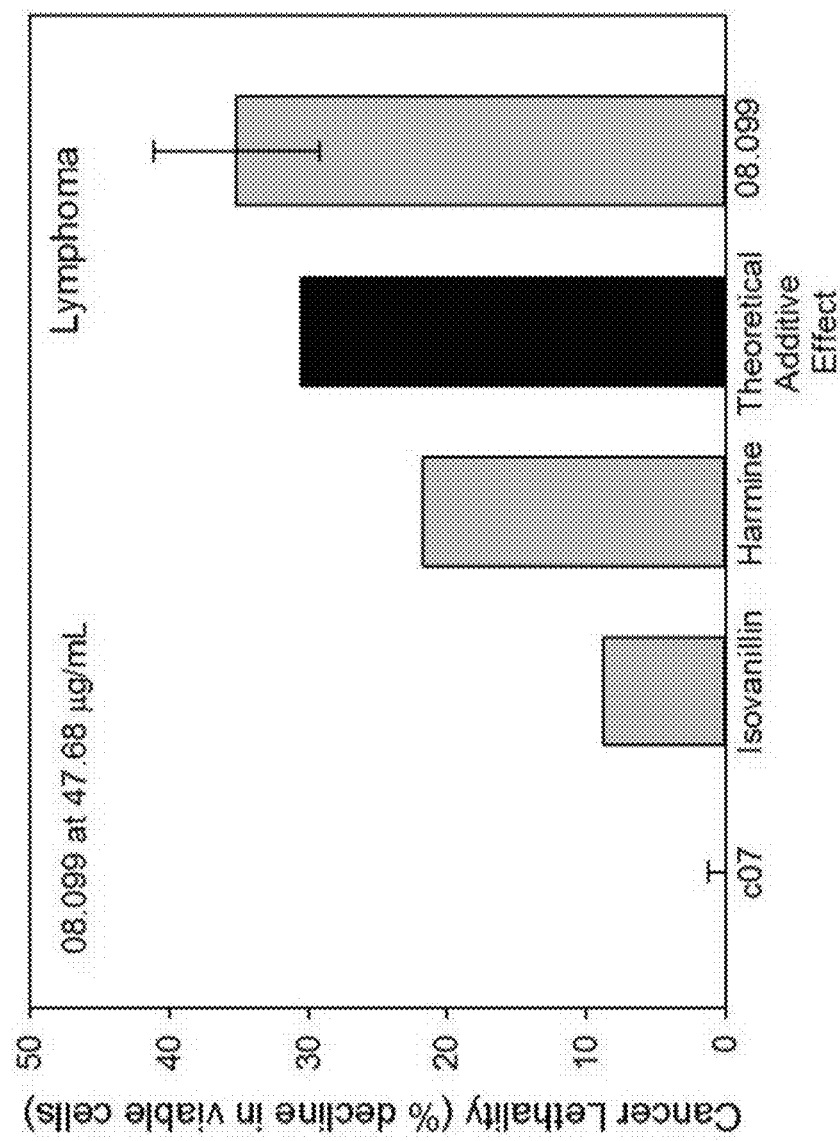
Figures 82, 159:
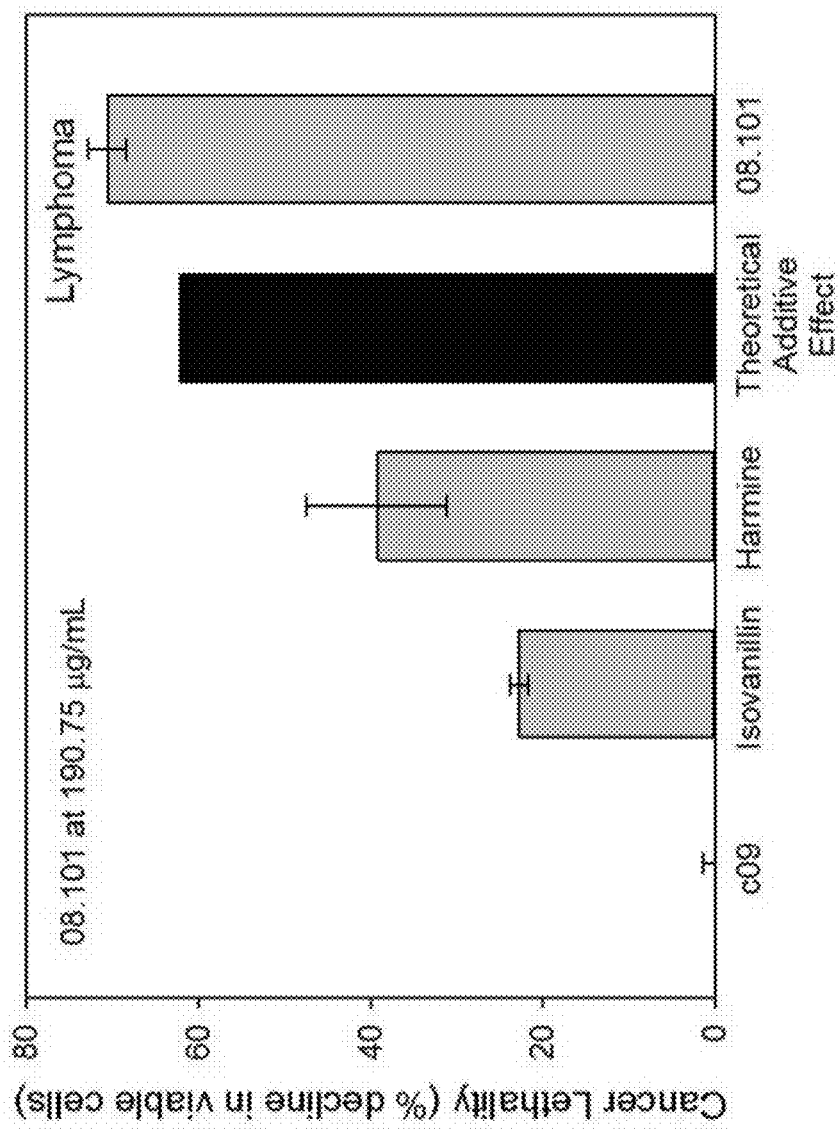
Figures 82, 160:
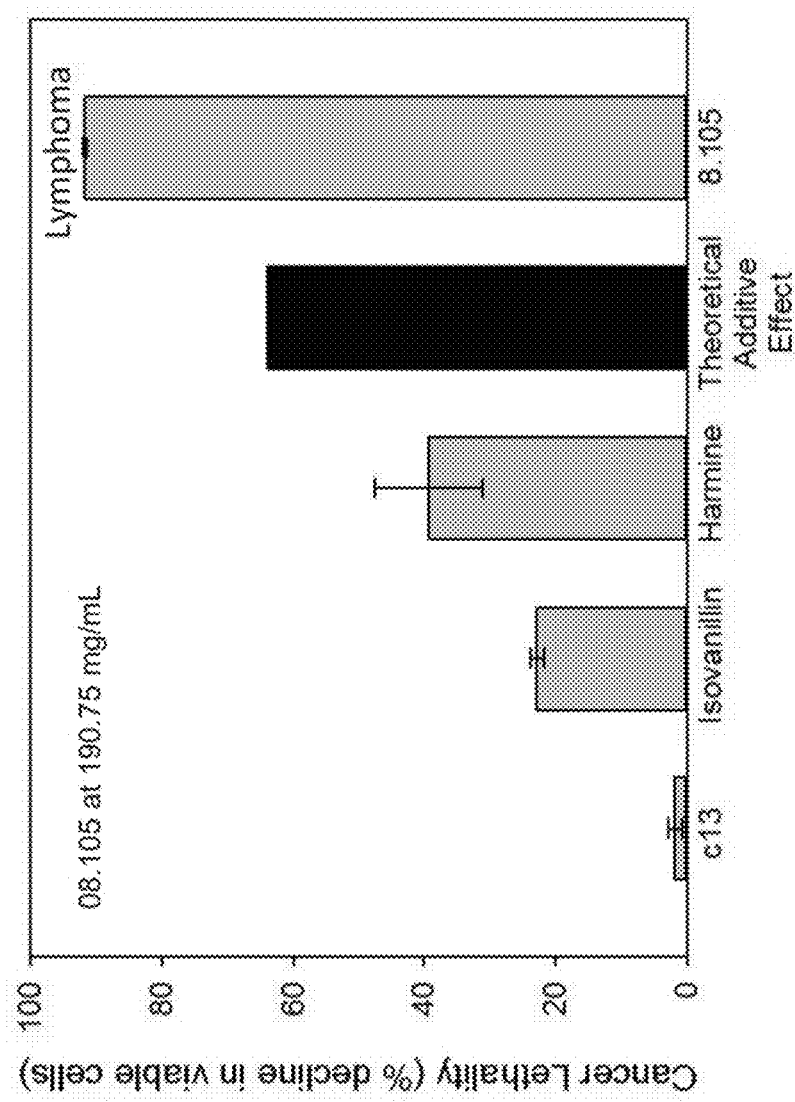
Figures 82, 161:
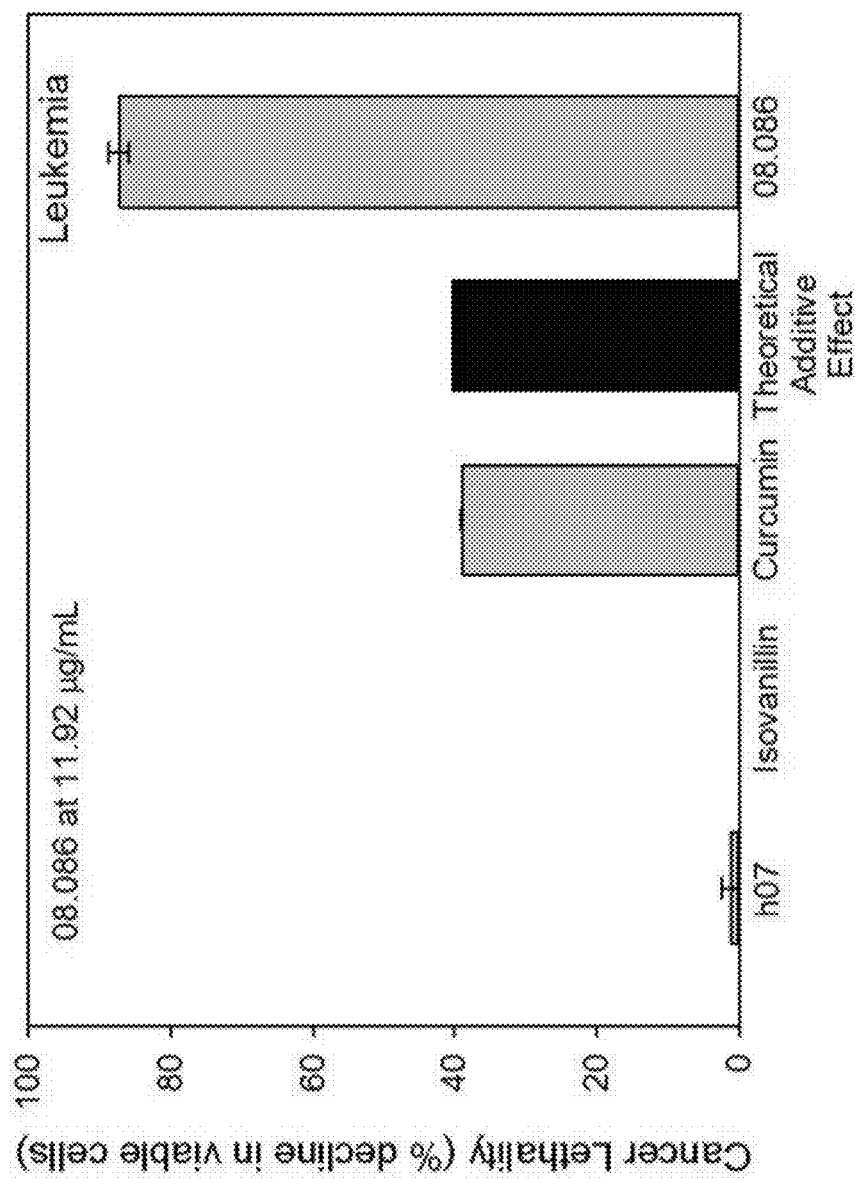
Figures 82, 162:
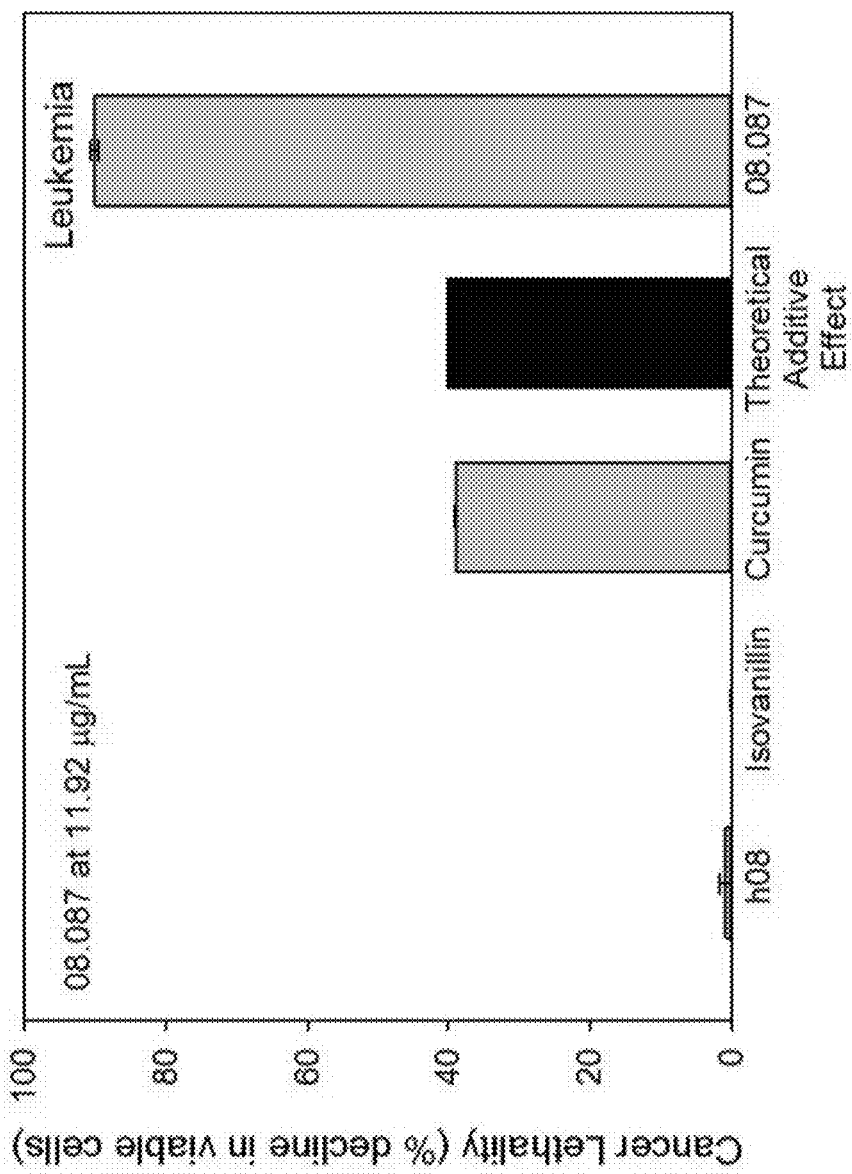
Figures 82, 163:
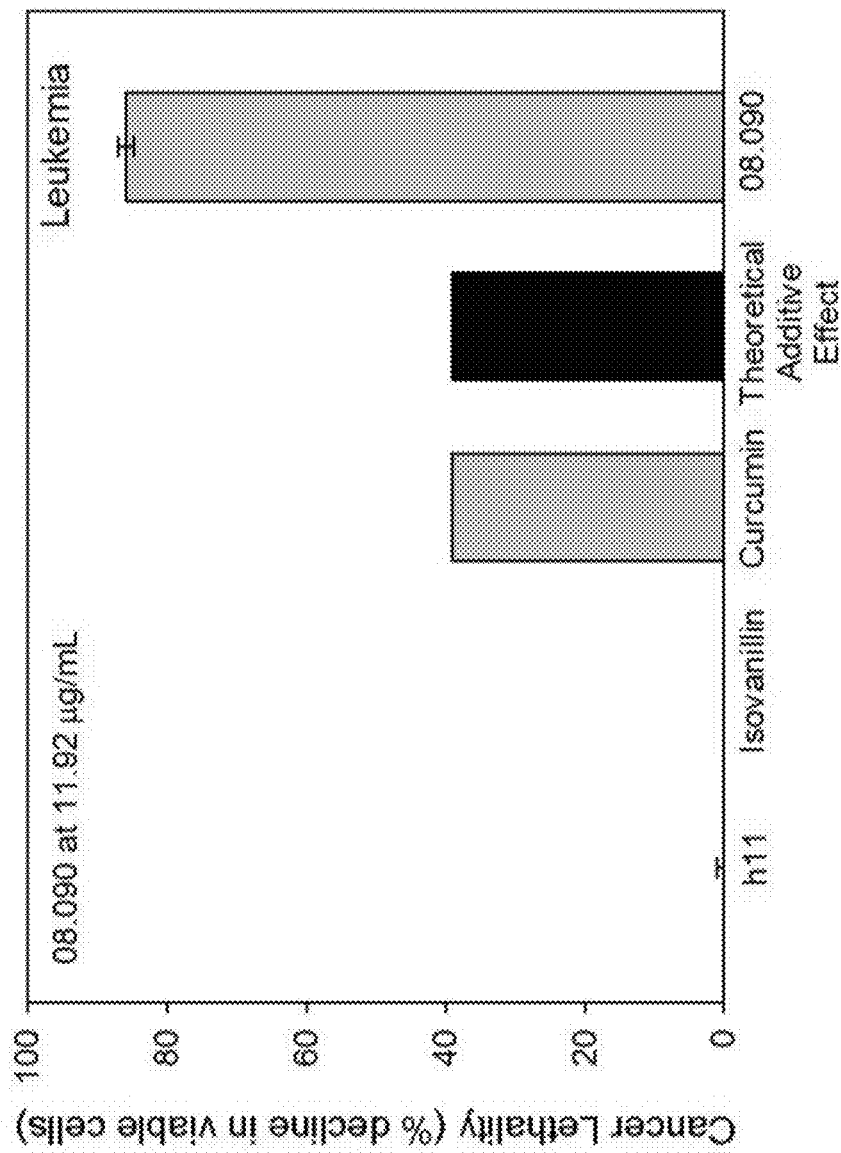
Figures 82, 164:
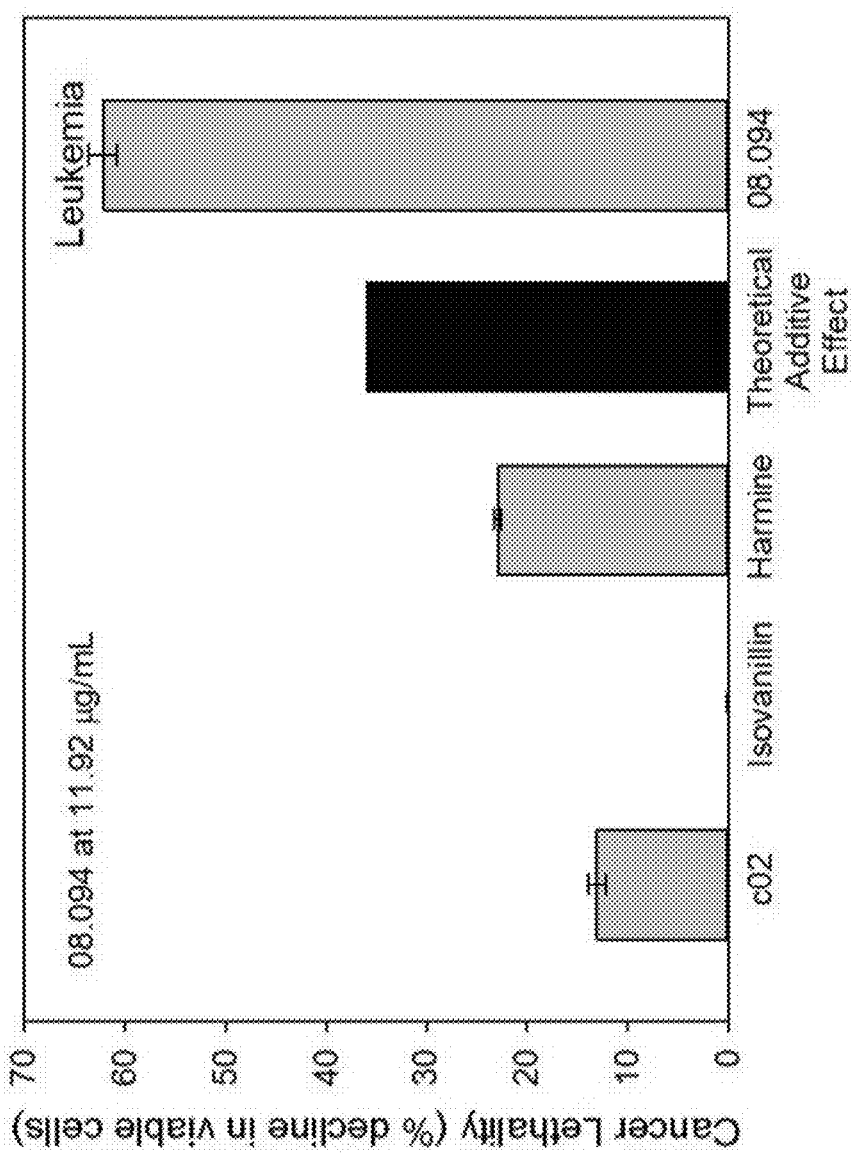
Figures 82, 165:
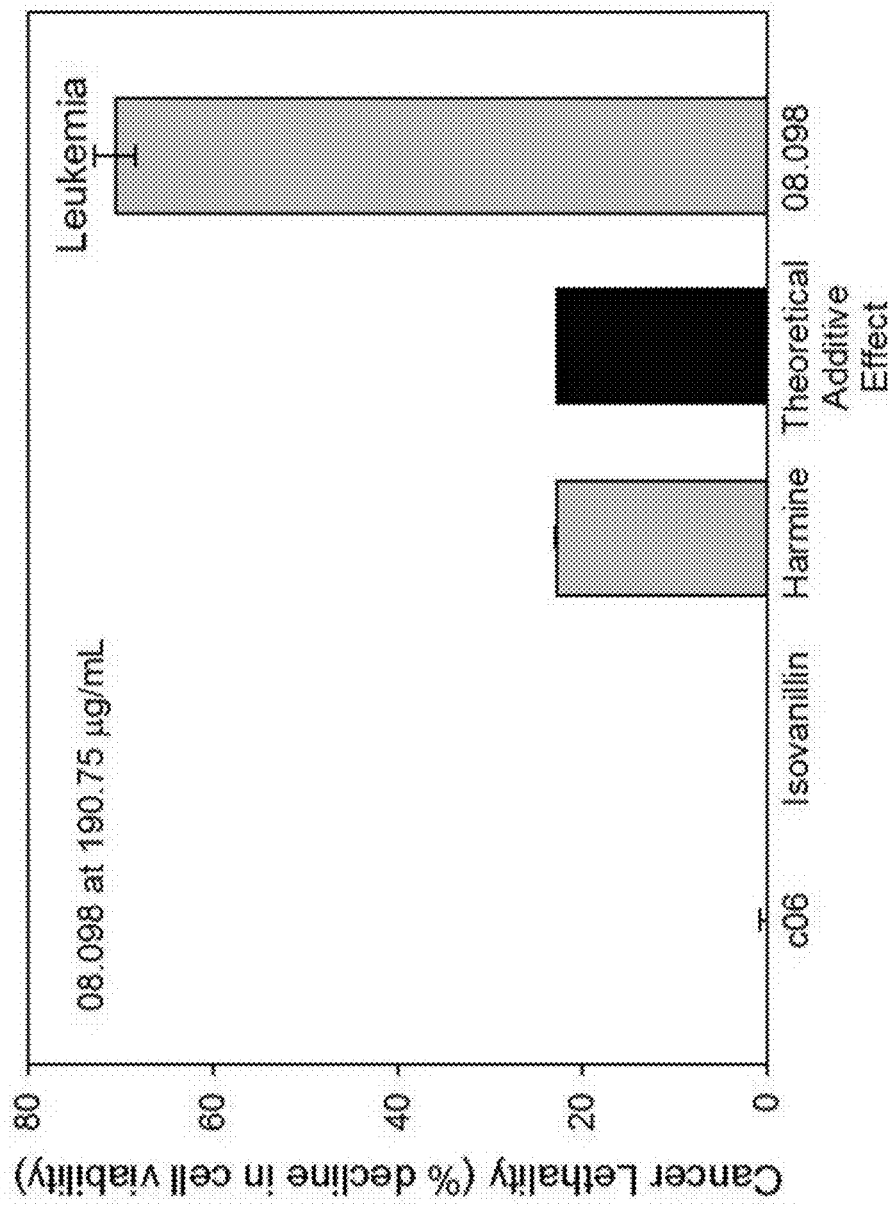
Figures 82, 166:
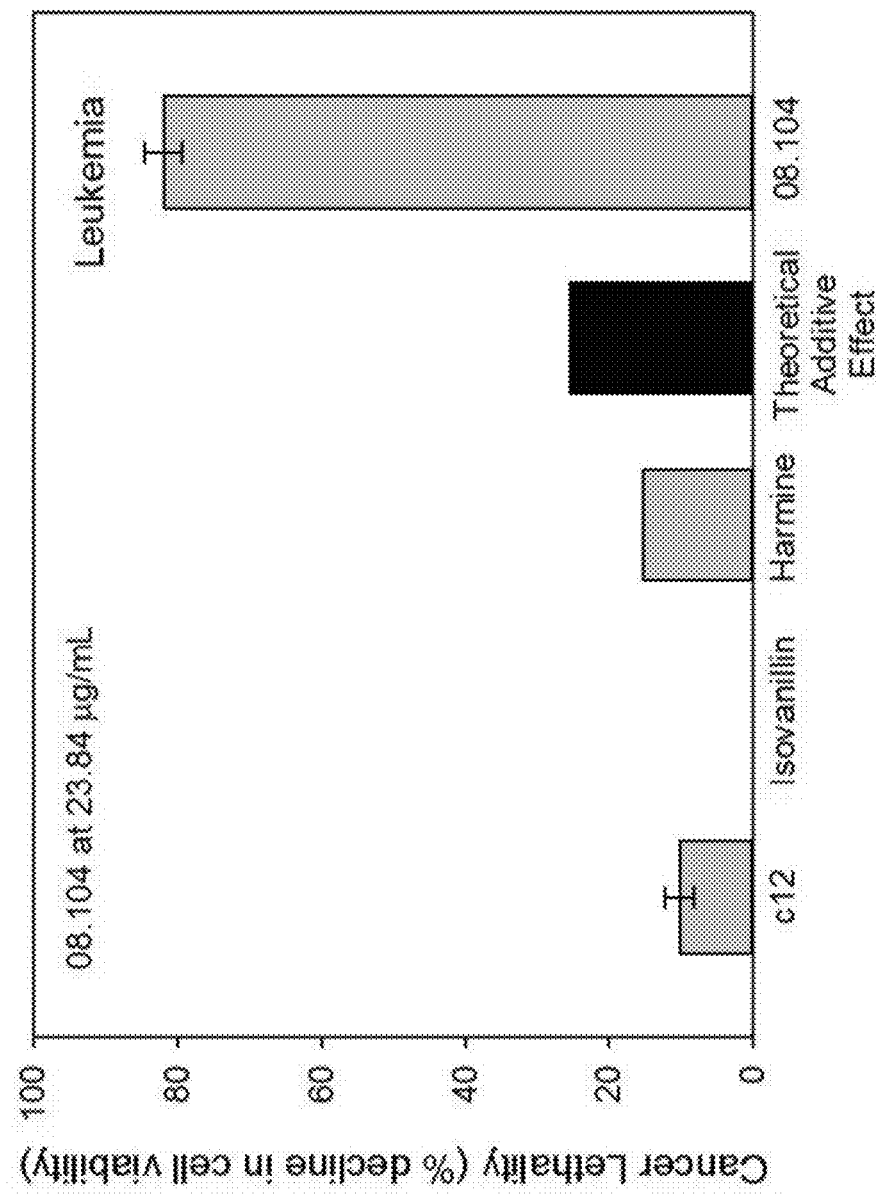
Figures 82, 167:
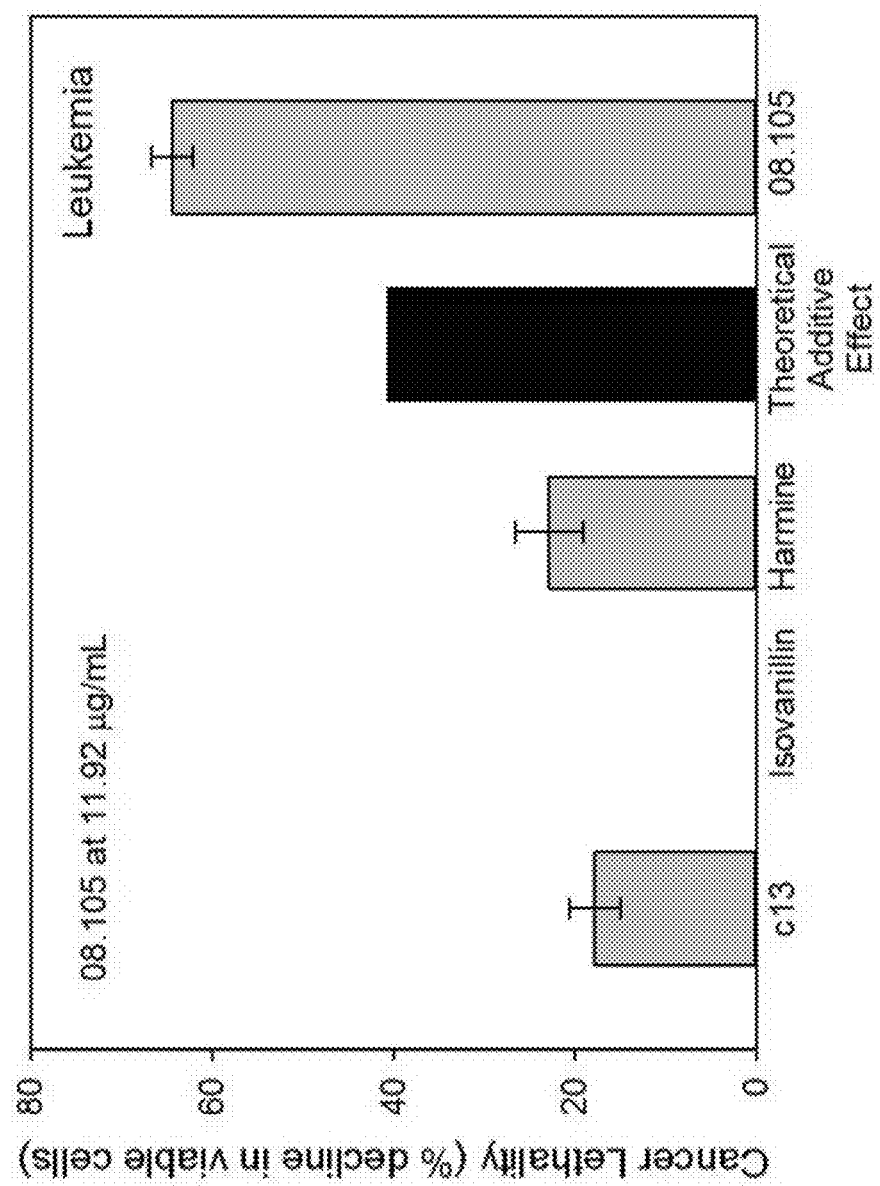
Figure 83A:
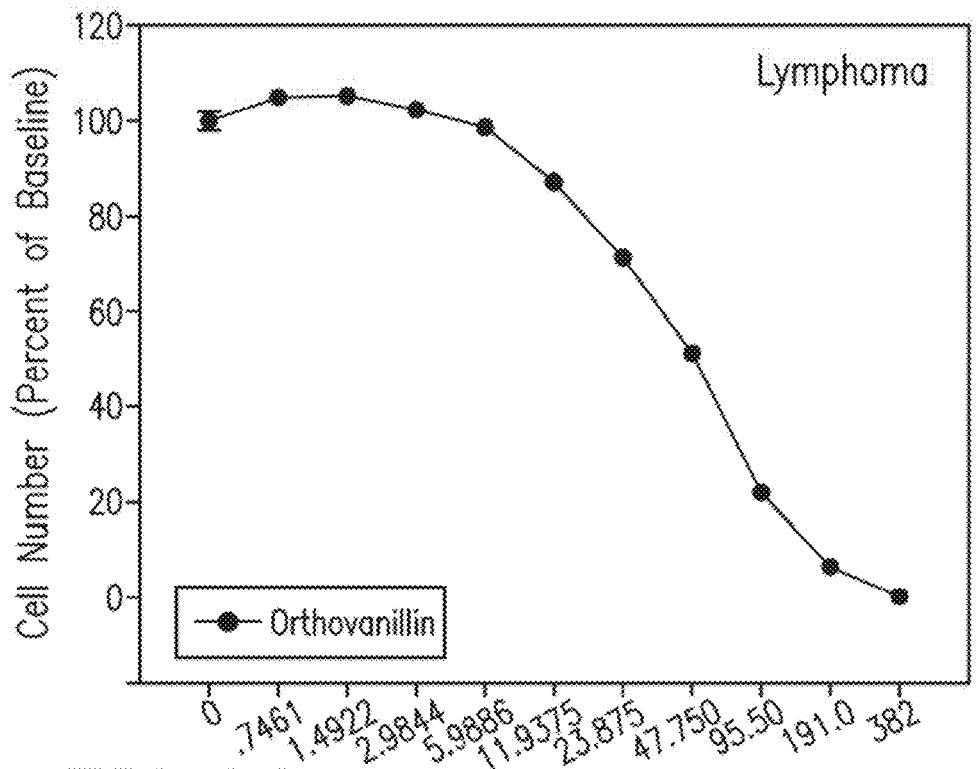
Figure 83B:
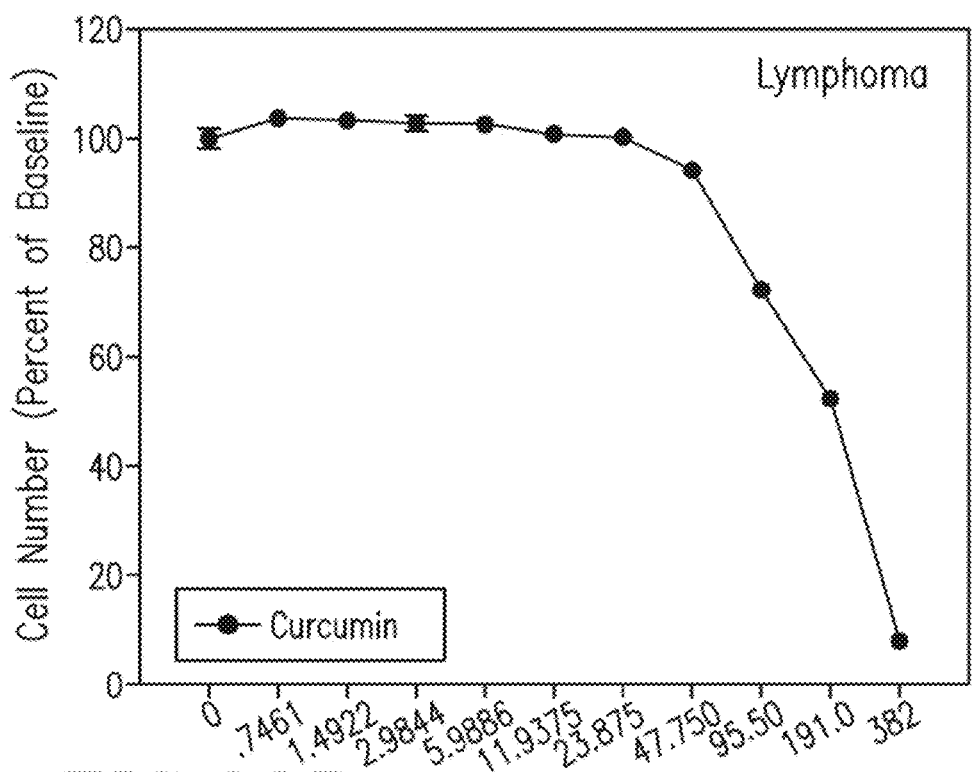
Figure 83C:
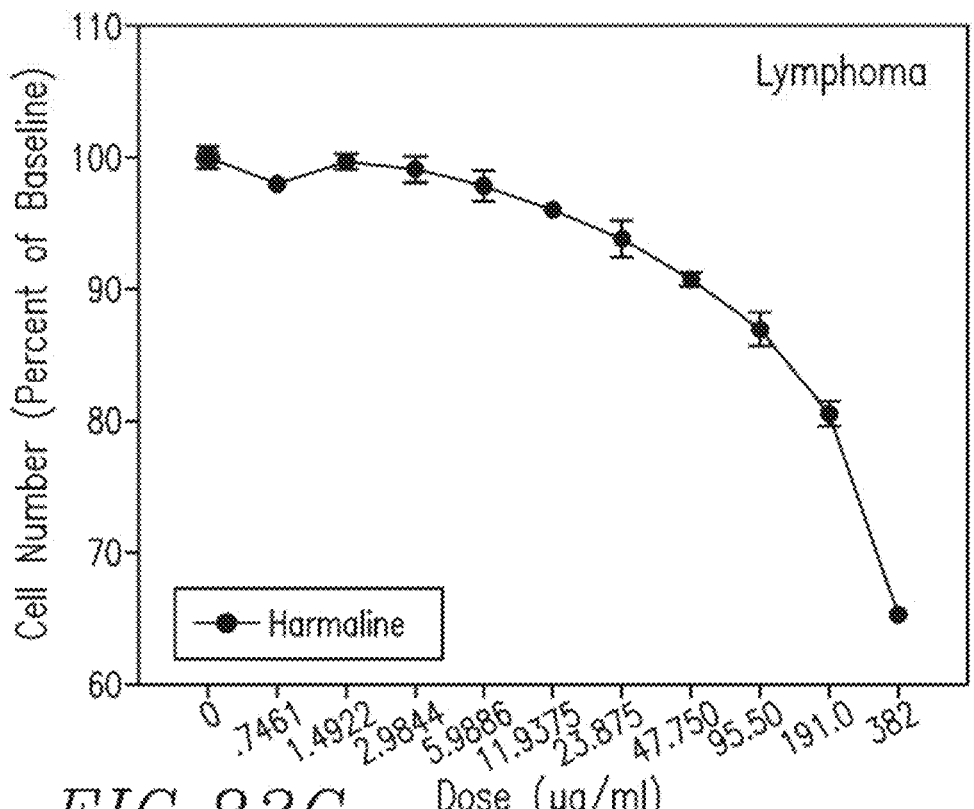
Figure 83D:
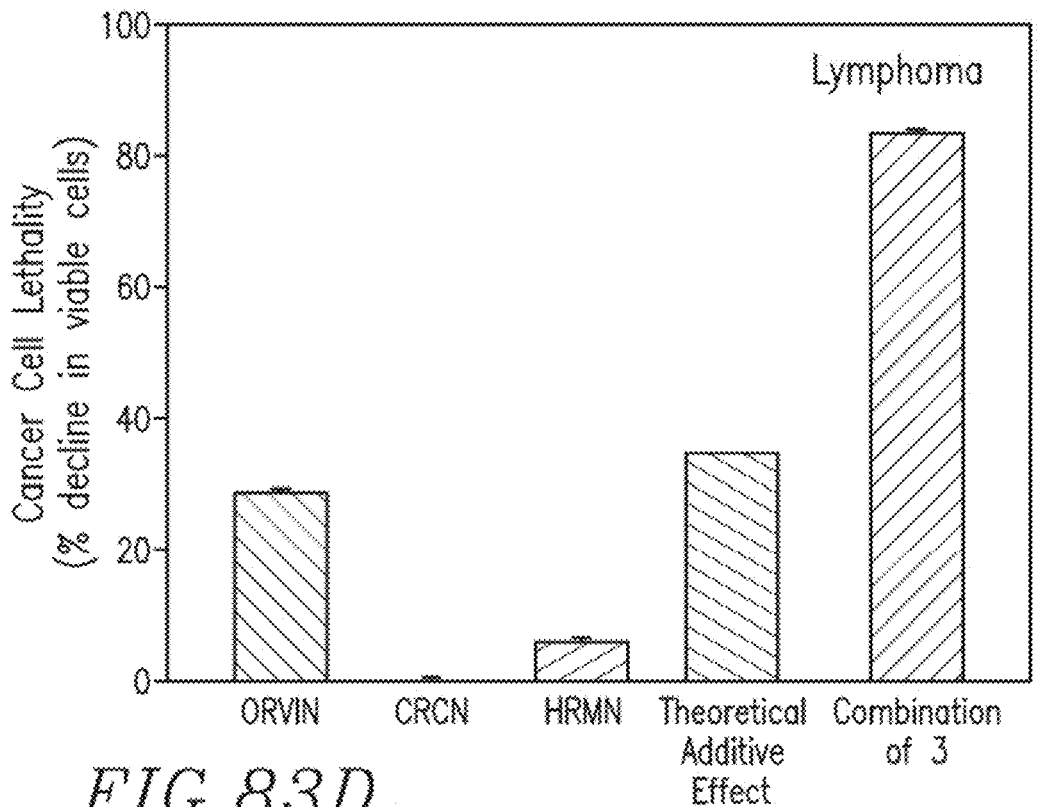
Figure 83E:
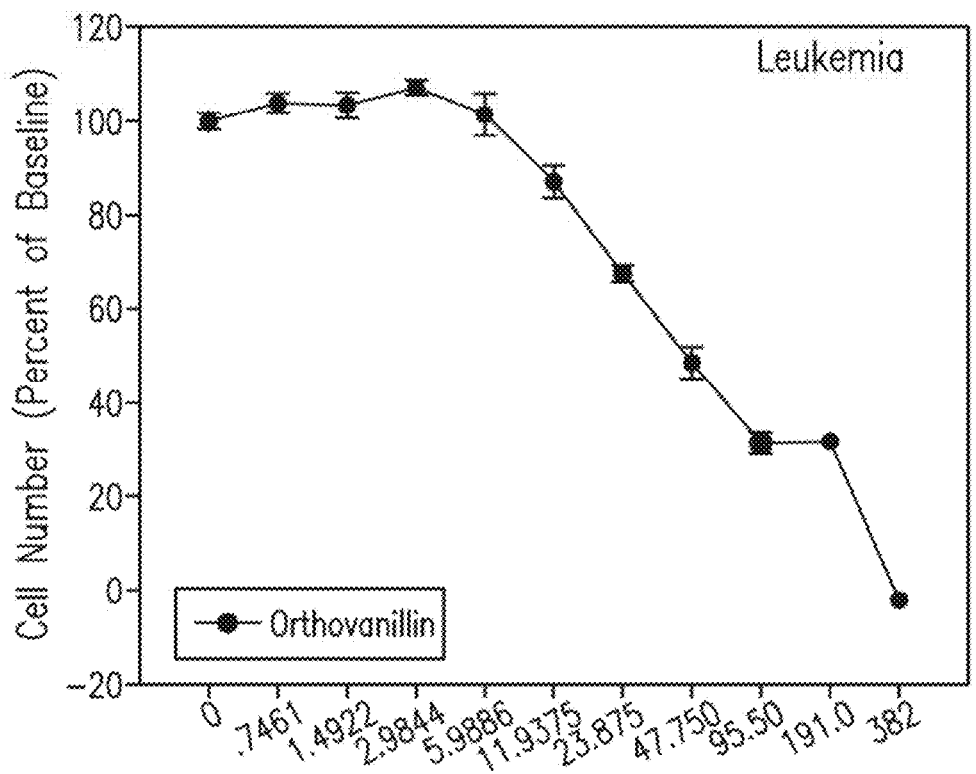
Figure 83F:
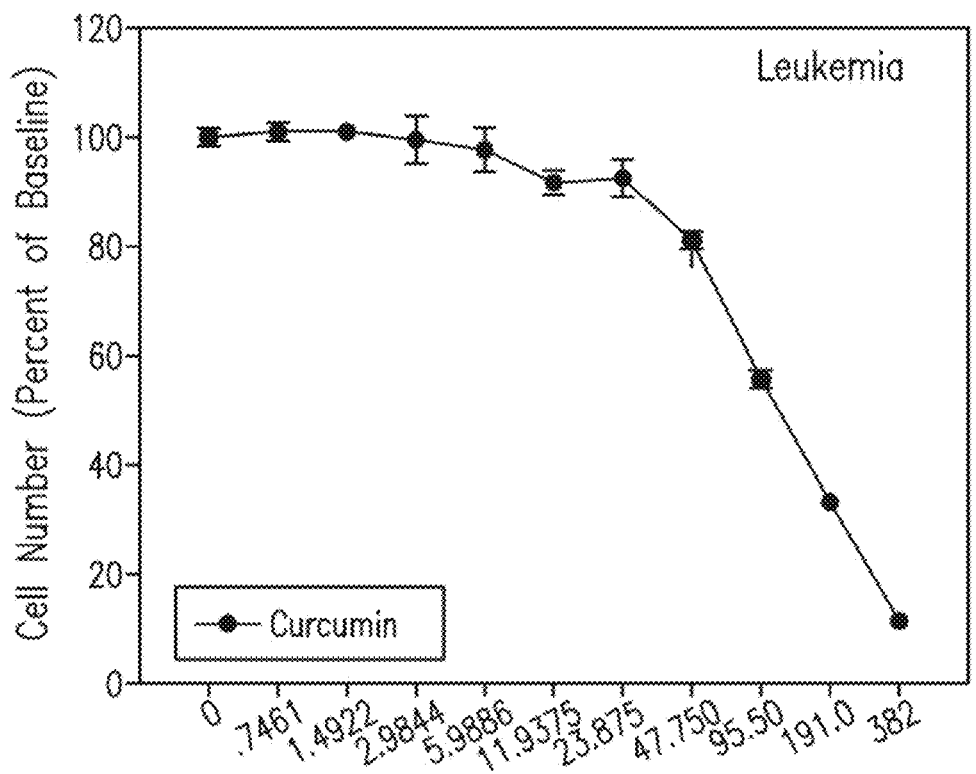
Figure 83G:
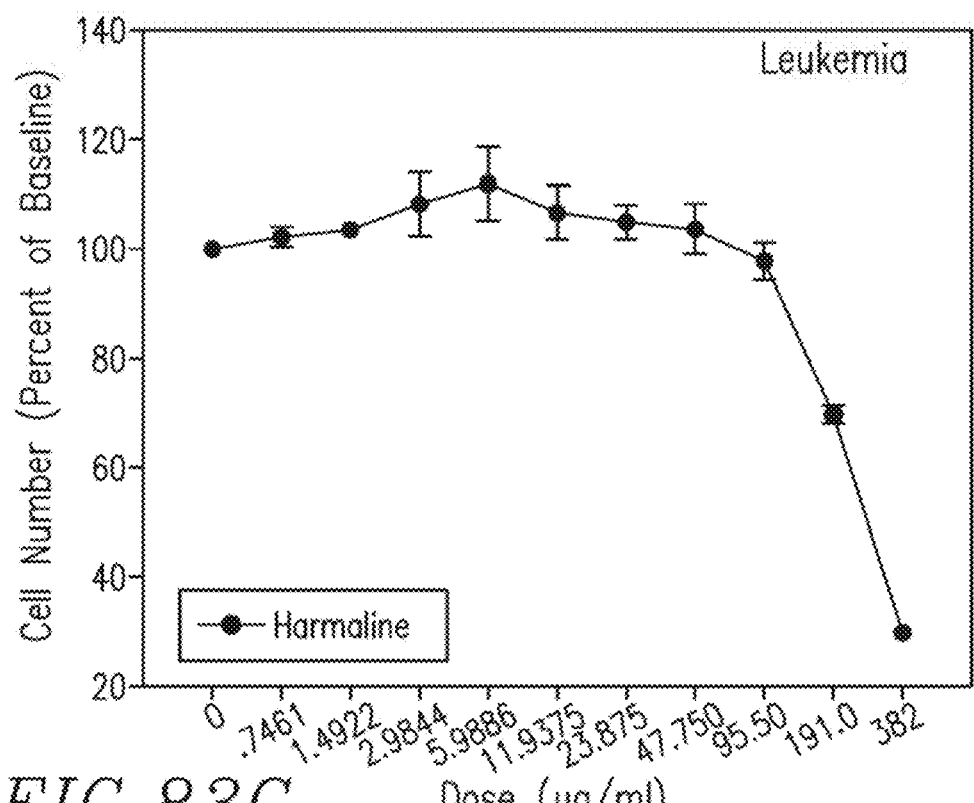
Figure 83H:
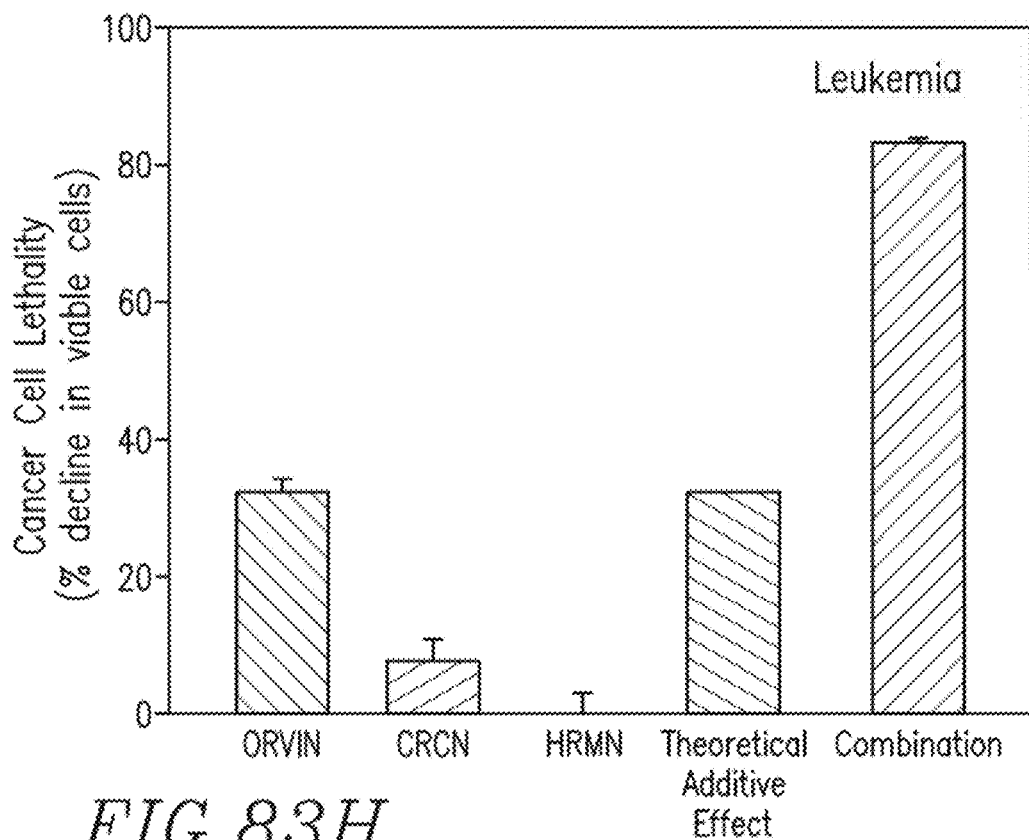
Figure 83I:
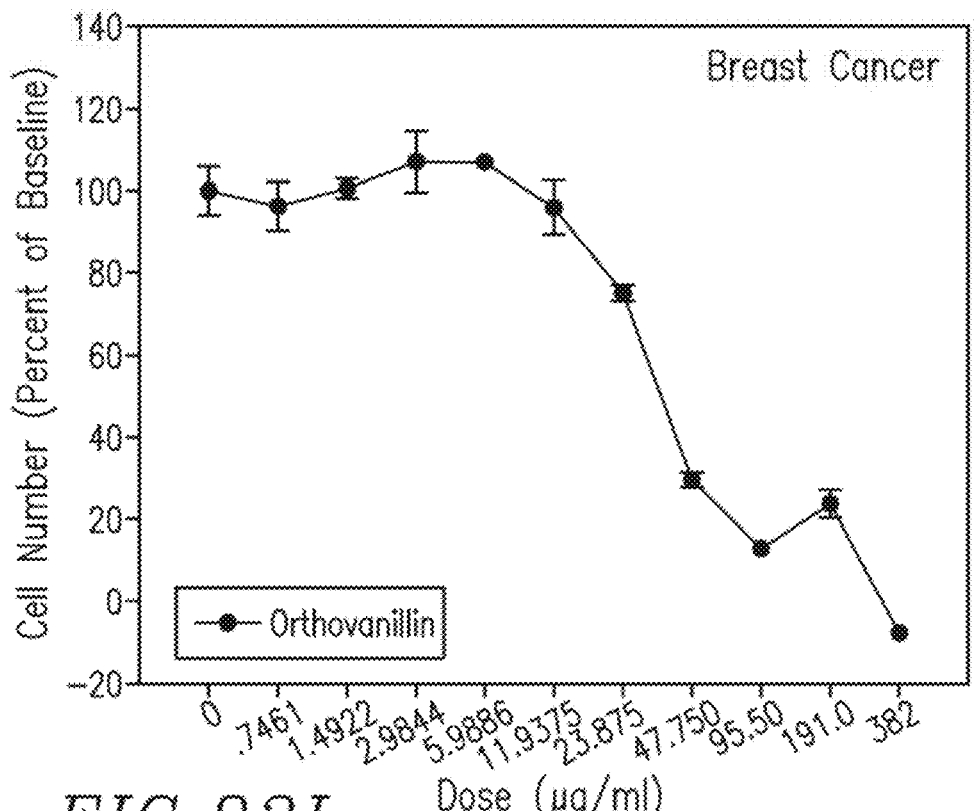
Figure 83J:
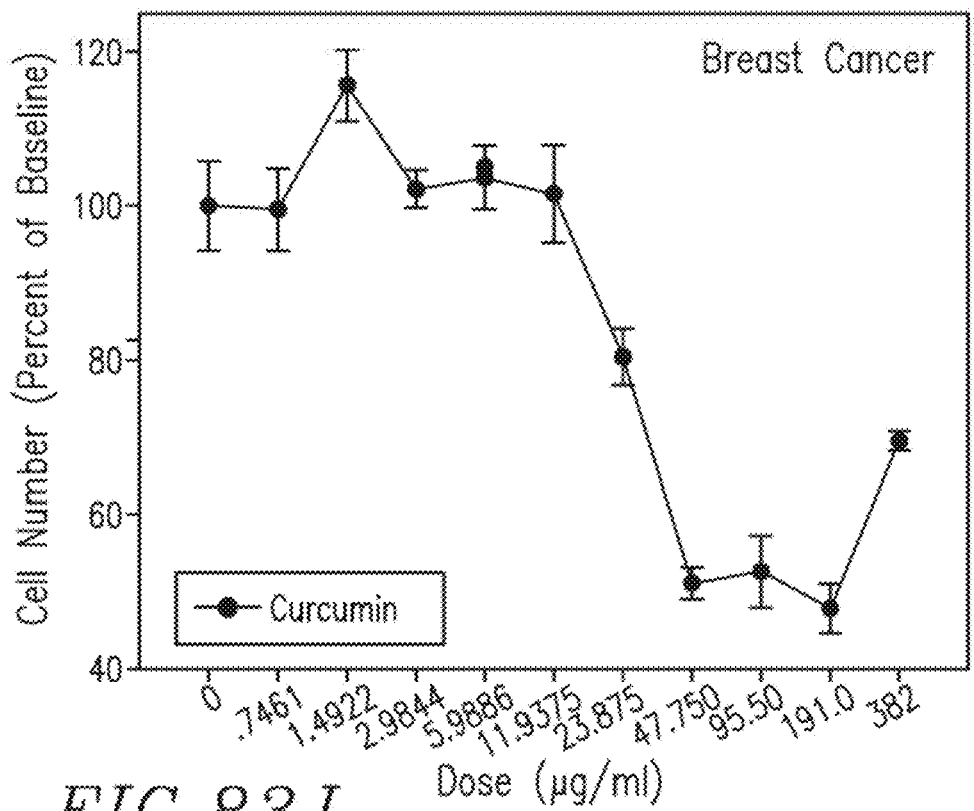
Figure 83K:
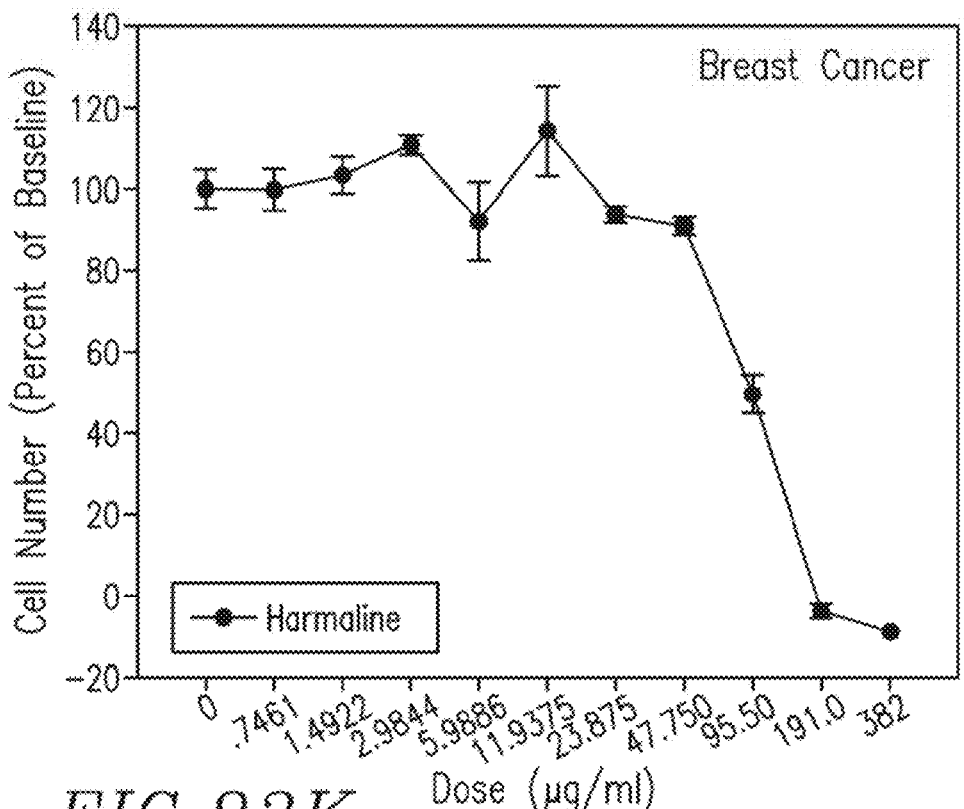
Figure 83L:
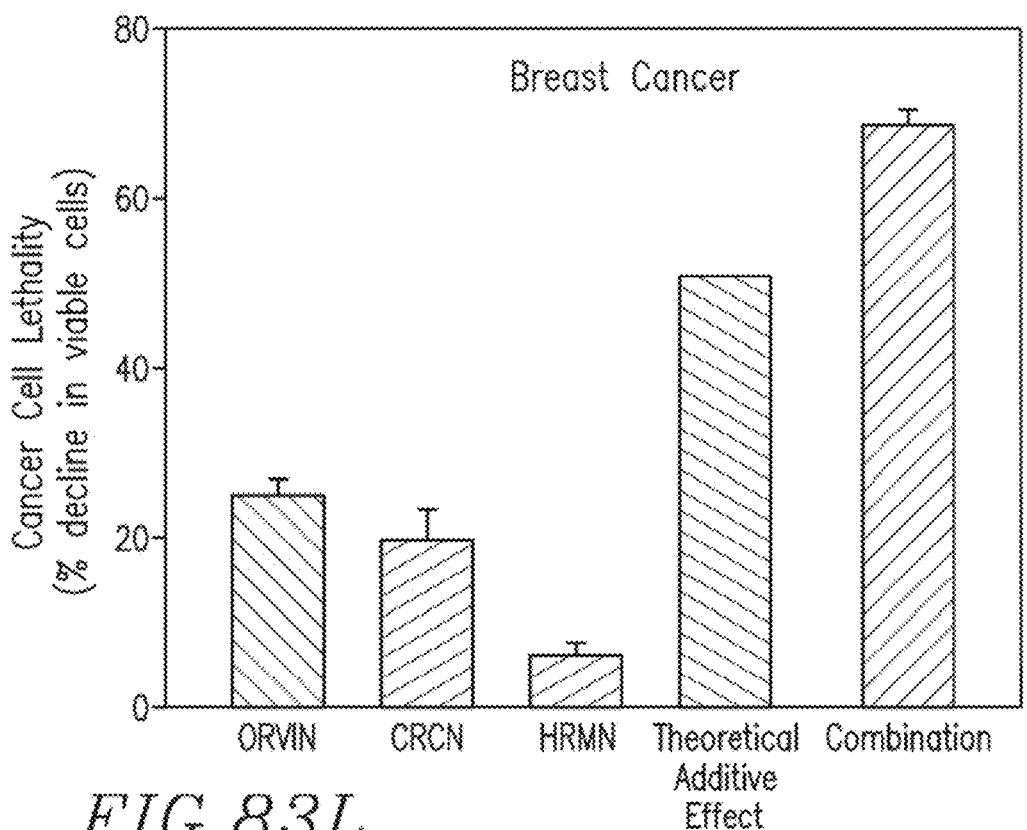
Figure 84A:
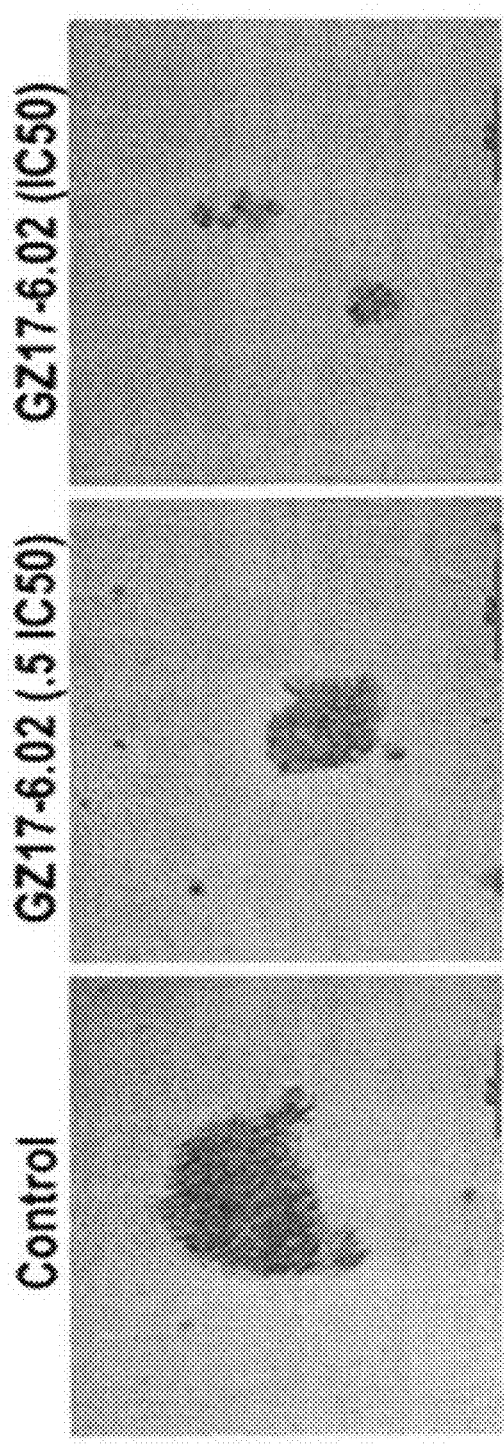
Figure 84C:
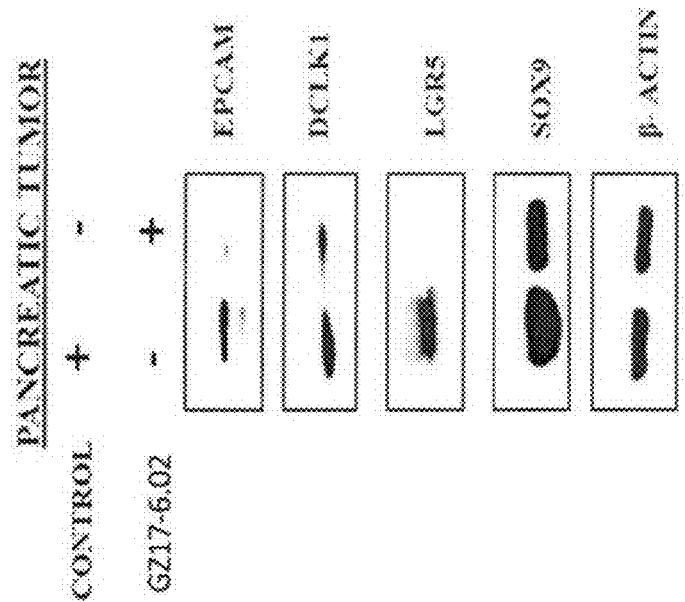
Figure 84B:
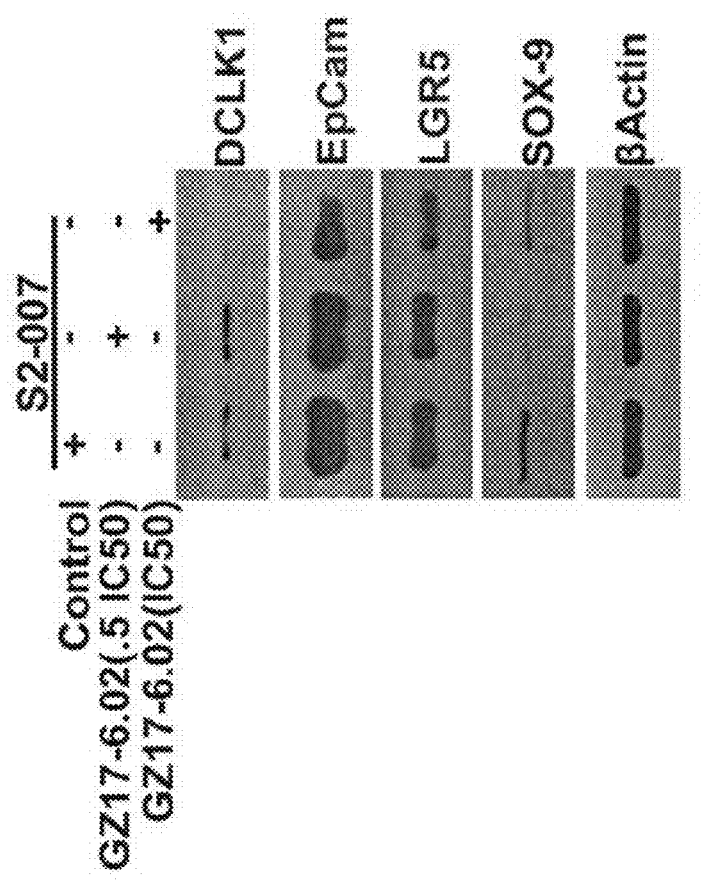
Figure 84D:
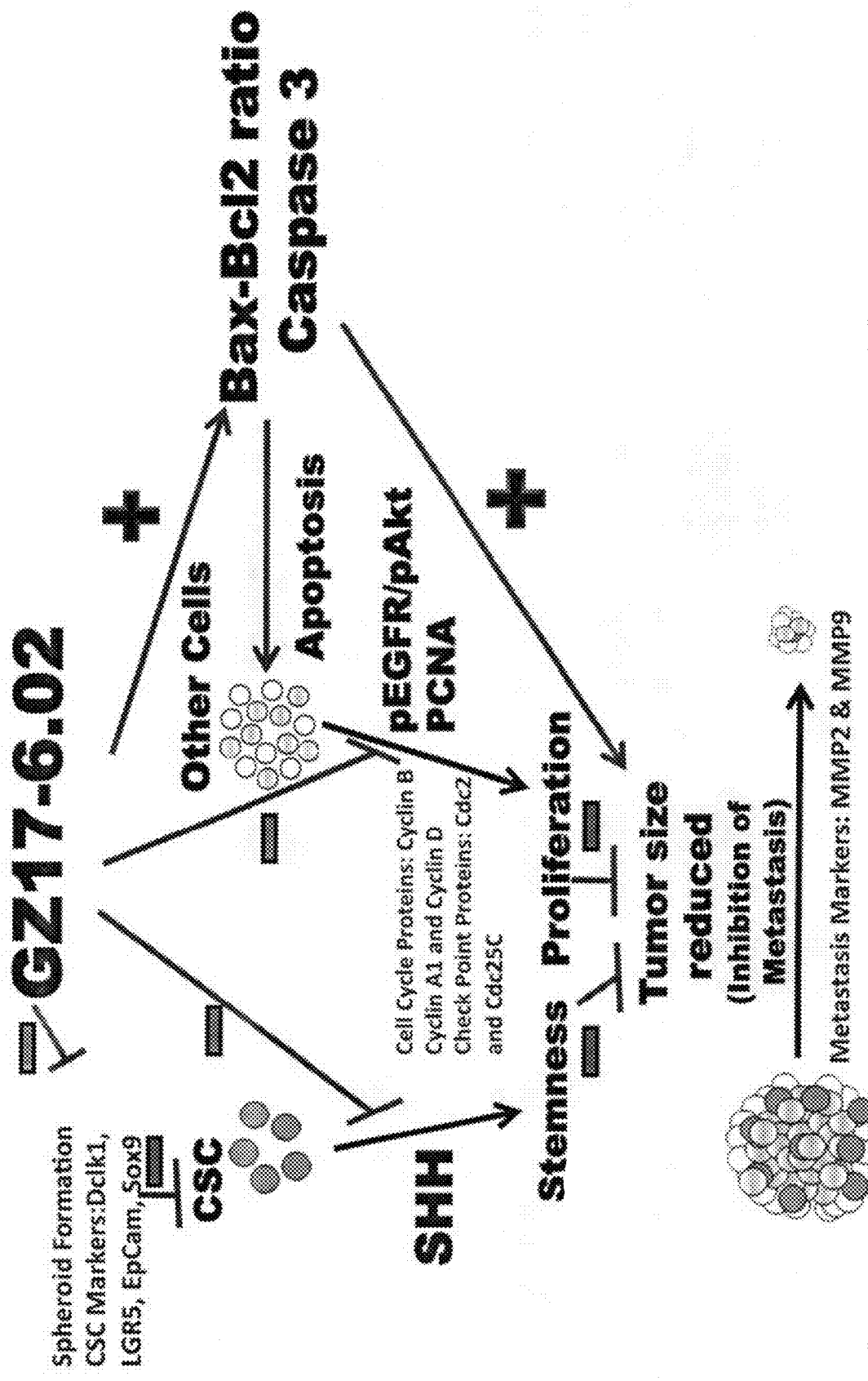

FIG. 33G is a graph of cell number versus dosage amounts of GZ17-8.15, illustrating the effect thereof in inducing the death of lymphoma;

FIG. 34A is a graph of cell number versus dosage amounts of GZ17-8.16, illustrating the effect thereof in inducing the death of ovarian cancer;

FIG. 34B is a graph of cell number versus dosage amounts of GZ17-8.16, illustrating the effect thereof in inducing the death of lung cancer;

FIG. 34C is a graph of cell number versus dosage amounts of GZ17-8.16, illustrating the effect thereof in inducing the death of prostate cancer;

FIG. 34D is a graph of cell number versus dosage amounts of GZ17-8.16, illustrating the effect thereof in inducing the death of head and neck cancer;

FIG. 34E is a graph of cell number versus dosage amounts of GZ17-8.16, illustrating the effect thereof in inducing the death of breast cancer;

FIG. 34F is a graph of cell number versus dosage amounts of GZ17-8.16, illustrating the effect thereof in inducing the death of leukemia;

FIG. 34G is a graph of cell number versus dosage amounts of GZ17-8.16, illustrating the effect thereof in inducing the death of lymphoma;

FIG. 35A is a graph of cell number versus dosage amounts of GZ17-8.17, illustrating the effect thereof in inducing the death of ovarian cancer;

FIG. 35B is a graph of cell number versus dosage amounts of GZ17-8.17, illustrating the effect thereof in inducing the death of lung cancer;

FIG. 35C is a graph of cell number versus dosage amounts of GZ17-8.17, illustrating the effect thereof in inducing the death of prostate cancer;

FIG. 35D is a graph of cell number versus dosage amounts of GZ17-8.17, illustrating the effect thereof in inducing the death of head and neck cancer;

FIG. 35E is a graph of cell number versus dosage amounts of GZ17-8.17, illustrating the effect thereof in inducing the death of breast cancer;

FIG. 35F is a graph of cell number versus dosage amounts of GZ17-8.17, illustrating the effect thereof in inducing the death of leukemia;

FIG. 35G is a graph of cell number versus dosage amounts of GZ17-8.17, illustrating the effect thereof in inducing the death of lymphoma;

FIG. 36A is a graph of cell number versus dosage amounts of GZ17-8.18, illustrating the effect thereof in inducing the death of ovarian cancer;

FIG. 36B is a graph of cell number versus dosage amounts of GZ17-8.18, illustrating the effect thereof in inducing the death of lung cancer;

FIG. 36C is a graph of cell number versus dosage amounts of GZ17-8.18, illustrating the effect thereof in inducing the death of prostate cancer;

FIG. 36D is a graph of cell number versus dosage amounts of GZ17-8.18, illustrating the effect thereof in inducing the death of head and neck cancer;

FIG. 36E is a graph of cell number versus dosage amounts of GZ17-8.18, illustrating the effect thereof in inducing the death of breast cancer;

FIG. 36F is a graph of cell number versus dosage amounts of GZ17-8.18, illustrating the effect thereof in inducing the death of leukemia;

FIG. 36G is a graph of cell number versus dosage amounts of GZ17-8.18, illustrating the effect thereof in inducing the death of lymphoma;

FIG. 37A is a graph of cell number versus dosage amounts of GZ17-8.19, illustrating the effect thereof in inducing the death of ovarian cancer;

FIG. 37B is a graph of cell number versus dosage amounts of GZ17-8.19, illustrating the effect thereof in inducing the death of lung cancer;

FIG. 37C is a graph of cell number versus dosage amounts of GZ17-8.19, illustrating the effect thereof in inducing the death of prostate cancer;

FIG. 37D is a graph of cell number versus dosage amounts of GZ17-8.19, illustrating the effect thereof in inducing the death of head and neck cancer;

FIG. 37E is a graph of cell number versus dosage amounts of GZ17-8.19, illustrating the effect thereof in inducing the death of breast cancer;

FIG. 37F is a graph of cell number versus dosage amounts of GZ17-8.19, illustrating the effect thereof in inducing the death of leukemia;

FIG. 37G is a graph of cell number versus dosage amounts of GZ17-8.19, illustrating the effect thereof in inducing the death of lymphoma;

FIG. 38A is a graph of cell number versus dosage amounts of GZ17-8.20, illustrating the effect thereof in inducing the death of ovarian cancer;

FIG. 38B is a graph of cell number versus dosage amounts of GZ17-8.20, illustrating the effect thereof in inducing the death of lung cancer;

FIG. 38C is a graph of cell number versus dosage amounts of GZ17-8.20, illustrating the effect thereof in inducing the death of prostate cancer;

FIG. 38D is a graph of cell number versus dosage amounts of GZ17-8.20, illustrating the effect thereof in inducing the death of head and neck cancer;

FIG. 38E is a graph of cell number versus dosage amounts of GZ17-8.20, illustrating the effect thereof in inducing the death of breast cancer;

FIG. 38F is a graph of cell number versus dosage amounts of GZ17-8.20, illustrating the effect thereof in inducing the death of leukemia;

FIG. 38G is a graph of cell number versus dosage amounts of GZ17-8.20, illustrating the effect thereof in inducing the death of lymphoma;

FIG. 39A is a graph of cell number versus dosage amounts of GZ17-8.21, illustrating the effect thereof in inducing the death of ovarian cancer;

FIG. 39B is a graph of cell number versus dosage amounts of GZ17-8.21, illustrating the effect thereof in inducing the death of lung cancer;

FIG. 39C is a graph of cell number versus dosage amounts of GZ17-8.21, illustrating the effect thereof in inducing the death of prostate cancer;

FIG. 39D is a graph of cell number versus dosage amounts of GZ17-8.21, illustrating the effect thereof in inducing the death of head and neck cancer;

FIG. 39E is a graph of cell number versus dosage amounts of GZ17-8.21, illustrating the effect thereof in inducing the death of breast cancer;

FIG. 39F is a graph of cell number versus dosage amounts of GZ17-8.21, illustrating the effect thereof in inducing the death of leukemia;

FIG. 39G is a graph of cell number versus dosage amounts of GZ17-8.21, illustrating the effect thereof in inducing the death of lymphoma;

FIG. 40A is a graph of cell number versus dosage amounts of GZ17-8.22, illustrating the effect thereof in inducing the death of ovarian cancer;

FIG. 40B is a graph of cell number versus dosage amounts of GZ17-8.22, illustrating the effect thereof in inducing the death of lung cancer;

FIG. 40C is a graph of cell number versus dosage amounts of GZ17-8.22, illustrating the effect thereof in inducing the death of prostate cancer;

FIG. 40D is a graph of cell number versus dosage amounts of GZ17-8.22, illustrating the effect thereof in inducing the death of head and neck cancer;

FIG. 40E is a graph of cell number versus dosage amounts of GZ17-8.22, illustrating the effect thereof in inducing the death of breast cancer;

FIG. 40F is a graph of cell number versus dosage amounts of GZ17-8.22, illustrating the effect thereof in inducing the death of leukemia;

FIG. 40G is a graph of cell number versus dosage amounts of GZ17-8.22, illustrating the effect thereof in inducing the death of lymphoma;

FIG. 41A is a graph of cell number versus dosage amounts of GZ17-8.23, illustrating the effect thereof in inducing the death of ovarian cancer;

FIG. 41B is a graph of cell number versus dosage amounts of GZ17-8.23, illustrating the effect thereof in inducing the death of lung cancer;

FIG. 41C is a graph of cell number versus dosage amounts of GZ17-8.23, illustrating the effect thereof in inducing the death of prostate cancer;

FIG. 41D is a graph of cell number versus dosage amounts of GZ17-8.23, illustrating the effect thereof in inducing the death of head and neck cancer;

FIG. 41E is a graph of cell number versus dosage amounts of GZ17-8.23, illustrating the effect thereof in inducing the death of breast cancer;

FIG. 41F is a graph of cell number versus dosage amounts of GZ17-8.23, illustrating the effect thereof in inducing the death of leukemia;

FIG. 41G is a graph of cell number versus dosage amounts of GZ17-8.23, illustrating the effect thereof in inducing the death of lymphoma;

FIG. 42A is a graph of cell number versus dosage amounts of GZ17-8.24, illustrating the effect thereof in inducing the death of ovarian cancer;

FIG. 42B is a graph of cell number versus dosage amounts of GZ17-8.24, illustrating the effect thereof in inducing the death of lung cancer;

FIG. 42C is a graph of cell number versus dosage amounts of GZ17-8.24, illustrating the effect thereof in inducing the death of prostate cancer;

FIG. 42D is a graph of cell number versus dosage amounts of GZ17-8.24, illustrating the effect thereof in inducing the death of head and neck cancer;

FIG. 42E is a graph of cell number versus dosage amounts of GZ17-8.24, illustrating the effect thereof in inducing the death of breast cancer;

FIG. 42F is a graph of cell number versus dosage amounts of GZ17-8.24, illustrating the effect thereof in inducing the death of leukemia;

FIG. 42G is a graph of cell number versus dosage amounts of GZ17-8.24, illustrating the effect thereof in inducing the death of lymphoma;

FIG. 43A is a graph of cell number versus dosage amounts of GZ17-8.25, illustrating the effect thereof in inducing the death of ovarian cancer;

FIG. 43B is a graph of cell number versus dosage amounts of GZ17-8.25, illustrating the effect thereof in inducing the death of lung cancer;

FIG. 43C is a graph of cell number versus dosage amounts of GZ17-8.25, illustrating the effect thereof in inducing the death of prostate cancer;

FIG. 43D is a graph of cell number versus dosage amounts of GZ17-8.25, illustrating the effect thereof in inducing the death of head and neck cancer;

FIG. 43E is a graph of cell number versus dosage amounts of GZ17-8.25, illustrating the effect thereof in inducing the death of breast cancer;

FIG. 43F is a graph of cell number versus dosage amounts of GZ17-8.25, illustrating the effect thereof in inducing the death of leukemia;

FIG. 43G is a graph of cell number versus dosage amounts of GZ17-8.25, illustrating the effect thereof in inducing the death of lymphoma;

FIG. 44A is a graph of cell number versus dosage amounts of GZ17-8.26, illustrating the effect thereof in inducing the death of ovarian cancer;

FIG. 44B is a graph of cell number versus dosage amounts of GZ17-8.26, illustrating the effect thereof in inducing the death of lung cancer;

FIG. 44C is a graph of cell number versus dosage amounts of GZ17-8.26, illustrating the effect thereof in inducing the death of prostate cancer;

FIG. 44D is a graph of cell number versus dosage amounts of GZ17-8.26, illustrating the effect thereof in inducing the death of head and neck cancer;

FIG. 44E is a graph of cell number versus dosage amounts of GZ17-8.26, illustrating the effect thereof in inducing the death of breast cancer;

FIG. 44F is a graph of cell number versus dosage amounts of GZ17-8.26, illustrating the effect thereof in inducing the death of leukemia;

FIG. 44G is a graph of cell number versus dosage amounts of GZ17-8.26, illustrating the effect thereof in inducing the death of lymphoma;

FIG. 45A is a graph of cell number versus dosage amounts of GZ17-8.27, illustrating the effect thereof in inducing the death of ovarian cancer;

FIG. 45B is a graph of cell number versus dosage amounts of GZ17-8.27, illustrating the effect thereof in inducing the death of lung cancer;

FIG. 45C is a graph of cell number versus dosage amounts of GZ17-8.27, illustrating the effect thereof in inducing the death of prostate cancer;

FIG. 45D is a graph of cell number versus dosage amounts of GZ17-8.27, illustrating the effect thereof in inducing the death of head and neck cancer;

FIG. 45E is a graph of cell number versus dosage amounts of GZ17-8.27, illustrating the effect thereof in inducing the death of breast cancer;

FIG. 45F is a graph of cell number versus dosage amounts of GZ17-8.27, illustrating the effect thereof in inducing the death of leukemia;

FIG. 45G is a graph of cell number versus dosage amounts of GZ17-8.27, illustrating the effect thereof in inducing the death of lymphoma;

FIG. 46A is a graph of cell number versus dosage amounts of GZ17-8.28, illustrating the effect thereof in inducing the death of ovarian cancer;

FIG. 46B is a graph of cell number versus dosage amounts of GZ17-8.28, illustrating the effect thereof in inducing the death of lung cancer;

FIG. 46C is a graph of cell number versus dosage amounts of GZ17-8.28, illustrating the effect thereof in inducing the death of prostate cancer;

FIG. 46D is a graph of cell number versus dosage amounts of GZ17-8.28, illustrating the effect thereof in inducing the death of head and neck cancer;

FIG. 46E is a graph of cell number versus dosage amounts of GZ17-8.28, illustrating the effect thereof in inducing the death of breast cancer;

FIG. 46F is a graph of cell number versus dosage amounts of GZ17-8.28, illustrating the effect thereof in inducing the death of leukemia;

FIG. 46G is a graph of cell number versus dosage amounts of GZ17-8.28, illustrating the effect thereof in inducing the death of lymphoma;

FIG. 47A is a graph of cell number versus dosage amounts of GZ17-8.29, illustrating the effect thereof in inducing the death of ovarian cancer;

FIG. 47B is a graph of cell number versus dosage amounts of GZ17-8.29, illustrating the effect thereof in inducing the death of lung cancer;

FIG. 47C is a graph of cell number versus dosage amounts of GZ17-8.29, illustrating the effect thereof in inducing the death of prostate cancer;

FIG. 47D is a graph of cell number versus dosage amounts of GZ17-8.29, illustrating the effect thereof in inducing the death of head and neck cancer;

FIG. 47E is a graph of cell number versus dosage amounts of GZ17-8.29, illustrating the effect thereof in inducing the death of breast cancer;

FIG. 47F is a graph of cell number versus dosage amounts of GZ17-8.29, illustrating the effect thereof in inducing the death of leukemia;

FIG. 47G is a graph of cell number versus dosage amounts of GZ17-8.29, illustrating the effect thereof in inducing the death of lymphoma;

FIG. 48A is a graph of cell number versus dosage amounts of GZ17-8.30, illustrating the effect thereof in inducing the death of ovarian cancer;

FIG. 48B is a graph of cell number versus dosage amounts of GZ17-8.30, illustrating the effect thereof in inducing the death of lung cancer;

FIG. 48C is a graph of cell number versus dosage amounts of GZ17-8.30, illustrating the effect thereof in inducing the death of prostate cancer;

FIG. 48D is a graph of cell number versus dosage amounts of GZ17-8.30, illustrating the effect thereof in inducing the death of head and neck cancer;

FIG. 48E is a graph of cell number versus dosage amounts of GZ17-8.30, illustrating the effect thereof in inducing the death of breast cancer;

FIG. 48F is a graph of cell number versus dosage amounts of GZ17-8.30, illustrating the effect thereof in inducing the death of leukemia;

FIG. 48G is a graph of cell number versus dosage amounts of GZ17-8.30, illustrating the effect thereof in inducing the death of lymphoma;

FIG. 49A is a graph of cell number versus dosage amounts of GZ17-8.31, illustrating the effect thereof in inducing the death of ovarian cancer;

FIG. 49B is a graph of cell number versus dosage amounts of GZ17-8.31, illustrating the effect thereof in inducing the death of lung cancer;

FIG. 49C is a graph of cell number versus dosage amounts of GZ17-8.31, illustrating the effect thereof in inducing the death of lymphoma;

FIG. 49D is a graph of cell number versus dosage amounts of GZ17-8.31, illustrating the effect thereof in inducing the death of leukemia;

FIG. 50A is a graph of cell number versus dosage amounts of GZ17-8.32, illustrating the effect thereof in inducing the death of ovarian cancer;

FIG. 50B is a graph of cell number versus dosage amounts of GZ17-8.32, illustrating the effect thereof in inducing the death of lung cancer;

FIG. 50C is a graph of cell number versus dosage amounts of GZ17-8.32, illustrating the effect thereof in inducing the death of lymphoma;

FIG. 50D is a graph of cell number versus dosage amounts of GZ17-8.32, illustrating the effect thereof in inducing the death of leukemia;

FIG. 51A is a graph of cell number versus dosage amounts of GZ17-8.33, illustrating the effect thereof in inducing the death of ovarian cancer;

FIG. 51B is a graph of cell number versus dosage amounts of GZ17-8.33, illustrating the effect thereof in inducing the death of lung cancer;

FIG. 51C is a graph of cell number versus dosage amounts of GZ17-8.33, illustrating the effect thereof in inducing the death of lymphoma;

FIG. 51D is a graph of cell number versus dosage amounts of GZ17-8.33, illustrating the effect thereof in inducing the death of leukemia;

FIG. 52A is a graph of cell number versus dosage amounts of GZ17-8.34, illustrating the effect thereof in inducing the death of ovarian cancer;

FIG. 52B is a graph of cell number versus dosage amounts of GZ17-8.34, illustrating the effect thereof in inducing the death of lung cancer;

FIG. 52C is a graph of cell number versus dosage amounts of GZ17-8.34, illustrating the effect thereof in inducing the death of lymphoma;

FIG. 52D is a graph of cell number versus dosage amounts of GZ17-8.34, illustrating the effect thereof in inducing the death of leukemia;

FIG. 53A is a graph of cell number versus dosage amounts of GZ17-8.35, illustrating the effect thereof in inducing the death of ovarian cancer;

FIG. 53B is a graph of cell number versus dosage amounts of GZ17-8.35, illustrating the effect thereof in inducing the death of lung cancer;

FIG. 53C is a graph of cell number versus dosage amounts of GZ17-8.35, illustrating the effect thereof in inducing the death of lymphoma;

FIG. 53D is a graph of cell number versus dosage amounts of GZ17-8.35, illustrating the effect thereof in inducing the death of leukemia;

FIG. 54A is a graph of cell number versus dosage amounts of GZ17-8.36, illustrating the effect thereof in inducing the death of ovarian cancer;

FIG. 54B is a graph of cell number versus dosage amounts of GZ17-8.36, illustrating the effect thereof in inducing the death of lung cancer;

FIG. 54C is a graph of cell number versus dosage amounts of GZ17-8.36, illustrating the effect thereof in inducing the death of lymphoma;

FIG. 54D is a graph of cell number versus dosage amounts of GZ17-8.36, illustrating the effect thereof in inducing the death of leukemia;

FIG. 55A is a graph of cell number versus dosage amounts of GZ17-8.37, illustrating the effect thereof in inducing the death of ovarian cancer;

FIG. 55B is a graph of cell number versus dosage amounts of GZ17-8.37, illustrating the effect thereof in inducing the death of lung cancer;

FIG. 55C is a graph of cell number versus dosage amounts of GZ17-8.37, illustrating the effect thereof in inducing the death of lymphoma;

FIG. 55D is a graph of cell number versus dosage amounts of GZ17-8.37, illustrating the effect thereof in inducing the death of leukemia;

FIG. 56A is a graph of cell number versus dosage amounts of GZ17-8.38, illustrating the effect thereof in inducing the death of ovarian cancer;

FIG. 56B is a graph of cell number versus dosage amounts of GZ17-8.38, illustrating the effect thereof in inducing the death of lung cancer;

FIG. 56C is a graph of cell number versus dosage amounts of GZ17-8.38, illustrating the effect thereof in inducing the death of lymphoma;

FIG. 56D is a graph of cell number versus dosage amounts of GZ17-8.38, illustrating the effect thereof in inducing the death of leukemia;

FIG. 57A is a graph of cell number versus dosage amounts of GZ17-8.39, illustrating the effect thereof in inducing the death of ovarian cancer;

FIG. 57B is a graph of cell number versus dosage amounts of GZ17-8.39, illustrating the effect thereof in inducing the death of lung cancer;

FIG. 57C is a graph of cell number versus dosage amounts of GZ17-8.39, illustrating the effect thereof in inducing the death of lymphoma;

FIG. 57D is a graph of cell number versus dosage amounts of GZ17-8.39, illustrating the effect thereof in inducing the death of leukemia;

FIG. 58A is a graph of cell number versus dosage amounts of GZ17-8.40, illustrating the effect thereof in inducing the death of ovarian cancer;

FIG. 58B is a graph of cell number versus dosage amounts of GZ17-8.40, illustrating the effect thereof in inducing the death of lung cancer;

FIG. 58C is a graph of cell number versus dosage amounts of GZ17-8.40, illustrating the effect thereof in inducing the death of lymphoma;

FIG. 58D is a graph of cell number versus dosage amounts of GZ17-8.40, illustrating the effect thereof in inducing the death of leukemia;

FIG. 59A is a graph of cell number versus dosage amounts of GZ17-8.41, illustrating the effect thereof in inducing the death of ovarian cancer;

FIG. 59B is a graph of cell number versus dosage amounts of GZ17-8.41, illustrating the effect thereof in inducing the death of lung cancer;

FIG. 59C is a graph of cell number versus dosage amounts of GZ17-8.41, illustrating the effect thereof in inducing the death of lymphoma;

FIG. 59D is a graph of cell number versus dosage amounts of GZ17-8.41, illustrating the effect thereof in inducing the death of leukemia;

FIG. 60A is a graph of cell number versus dosage amounts of GZ17-8.42, illustrating the effect thereof in inducing the death of ovarian cancer;

FIG. 60B is a graph of cell number versus dosage amounts of GZ17-8.42, illustrating the effect thereof in inducing the death of lung cancer;

FIG. 60C is a graph of cell number versus dosage amounts of GZ17-8.42, illustrating the effect thereof in inducing the death of lymphoma;

FIG. 60D is a graph of cell number versus dosage amounts of GZ17-8.42, illustrating the effect thereof in inducing the death of leukemia;

FIG. 61A is a graph of cell number versus dosage amounts of GZ17-8.43, illustrating the effect thereof in inducing the death of ovarian cancer;

FIG. 61B is a graph of cell number versus dosage amounts of GZ17-8.43, illustrating the effect thereof in inducing the death of lung cancer;

FIG. 61C is a graph of cell number versus dosage amounts of GZ17-8.43, illustrating the effect thereof in inducing the death of lymphoma;

FIG. 61D is a graph of cell number versus dosage amounts of GZ17-8.43, illustrating the effect thereof in inducing the death of leukemia;

FIG. 62A is a graph of cell number versus dosage amounts of GZ17-8.44, illustrating the effect thereof in inducing the death of ovarian cancer;

FIG. 62B is a graph of cell number versus dosage amounts of GZ17-8.44, illustrating the effect thereof in inducing the death of lung cancer;

FIG. 62C is a graph of cell number versus dosage amounts of GZ17-8.44, illustrating the effect thereof in inducing the death of lymphoma;

FIG. 62D is a graph of cell number versus dosage amounts of GZ17-8.44, illustrating the effect thereof in inducing the death of leukemia;

FIG. 63A is a graph of cell number versus dosage amounts of GZ17-8.45, illustrating the effect thereof in inducing the death of ovarian cancer;

FIG. 63B is a graph of cell number versus dosage amounts of GZ17-8.45, illustrating the effect thereof in inducing the death of lung cancer;

FIG. 63C is a graph of cell number versus dosage amounts of GZ17-8.45, illustrating the effect thereof in inducing the death of lymphoma;

FIG. 63D is a graph of cell number versus dosage amounts of GZ17-8.45, illustrating the effect thereof in inducing the death of leukemia;

FIG. 64A is a graph of cell number versus dosage amounts of GZ17-8.46, illustrating the effect thereof in inducing the death of ovarian cancer;

FIG. 64B is a graph of cell number versus dosage amounts of GZ17-8.46, illustrating the effect thereof in inducing the death of lung cancer;

FIG. 64C is a graph of cell number versus dosage amounts of GZ17-8.46, illustrating the effect thereof in inducing the death of lymphoma;

FIG. 64D is a graph of cell number versus dosage amounts of GZ17-8.46, illustrating the effect thereof in inducing the death of leukemia;

FIG. 65A is a graph of cell number versus dosage amounts of GZ17-8.47, illustrating the effect thereof in inducing the death of ovarian cancer;

FIG. 65B is a graph of cell number versus dosage amounts of GZ17-8.47, illustrating the effect thereof in inducing the death of lung cancer;

FIG. 65C is a graph of cell number versus dosage amounts of GZ17-8.47, illustrating the effect thereof in inducing the death of lymphoma;

FIG. 65D is a graph of cell number versus dosage amounts of GZ17-8.47, illustrating the effect thereof in inducing the death of leukemia;

FIG. 66A is a graph of cell number versus dosage amounts of GZ17-8.48, illustrating the effect thereof in inducing the death of ovarian cancer;

FIG. 66B is a graph of cell number versus dosage amounts of GZ17-8.48, illustrating the effect thereof in inducing the death of lung cancer;

FIG. 66C is a graph of cell number versus dosage amounts of GZ17-8.48, illustrating the effect thereof in inducing the death of lymphoma;

FIG. 66D is a graph of cell number versus dosage amounts of GZ17-8.48, illustrating the effect thereof in inducing the death of leukemia;

FIG. 67A is a graph of cell number versus dosage amounts of GZ17-8.49, illustrating the effect thereof in inducing the death of ovarian cancer;

FIG. 67B is a graph of cell number versus dosage amounts of GZ17-8.49, illustrating the effect thereof in inducing the death of lung cancer;

FIG. 67C is a graph of cell number versus dosage amounts of GZ17-8.49, illustrating the effect thereof in inducing the death of lymphoma;

FIG. 67D is a graph of cell number versus dosage amounts of GZ17-8.49, illustrating the effect thereof in inducing the death of leukemia;

FIG. 68A is a graph of cell number versus dosage amounts of GZ17-8.50, illustrating the effect thereof in inducing the death of ovarian cancer;

FIG. 68B is a graph of cell number versus dosage amounts of GZ17-8.50, illustrating the effect thereof in inducing the death of lung cancer;

FIG. 68C is a graph of cell number versus dosage amounts of GZ17-8.50, illustrating the effect thereof in inducing the death of lymphoma;

FIG. 68D is a graph of cell number versus dosage amounts of GZ17-8.50, illustrating the effect thereof in inducing the death of leukemia;

FIG. 69A is a graph of cell number versus dosage amounts of GZ17-8.51, illustrating the effect thereof in inducing the death of ovarian cancer;

FIG. 69B is a graph of cell number versus dosage amounts of GZ17-8.51, illustrating the effect thereof in inducing the death of lung cancer;

FIG. 69C is a graph of cell number versus dosage amounts of GZ17-8.51, illustrating the effect thereof in inducing the death of lymphoma;

FIG. 69D is a graph of cell number versus dosage amounts of GZ17-8.51, illustrating the effect thereof in inducing the death of leukemia;

FIG. 70A is a graph of cell number versus dosage amounts of GZ17-8.52, illustrating the effect thereof in inducing the death of ovarian cancer;

FIG. 70B is a graph of cell number versus dosage amounts of GZ17-8.52, illustrating the effect thereof in inducing the death of lung cancer;

FIG. 70C is a graph of cell number versus dosage amounts of GZ17-8.52, illustrating the effect thereof in inducing the death of lymphoma;

FIG. 70D is a graph of cell number versus dosage amounts of GZ17-8.52, illustrating the effect thereof in inducing the death of leukemia;

FIG. 71A is a graph of cell number versus dosage amounts of GZ17-8.53, illustrating the effect thereof in inducing the death of ovarian cancer;

FIG. 71B is a graph of cell number versus dosage amounts of GZ17-8.53, illustrating the effect thereof in inducing the death of lung cancer;

FIG. 71C is a graph of cell number versus dosage amounts of GZ17-8.53, illustrating the effect thereof in inducing the death of lymphoma;

FIG. 71D is a graph of cell number versus dosage amounts of GZ17-8.53, illustrating the effect thereof in inducing the death of leukemia;

FIG. 72A is a graph of cell number versus dosage amounts of GZ17-8.54, illustrating the effect thereof in inducing the death of ovarian cancer;

FIG. 72B is a graph of cell number versus dosage amounts of GZ17-8.54, illustrating the effect thereof in inducing the death of lung cancer;

FIG. 72C is a graph of cell number versus dosage amounts of GZ17-8.54, illustrating the effect thereof in inducing the death of lymphoma;

FIG. 72D is a graph of cell number versus dosage amounts of GZ17-8.54, illustrating the effect thereof in inducing the death of leukemia;

FIG. 73A is a graph of cell number versus dosage amounts of GZ17-8.55, illustrating the effect thereof in inducing the death of ovarian cancer;

FIG. 73B is a graph of cell number versus dosage amounts of GZ17-8.55, illustrating the effect thereof in inducing the death of lung cancer;

FIG. 73C is a graph of cell number versus dosage amounts of GZ17-8.55, illustrating the effect thereof in inducing the death of lymphoma;

FIG. 73D is a graph of cell number versus dosage amounts of GZ17-8.55, illustrating the effect thereof in inducing the death of leukemia;

FIG. 74A is a graph of cell number versus dosage amounts of GZ17-8.56, illustrating the effect thereof in inducing the death of ovarian cancer;

FIG. 74B is a graph of cell number versus dosage amounts of GZ17-8.56, illustrating the effect thereof in inducing the death of lung cancer;

FIG. 74C is a graph of cell number versus dosage amounts of GZ17-8.56, illustrating the effect thereof in inducing the death of lymphoma;

FIG. 74D is a graph of cell number versus dosage amounts of GZ17-8.56, illustrating the effect thereof in inducing the death of leukemia;

FIG. 75A is a graph of cell number versus dosage amounts of GZ17-8.57, illustrating the effect thereof in inducing the death of ovarian cancer;

FIG. 75B is a graph of cell number versus dosage amounts of GZ17-8.57, illustrating the effect thereof in inducing the death of lung cancer;

FIG. 75C is a graph of cell number versus dosage amounts of GZ17-8.57, illustrating the effect thereof in inducing the death of lymphoma;

FIG. 75D is a graph of cell number versus dosage amounts of GZ17-8.57, illustrating the effect thereof in inducing the death of leukemia;

FIG. 76A is a graph of cell number versus dosage amounts of GZ17-8.58, illustrating the effect thereof in inducing the death of ovarian cancer;

FIG. 76B is a graph of cell number versus dosage amounts of GZ17-8.58, illustrating the effect thereof in inducing the death of lung cancer;

FIG. 76C is a graph of cell number versus dosage amounts of GZ17-8.58, illustrating the effect thereof in inducing the death of lymphoma;

FIG. 76D is a graph of cell number versus dosage amounts of GZ17-8.58, illustrating the effect thereof in inducing the death of leukemia;

FIG. 77A is a graph of cell number versus dosage amounts of GZ17-8.59, illustrating the effect thereof in inducing the death of ovarian cancer;

FIG. 77B is a graph of cell number versus dosage amounts of GZ17-8.59, illustrating the effect thereof in inducing the death of lung cancer;

FIG. 77C is a graph of cell number versus dosage amounts of GZ17-8.59, illustrating the effect thereof in inducing the death of lymphoma;

FIG. 77D is a graph of cell number versus dosage amounts of GZ17-8.59, illustrating the effect thereof in inducing the death of leukemia;

FIG. 78A is a graph of cell number versus dosage amounts of GZ17-8.60, illustrating the effect thereof in inducing the death of ovarian cancer;

FIG. 78B is a graph of cell number versus dosage amounts of GZ17-8.60, illustrating the effect thereof in inducing the death of lung cancer;

FIG. 78C is a graph of cell number versus dosage amounts of GZ17-8.60, illustrating the effect thereof in inducing the death of lymphoma;

FIG. 78D is a graph of cell number versus dosage amounts of GZ17-8.60, illustrating the effect thereof in inducing the death of leukemia;

FIG. 79A is a graph of cell number versus dosage amounts of GZ17-8.61, illustrating the effect thereof in inducing the death of ovarian cancer;

FIG. 79B is a graph of cell number versus dosage amounts of GZ17-8.61, illustrating the effect thereof in inducing the death of lung cancer;

FIG. 79C is a graph of cell number versus dosage amounts of GZ17-8.61, illustrating the effect thereof in inducing the death of lymphoma;

FIG. 79D is a graph of cell number versus dosage amounts of GZ17-8.61, illustrating the effect thereof in inducing the death of leukemia;

FIG. 80A is a graph of cell number versus dosage amounts of GZ17-10.04, illustrating the effect thereof in inducing the death of ovarian cancer;

FIG. 80B is a graph of cell number versus dosage amounts of GZ17-10.05, illustrating the effect thereof in inducing the death of ovarian cancer;

FIG. 80C is a graph of cell number versus dosage amounts of GZ17-10.06, illustrating the effect thereof in inducing the death of ovarian cancer;

FIG. 80D is a graph of cell number versus dosage amounts of GZ17-10.04, illustrating the effect thereof in inducing the death of lymphoma;

FIG. 80E is a graph of cell number versus dosage amounts of GZ17-10.05, illustrating the effect thereof in inducing the death of lymphoma;

FIG. 80F is a graph of cell number versus dosage amounts of GZ17-10.06, illustrating the effect thereof in inducing the death of lymphoma;

FIG. 80G is a comparative bar graph illustrating the comparative lymphoma cell-killing effect of the individual components, GZ17-10.04-10.06, versus the theoretical additive effect of these components, and the actual effect thereof, demonstrating the synergism of the three-component composition;

FIG. 80H is a comparative bar graph illustrating the comparative lymphoma cell-killing effect of the individual components, GZ17-10.04 and 10.06, versus the theoretical additive effect of these components, and the actual effect thereof, demonstrating the synergism of the three-component composition;

FIG. 80I is a graph of cell number versus dosage amounts of GZ17-10.04, illustrating the effect thereof in inducing the death of leukemia;

FIG. 80J is a graph of cell number versus dosage amounts of GZ17-10.05, illustrating the effect thereof in inducing the death of leukemia;

FIG. 80K is a graph of cell number versus dosage amounts of GZ17-10.06, illustrating the effect thereof in inducing the death of leukemia;

FIG. 80L is a comparative bar graph illustrating the comparative leukemia cell-killing effect of the individual components, GZ17-10.04-10.06, versus the theoretical additive effect of these components, and the actual effect thereof, demonstrating the synergism of the three-component composition;

FIG. 80M is a comparative bar graph illustrating the comparative leukemia cell-killing effect of the individual components, GZ17-10.04 and 10.06, versus the theoretical additive effect of these components, and the actual effect thereof, demonstrating the synergism of the three-component composition;

FIG. 80N is a graph of cell number versus dosage amounts of GZ17-10.04, illustrating the effect thereof in inducing the death of breast cancer;

FIG. 80O is a graph of cell number versus dosage amounts of GZ17-10.05, illustrating the effect thereof in inducing the death of breast cancer;

FIG. 80P is a graph of cell number versus dosage amounts of GZ17-10.06, illustrating the effect thereof in inducing the death of breast cancer;

FIG. 80Q is a comparative bar graph illustrating the comparative breast cancer cell-killing effect of the individual components, GZ17-10.04-10.06, versus the theoretical additive effect of these components, and the actual effect thereof, demonstrating the synergism of the three-component composition;

FIG. 80R is a comparative bar graph illustrating the comparative breast cancer cell-killing effect of the individual components, GZ17-10.04 and 10.06, versus the theoretical additive effect of these components, and the actual effect thereof, demonstrating the synergism of the three-component composition;

FIG. 81A is a graph of cell number versus dosage amounts of GZ17-08.512, illustrating the effect thereof in inducing the death of ovarian cancer;

FIG. 81B is a graph of cell number versus dosage amounts of GZ17-08.512, illustrating the effect thereof in inducing the death of lymphoma;

FIG. 81C is a graph of cell number versus dosage amounts of GZ17-08.512, illustrating the effect thereof in inducing the death of head and neck cancer;

FIG. 81D is a graph of cell number versus dosage amounts of GZ17-08.513, illustrating the effect thereof in inducing the death of ovarian cancer;

FIG. 81E is a graph of cell number versus dosage amounts of GZ17-08.513, illustrating the effect thereof in inducing the death of lymphoma;

FIG. 81F is a graph of cell number versus dosage amounts of GZ17-08.513, illustrating the effect thereof in inducing the death of head and neck cancer;

FIG. 81G is a graph of cell number versus dosage amounts of GZ17-08.514, illustrating the effect thereof in inducing the death of ovarian cancer;

FIG. 81H is a graph of cell number versus dosage amounts of GZ17-08.514, illustrating the effect thereof in inducing the death of lymphoma;

FIG. 81I is a graph of cell number versus dosage amounts of GZ17-08.514, illustrating the effect thereof in inducing the death of head and neck cancer;

FIG. 81J is a graph of cell number versus dosage amounts of GZ17-08.515, illustrating the effect thereof in inducing the death of ovarian cancer;

FIG. 81K is a graph of cell number versus dosage amounts of GZ17-08.515, illustrating the effect thereof in inducing the death of lymphoma;

FIG. 81L is a graph of cell number versus dosage amounts of GZ17-08.515, illustrating the effect thereof in inducing the death of head and neck cancer;

FIG. 81M is a graph of cell number versus dosage amounts of GZ17-08.516, illustrating the effect thereof in inducing the death of ovarian cancer;

FIG. 81N is a graph of cell number versus dosage amounts of GZ17-08.516, illustrating the effect thereof in inducing the death of lymphoma;

FIG. 81O is a graph of cell number versus dosage amounts of GZ17-08.516, illustrating the effect thereof in inducing the death of head and neck cancer;

FIG. 81P is a graph of cell number versus dosage amounts of GZ17-08.517, illustrating the effect thereof in inducing the death of ovarian cancer;

FIG. 81Q is a graph of cell number versus dosage amounts of GZ17-08.517, illustrating the effect thereof in inducing the death of lymphoma;

FIG. 81R is a graph of cell number versus dosage amounts of GZ17-08.517, illustrating the effect thereof in inducing the death of head and neck cancer;

FIG. 81S is a graph of cell number versus dosage amounts of GZ17-08.518, illustrating the effect thereof in inducing the death of ovarian cancer;

FIG. 81T is a graph of cell number versus dosage amounts of GZ17-08.518, illustrating the effect thereof in inducing the death of lymphoma;

FIG. 81U is a graph of cell number versus dosage amounts of GZ17-08.518, illustrating the effect thereof in inducing the death of head and neck cancer;

FIG. 81V is a graph of cell number versus dosage amounts of GZ17-08.519, illustrating the effect thereof in inducing the death of ovarian cancer;

FIG. 81W is a graph of cell number versus dosage amounts of GZ17-08.519, illustrating the effect thereof in inducing the death of lymphoma;

FIG. 81X is a graph of cell number versus dosage amounts of GZ17-08.519, illustrating the effect thereof in inducing the death of head and neck cancer;

FIG. 81Y is a graph of cell number versus dosage amounts of GZ17-08.520, illustrating the effect thereof in inducing the death of ovarian cancer;

FIG. 81Z is a graph of cell number versus dosage amounts of GZ17-08.520, illustrating the effect thereof in inducing the death of lymphoma;

FIG. 81AA is a graph of cell number versus dosage amounts of GZ17-08.520, illustrating the effect thereof in inducing the death of head and neck cancer;

FIG. 81BB is a graph of cell number versus dosage amounts of GZ17-08.521, illustrating the effect thereof in inducing the death of ovarian cancer;

FIG. 81CC is a graph of cell number versus dosage amounts of GZ17-08.521, illustrating the effect thereof in inducing the death of lymphoma;

FIG. 81DD is a graph of cell number versus dosage amounts of GZ17-08.521, illustrating the effect thereof in inducing the death of head and neck cancer;

FIG. 82-1 is a graph of cell number versus dosage amounts of GZ08.065, illustrating the effect thereof in inducing the death of lung cancer, as described in Example 82;

FIG. 82-2 is a graph of cell number versus dosage amounts of GZ08.066, illustrating the effect thereof in inducing the death of lung cancer, as described in Example 82;

FIG. 82-3 is a graph of cell number versus dosage amounts of GZ08.067, illustrating the effect thereof in inducing the death of lung cancer, as described in Example 82;

FIG. 82-4 is a graph of cell number versus dosage amounts of GZ08.068, illustrating the effect thereof in inducing the death of lung cancer, as described in Example 82;

FIG. 82-5 is a graph of cell number versus dosage amounts of GZ08.069, illustrating the effect thereof in inducing the death of lung cancer, as described in Example 82;

FIG. 82-6 is a graph of cell number versus dosage amounts of GZ08.070, illustrating the effect thereof in inducing the death of lung cancer, as described in Example 82;

FIG. 82-7 is a graph of cell number versus dosage amounts of GZ08.071, illustrating the effect thereof in inducing the death of lung cancer, as described in Example 82;

FIG. 82-8 is a graph of cell number versus dosage amounts of GZ08.072, illustrating the effect thereof in inducing the death of lung cancer, as described in Example 82;

FIG. 82-9 is a graph of cell number versus dosage amounts of GZ08.073, illustrating the effect thereof in inducing the death of lung cancer, as described in Example 82;

FIG. 82-10 is a graph of cell number versus dosage amounts of GZ08.074, illustrating the effect thereof in inducing the death of lung cancer, as described in Example 82;

FIG. 82-11 is a graph of cell number versus dosage amounts of GZ08.075, illustrating the effect thereof in inducing the death of lung cancer, as described in Example 82;

FIG. 82-12 is a graph of cell number versus dosage amounts of GZ08.076, illustrating the effect thereof in inducing the death of lung cancer, as described in Example 82;

FIG. 82-13 is a graph of cell number versus dosage amounts of GZ08.077, illustrating the effect thereof in inducing the death of lung cancer, as described in Example 82;

FIG. 82-14 is a graph of cell number versus dosage amounts of GZ08.078, illustrating the effect thereof in inducing the death of lung cancer, as described in Example 82;

FIG. 82-15 is a graph of cell number versus dosage amounts of GZ08.079, illustrating the effect thereof in inducing the death of lung cancer, as described in Example 82;

FIG. 82-16 is a graph of cell number versus dosage amounts of GZ08.080, illustrating the effect thereof in inducing the death of lung cancer, as described in Example 82;

FIG. 82-17 is a graph of cell number versus dosage amounts of GZ08.081, illustrating the effect thereof in inducing the death of lung cancer, as described in Example 82;

FIG. 82-18 is a graph of cell number versus dosage amounts of GZ08.082, illustrating the effect thereof in inducing the death of lung cancer, as described in Example 82;

FIG. 82-19 is a graph of cell number versus dosage amounts of GZ08.083, illustrating the effect thereof in inducing the death of lung cancer, as described in Example 82;

FIG. 82-20 is a graph of cell number versus dosage amounts of GZ08.084, illustrating the effect thereof in inducing the death of lung cancer, as described in Example 82;

FIG. 82-21 is a graph of cell number versus dosage amounts of GZ08.085, illustrating the effect thereof in inducing the death of lung cancer, as described in Example 82;

FIG. 82-22 is a graph of cell number versus dosage amounts of GZ08.086, illustrating the effect thereof in inducing the death of lung cancer, as described in Example 82;

FIG. 82-23 is a graph of cell number versus dosage amounts of GZ08.087, illustrating the effect thereof in inducing the death of lung cancer, as described in Example 82;

FIG. 82-24 is a graph of cell number versus dosage amounts of GZ08.088, illustrating the effect thereof in inducing the death of lung cancer, as described in Example 82;

FIG. 82-25 is a graph of cell number versus dosage amounts of GZ08.089, illustrating the effect thereof in inducing the death of lung cancer, as described in Example 82;

FIG. 82-26 is a graph of cell number versus dosage amounts of GZ08.090, illustrating the effect thereof in inducing the death of lung cancer, as described in Example 82;

FIG. 82-27 is a graph of cell number versus dosage amounts of GZ08.091, illustrating the effect thereof in inducing the death of lung cancer, as described in Example 82;

FIG. 82-28 is a graph of cell number versus dosage amounts of GZ08.092, illustrating the effect thereof in inducing the death of lung cancer, as described in Example 82;

FIG. 82-29 is a graph of cell number versus dosage amounts of GZ08.093, illustrating the effect thereof in inducing the death of lung cancer, as described in Example 82;

FIG. 82-30 is a graph of cell number versus dosage amounts of GZ08.094, illustrating the effect thereof in inducing the death of lung cancer, as described in Example 82;

FIG. 82-31 is a graph of cell number versus dosage amounts of GZ08.095, illustrating the effect thereof in inducing the death of lung cancer, as described in Example 82;

FIG. 82-32 is a graph of cell number versus dosage amounts of GZ08.096, illustrating the effect thereof in inducing the death of lung cancer, as described in Example 82;

FIG. 82-33 is a graph of cell number versus dosage amounts of GZ08.097, illustrating the effect thereof in inducing the death of lung cancer, as described in Example 82;

FIG. 82-34 is a graph of cell number versus dosage amounts of GZ08.098, illustrating the effect thereof in inducing the death of lung cancer, as described in Example 82;

FIG. 82-35 is a graph of cell number versus dosage amounts of GZ08.099, illustrating the effect thereof in inducing the death of lung cancer, as described in Example 82;

FIG. 82-36 is a graph of cell number versus dosage amounts of GZ08.100, illustrating the effect thereof in inducing the death of lung cancer, as described in Example 82;

FIG. 82-37 is a graph of cell number versus dosage amounts of GZ08.101, illustrating the effect thereof in inducing the death of lung cancer, as described in Example 82;

FIG. 82-38 is a graph of cell number versus dosage amounts of GZ08.102, illustrating the effect thereof in inducing the death of lung cancer, as described in Example 82;

FIG. 82-39 is a graph of cell number versus dosage amounts of GZ08.103, illustrating the effect thereof in inducing the death of lung cancer, as described in Example 82;

FIG. 82-40 is a graph of cell number versus dosage amounts of GZ08.104, illustrating the effect thereof in inducing the death of lung cancer, as described in Example 82;

FIG. 82-41 is a graph of cell number versus dosage amounts of GZ08.105, illustrating the effect thereof in inducing the death of lung cancer, as described in Example 82;

FIG. 82-42 is a graph of cell number versus dosage amounts of GZ08.065, illustrating the effect thereof in inducing the death of lymphoma, as described in Example 82;

FIG. 82-43 is a graph of cell number versus dosage amounts of GZ08.066, illustrating the effect thereof in inducing the death of lymphoma, as described in Example 82;

FIG. 82-44 is a graph of cell number versus dosage amounts of GZ08.067, illustrating the effect thereof in inducing the death of lymphoma, as described in Example 82;

FIG. 82-45 is a graph of cell number versus dosage amounts of GZ08.068, illustrating the effect thereof in inducing the death of lymphoma, as described in Example 82;

FIG. 82-46 is a graph of cell number versus dosage amounts of GZ08.069, illustrating the effect thereof in inducing the death of lymphoma, as described in Example 82;

FIG. 82-47 is a graph of cell number versus dosage amounts of GZ08.070, illustrating the effect thereof in inducing the death of lymphoma, as described in Example 82;

FIG. 82-48 is a graph of cell number versus dosage amounts of GZ08.071, illustrating the effect thereof in inducing the death of lymphoma, as described in Example 82;

FIG. 82-49 is a graph of cell number versus dosage amounts of GZ08.072, illustrating the effect thereof in inducing the death of lymphoma, as described in Example 82;

FIG. 82-50 is a graph of cell number versus dosage amounts of GZ08.073, illustrating the effect thereof in inducing the death of lymphoma, as described in Example 82;

FIG. 82-51 is a graph of cell number versus dosage amounts of GZ08.074, illustrating the effect thereof in inducing the death of lymphoma, as described in Example 82;

FIG. 82-52 is a graph of cell number versus dosage amounts of GZ08.075, illustrating the effect thereof in inducing the death of lymphoma, as described in Example 82;

FIG. 82-53 is a graph of cell number versus dosage amounts of GZ08.076, illustrating the effect thereof in inducing the death of lymphoma, as described in Example 82;

FIG. 82-54 is a graph of cell number versus dosage amounts of GZ08.077, illustrating the effect thereof in inducing the death of lymphoma, as described in Example 82;

FIG. 82-55 is a graph of cell number versus dosage amounts of GZ08.078, illustrating the effect thereof in inducing the death of lymphoma, as described in Example 82;

FIG. 82-56 is a graph of cell number versus dosage amounts of GZ08.079, illustrating the effect thereof in inducing the death of lymphoma, as described in Example 82;

FIG. 82-57 is a graph of cell number versus dosage amounts of GZ08.080, illustrating the effect thereof in inducing the death of lymphoma, as described in Example 82;

FIG. 82-58 is a graph of cell number versus dosage amounts of GZ08.081, illustrating the effect thereof in inducing the death of lymphoma, as described in Example 82;

FIG. 82-59 is a graph of cell number versus dosage amounts of GZ08.082, illustrating the effect thereof in inducing the death of lymphoma, as described in Example 82;

FIG. 82-60 is a graph of cell number versus dosage amounts of GZ08.083, illustrating the effect thereof in inducing the death of lymphoma, as described in Example 82;

FIG. 82-61 is a graph of cell number versus dosage amounts of GZ08.084, illustrating the effect thereof in inducing the death of lymphoma, as described in Example 82;

FIG. 82-62 is a graph of cell number versus dosage amounts of GZ08.085, illustrating the effect thereof in inducing the death of lymphoma, as described in Example 82;

FIG. 82-63 is a graph of cell number versus dosage amounts of GZ08.086, illustrating the effect thereof in inducing the death of lymphoma, as described in Example 82;

FIG. 82-64 is a graph of cell number versus dosage amounts of GZ08.087, illustrating the effect thereof in inducing the death of lymphoma, as described in Example 82;

FIG. 82-65 is a graph of cell number versus dosage amounts of GZ08.088, illustrating the effect thereof in inducing the death of lymphoma, as described in Example 82;

FIG. 82-66 is a graph of cell number versus dosage amounts of GZ08.089, illustrating the effect thereof in inducing the death of lymphoma, as described in Example 82;

FIG. 82-67 is a graph of cell number versus dosage amounts of GZ08.090, illustrating the effect thereof in inducing the death of lymphoma, as described in Example 82;

FIG. 82-68 is a graph of cell number versus dosage amounts of GZ08.091, illustrating the effect thereof in inducing the death of lymphoma, as described in Example 82;

FIG. 82-69 is a graph of cell number versus dosage amounts of GZ08.092, illustrating the effect thereof in inducing the death of lymphoma, as described in Example 82;

FIG. 82-70 is a graph of cell number versus dosage amounts of GZ08.093, illustrating the effect thereof in inducing the death of lymphoma, as described in Example 82;

FIG. 82-71 is a graph of cell number versus dosage amounts of GZ08.094, illustrating the effect thereof in inducing the death of lymphoma, as described in Example 82;

FIG. 82-72 is a graph of cell number versus dosage amounts of GZ08.095, illustrating the effect thereof in inducing the death of lymphoma, as described in Example 82;

FIG. 82-73 is a graph of cell number versus dosage amounts of GZ08.096, illustrating the effect thereof in inducing the death of lymphoma, as described in Example 82;

FIG. 82-74 is a graph of cell number versus dosage amounts of GZ08.097, illustrating the effect thereof in inducing the death of lymphoma, as described in Example 82;

FIG. 82-75 is a graph of cell number versus dosage amounts of GZ08.098, illustrating the effect thereof in inducing the death of lymphoma, as described in Example 82;

FIG. 82-76 is a graph of cell number versus dosage amounts of GZ08.099, illustrating the effect thereof in inducing the death of lymphoma, as described in Example 82;

FIG. 82-77 is a graph of cell number versus dosage amounts of GZ08.100, illustrating the effect thereof in inducing the death of lymphoma, as described in Example 82;

FIG. 82-78 is a graph of cell number versus dosage amounts of GZ08.101, illustrating the effect thereof in inducing the death of lymphoma, as described in Example 82;

FIG. 82-79 is a graph of cell number versus dosage amounts of GZ08.102, illustrating the effect thereof in inducing the death of lymphoma, as described in Example 82;

FIG. 82-80 is a graph of cell number versus dosage amounts of GZ08.103, illustrating the effect thereof in inducing the death of lymphoma, as described in Example 82;

FIG. 82-81 is a graph of cell number versus dosage amounts of GZ08.104, illustrating the effect thereof in inducing the death of lymphoma, as described in Example 82;

FIG. 82-82 is a graph of cell number versus dosage amounts of GZ08.105, illustrating the effect thereof in inducing the death of lymphoma, as described in Example 82;

FIG. 82-83 is a graph of cell number versus dosage amounts of GZ08.065, illustrating the effect thereof in inducing the death of leukemia, as described in Example 82;

FIG. 82-84 is a graph of cell number versus dosage amounts of GZ08.066, illustrating the effect thereof in inducing the death of leukemia, as described in Example 82;

FIG. 82-85 is a graph of cell number versus dosage amounts of GZ08.067, illustrating the effect thereof in inducing the death of leukemia, as described in Example 82;

FIG. 82-86 is a graph of cell number versus dosage amounts of GZ08.068, illustrating the effect thereof in inducing the death of leukemia, as described in Example 82;

FIG. 82-87 is a graph of cell number versus dosage amounts of GZ08.069, illustrating the effect thereof in inducing the death of leukemia, as described in Example 82;

FIG. 82-88 is a graph of cell number versus dosage amounts of GZ08.070, illustrating the effect thereof in inducing the death of leukemia, as described in Example 82;

FIG. 82-89 is a graph of cell number versus dosage amounts of GZ08.071, illustrating the effect thereof in inducing the death of leukemia, as described in Example 82;

FIG. 82-90 is a graph of cell number versus dosage amounts of GZ08.072, illustrating the effect thereof in inducing the death of leukemia, as described in Example 82;

FIG. 82-91 is a graph of cell number versus dosage amounts of GZ08.073, illustrating the effect thereof in inducing the death of leukemia, as described in Example 82;

FIG. 82-92 is a graph of cell number versus dosage amounts of GZ08.074, illustrating the effect thereof in inducing the death of leukemia, as described in Example 82;

FIG. 82-93 is a graph of cell number versus dosage amounts of GZ08.075, illustrating the effect thereof in inducing the death of leukemia, as described in Example 82;

FIG. 82-94 is a graph of cell number versus dosage amounts of GZ08.076, illustrating the effect thereof in inducing the death of leukemia, as described in Example 82;

FIG. 82-95 is a graph of cell number versus dosage amounts of GZ08.077, illustrating the effect thereof in inducing the death of leukemia, as described in Example 82;

FIG. 82-96 is a graph of cell number versus dosage amounts of GZ08.078, illustrating the effect thereof in inducing the death of leukemia, as described in Example 82;

FIG. 82-97 is a graph of cell number versus dosage amounts of GZ08.079, illustrating the effect thereof in inducing the death of leukemia, as described in Example 82;

FIG. 82-98 is a graph of cell number versus dosage amounts of GZ08.080, illustrating the effect thereof in inducing the death of leukemia, as described in Example 82;

FIG. 82-99 is a graph of cell number versus dosage amounts of GZ08.081, illustrating the effect thereof in inducing the death of leukemia, as described in Example 82;

FIG. 82-100 is a graph of cell number versus dosage amounts of GZ08.082, illustrating the effect thereof in inducing the death of leukemia, as described in Example 82;

FIG. 82-101 is a graph of cell number versus dosage amounts of GZ08.083, illustrating the effect thereof in inducing the death of leukemia, as described in Example 82;

FIG. 82-102 is a graph of cell number versus dosage amounts of GZ08.084, illustrating the effect thereof in inducing the death of leukemia, as described in Example 82;

FIG. 82-103 is a graph of cell number versus dosage amounts of GZ08.085, illustrating the effect thereof in inducing the death of leukemia, as described in Example 82;

FIG. 82-104 is a graph of cell number versus dosage amounts of GZ08.086, illustrating the effect thereof in inducing the death of leukemia, as described in Example 82;

FIG. 82-105 is a graph of cell number versus dosage amounts of GZ08.087, illustrating the effect thereof in inducing the death of leukemia, as described in Example 82;

FIG. 82-106 is a graph of cell number versus dosage amounts of GZ08.088, illustrating the effect thereof in inducing the death of leukemia, as described in Example 82;

FIG. 82-107 is a graph of cell number versus dosage amounts of GZ08.089, illustrating the effect thereof in inducing the death of leukemia, as described in Example 82;

FIG. 82-108 is a graph of cell number versus dosage amounts of GZ08.090, illustrating the effect thereof in inducing the death of leukemia, as described in Example 82;

FIG. 82-109 is a graph of cell number versus dosage amounts of GZ08.091, illustrating the effect thereof in inducing the death of leukemia, as described in Example 82;

FIG. 82-110 is a graph of cell number versus dosage amounts of GZ08.092, illustrating the effect thereof in inducing the death of leukemia, as described in Example 82;

FIG. 82-111 is a graph of cell number versus dosage amounts of GZ08.093, illustrating the effect thereof in inducing the death of leukemia, as described in Example 82;

FIG. 82-112 is a graph of cell number versus dosage amounts of GZ08.094, illustrating the effect thereof in inducing the death of leukemia, as described in Example 82;

FIG. 82-113 is a graph of cell number versus dosage amounts of GZ08.095, illustrating the effect thereof in inducing the death of leukemia, as described in Example 82;

FIG. 82-114 is a graph of cell number versus dosage amounts of GZ08.096, illustrating the effect thereof in inducing the death of leukemia, as described in Example 82;

FIG. 82-115 is a graph of cell number versus dosage amounts of GZ08.097, illustrating the effect thereof in inducing the death of leukemia, as described in Example 82;

FIG. 82-116 is a graph of cell number versus dosage amounts of GZ08.098, illustrating the effect thereof in inducing the death of leukemia, as described in Example 82;

FIG. 82-117 is a graph of cell number versus dosage amounts of GZ08.099, illustrating the effect thereof in inducing the death of leukemia, as described in Example 82;

FIG. 82-118 is a graph of cell number versus dosage amounts of GZ08.100, illustrating the effect thereof in inducing the death of leukemia, as described in Example 82;

FIG. 82-119 is a graph of cell number versus dosage amounts of GZ08.101, illustrating the effect thereof in inducing the death of leukemia, as described in Example 82;

FIG. 82-120 is a graph of cell number versus dosage amounts of GZ08.102, illustrating the effect thereof in inducing the death of leukemia, as described in Example 82;

FIG. 82-121 is a graph of cell number versus dosage amounts of GZ08.103, illustrating the effect thereof in inducing the death of leukemia, as described in Example 82;

FIG. 82-122 is a graph of cell number versus dosage amounts of GZ08.104, illustrating the effect thereof in inducing the death of leukemia, as described in Example 82;

FIG. 82-123 is a graph of cell number versus dosage amounts of GZ08.105, illustrating the effect thereof in inducing the death of leukemia, as described in Example 82;

FIG. 82-124 is a comparative bar graph illustrating the comparative lung cancer cell-killing effect of the individual components of GZ08.065, versus the theoretical additive effect of these components, and the actual effect thereof at the indicted concentration, demonstrating the synergism of the three-component composition, as described in Example 82;

FIG. 82-125 is a comparative bar graph illustrating the comparative lung cancer cell-killing effect of the individual components of GZ08.067, versus the theoretical additive effect of these components, and the actual effect thereof at the indicted concentration, demonstrating the synergism of the three-component composition, as described in Example 82;

FIG. 82-126 is a comparative bar graph illustrating the comparative lung cancer cell-killing effect of the individual components of GZ08.068, versus the theoretical additive effect of these components, and the actual effect thereof at the indicted concentration, demonstrating the synergism of the three-component composition, as described in Example 82;

FIG. 82-127 is a comparative bar graph illustrating the comparative lung cancer cell-killing effect of the individual components of GZ08.079, versus the theoretical additive effect of these components, and the actual effect thereof at the indicted concentration, demonstrating the synergism of the three-component composition, as described in Example 82;

FIG. 82-128 is a comparative bar graph illustrating the comparative lung cancer cell-killing effect of the individual components of GZ08.080, versus the theoretical additive effect of these components, and the actual effect thereof at the indicted concentration, demonstrating the synergism of the three-component composition;

FIG. 82-129 is a comparative bar graph illustrating the comparative lung cancer cell-killing effect of the individual components of GZ08.084, versus the theoretical additive effect of these components, and the actual effect thereof at the indicted concentration, demonstrating the synergism of the three-component composition, as described in Example 82;

FIG. 82-130 is a comparative bar graph illustrating the comparative lung cancer cell-killing effect of the individual components of GZ08.085, versus the theoretical additive effect of these components, and the actual effect thereof at the indicted concentration, demonstrating the synergism of the three-component composition, as described in Example 82;

FIG. 82-131 is a comparative bar graph illustrating the comparative lung cancer cell-killing effect of the individual components of GZ08.086, versus the theoretical additive effect of these components, and the actual effect thereof at the indicted concentration, demonstrating the synergism of the three-component composition, as described in Example 82;

FIG. 82-132 is a comparative bar graph illustrating the comparative lung cancer cell-killing effect of the individual components of GZ08.087, versus the theoretical additive effect of these components, and the actual effect thereof at the indicted concentration, demonstrating the synergism of the three-component composition, as described in Example 82;

FIG. 82-133 is a comparative bar graph illustrating the comparative lung cancer cell-killing effect of the individual components of GZ08.088, versus the theoretical additive effect of these components, and the actual effect thereof at the indicted concentration, demonstrating the synergism of the three-component composition, as described in Example 82;

FIG. 82-134 is a comparative bar graph illustrating the comparative lung cancer cell-killing effect of the individual components of GZ08.089, versus the theoretical additive effect of these components, and the actual effect thereof at the indicted concentration, demonstrating the synergism of the three-component composition, as described in Example 82;

FIG. 82-135 is a comparative bar graph illustrating the comparative lung cancer cell-killing effect of the individual components of GZ08.090, versus the theoretical additive effect of these components, and the actual effect thereof at the indicted concentration, demonstrating the synergism of the three-component composition, as described in Example 82;

FIG. 82-136 is a comparative bar graph illustrating the comparative lung cancer cell-killing effect of the individual components of GZ08.091, versus the theoretical additive effect of these components, and the actual effect thereof at the indicted concentration, demonstrating the synergism of the three-component composition, as described in Example 82;

FIG. 82-137 is a comparative bar graph illustrating the comparative lung cancer cell-killing effect of the individual components of GZ08.092, versus the theoretical additive effect of these components, and the actual effect thereof at the indicted concentration, demonstrating the synergism of the three-component composition, as described in Example 82;

FIG. 82-138 is a comparative bar graph illustrating the comparative lung cancer cell-killing effect of the individual components of GZ08.093, versus the theoretical additive effect of these components, and the actual effect thereof at the indicted concentration, demonstrating the synergism of the three-component composition, as described in Example 82;

FIG. 82-139 is a comparative bar graph illustrating the comparative lung cancer cell-killing effect of the individual components of GZ08.094, versus the theoretical additive effect of these components, and the actual effect thereof at the indicted concentration, demonstrating the synergism of the three-component composition, as described in Example 82;

FIG. 82-140 is a comparative bar graph illustrating the comparative lung cancer cell-killing effect of the individual components of GZ08.097, versus the theoretical additive effect of these components, and the actual effect thereof at the indicted concentration, demonstrating the synergism of the three-component composition, as described in Example 82;

FIG. 82-141 is a comparative bar graph illustrating the comparative lung cancer cell-killing effect of the individual components of GZ08.098, versus the theoretical additive effect of these components, and the actual effect thereof at the indicted concentration, demonstrating the synergism of the three-component composition, as described in Example 82;

FIG. 82-142 is a comparative bar graph illustrating the comparative lung cancer cell-killing effect of the individual components of GZ08.100, versus the theoretical additive effect of these components, and the actual effect thereof at the indicted concentration, demonstrating the synergism of the three-component composition, as described in Example 82;

FIG. 82-143 is a comparative bar graph illustrating the comparative lung cancer cell-killing effect of the individual components of GZ08.101, versus the theoretical additive effect of these components, and the actual effect thereof at the indicted concentration, demonstrating the synergism of the three-component composition, as described in Example 82;

FIG. 82-144 is a comparative bar graph illustrating the comparative lung cancer cell-killing effect of the individual components of GZ08.102, versus the theoretical additive effect of these components, and the actual effect thereof at the indicted concentration, demonstrating the synergism of the three-component composition, as described in Example 82;

FIG. 82-145 is a comparative bar graph illustrating the comparative lung cancer cell-killing effect of the individual components of GZ08.103, versus the theoretical additive effect of these components, and the actual effect thereof at the indicted concentration, demonstrating the synergism of the three-component composition, as described in Example 82;

FIG. 82-146 is a comparative bar graph illustrating the comparative lung cancer cell-killing effect of the individual components of GZ08.104, versus the theoretical additive effect of these components, and the actual effect thereof at the indicted concentration, demonstrating the synergism of the three-component composition, as described in Example 82;

FIG. 82-147 is a comparative bar graph illustrating the comparative lung cancer cell-killing effect of the individual components of GZ08.105, versus the theoretical additive effect of these components, and the actual effect thereof at the indicted concentration, demonstrating the synergism of the three-component composition, as described in Example 82;

FIG. 82-148 is a comparative bar graph illustrating the comparative lymphoma cell-killing effect of the individual components of GZ08.067, versus the theoretical additive effect of these components, and the actual effect thereof at the indicted concentration, demonstrating the synergism of the three-component composition, as described in Example 82;

FIG. 82-149 is a comparative bar graph illustrating the comparative lymphoma cell-killing effect of the individual components of GZ08.073, versus the theoretical additive effect of these components, and the actual effect thereof at the indicted concentration, demonstrating the synergism of the three-component composition, as described in Example 82;

FIG. 82-150 is a comparative bar graph illustrating the comparative lymphoma cell-killing effect of the individual components of GZ08.076, versus the theoretical additive effect of these components, and the actual effect thereof at the indicted concentration, demonstrating the synergism of the three-component composition, as described in Example 82;

FIG. 82-151 is a comparative bar graph illustrating the comparative lymphoma cell-killing effect of the individual components of GZ08.077, versus the theoretical additive effect of these components, and the actual effect thereof at the indicted concentration, demonstrating the synergism of the three-component composition, as described in Example 82;

FIG. 82-152 is a comparative bar graph illustrating the comparative lymphoma cell-killing effect of the individual components of GZ08.080, versus the theoretical additive effect of these components, and the actual effect thereof at the indicted concentration, demonstrating the synergism of the three-component composition, as described in Example 82;

FIG. 82-153 is a comparative bar graph illustrating the comparative lymphoma cell-killing effect of the individual components of GZ08.083, versus the theoretical additive effect of these components, and the actual effect thereof at the indicted concentration, demonstrating the synergism of the three-component composition, as described in Example 82;

FIG. 82-154 is a comparative bar graph illustrating the comparative lymphoma cell-killing effect of the individual components of GZ08.086, versus the theoretical additive effect of these components, and the actual effect thereof at the indicted concentration, demonstrating the synergism of the three-component composition, as described in Example 82;

FIG. 82-155 is a comparative bar graph illustrating the comparative lymphoma cell-killing effect of the individual components of GZ08.088, versus the theoretical additive effect of these components, and the actual effect thereof at the indicted concentration, demonstrating the synergism of the three-component composition, as described in Example 82;

FIG. 82-156 is a comparative bar graph illustrating the comparative lymphoma cell-killing effect of the individual components of GZ08.092, versus the theoretical additive effect of these components, and the actual effect thereof at the indicted concentration, demonstrating the synergism of the three-component composition, as described in Example 82;

FIG. 82-157 is a comparative bar graph illustrating the comparative lymphoma cell-killing effect of the individual components of GZ08.095, versus the theoretical additive effect of these components, and the actual effect thereof at the indicted concentration, demonstrating the synergism of the three-component composition, as described in Example 82;

FIG. 82-158 is a comparative bar graph illustrating the comparative lymphoma cell-killing effect of the individual components of GZ08.099, versus the theoretical additive effect of these components, and the actual effect thereof at the indicted concentration, demonstrating the synergism of the three-component composition, as described in Example 82;

FIG. 82-159 is a comparative bar graph illustrating the comparative lymphoma cell-killing effect of the individual components of GZ08.101, versus the theoretical additive effect of these components, and the actual effect thereof at the indicted concentration, demonstrating the synergism of the three-component composition, as described in Example 82;

FIG. 82-160 is a comparative bar graph illustrating the comparative lymphoma cell-killing effect of the individual components of GZ08.105, versus the theoretical additive effect of these components, and the actual effect thereof at the indicted concentration, demonstrating the synergism of the three-component composition, as described in Example 82;

FIG. 82-161 is a comparative bar graph illustrating the comparative leukemia cell-killing effect of the individual components of GZ08.086, versus the theoretical additive effect of these components, and the actual effect thereof at the indicted concentration, demonstrating the synergism of the three-component composition, as described in Example 82;

FIG. 82-162 is a comparative bar graph illustrating the comparative leukemia cell-killing effect of the individual components of GZ08.087, versus the theoretical additive effect of these components, and the actual effect thereof at the indicted concentration, demonstrating the synergism of the three-component composition, as described in Example 82;

FIG. 82-163 is a comparative bar graph illustrating the comparative leukemia cell-killing effect of the individual components of GZ08.090, versus the theoretical additive effect of these components, and the actual effect thereof at the indicted concentration, demonstrating the synergism of the three-component composition, as described in Example 82;

FIG. 82-164 is a comparative bar graph illustrating the comparative leukemia cell-killing effect of the individual components of GZ08.094, versus the theoretical additive effect of these components, and the actual effect thereof at the indicted concentration, demonstrating the synergism of the three-component composition, as described in Example 82;

FIG. 82-165 is a comparative bar graph illustrating the comparative leukemia cell-killing effect of the individual components of GZ08.098, versus the theoretical additive effect of these components, and the actual effect thereof at the indicted concentration, demonstrating the synergism of the three-component composition, as described in Example 82;

FIG. 82-166 is a comparative bar graph illustrating the comparative leukemia cell-killing effect of the individual components of GZ08.104, versus the theoretical additive effect of these components, and the actual effect thereof at the indicted concentration, demonstrating the synergism of the three-component composition, as described in Example 82;

FIG. 82-167 is a comparative bar graph illustrating the comparative leukemia cell-killing effect of the individual components of GZ08.105, versus the theoretical additive effect of these components, and the actual effect thereof at the indicted concentration, demonstrating the synergism of the three-component composition, as described in Example 82;

FIG. 83A is a graph of cell number versus dosage amounts of orthovanillin, illustrating the effect thereof in inducing the death of lymphoma, as described in Example 83;

FIG. 83B is a graph of cell number versus dosage amounts of curcumin, illustrating the effect thereof in inducing the death of lymphoma, as described in Example 83;

FIG. 83C is a graph of cell number versus dosage amounts of harmaline, illustrating the effect thereof in inducing the death of lymphoma, as described in Example 83;

FIG. 83D is a comparative bar graph illustrating the comparative lymphoma cell-killing effect of the individual components, orthovanillin, curcumin, and harmaline, as shown in FIGS. 83A-83C, versus the theoretical additive effect of these components, and the actual effect thereof, demonstrating the synergism of the three-component composition;

FIG. 83E is a graph of cell number versus dosage amounts of orthovanillin, illustrating the effect thereof in inducing the death of leukemia, as described in Example 83;

FIG. 83F is a graph of cell number versus dosage amounts of curcumin, illustrating the effect thereof in inducing the death of leukemia, as described in Example 83;

FIG. 83G is a graph of cell number versus dosage amounts of harmaline, illustrating the effect thereof in inducing the death of leukemia, as described in Example 83;

FIG. 83H is a comparative bar graph illustrating the comparative leukemia cell-killing effect of the individual components, orthovanillin, curcumin, and harmaline, as shown in FIGS. 83E-83G, versus the theoretical additive effect of these components, and the actual effect thereof, demonstrating the synergism of the three-component composition;

FIG. 83I is a graph of cell number versus dosage amounts of orthovanillin, illustrating the effect thereof in inducing the death of breast cancer, as described in Example 83;

FIG. 83J is a graph of cell number versus dosage amounts of curcumin, illustrating the effect thereof in inducing the death of breast cancer, as described in Example 83;

FIG. 83K is a graph of cell number versus dosage amounts of harmaline, illustrating the effect thereof in inducing the death of breast cancer, as described in Example 83;

FIG. 83L is a comparative bar graph illustrating the comparative breast cancer cell-killing effect of the individual components, orthovanillin, curcumin, and harmaline, as shown in FIGS. 83I-83K, versus the theoretical additive effect of these components, and the actual effect thereof, demonstrating the synergism of the three-component composition;

FIG. 84A is series of photographs of pancreatic cancer spheres including a control, treatment of the spheres with GZ17-6.02 at levels of $0.5IC_{50}$ and $IC_{50}$, illustrating the effect of GZ17-6.02 in reducing the number and size of pancreatic cancer spheres, as set forth in Example 84;

FIG. 84B is a series of blots illustrating in vitro pancreatic cell treatment with GZ17-6.02 at levels of $0.5IC_{50}$ and $IC_{50}$, and depicting decreases in cancer stem cell markers owing to the treatment with GZ17-6.02, as set forth in Example 84;

FIG. 84C is a series of blots illustrating the treatment of mouse pancreatic cancer cells with GZ17-6.02, and depicting the decrease in cancer stem cell markers owing to the treatment with GZ17-6.02, as set forth in Example 84; and FIG. 84D is a possible pathway diagram illustrating the action of GZ17-6.02 on both cancer stem cells (CSC) and other cancer cells within a tumor, as set forth in Example 84.

DETAILED DESCRIPTION

The therapeutic agents of the invention are used in therapeutically effective amounts, i.e., amounts that will elicit the biological or medical response of a tissue, system, or subject that is being sought, and in particular to elicit some desired therapeutic effect against a variety of human diseases, and especially cancers; in the case of cancers, the agents operate by preventing and/or inhibiting proliferation and/or survival of cancerous cells, and/or by slowing the progression of cancers. Those skilled in the art recognize that an amount may be considered therapeutically effective even if the condition is not totally eradicated or prevented, but it or its symptoms and/or effects are improved or alleviated partially in the subject. Of course, the appropriate makeup of the agents hereof and dosing regimens using such agents will depend on the particular cancer being treated, the extent of the disease, and other factors related to the patient as determined by those skilled in the art. Hence, the terms "therapeutic" or "treat," as used herein, refer to products or processes in accordance with the invention that are intended to produce a beneficial change in an existing condition (e.g., cancerous tissue, tumor size, metastases, etc.) of a subject, such as by reducing the severity of the clinical symptoms and/or effects of the condition, and/or reducing the duration of the symptoms/effects of a subject.

Additional ingredients may be included with the chemotherapeutic agents of the invention for administration to the subject. Such additional ingredients include, other active agents, preservatives, buffering agents, salts, carriers, excipients, diluents, or other pharmaceutically-acceptable ingredients. The active agents that could be included in the compositions include antiviral, antibiotic, or other anticancer compounds.

The combined therapeutic agents of the invention preferably give synergistic results, which are entirely unexpected. Moreover, the lack of side effects when the agents are administered to patients is quite surprising and essentially unique. As used herein, the terms "combination" or "in combination" are intended to embrace compositions wherein the components are physically intermixed as dosage forms, and to situations where the individual components are separately administered to a subject over relatively short periods of time, which would have the same therapeutic effects as a single dosage form.

In use, a therapeutically effective amount of an agent in accordance with the invention is administered to a subject in need thereof. Such may comprise a single unit dosage or, more usually, periodic (e.g., daily) administration of lower dosages over time. Advantageously, administration of such therapeutically effective amounts achieves an unexpected therapeutic synergy. This means that the therapeutic two- or three-component compositions of the invention exhibit a joint action where one or more of the components supplements or enhances the action of at least one of the other components to produce an effect greater than that which may be obtained by use of individual components in equivalent quantities, or produce effects that could not be obtained with safe quantities of the other components, individually or in combination. Generally, one or more of the components working together produce an effect greater than the sum of their individual effects.

The dosages may be administered in any convenient manner, such as by oral, rectal, nasal, ophthalmic, parenteral (including intraperitoneal, gastrointestinal, intrathecal, intravenous, cutaneous (e.g., dermal patch), subcutaneous (e.g. injection or implant), or intramuscular) administrations. The dosage forms of the invention may be in the form of liquids, gels, suspensions, solutions, or solids (e.g., tablets, pills, or capsules). Moreover, therapeutically effective amounts of the agents of the invention may be co-administered with other chemotherapeutic agent(s), where the two products are administered substantially simultaneously or in any sequential manner.

Additional advantages of the various embodiments of the invention will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

In the ensuing discussion, the curcumin, harmine, and isovanillin component(s) will be individually described. In such discussions, where terms are used which specify or imply the presence of carbon-carbon chains (e.g., alkyl, alkenyl, alkoxy, alkyl amine, alkenyl amine, aldehyde, carboxylate, or the like), these disclosures should be understood to refer to primary (straight), branched chain, or cyclic carbon chain groups. Moreover, unless indicated otherwise, reference to aryl groups means phenyl, substituted phenyl, naphthyl, substituted naphthyl; and heteroatom aryl groups refers to aryl groups containing a nitrogen, oxygen, boron, or sulfur atom, such as pyridine; heterocyclic groups refers to cyclic groups containing from 3-7 atoms, one or more of which is a nitrogen, oxygen, boron, or sulfur heteroatom; and amine refers to primary, secondary, tertiary, or quaternary amines.

As used herein, pharmaceutically acceptable salts with reference to the components means salts of the component compounds of the present invention which are pharmaceutically acceptable, i.e., salts which are useful in preparing pharmaceutical compositions that are generally safe, non-toxic, and neither biologically nor otherwise undesirable and are acceptable for human pharmaceutical use, and which possess the desired degree of pharmacological activity. Such pharmaceutically acceptable salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiary-butylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts Properties*, and Use, P. H. Stahl & C. G. Wermuth eds., ISBN 978-3-90639-058-1 (2008).

As noted below, the curcumin, harmine, and isovanillin component(s) may be obtained as synthetic compounds of high purity, or from modified naturally occurring sources. In either case, however, it is preferred that the component(s) be purified to a level of at least about 50% by weight, more preferably at least about 70% by weight, still more preferably at least about 90% by weight, and most preferably at least about 98% by weight.

The individual discussions of the component(s) contain structural formulas. In order to be entirely clear, curcumin-based formulas are indicated "C-number," (not to be confused with carbon chain numbers, which are indicated as "Cnumber," without an intervening hyphen), harmine-based formulas are indicated as "H-number," and isovanillin-based formulas are indicated as "I-number."

Before discussing the individual components of the invention, it should be understood that use of unmodified, naturally occurring sources of the components is generally not appropriate or desirable, because these naturally occurring products contain relatively small amounts of the desired components and/or have potentially interfering compounds therein. For example, naturally occurring turmeric has only approximately 2-3% by weight curcumin therein and accordingly the straightforward use of unmodified turmeric would not be suitable for the invention. In like manner, naturally occurring harmala seed contains only a very minor amount of harmine and such a product would also be inappropriate.

Thus, the preferred components of the invention are either synthetically derived or derived from one or more naturally occurring product(s) which have been significantly modified so as to contain at least about 25% by weight (more preferably at least about 50% by weight, and still more preferably about 70% by weight) of the desired component. As used herein, "synthetically derived" means that the component in question was synthesized using specific starting ingredients and one or more chemical and/or biological reactions to obtain substantially pure compounds. Modification of naturally occurring products may involve extractions, or any other physical or chemical steps to achieve the desired end product, e.g., harmine components may be obtained from treatment of harmala seed, or curcumin components may be obtained from treatment of turmeric.

For example, curcumin can be synthetically derived to a high degree of purity. Alternately, curcumin can be obtained by extraction or other treatment of naturally occurring turmeric so that the curcumin content of the modified turmeric has the above-noted levels of curcumin therein.

The Curcumin Component(s)

As used herein, "curcumin component(s)" shall mean curcumin, its metabolites and derivatives, isomers and tautomers thereof, esters, metal complexes (e.g., Cu, Fe, Zn, Pt, V), and pharmaceutically acceptable salts of any of the foregoing. Curcumin derivatives include both naturally occurring and synthetic derivatives, e.g., the spontaneous degradation products of curcumin, curcumin metabolites, and synthetic curcumin derivative compounds.

1. Curcumin.

Curcumin (diferuloylmethane, 1,7-bis(4-hydroxy3-methoxyphenyl)-1,6-heptadiene-3,5-dione) is a symmetrical diphenolic dienone, see structure C-1 below. It exists in solution as an equilibrium mixture of the symmetrical dienone (diketo) and the keto-enol tautomer; the keto-enol form is strongly favored by intramolecular hydrogen bonding.

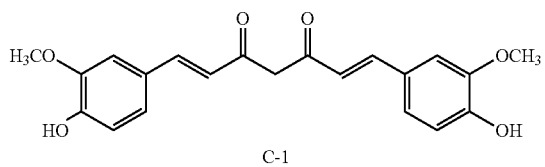
C-1

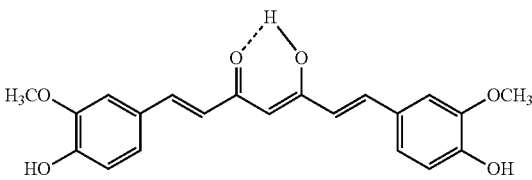
Curcumin

Curcumin contains two aryl rings separated by an unsaturated 7-carbon linker having a symmetrical β-diketone group (as used herein, "β-diketone" embraces both tautomeric forms, namely the diketo and enol forms). The aryl rings of curcumin contain a hydroxyl group in the para position and a methoxy group in the meta position.

2. Degradation Products of Curcumin.

It is known that, under certain pH and other conditions, curcumin will spontaneously form degradation products, and especially one or more of the following:

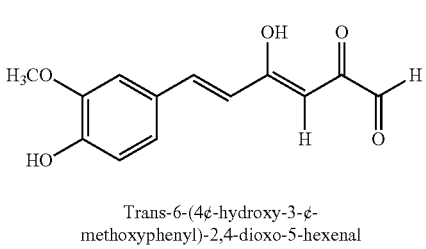

Trans-6-(4¢-hydroxy-3-¢-methoxyphenyl)-2,4-dioxo-5-hexenal

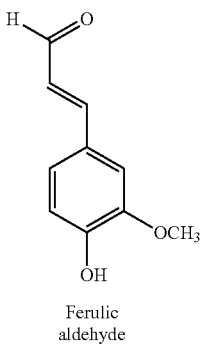

Ferulic aldehyde

-continued

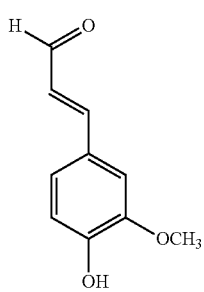

Ferulic acid

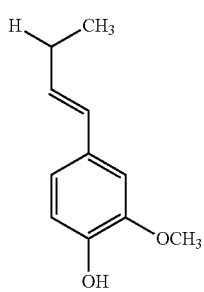

Feruloyl methane

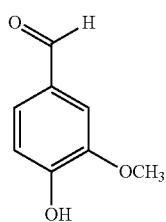

Vanillin

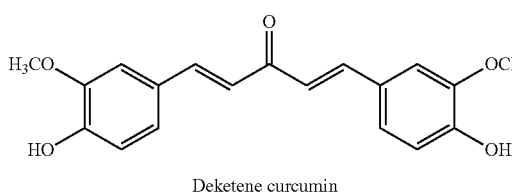

Deketene curcumin

3. Curcumin Metabolites

It has been determined that curcumin is differently metabolized in vivo depending upon the route of administration, see, Shen et al. *The Pharmacology of Curcumin: Is it the Degradation Products?* Trends in Molecular Medicine, March 2012 Vol. 18, No. 2, incorporated by reference herein it its entirety. Thus, when curcumin is orally administered, the metabolites normally include one or more of the following:

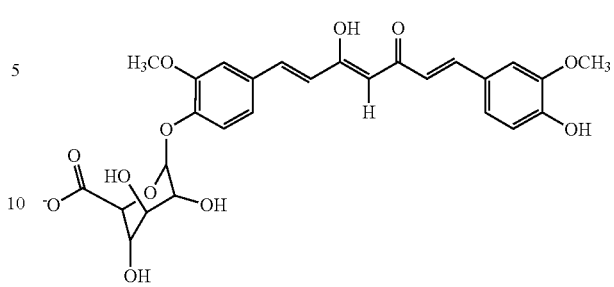

Curcumin glucuronide

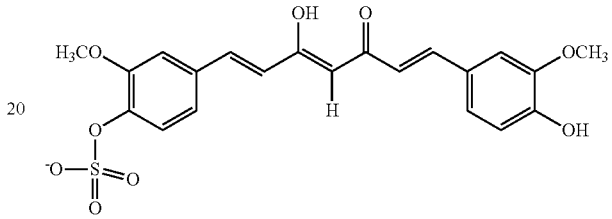

Curcuminsulfate

On the other hand, where the route of administration is intravenous/intraperitoneal, the metabolites generally include the following:

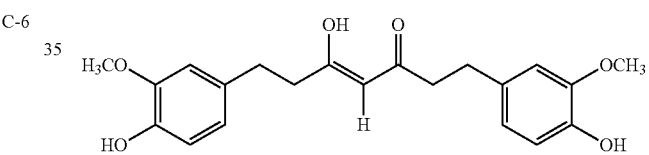

Tetrahydrocurcumin

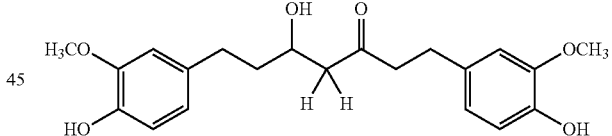

Hexahydrocurcumin

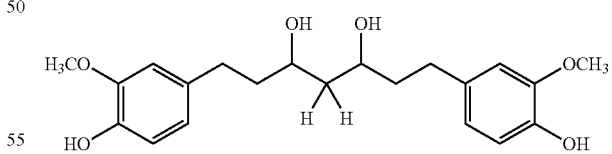

Octahydrocurcumin

Other naturally occurring curcumin derivatives include cyclocurcumin, bisdemethoxycurcumin, demethoxycurcumin, dihydrocurcumin, caffeic acid, cinnamic acid, isoeugenol, dibenzoylmethane, dehydrozingerone, capsaicin, [6]-gingerol, [6]-paradol, chlorogenic acid, yakuchinone A, oregonin, cassumuin A, and cassumuin B.

4. Synthetic Curcumin Derivatives.

Curcumin derivatives are expected to be beneficial for use in the treatment methods of the invention. The term "curcumin derivative" is used interchangeably with the term "curcumin analog" and "curcumin analogue" (alternative spelling) and includes, for example, curcumin derivatives, analogs, curcuminoids and chalcones. In one embodiment the curcumin derivative includes first and second aryl groups covalently attached by way of a linker or a linking group. In another embodiment, the second aryl group is absent, such that the curcumin derivative contains a first aryl group and the linker but no second aryl group at the distal end of the linker. Optionally, the first and/or second aryl group is a heteroaryl group. The first and second aryl groups may be independently substituted or unsubstituted.

Curcumin derivatives that exhibit improved pharmacokinetic properties and/or reduced toxicity are preferred. For example, curcumin derivatives that include heteroaryl groups and/or unsaturated linkers are expected to impart improved pharmacokinetic properties and/or reduced toxicity to the compounds, because they are expected to be less chemically reactive in vivo. One example of preferred curcumin derivatives includes those including one or two carbonyl groups in the linker region, including those derivatives that preserve the enone functionality of curcumin. Derivatives that include heteroaryl groups and/or unsaturated linkers are expected to be less likely to be degraded and/or form toxic adducts or intermediates under physiological conditions.

Thus, in one aspect, curcumin derivatives of the invention are generally encompassed by the formula:

  C-12 where Ar1 and Ar2 are independently aryl groups, and L is a divalent linking group that includes between 3 and 7 backbone carbon atoms, wherein one or more of the backbone carbon atoms include a carbonyl or hydroxyl moiety.

a. Aryl Groups

Preferred aryl groups include phenyl, naphthyl, thienyl, pyridinium, and pyridyl groups.

Aryl groups Ar1 and Ar2 may be substituted or unsubstituted, and one or more of the ring carbons may be substituted with a heteroatom, and especially N, S, B, or O.

For example, in one embodiment of the invention, Ar1 can be an aryl group according to the formula:

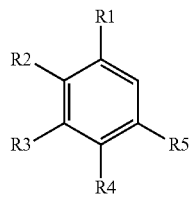  C-13 and Ar2 can be an aryl group according to the formula:

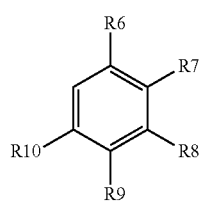  C-14 where one or more of the aryl ring carbons of Ar1 and Ar2 may be independently substituted with a heteroatom selected from N, S, B, or O, and R1-R10 are independently selected from the group consisting of H, hydroxyl, halogen, amine, nitro, sulfonate, sulfoxide, thio, ester, carboxylate, amide, borate, C1-C4 boronate, C1-C8 alkyl, C2-C8 alkenyl, C1-C6 haloalkyl, C1-C6 alkoxy, C1-C6 amine, C2-C8 carboxyl, C2-C8 ester, C1-C4 aldehyde, and glucuronide groups; L is a divalent linker including from 3-7 backbone carbon atoms that form a chain connecting the Ar1, Ar2, and R11 groups as the case may be, where L includes at least one of a carbonyl or hydroxyl group. In further embodiments, Ar1 and Ar2 are phenyl groups; R1-R10 are independently selected from the group consisting of H, hydroxyl, halogen, amine, nitro, sulfonate, thio, borate, C1-C2 boronate, sulfoxide, C1-C4 alkyl, C1-C4 alkoxy, C1-C4 alkylamine, C2-C6 alkenylamine, C1-C6 acetoxy, C1-C4 carboxyl, with at least one of R1-R5 and R6-R10 being hydroxyl.

b. Divalent Linking Groups

The linker L is a spacer that preferably includes 3, 4, 5, 6 or 7 carbon atoms that form a linear carbon chain connecting the first and second aryl groups. The carbons atoms in the carbon chain that trace out shortest path between the first and optional second aryl groups are referred to herein as the "backbone" carbon atoms. The number of backbone carbon atoms is readily determined in straight chain alkyl groups. In linkers that include a cyclic alkyl group as a constituent of the linear chain, the backbone carbon atoms include the least number of ring carbons possible. The number of backbone carbon atoms is used herein as a shorthand way to designate the length of the linker being used. For example, a 7-carbon linker is a divalent linker that includes 7 backbone carbon atoms.

Preferably at least one of the backbone carbon atoms is included in a carbonyl (C═O) or thio carbonyl (C═S) moiety. The linker may be substituted or unsubstituted. The linker may further be saturated or unsaturated. In a preferred embodiment, the linker contains an odd number of carbon atoms (i.e., 3, 5, or 7 carbon atoms), and at least one unsaturated carbon-carbon bond. In additional embodiments, the linker may include a hydroxyl moiety in place of, or in addition to, the at least one carbonyl moiety.

Curcumin derivatives of the invention include a linking group L that is preferably covalently attached at one end to aryl group Ar1. Optionally, the linking group L may also be covalently attached at the other end to a second aryl group, Ar2, which is selected independently from Ar1. The linking group L is a divalent linking group that preferably includes an alkylene or an alkenylene group having between 3 and 7 backbone carbon atoms, and more advantageously an odd number of backbone carbon atoms (i.e., 3, 5, or 7 carbon atoms). The linker also preferably has at least one carbonyl moiety, and may further include a hydroxyl moiety in place of, or in addition to, the at least one carbonyl moiety. The linking group may be substituted or unsubstituted, and may be saturated or unsaturated. Preferably, the linking group has a carbon-carbon double bond between the α and β carbons relative to Ar1 and/or Ar2 (e.g., see formulas C-1 and C-19 through C-33, which illustrate such a double bond. Still more preferably, the linking group includes conjugated double bonds. Table 1 shows compounds with 7-carbon linkers; Table 2 shows compounds with 5-carbon linkers; and Table 3 shows compounds with 3-carbon linkers.

A divalent linking group includes two carbons with unfilled valencies that provide valence points where a covalent bond can be formed to an adjacent alkyl or aryl group that also includes a carbon with an unfilled valency. Generally, a valence point is represented in a chemical formula by a bond that is shown as not being attached to another group (e.g., CH3-, wherein - represents the valence point).

In embodiments wherein the curcumin derivative lacks the second aryl group Ar2, the distal valence point on the linking group can be filled with any substituent of interest, preferably a short chain alkyl group (e.g., C1-C6, more preferably C1-C4) or a hydrogen (H). Compounds lacking a second aryl group may be represented by formula:

Ar1-L-R11        C-15

R11 can be, for example, a heterocyclic group or an alkyl group, preferably an alkyl group having four or fewer carbon atoms, e.g., a methyl group. R11 can alternately be an amine, a hydroxyl, a hydrogen, nitro, sulfonate, sulfoxide, thio, ester, carboxylate, amide, borate, or a C1-C4 boronate.

i. Curcumin Derivatives Including 7-Carbon Linking Groups.

In one embodiment of the invention, the curcumin derivatives include one or two aryl groups (Ar1 and optionally Ar2) and a linking group L that is a 7-carbon linking group (i.e., a linking group that includes 7 backbone carbon atoms). Preferably, the 7-carbon linking group includes at least one unsaturated carbon-carbon bond. Examples of 7-carbon linking groups include

—CH=CH—(CO)—CR12=C(OH)—CH=CH—,    C-16

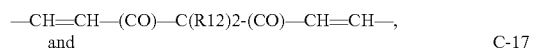
—CH=CH—(CO)—C(R12)2-(CO)—CH=CH—, and    C-17

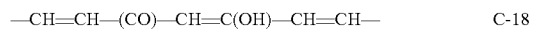
—CH=CH—(CO)—CH=C(OH)—CH=CH—    C-18 where R12 includes substituent alkyl, arylalkyl, or aryl groups comprising 10 carbon atoms or less. In some embodiments, R12 may be a methyl, ethyl, or benzyl group. These linking groups are the divalent forms of 4-alkyl-1,6 heptadiene-3,5-dione; 4,4-dialkyl-1,6 heptadiene-3,5-dione; and heptane-3,5-dione.

Table 1 shows a number of examples of curcumin derivatives that include a 7-carbon linker. The compounds shown contain two aryl rings separated by a 7-carbon linker having two carbonyls (or the equivalent keto-enol tautomer). In many, but not all, of the compounds, the linker is unsaturated. "Bn" refers to a benzyl group.

TABLE 1

7-Carbon Linker Analogs.

TABLE 1-continued
7-Carbon Linker Analogs.
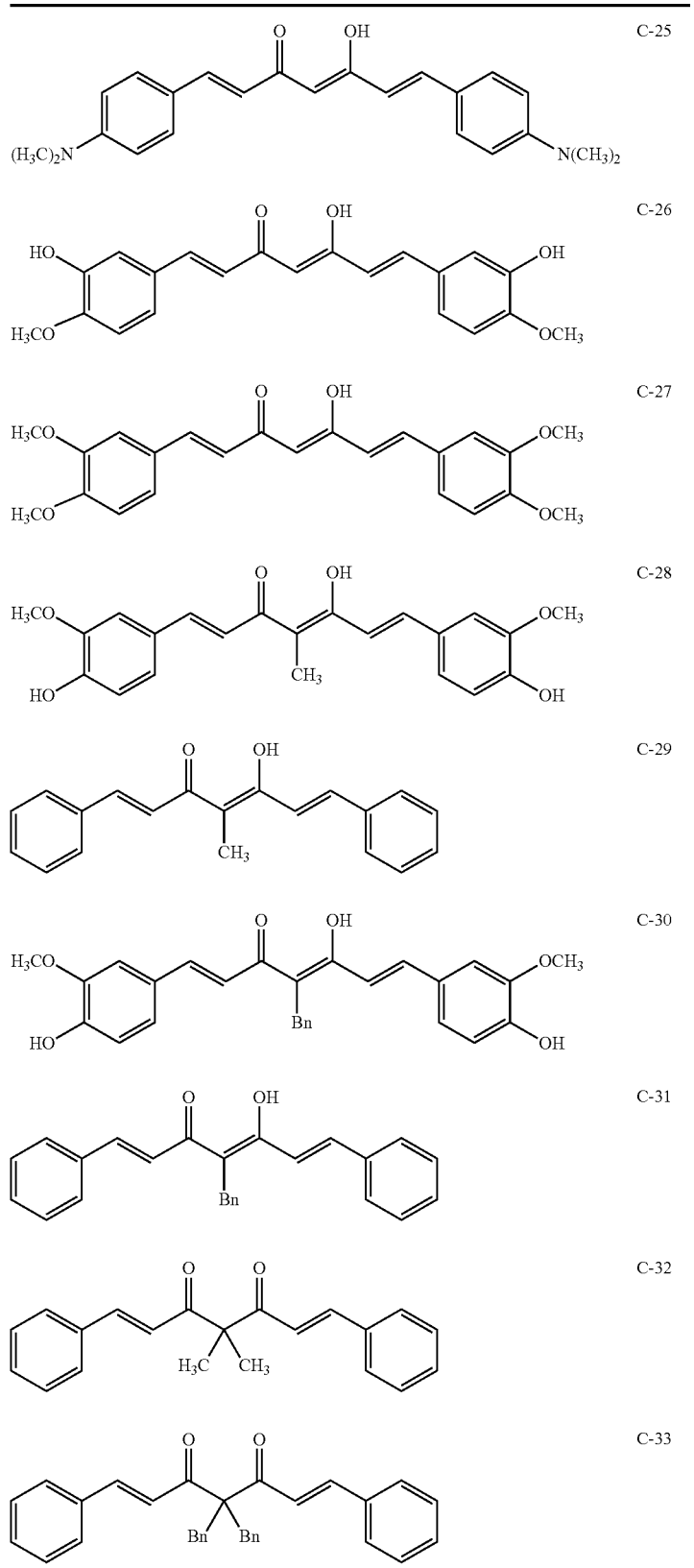

TABLE 1-continued

7-Carbon Linker Analogs.

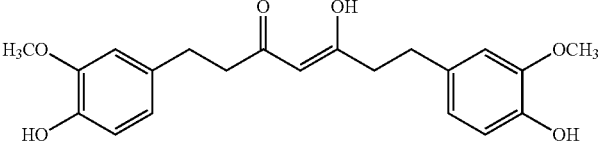 [SMILES: COc1cc(CCC(=O)/C=C(\O)CCc2ccc(O)c(OC)c2)ccc1O] C-34

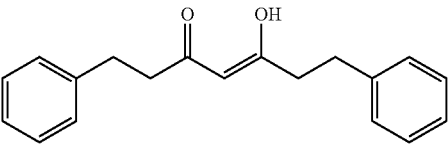 [SMILES: O=C(/C=C(\O)CCc1ccccc1)CCc1ccccc1] C-35

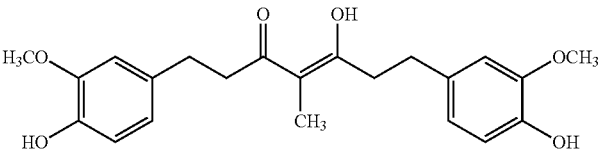 [SMILES: COc1cc(CCC(=O)/C(C)=C(\O)CCc2ccc(O)c(OC)c2)ccc1O] C-36

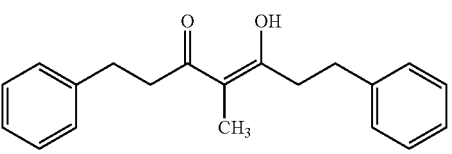 C-37

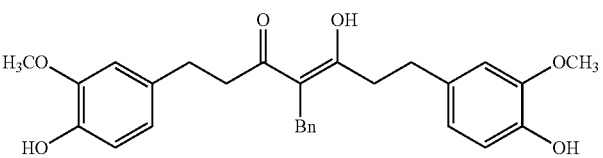 [SMILES: COc1cc(CCC(=O)/C(Cc2ccccc2)=C(\O)CCc2ccc(O)c(OC)c2)ccc1O] C-38

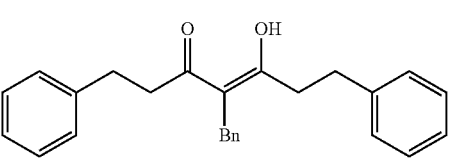 [SMILES: O=C(CCc1ccccc1)/C(Cc1ccccc1)=C(\O)CCc1ccccc1] C-39

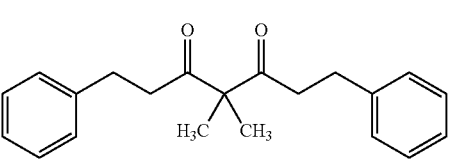 [SMILES: CC(C)(C(=O)CCc1ccccc1)C(=O)CCc1ccccc1] C-40

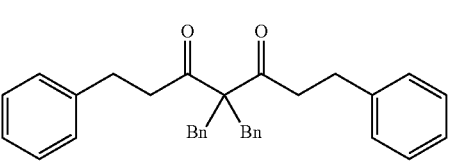 [SMILES: O=C(CCc1ccccc1)C(Cc1ccccc1)(Cc1ccccc1)C(=O)CCc1ccccc1] C-41 ii. Curcumin Derivatives Including 5-carbon Linking Groups

In a further embodiment of the invention, the curcumin derivatives include one or two aryl groups (Ar1 and optionally Ar2) that are linked by a linking group L that is a 5-carbon linking group (i.e., a linking group that includes 5 backbone carbon atoms). Preferably, the 5-carbon linking group includes at least one unsaturated carbon-carbon bond. Examples of 5-carbon linking groups include:

—CH=CH—(CO)—CH=CH—,  C-42

—CH2—CH2—(CO)—CH2—CH2—,  C-43

—CH2—CH2—CH(OH)—CH2—CH2—,  C-44

-continued

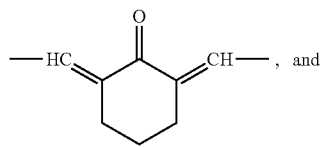, and

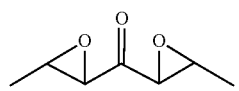

These linking groups are the divalent forms of 1,4-pentadiene-3-one; pentan-3-one; pentan-3-ol, 2,6; bis(methylene)cyclohexanone; and 1,2,4,5-diepoxy pentan-3-one. As noted herein, curcumin derivatives may include a cyclic linking group. For example, 1-methyl-2,6-diphenyl-4-piperidone provides a compound with a 5-carbon linking group that is bridged by a tertiary amine to form a cyclic alkylene linking group including the heteroatom nitrogen.

Table 2 shows a number of examples of curcumin derivatives that include a 5-carbon linker. The compounds shown contain two aryl rings separated by a 5-carbon linker having a single carbonyl or hydroxyl. In many, but not all, of the compounds, the linker is unsaturated.

TABLE 2

5-Carbon Linker Analogs.

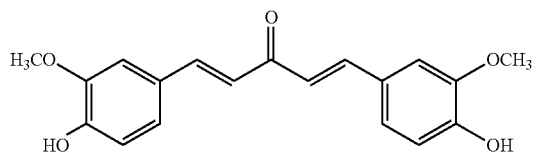 [SMILES: COc1cc(/C=C/C(=O)/C=C/c2ccc(O)c(OC)c2)ccc1O]

C-47

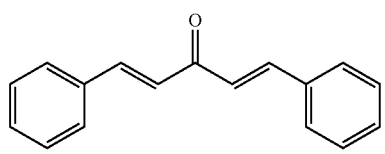 [SMILES: O=C(/C=C/c1ccccc1)/C=C/c1ccccc1]

C-48

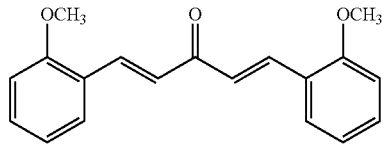 [SMILES: COc1ccccc1/C=C/C(=O)/C=C/c1ccccc1OC]

C-49

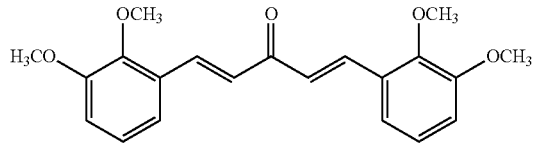 [SMILES: COc1cccc(/C=C/C(=O)/C=C/c2cccc(OC)c2OC)c1OC]

C-50

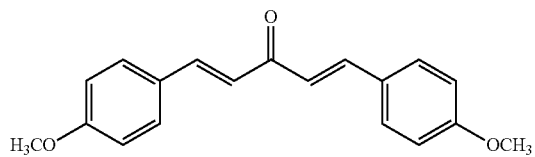 [SMILES: COc1ccc(/C=C/C(=O)/C=C/c2ccc(OC)cc2)cc1]

C-51

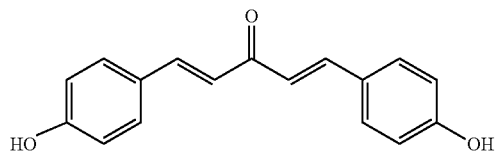 [SMILES: O=C(/C=C/c1ccc(O)cc1)/C=C/c1ccc(O)cc1]

C-52

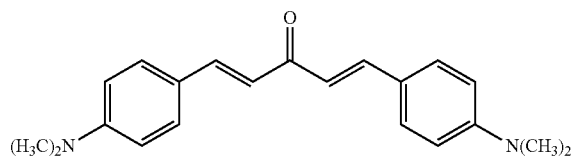

C-53

TABLE 2-continued
5-Carbon Linker Analogs.
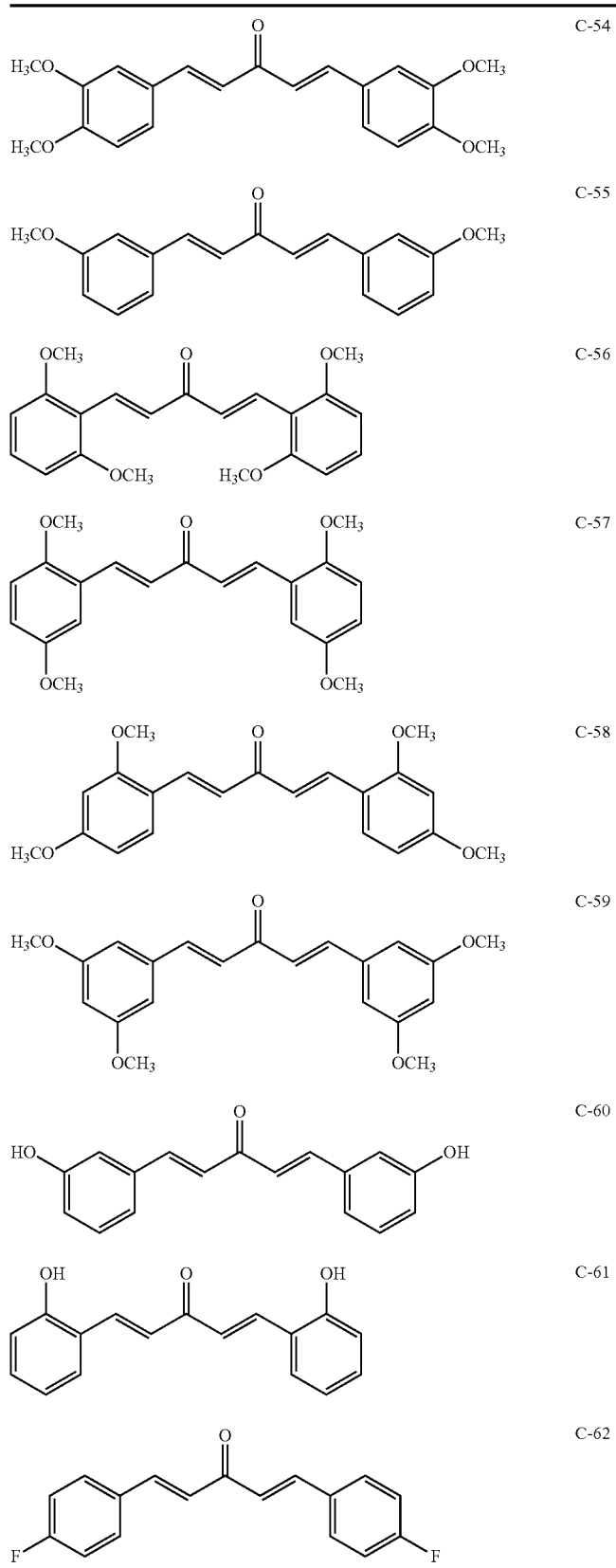

TABLE 2-continued
5-Carbon Linker Analogs.
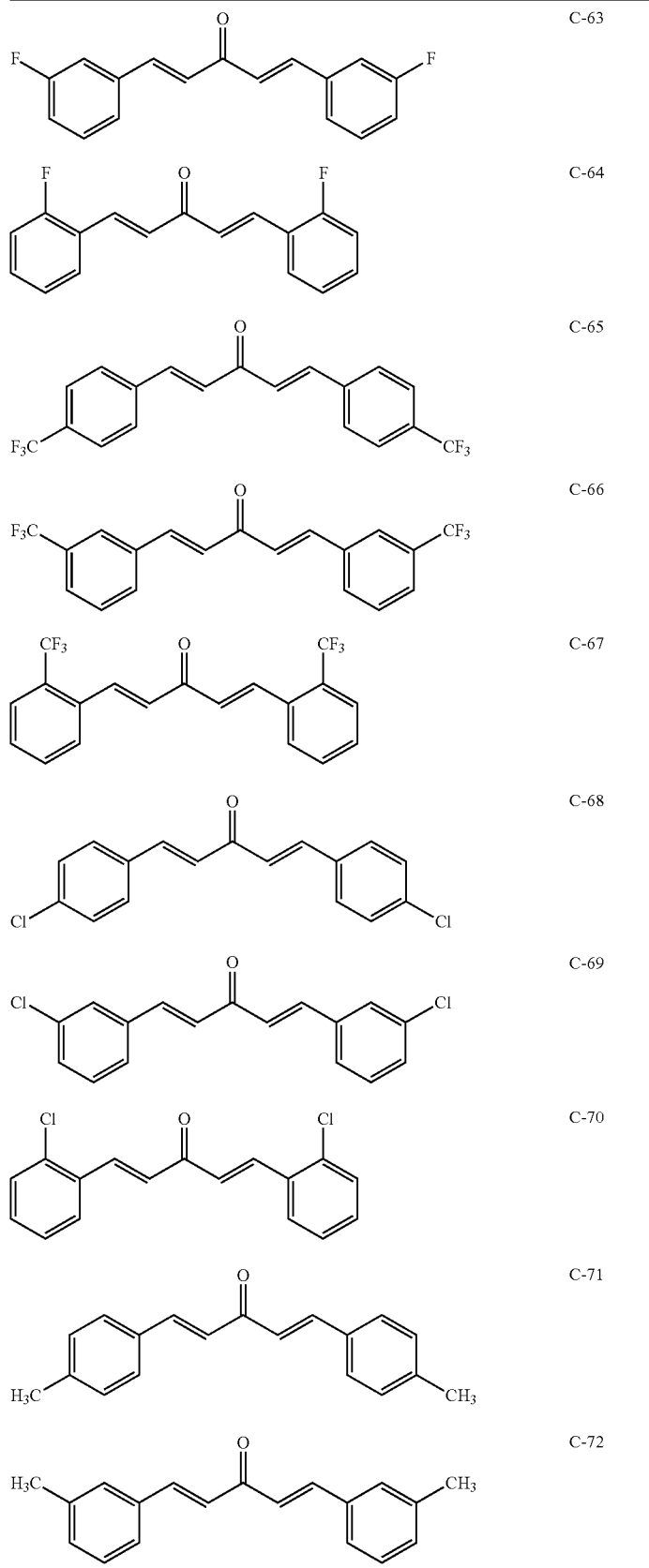

TABLE 2-continued
5-Carbon Linker Analogs.
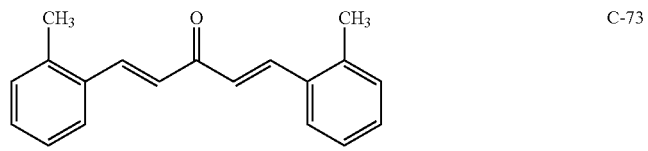
C-73
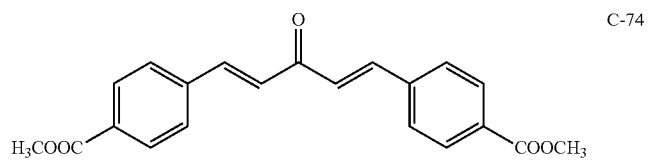
C-74
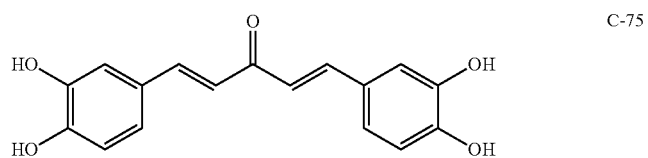
C-75
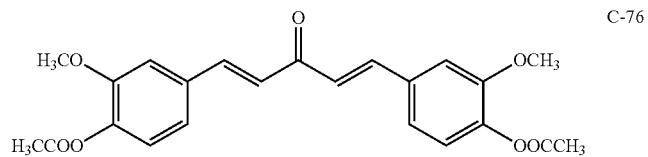
C-76
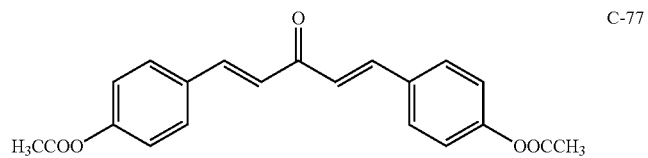
C-77
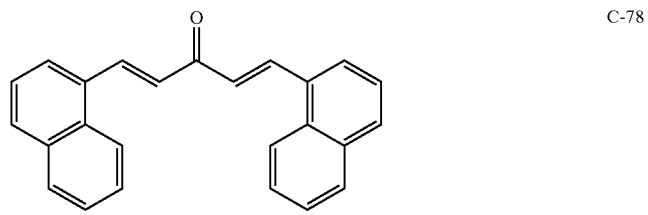
C-78
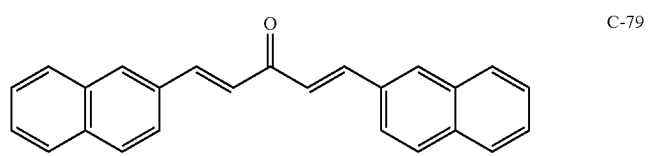
C-79
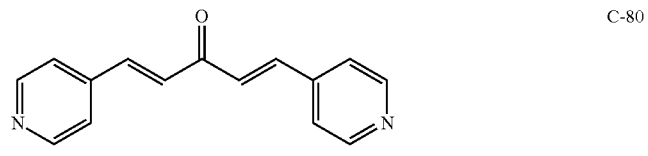
C-80
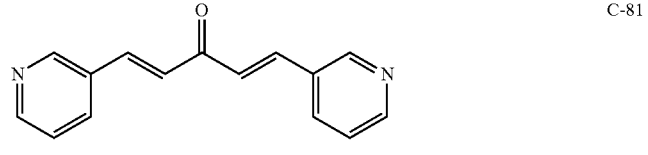
C-81

TABLE 2-continued

5-Carbon Linker Analogs.

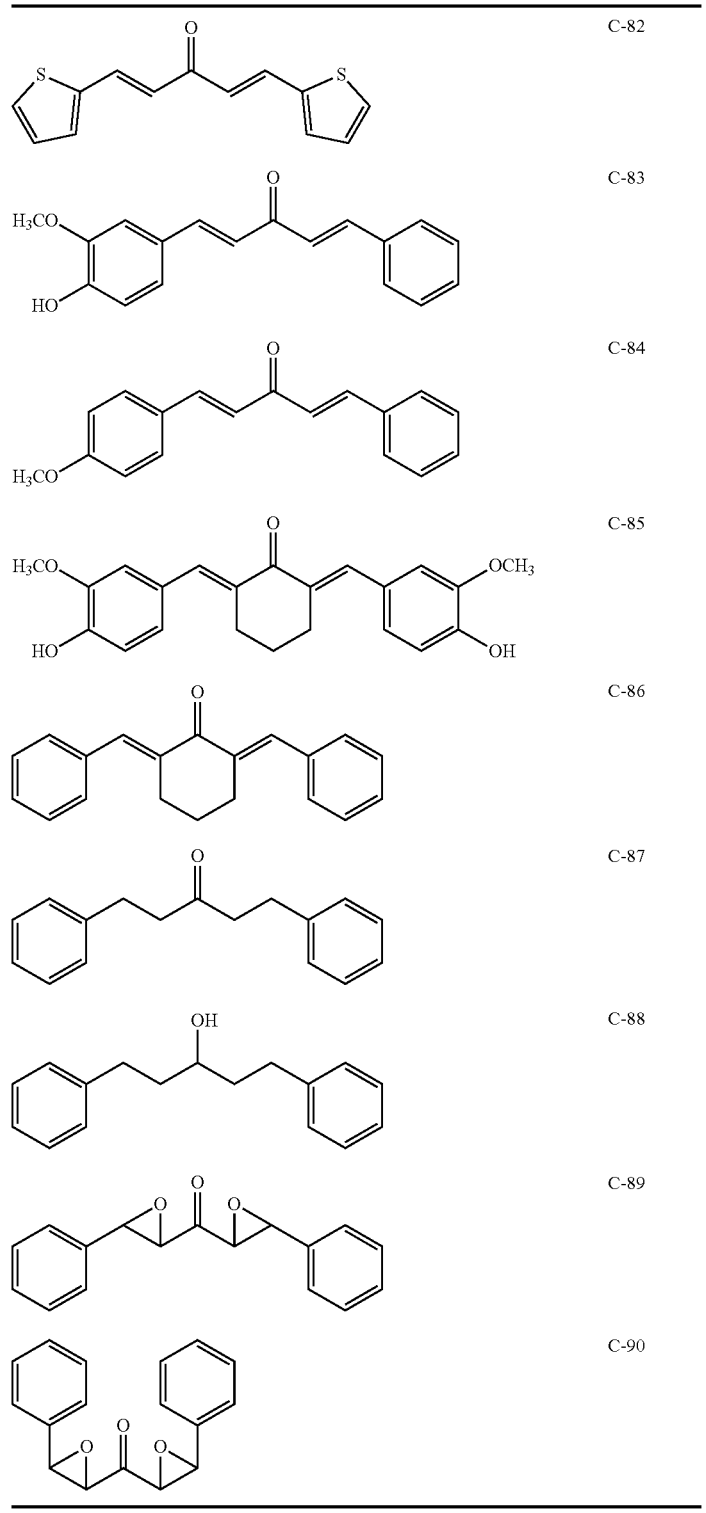

iii. Curcumin Derivatives Including 3-Carbon Linking Groups

In a further embodiment of the invention, the curcumin derivatives include one or two aryl groups (Ar1 and optionally Ar2) that are linked by a linking group L that is a 3-carbon linking group (i.e., a linking group that includes 3 backbone carbon atoms). Preferably, the 3-carbon linking group includes at least one unsaturated carbon-carbon bond. An example of a 3-carbon linking group is —CH═CH—(CO)—; i.e., a divalent form of propenone.

Table 3 shows a number of examples of curcumin derivatives that include a 3-carbon linker. The compounds shown generally have an unsaturated 3-carbon linker having a single carbonyl. While most of the examples shown have two aryl groups separated by the linker, several of the embodiments include only a single aryl group. In the examples that include only a single aryl group, a methyl group is provided at the other end of the linking group. One compound includes the heteroatom N in place of one of the backbone carbon atoms; however, this is still considered a 3-C linker in that 3 atoms (C, N, and C) are present along the shortest bridge between the two aryl groups.

TABLE 3

3-Carbon Linker Analogs.

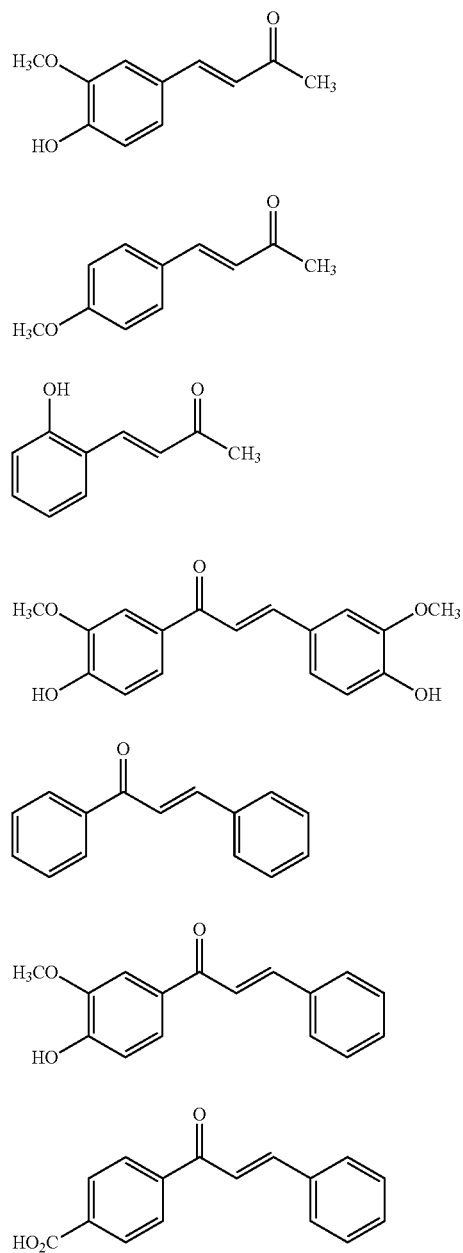

TABLE 3-continued

3-Carbon Linker Analogs.

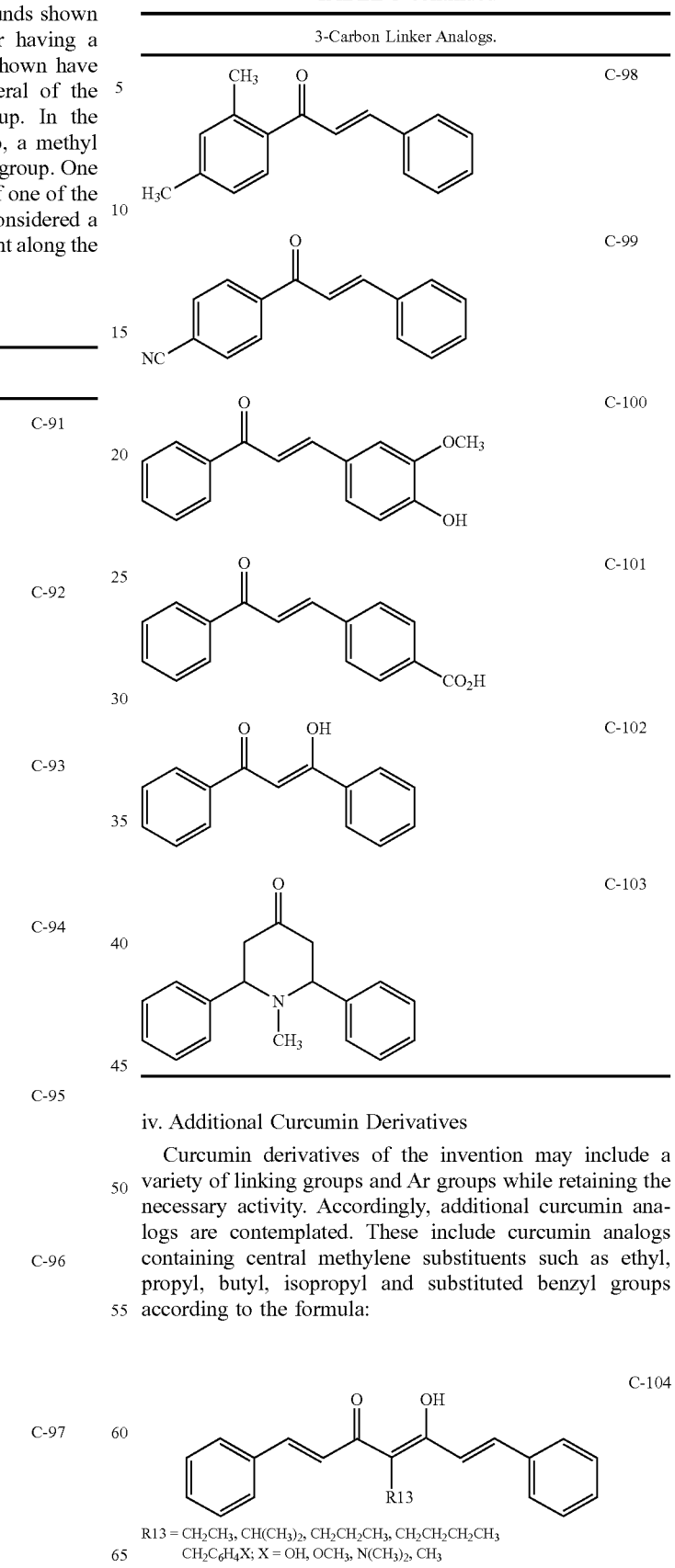

iv. Additional Curcumin Derivatives

Curcumin derivatives of the invention may include a variety of linking groups and Ar groups while retaining the necessary activity. Accordingly, additional curcumin analogs are contemplated. These include curcumin analogs containing central methylene substituents such as ethyl, propyl, butyl, isopropyl and substituted benzyl groups according to the formula:

Central Methylene Substituent Analogs

Additional analogs that are contemplated are those having a pyridine ring with and without a central methylene substituent on the 7-carbon linker such as those shown in the formulas:

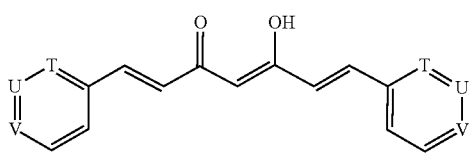
C-105

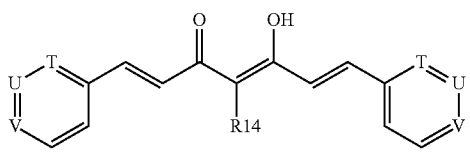
C-106 each T, U, V is independently selected from N, CH, such that each Ar ring is a pyridine; R14=CH$_2$CH$_3$, CH(CH$_3$)$_2$, CH$_2$CH$_2$CH$_3$, CH$_2$CH$_2$CH$_2$CH$_3$, CH$_2$C$_6$H$_4$X; X=OH, OCH$_3$, N(CH$_3$)$_2$, CH$_3$

Pyridine Aryl Ring Analogs

Many curcumin analogs which have a 5-carbon linker possess significant activity.

Additional active analogs in this series may contain substituents such as hydroxy and methoxy groups on the aryl rings. Examples of these analogs are shown in the formula:

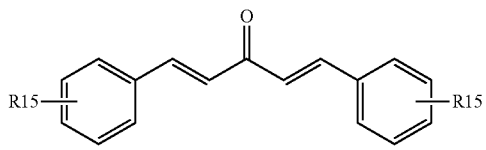
C-107 each R15 is independently selected from CH$_2$CH$_3$, CH(CH$_3$)$_2$, CH$_2$CH$_2$CH$_3$, CH$_2$CH$_2$CH$_2$CH$_3$

Aryl Substituent Analogs

Other analogs include heterocyclic moieties, which may be substituted or unsubstituted, as shown in the formulas:

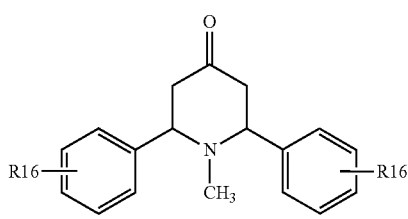
C-108 each R16 is independently selected from Cl, F, CF$_3$, OH

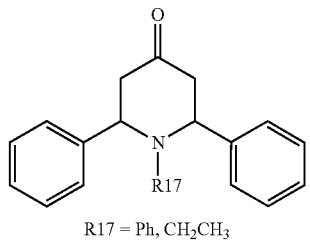
C-109

R17 = Ph, CH$_2$CH$_3$

Heterocyclic Analogs v. Synthetic Curcumin Derivatives Via Different Reaction Schemes A large number of naturally occurring and synthetic curcumin derivatives, the latter explicated by reference to the methods of synthesis thereof, are disclosed in Anand et al. "Biological Activities of Curcumin and Its Analogues (Congeners) Made By Man and Mother Nature." *Biochemical Pharmacology* 76 (2008):1590-1611, which is incorporated by reference herein its entirety. Representative synthetic curcumin derivatives are set forth below.

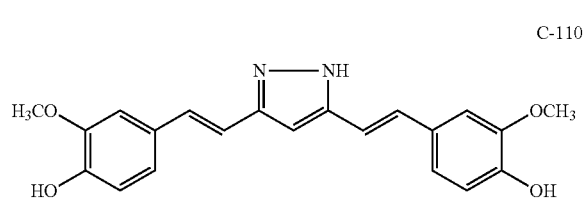
C-110

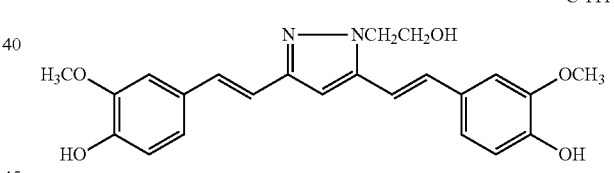
C-111

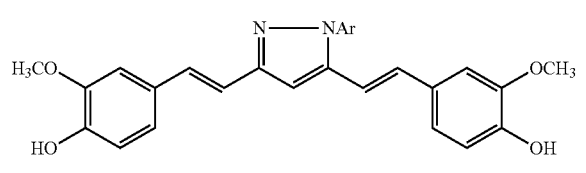
C-112

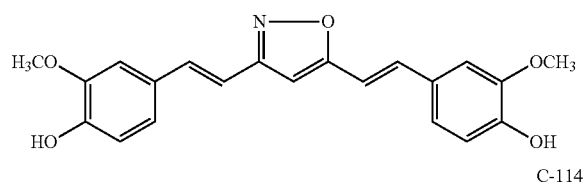
C-113

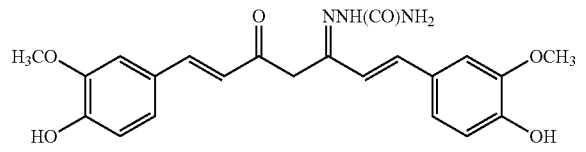
C-114

C-115
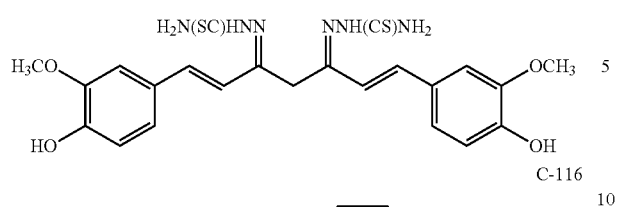
C-116
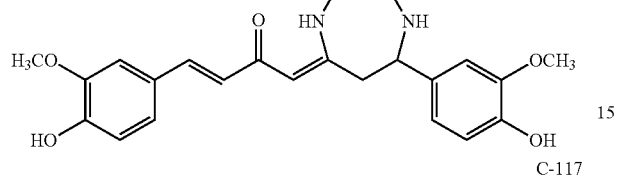
C-117
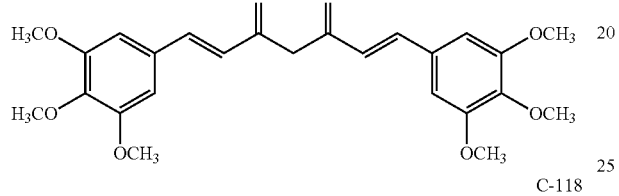
C-118
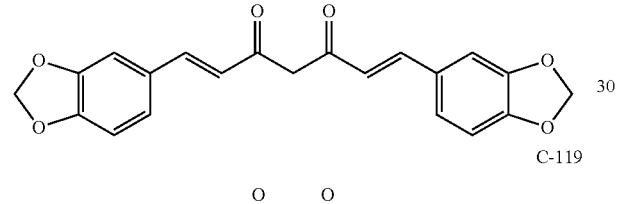
C-119
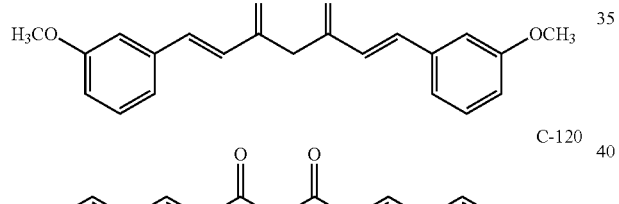
C-120
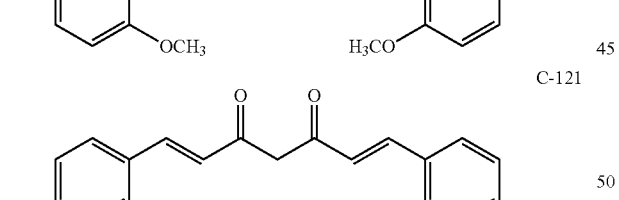
C-121
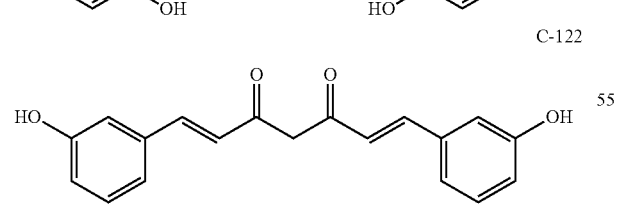
C-122
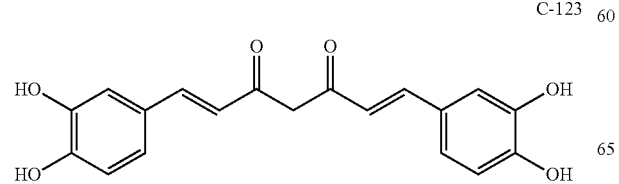
C-124
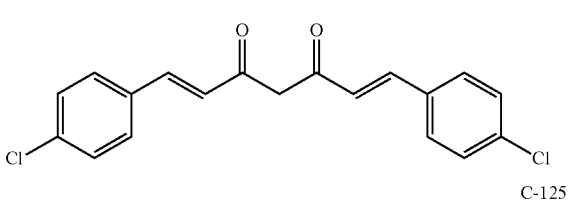
C-125
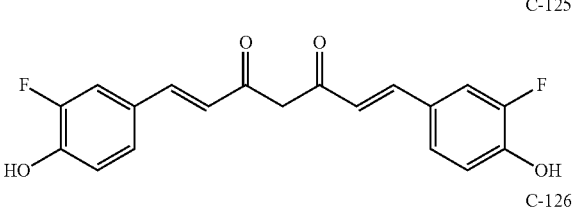
C-126
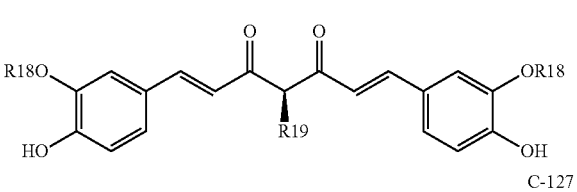
C-127
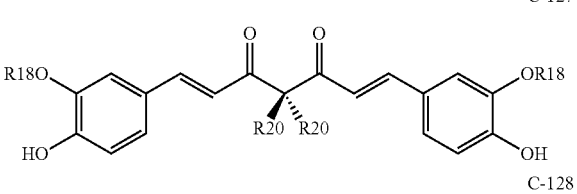
C-128
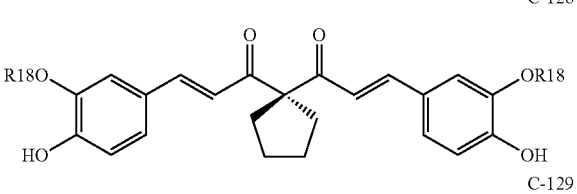
C-129
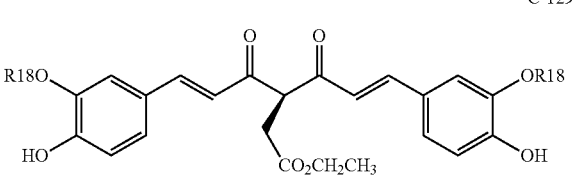
C-130
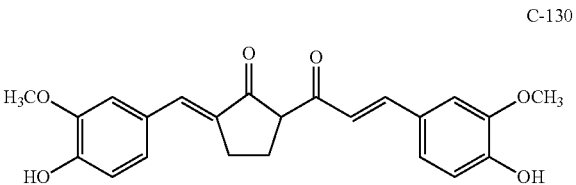
C-131
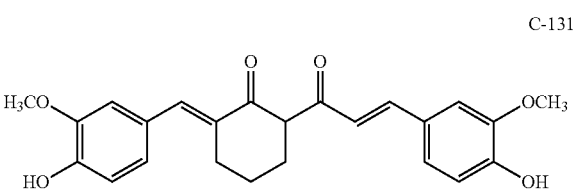
C-132
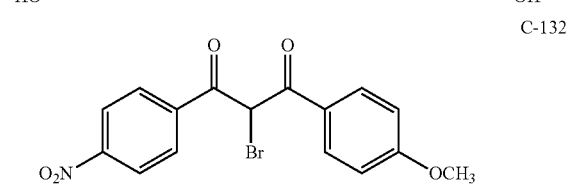

C-133
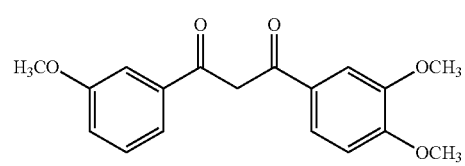
C-134
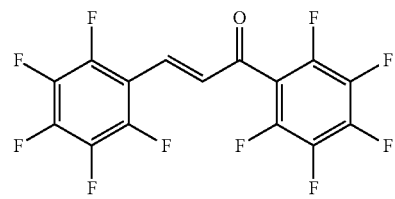
C-135
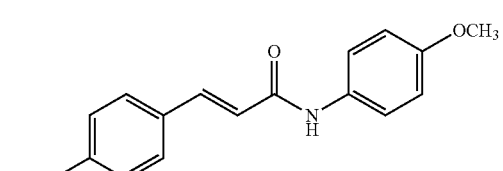
C-136
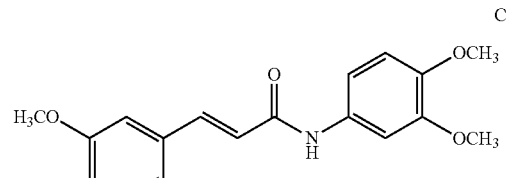
C-137
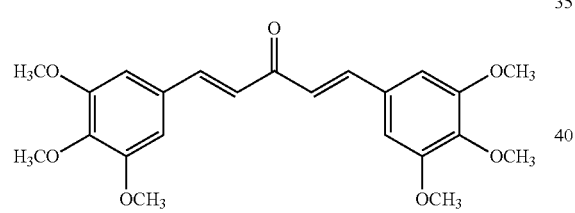
C-138
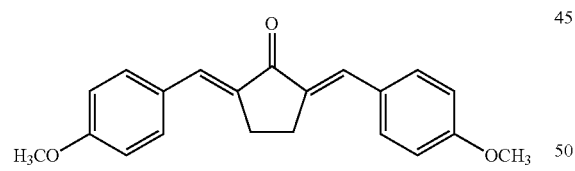
C-139
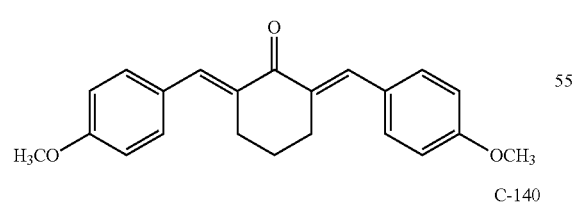
C-140
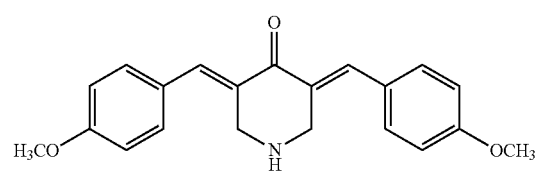
C-141
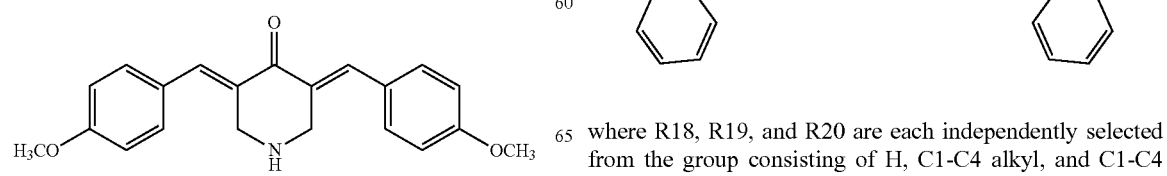
C-142
C-143
C-144
C-145
C-146
C-147
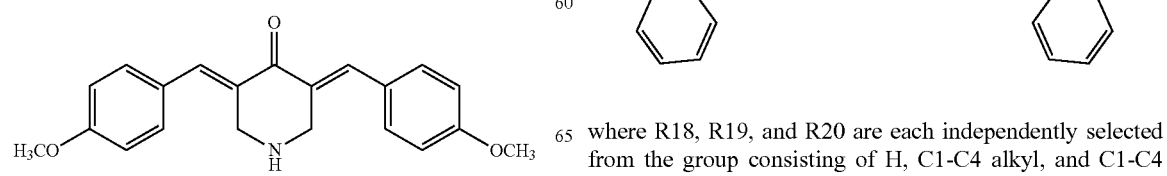
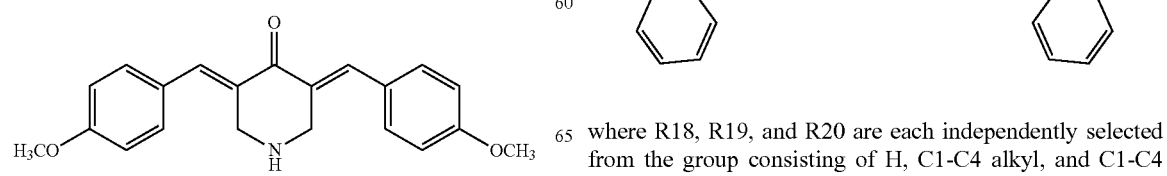
where R18, R19, and R20 are each independently selected from the group consisting of H, C1-C4 alkyl, and C1-C4 amine groups.

vi. Miscellaneous Curcumin Components

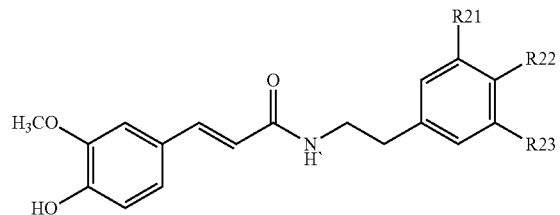

|       | R21  | R22 | R23  |
|-------|------|-----|------|
| C-148 | OCH₃ | OH  | OCH₃ |
| C-149 | OCH₃ | OH  | H    |
| C-150 | H    | OH  | H    |

C-151

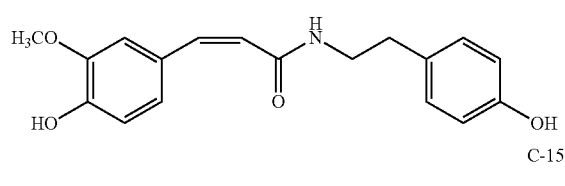

C-152

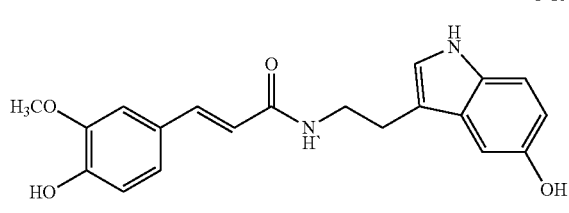

C-153

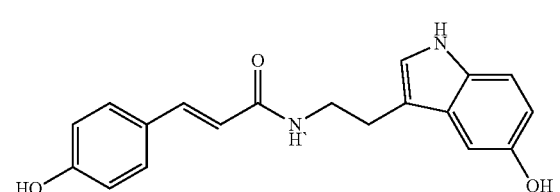

C-154

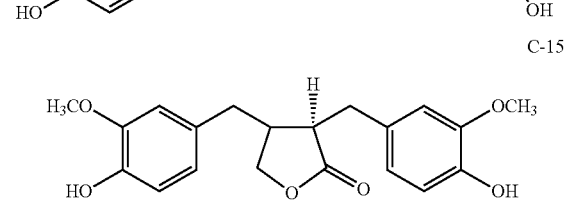

C-155

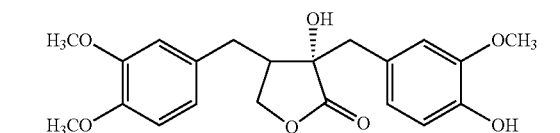

C-156

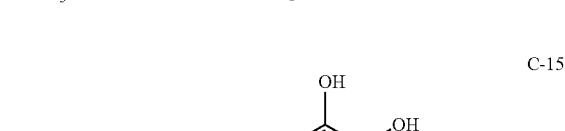

C-157

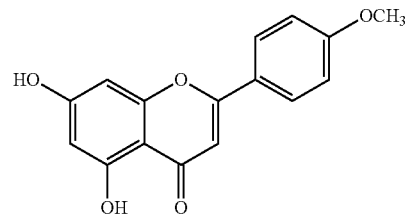

C-158

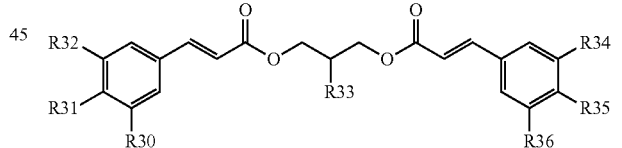

C-159

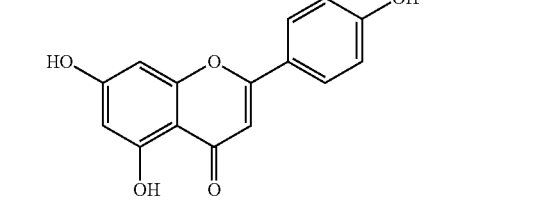

where R24 and R25 are independently selected from the group consisting of OH, C1-C4 alkoxy, and C1-C4 alkylcarbonyloxy; R26 and R27 are independently selected from the group consisting of H, OH, C1-C4 alkoxy, and C1-C4 alkylcarbonyloxy; R28 is selected from the group consisting of H, OH, and C1-C4 alkylcarbonyloxy; and R29 is selected from the group consisting of H and C1-C4 alkoxy.

C-160

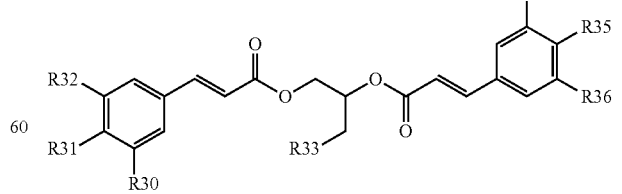

C-161 where R30, R31, R32, R33, R34, R35, and R36 are independently selected from the group consisting of H, OH, C1-C4 alkoxy, and C1-C4 alkylcarbonyloxy.

C-162

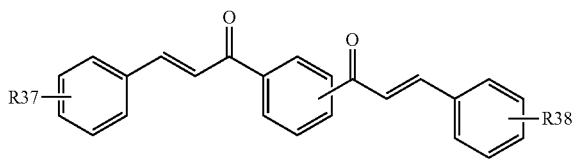

where R37 and R38 are independently selected from the group consisting of methoxy and OH, and the center benzene ring may be substituted in the 1,3- or the 1,4-position with the acryloyl groups.

Additionally, some or all of the carbonyl (C=O) moieties of formulae C-148 through C-162 may be substituted with thio carbonyl (C=S) moieties.

vii. Presently Preferred Curcumin Components

Based upon the structure activity relationships of curcumin and curcumin derivatives, curcumin components of formula C-13A are preferred:

C-13A

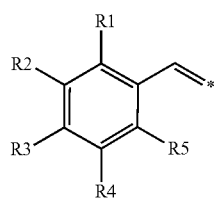

where R1-R5 are as previously defined, and the * denotes the valence point where the additional portion of the compounds are attached. That is, the preferred components have the moiety depicted in C-13A and additional portion exemplified by the foregoing disclosure, e.g., the remaining structure of the linker L and Ar2 or R11.

The most preferred curcumin components are exemplified by formula C-12 where:
 Ar1 and Ar2 are each aryl groups, and especially phenyl, naphthyl, thienyl, pyridinium, and pyridyl groups, and most preferably phenyl groups, wherein all of the foregoing may be substituted or unsubstituted;
 L contains either 5 or 7 backbone carbon atoms and at least one of a carbonyl or hydroxyl group;
 at least one of R1-R5 and R6-R10 is hydroxyl.
Still more preferably, the curcumin components should have:
 the R2 and R7, or R3 and R7, substituents of formulas C-13 and C-14 as hydroxyl;
 the R3 and R8 substituents of formulas C-13 and C-14 as methoxy or ethoxy (most preferably methoxy);
 a β-diketone group in the linker L of formula C-12; and/or
 at least one, and preferably two, carbon-carbon double bonds in the linker L of formula C-12, where at least one of the double bonds is located between the α and β carbons relative to Ar1 and/or Ar2;
 where the curcumin component is not apocynin.

In other embodiments, the curcumin component is taken from compounds of the general formula Ar1-L-Ar2    C-12 where Ar1 and Ar2 are independently selected form the group consisting phenyl and naphthyl groups, where the phenyl groups may be substituted with one or more substituents selected from the group consisting of OH, C1-C4 alkoxys (more preferably C1-C2 alkoxys), C1-C4 haloalkyls (more preferably C1-C2 haloalkyls), halo, and L has from 3-7 backbone carbon atoms including at least one carbonyl group therein.

Use has also been made of a commercially available, proprietary curcumin product sold under the designation "ResCu" by Davospharma, and which is asserted to be a more bioavailable form of standard curcumin. This commercial product has been tested in connection with the invention and found to be a suitable curcumin component.

The Harmine Component(s)

As used herein, "harmine component(s)" shall mean harmine, its metabolites and derivatives, isomers and tautomers thereof, and esters and pharmaceutically acceptable salts of any of the foregoing.

Harmine belongs to the family of β-carboline alkaloids, its chemical name is 7-methoxy-1-methyl 9H-pyrrole[3,4-b]indole, and its molecular formula is C13H12N2O. The base structure of β-carboline is shown in H-0.

H-0

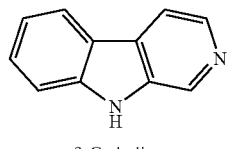

β-Carboline

Harmine has a molecular weight of 212.25 and a melting point of 261° C. Harmine was originally isolated from *Peganum harmala*, which is widely used as a traditional herbal drug in the Middle East and North Africa. The chemical structure of harmine, 1-methyl-7-methoxy-3-carboline, is shown as follows:

H-1

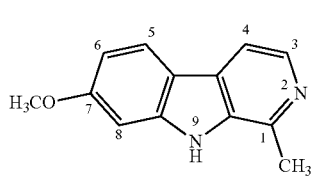

Harmine derivatives, which are variously substituted β-carbolines, are illustrated in the following formulas, which differ in that H-2 has a quaternary ammonium group at the 2-position, whereas H-3 has a tertiary nitrogen at the 2-position.

H-2

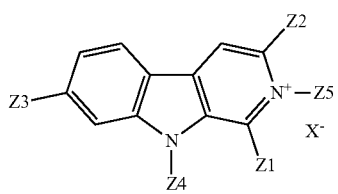

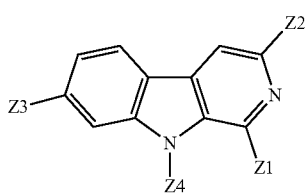

H-3

With reference to formulas H-2 and H-3:
- Z1 is hydrogen; a C1-C6 alkyl or haloalkyl, a C2-C6 alkenyl or haloalkenyl; an aryl group or an arylalkyl group, wherein the aryl group is optionally substituted at any position with halogen, nitro, hydroxyl, C1-C3 alkoxy, amino, sulfonate, sulfoxide, thio, ester, carboxylate, amide, borate, or C1-C4 boronate and wherein the alkyl group is selected from C1-C4 alkyl; or a heterocyclic group;
- Z2 is hydrogen; a C1-C6 carboxyl, ester, carboxylate, acylamino, acyl halide, sulfonate, sulfoxide, thio, amide or alkoxycarbonyl group; an aryloxycarbonyl group; alkyl group optionally substituted with hydroxyl or alkoxycarbonyl; carbamate; acylhydrazine; or a heterocyclic oxycarbonyl group, where the heterocyclic portion contains from 3-7 atoms and a nitrogen, oxygen, boron, or sulfur heteroatom;
- Z3 is hydrogen; a C1-C6 alkyl or haloalkyl; sulfonate, sulfoxide, thio, carboxylate, amide, C2-C6 alkenyl group; hydroxyl; a C1-C6 alkoxy group; a C1-C6 carboxylic ester group; an arylalkoxy group where the alkoxy portion contains from 1-6 carbon atoms; or a heterocyclic group containing from 3-7 atoms and a nitrogen, oxygen, boron, or sulfur heteroatom;
- Z4 is hydrogen; a C1-C6 alkyl, haloalkyl; C2-C6 alkenyl group; a hydroxyalkyl group where the alkyl portion contains from 1-6 carbon atoms; an arylalkyl group wherein the aryl group is optionally substituted at any position with halogen, nitro, hydroxyl, C1-C3 alkoxy, borate, C1-C4 boronate, sulfonate, sulfoxide, thio, ester, carboxylate, amide or amino, and wherein the alkyl group is selected from C1-C4 alkyl group; an arylalkanone; or a heterocyclic group containing from 3-7 atoms and a nitrogen, oxygen, boron or sulfur heteroatom;
- Z5 is hydrogen; a C1-C6 alkyl group; an aryl group substituted at any position with one or more of (1)-(2), where (1) is a C1-C4 alkyl group, and (2) is a C1-C6 carbonyl, hydroxycarbonyl, ester, sulfonate, sulfoxide, thio, ester, carboxylate, amide or amino group; arylalkyl where the alkyl group is a C1-C6 alkyl; 1-5 substituted arylalkyl; arylhydrocarbyl; arylcarboxyl; aryl ester group; arylamino group; or a heterocyclic group containing from 3-7 atoms and a nitrogen, oxygen, boron or sulfur heteroatom;
- X is a halogen; a sulfonic group, a sulfuric group, a nitric acid group or a carboxylate, in the compounds of the above formulas H-2 and H-3:
- Z1 is preferably hydrogen, a C1-C4 alkyl group, or an arylalkyl group; more preferably hydrogen, or a C1-C2 alkyl group; and most preferably methyl;
- Z2 is preferably hydrogen or a C1-C4 alkoxycarbonyl group; more preferably a C1-C2 alkoxycarbonyl group; and most preferably hydrogen;
- Z3 is preferably hydrogen, hydroxyl, or a C1-C4 alkyloxy group; more preferably methoxy;
- Z4 is preferably hydrogen, a C1-C4 alkyl group, a C1-C4 hydroxyalkyl group, or an optionally substituted arylalkyl group; more preferably hydrogen, a C1-C2 alkyl group, or a C1-C2 hydroxyalkyl group; still more preferably ethyl or benzyl; and most preferably hydrogen.

In certain embodiments where Z1 is hydrogen, a C1-C4 alkyl group, or an arylalkyl group, Z2 is hydrogen, hydroxyl, a C1-C4 carboxyl group, a C1-C4 ester group, a carboxylate group, a halogen, or a C1-C4 alkoxycarbonyl group; Z3 is hydrogen, hydroxyl, or a C1-4 alkoxy group; Z4 is hydrogen, a C1-C2 alkyl group, a C1-C2 hydroxyalkyl group, or an optionally substituted arylalkyl group; and Z5 is hydrogen, a C1-C6 alkyl group, or an optionally substituted aryl-alkyl group.

In certain embodiments where Z1 is hydrogen, Z2 is a C1-C2 alkoxycarbonyl group, Z3 is hydrogen, and Z4 is C1-C2 alkyl group, or an optionally substituted arylalkyl group.

In certain embodiments where Z1 is hydrogen, Z2 is ethoxycarbonyl, Z3 is hydrogen, and Z4 is ethyl or benzyl.

In certain embodiments where Z1 is methyl, Z2 is ethoxycarbonyl, Z3 is hydrogen, Z4 is pentafluorobenzyl, and Z5 is hydrogen.

In certain embodiments where Z1 is hydrogen, Z2 is hydrogen, Z3 is hydrogen, Z4 is benzyl, Z5 is benzyl, and X is bromine.

Certain preferred harmine components include β-carboline, tryptoline, pinoline, harmine, harmalol, harmalol hydrochloride hydrate, tetrahydroharmine, harmane, harmol, vasicine, and vasicinone.

Other harmine derivatives include:

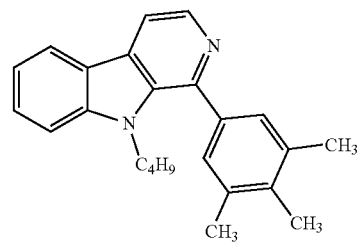

H-4

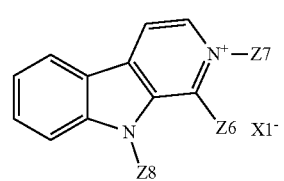

H-5 where Z1, Z2, and Z9 are set forth below, and X1 is a halogen preferably Cl, Br, and F or carboxylate anion.

Based upon the structure-activity relationships of harmine and harmine derivatives, preferred components are illustrated by formula H-6:

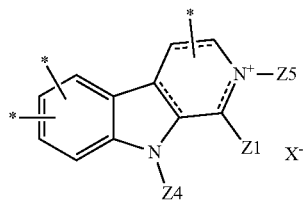

H-6 where the three * denote valence points where respective additional atoms or portions of the components are attached to give complete compounds; the dotted lines in the right-hand six-membered ring of H-6 indicate that the ring may optionally be aromatic; Z1 and Z4 are independently H or a C1-C6 alkyl group, more preferably a C1-C4 alkyl group, and most preferably methyl for Z1 and hydrogen for Z4; and the remaining unoccupied positions on the six-membered rings (i.e., the left-hand phenyl group and the right-hand six-membered ring) are each independently selected from the group consisting of Z1, as previously defined. That is, the preferred harmine components have the moiety depicted in H-1 and additional portions exemplified by the foregoing disclosure. N+ is optionally substituted with Z5, as previously defined. In some cases, X⁻ as previously defined is present. One of ordinary skill in the art would understand that ----- indicates a double or single bond is present. For example, where one of the -* substituents is OCH3 and is located at the No. 7 position as illustrated in formula H-1, the other -* substituents on the remaining unoccupied positions on the terminal 6-membered rings are all H, Z4 is H and Z1 is methyl, and Z5 and X⁻ not existing, the resulting compound is harmine.

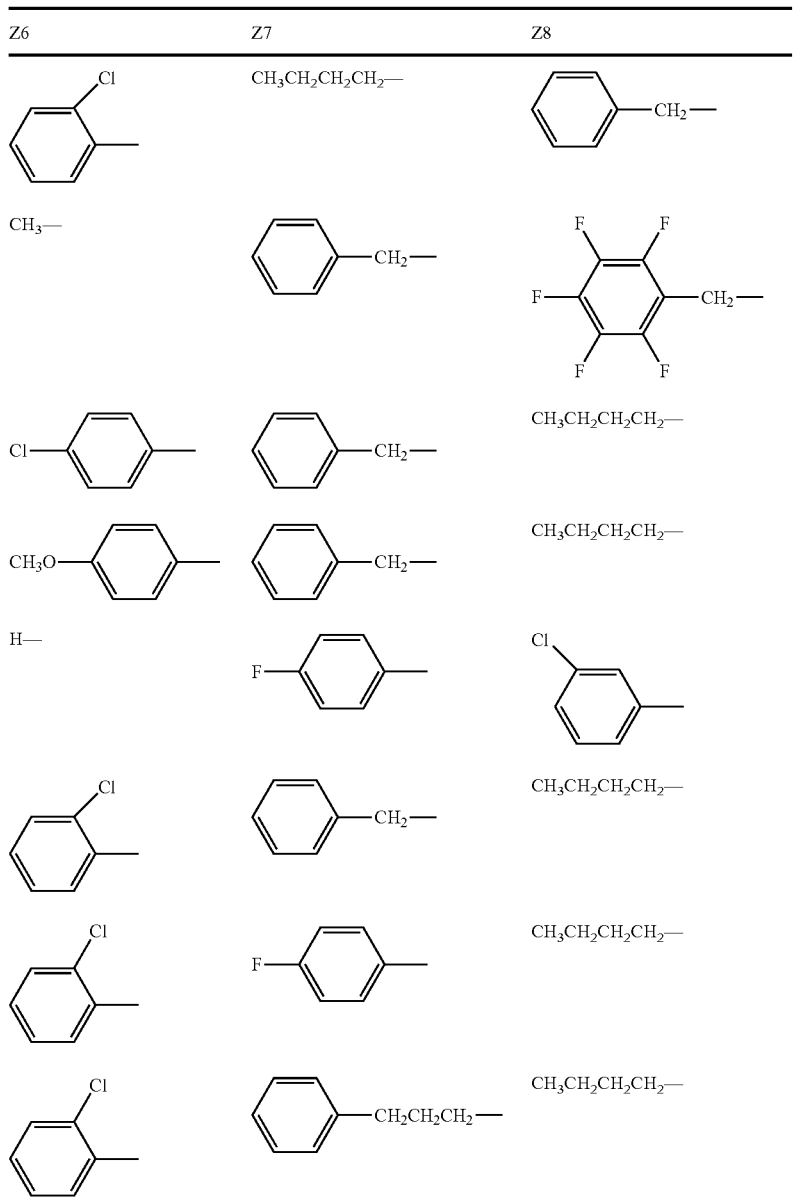

| Z6 | Z7 | Z8 |
|---|---|---|
| 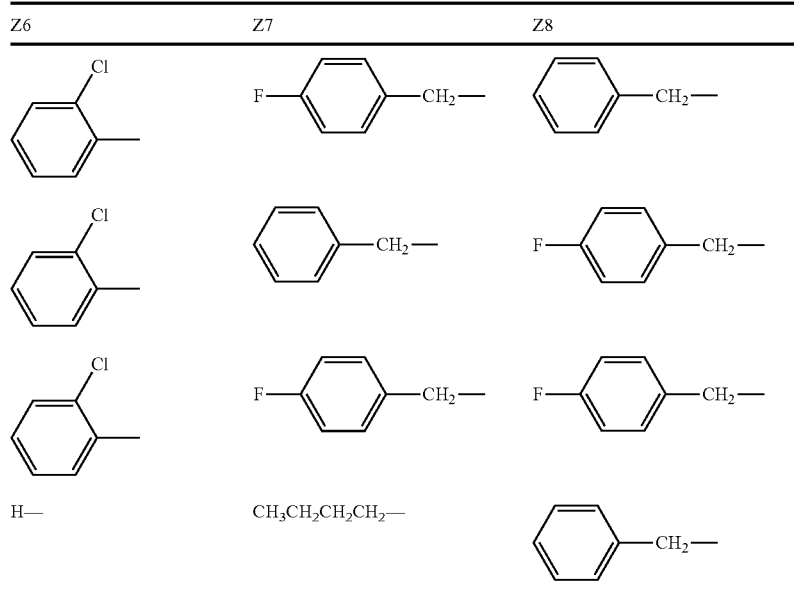 | | |
| H— | CH₃CH₂CH₂CH₂— | |

One class of preferred harmine components are shown in formula H-3, where Z3 is a methoxy or ethoxy group and Z4 is a benzyl group. A second preferred class of harmine components is shown in formula H-2, where Z1 is a methyl group, Z2 is hydrogen, Z3 is a benzyloxy group, Z4 and Z5 are benzyl groups.

In other embodiments, preferred harmine components include compounds of the formula

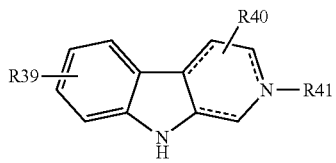

H-7

R39 is selected from the group consisting of H, C1-C4 alkoxys (more preferably C1-C2 alkoxys), O, and OH substituents, R40 is selected from the group consisting of H, C1-C4 alkyls (more preferably C1-C2 alkyls), C1-C4 haloalkyls (more preferably C1-C2 haloalkyls), C1-C4 alkoxys (more preferably C1-C2 alkoxys), nitrophenyls, C1-C4 organic acids (more preferably C1-C2 organic acids), C1-C4 alkylalcohols (more preferably C1-C2 alkylalcohols), and C1-C6 alkyl esters (more preferably C2-C4 alkyl esters), and R41 is selected from the group consisting of nothing, H, and nitrophenyls.

The Isovanillin Component(s)

As used herein, "isovanillin component(s)" refers to isovanillin, its metabolites and derivatives, isomers and tautomers thereof, and esters and pharmaceutically acceptable salts of any of the foregoing.

Isovanillin is a phenolic aldehyde having a hydroxyl group at the meta position and a methoxy group at the para position. Isovanillin is illustrated in the following structure:

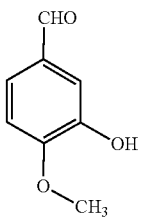

I-1

Isovanillin is metabolized in vivo to vanillin, which is the same as structure I-1, except that the hydroxyl and methoxy substituents are exchanged, i.e., in vanillin, the hydroxyl group is in the para position, and the methoxy group is in the meta position.

Useful derivatives of isovanillin have the following general formula:

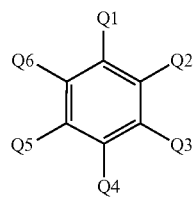

I-2 where at least one of Q1-Q6 is an alkoxy group and/or an aldehyde group, especially where the alkoxy and/or aldehyde groups contain from 1-6 carbon atoms; more preferably, where Q1 is an aldehyde, alcohol, amine, carbonyl, carboxylate, C1-C6 alkylhydroxy, ester, imidazole, nitro, sulfonate, sulfoxide, thio, amide, oxime, borate, or boronate, or semicarbazone group; the Q2-Q6 groups are independently selected from hydrogen, hydroxyl, halo, nitro, C1-C6 alkoxy, C1-C6 alkyl or alkenyl groups, with the proviso that at least one of the Q2-Q6 groups is an alkoxy group. In more preferred forms, the aldehyde, alcohol, amine, carbonyl, carboxylate, and ester groups should have a C1-C6 carbon chain length, the boronate is a C1-C4 boronate, and at least one of the Q2-Q6 groups is an alkoxy group (most preferably methoxy), and another is a hydroxyl group; advantageously, the alkoxy and hydroxyl groups are adjacent each other. In particularly preferred forms, the remainder of the Q2-Q6 groups, apart from the alkoxy and hydroxyl groups, are all H. Advantageously, the isovanillin components of the invention should include only one phenyl group and are free of any fused ring structures (as used herein, "fused ring structures" refer to structures such as found in naphthalene or anthracene where two rings share common atoms).

Some preferred isovanillin components are selected from isovanillin, vanillin, ethyl vanillin, ortho-vanillin, vanillic acid, isovanillic acid, vanillic alcohol, isovanillic alcohol, 6-bromine-5-hydroxy-4-methoxybenzaldehyde, 4-hydroxy-3,5-dimethoxybenzaldehyde, 4,5-dihydroxy-3-methoxybenzaldehyde, 5-hydroxy-4-methoxybenazldehyde, 2-Benzyloxy-3-methoxybenzaldehyde, 2-(2-benzyloxy-3-methoxyphenyl)-1H-benzimidazole, N–1-(2-benzyloxy-3-methoxybenzyl)-2-(2-benzyloxy-3-methoxyphenyl)-1H-benzimidazole, and (S)-1-(2-benzyloxy-3-methoxyphenyl)-2,2,2-trichloroethyl benzenesulfonate (regarding the last four compounds, see Al-Mudaris et al., *Anticancer Properties of Novel Synthetic Vanillin Derivatives* (2012)).

Certain imidazole derivatives (such as nitro-imidazoles) have been shown to have significant anticancer activity, see, e.g., Sharma et al., "Imidazole Derivatives Show Anticancer Potential by Inducing Apoptosis and Cellular Senescence," *Med. Chem. Commun.* 2014, 5, 1751, incorporated by reference herein. Representative imidazole derivatives include:

I-3
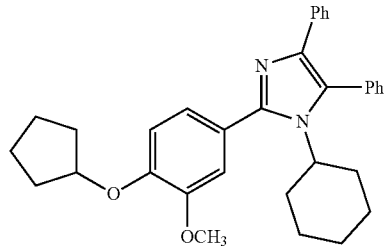

I-4
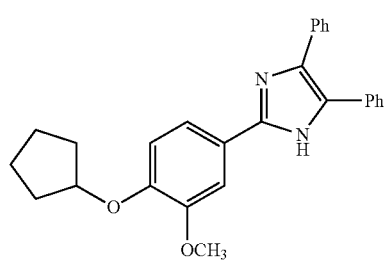

I-5
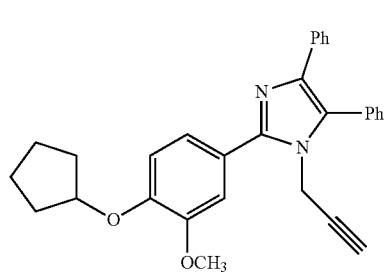

I-6
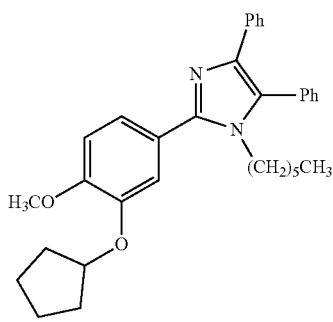

I-7
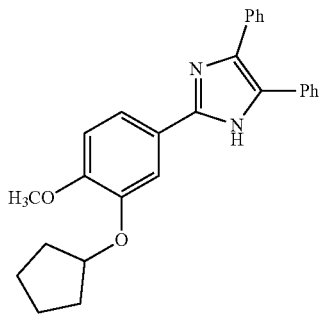

I-8
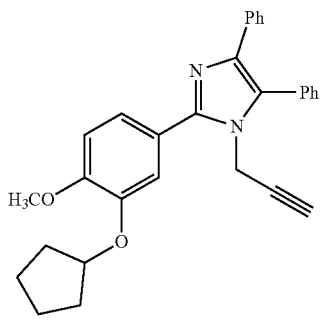

I-9
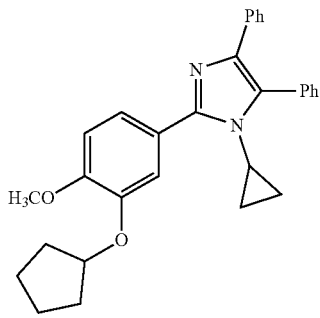

I-10
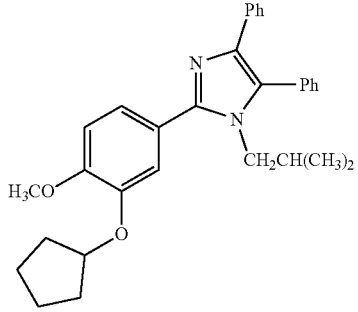

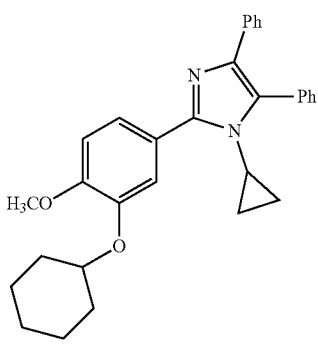

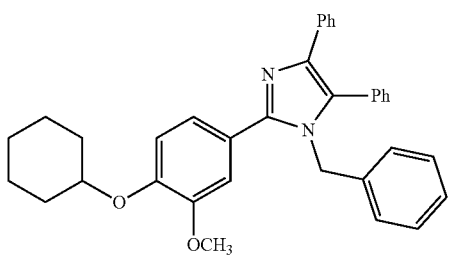

Additional isovanillin derivatives of interest are:

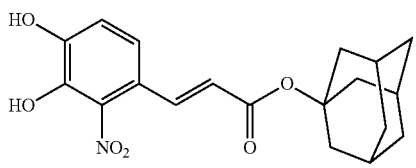

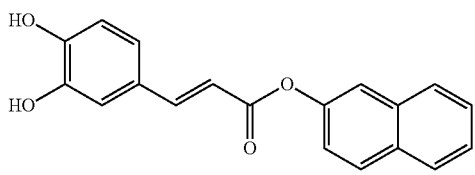

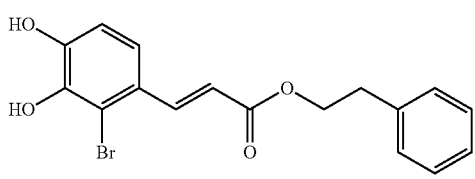

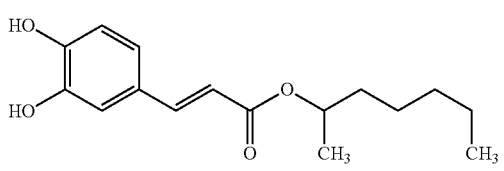

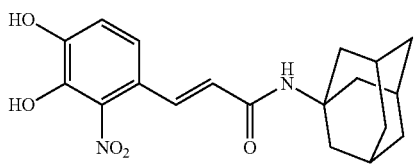

It will be appreciated that the aryl group substituents in formulas I-14-I18 can be at any desired position on the on the aryl rings, e.g., the —OH need not be adjacent and the heteroatom substituents may be at any desired location.

Based upon the structure-activity relationships of isovanillin and isovanillin derivatives, preferred components are illustrated by formula I-13:

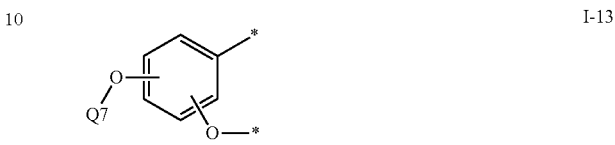

where the two * denote valence points where respective additional atoms or portions of the components are attached to form complete compounds, the remaining phenyl ring positions not taken by the two depicted moieties are independently R1 as previously defined with reference to formula C-13, and Q7 is H or a C1-C6 alkyl group, more preferably a C1-C4 alkyl group, and most preferably methyl. That is, the preferred isovanillin components have the moiety depicted in 1-13 and additional portions exemplified by the foregoing disclosure. For example, where * is CHO, the substituent —O-Q7 is located at the para position, Q7 is a methyl group, and the —O—* group is located at the meta position, the * of the —O—* moiety is H, and the remaining unoccupied positions on the phenyl ring are all H, the resulting compound is isovanillin. In preferred forms, the isovanillin component is not apocynin.

In other embodiments, the isovanillin components are selected from the compounds of the formula

where Q9 is selected from the group consisting of C1-C4 aldehydes (more preferably C1-C2 aldehydes), C1-C4 alkylalcohols (more preferably C1-C2 alkylalcohols), C1-C4 alkyl esters (more preferably C1-C2 alkyl esters), and C1-C4 organic acids (more preferably C1-C2 organic acids), Q10 is selected from the group consisting of OH, H, C1-C6 alkyl esters (more preferably C1-C4 alkyl esters), C1-C4 alkoxys (more preferably C1-C2 alkoxys), and benzyloxy, and Q11 is selected from the group consisting of H, C1-C4 alkoxys (more preferably C1-C2 alkoxys), and OH.

The Complete Compositions of the Invention

In the case of the preferred three-component compositions of the invention, made by combining individual quantities of normally highly purified curcumin component(s), harmine component(s), and isovanillin component(s), the as-added amounts should give weight ratios of about 10:1.7:0.85 (isovanillin component(s):harmine component(s):curcumin component(s)), but more broadly, the ratios are approximately 0.1-25:0.1-5:0.1-5 (isovanillin component(s): harmine component(s):curcumin component(s)). In this respect, it will be seen that the isovanillin component(s) of the preferred GZ17-6.02 product is/are the preponderant component(s) in the compositions on a weight basis, with the harmine and curcumin component(s) being present in lesser amounts on a weight basis. Generally, the isovanillin component(s) in the most preferred product should be present at a level at least three times (more preferably at least five times) greater than that of each of the harmine and curcumin component(s), again on a weight basis. However, the invention is not limited to such weight ratios. As noted in Example 17, an isovanillin component:harmine component:curcumin component weight ratio of 1:1:1 is also effective. In terms of amounts of the three components, the isovanillin component(s) should be present at a level of from about 25-85% by weight, the harmine component(s) should be present at a level of from about 7-50% by weight, and the curcumin component(s) should be present at a level of from about 5-40% by weight, based upon the total weight of the three components taken as 100% by weight.

In the case of two-component compositions in accordance with the invention made up of curcumin component(s) plus harmine component(s), the weight ratio of the curcumin component(s):harmine component(s) should range from about 0.01:1 to 10:1; and the weight amounts of the curcumin component(s) should range from about 20% to 75% by weight (more preferably from about 30-55% by weight, and most preferably about 45% by weight), and the weight amounts of the harmine component(s) should range from about 25% to 80% by weight (more preferably from about 45% to 70% by weight, and most preferably about 55% by weight), based upon the total weight of the two components in the compositions taken as 100% by weight. Generally, the amount of the harmine component should be greater than the amount of the curcumin component in these two-component compositions.

Two-component compositions made up of isovanillin component(s) plus curcumin component(s) should have a weight ratio of the isovanillin component(s):curcumin component(s) ranging from about 0.5:1 to 25:1; and the weight amounts of the isovanillin component(s) should range from about 25% to 95% by weight (more preferably from about 75% to 95% by weight, and most preferably about 88% by weight), and the weight amounts of the curcumin component(s) should range from about 5% to 75% by weight (more preferably from about 5% to 25% by weight, and most preferably about 12% by weight), based upon the total weight of the two components in the compositions taken as 100% by weight.

Finally, two-component compositions made up of isovanillin component(s) plus harmine component(s) should have a weight ratio of the isovanillin component(s):harmine component(s) should range from about 0.5:1 to 15:1; and the weight amounts of the isovanillin component(s) should range from about 25% to 95% by weight (more preferably from about 75% to 95% by weight, and most preferably about 85% by weight), and the weight amounts of the harmine component(s) should range from about 5% to 75% by weight (more preferably from about 5% to 25% by weight, and most preferably about 15% by weight) by weight, based upon the total weight of the two components in the compositions taken as 100% by weight.

In this connection, it should be understood that the isovanillin component(s) of any of the foregoing two- or three-component compositions containing isovanillin component(s) may be made up of initially added isovanillin component(s) plus any degradation products of the other component(s) yielding products within the ambit of the isovanillin component(s); for example, it is known that under certain circumstances curcumin will spontaneously degrade to give quantities of vanillin, and, in such circumstances, the total amount of the isovanillin component(s) would be the initially added amounts together with these degradation products. More broadly, the ultimate amounts of the curcumin, harmine, and isovanillin component(s) in the compositions of the invention should be determined based upon the actual contents of the component(s) in question, regardless of whether these component(s) are derived from the originally added component(s) or as degradation products of some or all of these originally added component(s).

As indicated previously, levels of dosing using the compositions of the invention is quite variable owing to factors such as the patient's age, patient's physical condition, the type of condition(s) being treated (e.g., specific cancer(s)), and the severity of the conditions. In general, however, regardless of the dosage form or route of administration employed, such as liquid solutions or suspensions, capsules, pills, or tablets, via oral, parenteral, or injection, the compositions should be dosed of from about 5 to 2000 mg per day, and more usually from about 100-800 mg per day. Such dosages may be based on a single administration per day, but more usually multiple administrations per day.

Finally, the invention also embraces compositions and methods where the individual components are provided and administered separately to subjects, so long as the therapeutic effects of the invention are substantially preserved.

Examples 1-28

The following Examples set forth preferred therapeutic agents and methods in accordance with the invention, but it is to be understood that these examples are given by way of illustration only, and nothing therein should be taken as a limitation upon the overall scope of the invention. A number of the Examples set forth various tests using the preferred drug of the invention, GZ17-6.02, which is sometimes referred to as GZ17Syn-6.02.

The GZ17-6.02 product of the Examples was made by dispersing quantities of solid synthetic isovanillin (771 mg, 98% by weight purity), synthetic harmine (130.3 mg, 99% by weight purity), and a commercially available curcumin product derived by the treatment of turmeric (98.7 mg, containing 99.76% by weight curcuminoids, namely 71.38% curcumin, 15.68% demethoxycurcumin, and 12.70% bisdemethoxycurcumin), in a 1 mL ethanol at a weight ratio of 771:130.3:98.7 (isovanillin:harmine:curcumin product) in ethanol followed by sonication of the dispersion. Aliquots of this stock solution were then used to create the different GZ17-6.02 dilutions using stock media of the cells in question.

The two-component products described in Example 23 were made in the same fashion as the GZ17-6.02 agent, and the weight ratios of the two components were as set forth immediately above, e.g., the isovanillin/harmine sub-combinations contained a weight ratio of 771:130.3, and so forth.

Example 1

In this example, the preferred GZ17-6.02 product was tested with two different human head and neck cancers (HN5 and OSC19), in order to determine the extent of cell death induced by the product.

Methods

The respective cells were individually cultured in a growth medium prepared using RPMI-1640 medium containing 11.1 mM D-glucose with 10% fetal bovine serum, 10 mM HEPES, 2 mM L-glutamine, 1 mM sodium pyruvate, 0.05 mM 2-mercaptoethanol, and Antibiotic-Antimycotic. These cells were maintained in T75 tissue culture flasks in a humidified incubator at 37° C. and 5% $CO_2$. The media were changed on a third day after cell plating, and the cells were passaged on day 5 by trypsinization.

Formation of Cancer Spheroids

Custom-made micromolds with 100 m diameter wells were loaded with the cells (U.S. Pat. No. 8,735,154, incorporated by reference herein). The media were changed every day by partial replacement. Cell aggregates were allowed to form in the micromolds for 72 hours and then were transferred to a 100 mm non-treated tissue culture dishes for 3 additional days. The spheroids were passed through 70 m and 100 m cell strainers (#3431751 and #43152, Corning, Tewksbury, Mass.) and maintained in HEPES Balanced Salt Solution comprised of: 20 mM HEPES, 114 mM NaCl, 4.7 mM KCl, 1.2 mM $KH_2PO_4$, 1.16 mM $MgSO_4$, 2.5 mM $CaCl_2$, 25.5 mM $NaHCO_3$ and 0.2% bovine serum albumin (fatty acid free), pH 7.2.

Testing of GZ17-6.02 on Head and Neck Cancer Spheroids

Individual wells of a 96 well plate were manually loaded with 15-20 cancer spheroids each, and exposed to selected doses of GZ17-6.02. Each trial was run with at least 4 replicates at each dose. After a 24 hour exposure to the selected dosages of GZ17-6.02, PrestoBlue (Life Technologies, Inc) was added to each well and fluorescence readings were taken 4-6 hours later with an excitation wavelength of 485 nm and an emission wavelength of 560 nm, using a microplate reader (Enspire Multimode, PerkinElmer). Results were averaged following background subtraction and normalized to untreated cell controls.

FIG. 1 demonstrated that GZ17-6.02 dramatically kills HN5 and OSC19 cancer cells in a dose-dependent manner. The X axis is the increasing dose of GZ17-6.02 and the Y axis is the average number of live cells in each well at the end of a 24 hour exposure to the stated dose of GZ17-6.02.

Example 2

In this example, GZ17-6.02 was found to induce significant cancer cell death in human pediatric leukemia cells and pediatric osteosarcoma in a dose-dependent manner.

Jurkat leukemia cells were grown in suspension in media (RPMI supplemented with 10% FBS), maintained at approximately 500,000 cells/mL. The cells were plated in 96-well plates, and each well was exposed to a selected dose of GZ17-6.02 for 24 hours (a minimum of 4 replicates for each dosage). These cells were not treated to generate spheroids, but were directly plated onto the well plates. After a 24 hour exposure to the selected dosages of GZ17-6.02, PrestoBlue (Life Technologies, Inc) was added to each well and fluorescence readings were taken 4-6 hours later with an excitation wavelength of 485 nm and an emission wavelength of 560 nm, using a microplate reader (Enspire Multimode, PerkinElmer). Results were averaged following background subtraction and normalized to untreated cell controls.

Human osteosarcoma cells (HOS) also had a significant dose-dependent increase in cell death when exposed to GZ17-6.02 for 24 hours. The methods to create and test osteosarcoma spheroids were the same as the methods described in Example 1.

As illustrated in FIGS. 2A and 2B, increasing doses of GZ17-6.02 induced significant cell death in both leukemia and osteosarcoma cell types tested.

Example 3

In this example, the effect of increasing doses of GZ17-6.02 in killing human lymphoma cells (mo205) and human lung cancer cells (H358) was tested.

The lymphomas treatment methods used were identical to those described in Example 2 relative to the pediatric leukemia cells, whereas the lung cancer treatment method was the same as described in Example 1.

FIGS. 3A and 3B set forth the results of these tests, and demonstrate the effectiveness of GZ17-6.02 in inducing lymphoma and lung cancer cell death.

Example 4

In this example, the effect of increasing doses of GZ17-6.02 in killing human ovarian cancer cells (A1847) and human prostate cancer cells (22rv1) was tested.

The cells were treated and tested as set forth in Example 1.

Figure 4A:
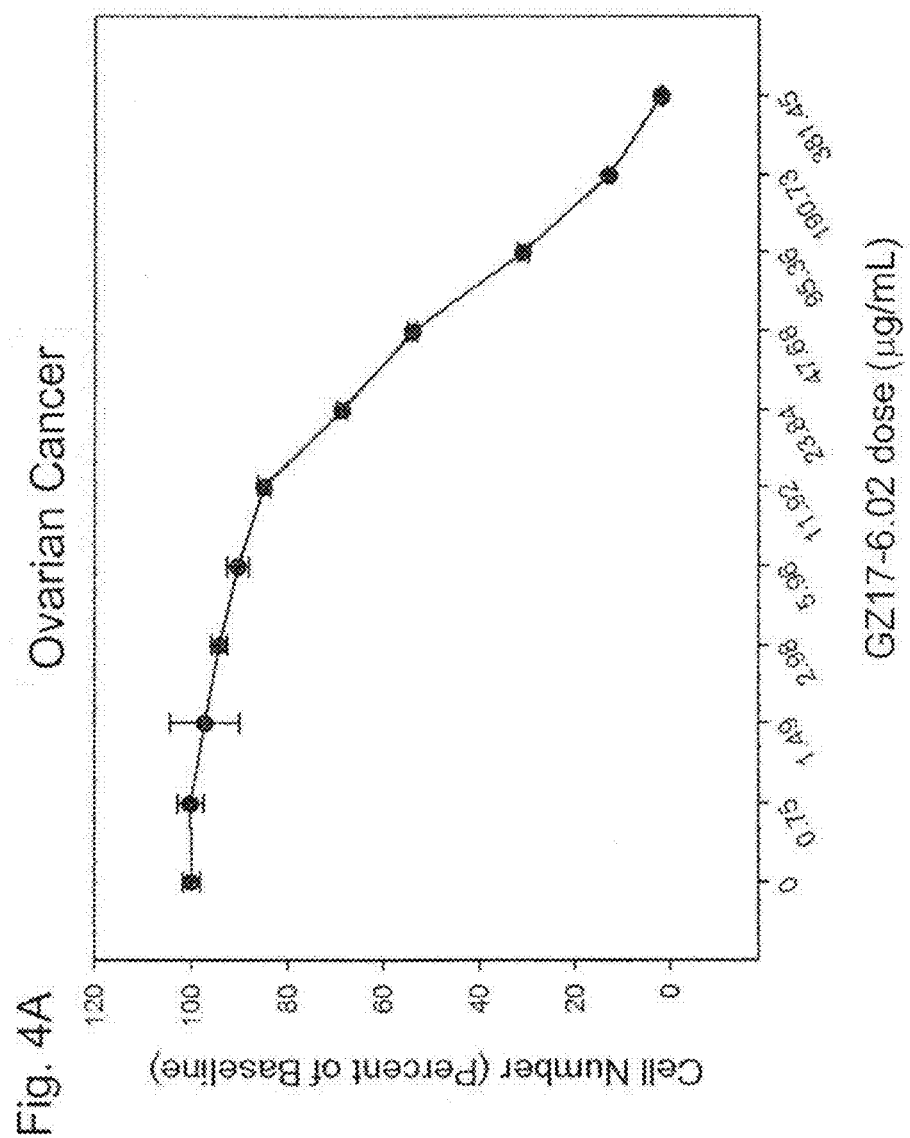
FIG. 4A is a graph of cell number versus dosage amounts of GZ17-6.02, illustrating the effect thereof GZ17-6.02 in inducing the death of ovarian cancer cells, as described in Example 4.

This test confirmed that both types of cells experienced dose-dependent death when exposed to GZ17-6.02, see FIGS. 4A and 4B.

Example 5

In this example, the effect of increasing doses of GZ17-6.02 in killing human breast cancer cells (du4475) and human pancreatic cancer cells (panc-1) was tested.

The cells were treated and tested as set forth in Example 1, except that a different growth medium was used, namely Dulbecco's Modified Eagle Medium (DMEM) with 10% fetal bovine serum, and 1% penicillin/streptomycin mix (Sigma-Aldrich).

Figure 5B:
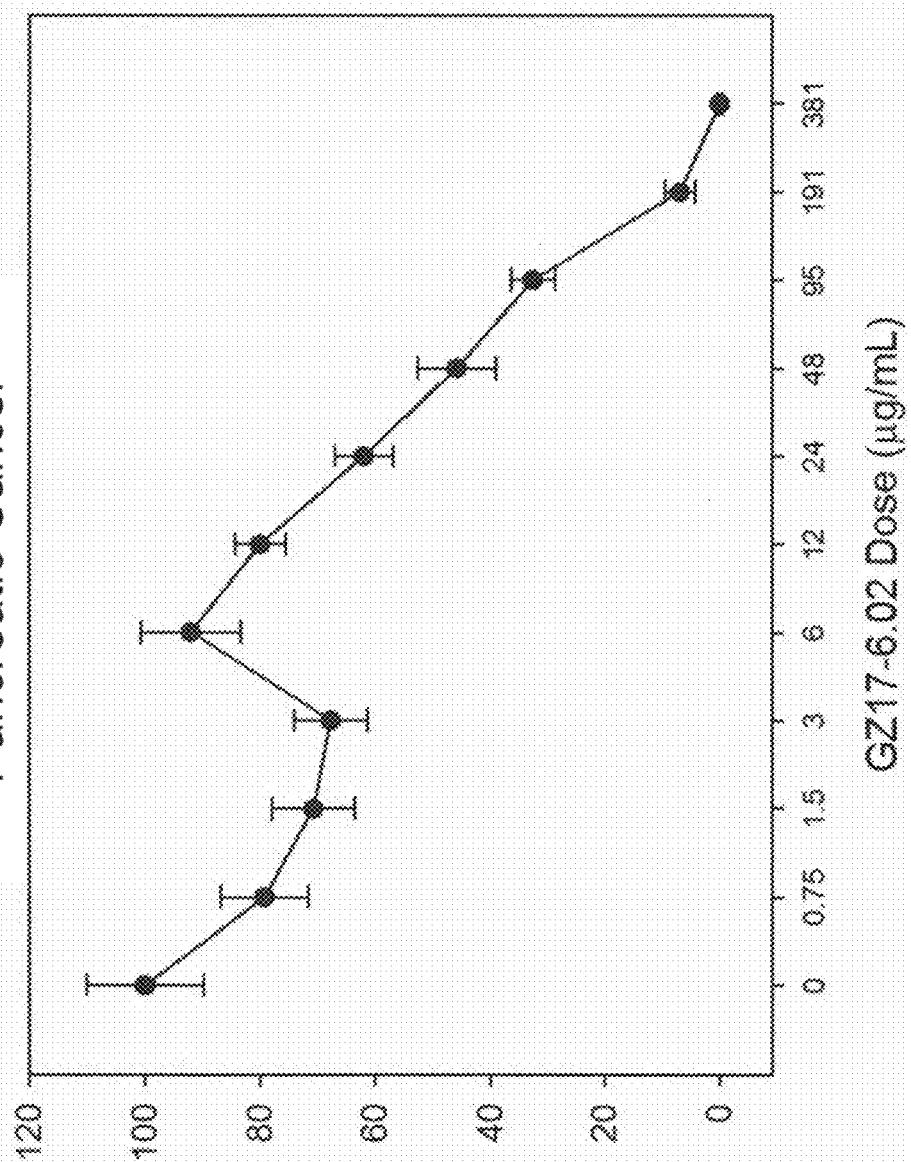
FIG. 5B is a graph of cell number versus dosage amounts of GZ17-6.02, illustrating the effect thereof in inducing the death of pancreatic cancer cells, as described in Example 5.

This test confirmed that both types of cells experienced dose-dependent death when exposed to GZ17-6.02, see FIGS. 5A and 5B.

As is evident from Examples 1-5, ten different cancer types were tested with GZ17-6.02 and they all were sensitive to the therapeutic agent. In most of the cancers (head and neck cancer (OSC19), leukemia, osteosarcoma (bone cancer), lymphoma, lung cancer, ovarian, prostate, breast, and pancreatic cancer), the compound killed nearly all of the cells in the dish at a dose of 3.13-6.25 mg/mL. This array of cancer types represents a substantial portion of human cancers. Moreover, the results confirm that the therapeutic agent is effective in both solid tumor cancers and blood cancers.

Example 6

In this test, non-cancerous integumental (dermal) fibroblasts (hgf-1) were tested with GZ17-6.02 and compared with prostate cancer (22rv1) and ovarian cancer cells (A1847), to determine the effect of GZ17-6.02 on the non-cancerous cells versus the prostate cancer and ovarian cancer cells.

The fibroblasts were treated as follows: The cells were grown to confluence in the DMEM medium of Example 5, and then placed in 96-well plates where they adhered to the bottom of the plates. Each well was then exposed to a selected dose of GZ17-6.02 for 24 hours (a minimum of 4 replicates each), and tested according to Example 1. The prostate cancer and ovarian cancer results were taken from the previous Example 4.

As illustrated in FIG. 6, the cancer cells begin to die at lower GZ17-6.02 doses than the non-cancerous fibroblast cells, demonstrating that GZ17-6.02 is more toxic to cancer cells versus the non-cancerous fibroblasts.

Example 7

Migration of cells away from a primary tumor, followed by invasion of those tumor cells first into the blood vessels and later out of the blood vessels and into other tissues, are the two steps essential for metastases to form from a primary tumor. The cells were grown in the DMEM media of Example 5.

Head and neck cancer cells (OSC19) were tested using a commercially available migration assay kit, Cultrex 96 Well Migration Assay (R&D Systems). The cell movement from the upper compartment to the lower compartment was measured as representative of cell migration. A negative control migration was also measured, using the GZ17-6.02 vehicle, namely a dilution of ethanol in the growth media to the same concentration as GZ17-6.02 in the growth media.

The head and neck cancer cells were also assayed for migration using a Cultrex Cell Invasion Assay (R&D Systems). The ability of the head and neck cancer cells to invade a collagen matrix was measured by counting cells that exited the upper chamber and passed through a collagen-surrounded lower chamber. Similarly, a negative control for invasion was also measured, using the same ethanol vehicle employed in the migration assay.

Figure 7A:
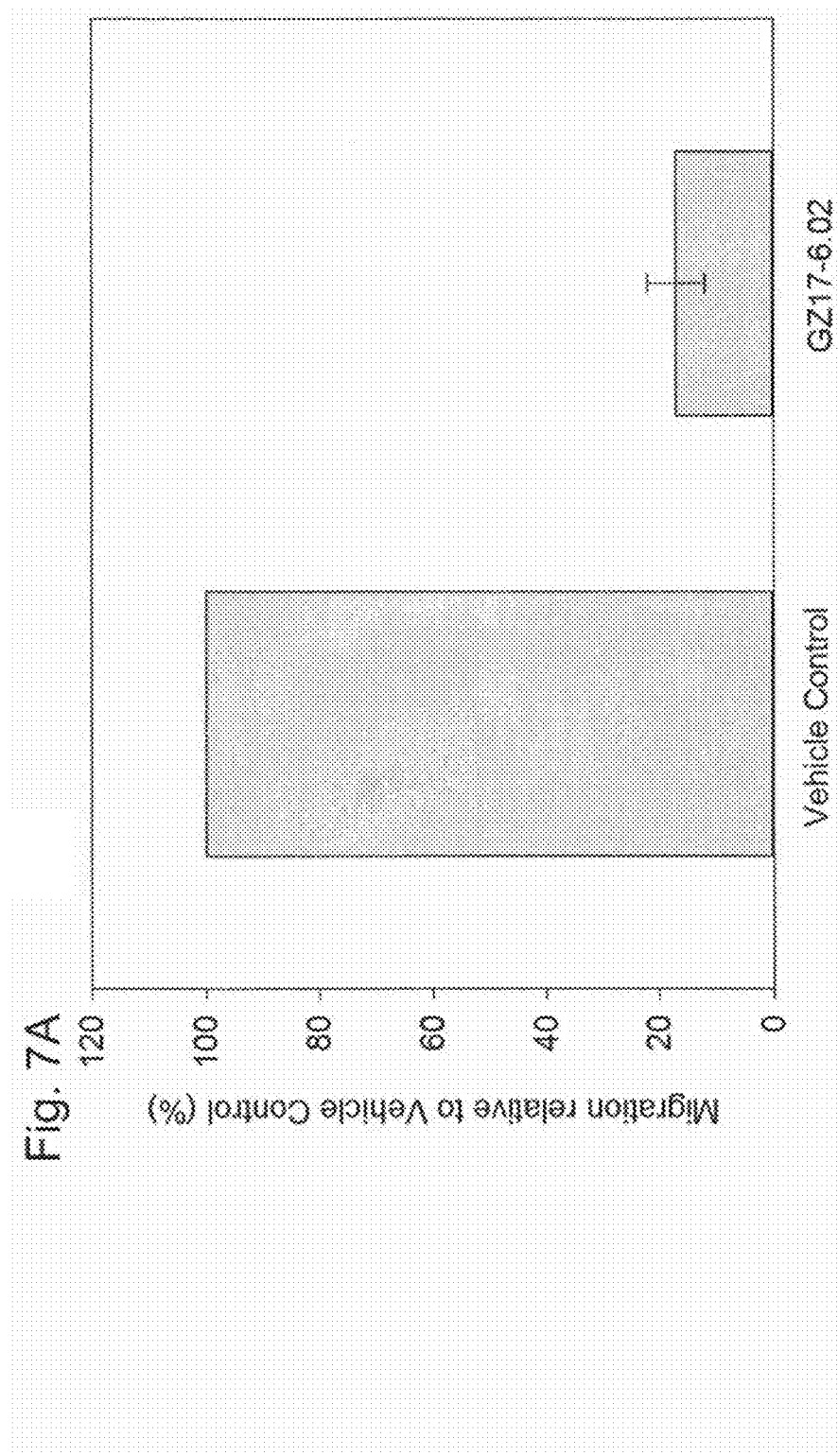
FIG. 7A is a graph illustrating the effect of GZ17-6.02 in preventing migration of head and neck cancer cells, as described in Example 7.

As illustrated in FIG. 7A, the GZ17-6.02 significantly inhibited migration so that almost no head and neck cancer cells could migrate from the site of origin. Likewise, GZ17-6.02 significantly inhibited invasion (FIG. 7B) by more than 60%.

Example 8

In this test, the synergism of GZ17-6.02 with doxorubicin (a common chemotherapy drug) was tested on ovarian cancer cells. In this test, increasing doses of doxorubicin were administered to ovarian cancer spheroids and cell deaths were measured, as described in Example 1. The protocol involved testing doxorubicin alone at various dosages (FIG. 8, doxorubicin alone—closed circles), with comparative tests using the various dosages of doxorubicin in combination with either 0.2 mg/mL (FIG. 8 open circles) or 0.4 mg/mL (FIG. 8 closed triangles) GZ17-6.02. Additionally, the induced cell death results from use of 0.2 mg/mL GZ17-6.02 alone (FIG. 8, line A) and 0.4 mg/mL GZ17-6.02 alone (FIG. 8, line B) were determined.

As is evident from FIG. 8, even at the lowest dose of doxorubicin (0.002 µM), the addition of GZ17-6.02 at 0.2 and 0.4 mg/mL increased cell death significantly below the level of either compound alone. At low doses of doxorubicin alone (up to 0.158 µM), doxorubicin was ineffective. GZ17-6.02 administered alone at a dose of 0.2 mg/mL resulted in cell death at a level represented by the upper horizontal dotted line in FIG. 8. Moreover, GZ17-6.02 administered alone at a dose of 0.4 mg/mL resulted in cell death at a level represented by the lower horizontal dotted line in FIG. 8. Thus, even at these low dosages, addition of GZ17-6.02 significantly increased cell death (see data points under both of the horizontal dotted lines in FIG. 8). This demonstrates the synergy of the combination of GZ17-6.02 and doxorubicin, even at low dosages of both GZ17-6.02 and doxorubicin. This trend is confirmed at higher dosages of doxorubicin, where the combined products were always more effective than doxorubicin alone.

Example 9

Figure 9A:
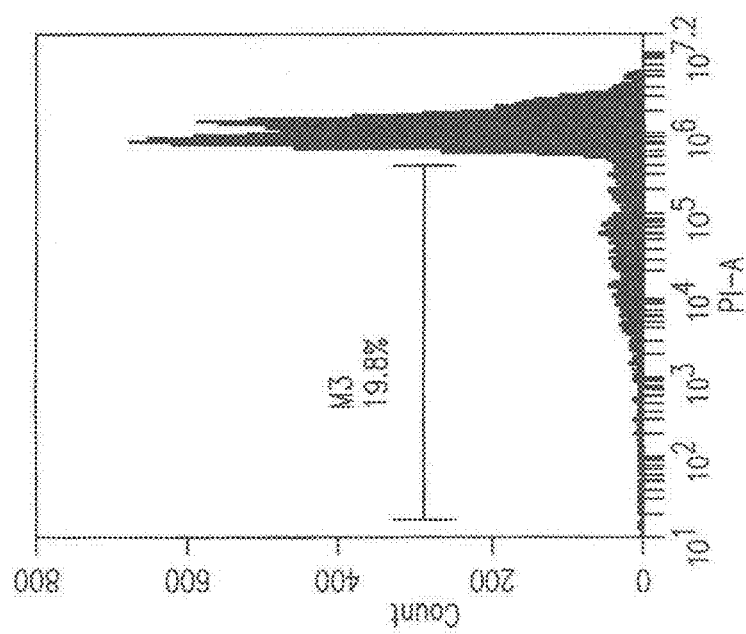
FIG. 9A is a graph illustrating extent of apoptosis in a control test, as described in Example 9, and illustrating about 19.8% cell death via apoptosis.
Figure 9B:
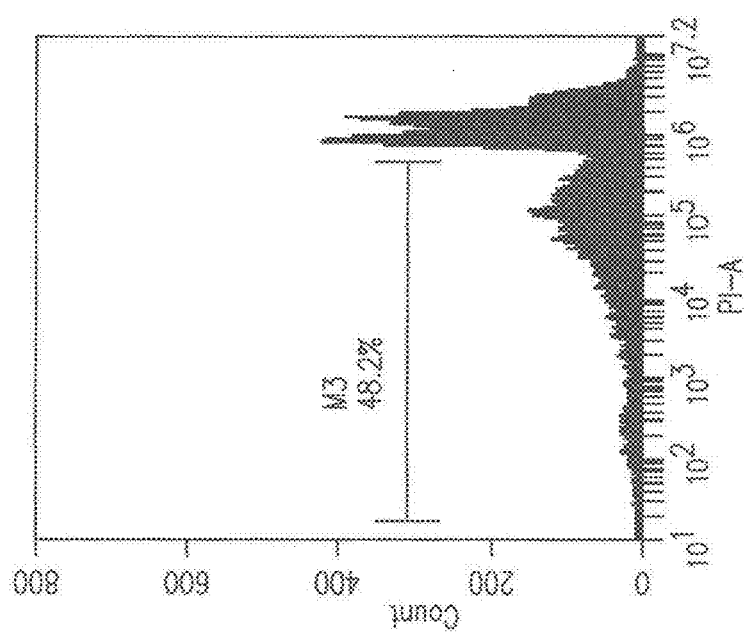
FIG. 9B is a graph illustrating extent of apoptosis in a test identical to the control test of FIG. 9A, but including GZ17-6.02, as described in Example 9, and illustrating about 48.2% cell death via apoptosis.

There are multiple general ways in which cancer (blood or solid tumors) can be blocked by chemotherapy. One is to actually induce death in the cancer cells (apoptosis), and a second is to block the ability of cells to receive nutrients, basically starving them to death (necrosis). This test demonstrates that at the $ED_{50}$ of GZ17-6.02 on head and neck cancer cells (OSC19) caused cell death via apoptosis. In the test, head and neck cancer cells were stained with an apoptotic fluorophore and sorted by flow cytometry, which allows a single cell to be counted and measured for fluorescence simultaneously. This histograms in FIGS. 9A and 9B illustrate the shift in fluorescence intensity to a lower level, indicating apoptotic cell death. While the control (FIG. 9A, head and neck cancer cells without GZ17-6.02) had little apoptotic cell death (19.8%), 48.2% of the cells exposed to GZ17-6.02 died of apoptosis (FIG. 9B). This indicates one type of mechanism of action of GZ17-6.02.

Example 10

Caspase proteins are intracellular proteins involved in the apoptotic programmed cell death pathway. In instances where live lung cancer cell number decrease while a caspase protein increases, it can be inferred by association that the caspase was activated, and was thus associated with the molecular pathway of the cell death.

In these tests, the lung cancer cells (H358) were assayed using caspase testing kits (Promega Caspase-Glo 3/7, -Glo 2, -Glo 6, -Glo 8, and -Glo 9). Sample lung cancer cells were homogenized on ice in the provided preparation buffer and agitated on a plate shaker at low speeds (around 300 rpm). The supernatants were exposed to the provided assay solutions and read on a microplate reader for luminescent output (Enspire Multimode, PerkinElmer).

Figure 10A:
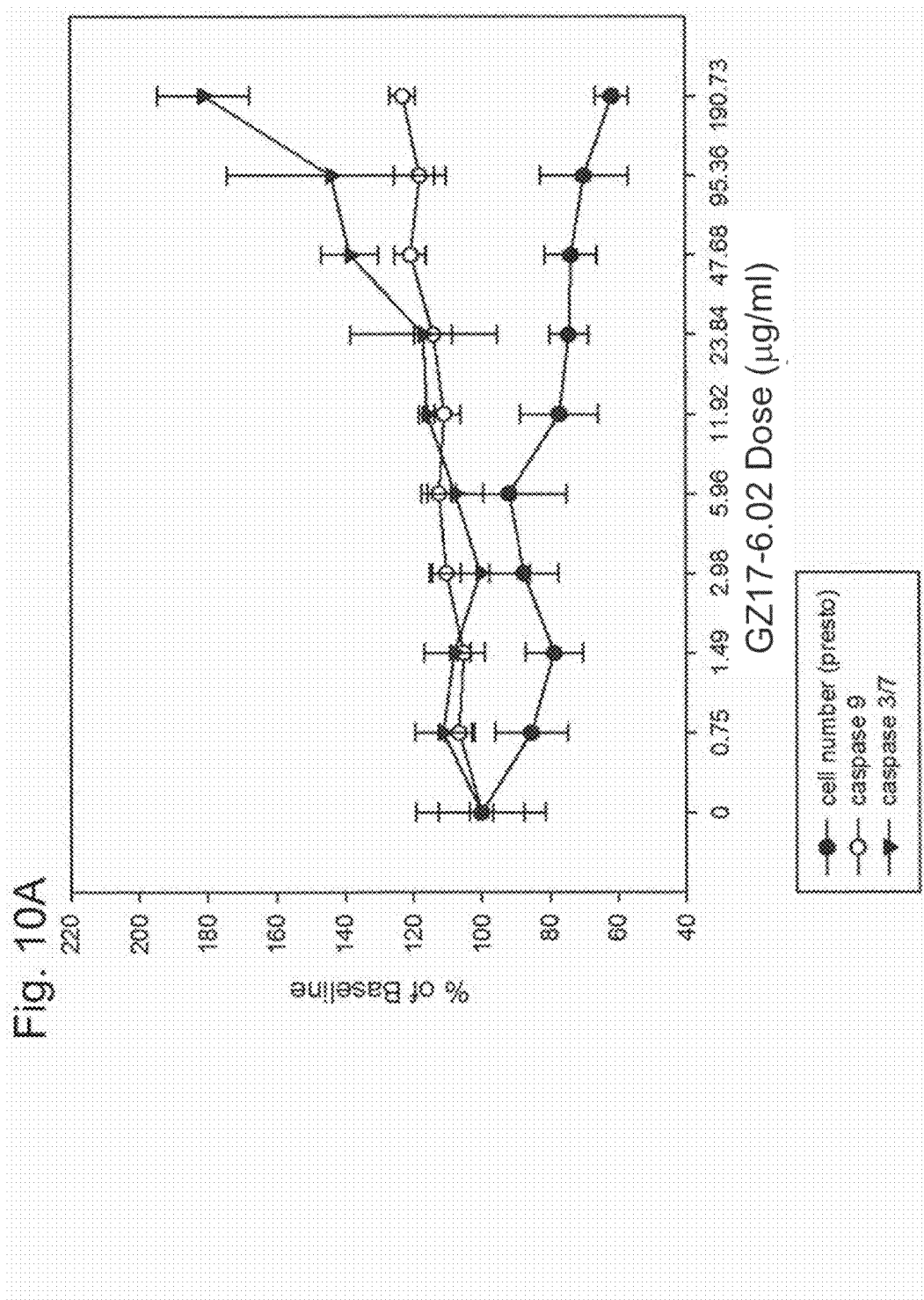
FIG. 10A is a graph illustrating that caspase 3 and 7 concentrations increased in response to GZ17-6.02, but caspase 9 levels did not change in response to GZ17-6.02 in lung cancer cells, as described in Example 10.

The test results indicated that caspases 3 and 7 (FIG. 10A, filled triangles) increased dramatically in association with cell death (filled circles). In addition, results indicated that caspase 6 (FIG. 10B, open circles) increased in association with cell death (filled circles). In contrast, caspase 9 was not activated (FIG. 10A, open circles). This implies a receptor-mediated cell death pathway and not a mitochondrial cell death pathway. In order to confirm this, an ATP assay (CellTiter-Glo, Promega) was conducted in which toxicity of the mitochondria were measured at the same time as cell death, based upon ATP concentrations. If a mitochondrial toxicity were responsible for cell death, it would happen at lower doses or prior in time to the cell death. FIG. 10C confirms that there was no significant mitochondrial toxicity (filled circles) while there was cell death (open circles).

Example 11

Figure 11A:
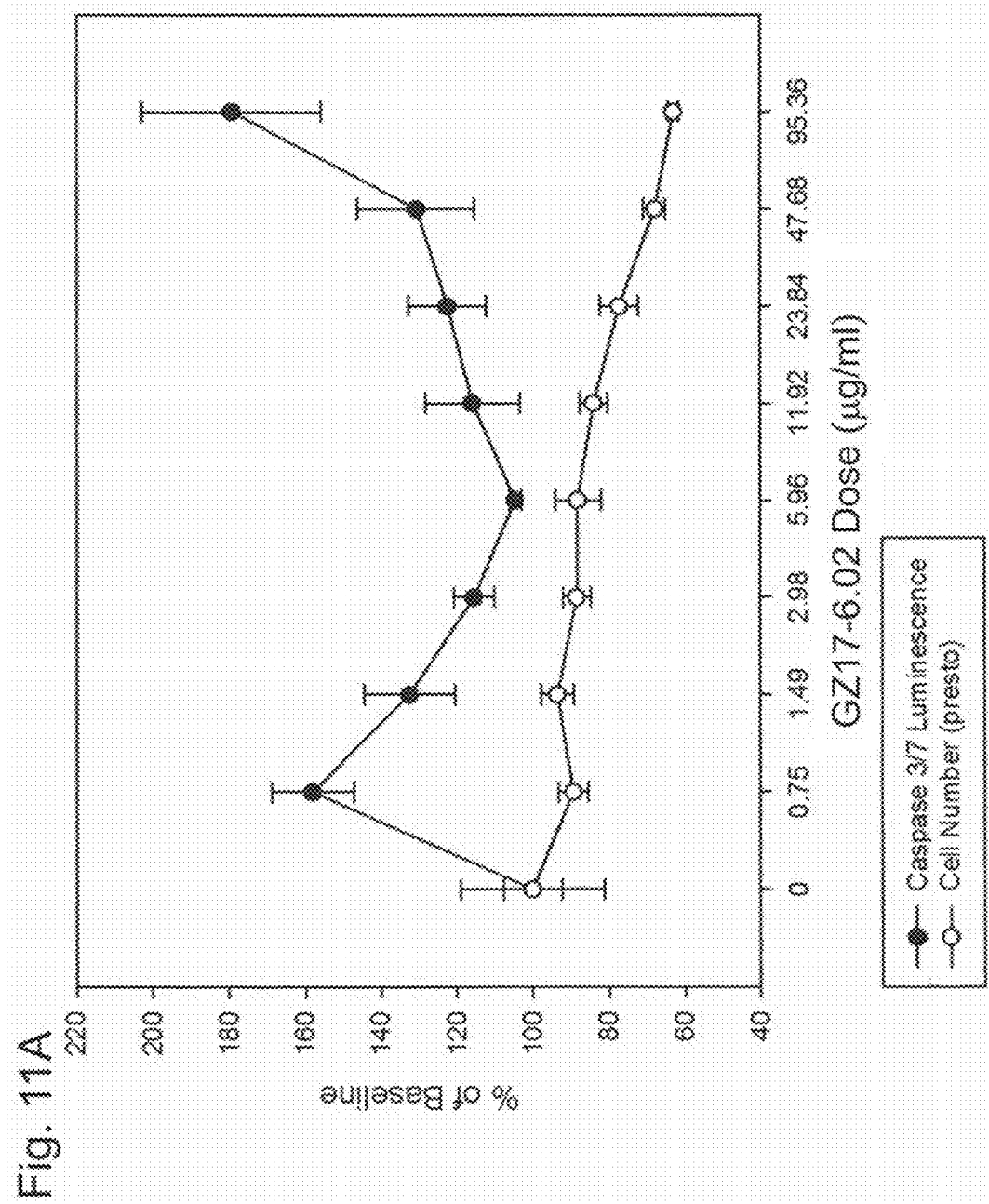
FIG. 11A is a graph illustrating the mechanisms of ovarian cancer cells death by application of GZ17-6.02, as explained in Example 11.
Figure 11B:
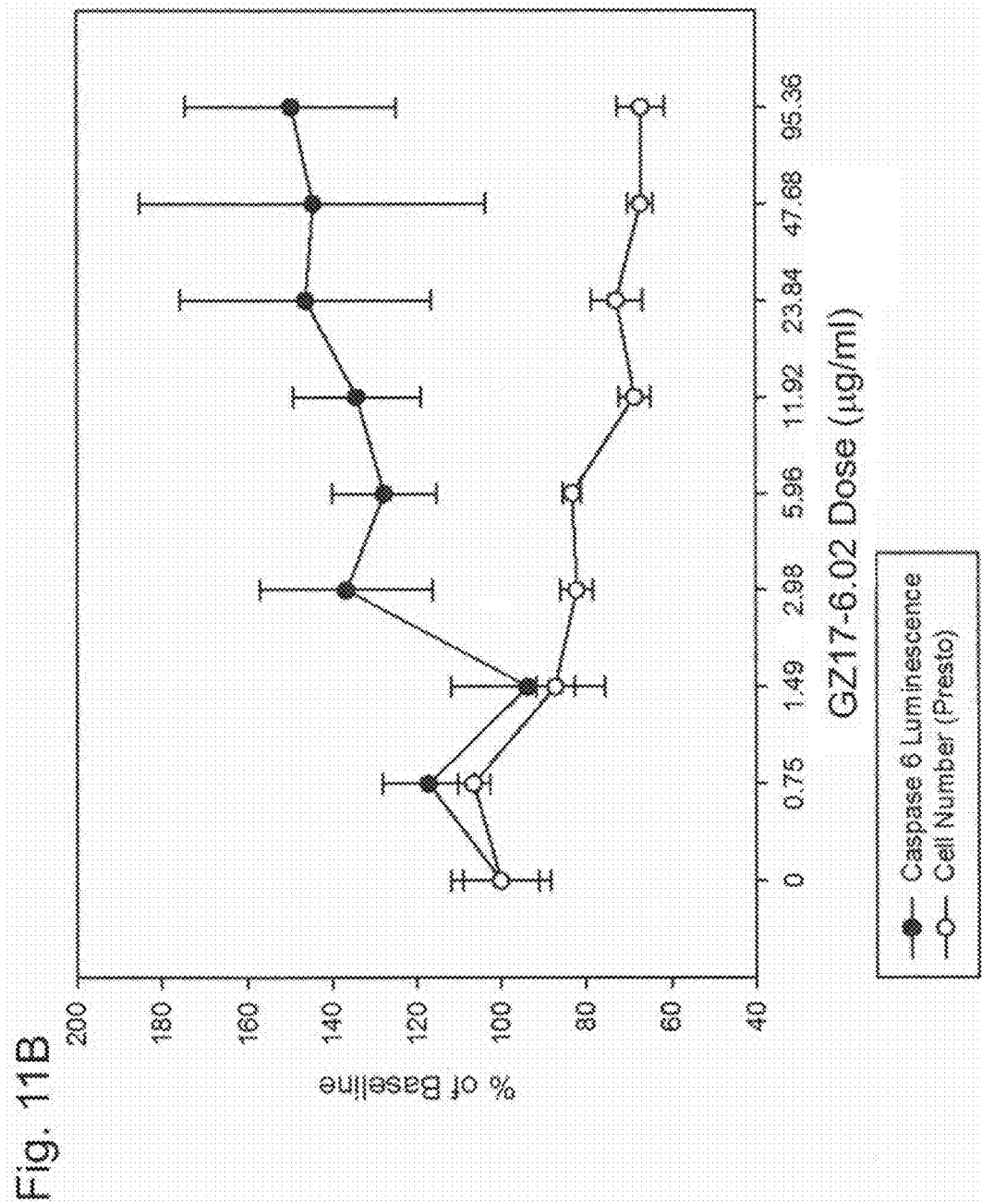
FIG. 11B is a graph illustrating the mechanisms of ovarian cancer cells death by application of GZ17-6.02, as explained in Example 11.
Figure 11D:
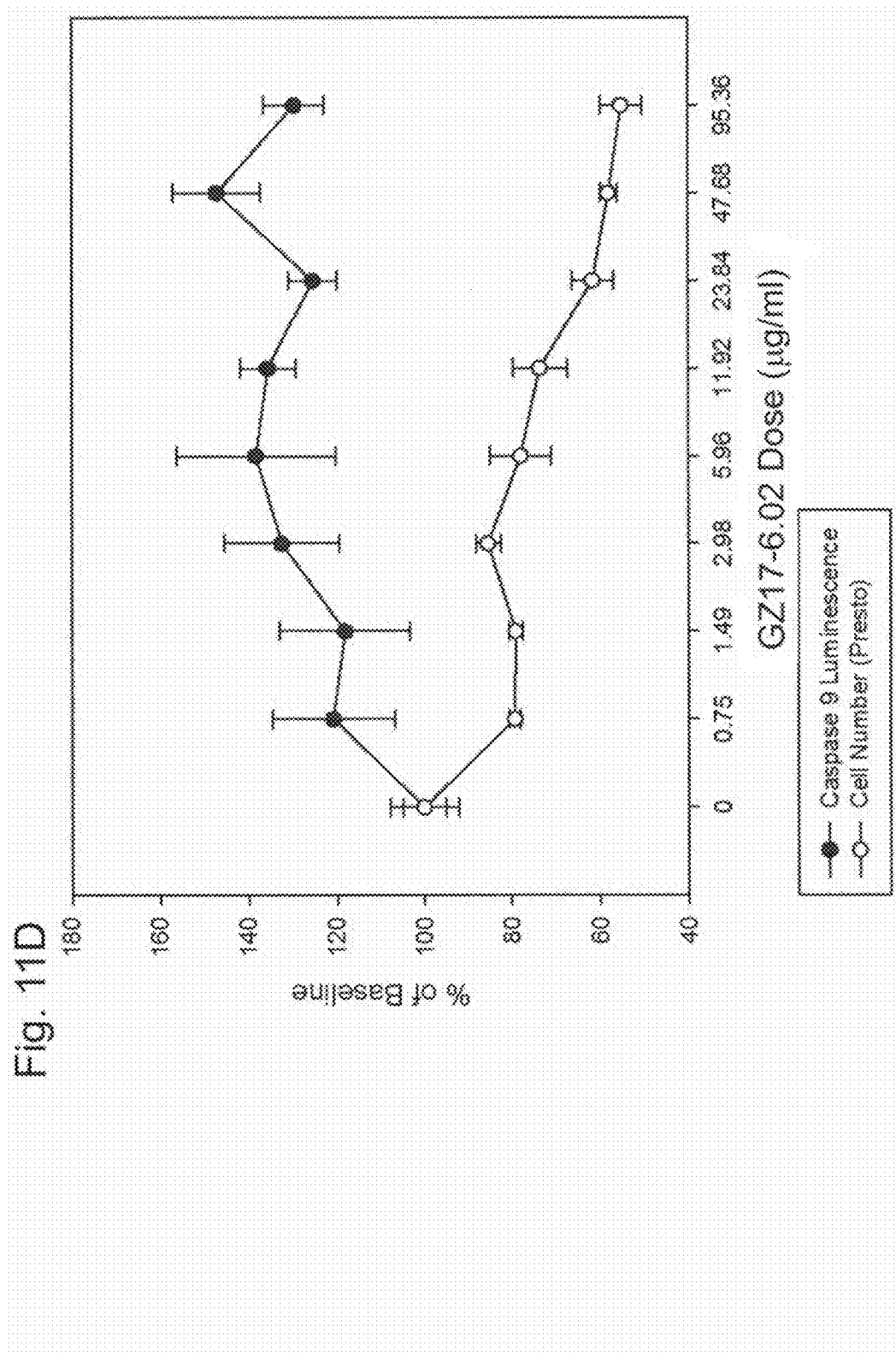
FIG. 11D is a graph illustrating the mechanisms of ovarian cancer cells death by application of GZ17-6.02, as explained in Example 11.

The procedures of Example 10 were followed, with testing of GZ17-6.02 on ovarian cancer cells (A1847). Caspases 3 and 7 were activated at low doses of GZ17-6.02, indicating a receptor-mediated cell death (FIG. 11A, filled circles). Caspase 6 was active at low doses of GZ17-6.02 (FIG. 11B, filled circles). However, caspase 8 was activated, which typically signals cell death via the mitochondria (FIG. 11C, filled circles) and caspase 9 was also activated (FIG. 11D, filled circles). In order to confirm the mitochondrial cell death pathway, mitochondrial toxicity was monitored in comparison to cell death (FIG. 11E, filled circles), indicating that the mitochondrial toxicity was at least partially involved in the subsequent cell death.

Example 12

Figure 12A:
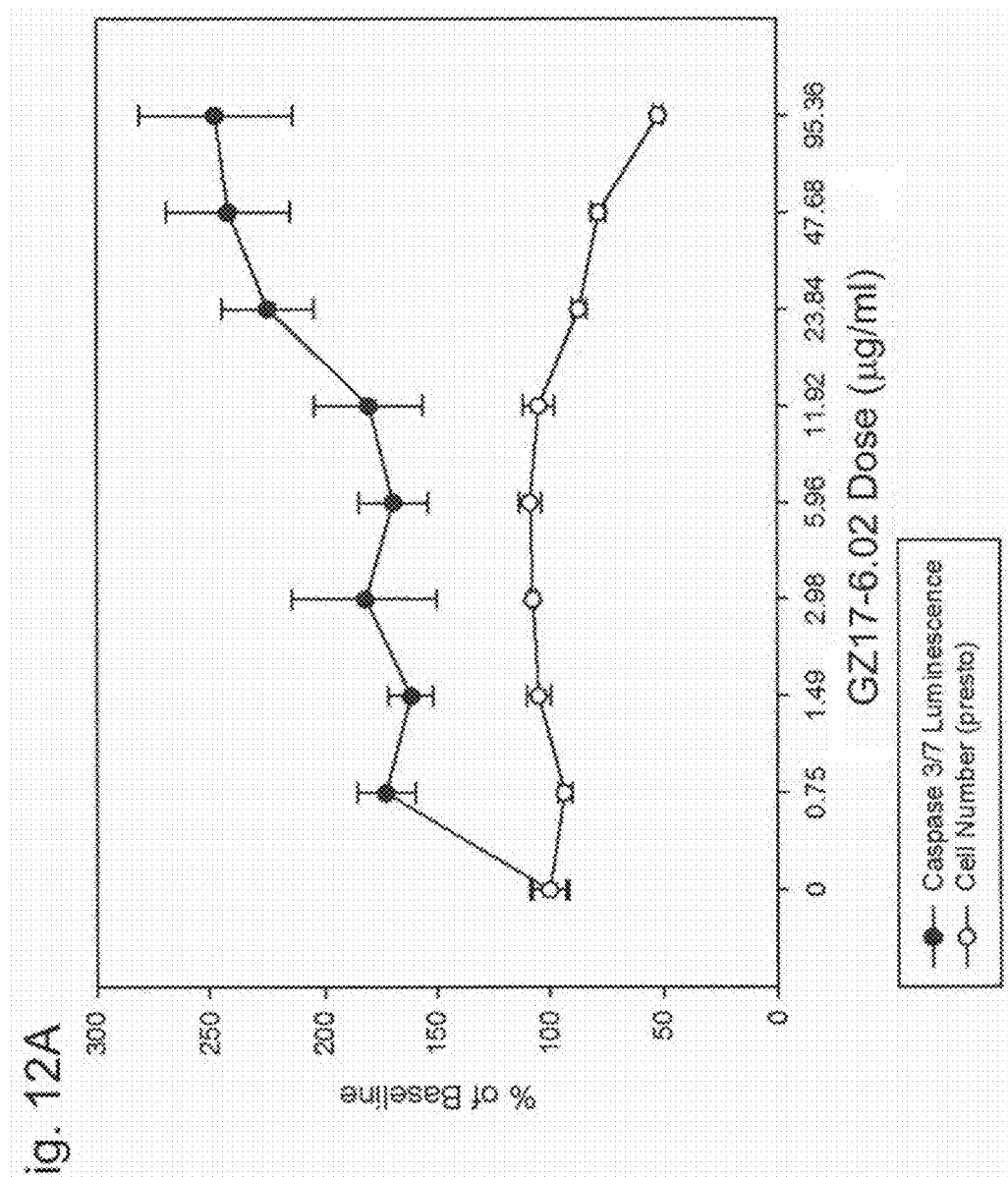
FIG. 12A is a graph illustrating the mechanisms of osteosarcoma cells death by application of GZ17-6.02, as explained in Example 12.
Figure 12B:
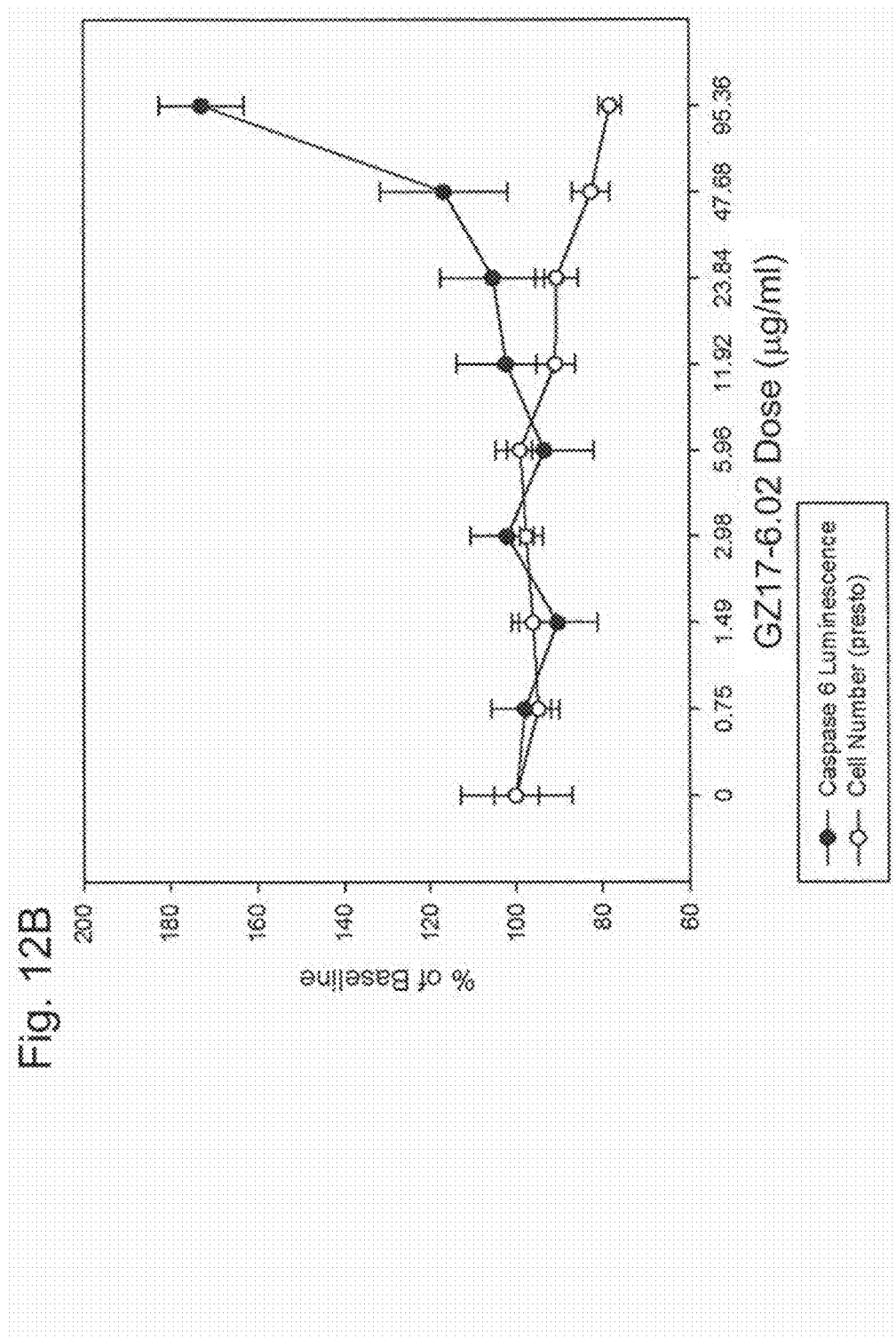
FIG. 12B is a graph illustrating the mechanisms of osteosarcoma cells death by application of GZ17-6.02, as explained in Example 12.
Figure 12D:
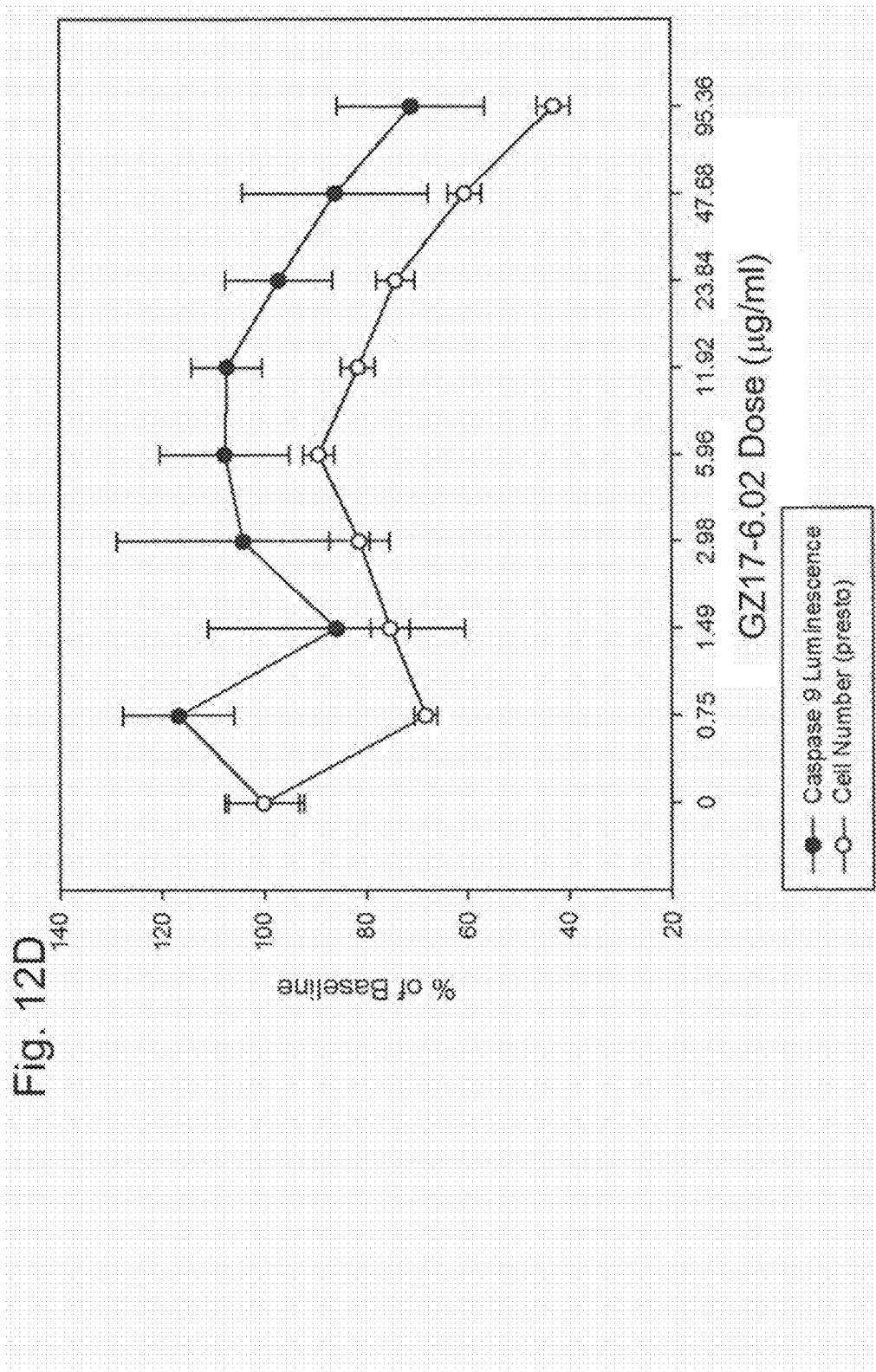
FIG. 12D is a graph illustrating the mechanisms of osteosarcoma cells death by application of GZ17-6.02, as explained in Example 12.

The procedures of Example 10 were followed, with testing of GZ17-6.02 on osteosarcoma cells (HOS). These tests indicated that levels of caspases 3 and 7 were significantly higher when exposed to doses of GZ17-6.02 over 0.4 mg/mL before or during cell death (FIG. 12A, filled circles). Caspase 6 was activated at high doses of GZ17-6.02 (FIG. 12B, filled circles). In contrast, caspase 2 (FIG. 12C, filled circles) and caspase 9 (FIG. 12D, filled circles) showed no activation that would indicate that they were involved in the cell death pathways induced by GZ17-6.02.

Example 13

The procedures of Example 10 were followed, with testing of GZ17-6.02 on human head and neck cancer cells (OSC19). FIG. 13 (filled circles) indicates that there is no mitochondrial toxicity involved in GZ17-6.02 induced cell death in the head and neck cancer cells.

Example 14

In addition to directly killing cancer cells, chemotherapeutic agents can work by blocking the rapid proliferation of cancer cells, thus eventually halting the progression of the cancer.

In this test, a multiplex dot-based Western assay for proliferative proteins was used to measure the relative amounts of proteins known to be involved in cell proliferation signaling, in both a control test (no GZ17-6.02) and an inactivation test (with GZ17-6.02, at the $ED_{50}$ for head and neck cancer cells).

Following a 24 hour exposure to GZ17-6.02 or vehicle head and neck cancer cells (OSC19) were homogenized and the lysate loaded onto the Human Phospho-Kinase Array Kit (R&D Systems) using the following procedure. The antibody-attached membranes were incubated overnight at 4° C. with the respective cell lysates, followed by repeated washing and incubation in the detection antibodies for 24 hours. After subsequent repeated washes, streptavidin-HRP was applied for 30 minutes. Membranes were washed and exposed to film after applying chemiluminescence reagent mix.

Cellular proteins specific to a pathway of cell proliferation were tested in duplicate (resulting in 2 side-by-side dots for each protein in FIG. 14A). The darker the dot, the more relative protein was present in the homogenate. As shown in FIG. 14B, cell proliferation proteins showed a dramatic reduction in amount when exposed to the head and neck cancer cell $ED_{50}$ dose of GZ17-6.02. The proteins showing the greatest reduction included epidermal growth factor receptor (block a compared to block a'), extracellular-signal-regulated kinase (block b compared to block b'), the catalytic subunit of AMP-activated kinase (block c compared to block c'), β-catenin (block d compared to block d'), STAT2 (block e compared to block e') and Chk-2 (block f compared to block f').

Example 15

Figure 15A:
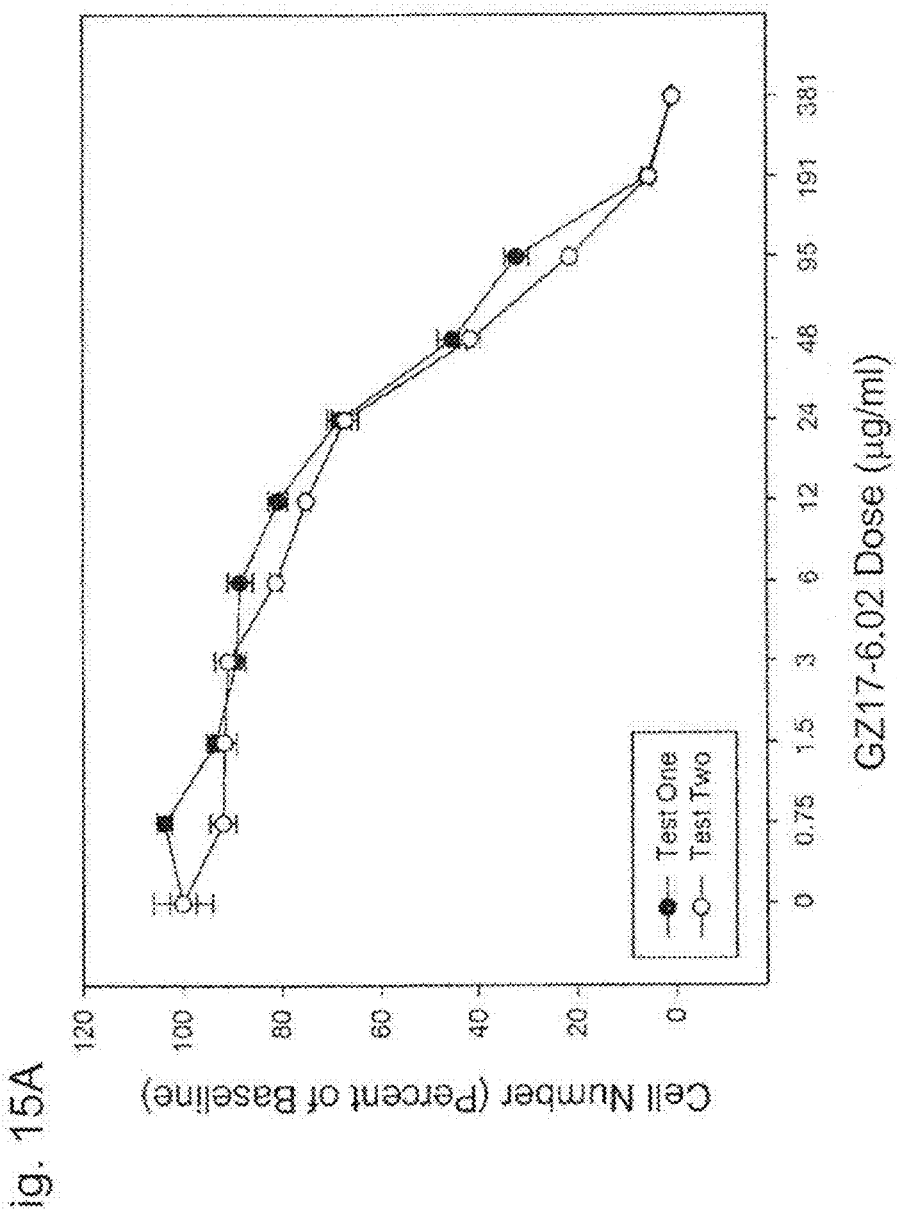
FIG. 15A is a graph depicting the results of two independent scientists, each carrying out an identical induced cell death test with GZ17-6.02 on ovarian cancer cells, as described in Example 15.
Figure 15B:
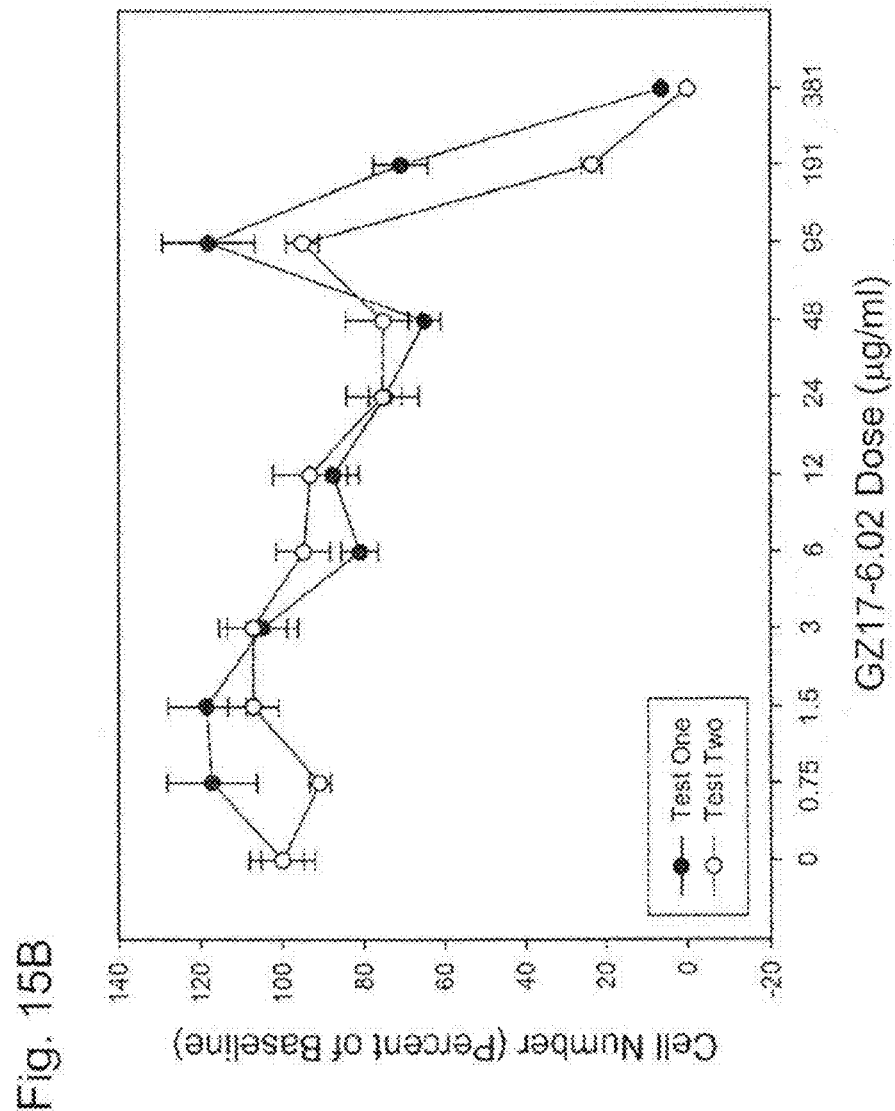
FIG. 15B is a graph depicting the results of two independent scientists, each carrying out an identical induced cell death test with GZ17-6.02 on lung cancer cells, as described in Example 4.

In this example, two independent scientists conducted identical tests with ovarian cancer and lung cancer cells (A1847 and H358) using the techniques described in Example 1, in order to determine induced cell death upon application of GZ17-6.02. The nearly identical results (filled circles versus open circles) confirm the reliability of the testing as a determination of GZ17-6.02 effectiveness. FIG. 15A sets forth the ovarian cancer results, whereas FIG. 15B gives the lung cancer cell results.

Example 16

Six-week old FOXN1 mice were inoculated with human head and neck cancer cells (OSC19) bilaterally into the flank region, in order to induce the formation of palpable tumors. The bilateral tumors were measured at one week after cell injection, and had each grown to an average volume of approximately 9 mm³. Half of the mice were injected daily with 15 mg/kg body weight GZ17-6.02 stock solution into the right side tumors, starting on day 7 after inoculation of the tumor cells. The other half of the mice were injected with the same volume of the ethanol carrier of the stock solution into the right side tumors. Thus, each mouse had 2 palpable tumors, one on either flank, but only one side was injected with GZ17-6.02. Every 2-4 days, the tumors on both sides of each mouse were measured with vernier calipers in 2 perpendicular dimensions and the volumes calculated.

Figure 16B:
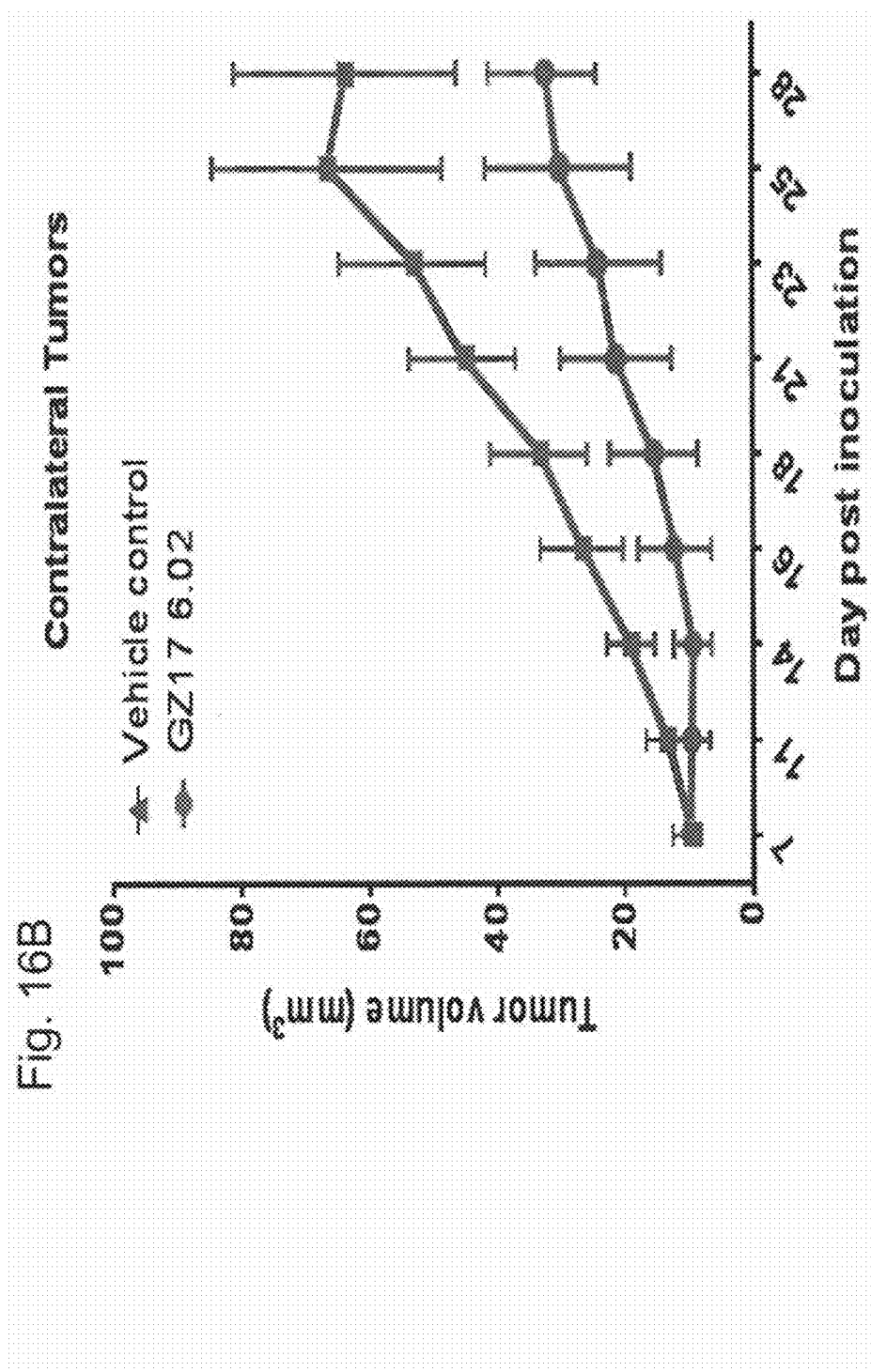
FIG. 16B is a comparative graph of contralateral tumor volume versus days after cancer cell inoculation in mice, indicating a systemic effect of use of GZ17-6.02, as explained in Example 16.

FIG. 16A shows that GZ17-6.02 dramatically halted tumor growth in the treated mice, so that by 3 weeks there was a distinct and statistically significant difference between the vehicle-treated controls and the GZ17-6.02 treated mice. Further, the trend in the GZ17-6.02 treated mice was that the tumors began to decrease in volume from day 21 (although the decrease was not statistically significant) from tumor size at day 28. FIG. 16A shows the decline in tumor volume in the tumors that were directly injected with GZ17-6.02. FIG. 16B shows the halt in tumor growth that occurred in the non-injected tumors on the contralateral side of the neck of the treated mice. FIG. 16B demonstrates that GZ17-6.02 has a systemic anticancer effect, i.e., the contralateral tumor size decrease without direct injection of GZ17-6.02 indicates that the agent traveled through the bloodstream of the mice.

Throughout the study, the animals showed no signs of complications, distress, or toxicity. Thus, none of the over 30 mice in the study exhibited any observable adverse reactions. Daily observation of the mice documented that none suffered any weight loss, new tumor formation, loss of appetite, change in fur appearance or grooming behavior, or change in activity owing to lethargy. Moreover, there were no gross abnormalities of any of the internal organs of the mice upon necropsy. It was thus concluded that there were no drug-drug interactions, which are common with multiple-drug anti-cancer compositions.

In another mice study, a head and neck tumor was surgically removed from a human patient, and approximate 35 mg-portions of the tumor were implanted in a first randomized group of ten nude-FOXN1 mice using a 5% ethanol in saline vehicle via oral gavage. A second randomized group of ten mice was treated only with the vehicle as a control, in the same manner as the first group. The first mice group was treated with 30 mg/kg/day doses of GZ17-6.02 five days/week, and the doses were increased to 50 mg/kg/day during the second week of treatment.

Figure 16C:
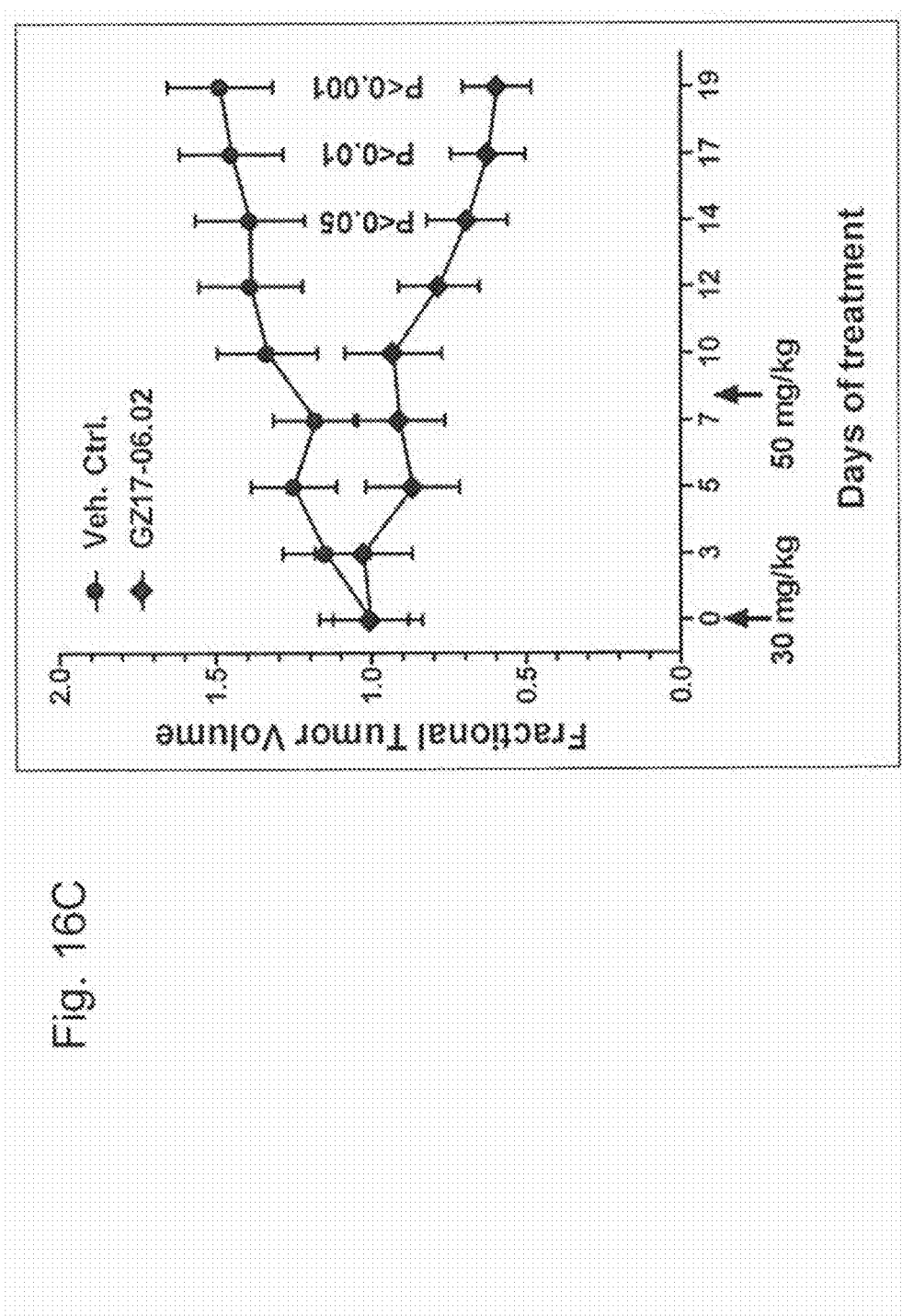
FIG. 16C is a graph of fractional tumor volume versus days after treatment wherein one group of mice was implanted with human head and neck tumor cells using an implantation vehicle, and a control group of mice was implanted with only the vehicle, in order to determine tumor volume over time, as set forth in Example 16.

The two groups of mice were treated for a total of three weeks, and tumor volumes were measured twice a week using a Vernier caliper. The results of this study are set forth in FIG. 16C, which illustrates that the fractional tumor volumes relative to the pretreatment tumor size were reduced in the first group of mice, while the control mice exhibited gradually increasing tumor burdens.

Example 17

Figure 17B:
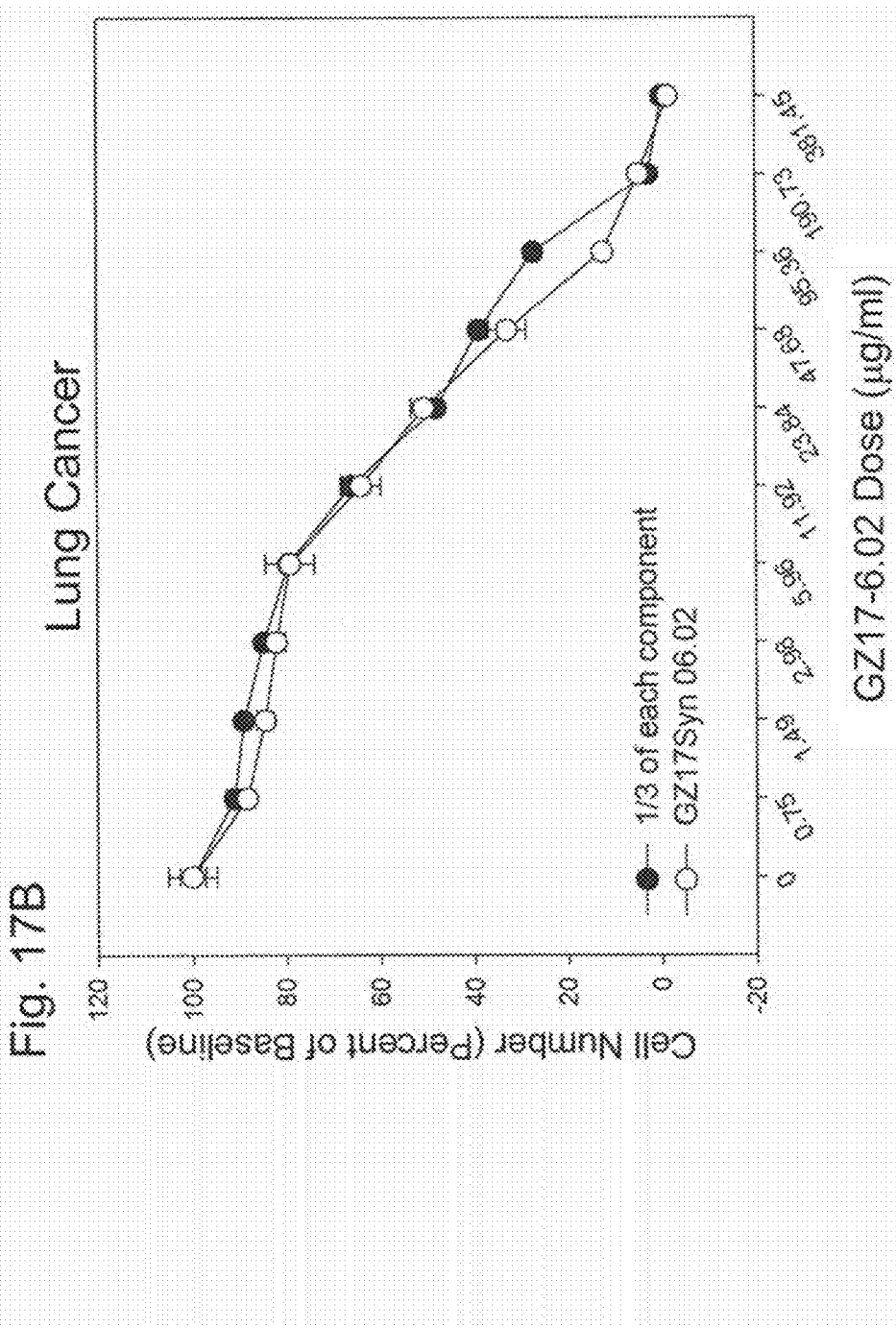
FIG. 17B is a graph of cell number versus dosage amounts of GZ17-6.02 (open circles) versus a combined product including ⅓ by weight of each GZ17-6.02 component (filled circles), tested on lung cancer cells, as described in Example 3.
Figure 17C:
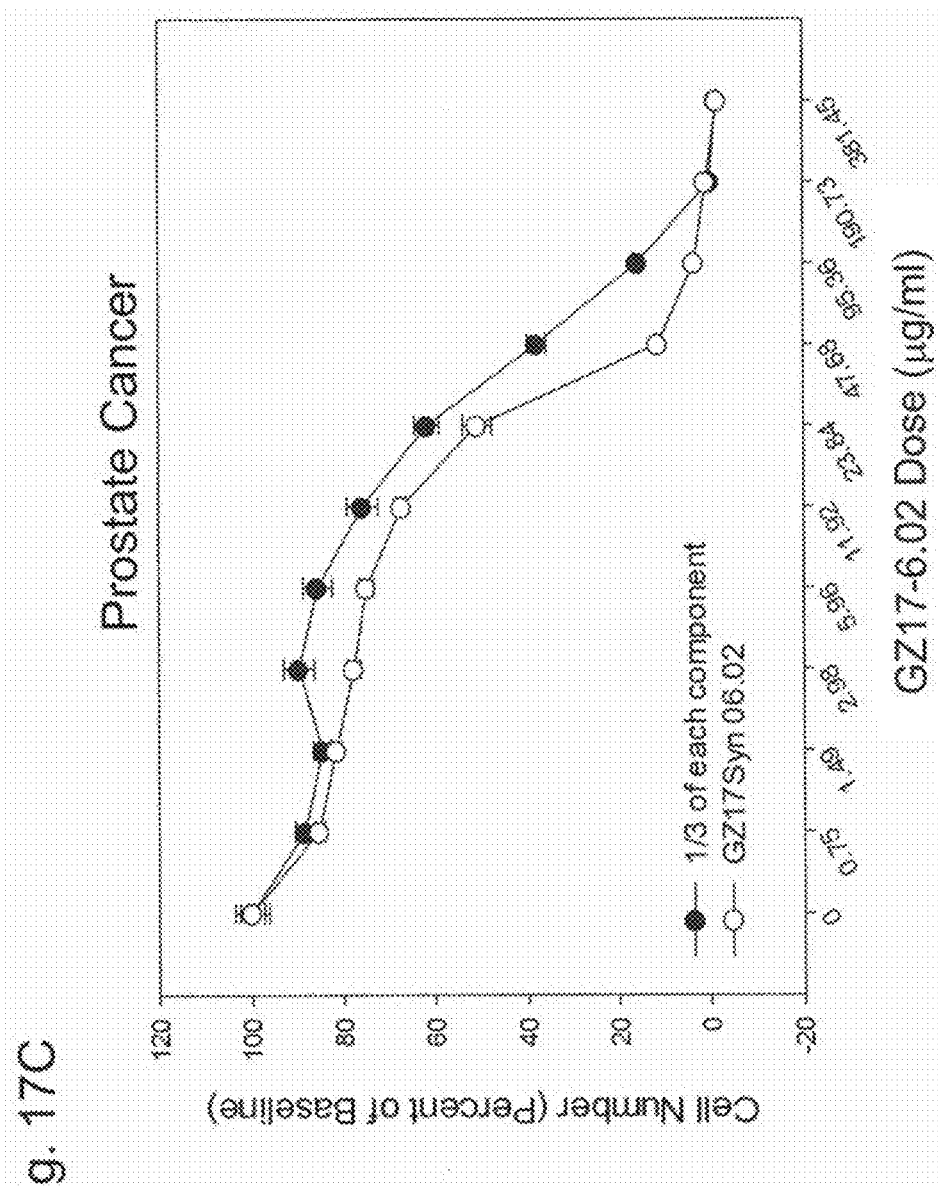
FIG. 17C is a graph of cell number versus dosage amounts of GZ17-6.02 (open circles) versus a combined product including ⅓ by weight of each GZ17-6.02 component (filled circles), tested on prostate cancer cells, as described in Example 4.
Figure 18A:
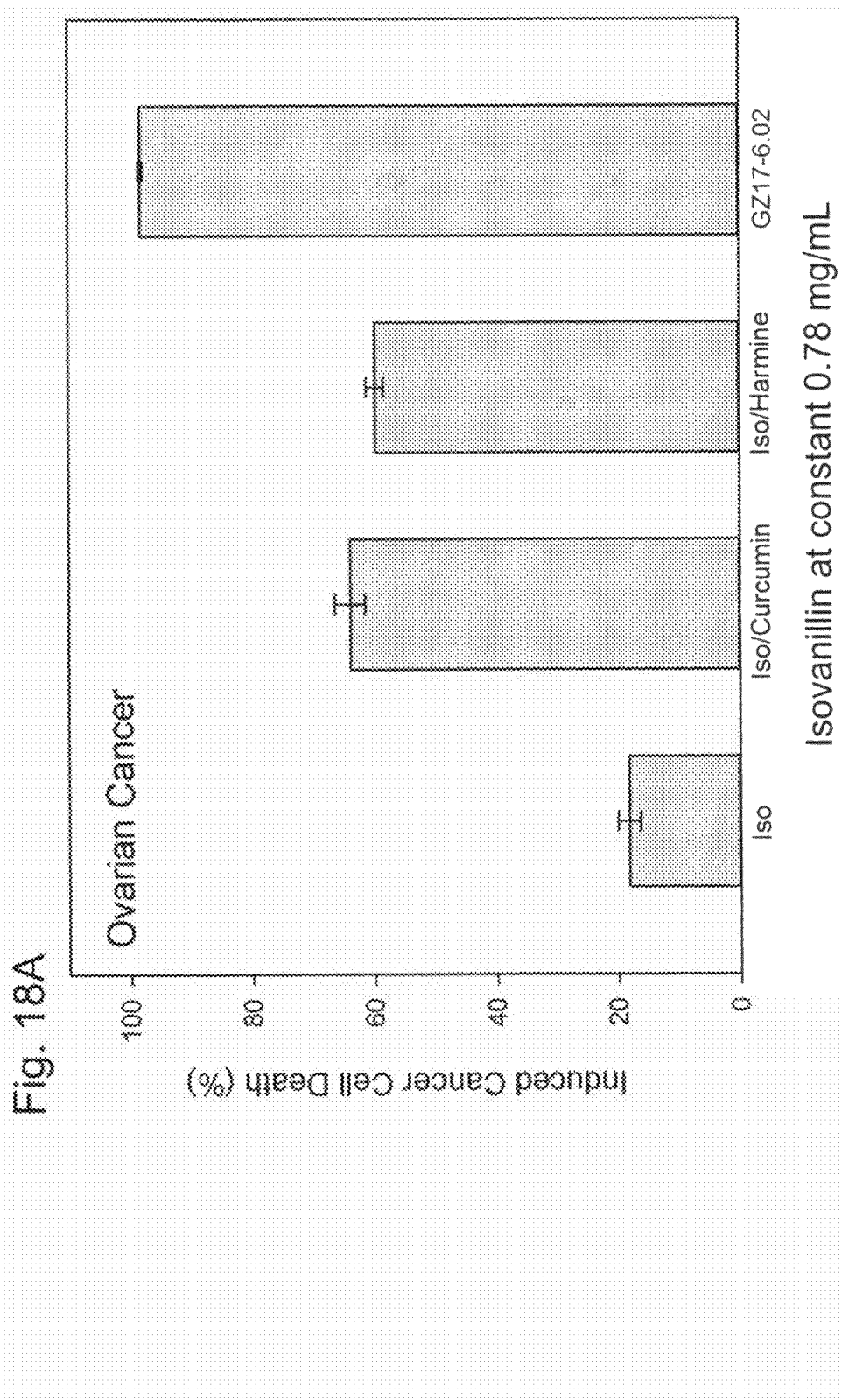
FIG. 18A is a graph of percent ovarian cancer cell death versus different component combinations of GZ17-6.02, illustrating results using isovanillin alone, and two-component products respectively including isovanillin plus curcumin, and isovanillin plus harmine, where the isovanillin concentration was held constant throughout.
Figure 18B:
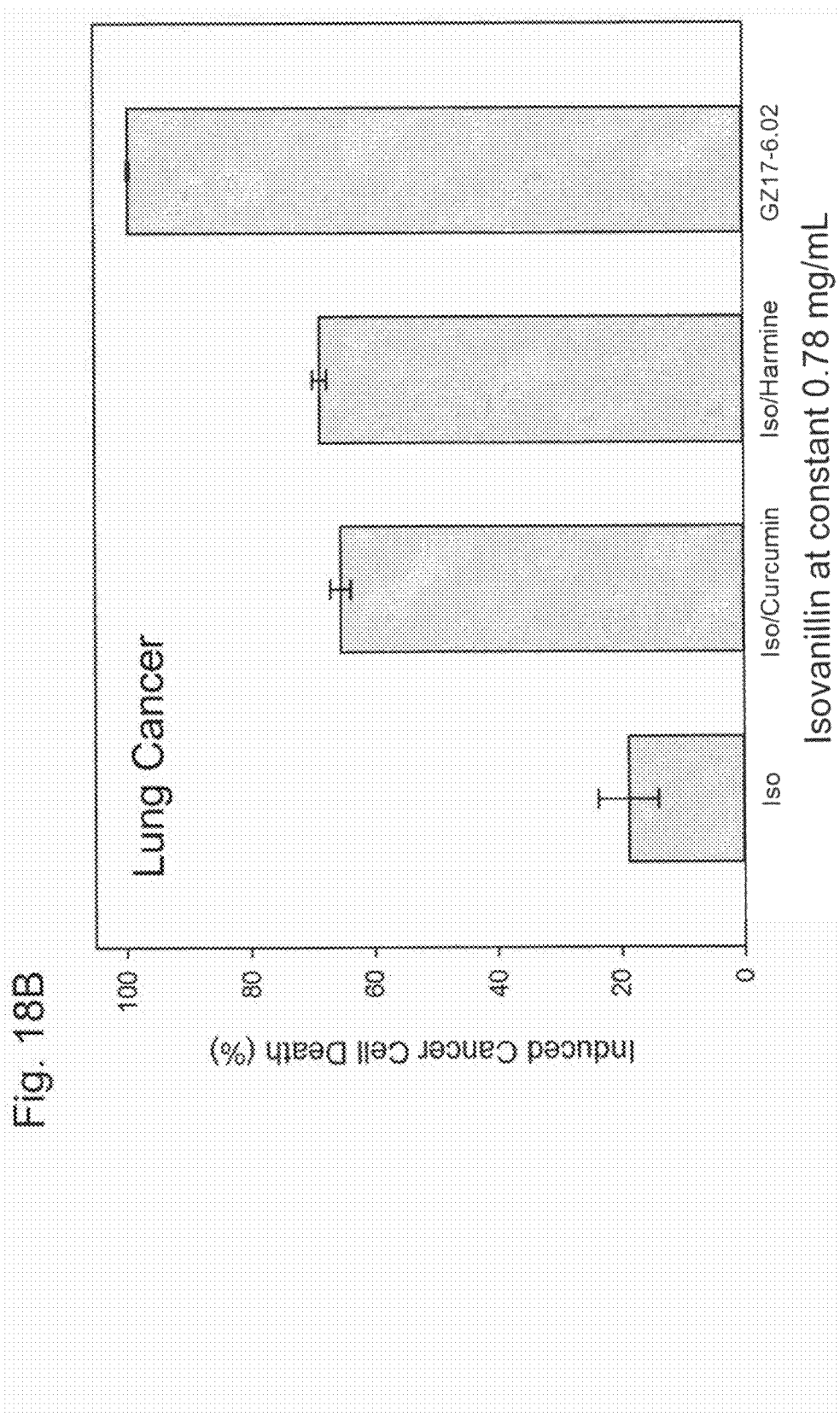
FIG. 18B is a graph of percent lung cancer cell death versus different component combinations of GZ17-6.02, illustrating results using isovanillin alone, and two-component products respectively including isovanillin plus curcumin, and isovanillin plus harmine, where the isovanillin concentration was held constant throughout.
Figure 18C:
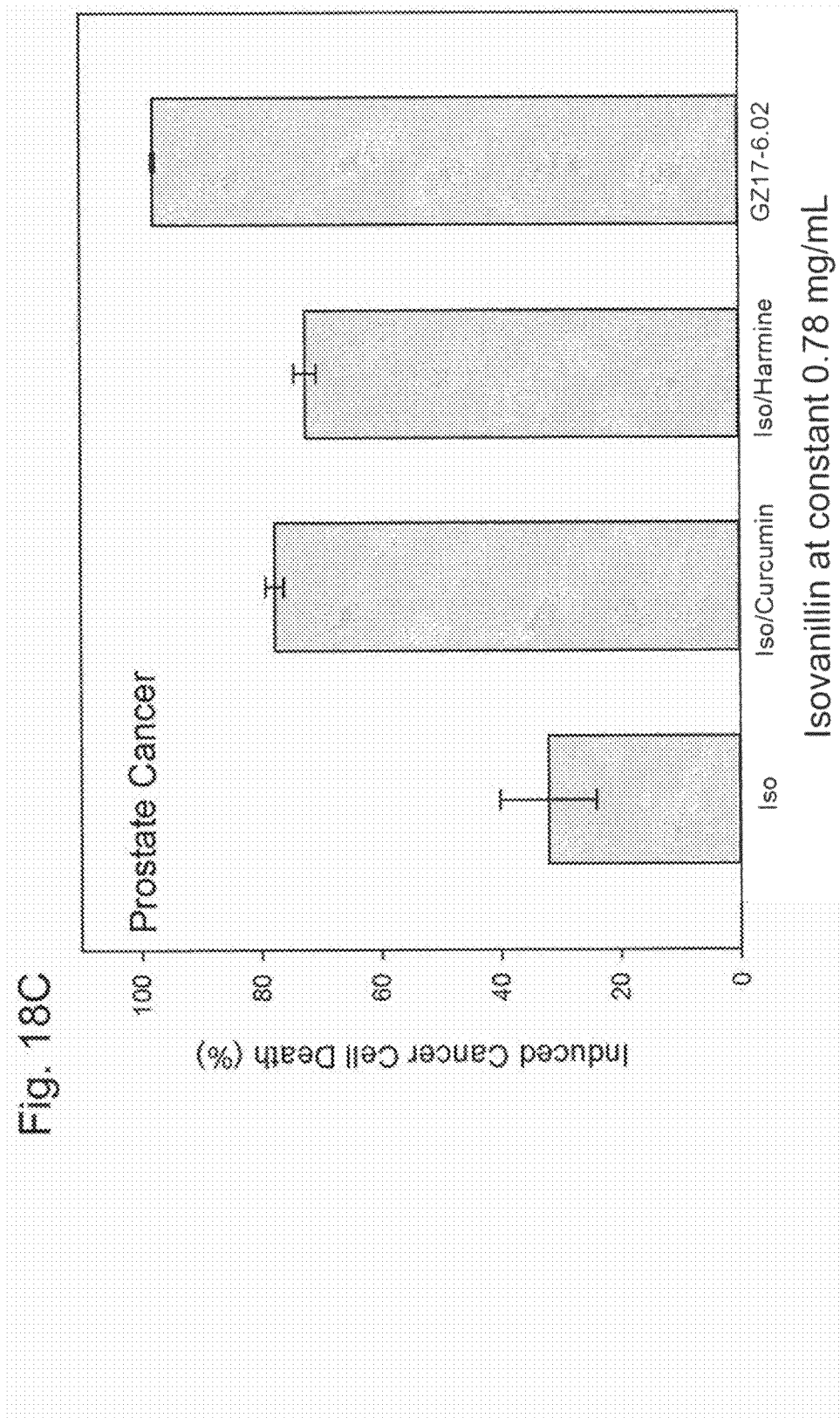
FIG. 18C is a graph of percent prostate cancer cell death versus different component combinations of GZ17-6.02, illustrating results using isovanillin alone, and two-component products respectively including isovanillin plus curcumin, and isovanillin plus harmine, where the isovanillin concentration was held constant throughout.
Figure 19B:
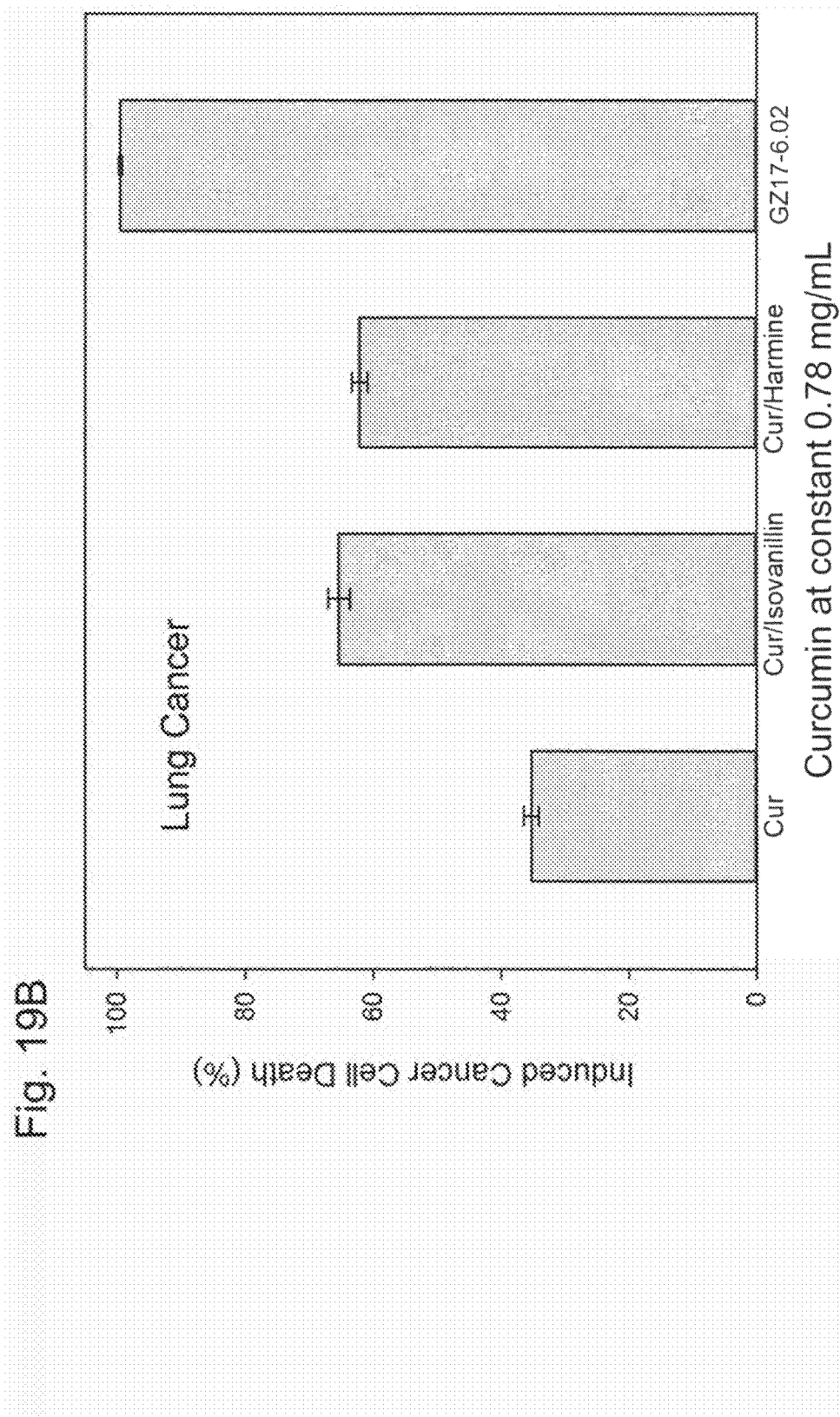
FIG. 19B is a graph of percent lung cancer cell death versus different component combinations of GZ17-6.02, illustrating results using curcumin alone, and two-component products respectively including curcumin plus isovanillin, and curcumin plus harmine, where the curcumin concentration was held constant throughout.
Figure 19C:
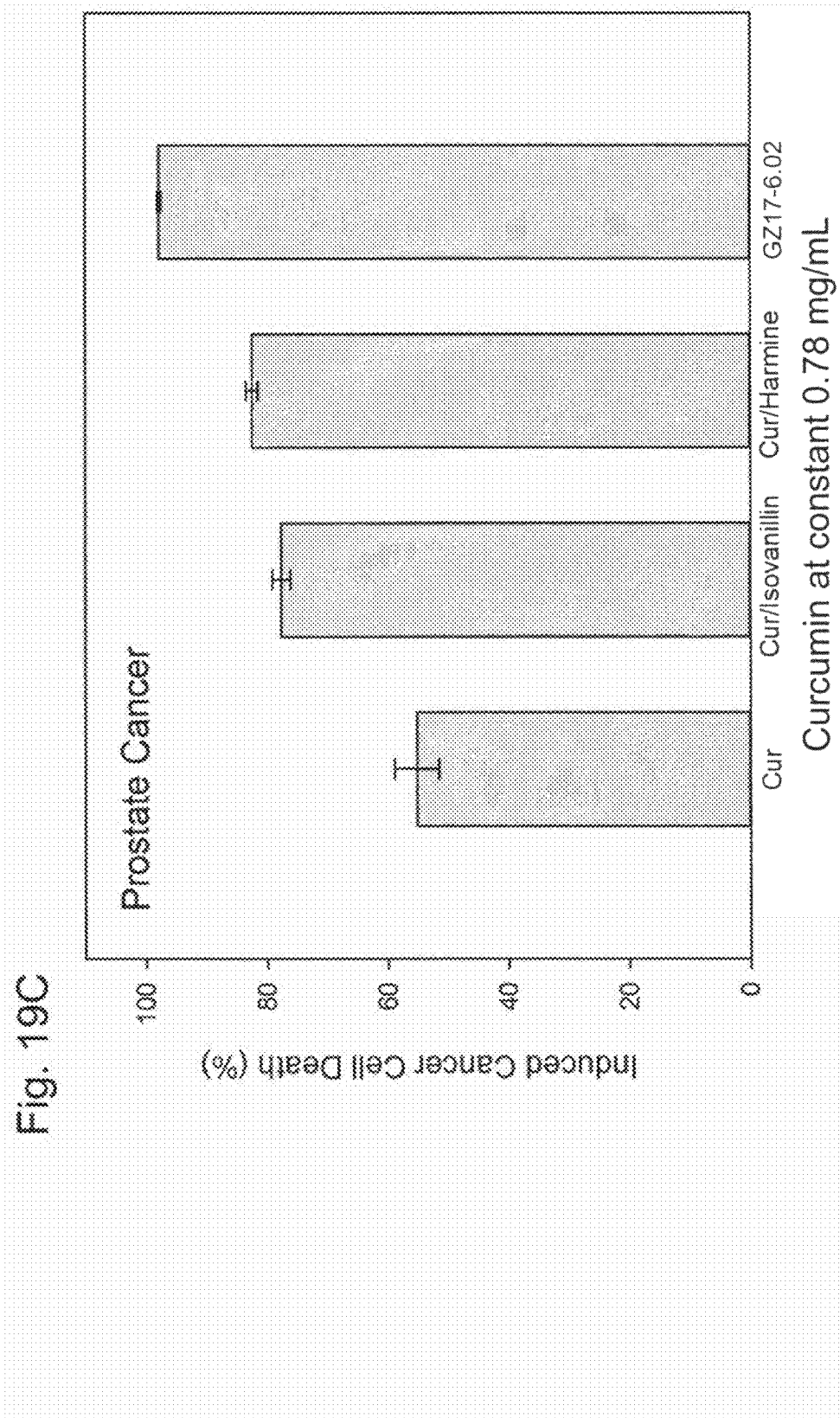
FIG. 19C is a graph of percent prostate cancer cell death versus different component combinations of GZ17-6.02, illustrating results using curcumin alone, and two-component products respectively including curcumin plus isovanillin, and curcumin plus harmine, where the curcumin concentration was held constant throughout.
Figure 20B:
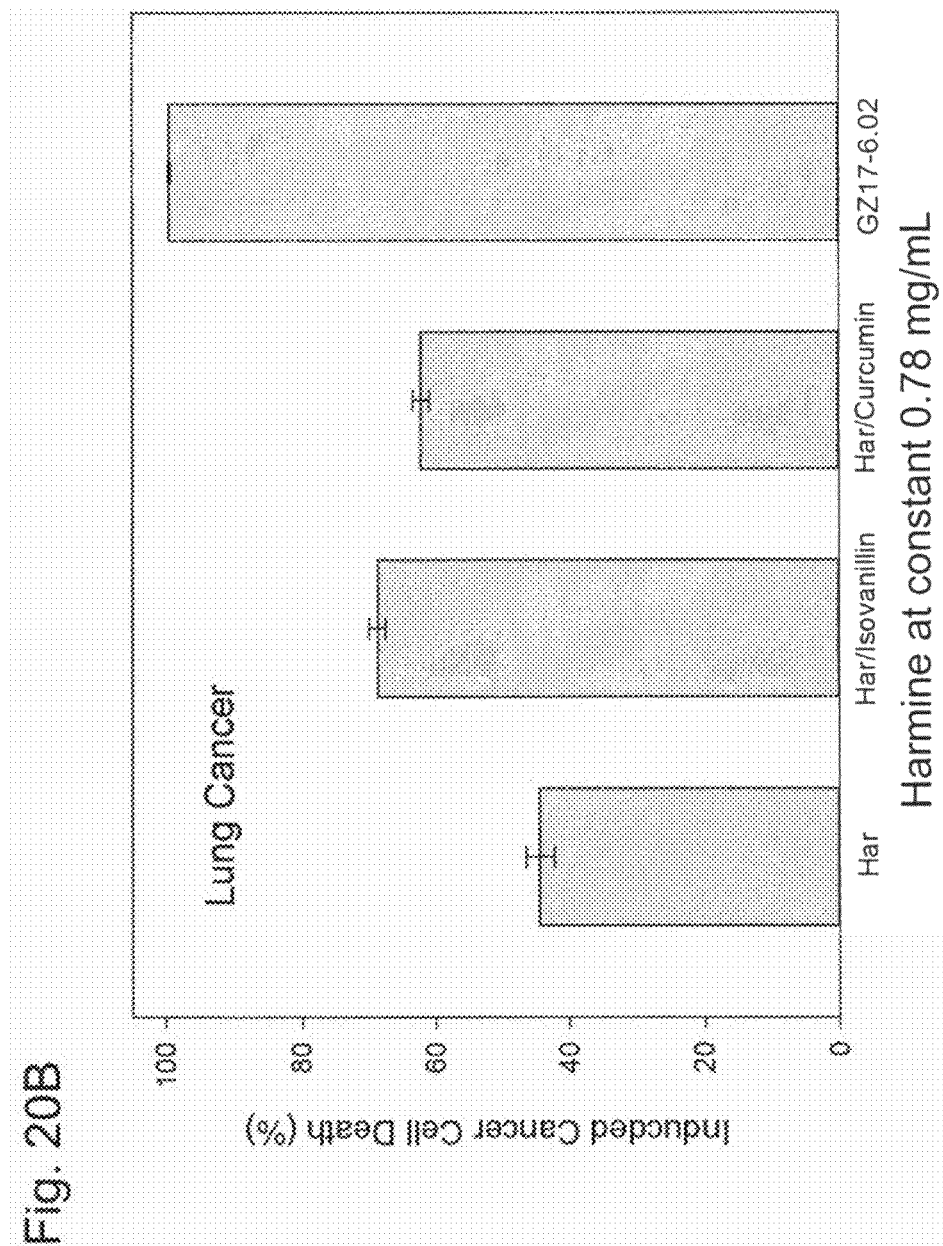
FIG. 20B is a graph of percent lung cancer cell death versus different component combinations of GZ17-6.02, illustrating results using harmine alone, and two-component products respectively including harmine plus isovanillin, and harmine plus curcumin, where the harmine concentration was held constant throughout.
Figure 20C:
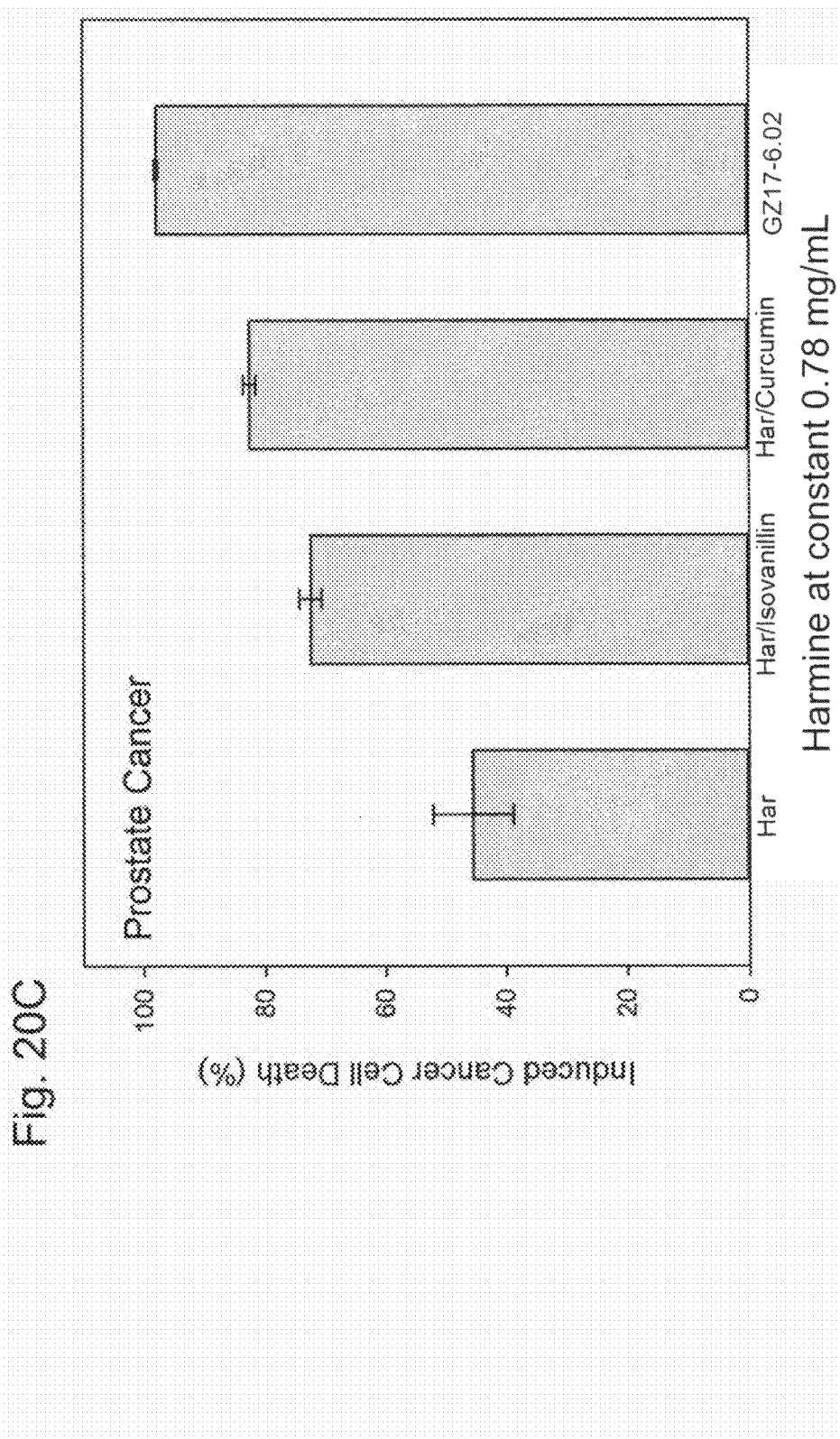
FIG. 20C is a graph of percent prostate cancer cell death versus different component combinations of GZ17-6.02, illustrating results using harmine alone, and two-component products respectively including harmine plus isovanillin, and harmine plus curcumin, where the harmine concentration was held constant throughout.
Figure 20D:
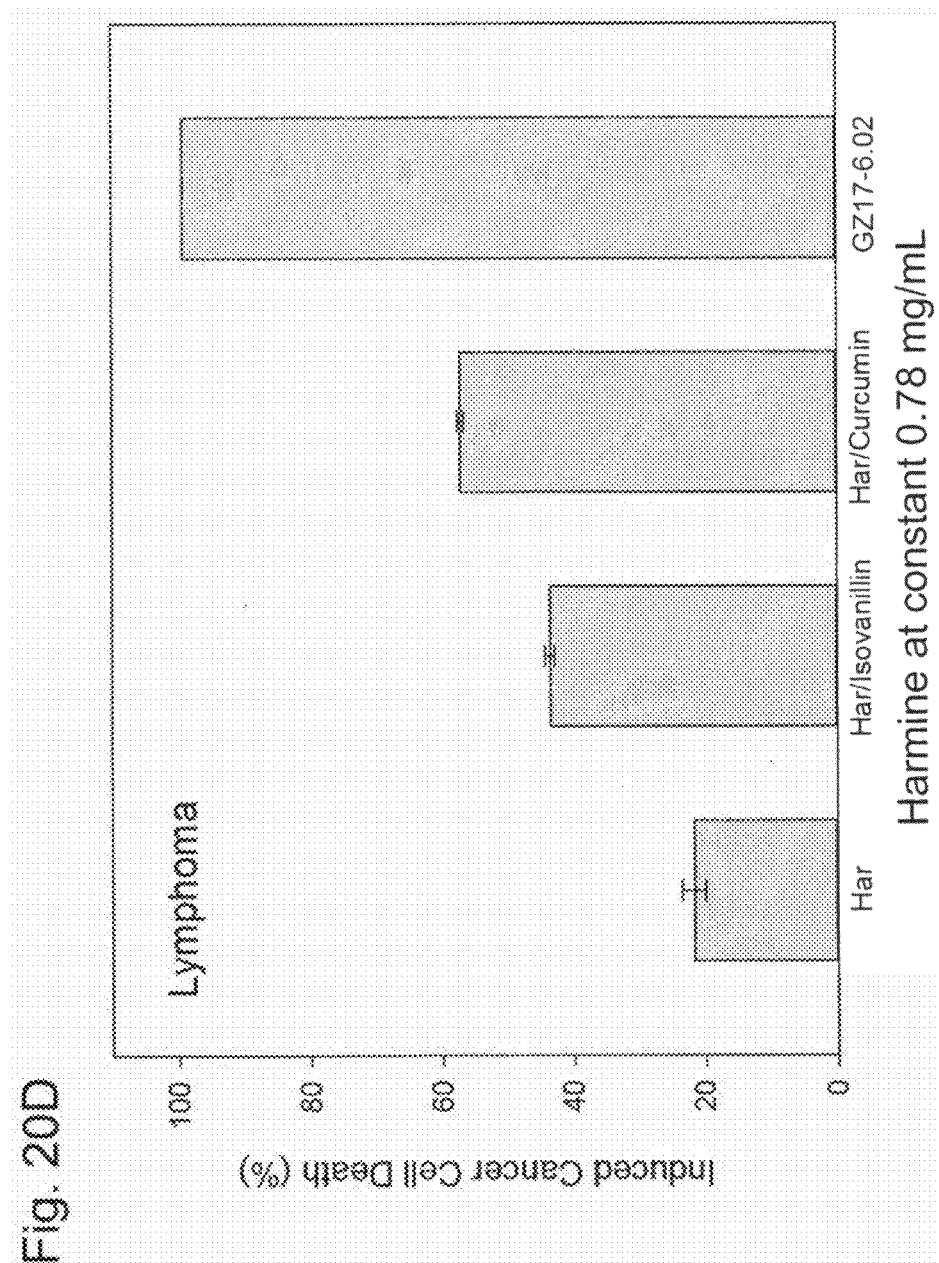
FIG. 20D is a graph of percent lymphoma cancer cell death versus different component combinations of GZ17-6.02, illustrating results using harmine alone, and two-component products respectively including harmine plus isovanillin, and harmine plus curcumin, where the harmine concentration was held constant throughout.
Figure 21B:
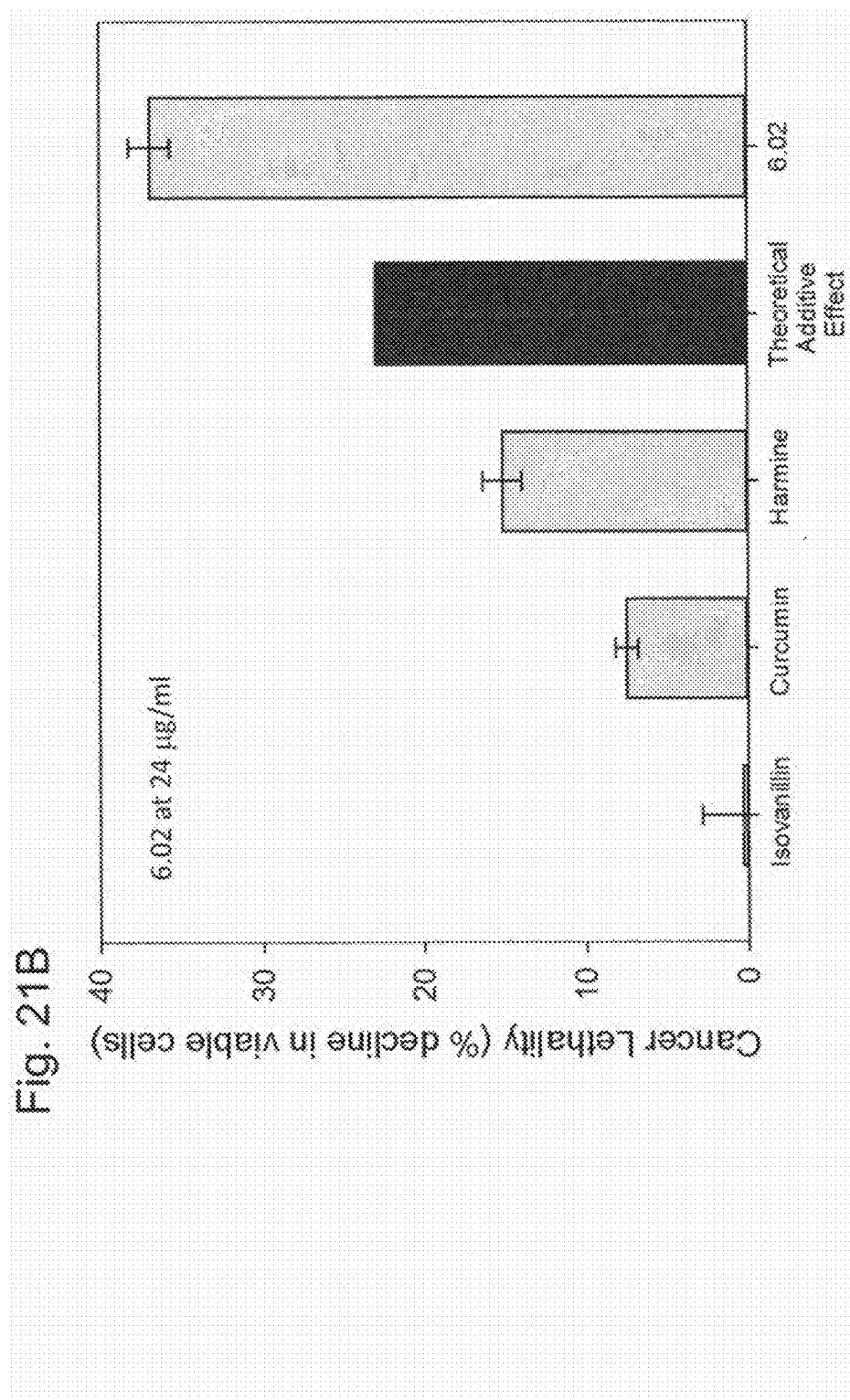
FIG. 21B is a graph of lymphoma cancer cell lethality using GZ17-6.02 at a dosage rate of 24 μg/mL, and using the three components of GZ17-6.02 individually at the concentration present in GZ17-6.02, and further illustrating the theoretical additive effect of the three components versus GZ17-6.02.

In this Example, a different ratio of isovanillin, harmine, and curcumin was used, as compared with GZ17-6.02, namely ⅓ by weight of each component. This formulation was prepared by mixing the three GZ17-6.02 components in 1 mL of ethanol to obtain a secondary stock solution. FIG. 17A shows that the original stock solution (filled circles) and the secondary stock solution (open circles) are bioequivalent in terms of ovarian cancer cell (A1847) kill rate. FIGS. 17B and 17C show the same general effect for lung cancer cells (H358) and prostate cancer cells (22rv1).

Example 18

In this Example, a known ovarian cancer cell kill rate for GZ17-6.02 was selected, and the amount of isovanillin in this dosage (0.78 mg/mL) was tested against GZ17-6.02. Additionally, sub-combinations of isovanillin:curcumin and isovanillin:harmine were tested, where the concentrations of the two ingredients were identical to those in the GZ17-6.02. Thus, the concentration of the isovanillin:curcumin product was 0.78 mg/mL isovanillin and 0.13 mg/mL curcumin, and the concentration of the isovanillin:harmine product was 0.78 mg/mL isovanillin and 0.099 mg/mL harmine. FIGS. 18A-18D illustrate these results with ovarian cancer cells (A1847), lung cancer cells (H358), prostate cancer cells (22rv1), and lymphoma cells (M0205). As is evident, the two-component products each exhibited greater kill rates as compared with isovanillin alone.

Example 19

The procedures of Example 18 were followed, except that curcumin was tested alone versus GZ17-6.02, together with curcumin:isovanillin and curcumin:harmine two-component products. In this test, the curcumin was present at a level of 0.78 mg/mL and the concentrations in the curcumin:isovanillin product were 0.78 mg/mL curcumin and 3.59 mg/mL isovanillin, and in the curcumin:harmine product the concentrations were 0.78 mg/mL curcumin and 0.59 mg/mL harmine. FIGS. 19A-19D illustrate the results of this test, and confirm that the two-component products give better results than curcumin alone.

Example 20

The procedures of Example 18 were followed, except that harmine was tested alone versus GZ17-6.02, together with harmine:isovanillin and harmine:curcumin two-component products. In this test, the harmine was present at a level of 0.78 mg/mL and the concentrations in the harmine:isovanillin product were 0.78 mg/mL harmine and 6.09 mg/mL isovanillin, and in the harmine:curcumin product the concentrations were 0.78 mg/mL curcumin and 1.03 mg/mL curcumin. FIGS. 20A-20D illustrate the results of this test, and confirm that the two-component products give better results than harmine alone.

Example 21

In this example, the individual components of GZ17-6.02 were tested against lymphoma cancer cells (MO205) at the component concentrations found in GZ17-6.02, at dosage rates of 12, 24, 48, and 96 µg/mL. The theoretical additive effect (black bar) of the 3 components was also calculated in each case and shown versus the actual test results found using GZ17-6.02. FIGS. 21A-21D illustrate the results of these tests, and confirm that, at the tested dosages, the GZ17-6.02 product had a greater effect than the individual components and the theoretical additive effect thereof, thus establishing synergistic effects. In this regard, those skilled in the art understand that dosages of anticancer products actually administered to patients depend on a number of factors, including age, weight, sex, physical conditions, types of cancers, and stages of cancers. By the same token, it should also be understood that at some dosage levels and/or specific concentrations of components, the results of FIGS. 21A-21D may not be duplicated. These same considerations apply to the tests set forth in Examples 22 and 23 below. In most cases, however, compositions giving therapeutic synergies at the selected dosages are preferred.

Example 22

Figure 22B:
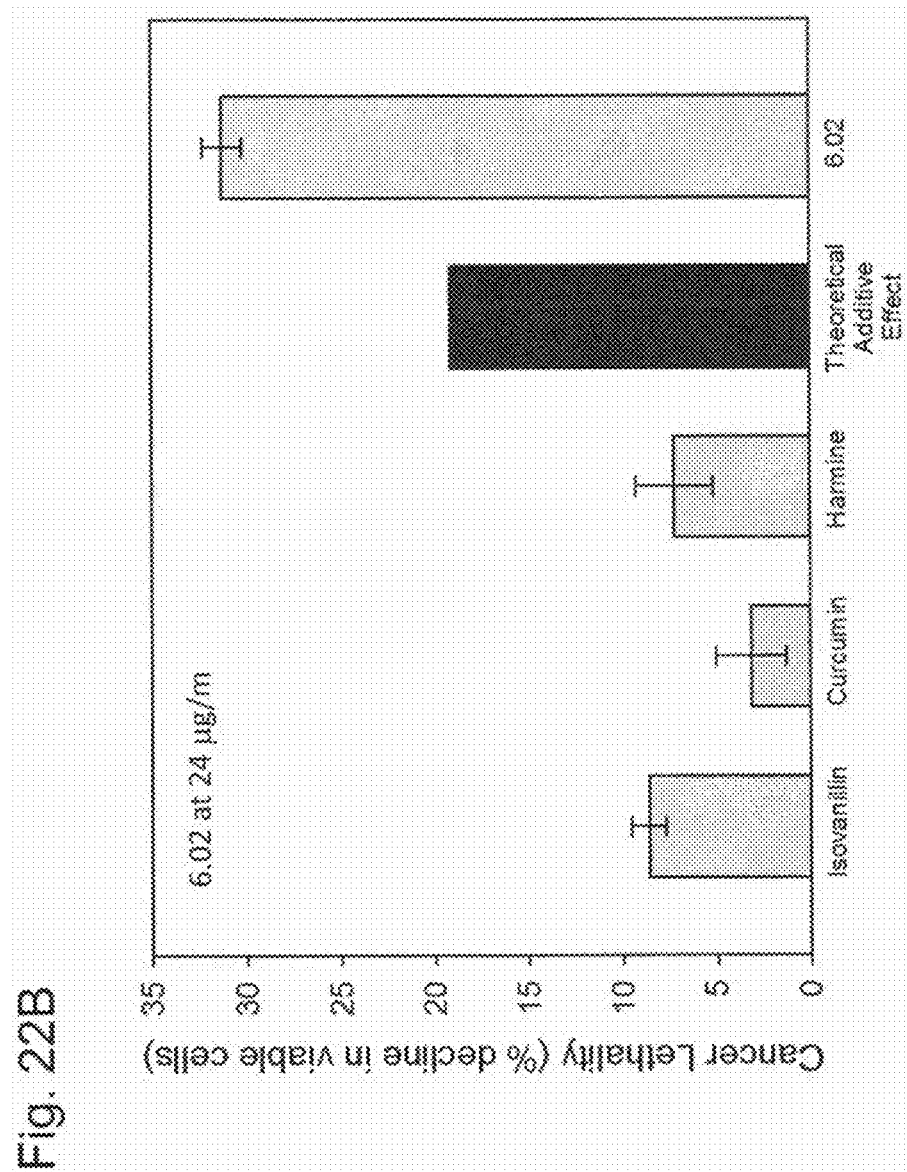
FIG. 22B is a graph of ovarian cancer cell lethality using GZ17-6.02 at a dosage rate of 24 μg/mL, and using the three components of GZ17-6.02 individually at the concentration present in GZ17-6.02, and further illustrating the theoretical additive effect of the three components versus GZ17-6.02.
Figure 22C:
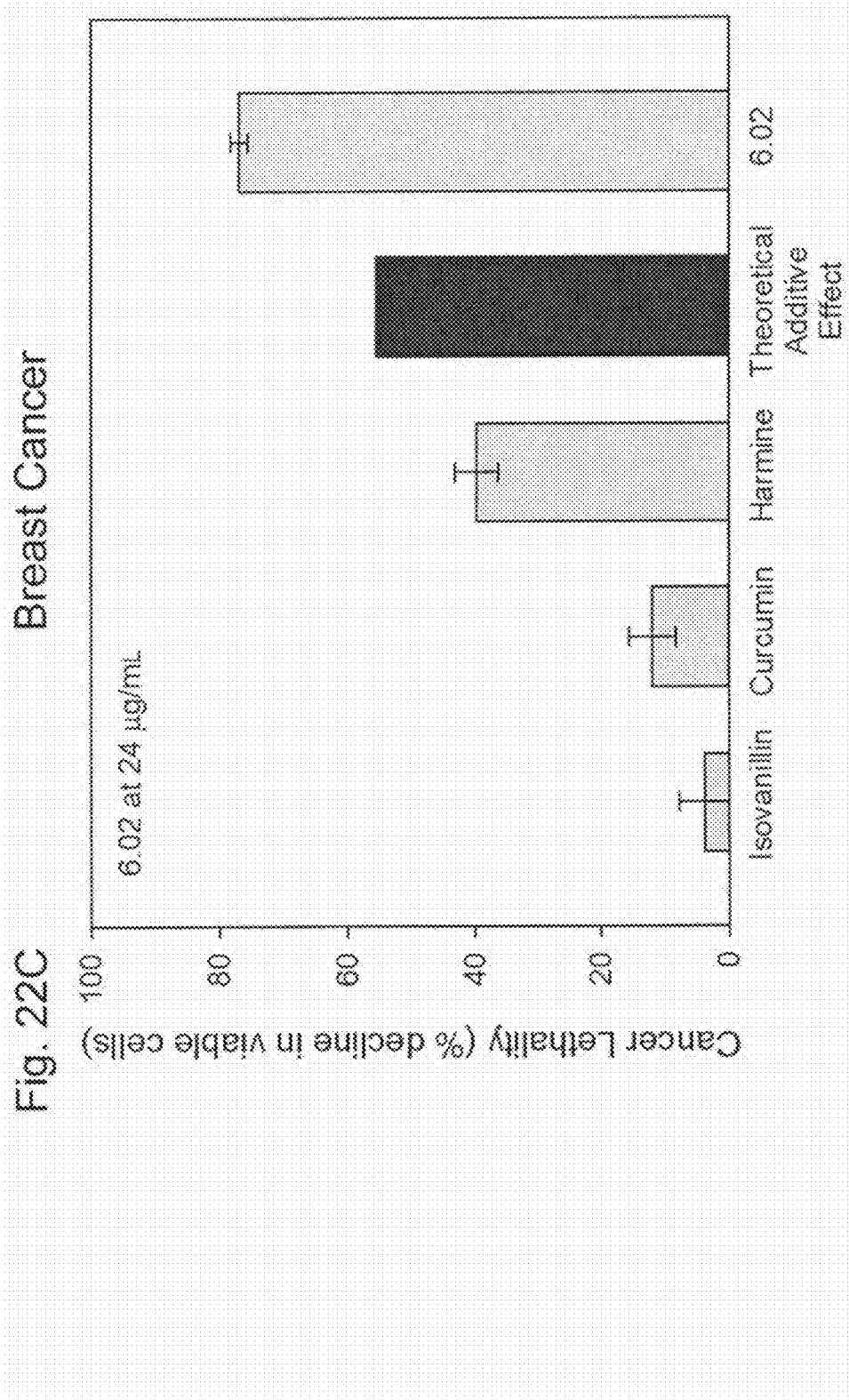
FIG. 22C is a graph of breast cancer cell lethality using GZ17-6.02 at a dosage rate of 24 μg/mL, and using the three components of GZ17-6.02 individually at the concentration present in GZ17-6.02, and further illustrating the theoretical additive effect of the three components versus GZ17-6.02.
Figure 23B:
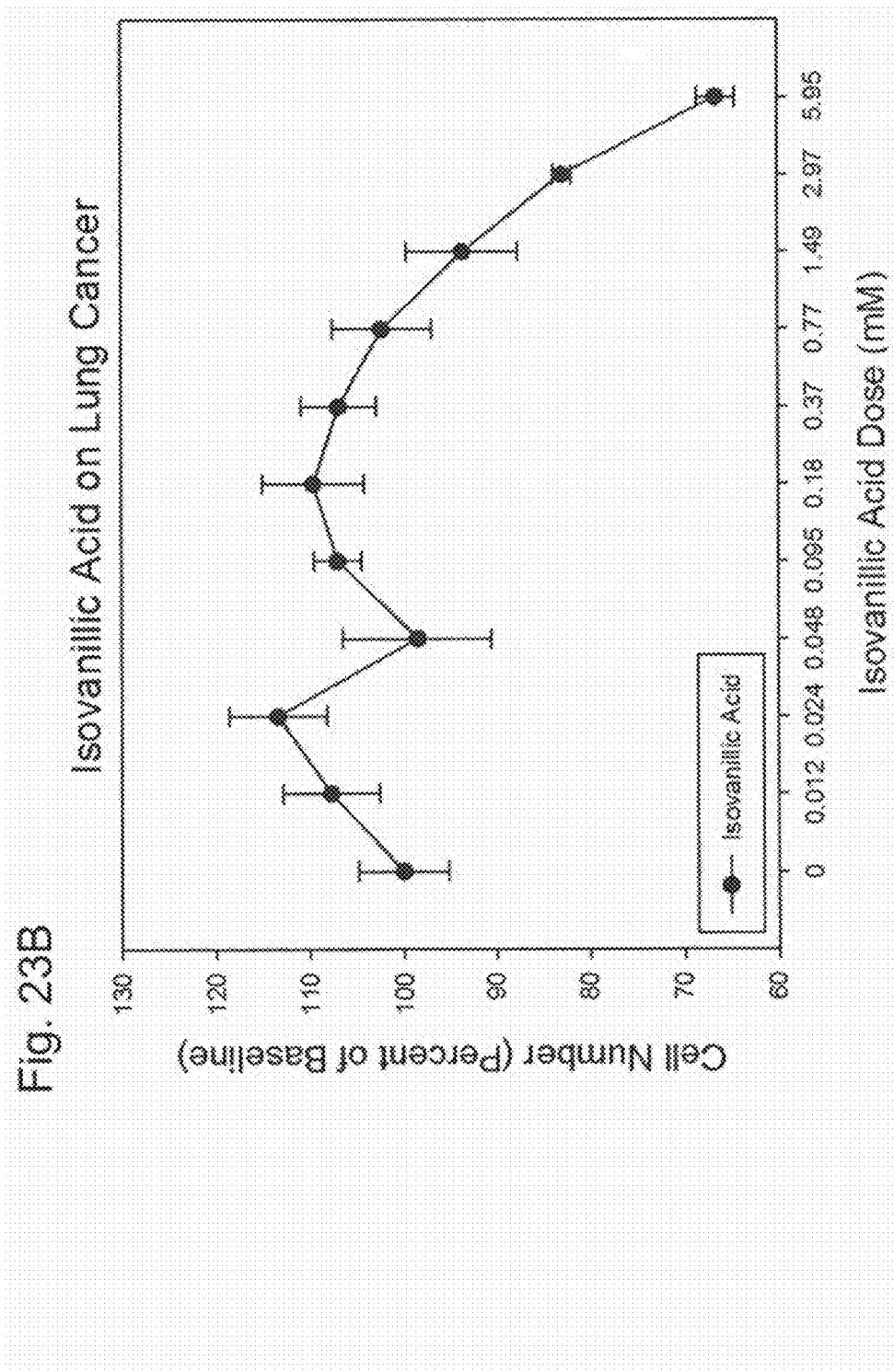
FIG. 23B is a graph of lung cancer cell number versus increasing dosage amounts of isovanillic acid alone, as described in Example 1.
Figure 23D:
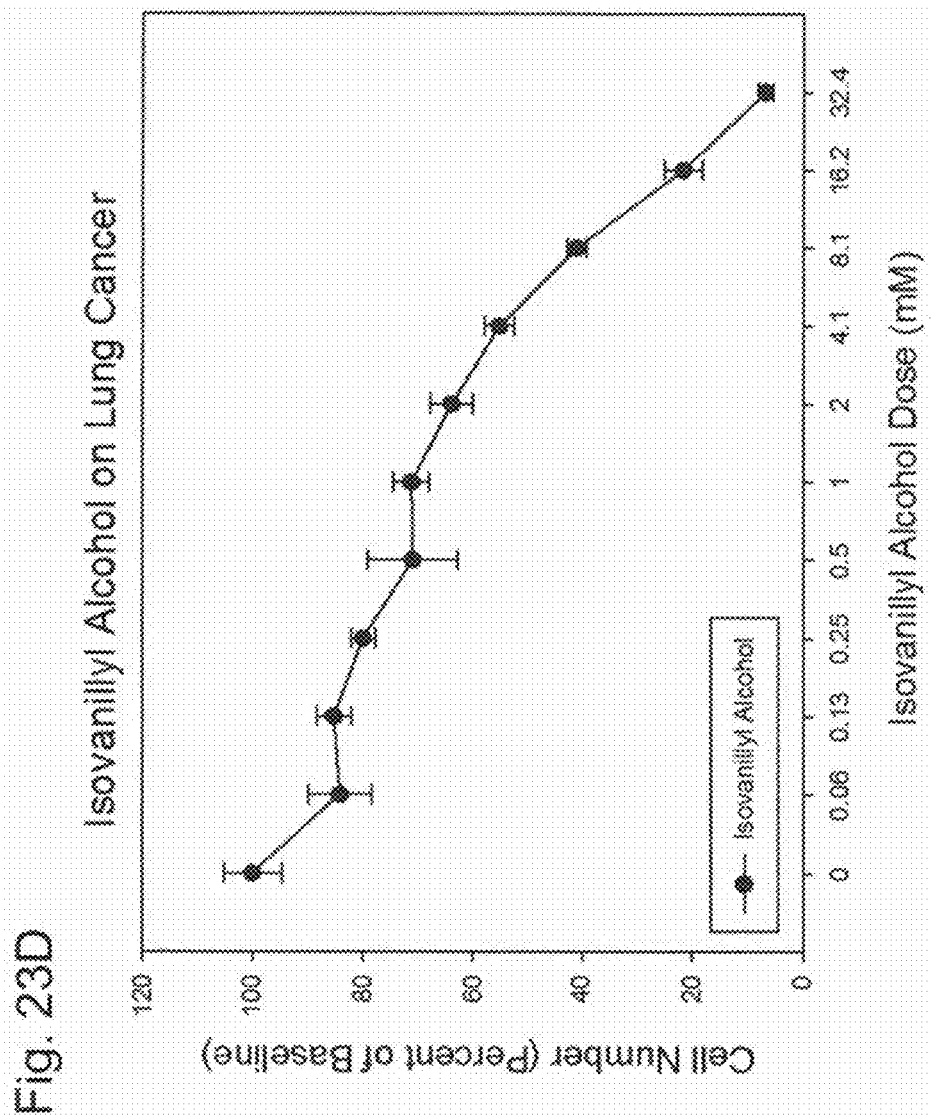
FIG. 23D is a graph of lung cancer cell number versus increasing dosage amounts of isovanillyl alcohol alone, as described in Example 1.
Figure 23E:
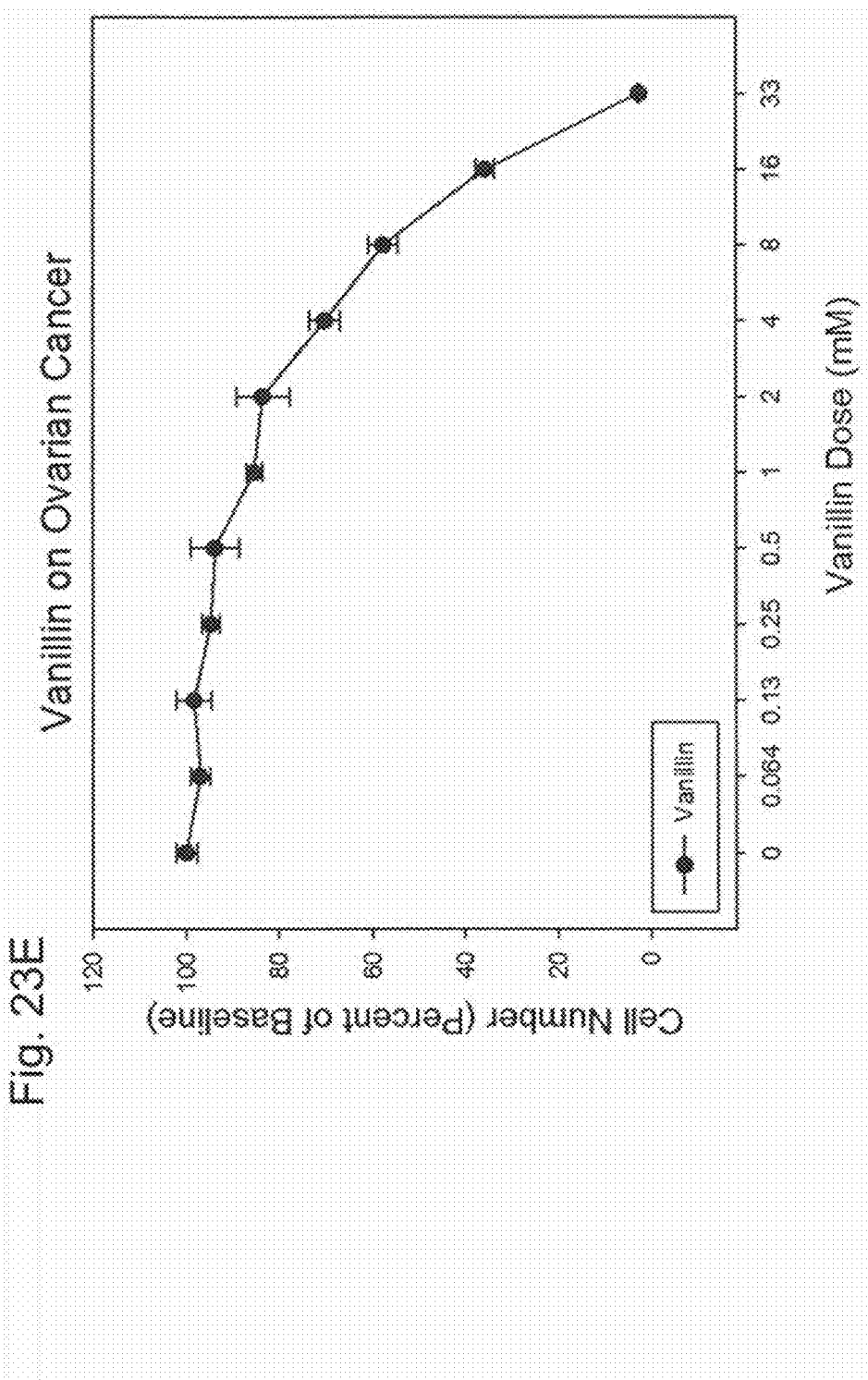
FIG. 23E is a graph of ovarian cancer cell number versus increasing dosage amounts of vanillin alone, as described in Example 1.
Figure 23F:
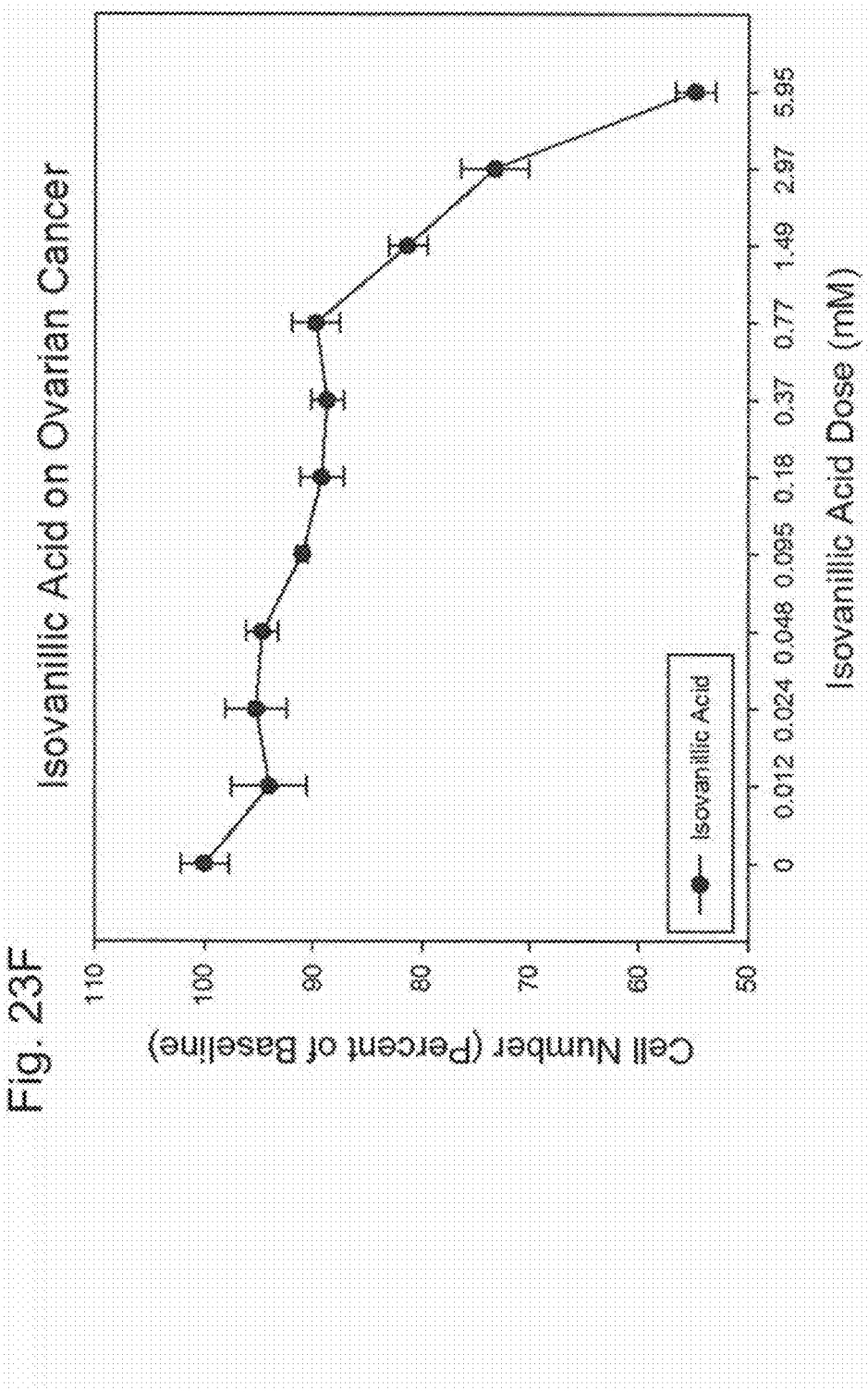
FIG. 23F is a graph of ovarian cancer cell number versus increasing dosage amounts of isovanillic acid alone, as described in Example 1.
Figure 23H:
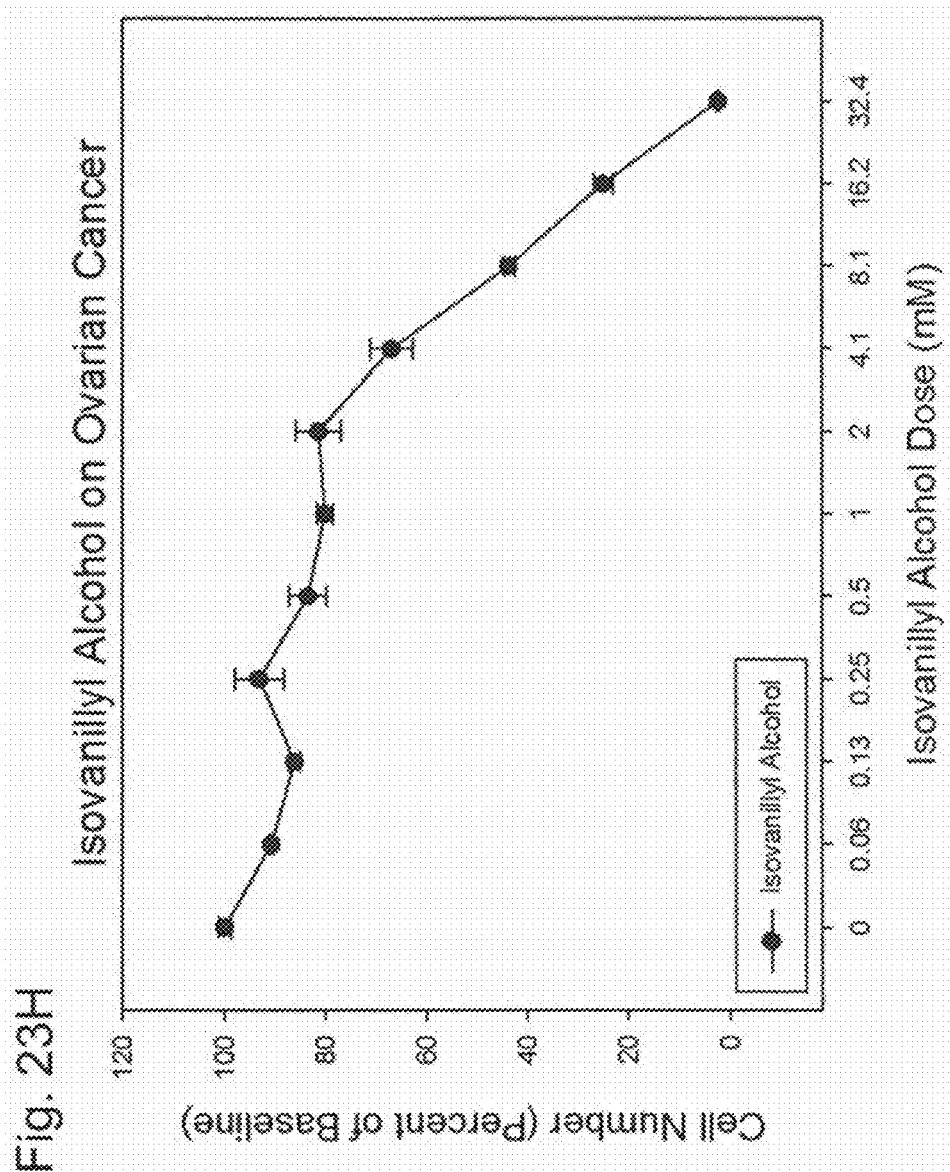
FIG. 23H is a graph of ovarian cancer cell number versus increasing dosage amounts of isovanillyl alcohol alone, as described in Example 1.
Figure 23I:
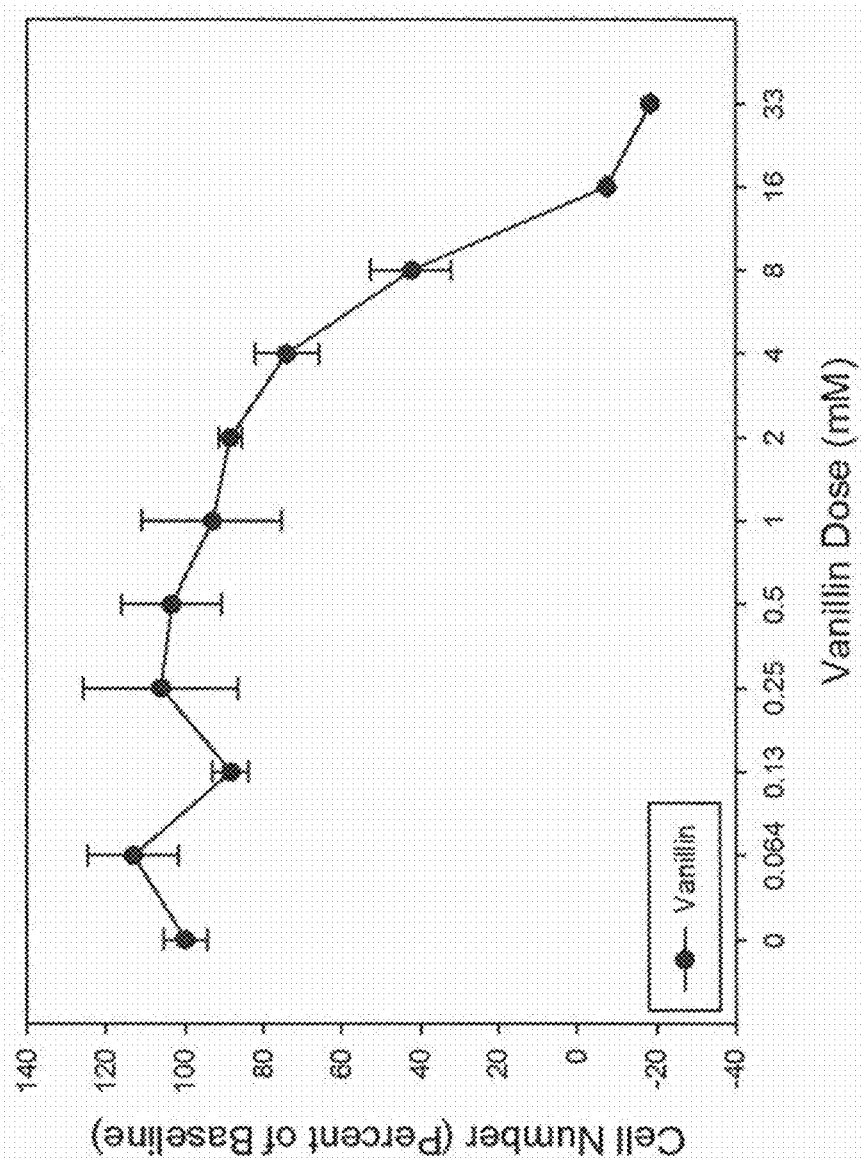
FIG. 23I is a graph of prostate cancer cell number versus increasing dosage amounts of vanillin alone, as described in Example 1.
Figure 23K:
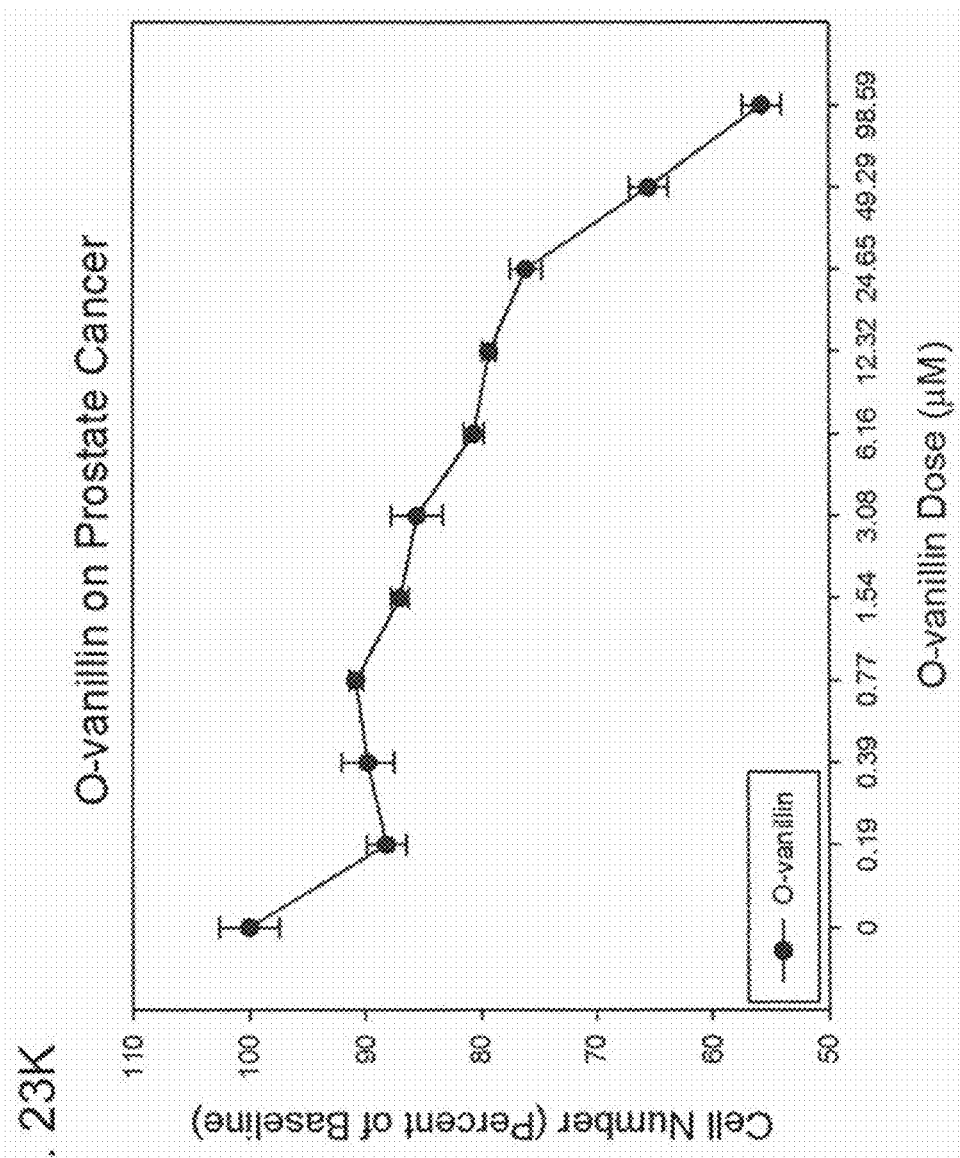
FIG. 23K is a graph of prostate cancer cell number versus increasing dosage amounts of O-vanillin alone, as described in Example 1.
Figure 23L:
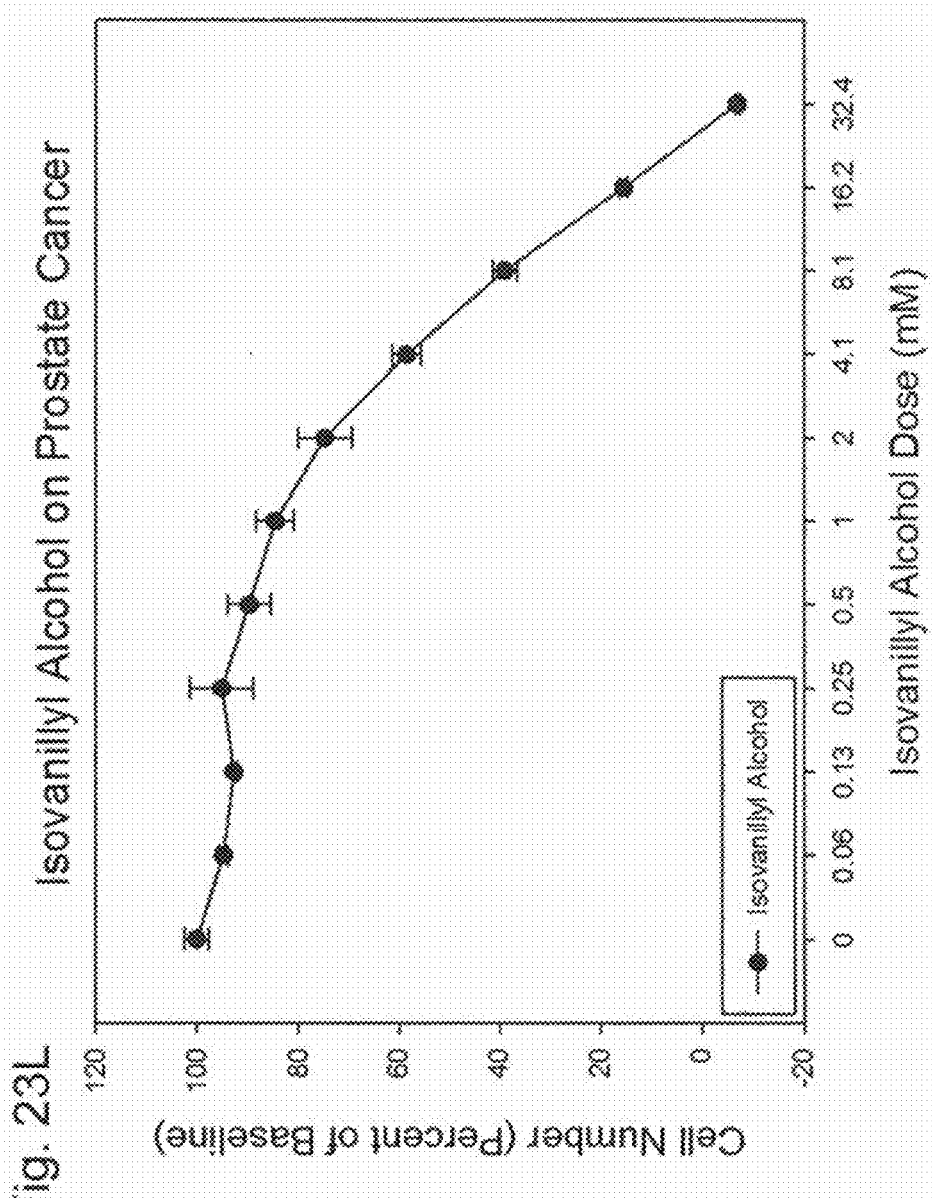
FIG. 23L is a graph of prostate cancer cell number versus increasing dosage amounts of isovanillyl alcohol alone, as described in Example 1.

In this example, the individual components of GZ17-6.02 were tested against ovarian cancer cells (A1847) and breast cancer cells (du4475) at the component concentrations found in GZ17-6.02, at dosage rates of 12 and 24 µg/mL. The theoretical additive effect (black bar) of the 3 components was also calculated in each case and shown versus the actual test results found using GZ17-6.02. FIGS. 22A and 22B illustrate the results of these ovarian cancer tests, and confirm that, at the tested dosages, the GZ17-6.02 product had a greater effect than the individual components and the theoretical additive effect thereof. In an additional test at 48 µg/mL dosage rate, this effect was not observed. FIG. 22C sets forth the results using breast cancer cells.

Example 23

In this example, increasing concentrations of different isovanillin derivatives or metabolites were tested using lung cancer cells (H358), ovarian cancer cells (A1847), and prostate cancer cells (22rv1), to determine the anticancer effects of the derivatives/metabolites, using the techniques of Example 1. Each of the derivatives/metabolites (vanillin, isovanillic acid, 0-vanillin, and isovanillyl alcohol) demonstrated anticancer effects (see FIGS. 23A-23L).

Example 24

Figure 24A:
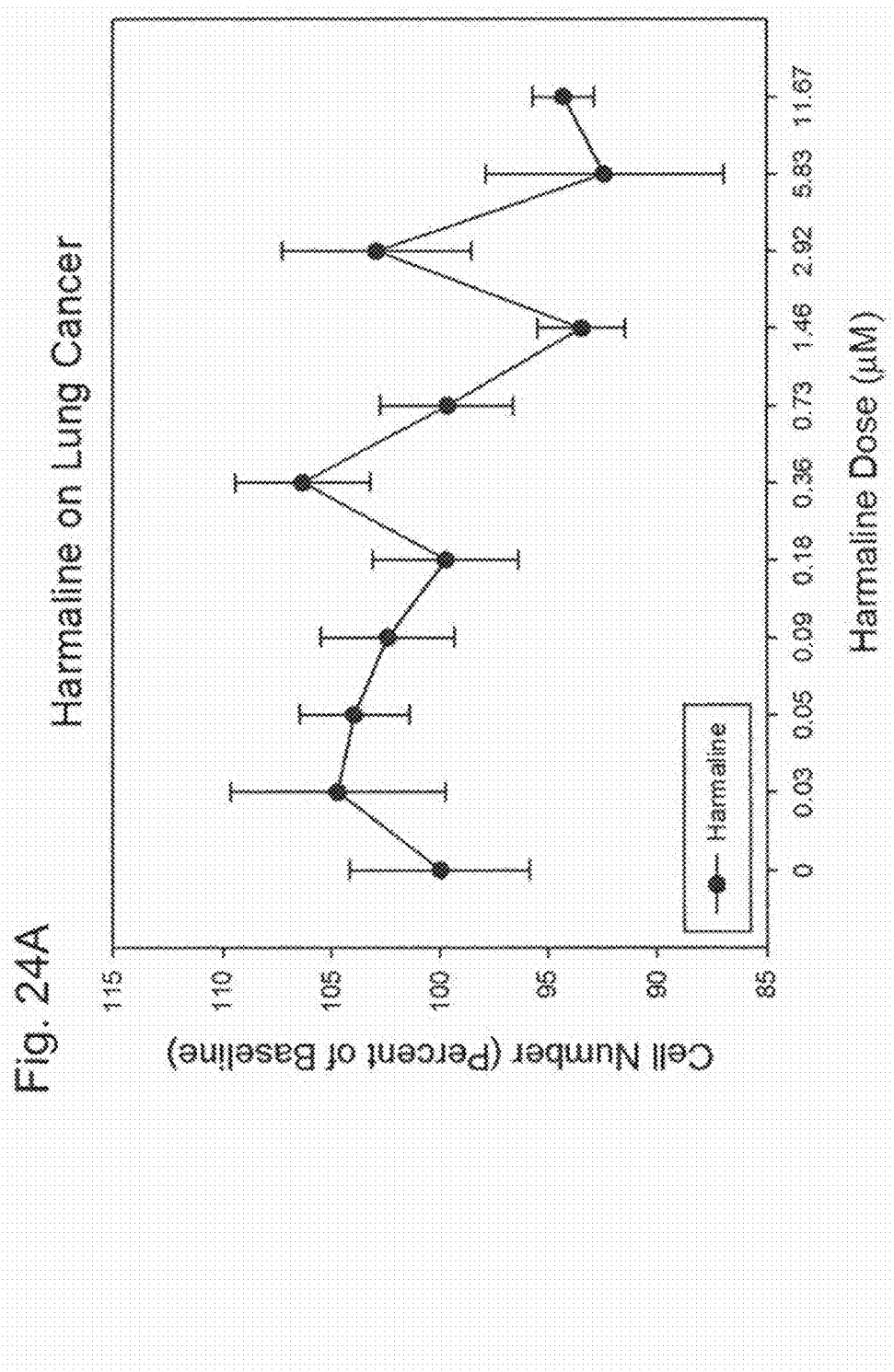
FIG. 24A is a graph of lung cancer cell number versus increasing dosage amounts of harmaline alone, as described in Example 1.
Figure 24B:
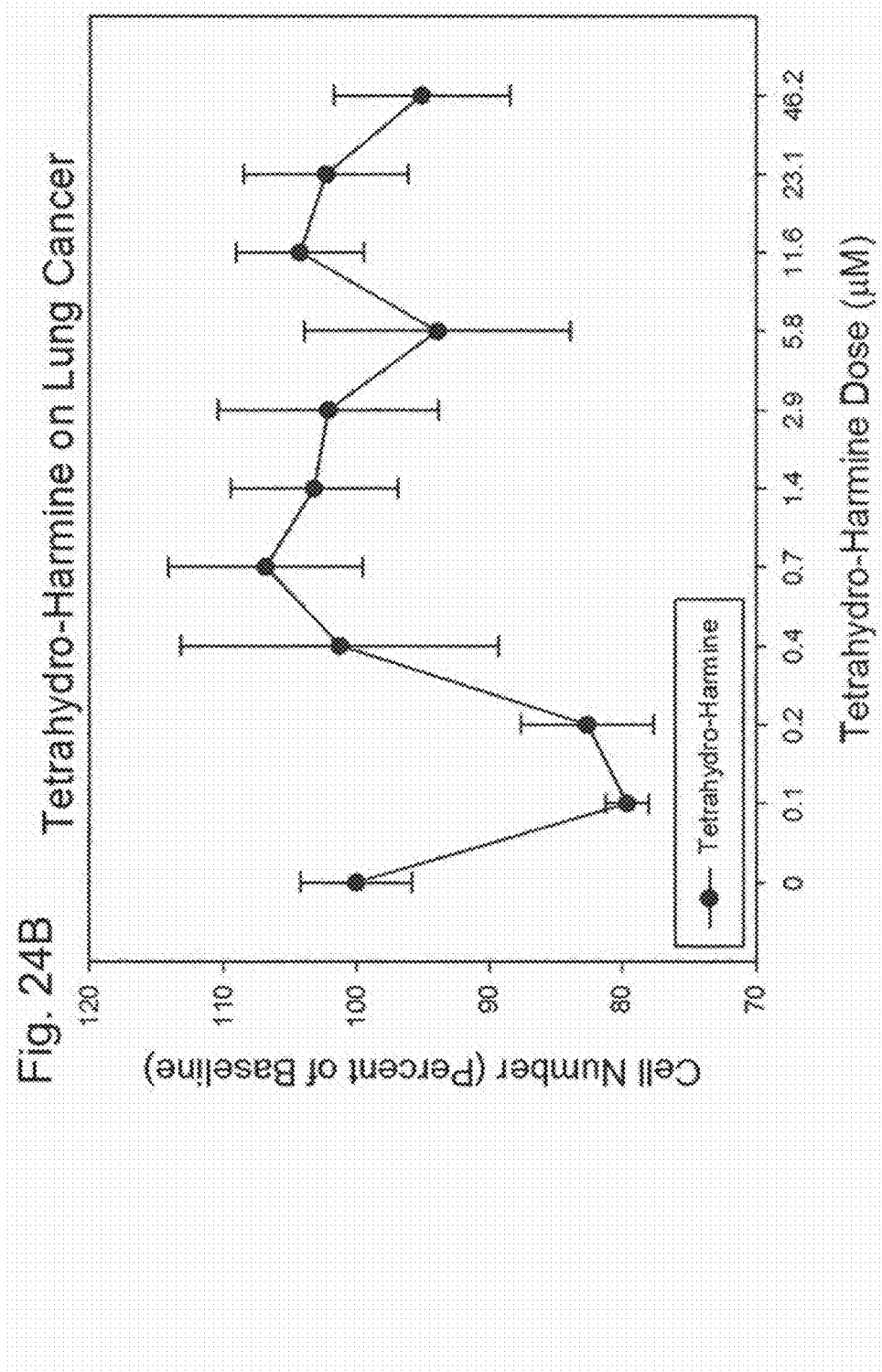
FIG. 24B is a graph of lung cancer cell number versus increasing dosage amounts of tetrahydro-harmine alone, as described in Example 1.
Figure 24C:
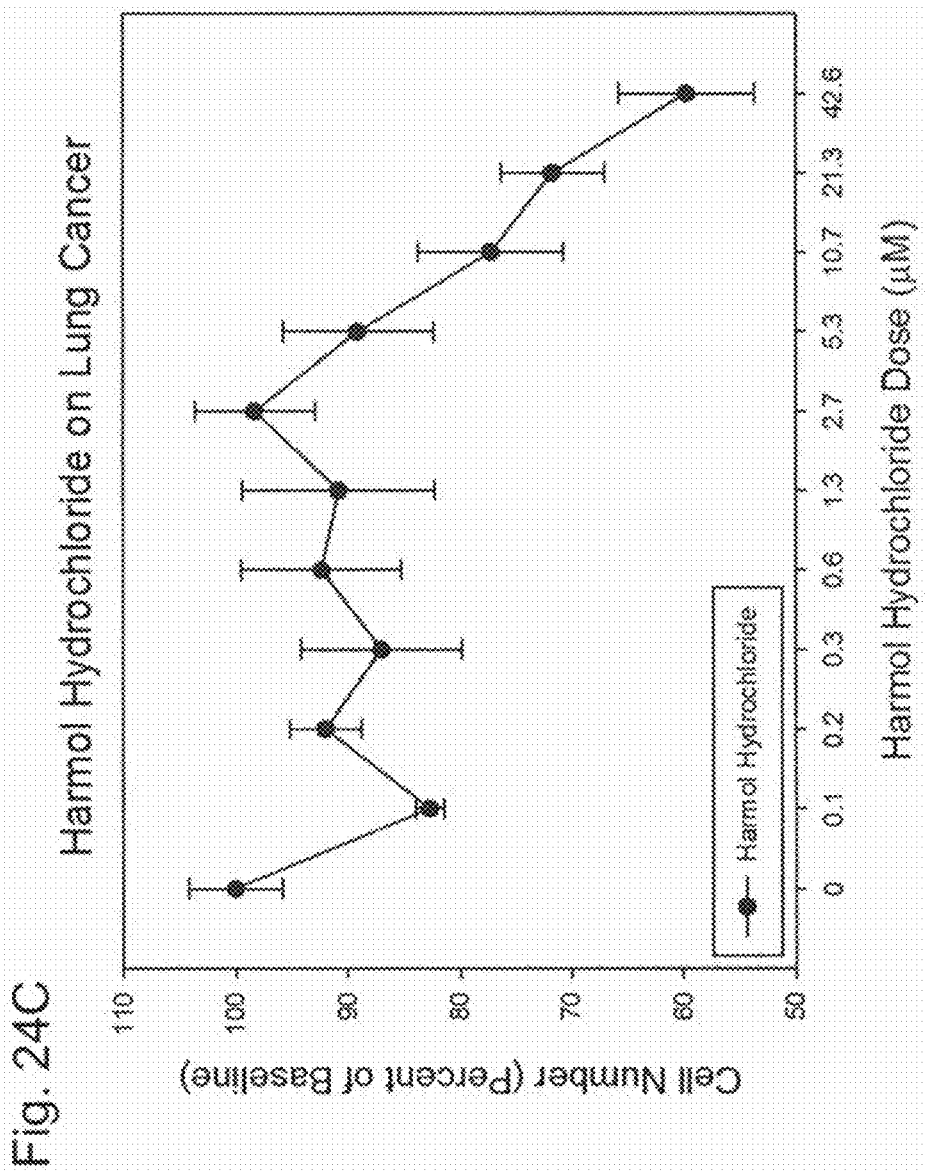
FIG. 24C is a graph of lung cancer cell number versus increasing dosage amounts of harmol hydrochloride alone, as described in Example 1.
Figure 24D:
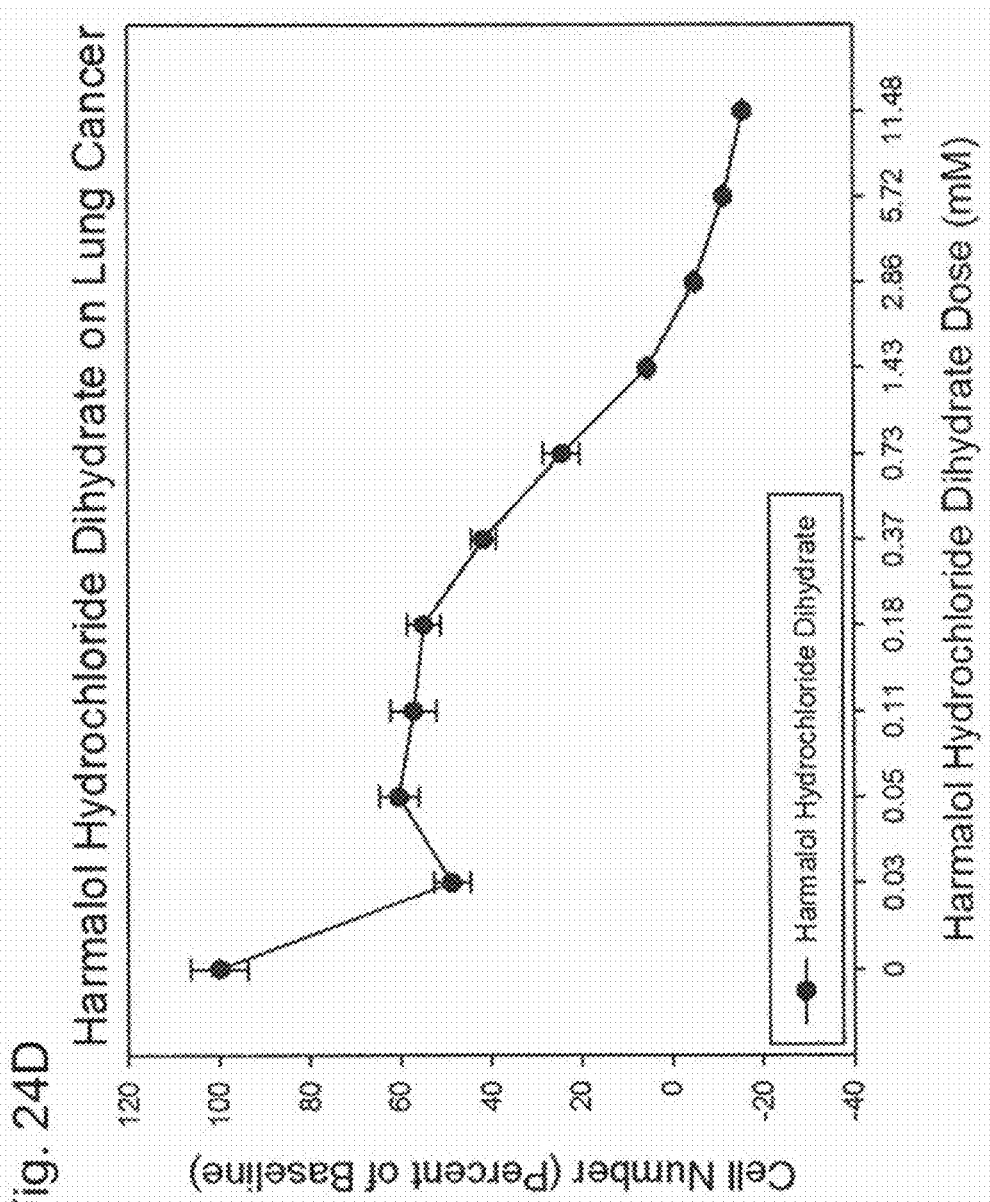
FIG. 24D is a graph of lung cancer cell number versus increasing dosage amounts of harmalol hydrochloride dihydrate alone, as described in Example 1.
Figure 24E:
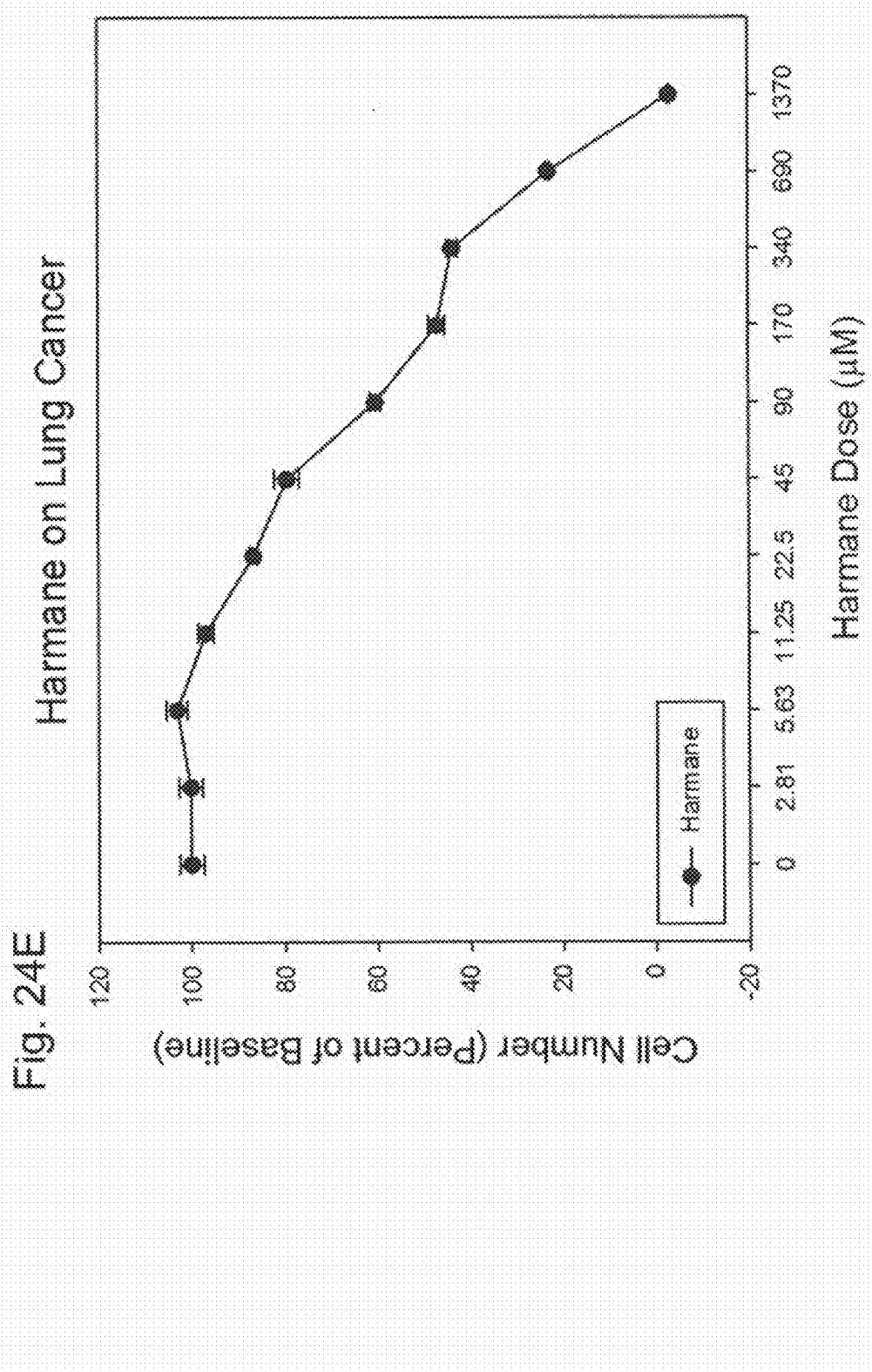
FIG. 24E is a graph of lung cancer cell number versus increasing dosage amounts of harmane alone, as described in Example 1.
Figure 24F:
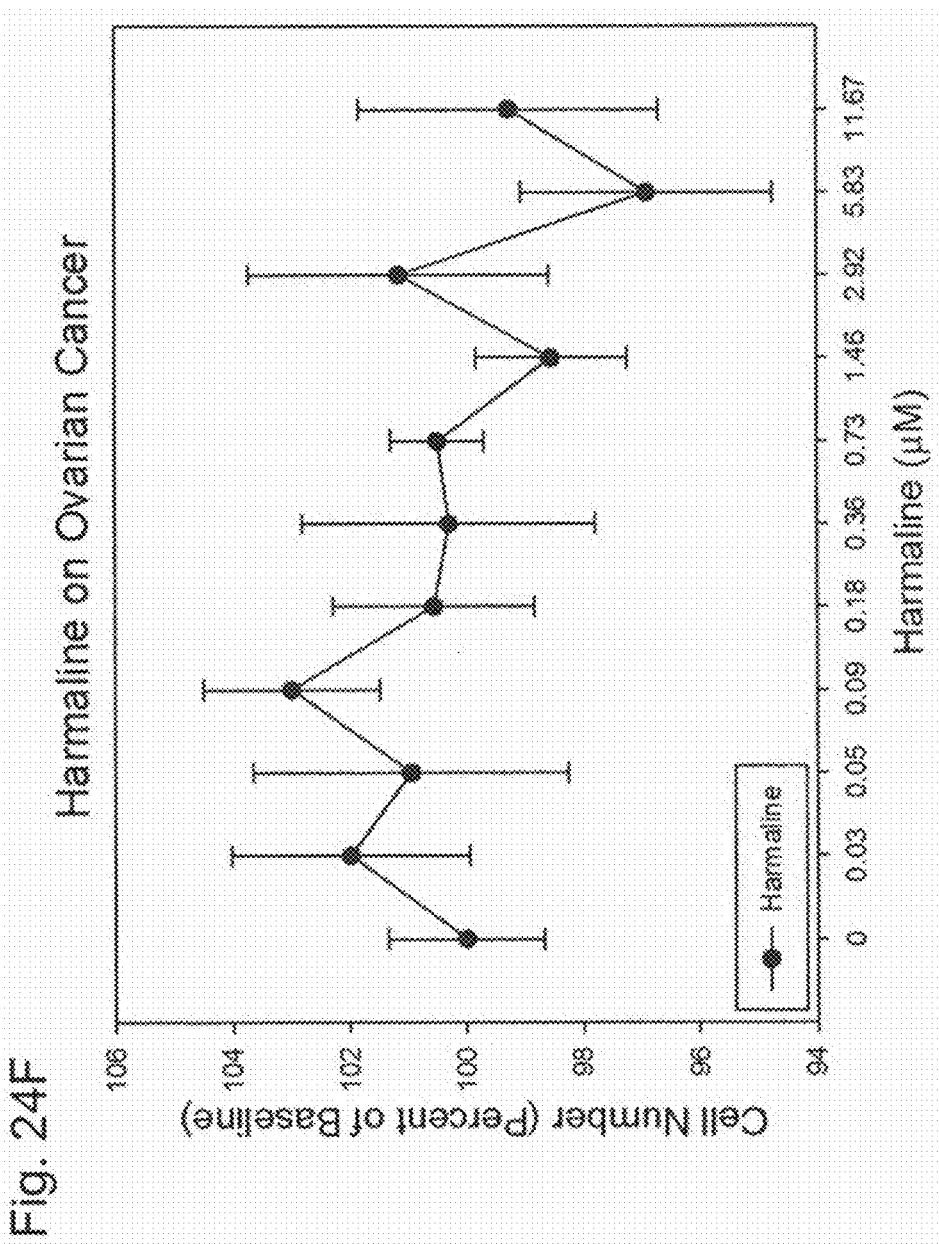
FIG. 24F is a graph of ovarian cancer cell number versus increasing dosage amounts of harmaline alone, as described in Example 1.
Figure 24G:
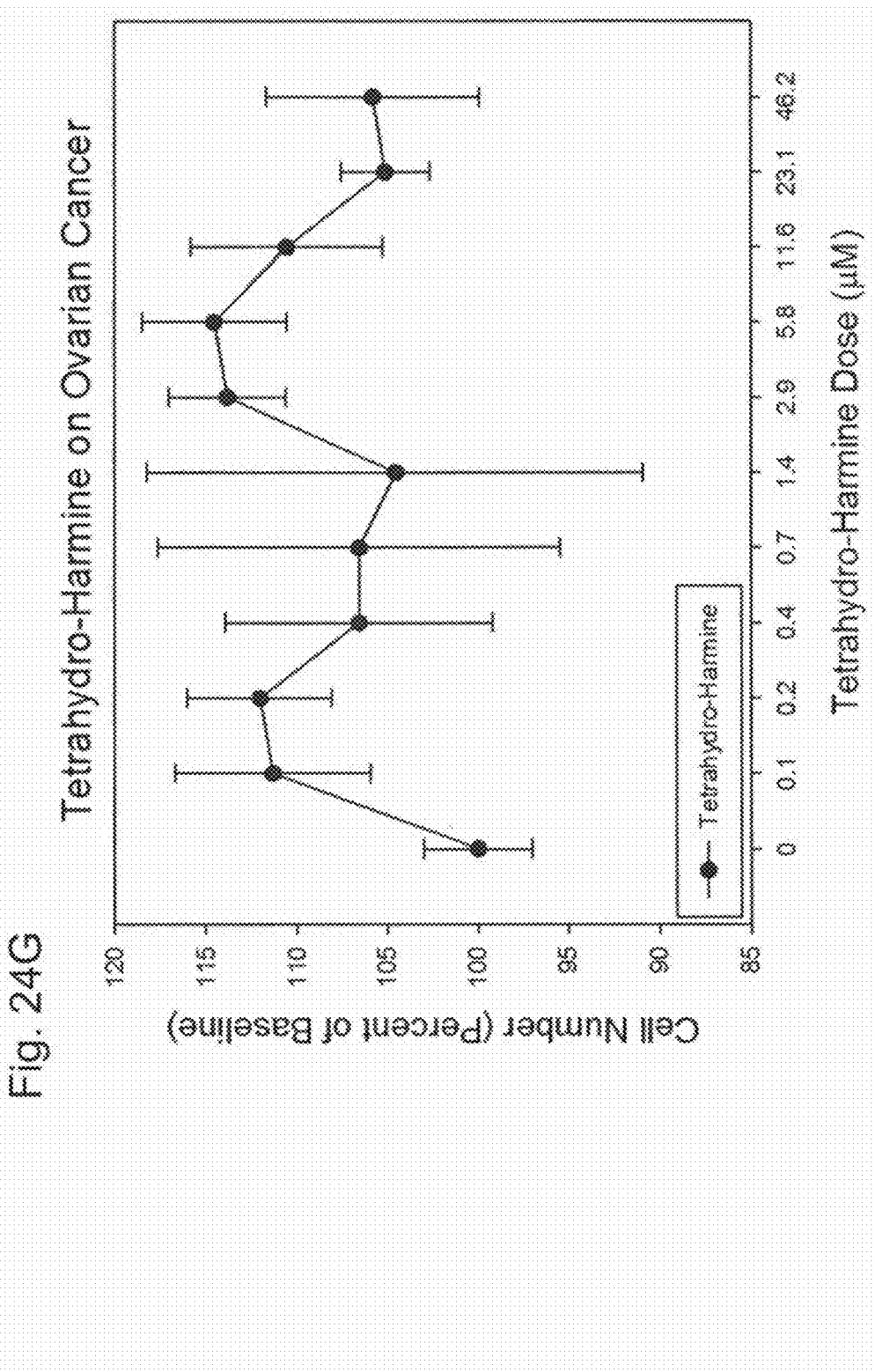
FIG. 24G is a graph of ovarian cancer cell number versus increasing dosage amounts of tetrahydro-harmine alone, as described in Example 1.
Figure 24H:
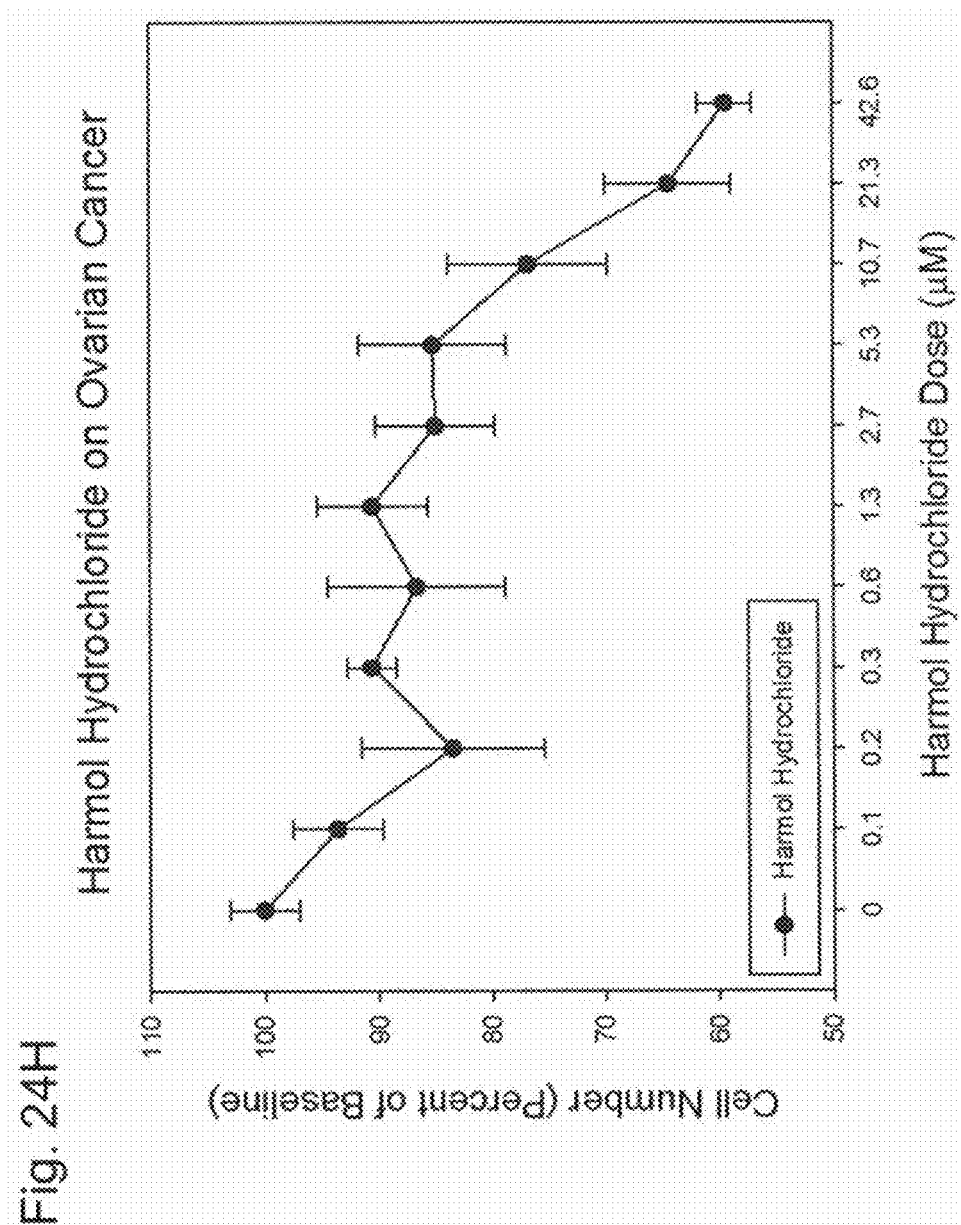
FIG. 24H is a graph of ovarian cancer cell number versus increasing dosage amounts of harmol hydrochloride alone, as described in Example 1.
Figure 24I:
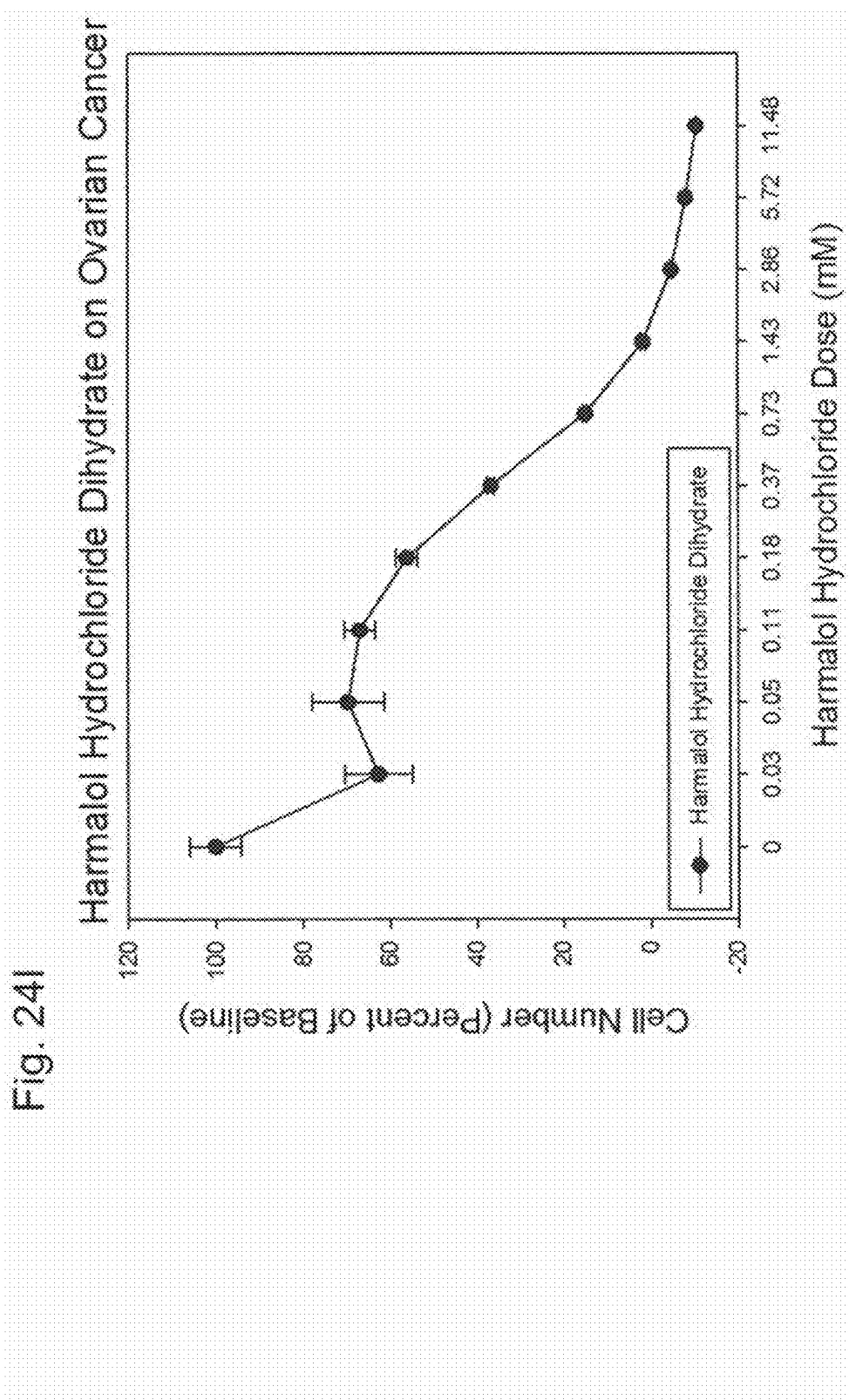
FIG. 24I is a graph of ovarian cancer cell number versus increasing dosage amounts of harmalol hydrochloride dihydrate alone, as described in Example 1.
Figure 24J:
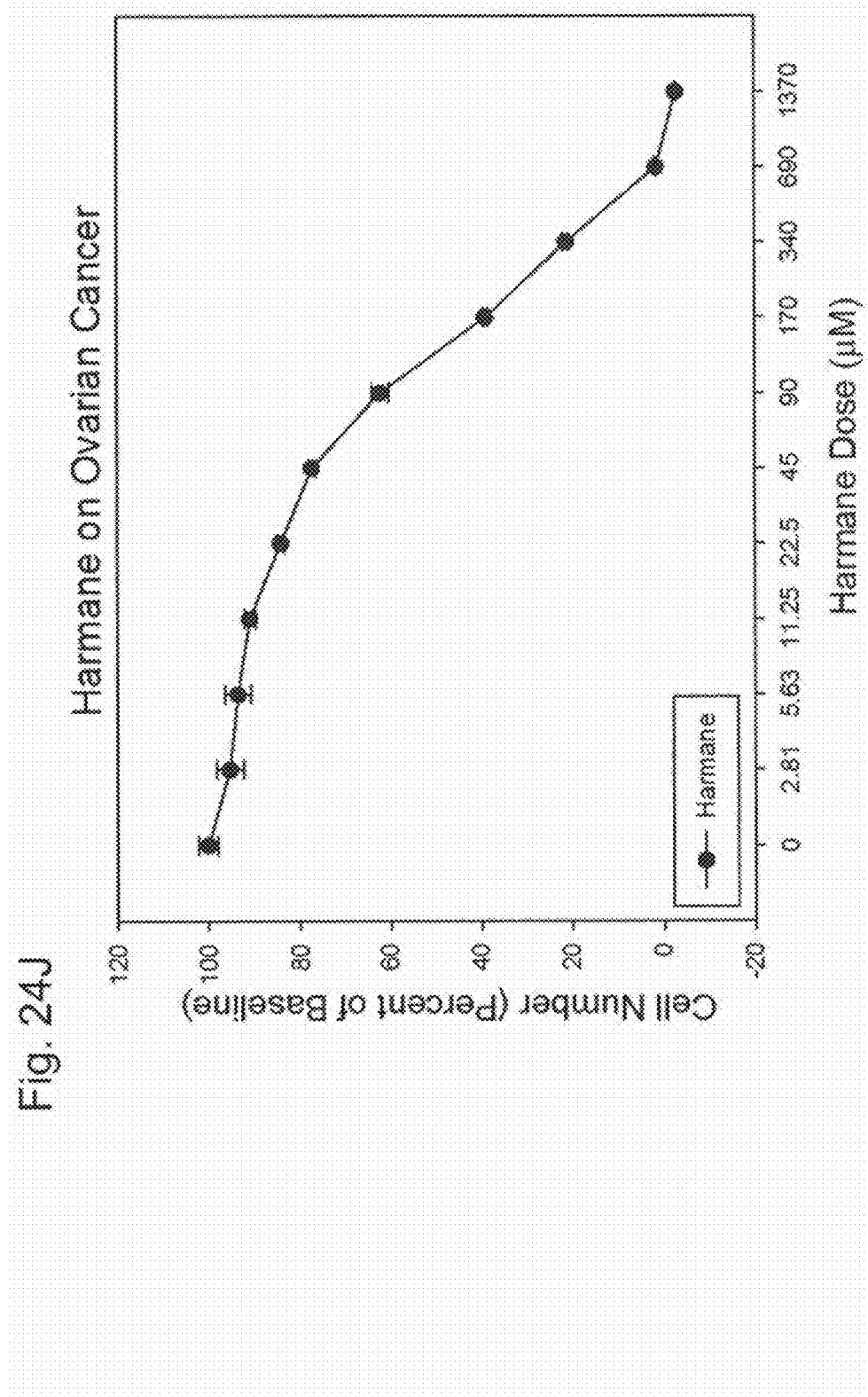
FIG. 24J is a graph of ovarian cancer cell number versus increasing dosage amounts of harmane alone, as described in Example 1.
Figure 24L:
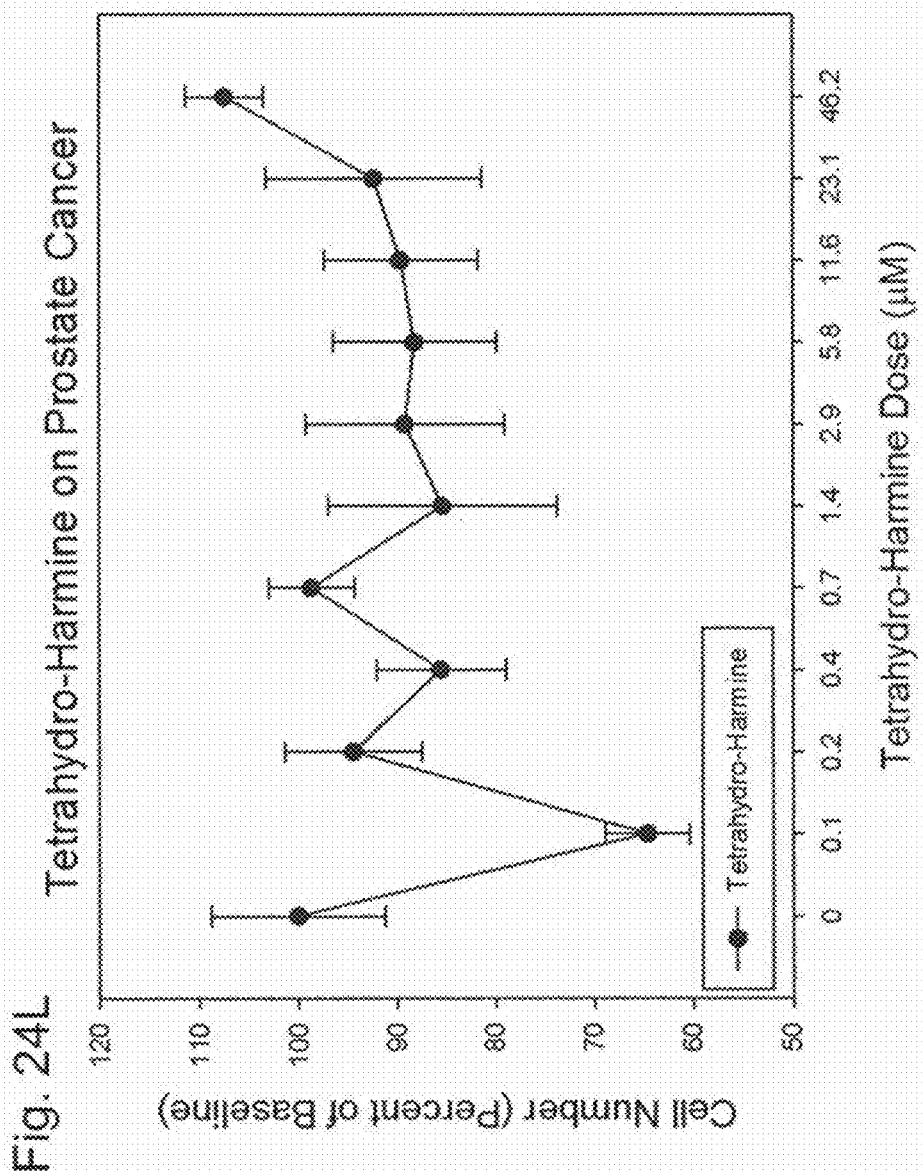
FIG. 24L is a graph of prostate cancer cell number versus increasing dosage amounts of tetrahydro-harmine alone, as described in Example 1.
Figure 24N:
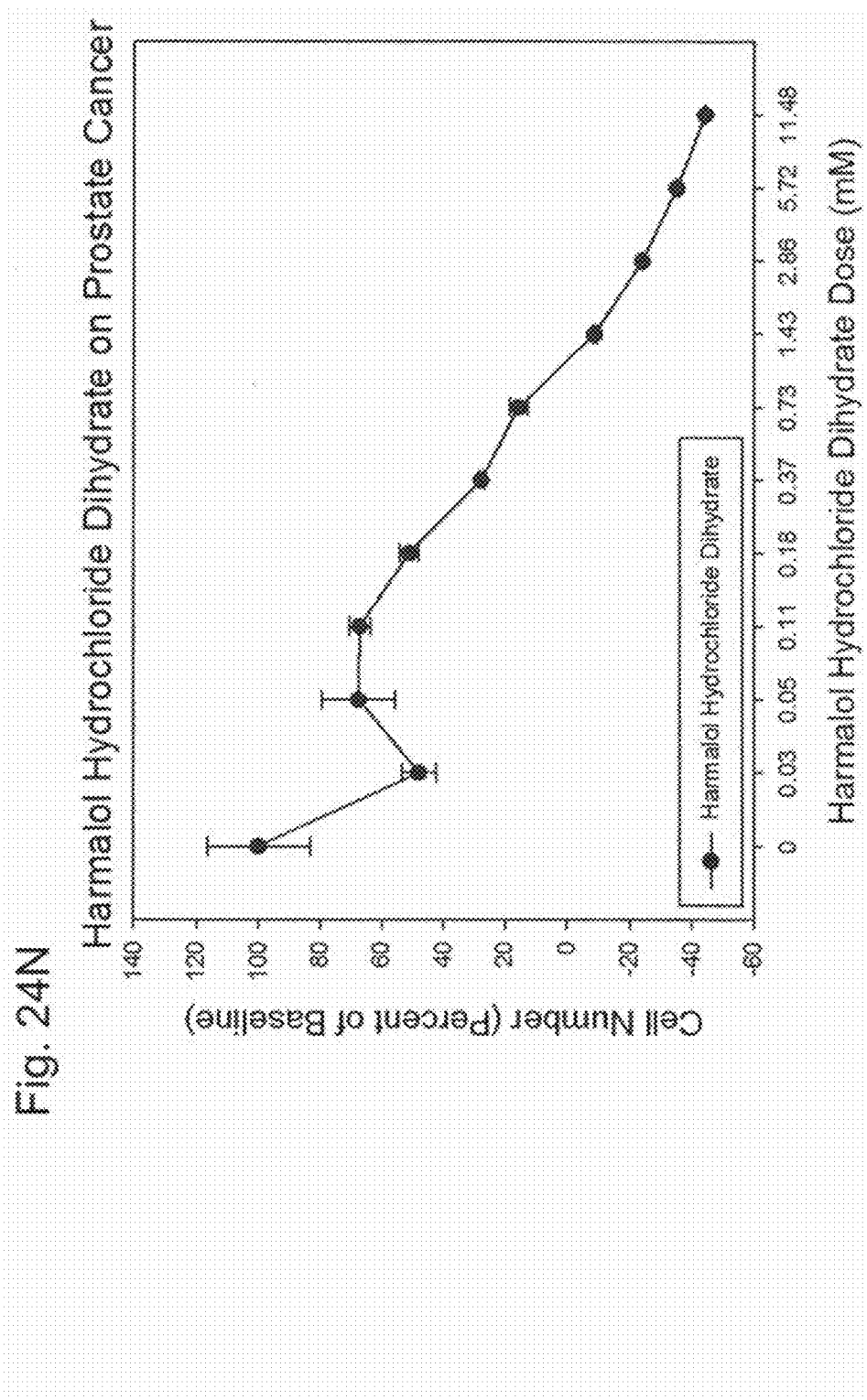
FIG. 24N is a graph of prostate cancer cell number versus increasing dosage amounts of harmalol hydrochloride dihydrate alone, as described in Example 1.
Figure 24O:
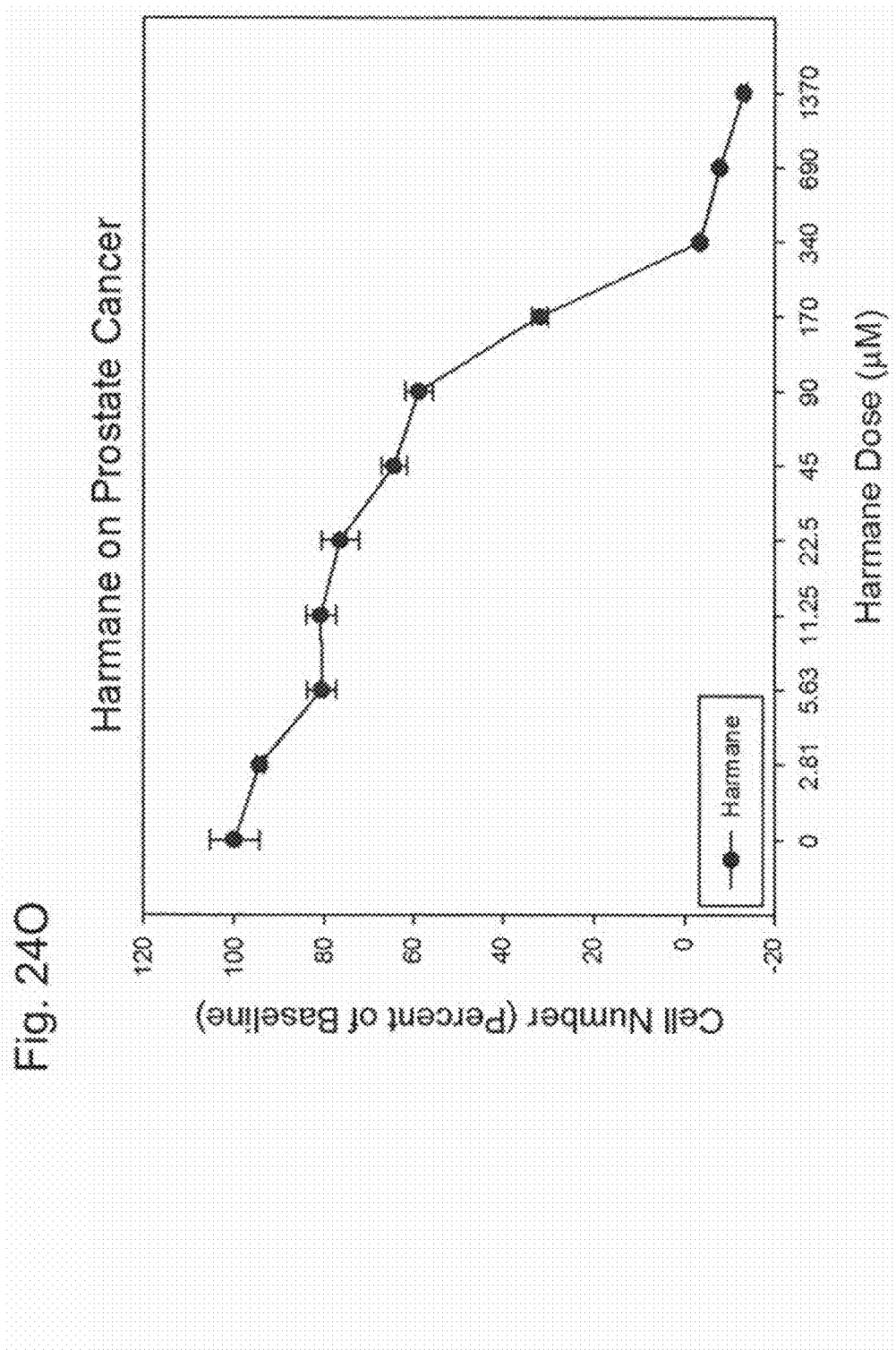
FIG. 24O is a graph of prostate cancer cell number versus increasing dosage amounts of harmane alone, as described in Example 1.

In this example, increasing concentrations of different harmine derivatives or metabolites were tested using lung cancer cells (H358), ovarian cancer cells (A1847), and prostate cancer cells (22rv1), to determine the anticancer effects of the derivatives/metabolites, using the techniques of Example 1. Each of the derivatives/metabolites (harmaline, tetrahydro-harmine, harmole hydrochloride, harmalol hydrochloride, and harmane) demonstrated anticancer effects (see FIGS. 24A-24O).

Example 25

Figure 25A:
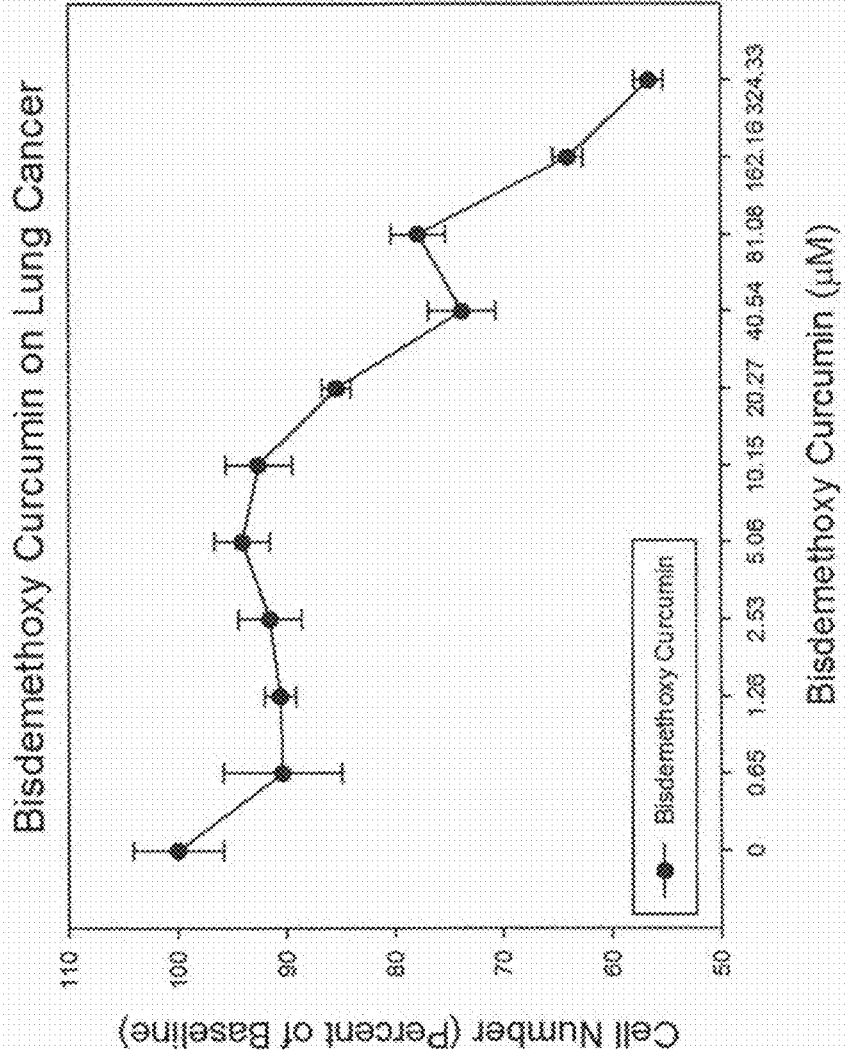
FIG. 25A is a graph of lung cancer cell number versus increasing dosage amounts of bisdemethoxy curcumin alone, as described in Example 1.
Figure 25C:
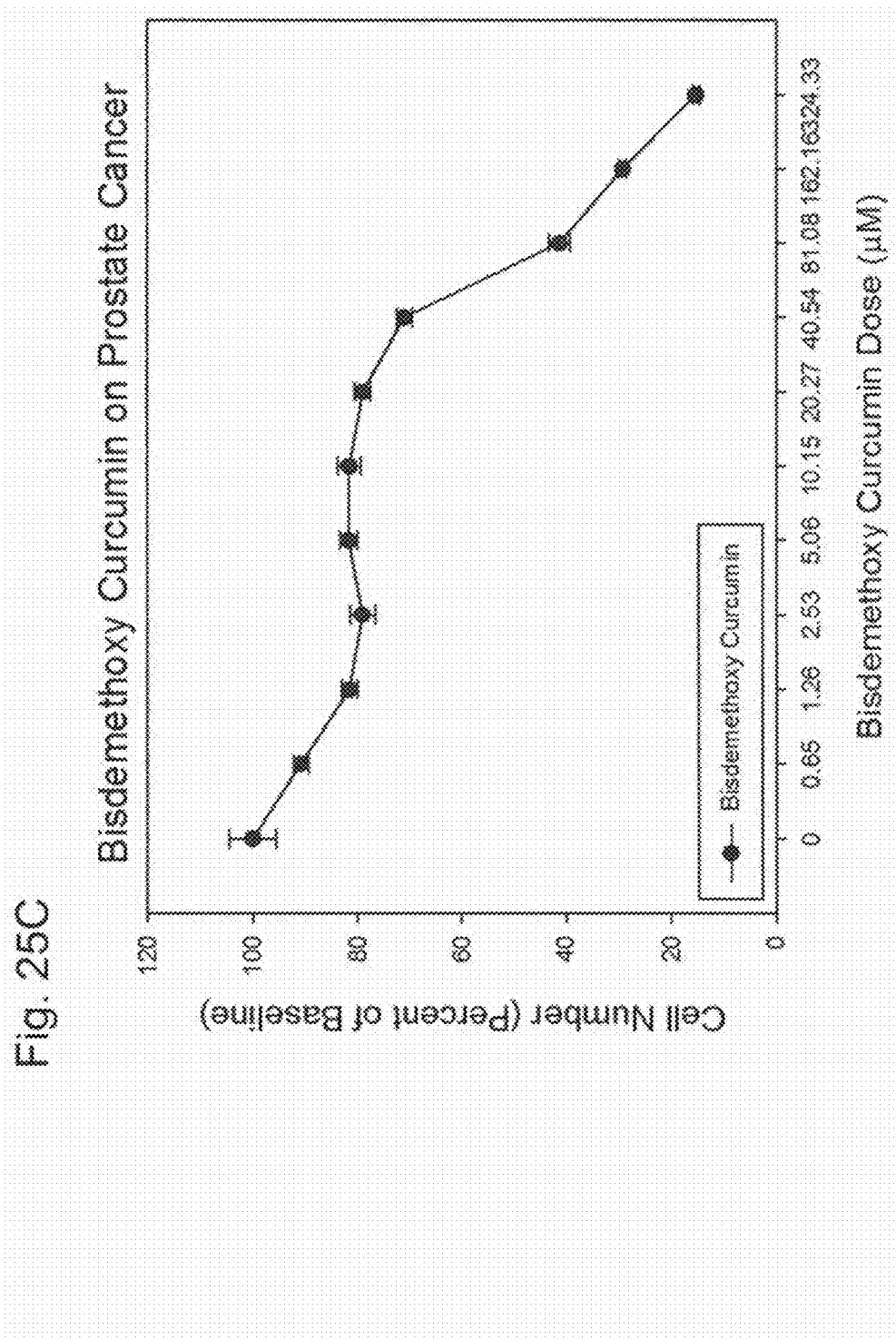
FIG. 25C is a graph of prostate cancer cell number versus increasing dosage amounts of bisdemethoxy curcumin alone, as described in Example 1.

In this example, increasing concentrations of a curcumin derivative, bisdemethoxy curcumin, were tested using lung cancer cells (H358), ovarian cancer cells (A1847), and prostate cancer cells (22rv1), to determine the anticancer effects of the derivative, using the techniques of Example 1. The results confirmed the anticancer effects of this derivative (see FIGS. 25A-25C).

Example 26

In this test, the preferred GZ17-6.02 product was stored at various temperatures over a two-month period, and then tested against ovarian cancer cells (A1847). The results are set forth in FIG. 26, which illustrates that at storage temperatures of −20° C. and 4° C., the product maintained its potency.

Example 27

In this test, the GZ17-6.02 product was subjected to successive freeze/thaw cycles. In each cycle, the product was frozen at −20° C., followed by allowing the product temperature to equilibrate at room temperature. At the end of each cycle, the product was tested against ovarian cancer cells (A1847) using the methods of Example 1. A total of 10 successive freeze/thaw cycles were performed on the same sample. FIG. 27 illustrates that there was no significant change in the efficacy of the GZ17-6.02 against ovarian cancer cells.

Example 28

Figure 28A:
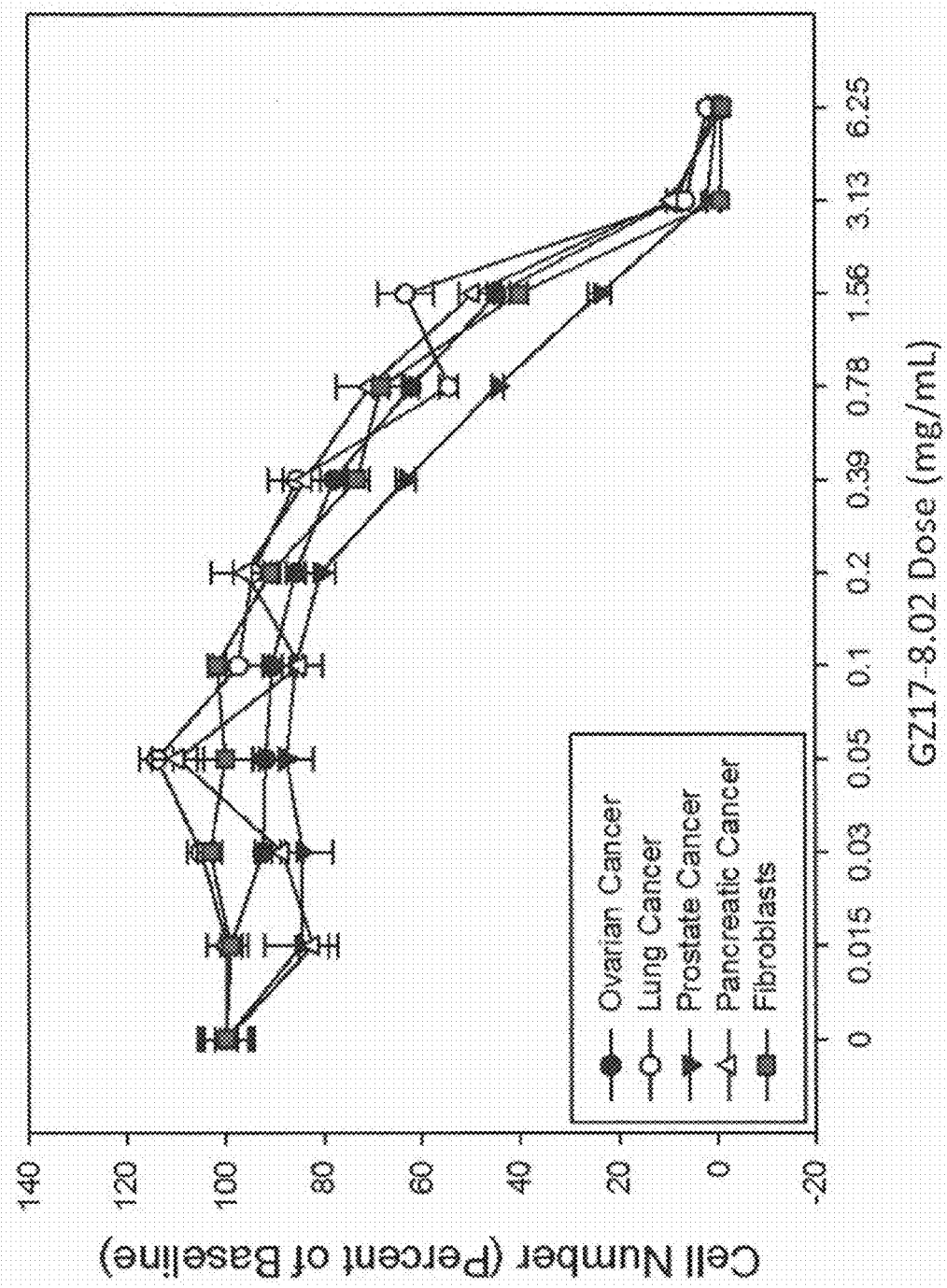
FIG. 28A is a graph of cell number versus dosage amounts of GZ17-8.02, illustrating the effect thereof in inducing the death of two different types ovarian cancer, lung cancer, prostate cancer, pancreatic cancer and fibroblast cells, as described in Example 28.
Figure 28B:
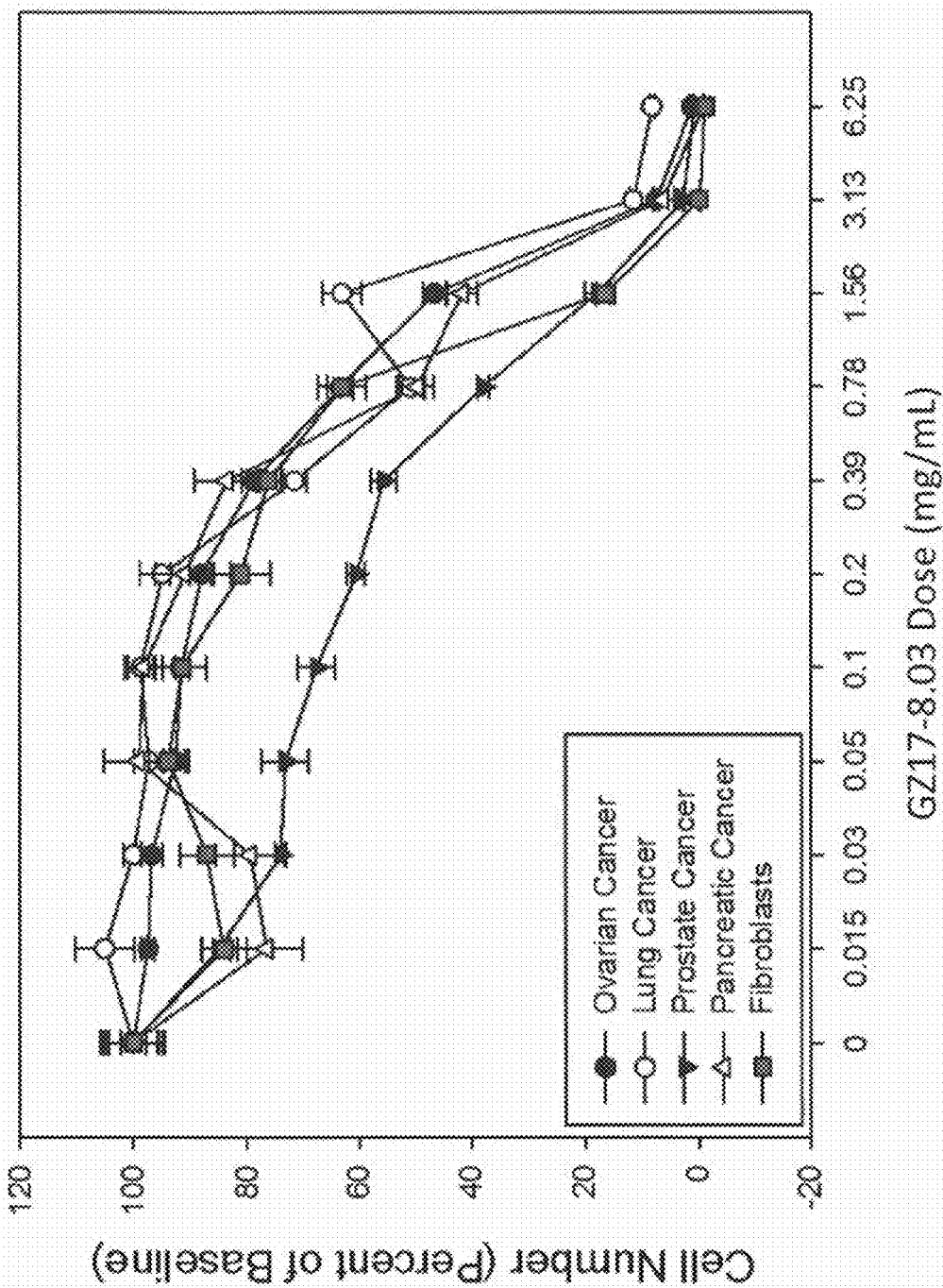
FIG. 28B is a graph of cell number versus dosage amounts of GZ17-8.03, illustrating the effect thereof in inducing the death of ovarian cancer, lung cancer, prostate cancer, pancreatic cancer and fibroblast cells, as described in Example 28.
Figure 28C:
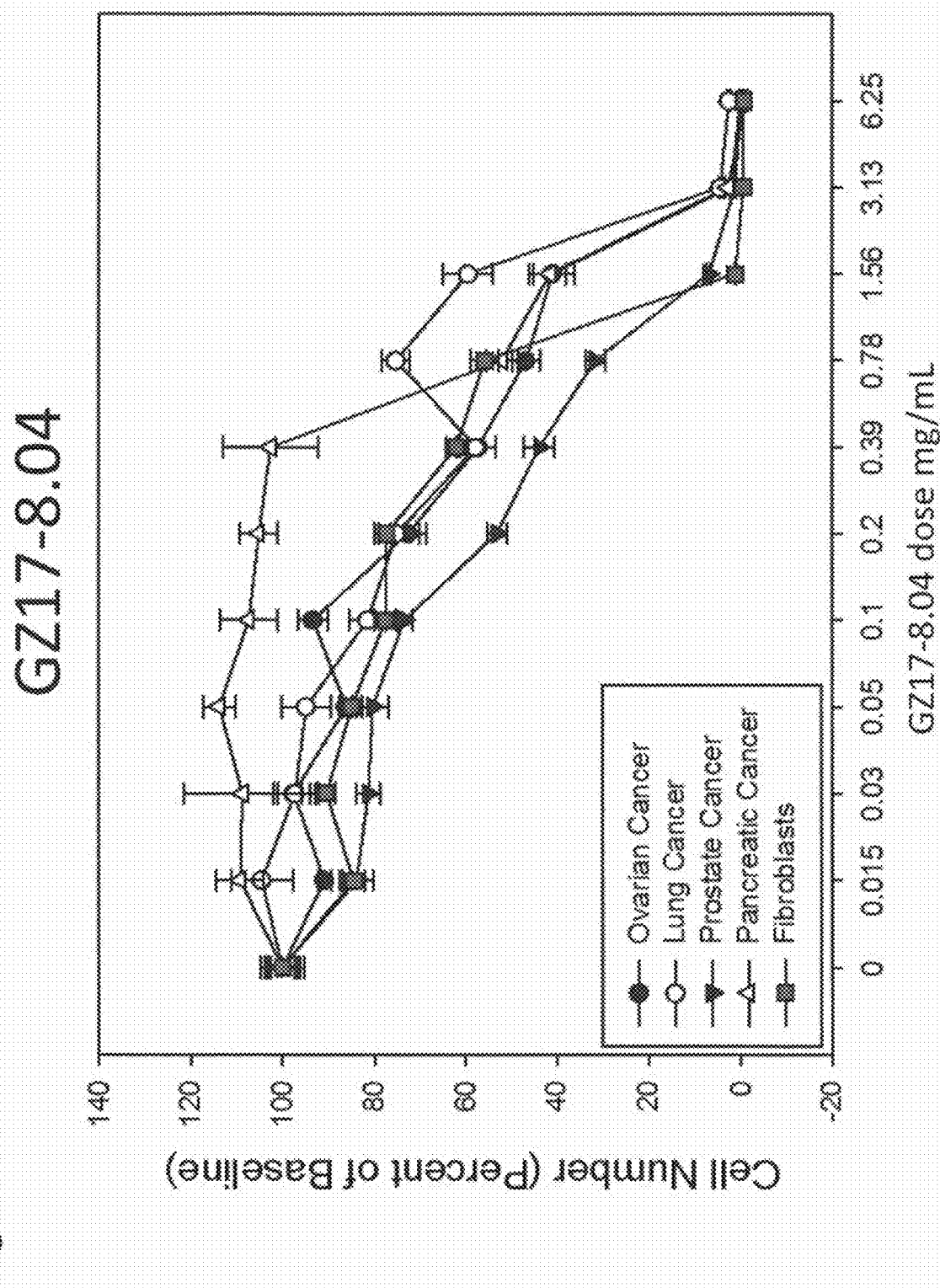
FIG. 28C is a graph of cell number versus dosage amounts of GZ17-8.04, illustrating the effect thereof in inducing the death of ovarian cancer, lung cancer, prostate cancer, pancreatic cancer and fibroblast cells, as described in Example 28.
Figure 28D:
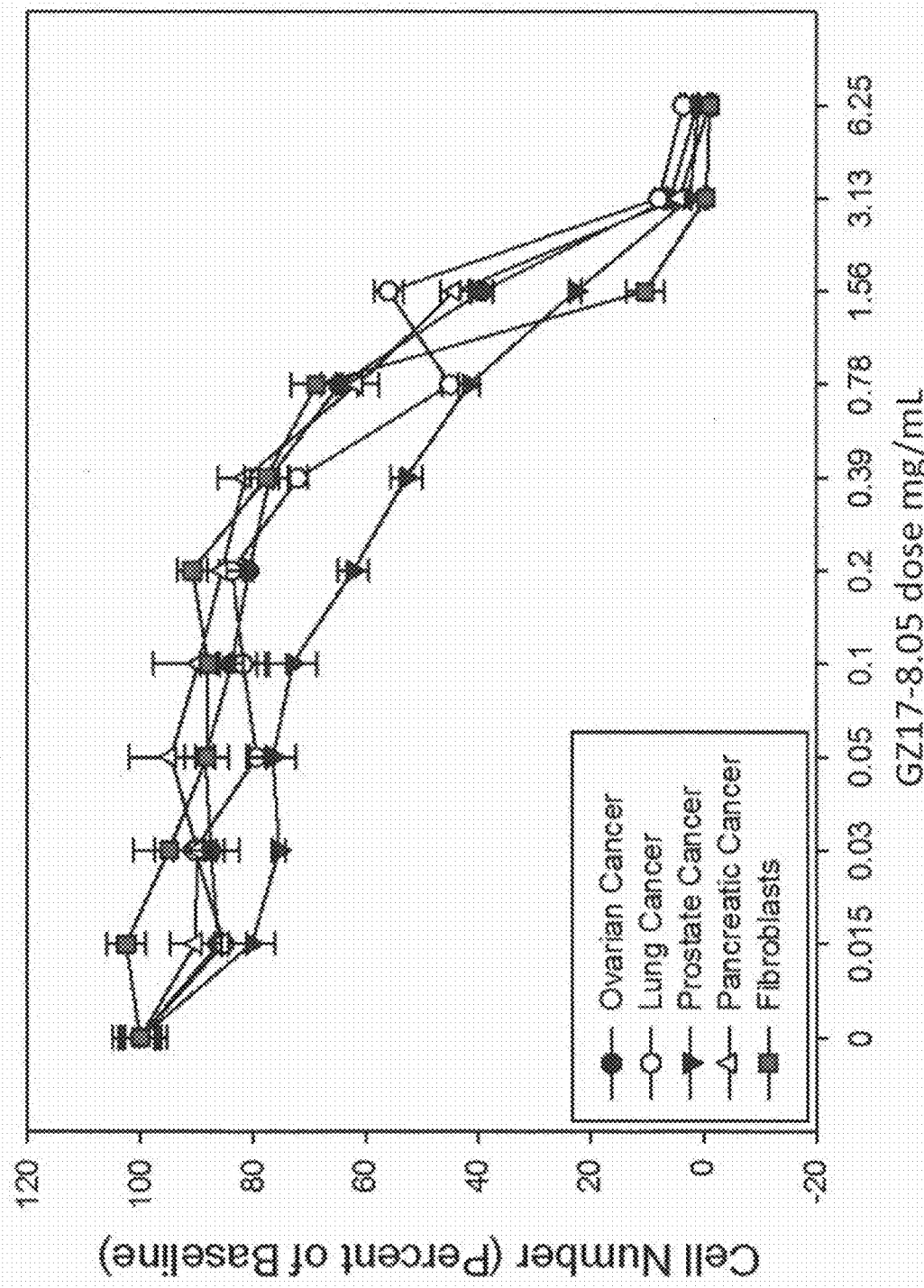
FIG. 28D is a graph of cell number versus dosage amounts of GZ17-8.05, illustrating the effect thereof in inducing the death of ovarian cancer, lung cancer, prostate cancer, pancreatic cancer and fibroblast cells, as described in Example 28.
Figure 28E:
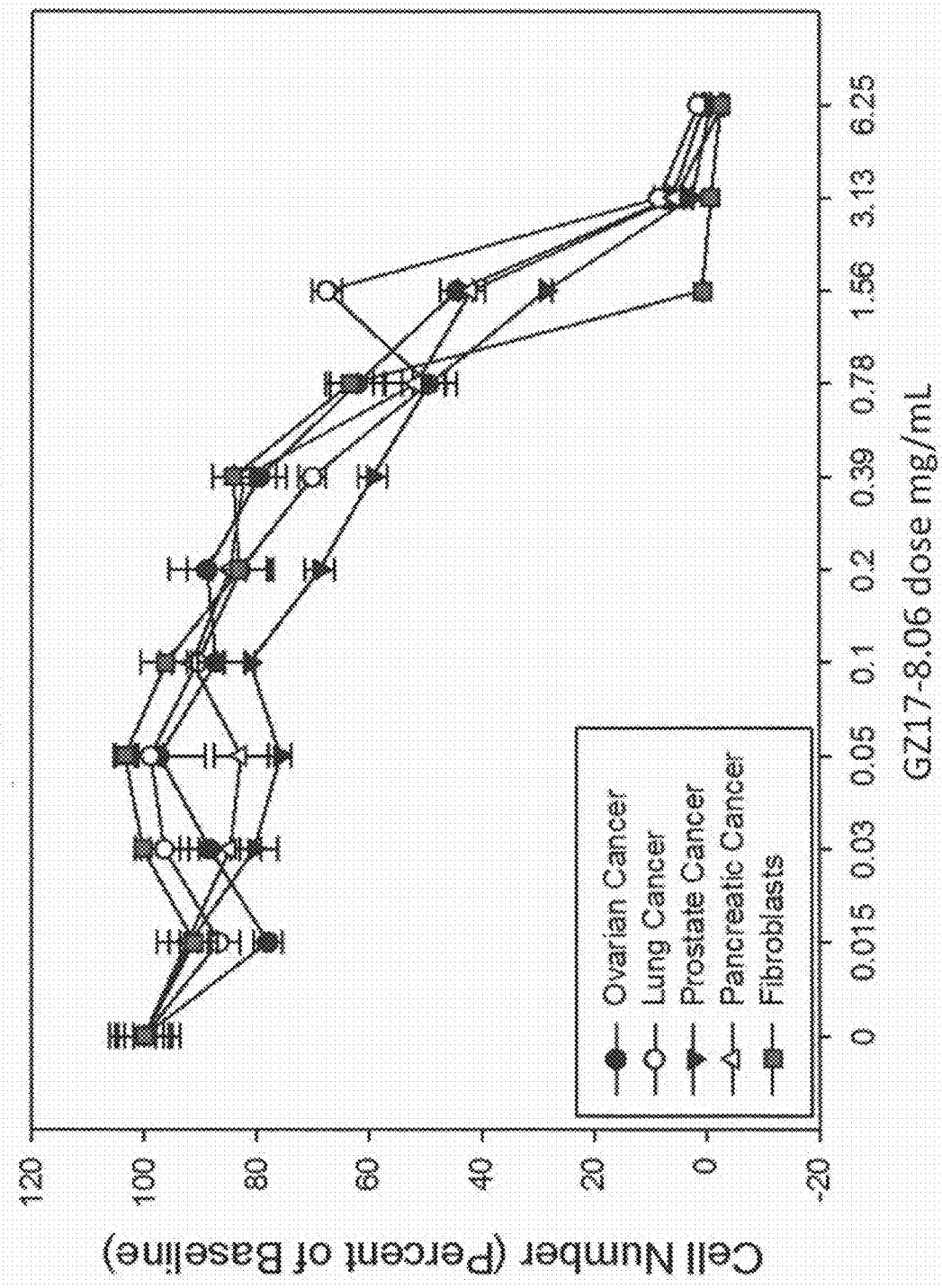
FIG. 28E is a graph of cell number versus dosage amounts of GZ17-8.06, illustrating the effect thereof in inducing the death of ovarian cancer, lung cancer, prostate cancer, pancreatic cancer and fibroblast cells, as described in Example 28.
Figure 28F:
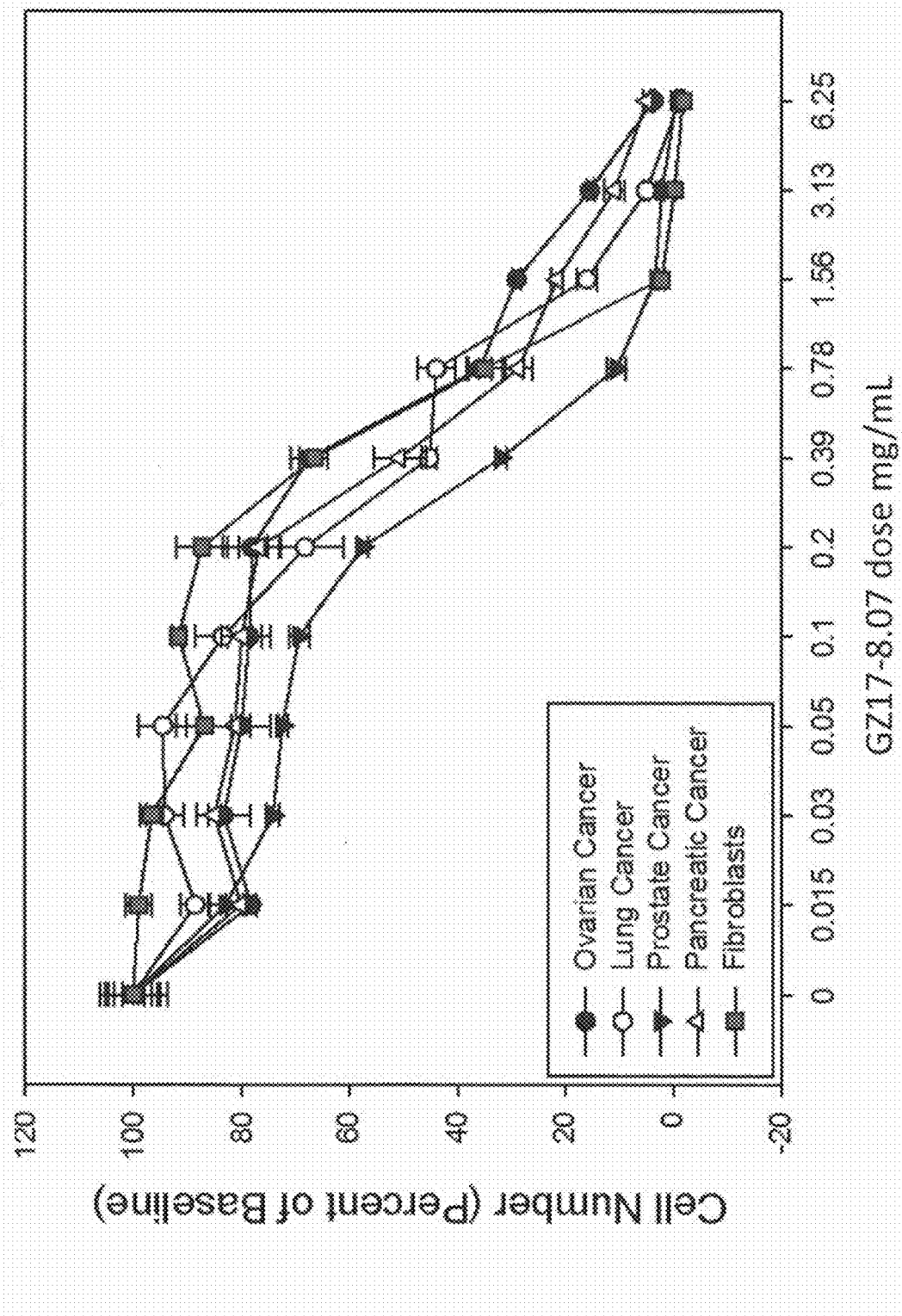
FIG. 28F is a graph of cell number versus dosage amounts of GZ17-8.07, illustrating the effect thereof in inducing the death of ovarian cancer, lung cancer, prostate cancer, pancreatic cancer and fibroblast cells, as described in Example 28.
Figure 28G:
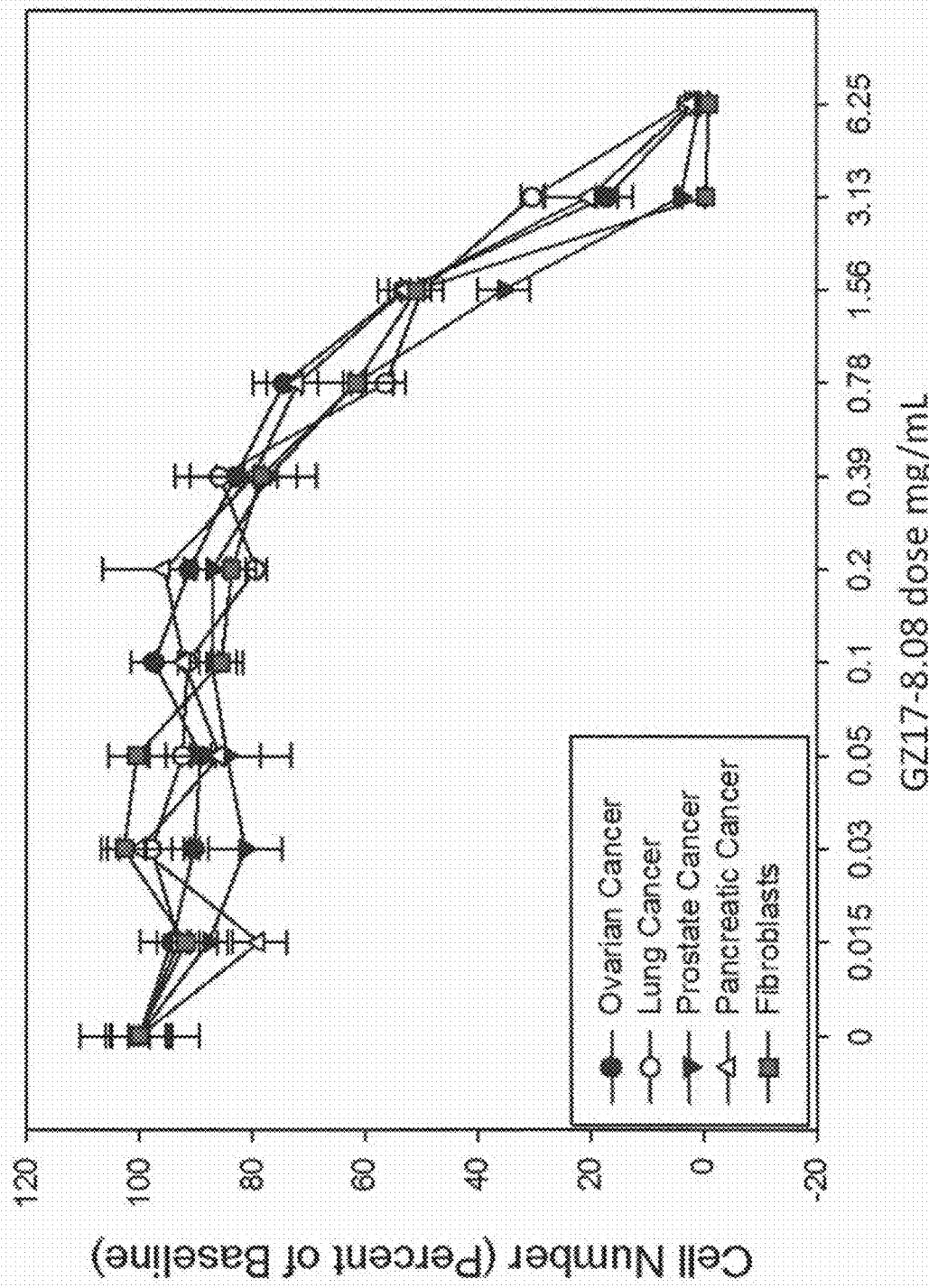
FIG. 28G is a graph of cell number versus dosage amounts of GZ17-8.08, illustrating the effect thereof in inducing the death of ovarian cancer, lung cancer, prostate cancer, pancreatic cancer and fibroblast cells, as described in Example 28.
Figure 28H:
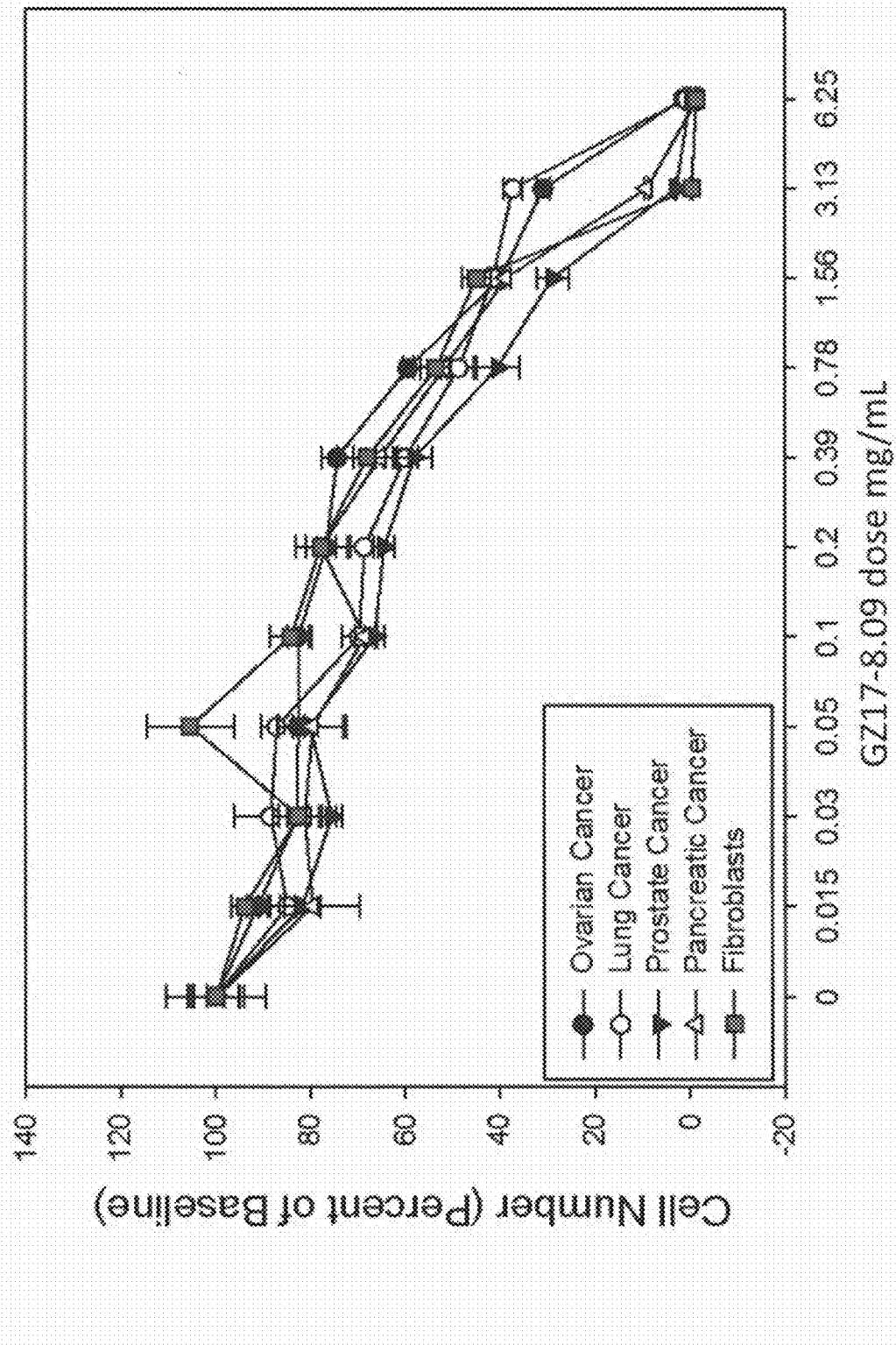
FIG. 28H is a graph of cell number versus dosage amounts of GZ17-8.09, illustrating the effect thereof in inducing the death of ovarian cancer, lung cancer, prostate cancer, pancreatic cancer and fibroblast cells, as described in Example 28.
Figure 28I:
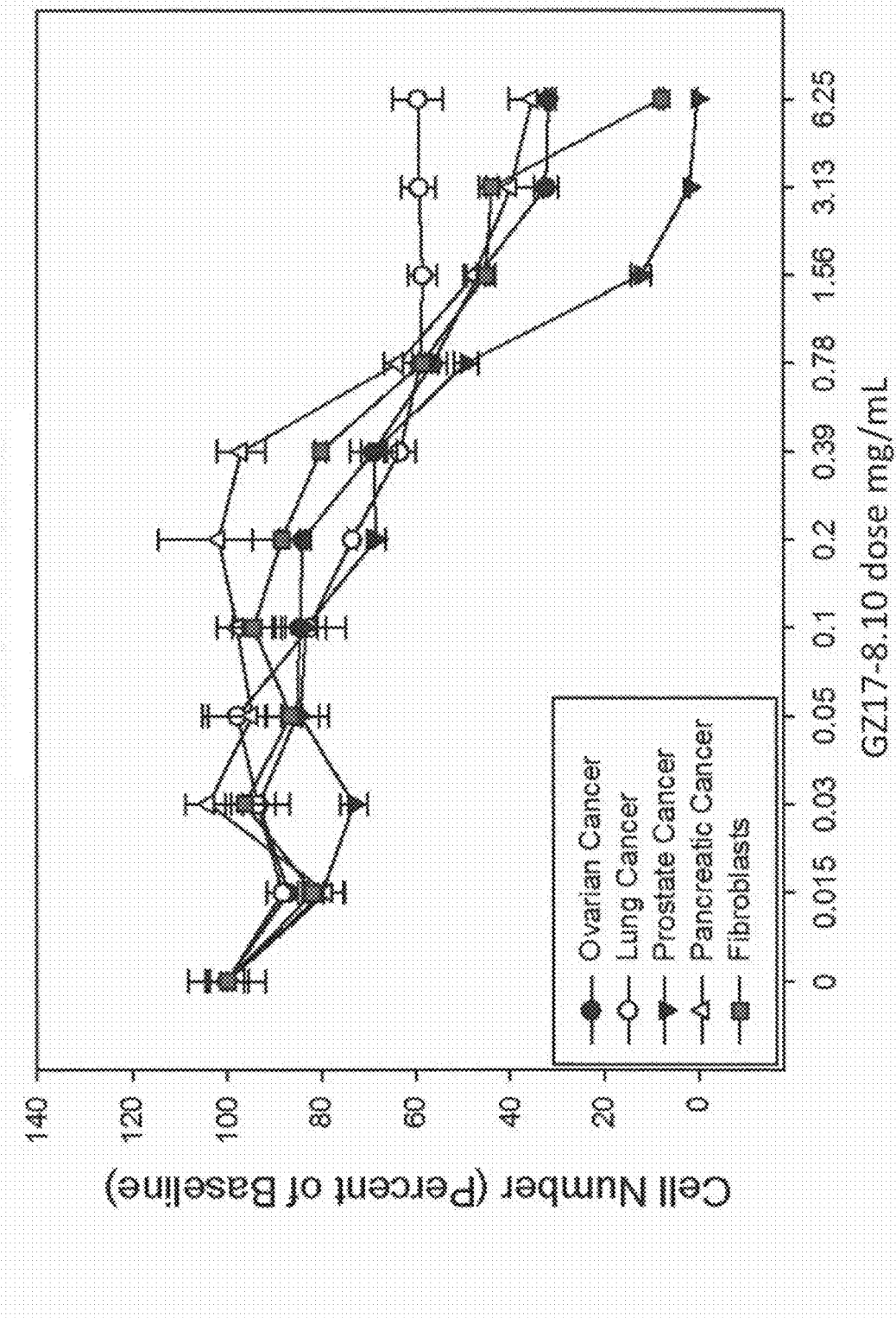
FIG. 28I is a graph of cell number versus dosage amounts of GZ17-8.10, illustrating the effect thereof in inducing the death of ovarian cancer, lung cancer, prostate cancer, pancreatic cancer and fibroblast cells, as described in Example 28.
Figure 29A:
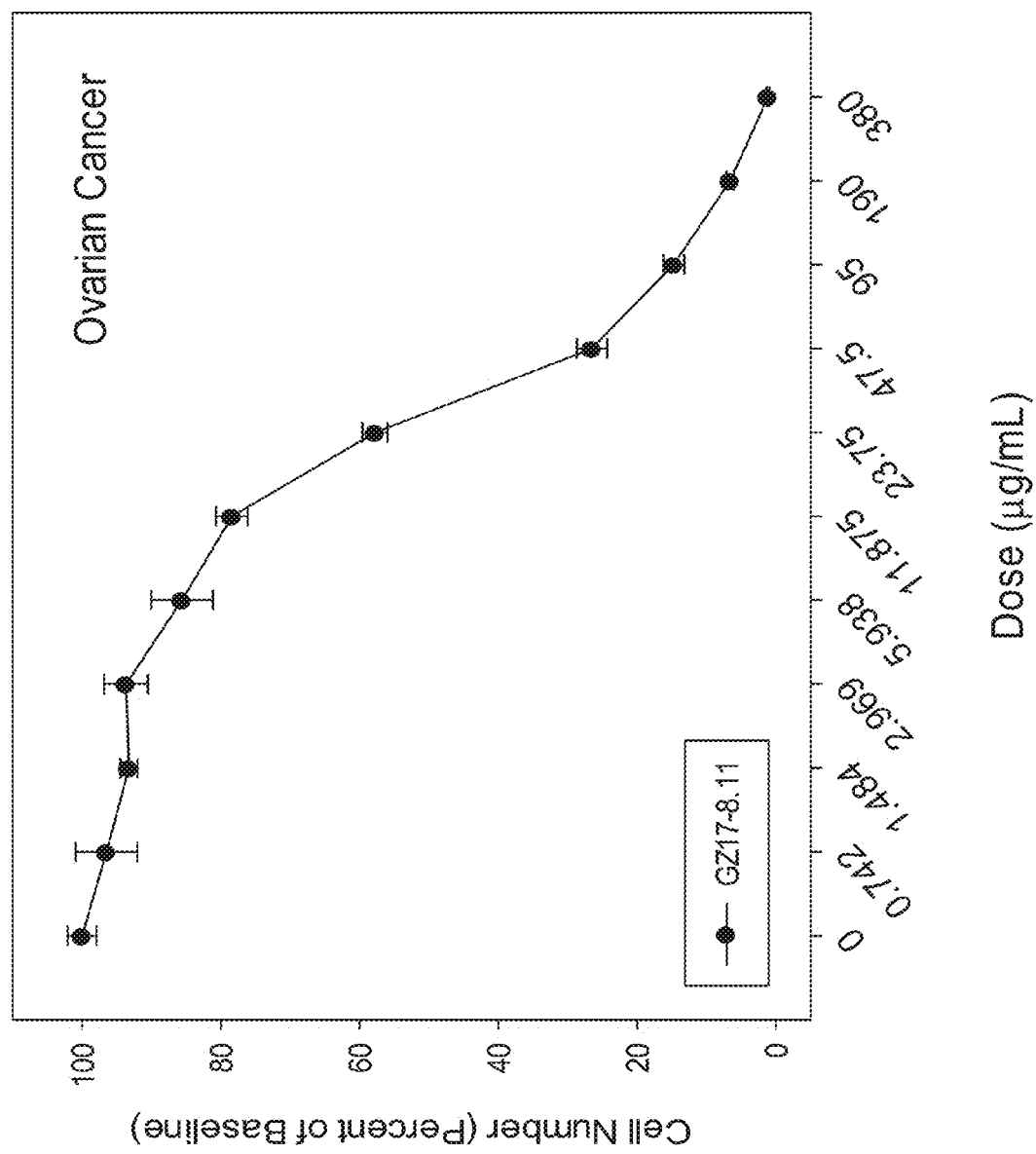
FIG. 29A is a graph of cell number versus dosage amounts of GZ17-8.11, illustrating the effect thereof in inducing the death of ovarian cancer.
Figure 29B:
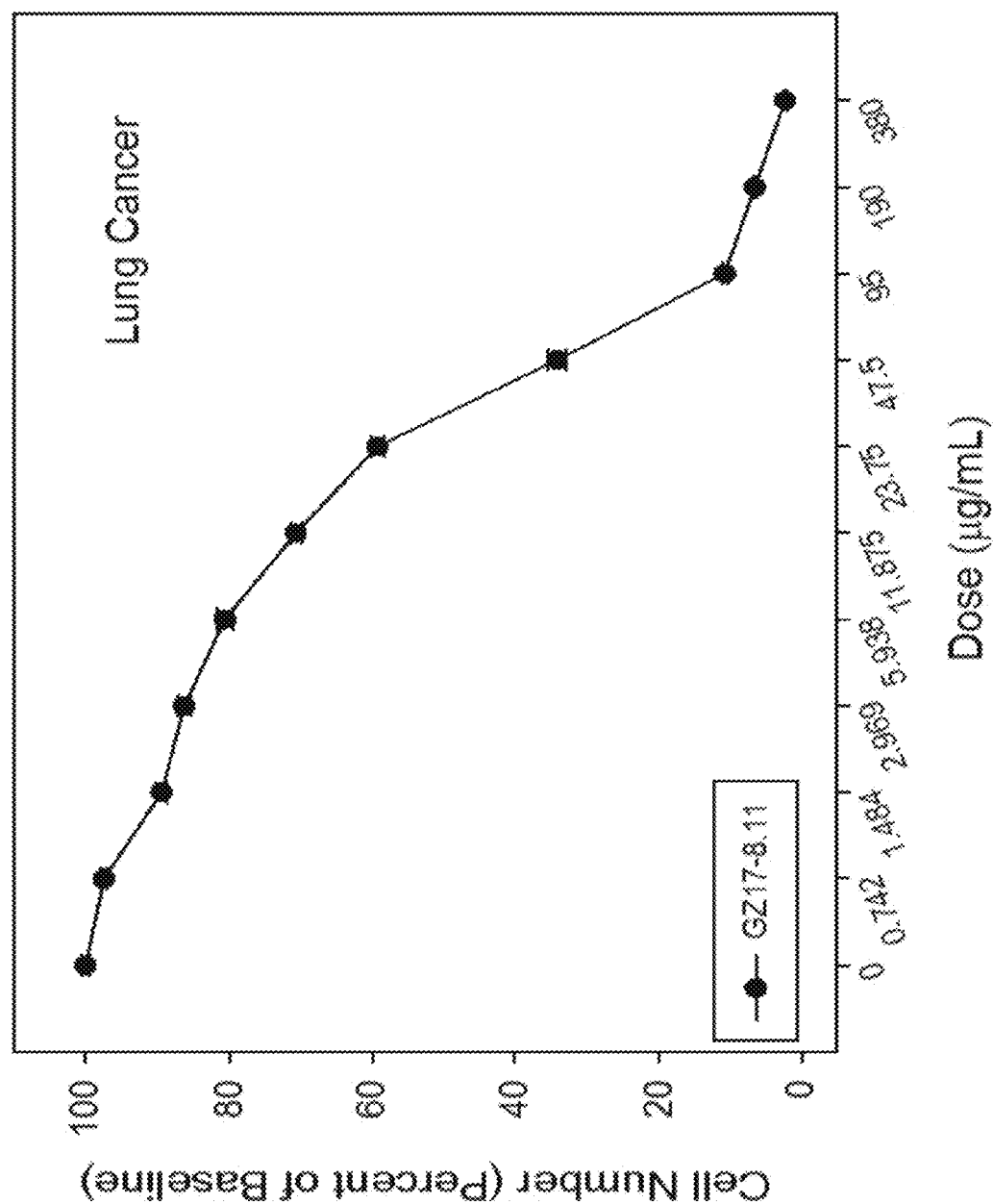
FIG. 29B is a graph of cell number versus dosage amounts of GZ17-8.11, illustrating the effect thereof in inducing the death of lung cancer.
Figure 29C:
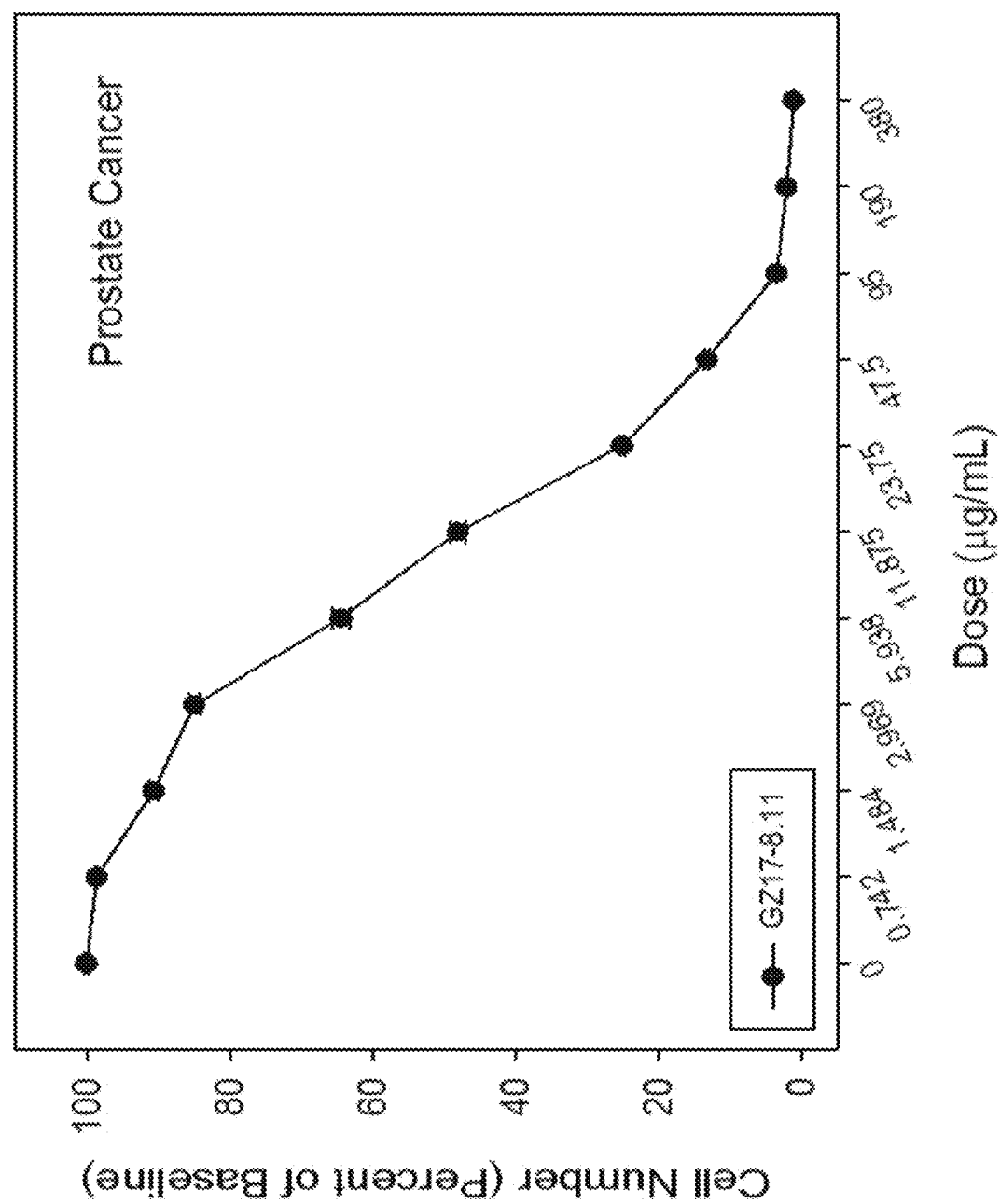
FIG. 29C is a graph of cell number versus dosage amounts of GZ17-8.11, illustrating the effect thereof in inducing the death of prostate cancer.
Figure 29D:
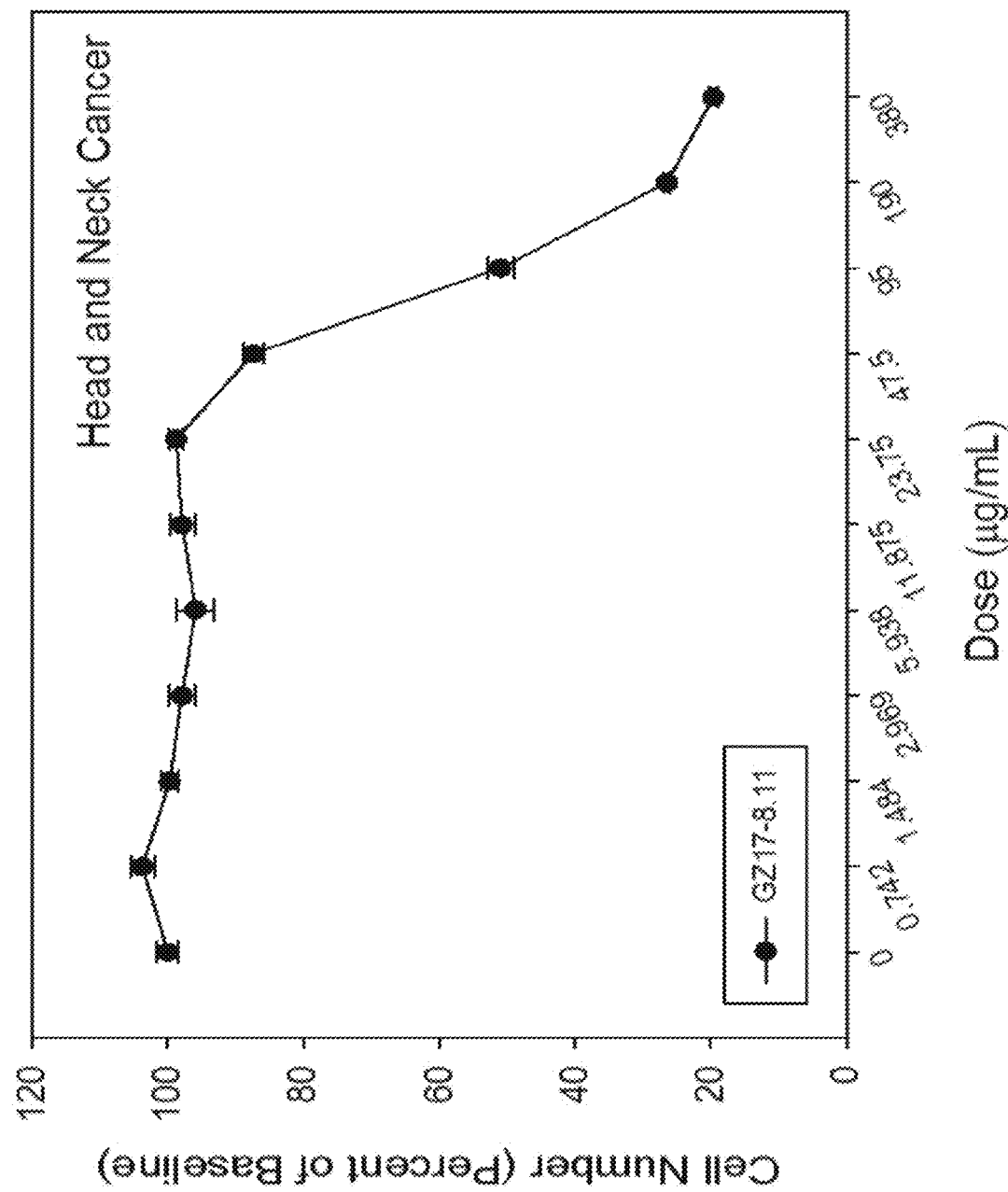
FIG. 29D is a graph of cell number versus dosage amounts of GZ17-8.11, illustrating the effect thereof in inducing the death of head and neck cancer.
Figure 29E:
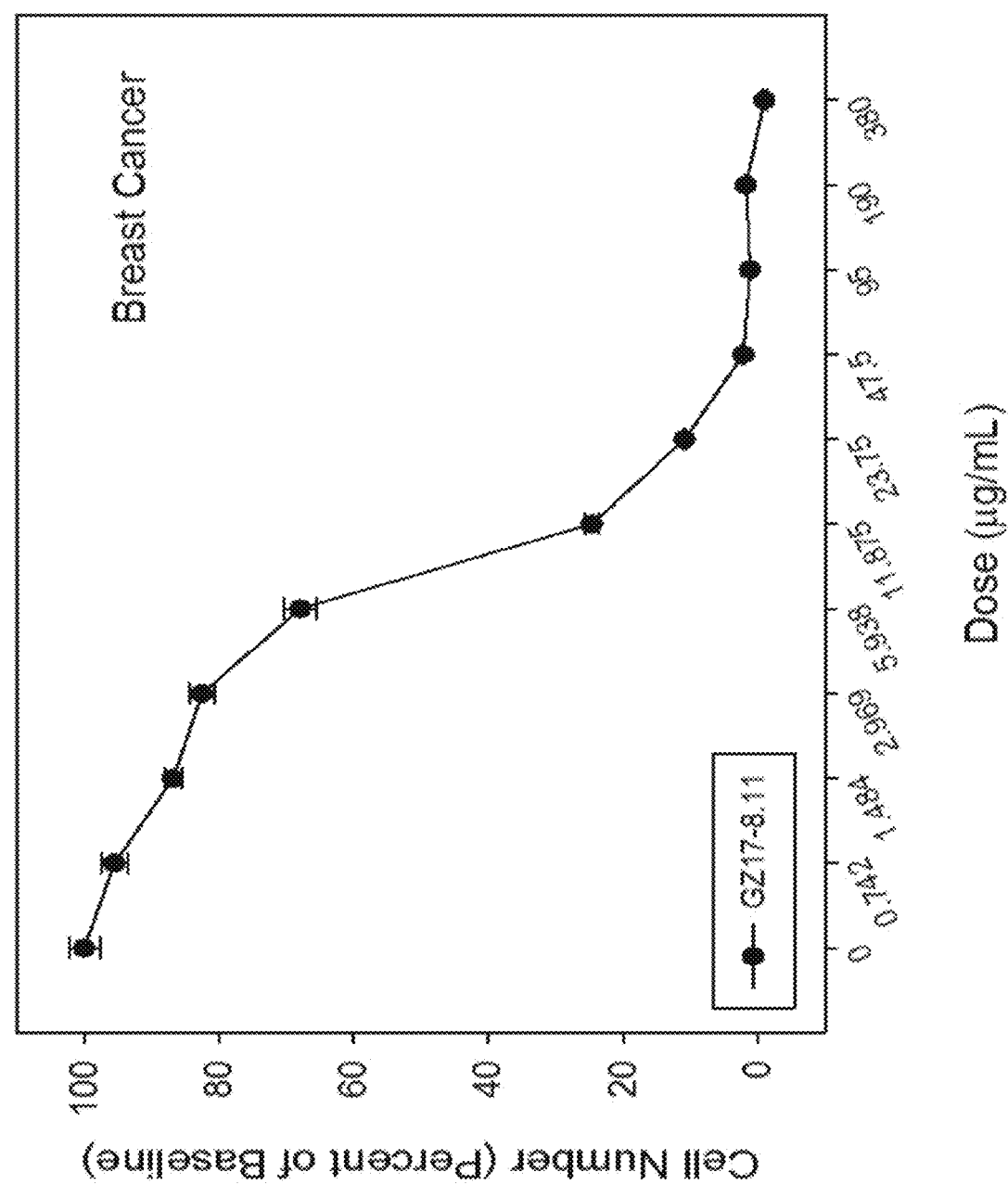
FIG. 29E is a graph of cell number versus dosage amounts of GZ17-8.11, illustrating the effect thereof in inducing the death of breast cancer.
Figure 29F:
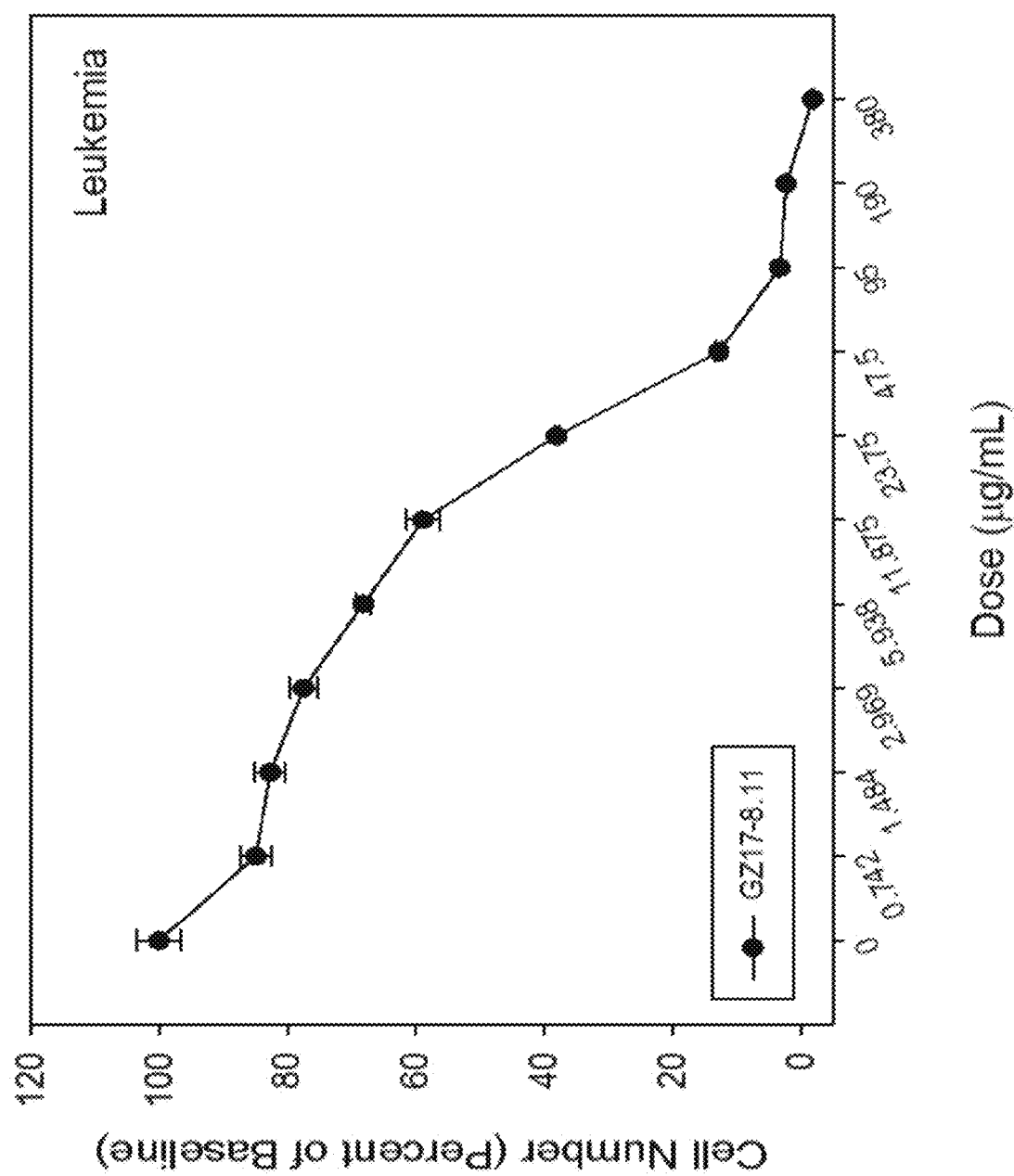
FIG. 29F is a graph of cell number versus dosage amounts of GZ17-8.11, illustrating the effect thereof in inducing the death of leukemia.
Figure 29G:
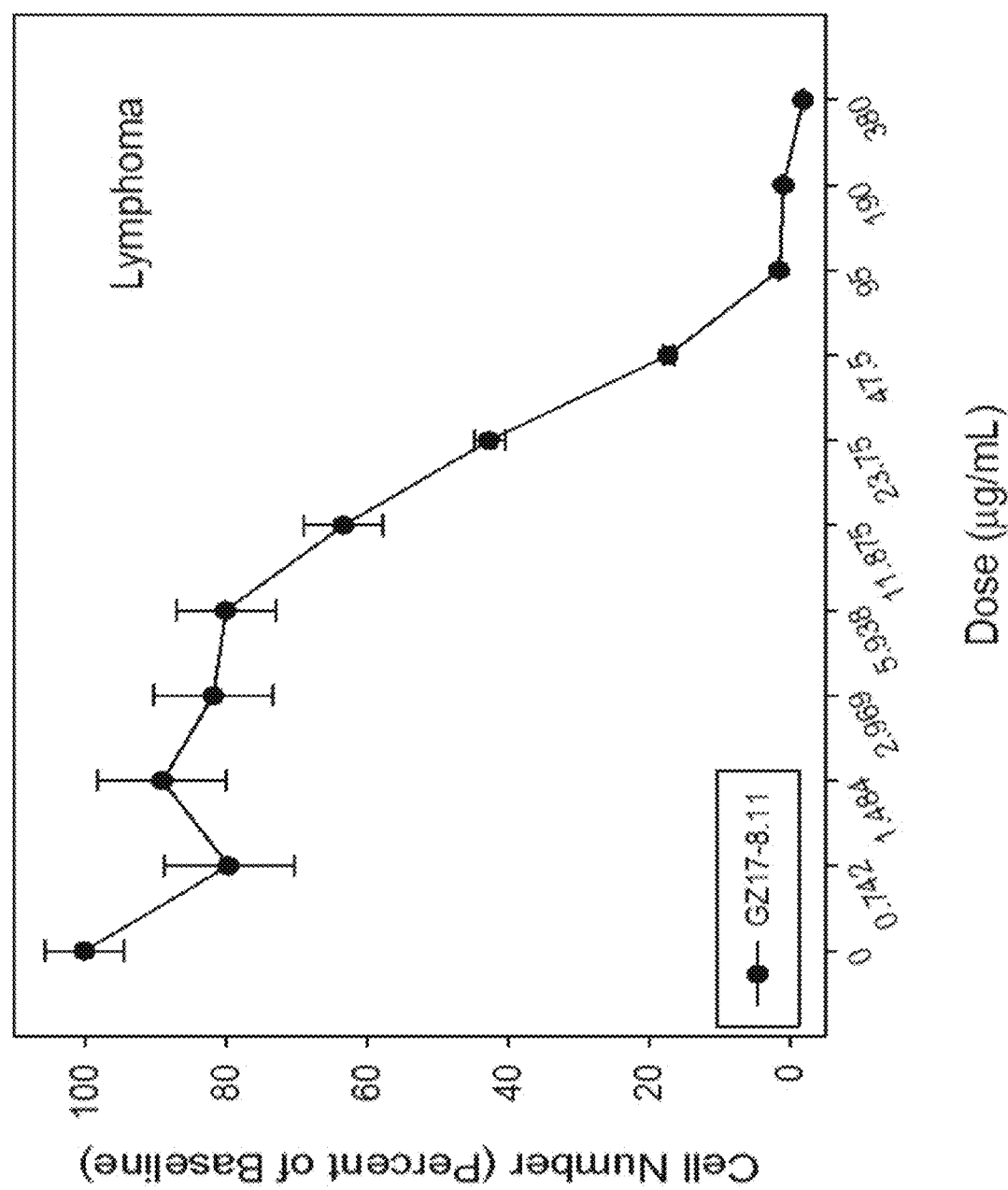
FIG. 29G is a graph of cell number versus dosage amounts of GZ17-8.11, illustrating the effect thereof in inducing the death of lymphoma.
Figure 30A:
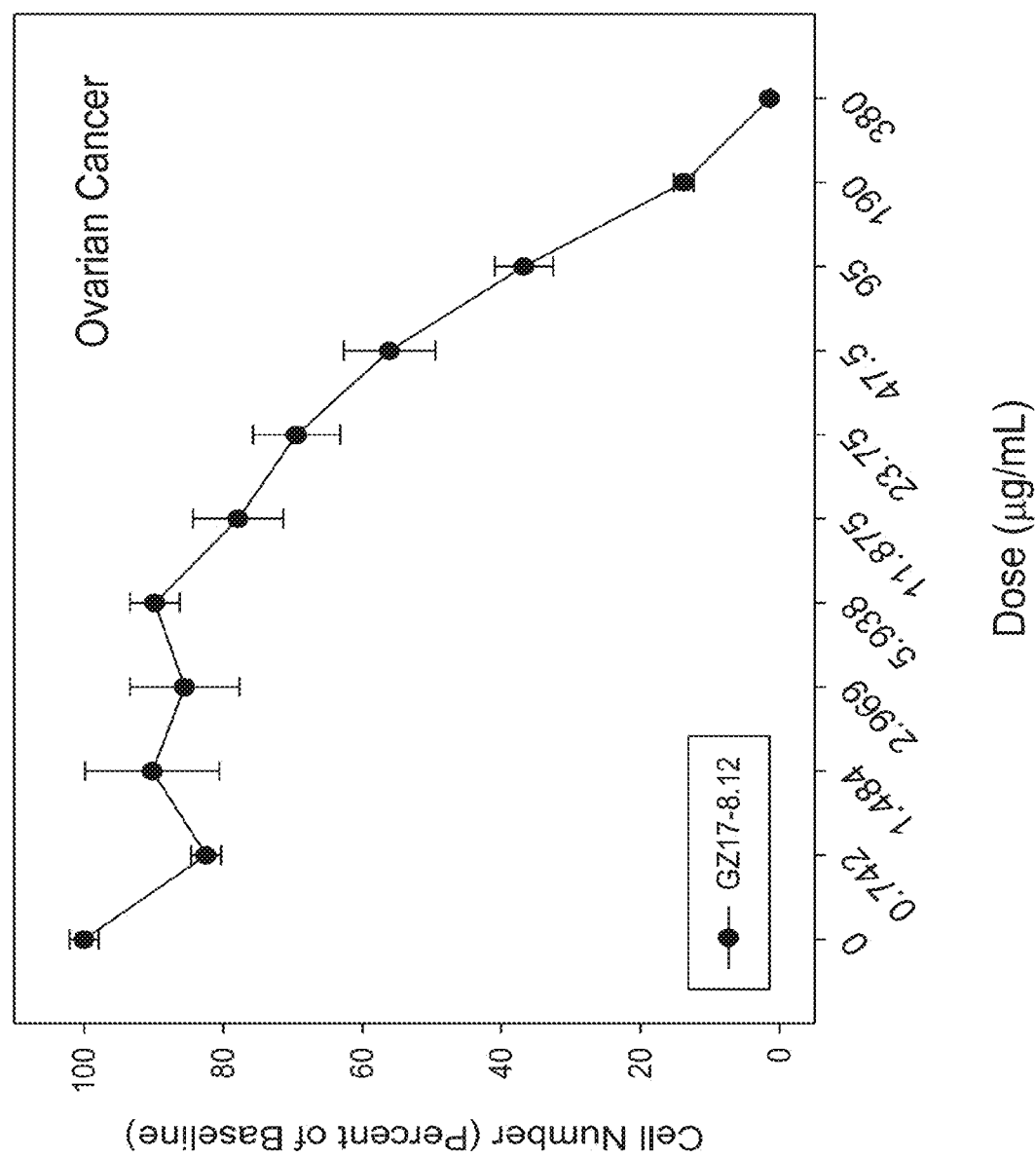
FIG. 30A is a graph of cell number versus dosage amounts of GZ17-8.12, illustrating the effect thereof in inducing the death of ovarian cancer.
Figure 30B:
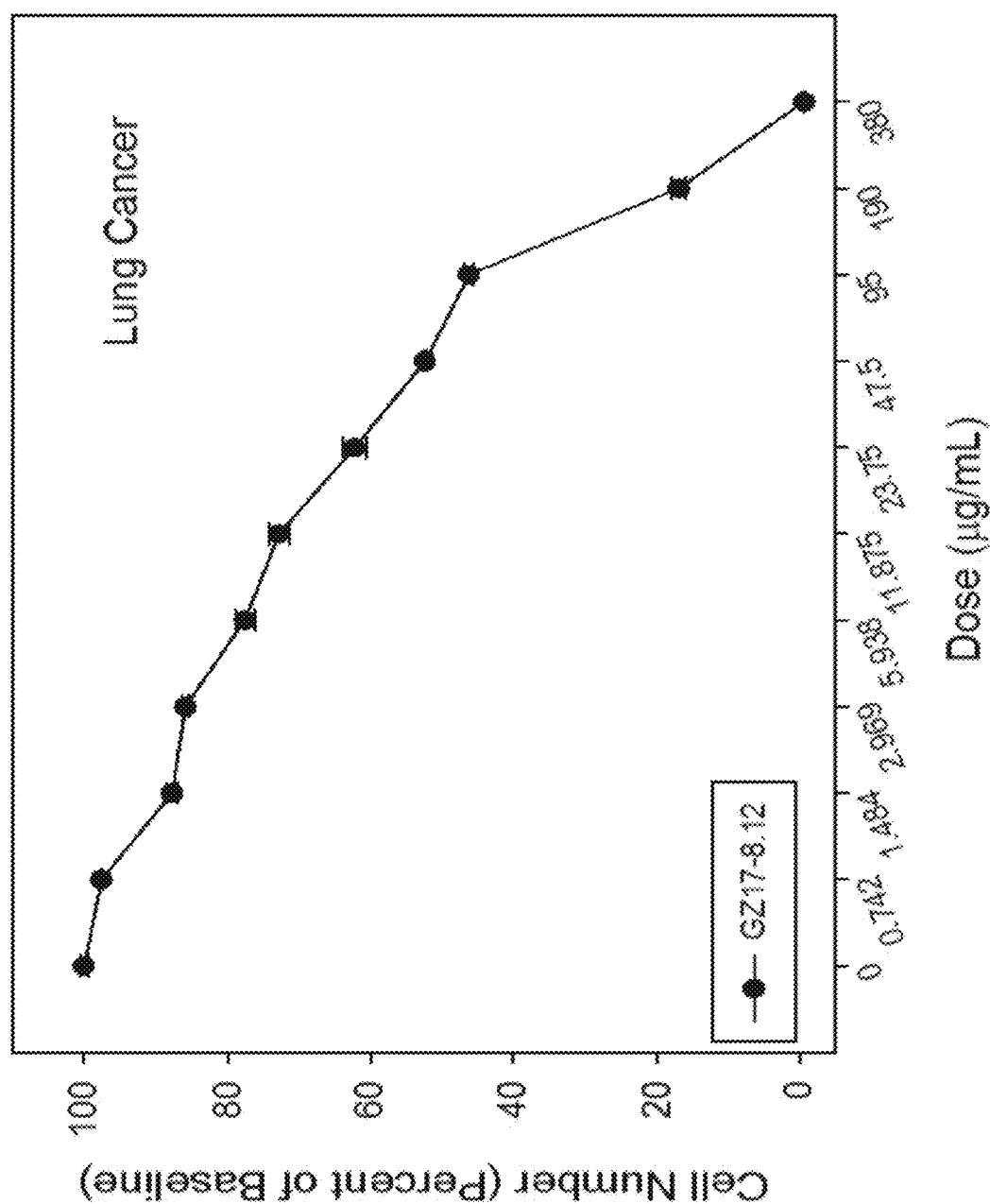
FIG. 30B is a graph of cell number versus dosage amounts of GZ17-8.12, illustrating the effect thereof in inducing the death of lung cancer.
Figure 30C:
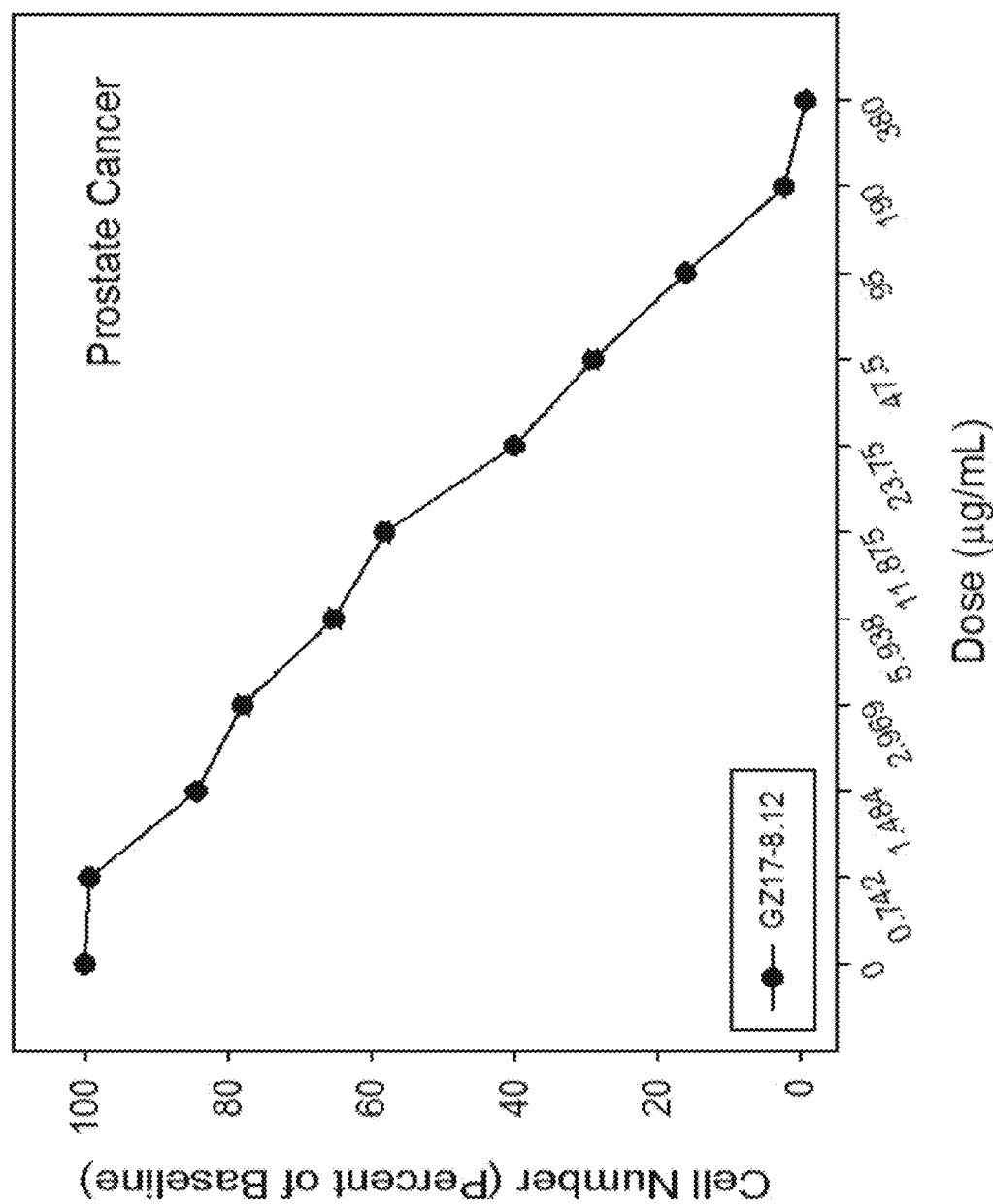
FIG. 30C is a graph of cell number versus dosage amounts of GZ17-8.12, illustrating the effect thereof in inducing the death of prostate cancer.
Figure 30D:
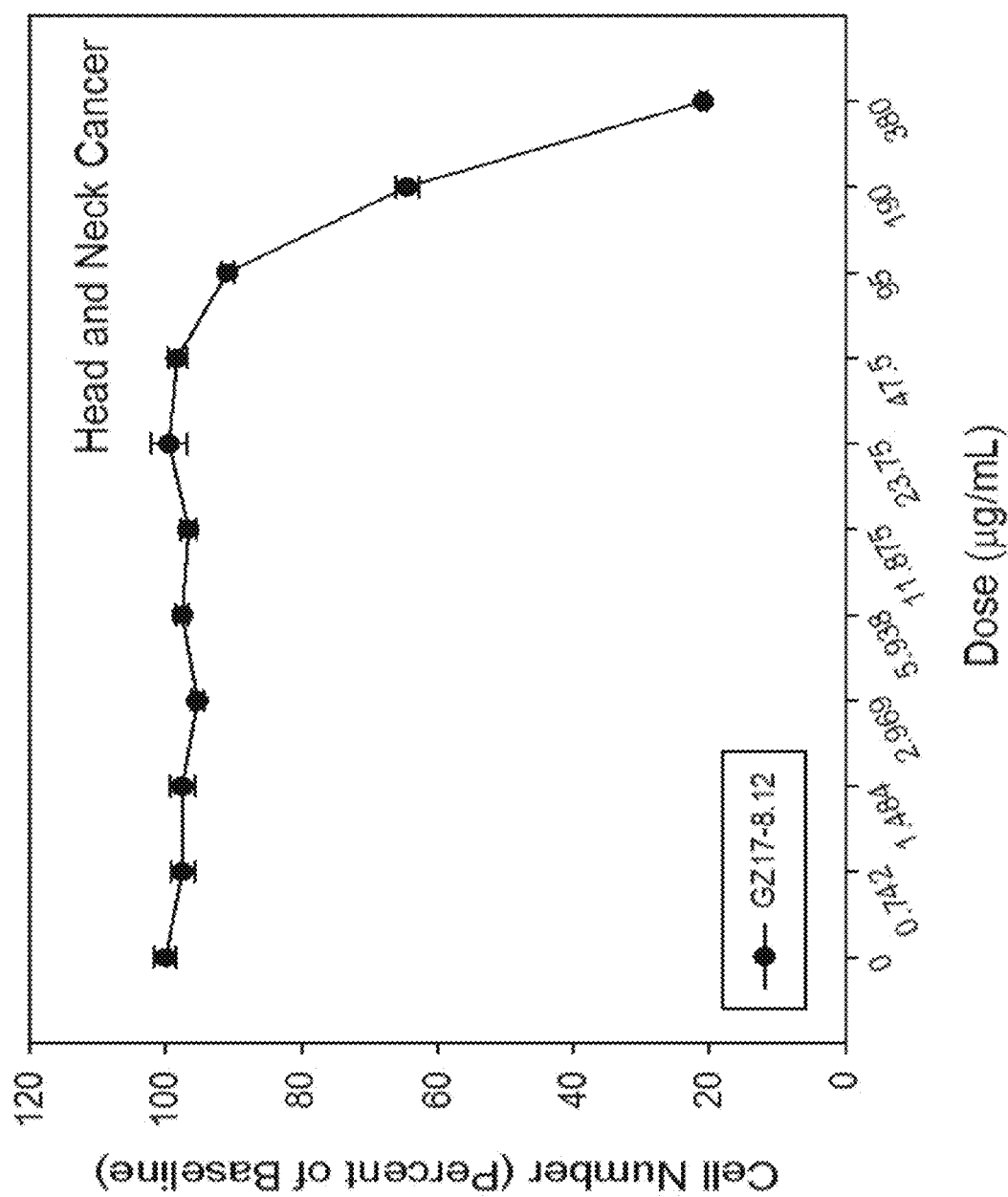
FIG. 30D is a graph of cell number versus dosage amounts of GZ17-8.12, illustrating the effect thereof in inducing the death of head and neck cancer.
Figure 30E:
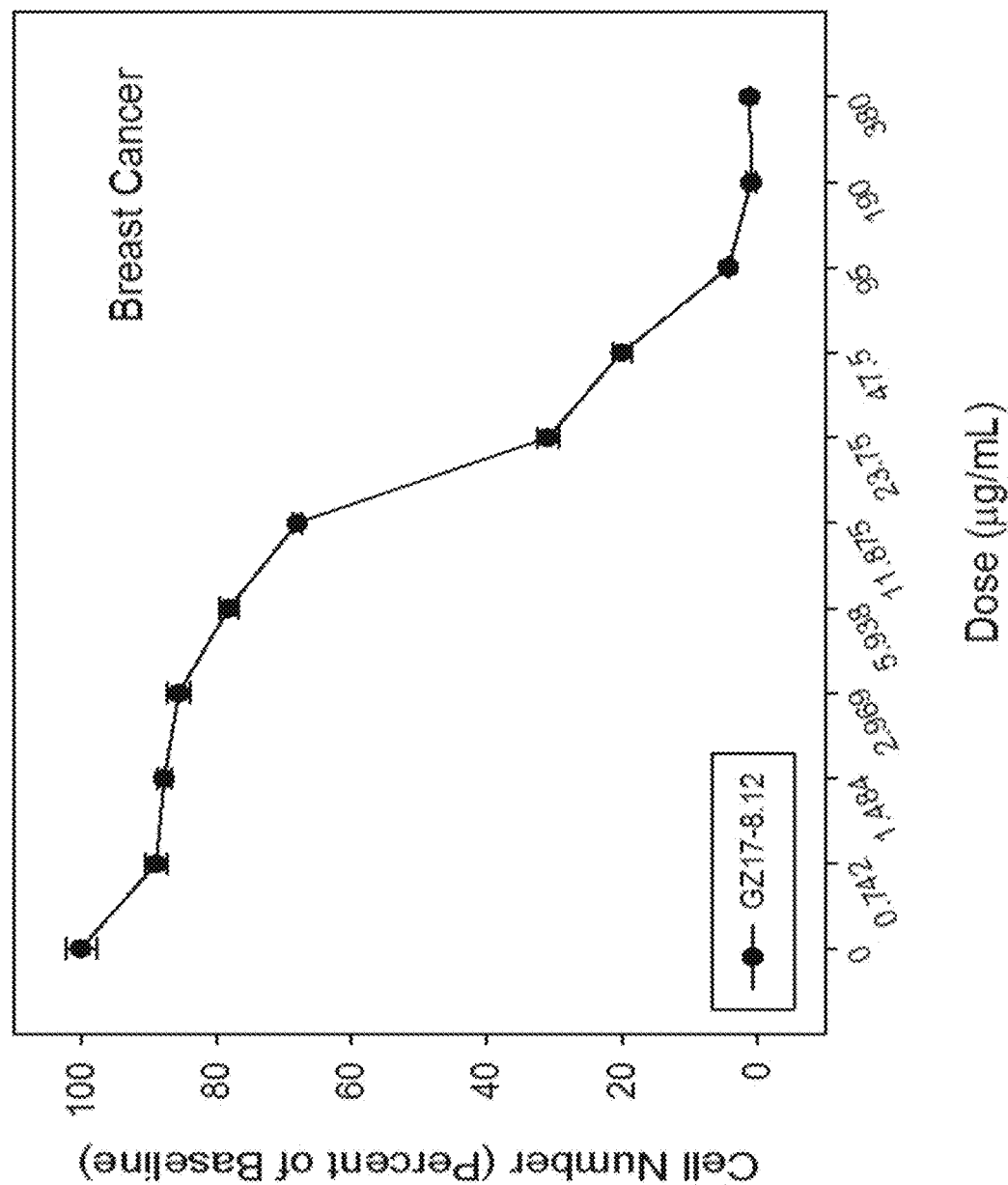
FIG. 30E is a graph of cell number versus dosage amounts of GZ17-8.12, illustrating the effect thereof in inducing the death of breast cancer.
Figure 30F:
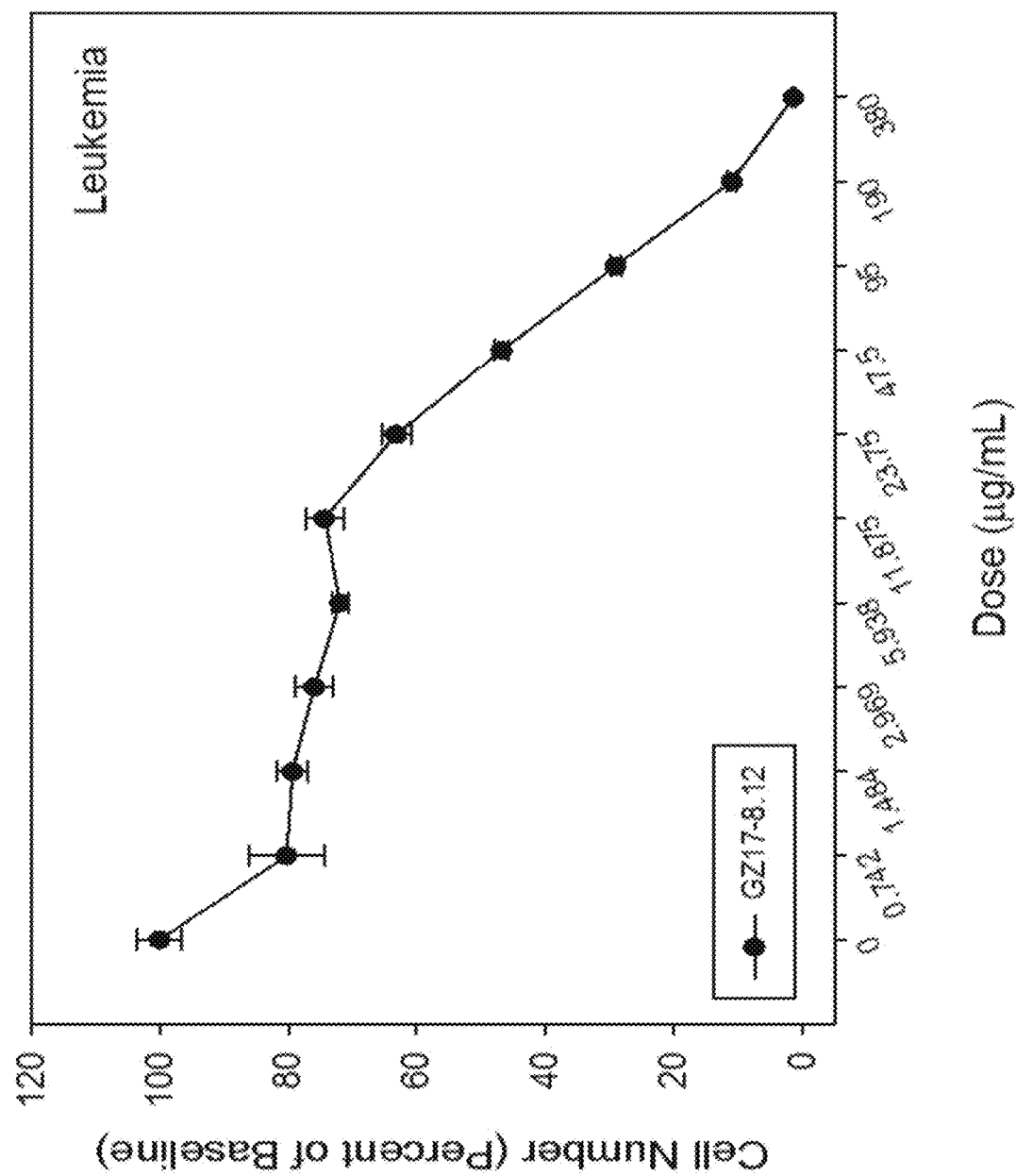
FIG. 30F is a graph of cell number versus dosage amounts of GZ17-8.12, illustrating the effect thereof in inducing the death of leukemia.
Figure 30G:
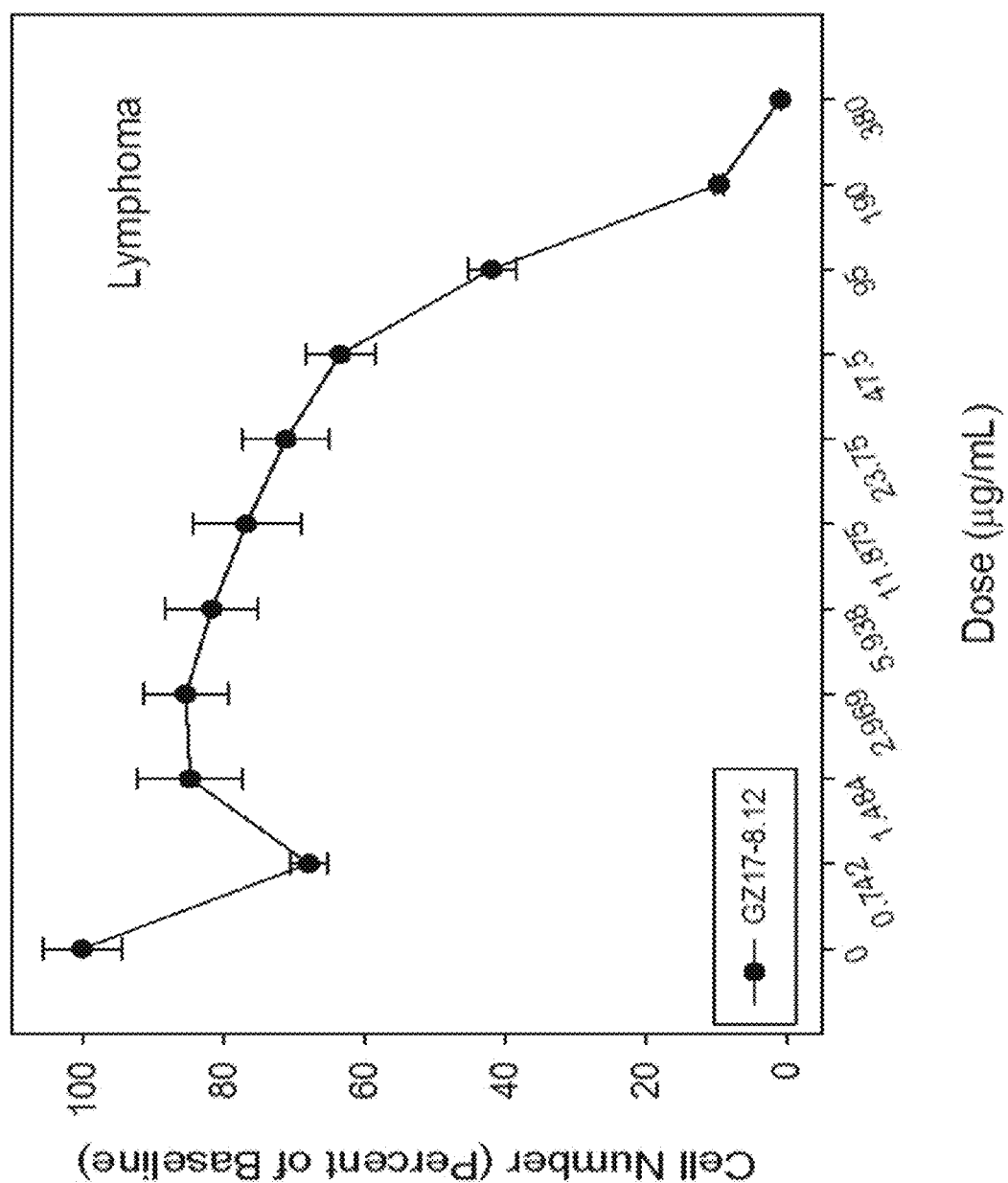
FIG. 30G is a graph of cell number versus dosage amounts of GZ17-8.12, illustrating the effect thereof in inducing the death of lymphoma.
Figure 31A:
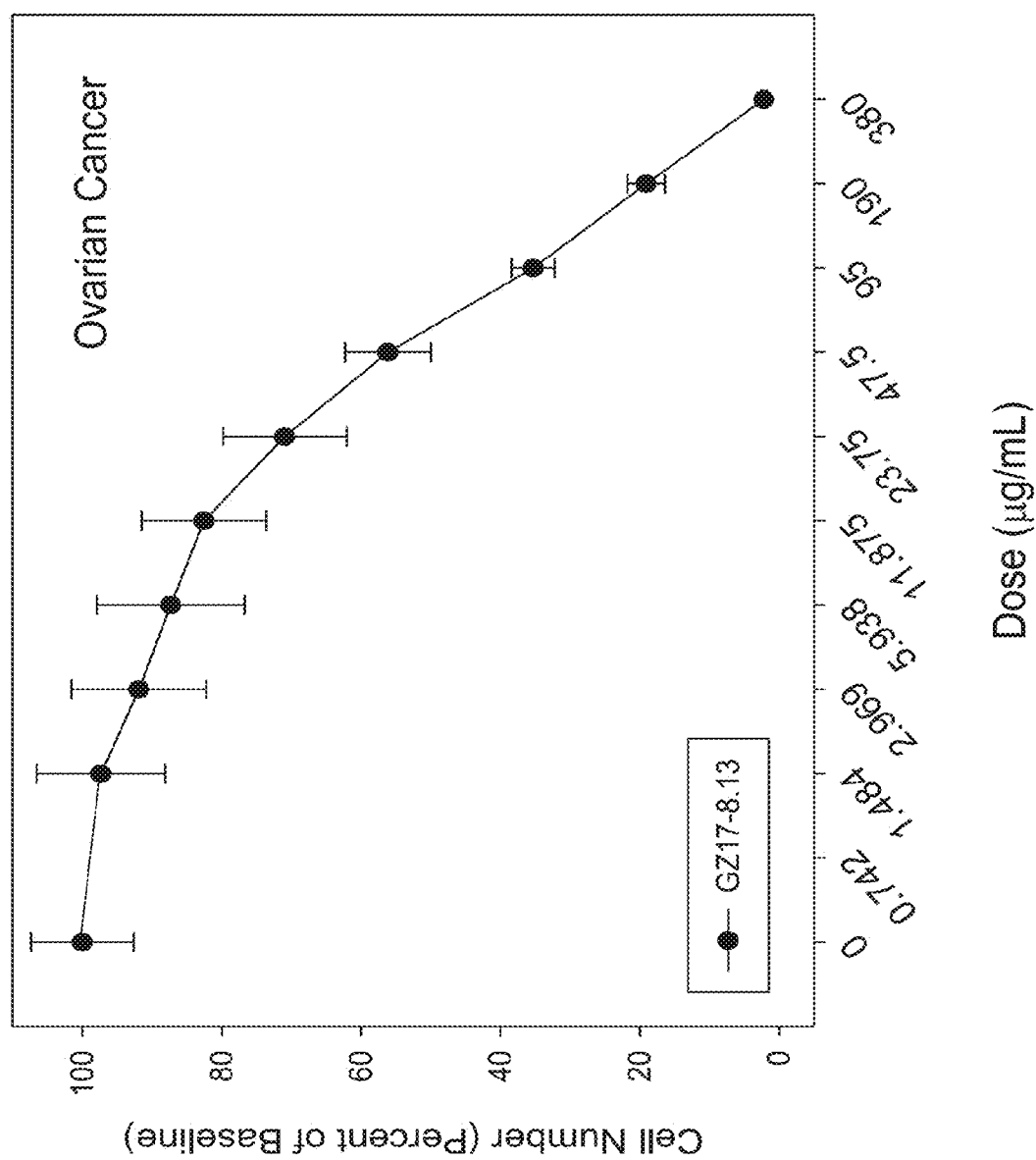
FIG. 31A is a graph of cell number versus dosage amounts of GZ17-8.13, illustrating the effect thereof in inducing the death of ovarian cancer.
Figure 31B:
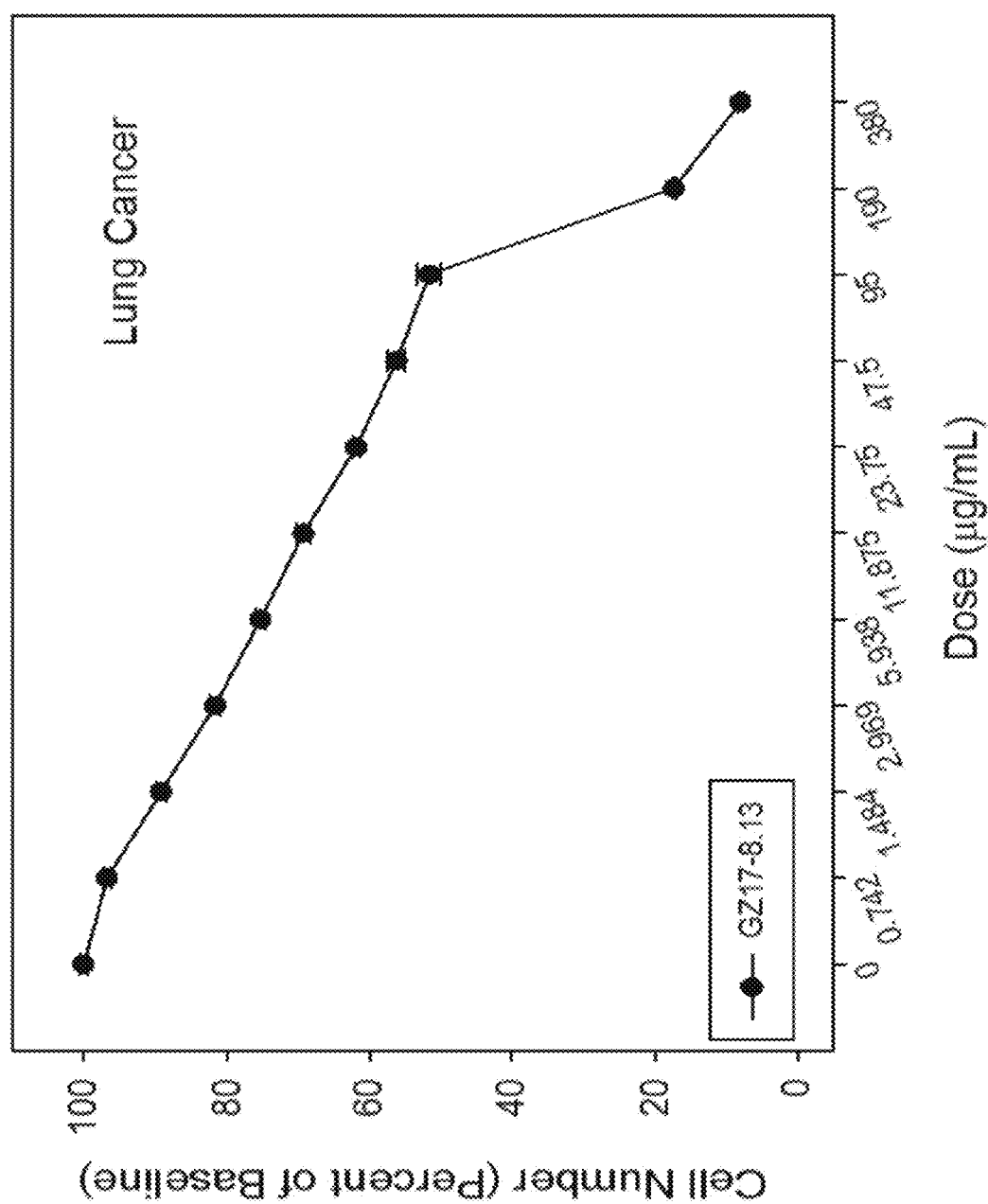
FIG. 31B is a graph of cell number versus dosage amounts of GZ17-8.13, illustrating the effect thereof in inducing the death of lung cancer.
Figure 31C:
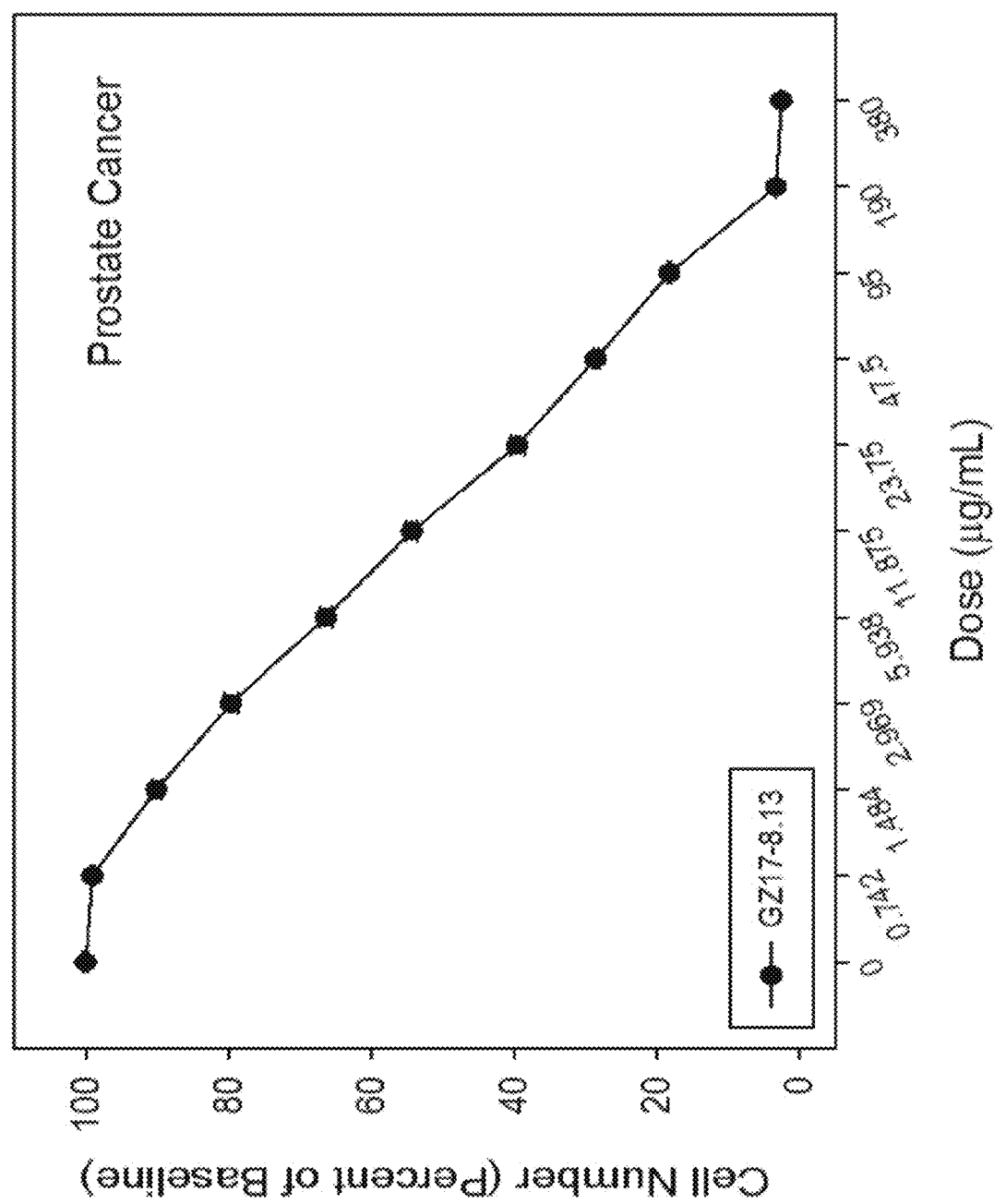
FIG. 31C is a graph of cell number versus dosage amounts of GZ17-8.13, illustrating the effect thereof in inducing the death of prostate cancer.
Figure 31D:
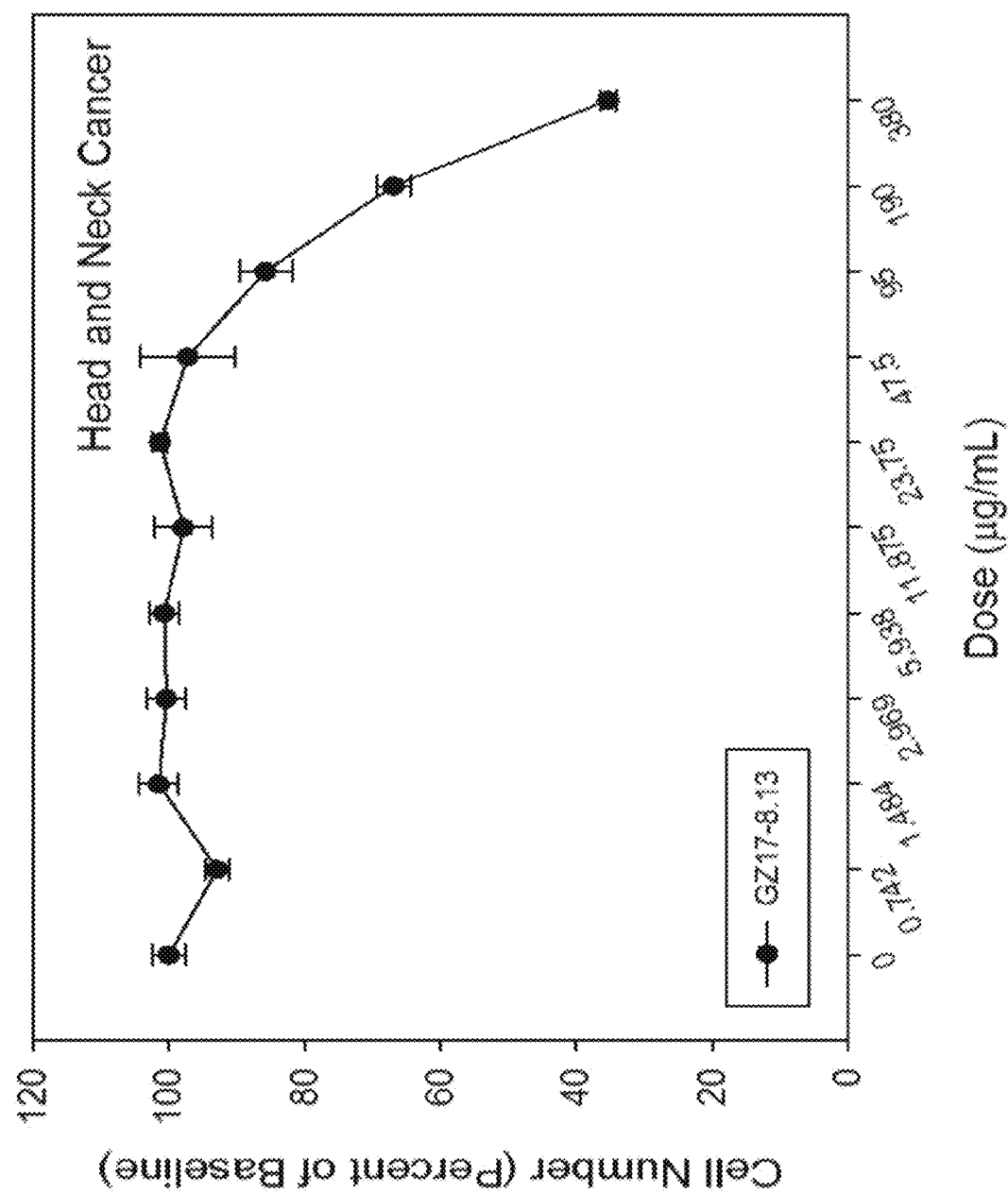
FIG. 31D is a graph of cell number versus dosage amounts of GZ17-8.13, illustrating the effect thereof in inducing the death of head and neck cancer.
Figure 31E:
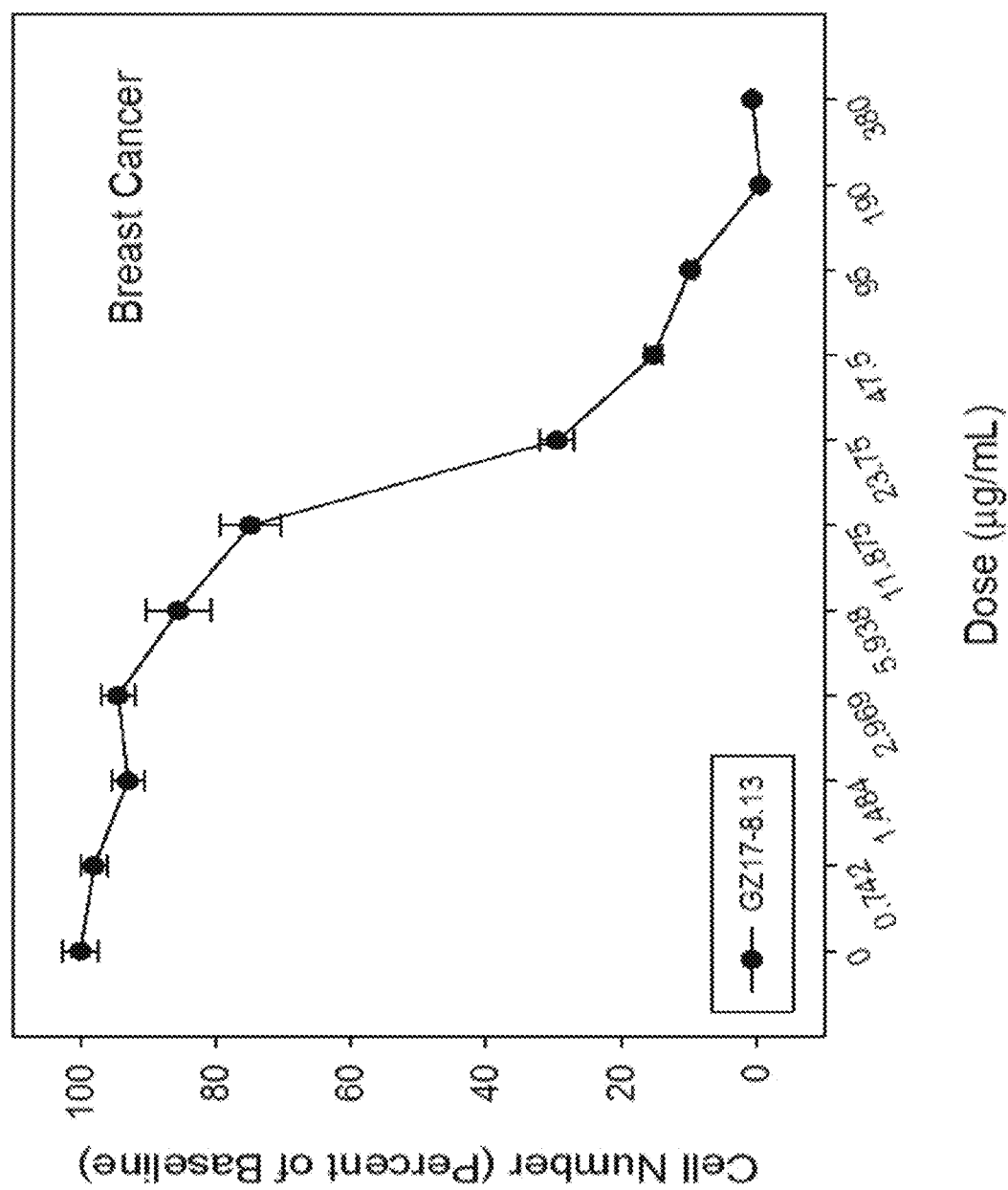
FIG. 31E is a graph of cell number versus dosage amounts of GZ17-8.13, illustrating the effect thereof in inducing the death of breast cancer.
Figure 31F:
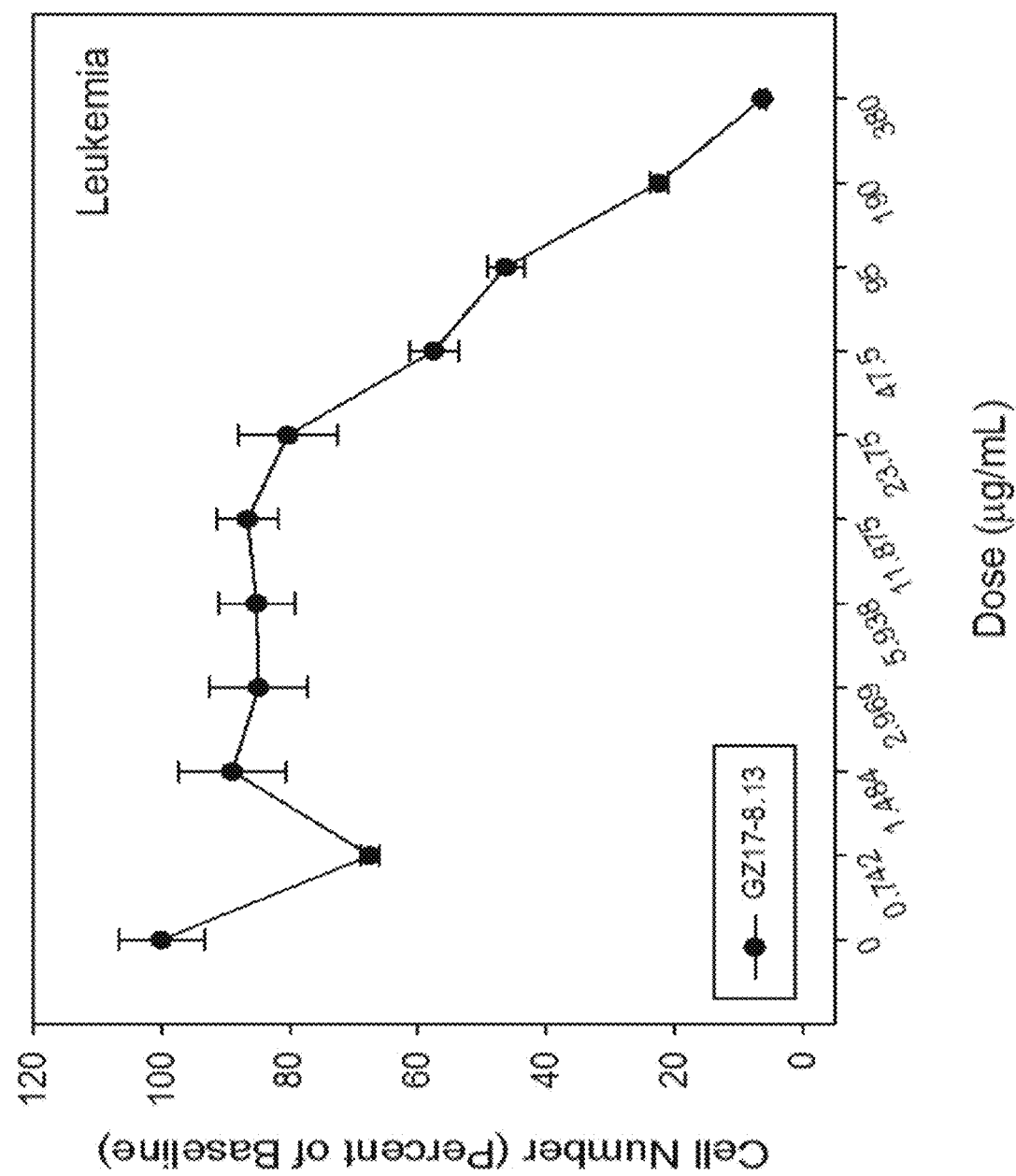
FIG. 31F is a graph of cell number versus dosage amounts of GZ17-8.13, illustrating the effect thereof in inducing the death of leukemia.
Figure 31G:
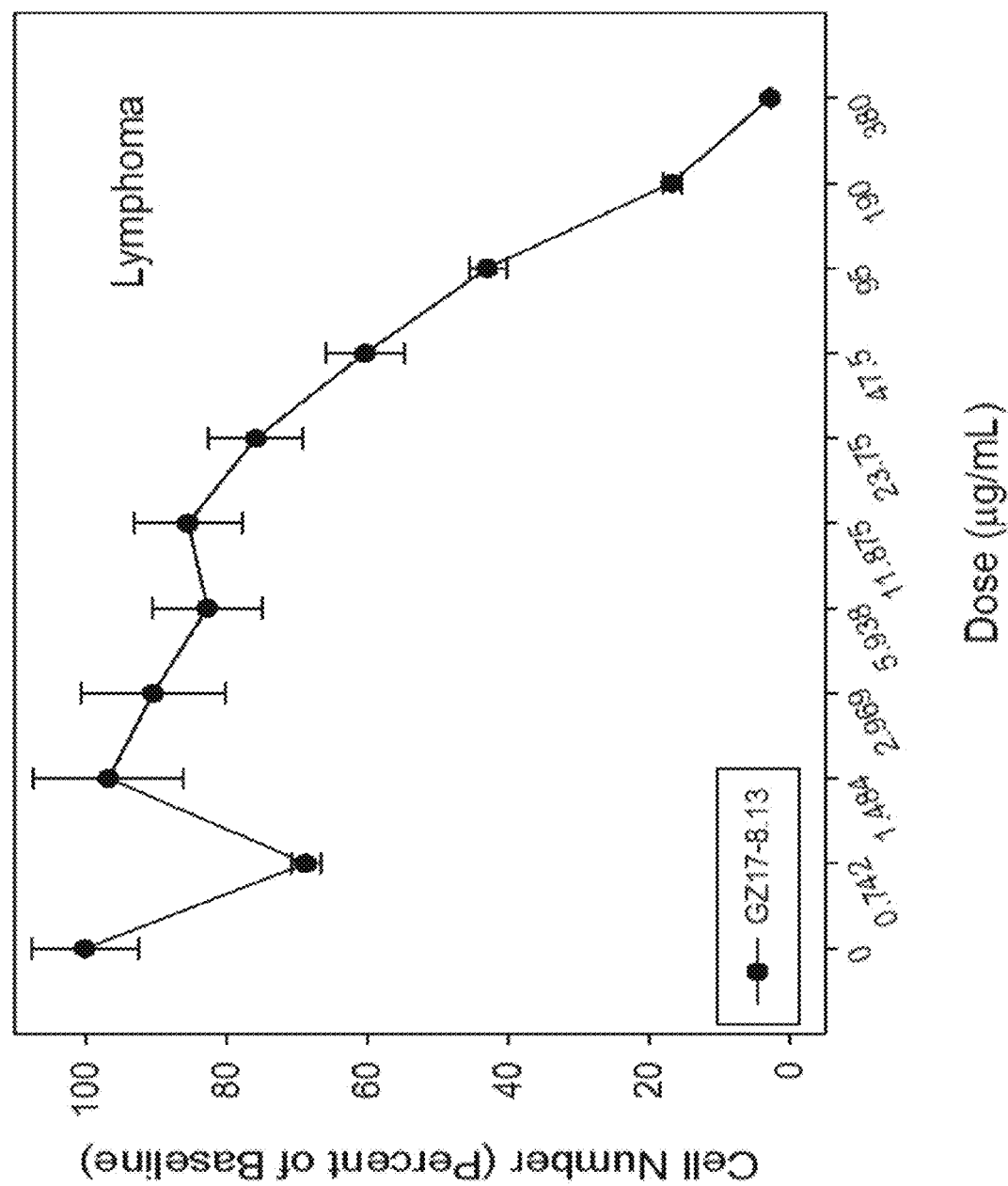
FIG. 31G is a graph of cell number versus dosage amounts of GZ17-8.13, illustrating the effect thereof in inducing the death of lymphoma.
Figure 32A:
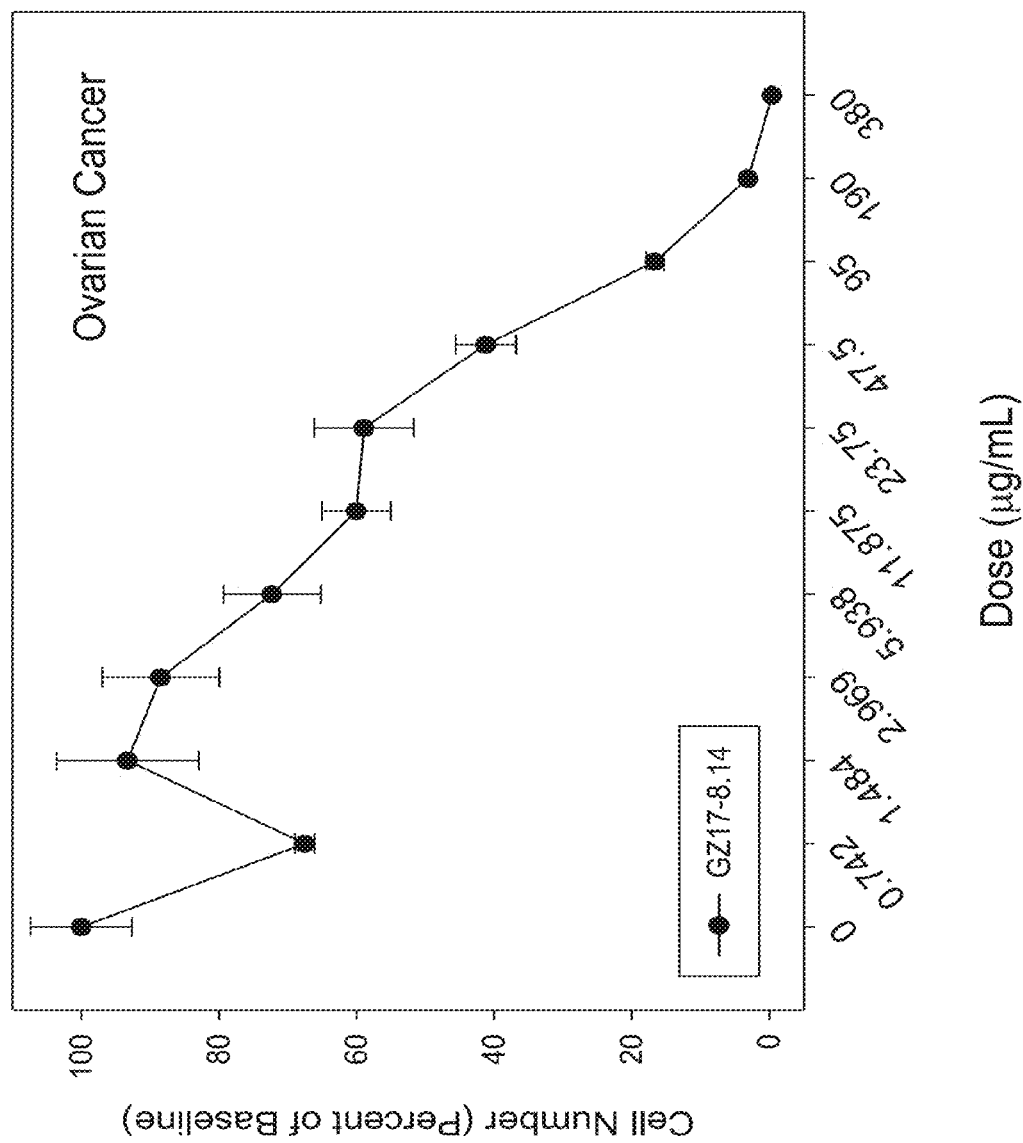
FIG. 32A is a graph of cell number versus dosage amounts of GZ17-8.14, illustrating the effect thereof in inducing the death of ovarian cancer.
Figure 32B:
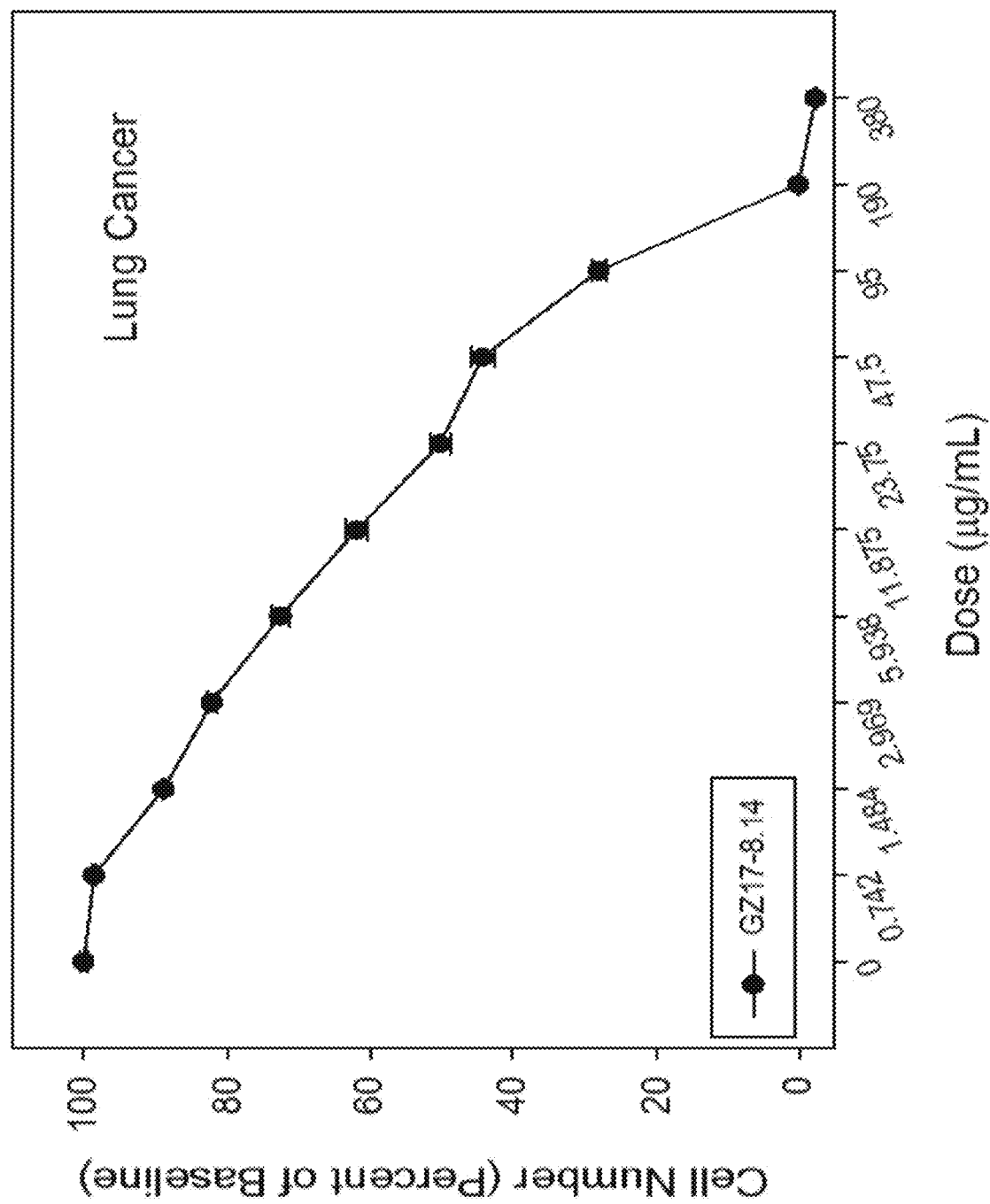
Figure 32C:
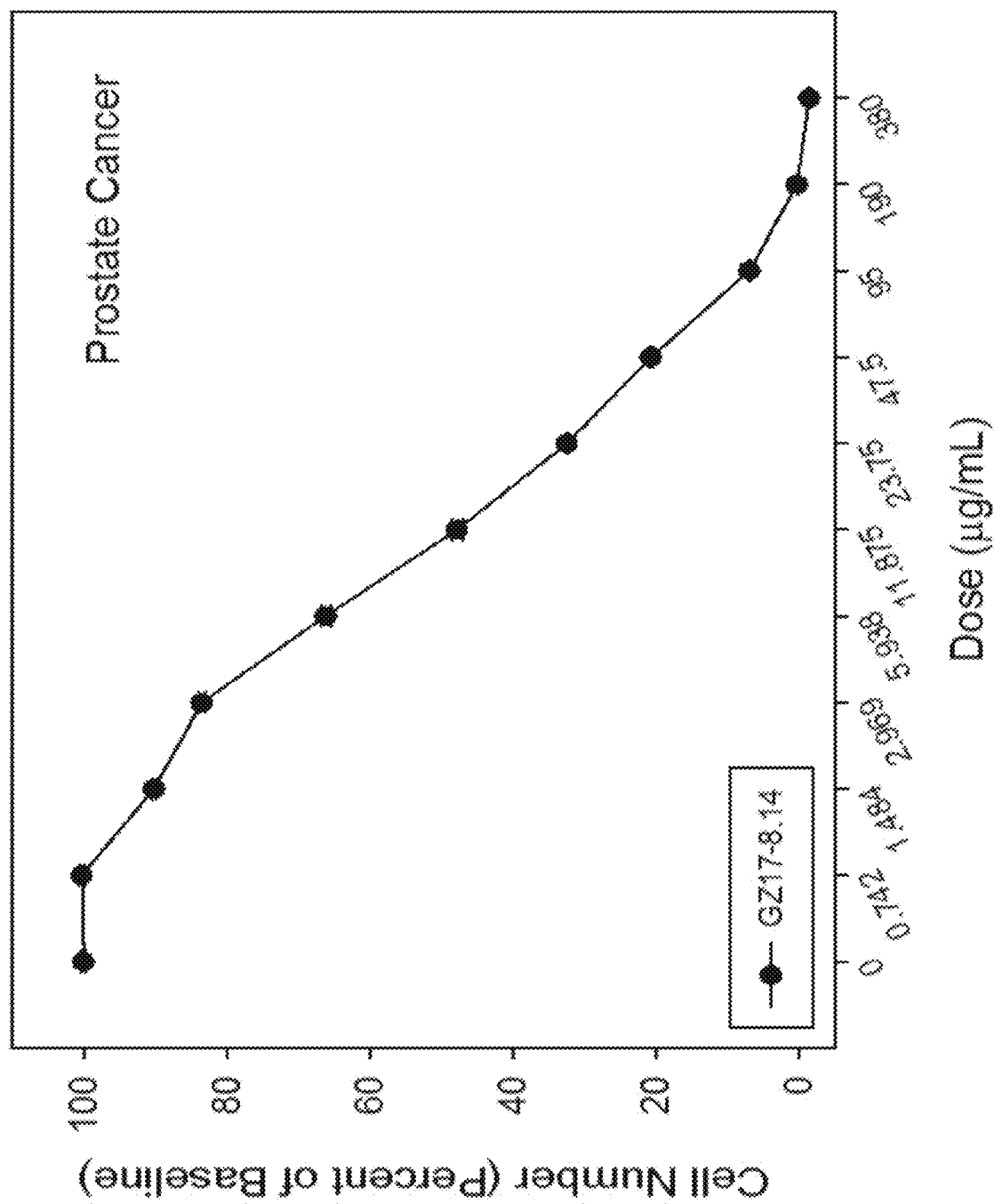
Figure 32D:
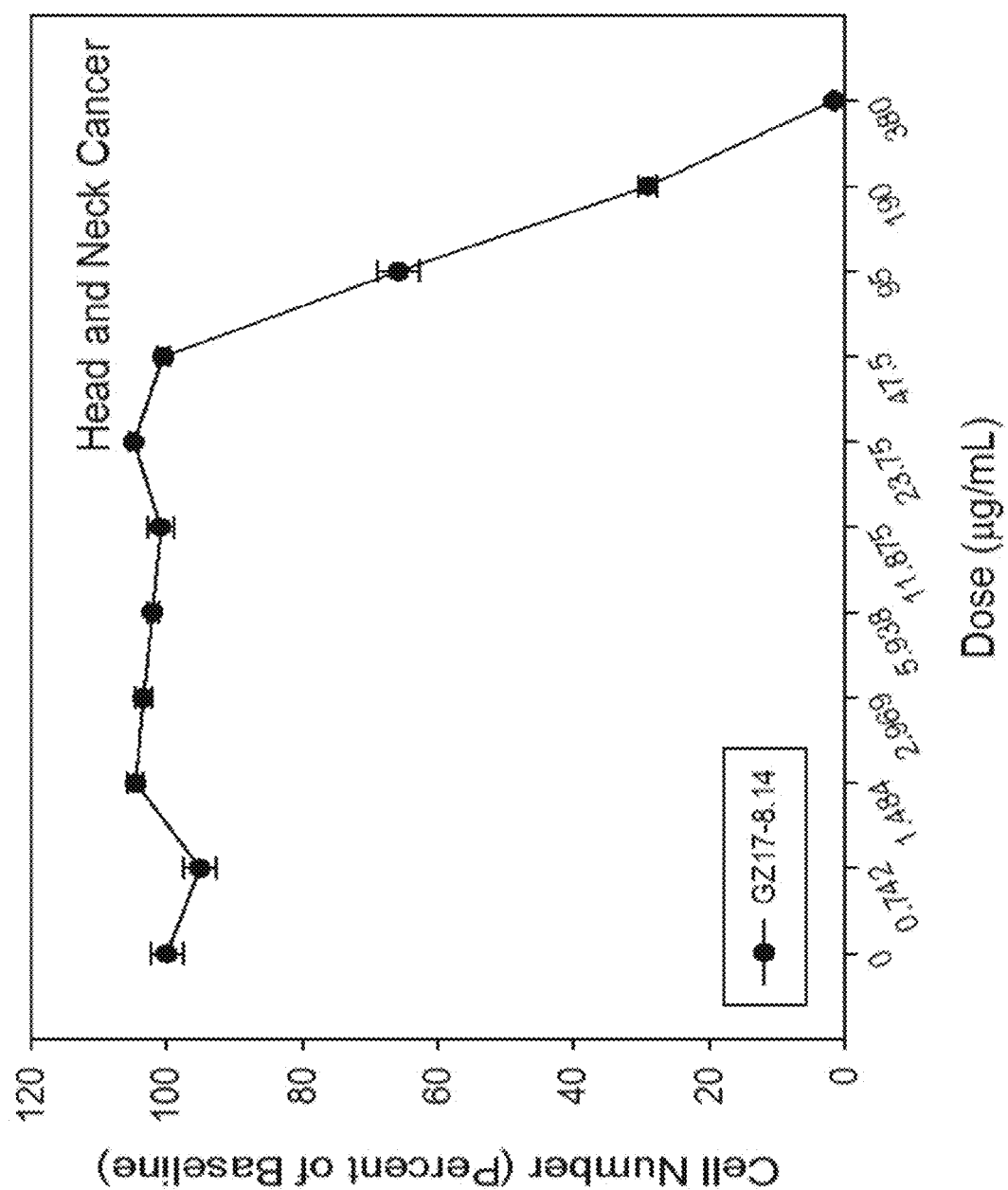
Figure 32E:
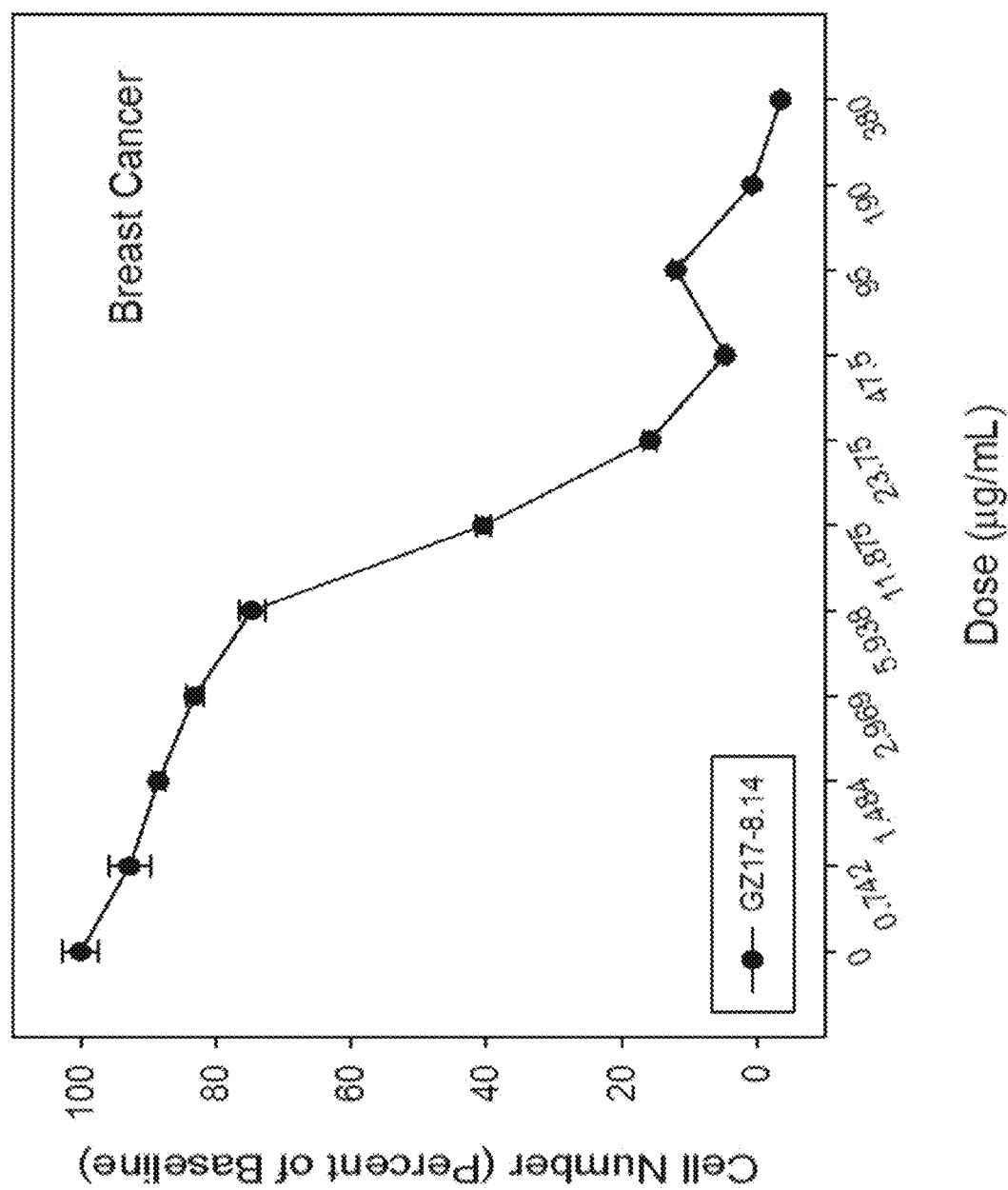
Figure 32F:
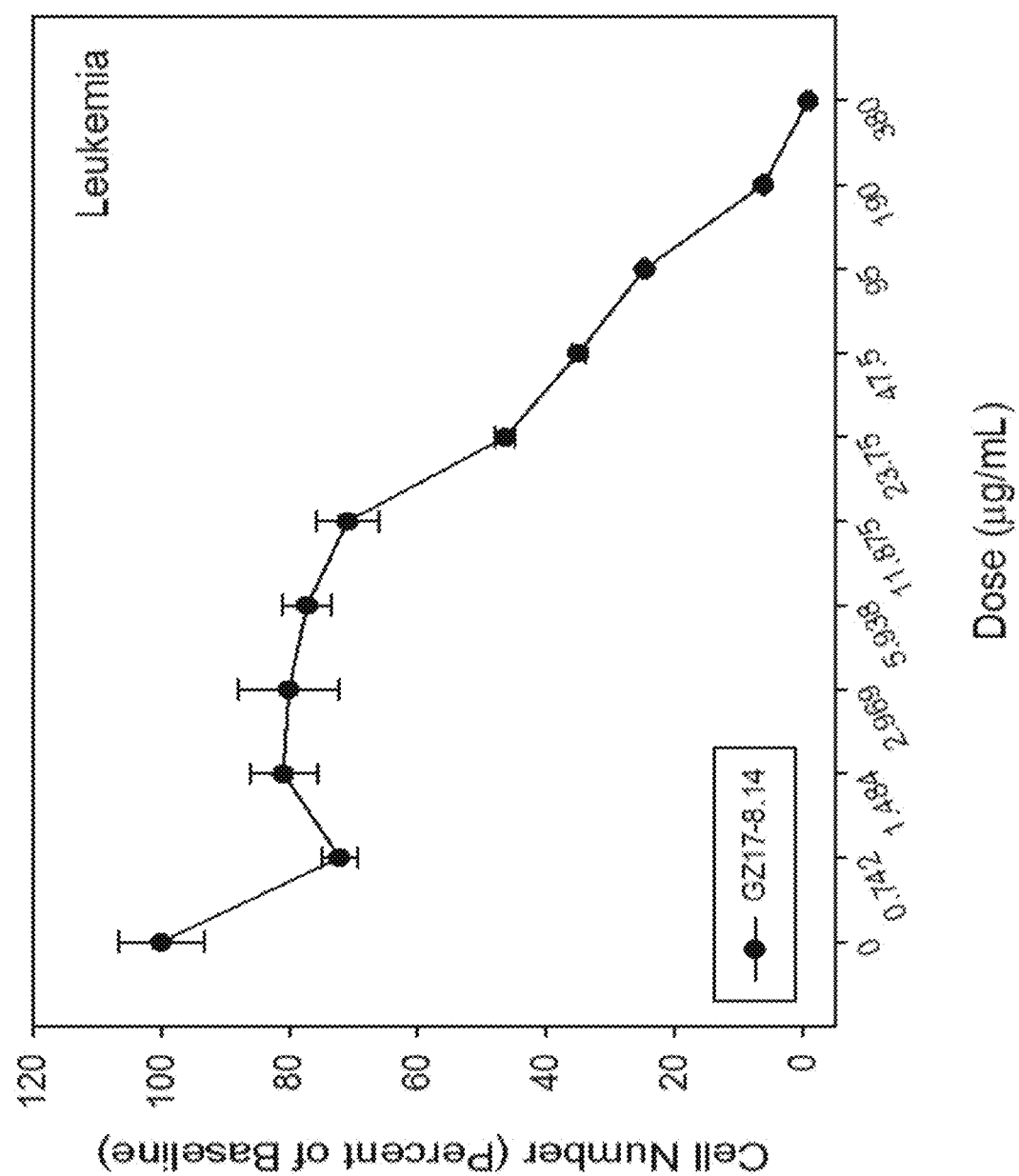
Figure 32G:
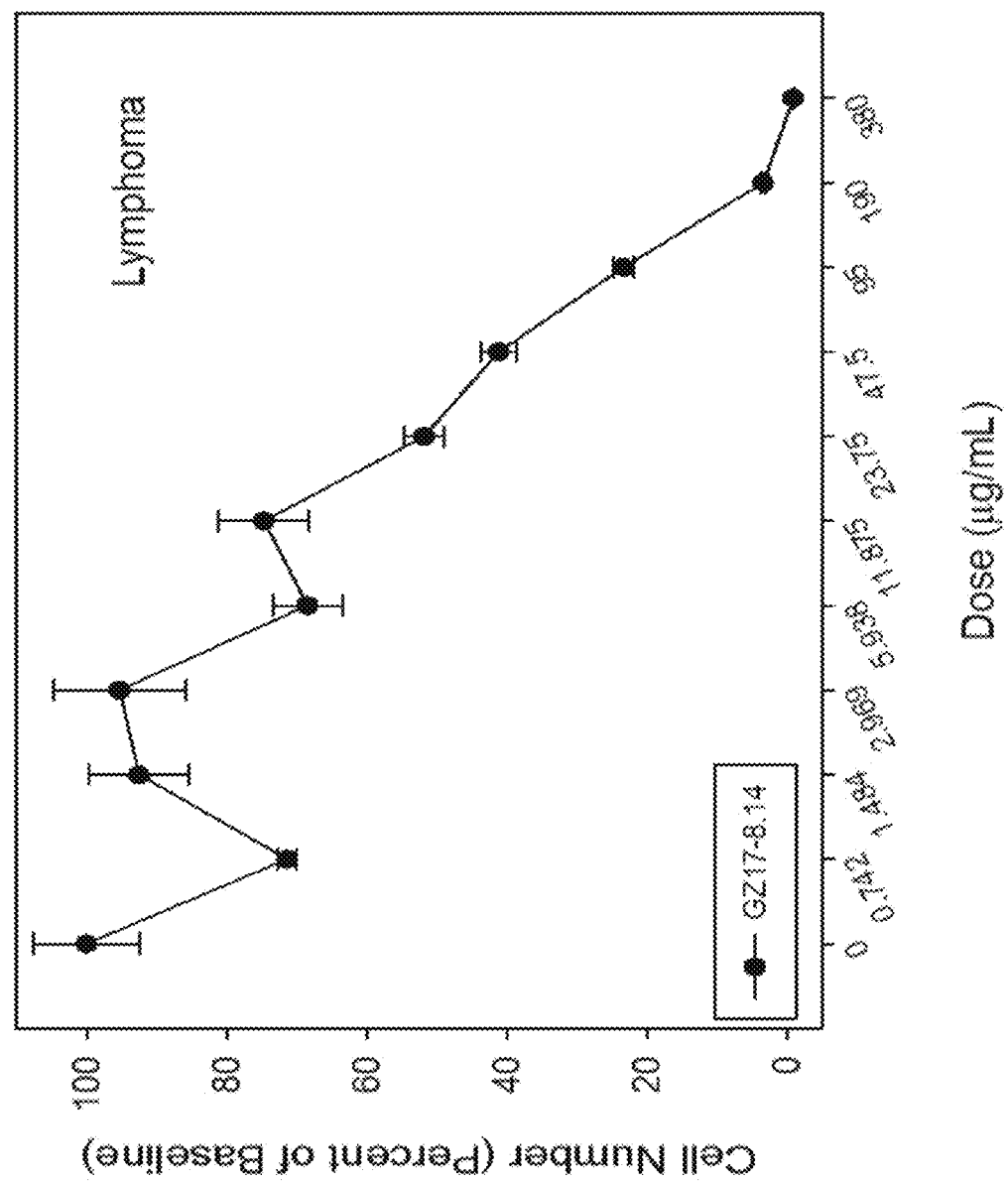

In this series of tests, GZ17-8.02 (which is identical with the preferred GZ17-6.02 composition), and several different combinations of curcumin, harmine, and isovanillin derivatives were tested against ovarian cancer (A1847), lung cancer (H358), prostate cancer (22rv1), pancreatic cancer, and fibroblast cells (hgf-1), in order to confirm that such derivative combinations were effective. In each case, the weight ratio of the isovanillin component:curcumin component:harmine component was 7.7:1:1.3, and the compositions were prepared as described above and the tests were carried out as described in Examples 1, 2, and 6. The compositions are identified below, including the respective graphs giving the results of the tests:

GZ17-8.02 (FIG. 28A)
GZI7-8.03 contained vanillin, turmeric-derived curcumin, and harmine (FIG. 28B)
GZI7-8.04 contained orthovanillin, turmeric-derived curcumin, and harmine, and (FIG. 28C)
GZI7-8.05 contained isovanillyl alcohol, turmeric-derived curcumin, and harmine (FIG. 28D)
GZI7-8.06 contained isovanillic acid, turmeric-derived curcumin, and harmine (FIG. 28E)
GZI7-8.07 contained isovanillin, turmeric-derived curcumin, and harmaline (FIG. 28F)
GZI7-8.08 contained isovanillin, turmeric-derived curcumin, and harmane (FIG. 28G)
GZI7-8.09 contained isovanillin, 100% synthetic curcumin, and harmine (FIG. 28H)
GZI7-8.10 contained isovanillin, bisdemethoxy curcumin, and harmine (FIG. 28I)

Examples 29-79

In each of the following examples, respective compositions having different combinations of isovanillin, curcumin, and harmine components were tested as set forth in Examples 1-6, against cancer cells to determine the anticancer effectiveness thereof. The specific cancer cell lines used in each case were those previously described. In all cases, the weight ratio of the isovanillin component:curcumin component:harmine component was 7.7:1:1.3, and the compositions were prepared as described above in connection with the preparation of GZ17-6.02. A separate graph is provided for each test, which identifies the cancer cells tested.

The following Table sets forth the Example numbers, composition designation, components, and corresponding Figure numbers for this series of tests. Where "curcumin" is specified, this refers to turmeric-derived curcumin, and where "curcumin (syn)" is specified, this refers to essentially pure synthetically-derived curcumin.

| Example No. | Composition | Isovanillin Component | Curcumin Component | Harmine Component | Figure Nos. |
|---|---|---|---|---|---|
| 29 | GZ17-08.11 | isovanillin | bisdemethoxy curcumin | harmaline | 29 A-G |
| 30 | GZ17-08.12 | isovanillin | bisdemethoxy curcumin | harmane | 30 A-G |
| 31 | GZ17-08.13 | isovanillin | bisdemethoxy curcumin | harmalol | 31 A-G |
| 32 | GZ17-08.14 | isovanillin | bisdemethoxy curcumin | harmol | 32 A-G |
| 33 | GZ17-08.15 | vanillin | bisdemethoxy curcumin | harmine | 33 A-G |
| 34 | GZ17-08.16 | vanillin | bisdemethoxy curcumin | harmaline | 34 A-G |
| 35 | GZ17-08.17 | vanillin | bisdemethoxy curcumin | harmane | 35 A-G |
| 36 | GZ17-08.18 | vanillin | bisdemethoxy curcumin | harmalol | 36 A-G |
| 37 | GZ17-08.19 | vanillin | bisdemethoxy curcumin | harmol | 37 A-G |
| 38 | GZ17-08.20 | isovanillin | curcumin (syn) | harmalol | 38 A-G |
| 39 | GZ17-08.21 | isovanillin | curcumin (syn) | harmol | 39 A-G |
| 40 | GZ17-08.22 | vanillin | curcumin (syn) | harmaline | 40 A-G |
| 41 | GZ17-08.23 | vanillin | curcumin (syn) | harmane | 41 A-G |
| 42 | GZ17-08.24 | vanillin | curcumin (syn) | harmalol | 42 A-G |
| 43 | GZ17-08.25 | vanillin | curcumin (syn) | harmol | 43 A-G |
| 44 | GZ17-08.26 | orthovanillin | bisdemethoxy curcumin | harmine | 44 A-G |
| 45 | GZ17-08.27 | orthovanillin | bisdemethoxy curcumin | harmaline | 45 A-G |
| 46 | GZ17-08.28 | orthovanillin | bisdemethoxy curcumin | harmane | 46 A-G |
| 47 | GZ17-08.29 | orthovanillin | bisdemethoxy curcumin | harmalol | 47 A-G |
| 48 | GZ17-08.30 | orthovanillin | bisdemethoxy curcumin | harmol | 48 A-G |
| 49 | GZ17-08.31 | isovanillyl alcohol | bisdemethoxy curcumin | harmine | 49 A-D |
| 50 | GZ17-08.32 | isovanillyl alcohol | bisdemethoxy curcumin | harmaline | 50 A-D |

| Example No. | Composition | Isovanillin Component | Curcumin Component | Harmine Component | Figure Nos. |
|---|---|---|---|---|---|
| 51 | GZ17-08.33 | isovanillyl alcohol | bisdemethoxy curcumin | harmane | 51 A-D |
| 52 | GZ17-08.34 | isovanillyl alcohol | bisdemethoxy curcumin | harmalol | 52 A-D |
| 53 | GZ17-08.35 | isovanillyl alcohol | bisdemethoxy curcumin | harmol | 53 A-D |
| 54 | GZ17-08.36 | orthovanillin | curcumin (syn) | harmaline | 54 A-D |
| 55 | GZ17-08.37 | orthovanillin | curcumin (syn) | harmane | 55 A-D |
| 56 | GZ17-08.38 | orthovanillin | curcumin (syn) | harmalol | 56 A-D |
| 57 | GZ17-08.39 | orthovanillin | curcumin (syn) | harmol | 57 A-D |
| 58 | GZ17-08.40 | isovanillyl alcohol | curcumin (syn) | harmaline | 58 A-D |
| 59 | GZ17-08.41 | isovanillyl alcohol | curcumin (syn) | harmane | 59 A-D |
| 60 | GZ17-08.42 | isovanillyl alcohol | curcumin (syn) | harmalol | 60 A-D |
| 61 | GZ17-08.43 | isovanillyl alcohol | curcumin (syn) | harmol | 61 A-D |
| 62 | GZ17-08.44 | isovanillic acid | bisdemethoxy curcumin | harmine | 62 A-D |
| 63 | GZ17-08.45 | isovanillic acid | bisdemethoxy curcumin | harmaline | 63 A-D |
| 64 | GZ17-08.46 | isovanillic acid | bisdemethoxy curcumin | harmane | 64 A-D |
| 65 | GZ17-08.47 | isovanillic acid | bisdemethoxy curcumin | harmalol | 65 A-D |
| 66 | GZ17-08.48 | isovanillic acid | bisdemethoxy curcumin | harmol | 66 A-D |
| 67 | GZ17-08.49 | isovanillic acid | curcumin (syn) | harmaline | 67 A-D |
| 68 | GZ17-08.50 | isovanillic acid | curcumin (syn) | harmane | 68 A-D |
| 69 | GZ17-08.51 | isovanillic acid | curcumin (syn) | harmalol | 69 A-D |
| 70 | GZ17-08.52 | isovanillic acid | curcumin (syn) | harmol | 70 A-D |
| 71 | GZ17-08.53 | 5-bromovanillin | curcumin | harmine | 71 A-D |
| 72 | GZ17-08.54 | 2-bromo-3-hydroxy-4-methoxy benzaldehyde | curcumin | harmine | 72 A-D |
| 73 | GZ17-08.55 | 2-iodo-3-hydroxy-4-methoxy benzaldehyde | curcumin | harmine | 73 A-D |
| 74 | GZ17-08.56 | isovanillin | (1E,4E)-1,5-bis(3,5-dimethoxyphenyl)-1,4-pentadien-3-one | harmine | 74 A-D |
| 75 | GZ17-08.57 | isovanillin | cardamonin | harmine | 75 A-D |
| 76 | GZ17-08.58 | isovanillin | 2'-hydroxy-3,4,4',5'-tetramethoxychalcone | harmine | 76 A-D |
| 77 | GZ17-08.59 | isovanillin | 2,2'-dihydroxy-4',6'-dimethoxychalcone | harmine | 77 A-D |
| 78 | GZ17-08.60 | isovanillin | (1E,4E)-1,5-Bis(2-Hydroxyphenyl)-1,4-pentadien-3-one | harmine | 78 A-D |
| 79 | GZ17-08.61 | isovanillin | curcumin | 1,2,3,4-tetrahydro-harmane-3-carboxylic acid | 79 A-D |

These test results confirm that all of the compositions were effective anti-cancer agents.

Example 80

In this series of tests, the following compositions were prepared:

| Composition | Isovanillin Component | Curcumin Component | Harmine Component |
|---|---|---|---|
| GZ17-10.00 | orthovanillin | curcumin | harmaline |
| GZ17-10.01 | orthovanillin | — | harmaline |
| GZ17-10.02 | orthovanillin | curcumin | — |
| GZ17-10.03 | — | curcumin | harmaline |
| GZ17-10.04 | orthovanillin | — | — |
| GZ17-10.05 | — | curcumin | — |
| GZ17-10.06 | — | — | harmaline |

GZ17-10.00 is identical with the above-described GZ17-6.02, having the identical amounts of the components and method of preparation. The two-component compositions have the same relative ratios, namely 7.7:1.3 for GZ17-10.01, 7.7:1 for GZ17-10.02, and 1:1.3 for GZ17-10.03. The single-component compositions contain the same amount of component as used in the three- and two-component compositions.

The respective compositions of this Example were tested against different cancer cell lines, as previously identified, using the methods of Examples 1-6, as set forth in the accompanying relevant graphs, 80A-80R. Six of these (FIGS. 80G, H, L, M, Q, and R) are comparative bar graphs setting forth the theoretical additive effect of the components, and the results obtained using the complete formulations, thereby demonstrating the synergistic effects of the compositions of the invention.

These test results confirm that all of the compositions were effective anti-cancer agents.

Example 81

In this series of tests, the following compositions were prepared:

| Composition | Isovanillin Component (ratio component = 7.7) | Harmine Component (ratio component = 1.3) |
|---|---|---|
| GZ17-08.512 | isovanillin | harmine |
| GZ17-08.513 | isovanillin | harmaline |
| GZ17-08.514 | isovanillin | harmane |
| GZ17-08.515 | isovanillin | harmalol |
| GZ17-08.516 | isovanillin | harmol |
| GZ17-08.517 | vanillin | harmine |
| GZ17-08.518 | vanillin | harmaline |
| GZ17-08.519 | vanillin | harmane |
| GZ17-08.520 | vanillin | harmalol |
| GZ17-08.521 | vanillin | harmol |

The respective compositions of this Example were tested against different cancer cell lines, as previously identified, using the methods of Examples 1-6, as set forth in the accompanying relevant graphs, 81A-81DD.

These test results confirm that all of the compositions were effective anti-cancer agents.

Example 82

In each of the following examples, respective compositions having different combinations of isovanillin, curcumin, and harmine components were tested as set forth in Examples 1-3, against lung cancer, lymphoma, and leukemia cells to determine the anti-cancer effectiveness thereof. The compositions were prepared by individually mixing the listed components in 3 mL of ethanol followed by adding the so-mixed components together to form the resultant compositions. A separate graph is provided for each test, which identifies the cancer cells tested. Specifically, FIGS. 82-1 through 82-41 set forth the results of the lung cancer (LC) tests using the compositions, FIGS. 82-42 through 82-82 give the results for the lymphoma (LY) tests, and FIGS. 82-83 through 82-123 give the results of the leukemia (LK) tests.

The first Table below sets forth the identities of the isovanillin components i01-i15, the harmine components h01-h13, and the curcumin components c01-c13, used in these tests. The second Table below sets forth the multiple-component compositions tested, GZ08.065-GZ08.105, for lung cancer, lymphoma, and leukemia cells and the respective Figure numbers associated with each such composition and cell line. The recitation "curcumin (syn)" refers to essentially pure synthetically-derived curcumin.

All of the second Table compositions exhibited anti-cancer activity against lung cancer, lymphoma, and leukemia cells. In addition, FIGS. 82-124 through 82-167 are comparative bar graphs confirming the synergism found in exemplary compositions of this Example, at various concentration levels, against lung cancer, lymphoma, and leukemia cells.

| Code | Compound | CAS# | MW |
|---|---|---|---|
| i01 | o-anisaldehyde | 135-02-4 | 136.15 |
| i02 | isovanillin oxime | 51673-94-0 | 167.166 |
| i03 | ethyl vanillin | 121-32-4 | 166.18 |
| i04 | vanillin isobutyrate | 20665-85-4 | 222.24 |
| i05 | veratraldehyde | 120-14-9 | 166.18 |
| i06 | 5-nitrovanillin | 6635-20-7 | 197.14 |
| i07 | vanillin acetate | 881-68-5 | 194.18 |
| i08 | 3-benzyloxy-4-methoxybenzaldehyde | 6346-05-0 | 242.27 |
| i09 | 3-hydroxy-5-methoxybenzaldehyde | 672-13-9 | 152.15 |
| i10 | methyl isovanillate | 6702-50-7 | 182.18 |
| i11 | acetovanillone (apocynin) | 498-02-2 | 166.17 |
| i12 | 2-hydroxy-4-methoxybenzaldehyde | 673-22-3 | 152.15 |
| i13 | trans-ferulic acid | 537-98-4 | 194.18 |
| i14 | 3-hydroxy-4-methoxycinnamic acid | 537-73-5 | 194.18 |
| i15 | caffeic acid | 331-39-5 | 180.16 |
| h01 | norharmane | 244-63-3 | 168.19 |
| h02 | 6-methoxyharmalan | 3589-73-9 | 214.26 |
| h03 | bromo harmine | na | 372.06 |
| h04 | 2-methyl harmine | 21236-68-0 | 227.28 |
| h05 | 4,9-dihydro-3H-beta-carbolin-1-yl methyl ether | na | 200.24 |
| h06 | 1-(4(nitrophenyl)-2,3,4,9-tetrahydro-1H-beta-carboline hydrochloride | 3380-77-6 | 329.79 |
| h07 | 1,2,3,4-tetrahydro-9H-pyrido[3,4-b]indole {THbC} | 16502-01-5 | 172.23 |
| h08 | 1,2,3,4-tetrahydro-beta-carboline-1-carboxylic acid | na | 216.24 |
| h09 | 6-Methoxy-1,2,3,4-tetrahydro-9H-pyrido[3,4-b]indole | 20315-68-8 | 202.25 |
| h10 | 3-hydroxymethyl-b-carboline | 65474-79-5 | 198.22 |
| h11 | 2,3,4,5-tetrahydro-8-methoxy-1H-pyrido[4,3-b]indole | na | 202.25 |
| h12 | 6-Methoxy-1,2,3,4-tetrahydro-9H-pyrido[3,4-b]indole-1-carboxylic acid | 17952-63-5 | 246.26 |
| h13 | ethyl b-carboline-3-carboxylate | 74214-62-3 | 240.26 |
| c01 | tetrahydro curcumin | 36062-04-1 | 372.41 |
| c02 | demethyl curcumin | 149732-51-4 | 354.35 |
| c03 | demethoxy curcumin | 22608-11-3 | 338.35 |
| c04 | 1,3-diphenyl-2-propanone | 102-04-5 | 210.27 |
| c05 | caffeic acid phenethyl ester | 104594-70-9 | 284.31 |
| c06 | (1E,4E)-1,5-bis[3,5-bis(methoxymethoxy)phenyl]-1,4-pentadiene-3-one | 917813-62-8 | 474.51 |
| c07 | 1,7-di(1-naphthyl)-2,6-heptanedione | na | 380.49 |
| c08 | trans,trans-1,5-Bis[4-(trifluoromethyl)phenyl]-1,4-pentadien-3-one | 103836-71-1 | 370.29 |
| c09 | 1,5-dibenzoylpentane | 28861-22-5 | 280.36 |
| c10 | (2E,5E)-2,5-dibenzylidenecyclopentanone | 895-80-7 | 260.33 |
| c11 | 2,6-bis(4-fluorobenzal)cyclohexanone | 62085-74-9 | 310.34 |
| c12 | (1E,4E)-1,5-bis(4-fluorophenyl)-1,4-pentadien-3-one | na | 354.4 |
| c13 | FLLL31 | 52328-97-9 | 424.49 |

| Comp. | Isovanillin Component (176 mg/3 mL EtOH) | Harmine Component (30 mg/3 mL EtOH) | Curcumin Component (23 mg/3 mL EtOH) | Total (mg/mL) | Total (mM) | LC FIG. Nos. | LY FIG. Nos. | LK FIG. Nos. |
|---|---|---|---|---|---|---|---|---|
| 08.065 | i01 | harmine | curcumin (syn) | 76.3 | 498.8 | 82-1 | 82-42 | 82-83 |
| 08.066 | i02 | harmine | curcumin (syn) | 76.3 | 418.8 | 82-2 | 82-43 | 82-84 |
| 08.067 | i03 | harmine | curcumin (syn) | 76.3 | 420.9 | 82-3 | 82-44 | 82-85 |
| 08.068 | i04 | harmine | curcumin (syn) | 76.3 | 331.9 | 82-4 | 82-45 | 82-86 |
| 08.069 | i05 | harmine | curcumin (syn) | 76.3 | 420.9 | 82-5 | 82-46 | 82-87 |
| 08.070 | i06 | harmine | curcumin (syn) | 76.3 | 365.5 | 82-6 | 82-47 | 82-88 |
| 08.071 | i07 | harmine | curcumin (syn) | 76.3 | 370.0 | 82-7 | 82-48 | 82-89 |
| 08.072 | i08 | harmine | curcumin (syn) | 76.3 | 310.1 | 82-8 | 82-49 | 82-90 |
| 08.073 | i09 | harmine | curcumin (syn) | 76.3 | 453.5 | 82-9 | 82-50 | 82-91 |
| 08.074 | i10 | harmine | curcumin (syn) | 76.3 | 389.9 | 82-10 | 82-51 | 82-92 |
| 08.075 | i11 | harmine | curcumin (syn) | 76.3 | 421.0 | 82-11 | 82-52 | 82-93 |
| 08.076 | i12 | harmine | curcumin (syn) | 76.3 | 453.5 | 82-12 | 82-53 | 82-94 |
| 08.077 | i13 | harmine | curcumin (syn) | 76.3 | 370.0 | 82-13 | 82-54 | 82-95 |
| 08.078 | i14 | harmine | curcumin (syn) | 76.3 | 370.0 | 82-14 | 82-55 | 82-96 |
| 08.079 | i15 | harmine | curcumin (syn) | 76.3 | 393.5 | 82-15 | 82-56 | 82-97 |
| 08.080 | isovanillin | h01 | curcumin (syn) | 76.3 | 465.9 | 82-16 | 82-57 | 82-98 |
| 08.081 | isovanillin | h02 | curcumin (syn) | 76.3 | 453.1 | 82-17 | 82-58 | 82-99 |
| 08.082 | isovanillin | h03 | curcumin (syn) | 76.3 | 433.3 | 82-18 | 82-59 | 82-100 |
| 08.083 | isovanillin | h04 | curcumin (syn) | 76.3 | 450.4 | 82-19 | 82-60 | 82-101 |
| 08.084 | isovanillin | h05 | curcumin (syn) | 76.3 | 456.3 | 82-20 | 82-61 | 82-102 |
| 08.085 | isovanillin | h06 | curcumin (syn) | 76.3 | 436.7 | 82-21 | 82-62 | 82-103 |
| 08.086 | isovanillin | h07 | curcumin (syn) | 76.3 | 464.5 | 82-22 | 82-63 | 82-104 |
| 08.087 | isovanillin | h08 | curcumin (syn) | 76.3 | 452.6 | 82-23 | 82-64 | 82-105 |
| 08.088 | isovanillin | h09 | curcumin (syn) | 76.3 | 455.8 | 82-24 | 82-65 | 82-106 |
| 08.089 | isovanillin | h10 | curcumin (syn) | 76.3 | 456.8 | 82-25 | 82-66 | 82-107 |
| 08.090 | isovanillin | h11 | curcumin (syn) | 76.3 | 455.8 | 82-26 | 82-67 | 82-108 |
| 08.091 | isovanillin | h12 | curcumin (syn) | 76.3 | 447.0 | 82-27 | 82-68 | 82-109 |
| 08.092 | isovanillin | h13 | curcumin (syn) | 76.3 | 448.0 | 82-28 | 82-69 | 82-110 |
| 08.093 | isovanillin | harmine | c01 | 76.3 | 453.3 | 82-29 | 82-70 | 82-111 |
| 08.094 | isovanillin | harmine | c02 | 76.3 | 454.3 | 82-30 | 82-71 | 82-112 |
| 08.095 | isovanillin | harmine | c03 | 76.3 | 455.4 | 82-31 | 82-72 | 82-113 |
| 08.096 | isovanillin | harmine | c04 | 76.3 | 469.2 | 82-32 | 82-73 | 82-114 |
| 08.097 | isovanillin | harmine | c05 | 76.3 | 459.7 | 82-33 | 82-74 | 82-115 |
| 08.098 | isovanillin | harmine | c06 | 76.3 | 448.9 | 82-34 | 82-75 | 82-116 |
| 08.099 | isovanillin | harmine | c07 | 76.3 | 452.8 | 82-35 | 82-76 | 82-117 |
| 08.100 | isovanillin | harmine | c08 | 76.3 | 453.4 | 82-36 | 82-77 | 82-118 |
| 08.101 | isovanillin | harmine | c09 | 76.3 | 460.0 | 82-37 | 82-78 | 82-119 |
| 08.102 | isovanillin | harmine | c10 | 76.3 | 462.1 | 82-38 | 82-79 | 82-120 |
| 08.103 | isovanillin | harmine | c11 | 76.3 | 457.4 | 82-39 | 82-80 | 82-121 |
| 08.104 | isovanillin | harmine | c12 | 76.3 | 454.3 | 82-40 | 82-81 | 82-122 |
| 08.105 | isovanillin | harmine | c13 | 76.3 | 450.8 | 82-41 | 82-82 | 82-123 |

All of the foregoing tests confirmed significant anti-cancer activity against lung cancer cells, H358, lymphoma cells, MO205, and leukemia cells, jurkat E6-1. Accordingly, all combinations of i01-i15, h01-h13, and c01-c13, whether three-component or two-component, would exhibit such anti-cancer activity. Moreover, as shown above, the combinations of harmine and curcumin with i01-15, isovanillin and curcumin with h01-h13, and isovanillin and harmine with c01-c13 all have useful anti-cancer activity.

Moreover, as noted previously, the compounds i01-i15, h01-h13, and c01-c13 may be individually and independently in the form of the corresponding esters, metal complexes, pharmaceutically acceptable salts, and mixtures thereof. That is, e.g., a given curcumin component may be in the form of an ester, complex, or salt, independently of the form of the remaining components of the composition.

Example 83

In another series of tests, compositions were prepared containing: (1) orthovanillin+curcumin+harmaline; and (2) single-component compositions containing orthovanillin, curcumin, and harmaline, respectively. The three-component composition had a weight ratio of orthovanillin:curcumin:harmaline of 771:130.3:98.7, and the single-component compositions contained varying amounts of orthovanillin, curcumin, and harmaline.

These compositions were prepared by mixing together quantities of solid synthetic orthovanillin (99% by weight purity), synthetic harmaline (92% by weight purity), and a commercial turmeric product (ResCu) in ethanol, and allowing the mixtures to react for a period of 24 hours.

These compositions were tested against lymphoma (M0205), leukemia (jurkat E6-1), and breast cancer (du4475) cell lines, using the assays described in Examples 1-3.

The results of the lymphoma tests are set forth in FIGS. 83A-83D. These tests confirmed that the combination of orthovanillin+curcumin+harmaline (FIG. 83D) exhibited synergistic results as compared with the individual tests of orthovanillin, curcumin, and harmaline (FIGS. 83A-83C).

In like manner, the leukemia tests (FIGS. 83E-83H) confirmed that the combination of orthovanillin+curcumin+harmaline (FIG. 83H) exhibited synergistic results as compared with the individual tests of orthovanillin, curcumin, and harmaline (FIGS. 83E-83G).

To a similar effect, the breast cancer tests (FIGS. 83I-83L) confirmed that the combination of orthovanillin+curcumin+harmaline (FIG. 83L) exhibited synergistic results as compared with the individual tests of orthovanillin, curcumin, and harmaline (FIGS. 83I-83K).

Example 84

In this Example, GZ17-6.02 was tested with pancreatic cancer cells (S2-007) to determine whether it had an effect on cancer stem cell proteins using the techniques described in Examples 1-3, and it was found that the treatment decreased the number and size of the pancreatic cancer spheres at both the $IC_{50}$ concentration and a concentration of half that amount (see FIG. 84A). In additional tests (FIG. 84B), treated cells exhibited a dose-dependent decline in doublecortin calmodulin-like kinase 1 (Dclk-1), a microtubule-associated protein that serves as a marker for intestinal and pancreatic cancer stem cells (Mwangi, S. M. et al. "DCAMKL-1: a new horizon for pancreatic progenitor identification." *Am J Phys—Gastro Liver Physiol* 299 (2010):G301-302), and also differentiates between tumor stem cells and normal stem cells (Nakanishi, Y. et al. "Dclk1 distinguishes between tumor and normal stem cells in the intestine." *Nature Gen* 45 (2013):98-103). Epithelial cell adhesion molecule (EpCAM) is another cancer stem cell marker and it also decreased in level with GZ17-6.02 exposure. Likewise, the leucine-rich-repeat containing G-protein-coupled receptor 5 (LGR5) is another cancer stem cell marker and its levels decreased with the GZ17-6.02 treatment (FIG. 84B).

When tumors from treated mice were analyzed, the tumors also showed a clear reduction in EPCAM, DCLK1, LGR5, and SOX9 (FIG. 84C). GZ17-6.02 is thus seen to block pancreatic spheroid formation and cancer stem cell marker expression, both in cancer cells grown and treated in vitro and in tumor samples from mice treated with GZ17-6.02.

GZ17-6.02 significantly reduced tumorigenesis both with in vitro and in vivo pancreatic cancer cell models, partially via a route that inhibits the presence of cancer stem cells. In this regard, it appears that GZ17-6.02 has several different mechanisms of action resulting in decreased tumor growth and inhibition of metastases. FIG. 84D illustrates a possible pathway for the action of GZ17-6.02 on both cancer stem cells (CSC) and on the other cancer cells within the tumor. With respect to the cancer stem cells, the GZ17-6.02 decreased the common biomarkers of cancer stem cells (Dclk1, LGR5, EpCam, and Sox9). It apparently did this by acting through the Sonic Hedgehog pathway (FIG. 84D, SHH). Simultaneously, GZ17-6.02 blocked the bulk tumor cells in two ways by directly inducing apoptosis via the caspase pathway, as measured by the BAX/Bcl2 ratio, and through the EGFR pathway. All three of these mechanisms led to reduced tumor size, inhibition of metastasis and decline in the presence of cancer stem cells. Thus, the compositions of the invention are effective for killing or inhibiting the growth of cancer stem cells.

Example 85

The purpose of this study was to determine the effect of GZ17-6.02 on the regression of growth and the inhibition of metastases in a pancreatic cancer mouse model. Twelve immunocompromised (nude) mice were treated injected with MiaPaCa-2 cells (a pancreatic cancer cell line) that had been genetically transformed to express TdTomato and luciferin for in vivo tumor imaging. After tumors reached a measurable size (approximately 2 weeks), half of the mice were randomly assigned to the experimental group and the other half to the control group.

The experimental group was treated with GZ17-6.02 at a daily dose of 100 mg/kg body weight. The drug administration was oral, dissolved in peptamen. Control mice were fed the vehicle (peptamen) alone. Once a week mice were lightly anesthetized in order to use IVIS imaging to detect the tumor sizes. On day 5, there was no statistical difference in the amount of fluorescence measured from the control (placebo-fed) and GZ17-6.02-fed mice. However, by day 20, there was a statistically significant decrease in the amount of fluorescence, indicating a decreased total tumor burden, in the mice fed GZ17-6.02, as compared with the control. In addition, the placebo-treated mice had dramatic levels of peritoneal ascites that were not present in the GZ17-6.02 group.

At the end of 21 days of treatment with GZ17-6.02 or the placebo, the mice were sacrificed and tumor samples removed from the pancreas, liver, and lungs. The primary pancreatic tumors were weighed. The placebo-fed animals had pancreatic tumors that averaged 2.4 times statistically larger than the GZ17-6.02 fed mice.

Example 86

A 63-year-old male patient having a Prostate-Specific Antigen (PSA) count of 8.2 began a treatment regimen using a dosage form of GZ17-6.02. Specifically, solid GZ17-6.02 prepared by evaporating the ethanol from the previously described GZ17-6.02 agent was dispersed in water in equal weight amounts, e.g., 5 grams solid GZ17-6.02 in 5 grams water. This dosage form was taken three times daily for six weeks, with each dose being four fluid ounces of the 50%:50% dispersion. At the end of six weeks, the patient's PSA count had dropped to 2.1, and all prostate and urological tests were normal. The treating physician had no explanation for the decline in PSA. The patient experienced no observable adverse reactions to the treatment with GZ17-6.02.

Although not wishing to be bound by any theory of operation, the inventors believe that the therapeutic agents of the invention ameliorate a number of conditions or illnesses, and especially reduce and/or eliminate cancer and/or the symptoms thereof by augmenting or stimulating the patients' immune systems. In this sense, the invention is believed to be a form of biological therapy. As such, it is considered that the invention is applicable to virtually all cancers, such as the following: Acute Lymphoblastic Leukemia, Adult; Acute Lymphoblastic Leukemia, Childhood; Acute Myeloid Leukemia, Adult; Acute Myeloid Leukemia, Childhood; Adrenocortical Carcinoma; Adrenocortical Carcinoma, Childhood; Adolescents, Cancer in; AIDS-Related Cancers; AIDS-Related Lymphoma; Anal Cancer; Appendix Cancer; Astrocytomas, Childhood; Atypical Teratoid/Rhabdoid Tumor, Childhood, Central Nervous System; Basal Cell Carcinoma; Bile Duct Cancer, Extrahepatic; Bladder Cancer; Bladder Cancer, Childhood; Bone Cancer, Osteosarcoma and Malignant Fibrous Histiocytoma; Brain Stem Glioma, Childhood; Brain Tumor, Adult; Brain Tumor, Brain Stem Glioma, Childhood; Brain Tumor, Central Nervous System Atypical Teratoid/Rhabdoid Tumor, Childhood; Brain Tumor, Central Nervous System Embryonal Tumors, Childhood; Brain Tumor, Astrocytomas, Childhood; Brain Tumor, Craniopharyngioma, Childhood; Brain Tumor, Ependymoblastoma, Childhood; Brain Tumor, Ependymoma, Childhood; Brain Tumor, Medulloblastoma, Childhood; Brain Tumor, Medulloepithelioma, Childhood; Brain Tumor, Pineal Parenchymal Tumors of Intermediate Differentiation, Childhood; Brain Tumor, Supratentorial Primitive Neuroectodermal Tumors and Pineoblastoma, Childhood; Brain and Spinal Cord Tumors, Childhood (Other); Breast Cancer; Breast Cancer and Pregnancy; Breast Cancer, Childhood; Breast Cancer, Male; Bronchial Tumors, Childhood; Burkitt Lymphoma; Carcinoid Tumor, Childhood; Carcinoid Tumor, Gastrointestinal; Carcinoma of Unknown Primary; Central Nervous System Atypical Teratoid/Rhabdoid Tumor, Childhood; Central Nervous System Embryonal Tumors, Childhood; Central Nervous System (CNS) Lymphoma, Primary; Cervical Cancer; Cervical Cancer, Childhood; Childhood Cancers; Chordoma, Childhood; Chronic Lymphocytic Leukemia; Chronic Myelogenous Leukemia; Chronic Myeloproliferative Disorders; Colon Cancer; Colorectal Cancer, Childhood; Craniopharyngioma, Childhood; Cutaneous T-Cell Lymphoma; Embryonal Tumors, Central Nervous System, Childhood; Endometrial Cancer; Ependymoblastoma, Childhood; Ependymoma, Childhood; Esophageal Cancer; Esophageal Cancer, Childhood; Esthesioneuroblastoma, Childhood; Ewing Sarcoma Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Gastrointestinal Stromal Tumor (GIST); Gastrointestinal Stromal Cell Tumor, Childhood; Germ Cell Tumor, Extracranial, Childhood; Germ Cell Tumor, Extragonadal; Germ Cell Tumor, Ovarian; Gestational Trophoblastic Tumor; Glioma, Adult; Glioma, Childhood Brain Stem; Hairy Cell Leukemia; Head and Neck Cancer; Heart Cancer, Childhood; Hepatocellular (Liver) Cancer, Adult (Primary); Hepatocellular (Liver) Cancer, Childhood (Primary); Histiocytosis, Langerhans Cell; Hodgkin Lymphoma, Adult; Hodgkin Lymphoma, Childhood; Hypopharyngeal Cancer; Intraocular Melanoma; Islet Cell Tumors (Endocrine Pancreas); Kaposi Sarcoma; Kidney (Renal Cell) Cancer; Kidney Cancer, Childhood; Langerhans Cell Histiocytosis; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoma, AIDS-Related; Lymphoma, Burkitt; Lymphoma, Cutaneous T-Cell; Lymphoma, Hodgkin, Adult; Lymphoma, Hodgkin, Childhood; Lymphoma, Non-Hodgkin, Adult; Lymphoma, Non-Hodgkin, Childhood; Lymphoma, Primary Central Nervous System (CNS); Macroglobulinemia, Waldenstrom; Malignant Fibrous Histiocytoma of Bone and Osteosarcoma; Medulloblastoma, Childhood; Medulloepithelioma, Childhood; Melanoma; Melanoma, Intraocular (Eye); Merkel Cell Carcinoma; Mesothelioma, Adult Malignant; Mesothelioma, Childhood; Metastatic Squamous Neck Cancer with Occult Primary; Mouth Cancer; Multiple Endocrine Neoplasia Syndromes, Childhood; Multiple Myeloma/Plasma Cell Neoplasm; Mycosis Fungoides; Myelodysplastic Syndromes; Myelodysplastic/Myeloproliferative Neoplasms; Myelogenous Leukemia, Chronic; Myeloid Leukemia, Adult Acute; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Non-Hodgkin Lymphoma, Adult; Non-Hodgkin Lymphoma, Childhood; Non-Small Cell Lung Cancer; Oral Cancer, Childhood; Oral Cavity Cancer, Lip and; Oropharyngeal Cancer; Osteosarcoma and Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood; Pancreatic Cancer, Islet Cell Tumors; Papillomatosis, Childhood; Paranasal Sinus and Nasal Cavity Cancer; Parathyroid Cancer; Penile Cancer; Pharyngeal Cancer; Pineal Parenchymal Tumors of Intermediate Differentiation, Childhood; Pineoblastoma and Supratentorial Primitive Neuroectodermal Tumors, Childhood; Pituitary Tumor; Plasma Cell Neoplasm/Multiple Myeloma; Pleuropulmonary Blastoma, Childhood; Pregnancy and Breast Cancer; Primary Central Nervous System (CNS) Lymphoma; Prostate Cancer; Rectal Cancer; Renal Cell (Kidney) Cancer; Renal Pelvis and Ureter, Transitional Cell Cancer; Respiratory Tract Cancer with Chromosome 15 Changes; Retinoblastoma; Rhabdomyosarcoma, Childhood; Salivary Gland Cancer; Salivary Gland Cancer, Childhood; Sarcoma, Ewing Sarcoma Family of Tumors; Sarcoma, Kaposi; Sarcoma, Soft Tissue, Adult; Sarcoma, Soft Tissue, Childhood; Sarcoma, Uterine; Sezary Syndrome; Skin Cancer (Nonmelanoma); Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Cell Carcinoma; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T-Cell Lymphoma, Cutaneous; Testicular Cancer; Testicular Cancer, Childhood; Throat Cancer; Thymoma and Thymic Carcinoma; Thymoma and Thymic Carcinoma, Childhood; Thyroid Cancer; Thyroid Cancer, Childhood; Transitional Cell Cancer of the Renal Pelvis and Ureter; Trophoblastic Tumor, Gestational; Unknown Primary Site, Carcinoma of, Adult; Unknown Primary Site, Cancer of, Childhood; Unusual Cancers of Childhood; Ureter and Renal Pelvis, Transitional Cell Cancer; Urethral Cancer; Uterine Cancer, Endometrial; Uterine Sarcoma; Vaginal Cancer; Vaginal Cancer, Childhood; Vulvar Cancer; Waldenstrom Macroglobulinemia; Wilms Tumor; Women's Cancers.

We claim:

1. A method of treating a cancer patient comprising the step of administering to the patient a therapeutic anti-cancer composition comprising at least one each of a curcumin a component, a harmine component, and an isovanillin component, where said curcumin component is selected from the group consisting of curcumin, tetrahydro curcumin, demethyl curcumin, demethoxy curcumin, disdemethoxy curcumin, 1,3-diphenyl-2-propanone, caffeic acid phenethyl ester, (1E,4E)-1,5-bis[3,5-bis(methoxymethoxy)phenyl]-1,4-pentadiene-3-one, 1,7-di(1-naphthyl)-2,6-heptanedione, trans,trans-1,5-Bis[4-(trifluoromethyl)phenyl]-1,4-pentadien-3-one, 1,5-dibenzoylpentane, (2E,5E)-2,5-dibenzylidenecyclopentanone, 2,6-bis(4-fluorobenzal)cyclohexanone, (1E,4E)-1,5-bis(4-fluorophenyl)-1,4-pentadien-3-one, FLLL31, and mixtures thereof, said harmine component is selected from the group consisting of harmine, harmaline, harmane, hamalol, harmol, norharmane, 6-methoxyharmalan, bromo harmine, 2-methyl harmine, 4,9-dihydro-3H-beta-carbolin-1-yl methyl ether, 1-(4-nitrophenyl)-2,3,4,9-tetrahydro-1H-beta-carboline hydrochloride, 1,2,3,4-tetrahydro-9H-pyrido[3,4-b]indole {THbC}, 1,2,3,4-tetrahydro-beta-carboline-1-carboxylic acid, 6-Methoxy-1,2,3,4-tetrahydro-9H-pyrido[3,4-b]indole, 3-hydroxymethyl-b-carboline, 2,3,4,5-tetrahydro-8-methoxy-1H-pyrido[4,3-b]indole, 6-Methoxy-1,2,3,4-tetrahydro-9H-pyrido[3,4-b]indole-1-carboxylic acid, ethyl b-carboline-3-carboxylate, and mixtures thereof, and said isovanillin component is selected from the group consisting of isovanillin, orthovanillin, isovanillyl alcohol, isovanillic acid, 2-bromo-3-hydroxy-4-methoxy benzaldehyde, 2-iodo-3-hydroxy-4-methoxy benzaldehyde, o-anisaldehyde, isovanillin oxime, ethyl vanillin, vanillin isobutyrate, veratraldehyde, 5-nitrovanillin, vanillin acetate, 3-benzyloxy-4-methoxybenzaldehyde, 3-hydroxy-5-methoxybenzaldehyde, methyl isovanillate, acetovanillone (apocynin), 2-hydroxy-4-methoxybenzaldehyde, trans-ferulic acid, 3-hydroxy-4-methoxycinnamic acid, caffeic acid, and mixtures thereof, with the total weight amount of isovanillin component(s) being preponderant, and with the total weight amounts of curcumin component(s) and harmine component(s) being present in lesser amounts, the curcumin, harmine, and isovanillin components being selected and present in amounts to provide anti-cancer synergy for the composition, wherein said cancer is selected from the group consisting of leukemia, lymphoma, ovarian cancer, lung cancer, breast cancer and prostate cancer.

2. The method of claim 1, wherein said components are individually and independently in the form of esters, metal complexes, pharmaceutically acceptable salts, and mixtures thereof.

3. The method of claim 1, said composition exhibiting anti-cancer activity against lung cancer cells, lymphoma cells, and leukemia cells.

4. The method of claim 3, said composition exhibiting anti-cancer activity against lung cancer cells, H358, lymphoma cells, M0205, and leukemia cells, jurkat E6-1.

5. The method of claim 1, the weight ratios of isovanillin component(s):harmine component(s):curcumin component(s) being approximately 0.1-25:0.1-5:0.1-5.

6. The method of claim 5, said ratio being about 10:1.7:0.85.

7. The method of claim 1, wherein said isovanillin component(s) are present at a level of from about 25-85% by weight, said harmine component(s) are present at a level of from about 7-50% by weight, and said curcumin component(s) are present at a level of from about 5-40% by weight, based upon the total weight of the three components taken as 100% by weight.

8. The method of claim 1, said composition exhibiting anti-cancer synergy with lymphoma, ovarian cancer, or breast cancer cells.

9. The method of claim 8, said composition exhibiting anti-cancer synergy with lymphoma cancer cells, M0205.

10. The method of claim 8, said composition exhibiting anti-cancer synergy with ovarian cancer cells, A1847.

11. The method of claim 8, said composition exhibiting anti-cancer synergy with breast cancer cells, du4475.

12. The method of claim 1, said composition being in the form of liquids, gels, suspensions, solutions, solids, capsules, pills, or tablets.

13. The method of claim 1, including the step of administering said composition by oral, rectal, nasal, ophthalmic, parenteral, cutaneous, subcutaneous, or intramuscular administration.

14. A method of inhibiting the growth of cancer cells comprising the step of contacting said cells with an anti-cancer composition comprising at least one each of a curcumin a component, a harmine component, and an isovanillin component, where said curcumin component is selected from the group consisting of curcumin, tetrahydro curcumin, demethyl curcumin, demethoxy curcumin, disdemethoxy curcumin, 1,3-diphenyl-2-propanone, caffeic acid phenethyl ester, (1E,4E)-1,5-bis[3,5-bis(methoxymethoxy)phenyl]-1,4-pentadiene-3-one, 1,7-di(1-naphthyl)-2,6-heptanedione, trans,trans-1,5-Bis[4-(trifluoromethyl)phenyl]-1,4-pentadien-3-one, 1,5-dibenzoylpentane, (2E,5E)-2,5-dibenzylidenecyclopentanone, 2,6-bis(4-fluorobenzal)cyclohexanone, (1E,4E)-1,5-bis(4-fluorophenyl)-1,4-pentadien-3-one, FLLL31, and mixtures thereof, said harmine component is selected from the group consisting of harmine, harmaline, harmane, hamalol, harmol, norharmane, 6-methoxyharmalan, bromo harmine, 2-methyl harmine, 4,9-dihydro-3H-beta-carbolin-1-yl methyl ether, 1-(4-nitrophenyl)-2,3,4,9-tetrahydro-1H-beta-carboline hydrochloride, 1,2,3,4-tetrahydro-9H-pyrido[3,4-b]indole {THbC}, 1,2,3,4-tetrahydro-beta-carboline-1-carboxylic acid, 6-Methoxy-1,2,3,4-tetrahydro-9H-pyrido[3,4-b]indole, 3-hydroxymethyl-b-carboline, 2,3,4,5-tetrahydro-8-methoxy-1H-pyrido[4,3-b]indole, 6-Methoxy-1,2,3,4-tetrahydro-9H-pyrido[3,4-b]indole-1-carboxylic acid, ethyl b-carboline-3-carboxylate, and mixtures thereof, and said isovanillin component is selected from the group consisting of isovanillin, orthovanillin, isovanillyl alcohol, isovanillic acid, 2-bromo-3-hydroxy-4-methoxy benzaldehyde, 2-iodo-3-hydroxy-4-methoxy benzaldehyde, o-anisaldehyde, isovanillin oxime, ethyl vanillin, vanillin isobutyrate, veratraldehyde, 5-nitrovanillin, vanillin acetate, 3-benzyloxy-4-methoxybenzaldehyde, 3-hydroxy-5-methoxybenzaldehyde, methyl isovanillate, acetovanillone (apocynin), 2-hydroxy-4-methoxybenzaldehyde, trans-ferulic acid, 3-hydroxy-4-methoxycinnamic acid, caffeic acid, and mixtures thereof, with the total weight amount of isovanillin component(s) being preponderant, and with the total weight amounts of curcumin component(s) and harmine component(s) being present in lesser amounts, the curcumin, harmine, and isovanillin components being selected and present in amounts to provide anti-cancer synergy for the composition, wherein said cancer is selected from the group consisting of leukemia, lymphoma, ovarian cancer, lung cancer, breast cancer and prostate cancer.

15. The method of claim 14 wherein said components are individually and independently in the form of esters, metal complexes, pharmaceutically acceptable salts, and mixtures thereof.

16. The method of claim 14, said composition exhibiting anti-cancer activity against lung cancer cells, lymphoma cells, and leukemia cells.

17. The method of claim 16, said composition exhibiting anti-cancer activity against lung cancer cells, H358, lymphoma cells, M0205, and leukemia cells, jurkat E6-1.

18. The method of claim 14, the weight ratios of isovanillin component(s):harmine component(s):curcumin component(s) being approximately 0.1-25:0.1-5:0.1-5.

19. The method of claim 18, said ratio being about 10:1.7:0.85.

20. The method of claim 14, wherein said isovanillin component(s) are present at a level of from about 25-85% by weight, said harmine component(s) are present at a level of from about 7-50% by weight, and said curcumin component(s) are present at a level of from about 5-40% by weight, based upon the total weight of the three components taken as 100% by weight.

21. The method of claim 14, said composition exhibiting anti-cancer synergy with lymphoma, ovarian cancer, or breast cancer cells.

22. The method of claim 21, said composition exhibiting anti-cancer synergy with lymphoma cancer cells, M0205.

23. The method of claim 21, said composition exhibiting anti-cancer synergy with ovarian cancer cells, A1847.

24. The method of claim 21, said composition exhibiting anti-cancer synergy with breast cancer cells, du4475.

* * * * *